US006737383B1

(12) United States Patent
Annis et al.

(10) Patent No.: US 6,737,383 B1
(45) Date of Patent: May 18, 2004

(54) HERBICIDAL OXADIAZOLIDINES

(75) Inventors: Gary David Annis, Landenberg, PA (US); George Chih-Shu Chiang, Wilmington, DE (US); David Raymond Forney, Elkton, MD (US); Kanu Maganbhai Patel, Wilmington, DE (US); Morris Padgett Rorer, Newark, DE (US); William Francis Smith, III, Elkton, MD (US); Thomas Martin Stevenson, Newark, DE (US); King-Mo Sun, Hockessin, DE (US); Chi-Ping Tseng, Wilmington, DE (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/869,771

(22) PCT Filed: Jan. 20, 2000

(86) PCT No.: PCT/US00/01283

§ 371 (c)(1),
(2), (4) Date: Jun. 29, 2001

(87) PCT Pub. No.: WO00/43377

PCT Pub. Date: Jul. 27, 2000

Related U.S. Application Data

(60) Provisional application No. 60/117,210, filed on Jan. 25, 1999.

(51) Int. Cl.[7] ........................ C07D 271/07; A01N 47/38
(52) U.S. Cl. ........................................ 504/265; 548/132
(58) Field of Search ........................... 548/132; 504/265

(56) References Cited

U.S. PATENT DOCUMENTS

| | | |
|---|---|---|
| 3,950,367 A | 4/1976 | Botta |
| 5,356,865 A | 10/1994 | Miller et al. |

FOREIGN PATENT DOCUMENTS

| | | |
|---|---|---|
| DE | 1259871 | 2/1968 |
| EP | 0477646 A1 | 4/1992 |
| GB | 1168721 | 10/1969 |

OTHER PUBLICATIONS

Database Crossfire Online—Beilstein Institut zur Foerderung der Chemischen Wissenschaften; XP002141082 Beilstein Registry No. 5973265, 5944839, 5942772, 5940606, 5927572 & Arch. Pharm., vol. 314, No. 4, 1981, pp. 294–302.

Database Crossfire Online—Beilstein Institut zur Foerderung der Chemischen Wissenschaften; XP992141083 Beilstein Registry No. 513318, 611515, 519232, 509077, 510600, 511401 & Arch. Pham. Ber. DTSCH. Pharm. GES., vol. 303, 1970, pp. 139–144.

Database Crossfire Online Beilstein Institut zur Foerderung der Chemischen Wissenschaften; XP002141084 Beilstein Registry No. 972970, 973571, 974317, 975960, 981328 & Arch Pharm Ber. DTSCH. Pharm GES., vol. 303, 1970, pp. 385–390.

Database Crossfire Online Bellstein Institut zur Foerderung der Chemischen Wissenschaften; XP002141085 Beilstein Registry No. 519889, 521425, 5222254, 534767, 4937992 & Chem. Ber., vol. 98, 1965, pp. 144–154.

Chemical Abstracts, vol. 80, No. 19, May 13, 1974 Columbus, Ohio, US; abstract No. 108148v, Zinner G et al: "Hydroxylamine derivatives. 56. Synthesis and acylations of 1,1–Dialkyl-3–hydroxyureas" p. 383; XP0021164 cited in the application abstract & Arch. Pharm., vol. 307, No. 1, 1974, pp. 7–12, Weinheim, DE Arch. Pharm (1974), 307, 7–12.

*Primary Examiner*—Robert Gerstl
(74) *Attorney, Agent, or Firm*—Paul Littlepage; Quine Intellectual Property Law Group, P.C.

(57) ABSTRACT

Compounds of Formula (1) and processes for their preparation, their N-oxides and agriculturally suitable salts, are disclosed which are useful for controlling undesired vegetation wherein Q, $X^1$, $X^2$, $X^3$, $R^1$, $R^2$, $R^6$ and $R^7$ are as defined in the disclosure. Also disclosed are novel intermediates of Formula (5), Formula (8) and Formula (20) wherein $R^{27}$ is $—(CR^6R^7)_q—Q$; $R^6$, $R^7$, q, Q, $X^1$ and $X^2$ are as defined in the disclosure. Also disclosed are compositions containing the compounds of Formula (1) and a method for controlling undesired vegetation which involves contacting the vegetation or its environment with an effective amount of a compound of Formula (1).

(1)

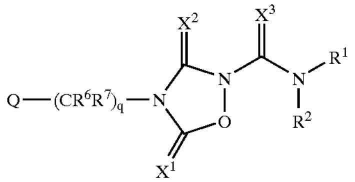

(5)

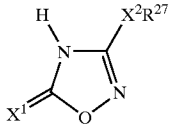

(8)

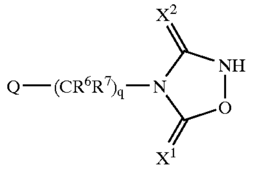

(20)

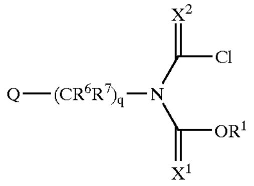

25 Claims, No Drawings

HERBICIDAL OXADIAZOLIDINES

This application claims the benefit of Provisional Application Ser. No. 60/117,210 filed Jan. 25, 1999.

BACKGROUND OF THE INVENTION

This invention relates to certain oxadiazolidines, processes for their preparation, their N-oxides, agriculturally suitable salts and compositions, and methods of their use for controlling undesirable vegetation. This invention also relates to mixtures of herbicides that have a synergistic effect on weeds or have a safening effect on crops while retaining or increasing weed control.

The control of undesired vegetation is extremely important in achieving high crop efficiency. Achievement of selective control of the growth of weeds especially in such useful crops as rice, soybean, sugar beet, corn (maize), potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds which are more effective, less costly, less toxic, environmentally safer or have different modes of action. *Arch. Pharm.* (1974), 307, 7–12 discloses the chemical structures of N,N-substituted 4-aryloxazolidindiones. However, it does not disclose the compounds of the present invention.

SUMMARY OF THE INVENTION

This invention is directed to compounds and processes to prepare compounds of Formula 1 including all geometric and stereoisomers, N-oxides, and agriculturally suitable salts thereof, agricultural compositions containing them and their use for controlling undesirable vegetation:

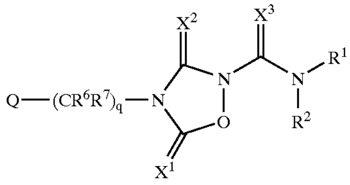

1 wherein

- Q is H; or $C_1$–$C_{12}$ alkyl, $C_3$–$C_{10}$ cycloalkyl, $C_6$–$C_{14}$ bicycloalkyl, $C_3$–$C_{12}$ alkenyl, $C_3$–$C_{10}$ cycloalkenyl, $C_6$–$C_{14}$ bicycloalkenyl or $C_3$–$C_{12}$ alkynyl, each optionally substituted with one or more $R^{21}$; or
- Q is a 3- to 7-membered fully saturated or 5- to 7-membered partially saturated heterocyclic ring containing one or two X, provided that (a) when X is other than O or $S(O)_n$, then only one X may be present and (b) when two X are present in the ring, they cannot be bonded directly to each other; or
- Q is a 5- or 6-membered aromatic heterocyclic ring system containing 1 to 3 heteroatoms independently selected from the group consisting of nitrogen, oxygen and sulfur, provided that the heterocyclic ring system contains no more than one oxygen and no more than one sulfur, and each heterocyclic ring system is optionally substituted with one or more $R^{16}$; and when Q is a 5- or 6-membered aromatic heterocyclic ring system containing a nitrogen, then Q is bonded through any available carbon or nitrogen atom by replacement of a hydrogen on said carbon or nitrogen atom; or
- Q is phenyl optionally substituted with one or more substituents independently selected from the group consisting of $R^{16}$, phenoxy and Z; or
- Q is

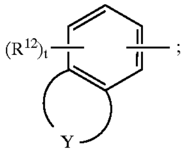
;
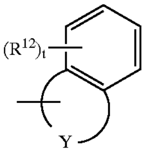
or
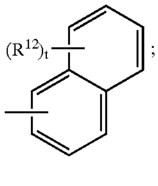
; or

- Q is —$C(R^{14})(=NOR^{15})$, —$C(O)R^{19}$, —$C(O)OR^{19}$, —$C(O)SR^{19}$, —$C(S)R^{19}$, —$C(S)OR^{19}$, —$C(S)SR^{19}$, —$C(O)NR^{23}R^{24}$, —$C(S)NR^{23}R^{24}$, —$OR^{19}$, —$NR^{19}R^{20}$, —$S(O)_nR^{19}$ or —$S(O)_nNR^{19}R^{20}$;
- each X is —O—, —$S(O)_n$—, —N=, —$NR^{10}$— or —Si$(R^{11})_2$—;
- Y is, together with the carbons to which it is attached, a fully or partially saturated 5-, 6- or 7-membered carbocyclic ring optionally substituted with one or more $C_1$–$C_4$ alkyl groups; or
- Y is, together, with the carbons to which it is attached, a fully or partially saturated 5-, 6- or 7-membered heterocyclic ring which contains one or two X and is optionally substituted with one or more $R^{12}$, provided that when said heterocyclic ring contains two X, then one X is other than O;
- Z is phenyl or a 5- or 6-membered aromatic heterocyclic ring system containing 1 to 3 heteroatoms independently selected from the group consisting of nitrogen, oxygen and sulfur, provided that the heterocyclic ring system contains no more than one oxygen and no more than one sulfur, and each phenyl and heterocyclic ring system is optionally substituted with one or more $R^{16}$;
- $R^1$ is $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl, $C_3$–$C_6$ haloalkynyl, $C_1$–$C_6$ alkoxy, $C_2$–$C_6$ alkoxyalkyl or $C_2$–$C_6$ haloalkoxyalkyl; or $R^1$ is $C_3$–$C_7$ cycloalkyl or $C_3$–$C_7$ cycloalkenyl, each optionally substituted with one or more $R^5$; or
- $R^1$ is phenyl optionally substituted with one or more $R^{13}$; or
- $R^1$ is a 5- or 6-membered aromatic heterocyclic ring system containing 1 to 3 heteroatoms independently selected from the group consisting of nitrogen, oxygen and sulfur, provided that the heterocyclic ring system contains no more than one oxygen and no more than one sulfur, and each heterocyclic ring system is optionally substituted with one or more $R^{16}$;
- $R^2$ is $C_1$–$C_6$ alkyl, $C_1$–$C_6$ haloalkyl, $C_3$–$C_7$ cycloalkyl, $C_3$–$C_6$ alkenyl, $C_3$–$C_6$ haloalkenyl, $C_3$–$C_6$ alkynyl, $C_3$–$C_6$ haloalkynyl, $C_1$–$C_6$ alkoxy, $C_2$–$C_6$ alkoxyalkyl, $C_2$–$C_6$ haloalkoxyalkyl or $NR^3R^4$; or $R^2$ is

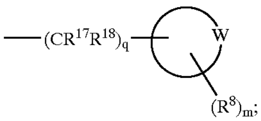

$(R^8)_m$; or $R^1$ and $R^2$ are taken together as $-CH_2CH_2-$, $-CH_2CH_2CH_2-$, $-CH_2CH_2CH_2CH_2-$, $-CH_2CH_2CH_2CH_2CH_2-$ or $-CH_2CH_2OCH_2CH_2-$;

$R^3$ is $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl, $C_3$–$C_6$ haloalkynyl; or $R^3$ is $C_3$–$C_7$ cycloalkyl or $C_3$–$C_7$ cycloalkenyl, each optionally substituted with one or more $R^5$; or $R^3$ is a saturated or partially saturated 5-, 6- or 7-membered heterocyclic ring containing 1 to 2 heteroatoms independently selected from the group consisting of nitrogen, oxygen and sulfur, and each heterocyclic ring is optionally substituted with one or more $R^5$; or $R^3$ is phenyl optionally substituted with one or more $R^{26}$ groups; or $R^1$ and $R^3$ are taken together with the two nitrogen atoms to which they are attached to form a saturated or partially saturated 5-, 6- or 7-membered heterocyclic ring containing an optional third heteroatom selected from the group consisting of oxygen sulfur and nitrogen, and said heterocyclic ring is optionally substituted with one, or more $R^9$; or $R^2$ and $R^{13}$, together with the two atoms to which they are attached and the atom between them, form a fully saturated 5-, 6- or 7-membered carbocyclic or heterocyclic ring containing one oxygen, one sulfur or one or two nitrogen atoms, said heterocyclic ring is optionally substituted with one or more $R^{12}$, provided that when said heterocyclic ring contains two nitrogen atoms, they are other than bonded directly to each other;

$R^4$ is H or $C_1$–$C_4$ alkyl; or $R^3$ and $R^4$ are taken together with the nitrogen atom to which they are attached to form a saturated or partially saturated 5-, 6- or 7-membered heterocyclic ring containing an optional second heteroatom selected from the group consisting of oxygen, sulfur and nitrogen, and said heterocyclic ring is optionally substituted with 1–4 $R^9$;

each $R^5$ is independently halogen, $C_1$–$C_4$ alkyl or $C_1$–$C_4$ alkoxy; or when two $R^5$ are attached to the same carbon, then said two $R^5$ groups are taken together as (=O);

each $R^6$ and $R^7$ are independently H or $C_1$–$C_4$ alkyl;

$R^8$ is independently $C_1$–$C_4$ alkyl, $C_1$–$C_4$ haloalkyl or $C_1$–$C_4$ alkoxy, each $R^9$ is independently $C_1$–$C_4$ alkyl or $C_1$–$C_4$ alkoxy; or when two $R^9$ are attached to the same carbon, then said two $R^9$ groups are taken together as (=O);

W is, together with the carbons to which it is attached, a fully or partially saturated 5-, 6- or 7-membered heterocyclic ring containing one or two X, provided that (a) when X is other than O or $S(O)_n$, then only one X may be present; (b) when two X are present in the ring, they cannot be bonded directly to each other; and (c) said heterocyclic ring is bonded to the group $(CR^{17}R^{18})_q$ through other than X;

$R^{10}$ is H, $C_1$–$C_4$ alkyl, $C_1$–$C_4$ haloalkyl, $C_3$–$C_4$ alkenyl, $C_3$–$C_4$ alkynyl, $C_2$–$C_4$ alkoxycarbonyl or $C_2$–$C_4$ alkylcarbonyl; or $R^{10}$ is phenyl optionally substituted with $C_1$–$C_3$ alkyl, halogen, cyano, nitro or $C_2$–$C_4$ alkoxycarbonyl;

each $R^{11}$ is $C_1$–$C_4$ alkyl;

each $R^{12}$ is independently halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ haloalkylthio, $C_1$–$C_4$ alkylsufinyl, $C_1$–$C_4$ alkylsufonyl or $C_2$–$C_4$ alkoxycarbonyl;

each $R^{13}$ is independently halogen, $C_1$–$C_3$ alkyl, $C_1$–$C_3$ haloalkyl, $C_1$–$C_3$ alkoxy, $C_1$–$C_3$ haloalkoxy, $C_3$–$C_6$ alkenyloxy, $C_3$–$C_6$ alkynyloxy, $C_1$–$C_4$ alkylthio, $C_1$–$C_4$ haloalkylthio, $C_1$–$C_4$ alkylsufinyl, $C_1$–$C_4$ alkylsufonyl, cyano, amino, nitro or $C_2$–$C_4$ alkoxycarbonyl;

$R^{14}$ is H, $C_1$–$C_6$ alkyl, $C_1$–$C_6$ haloalkyl or $C_2$–$C_6$ alkoxyalkyl; or $R^{14}$ and $R^6$, together with the carbon atoms to which they are bonded, form a 5- or 6-membered saturated carbocyclic ring optionally substituted with one or more $C_1$–$C_4$ alkyl groups;

$R^{15}$ is H, $C_1$–$C_6$ alkyl, $C_1$–$C_6$ haloalkyl, $C_3$–$C_4$ alkenyl or $C_3$–$C_4$ alkynyl;

each $R^{16}$ is independently halogen, nitro, cyano, $C_1$–$C_4$ alkyl, $C_1$–$C_4$ haloalkyl, $C_3$–$C_4$ alkenyl, $C_3$–$C_4$ alkynyl, $OR^{22}$, $NR^{23}R^{24}$ or $S(O)_nR^{19}$;

each $R^{17}$ and $R^{18}$ are independently H or $C_1$–$C_4$ alkyl;

each $R^{19}$ and $R^{20}$ are independently $C_1$–$C_{12}$ alkyl, $C_3$–$C_8$ cycloalkyl, $C_3$–$C_{12}$ alkenyl, $C_3$–$C_8$ cycloalkenyl or $C_3$–$C_{12}$ alkynyl, each optionally substituted with one or more $R^{21}$;

each $R^{21}$ is halogen, $C_4$–$C_8$ trialkylsilylalkyl, CN, $NO_2$, $-OR^{22}$, $-NR^{23}R^{24}$, $-S(O)_nR^{22}$, $-S(O)_nNR^{23}R^{24}$, $-C(O)R^{22}$, $-C(S)R^{22}$, $-C(O)OR^{22}$, $-C(S)OR^{22}$, $-C(S)SR^{22}$, $-C(O)NR^{23}R^{24}$, $-C(S)NR^{23}R^{24}$, $-CHR^{25}COR^{22}$, $-CHR^{25}P(O)(OR^{22})_2$, $-CHR^{25}P(S)(OR^{22})_2$, $-CHR^{25}C(O)NR^{23}R^{24}$, $-CHR^{25}C(O)NH_2$, $-CHR^{25}CO_2R^{22}$, phenyl optionally substituted with one or more $R^{26}$ groups or benzyl optionally substituted with one or more $R^{26}$ groups;

each $R^{22}$ is $C_1$–$C_8$ alkyl, $C_3$–$C_8$ cycloalkyl, $C_3$–$C_8$ alkenyl, $C_3$–$C_8$ alkynyl, $C_1$–$C_8$ haloalkyl, $C_2$–$C_8$ alkoxyalkyl, $C_2$–$C_8$ alkylthioalkyl, $C_2$–$C_8$ alkylsulfinylalkyl, $C_2$–$C_8$ alkylsulfonylalkyl, $C_4$–$C_8$ alkoxyalkoxyalkyl, $C_4$–$C_8$ cycloalkylalkyl, $C_4$–$C_8$ alkenoxyalkyl, $C_4$–$C_8$ alkynyloxyalkyl, $C_6$–$C_8$ cycloalkoxyalkyl, $C_4$–$C_8$ alkenyloxyalkyl, $C_4$–$C_8$ alkynyloxyalkyl, $C_3$–$C_8$ haloalkoxyalkyl, $C_4$–$C_8$ haloalkenoxyalkyl, $C_4$–$C_8$ haloalkynyloxyalkyl, $C_6$–$C_8$ cycloalkylthioalkyl, $C_4$–$C_8$ alkenylthioalkyl, $C_4$–$C_8$ alkynylthioalkyl, $C_1$–$C_4$ alkyl substituted with phenoxy or benzyloxy, each ring optionally substituted with halogen, $C_1$–$C_3$ alkyl or $C_1$–$C_3$ haloalkyl, $C_4$–$C_8$ trialkylsilylalkyl, $C_3$–$C_8$ cyanoalkyl, $C_3$–$C_8$ halocycloalkyl, $C_3$–$C_8$ haloalkenyl, $C_5$–$C_8$ alkoxyalkenyl, $C_5$–$C_8$ haloalkoxyalkenyl, $C_5$–$C_8$ alkylthioalkenyl, $C_3$–$C_8$ haloalkynyl, $C_5$–$C_8$ alkoxyalkynyl, $C_5$–$C_8$ haloalkoxyalkynyl, $C_5$–$C_8$ alkylthioalkynyl, $C_2$–$C_8$ alkyl carbonyl, $C_2$–$C_8$ alkoxy carbonyl, phenyl optionally substituted with halogen, CN, $C_1$–$C_2$ haloalkyl and $C_1$–$C_2$ haloalkoxy or benzyl optionally substituted with halogen, $C_1$–$C_3$ alkyl and $C_1$–$C_3$ haloalkyl;

each $R^{23}$ is H or $C_1$–$C_4$ alkyl;

each $R^{24}$ is $C_1$–$C_4$ alkyl or phenyl optionally substituted with one or more $R^{26}$ groups;

$R^{23}$ and $R^{24}$ may be taken together as $-(CH_2)_5-$, $-(CH_2)_4-$ or $-CH_2CH_2OCH_2CH_2-$, each ring optionally substituted with $C_1$–$C_3$ alkyl, phenyl or benzyl;

each $R^{25}$ is H or $C_1$–$C_4$ alkyl;

each $R^{26}$ is $C_1$–$C_3$ alkyl, $C_1$–$C_3$ haloalkyl, $C_1$–$C_3$ alkoxy, $C_1$–$C_3$ haloalkoxy, $C_1$–$C_3$ alkylthio, $C_2$–$C_5$ alkylcarbonyl, $C_2$–$C_5$ alkoxycarbonyl, halogen, amino, cyano or nitro;

$R^{28}$ is H or $C_1$–$C_4$ alkyl;

$X^1$ and $X^2$ are independently O or S;

$X^3$ is O, S or $NR^{28}$;

m is 0, 1, 2, 3 or 4;

each n is independently 0, 1 or 2;

p is 0 or 1;

each q is independently 0, 1 or 2; and t is 0, 1 or 2;

provided that when Q is unsubstituted phenyl, $X^1$, $X^2$ and $X^3$ are O, q is 0 and $R^2$ is methyl, then $R^1$ is other than methyl.

In the above recitations, the term "alkyl"used either alone or in compound words such as "alkylthio" or "haloalkyl" includes straight-chain or branched alkyl, such as, methyl, ethyl, n-propyl, i-propyl, or the different butyl, pentyl or hexyl isomers. The term "1-2 alkyl" indicates that one or two of the available positions for that substituent may be alkyl. "Alkenyl" includes straight-chain or branched alkenes such as 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkylthio" includes branched or straight-chain alkylthio moieties such as methylthio, ethylthio, and the different propylthio, butylthio, pentylthio and hexylthio isomers. "Cycloalkyl" includes, for example, cyclopropyl, cyclobutyl, cyclopentyl and cyclohexyl. "Saturated Carbocyclic" ring denotes a ring having a backbone consisting of carbon atoms linked to one another by single bonds; unless otherwise specified, the remaining carbon valences are occupied by hydrogen atoms.

The term "halogen"either alone or in compound words such as "haloalkyl"includes fluorine, chlorine, bromine or iodine. Further, when used in compound words such as "haloalkyl"said alkyl may be partially or fully substituted with halogen atoms which may be the same or different. Examples of"haloalkyl" include $F_3C$, $ClCH_2$, $CF_3CH_2$ and $CF_3CCl_2$. The terms "haloalkenyl""haloalkynyl", "haloalkoxy"and the like, are defined analogously to the term "haloalkyl". Examples of "haloalkenyl" include $(Cl)_2C{=}CHCH_2$ and $CF_3CH_2CH{=}CHCH_2$. Examples of "haloalkynyl" include $HC{\equiv}CCHCl$, $CF_3C{\equiv}C$, $CCl_3C{\equiv}C$ and $FCH_2C{\equiv}CCH_2$. Examples of "haloalkoxy" include $CF_3O$, $CCl_3CH_2O$, $HCF_2CH_2CH_2O$ and $CF_3CH_2O$.

The total number of carbon atoms in a substituent group is indicated by the "$C_i$–$C_j$" prefix where i and j are numbers from 1 to 12. For example, $C_1$–$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$. In the above recitations, when a compound of Formula 1 contains a heterocyclic ring, all substituents are attached to this ring through any available carbon or nitrogen by replacement of a hydrogen on said carbon or nitrogen.

When a group contains a substituent which can be hydrogen, for example $R^3$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art ,will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula 1, N-oxides and agriculturally suitable salts thereof The compounds of the invention may be present as a mixture of stereoisomers, individual stereoisomers, or as an optically active form.

One skilled in the art will appreciate that not all nitrogen containing heterocycles can form N-oxides since the nitrogen requires an available lone pair for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethydioxirane. These methods for the preparation of N-oxides have been extensively described and reviewed in the literature, see for example: T. L. Gilchrist in *Comprehensive Organic Synthesis*, vol. 7, pp 748–750, S. V. Ley, Ed, Pergamon Press; M. Tisler and B. Stanovnik in *Comprehensive Heterocyclic Chemistry*, vol. 3, pp 18–20, A. J. Boulton and A. McKillop, Eds., Pergamon Press; M. R. Grimmett and B. R. T. Keene in *Advances in Heterocyclic Chemistry*, vol. 43, pp 149–161, A. R. Katritzky, Ed., Academic Press; M. Tisler and B. Stanovnik in *Advances in Heterocyclic Chemistry*, vol. 9, pp 285–291, A. R. Katritzky and A. J. Boulton, Eds., Academic Press; and G. W. H. Cheeseman and E. S. G. Werstiuk in *Advances in Heterocyclic Chemistry*, vol. 22, pp 390–392, A. CR. Katritzky and A. J. Boulton, Eds., Academic Press.

The salts of the compounds of the invention include acid-addition salts with inorganic or organic acids such as hydrobrornic, hydrochloric, nitric, phosphoric, sulfuric, acetic, butyric, fumaric, lactic, maleic, malonic, oxalic, propionic, salicylic, tartaric, 4-toluenesulfonic or valeric acids.

Preferred compounds for reasons of better activity and/or ease of synthesis are:

Preferred 1. Compounds of Formula 1 wherein

Q is H; or $C_1$–$C_{12}$ alkyl, $C_3$–$C_8$ cycloalkyl, $C_3$–$C_{12}$ alkenyl, $C_3$–$C_8$ cycloalkenyl or $C_3$–C 12 alkynyl, each optionally substituted with one or more $R^{21}$; or Q is a 3- to 7-membered fully saturated or 5- to 7-membered partially saturated heterocyclic ring containing one or two X, provided that (a) when X is other than O or $S(O)_n$, then only one X may be present and (b) when two X are present in the ring, they cannot be bonded directly to each other; or Q is a 5- or 6-membered aromatic heterocyclic ring system containing 1 to 3 heteroatoms independently selected from the group consisting of nitrogen, oxygen and sulfur, provided that the heterocyclic ring system contains no more than one oxygen and no more than one sulfur, and each heterocyclic ring system is optionally substituted with one or more $R^{16}$; and when Q is a 5- or 6-membered aromatic heterocyclic ring system containing a nitrogen, then Q is bonded through any available carbon or nitrogen atom by replacement of a hydrogen on said carbon or nitrogen atom; or Q is phenyl optionally substituted with one or more substituents independently selected from the group consisting of $R^{16}$, phenoxy and Z.

Preferred 2. Compounds of Preferred 1 wherein

Q is $C_1$–$C_{12}$ alkyl, $C_3$–$C_8$ cycloalkyl, $C_3$–$C_{12}$ alkenyl, $C_3$–$C_8$ cycloalkenyl or $C_3$–$C_{12}$ alkynyl, each optionally substituted with one or more $R^{21}$.

Preferred 3. Compounds of Preferred 1 wherein

Q is a 3- to 7-membered fully saturated or 5- to 7-membered partially saturated heterocyclic ring containing one or two X, provided that (a) when X is other than O or $S(O)_n$, then only one X may be present and (b) when two X are present in the ring, they cannot be bonded directly to each other, or Q is a 5- or 6-membered aromatic heterocyclic ring system containing 1 to 3 heteroatoms independently selected from the group consisting of nitrogen, oxygen and sulfur, provided that the heterocyclic ring system contains no more than one oxygen and no more than one sulfur, and each heterocyclic ring system is optionally substituted with one or more $R^{16}$; and when Q is a 5- or 6-membered aromatic heterocyclic ring system containing a nitrogen, then Q is bonded through any available carbon or nitrogen atom by replacement of a hydrogen on said carbon or nitrogen atom.

Preferred 4. Compounds of Preferred 1 wherein

Q is phenyl optionally substituted with one or more substituents independently selected from the group consisting of $R^{16}$, phenoxy and Z.

Preferred 5. Compounds of Preferred 2 wherein

Q is $C_1$–$C_6$ alkyl optionally substituted with one or more $R^{21}$, $C_5$–$C_7$ cycloalkyl, $C_3$–$C_7$ alkenyl or $C_3$–$C_6$ alkynyl.

Preferred 6. Compounds of Preferred 3 wherein

Q is a 5- or 6-membered aromatic heterocyclic ring system containing 1 to 3 heteroatoms independently selected from the group consisting of nitrogen, oxygen and sulfur, provided that the heterocyclic ring system contains no more than one oxygen and no more than one sulfur, and each heterocyclic ring system is optionally substituted with one or more $R^{16}$; and when Q is a 5- or 6-membered aromatic heterocyclic ring system containing a nitrogen, then Q is bonded through any available carbon or nitrogen atom by replacement of a hydrogen on said carbon or nitrogen atom.

Preferred 7. Compounds of Preferred 4 wherein

Q is phenyl optionally substituted with one or more substituents independently selected from the group consisting of $R^{16}$.

Preferred 8. Compounds of Preferred 2, Preferred 3 or Preferred 4 wherein $X^1$, X2 and $X^3$ are O.

Preferred 9. Compounds of Preferred 7 wherein

Q is phenyl with substituents on the 2-, and 6-position independently selected from the group consisting of $R^{16}$.

Preferred 10. Compounds of Preferred 5 wherein q is 0 or 1.

Preferred 11. Compounds of Preferred 6 wherein q is 0 or 1.

Preferred 12. Compounds of Preferred 7 wherein q is 0 or 1.

Preferred 13. Compounds of Preferred 1 wherein $R^1$ is phenyl substituted with one or more $R^{13}$.

Preferred 14. Compounds of Preferred 1 wherein $R^2$ is $C_2$–$C_6$ alkyl, $C_2$–$C_6$ haloalkyl or $C_2$–$C_6$ alkoxyalkyl.

Most preferred is the compound of Formula 1 which is selected from the group consisting of:

(a) N-(4-fluorophenyl)-N-(1-methylethyl)-4-(2-methylphenyl)-3,5-dioxo-1,2,4-oxadiazolidine-2-carboxamide;

(b) 4-(2,6-dimethylphenyl)-N-(4-fluorophenyl)-N-(1-methylethyl)-3,5-dioxo1,2,4-oxadiazolidine-2-carboxamiide;

(c) 4-(2,6-dimethylphenyl)N-(1-methylethyl)-3,5-dioxo-N-phenyl-1,2,4-oxadiazolidine-2-carboxamide;

(d) 4-cyclohexyl-N-(1-methylethyl)-3,5-dioxo-N-phenyl-1,2,4-oxadiazolidine-2-carboxamide;

(e) 4-cyclohexyl-N-(4-fluorophenyl)-N-(1-methylethyl)-3,5-dioxo-1,2,4-oxadiazolidine-2-carboxamide (f) N,4-bis(1-methylethyl)-3,5-dioxo-N-phenyl-1,2,4-oxadiazolidine-2-carboxamiide;

(g) N-(4-fluorophenyl)-N-(1-methylethyl)-3,5-dioxo-4-(cyclopropyl)-1,2,4-oxadiazolidine-2-carboxamide; and (h) N-(4-fluorophenyl)-N,4-bis(1-methylethyl)-3,5-dioxo-1,2,4-oxadiazolidine-carboxamide.

The oxadiazolidines of Formula 1 are useful as herbicides. The present invention also relates to processes for preparing an oxadiazolidine of Formula 1. The present processes for preparing the oxadiazolidines of Formula 1 provided herein are characterized by employing a process sequence selected from process sequences A, B, C, D or E as described below.

PROCESS SEQUENCE A

A process for preparing a compound of Formula 1

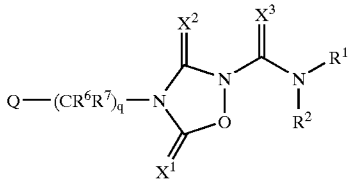

1 wherein Q, $R^6$, $R^7$, q, $X^1$, $X^2$, $X^3$, $R^1$ and $R^2$ are as defined above, comprising:

(a) contacting a compound of Formula 5

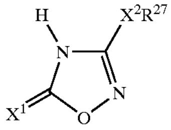
5 wherein $R^{27}$ is —$(CR^6R^7)_q$—Q, with a compound of Formula 4

Q—$(CR^6R^7)_q$—$X^4$ 4 wherein $X^4$ is halogen or mesylate, in the presence of a base to provide a compound of Formula3

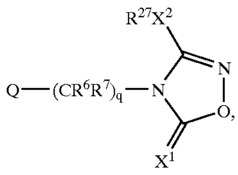
, and 3

(b) contacting the compound of Formula 3 with a carbamoyl or thiocarbamoyl chloride of Formula 2

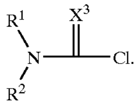
2

PROCESS SEQUENCE B

A process for preparing a compound of Formula 1

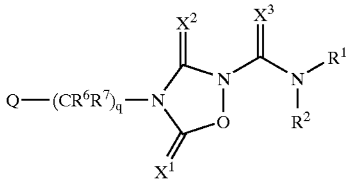
1 wherein Q, $R^6$, $R^7$, q, $X^1$, X2, $X^3$, $R^1$ and $R^2$ are as defined above, comprising:

(a) contacting a compound of Formula 5

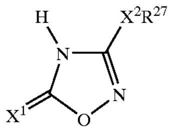
5 wherein $R^{27}$ is —$(CR^6R^7)_q$—Q, with an alcohol of Formula 6

Q—$(CR^6R^7)_q$—OH 6 under reaction conditions involving a tertiary phosphine and an azo compound to provide a compound of Formula 3

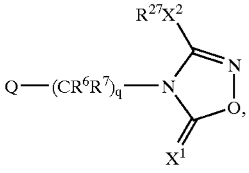
, and 3

(b) contacting the compound of Formula 3 with a carbamoyl or thiocarbamoyl chloride of Formula 2

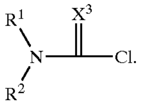
2

PROCESS SEQUENCE C

A process for preparing a compound of Formula 1

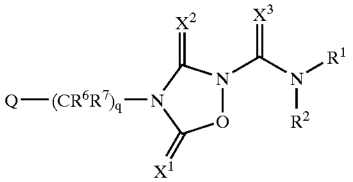
1 wherein Q, $R^6$, $R^7$, q, $X^1$, $X^2$, $X^3$, $R^1$ and $R^2$ are as defined above, comprising:

(a) contacting a compound of Formula 5

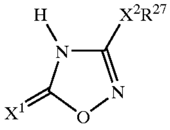
5 wherein $R^{27}$ is —$(CR^6R^7)_q$—Q, with a carbamoyl or thiocarbamoyl chloride of Formula 2

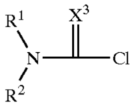
2 in the presence of a base to provide the compound of Formula 1

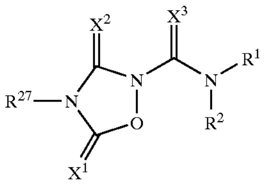
1 directly or a compound of Formula 7

7

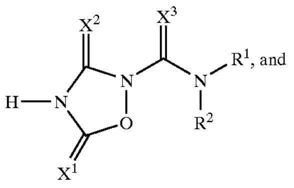

and (b) contacting the compound of Formula 7 with an alcohol of Formula 6

$Q—(CR^6R^7)_q—OH$ 6 under reaction conditions involving a tertiary phosphine and an azo compound or with a compound of Formula 4

$Q—(CR^6R^7)_q—X^4$ 4 in the presence of a base.

PROCESS SEQUENCE D

A process for preparing a compound of Formula 1

1

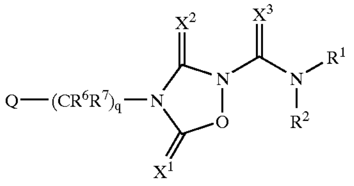

wherein Q, $R^6$, $R^7$, q, $X^2$, $X^3$, $R^1$ and $R^2$ are as defined above, and $X^1$ is O, comprising:

(a) contacting a compound of Formula 19

19

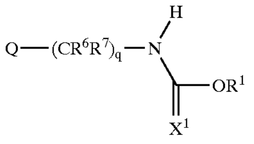

with phosgene or thiophosgene to provide a compound of Formula 20

20

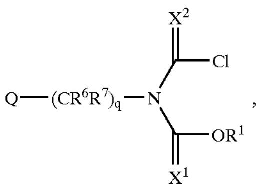

(b) contacting the compound of Formula 20 with hydroxylamine, following by treatment with a base, and then an acid, to provide a compound of Formula 8

8

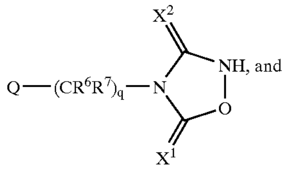

and (c) contacting the compound of Formula 8 with a compound of Formula 2

2

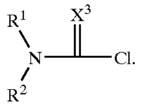

PROCESS SEQUENCE E

A process for preparing a compound of Formula 1

1

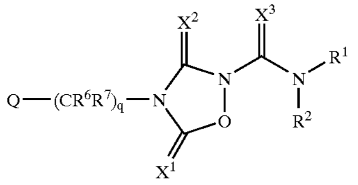

wherein Q, $R^6$, $R^7$, q, $X^1$, $X^2$, $X^3$, $R^1$ and $R^2$ are as defined above, comprising:

(a) contacting a compound of Formula 2

2

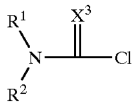

with hydroxylamine in the presence of a base to provide a compound of Formula 22

22

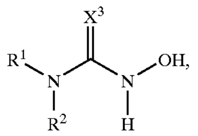

(b) contacting the compound of Formula 22 with a compound of Formula 23

23

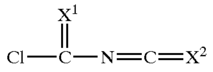

in the presence of a base to provide a compound of Formula 7

7

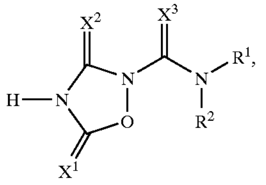

and (c) contacting the compound of Formula 7 with an alcohol of Formula 6

$Q—(CR^6R^7)_q—OH$ 6 under reaction conditions involving a tertiary phosphine and an azo compound or with a compound of Formula 4

$Q—(CR^6R^7)_q—X^4$ 4 in the presence of a base.

PROCESS SEQUENCE F

A process for preparing a compound of Formula 1

1

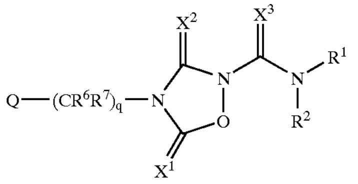

wherein Q, $R^6$, $R^7$, q, $X^1$, $X^2$, $X^3$, $R^1$ and $R^2$ are as defined above, comprising contacting a compound of Formula 7

7

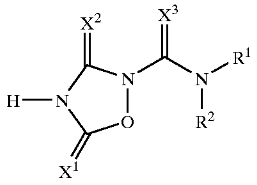

with an orthoformate of Formula 24

$(R^{27}O)_3CH$ 24 wherein $R^{27}$ is $—(CR^6R^7)_q—Q$, in the presence of a base.

PROCESS SEQUENCE G

A process for preparing a compound of Formula 1

1

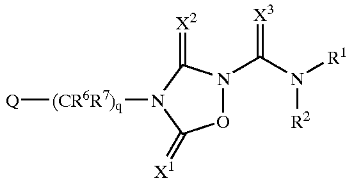

wherein Q, $R^6$, $R^7$, q, $X^1$, $X^2$, $X^3$, $R^1$ and $R^2$ are as defined above, comprising:

(a) contacting a compound of Formula 8

8

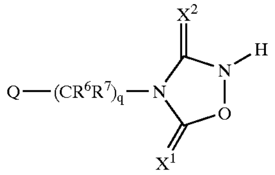

with a compound of Formula 26

26

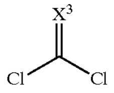

to provide a compound of Formula 25

25

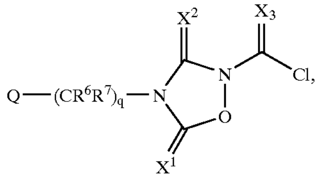

or a compound of Formula 27

27

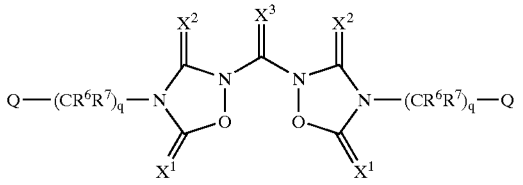

in the presence of a catalyst such as hexamethylguanidinium chloride; and (b) contacting the compound of Formula 25 or Formula 27 with an amine of Formula 13

13

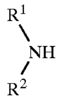

in the presence of a base.

The present invention also relates to an intermediate compound of Formula 5

5

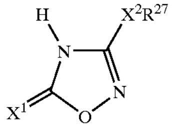

wherein $R^{27}$ is $—(CR^6R^7)_q—Q$; $R^6$, $R^7$, q, Q, $X^1$ and $X^2$ are as defined above for Formula 1;

provided that when $X^1$ and $X^2$ are O and q is 0, then Q is other than unsubstituted benzyl. The present invention also relates to intermediate compounds of Formula 8 and Formula 20

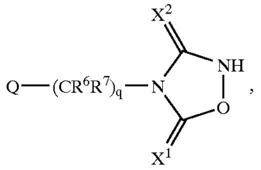

8

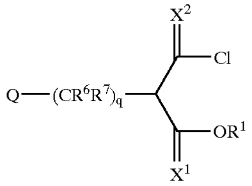

20 wherein $R^6$, $R^7$, q, Q and $X^2$ are as defined above for Formula 1; and $X^1$ is O;

provided that when $X^2$ is O and q is 0, then Q is other than unsubstituted benzyl.

The oxadiazolidines of Formula 1 can be used alone or in combination with other commercial pesticides. The present invention also relates to certain rare combinations that surprisingly give greater-than-expected or synergistic effect, or give a less-than-additive or safening effect on crops while retaining or increasing synergistically weed control. The mixtures of compounds of Formula 1 and certain sulfonylureas have now been discovered to synergistically control weeds. Also, the mixtures of compounds of Formula 1 and safeners such as dichlormid or naphthalic anhydride have now been discovered to exhibit a crop safening effect while retaining or synergistically increasing weed control.

This invention also relates to a herbicidal composition comprising a herbicidally effective amount of a compound of Formula 1 and at least one of a surfactant, a solid diluent or a liquid diluent. The preferred compositions of the present invention are those which comprise the above preferred compounds.

This invention also relates to a method for controlling the growth of undesired vegetation comprising contacting the vegetation or its environment with a herbicidally effective amount of a compound of Formula 1.

DETAILS OF THE INVENTION

Compounds of the Formula 1 can be readily prepared by one skilled in the art by using the reactions and techniques described in Scheme 1 to Scheme 10 below. In cases where a substituent of the starting material is not compatible with the reaction conditions described for any of the reaction schemes, the substituent can be converted to a protected form prior to the described reaction scheme and then deprotected after the reaction using commonly accepted protection/deprotection techniques (see Green, T. W and Wuts, P. G., *Protecting Groups in Organic Transformations*, 2nd Edition, John Wiley and Sons, New York, 1991). Otherwise, alternative approaches known to one skilled in the art are available. The definitions of Q, $X^1$, $X^2$, $X^3$, $R^1$, $R^2$, $R^6$, $R^7$, and q in compounds of Formulae 1–21 below are as defined in the Summary of the Invention.

As shown in Scheme 1, compounds of Formula 1 can be obtained by the reaction of oxadiazolidines of Formula 8 with carbamyl chlorides of Formula 2. The preferred solvent for the carbamoylation reaction is an inert solvent such as tetrahydrofuran, toluene, benzene or dioxane. The presence of a tertiary amine base such as triethylaamine or diisopropylethylarnine is preferable. Use of an acylation catalyst such as 4-dimethylaminopyridine or 4-pyrrolidinopyridine in a catalytic or stoichiometric amount is preferred. Other bases such as alkali hydroxide, carbonates or hydrides may also be employed. The reaction can be carried out at temperatures between 20 to 150° C.

SCHEME 1

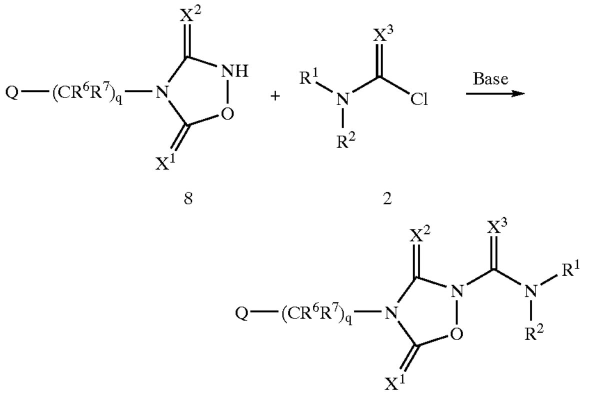

8 2

1

Oxadiazolidines of Formula 8 can be prepared by methods known in the literature. Zinner reported the preparation of a wide variety of oxadiazolidines. See, for example: *Arch. Pharm.* (1965), 298, 580–587; *Arch. Pharm.* (1971), 303, 139–144, German patent application, DE 2010396 (1971). As shown in Scheme 2, a hydroxyurea or hydroxythiourea of Formula 9 is reacted with an activated carbonyl or thiocarbonyl compound of Formula 10 in the presence of a base to give compounds of Formula 8. Examples of suitable activated carbonyl compounds are ethyl chloroformate, phenyl chloroformate, carbonyl diimidazole, phosgene, diphosgene or triphosgene. Examples of suitable activated thiocarbonyl compounds are carbon disulfide, thiophosgene and thiocarbonyldiimidazole. Suitable bases include alkali carbonates, tertiary amines such as triethylamine and alkali hydroxides. The reaction can be carried out in a variety of solvents including tetrahydrofuran, toluene, dichloromethane, chloroform, acetonitrile or dioxane. The reaction may also be carried out in two-phase mixtures of water and an organic solvent such as dichloromethane, ethyl acetate or toluene. Depending on the reactivity of the carbonyl or thiocarbonyl compound, the reaction may be carried out at temperatures from 0 to 150° C.

SCHEME 2

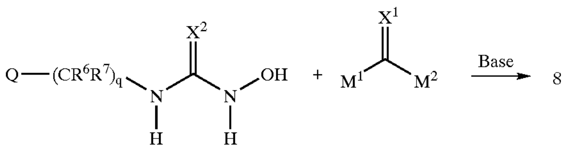

9 10

$M^1$, $M^2$ is halogen, phenoxy, $OCH_3$, $OC_2H_5$ or imidazole

As shown in Scheme 3, compounds of Formula 8a wherein $X^1$ and $X^2$ are O can be made via the method of Zinner, *Arch. Pharm.* (1981), 314, 294–302. The reaction of isocyanates of Formula 11 with hydroxyurethanes of Formula 12 gives compounds of Formula 8a. The cyclization can be carried out in a variety of solvents such as acetone, dichloromethane, tetrahydrofuran, dioxane, ethyl acetate, and other solvents inert to isocyanates. The presence of a base such as triethylamine or sodium hydroxide is also useful. The reaction may be carried out at temperatures from 20 to 150° C.

SCHEME 3

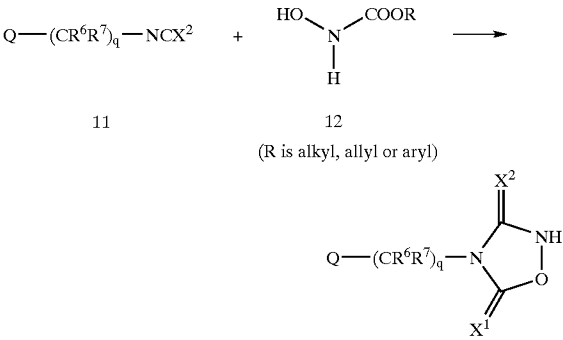

11 12

(R is alkyl, allyl or aryl)

8a (wherein $X^1$ and $X^2$ are O)

Carbamyl chlorides of Formula 2a (which are compounds of Formula 2 wherein $X^3$ is O) are well known in the literature and can be made by the reaction of amines of Formula 13 with phosgene or a phosgene equivalent such as di- or triphosgene as shown in Scheme 4. The presence of a base is useful and the use of hindered tertiary amines such as diisopropylethyl amine is preferred. The reaction can be carried out in a variety of solvents such as toluene or benzene that are inert to phosgene and its equivalents. The reaction can be carried out at temperatures from 0 to 120° C.

SCHEME 4

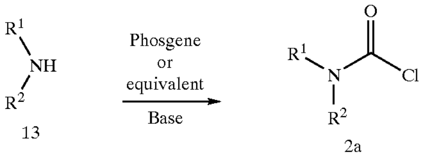

13 2a

As shown in Scheme 5, hydroxyureas and thioureas of Formula 9 can be prepared from the reaction of hydroxylamine with isocyanates or isothiocyanates of Formula 11. The reaction is carried out in a two-phase reaction medium consisting of water and an organic solvent such as toluene, benzene, dichloroethane, dichloromethane, ethyl acetate or chlorobutane. The hydroxylamine employed can be a commercially available aqueous solution or can be prepared in situ from the reaction of an acid addition salt of hydroxylamine with an alkali hydroxide or carbonate. The reaction is generally carried out at temperatures between 0 and 40° C.

SCHEME 5

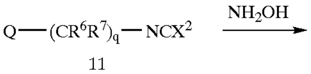

11

-continued

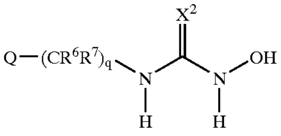

9

Isocyanates of Formula 11a are commercially available or can be prepared from amines of Formula 14 as shown in Scheme 6. The reaction of phosgene or its equivalents (such as di- and triphosgene) with amines or amine hydrochlorides of Formula 14 gives the isocyanates of Formula 11a. This reaction is well known in the literature and can be carried out in a variety of solvents such as toluene, benzene, ethyl acetate or dichloroethane which are inert to phosgene. Depending upon the reactivity of the amine of Formula 14, the reaction may be carried out at temperatures from 0 to 200° C.

SCHEME 6

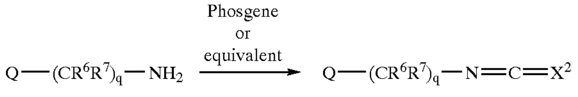

14 11a (wherein $X^2$ is O)

As shown in Scheme 7, isocyanates of Formula 11a can also be formed from activated acids of Formula 15. Acid halides, anhydrides, imidazolides and the like can be reacted with various azides to provide, after a Curtius rearrangement, the isocyanates of Formula 11a. The azide used may be an alkali azide, trialkylsilyl azide or trialkylstannyl azide. The reaction may be carried out in solvents such as toluene, tetrahydrofuran, ethyl acetate, dioxane, benzene, or methyl tert-butyl ether. When an alkali azide is employed, biphasic aqueous solvents or miscible aqueous containing mixtures are preferred in the formation of the acyl azide intermediate. For further examples of Curtius rearrangements, see: March, *J. Advanced Organic Chemistry*, 3rd edition; John Wiley & Sons, 1985; pp 984–985 and 380. See also Kim, World Patent Application 98/51683 (1998) and Larock, *Comprehensive Organic Transformations*, VCH, 1989, pp 931–932.

SCHEME 7

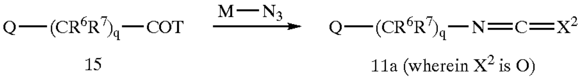

15 11a (wherein $X^2$ is O)

T is halogen, imidazole, etc.
M is alkali metal, trialkylsilyl or trialkylstannyl As shown in Scheme 8, compounds of Formula 9 can also be made by the reaction of compounds of Formula 16 with hydroxylamine. The reaction may be carried out in a number of different solvents including tetrahydrofuran, dioxane, acetonitrile, dimethylformamide and dimethylsulfoxide. Temperatures from 0 to 160° C. may be employed in this transformation. Many compounds of Formula 16 are known, and can be made by the reaction of commercially available chlorofornates and chlorothioformates with compounds of Formula 14.

SCHEME 8

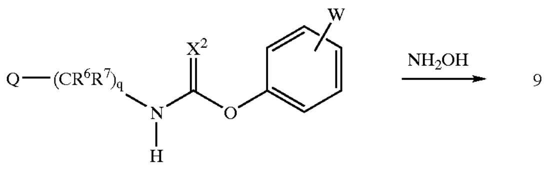

16

(W is H, halogen or $NO_2$)

As shown in Scheme 9, compounds of Formula 9 can also be made by the reaction of activated hydroxylamines of Formula 17 with amines of Formula 14. The reaction may be carried out in a number of different solvents including tetrahydrofuran, dioxane, acetonitrile, dimethylformamide and dimethylsulfoxide. In some cases lower alcohols or even mixtures of water and alcohols may also be employed. Temperatures from 0 to 160° C. may be employed in this transformation. Compounds of Formula 17 are known in the literature and can be made from hydroxylamine and activated esters or thioesters (See Oesper and Broker, *J. Am. Chem. Soc.*, 1925, 47, 2607; Defoin et. al., *Helv. Chim. Acta.*, 1992, 75, 109–123; and Stewart and Brooks, *J. Org. Chem.*, 1992, 57, 5020–5023).

SCHEME 9

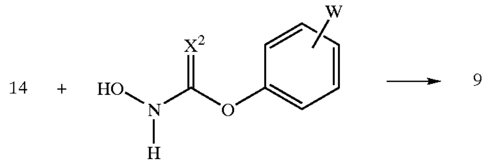

(W is H, halogen or $NO_2$)

Compounds of Formula 2b (which are compounds of Formula 2 wherein $X^3$ is $NR^{23}$) can be made by the chlorination of ureas of Formula 18 as shown in Scheme 10. The chlorination may be carried out with a wide variety of reagents such as phosphorus oxychloride, thionyl chloride, phosphorous pentachloride, or triphenylphosphine reagents with carbon tetrachloride or chlorine. A variety of solvents may be used including halogenated solvents such as dichloromethane, dichloroethane, or trichloroethane. A preferred solvent of the transformation is dimethylformamide. The reaction may be carried out from 0 to 150° C. Some known chloroamidine compounds and their synthesis may be found in Reid, *Chem. Ber.*, 1975, 108, 2290–2299; Kuehle et al.; *Angew. Chem.*; 1969; 81; 18; and Shevchenko, V. I. et al.; *J. Gen. Chem. USSR* (Engl.Transl.); 1976;46;535–539.

SCHEME 10

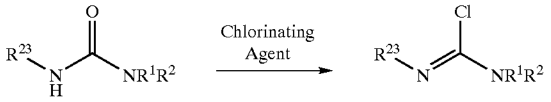

18

2b

Wherein $X^3$ is $NR^{23}$

Many isothiocyanates of Formula 11a are commercially available. Amines of Formula 13 are commercially available or can be prepared by methods disclosed in the literature. See the following references and references cited therein for synthesis of these materials: Kim, World Patent Application 98/51683 (1998); Dhar, World Patent Application 98/35961 (1998); Rorer, World Patent Application 98/25912 (1998); and Morita et. al., World Patent Application WO 98/11079 (1998).

Amines of Formula 14 are commercially available or can be synthesized by methods known in the art. See the following references and references cited therein for synthesis of these materials: Kim, World Patent Application 98/51683 (1998); Dhar, World Patent Application 98/35961 (1998); Rorer, World Patent Application 98/25912 (1998), Goto et. al., European Patent Application EP 695748 (1996); Goto et. al., European Patent Application EP 771,797 (1997); and Goto et. al. U.S. Pat. No. 5,589,439 (1996).

Activated carboxylic acids of Formula 10 are commercially available or can be prepared by methods disclosed in the literature. See the following references and references cited therein for the synthesis of these materials: Kim, World Patent Application 98/51683 (1998); Dhar, World Patent Application 98/35961(1998); Rorer World Patent Application 98/25912 (1998); and Goto et. al., European Patent Application EP 695748.(1996). See also Larock, *Comprehensive Organic Transformations*, VCH, 1989, p 821 for a list of comprehensive references for the synthesis and chemistry of carboxylic acids and activated derivatives.

This invention is further directed to processes for the preparation of compounds of Formula 1 using process sequences described below.

PROCESS SEQUENCE A

STEP 1

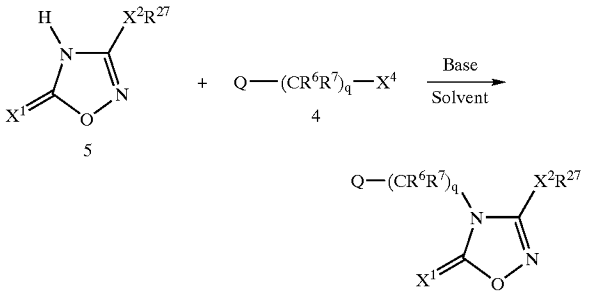

5

4

3

Step 1 forms compounds of Formula 3 by contacting compounds of Formula 5 with compounds of Formula 4 in the presence of a suitable base either neat or in a suitable solvent.

Compounds of Formula 5 may be prepared, for example, by methods described in *Synthesis*, 1991, 265.

For Step 1, the reaction temperature is generally from −10 to 250° C., preferably from 0 to 100° C. The reaction times are generally from 0.25 to 48 h, preferably from 0.25 to 24 h. Generally, the pressure is in the range of $1.013 \times 10^2$ to $2.026 \times 10^2$ KPa, preferably ambient pressure. Suitable solvents include typical organic solvents in which the reactants can be dissolved and the process of Step 1 can proceed without interference. Examples of such reactants include aromatics such as benzene, toluene, xylene, chlorobenzene and dichlorobenzene, ethers such as dioxane and tetrahydrofuran, nitriles such as acetonitrile and propionitrile, ethyl acetate, dichloromethane, dichloroethane, and polar aprotic solvents such as dimeth-ylformarnide and dimethylsulfoxide.

Suitable bases include organic trialkylamines such as trimethylamine, triethylamine, diisopropylethylamnine, tributylamine and the like, dimethylaniline, N,N-dimethylaminopyridine, N-methylmorpholine, 1,8-diazabicyclo[5.4.0]undec-7-ene, 1,4-diazabicyclo[2.2.2]octane and 1,5-diazabicyclo[4.3.0]non-5-ene. 1,8-Diazabicyclo[5.4.0]undec-7-ene is a particularly useful organic base for this reaction. Inorganic bases include, but are not limited to, potassium carbonate, sodium carbonate, potassium hydride, sodium hydride, lithium carbonate and cesium carbonate.

A phase transfer catalyst can accelerate the reaction in the presence of inorganic bases. Phase transfer catalysts include tetraalkylammonium halides, crown ethers, phosphonium salts, silicon analogs of crown ethers and acyclic analogs of crown ethers. Particularly useful as a base is the combination of potassium carbonate and a phase transfer catalyst.

Generally at least an equimolar amount of the Formula 4 compound is used in respect to the Formula 5 compound, and preferably at least a small molar excess of the Formula 4 compound is used. More particularly, the molar ratio of the Formula 4 compound to the Formula 5 compound is usually in the range of 1.05:1 to 10:1. In most cases, the molar ratio of the Formula 5 compound to the Formula 4 compound is preferably in the range of 1.1:1 to 1.5:1. Generally at least an equivalent of base is used in respect to the Formula 5 compound, and preferably at least a small equivalent excess of the base is used. More particularly, the ratio of the number of equivalents of base to number of moles of the Formula 5 compound is usually in the range of 1.05:1 to 10:1. In most cases, the ratio of the number of equivalents of base to number of moles of the Formula 5 compound is preferably in the range of 1.1:1 to 1.5:1. The equivalent amount of base may be similar to the molar amount of the Formula 4 compound, but this is not necessary.

The compound of Formula 4 is preferably added to the reaction mixture containing the compound of Formula 5 and a base either neat or in a solvent. The reaction temperature is maintained during and after the addition and until the reaction reaches completion.

Isolation of product of Step 1 can be accomplished by standard workup procedures or the resultant mixture can be used directly in Step 2.

STEP 2

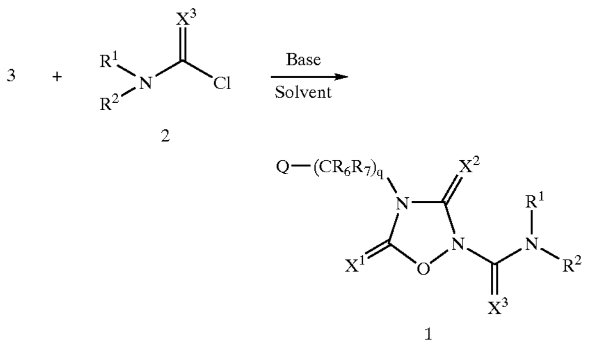

Step 2 forms compounds of Formula 1 from the reaction of compounds of Formula 3 with compounds of Formula 2 in the presence of a suitable base in a suitable solvent.

For Step 2, the general and preferred reaction conditions are the same as the ones described above for Step 1.

Alternatively, the processes of Step 1 and 2 can be combined without isolating product of Step 1 and preferably, the reaction conditions (e.g. temperature, mole ratio, reaction time etc) are balanced to achieve a high yield of compound of Formula 1.

The compound of Formula 1 can be isolated by standard procedures.

PROCESS SEQUENCE B

STEP 1

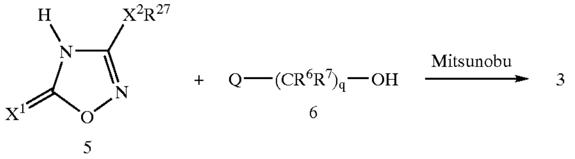

Step 1 forms the compounds of Formula 3 from the reaction of compounds of Formula 5 with compounds of Formula 6 under Mitsunobu reaction conditions involving a tertiary phosphine and an azo compound. One skilled in the art can find a variety of the tertiary phosphine and azo compounds as well as solvents useful for this transformation in *Synthesis*, 1981, 1 and *Org. Reactions*, 1992, 42, 335.

For the process of Step 1, the reaction temperature is generally from about −40 to 250° C., preferably from −20 to 80° C. The reaction times are generally from about 0.20 to 24 h, preferably from 0.5 to 12 h. Generally, the pressure is from $1.013 \times 10^2$ to $5.065 \times 10^2$ KPa; preferably ambient pressure.

Generally at least an equimolar amount of the Formula 5 compound is used in respect to the Formula 6 compound, and preferably at least a small molar excess of the Formula 6 compound is used. More particularly, the molar ratio of the Formula 6 compound to the Formula 5 compound is usually in the range of 1.05:1 to 10:1. In most cases, the molar ratio of the Formula 6 compound to the Formula 5 compound is preferably in the range of 1.1:1 to 1.5:1.

Isolation of product of Step 1 can be accomplished by standard workup procedures.

Step 2

Compounds of Formula 1 are then obtained by the reaction of the compounds of Formula 3 prepared in Step 1 and compounds of Formula 2 under the same reaction conditions as already described in Step 2 for Sequence A.

PROCESS SEQUENCE C

STEP 1a

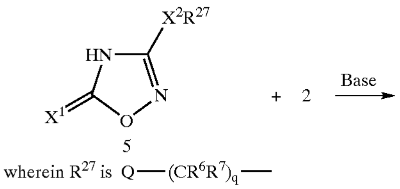

wherein $R^{27}$ is $Q—(CR^6R^7)_q—$

-continued

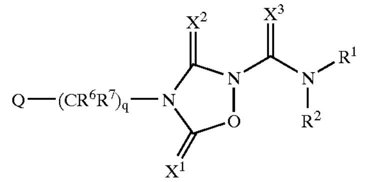

1

Step 1a forms the compounds of Formula 1 by contacting compounds of Formula 5 with compounds of Formula 2 in the presence of a suitable base either neat or in a suitable solvent.

For the process of Step 1a, the general and preferred reaction conditions are the same as the ones described above for Step 1 in Process Sequence A.

A solution of compound of Formula 2 can be added to a solution/suspension of compound of Formula 5 and a base in a solvent. Reaction temperature is maintained during and after the addition and until the reaction reaches completion. Isolation of product of Step 1a can be accomplished by standard workup procedures.

STEP 1b

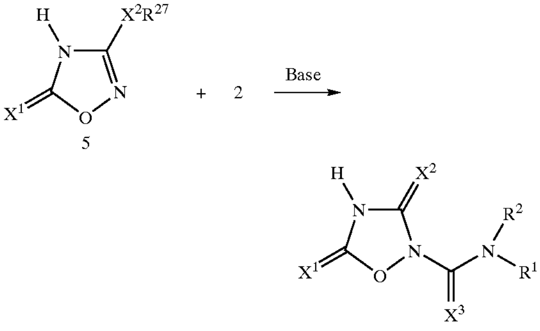

7

Step 1b forms the compounds of Formula 7 from the reaction of compounds of Formula 5 and compounds of Formula 2 in the presence of a base either neat or in a suitable solvent.

For the process of Step 1b, the general and preferred reaction conditions are the same as the ones described above for Step 1 in Process Sequence A.

The product of Step 1b can be isolated by standard workup procedures.

STEP 2a

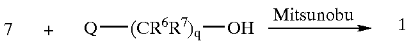

6

Step 2a forms the compounds of Formula 1 from the reaction of compounds of Formula 7 and compounds of Formula 6 under Mitsunobu reaction conditions involving a tertiary phosphine and an azo compound. One skilled in the art can find a variety of the tertiary phosphine and azo compounds as well as solvents useful for this transformation in *Synthesis*, 1981, 1 and *Org. Reactions*, 1992, 42, 335.

For the process of Step 2a, the reaction temperature is generally from about −40 to 250° C., preferably from −20 to 80° C. The reaction times are generally from about 0.20 to 24 h, preferably from 0.5 to 12 h. Generally, the pressure is from $1.013\times10^2$ to $5.065\times10^2$ KPa; preferably ambient pressure.

Generally at least an equimolar amount of the Formula 7 compound is used in respect to the Formula 6 compound, and preferably at least a small molar excess of the Formula 6 compound is used. More particularly, the molar ratio of the Formula 6 compound to the Formula 7 compound is usually in the range of 1.05:1 to 10:1. In most cases, the molar ratio of the Formula 7 compound to the Formula 6 compound is preferably in the range of 1.1:1 to 1.5:1.

Isolation of product of Step 2a can be accomplished by standard workup procedures.

STEP 2b

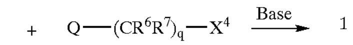

4

Step 2b forms compounds of Formula 1 by contacting compounds of Formula 7 with compounds of Formula 4 in the presence of a suitable base either neat or in a suitable solvent.

For the process of Step 2b, the general and preferred reaction conditions are similar to the ones described above for Step 1 in Process Sequence A.

Isolation of product of Step 2b can be accomplished by standard workup procedures.

PROCESS SEQUENCE D

Compounds of the Formula 8 can be readily prepared by one skilled in the art by using the reactions and techniques described in Steps 1 and 2. In cases where a substituent of the starting material is not compatible with the reaction conditions described for any of the reaction schemes, the substituent can be converted to a protected form prior to the described reaction scheme and then deprotected after the reaction using commonly accepted protection/deprotection techniques (see Green, T. W. and Wuts, P. G., *Protecting Groups in Organic Transformations*, 2nd Edition, John Wiley and Sons, New York, 1991). Otherwise, alternative approaches known to one skilled in the art are available.

STEP 1

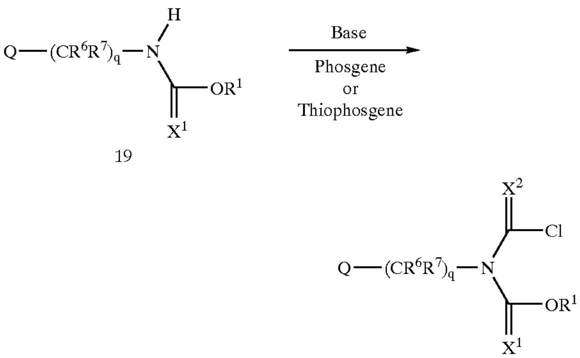

19

20

(wherein $X^1$ is O)

Step 1 forms compounds of Formula 20 from the reaction of compounds of Formula 19 with phosgene or thiophosgene in the presence of a base. For general reaction conditions for this transformation, see: U.S. Pat. No. 5,602,251. Compounds of Formula 19 are well known in the literature. See: for example, *J. Chem. Soc. Perkin I* (1997), 1041.

STEP 2

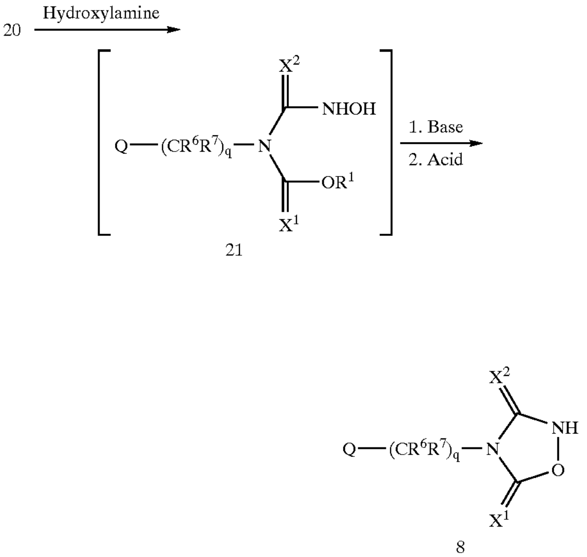

20

21

8

(wherein $X^2$ is O or S and $X^1$ is O)

Step 2 forms compounds of Formula 8 in the form of a salt by treatment of compounds of Formula 20 with hydroxylamine and a base. The salt is then converted to compound of Formula 8 by treatment with an acid.

The reaction is conducted in a suitable organic solvent such as, but not limited to, tetrahydrofuran, dioxane or toluene at a temperature between −20 and 100° C. with 10–50° C. being the preferred temperature. Hydroxylamine may be generated from one of its salts by use of a suitable base such as, but not limited to, potassium carbonate, potassium hydroxide or sodium hydroxide. Alternatively, hydroxylamine in water may be used. Judicious use of an appropriate co-solvent such as water or a phase transfer catalyst may be effective in facilitating the reaction. Further amounts of the base (vide supra) can be added to scavenge the HCl formed in the reaction. Alternatively, an excess amount of hydroxylaniine can be used to achieve the same purpose.

The intermediate compound of Formula 21 is not usually isolated, but converted directly to compounds of Formula 8 by addition of further quantities of base. It is apparent to one skilled in the art that salts of compounds of Formula 8 generated from this reaction may be used directly in the preparation of compounds of Formula 1 as described in Scheme 1. To facilitate the transformation, it may be desirable to adjust the solvent composition by removal of co-solvents such as water prior to the reaction. Alternatively, compounds of Formula 8 may be isolated from their salts by addition of an appropriate mineral acid such as, but not limited to, HCl before being subjected to the reaction conditions as described in Scheme 1 to produce compounds of Formula 1.

PROCESS SEQUENCE E

Compounds of the Formula 7 can be readily prepared by one skilled in the art by using the reactions and techniques described in Steps 1 and 2. Since hydroxylamine is unstable upon heating, this sequence allows a safe and efficient route to the compounds of the Formula 7 under mild conditions.

STEP 1

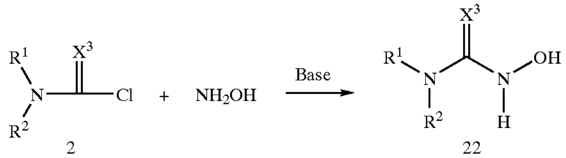

2

22

Step 1 forms the compounds of Formula 22 by contacting a compound of Formula 2 with hydroxylamine in the presence of a suitable base in a suitable solvent. Hydroxylamine may be generated from one of its salts or hydroxylamine in water may be used.

For Step 1, the reaction temperature is generally from −10 to 150° C., preferably from 0 to 100° C. The reaction times are generally from 0.10 to 24 h, preferably from 0.10 to 2 h. Generally, the pressure is in the range of $1.013\times10^2$ to $2.026\times10^2$ KPa; preferably ambient pressure. Suitable solvents include typical organic solvents in which the reactants can be dissolved and the process of Step 1 can proceed without interference. Examples of such solvents include aromatics such as benzene, toluene, xylene, chlorobenzene and dichlorobenzene, ethers such as dioxane and tetrahydrofuran, nitriles such as acetonitrile and propionitrile, ethyl acetate, dichloromethane, dichloroethane, and polar aprotic solvents such as dimethylformamide and dimethylsulfoxide. Judicious use of an appropriate co-solvent such as water or a phase transfer catalyst may be effective in facilitating the reaction.

Suitable bases include organic trialkylamines such as trimethylamine, triethylamine, diisopropylethylamine, tributylamine and the like, dimethylaniline, N,N-dimethylaminopyridine, N-methylmorpholine, 1,8-diazabicyclo[5.4.0]undec-7-ene, 1,4 diazabicyclo[2.2.2]octane and 1,5-diazabicyclo[4.3.0]non-5-ene. Trialkylamines is a particularly useful organic base for this reaction. When an excess quantity of hydroxylamine is employed, the excess hydroxylamine can also serve as a base. Inorganic bases include, but are not limited to, potassium hydroxide, sodium hydroxide, potassium carbonate, sodium carbonate, lithium carbonate and cesium carbonate.

Generally at least an equimolar amount of the Formula 2 compound is used in respect to hydroxylamine, and preferably at least a small molar excess of hydroxylamine is used. More particularly, the molar ratio of the Formula 2 compound to hydroxylamine is usually in the range of 1:1.05 to 1:10. In most cases, the molar ratio of the Formula 2 compound to hydroxylamine is preferably in the range of 1:1.1 to 1:1.5. Generally at least an equivalent of base is used in respect to the Formula 2 compound, and preferably at least a small equivalent excess of the base is used. More particularly, the ratio of the number of equivalents of base to number of moles of the Formula 2 compound is usually in the range of 1.05:1 to 10:1. In most cases, the ratio of the number of equivalents of base to number of moles of the Formula 2 compound is preferably in the range of 1.1:1 to 1.5:1. The equivalent amount of base may be similar to the molar amount of the Formula 2 compound, but this is not necessary.

Isolation of product of Step 1 can be accomplished by standard workup procedures. In the scenario that the reaction is carried our in an aqueous solution, a filtration can be employed to collect compounds of Formula 22.

STEP 2

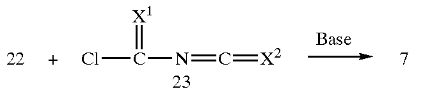

Compounds of Formula 7 are synthesized by contacting compounds of Formula 22 with chlorocarbonyl isocyanate ($X^1$ and $X^2$ are O) or chlorocarbonyl isothiocyanate ($X^1$ is O and $X^2$ is S) or chlorothiocarbonyl isocyanate ($X^1$ is S and $X^2$ is O) or chlorothiocarbonyl isothiocyanate ($X^1$ and $X^2$ are S) in the presence of a base to scavange the HCl byproduct. Similar examples of such reactions using N-alkyl-N-hydroxylamine and chlorocarbonyl isocyanate have been reported in *Syn*., 1982, 781–2 and in WO 9741097 but there is no example of compound like 22 and chlorocarbonyl isocyanate in the literature.

Compounds of Formula 23 are either commercially available or may be prepared by one skilled in the art using methods known in the art (or slight modification of these methods); for example, see: *Chem. Ber*. 1981, 114, 1746–51, *Chem. Ber*. 1973, 106, 1487–95, and *Chem. Ber*. 1966, 99,3572–81.

For Step 2, the reaction temperature is generally from −10 to 150° C., preferably from 0 to 100° C. The reaction times are generally from 0.10 to 24 h, preferably from 0.10 to 2 h. Generally, the pressure is in the range of $1.013 \times 10^2$ to $2.026 \times 10^2$ KPa; preferably ambient pressure. Suitable solvents include typical organic solvents in which the reactants can be dissolved and the process of Step 1 can proceed without interference. Examples of such reactants include aromatics such as benzene, toluene, xylene, chlorobenzene and dichlorobenzene, ethers such as dioxane and tetrahydrofuran, nitriles such as acetonitrile and propionitrile, ethyl acetate, dichloromethane, dichloroethane, and polar aprotic solvents such as dimethylformamide and dimethylsulfoxide.

Suitable bases for Step 2 are similar to the ones described above for Step 1.

Generally at least an equimolar amount of the Formula 22 compound is used in respect to the Formula 23 compound, and preferably at least a small molar excess of the Formula 23 compound is used. More particularly, the molar ratio of the Formula 22 compound to the Formula 23 compound is usually in the range of 1:1.05 to 1:10. In most cases, the molar ratio of the Formula 22 compound to the Formula 23 compound is preferably in the range of 1:1.1 to 1:1.5. Generally at least an equivalent of base is used in respect to the Formula 22 compound, and preferably at least a small equivalent excess of the base is used. More particularly, the ratio of the number of equivalents of base to number of moles of the Formula 22 compound is usually in the range of 1.05:1 to 10:1. In most cases, the ratio of the number of equivalents of base to number of moles of the Formula 22 compound is preferably in the range of 1.1:1 to 1.5:1. The equivalent amount of base may be similar to the molar amount of the Formula 22 compound, but this is not necessary.

Isolation of product of Step 2 can be accomplished by standard workup procedures.

Compounds 7 can be readily converted into alkali salts when treated with potassium carbonate or sodium carbonate in water. The salts may be useful in alkylation reactions.

Compounds of Formula 1 are then obtained by the reaction of compounds of Formula 7 under the same reaction conditions as already described in Step 2a/2b in Sequence C.

PROCESS SEQUENCE F

Compounds of the Formula 1 can be readily prepared by one skilled in the art by using the reactions and techniques described in the scheme below.

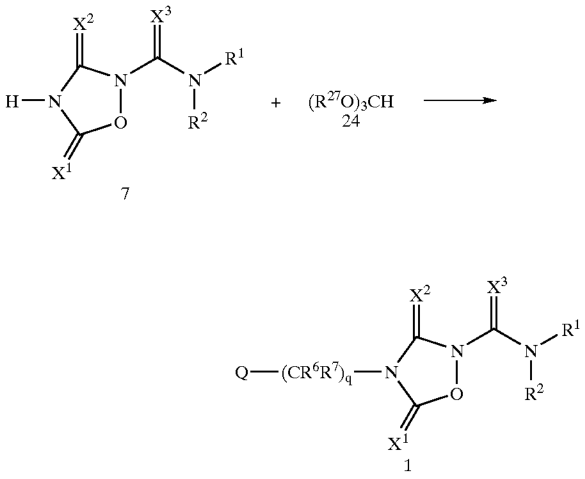

wherein $R^{27}$ is —$(CR^6R^7)$—Q

The compounds of Formula 1 are formed by contacting a compound of Formula 7 with an orthoformate of Formula 24 either neat or in the presence of a suitable solvent.

The reaction temperature is generally from −10 to 150° C., preferably from 0 to 100° C. The reaction times are generally from 0.10 to 24 h, preferably from 0.10 to 2 h. Generally, the pressure is in the range of $1.013 \times 10^2$ to $2.026 \times 10^2$ KPa; preferably ambient pressure. Suitable solvents include typical organic solvents in which the reactants can be dissolved and the process can proceed without interference. Examples of such reactants include aromatics such as benzene, toluene, xylene, chlorobenzene and dichlorobenzene, ethers such as dioxane and tetrahydrofuran, nitriles such as acetonitrile and propionitrile, ethyl acetate, dichloromethane, dichloroethane, and polar aprotic solvents such as dimethylformamide and dimethylsulfoxide.

Generally at least an equimolar amount of the Formula 24 compound is used in respect to the Formula 7 compound, and preferably at least a small molar excess of Formula 24 compound is used. More particularly, the molar ratio of the Formula 7 compound to the Formula 24 compound is usually in the range of 1:1.05 to 1:10. In most cases, the molar ratio of the Formula 7 compound to the Formula 24 compound is preferably in the range of 1:1.1 to 1:1.5.

PROCESS SEQUENCE G

Compounds of the Formula 1 can be readily prepared by one skilled in the art by using the reactions and techniques described in Steps 1 and 2.

STEP 1

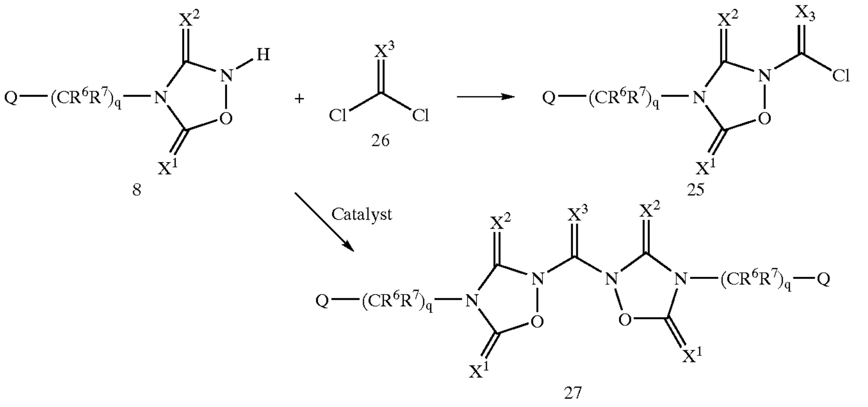

Step 1 forms the compounds of Formula 25 by contacting a compound of Formula 8 with a compound of Formula 26 either neat or in a suitable solvent.

For Step 1, the reaction temperature is generally from −10 to 150° C., preferably from 0 to 100° C. The reaction times are generally from 0.10 to 24 h, preferably from 0.10 to 2 h. Generally, the pressure is in the range of $1.013\times10^2$ to $2.026\times10^2$ KPa; preferably ambient pressure. Suitable solvents include typical organic solvents in which the reactants can be dissolved and the process of Step 1 can proceed without interference. Examples of such reactants include aromatics such as benzene, toluene, xylene, chlorobenzene and dichlorobenzene, ethers such as dioxane and tetraydrofuran, nitriles such as acetonitrile and propionitrile, ethyl acetate, dichloromethane and dichloroethane.

Generally at least an equimolar amount of the Formula 26 compound is used in respect to the Formula 8 compound, and preferably at least a small molar excess of the Formula 26 compound is used. More particularly, the molar ratio of the Formula 8 compound to the Formula 26 compound is usually in the range of 1:1.05 to 1:10. In most cases, the molar ratio of the Formula 8 compound to the Formula 26 compound is preferably in the range of 1:1.1 to 1:1.5.

In the presence of a catalyst such as hexamethylguanidinium chloride, the reaction of compounds of Formula 8 and compounds of Formula 26 produces compounds of Formula 27. For general and preferred conditions, see *Tet. Lett.* 1987, 5823–5826.

Isolation of product of Step 1 can be accomplished by standard workup procedures.

STEP 2

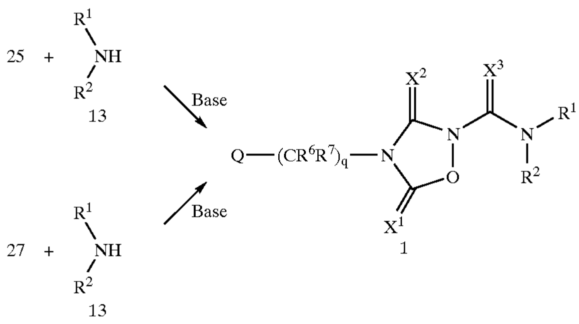

Compounds of Formula 1 are synthesized by contacting compounds of either Formula 25 or Formula 27 with amines of Formula 13 in the presence of a suitable base in a suitable solvent.

For Step 2, the general and preferred reaction conditions are the same as the ones described above for Step 1 in Process Sequence A.

One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s=singlet, d=doublet, t=triplet, q=quartet, m=multiplet, dd=doublet of doublets, dt=doublet of triplets, br s=broad singlet.

EXAMPLE 1

Step A: Preparation of N-(2,4-Dichlorophenyl)-N'-hydroxyurea

A solution of 14.2 g (75 mmol) of 2,4-dichlorophenylisocyanate in 50 mL of toluene was added to a mixture of 8.26 g (120 mmol) of hydroxylamine hydrochloride and 4.8 g (120 mmol) of sodium hydroxide in a two-phase solvent mixture consisting of 50 mL of water and 50 mL of toluene. The resulting mixture was stirred at 25° C. for 30 minutes and filtered. The solid thus obtained was washed with water and then dissolved in 200 mL of ethyl acetate. The solution was dried over magnesium sulfate and the solvent was removed under reduced pressure to yield 12.7 g of the title compound of Step A as a white solid melting at 157–158° C. It was used directly in the next step without further purification.

Step B: Preparation of 4-(2,4-Dichlorophenyl)-1,2,4-oxadiazolidine-3,5-dione

A solution of 4.2 g (19 mmol) of the compound of step A in tetrahydrofuran (20 mL) was treated with carbonyldiimidazole (3.2 g, 19 mmol). The mixture was stirred at 25° C. for 16 h. Some precipitated imidazole was filtered off and the filtrate was concentrated under reduced pressure. The residue was partitioned between 1N HCl (20 mL) and ethyl acetate (50 mL). The organic layer was dried over magnesium sulfate and concentrated to an oil which solidified to give 3.8 g of the title compound of Step B as a solid melting at 104–107° C. It was used directly for the next step without further purification.

Step C: Preparation of 4-Fluoro-N-Propylbenzenamine

A 3 L three neck round bottom flask equipped with a nitrogen inlet, a thermometer, an overhead stirrer and a solid addition funnel was charged with 250 mL acetic acid, 50 mL absolute ethanol and 29.5 g (0.27 mol) of 4-fluoroaniline. To this mixture was added acetone (23 mL, 6.31 mol) in one portion followed by the portion-wise addition of sodium acetate trihydrate over 5 min. This vigorously stirred mixture was cooled to 0° C. (dry-ice/acetone) and 4.5 g of sodium borohydride (1.2 mol) was added portion-wise via a solid addition funnel over 50 min while keeping the internal temperature below 10° C. During this addition, acetic acid (100 mL) and absolute ethanol (50 mL) were added to facilitate stirring. After the addition, the mixture was allowed to warm to room temperature, and then stirred at ambient temperature for 12 h. Sufficient ammonium hydroxide (30% aqueous) was added to adjust the pH to ~8 while maintaining the internal temperature below 30° C. using an ice/water bath. The mixture was extracted with ether (4×400 mL). The combined organic layers were washed with brine, dried over $MgSO_4$, filtered, then concentrated under reduced pressure to give the desired product as a black/brown oil (38 g).

$^1$H NMR: (300 MHz, $CDCl_3$) δ 6.8–6.9 (t, 2H), 6.5 (m, 2H), 3.5 (m, 1H), 1.2 (d, 6H).

Step D: Preparation of 4-(Fluorophenyl) propylcarbamic Chloride

A 1 L three neck round bottom flask equipped with a nitrogen inlet, a thermometer and two addition funnels was charged with 600 mL of toluene and 36.0 g (0.22 mol) of the compound of Step C. This stirred mixture was cooled to 3° C., and then 116 mL (0.22 mol) of a 20% solution of phosgene in toluene was added dropwise over 15 min while maintaining the temperature below 10° C. Ten min after the addition, diisopropyl ethylamine (39 mL, 0.22 mol) was added dropwise over 15 min while maintaining the temperature below 7° C. The reaction mixture was allowed to warm to room temperature and stirred for 14 hours. The resulting brown solution was flooded with $CH_2Cl_2$ (700 mL), and then saturated $NaHCO_3$ solution. The organic layer was separated and washed with saturated $NaHCO_3$ solution (3×500 mL), dried over $MgSO_4$, and filtered. The solvent was removed under reduced pressure, then in vacuo, during which time the resulting oil slowly crystallized. This solid was triturated with hexanes to give 36 g (78%) of a gray solid melting at 50–55° C.

$^1$H NMR: (300 MHz, $CDCl_3$) δ 7.1–7.2 (m, 4H), 4.68 (m, 1H), 1.1–1.2 (d, 6H).

Step E: Preparation of 4-(2,4-Dichlorophenyl)-N-(4-fluorophenyl)-N-(1-methylethyl)-3,5-dioxo-1,2,4-oxadiazolidine-2-carboxamide A solution of 0.6 g (2.4 mmol) of the compound of Step B in toluene (25 mL) was treated with 0.42 g (1.9 mmol) of the compound of Step D and 0.35 g (2.9 mmol) of 4-dimethylaminopyridine. The resulting mixture was heated at 80° C. for 1 hour, and subsequently diluted with 1N hydrochloric acid (20 mL) and ethyl acetate (50 mL). The organic layer was separated and washed with saturated brine solution (30 mL). It was then dried over magnesium sulfate and concentrated under reduced pressure. The residue was subjected to column chromatography on silica gel with 85:15 hexanes-ethyl acetate as eluent. Appropriate fractions were combined and concentrated to give 0.32 g of the title compound of Step E, a compound of this invention, as an oil which solidified on standing to give a solid melting at 57–60° C.

$^1$H NMR ($CDCl_3$) δ 1.22 (m, 6H), 4.7 (m, 1H), 7.04–7.17 (m, 2H), 7.2–7.3 (m, 3H), 7.39 (d, 1H), 7.58 (s, 1H).

EXAMPLE 2

Step A: Preparation of N-(2,6-Dimethylphenyl)-N'-hydroxylurea

A 500 mL side arm flask equipped with a thermometer and an addition funnel with a nitrogen inlet was charged with 100 mL of toluene and 2.00 g (0.10 mol) of 50% hydroxylamine in water. A solution of 4.41 g of 2,6-dimethylphenyl isocyanate (0.03 mol) dissolved in 50 mL of toluene was added dropwise over 15 min. External cooling was used to maintain the, internal reaction temperature below 25° C. Stirring was continued at room temp for 18 h. The solvent was removed under reduced pressure to give a white solid. The residual solvent was further co-evaporated twice with toluene, then oven dried overnight to give the desired product (5.25 g) as a white solid melting at 192–193° C.

$^1$H NMR: (300 MHz, DMSO-$d_6$) δ 8.85 (d, 1H), 8.58 (s, 1H), 8.14 (s, 1H), 7.00–7.08 (m, 3H), 2.15 (s, 6H).

Step B: Preparation of 4-(2,6-Dimethylphenyl)-1,2,4-oxadiazolidine-3,5-dione

A 300 mL flask with side arm equipped with a nitrogen inlet and a thermometer was charged with 25 mL of tetrahydrofuran followed by 5.00 g (0.0277 mol) of 2,6-dimethylphenyl hydroxyurea. To this stirred suspension was added portion-wise 4.41 g (0.0277 mol) of carbonyl diimidazole over 5 min. While stirring at room temperature, the suspension turned into a solution before precipitate started to form slowly. After 18 h, the mixture was quenched with 50 mL of 1N HCl which caused the suspension to turn into a solution. It was partitioned between ethyl acetate (250 mL) and 1N HCl (50 mL). The organic layer was separated and washed with brine, then dried over $MgSO_4$ and filtered. The solvent was removed under reduced pressure to give the title compound as a red oil (5.20 g) which slowly crystallized upon standing at room temperature to give a solid melting at 90–100° C.

$^1$H NMR: (300 MHz, $CDCl_3$) δ 7.30 (t, 1H), 7.20 (d, 2H), 2.24 (s, 6H).

Step C: Preparation of 4-(2,6-Dimethylphenyl)-N-(4-fluorophenyl)-N-(1-methylethyl)-3,5-dioxo-1,2,4-oxadiazolidine-2-carboxamide To a 500 mL two neck round bottom flask equipped with a thermometer and a reflux condenser with nitrogen inlet was charged sequentially 30 mL of toluene, 1.50 g (0.0072 mol) of the compound of Step B, 1.60 g (0.0074 mol) of the compound of Step D in Example 1, and lastly 0.90 g of 4-dimethylaminopyridine (0.072 mol). The reaction became homogeneous upon heating to 85° C. Heating was continued at 85° C. for 2 h during which time a precipitate was formed. The reaction mixture was then cooled to room temperature, filtered and the solid was washed with toluene (2×25 mL). The toluene was removed under reduced pressure to give a tan solid. The product was washed with cool isopropyl alcohol (2×10 mL) to give 2.16 g of the title compound, a compound of the invention, as a white solid melting at 134–136° C.

$^1$H NMR: (300 MHz, DMSO-$d_6$) δ 7.20–7.47 (m, 7H), 4.52–4.65 (m, 1H), 2.03 (s, 6H).

EXAMPLE 3

Step A: Preparation of 4-(2-Propenyl)-1,2,4-oxadiazolidine-3,5-dione

To a 500 mL round-bottom flask were added acetone (300 mL), allyl isocyanate (12.0 g, 0.145 mol), N-hydroxyurethane (6.1 g, 0.058 mol) and triethylamine (11.7 g, 0.116 mol) respectively at room temperature under nitrogen with efficient stirring. The reaction mixture was allowed to stir at room temperature for 6 d. The solvent was removed under reduced pressure. The residue was suspended in 100 mL of 1N HCl, extracted with ethyl acetate (3×150 mL). The organic solution was washed with water, brine, dried over $MgSO_4$ and concentrated to a clear yellow oil. The crude product was dried under high vacuum for 4 h to give the title compound as an oil (13.1 g) which was used in the next step without further purification.

$^1$H NMR: (300 MHz, $CDCl_3$) δ: 5.87 (m, 1H), 5.27 (m, 2H), 4.17 (m, 1H), 3.82 (bs, 1H).

Step B: Preparation of N-(4-Fluoroyhenyl)-N-(1-methylethyl)-3,5-dioxo-4-(2-propenyl)-1,2,4-oxadiazolidine-2-carboxamide A dry 100 mL round-bottom flask was changed with dry tetrahydrofuran (20 mL), the compound of step A (1.0 g, 7.0 mmol), the compound of Step D in Example 1 (1.5 g, 7.0 mmol), triethylamine (1.0 g, 10.0 mmol) and 4-dimethylaminopyridine (0.2 g, 1.6 mmol) respectively at room temperature under nitrogen atmosphere with stirring. The reaction mixture was heated at reflux for 1.5 h during which time a white solid precipitated out. The reaction mixture was cooled to room temperature and diluted with 150 mL of ethyl acetate. The organic layer was washed with 1N HCl, water, brine, and dried over $MgSO_4$. Upon concentration, a yellow syrup (1.8 g) was obtained. The crude product was purified by flash chromatography on silica gel with ethyl acetate/hexanes 1:9 as eluent to provide 1.22 g of the title compound, a compound of the invention, as a white solid melting at 65–66° C.

$^1$H NMR: (300 MHz, $CDCl_3$) δ 7.22 (m, 2H), 7.11 (m, 2H), 5.78 (m, 1H), 5.26 (m, 2H), 4.42 (m, 1H), 4.07 (d, 2H), 1.20 (d, 6H).

EXAMPLE 4

Step A: Preparation of Phenylhydroxycarbamate

To a stirred solution of $NaHCO_3$ (60.5 g) in water (200 mL) in a 2 L beaker was added portion-wise over 15 min 27.5 g of hydroxylamine hydrochloride. Once the bubbling subsided, dichloromethane (200 mL) was added to the reaction mixture and cooled to 5° C. Phenyl chloroformate (50 g) was then added at a steady rate to the reaction mixture. The reaction mixture was allowed to warm to room temperature and stirred for 1 h. Ethyl acetate (100 mL) was employed to bring the reaction mixture to a transparent solution. The organic layer was separated, washed with brine (200 mL) and dried over $MgSO_4$. The organic solvent was removed under reduced pressure to give the title compound (38.20 g) as a white solid melting at 104–107° C.

Step B: Preparation of N-Hydroxy-2,2-dimethylhydrazinecarboxamide

To a solution of 37.3 g of the compound of Step A in tetrahydrofuran (200 mL) at room temperature under nitrogen was added 22 mL of 1,1-dimethylhydrazine. The reaction mixture was then heated at reflux overnight. The solvent was removed under reduced pressure to afford an oil which was purified by column chromatography with 9:1 ethyl acetate-methanol as eluent to give a semi-solid. Triturating of the residue with dichloromethane gave the title compound (7.25 g) as a white solid melting at 115–118° C.

$^1$H NMR (DMSO-$d_6$) δ 8.5 (brs, 1H), 8.27 (brs, 1H), 7.4 (brs, 1H), 2.4 (s, 6H).

Step C: Preparation of 4-(Dimethylamino)-1,2,4-oxadiazolinedine-3,5-dione

The compound of Step B (4.25 g, 29 mmol) was suspended in tetrahydrofuran (25 mL) at 5° C. under nitrogen. To the mixture was added portion-wise 1,1'-carbonyldiimidazole (5.78 g, 29 mmol) while maintaining the reaction temperature under 10° C. The reaction was partitioned between ethyl acetate (125 mL) and 1N HCl (60 mL). The organic layer was separated. The aqueous layer was further extracted with ethyl acetate (2×100 mL). The combined organic layers were dried over $MgSO_4$ and concentrated under reduced pressure to afford the title compound as an oil (2.9 g).

$^1$H NMR ($CDCl_3$) δ 5.1 (br s, 1H), 2.9 (s, 6H).

Step D: Preparation of 4-(Dimethylamino)-N-(4-fluorophenyl)-N-(1-methylethyl)-3,5-dioxo-1,2,4-oxadiazolidine-2-carboxamide The compound of Step D, Example 1 (1.48 g, 6.9 mmol), 4-dimethylaminopyridine (0.84 g, 6.9 mmol), and the compound of Step C (1.00 g, 6.9 mmol) were combined in toluene (25 mL) at room temperature. The reaction mixture was heated to 80° C. for 3 h. Acetonitrile (20 mL) and silica gel (5 g) were added and the solvent was removed under reduced pressure. After column chromatography with 8:2 hexanes-ethyl acetate as eluent, the title compound, a compound of the invention, was isolated as a white solid (1.23 g) melting at 69–71° C.

$^1$H NMR ($CDCl_3$) δ 7.2 (m, 2H), 7.1 (m, 2H), 4.6 (m, 1H), 2.9 (s, 6H), 1.2 (d, 6H).

EXAMPLE 5

Step A: Preparation of 4-[(2-Methylphenyl)methyl]-3-phenylmethoxy)-1,2,4-oxadiazol-5(4H)-one A 50 mL round bottom flask equipped with a thermometer, a stirrer, and a nitrogen inlet was charged with 3-(phenylmethoxy)-1,2,4-oxadiazol-5(4H)-one (*Synthesis*, (1991), 265 0.5 g, 2.6 mmol), potassium carbonate (0.5 g, 3.6 mmol), tetrabutylammonium bromide (0.022 g, 0.1 mmol), 2-methylbenzyl bromide (0.6 g, 3.2 mmol) and acetonitrile (10 mL). The reaction mixture was stirred at room temperature for 18 h. The reaction mixture was poured into water (25 mL) and extracted with dichloromethane (3×20 mL), dried over $MgSO_4$ and concentrated under reduced pressure to provide a solid. The solid was further purified by flashichromatography on silica gel using 9:1 hexane-ethyl acetate to provide 0.3 g (40%) of the title compound as a white solid melting at 77–78° C.

$^1$H NMR ($CDCl_3$): δ 7.39 (m, 3H), 7.27 (m, 3H), 7.17 (m, 3H), 5.26 (s, 2H), 4.69 (s, 2H), 2.31 (s, 3H).

Step B: Preparation of N-(4-Chlorophenyl)-N-(1-methylethyl)-4-[(2-methylphenyl)methyl]-3,5-dioxo-1,2,4-oxadiazolidine-2-carboxamide A 50 mL round bottom flask equipped with a stirrer, a thermometer, and a nitrogen inlet was charged with the compound of Step A (0.6 g, 2.05 mmol), (4-chlorophenyl)(1-methylethyl)carbamic chloride (0.5 g, 2.155 mmol), N,N'-dimethylaminopyridine (0.26 g, 2.13 mmol) and tetrahydrofuran (20 mL). The mixture was heated to reflux for 3 hours, then cooled to room temperature and poured into 1N HCl (50 mL). The mixture was extracted with diethyl ether (3×25 mL). The organic layer was dried over $MgSO_4$ and concentrated under reduced pressure to provide a thick oil. The oil was purified by flash chromatography on silica gel using 9:1 hexane-ethyl acetate to provide 0.22 g (28%) of the title compound as a white solid melting at 90–91° C.

$^1$H NMR ($CDCl_3$): δ 7.5–7.0 (m, 8H), 4.63 (s, 2H), 4.6 (m, 1H), 2.36 (s, 3H), 1.18 (d, 6H).

EXAMPLE 6

Step A: Preparation of 4-Methyl-3-(phenylmethoxy)-1,2-oxadiazol-5(4H)-one

A 50 mL round bottom flask equipped with a thermometer, a stirrer and a nitrogen inlet was charged with 3-(phenylmethoxy)-1,2,4-oxadiazol-5(4H)-one (1 g, 5.2 mmol), iodomethane (0.916 g, 6.5 mmol), 1,8-diazabicyclo[5.4.0]undec-7-ene (1 g, 6.5 mmol) and acetonitrile (10 mL). The mixture was stirred at room temperature for 18 h. The entire reaction mixture was flash chromatographed (silica gel, 8:2 hexane-ethyl acetate) to provide 1 g (37.5%) of the title compound as a white solid melting at 80–83° C.

$^1$H NMR ($CDCl_3$): δ 7.43 (m, 5H), 5.32 (s, 2H), 3.09 (s, 3H).

Step B: Preparation of N-(4-Fluorophenyl)-4-methyl-N-(1-methylethyl)-3,5-dioxo-1,2,4-oxadiazolidine-2-carboxamide A 50 mL round bottom flask equipped with a thermometer, a stirrer and a nitrogen inlet was charged with 4-methyl-3-(phenylmethoxy)-1,2,4-oxadiazol-5(4H)-one (0.55 g, 2.66 mmol), (4-fluorophenyl)(1-methylethyl)carbamic chloride (0.581 g, 2.7 mmol), N,N'-dimethylaminopyridine (0.329 g, 2.7 mmol) and acetonitrile (10 mL). The reaction mixture was heated to reflux 2 h, and allowed to cool to room temperature. The entire mixture was flash chromatographed (silica gel, 9: 1, then 8:2 hexane-ethyl acetate) to provide 0.6 g (76%) of the title compound as a white solid melting at 135–136° C.

$^1$H NMR ($CDCl_3$) δ 7.29 (m, 2H), 7.11 (m, 2H), 4.64 (m, 1H), 3.05 (s, 3H), 1.18 (d, 6H).

EXAMPLE 7

Step A: Preparation of N-(4-Chlorophenyl)-4-methyl-N-(1-methylethyl)-3,5-dioxo-1,2,4-oxadiazolidine-2-carboxamide A 50 mL round bottom flask, equipped with a thermometer, a stirrer and nitrogen inlet was charged with 3-(phenylmethoxy)-1,2,4-oxadiazol-5(4H)-one (0.5 g, 2.6 mmol), 1,8-diazabicyclo[5.4.0]unded-7-ene (0.5 g, 3.28 mmol), iodomethane (0.5 g, 3.54 mmol) and acetonitrile (5 mL). The mixture was stirred at room temperature for 18 h. To the mixture was added (4-chlorophenyl)(1-methylethyl) carbamic chloride (0.7 g, 3 mmol) and N,N'-dimethylamino-pyridine (0.367 g, 3 mmol), and the resulting mixture was heated to reflux for 2 h. It was then cooled to room temperature and flash chromatographed (silica gel, 9:1 hexane-ethyl acetate) to provide 150 mg (18%) of the title compound as a white solid melting at 121–123° C.

$^1$H NMR ($CDCl_3$): δ 7.36 (m, 2H), 7.2 (m, 2H), 4.6 (m, 1H), 3.05 (s, 3H), 1.21 (d, 6H).

EXAMPLE 8

Step A: Preparation of 4-(2-Methylproyl)-3-(phenylmethoxy)-1,2,4-oxadiazol-5(4H)-one A 50 mL round bottom flask equipped with a thermometer, a stirrer, addition funnel and nitrogen inlet was charged with 3-(phenylmethoxy)-1,2,4-oxadiazol-5(4H)-one (1 g, 5.2 mmol), 2-methyl propanol (0.45 g, 6 mmol), triphenylphosphine (1.57 g, 6 mmol) and tetrahydrofuran (5 mL). The mixture was cooled to 0° C. and a solution of diethyl azodicarboxylate (1.04 g, 6 mmol) in tetrahydrofuran (2 mL) was added dropwise over a period of 10 min. The reaction mixture was allowed to warm to room temperature, and stirred for 18 h. The entire mixture was flash chromatographed (silica gel, 8:2 hexane-ethyl acetate) to provide 1.1 g (84%) of the title compound as a white solid melting at 53–60° C.

$^1$H NMR ($CDCl_3$): δ 7.42 (m, 5H), 5.31 (s, 2H), 3.34 (d, 2H), 2.01 (m, 1H), 0.89 (d, 6H).

Step B: Preparation of N-(4-Fluororhenyl)-N-(1-methylethyl)-4-(2-methylpropyl)-3,5-dioxo-1,2,4-oxadiazolidine-2-carboxamide A 50 mL round bottom flask equipped with a stirrer, a thermometer and a nitrogen inlet was charged with 4-(2-methylpropyl)-3-(phenylmethoxy)-1,2,4-oxadiazol-5(4H)-one (0.25 g, 1 mmol), (4-fluorophenyl)(1-methylethyl) carbamic chloride (0.24 g, 1.1 mmol), N,N'-dimethylaminopyridine (0.14 g, 1.1 mmol) and acetonitrile (10 mL). The mixture was heated to reflux; for 2 h and allowed to cool to room temperature. The entire mixture was flashed chromatographed (silica gel, 9:1 hexane-ethyl acetate) to provide 0.18 (53%) of the title compound as a white solid melting at 80–81° C.

$^1$H NMR ($CDCl_3$): δ 7.24 (m, 2H), 7.11 (m, 2H), 4.65 (m, 1H), 3.29 (d, 2H), 2.0 (m, 1H), 1.2 (d, 6H), 0.89 (d, 6H).

EXAMPLE 9

Step A: Preparation of N-(4-Fluorophenyl)-N-(1-methylethyl)-3,5-dioxo-4-(phenylmethyl)-1,2,4-oxadiazolidine-2-carboxamide A 50 mL round bottom flask equipped with a thermometer, a stirrer and a nitrogen inlet was charged with 3-(phenyhnethoxy)-1,2,4-oxadiazol-5(4H)-one (0.5 g, 2.6 mmol), (4-fluorophenyl)(1-methylethyl)carbamic chloride (0.58 g, 27 mmol), N,N'-dimethylaminopyridine (0.33 g, 2.7 mmol) and acetonitrile (5 mL). The mixture was heated to reflux for 3 h and allowed to cool to room temperature. The mixture was flash chromatographed (silica gel, 9:1 hexane-ethyl acetate) to provide 0.24 g (25%) of the title compound as a white solid melting at 95–96° C.

$^1$H NMR ($CDCl_3$): δ 7.22 (s, 5H), 7.2 (m, 2H), 7.06 (m, 2H), 4.6 (m, 1H), 4.59 (s, 2H), 1.17 (d, 6H).

EXAMPLE 10

Step A: Preparation of N-(4-Fluorophenyl)-N-(1-methylethyl)-3,5-dioxo-1,2,4-oxadiazolidine-2-carboxamide and N-(4-fluorophenyl)-4-methyl-N-(1-methylethyl)-3,5-dioxo-1,2,4-oxadiazolidine-2-carboxamide A 50 mL round bottom flask equipped with a thermometer, a stirrer and nitrogen inlet was charged with 3-methoxy-1,2,4-oxadiazol-5(4H)-one (1.16 g, 0.01 m), (4-fluorophenyl)(1-methylethy)carbamic chloride (2.4 g, 0.011 m), N,N'-dimethylaminopyridine (1.35 g, 0.011 m) and acetonitrile (20 mL). The mixture was heated to reflux for 18 h. The mixture was allowed to cool to room temperature, poured into 1N HCl (20 mL) and extracted with ethyl acetate (3×25 mL). The organic phase was dried over $MgSO_4$ and concentrated under reduced pressure to provide a thick oil. The oil was flash chromatographed (silica gel, 7:3 dichloromethane-ethyl acetate) to provide two fractions. Fraction A contained 0.42 g (15%) of N-(4-fluorophenyl)-4-methyl-N-(1-methylethyl)-3,5-dioxo-1,2,4-oxadiazolidine-2-carboxamide as a white solid melting at 135–136° C. $^1$H NMR ($CDCl_3$): δ 7.26 (m, 2H), 7.11 (m, 2H), 4.6 (m, 1H), 3.05 (s, 3H), 1.17 (m, 6H). Fraction B contained 1.1 g (40%) of N-(4-fluorophenyl)-N-(1-methylethyl)-3,5-dioxo-1,2,4-oxadiazolidine-2-carboxamide as a solid melting at 55–60° C.

1H NMR ($CDCl_3$): δ 7.24 (m, 2H), 7.19 (m, 2H), 4.6 (m, 1H), 1.2 (d, 6H). IR ($CH_2Cl_2$); 3200, 3300, 1776, 1715 $cm^{-1}$. MS (M+1): 281, 257.

Step B: Preparation of N-(4-Fluorophenyl)-N-(1-methylethyl)-4-(2-methylpropyl)-3,5-dioxo-1,2,4-oxadiazolidine-2-carboxamide A 50 mL round bottom flask equipped with a thermometer, a stirrer, an addition funnel, and a nitrogen inlet was charged with N-(4-fluorophenyl)-N-(1-methylethyl)-3,5-dioxo-1,2,4-oxadiazolidine-2-carboxamide (5.5 g, 0.019 m), 2-methyl-1-propanol (3 g, 0.04 mol), triphenylphosphine (6.3 g, 0.021 mol) and tetrahydrofuran (60 mL). The reaction solution was cooled to 15° C. and diethyl azodicarboxylate (4.2 g, 0.024 mol) in tetrahydrofuran (10 mL) was added dropwise over a period of 10 min. The reaction mixture was stirred at room temperature for 18 h. The solvent was removed under reduced pressure and the residue was flash chromatographed (silica gel, 9:1 hexane-ethyl acetate) to provide the title compound as a white solid (5.6 g, 88%). The solid has a melting range of 80–81° C., and was identical to the material prepared in Example 8, Step B.

EXAMPLE 11

Step A: Preparation of Methyl (Chlorocarbonyl)(2,6-dimethylphenyl)carbamate

A mixture of toluene (150 mL), biphenyl (0.2 g) and sodium methoxide in methanol (23.76 g, 0.11 mol, 25% by weight) was heated at reflux, and the methanol-toluene azeotrope was removed. The mixture was allowed to cool to 80° C., and toluene (80 mL) was added. To the resulting mixture was added in five portions methyl (2,6-dimethylphenyl)carbamate (17.9 g, 0.1 mol). The methanol formed in the reaction was removed as the above azeotrope. When most of the methanol had been removed, ethylene glycol dimethyl ether (8 mL) was added, and the mixture was distilled until the head temperature reached 110° C. The mixture was allowed to cool to 25° C., and ethylene glycol dimethyl ether (3 mL) was added. The mixture was then added to phosgene in toluene (22.5 g, 0.56 mol, 25% by weight). When the addition was complete, excess phosgene was removed by distillation. The mixture was allowed to cool to 25° C., and then washed with sodium bicarbonate solution (40 mL, saturated). The organic layer was dried and the volatiles removed by evaporation to give 17.21 g (64.5%) of the title compound as a solid. An analytical sample was prepared by column chromatography on silica gel using 1:3 ethyl acetate-hexanes as the eluent.

M.P. 84.5–86° C.; IR (Nujol): 1814, 1437, 1252, 1229, 1209, 1182, 1013, 982, 845 $cm^{-1}$; 1H NMR ($CDCl_3$): δ 7.28–7.12 (m, 3H), 3.82 (s, 3H), 2.23 (s, 6H).

Step B: Preparation of 4-(2,6-Dimethylphenyl)-2-methyl-1,2,4-oxadiazolidine-3,5-dione A portion of the compound from Step A (3.72 g, 15.4 mmol) in dioxane (15 mL) was added to a mixture of aqueous hydroxylainie (2.03 g, 30.7 mmol, 50% by weight) in dioxane (1 5 mL). When the addition was complete, a solution of potassium hydroxide (2.22 g, 33.6 mmol, 85%) in water (5 mL) was added dropwise to the mixture so that the temperature did, not rise beyond 30° C. When the addition was complete, the solvent was removed until the volume was reduced to about 5 mL. The mixture was poured into water (100 mL), and the aqueous mixture was extracted with ethyl acetate (2×50 mL). The aqueous mixture was acidified with HCl and further extracted with ethyl acetate (2×50 mL). The combined organic extracts from the second extraction were dried and evaporated to give the title compound as a solid (2.34 g, 73.7%). The solid has a melting point range of 92–93.5° C. after crystallization from ether/hexanes, and was identical to material prepared in Example 2, Step B.

EXAMPLE 12

Step A: Preparation of N'-Hydroxy-N-(1-methylethyl)-N-phenylurea

A solution, of 50% aqueous hydroxylamine (16.8 g, 0.25 mol) was added dropwise to a solution of (1-methylethyl) phenylcarbamic chloride (20.0 g, 0.1 mol) in 200 mL of THF in an ice bath so that the reaction temperature was kept below 30° C. Precipitate began to form halfway through the addition. The resulting slurry was stirred overnight. The mixture was filtered, and the solids collected were first washed with water and then with hexane/ether. After air-drying, 14.56 g of the title compound was obtained. Its structure was confirmed by an analysis of the NMR spectra. The filtrate was stripped down to afford a residue which was washed sequentially with 1N HCl, water and hexane/ether to yield a second crop of the title compound (5.38 g) melting at 165–166° C. The combined yield was 100%.

$^1$H NMR.(300 MHz, DMSO-$d_6$): δ 8.10 (br s, 1H), 7.74 (s, 1H), 7.38 (m, 3H), 7.12 (m, 2H), 4.55 (m, 1H), 0.97 (d, 6H)

Step B: Preparation of N-(1-Methylethyl)-3,5-dioxo-N-phenyl-1,2,4-oxadiazolidine-2-carboxamide A solution of chlorocarbonyl isocyanate (5.0 g, 0.047 mol) was added dropwise to a slurry of the title compound of Step A (9.2 g, 0.047 mol) and triethylamine (5.3 g, 0.052 mol) in 200 mL of THF while maintaining the reaction temperature below 30° C. using an ice bath. After 2 hours, TLC showed the presence of starting material. Another 0.5 g of chlorocarbonyl isocyanate was added, and the reaction mixture was stirred for another hour. At that point, TLC showed still the presence of starting material. The reaction mixture was filtered to, remove solids, and the filtrate was stripped to dryness and then extracted with 1N HCl and ether. Upon evaporation of volatiles, a gummy product was obtained which was taken into methylene chloride and potassium carbonate solution. Solids were collected by a filtration, washed with methylene chloride and air dried. The solids (5.3 g) were found to be the potassium salt of the title compound. The basic aqueous filtrate was acidified with concentrated HCl and extracted with methylene chloride to afford 4 g of the title compound, an intermediate useful for the preparation of the compounds of the present invention, melting at 116–7° C. From the methylene chloride used to wash the solids, 2.6 g of the title compound of Step A was recovered. This represented a 71.7% conversion. The combined yield was therefore 96% based on the 71.7% conversion.

$^1$H NMR (300 MHz, DMSO-$d_6$): δ 9.60 (brs, 1H), 7.37 (m, 3H), 7.23 (m, 2H), 4.60 (m, 1H), 1.19 (d, 6H).

EXAMPLE 13

Step A: Preparation of N-(4-Fluorophenyl)-N-(1-methylethyl)-3,5-dioxo-1,2,4-oxadiazolidine-2-carboxamide A 1 L three neck round bottom flask equipped with nitrogen inlet, thermometer and water condenser was charged with dioxanes (400 mL), 1,2,4-oxadiazole-3,5-dione (30 g 0.29 moles, prepared according to Srivastava, P. and Robins, R., *J. Med. Chem.* 1981, 24, 1172–1177), 4-dimethylaminopyridine (36 g, 0.29 mole), and N-isopropyl-4-flourophenylcarbamoyl chloride (63 g, 0.29 moles) at room temperature. The yellow mixture was heated at reflux for 4 hours. When no starting material was detected by thin layer chromatography, heat was tuned off and mixture was cooled to room temperature. The solvent was removed under reduced pressure and the resulting solids were suspended in ethyl acetate. The mixture was washed with 1N HCl, and the aqueous layer was extracted twice with ethyl acetate. The combined organic solutions were washed with brine, dried over anhydrous magnesium sulfate, and concentrated under reduced pressure. The product was crystallized from chlorobutane and hexanes, and filtered to give 47 g (57%) of the title compound as a white solid melting at 94–95° C.

$^1$H NMR: (300 MHz, $CDCl_3$) δ 7.24 (m, 2H), 7.09 (m, 2H), 4.63 (m, 1H), 1.18 (d, 6H).

Step B: Preparation of N-(4-Fluorophenyl)-N,4-bis (1-methylethyl)-3,5-dioxo-1,2,4-oxadiazolidine-2-carboxamide A solution of the compound of Step A (1.0 g, 3.6 mmol) in 20 mL of triisopropylorthoformate was heated at 145° C. for 2 h and then allowed to stir at ambient temperature overnight. The volatiles were removed under reduced pressure, and the residue recrystallized from methanol to give 0.99 g (86%) of the title compound, a compound of this invention, as a solid melting at 78–80° C.

$^1$H NMR (300 MHz, $CDCl_3$): δ 7.26(m, 2H), 7.11(m, 2H), 4.62(m, 1H), 4.18(m, 1H), 1.40(d, 6H), 1.20 (d, 6H).

EXAMPLE 14

Step A: Preparation of 2,2'-Carbonylbis[4-(1-methylethyl)-1,2,4-oxadiazolidine-3,5-dione To a solution of 4-(1-methylethyl)-1,2,4-oxadiazolidine-3,5-dione (20 g, 139 mmol) and hexamethylguanidinium chloride (0.25 g, 1.39 mmol) in 150 mL of toluene was added phosgene (6.88 g, 69 mmol, 20% by weight in toluene). The resulting mixture was heated at reflux for 1.5 h with the use of a dry ice/acetone condenser. The volatiles were removed under reduced pressure, and the residue recrystallized from 150 mL of n-BuCl to give 14 g (64%) of the title compound as a white solid melting at 150° C.

$^1$H NMR (300 MHz, $CDCl_3$): δ 1.52 (d, 6H), 4.36 (m, 1H).

Step B: Preparation of N,4-bis(1-Methylethyl)-3,5-dioxo-N-phenyl-1,2,4-oxadiazolidine-2-carboxamide A solution of the compound of Step A (0.5 g, 1.6 mmol), N-phenyl-N-(2-methylethyl)amine (0.215 g, 1.6 mmol) and 4-dimethylaminopyridine (0.19 g, 1.6 mmol) in 10 mL of acetonitrile was heated at reflux under a nitrogen atmosphere. The resulting mixture was allowed to cool to ambient temperature and poured into 25 mL of water. It was then extracted with ethylacetate (4×25 mL). Condensation gave an oil which was purified by flash chromatography using 1:3 EtOAc-Hexanes as the eluant to give the title compound, a compound of this invention, as a white solid melting at 83–84° C.

$^1$H NMR (300 MHz, $CDCl_3$): δ 1.20 (d, 6H), 1.38 (d, 6H), 4.16 (m, 1H), 4.63 (m, 1H), 7.26 (m, 2H), 7.39 (m, 3H).

EXAMPLE 15

Step A: N-(4-Fluorophenyl)-4-(methoxymethyl)-N-(1-methylethyl)-3,5-dioxo-1,2,4-oxadiazolidine-2-carboxamide To a solution of 308 uL of bromomethyl methyl ether (1 eq, 90% tech.) in 8 mL dry acetonitrile was added 995 mg of the title compound of Step A in Example 13. To this mixture was then added 508 uL (1 eq) of 1,8-diazabicyclo [5.4.0]undec-7-ene (DBU). The resulting solution was heated at reflux under a nitrogen atmosphere for 3 h. The reaction mixture was allowed to cool to room temperature and the volatiles removed under reduced pressure. The residue was dissolved in 1 mL of dichloromethane and loaded onto a 70 mL solid phase extraction (SPE) cartridge containing 10 g of silica gel (230–400 mesh). The title compound (260 mg), a compound of this invention, was obtained after elution using a 20% ethyl acetate/hexane solution.

$^1$H NMR (300 MHz, $CDCl_3$): δ 7.22(m, 2H), 7.09 (m, 2H), 4.89 (s, 2H), 4.65 (m, 1H), 3.39 (s, 3H), 1.2 (d, 6H).

By the procedures described herein together with methods known in the art, the following compounds of Tables 1 to 3 can be prepared. The following notations have been used in Tables.

| | |
|---|---|
| Q-1 | Ph |
| Q-2 | 2-Cl—Ph |
| Q-3 | 3-Cl—Ph |
| Q-4 | 4-Cl—Ph |
| Q-5 | 2-Br—Ph |
| Q-6 | 2-F—Ph |
| Q-76 | 2,4-di-F—Ph |
| Q-8 | 2,6-di-F—Ph |
| Q-9 | 2,3-di-Cl—Ph |
| Q-10 | 2,4-di-Cl—Ph |
| Q-11 | 2,6-di-Cl—Ph |
| Q-12 | 2,6-di-Et-Ph |
| Q-13 | 2,6-di-OMe |

-continued

| | |
|---|---|
| Q-14 | 2-Cl-4-F—Ph |
| Q-15 | 2-Cl-6-F—Ph |
| Q-16 | 2-Me-Ph |
| Q-17 | 3-Me-Ph |
| Q-18 | 4-Me-Ph |
| Q-19 | 2-Et-Ph |
| Q-20 | 2-Pr—Ph |
| Q-21 | 2,5-di-Me-Ph |
| Q-22 | 4-OMe-Ph |
| Q-23 | 2-Cl-6-Me-Ph |
| Q-24 | 2,6-di-Me-Ph |
| Q-25 | 2,4-Me-Ph |
| Q-26 | 2,5-di-Me-Ph |
| Q-27 | 2,3-di-Me-Ph |
| Q-28 | 2-Me-6-Et-Ph |
| Q-29 | 2-$CF_3$—Ph |
| Q-30 | 4-$CF_3$—Ph |
| Q-31 | 2-$OCF_2H$—Ph |
| Q-32 | 2-$OCF_3$—Ph |
| Q-33 | 2,4,6-tri-Me-Ph |
| Q-34 | 4-Cl-2,6-di-Me-Ph |
| Q-35 | 2-OPh—Ph |
| Q-36 | 2-$SCH_3$—Ph |
| Q-37 | 2-Me-6-(i-Pr)—Ph |
| Q-38 | 2-Cl-4-Me-Ph |
| Q-39 | 2-CN-Ph |
| Q-40 | 4-Cl-2-Me-Ph |
| Q-41 | 2-Cl-6-Me-Ph |
| Q-42 | 2-Me-5-Cl—Ph |
| Q-43 | 2-Cl-5-Me-Ph |
| Q-44 | 2-Cl-3-Me-Ph |
| Q-45 | 2-$NO_2$—Ph |
| Q-46 | 1-tetrahydronaphthyl |
| Q-47 | 4-(2,3-dihydro-1H-indene) |
| Q-48 | 7-(2,3-diH-2,2-di-Me-7-benzofuran) |
| Q-49 | 2-Vinyl-Ph |
| Q-50 | 2-Ph—Ph |
| Q-51 | 1-(2-Me-tetrahydronaphthyl) |
| Q-52 | 3-(2-Cl-Pyridine) |
| Q-53 | 4,6-di-Me-Pyrimidin-5-yl |
| Q-54 | 4,6-di-OMe-Pyrimidin-5-yl |
| Q-55 | $PhCH_2$— |
| Q-56 | $PhC(CH_3)$— |
| Q-57 | (2-Cl—Ph)$CH_2$— |
| Q-58 | (2,6-di-Cl—Ph)$CH_2$— |
| Q-59 | (2,3-di-Cl—Ph)$CH_2$— |
| Q-60 | (2-Me-Ph)$CH_2$— |
| Q-61 | (2-$OCH_3$—Ph)$CH_2$— |
| Q-62 | (2,4-di-Cl—Ph)$CH_2$— |
| Q-63 | (2-$CF_3$—Ph)$CH_2$— |
| Q-64 | (2-$OCF_3$—Ph)$CH_2$— |
| Q-65 | (2-CN-Ph)$CH_2$— |
| Q-66 | (2-Cl—Ph)$CH(CH_3)$— |
| Q-67 | (2-Me-Ph)$CH(CH_3)$— |
| Q-68 | $PhCH_2CH_2$— |
| Q-69 | (2-Cl—Ph)$CH_2CH_2$— |
| Q-70 | (2-Me-Ph)$CH_2CH_2$— |

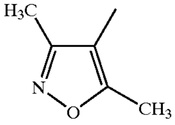

Q-71

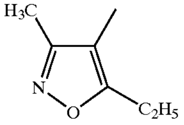

Q-72

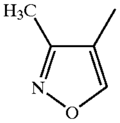

Q-73

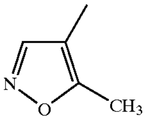

Q-74

-continued

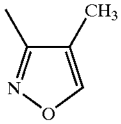

Q-75

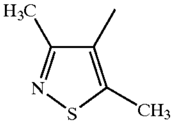

Q-76

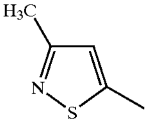

Q-77

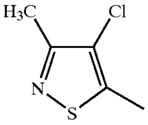

Q-78

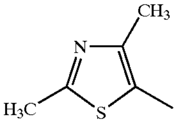

Q-79

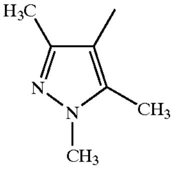

Q-80

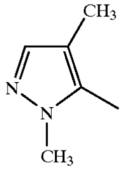

Q-81

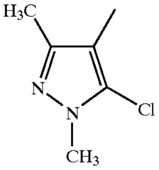

Q-82

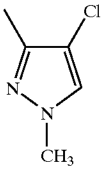

Q-83

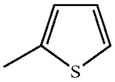

Q-84

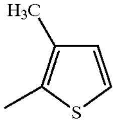

Q-85

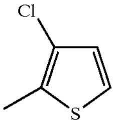

Q-86

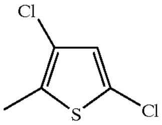

Q-87

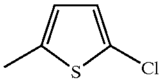

Q-88

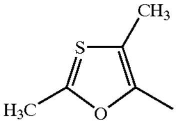

Q-89

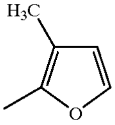

Q-90

-continued

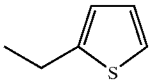

Q-91

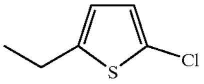

Q-92

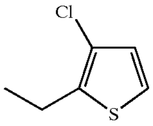

Q-93

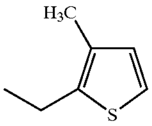

Q-94

| | |
|---|---|
| Q-95 | n-Pr |
| Q-96 | n-Bu |
| Q-97 | i-Bu |
| Q-98 | n-hex |
| Q-99 | c-Pr |
| Q-100 | Allyl |
| Q-101 | Propargyl |
| Q-102 | 3-(2-Cl-Propenyl) |
| Q-103 | Cyclohexyl |
| Q-104 | 1-cyclohexenyl |
| Q-105 | 2-Me-1-cyclohexenyl |
| Q-106 | $MeOCH_2CH_2$— |
| Q-107 | $MeOCH_2$— |
| Q-108 | 3-Cl—Pr |
| Q-109 | 4-(1,1-di-F-butenyl) |
| Q-110 | 3-(1,1-di-Cl-propenyl) |
| Q-111 | i-Pr |
| Q-112 | 2-OMe-Ph |
| Q-113 | 2-Me-6-OMe-Ph |
| Q-114 | 2-Cl-Et |
| Q-115 | 3-(2-Me-Propenyl) |
| Q-116 | t-Bu |
| Q-117 | $MeC(=NOMe)CH_2$— |
| Q-118 | 2-Me-(c-Hex) |
| Q-119 | Et |
| Q-120 | c-Pentyl |
| Q-121 | c-Butyl |
| Q-122 | $EtC(Me)_2$— |
| Q-123 | $CF_3CH_2$— |
| Q-124 | 4-(1-Butenyl) |
| Q-125 | 3-Me-Propargyl |
| Q-126 | 1-(3-Me-1-Propenyl) |
| Q-127 | $NCCH_2$— |
| Q-128 | $(i-C_3H_7)O$— |
| Q-129 | (Allyl)O— |
| Q-130 | $(Me)_2N$— |
| Q-131 | 1-piperidino |
| Q-132 | $MeO_2S$— |
| Q-133 | $MeSCH_2CH_2$— |
| Q-134 | $Me2NS(O)_2$— |
| Q-135 | $O_2NCH_2$— |
| Q-136 | MeC(=O)— |
| Q-137 | (i-Pr)OC(=O)— |
| Q-138 | EtOC(=O)— |
| Q-139 | $Me_2NC(=O)$— |
| Q-140 | $EtOC(=O)CH_2$— |
| Q-141 | $(MeO)_2P(=O)CH_2$— |
| Q-142 | $Me_2NC(=O)CH_2$— |
| Q-143 | 2-(Tetrahydropyranyl) |
| Q-144 | (Oxirane)-$CH_2$— |

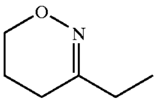

Q-145

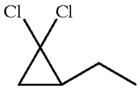

Q-146

-continued

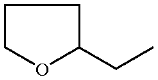

Q-147

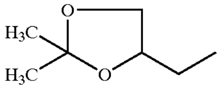

Q-148

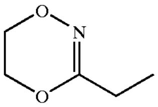

Q-149

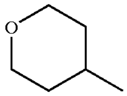

Q-150

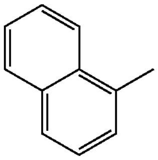

Q-151

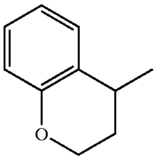

Q-152

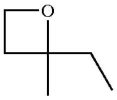

Q-153

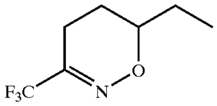

Q-154

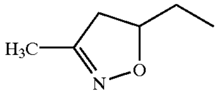

Q-155

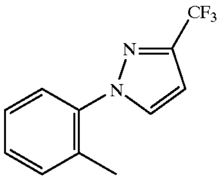

Q-156

| | |
|---|---|
| Q-157 | $Me_2NCH_2CH_2$— |
| Q-158 | $Me_2NCH_2$— |
| Q-159 | $Me_3SiCH_2$— |
| Q-160 | $Me_2NC(=S)$— |
| Q-161 | 3-oxetanyl |
| Q-162 | $NCCH_2CH_2$ |
| Q-163 | $MeOC(=O)CH(CH_3)$— |
| Q-164 | MeOC(=O)CH(i-Pr)— |
| Q-165 | MeNH |
| Q-166 | $2-(NMe_2)$—Ph |
| Q-167 | $2-(SF_5)$—Ph |
| Q-168 | 1-(Morpholino) |
| Q-169 | EtCH(Me)— |
| Q-170 | $Me_3CCH_2$ |
| Q-171 | $(Et)_2N$— |
| Q-172 | MeS— |
| Q-173 | MeSC(=S)— |
| Q-174 | 4-(2-Butynyl) |
| Q-175 | $F_3CS$— |

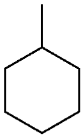

B-1

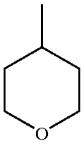

B-2

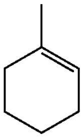

B-3

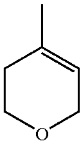

B-4

-continued

| | | | |
|---|---|---|---|
| 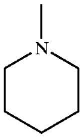 | 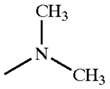 | 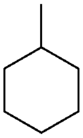 | 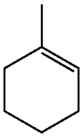 |
| B-5 | B-6 | B-7 | B-8 |
| 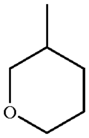 | 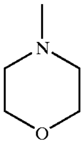 | i-$C_3H_7$ | $C_2H_5$ |
| B-9 | B-10 | B-11 | B-12 |

-continued

| | | | |
|---|---|---|---|
| 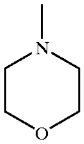 | 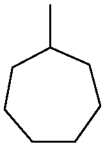 | 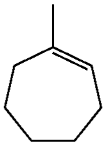 | 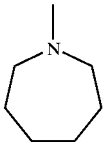 |
| B-13 | B-14 | B-15 | B-16 |
| Allyl | Propargyl | | |
| B-17 | B-18 | | |

TABLE 1

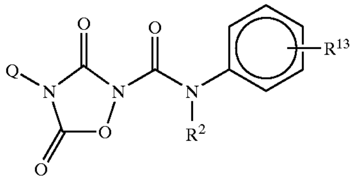

$R^2$ is i-$C_3H_7$, $R^{13}$ is 4-F

| Q | Q | Q | Q | Q | Q | Q | Q | Q |
|---|---|---|---|---|---|---|---|---|
| Q-1 | Q-2 | Q-3 | Q-4 | Q-5 | Q-6 | Q-7 | Q-8 | Q-9 |
| Q-10 | Q-11 | Q-12 | Q-13 | Q-14 | Q-15 | Q-16 | Q-17 | Q-18 |
| Q-19 | Q-20 | Q-21 | Q-22 | Q-23 | Q-24 | Q-25 | Q-26 | Q-27 |
| Q-28 | Q-29 | Q-30 | Q-31 | Q-32 | Q-33 | Q-34 | Q-35 | Q-36 |
| Q-37 | Q-38 | Q-39 | Q-40 | Q-41 | Q-42 | Q-43 | Q-44 | Q-45 |
| Q-46 | Q-47 | Q-48 | Q-49 | Q-50 | Q-51 | Q-52 | Q-53 | Q-54 |
| Q-55 | Q-56 | Q-57 | Q-58 | Q-59 | Q-60 | Q-61 | Q-62 | Q-63 |
| Q-64 | Q-65 | Q-66 | Q-67 | Q-68 | Q-69 | Q-70 | Q-71 | Q-72 |
| Q-73 | Q-74 | Q-75 | Q-76 | Q-77 | Q-78 | Q-79 | Q-80 | Q-81 |
| Q-82 | Q-83 | Q-84 | Q-85 | Q-86 | Q-87 | Q-88 | Q-89 | Q-90 |
| Q-91 | Q-92 | Q-93 | Q-94 | Q-95 | Q-96 | Q-97 | Q-98 | Q-99 |
| Q-100 | Q-101 | Q-102 | Q-103 | Q-104 | Q-105 | Q-106 | Q-107 | Q-108 |
| Q-109 | Q-110 | Q-111 | Q-112 | Q-113 | Q-114 | Q-115 | Q-116 | Q-117 |
| Q-118 | Q-119 | Q-120 | Q-121 | Q-122 | Q-123 | Q-124 | Q-125 | Q-126 |
| Q-127 | Q-128 | Q-129 | Q-130 | Q-131 | Q-132 | Q-133 | Q-134 | Q-135 |
| Q-136 | Q-137 | Q-138 | Q-139 | Q-140 | Q-141 | Q-142 | Q-143 | Q-144 |
| Q-145 | Q-146 | Q-147 | Q-148 | Q-149 | Q-150 | Q-151 | Q-152 | Q-153 |
| Q-154 | Q-155 | Q-156 | Q-157 | Q-158 | Q-159 | Q-160 | Q-161 | Q-162 |
| Q-163 | Q-164 | Q-165 | Q-166 | Q-167 | Q-168 | Q-169 | Q-170 | Q-171 |
| Q-172 | Q-173 | Q-174 | Q-175 | | | | | |

$R^2$ is i-$C_3H_7$, $R^{13}$ is 2,4-di-F

| Q | Q | Q | Q | Q | Q | Q | Q | Q |
|---|---|---|---|---|---|---|---|---|
| Q-1 | Q-2 | Q-3 | Q-4 | Q-5 | Q-6 | Q-7 | Q-8 | Q-9 |
| Q-10 | Q-11 | Q-12 | Q-13 | Q-14 | Q-15 | Q-16 | Q-17 | Q-18 |
| Q-19 | Q-20 | Q-21 | Q-22 | Q-23 | Q-24 | Q-25 | Q-26 | Q-27 |
| Q-28 | Q-29 | Q-30 | Q-31 | Q-32 | Q-33 | Q-34 | Q-35 | Q-36 |
| Q-37 | Q-38 | Q-39 | Q-40 | Q-41 | Q-42 | Q-43 | Q-44 | Q-45 |
| Q-46 | Q-47 | Q-48 | Q-49 | Q-50 | Q-51 | Q-52 | Q-53 | Q-54 |
| Q-55 | Q-56 | Q-57 | Q-58 | Q-59 | Q-60 | Q-61 | Q-62 | Q-63 |
| Q-64 | Q-65 | Q-66 | Q-67 | Q-68 | Q-69 | Q-70 | Q-71 | Q-72 |
| Q-73 | Q-74 | Q-75 | Q-76 | Q-77 | Q-78 | Q-79 | Q-80 | Q-81 |
| Q-82 | Q-83 | Q-84 | Q-85 | Q-86 | Q-87 | Q-88 | Q-89 | Q-90 |
| Q-91 | Q-92 | Q-93 | Q-94 | Q-95 | Q-96 | Q-97 | Q-98 | Q-99 |
| Q-100 | Q-101 | Q-102 | Q-103 | Q-104 | Q-105 | Q-106 | Q-107 | Q-108 |
| Q-109 | Q-110 | Q-111 | Q-112 | Q-113 | Q-114 | Q-115 | Q-116 | Q-117 |

TABLE 1-continued

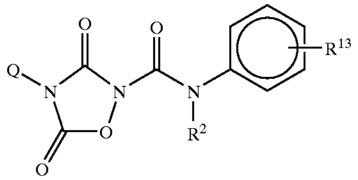

| | | | | | | | | |
|---|---|---|---|---|---|---|---|---|
| Q-118 | Q-119 | Q-120 | Q-121 | Q-122 | Q-123 | Q-124 | Q-125 | Q-126 |
| Q-127 | Q-128 | Q-129 | Q-130 | Q-131 | Q-132 | Q-133 | Q-134 | Q-135 |
| Q-136 | Q-137 | Q-138 | Q-139 | Q-140 | Q-141 | Q-142 | Q-143 | Q-144 |
| Q-145 | Q-146 | Q-147 | Q-148 | Q-149 | Q-150 | Q-151 | Q-152 | Q-153 |
| Q-154 | Q-155 | Q-156 | Q-157 | Q-158 | Q-159 | Q-160 | Q-161 | Q-162 |
| Q-163 | Q-164 | Q-165 | Q-166 | Q-167 | Q-168 | Q-169 | Q-170 | Q-171 |
| Q-172 | Q-173 | Q-174 | Q-175 | | | | | |

$R^2$ is i-$C_3H_7$, $R^{13}$ is 4-Cl

| Q | Q | Q | Q | Q | Q | Q | Q | Q |
|---|---|---|---|---|---|---|---|---|
| Q-1 | Q-2 | Q-3 | Q-4 | Q-5 | Q-6 | Q-7 | Q-8 | Q-9 |
| Q-10 | Q-11 | Q-12 | Q-13 | Q-14 | Q-15 | Q-16 | Q-17 | Q-18 |
| Q-19 | Q-20 | Q-21 | Q-22 | Q-23 | Q-24 | Q-25 | Q-26 | Q-27 |
| Q-28 | Q-29 | Q-30 | Q-31 | Q-32 | Q-33 | Q-34 | Q-35 | Q-36 |
| Q-37 | Q-38 | Q-39 | Q-40 | Q-41 | Q-42 | Q-43 | Q-44 | Q-45 |
| Q-46 | Q-47 | Q-48 | Q-49 | Q-50 | Q-51 | Q-52 | Q-53 | Q-54 |
| Q-55 | Q-56 | Q-57 | Q-58 | Q-59 | Q-60 | Q-61 | Q-62 | Q-63 |
| Q-64 | Q-65 | Q-66 | Q-67 | Q-68 | Q-69 | Q-70 | Q-71 | Q-72 |
| Q-73 | Q-74 | Q-75 | Q-76 | Q-77 | Q-78 | Q-79 | Q-80 | Q-81 |
| Q-82 | Q-83 | Q-84 | Q-85 | Q-86 | Q-87 | Q-88 | Q-89 | Q-90 |
| Q-91 | Q-92 | Q-93 | Q-94 | Q-95 | Q-96 | Q-97 | Q-98 | Q-99 |
| Q-100 | Q-101 | Q-102 | Q-103 | Q-104 | Q-105 | Q-106 | Q-107 | Q-108 |
| Q-109 | Q-110 | Q-111 | Q-112 | Q-113 | Q-114 | Q-115 | Q-116 | Q-117 |
| Q-118 | Q-119 | Q-120 | Q-121 | Q-122 | Q-123 | Q-124 | Q-125 | Q-126 |
| Q-127 | Q-128 | Q-129 | Q-130 | Q-131 | Q-132 | Q-133 | Q-134 | Q-135 |
| Q-136 | Q-137 | Q-138 | Q-139 | Q-140 | Q-141 | Q-142 | Q-143 | Q-144 |
| Q-145 | Q-146 | Q-147 | Q-148 | Q-149 | Q-150 | Q-151 | Q-152 | Q-153 |
| Q-154 | Q-155 | Q-156 | Q-157 | Q-158 | Q-159 | Q-160 | Q-161 | Q-162 |
| Q-163 | Q-164 | Q-165 | Q-166 | Q-167 | Q-168 | Q-169 | Q-170 | Q-171 |
| Q-172 | Q-173 | Q-174 | Q-175 | | | | | |

$R^2$ is i-$C_3H_7$, $R^{13}$ is H

| Q | Q | Q | Q | Q | Q | Q | Q | Q |
|---|---|---|---|---|---|---|---|---|
| Q-1 | Q-2 | Q-3 | Q-4 | Q-5 | Q-6 | Q-7 | Q-8 | Q-9 |
| Q-10 | Q-11 | Q-12 | Q-13 | Q-14 | Q-15 | Q-16 | Q-17 | Q-18 |
| Q-19 | Q-20 | Q-21 | Q-22 | Q-23 | Q-24 | Q-25 | Q-26 | Q-27 |
| Q-28 | Q-29 | Q-30 | Q-31 | Q-32 | Q-33 | Q-34 | Q-35 | Q-36 |
| Q-37 | Q-38 | Q-39 | Q-40 | Q-41 | Q-42 | Q-43 | Q-44 | Q-45 |
| Q-46 | Q-47 | Q-48 | Q-49 | Q-50 | Q-51 | Q-52 | Q-53 | Q-54 |
| Q-55 | Q-56 | Q-57 | Q-58 | Q-59 | Q-60 | Q-61 | Q-62 | Q-63 |
| Q-64 | Q-65 | Q-66 | Q-67 | Q-68 | Q-69 | Q-70 | Q-71 | Q-72 |
| Q-73 | Q-74 | Q-75 | Q-76 | Q-77 | Q-78 | Q-79 | Q-80 | Q-81 |
| Q-82 | Q-83 | Q-84 | Q-85 | Q-86 | Q-87 | Q-88 | Q-89 | Q-90 |
| Q-91 | Q-92 | Q-93 | Q-94 | Q-95 | Q-96 | Q-97 | Q-98 | Q-99 |
| Q-100 | Q-101 | Q-102 | Q-103 | Q-104 | Q-105 | Q-106 | Q-107 | Q-108 |
| Q-109 | Q-110 | Q-111 | Q-112 | Q-113 | Q-114 | Q-115 | Q-116 | Q-117 |
| Q-118 | Q-119 | Q-120 | Q-121 | Q-122 | Q-123 | Q-124 | Q-125 | Q-126 |
| Q-127 | Q-128 | Q-129 | Q-130 | Q-131 | Q-132 | Q-133 | Q-134 | Q-135 |
| Q-136 | Q-137 | Q-138 | Q-139 | Q-140 | Q-141 | Q-142 | Q-143 | Q-144 |
| Q-145 | Q-146 | Q-147 | Q-148 | Q-149 | Q-150 | Q-151 | Q-152 | Q-153 |
| Q-154 | Q-155 | Q-156 | Q-157 | Q-158 | Q-159 | Q-160 | Q-161 | Q-162 |
| Q-163 | Q-164 | Q-165 | Q-166 | Q-167 | Q-168 | Q-169 | Q-170 | Q-171 |
| Q-172 | Q-173 | Q-174 | Q-175 | | | | | |

| Q | $R^2$ | $R^{13}$ | Q | $R^2$ | $R^{13}$ | Q | $R^2$ | $R^{13}$ |
|---|---|---|---|---|---|---|---|---|
| Q-2 | $CH_3$ | 4-F | Q-2 | $CH_3$ | 2,4-di-F | Q-2 | $CH_3$ | 4-Cl |
| Q-16 | $CH_3$ | 4-F | Q-16 | $CH_3$ | 2,4-di-F | Q-16 | $CH_3$ | 4-Cl |
| Q-24 | $CH_3$ | 4-F | Q-24 | $CH_3$ | 2,4-di-F | Q-24 | $CH_3$ | 4-Cl |
| Q-29 | $CH_3$ | 4-F | Q-29 | $CH_3$ | 2,4-di-F | Q-29 | $CH_3$ | 4-Cl |
| Q-57 | $CH_3$ | 4-F | Q-57 | $CH_3$ | 2,4-di-F | Q-57 | $CH_3$ | 4-Cl |
| Q-71 | $CH_3$ | 4-F | Q-71 | $CH_3$ | 2,4-di-F | Q-71 | $CH_3$ | 4-Cl |
| Q-100 | $CH_3$ | 4-F | Q-100 | $CH_3$ | 2,4-di-F | Q-100 | $CH_3$ | 4-Cl |
| Q-119 | $CH_3$ | 4-F | Q-119 | $CH_3$ | 2,4-di-F | Q-119 | $CH_3$ | 4-Cl |
| Q-120 | $CH_3$ | 4-F | Q-120 | $CH_3$ | 2,4-di-F | Q-120 | $CH_3$ | 4-Cl |

TABLE 1-continued

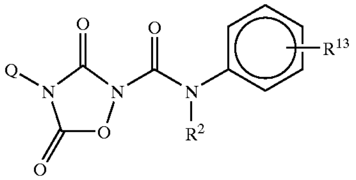

| | | | | | | | | |
|---|---|---|---|---|---|---|---|---|
| Q-126 | $CH_3$ | 4-F | Q-126 | $CH_3$ | 2,4-di-F | Q-126 | $CH_3$ | 4-Cl |
| Q-130 | $CH_3$ | 4-F | Q-130 | $CH_3$ | 2,4-di-F | Q-130 | $CH_3$ | 4-Cl |
| Q-144 | $CH_3$ | 4-F | Q-144 | $CH_3$ | 2,4-di-F | Q-144 | $CH_3$ | 4-Cl |
| Q-162 | $CH_3$ | 4-F | Q-162 | $CH_3$ | 2,4-di-F | Q-162 | $CH_3$ | 4-Cl |
| Q-169 | $CH_3$ | 4-F | Q-169 | $CH_3$ | 2,4-di-F | Q-169 | $CH_3$ | 4-Cl |
| Q-2 | $C_2H_5$ | 4-F | Q-2 | $C_2H_5$ | 2,4-di-F | Q-2 | $C_2H_5$ | 4-Cl |
| Q-16 | $C_2H_5$ | 4-F | Q-16 | $C_2H_5$ | 2,4-di-F | Q-16 | $C_2H_5$ | 4-Cl |
| Q-24 | $C_2H_5$ | 4-F | Q-24 | $C_2H_5$ | 2,4-di-F | Q-24 | $C_2H_5$ | 4-Cl |
| Q-29 | $C_2H_5$ | 4-F | Q-29 | $C_2H_5$ | 2,4-di-F | Q-29 | $C_2H_5$ | 4-Cl |
| Q-57 | $C_2H_5$ | 4-F | Q-57 | $C_2H_5$ | 2,4-di-F | Q-57 | $C_2H_5$ | 4-Cl |
| Q-71 | $C_2H_5$ | 4-F | Q-71 | $C_2H_5$ | 2,4-di-F | Q-71 | $C_2H_5$ | 4-Cl |
| Q-100 | $C_2H_5$ | 4-F | Q-100 | $C_2H_5$ | 2,4-di-F | Q-100 | $C_2H_5$ | 4-Cl |
| Q-119 | $C_2H_5$ | 4-F | Q-119 | $C_2H_5$ | 2,4-di-F | Q-119 | $C_2H_5$ | 4-Cl |
| Q-120 | $C_2H_5$ | 4-F | Q-120 | $C_2H_5$ | 2,4-di-F | Q-120 | $C_2H_5$ | 4-Cl |
| Q-126 | $C_2H_5$ | 4-F | Q-126 | $C_2H_5$ | 2,4-di-F | Q-126 | $C_2H_5$ | 4-Cl |
| Q-130 | $C_2H_5$ | 4-F | Q-130 | $C_2H_5$ | 2,4-di-F | Q-130 | $C_2H_5$ | 4-Cl |
| Q-144 | $C_2H_5$ | 4-F | Q-144 | $C_2H_5$ | 2,4-di-F | Q-144 | $C_2H_5$ | 4-Cl |
| Q-162 | $C_2H_5$ | 4-F | Q-162 | $C_2H_5$ | 2,4-di-F | Q-162 | $C_2H_5$ | 4-Cl |
| Q-169 | $C_2H_5$ | 4-F | Q-169 | $C_2H_5$ | 2,4-di-F | Q-169 | $C_2H_5$ | 4-Cl |
| Q-2 | i-$C_4H_9$ | 4-F | Q-2 | i-$C_4H_9$ | 2,4-di-F | Q-2 | i-$C_4H_9$ | 4-Cl |
| Q-16 | i-$C_4H_9$ | 4-F | Q-16 | i-$C_4H_9$ | 2,4-di-F | Q-16 | i-$C_4H_9$ | 4-Cl |
| Q-24 | i-$C_4H_9$ | 4-F | Q-24 | i-$C_4H_9$ | 2,4-di-F | Q-24 | i-$C_4H_9$ | 4-Cl |
| Q-29 | i-$C_4H_9$ | 4-F | Q-29 | i-$C_4H_9$ | 2,4-di-F | Q-29 | i-$C_4H_9$ | 4-Cl |
| Q-57 | i-$C_4H_9$ | 4-F | Q-57 | i-$C_4H_9$ | 2,4-di-F | Q-57 | i-$C_4H_9$ | 4-Cl |
| Q-71 | i-$C_4H_9$ | 4-F | Q-71 | i-$C_4H_9$ | 2,4-di-F | Q-71 | i-$C_4H_9$ | 4-Cl |
| Q-100 | i-$C_4H_9$ | 4-F | Q-100 | i-$C_4H_9$ | 2,4-di-F | Q-100 | i-$C_4H_9$ | 4-Cl |
| Q-119 | i-$C_4H_9$ | 4-F | Q-119 | i-$C_4H_9$ | 2,4-di-F | Q-119 | i-$C_4H_9$ | 4-Cl |
| Q-120 | i-$C_4H_9$ | 4-F | Q-120 | i-$C_4H_9$ | 2,4-di-F | Q-120 | i-$C_4H_9$ | 4-Cl |
| Q-126 | i-$C_4H_9$ | 4-F | Q-126 | i-$C_4H_9$ | 2,4-di-F | Q-126 | i-$C_4H_9$ | 4-Cl |
| Q-130 | i-$C_4H_9$ | 4-F | Q-130 | i-$C_4H_9$ | 2,4-di-F | Q-130 | i-$C_4H_9$ | 4-Cl |
| Q-144 | i-$C_4H_9$ | 4-F | Q-144 | i-$C_4H_9$ | 2,4-di-F | Q-144 | i-$C_4H_9$ | 4-Cl |
| Q-162 | i-$C_4H_9$ | 4-F | Q-162 | i-$C_4H_9$ | 2,4-di-F | Q-162 | i-$C_4H_9$ | 4-Cl |
| Q-169 | i-$C_4H_9$ | 4-F | Q-169 | i-$C_4H_9$ | 2,4-di-F | Q-169 | i-$C_4H_9$ | 4-Cl |
| Q-2 | n-$C_3H_7$ | 4-F | Q-2 | n-$C_3H_7$ | 2,4-di-F | Q-2 | n-$C_3H_7$ | 4-Cl |
| Q-16 | n-$C_3H_7$ | 4-F | Q-16 | n-$C_3H_7$ | 2,4-di-F | Q-16 | n-$C_3H_7$ | 4-Cl |
| Q-24 | n-$C_3H_7$ | 4-F | Q-24 | n-$C_3H_7$ | 2,4-di-F | Q-24 | n$C_3H_7$ | 4-Cl |
| Q-29 | n-$C_3H_7$ | 4-F | Q-29 | n-$C_3H_7$ | 2,4-di-F | Q-29 | n-$C_3H_7$ | 4-Cl |
| Q-57 | n-$C_3H_7$ | 4-F | Q-57 | n-$C_3H_7$ | 2,4-di-F | Q-57 | n-$C_3H_7$ | 4-Cl |
| Q-71 | n-$C_3H_7$ | 4-F | Q-71 | n-$C_3H_7$ | 2,4-di-F | Q-71 | n-$C_3H_7$ | 4-Cl |
| Q-100 | n-$C_3H_7$ | 4-F | Q-100 | n-$C_3H_7$ | 2,4-di-F | Q-100 | n-$C_3H_7$ | 4-Cl |
| Q-119 | n-$C_3H_7$ | 4-F | Q-119 | n-$C_3H_7$ | 4-F | Q-119 | n-$C_3H_7$ | 4-F |
| Q-120 | n-$C_3H_7$ | 4-F | Q-120 | n-$C_3H_7$ | 4-F | Q-120 | n-$C_3H_7$ | 4-F |
| Q-126 | n-$C_3H_7$ | 4-F | Q-126 | n-$C_3H_7$ | 4-F | Q-126 | n-$C_3H_7$ | 4-F |
| Q-130 | n-$C_3H_7$ | 4-F | Q-130 | n-$C_3H_7$ | 4-F | Q-130 | n-$C_3H_7$ | 4-F |
| Q-144 | n-$C_3H_7$ | 4-F | Q-144 | n-$C_3H_7$ | 4-F | Q-144 | n-$C_3H_7$ | 4-F |
| Q-162 | n-$C_3H_7$ | 4-F | Q-162 | n-$C_3H_7$ | 4-F | Q-162 | n-$C_3H_7$ | 4-F |
| Q-169 | n-$C_3H_7$ | 4-F | Q-169 | n-$C_3H_7$ | 4-F | Q-169 | n-$C_3H_7$ | 4-F |
| Q-2 | Cyclopropyl | 4-F | Q-2 | Cyclopropyl | 2,4-di-F | Q-2 | Cyclopropyl | 4-Cl |
| Q-16 | Cyclopropyl | 4-F | Q-16 | Cyclopropyl | 2,4-di-F | Q-16 | Cyclopropyl | 4-Cl |
| Q-24 | Cyclopropyl | 4-F | Q-24 | Cyclopropyl | 2,4-di-F | Q-24 | Cyclopropyl | 4-Cl |
| Q-29 | Cyclopropyl | 4-F | Q-29 | Cyclopropyl | 2,4-di-F | Q-29 | Cyclopropyl | 4-Cl |
| Q-57 | Cyclopropyl | 4-F | Q-57 | Cyclopropyl | 2,4-di-F | Q-57 | Cyclopropyl | 4-Cl |
| Q-71 | Cyclopropyl | 4-F | Q-71 | Cyclopropyl | 2,4-di-F | Q-71 | Cyclopropyl | 4-Cl |
| Q-100 | Cyclopropyl | 4-F | Q-100 | Cyclopropyl | 2,4-di-F | Q-100 | Cyclopropyl | 4-Cl |
| Q-119 | Cyclopropyl | 4-F | Q-119 | Cyclopropyl | 2,4-di-F | Q-119 | Cyclopropyl | 4-Cl |
| Q-120 | Cyclopropyl | 4-F | Q-120 | Cyclopropyl | 2,4-di-F | Q-120 | Cyclopropyl | 4-Cl |
| Q-126 | Cyclopropyl | 4-F | Q-126 | Cyclopropyl | 2,4-di-F | Q-126 | Cyclopropyl | 4-Cl |
| Q-130 | Cyclopropyl | 4-F | Q-130 | Cyclopropyl | 2,4-di-F | Q-130 | Cyclopropyl | 4-Cl |
| Q-144 | Cyclopropyl | 4-F | Q-144 | Cyclopropyl | 2,4-di-F | Q-144 | Cyclopropyl | 4-Cl |
| Q-162 | Cyclopropyl | 4-F | Q-162 | Cyclopropyl | 2,4-di-F | Q-162 | Cyclopropyl | 4-Cl |
| Q-169 | Cyclopropyl | 4-F | Q-169 | Cyclopropyl | 2,4-di-F | Q-169 | Cyclopropyl | 4-Cl |

| Q | $R^2$ | $R^{13}$ | Q | $R^2$ | $R^{13}$ | Q | $R^2$ | $R^{13}$ |
|---|---|---|---|---|---|---|---|---|
| Q-2 | i-$C_3H_7$ | 4-$OCF_3$ | Q-2 | i-$C_3H_7$ | 4-$COOCH_3$ | Q-2 | i-$C_3H_7$ | 3,5-di-F |
| Q-16 | i-$C_3H_7$ | 4-$OCF_3$ | Q-16 | i-$C_3H_7$ | 4-$COOCH_3$ | Q-16 | i-$C_3H_7$ | 3,5-di-F |
| Q-24 | i-$C_3H_7$ | 4-$OCF_3$ | Q-24 | i-$C_3H_7$ | 4-$COOCH_3$ | Q-24 | i-$C_3H_7$ | 3,5-di-F |
| Q-29 | i-$C_3H_7$ | 4-$OCF_3$ | Q-29 | i-$C_3H_7$ | 4-$COOCH_3$ | Q-29 | i-$C_3H_7$ | 3,5-di-F |
| Q-57 | i-$C_3H_7$ | 4-$OCF_3$ | Q-57 | i-$C_3H_7$ | 4-$COOCH_3$ | Q-57 | i-$C_3H_7$ | 3,5-di-F |

TABLE 1-continued

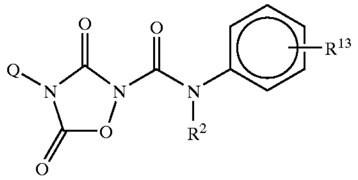

| | | | | | | | | | | | |
|---|---|---|---|---|---|---|---|---|---|---|---|
| Q-71 | i-$C_3H_7$ | 4-$OCF_3$ | Q-71 | i-$C_3H_7$ | 4-$COOCH_3$ | Q-71 | i-$C_3H_7$ | 3,5-di-F |
| Q-100 | i-$C_3H_7$ | 4-$OCF_3$ | Q-100 | i-$C_3H_7$ | 4-$COOCH_3$ | Q-100 | i-$C_3H_7$ | 3,5-di-F |
| Q-119 | i-$C_3H_7$ | 4-$OCF_3$ | Q-119 | i-$C_3H_7$ | 4-$COOCH_3$ | Q-119 | i-$C_3H_7$ | 3,5-di-F |
| Q-120 | i-$C_3H_7$ | 4-$OCF_3$ | Q-120 | i-$C_3H_7$ | 4-$COOCH_3$ | Q-120 | i-$C_3H_7$ | 3,5-di-F |
| Q-126 | i-$C_3H_7$ | 4-$OCF_3$ | Q-126 | i-$C_3H_7$ | 4-$COOCH_3$ | Q-126 | i-$C_3H_7$ | 3,5-di-F |
| Q-130 | i-$C_3H_7$ | 4-$OCF_3$ | Q-130 | i-$C_3H_7$ | 4-$COOCH_3$ | Q-130 | i-$C_3H_7$ | 3,5-di-F |
| Q-144 | i-$C_3H_7$ | 4-$OCF_3$ | Q-144 | i-$C_3H_7$ | 4-$COOCH_3$ | Q-144 | i-$C_3H_7$ | 3,5-di-F |
| Q-162 | i-$C_3H_7$ | 4-$OCF_3$ | Q-162 | i-$C_3H_7$ | 4-$COOCH_3$ | Q-162 | i-$C_3H_7$ | 3,5-di-F |
| Q-169 | i-$C_3H_7$ | 4-$OCF_3$ | Q-169 | i-$C_3H_7$ | 4-$COOCH_3$ | Q-169 | i-$C_3H_7$ | 3,5-di-F |
| Q-2 | i-$C_3H_7$ | 4-$CF_3$ | Q-2 | i-$C_3H_7$ | 4-$CH_3$ | Q-2 | i-$C_3H_7$ | 2,4,6-tri-F |
| Q-16 | i-$C_3H_7$ | 4-$CF_3$ | Q-16 | i-$C_3H_7$ | 4-$CH_3$ | Q-16 | i-$C_3H_7$ | 2,4,6-tri-F |
| Q-24 | i-$C_3H_7$ | 4-$CF_3$ | Q-24 | i-$C_3H_7$ | 4-$CH_3$ | Q-24 | i-$C_3H_7$ | 2,4,6-tri-F |
| Q-29 | i-$C_3H_7$ | 4-$CF_3$ | Q-29 | i-$C_3H_7$ | 4-$CH_3$ | Q-29 | i-$C_3H_7$ | 2,4,6-tri-F |
| Q-57 | i-$C_3H_7$ | 4-$CF_3$ | Q-57 | i-$C_3H_7$ | 4-$CH_3$ | Q-57 | i-$C_3H_7$ | 2,4,6-tri-F |
| Q-71 | i-$C_3H_7$ | 4-$CF_3$ | Q-71 | i-$C_3H_7$ | 4-$CH_3$ | Q-71 | i-$C_3H_7$ | 2,4,6-tri-F |
| Q-100 | i-$C_3H_7$ | 4-$CF_3$ | Q-100 | i-$C_3H_7$ | 4-$CH_3$ | Q-100 | i-$C_3H_7$ | 2,4,6-tri-F |
| Q-119 | i-$C_3H_7$ | 4-$CF_3$ | Q-119 | i-$C_3H_7$ | 4-$CH_3$ | Q-119 | i-$C_3H_7$ | 2,4,6-tri-F |
| Q-120 | i-$C_3H_7$ | 4-$CF_3$ | Q-120 | i-$C_3H_7$ | 4-$CH_3$ | Q-120 | i-$C_3H_7$ | 2,4,6-tri-F |
| Q-126 | i-$C_3H_7$ | 4-$CF_3$ | Q-126 | i-$C_3H_7$ | 4-$CH_3$ | Q-126 | i-$C_3H_7$ | 2,4,6-tri-F |
| Q-130 | i-$C_3H_7$ | 4-$CF_3$ | Q-130 | i-$C_3H_7$ | 4-$CH_3$ | Q-130 | i-$C_3H_7$ | 2,4,6-tri-F |
| Q-144 | i-$C_3H_7$ | 4-$CF_3$ | Q-144 | i-$C_3H_7$ | 4-$CH_3$ | Q-144 | i-$C_3H_7$ | 2,4,6-tri-F |
| Q-162 | i-$C_3H_7$ | 4-$CF_3$ | Q-162 | i-$C_3H_7$ | 4-$CH_3$ | Q-162 | i-$C_3H_7$ | 2,4,6-tri-F |
| Q-169 | i-$C_3H_7$ | 4-$CF_3$ | Q-169 | i-$C_3H_7$ | 4-$CH_3$ | Q-169 | i-$C_3H_7$ | 2,4,6-tri-F |
| Q-2 | i-$C_3H_7$ | 4-$OCH_3$ | Q-2 | i-$C_3H_7$ | 2,4-di-Cl | Q-2 | i-$C_3H_7$ | 2,5-di-F |
| Q-16 | i-$C_3H_7$ | 4-$OCH_3$ | Q-16 | i-$C_3H_7$ | 2,4-di-Cl | Q-16 | i-$C_3H_7$ | 2,5-di-F |
| Q-24 | i-$C_3H_7$ | 4-$OCH_3$ | Q-24 | i-$C_3H_7$ | 2,4-di-Cl | Q-24 | i-$C_3H_7$ | 2,5-di-F |
| Q-29 | i-$C_3H_7$ | 4-$OCH_3$ | Q-29 | i-$C_4H_9$ | 2,4-di-Cl | Q-29 | i-$C_3H_7$ | 2,5-di-F |
| Q-57 | i-$C_3H_7$ | 4-$OCH_3$ | Q-57 | i-$C_3H_7$ | 2,4-di-Cl | Q-57 | i-$C_3H_7$ | 2,5-di-F |
| Q-71 | i-$C_3H_7$ | 4-$OCH_3$ | Q-71 | i-$C_3H_7$ | 2,4-di-Cl | Q-71 | i-$C_3H_7$ | 2,5-di-F |
| Q-100 | i-$C_3H_7$ | 4-$OCH_3$ | Q-100 | i-$C_3H_7$ | 2,4-di-Cl | Q-100 | i-$C_3H_7$ | 2,5-di-F |
| Q-119 | i-$C_3H_7$ | 4-$OCH_3$ | Q-119 | i-$C_3H_7$ | 2,4-di-Cl | Q-119 | i-$C_3H_7$ | 2,5-di-F |
| Q-120 | i-$C_3H_7$ | 4-$OCH_3$ | Q-120 | i-$C_3H_7$ | 2,4-di-Cl | Q-120 | i-$C_3H_7$ | 2,5-di-F |
| Q-126 | i-$C_3H_7$ | 4-$OCH_3$ | Q-126 | i-$C_3H_7$ | 2,4-di-Cl | Q-126 | i-$C_3H_7$ | 2,5-di-F |
| Q-130 | i-$C_3H_7$ | 4-$OCH_3$ | Q-130 | i-$C_4H_9$ | 2,4-di-Cl | Q-130 | i-$C_3H_7$ | 2,5-di-F |
| Q-144 | i-$C_3H_7$ | 4-$OCH_3$ | Q-144 | i-$C_3H_7$ | 2,4-di-Cl | Q-144 | i-$C_3H_7$ | 2,5-di-F |
| Q-162 | i-$C_3H_7$ | 4-$OCH_3$ | Q-162 | i-$C_3H_7$ | 2,4-di-Cl | Q-162 | i-$C_3H_7$ | 2,5-di-F |
| Q-169 | i-$C_3H_7$ | 4-$OCH_3$ | Q-169 | i-$C_3H_7$ | 2,4-di-Cl | Q-169 | i-$C_3H_7$ | 2,5-di-F |
| Q-2 | i-$C_3H_7$ | 4-CN | Q-2 | i-$C_3H_7$ | 2-F, 4-Cl | Q-2 | i-$C_3H_7$ | 4-$OCF_2H$ |
| Q-16 | i-$C_3H_7$ | 4-CN | Q-16 | i-$C_3H_7$ | 2-F, 4-Cl | Q-16 | i-$C_3H_7$ | 4-$OCF_2H$ |
| Q-24 | i-$C_3H_7$ | 4-CN | Q-24 | i-$C_3H_7$ | 2-F, 4-Cl | Q-24 | i-$C_3H_7$ | 4-$OCF_2H$ |
| Q-29 | i-$C_3H_7$ | 4-CN | Q-29 | i-$C_3H_7$ | 2-F, 4-Cl | Q-29 | i-$C_3H_7$ | 4-$OCF_2H$ |
| Q-57 | i-$C_3H_7$ | 4-CN | Q-57 | i-$C_3H_7$ | 2-F, 4-Cl | Q-57 | i-$C_3H_7$ | 4-$OCF_2H$ |
| Q-71 | i-$C_3H_7$ | 4-CN | Q-71 | i-$C_3H_7$ | 2-F, 4-Cl | Q-71 | i-$C_3H_7$ | 4-$OCF_2H$ |
| Q-100 | i-$C_3H_7$ | 4-CN | Q-100 | i-$C_3H_7$ | 2-F, 4-Cl | Q-100 | i-$C_3H_7$ | 4-$OCF_2H$ |
| Q-119 | i-$C_3H_7$ | 4-CN | Q-119 | i-$C_3H_7$ | 2-F, 4-Cl | Q-119 | i-$C_3H_7$ | 4-$OCF_2H$ |
| Q-120 | i-$C_3H_7$ | 4-CN | Q-120 | i-$C_3H_7$ | 2-F, 4-Cl | Q-120 | i-$C_3H_7$ | 4-$OCF_2H$ |
| Q-126 | i-$C_3H_7$ | 4-CN | Q-126 | i-$C_3H_7$ | 2-F, 4-Cl | Q-126 | i-$C_3H_7$ | 4-$OCF_2H$ |
| Q-130 | i-$C_3H_7$ | 4-CN | Q-130 | i-$C_3H_7$ | 2-F, 4-Cl | Q-130 | i-$C_3H_7$ | 4-$OCF_2H$ |
| Q-144 | i-$C_3H_7$ | 4-CN | Q-144 | i-$C_3H_7$ | 2-F,4-Cl | Q-144 | i-$C_3H_7$ | 4-$OCF_2H$ |
| Q-162 | i-$C_3H_7$ | 4-CN | Q-162 | i-$C_3H_7$ | 2-F, 4-Cl | Q-162 | i-$C_3H_7$ | 4-$OCF_2H$ |
| Q-169 | i-$C_3H_7$ | 4-CN | Q-169 | i-$C_3H_7$ | 2-F, 4-Cl | Q-169 | i-$C_3H_7$ | 4-$OCF_2H$ |
| Q-2 | i-$C_3H_7$ | 4-$NO_2$ | Q-2 | i-$C_3H_7$ | 3,4-di-F | Q-2 | i-$C_3H_7$ | 4-$SCH_3$ |
| Q-16 | i-$C_3H_7$ | 4-$NO_2$ | Q-16 | i-$C_3H_7$ | 3,4-di-F | Q-16 | i-$C_3H_7$ | 4-$SCH_3$ |
| Q-24 | i-$C_3H_7$ | 4-$NO_2$ | Q-24 | i-$C_3H_7$ | 3,4-di-F | Q-24 | i-$C_3H_7$ | 4-$SCH_3$ |
| Q-29 | i-$C_3H_7$ | 4-$NO_2$ | Q-29 | i-$C_3H_7$ | 3,4-di-F | Q-29 | i-$C_3H_7$ | 4-$SCH_3$ |
| Q-57 | i-$C_3H_7$ | 4-$NO_2$ | Q-57 | i-$C_3H_7$ | 3,4-di-F | Q-57 | i-$C_3H_7$ | 4-$SCH_3$ |
| Q-71 | i-$C_3H_7$ | 4-$NO_2$ | Q-71 | i-$C_3H_7$ | 3,4-di-F | Q-71 | i-$C_3H_7$ | 4-$SCH_3$ |
| Q-100 | i-$C_3H_7$ | 4-$NO_2$ | Q-100 | i-$C_3H_7$ | 3,4-di-F | Q-100 | i-$C_3H_7$ | 4-$SCH_3$ |
| Q-119 | i-$C_3H_7$ | 4-$NO_2$ | Q-119 | i-$C_3H_7$ | 3,4-di-F | Q-119 | i-$C_3H_7$ | 4-$SCH_3$ |
| Q-120 | i-$C_3H_7$ | 4-$NO_2$ | Q-120 | i-$C_3H_7$ | 3,4-di-F | Q-120 | i-$C_3H_7$ | 4-$SCH_3$ |
| Q-126 | i-$C_3H_7$ | 4-$NO_2$ | Q-126 | i-$C_3H_7$ | 3,4-di-F | Q-126 | i-$C_3H_7$ | 4-$SCH_3$ |
| Q-130 | i-$C_3H_7$ | 4-$NO_2$ | Q-130 | i-$C_3H_7$ | 3,4-di-F | Q-130 | i-$C_3H_7$ | 4-$SCH_3$ |
| Q-144 | i-$C_3H_7$ | 4-$NO_2$ | Q-144 | i-$C_3H_7$ | 3,4-di-F | Q-144 | 1-$C_3H_7$ | 4-$SCH_3$ |
| Q-162 | i-$C_3H_7$ | 4-$NO_2$ | Q-162 | i-$C_3H_7$ | 3,4-di-F | Q-162 | i-$C_3H_7$ | 4-$SCH_3$ |
| Q-169 | i-$C_3H_7$ | 4-$NO_2$ | Q-169 | i-$C_3H_7$ | 3,4-di-F | Q-169 | i-$C_3H_7$ | 4-$SCH_3$ |

TABLE 1-continued

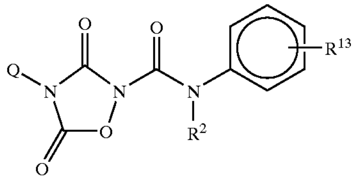

| Q | $R^2$ | $R^{13}$ | Q | $R^2$ | $R^{13}$ | Q | $R^2$ | $R^{13}$ |
|---|---|---|---|---|---|---|---|---|
| Q-2 | Allyl | 4-F | Q-2 | Allyl | 2,4-di-F | Q-2 | Allyl | 4-Cl |
| Q-16 | Allyl | 4-F | Q-16 | Allyl | 2,4-di-F | Q-16 | Allyl | 4-Cl |
| Q-24 | Allyl | 4-F | Q-24 | Allyl | 2,4-di-F | Q-24 | Allyl | 4-Cl |
| Q-29 | Allyl | 4-F | Q-29 | Allyl | 2,4-di-F | Q-29 | Allyl | 4-Cl |
| Q-57 | Allyl | 4-F | Q-57 | Allyl | 2,4-di-F | Q-57 | Allyl | 4-Cl |
| Q-71 | Allyl | 4-F | Q-71 | Allyl | 2,4-di-F | Q-71 | Allyl | 4-Cl |
| Q-100 | Allyl | 4-F | Q-100 | Allyl | 2,4-di-F | Q-100 | Allyl | 4-Cl |
| Q-119 | Allyl | 4-F | Q-119 | Allyl | 2,4-di-F | Q-119 | Allyl | 4-Cl |
| Q-120 | Allyl | 4-F | Q-120 | Allyl | 2,4-di-F | Q-120 | Allyl | 4-Cl |
| Q-126 | Allyl | 4-F | Q-126 | Allyl | 2,4-di-F | Q-126 | Allyl | 4-Cl |
| Q-130 | Allyl | 4-F | Q-130 | Allyl | 2,4-di-F | Q-130 | Allyl | 4-Cl |
| Q-144 | Allyl | 4-F | Q-144 | Allyl | 2,4-di-F | Q-144 | Allyl | 4-Cl |
| Q-162 | Allyl | 4-F | Q-162 | Allyl | 2,4-di-F | Q-162 | Allyl | 4-Cl |
| Q-169 | Allyl | 4-F | Q-169 | Allyl | 2,4-di-F | Q-169 | Allyl | 4-Cl |
| Q-2 | $OCH_3$ | 4-F | Q-2 | $OCH_3$ | 2,4-di-F | Q-2 | $OCH_3$ | 4-Cl |
| Q-16 | $OCH_3$ | 4-F | Q-16 | $OCH_3$ | 2,4-di-F | Q-16 | $OCH_3$ | 4-Cl |
| Q-24 | $OCH_3$ | 4-F | Q-24 | $OCH_3$ | 2,4-di-F | Q-24 | $OCH_3$ | 4-Cl |
| Q-29 | $OCH_3$ | 4-F | Q-29 | $OCH_3$ | 2,4-di-F | Q-29 | $OCH_3$ | 4-Cl |
| Q-57 | $OCH_3$ | 4-F | Q-57 | $OCH_3$ | 2,4-di-F | Q-57 | $OCH_3$ | 4-Cl |
| Q-71 | $OCH_3$ | 4-F | Q-71 | $OCH_3$ | 2,4-di-F | Q-71 | $OCH_3$ | 4-Cl |
| Q-100 | $OCH_3$ | 4-F | Q-100 | $OCH_3$ | 2,4-di-F | Q-100 | $OCH_3$ | 4-Cl |
| Q-119 | $OCH_3$ | 4-F | Q-119 | $OCH_3$ | 2,4-di-F | Q-119 | $OCH_3$ | 4-Cl |
| Q-120 | $OCH_3$ | 4-F | Q-120 | $OCH_3$ | 2,4-di-F | Q-120 | $OCH_3$ | 4-Cl |
| Q-126 | $OCH_3$ | 4-F | Q-126 | $OCH_3$ | 2,4-di-F | Q-126 | $OCH_3$ | 4-Cl |
| Q-130 | $OCH_3$ | 4-F | Q-130 | $OCH_3$ | 2,4-di-F | Q-130 | $OCH_3$ | 4-Cl |
| Q-144 | $OCH_3$ | 4-F | Q-144 | $OCH_3$ | 2,4-di-F | Q-144 | $OCH_3$ | 4-Cl |
| Q-162 | $OCH_3$ | 4-F | Q-162 | $OCH_3$ | 2,4-di-F | Q-162 | $OCH_3$ | 4-Cl |
| Q-169 | $OCH_3$ | 4-F | Q-169 | $OCH_3$ | 2,4-di-F | Q-169 | $OCH_3$ | 4-Cl |
| Q-2 | $N(CH_3)_2$ | 4-F | Q-2 | $N(CH_3)_2$ | 2,4-di-F | Q-2 | $N(CH_3)_2$ | 4-Cl |
| Q-16 | $N(CH_3)_2$ | 4-F | Q-16 | $N(CH_3)_2$ | 2,4-di-F | Q-16 | $N(CH_3)_2$ | 4-Cl |
| Q-24 | $N(CH_3)_2$ | 4-F | Q-24 | $N(CH_3)_2$ | 2,4-di-F | Q-24 | $N(CH_3)_2$ | 4-Cl |
| Q-29 | $N(CH_3)_2$ | 4-F | Q-29 | $N(CH_3)_2$ | 2,4-di-F | Q-29 | $N(CH_3)_2$ | 4-Cl |
| Q-57 | $N(CH_3)_2$ | 4-F | Q-57 | $N(CH_3)_2$ | 2,4-di-F | Q-57 | $N(CH_3)_2$ | 4-Cl |
| Q-71 | $N(CH_3)_2$ | 4-F | Q-71 | $N(CH_3)_2$ | 2,4-di-F | Q-71 | $N(CH_3)_2$ | 4-Cl |
| Q-100 | $N(CH_3)_2$ | 4-F | Q-100 | $N(CH_3)_2$ | 2,4-di-F | Q-100 | $N(CH_3)_2$ | 4-Cl |
| Q-119 | $N(CH_3)_2$ | 4-F | Q-119 | $N(CH_3)_2$ | 2,4-di-F | Q-119 | $N(CH_3)_2$ | 4-Cl |
| Q-120 | $N(CH_3)_2$ | 4-F | Q-120 | $N(CH_3)_2$ | 2,4-di-F | Q-120 | $N(CH_3)_2$ | 4-Cl |
| Q-126 | $N(CH_3)_2$ | 4-F | Q-126 | $N(CH_3)_2$ | 2,4-di-F | Q-126 | $N(CH_3)_2$ | 4-Cl |
| Q-130 | $N(CH_3)_2$ | 4-F | Q-130 | $N(CH_3)_2$ | 2,4-di-F | Q-130 | $N(CH_3)_2$ | 4-Cl |
| Q-144 | $N(CH_3)_2$ | 4-F | Q-144 | $N(CH_3)_2$ | 2,4-di-F | Q-144 | $N(CH_3)_2$ | 4-Cl |
| Q-162 | $N(CH_3)_2$ | 4-F | Q-162 | $N(CH_3)_2$ | 2,4-di-F | Q-162 | $N(CH_3)_2$ | 4-Cl |
| Q-169 | $N(CH_3)_2$ | 4-F | Q-169 | $N(CH_3)_2$ | 2,4-di-F | Q-169 | $N(CH_3)_2$ | 4-Cl |
| Q-2 | $CH_2OCH_3$ | 4-F | Q-2 | $CH_2OCH_3$ | 2,4-di-F | Q-2 | $CH_2OCH_3$ | 4-Cl |
| Q-16 | $CH_2OCH_3$ | 4-F | Q-16 | $CH_2OCH_3$ | 2,4-di-F | Q-16 | $CH_2OCH_3$ | 4-Cl |
| Q-24 | $CH_2OCH_3$ | 4-F | Q-24 | $CH_2OCH_3$ | 2,4-di-F | Q-24 | $CH_2OCH_3$ | 4-Cl |
| Q-29 | $CH_2OCH_3$ | 4-F | Q-29 | $CH_2OCH_3$ | 2,4-di-F | Q-29 | $CH_2OCH_3$ | 4-Cl |
| Q-57 | $CH_2OCH_3$ | 4-F | Q-57 | $CH_2OCH_3$ | 2,4-di-F | Q-57 | $CH_2OCH_3$ | 4-Cl |
| Q-71 | $CH_2OCH_3$ | 4-F | Q-71 | $CH_2OCH_3$ | 2,4-di-F | Q-71 | $CH_2OCH_3$ | 4-Cl |
| Q-100 | $CH_2OCH_3$ | 4-F | Q-100 | $CH_2OCH_3$ | 2,4-di-F | Q-100 | $CH_2OCH_3$ | 4-Cl |
| Q-119 | $CH_2OCH_3$ | 4-F | Q-119 | $CH_2OCH_3$ | 2,4-di-F | Q-119 | $CH_2OCH_3$ | 4-Cl |
| Q-120 | $CH_2OCH_3$ | 4-F | Q-120 | $CH_2OCH_3$ | 2,4-di-F | Q-120 | $CH_2OCH_3$ | 4-Cl |
| Q-126 | $CH_2OCH_3$ | 4-F | Q-126 | $CH_2OCH_3$ | 2,4-di-F | Q-126 | $CH_2OCH_3$ | 4-Cl |
| Q-130 | $CH_2OCH_3$ | 4-F | Q-130 | $CH_2OCH_3$ | 2,4-di-F | Q-130 | $CH_2OCH_3$ | 4-Cl |
| Q-144 | $CH_2OCH_3$ | 4-F | Q-144 | $CH_2OCH_3$ | 2,4-di-F | Q-144 | $CH_2OCH_3$ | 4-Cl |
| Q-162 | $CH_2OCH_3$ | 4-F | Q-162 | $CH_2OCH_3$ | 2,4-di-F | Q-162 | $CH_2OCH_3$ | 4-Cl |
| Q-169 | $CH_2OCH_3$ | 4-F | Q-169 | $CH_2OCH_3$ | 2,4-di-F | Q-169 | $CH_2OCH_3$ | 4-Cl |
| Q-2 | $CH_2CF_3$ | 4-F | Q-2 | $CH_2CF_3$ | 2,4-di-F | Q-2 | $CH_2CF_3$ | 4-Cl |
| Q-16 | $CH_2CF_3$ | 4-F | Q-16 | $CH_2CF_3$ | 2,4-di-F | Q-16 | $CH_2CF_3$ | 4-Cl |
| Q-24 | $CH_2CF_3$ | 4-F | Q-24 | $CH_2CF_3$ | 2,4-di-F | Q-24 | $CH_2CF_3$ | 4-Cl |
| Q-29 | $CH_2CF_3$ | 4-F | Q-29 | $CH_2CF_3$ | 2,4-di-F | Q-29 | $CH_2CF_3$ | 4-Cl |
| Q-57 | $CH_2CF_3$ | 4-F | Q-57 | $CH_2CF_3$ | 2,4-di-F | Q-57 | $CH_2CF_3$ | 4-Cl |
| Q-71 | $CH_2CF_3$ | 4-F | Q-71 | $CH_2CF_3$ | 2,4-di-F | Q-71 | $CH_2CF_3$ | 4-Cl |
| Q-100 | $CH_2CF_3$ | 4-F | Q-100 | $CH_2CF_3$ | 2,4-di-F | Q-100 | $CH_2CF_3$ | 4-Cl |
| Q-119 | $CH_2CF_3$ | 4-F | Q-119 | $CH_2CF_3$ | 2,4-di-F | Q-119 | $CH_2CF_3$ | 4-Cl |
| Q-120 | $CH_2CF_3$ | 4-F | Q-120 | $CH_2CF_3$ | 2,4-di-F | Q-120 | $CH_2CF_3$ | 4-Cl |
| Q-126 | $CH_2CF_3$ | 4-F | Q-126 | $CH_2CF_3$ | 2,4-di-F | Q-126 | $CH_2CF_3$ | 4-Cl |
| Q-130 | $CH_2CF_3$ | 4-F | Q-130 | $CH_2CF_3$ | 2,4-di-F | Q-130 | $CH_2CF_3$ | 4-Cl |

TABLE 1-continued

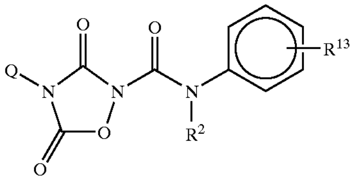

| | | | | | | | | |
|---|---|---|---|---|---|---|---|---|
| Q-144 | $CH_2CF_3$ | 4-F | Q-144 | $CH_2CF_3$ | 2,4-di-F | Q-144 | $CH_2CF_3$ | 4-Cl |
| Q-162 | $CH_2CF_3$ | 4-F | Q-162 | $CH_2CF_3$ | 2,4-di-F | Q-162 | $CH_2CF_3$ | 4-Cl |
| Q-169 | $CH_2CF_3$ | 4-F | Q-169 | $CH_2CF_3$ | 2,4-di-F | Q-169 | $CH_2CF_3$ | 4-Cl |

TABLE 2

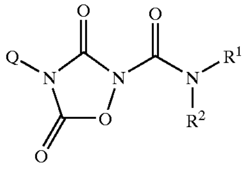

$R^1$ is $C_2H_5$, $R^2$ is B-1

| Q | Q | Q | Q | Q | Q | Q | Q | Q |
|---|---|---|---|---|---|---|---|---|
| Q-1 | Q-2 | Q-3 | Q-4 | Q-5 | Q-6 | Q-7 | Q-8 | Q-9 |
| Q-10 | Q-11 | Q-12 | Q-13 | Q-14 | Q-15 | Q-16 | Q-17 | Q-18 |
| Q-19 | Q-20 | Q-21 | Q-22 | Q-23 | Q-24 | Q-25 | Q-26 | Q-27 |
| Q-28 | Q-29 | Q-30 | Q-31 | Q-32 | Q-33 | Q-34 | Q-35 | Q-36 |
| Q-37 | Q-38 | Q-39 | Q-40 | Q-41 | Q-42 | Q-43 | Q-44 | Q-45 |
| Q-46 | Q-47 | Q-48 | Q-49 | Q-50 | Q-51 | Q-52 | Q-53 | Q-54 |
| Q-55 | Q-56 | Q-57 | Q-58 | Q-59 | Q-60 | Q-61 | Q-62 | Q-63 |
| Q-64 | Q-65 | Q-66 | Q-67 | Q-68 | Q-69 | Q-70 | Q-71 | Q-72 |
| Q-73 | Q-74 | Q-75 | Q-76 | Q-77 | Q-78 | Q-79 | Q-80 | Q-81 |
| Q-82 | Q-83 | Q-84 | Q-85 | Q-86 | Q-87 | Q-88 | Q-89 | Q-90 |
| Q-91 | Q-92 | Q-93 | Q-94 | Q-95 | Q-96 | Q-97 | Q-98 | Q-99 |
| Q-100 | Q-101 | Q-102 | Q-103 | Q-104 | Q-105 | Q-106 | Q-107 | Q-108 |
| Q-109 | Q-110 | Q-111 | Q-112 | Q-113 | Q-114 | Q-115 | Q-116 | Q-117 |
| Q-118 | Q-119 | Q-120 | Q-121 | Q-122 | Q-123 | Q-124 | Q-125 | Q-126 |
| Q-127 | Q-128 | Q-129 | Q-130 | Q-131 | Q-132 | Q-133 | Q-134 | Q-135 |
| Q-136 | Q-137 | Q-138 | Q-139 | Q-140 | Q-141 | Q-142 | Q-143 | Q-144 |
| Q-145 | Q-146 | Q-147 | Q-148 | Q-149 | Q-150 | Q-151 | Q-152 | Q-153 |
| Q-154 | Q-155 | Q-156 | Q-157 | Q-158 | Q-159 | Q-160 | Q-161 | Q-162 |
| Q-163 | Q-164 | Q-165 | Q-166 | Q-167 | Q-168 | Q-169 | Q-170 | Q-171 |
| Q-172 | Q-173 | Q-174 | Q-175 | | | | | |

$R^1$ is i-$C_3H_7$, $R^2$ is B-4

| Q | Q | Q | Q | Q | Q | Q | Q | Q |
|---|---|---|---|---|---|---|---|---|
| Q-1 | Q-2 | Q-3 | Q-4 | Q-5 | Q-6 | Q-7 | Q-8 | Q-9 |
| Q-10 | Q-11 | Q-12 | Q-13 | Q-14 | Q-15 | Q-16 | Q-17 | Q-18 |
| Q-19 | Q-20 | Q-21 | Q-22 | Q-23 | Q-24 | Q-25 | Q-26 | Q-27 |
| Q-28 | Q-29 | Q-30 | Q-31 | Q-32 | Q-33 | Q-34 | Q-35 | Q-36 |
| Q-37 | Q-38 | Q-39 | Q-40 | Q-41 | Q-42 | Q-43 | Q-44 | Q-45 |
| Q-46 | Q-47 | Q-48 | Q-49 | Q-50 | Q-51 | Q-52 | Q-53 | Q-54 |
| Q-55 | Q-56 | Q-57 | Q-58 | Q-59 | Q-60 | Q-61 | Q-62 | Q-63 |
| Q-64 | Q-65 | Q-66 | Q-67 | Q-68 | Q-69 | Q-70 | Q-71 | Q-72 |
| Q-73 | Q-74 | Q-75 | Q-76 | Q-77 | Q-78 | Q-79 | Q-80 | Q-81 |
| Q-82 | Q-83 | Q-84 | Q-85 | Q-86 | Q-87 | Q-88 | Q-89 | Q-90 |
| Q-91 | Q-92 | Q-93 | Q-94 | Q-95 | Q-96 | Q-97 | Q-98 | Q-99 |
| Q-100 | Q-101 | Q-102 | Q-103 | Q-104 | Q-105 | Q-106 | Q-107 | Q-108 |
| Q-109 | Q-110 | Q-111 | Q-112 | Q-113 | Q-114 | Q-115 | Q-116 | Q-117 |
| Q-118 | Q-119 | Q-120 | Q-121 | Q-122 | Q-123 | Q-124 | Q-125 | Q-126 |
| Q-127 | Q-128 | Q-129 | Q-130 | Q-131 | Q-132 | Q-133 | Q-134 | Q-135 |
| Q-136 | Q-137 | Q-138 | Q-139 | Q-140 | Q-141 | Q-142 | Q-143 | Q-144 |
| Q-145 | Q-146 | Q-147 | Q-148 | Q-149 | Q-150 | Q-151 | Q-152 | Q-153 |
| Q-154 | Q-155 | Q-156 | Q-157 | Q-158 | Q-159 | Q-160 | Q-161 | Q-162 |
| Q-163 | Q-164 | Q-165 | Q-166 | Q-167 | Q-168 | Q-169 | Q-170 | Q-171 |
| Q-172 | Q-173 | Q-174 | Q-175 | | | | | |

TABLE 2-continued

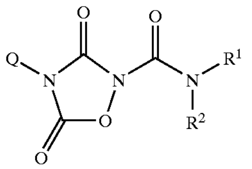

R¹ is $C_2H_5$, $R^2$ is B-4

| Q | Q | Q | Q | Q | Q | Q | Q | Q |
|---|---|---|---|---|---|---|---|---|
| Q-1 | Q-2 | Q-3 | Q-4 | Q-5 | Q-6 | Q-7 | Q-8 | Q-9 |
| Q-10 | Q-11 | Q-12 | Q-13 | Q-14 | Q-15 | Q-16 | Q-17 | Q-18 |
| Q-19 | Q-20 | Q-21 | Q-22 | Q-23 | Q-24 | Q-25 | Q-26 | Q-27 |
| Q-28 | Q-29 | Q-30 | Q-31 | Q-32 | Q-33 | Q-34 | Q-35 | Q-36 |
| Q-37 | Q-38 | Q-39 | Q-40 | Q-41 | Q-42 | Q-43 | Q-44 | Q-45 |
| Q-46 | Q-47 | Q-48 | Q-49 | Q-50 | Q-51 | Q-52 | Q-53 | Q-54 |
| Q-55 | Q-56 | Q-57 | Q-58 | Q-59 | Q-60 | Q-61 | Q-62 | Q-63 |
| Q-64 | Q-65 | Q-66 | Q-67 | Q-68 | Q-69 | Q-70 | Q-71 | Q-72 |
| Q-73 | Q-74 | Q-75 | Q-76 | Q-77 | Q-78 | Q-79 | Q-80 | Q-81 |
| Q-82 | Q-83 | Q-84 | Q-85 | Q-86 | Q-87 | Q-88 | Q-89 | Q-90 |
| Q-91 | Q-92 | Q-93 | Q-94 | Q-95 | Q-96 | Q-97 | Q-98 | Q-99 |
| Q-100 | Q-101 | Q-102 | Q-103 | Q-104 | Q-105 | Q-106 | Q-107 | Q-108 |
| Q-109 | Q-110 | Q-111 | Q-112 | Q-113 | Q-114 | Q-115 | Q-116 | Q-117 |
| Q-118 | Q-119 | Q-120 | Q-121 | Q-122 | Q-123 | Q-124 | Q-125 | Q-126 |
| Q-127 | Q-128 | Q-129 | Q-130 | Q-131 | Q-132 | Q-133 | Q-134 | Q-135 |
| Q-136 | Q-137 | Q-138 | Q-139 | Q-140 | Q-141 | Q-142 | Q-143 | Q-144 |
| Q-145 | Q-146 | Q-147 | Q-148 | Q-149 | Q-150 | Q-151 | Q-152 | Q-153 |
| Q-154 | Q-155 | Q-156 | Q-157 | Q-158 | Q-159 | Q-160 | Q-161 | Q-162 |
| Q-163 | Q-164 | Q-165 | Q-166 | Q-167 | Q-168 | Q-169 | Q-170 | Q-171 |
| Q-172 | Q-173 | Q-174 | Q-175 | | | | | |

$R^1$ is $C_2H_5$, $R^2$ is B-10

| Q | Q | Q | Q | Q | Q | Q | Q | Q |
|---|---|---|---|---|---|---|---|---|
| Q-1 | Q-2 | Q-3 | Q-4 | Q-5 | Q-6 | Q-7 | Q-8 | Q-9 |
| Q-10 | Q-11 | Q-12 | Q-13 | Q-14 | Q-15 | Q-16 | Q-17 | Q-18 |
| Q-19 | Q-20 | Q-21 | Q-22 | Q-23 | Q-24 | Q-25 | Q-26 | Q-27 |
| Q-28 | Q-29 | Q-30 | Q-31 | Q-32 | Q-33 | Q-34 | Q-35 | Q-36 |
| Q-37 | Q-38 | Q-39 | Q-40 | Q-41 | Q-42 | Q-43 | Q-44 | Q-45 |
| Q-46 | Q-47 | Q-48 | Q-49 | Q-50 | Q-51 | Q-52 | Q-53 | Q-54 |
| Q-55 | Q-56 | Q-57 | Q-58 | Q-59 | Q-60 | Q-61 | Q-62 | Q-63 |
| Q-64 | Q-65 | Q-66 | Q-67 | Q-68 | Q-69 | Q-70 | Q-71 | Q-72 |
| Q-73 | Q-74 | Q-75 | Q-76 | Q-77 | Q-78 | Q-79 | Q-80 | Q-81 |
| Q-82 | Q-83 | Q-84 | Q-85 | Q-86 | Q-87 | Q-88 | Q-89 | Q-90 |
| Q-91 | Q-92 | Q-93 | Q-94 | Q-95 | Q-96 | Q-97 | Q-98 | Q-99 |
| Q-100 | Q-101 | Q-102 | Q-103 | Q-104 | Q-105 | Q-106 | Q-107 | Q-108 |
| Q-109 | Q-110 | Q-111 | Q-112 | Q-113 | Q-114 | Q-115 | Q-116 | Q-117 |
| Q-118 | Q-119 | Q-120 | Q-121 | Q-122 | Q-123 | Q-124 | Q-125 | Q-126 |
| Q-127 | Q-128 | Q-129 | Q-130 | Q-131 | Q-132 | Q-133 | Q-134 | Q-135 |
| Q-136 | Q-137 | Q-138 | Q-139 | Q-140 | Q-141 | Q-142 | Q-143 | Q-144 |
| Q-145 | Q-146 | Q-147 | Q-148 | Q-149 | Q-150 | Q-151 | Q-152 | Q-153 |
| Q-154 | Q-155 | Q-156 | Q-157 | Q-158 | Q-159 | Q-160 | Q-161 | Q-162 |
| Q-163 | Q-164 | Q-165 | Q-166 | Q-167 | Q-168 | Q-169 | Q-170 | Q-171 |
| Q-172 | Q-173 | Q-174 | Q-175 | | | | | |

$R^1$ i-$C_3H_7$, $R^2$ is B-10

| Q | Q | Q | Q | Q | Q | Q | Q | Q |
|---|---|---|---|---|---|---|---|---|
| Q-1 | Q-2 | Q-3 | Q-4 | Q-5 | Q-6 | Q-7 | Q-8 | Q-9 |
| Q-10 | Q-11 | Q-12 | Q-13 | Q-14 | Q-15 | Q-16 | Q-17 | Q-18 |
| Q-19 | Q-20 | Q-21 | Q-22 | Q-23 | Q-24 | Q-25 | Q-26 | Q-27 |
| Q-28 | Q-29 | Q-30 | Q-31 | Q-32 | Q-33 | Q-34 | Q-35 | Q-36 |
| Q-37 | Q-38 | Q-39 | Q-40 | Q-41 | Q-42 | Q-43 | Q-44 | Q-45 |
| Q-46 | Q-47 | Q-48 | Q-49 | Q-50 | Q-51 | Q-52 | Q-53 | Q-54 |
| Q-55 | Q-56 | Q-57 | Q-58 | Q-59 | Q-60 | Q-61 | Q-62 | Q-63 |
| Q-64 | Q-65 | Q-66 | Q-67 | Q-68 | Q-69 | Q-70 | Q-71 | Q-72 |
| Q-73 | Q-74 | Q-75 | Q-76 | Q-77 | Q-78 | Q-79 | Q-80 | Q-81 |
| Q-82 | Q-83 | Q-84 | Q-85 | Q-86 | Q-87 | Q-88 | Q-89 | Q-90 |
| Q-91 | Q-92 | Q-93 | Q-94 | Q-95 | Q-96 | Q-97 | Q-98 | Q-99 |
| Q-100 | Q-101 | Q-102 | Q-103 | Q-104 | Q-105 | Q-106 | Q-107 | Q-108 |
| Q-109 | Q-110 | Q-111 | Q-112 | Q-113 | Q-114 | Q-115 | Q-116 | Q-117 |
| Q-118 | Q-119 | Q-120 | Q-121 | Q-122 | Q-123 | Q-124 | Q-125 | Q-126 |
| Q-127 | Q-128 | Q-129 | Q-130 | Q-131 | Q-132 | Q-133 | Q-134 | Q-135 |
| Q-136 | Q-137 | Q-138 | Q-139 | Q-140 | Q-141 | Q-142 | Q-143 | Q-144 |

TABLE 2-continued

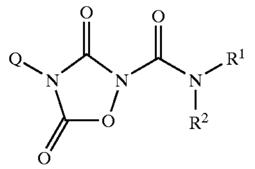

| | | | | | | | | |
|---|---|---|---|---|---|---|---|---|
| Q-145 | Q-146 | Q-147 | Q-148 | Q-149 | Q-150 | Q-151 | Q-152 | Q-153 |
| Q-154 | Q-155 | Q-156 | Q-157 | Q-158 | Q-159 | Q-160 | Q-161 | Q-162 |
| Q-163 | Q-164 | Q-165 | Q-166 | Q-167 | Q-168 | Q-169 | Q-170 | Q-171 |
| Q-172 | Q-173 | Q-174 | Q-175 | | | | | |

| Q | $R^1$ | $R^2$ | Q | $R^1$ | $R^2$ | Q | $R^1$ | $R^2$ |
|---|---|---|---|---|---|---|---|---|
| Q-2 | Cyclopropyl | B-10 | Q-2 | Allyl | B-4 | Q-2 | Cyclohexyl | B-18 |
| Q-16 | Cyclopropyl | B-10 | Q-16 | Allyl | B-4 | Q-16 | Cyclohexyl | B-18 |
| Q-24 | Cyclopropyl | B-10 | Q-24 | Allyl | B-4 | Q-24 | Cyclohexyl | B-18 |
| Q-29 | Cyclopropyl | B-10 | Q-29 | Allyl | B-4 | Q-29 | Cyclohexyl | B-18 |
| Q-57 | Cyclopropyl | B-10 | Q-57 | Allyl | B-4 | Q-57 | Cyclohexyl | B-18 |
| Q-71 | Cyclopropyl | B-10 | Q-71 | Allyl | B-4 | Q-71 | Cyclohexyl | B-18 |
| Q-100 | Cyclopropyl | B-10 | Q-100 | Allyl | B-4 | Q- 100 | Cyclohexyl | B-18 |
| Q-119 | Cyclopropyl | B-10 | Q-119 | Allyl | B-4 | Q-119 | Cyclohexyl | B-18 |
| Q-120 | Cyclopropyl | B-10 | Q-120 | Allyl | B-4 | Q-120 | Cyclohexyl | B-18 |
| Q-126 | Cyclopropyl | B-10 | Q-126 | Allyl | B-4 | Q-126 | Cyclohexyl | B-18 |
| Q-130 | Cyclopropyl | B-10 | Q-130 | Allyl | B-4 | Q-130 | Cyclohexyl | B-18 |
| Q-144 | Cyclopropyl | B-10 | Q-144 | Allyl | B-4 | Q-144 | Cyclohexyl | B-18 |
| Q-162 | Cyclopropyl | B-10 | Q-162 | Allyl | B-4 | Q-162 | Cyclohexyl | B-18 |
| Q-169 | Cyclopropyl | B-10 | Q-169 | Allyl | B-4 | Q-169 | Cyclohexyl | B-18 |
| Q-2 | n-$C_4H_9$ | B-10 | Q-2 | Cyclopropyl | B-4 | Q-2 | i-$C_3H_7$ | B-18 |
| Q-16 | n-$C_4H_9$ | B-10 | Q-16 | Cyclopropyl | B-4 | Q-16 | i-$C_3H_7$ | B-18 |
| Q-24 | n-$C_4H_9$ | B-10 | Q-24 | Cyclopropyl | B-4 | Q-24 | i-$C_3H_7$ | B-18 |
| Q-29 | n-$C_4H_9$ | B-10 | Q-29 | Cyclopropyl | B-4 | Q-29 | i-$C_3H_7$ | B-18 |
| Q-57 | n-$C_4H_9$ | B-10 | Q-57 | Cyclopropyl | B-4 | Q-57 | i-$C_3H_7$ | B-18 |
| Q-71 | n-$C_4H_9$ | B-10 | Q-71 | Cyclopropyl | B-4 | Q-71 | i-$C_3H_7$ | B-18 |
| Q-100 | n-$C_4H_9$ | B-10 | Q-100 | Cyclopropyl | B-4 | Q-100 | i-$C_3H_7$ | B-18 |
| Q-119 | n-$C_4H_9$ | B-10 | Q-119 | Cyclopropyl | B-4 | Q-119 | i-$C_3H_7$ | B-18 |
| Q-120 | n-$C_4H_9$ | B-10 | Q-120 | Cyclopropyl | B-4 | Q-120 | i-$C_3H_7$ | B-18 |
| Q-126 | n-$C_4H_9$ | B-10 | Q-126 | Cyclopropyl | B-4 | Q-126 | i-$C_3H_7$ | B-18 |
| Q-130 | n-$C_4H_9$ | B-10 | Q-130 | Cyclopropyl | B-4 | Q-130 | i-$C_3H_7$ | B-18 |
| Q-144 | n-$C_4H_9$ | B-10 | Q-144 | Cyclopropyl | B-4 | Q-144 | i-$C_3H_7$ | B-18 |
| Q-162 | n-$C_4H_9$ | B-10 | Q-162 | Cyclopropyl | B-4 | Q-162 | i-$C_3H_7$ | B-18 |
| Q-169 | n-$C_4H_9$ | B-10 | Q-169 | Cyclopropyl | B-4 | Q-169 | i-$C_3H_7$ | B-18 |
| Q-2 | $CH_2CH_2OCH_3$ | B-10 | Q-2 | $CH_3$ | B-4 | Q-2 | Cyclohexyl | B-17 |
| Q-16 | $CH_2CH_2OCH_3$ | B-10 | Q-16 | $CH_3$ | B-4 | Q-16 | Cyclohexyl | B-17 |
| Q-24 | $CH_2CH_2OCH_3$ | B-10 | Q-24 | $CH_3$ | B-4 | Q-24 | Cyclohexyl | B-17 |
| Q-29 | $CH_2CH_2OCH_3$ | B-10 | Q-29 | $CH_3$ | B-4 | Q-29 | Cyclohexyl | B-17 |
| Q-57 | $CH_2CH_2OCH_3$ | B-10 | Q-57 | $CH_3$ | B-4 | Q-57 | Cyclohexyl | B-17 |
| Q-71 | $CH_2CH_2OCH_3$ | B-10 | Q-71 | $CH_3$ | B-4 | Q-71 | Cyclohexyl | B-17 |
| Q-100 | $CH_2CH_2OCH_3$ | B-10 | Q-100 | $CH_3$ | B-4 | Q-100 | Cyclohexyl | B-17 |
| Q-119 | $CH_2CH_2OCH_3$ | B-10 | Q-119 | $CH_3$ | B-4 | Q-119 | Cyclobexyl | B-17 |
| Q-120 | $CH_2CH_2CCH_3$ | B-10 | Q-120 | $CH_3$ | B-4 | Q-120 | Cyclohexyl | B-17 |
| Q-126 | $CH_2CH_2OCH_3$ | B-10 | Q-126 | $CH_3$ | B-4 | Q-126 | Cyclohexyl | B-17 |
| Q-130 | $CH_2CH_2OCH_3$ | B-10 | Q-130 | $CH_3$ | B-4 | Q-130 | Cyclohexyl | B-17 |
| Q-144 | $CH_2CH_2OCH_3$ | B-10 | Q-144 | $CH_3$ | B-4 | Q-144 | Cyclohexyl | B-17 |
| Q-162 | $CH_2CH_2OCH_3$ | B-10 | Q-162 | $CH_3$ | B-4 | Q-162 | Cyclohexyl | B-17 |
| Q-169 | $CH_2CH_2OCH_3$ | B-10 | Q-169 | $CH_3$ | B-4 | Q-169 | Cyclohexyl | B-17 |
| Q-2 | $CH_3$ | B-10 | Q-2 | $CH_3$ | B-4 | Q-2 | $C_2H_5$ | B-17 |
| Q-16 | $CH_3$ | B-10 | Q-16 | $CH_3$ | B-4 | Q-16 | $C_2H_5$ | B-17 |
| Q-24 | $CH_3$ | B-10 | Q-24 | $CH_3$ | B-4 | Q-24 | $C_2H_5$ | B-17 |
| Q-29 | $CH_3$ | B-10 | Q-29 | $CH_3$ | B-4 | Q-29 | $C_2H_5$ | B-17 |
| Q-57 | $CH_3$ | B-10 | Q-57 | $CH_3$ | B-4 | Q-57 | $C_2H_5$ | B-17 |
| Q-71 | $CH_3$ | B-10 | Q-71 | $CH_3$ | B-4 | Q-71 | $C_2H_5$ | B-17 |
| Q-100 | $CH_3$ | B-10 | Q-100 | $CH_3$ | B-4 | Q-100 | $C_2H_5$ | B-17 |
| Q-119 | $CH_3$ | B-10 | Q-119 | $CH_3$ | B-4 | Q-119 | $C_2H_5$ | B-17 |
| Q-120 | $CH_3$ | B-10 | Q-120 | $CH_3$ | B-4 | Q-120 | $C_2H_5$ | B-17 |
| Q-126 | $CH_3$ | B-10 | Q-126 | $CH_3$ | B-4 | Q-126 | $C_2H_5$ | B-17 |
| Q-130 | $CH_3$ | B-10 | Q-130 | $CH_3$ | B-4 | Q-130 | $C_2H_5$ | B-17 |
| Q-144 | $CH_3$ | B-10 | Q-144 | $CH_3$ | B-4 | Q-144 | $C_2H_5$ | B-17 |
| Q-162 | $CH_3$ | B-10 | Q-162 | $CH_3$ | B-4 | Q-162 | $C_2H_5$ | B-17 |
| Q-169 | $CH_3$ | B-10 | Q-169 | $CH_3$ | B-4 | Q-169 | $C_2H_5$ | B-17 |
| Q-2 | n-$C_6H_{13}$ | B-10 | Q-2 | $CH_2CF_3$ | B-4 | Q-2 | n-$C_3H_7$ | B-6 |
| Q-16 | n-$C_6H_{13}$ | B-10 | Q-16 | $CH_2CF_3$ | B-4 | Q-16 | n-$C_3H_7$ | B-6 |
| Q-24 | n-$C_6H_{13}$ | B-10 | Q-24 | $CH_2CF_3$ | B-4 | Q-24 | n-$C_3H_7$ | B-6 |
| Q-29 | n-$C_6H_{13}$ | B-10 | Q-29 | $CH_2CF_3$ | B-4 | Q-29 | n-$C_3H_7$ | B-6 |
| Q-57 | n-$C_6H_{13}$ | B-10 | Q-57 | $CH_2CF_3$ | B-4 | Q-57 | n-$C_3H_7$ | B-6 |
| Q-71 | n-$C_6H_{13}$ | B-10 | Q-71 | $CH_2CF_3$ | B-4 | Q-71 | n-$C_3H_7$ | B-6 |
| Q-100 | n-$C_6H_{13}$ | B-10 | Q-100 | $CH_2CF_3$ | B-4 | Q-100 | n-$C_3H_7$ | B-6 |

TABLE 2-continued

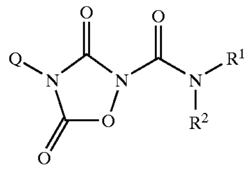

| | | | | | | | | |
|---|---|---|---|---|---|---|---|---|
| Q-119 | n-$C_6H_{13}$ | B-10 | Q-119 | $CH_2CF_3$ | B-4 | Q-119 | n-$C_3H_7$ | B-6 |
| Q-120 | n-$C_6H_{13}$ | B-10 | Q-120 | $CH_2CF_3$ | B-4 | Q-120 | n-$C_3H_7$ | B-6 |
| Q-126 | n-$C_6H_{13}$ | B-10 | Q-126 | $CH_2CF_3$ | B-4 | Q-126 | n-$C_3H_7$ | B-6 |
| Q-130 | n-$C_6H_{13}$ | B-10 | Q-130 | $CH_2CF_3$ | B-4 | Q-130 | n-$C_3H_7$ | B-6 |
| Q-144 | n-$C_6H_{13}$ | B-10 | Q-144 | $CH_2CF_3$ | B-4 | Q-144 | n-$C_3H_7$ | B-6 |
| Q-162 | n-$C_6H_{13}$ | B-10 | Q-162 | $CH_2CF_3$ | B-4 | Q-162 | n-$C_3H_7$ | B-6 |
| Q-169 | n-$C_6H_{13}$ | B-10 | Q-169 | $CH_2CF_3$ | B-4 | Q-169 | n-$C_3H_7$ | B-6 |

| Q | $R^1$ | $R^2$ | Q | $R^1$ | $R^2$ | Q | $R^1$ | $R^2$ |
|---|---|---|---|---|---|---|---|---|
| Q-2 | $C_2H_5$ | B-2 | Q-2 | $C_2H_5$ | B-5 | Q-2 | $C_2H_5$ | B-8 |
| Q-16 | $C_2H_5$ | B-2 | Q-16 | $C_2H_5$ | B-5 | Q-16 | $C_2H_5$ | B-8 |
| Q-24 | $C_2H_5$ | B-2 | Q-24 | $C_2H_5$ | B-5 | Q-24 | $C_2H_5$ | B-8 |
| Q-29 | $C_2H_5$ | B-2 | Q-29 | $C_2H_5$ | B-5 | Q-29 | $C_2H_5$ | B-8 |
| Q-57 | $C_2H_5$ | B-2 | Q-57 | $C_2H_5$ | B-5 | Q-57 | $C_2H_5$ | B-8 |
| Q-71 | $C_2H_5$ | B-2 | Q-71 | $C_2H_5$ | B-5 | Q-71 | $C_2H_5$ | B-8 |
| Q-100 | $C_2H_5$ | B-2 | Q-100 | $C_2H_5$ | B-5 | Q-100 | $C_2H_5$ | B-8 |
| Q-119 | $C_2H_5$ | B-2 | Q-119 | $C_2H_5$ | B-5 | Q-119 | $C_2H_5$ | B-8 |
| Q-120 | $C_2H_5$ | B-2 | Q-120 | $C_2H_5$ | B-5 | Q-120 | $C_2H_5$ | B-8 |
| Q-126 | $C_2H_5$ | B-2 | Q-126 | $C_2H_5$ | B-5 | Q-126 | $C_2H_5$ | B-8 |
| Q-130 | $C_2H_5$ | B-2 | Q-130 | $C_2H_5$ | B-5 | Q-130 | $C_2H_5$ | B-8 |
| Q-144 | $C_2H_5$ | B-2 | Q-144 | $C_2H_5$ | B-5 | Q-144 | $C_2H_5$ | B-8 |
| Q-162 | $C_2H_5$ | B-2 | Q-162 | $C_2H_5$ | B-5 | Q-162 | $C_2H_5$ | B-8 |
| Q-169 | $C_2H_5$ | B-2 | Q-169 | $C_2H_5$ | B-5 | Q-169 | $C_2H_5$ | B-8 |
| Q-2 | $C_3H_7$ | B-2 | Q-2 | i-$C_3H_7$ | B-6 | Q-2 | Cyclopropyl | B-8 |
| Q-16 | $C_3H_7$ | B-2 | Q-16 | i-$C_3H_7$ | B-6 | Q-16 | Cyclopropyl | B-8 |
| Q-24 | $C_3H_7$ | B-2 | Q-24 | i-$C_3H_7$ | B-6 | Q-24 | Cyclopropyl | B-8 |
| Q-29 | $C_3H_7$ | B-2 | Q-29 | i-$C_3H_7$ | B-6 | Q-29 | Cyclopropyl | B-8 |
| Q-57 | $C_3H_7$ | B-2 | Q-57 | i-$C_3H_7$ | B-6 | Q-57 | Cyclopropyl | B-8 |
| Q-71 | $C_3H_7$ | B-2 | Q-71 | i-$C_3H_7$ | B-6 | Q-71 | Cyclopropyl | B-8 |
| Q-100 | $C_3H_7$ | B-2 | Q-100 | i-$C_3H_7$ | B-6 | Q-100 | Cyclopropyl | B-8 |
| Q-119 | $C_3H_7$ | B-2 | Q-119 | i-$C_3H_7$ | B-6 | Q-119 | Cyclopropyl | B-8 |
| Q-120 | $C_3H_7$ | B-2 | Q-120 | i-$C_3H_7$ | B-6 | Q-120 | Cyclopropyl | B-8 |
| Q-126 | $C_3H_7$ | B-2 | Q-126 | i-$C_3H_7$ | B-6 | Q-126 | Cyclopropyl | B-8 |
| Q-130 | $C_3H_7$ | B-2 | Q-130 | i-$C_3H_7$ | B-6 | Q-130 | Cyclopropyl | B-8 |
| Q-144 | $C_3H_7$ | B-2 | Q-144 | i-$C_3H_7$ | B-6 | Q-144 | Cyclopropyl | B-8 |
| Q-162 | $C_3H_7$ | B-2 | Q-162 | i-$C_3H_7$ | B-6 | Q-162 | Cyclopropyl | B-8 |
| Q-169 | $C_3H_7$ | B-2 | Q-169 | i-$C_3H_7$ | B-6 | Q-169 | Cyclopropyl | B-8 |
| Q-2 | $C_2H_5$ | B-3 | Q-2 | $C_2H_5$ | B-6 | Q-2 | $C_2H_5$ | B-9 |
| Q-16 | $C_2H_5$ | B-3 | Q-16 | $C_2H_5$ | B-6 | Q-16 | $C_2H_5$ | B-9 |
| Q-24 | $C_2H_5$ | B-3 | Q-24 | $C_2H_5$ | B-6 | Q-24 | $C_2H_5$ | B-9 |
| Q-29 | $C_2H_5$ | B-3 | Q-29 | $C_2H_5$ | B-6 | Q-29 | $C_2H_5$ | B-9 |
| Q-57 | $C_2H_5$ | B-3 | Q-57 | $C_2H_5$ | B-6 | Q-57 | $C_2H_5$ | B-9 |
| Q-71 | $C_2H_5$ | B-3 | Q-71 | $C_2H_5$ | B-6 | Q-71 | $C_2H_5$ | B-9 |
| Q-100 | $C_2H_5$ | B-3 | Q-100 | $C_2H_5$ | B-6 | Q-100 | $C_2H_5$ | B-9 |
| Q-119 | $C_2H_5$ | B-3 | Q-119 | $C_2H_5$ | B-6 | Q-119 | $C_2H_5$ | B-9 |
| Q-120 | $C_2H_5$ | B-3 | Q-120 | $C_2H_5$ | B-6 | Q-120 | $C_2H_5$ | B-9 |
| Q-126 | $C_2H_5$ | B-3 | Q-126 | $C_2H_5$ | B-6 | Q-126 | $C_2H_5$ | B-9 |
| Q-130 | $C_2H_5$ | B-3 | Q-130 | $C_2H_5$ | B-6 | Q-130 | $C_2H_5$ | B-9 |
| Q-144 | $C_2H_5$ | B-3 | Q-144 | $C_2H_5$ | B-6 | Q-144 | $C_2H_5$ | B-9 |
| Q-162 | $C_2H_5$ | B-3 | Q-162 | $C_2H_5$ | B-6 | Q-162 | $C_2H_5$ | B-9 |
| Q-169 | $C_2H_5$ | B-3 | Q-169 | $C_2H_5$ | B-6 | Q-169 | $C_2H_5$ | B-9 |
| Q-2 | i-$C_3H_7$ | B-3 | Q-2 | $C_2H_5$ | B-7 | Q-2 | i-$C_3H_7$ | B-9 |
| Q-16 | i-$C_3H_7$ | B-3 | Q-16 | $C_2H_5$ | B-7 | Q-16 | i-$C_3H_7$ | B-9 |
| Q-24 | i-$C_3H_7$ | B-3 | Q-24 | $C_2H_5$ | B-7 | Q-24 | i-$C_3H_7$ | B-9 |
| Q-29 | i-$C_3H_7$ | B-3 | Q-29 | $C_2H_5$ | B-7 | Q-29 | I-$C_3H_7$ | B-9 |
| Q-57 | i-$C_3H_7$ | B-3 | Q-57 | $C_2H_5$ | B-7 | Q-57 | i-$C_3H_7$ | B-9 |
| Q-71 | i-$C_3H_7$ | B-3 | Q-71 | $C_2H_5$ | B-7 | Q-71 | i-$C_3H_7$ | B-9 |
| Q-100 | i-$C_3H_7$ | B-3 | Q-100 | $C_2H_5$ | B-7 | Q-100 | i-$C_3H_7$ | B-9 |
| Q-119 | i-$C_3H_7$ | B-3 | Q-119 | $C_2H_5$ | B-7 | Q-119 | i-$C_3H_7$ | B-9 |
| Q-120 | i-$C_3H_7$ | B-3 | Q-120 | $C_2H_5$ | B-7 | Q-120 | i-$C_3H_7$ | B-9 |
| Q-126 | i-$C_3H_7$ | B-3 | Q-126 | $C_2H_5$ | B-7 | Q-126 | i-$C_3H_7$ | B-9 |
| Q-130 | i-$C_3H_7$ | B-3 | Q-130 | $C_2H_5$ | B-7 | Q-130 | i-$C_3H_7$ | B-9 |
| Q-144 | i-$C_3H_7$ | B-3 | Q-144 | $C_2H_5$ | B-7 | Q-144 | i-$C_3H_7$ | B-9 |
| Q-162 | i-$C_3H_7$ | B-3 | Q-162 | $C_2H_5$ | B-7 | Q-162 | i-$C_3H_7$ | B-9 |
| Q-169 | i-$C_3H_7$ | B-3 | Q-169 | $C_2H_5$ | B-7 | Q-169 | i-$C_3H_7$ | B-9 |
| Q-2 | $C_2H_5$ | B-4 | Q-2 | i-$C_3H_7$ | B-7 | Q-2 | $C_2H_5$ | B-11 |
| Q-16 | $C_2H_5$ | B-4 | Q-16 | i-$C_3H_7$ | B-7 | Q-16 | $C_2H_5$ | B-11 |
| B-24 | $C_2H_5$ | B-4 | Q-24 | i-$C_3H_7$ | B-7 | Q-24 | $C_2H_5$ | B-11 |
| Q-29 | $C_2H_5$ | B-4 | Q-29 | i-$C_3H_7$ | B-7 | Q-29 | $C_2H_5$ | B-11 |

TABLE 2-continued

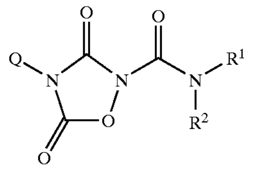

| | | | | | | | | |
|---|---|---|---|---|---|---|---|---|
| Q-57 | $C_2H_5$ | B-4 | Q-57 | i-$C_3H_7$ | B-7 | Q-57 | $C_2H_5$ | B-11 |
| Q-71 | $C_2H_5$ | B-4 | Q-71 | i-$C_3H_7$ | B-7 | Q-71 | $C_2H_5$ | B-11 |
| Q-100 | $C_2H_5$ | B-4 | Q-100 | i-$C_3H_7$ | B-7 | Q-100 | $C_2H_5$ | B-11 |
| Q-119 | $C_2H_5$ | B-4 | Q-119 | i-$C_3H_7$ | B-7 | Q-119 | $C_2H_5$ | B-11 |
| Q-120 | $C_2H_5$ | B-4 | Q-120 | i-$C_3H_7$ | B-7 | Q-120 | $C_2H_5$ | B-11 |
| Q-126 | $C_2H_5$ | B-4 | Q-126 | i-$C_3H_7$ | B-7 | Q-126 | $C_2H_5$ | B-11 |
| Q-130 | $C_2H_5$ | B-4 | Q-130 | i-$C_3H_7$ | B-7 | Q-130 | $C_2H_5$ | B-11 |
| Q-144 | $C_2H_5$ | B-4 | Q-144 | i-$C_3H_7$ | B-7 | Q-144 | $C_2H_5$ | B-11 |
| Q-162 | $C_2H_5$ | B-4 | Q-162 | i-$C_3H_7$ | B-7 | Q-162 | $C_2H_5$ | B-11 |
| Q-169 | $C_2H_5$ | B-4 | Q-169 | i-$C_3H_7$ | B-7 | Q-169 | $C_2H_5$ | B-11 |
| Q | $R^1$ | $R^2$ | Q | $R^1$ | $R^2$ | Q | $R^1$ | $R^2$ |
| Q-2 | Cyclopropyl | B-11 | Q-2 | $C_2H_5$ | B-14 | Q-2 | i-$C_3H_7$ | B-16 |
| Q-16 | Cyclopropyl | B-11 | Q-16 | $C_2H_5$ | B-14 | Q-16 | i-$C_3H_7$ | B-16 |
| Q-24 | Cyclopropyl | B-11 | Q-24 | $C_2H_5$ | B-14 | Q-24 | i-$C_3H_7$ | B-16 |
| Q-29 | Cyclopropyl | B-11 | Q-29 | $C_2H_5$ | B-14 | Q-29 | i-$C_3H_7$ | B-16 |
| Q-57 | Cyclopropyl | B-11 | Q-57 | $C_2H_5$ | B-14 | Q-57 | i-$C_3H_7$ | B-16 |
| Q-71 | Cyclopropyl | B-11 | Q-71 | $C_2H_5$ | B-14 | Q-71 | i-$C_3H_7$ | B-16 |
| Q-100 | Cyclopropyl | B-11 | Q-100 | $C_2H_5$ | B-14 | Q-100 | i-$C_3H_7$ | B-16 |
| Q-119 | Cyclopropyl | B-11 | Q-119 | $C_2H_5$ | B-14 | Q-119 | i-$C_3H_7$ | B-16 |
| Q-120 | Cyclopropyl | B-11 | Q-120 | $C_2H_5$ | B-14 | Q-120 | i-$C_3H_7$ | B-16 |
| Q-126 | Cyclopropyl | B-11 | Q-126 | $C_2H_5$ | B-14 | Q-126 | i-$C_3H_7$ | B-16 |
| Q-130 | Cyclopropyl | B-11 | Q-130 | $C_2H_5$ | B-14 | Q-130 | i-$C_3H_7$ | B-16 |
| Q-144 | Cyclopropyl | B-11 | Q-144 | $C_2H_5$ | B-14 | Q-144 | i-$C_3H_7$ | B-16 |
| Q-162 | Cyclopropyl | B-11 | Q-162 | $C_2H_5$ | B-14 | Q-162 | i-$C_3H_7$ | B-16 |
| Q-169 | Cyclopropyl | B-11 | Q-169 | $C_2H_5$ | B-14 | Q-169 | i-$C_3H_7$ | B-16 |
| Q-2 | $C_2H_5$ | B-12 | Q-2 | i-$C_3H_7$ | B-14 | Q-2 | t-$C_4H_9$ | B-10 |
| Q-16 | $C_2H_5$ | B-12 | Q-16 | i-$C_3H_7$ | B-14 | Q-16 | t-$C_4H_9$ | B-10 |
| Q-24 | $C_2H_5$ | B-12 | Q-24 | i-$C_3H_7$ | B-14 | B-24 | t-$C_4H_9$ | B-10 |
| Q-29 | $C_2H_5$ | B-12 | Q-29 | i-$C_3H_7$ | B-14 | B-29 | t-$C_4H_9$ | B-10 |
| Q-57 | $C_2H_5$ | B-12 | Q-57 | i-$C_3H_7$ | B-14 | Q-57 | t-$C_4H_9$ | B-10 |
| Q-71 | $C_2H_5$ | B-12 | Q-71 | i-$C_3H_7$ | B-14 | Q-71 | t-$C_4H_9$ | B-10 |
| Q-100 | $C_2H_5$ | B-12 | Q-100 | i-$C_3H_7$ | B-14 | Q-100 | t-$C_4H_9$ | B-10 |
| Q-119 | $C_2H_5$ | B-12 | Q-119 | i-$C_3H_7$ | B-14 | Q-119 | t-$C_4H_9$ | B-10 |
| Q-120 | $C_2H_5$ | B-12 | Q-120 | i-$C_3H_7$ | B-14 | Q-120 | t-$C_4H_9$ | B-10 |
| Q-126 | $C_2H_5$ | B-12 | Q-126 | i-$C_3H_7$ | B-14 | Q-126 | t-$C_4H_9$ | B-10 |
| Q-130 | $C_2H_5$ | B-12 | Q-130 | i-$C_3H_7$ | B-14 | Q-130 | t-$C_4H_9$ | B-10 |
| Q-144 | $C_2H_5$ | B-12 | Q-144 | i-$C_3H_7$ | B-14 | Q-144 | t-$C_4H_9$ | B-10 |
| Q-162 | $C_2H_5$ | B-12 | Q-162 | i-$C_3H_7$ | B-14 | Q-162 | t-$C_4H_9$ | B-10 |
| Q-169 | $C_2H_5$ | B-12 | Q-169 | i-$C_3H_7$ | B-14 | Q-169 | t-$C_4H_9$ | B-10 |
| Q-2 | i-$C_3H_7$ | B-12 | Q-2 | $C_2H_5$ | B-15 | Q-2 | i-$C_4H_9$ | B-10 |
| Q-16 | i-$C_3H_7$ | B-12 | Q-16 | $C_2H_5$ | B-15 | Q-16 | i-$C_4H_9$ | B-10 |
| Q-24 | i-$C_3H_7$ | B-12 | Q-24 | $C_2H_5$ | B-15 | Q-24 | i-$C_4H_9$ | B-10 |
| Q-29 | i-$C_3H_7$ | B-12 | Q-29 | $C_2H_5$ | B-15 | Q-29 | i-$C_4H_9$ | B-10 |
| Q-57 | i-$C_3H_7$ | B-12 | Q-57 | $C_2H_5$ | B-15 | Q-57 | i-$C_4H_9$ | B-10 |
| Q-71 | i-$C_3H_7$ | B-12 | Q-71 | $C_2H_5$ | B-15 | Q-71 | i-$C_4H_9$ | B-10 |
| Q-100 | i-$C_3H_7$ | B-12 | Q-100 | $C_2H_5$ | B-15 | Q-100 | i-$C_4H_9$ | B-10 |
| Q-119 | i-$C_3H_7$ | B-12 | Q-119 | $C_2H_5$ | B-15 | Q-119 | i-$C_4H_9$ | B-10 |
| Q-120 | i-$C_3H_7$ | B-12 | Q-120 | $C_2H_5$ | B-15 | Q-120 | i-$C_4H_9$ | B-10 |
| Q-126 | i-$C_3H_7$ | B-12 | Q-126 | $C_2H_5$ | B-15 | Q-126 | i-$C_4H_9$ | B-10 |
| Q-130 | i-$C_3H_7$ | B-12 | Q-130 | $C_2H_5$ | B-15 | Q-130 | i-$C_4H_9$ | B-10 |
| Q-144 | i-$C_3H_7$ | B-12 | Q-144 | $C_2H_5$ | B-15 | Q-144 | i-$C_4H_9$ | B-10 |
| Q-162 | i-$C_3H_7$ | B-12 | Q-162 | $C_2H_5$ | B-15 | Q-162 | i-$C_4H_9$ | B-10 |
| Q-169 | i-$C_3H_7$ | B-12 | Q-169 | $C_2H_5$ | B-15 | Q-169 | i-$C_4H_9$ | B-10 |
| Q-2 | $C_2H_5$ | B-13 | Q-2 | i-$C_3H_7$ | B-15 | Q-2 | $CH_2CF_3$ | B-10 |
| Q-16 | $C_2H_5$ | B-13 | Q-16 | i-$C_3H_7$ | B-15 | Q-16 | $CH_2CF_3$ | B-10 |
| Q-24 | $C_2H_5$ | B-13 | Q-24 | i-$C_3H_7$ | B-15 | Q-24 | $CH_2CF_3$ | B-10 |
| Q-29 | $C_2H_5$ | B-13 | Q-29 | i-$C_3H_7$ | B-15 | Q-29 | $CH_2CF_3$ | B-10 |
| Q-57 | $C_2H_5$ | B-13 | Q-57 | i-$C_3H_7$ | B-15 | Q-57 | $CH_2CF_3$ | B-10 |
| Q-71 | $C_2H_5$ | B-13 | Q-71 | i-$C_3H_7$ | B-15 | Q-71 | $CH_2CF_3$ | B-10 |
| Q-100 | $C_2H_5$ | B-13 | Q-100 | i-$C_3H_7$ | B-15 | Q-100 | $CH_2CF_3$ | B-10 |
| Q-119 | $C_2H_5$ | B-13 | Q-119 | i-$C_3H_7$ | B-15 | Q-119 | $CH_2CF_3$ | B-10 |
| Q-120 | $C_2H_5$ | B-13 | Q-120 | i-$C_3H_7$ | B-15 | Q-120 | $CH_2CF_3$ | B-10 |
| Q-126 | $C_2H_5$ | B-13 | Q-126 | i-$C_3H_7$ | B-15 | Q-126 | $CH_2CF_3$ | B-10 |
| Q-130 | $C_2H_5$ | B-13 | Q-130 | i-$C_3H_7$ | B-15 | Q-130 | $CH_2CF_3$ | B-10 |
| Q-144 | $C_2H_5$ | B-13 | Q-144 | i-$C_3H_7$ | B-15 | Q-144 | $CH_2CF_3$ | B-10 |
| Q-162 | $C_2H_5$ | B-13 | Q-162 | i-$C_3H_7$ | B-15 | Q-162 | $CH_2CF_3$ | B-10 |
| Q-169 | $C_2H_5$ | B-13 | Q-169 | i-$C_3H_7$ | B-15 | Q-169 | $CH_2CF_3$ | B-10 |
| Q-2 | i-$C_3H_7$ | B-13 | Q-2 | $C_2H_5$ | B-16 | Q-2 | n-$C_3H_7$ | B-10 |

TABLE 2-continued

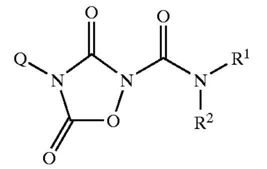

| | | | | | | | | |
|---|---|---|---|---|---|---|---|---|
| Q-16 | i-$C_3H_7$ | B-13 | Q-16 | $C_2H_5$ | B-16 | Q-16 | n-$C_3H_7$ | B-10 |
| Q-24 | i-$C_3H_7$ | B-13 | Q-24 | $C_2H_5$ | B-16 | Q-24 | n-$C_3H_7$ | B-10 |
| Q-29 | i-$C_3H_7$ | B-13 | Q-29 | $C_2H_5$ | B-16 | Q-29 | n-$C_3H_7$ | B-10 |
| Q-57 | i-$C_3H_7$ | B-13 | Q-57 | $C_2H_5$ | B-16 | Q-57 | n-$C_3H_7$ | B-10 |
| Q-71 | i-$C_3H_7$ | B-13 | Q-71 | $C_2H_5$ | B-16 | Q-71 | n-$C_3H_7$ | B-10 |
| Q-100 | i-$C_3H_7$ | B-13 | Q-100 | $C_2H_5$ | B-16 | Q-100 | n-$C_3H_7$ | B-10 |
| Q-119 | i-$C_3H_7$ | B-13 | Q-119 | $C_2H_5$ | B-16 | Q-119 | n-$C_3H_7$ | B-10 |
| Q-120 | i-$C_3H_7$ | B-13 | Q-120 | $C_2H_5$ | B-16 | Q-120 | n-$C_3H_7$ | B-10 |
| Q-126 | i-$C_3H_7$ | B-13 | Q-126 | $C_2H_5$ | B-16 | Q-126 | n-$C_3H_7$ | B-10 |
| Q-130 | i-$C_3H_7$ | B-13 | Q-130 | $C_2H_5$ | B-16 | Q-130 | n-$C_3H_7$ | B-10 |
| Q-144 | i-$C_3H_7$ | B-13 | Q-144 | $C_2H_5$ | B-16 | Q-144 | n-$C_3H_7$ | B-10 |
| Q-162 | i-$C_3H_7$ | B-13 | Q-162 | $C_2H_5$ | B-16 | Q-162 | n-$C_3H_7$ | B-10 |
| Q-169 | i-$C_3H_7$ | B-13 | Q-169 | $C_2H_5$ | B-16 | Q-169 | n-$C_3H_7$ | B-10 |

TABLE 3

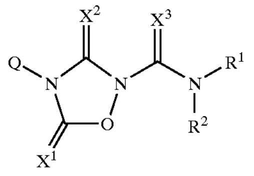

| Q | $X^1$ | $X^2$ | $X^3$ | $R^1$ | $R^2$ |
|---|---|---|---|---|---|
| i-Pr | S | O | O | i-Pr | 4-F-Phenyl |
| i-Pr | O | S | O | i-Pr | 4-F-Phenyl |
| i-Pr | O | O | S | i-Pr | 4-F-Phenyl |
| i-Pr | NMe | O | O | i-Pr | 4-F-Phenyl |
| i-Pr | O | NMe | O | i-Pr | 4-F-Phenyl |
| i-Pr | O | O | NMe | i-Pr | 4-F-Phenyl |
| i-Pr | NCN | O | O | i-Pr | 4-F-Phenyl |
| i-Pr | O | NCN | O | i-Pr | 4-F-Phenyl |
| i-Pr | O | O | NCN | i-Pr | 4-F-Phenyl |
| i-Pr | S | S | O | i-Pr | 4-F-Phenyl |
| i-Pr | S | O | S | i-Pr | 4-F-Phenyl |
| i-Pr | O | S | S | i-Pr | 4-F-Phenyl |
| i-Pr | S | S | S | i-Pr | 4-F-Phenyl |
| c-Pr | S | O | O | i-Pr | 4-F-Phenyl |
| c-Pr | O | S | O | i-Pr | 4-F-Phenyl |
| c-Pr | O | O | S | i-Pr | 4-F-Phenyl |
| c-Pr | NMe | O | O | i-Pr | 4-F-Phcnyl |
| c-Pr | O | NMe | O | i-Pr | 4-F-Phenyl |
| c-Pr | O | O | NMe | i-Pr | 4-F-Phenyl |
| c-Pr | NCN | O | O | i-Pr | 4-F-Phenyl |
| c-Pr | O | NCN | O | i-Pr | 4-F-Phenyl |
| c-Pr | O | O | NCN | i-Pr | 4-F-Phenyl |
| c-Pr | S | S | O | i-Pr | 4-F-Phenyl |
| c-Pr | S | O | S | i-Pr | 4-F-Phenyl |
| c-Pr | O | S | S | i-Pr | 4-F-Phenyl |
| c-Pr | S | S | S | i-Pr | 4-F-Phenyl |
| i-Pr | O | O | O | i-Pr | 2-Cl-Pyridin-5-yl |
| i-Pr | O | O | O | i-Pr | 2-F-Pyridin-5-yl |
| i-Pr | O | O | O | i-Pr | 2-Br-Pyridin-5-yl |
| i-Pr | O | O | O | i-Pr | 2-Me-Pyridin-5-yl |
| i-Pr | O | O | O | i-Pr | 2-$CF_3$-Pyridin-5-yl |
| i-Pr | O | O | O | i-Pr | 2-Cl-Pyrimidin-5-yl |
| i-Pr | O | O | O | i-Pr | 2-F-Pyrimidin-5-yl |
| i-Pr | O | O | O | i-Pr | 2-Br-Pyrimidin-5-yl |
| i-Pr | O | O | O | i-Pr | 2-Me-Pyrimidin-5-yl |
| i-Pr | O | O | O | i-Pr | 2-$CF_3$-Pyrimidin-5-yl |
| i-Pr | O | O | O | i-Pr | 2-Cl-Thien-5-yl |
| i-Pr | O | O | O | i-Pr | 2-F-Thien-5-yl |
| i-Pr | O | O | O | i-Pr | 2-Me-Thien-5-yl |

TABLE 3-continued

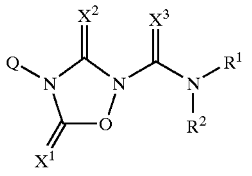

| Q | $X^1$ | $X^2$ | $X^3$ | $R^1$ | $R^2$ |
|---|---|---|---|---|---|
| i-Pr | O | O | O | i-Pr | Thien-2-yl |
| i-Pr | O | O | O | i-Pr | Pyrimidin-5-yl |
| i-Pr | O | O | O | i-Pr | 2-Cl-Pyridazin-5-yl |
| i-Pr | O | O | O | i-Pr | 2-Cl-1,3,4-Thiadiazol-5-yl |
| i-Pr | O | O | O | i-Pr | 2-$CF_3$-1,3,4-Thiadiazol-5-yl |
| i-Pr | O | O | O | i-Pr | 2-Cl-Thiazol-5-yl |
| i-Pr | O | O | O | i-Pr | 5-Cl-Thiazol-2-yl |
| c-Pr | O | O | O | i-Pr | Thien-2-yl |
| Et | O | O | O | i-Pr | Thien-2-yl |
| n-Pr | O | O | O | i-Pr | Thien-2-yl |
| Me | O | O | O | i-Pr | Thien-2-yl |
| i-Bu | O | O | O | i-Pr | Thien-2-yl |
| Allyl | O | O | O | i-Pr | Thien-2-yl |
| c-Hexyl | O | O | O | i-Pr | Thien-2-yl |
| c-Pr | O | O | O | i-Pr | 2-Cl-Pyridin-5-yl |
| Et | O | O | O | i-Pr | 2-Cl-Pyridin-5-yl |
| n-Pr | O | O | O | i-Pr | 2-Cl-Pyridin-5-yl |
| Me | O | O | O | i-Pr | 2-Cl-Pyridin-5-yl |
| i-Bu | O | O | O | i-Pr | 2-Cl-Pyridin-5-yl |
| Allyl | O | O | O | i-Pr | 2-Cl-Pyridin-5-yl |
| c-Hexyl | O | O | O | i-Pr | 2-Cl-Pyridin-5-yl |
| s-Bu | O | O | O | i-Pr | 2-Cl-Pyridin-5-yl |
| s-Bu | O | O | O | i-Pr | Thien-2-yl |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carrers*, 2nd Ed., Dorland Books, Caldwell, N.J. Typical liquid diluents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydroflrfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon performed granular carriers or by agglomeration techniques. See Browning, "Agglomeration", *Chemical Engineering*, Dec. 4, 1967, pp 147–48, *Perry's Chemical Engineer's Handbook*, 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook*, 8th Ed., Blackwell Scientific Publications, Oxford, 1989.

In the following Examples, all percentages are by weight and all formulations are prepared in conventional ways. Compound numbers refer to compounds in Index Tables A–D below.

| Example A | |
|---|---|
| High Strength Concentrate | |
| Compound 2 | 98.5% |
| silica aerogel | 0.5% |
| synthetic amorphous fine silica | 1.0%. |

| Example B | |
|---|---|
| Wettable Powder | |
| Compound 2 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

| Example C | |
|---|---|
| Granule | |
| Compound 2 | 10.0% |
| attapulgite granules (low volatile matter, 0.71/0.30 mm; U.S.S. No. 25–50 sieves) | 90.0%. |

| Example D | |
|---|---|
| Extruded Pellet | |
| Compound 2 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.00%. |

Test results indicate that the compounds of the present invention are highly active preemergent and postemergent herbicides or plant growth regulants. Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Some of the compounds are useful for the control of selected grass and broadleaf weeds with tolerance to important agronomic crops which include but are not limited to alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as eucalyptus and conifers (e.g., loblolly pine), and turf species (e.g., Kentucky bluegrass, St. Augustine grass, Kentucky fescue and Bermuda grass). Those skilled in the art will appreciate that not all compounds are equally effective against all weeds. Alternatively, the subject compounds are useful to modify plant growth.

A herbicidally effective amount of the compounds of this invention is determined by a number of factors. These factors include: formulation selected, method of application, amount and type of vegetation present, growing conditions, etc. In general, a herbicidally effective amount of compounds of this invention is 0.001 to 20 kg/ha with a preferred range of 0.004 to 1.0 kg/ha. One skilled in the art can easily determine the herbicidally effective amount necessary for the desired level of weed control.

Compounds of this invention can be used alone or in combination with other commercial herbicides, insecticides or fungicides. Compounds of this invention can also be used in combination with commercial herbicide safeners such as benoxacor, dichlormid and furilazole to increase safety to certain crops. A mixture of one or more of the following herbicides with a compound of this invention may be particularly useful for weed control: acetochlor, acifluorfen and its sodium salt, aclonifen, acrolein (2-propenal), alachlor, ametryn, amidosulfuron, amitrole, ammonium sulfamate, anilofos, asulam, atrazine, azafenidin, azimsulfuron, benazolin, benazolin-ethyl, benfluralin, benfuresate, bensulfuron-methyl, bensulide, bentazone, bifenox, bispyribac and its sodium salt, bromacil, bromoxynil, bromoxynil octanoate, butachlor, butralin, butroxydim (ICIA0500), butylate, caloxydim (BAS 620H), carfentrazone-ethyl, chlomethoxyfen, chloramben, chlorbromuron, chloridazon, chlorimuron-ethyl, chlornitrofen, chlorotoluron, chlorpropham, chlorsulfuron, chlorthal-dimethyl, cinmethylin, cinosulfuron, clethodim, clomazone, clopyralid, clopyralid-olamine, cyanazine, cycloate, cyclosulfamuron, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, 2-[4,5-dihydro4 methyl-4-(1-methylethyl)-5-oxo-1H-imidazol-2-yl]-5-methyl-3-pyridinecarboxylic acid (AC 263,222), difenzoquat metilsulfate, diflufenican, dimepiperate, dimethenamid, dimethylarsinic acid and its sodium salt, dinitramine, diphenamid, diquat dibromide, dithiopyr, diuron, DNOC, endothal, EPTC, esprocarb, ethalfluralin, ethametsulfuron-methyl, ethofumesate, ethoxysulfuron, fenoxaprop-ethyl, fenoxaprop-P-ethyl, fenuron, fenuron-TCA, flamprop-methyl, flamprop-M-isopropyl, flamprop-M-methyl, flazasulfuron, fluazifop-butyl, fluazifop-P-butyl, fluchloralin, flufenacet, flumetsulam, flumiclorac-pentyl, flumioxazin, fluometuron, fluoroglycofen-ethyl, flupoxam, flupyrsulfuron-methyl and its sodium salt, fluridone, flurochloridone, fluroxypyr, fluthiacet-methyl, fomesafen, fosamine-ammonium, glufosinate, glufosinate-ammonium, glyphosate, glyphosate-isopropylammonium, glyphosate-sesquisodium, glyphosate-trimesium, halosulfuron-methyl, haloxyfop-etotyl, haloxyfop-methyl, hexazinone, imazamethabenz-methyl, imazamox, imazapyr, imazaquin, imazaquin-ammonium, imazethapyr, imazethapyr-ammonium, imazosulfuron, ioxynil, ioxynil octanoate, ioxynil-sodium, isoproturon, isouron, isoxaben, isoxaflutole, lactofen, lenacil, linuron, maleic hydrazide, MCPA and its dimethylammonium, potassium and sodium salts, MCPA-isoctyl, mecoprop, mecoprop-P, mefenacet, mefluidide, metam-sodium, methabenzthiazuron, methylarsonic acid and its calcium, monoammonium, monosodium and disodium salts, methyl [[[1-[5-[2-chloro-4-(trifluoromethyl) phenoxy]-2-nitrophenyl]-2-methoxyethylidene]amino]oxy] acetate (AKH-7088), methyl 5-[[[[(4,6-dimethyl-2-pyrimidinyl)amino]carbonyl]amino]sulfonyl]-1-(2-pyridin)-1H-pyrazole-4-carboxylate (NC-330), metobenzuron, metolachlor, metosulam, metoxuron, metribuzin, metsulfuron-methyl, molinate, monolinuron, napropamide, naptalam, neburon, nicosulfuron, norflurazon, oryzalin, oxadiazon, oxasulfuron, oxyfluorfen, paraquat dichloride, pebulate, pendimethalin, pentoxazone (KPP-314), perfluidone, phenmediphali, picloram, picloram-potassium, pretilachlor, primisulfuron-methyl, prometon, prometryn, propachlor, propanil, propaquizafop, propazine, propham, propyzamide, prosulfuron, pyrazolynate, pyrazosulfuron-ethyl, pyridate, pyriminobac-methyl, pyrithiobac, pyrithiobac-sodium, quinclorac, quizalofop-ethyl, quizalofop-P-ethyl, quizalofop-P-tefuryl, rimsulfuron, sethoxydim, siduron, simazine, sulcotrione (ICIA0051), sulfentrazone, sulfometuron-methyl, TCA, TCA-sodium, tebuthiuron, terbacil, terbuthylazine, terbutryn, thenylchlor, thiafluamide (BAY 11390), thifensulfuron-methyl, thiobencarb, tralkoxydim, tri-allate, triasulfuron, triaziflam, tribenuron-methyl, triclopyr, triclopyr-butotyl, triclopyr-triethylammonium, tridiphane, trifluralin, triflusulfuron-methyl, and vernolate.

In certain instances, combinations with other herbicides having a similar spectrum of control but a different mode of action will be particularly advantageous for preventing the development of resistant weeds. Certain combinations of compounds of this invention with other herbicides may provide synergistic herbicidal effects on weeds or may provide enhanced crop safety.

Preferred for better control of undesired vegetation in corn (e.g., lower use rate, broader spectrum of weeds controlled, or enhanced crop safety) or for preventing the development of resistant weeds in corn are mixtures of a compound of this invention with one or more of the herbicides selected from the group rimsulfuron, nicosulfuron, thifensulfuron, prosulfuron, halosulfuron, naphthalic anhydride, flurazole, dichlormid, fenchlorazole ethyl, naphthalic anhydride, MG-191 (2-dichloromethyl)-2-methyl-1,3-dioxolane), dicyclonon, benoxacor, cyometrinil, furilazole, oxabetrinil, cloquintocet mexyl, fluxofenim, fenclorim, menfenpyr diethyl, and R-29148 (3-(dichloroacetyl)-2,2,5-trimethyloxazolidine).

Specifically preferred mixtures for use in corn are selected from the group consisting of:

a) Compound 113 (Index Table C, mixture partner A, generally applied at a rate of 10 to 1000 g/ha, preferably applied at a rate of 50 to 500 g/ha) in combination with:

| Combination Number | Mixture partner B |
|---|---|
| 1 | rimsulfuron |
| 2 | nicosulfuron |
| 3 | dichlormid |

-continued

| Combination Number | Mixture partner B |
|---|---|
| 4 | benoxacor |
| 5 | naphthalic anhydride |
| 6 | rimsulfuron (B1) in combination with dichlormid (B2) |
| 7 | nicosulfuron (B3) in combination with dichlormid (B4) |

Combination 1 is generally used in a ratio of A to B of 3:1 to 50:1, preferably 5:1 to 30:1, with B being applied at a rate of 1 to 100 g/ha, preferably 5 to 50 g/ha. Combination 2 is generally used in a ratio of A to B of 2:1 to 20:1, preferably 4:1 to 10:1, with B being applied at a rate of 1 to 100 g/ha, preferably 20 to 70 g/ha. Combination 3 is generally used in a ratio of A to B of 1:10 to 10:1, preferably 1:2 to 2:1, with B being applied at a rate of 10 to 1000 g/ha, preferably 50 to 500 g/ha. Combination 4 is generally used in a ratio of A to B of 1:10 to 10:1, preferably 1:2 to 4:1, with B being applied at a rate of 1 to 1000 g/ha, preferably 20 to 5:00 g/ha. Combination 5 is generally used in a ratio of A to B of 1:500 to 50:1, preferably 1:20 to 10:1, with B being applied at a rate of 10 to 1000 g/ha, preferably 50 to 500 g/ha. Combination 6 is generally used in a ratio of A to B1 of 3:1 to 50:1, preferably 5:1 to 30:1, and a ratio of A to B2 of 1:10 to 10:1, preferably 1:2 to 2:1, with B1 being applied at a rate of 1 to 100 g/ha, preferably 5 to 50 g/ha, and B2 being applied at a rate of 10 to 1000 g/ha, preferably 50 to 500 g/ha. Combination 7 is generally used in a ratio of A to B3 of 2:1 to 20:1, preferably 4:1 to 10:1, and a ratio of A to B4 of 1:10 to 10:1, preferably 1:2 to 2:1, with B3 being applied at a rate of 1 to 100 g/ha, preferably 20 to 70 g/ha, and B4 being applied at a rate of 10 to 1000 g/ha, preferably 50 to 500 g/ha.

b) Compound 131 (Index Table C, mixture partner A, generally applied at a rate of 10 to 1000 g/ha, preferably applied at a rate of 50 to 500 g/ha) in combination with:

| Combination Number | Mixture partner B |
|---|---|
| 1 | rimsulfuron |
| 2 | nicosulfuron |
| 3 | dichlormid |
| 4 | benoxacor |
| 5 | naphthalic anhydride |
| 6 | rimsulfuron (B1) in combination with dichlormid (B2) |
| 7 | nicosulfuron (B3) in combination with dichlormid (B4) |

Combination 1 is generally used in a ratio of A to B of 3:1 to 50:1, preferably 5:1 to 30:1, with B being applied at a rate of 1 to 100 g/ha, preferably 5 to 50 g/ha Combination 2 is generally used in a ratio of A to B of 2:1 to 20:1, preferably 4:1 to 10:1, with B being applied at a rate of 1 to 100 g/ha, preferably 20 to 70 g/ha. Combination 3 is generally used in a ratio of A to B of 1:10 to 10:1, preferably 1:2 to 2:1, with B being applied at a rate of 10 to 1000 g/ha, preferably 50 to 500 g/ha. Combination 4 is generally used in a ratio of A to B of 1:10 to 10:1, preferably 1:2 to 4:1, with B being applied at a rate of 1 to 1000 g/ha, preferably 20 to 500 g/ha. Combination 5 is generally used in a ratio of A to B of 1:500 to 50:1, preferably 1:20 to 10:1, with B being applied at a rate of 10 to 1000 g/ha, preferably 50 to 500 g/ha. Combination 6 is generally used in a ratio of A to B1 of 3:1 to 50:1, preferably 5:1 to 30:1, and a ratio of A to B2 of 1:10 to 10:1, preferably 1:2 to 2:1, with B1 being applied at a rate of 1 to 100 g/ha, preferably 5 to 50 g/ha, and B2 being applied at a rate of 10 to 1000 g/ha, preferably 50 to 500 g/ha. Combination 7 is generally used in a ratio of A to B3 of 2:1 to 20:1, preferably 4:1 to 10:1, and a ratio of A to B4 of 1:10 to 10:1, preferably 1:2 to 2:1, with B3 being applied at a rate of 1 to 100 g/ha, preferably 20 to 70 g/ha, and B4 being applied at a rate of 10 to 1000 g/ha, preferably 50 to 500 g/ha c) Compound 242 (Index Table C, mixture partner A, generally applied at a rate of 10 to 1000 g/ha, preferably applied at a rate of 50 to 500 g/ha) in combination with:

| Combination Number | Mixture partner B |
|---|---|
| 1 | Rimsulfuron |
| 2 | Nicosulfuron |
| 3 | Dichlormid |
| 4 | Benoxacor |
| 5 | naphthalic anhydride |
| 6 | rimsulfuron (B1) in combination with dichlormid (B2) |
| 7 | nicosulfuron (B3) in combination with dichlormid (B4) |

Combination 1 is generally used in a ratio of A to B of 3:1 to 50:1, preferably 5:1 to 30:1, with B being applied at a rate of 1 to 100 g/ha, preferably 5 to 50 g/ha. Combination 2 is generally used in a ratio of A to B of 2:1 to 20:1, preferably 4:1 to 10:1, with B being applied at a rate of 1 to 100 g/ha, preferably 20 to 70 g/ha. Combination 3 is generally used in a ratio of A to B of 1:10 to 10:1, preferably 1:2 to 2:1, with B being applied at a rate of 10 to 1000 g/ha, preferably 50 to 500 g/ha. Combination 4 is generally used in a ratio of A to B of 1:10 to 10:1, preferably 1:2 to 4:1, with B being applied at a rate of 1 to 1000 g/ha, preferably 20 to 500 g/ha. Combination 5 is generally used in a ratio of A to B of 1:500 to 50:1, preferably 1:20 to 10:1, with B being applied at a rate of 10 to 1000 g/ha, preferably 50 to 500 g/ha. Combination 6 is generally used in a ratio of A to B1 of 3:1 to 50:1, preferably 5:1 to 30:1, and a ratio of A to B2 of 1:10 to 10:1, preferably 1:2 to 2:1, with B1 being applied at a rate of 1 to 100 g/ha, preferably 5 to 50 g/ha, and B2 being applied at a rate of 10 to 1000 g/ha, preferably 50 to 500 g/ha. Combination 7 is generally used in a ratio of A to B3 of 2:1 to 20:1, preferably 4:1 to 10:1, and a ratio of A to B4 of 1:10 to 10:1, preferably 1:2 to 2:1, with B3 being applied at a rate of 1 to 100 g/ha, preferably 20 to 70 g/ha, and B4 being applied at a rate of 10 to 1000 g/ha, preferably 50 to 500 g/ha.

d) Compound 146 (Index Table C, mixture partner A, generally applied at a rate of 10 to 1000 g/ha, preferably applied at a rate of 50 to 500 g/ha) in combination with:

| Combination Number | Mixture partner B |
|---|---|
| 1 | Rimsulfuron |
| 2 | Nicosulfuron |
| 3 | Dichlormid |
| 4 | Benoxacor |
| 5 | naphthalic anhydride |
| 6 | rimsulfuron (B1) in combination with dichlormid (B2) |
| 7 | nicosulfuron (B3) in combination with dichlormid (B4) |

Combination 1 is generally used in a ratio of A to B of 3:1 to 50:1, preferably 5:1 to 30:1, with B being applied at a rate of 1 to 100 g/ha, preferably 5 to 50 g/ha. Combination 2 is generally used in a ratio of A to B of 2:1 to 20:1, preferably 4:1 to 10:1, with B being applied at a rate of 1 to 100 g/ha, preferably 20 to 70 g/ha. Combination 3 is generally used in a ratio of A to B of 1:10 to 10:1, preferably 1:2 to 2:1, with B being applied at a rate of 10 to 1000 g/ha, preferably 50 to 500 g/ha. Combination 4 is generally used in a ratio of A to B of 1:10 to 10:1, preferably 1:2 to 4:1, with B being applied at a rate of 1 to 1000 g/ha, preferably 20 to 500 g/ha. Combination 5 is generally used in a ratio of A to B of 1:500 to 50:1, preferably 1:20 to 10:1, with B being applied at a rate of 10 to 1000 g/ha, preferably 50 to 500 g/ha. Combination 6 is generally used in a ratio of A to B 1 of 3:1 to 50:1, preferably 5:1 to 30:1, and a ratio of A to B2 of 1:I0 to 10:1, preferably 1:2 to 2:1, with B1 being applied at a rate of 1 to 100 g/ha, preferably 5 to 50 g/ha, and B2 being applied at a rate of 10 to 1000 g/ha, preferably 50 to 500 g/ha. Combination 7 is generally used in a ratio of A to B3 of 2:1 to 20:1, preferably 4:1 to 10:1, and a ratio of A to B4 of1:10 to 10:1, preferably 1:2 to 2:1, with B3 being applied at a rate of 1 to 100 g/ha, preferably 20 to 70 g/ha, and B4 being applied at a rate of 10 to 1000 g/ha, preferably 50 to 500 g/ha.

The following Tests demonstrate the control efficacy of the compounds of this invention against specific weeds. The weed control afforded by the compounds is not limited, however, to these species. See Index Tables A–D for compound descriptions. The abbreviation "dec" indicates that the compound appeared to decompose on melting. The abbreviation "Ex." stands for "Example" and is followed by a number indicating in which example the compound is prepared.

INDEX TABLE A

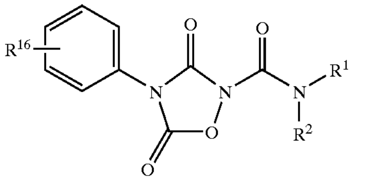

| Cmpd No. | $R^1$ | $R^2$ | $R^{16}$ | MP (° C.) |
|---|---|---|---|---|
| 1 | Et | Et | $4\text{-}OCH_3$ | 113–116 |
| 2 | Et | Et | 2,6-dimethyl | 90–93 |
| 3 | Et | Et | 4-F | 71–76 |
| 4 | i-Pr | 4-F-Phenyl | $2\text{-}CH_3$ | 122–124 |
| 5 | i-Pr | 4-F-Phenyl | $4\text{-}OCH_3$ | 145–148 |
| 6 | i-Pr | 3,6-dihydro-2H-pyran | $4\text{-}OCH_3$ | 98–100 |
| 7 (Ex. 1) | i-Pr | 4-F-Phenyl | 2,4-di-Cl | 57–60 |
| 8 | i-Pr | 4-F-Phenyl | 2-Cl | 80–83 |
| 9 | i-Pr | 3,6-dihydro-2H-pyran | 3,5-di-Cl | 137–139 |
| 10 | i-Pr | 3,6-dihydro-2H-pyran | $2\text{-}CH_3$ | 143–145 |
| 11 | Et | Et | 3,5-di-Cl | oil* |
| 12 | Et | Et | $4\text{-}OCF_3$ | oil* |
| 13 | i-Pr | 3,6-dihydro-2H-pyran | $4\text{-}OCF_3$ | oil* |
| 14 | i-Pr | 4-F-Phenyl | $2\text{-}OCF_3$ | 129–131 |
| 15 | i-Pr | 4-F-Phenyl | $2\text{-}CF_3$ | 131–134 |
| 16 | i-Pr | 4-F-Phenyl | 2, 5-di-Cl | 120–122 |
| 17 | i-Pr | 4-F-Phenyl | 1, 4-di-Me | 154–156 |
| 18 | i-Pr | 4-F-Phenyl | 2,6-di-Me | 103–105 |
| 19 | i-Pr | 4-F-Phenyl | 2,6-di-Cl | 130–132 |
| 20 | i-Pr | 4-F-Phenyl | $4\text{-}Cl\text{-}2\text{-}CF_3$ | 128–131 |
| 21 | i-Pr | 4-F-Phenyl | 3-Cl-2-Me | 170–172 |
| 22 | i-Pr | 2,4-di-F-Phenyl | 2,4-di-F | 108–110 |
| 23 | Et | c-Hex | 2,4-di-F | oil* |
| 24 | i-Pr | 2,4-di-F-Phenyl | 2,4-di-Me | 103–106 |
| 25 | i-Pr | 2,4-di-F-Phenyl | 2-Me | 85–89 |
| 26 | Et | c-Hex | 2,4-di-Me | 118–120 |
| 27 | Et | c-Hex | 2,6-di-Me | 120–122 |
| 28 | i-Pr | 2,4-di-F-Phenyl | 2,6-di-Me | 129–131 |
| 29 | Et | c-Hex | 2-OMe | 111–114 |
| 30 | i-Pr | 4-F-Phenyl | 2-OMe | 109–111 |
| 31 | i-Pr | 2,4-di-F-Phenyl | 2-OMe | 55–60 |
| 32 | i-Pr | 2,4-di-F-Phenyl | 2,4-di-OMe | 134–137 |

INDEX TABLE A-continued

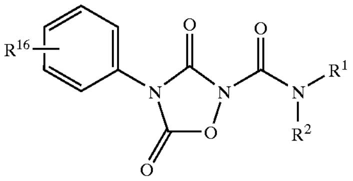

| Cmpd No. | $R^1$ | $R^2$ | $R^{16}$ | MP (° C.) |
|---|---|---|---|---|
| 33 | i-Pr | 4-F-Phenyl | 2,4-di-OMe | 175–177 |
| 34 | i-Pr | 4-F-Phenyl | 2-Et | 94–97 |
| 35 | i-Pr | 4-F-Phenyl | 2-Me-4-OMe | 112–115 |
| 36 | i-Pr | Phenyl | 2-Me | 148–150 |
| 37 | c-Pr | 4-F-Phenyl | 2-Me | oil* |
| 38 | i-Pr | 4-F-Phenyl | H | oil* |
| 39 | i-Pr | $4\text{-}CF_3\text{-}Phenyl$ | 2-Me | 85 |
| 40 | i-Pr | 4-Me-Phenyl | 2-Me | 128 |
| 41 | i-Pr | 4-Cl-Phenyl | 2-Me | 139–141 |
| 42 | i-Pr | 2,4-di-Cl-5-O-i-Pr-Phenyl | 2-Me | 68–70 |
| 43 | i-Pr | 4-F-Phenyl | 2,4-di-Cl-5-O-i-Pr | 148–150 |
| 44 | i-Pr | $4\text{-}NO_2\text{-}Phenyl$ | 2-Me | 148 |
| 45 | i-Pr | 2,4-di-F-Phenyl | 2-Et | 93–97 |
| 46 (Ex. 2) | i-Pr | Phenyl | 2,6-di-Me | 146–148 |
| 47 | i-Pr | 4-Cl-Phenyl | 2,6-di-Me | 143–147 |
| 48 | i-Pr | 3,4-di-F-Phenyl | 2-Me | 124 |
| 49 | i-Pr | 4-OMe-Phenyl | 2-Me | 95 |
| 50 | c-Pr | 2,4-diF-Phenyl | 2-Me | oil* |
| 51 | i-Pr | 4-CN-Phenyl | 2-Me | 205 |
| 52 | i-Pr | 4-F-Phenyl | 2-Et-6-Me | oil* |
| 53 | i-Pr | 4-F-Phenyl | 2-Cl-6-Me | oil* |
| 54 | i-Pr | 4-Cl-Phenyl | 2-Cl-6-Me | oil* |
| 55 | i-Pr | Pyrrolidinyl | 2,4-di-Cl | 120–122 |
| 56 | i-Pr | Pyrrolidinyl | $2\text{-}OCF_3$ | oil* |
| 57 | i-Pr | Pyrrolidinyl | $2\text{-}CF_3$ | 120–122 |
| 58 | i-Pr | Pyrrolidinyl | 2, 5-di-Cl | 139–140 |
| 59 | i-Pr | Pyrrolidinyl | 2-Me | 103–106 |
| 60 | i-Pr | 4-F-Phenyl | 2,4, 6-tri-Me | 181–183 |
| 61 | i-Pr | 4-Cl-Phenyl | 2,4, 6-tri-Me | 121–122 |
| 62 | i-Pr | 4-F-Phenyl | 2-Me-6-OMe | 100–102 |
| 63 | Et | c-Hex | 2,4, 6-tri-Me | 122–123 |
| 64 | i-Pr | 4-Cl-Phenyl | 2-i-Pr, 6-Me | oil* |
| 65 | i-Pr | 4-F-Phenyl | 2-i-Pr, 6-Me | oil* |
| 66 | i-Pr | Phenyl | 2-i-Pr, 6-Me | oil* |
| 67 | i-Pr | 3,5-di-F | 2-Me | 120 |
| 68 | i-Pr | 2, 5-di-F | 2-Me | 98 |
| 69 | i-Pr | Benzyl | 2,6-di-Me | oil* |
| 70 | Et | Benzyl | 2,6-di-Me | oil* |
| 71 | Et | Benzyl | 2-Me | oil* |
| 72 | i-Pr | Benzyl | 2-Me | oil* |
| 73 | i-Pr | Phenyl | 2-OMe, 6-Me | 132–134 |
| 74 | i-Pr | 2,4-di-F-Phenyl | 2-OMe, 6-Me | 107–109 |

*see Index Table B for $^1H$ NMR data.

INDEX TABLE B

| Cmpd No. | $^1H$ NMR Data ($CDCl_3$ solution unless indicated otherwise)[a] |
|---|---|
| 11 | δ 1.25(t, 6H), 3.40(m, 4H), 6.96(s, 1H), 7.55(s, 1H), 8.59(s, 1H). |
| 12 | δ 1.26(t, 6H), 3.58(m, 4H), 7.36(d, 2H), 7.61(d, 2H). |
| 13 | δ 1.33(d, 6H) 2.3–2.4(m, 2H), 3.86(t, 2H), 4.2–4.3(m, 2H), 4.38–4.45(m, 1H), 5.83–5.90 7.38(m, 2H), 7.60(m, 2H). |
| 23 | δ 7.5–7.4(m, 1H), 7.1(t, 2H), 4.2–3.8(m, 1H), 3.5–3.2(m, 2H), 2.0–1.8(m, 3H), 1.8–1.0(m |
| 37 | δ 7.3–7.4(m, 6H), 7.0–7.1(t, 2H), 3.4(m, 1H), 2.21(s, 3H), 0.9(m, 2H), 0.7–0.8(m, 2H). |
| 38 | δ 7.4–7.6(m, 4H), 7.3(m, 1H), 7.0–7.2(m, 2H), 4.7(m, 1H), 1.2(d, 6H). |

INDEX TABLE B-continued

| Cmpd No. | $^1$H NMR Data ($CDCl_3$ solution unless indicated otherwise)[a] |
|---|---|
| 50 | δ 7.3–7.4(m, 4H), 7.2(d, 1H), 6.8–7.0(q, 2H), 3.4(m, 1H), 2.2(s, 3H), 0.9(d, 2H), 0.8(d, |
| 52 | δ 7.2–7.4(m, 3H), 7.0–7.2(m, 4H), 4.7(m, 1H), 2.3–2.4(q, 2H), 2.1(s, 3H), 1.2(d, 6H), 1. (t, 3H). |
| 53 | δ 7.3(m, 3H), 7.2(m, 2H), 7.1(t, 2H), 4.6–4.7(m, 1H), 2.19(s, 3H), 1.2(d, 6H). |
| 54 | δ 7.3–7.4(q, 4H), 7.2(m, 3H), 4.6–4.7(m, 1H), 2.198(s, 3H), 1.2(d, 6H). |

INDEX TABLE B-continued

| Cmpd No. | $^1$H NMR Data ($CDCl_3$ solution unless indicated otherwise)[a] |
|---|---|
| 69 | δ 7.4–7.1(m, 8H), 4.68(s, 2H), 4.5(bs, 1H), 2.23(s, 6H), 1.27(d, 6H). |
| 70 | δ 7.4–7.1(m, 8H), 4.74(s, 2H), 3.6–3.4(bs, 2H), 2.26(s, 6H), 1.2(m, 3H). |
| 71 | δ 7.5–7.3(m, 9H), 4.74(m, 2H), 3.6–3.4(bm, 2H), 2.30(s, 3H), 1.2(bt, 3H). |
| 72 | δ 7.5–7.1(m, 9H), 4.67(s, 2H), 4.5(bs, 1H), 2.27(s, 3H), 1.28(d, 6H). |

[a]$^1$H NMR data are in ppm downfield from tetramethylsilane. Couplings are designated by (s)-singlet, (d)-doublet, (t)-triplet, (q)-quartet, (m)-multiplet, (dd)-doublet of doublets, (dt)-doublet of triplets, (br s)-broad singlet.

INDEX TABLE C

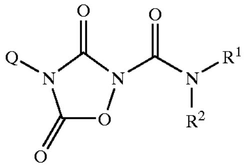

| Cmpd. | Q | $R^1$ | $R^2$ | MP ° C. |
|---|---|---|---|---|
| 75 | 1,3,5-Trimethylpyrazol-4-yl | i-Pr | 4-F-Phenyl | 152–154 |
| 76 | 1,3,5-Trimethylpyrazol-4-yl | i-Pr | 2,4-diF-Phenyl | 45–50 |
| 77 | 2-Thienylmethyl | Et | Et | oil* |
| 78 (Ex. 9) | Benzyl | i-Pr | 4-F-Phenyl | 95–96 |
| 79 | Benzyl | i-Pr | 2,4-diF-Phenyl | 93–95 |
| 80 | 2-Thienylmethyl | i-Pr | 4-F-Phenyl | oil* |
| 81 | 2-Thienylmethyl | i-Pr | 2-Dihydropyranyl | oil* |
| 82 | 2-Thienylmethyl | Et | c-Hexyl | oil* |
| 83 | 2-Thienylmethyl | Me | Phenyl | oil* |
| 84 | 2-Methylbenzyl | Et | Et | oil* |
| 85 | 2-Methylbenzyl | Me | Ph | oil* |
| 86 | 2-Thienylmethyl | i-Pr | 2,4-diF-Ph | 77–80 |
| 87 | 2-Methylbenzyl | i-Pr | 2,4-diF-Phenyl | oil* |
| 88 | 2-Methylbenzyl | i-Pr | 4-F-Phenyl | 118–120 |
| 89 | 5-Tetrahydronaphthyl | Et | Et | oil* |
| 90 | 5-Tetrahydronaphthyl | i-Pr | 4-F-Phenyl | oil* |
| 91 | n-Propyl | i-Pr | 4-F-Phenyl | oil* |
| 92 | n-Propyl | i-Pr | Phenyl | oil* |
| 93 | Allyl | i-Pr | Phenyl | 68–70 |
| 94 | Benzyl | i-Pr | Phenyl | 90–94 |
| 95 | 1,3-Dimethyl-5-chloropyrazol-4-yl | i-Pr | 4-F-Phenyl | 109-112 |
| 96 | 1,3-Dimethyl-5-chloropyrazol-4-yl | i-Pr | 2,4-diF-Phenyl | 55–59 |
| 97 | 1-Methyl-5-chloropyrazol-4-yl | i-Pr | 4-F-Phenyl | 55–60 |
| 98 | 1-Methylpyrazol-4-yl | i-Pr | 4-F-Phenyl | 145–146 |
| 99 | 2-Trifluoromethylcyclohexyl | i-Pr | 4-F-Phenyl | oil* |
| 100 | 3-Phenyl-5-methylisoxazol-4-yl | i-Pr | 4-F-Phenyl | 206–209 |
| 101 | 3-Ethyl-5-methylisoxazol-4-yl | i-Pr | 4-F-Phenyl | oil* |
| 102 | 3-Ethyl-5-ethylisoxazol-4-yl | i-Pr | 4-F-Phenyl | 74–77 |
| 103 | 2-Thienylmethyl | i-Pr | Phenyl | 90–95 |
| 104 | 2-Methoxybenzyl | i-Pr | Phenyl | 115–117 |
| 105 | Allyl | i-Pr | 4-Cl-Phenyl | oil* |
| 106 | Benzyl | i-Pr | 4-Cl-Phenyl | oil* |
| 107 | Ethyl | i-Pr | 4-F-Phenyl | 78–81 |
| 108 | Ethyl | i-Pr | 4-Cl-Phenyl | 83–86 |
| 109 | Isopropyl | i-Pr | 2,4-diF-Phenyl | 82–85 |
| 110 | c-Hexyl | i-Pr | 4-F-Phenyl | 128–131 |
| 111 | c-Hexyl | i-Pr | 4-Cl-Phenyl | 126–130 |
| 112 | c-Hexyl | i-Pr | Phenyl | 136–139 |
| 113 (Ex. 14) | Isopropyl | i-Pr | Phenyl | 82–86 |

INDEX TABLE C-continued

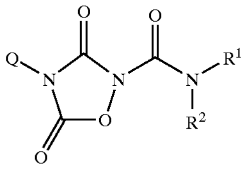

| Cmpd. | Q | $R^1$ | $R^2$ | MP ° C. |
|---|---|---|---|---|
| 114 | Isopropyl | i-Pr | 4-Cl-Phenyl | 76–80 |
| 115 | c-Hexyl | i-Pr | 2,4-diF-Phenyl | 88–90 |
| 116 | Ethyl | i-Pr | 2,4-diF-Phenyl | 75–77 |
| 117 | Ethyl | i-Pr | Phenyl | 74–76 |
| 118 | t-Bu | i-Pr | 4-Cl-Phenyl | 88–90 |
| 119 | n-Pr | i-Pr | 4-Cl-Phenyl | oil* |
| 120 | 1,3,5-Trimethylpyrazol-4-yl | i-Pr | Phenyl | 48–52 |
| 121 | 1,3-Dimethyl-5-chloropyrazol-4-yl | i-Pr | Phenyl | 54–56 |
| 122 | 1-Methyl-5-chloropyrazol-4-yl | i-Pr | Phenyl | 94–97 |
| 123 | 1-Methylpyrazol-4-yl | i-Pr | Phenyl | 111–112 |
| 124 | 1-Methylpyrazol-5-yl | i-Pr | 4-F-Phenyl | 52–59 |
| 125 | 1,4-Dimethylpyrazol-5-yl | i-Pr | 4-F-Phenyl | 45–49 |
| 126 | 3,5-di-Me-isoxazol-4-yl | i-Pr | 2-Dihydropyranyl | oil* |
| 127 | Allyl | c-Pr | 2,4-F-Phenyl | oil* |
| 128 | $CH_2CO_2Et$ | i-Pr | 4-F-Phenyl | oil* |
| 129 | t-Bu | i-Pr | Phenyl | oil* |
| 130 | n-Pr | i-Pr | 2,4-diF-Phenyl | oil* |
| 131 (Ex. 13) | i-Pr | i-Pr | 4-F-Phenyl | 78–80 |
| 132 | i-Pr | i-Pr | 4-Me-Phenyl | 68-71 |
| 133 | α-Me-Benzyl | i-Pr | 4-Cl-Phenyl | oil* |
| 134 | α-Me-Benzyl | i-Pr | 4-F-Phenyl | oil* |
| 135 | 3,5-Diisopropylisoxazol-4-yl | i-Pr | 4-F-Phenyl | oil* |
| 136 (Ex. 5) | 2-Methylbenzyl | i-Pr | 4-Cl-Phenyl | oil* |
| 137 (Ex. 7) | Methyl | i-Pr | 4-Cl-Phenyl | 121–123 |
| 138 (Ex. 6) | Methyl | i-Pr | 4-F-Phenyl | 135–136 |
| 139 | 2-Methylallyl | i-Pr | 4-F-Phenyl | oil* |
| 140 | 2-Chlorobenzyl | i-Pr | 4-F-Phenyl | oil* |
| 141 | 2-Chlorobenzyl | i-Pr | Pyrrolidinyl | oil* |
| 142 | 2-Methoxybenzyl | i-Pr | Pyrrolidinyl | oil* |
| 143 | 2-Methoxybenzyl | i-Pr | 4-F-Phenyl | 104–106 |
| 144 | 2-Chlorobenzyl | i-Pr | 2-Dihydropyrinyl | oil* |
| 145 | 2-Chlorobenzyl | i-Pr | c-Hexenyl | oil* |
| 146 (Ex. 3) | Allyl | i-Pr | 4-F-Phenyl | 65–66 |
| 147 | Allyl | i-Pr | 2-Dihydropyranyl | oil* |
| 148 | 2-Chloroethyl | i-Pr | 4-F-Phenyl | oil* |
| 149 | 2-Chloroethyl | i-Pr | 2-Dihydropyranyl | oil* |
| 150 | Allyl | Et | Pyrrolidinyl | oil* |
| 151 | Allyl | i-Pr | 2,4-diF-Phenyl | oil* |
| 152 | Benzyl | Et | Et | oil* |
| 153 | Benzyl | Me | Phenyl | oil* |
| 154 | Allyl | c-Pr | 4-F-Phenyl | oil* |
| 155 | 3,5-Dimethylisoxazol-4-yl | i-Pr | 4-F-Phenyl | 133–136 |
| 156 | 3,5-Dimethylisoxazol-4-yl | i-Pr | 2,4-diF-Phenyl | 175–178 |
| 157 | 3,5-Dimethylisothiazol-4-yl | i-Pr | 4-F-Phenyl | oil* |
| 158 | 3,5-Dimethylisothiazol-4-yl | i-Pr | 2,4-di-F-Phenyl | 158–161 |
| 159 | 3,5-Dimethylisothiazol-4-yl | i-Pr | 4-Cl-Phenyl | 124–127 |
| 160 | 2, 5-Dichlorothiazoly-4-yl | i-Pr | 4-F-Phenyl | oil* |
| 161 | 2-Me-c-Hex | i-Pr | 4-F-Phenyl | 78–81 |
| 162 | 2-Me-c-Hex | i-Pr | Phenyl | oil* |
| 163 | $CF_3CH_2$ | i-Pr | 4-F-Phenyl | 122–124 |
| 164 | H | i-Pr | 4-F-Phenyl | 55–60 |
| 165 | i-Pr | i-Pr | Benzyl | oil* |
| 166 | i-Pr | Et | Benzyl | oil* |
| 167 | α-Me-Benzyl (S) | i-Pr | 4-F-Phenyl | oil* |
| 168 | α-Me-Benzyl (S) | i-Pr | Phenyl | oil* |
| 169 (Ex. 8) | i-Bu | i-Pr | 4-F-Phenyl | 80–81 |
| 170 (Ex. 4) | NMe2 | i-Pr | 4-F-Phenyl | 69–71 |
| 171 | 2-Methylphenyl | i-Pr | 2, 3-DiF-Phenyl | 88 |
| 172 | 2-Methyl-c-hexyl | i-Pr | 2,4-DiF-Phenyl | oil* |
| 173 | α-Methylbenzyl (S) | i-Pr | Phenyl | 72–74 |
| 174 | α-Methylbenzyl (S) | i-Pr | 4-Cl-Phenyl | oil* |

INDEX TABLE C-continued

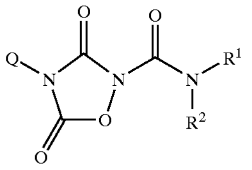

| Cmpd. | Q | $R^1$ | $R^2$ | MP ° C. |
|---|---|---|---|---|
| 175 | 2-Methylphenyl | i-Pr | 4-Br-Phenyl | 117 |
| 176 | 2-Methylphenyl | i-Pr | 2,6-di-F-Phenyl | 91 |
| 177 | Phenyl (Me)N | i-Pr | 4-F-Phenyl | 62–64 |
| 178 | α-Methylbenzyl (R) | i-Pr | 4-Cl-Phenyl | oil* |
| 179 | α-Methylbenzyl (R) | i-Pr | 4-F-Phenyl | 64–67 |
| 180 | 2,6-DiMe-Phenyl | i-Pr | 4, 6-Dimethoxy-1,3,5-Triazine-2-yl | oil* |
| 181 | 2-Me-Phenyl | i-Pr | 4, 6-Dimethoxy-1,3,5-Triazine-2-yl | oil* |
| 182 | i-Propyl | i-Pr | 4, 6-Dimethoxy-1,3,5-Triazine-2-yl | oil* |
| 183 | Phenyl (Me)N | Et | c-Hexyl | oil* |
| 184 | 3-Trifluoromethylcyclohexyl | i-Pr | 4-F-Phenyl | oil* |
| 185 | 2-Methylphenyl | i-Pr | 2,4-DiCl-Phenyl | 54 |
| 186 | 2-Methylphenyl | i-Pr | 2-Cl, 4-F-Phenyl | 48–51 |
| 187 | 2-Methylphenyl | i-Pr | 4-Ph-Phenyl | 63 |
| 188 | Oxiranylmethyl | i-Pr | 4-F-Phenyl | oil* |
| 189 | i-Propyl | Et | 4-Pyridylmethyl | oil* |
| 190 | i-Propyl | Et | 1,3,4-Thiadiazol-2-yl | oil* |
| 191 | (2,4-Dimethylthiazol-5-yl)methyl | i-Pr | 4-Cl-Phenyl | oil* |
| 192 | (2,4-Dimethylthiazol-5-yl)methyl | i-Pr | 4-F-Phenyl | oil* |
| 193 | 2-Methylphenyl | 3-Pentyl | 4-F-Phenyl | 142–145 |
| 194 | Allyl | c-Bu | 4-F-Phenyl | 61–63 |
| 195 | 2-Methylphenyl | i-Pr | 4-Cl, 2-F-Phenyl | 50 |
| 196 | 2,4-Dimethylthiazol-5-yl | i-Pr | 4-Cl-Phenyl | oil* |
| 197 | 2,4-Dimethylthiazol-5-yl | i-Pr | Phenyl | oil* |
| 198 | 2,4-Dimethylthiazol-5-yl | i-Pr | 4-F-Phenyl | oil* |
| 199 | 1-(3-Methyl-3-Butenyl) | i-Pr | 4-F-Phenyl | 77–78 |
| 200 | 2-Methylphenyl | c-Bu | 4-F-Phenyl | 108–110 |
| 201 | 2-Et-6-Me-Phenyl | i-Pr | 4-F-Phenyl | oil* |
| 202 | 4-Trifluoromethoxyphenyl | i-Pr | 4-F-Phenyl | 88–92 |
| 203 | 2-Methylphenyl | i-Pr | 4-Methylsulfonylphenyl | 153 |
| 204 | 2-Methylphenyl | i-Pr | 2-F-Phenyl | 42 |
| 205 | 2-Methylphenyl | i-Pr | 4-Methylthiophenyl | 104 |
| 206 | 2-Furanylmethyl | i-Pr | 4-Cl-Phenyl | oil* |
| 207 | 2-Furanylmethyl | i-Pr | 4-F-Phenyl | oil* |
| 208 | 2-Furanylmethyl | i-Pr | 2,4-diF-Phenyl | oil* |
| 209 | 2-Furanylmethyl | i-Pr | Phenyl | 67–70 |
| 210 | Cinnamyl | i-Pr | 4-F-Phenyl | oil* |
| 211 | 4-Acetoxybutyl | i-Pr | 4-F-Phenyl | 93–95 |
| 212 | Propargyl | i-Pr | 4-F-Phenyl | 74–75 |
| 213 | 3-Trimethylsilylpropargyl | i-Pr | 4-F-Phenyl | oil* |
| 214 | 1-(3-Ethoxycarbonyl-2-Propenyl) | i-Pr | 4-F-Phenyl | oil* |
| 215 | $MeO_2CCH_2$ | i-Pr | 4-F-Phenyl | oil* |
| 216 | $t-BuCOCH_2$ | i-Pr | 4-F-Phenyl | oil* |
| 217 | $MeCOCH_2$ | i-Pr | 4-F-Phenyl | oil* |
| 218 | 1-(3,4,4-Trifluoro-3-Butenyl) | i-Pr | 4-F-Phenyl | oil* |
| 219 | 2-(1,3-Dioxolan-2-yl)ethyl | i-Pr | 4-F-Phenyl | 94–96 |
| 220 | $CH_3OCH_2CH_2OCH_2$ | i-Pr | 4-F-Phenyl | oil* |
| 221 | n-Butyl | i-Pr | 4-F-Phenyl | oil* |
| 222 | 2,4-DiMe-6-OMe-Phenyl | i-Pr | 4-F-Phenyl | oil* |
| 223 | 2,4-DiMe-6-OMe-Phenyl | i-Pr | 2,4-diF-Phenyl | oil* |
| 224 | 2-Br-4, 6-diMe-Phenyl | i-Pr | 4-F-Phenyl | 141–144 |
| 225 | $Me_2N$ | i-Pr | Phenyl | oil* |
| 226 | 3-Methyl-3-oxetanylmethyl | i-Pr | 4-F-Phenyl | 65–77 |
| 227 | 1-(3,3,3-Trifluoro-2-methoximino)propyl | i-Pr | 4-F-Phenyl | 80–105 |
| 228 | Methyl | Et | c-Hex | 65–74 |
| 229 | 2-Methylphenyl | i-Pr | 4-n-Bu-Phenyl | oil* |
| 230 | 2-Methylphenyl | i-Pr | 4-Et-Phenyl | oil* |
| 231 | 2-Methylphenyl | i-Pr | 4-i-Pr-Phenyl | 94 |
| 232 | (2,4-DiMe-Thiazol-5-yl)methyl | i-Pr | 4-F-Phenyl | oil* |
| 233 | (2,4-DiMe-Thiazol-5-yl)methyl | i-Pr | 2,4-diF-Phenyl | oil* |
| 234 | 3-Pyridyl | i-Pr | 4-F-Phenyl | 109–112 |
| 235 | 3-Pyridyl | i-Pr | Phenyl | 116–118 |
| 236 | 2-Methylphenyl | i-Pr | 2-Me-Phenyl | oil* |
| 237 | 2-Methylphenyl | i-Pr | 4-Dimethylamino-Phenyl | 115 |
| 238 | α-Me-Benzyl (R) | i-Pr | 2,4-diF-Phenyl | oil* |
| 239 | 2-Methylphenyl | s-Bu | 4-F-Phenyl | 79–82 |
| 240 | 2-Methylphenyl | 1-c-Pr-ethyl | 4-F-Phenyl | 90–93 |
| 241 | c-Propyl | i-Pr | 4-Cl-Phenyl | oil* |
| 242 | c-Propyl | i-Pr | 4-F-Phenyl | 65–67 |

INDEX TABLE C-continued

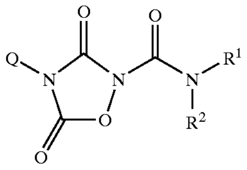

| Cmpd. | Q | $R^1$ | $R^2$ | MP ° C. |
|---|---|---|---|---|
| 243 | c-Propyl | i-Pr | Phenyl | 70–74 |
| 244 | 2,6-DiMe-Phenyl | 1-Ethoxycarbonylethyl | 4-F-Phenyl | 97–99 |
| 245 | $D_3C$ | i-Pr | 4-F-Phenyl | 141–143 |
| 246 | Neopentyl | i-Pr | 4-F-Phenyl | 106–108 |
| 247 | 2-Methylphenyl | 1-Ethoxycarbonylethyl | 4-F-Phenyl | 97–99 |
| 248 | Ethyl | 1-Ethoxycarbonylethyl | 4-F-Phenyl | oil* |
| 249 | Allyl | c-Heptyl | 4-F-Phenyl | 72–79 |
| 250 | 2-Phenethyl | i-Pr | 4-F-Phenyl | 95–96 |
| 251 | c-Propylmethyl | i-Pr | 4-F-Phenyl | oil* |
| 252 | $CH_3CH_2C(O)CH_2$ | i-Pr | 4-F-Phenyl | oil* |
| 253 | n-$C_{19}H_{39}$ | i-Pr | 4-F-Phenyl | oil* |
| 254 | 1-(2-Octynyl) | i-Pr | 4-F-Phenyl | oil* |
| 255 | 2-(1,3-Dioxan-2-yl)ethyl | i-Pr | 4-F-Phenyl | 82–83 |
| 256 | 1-(2-Trimethylsilylmethyl-2-propenyl) | i-Pr | 4-F-Phenyl | oil* |
| 257 | 2-Cyclohexylethyl | i-Pr | 4-F-Phenyl | oil* |
| 258 | $CH_3OCH_2CH_2OCH_2$ | i-Pr | 4-F-Phenyl | 119–120 |
| 259 | (3,5-dimethylisoxazol-4-yl)methyl | i-Pr | 4-F-Phenyl | oil* |
| 260 | PhC(O)CH(Me) | i-Pr | 4-F-Phenyl | oil* |
| 261 | $PhCH_2OCH_2$ | i-Pr | 4-F-Phenyl | 110–112 |
| 262 | Geranyl | i-Pr | 4-F-Phenyl | oil* |
| 263 | 1-(3-Methoxycarbonyl-2-Propenyl) | i-Pr | 4-F-Phenyl | oil* |
| 264 | $Et_2NC(O)CH_2$ | i-Pr | 4-F-Phenyl | oil* |
| 265 | t-$BuO_2CCH_2$ | i-Pr | 4-F-Phenyl | oil* |
| 266 | $MeO_2CCH_2CH_2CH_2$ | i-Pr | 4-F-Phenyl | oil* |
| 267 | 2-Pyridylmethyl | i-Pr | 4-F-Phenyl | oil* |
| 268 | 2-Methylphenyl | i-Pr | 4-Phenoxy-Phenyl | 51 |
| 269 | 2-Methylphenyl | i-Pr | 3-F-Phenyl | 128 |
| 270 | 2-Methylphenyl | i-Pr | 4-t-Bu-Phenyl | oil* |
| 271 | c-Pentyl | i-Pr | 4-F-Phenyl | 79–80 |
| 272 | 3-Thienyl | i-Pr | 4-F-Phenyl | 125–128 |
| 273 | 2,6-DiMe-Phenyl | i-Pr | 2-Cyclohexenyl | 105–112 |
| 274 | $Me_2N$ | Et | c-Hex | oil* |
| 275 | Neopentyl | Et | c-Hex | oil* |
| 276 | Neopentyl | i-Pr | Phenyl | 116–118 |
| 277 | Neopentyl | i-Pr | 2,4-DiF-Phenyl | oil* |
| 278 | 2-Methylphenyl | i-Pr | 5-Indanyl | 115 |
| 279 | Allyl | 1-Ethoxycarbonylethyl | 4-F-Phenyl | oil* |
| 280 | c-Hexyl | 1-Ethoxycarbonylethyl | 4-F-Phenyl | oil* |
| 281 | 2, 3-Dihydro-2-Me-benzofuran-7-yl | i-Pr | 4-F-Phenyl | 148–150 |
| 282 | c-Pentyl | i-Pr | 4-Cl-Phenyl | 104–106 |
| 283 | c-Pentyl | i-Pr | Phenyl | oil* |
| 284 | c-Pentyl | i-Pr | 2,4-DiF-Phenyl | oil* |
| 285 | 1-(3-Chlorobutenyl) | i-Pr | 4-F-Phenyl | oil* |
| 286 | 1-(2-Pentenyl) | i-Pr | 4-F-Phenyl | oil* |
| 287 | 3-Fluoropropyl | i-Pr | 4-F-Phenyl | oil* |
| 288 | 1-(3-Methyl-2-butenyl) | i-Pr | 4-F-Phenyl | oil* |
| 289 | 1-(4-Fluorobutyl) | i-Pr | 4-F-Phenyl | oil* |
| 290 | n-Pentyl | i-Pr | 4-F-Phenyl | oil* |
| 291 | 1-(4-Pentenyl) | i-Pr | 4-F-Phenyl | oil* |
| 292 | Acetoxymethyl | i-Pr | 4-F-Phenyl | oil* |
| 293 (Ex. 15) | Methoxymethyl | i-Pr | 4-F-Phenyl | oil* |
| 294 | Trimethylsilylmethyl | i-Pr | 4-F-Phenyl | oil* |
| 295 | Ethoxymethyl | i-Pr | 4-F-Phenyl | oil* |
| 296 | i-Propyl | i-Pr | 2-Pyrazinyl | oil* |
| 297 | c-Propyl | Et | Et | oil* |
| 298 | c-Propyl | Et | c-Hex | oil* |
| 299 | c-Propyl | i-Pr | 2,4-DiF-Phenyl | 83–85 |
| 300 | 2-Methylphenyl | i-Pr | 4-$CF_3O$-Phenyl | 109 |
| 301 | 2-Methylphenyl | i-Pr | 4-Pyridinyl | 152–154 |
| 302 | i-Propyl | 1-Ethoxycarbonylethyl | 4-F-Phenyl | oil* |
| 303 | 2-t-Bu-6-Me-Phenyl | i-Pr | Phenyl | oil* |
| 304 | 2,6-DiEt-Phenyl | i-Pr | 4-F-Phenyl | oil* |
| 305 | 2,6-DiEt-Phenyl | i-Pr | Phenyl | 77–83 |
| 306 | 2-Methylphenyl | i-Pr | 2-Naphthyl | 49 |
| 307 | Allyl | Et | c-Hex | 62–65 |
| 308 | c-Hexyl | Et | c-Hex | oil* |
| 309 | i-Propyl | Et | c-Hex | oil* |

INDEX TABLE C-continued

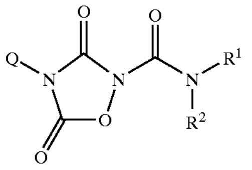

| Cmpd. | Q | $R^1$ | $R^2$ | MP ° C. |
|---|---|---|---|---|
| 310 | 4-Tetrahydropyranyl | i-Pr | 4-F-Phenyl | 101–103 |
| 311 | 2-Tetrahydropyranyl | i-Pr | 4-F-Phenyl | 103–105 |
| 312 | 2-Furanylmethyl | Et | c-Hex | oil* |
| 313 | 2-Biphenylylmethyl | i-Pr | 4-F-Phenyl | 113–126 |
| 314 | 1-(2-Methylthioethyl) | i-Pr | 4-F-Phenyl | 101–106 |
| 315 | 2,6-DiMe-Phenyl | i-Pr | 2-Dihydropyrinyl | 122–124 |
| 316 | 2-(3-Methylbutyl) | i-Pr | 4-F-Phenyl | 62–64 |
| 317 | 1-(2,2-Dimethoxyethyl) | i-Pr | 4-F-Phenyl | oil* |
| 318 | 2,6-DiMe-Phenyl | c-Bu | 2,4-DiCl-Phenyl | 127–131 |
| 319 | i-Propyl | c-Bu | 2,4-DiCl-Phenyl | 103–106 |
| 320 | (5-Cl-1,2,3-thiadiazol-4-yl)methyl | i-Pr | 2,4-DiF-Phenyl | 103–108 |
| 321 | (5-Cl-1,2,3-thiadiazol-4-yl)methyl | i-Pr | Phenyl | 128–131 |
| 322 | Cyclopentylmethyl | i-Pr | 4-F-Phenyl | 83–90 |
| 323 | 1-(3-Dimethylaminopropyl) | i-Pr | 4-F-Phenyl | oil* |
| 324 | 2-Methylphenyl | 2-(3-OMe-propyl) | 4-F-Phenyl | 115–121 |
| 325 | Allyl | 1-c-Pr-ethyl | 4-Cl-Phenyl | oil* |
| 326 | [2.2.1]-Bicyclohept-2-yl | i-Pr | 2,4-DiF-Phenyl | 103–105 |
| 327 | [2.2.1]-Bicyclohept-2-yl | i-Pr | 4-F-Phenyl | 90–94 |
| 328 | [2.2.1]-Bicyclohept-2-yl | i-Pr | Phenyl | 90–91 |
| 329 | 2-Naphthyl | i-Pr | 4-F-Phenyl | 150–151 |
| 330 | 2-Methylphenyl | 1-c-Pr-ethyl | 4-Cl-Phenyl | 111–115 |
| 331 | 2-MeO-6-Me-Phenyl | 1-Ethoxycarbonylethyl | 4-F-Phenyl | oil* |
| 332 | 2-Naphthyl | i-Pr | Phenyl | 134–135 |
| 333 | 2-Naphthyl | i-Pr | 4-Cl-Phenyl | 142–143 |
| 334 | 2-Naphthyl | i-Pr | 4-Me-Phenyl | 172–173 |
| 335 | 2-Naphthyl | i-Pr | 2,4-DiF-Phenyl | oil* |
| 336 | 1-Me-2-Naphthyl | i-Pr | 4-Cl-Phenyl | oil* |
| 337 | 1-Me-2-Naphthyl | i-Pr | 2,4-DiF-Phenyl | oil* |
| 338 | 1-Me-2-Naphthyl | i-Pr | 4-F-Phenyl | oil* |
| 339 | c-Heptyl | i-Pr | 4-Cl-Phenyl | 125–135 |
| 340 | c-Heptyl | i-Pr | 4-F-Phenyl | 104–105 |
| 341 | c-Heptyl | i-Pr | Phenyl | 100–102 |
| 342 | c-Heptyl | i-Pr | 2,4-DiF-Phenyl | 87–90 |
| 343 | 2-Tetrahydrofuranylmethyl | i-Pr | 4-F-Phenyl | 95–96 |
| 344 | 1-Me-2-Naphthyl | i-Pr | Phenyl | oil* |
| 345 | 2-Tetrahydrofuranyl | i-Pr | 4-F-Phenyl | oil* |
| 346 | (3,5-Dimethylpyrazol-1-yl)methyl | i-Pr | Phenyl | 138–148 |
| 347 | (3,5-Dimethylpyrazol-1-yl)methyl | i-Pr | 4-F-Phenyl | 140–144 |
| 348 | c-Butyl | i-Pr | Phenyl | 70–72 |
| 349 | c-Butyl | i-Pr | 4-Cl-Phenyl | 64–68 |
| 350 | c-Butyl | i-Pr | 4-F-Phenyl | 97–100 |
| 351 | c-Butyl | i-Pr | 2,4-diF-Phenyl | 65–67 |
| 352 | $MeOCH_2CH(Me)$ | i-Pr | 2,4-diF-Phenyl | oil* |
| 353 | 3-Pentyl | i-Pr | 2,4-diF-Phenyl | 72–75 |
| 354 | 3-Pentyl | i-Pr | Phenyl | oil* |
| 355 | 2-(3-Methylbutyl) | i-Pr | Phenyl | oil* |
| 356 | 2-(3-Methylbutyl) | i-Pr | 2,4-diF-Phenyl | oil* |
| 357 | $MeOCH_2CH(Me)$ | i-Pr | 2,4-diF-Phenyl | 81–85 |
| 358 | 3-Pentyl | i-Pr | 4-F-Phenyl | oil* |
| 359 | 2-t-Bu-6-Me-Phenyl | i-Pr | 4-F-Phenyl | oil* |
| 360 | 1-(1-Me-c-propyl) | i-Pr | Phenyl | 82–83 |
| 361 | 1-(1-Me-c-propyl) | i-Pr | 4-Cl-Phenyl | oil* |
| 362 | 1-(1-Me-c-propyl) | i-Pr | 4-F-Phenyl | oil* |
| 363 | 1-(1-Me-c-propyl) | i-Pr | 2,4-diF-Phenyl | oil* |
| 364 | 2-Methylphenyl | Et | Et | oil* |
| 365 | Methyl | 1-Ethoxycarbonylethyl | 4-F-Phenyl | oil* |
| 366 | 3-Pyridylmethyl | i-Pr | 4-F-Phenyl | oil* |
| 367 | 2-(3-Chloropropyl) | i-Pr | 4-F-Phenyl | oil* |
| 368 | Methyl | i-Pr | 2,4-diF-Phenyl | oil* |
| 369 | 1-(2-Me-c-propyl) | i-Pr | 4-Cl-Phenyl | oil* |
| 370 | 1-(2-Me-c-propyl) | i-Pr | Phenyl | oil* |
| 371 | 1-(2-Me-c-propyl) | i-Pr | 4-F-Phenyl | 95–97 |
| 372 | 1-(2-Me-c-propyl) | i-Pr | 2,4-diF-Phenyl | oil* |
| 373 | (5-Cl-3-Me-isothiazol-4-yl)methyl | i-Pr | 4-F-Phenyl | 126–129 |
| 374 | (5-Cl-3-Me-isothiazol-4-yl)methyl | i-Pr | Phenyl | 133–136 |
| 375 | 3-Tetrahydrofurylmethyl | i-Pr | 4-F-Phenyl | 84–86 |
| 376 | Chloromethyl | i-Pr | 4-F-Phenyl | 83–86 |
| 377 | H | i-Pr | 4-Cl-Phenyl | 137–138 |

INDEX TABLE C-continued

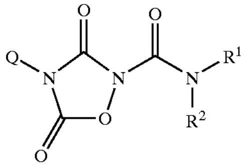

| Cmpd. | Q | $R^1$ | $R^2$ | MP ° C. |
|---|---|---|---|---|
| 378 | (4-Methyl-1,2,3-thiadiazol-5-yl)methyl | i-Pr | Phenyl | 109–113 |
| 379 | (2-Ethoxy-4-$CF_3$-thiazol-5-yl)methyl | i-Pr | Phenyl | oil* |
| 380 | (4-Methyl-1,2,3-thiadiazol-5-yl)methyl | i-Pr | 4-F-Phenyl | 54–55 |
| 381 | (2-Ethoxy-4-$CF_3$-thiazol-5-yl)methyl | i-Pr | 4-F-Phenyl | oil* |
| 382 | 1-(2,6-Dimethylpiperidine) | i-Pr | 4-F-Phenyl | 97–100 |
| 383 | 1-(2,6-Dimethylpiperidine) | i-Pr | 2,4-diF-Phenyl | 81–84 |
| 384 | 4-(Morpholino) | i-Pr | 2,4-diF-Phenyl | 62–68 |
| 385 | 4-(Morpholino) | i-Pr | 4-F-Phenyl | 173–175 |
| 386 | H | i-Pr | Phenyl | 116–117 |
| 387 | 2-(2-Cyanoethyl) | i-Pr | 4-F-Phenyl | oil* |
| 388 | 1-(2-Cyanoethyl) | i-Pr | 4-F-Phenyl | 125–128 |
| 389 | n-Hexyl | i-Pr | 4-F-Phenyl | oil* |
| 390 | 2-(1,3-Difluoropropyl) | i-Pr | 4-F-Phenyl | 99–101 |
| 391 | H | i-Pr | 2,4-diF-Phenyl | 110–112 |
| 392 | Trans-1-(2-Me-c-propyl) | i-Pr | 4-F-Phenyl | 90–91 |
| 393 | 1-(1-Chloroethyl) | i-Pr | 4-F-Phenyl | 70–73 |
| 394 | i-Butyl | i-Pr | 2,4-diF-Phenyl | oil* |
| 395 | Cyanomethyl | i-Pr | 4-F-Phenyl | 120–123 |
| 396 | 1-(2-Ethoxy-3-ethoxycarbonyl-2-propenyl) | i-Pr | 4-F-Phenyl | 112–114 |
| 397 | 1-(3,3,3-trifluoropropyl) | i-Pr | 4-F-Phenyl | 99–100 |
| 398 | 1-(4,4,4-trifluorobutyl) | i-Pr | 4-F-Phenyl | 71–72 |
| 399 | 1-(3,4,4, 4-Tetrafluoro-3-trifluoromethylbutyl) | i-Pr | 4-F-Phenyl | oil* |
| 400 | $CH_3C(O)CH(CH_3)$ | i-Pr | 4-F-Phenyl | oil* |
| 401 | 1-(2-Cl-4-Me-thiazol-5-yl)ethyl | i-Pr | 4-F-Phenyl | oil* |
| 402 | 2-Methyl-c-propylmethyl | i-Pr | 4-F-Phenyl | 81–83 |
| 403 | c-Butylmethyl | i-Pr | 4-F-Phenyl | 74–76 |
| 404 | 1-(c-Propylethyl) | i-Pr | 4-F-Phenyl | 97–99 |
| 405 | 1-(2-Cl-4-Me-thiazol-5-yl)ethyl | i-Pr | 2,4-F-Phenyl | 122–125 |
| 406 | 1-(2-Cl-4-Me-thiazol-5-yl)ethyl | i-Pr | 4-Cl-Phenyl | 128–131 |
| 407 | 1-(2-Cl-4-Me-thiazol-5-yl)ethyl | i-Pr | Phenyl | 128–131 |
| 408 | 2-(3-Chloropropyl) | i-Pr | 2,4-diF-Phenyl | oil* |
| 409 | Methyl | i-Pr | Phenyl | 105–114 |
| 410 | i-Butyl | i-Pr | Phenyl | 55–67 |
| 411 | 2-(3-Chloropropyl) | i-Pr | Phenyl | 95–105 |
| 412 | 1-(2-Butenyl) | i-Pr | 4-F-Phenyl | oil* |
| 413 | 2-(3-Butenyl) | i-Pr | 4-F-Phenyl | oil* |
| 414 | Allyldimethylsilylmethyl | i-Pr | 4-Cl-Phenyl | oil* |
| 415 | 1-(2-Bromoethyl) | i-Pr | Phenyl | 90–92 |
| 416 | 4-Tetrahydropyranyl | i-Pr | Phenyl | 80–93 |
| 417 | i-Butyl | i-Pr | 4-Cl-Phenyl | oil* |
| 418 | 1-(3-Methyl-3-Butenyl) | i-Pr | Phenyl | oil* |
| 419 | 1-(2-Methylthioethyl) | i-Pr | Phenyl | oil* |
| 420 | (3-Methyl-3-oxetanyl)methyl | i-Pr | Phenyl | oil* |
| 421 | 2-(1,3-difluoropropyl) | i-Pr | Phenyl | 95–107 |
| 422 | Chloromethyl | i-Pr | 4-Cl-Phenyl | 75–77 |
| 423 | Chloromethyl | i-Pr | Phenyl | 75–77 |
| 424 | Phenyldimethylsilylmethyl | i-Pr | 4-Cl-Phenyl | oil* |
| 425 | Vinyldimethylsilylmethyl | i-Pr | 4-Cl-Phenyl | oil* |
| 426 | Allyldimethylsilylmethyl | i-Pr | 4-F-Phenyl | oil* |
| 427 | c-Heptyl | i-Pr | 3, 6-dihydro-2H-pyran | oil* |
| 428 | c-Heptyl | i-Pr | 1-Cyclohexenyl | oil* |
| 429 | c-Heptyl | Et | c-Hexyl | oil* |
| 430 | (5,6-Dihydro-1,2-Oxazin-3-yl)methyl | i-Pr | Phenyl | 95–97 |
| 431 | Cyanomethyl | i-Pr | 2,4-diF-Phenyl | 123–126 |
| 432 | 1-(1-Cyanoethyl) | i-Pr | 2,4-diF-Phenyl | oil* |
| 433 | 1-(2-Cyanoethyl) | i-Pr | 2,4-diF-Phenyl | 112–114 |
| 434 | Cyanomethyl | i-Pr | Phenyl | 90–91 |
| 435 | 1-(1-Cyanoethyl) | i-Pr | Phenyl | oil* |
| 436 | 1-(2-Cyanoethyl) | i-Pr | Phenyl | 74–77 |
| 437 | Chloromethyl | i-Pr | 2,4-diF-Phenyl | 69–71 |
| 438 | 1-(1-Chloroethyl) | i-Pr | Phenyl | 73–75 |
| 439 | 1-(1-Methoxyethyl) | i-Pr | 4-F-Phenyl | 77–79 |
| 440 | $Me_2NC(O)CH_2$ | i-Pr | 2,4-diF-Phenyl | 111 |
| 441 | 1-(1-Methoxyethyl) | i-Pr | Phenyl | oil* |
| 442 | 1-(2,4-Dimethylthiazol-5-yl)ethyl | i-Pr | Phenyl | oil* |
| 443 | 1-(2,4-Dimethylthiazol-5-yl)ethyl | i-Pr | 2,4-diF-Phenyl | oil* |
| 444 | 1-(2-Cyanoethyl) | i-Pr | 4-Cl-Phenyl | 139–142 |
| 445 | $PhCONHCH_2$ | i-Pr | 4-F-Phenyl | 161–163 |

INDEX TABLE C-continued

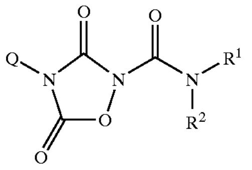

| Cmpd. | Q | $R^1$ | $R^2$ | MP ° C. |
|---|---|---|---|---|
| 446 | 1-(1,2-Dimethoxyethyl) | i-Pr | 4-F-Phenyl | oil* |
| 447 | $(EtO)_2P(O)CH_2$ | i-Pr | Phenyl | oil* |
| 448 | $(EtO)_2P(O)CH(CH_3)$ | i-Pr | Phenyl | oil* |
| 449 | 1-(2-Ethyl-4-methylthiazol-5-yl)ethyl | i-Pr | 4-F-Phenyl | 106–109 |
| 450 | (5,6-Dihydro-1,2-Oxazin-3-yl)methyl | i-Pr | 4-Cl-Phenyl | 105–108 |
| 451 | 1-(1-Cyanoethyl) | i-Pr | 4-Cl-Phenyl | 117–127 |
| 452 | 1-(1-Methoxy-2-propenyl) | i-Pr | 4-F-Phenyl | oil* |
| 453 | 1-(2-Methylsulfonylethyl) | i-Pr | 4-F-Phenyl | oil* |
| 454 | 1-(2-Pentenyl) | i-Pr | Phenyl | oil* |
| 455 | 3-(4-Pentenyl) | i-Pr | Phenyl | oil* |
| 456 | 2-(3-Chloropropyl) | i-Pr | 4-Cl-Phenyl | oil* |
| 457 | Hydroxymethyl | i-Pr | 4-Cl-Phenyl | oil* |
| 458 | 1-(2-Chloro-1-methoxyethyl) | i-Pr | 4-Cl-Phenyl | oil* |
| 459 | Ethyldimethylsilylmethyl | i-Pr | 4-F-Phenyl | 54–55 |
| 460 | Ethyldimethylsilylmethyl | i-Pr | 4-Cl-Phenyl | 68–71 |
| 461 | 1-(3-Trimethylsilylpropyl) | i-Pr | 4-F-Phenyl | oil* |
| 462 | $t\text{-}BuC(O)OCH_2$ | i-Pr | 4-F-Phenyl | 87–90 |
| 463 | $CH_3O_2CCH(CH_3)$ | i-Pr | 2,4-diF-Phenyl | oil* |
| 464 | $CH_3O_2CCH(CH_3)$ | i-Pr | Phenyl | oil* |
| 465 | $EtO_2CCH_2CH(CO_2Et)$ | i-Pr | 2,4-diF-Phenyl | oil* |
| 466 | (3,4-Dihydroisoxazol-3-yl)methyl | i-Pr | 4-F-Phenyl | 93–95 |
| 467 | $Me_3SiCH_2CH_2OCH_2$ | i-Pr | 4-Cl-Phenyl | oil* |
| 468 | 2-(1,3-Difluoropropyl) | i-Pr | 4-Cl-Phenyl | 93–96 |
| 469 | 1-(2-Chloroethyl) | i-Pr | Phenyl | 80–83 |
| 470 | Hydroxymethyl | i-Pr | 4-F-Phenyl | 89–95 |
| 471 | 2-(3, 3-Dimethoxypropyl) | i-Pr | 4-F-Phenyl | 60–63 |
| 472 | 2-(3, 3-Dimethoxypropyl) | i-Pr | 2,4-diF-Phenyl | oil* |
| 473 | $MeCONHCH_2$ | i-Pr | 4-F-Phenyl | 150–168 |
| 474 | 1-(2-Chloroethyl) | i-Pr | 4-Cl-Phenyl | 100–101 |
| 475 | 1-(2-Chloroethyl) | i-Pr | 2,4-diF-Phenyl | 70–72 |
| 476 | Cyanomethyl | i-Pr | 4-Cl-Phenyl | 173–179 |
| 477 | $Me_2NC(O)CH_2$ | i-Pr | 4-Cl-Phenyl | 152–153 |
| 478 | $Me_2NC(O)CH(CH_3)$ | i-Pr | 4-F-Phenyl | oil* |
| 479 | $Me_2NC(O)CH(CH_3)$ | i-Pr | Phenyl | oil* |
| 480 | $Me_2NC(O)CH(CH_3)$ | i-Pr | 4-Cl-Phenyl | 102 |
| 481 | $Me_2NC(O)CH(CH_3)$ | i-Pr | 2,4-diF-Phenyl | oil* |
| 482 | (2-Chlorothiazol-5-yl)methyl | i-Pr | 4-F-Phenyl | 69–70 |
| 483 | 1-(2-nitroethyl) | i-Pr | 4-Cl-Phenyl | 119–122 |
| 484 | $i\text{-}PrC(CO)CH_2$ | i-Pr | 4-F-Phenyl | 79–81 |
| 485 | $i\text{-}PrC(CO)CH_2$ | i-Pr | Phenyl | oil* |
| 486 | $i\text{-}PrC(CO)CH_2$ | i-Pr | 2,4-diF-Phenyl | oil* |
| 487 | $i\text{-}PrC(CO)CH_2$ | i-Pr | 4-Cl-Phenyl | oil* |
| 488 | $c\text{-}PrC(CO)CH_2$ | i-Pr | 4-F-Phenyl | oil* |
| 489 | $c\text{-}PrC(CO)CH_2$ | i-Pr | Phenyl | 87–89 |
| 490 | $c\text{-}PrC(CO)CH_2$ | i-Pr | 2,4-diF-Phenyl | oil* |
| 491 | $HC(O)CH_2$ | i-Pr | 4-F-Phenyl | oil* |
| 492 | $ClCH_2C(O)NHCH_2CH_2$ | i-Pr | Phenyl | oil* |
| 493 | $ClCH_2C(O)NHCH_2CH_2CH_2$ | i-Pr | Phenyl | oil* |
| 494 | (5,6-Dihydro-1,3-oxazin-2-yl)methyl | i-Pr | Phenyl | oil* |
| 495 | (3,4-Dihydrooxazol-2-yl)methyl | i-Pr | Phenyl | oil* |
| 496 | (1-Cyclohexenyl)methyl | i-Pr | Phenyl | oil* |
| 497 | (1-Methyl-1,2,5,6-tetrahydropyridin-3-yl)methyl | i-Pr | Phenyl | oil* |
| 498 | 1-(2-(3-Pyridyl)-2-propenyl) | i-Pr | Phenyl | oil* |
| 499 | 1-(2-Ethyl-4-methylthiazol-5-yl)methyl | i-Pr | 4-Cl-Phenyl | 103–104 |
| 500 | 1-(3-Fluoropropyl) | i-Pr | 2,4-diF-Phenyl | oil* |
| 501 | 2-(1,3-Dioxolan-2-yl)methyl | i-Pr | 2,4-diF-Phenyl | oil* |
| 502 | 2-(1,3-Dioxan-2-yl)ethyl | i-Pr | 2,4-diF-Phenyl | oil* |
| 503 | Methoxymethyl | i-Pr | 2,4-diF-Phenyl | oil* |
| 504 | Ethoxymethyl | i-Pr | 2,4-diF-Phenyl | oil* |
| 505 | $CH_3OCH_2CH_2OCH_2$ | i-Pr | 2,4-diF-Phenyl | oil* |
| 506 | 1-(4-Acetoxybutyl) | i-Pr | 2,4-diF-Phenyl | oil* |
| 507 | 1-(3,4,4-Trifluoro-3-butenyl) | i-Pr | 2,4-diF-Phenyl | oil* |
| 508 | 1-(2-Phenylethyl) | i-Pr | 2,4-diF-Phenyl | oil* |
| 509 | Cyclopropylmethyl | i-Pr | 2,4-diF-Phenyl | oil* |
| 510 | (3,5-Dimethyloxazol-4-yl)methyl | i-Pr | 2,4-diF-Phenyl | oil* |
| 511 | $PhCOCH(CH_3)$ | i-Pr | 2,4-diF-Phenyl | oil* |
| 512 | $Et_2NC(O)CH_2$ | i-Pr | 2,4-diF-Phenyl | oil* |
| 513 | $MeO_2CCH_2CH_2CH_2$ | i-Pr | 2,4-diF-Phenyl | oil* |

INDEX TABLE C-continued

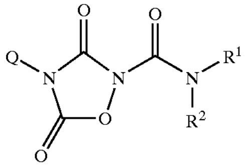

| Cmpd. | Q | $R^1$ | $R^2$ | MP ° C. |
|---|---|---|---|---|
| 514 | 1-(3-Chloro-2-butenyl) | i-Pr | 2,4-diF-Phenyl | oil* |
| 515 | 1-(3-Methyl-2-butenyl) | i-Pr | 2,4-diF-Phenyl | oil* |
| 516 | 1-(4-Pentenyl) | i-Pr | 2,4-diF-Phenyl | oil* |
| 517 | $CH_3C(O)CH(CH_3)$ | i-Pr | 2,4-diF-Phenyl | oil* |
| 518 | Trimethylsilylmethyl | i-Pr | 2,4-diF-Phenyl | oil* |
| 519 | 1-(2-Ethoxy-3-ethoxycarbonyl-2-propenyl) | i-Pr | 2,4-diF-Phenyl | oil* |
| 520 | $PhCH_2OCH_2$ | i-Pr | 2,4-diF-Phenyl | oil* |
| 521 | Cyclobutylmethyl | i-Pr | 2,4-diF-Phenyl | oil* |
| 522 | 1-(4-Fluorobutyl) | i-Pr | 2,4-diF-Phenyl | oil* |
| 523 | 1-(2-Pentenyl) | i-Pr | 2,4-diF-Phenyl | oil* |
| 524 | $CH_3CH_2C(O)CH_2$ | i-Pr | 2,4-diF-Phenyl | oil* |
| 525 | 1-(3,3,3-Trifluoropropyl) | i-Pr | 2,4-diF-Phenyl | oil* |
| 526 | 1-(4,4,4-Trifluorobutyl) | i-Pr | 2,4-diF-Phenyl | oil* |
| 527 | n-Butyl | i-Pr | 4-Cl-Phenyl | oil* |
| 528 | n-Pentyl | i-Pr | 4-Cl-Phenyl | oil* |
| 529 | n-Hexyl | i-Pr | 4-Cl-Phenyl | oil* |
| 530 | 1-(3-Fluoropropyl) | i-Pr | 4-Cl-Phenyl | oil* |
| 531 | 2-(1,3-Dioxolan-2-yl)ethyl | i-Pr | 4-Cl-Phenyl | oil* |
| 532 | 2-(1,3-Dioxan-2-yl)ethyl | i-Pr | 4-Cl-Phenyl | oil* |
| 533 | Methoxymethyl | i-Pr | 4-Cl-Phenyl | oil* |
| 534 | Ethoxymethyl | i-Pr | 4-Cl-Phenyl | oil* |
| 535 | $CH_3OCH_2CH_2OCH_2$ | i-Pr | 4-Cl-Phenyl | oil* |
| 536 | 1-(4-Acetoxybutyl) | i-Pr | 4-Cl-Phenyl | oil* |
| 537 | 1-(3,4,4-Trifluoro-3-butenyl) | i-Pr | 4-Cl-Phenyl | oil* |
| 538 | 1-(2-Phenylethyl) | i-Pr | 4-Cl-Phenyl | oil* |
| 539 | Cyclopropylmethyl | i-Pr | 4-Cl-Phenyl | oil* |
| 540 | (3,5-Dimethyloxazol-4-yl)methyl | i-Pr | 4-Cl-Phenyl | oil* |
| 541 | $PhCOCH(CH_3)$ | i-Pr | 4-Cl-Phenyl | oil* |
| 542 | $Et_2NC(O)CH_2$ | i-Pr | 4-Cl-Phenyl | oil* |
| 543 | $MeO_2CCH_2CH_2CH_2$ | i-Pr | 4-Cl-Phenyl | oil* |
| 544 | 1-(3-Chloro-2-butenyl) | i-Pr | 4-Cl-Phenyl | oil* |
| 545 | 1-(3-Methyl-2-butenyl) | i-Pr | 4-Cl-Phenyl | oil* |
| 546 | 1-(4-Pentenyl) | i-Pr | 4-Cl-Phenyl | oil* |
| 547 | $CH_3C(O)CH(CH_3)$ | i-Pr | 4-Cl-Phenyl | oil* |
| 548 | Trimethylsilylmethyl | i-Pr | 4-Cl-Phenyl | oil* |
| 549 | 1-(2-Ethoxy-3-ethoxycarbonyl-2-propenyl) | i-Pr | 4-Cl-Phenyl | oil* |
| 550 | Cyclobutylmethyl | i-Pr | 4-Cl-Phenyl | oil* |
| 551 | 1-(4-Fluorobutyl) | i-Pr | 4-Cl-Phenyl | oil* |
| 552 | 1-(2-Pentenyl) | i-Pr | 4-Cl-Phenyl | oil* |
| 553 | $CH_3CH_2C(O)CH_2$ | i-Pr | 4-Cl-Phenyl | oil* |
| 554 | 1-(3,3,3-Trifluoropropyl) | i-Pr | 4-Cl-Phenyl | oil* |
| 555 | 1-(4,4,4-Trifluorobutyl) | i-Pr | 4-Cl-Phenyl | oil* |
| 556 | n-Butyl | i-Pr | Phenyl | oil* |
| 557 | n-Pentyl | i-Pr | Phenyl | oil* |
| 558 | n-Hexyl | i-Pr | Phenyl | oil* |
| 559 | 1-(3-Fluoropropyl) | i-Pr | Phenyl | oil* |
| 560 | 2-(1,3-Dioxolan-2-yl)ethyl | i-Pr | Phenyl | oil* |
| 561 | 2-(1,3-Dioxan-2-yl)ethyl | i-Pr | Phenyl | oil* |
| 562 | Methoxymethyl | i-Pr | Phenyl | oil* |
| 563 | Ethoxymethyl | i-Pr | Phenyl | oil* |
| 564 | $CH_3OCH_2CH_2OCH_2$ | i-Pr | Phenyl | oil* |
| 565 | 1-(4-Acetoxybutyl) | i-Pr | Phenyl | oil* |
| 566 | 1-(3,4,4-Trifluoro-3-butenyl) | i-Pr | Phenyl | oil* |
| 567 | 1-(2-Phenylethyl) | i-Pr | Phenyl | oil* |
| 568 | Cyclopropylmethyl | i-Pr | Phenyl | oil* |
| 569 | (3,5-Dimethyloxazol-4-yl)methyl | i-Pr | Phenyl | oil* |
| 570 | $PhCOCH(CH_3)$ | i-Pr | Phenyl | oil* |
| 571 | $Et_2NC(O)CH_2$ | i-Pr | Phenyl | oil* |
| 572 | $MeO_2CCH_2CH_2CH_2$ | i-Pr | Phenyl | oil* |
| 573 | 1-(3-Chloro-2-butenyl) | i-Pr | Phenyl | oil* |
| 574 | 1-(3-Methyl-2-butenyl) | i-Pr | Phenyl | oil* |
| 575 | 1-(4-Pentenyl) | i-Pr | Phenyl | oil* |
| 576 | $CH_3C(O)CH(CH_3)$ | i-Pr | Phenyl | oil* |
| 577 | Trimethylsilylmethyl | i-Pr | Phenyl | oil* |
| 578 | 1-(2-Ethoxy-3-ethoxycarbonyl-2-propenyl) | i-Pr | Phenyl | oil* |
| 579 | $PhCH_2OCH_2$ | i-Pr | Phenyl | oil* |
| 580 | Cyclobutylmethyl | i-Pr | Phenyl | oil* |
| 581 | 1-(4-Fluorobutyl) | i-Pr | Phenyl | oil* |

INDEX TABLE C-continued

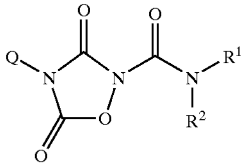

| Cmpd. | Q | $R^1$ | $R^2$ | MP ° C. |
|---|---|---|---|---|
| 582 | 1-(2-Pentenyl) | i-Pr | Phenyl | oil* |
| 583 | $CH_3CH_2C(O)CH_2$ | i-Pr | Phenyl | oil* |
| 584 | 1-(3,3,3-Trifluoropropyl) | i-Pr | Phenyl | oil* |
| 585 | 1-(4,4,4-Trifluorobutyl) | i-Pr | Phenyl | oil* |
| 586 | $Me_2NC(O)CH_2$ | i-pr | 4-F-Phenyl | 117 |
| 587 | $(EtO)_2P(O)CH_2$ | i-Pr | 4-F-Phenyl | oil* |
| 588 | $Me_2NC(O)CH_2$ | i-Pr | Phenyl | 152 |
| 589 | 1-(2-Ethyl-4-methylthiazol-5-yl)ethyl | i-Pr | 2,4-diF-Phenyl | 87–90 |
| 590 | 1-(2-Ethyl-4-methylthiazol-5-yl)ethyl | i-Pr | 4-Cl-Phenyl | 93–97 |
| 591 | 1-(2-Nitroethyl) | i-Pr | 2,4-diF-Phenyl | 92–98 |
| 592 | 1-(1-Methoxyethyl) | i-Pr | 4-Cl-Phenyl | oil* |
| 593 | 1-(1-Methoxyethyl) | i-Pr | 2,4-diF-Phenyl | oil* |
| 594 | 2-(3-Bromopropyl) | i-Pr | 2,4-diF-Phenyl | oil* |
| 595 | 2-(1,3-Difluoropropyl) | i-Pr | 2,4-diF-Phenyl | 91–96 |
| 596 | 2-(3-Acetoxy-1-chloropropyl) | i-Pr | 4-F-Phenyl | oil* |
| 597 | $F_3CC(O)CH_2$ | i-Pr | 4-Cl-Phenyl | oil* |
| 598 | $F_3CC(O)CH_2$ | i-Pr | 2,4-diF-Phenyl | oil* |
| 599 | $(EtO)_2P(O)CH_2$ | i-Pr | 4-Cl-Phenyl | oil* |
| 600 | Allyl | 2-(3-OMe-propyl) | 2,6-DiMe-Phenyl | oil* |
| 601 | (5,6-Dihydro-1,2-Oxazin-3-yl)methyl | i-Pr | 4-F-Phenyl | 108–112 |
| 602 | (5,6-Dihydro-1,2-Oxazin-3-yl)methyl | i-Pr | 2,4-diF-Phenyl | 87–95 |
| 603 | 1-(2-Nitropropyl) | i-Pr | 2,4-diF-Phenyl | oil* |
| 604 | 1-(2-Nitropropyl) | i-Pr | Phenyl | oil* |
| 605 | 1-(2-(6-Chloro-2-pyridyl)-2-propenyl) | i-Pr | Phenyl | oil* |
| 606 | 1-(2-(4-Fluorophenyl)-2-propenyl) | i-Pr | Phenyl | oil* |
| 607 | 1-(2-Methyl-2-propenyl) | i-Pr | Phenyl | oil* |
| 608 | 1-(2-Chlorol-2-propenyl) | i-Pr | Phenyl | oil* |
| 609 | 2-(3-Butynyl) | i-Pr | Phenyl | oil* |
| 610 | s-Butyl (R) | i-Pr | Phenyl | 53–55 |
| 611 | s-Butyl (S) | i-Pr | Phenyl | 55–57 |
| 612 | s-Butyl (S) | i-Pr | Phenyl | 41–43 |
| 613 | s-Butyl (R) | i-Pr | 4-F-Phenyl | 41–43 |
| 614 | $EtO_2CCH_2CH(CO_2Et)$ | i-Pr | Phenyl | oil* |
| 615 | $EtO_2CCH_2CH(CO_2Et)$ | i-Pr | 4-F-Phenyl | oil* |
| 616 | $MeO_2CCH(CH_3)$ | i-Pr | 4-F-Phenyl | oil* |
| 617 | $(EtO)_2P(O)CH(CH_3)$ | i-Pr | 4-F-Phenyl | oil* |
| 618 | Thiocyanatomethyl | i-Pr | 4-F-Phenyl | 125–127 |
| 619 | $PhC(O)NHCH_2$ | i-Pr | 2,4-diF-Phenyl | 120–123 |
| 620 | $PhC(O)NHCH_2$ | i-Pr | Phenyl | 145–146 |
| 621 | $MeC(O)NHCH_2$ | i-Pr | Phenyl | 122–126 |
| 622 | $MeC(O)NHCH_2$ | i-Pr | 2,4-diF-Phenyl | 173–175 |
| 623 | $MeO_2CCH(CH_3)$ | i-Pr | 4-Cl-Phenyl | oil* |
| 624 | (2-Tetrahydropyranyl)methyl | i-Pr | 4-F-Phenyl | 80–82 |
| 625 | $CH_3C(O)N(CH_3)CH_2CH_2$ | i-Pr | 4-F-Phenyl | 112–126 |
| 626 | 1-(2-Fluoroethyl) | i-Pr | 4-F-Phenyl | 95–96 |
| 627 | 1-(2-Methoxyethyl) | i-Pr | 4-F-Phenyl | oil* |
| 628 | 1-(2-Methoxyethyl) | i-Pr | 2,4-diF-Phenyl | 94–97 |
| 629 | 1-(2,2-Diethoxyethyl) | i-Pr | 4-F-Phenyl | oil* |
| 630 | 1-(2,2-Diethoxyethyl) | i-Pr | 2,4-diF-Phenyl | 84–88 |
| 631 | 1-(2-Methoxyethyl) | i-Pr | Phenyl | oil* |
| 632 | 1-(2,2-Diethoxyethyl) | i-Pr | Phenyl | oil* |
| 633 | 1-(2,2-Diethoxyethyl) | i-Pr | 4-Cl-Phenyl | 73–75 |
| 634 | 1-(2-Chloro-2-propenyl) | i-Pr | 2,4-diF-Phenyl | oil* |
| 635 | n-Butyl | i-Pr | 2,4-diF-Phenyl | oil* |
| 636 | n-Pentyl | i-Pr | 2,4-diF-Phenyl | oil* |
| 637 | n-Hexyl | i-Pr | 2,4-diF-Phenyl | oil* |
| 638 | $Me_2NC(O)CH_2CH_2$ | i-Pr | 4-F-Phenyl | 100 |
| 639 | $c-PrC(O)CH_2$ | i-Pr | 4-Cl-Phenyl | oil* |
| 640 | $c-BuC(O)CH_2$ | i-Pr | 4-F-Phenyl | oil* |
| 641 | $c-BuC(O)CH_2$ | i-Pr | Phenyl | 115–117 |
| 642 | $c-BuC(O)CH_2$ | i-Pr | 2,4-diF-Phenyl | oil* |
| 643 | $c-BuC(O)CH_2$ | i-Pr | 4-Cl-Phenyl | oil* |
| 644 | $(EtO)_2P(O)CH(CH_3)$ | i-Pr | 4-Cl-Phenyl | oil* |
| 645 | (2-Chloro-1,3,4-thiadiazol-5-yl)methyl | i-Pr | 2,4-diF-Phenyl | 106–109 |
| 646 | (2-Chloro-1,3,4-thiadiazol-5-yl)methyl | i-Pr | 4-F-Phenyl | 110–112 |
| 647 | 1-(3-Cyanopropyl) | i-Pr | 4-F-Phenyl | oil* |
| 648 | 1-(2-t-Butyl-2-propenyl) | i-Pr | Phenyl | oil* |
| 649 | 1-(2-i-Propyl-2-propenyl) | i-Pr | Phenyl | oil* |

INDEX TABLE C-continued

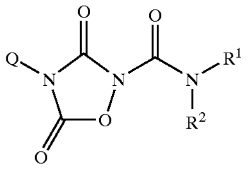

| Cmpd. | Q | $R^1$ | $R^2$ | MP ° C. |
|---|---|---|---|---|
| 650 | 1-(2-Benzyl-2-propenyl) | i-Pr | Phenyl | oil* |
| 651 | 2-(3-Carbomethoxy-3-butenyl) | i-Pr | Phenyl | oil* |
| 652 | 1-(1-Ethynyl-3-methyl-2-butenyl) | i-Pr | Phenyl | oil* |
| 653 | (2-Chloro-1,3,4-thiadiazol-5-yl)methyl | i-Pr | 4-Cl-Phenyl | oil* |
| 654 | (2-Chloro-1,3,4-thiadiazol-5-yl)methyl | i-Pr | Phenyl | oil* |
| 655 | 2-(4-Ethynyl-2-methyl-3-butenyl) | i-Pr | Phenyl | oil* |
| 656 | 2-(5,6-Dihydro-1,2-Oxazin-3-yl)ethyl | i-Pr | 4-F-Phenyl | oil* |
| 657 | 2-(3-Butynyl) | i-Pr | 2,4-diF-Phenyl | oil* |
| 658 | 2-(3-Butynyl) | i-Pr | 4-Cl-Phenyl | oil* |
| 659 | (2-Tetrahydropyranyl)methyl | i-Pr | Phenyl | 97–100 |
| 660 | (2-Tetrahydropyranyl)methyl | i-Pr | 4-Cl-Phenyl | 82–84 |
| 661 | (3,4-Dihydroisoxazol-3-yl)methyl | i-Pr | 4-Cl-Phenyl | 105–107 |
| 662 | $(MeO)_2P(O)CH_2CH_2$ | i-Pr | 4-F-Phenyl | 79–85 |
| 663 | i-Propyl | i-Pr | 4-Pyridyl | 85–89 |
| 664 | s-Butyl (S) | i-Pr | 4-Cl-Phenyl | 53–56 |
| 665 | s-Butyl (R) | i-Pr | 4-Cl-Phenyl | 54–56 |
| 666 | s-Butyl (S) | i-Pr | 2,4-diF-Phenyl | 59–61 |
| 667 | s-Butyl (R) | i-Pr | 2,4-diF-Phenyl | 58–60 |
| 668 | 1-(2-Fluoroethyl) | i-Pr | 4-Cl-Phenyl | 120–121 |
| 669 | 1-(2-Fluoroethyl) | i-Pr | Phenyl | 88–89 |
| 670 | 1-(2-Fluoroethyl) | i-Pr | 2,4-diF-Phenyl | 90–91 |
| 671 | $Me_2NC(O)CH_2CH_2$ | i-Pr | Phenyl | 91 |
| 672 | 2-(1,3-Dichloropropyl) | i-Pr | 4-F-Phenyl | oil* |
| 673 | 1-(2,2-Dichloroethyl) | i-Pr | 2,4-diF-Phenyl | 121–122 |
| 674 | 1-(3-Cyanopropyl) | i-Pr | Phenyl | 89–92 |
| 675 | 1-(3-Cyanopropyl) | i-Pr | 2,4-diF-Phenyl | oil* |
| 676 | (3,4-Dihydroisoxazol-3-yl)methyl | i-Pr | 2,4-diF-Phenyl | 66–68 |
| 677 | $PhCH(CO_2Me)$ | i-Pr | 4-F-Phenyl | oil* |
| 678 | $HOCH_2CH_2CH(CO_2Me)$ | i-Pr | Phenyl | 120–123 |
| 679 | $HOCH_2CH_2CH(CO_2Me)$ | i-Pr | 4-Cl-Phenyl | 107–110 |
| 680 | $HOCH_2CH_2CH(CO_2Me)$ | i-Pr | 4-F-Phenyl | 102–106 |
| 681 | $EtO_2CCH_2CH(CO_2Et)$ | i-Pr | 4-Cl-Phenyl | oil* |
| 682 | (1-Ethyl-5-Chloropyrazol-4-yl)methyl | i-Pr | 2,4-diF-Phenyl | oil* |
| 683 | (1-Ethyl-5-Chloropyrazol-4-yl)methyl | i-Pr | Phenyl | oil* |
| 684 | (1-Ethyl-5-Chloropyrazol-4-yl)methyl | i-Pr | 4-Cl-Phenyl | oil* |
| 685 | (1-Ethyl-5-Chloropyrazol-4-yl)methyl | i-Pr | 4-F-Phenyl | oil* |
| 686 | (1-Ethyl-5-Chloropyrazol-4-yl)methyl | i-Pr | 4-F-Phenyl | oil* |
| 687 | $Me_2NC(O)CH_2CH_2$ | i-Pr | 2,4-diF-Phenyl | oil* |
| 688 | i-Propyl | s-Butyl (S) | 4-F-Phenyl | 59–61 |
| 689 | i-Propyl | s-Butyl | 4-F-Phenyl | 74–75 |
| 690 | i-Propyl | s-Butyl (R) | 4-F-Phenyl | 64–65 |
| 691 | i-Propyl | i-Pr | 4-Br-Phenyl | 75–76 |
| 692 | 3-Cyclohexenyl | i-Pr | 4-F-Phenyl | 80–82 |
| 693 | $HC(O)CH(CH_3)$ | i-Pr | Phenyl | oil* |
| 694 | 3-Cyclohexenyl | i-Pr | 2,4-diF-Phenyl | oil* |
| 695 | 3-Cyclohexenyl | i-Pr | 4-Cl-Phenyl | 87–89 |
| 696 | 3-Cyclohexenyl | i-Pr | Phenyl | oil* |
| 697 | $(MeO)_2P(O)CH_2CH_2$ | i-Pr | Phenyl | oil* |
| 698 | $(MeO)_2P(O)CH_2CH_2$ | i-Pr | 4-Cl-Phenyl | oil* |
| 699 | 1-(Cyclopropyl)ethyl | i-Pr | Phenyl | 65–67 |
| 700 | 1-(Cyclopropyl)ethyl | i-Pr | 4-Cl-Phenyl | 52–54 |
| 701 | 1-(Cyclobutyl)ethyl | i-Pr | 4-Cl-Phenyl | oil* |
| 702 | 1-(Cyclobutyl)ethyl | i-Pr | 2,4-diF-Phenyl | oil* |
| 703 | 1-(Morpholinocarbonyl)ethyl | i-Pr | 4-Cl-Phenyl | 163 |
| 704 | $Me_2NC(S)CH(CH_3)$ | i-Pr | Phenyl | 141 |
| 705 | 1-(Morpholinocarbonyl)ethyl | i-Pr | 4-F-Phenyl | oil* |
| 706 | (3,4-Dihydroisoxazol-3-yl)methyl | i-Pr | Phenyl | oil* |
| 707 | 2-(1-Chloro-3-fluoropropyl) | i-Pr | 4-F-Phenyl | 85–86 |
| 708 | 2-(1-Acetoxy-3-chloropropyl) | i-Pr | 2,4-diF-Phenyl | oil* |
| 709 | Fluoromethyl | i-Pr | 4-F-Phenyl | 126–127 |
| 710 | 2,2-Difluoroethyl | i-Pr | 4-F-Phenyl | 94–96 |
| 711 | 2,2-Difluoroethyl | i-Pr | 2,4-diF-Phenyl | 105–108 |
| 712 | 1-(4-Chlorobutyl) | i-Pr | 4-F-Phenyl | oil* |
| 713 | 1-(3-Chloropropyl) | i-Pr | 4-F-Phenyl | oil* |
| 714 | 1-(2-Chloropropyl) (S) | i-Pr | 2,4-diF-Phenyl | oil* |
| 715 | (2-Tetrahydropyranyl)methyl | i-Pr | 2,4-diF-Phenyl | oil* |
| 716 | (2-Phenyl-1,3,4-oxadiazol-5-yl)methyl | i-Pr | Phenyl | 130–132 |
| 717 | 1-(Cyclobutyl)ethyl | i-Pr | Phenyl | oil* |

INDEX TABLE C-continued

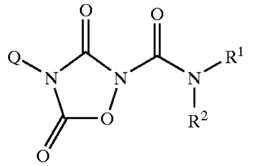

| Cmpd. | Q | $R^1$ | $R^2$ | MP ° C. |
|---|---|---|---|---|
| 718 | 1-(Cyclobutyl)ethyl | i-Pr | 4-F-Phenyl | oil* |
| 719 | $Me_2NC(O)CH_2CH_2$ | i-Pr | 4-Cl-Phenyl | 82–83 |
| 720 | 1-(Cyclopropyl)ethyl | i-Pr | 2,4-diF-Phenyl | oil* |
| 721 | 1-(3,4-Dihydroisoxazol-3-yl)ethyl | i-Pr | 4-F-Phenyl | oil* |
| 722 | (5-Phenyl-1, 2, 5-oxadiazol-2-yl)methyl | i-Pr | Phenyl | 120–121 |
| 723 | $PhCH(CO_2Me)$ | i-Pr | Phenyl | oil* |
| 724 | $PhCH(CO_2Me)$ | i-Pr | 4-Cl-Phenyl | oil* |
| 725 | 1-(2-Chloro-1-methoxyethyl) | i-Pr | 4-Cl-Phenyl | oil* |
| 726 | 1-(1,2-Dimethoxyethyl) | i-Pr | 4-Cl-Phenyl | oil* |
| 727 | $CH_3C(O)NHCH_2CH_2$ | i-Pr | 4-F-Phenyl | oil* |
| 728 | $Me_2NC(S)CH(CH_3)$ | i-Pr | 4-F-Phenyl | 130 |
| 729 | 1-(3,4-Dihydroisoxazol-3-yl)ethyl | i-Pr | Phenyl | oil* |
| 730 | 1-(3,4-Dihydroisoxazol-3-yl)ethyl | i-Pr | 2,4-diF-Phenyl | oil* |
| 731 | 1-(2-(6-Chloro-2-pyridyl)-2-propenyl) | i-Pr | Phenyl | oil* |
| 732 | 1-(2-Carbomethoxy-2-propenyl) | i-Pr | 4-F-Phenyl | oil* |
| 733 | $Me_2NC(S)CH(CH_3)$ | i-Pr | 4-Cl-Phenyl | 136 |
| 734 | 1-(1,2-Dimethoxyethyl) | i-Pr | Phenyl | oil* |
| 735 | 1-(2-Chloro-1-methoxyethyl) | i-Pr | Phenyl | oil* |
| 736 | $(EtO)_2P(O)CH_2$ | i-Pr | 2,4-diF-Phenyl | 113–115 |
| 737 | 1-(2-Chloro-1-methoxyethyl) | i-Pr | 2,4-diF-Phenyl | oil* |
| 738 | 1-(1,2-Dimethoxyethyl) | i-Pr | 2,4-diF-Phenyl | oil* |
| 739 | $Me_2NC(S)CH(CH_3)$ | i-Pr | 2,4-diF-Phenyl | 107 |
| 740 | (5,6-Dihydro-1,2,4-Dioxazin-3-yl)methyl | i-Pr | 4-Cl-Phenyl | 107 |
| 741 | $PhCON(CH_3)CH_2CH_2$ | i-Pr | 4-F-Phenyl | 141–146 |
| 742 | 1-(1-Ethoxypropyl) | i-Pr | 4-F-Phenyl | oil* |
| 743 | Propargyl | i-Pr | 4-F-Phenyl | oil* |
| 744 | 1-(3-Butynyl) | i-Pr | 2,4-diF-Phenyl | oil* |
| 745 | 2,2-Difluoroethyl | i-Pr | 4-Cl-Phenyl | 104–107 |
| 746 | 2,2-Difluoroethyl | i-Pr | Phenyl | oil* |
| 747 | 1-(2-Chloropropyl) (S) | i-Pr | Phenyl | oil* |
| 748 | 1-(2-Chloropropyl) (S) | i-Pr | 4-Cl-Phenyl | oil* |
| 749 | 1-(3-Chloropropyl) | i-Pr | 4-Cl-Phenyl | 68–72 |
| 750 | 1-(3-Chloropropyl) | i-Pr | Phenyl | oil* |
| 751 | s-Butyl | i-Pr | 4-F-Phenyl | 42–44 |
| 752 | 1-(3-Bromo-2-methylpropyl) | i-Pr | 4-F-Phenyl | 96–100 |
| 753 | 3-(4-Pentynyl) | i-Pr | 4-F-Phenyl | oil* |
| 754 | Propargyl | i-Pr | Phenyl | 75–76 |
| 755 | Bromomethyl | i-Pr | Phenyl | 82–84 |
| 756 | 1-(4,5-Dimethylthiazol-2-yl)ethyl | i-Pr | Phenyl | 101–104 |
| 757 | 1-(4,5-Dimethylthiazol-2-yl)ethyl | i-Pr | 4-F-Phenyl | 103–105 |
| 758 | (5,6-Dihydro-1,2,4-Dioxzain-3-yl)methyl | i-Pr | 2,4-diF-Phenyl | oil* |
| 759 | 1-(3,4-Dihydroisoxazol-3-yl)ethyl | i-Pr | 4-Cl-Phenyl | oil* |
| 760 | (5,6-Dihydro-6-OMe-1,2-oxazin-3-yl)methyl | i-Pr | 4-Cl-Phenyl | 107–109 |
| 761 | $PhCON(CH_3)CH_2CH_2$ | i-Pr | Phenyl | 124–127 |
| 762 | $PhCON(CH_3)CH_2CH_2$ | i-Pr | 2,4-diF-Phenyl | 106–108 |
| 763 | 2-(3-Butynyl) | i-Pr | 4-F-Phenyl | oil* |
| 764 | Propargyl | i-Pr | 2,4-diF-Phenyl | oil* |
| 765 | (5,6-Dihydro-1,2,4-Dioxazin-3-yl)methyl | i-Pr | 4-F-Phenyl | oil* |
| 766 | (Dihydro-6-OMe-1,2-oxazin-3-yl)methyl | i-Pr | 4-F-Phenyl | oil* |
| 767 | 1-(3-Butynyl) | i-Pr | 4-F-Phenyl | oil* |
| 768 | 1-(3-Butynyl) | i-Pr | Phenyl | oil* |
| 769 | (5-i-Propyl-1, 2, 5-oxadiazol-2-yl)methyl | i-Pr | Phenyl | oil* |
| 770 | (5-c-Hexyl-1, 2, 5-oxadiazol-2-yl)methyl | i-Pr | Phenyl | 106–108 |
| 771 | i-Propyl | i-Pr | 2-Cl-5-Pyridiyl | oil* |
| 772 | 1-(1-Ethoxypropyl) | i-Pr | 4-Cl-Phenyl | oil* |
| 773 | 1-(1-Ethoxypropyl) | i-Pr | Phenyl | oil* |
| 774 | 1-(1-Ethoxypropyl) | i-Pr | 2,4-diF-Phenyl | oil* |
| 775 | $CH_3O_2CN(CH_3)CH_2CH_2$ | i-Pr | Phenyl | oil* |
| 776 | $(EtO)_2P(O)CH(CH_3)$ | i-Pr | 2,4-diF-Phenyl | oil* |
| 777 | $(CH_3O)_2P(O)CH_2CH_2$ | i-Pr | 2,4-diF-Phenyl | oil* |
| 778 | $CH_3O_2CN(CH_3CH_2CH_2$ | i-Pr | 2,4-diF-Phenyl | oil* |
| 779 | $CH_3O_2CN(CH_3CH_2CH_2$ | i-Pr | 4-Cl-Phenyl | oil* |
| 780 | i-Propyl | i-Pr | 4-OMe-Phenyl | 93–94 |
| 781 | 1-(3-Methyl-3-nitropropyl) | i-Pr | 2,4-diF-Phenyl | 118–120 |
| 782 | 1-(3, 3-Dichloro-2-propenyl) | i-Pr | 4-F-Phenyl | oil* |
| 783 | 3-(4-Pentynyl) | i-Pr | 2,4-diF-Phenyl | oil* |
| 784 | Propargyl | i-Pr | 4-Cl-Phenyl | oil* |
| 785 | 1-(4,5-Dimethylthiazol-2-yl)ethyl | i-Pr | 2,4-diF-Phenyl | oil* |

INDEX TABLE C-continued

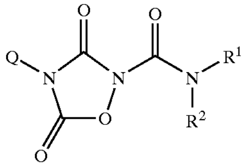

| Cmpd. | Q | $R^1$ | $R^2$ | MP ° C. |
|---|---|---|---|---|
| 786 | Pyrrolidinothiocarbonylmethyl | i-Pr | 2,4-diF-Phenyl | 68 |
| 787 | Pyrrolidinothiocarbonylmethyl | i-Pr | 4-Cl-Phenyl | 144 |
| 788 | Pyrrolidinothiocarbonylmethyl | i-Pr | Phenyl | 117 |
| 789 | Pyrrolidinothiocarbonylmethyl | i-Pr | 4-F-Phenyl | 142 |
| 790 | 2-(3-Methoximinopropyl) | i-Pr | Phenyl | 82–87 |
| 791 | 1-(4-Chlorobutyl) | i-Pr | 4-Cl-Phenyl | 103–109 |
| 792 | 1-(4-Chlorobutyl) | i-Pr | Phenyl | oil* |
| 793 | 4-Cyclohexenyl | i-Pr | 4-F-Phenyl | 107–108 |
| 794 | 1-(2-Bromoethyl) | i-Pr | 4-F-Phenyl | 105–106 |
| 795 | 1-(2-Bromoethyl) | i-Pr | 2,4-diF-Phenyl | 77–80 |
| 796 | 1-(2-Bromoethyl) | i-Pr | 4-Cl-Phenyl | 85–87 |
| 797 | (Pinenyl)methyl | i-Pr | Phenyl | oil* |
| 798 | i-Propyl | i-Pr | (3,5-Dimethylisoxazol-4-yl)methyl | oil* |
| 799 | 1-(2,2-Dimethylcyclopropyl) | i-Pr | 4-F-Phenyl | 69–72 |
| 800 | 1-(2,2-Dimethylcyclopropyl) | i-Pr | Phenyl | oil* |
| 801 | 1-(2,2-Dimethylcyclopropyl) | i-Pr | 4-Cl-Phenyl | oil* |
| 802 | 1-(2,2-Dimethylcyclopropyl) | i-Pr | 2,4-diF-Phenyl | oil* |
| 803 | 3-(4-Pentynyl) | i-Pr | Phenyl | oil* |
| 804 | 1-(3-Butynyl) | i-Pr | 4-Cl-Phenyl | oil* |
| 805 | 2-(1,3-Dibromopropyl) | i-Pr | 4-F-Phenyl | oil* |
| 806 | 1-(3-Bromo-2,2-dimethylpropyl) | i-Pr | 4-F-Phenyl | 122–126 |
| 807 | (5,6-Dihydro-6-methoxy-,2-oxazin-3-yl)methyl | i-Pr | 2,4-diF-Phenyl | 110–115 |
| 808 | 3-(4-Pentynyl) | i-Pr | 4-Cl-Phenyl | oil* |
| 809 | (5,6-Dihydro-6-methoxy-1,2-oxazin-3-yl)methyl | i-Pr | Phenyl | 96–98 |
| 810 | 1-(4,5-Dihydro-5-methoxyisoxazol-3-yl)ethyl | i-Pr | 4-F-Phenyl | oil* |
| 811 | 1-(4,5-Dihydroisoxazol-5-yl)ethyl | i-Pr | 4-F-Phenyl | oil* |
| 812 | 1-(4,5-Dihydro-5-methoxyisoxazol-3-yl)ethyl | i-Pr | Phenyl | oil* |
| 813 | i-Pr | c-$PrCH_2$ | 4-F-Phenyl | 76–77 |
| 814 | 1-(4,5-Dihydroisoxazol-5-yl)ethyl | i-Pr | 4-Cl-Phenyl | oil* |
| 815 | 1-(4,5-Dihydroisoxazol-5-yl)ethyl | i-Pr | 2,4-diF-Phenyl | oil* |
| 816 | 1-(4,5-Dihydroisoxazol-5-yl)ethyl | i-Pr | Phenyl | oil* |
| 817 | 2-(1,1,1-Trifluoropropyl) | i-Pr | 2,4-diF-Phenyl | oil* |
| 818 | 3-(1-Trimethylsilylpropyl) | i-Pr | 4-F-Phenyl | oil |
| 819 | 1-(2,3-Epoxy-2-methylpropyl) (R) | i-Pr | 4-F-Phenyl | oil* |
| 820 | 1-(2,3-Epoxy-2-methylpropyl) (S) | i-Pr | 4-F-Phenyl | 78–80 |
| 821 | $(MeO_2C)_2CH$ | i-Pr | Phenyl | oil |
| 822 | 1-(3-Chloropropyl) | i-Pr | 2,4-diF-Phenyl | oil* |
| 823 | 1-(4-Chlorobutyl) | i-Pr | 2,4-diF-Phenyl | oil* |
| 824 | 2-(3-Chloro-3-methoxypropyl) | i-Pr | Phenyl | oil* |
| 825 | 2-(3-Chloro-3-methoxypropyl) | i-Pr | 4-F-Phenyl | oil* |
| 826 | 1-(2,2-Dichloroethyl) | i-Pr | 4-F-Phenyl | 95–98 |
| 827 | 1-(2-Butynyl) | i-Pr | 2,4-diF-Phenyl | 131–132 |
| 828 | 1-(2-Butynyl) | i-Pr | 4-F-Phenyl | 115–116.5 |
| 829 | i-Pr | i-Pr | (5-t-Butyl-1,2,4-oxadiazol-3-yl)methyl | oil* |
| 830 | 1-(2-Butynyl) | i-Pr | 4-Cl-Phenyl | 24–25 |
| 831 | 1-(2-Cyclopropylethyl) | i-Pr | 4-F-Phenyl | 70–72 |
| 832 | 1-(2-Cyclopropylethyl) | i-Pr | Phenyl | 70–72 |
| 833 | 1-(2-Butynyl) | i-Pr | Phenyl | 90.5–92 |
| 834 | 1-(1,3-Dioxolan-2-yl)ethyl | i-Pr | 4-F-Phenyl | 104–107 |
| 835 | 1-(1,3-Dioxan-2-yl)ethyl | i-Pr | 4-F-Phenyl | 94–96 |
| 836 | 1-(5,5-Dimethyl-1,3-dioxan-2-yl)ethyl | i-Pr | 4-F-Phenyl | 90–93 |
| 837 | 1-(1,3-Dioxepin-5-en-2-yl)ethyl | i-Pr | 4-F-Phenyl | oil* |
| 838 | i-Pr | i-Pr | 2,6-DiF-Phenyl | 80–83 |
| 839 | i-Pr | i-Pr | 2,3-DiF-Phenyl | oil* |
| 840 | i-Pr | Et | 4-F-Phenyl | oil* |
| 841 | 2-(3-Butenyl) | i-Pr | 4-Cl-Phenyl | oil* |
| 842 | 2-(3-Butenyl) | i-Pr | 2,4-diF-Phenyl | oil* |
| 843 | 2-(3-Butenyl) | i-Pr | Phenyl | oil* |
| 844 | 1-(3-Methylenecyclobutane) | i-Pr | 4-F-Phenyl | 60–61 |
| 845 | 1-(3-Methylenecyclobutane) | i-Pr | 2,4-diF-Phenyl | oil* |
| 846 | 1-(3-Methylenecyclobutane) | i-Pr | Phenyl | oil* |
| 847 | 1-(3-Methylenecyclobutane) | i-Pr | 4-Cl-Phenyl | 81–84 |
| 848 | 3-Cyclopentene | i-Pr | 4-F-Phenyl | 71–74 |
| 849 | $HC(O)CH(CH_3)$ | i-Pr | 4-Cl-Phenyl | oil* |
| 850 | $HC(O)CH(CH_3)$ | i-Pr | Phenyl | oil* |
| 851 | (3-Chloro-1-methylpyrazol-4-yl)methyl | i-Pr | 4-F-Phenyl | 105–107 |
| 852 | (3-Chloro-1-methylpyrazol-4-yl)methyl | i-Pr | 4-Cl-Phenyl | oil* |
| 853 | (3-Chloro-1-methylpyrazol-4-yl)methyl | i-Pr | Phenyl | oil* |

INDEX TABLE C-continued

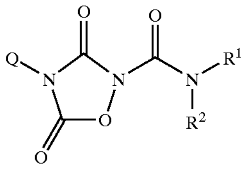

| Cmpd. | Q | $R^1$ | $R^2$ | MP ° C. |
|---|---|---|---|---|
| 854 | (3-Chloro-1-methylpyrazol-4-yl)methyl | i-Pr | 2,4-diF-Phenyl | oil* |
| 855 | (1-Methyl-5-chloro-3-trifluoromethylpyrazol-4-yl)methyl | i-Pr | Phenyl | 152–154 |
| 856 | (1-Methyl-5-chloro-3-trifluoromethylpyrazol-4-yl)methyl | i-Pr | 4-F-Phenyl | 148–149 |
| 857 | (1-Methyl-5-chloro-3-trifluoromethylpyrazol-4-yl)methyl | i-Pr | 2,4-diF-Phenyl | 112–114 |
| 858 | (1-Methyl-5-chloro-3-trifluoromethylpyrazol-4-yl)methyl | i-Pr | 4-Cl-Phenyl | 132–136 |
| 859 | (1-Methyl-4-bromopyrazol-3-yl)methyl | i-Pr | Phenyl | 161–165 |
| 860 | (1-Methyl-4-bromopyrazol-3-yl)methyl | i-Pr | 4-F-Phenyl | 124–132 |
| 861 | 1-(1-Methyl-4-bromopyrazol-3-yl)ethyl | i-Pr | Phenyl | 123–124 |
| 862 | 1-(1-Methyl-4-bromopyrazol-3-yl)ethyl | i-Pr | 4-F-Phenyl | 122–124 |
| 863 | (1-Methyl-4-bromopyrazol-3-yl)methyl | i-Pr | 4-Cl-Phenyl | 147–150 |
| 864 | 1-(1-Methyl-4-bromopyrazol-3-yl)ethyl | i-Pr | 4-Cl-Phenyl | 119–121 |
| 865 | (1-Methyl-4-bromopyrazol-3-yl)methyl | i-Pr | 2,4-diF-Phenyl | 116–117 |
| 866 | 1-(1-Methyl-4-bromopyrazol-3-yl)ethyl | i-Pr | 2,4-diF-Phenyl | oil* |
| 867 | Cyclooctyl | i-Pr | 4-F-Phenyl | 81–84 |
| 868 | i-Pr | 2-(3-MeO-propyl) | Phenyl | 73–77 |
| 869 | i-Pr | 2-(3-MeO-propyl) | 4-F-Phenyl | 119–125 |
| 870 | i-Pr | 2-(3-MeO-propyl) | 4-Cl-Phenyl | 76–81 |
| 871 | 2-(3-Chloro-3-methoxypropyl) | i-Pr | 4-Cl-Phenyl | oil* |
| 872 | 2-(3-Chloro-3-methoxypropyl) | i-Pr | 2,4-diF-Phenyl | oil* |
| 873 | 1-(2,2-Dichloroethyl) | i-Pr | 4-Cl-Phenyl | 80–88 |
| 874 | 1-(2,2-Dichloroethyl) | i-Pr | Phenyl | 95–96 |
| 875 | 1-(2-Chloropropyl) (S) | i-Pr | 4-F-Phenyl | 55-60 |
| 876 | 2-(1,1,1-Trifluoropropyl) | i-Pr | 4-Cl-Phenyl | — |
| 877 | Cyclooctyl | i-Pr | Phenyl | 50–58 |
| 878 | i-Pr | Allyl | Phenyl | 58–60 |
| 879 | Cyclooctyl | i-Pr | 4-Cl-Phenyl | 99–103 |
| 880 | Cyclooctyl | i-Pr | 2,4-diF-Phenyl | 89–93 |
| 881 | $Me_2NC(O)OCH_2CH_2$ | i-Pr | 4-F-Phenyl | 94–96 |
| 882 | 3-(1-Hexynyl) | i-Pr | Phenyl | oil* |
| 883 | i-Pr | $(CD_3)_2CH$ | 4-F-Phenyl | 66–68 |
| 884 | 1-(3-Allyloxy-2-methoximinopropyl) | i-Pr | 4-F-Phenyl | oil* |
| 885 | 1-(3-Allyloxy-2-methoximinopropyl) | i-Pr | Phenyl | oil* |
| 886 | 1-(3-Allyloxy-2-methoximinopropyl) | i-Pr | 2,4-diF-Phenyl | oil* |
| 887 | 1-(3-Allyloxy-2-methoximinopropyl) | i-Pr | 4-Cl-Phenyl | oil* |
| 888 | i-Pr | 2-(1-Chloropropyl) | 4-Cl-Phenyl | oil* |
| 889 | (1,3-Dioxolan-4-yl)methyl | i-Pr | 4-F-Phenyl | 75–78 |
| 890 | (2,2-Dimethyl-1,3-dioxolan-4-yl)methyl | i-Pr | 4-F-Phenyl | 110–113 |
| 891 | (1,3-Dioxolan-4-yl)methyl | i-Pr | Phenyl | 91–96 |
| 892 | 2-Methoxymethylpyrrolidin-1-yl | i-Pr | 4-F-Phenyl | oil* |
| 893 | 1-(3-Methylbutyl) | i-Pr | Phenyl | 63–65 |
| 894 | 1-(3-Methylbutyl) | i-Pr | 4-Cl-Phenyl | 64–66 |
| 895 | 1-(3-Methylbutyl) | i-Pr | 4-F-Phenyl | 88–91 |
| 896 | 1-(3-Methylbutyl) | i-Pr | 2,4-diF-Phenyl | 54–56 |
| 897 | 3-(1-Hexynyl) | i-Pr | 2,4-diF-Phenyl | 63–64 |
| 898 | 1-(1,3-Dioxepin-2-yl)ethyl | i-Pr | 4-F-Phenyl | oil* |
| 899 | (1,3-Dioxolan-2-yl)methyl | i-Pr | 4-F-Phenyl | 84–87 |
| 900 | 1-(3-Benzyloxy-2-methoximinopropyl) | i-Pr | 4-F-Phenyl | oil* |
| 901 | 1-(3-Benzyloxy-2-methoximinopropyl) | i-Pr | Phenyl | oil* |
| 902 | 1-(3-Methoxy-2-methoximinopropyl) | i-Pr | 4-F-Phenyl | oil* |
| 903 | 1-(3-Methoxy-2-methoximinopropyl) | i-Pr | Phenyl | oil* |
| 904 | 1-(3-Methoxy-2-methoximinopropyl) | i-Pr | Phenyl | oil* |
| 905 | i-Pr | 2-(1,1-Dimethoxypropyl) | 4-Cl-Phenyl | oil* |
| 906 | i-Pr | 2-(1-Chloropropyl) | Phenyl | 92–94 |
| 907 | i-Pr | 2-(1-Chloropropyl) | 4-F-Phenyl | 95–97 |
| 908 | i-Pr | 2-(3-Chloropropyl) | Phenyl | oil* |
| 909 | i-Pr | 2-(3-Chloropropyl) | 4-F-Phenyl | oil* |
| 910 | i-Pr | n-Bu | 4-F-Phenyl | 72–73 |
| 911 | i-Pr | n-Pr | 4-F-Phenyl | 63–64 |
| 912 | i-Pr | i-Bu | 4-F-Phenyl | 66–67 |
| 913 | $CH_3C(O)CH_2CH_2$ | i-Pr | Phenyl | oil* |
| 914 | $HC(O)CH_2CH_2$ | i-Pr | 4-F-Phenyl | oil* |
| 915 | $CH_3C(O)CH_2CH_2CH_2$ | i-Pr | 2,4-diF-Phenyl | oil* |
| 916 | $CH_3C(O)CH_2CH_2CH_2$ | i-Pr | 4-Cl-Phenyl | oil* |
| 917 | 3-(1-Hexynyl) | i-Pr | 4-Cl-Phenyl | oil* |
| 918 | i-Pr | 2-(1,1,1-Trifluoropropyl) | Phenyl | 92–94 |
| 919 | i-Pr | 2-(1,1-Dimethoxypropyl) | Phenyl | oil* |
| 920 | i-Pr | 2-(1,1-Dimethoxypropyl) | 4-F-Phenyl | oil* |
| 921 | i-Pr | 1-(1-Cyanoethyl) | 4-F-Phenyl | 80–82 |

INDEX TABLE C-continued

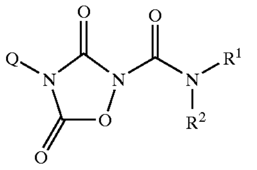

| Cmpd. | Q | $R^1$ | $R^2$ | MP ° C. |
|---|---|---|---|---|
| 922 | 1-(3-Methoxy-2-methoximinopropyl) | i-Pr | 4-Cl-Phenyl | oil* |
| 923 | 1-(3-Methoxy-2-methoximinopropyl) | i-Pr | 2,4-diF-Phenyl | oil* |
| 924 | i-Pr | Allyl | 4-F-Phenyl | 57–59 |
| 925 | i-Pr | c-Hexyl | 4-F-Phenyl | 126–131 |
| 926 | i-Pr | c-Pentyl | 4-F-Phenyl | 93–95 |
| 927 | 3-(Cyclopentene) | i-Pr | 2,4-diF-Phenyl | oil* |
| 928 | 3-(Cyclopentene) | i-Pr | 4-Cl-Phenyl | 100–103 |
| 929 | 3-(Cyclopentene) | i-Pr | Phenyl | oil* |
| 930 | 1-(3-Oxocyclobutyl) | i-Pr | 4-F-Phenyl | oil* |
| 931 | 1-(3-Oxocyclobutyl) | i-Pr | 2,4-diF-Phenyl | 95–97 |
| 932 | 1-(3-Oxocyclobutyl) | i-Pr | Phenyl | 148–150 |
| 933 | 1-(3-Oxocyclobutyl) | i-Pr | 4-Cl-Phenyl | 120–122 |
| 934 | $CH_3C(O)CH_2CH_2$ | i-Pr | 4-F-Phenyl | 94–95 |
| 935 | $CH_3C(O)CH_2CH_2$ | i-Pr | 2,4-diF-Phenyl | oil* |
| 936 | $CH_3C(O)CH_2CH_2$ | i-Pr | 4-Cl-Phenyl | 111–113 |
| 937 | 1-(3-Butenyl) | i-Pr | 4-F-Phenyl | 40–42 |
| 938 | 1-(3-Butenyl) | i-Pr | 2,4-diF-Phenyl | 58–60 |
| 939 | 1-(3-Butenyl) | i-Pr | Phenyl | 43–45 |
| 940 | 1-(3-Butenyl) | i-Pr | 4-Cl-Phenyl | 50–51 |
| 941 | i-Pr | Neopentyl | 4-F-Phenyl | 88–89 |
| 942 | i-Pr | $(CH_3)_3CCH_2CH_2$ | 4-F-Phenyl | 79–80 |
| 943 | 2-(1-Chloro-3-Fluoropropyl) | i-Pr | 4-Cl-Phenyl | 87–90 |
| 944 | 2-(1,3-Dichloropropyl) | i-Pr | 4-Cl-Phenyl | 79–82 |
| 945 | 4-(2,3,5,6-Tetrahydrothiopyranyl) | i-Pr | 4-F-Phenyl | 163–165 |
| 946 | 4-(2,3,5,6-Tetrahydrothiopyranyl) | i-Pr | Phenyl | 145–148 |
| 947 | 4-(2,3,5,6-Tetrahydrothiopyranyl) | i-Pr | 2,4-diF-Phenyl | oil* |
| 948 | 4-(2,3,5,6-Tetrahydrothiopyranyl) | i-Pr | 4-Cl-Phenyl | 153–157 |
| 949 | 3-(2,3,4,5-Tetrahydrothienyl) | i-Pr | 4-F-Phenyl | 67–70 |
| 950 | 2-(1-Chloro-3-Fluoropropyl) | i-Pr | Phenyl | 100–103 |
| 951 | i-Pr | 3-(2,3,4,5-Tetrahydrothienyl) | 4-F-Phenyl | 114–117 |
| 952 | i-Pr | N=CHMe | Phenyl | oil* |
| 953 | i-Pr | $N=CMe_2$ | Phenyl | oil* |
| 954 | $PyrrolidinoC(O)OCH_2CH_2$ | i-Pr | Phenyl | 100–104 |
| 955 | i-Pr | 2-(1,3-DiCl-propyl) | Phenyl | oil* |
| 956 | i-Pr | (2-(1,3-DiCl-propyl) | 4-F-Phenyl | oil* |
| 957 | i-Pr | 3-(2-Me-butyl) | 4-F-Phenyl | 109–110 |
| 958 | c-Pr | $(CD_3)_2CH$ | 4-F-Phenyl | 69–70 |
| 959 | 3-(2-Methyl-4-pentynyl) | i-Pr | Phenyl | oil* |
| 960 | $EtOC(O)OCH_2CH_2$ | i-Pr | 4-F-Phenyl | 105–108 |
| 961 | i-Pr | 3-Pentyl | 4-F-Phenyl | 55–57 |
| 962 | $CH_3C(O)CH_2CH_2CH_2$ | i-Pr | 4-F-Phenyl | oil* |
| 963 | $CH_3C(O)CH_2CH_2CH_2$ | i-Pr | Phenyl | oil* |
| 964 | $HC(O)CH_2CH_2$ | i-Pr | 2,4-diF-Phenyl | oil* |
| 965 | $HC(O)CH_2CH_2$ | i-Pr | Phenyl | oil* |
| 966 | $HC(O)CH_2CH_2$ | i-Pr | 4-Cl-Phenyl | 98–100 |
| 967 | 4-(1-Hexynyl) | i-Pr | 4-F-Phenyl | oil* |

*see Index Table D for $^1H$ NMR data.

INDEX TABLE D

| Cmpd No. | $^1H$ NMR Data ($CDCl_3$ solution unless indicated otherwise)[a] |
|---|---|
| 77 | δ 7.30(d, 1H), 7.20(d, 1H), 6.99(m, 1H), 4.89(s, 2H), 3.50(q, 4H), 1.24(t, 6H). |
| 80 | δ 7.22(m, 4H), 7.09(m, 2H), 6.96(m, 1H), 4.78(s, 2H), 4.42(m, 1H), 1.20(d, 6H). |
| 82 | δ 7.32(d, 1H), 7.20(d, 1H), 7.00(m, 1H), 4.90(s, 2H), 3.95(m, 1H), 3.40(m, 2H), 1.82(m, 4H), 1.70–1.50(m, 2H), 1.40–1.20(m, 7H). |
| 83 | δ 7.3(d, 1H), 7.19(d, 1H), 6.96(m, 1H), 4.88(s, 2H), 4.38(m, 1H), 4.20(s,2H), 3.80(t, 2H) 2.30(br.s, 2H), 1.28(d, 6H). |

INDEX TABLE D-continued

| Cmpd No. | $^1H$ NMR Data ($CDCl_3$ solution unless indicated otherwise)[a] |
|---|---|
| 84 | δ 7.41(d, 1H), 7.10(m, 4H), 4.75(s, 2H), 3.50(q, 4H), 3.45(s, 3H), 1.24(t, 6H). |
| 85 | δ 7.41–7.14(m, 9H), 4.66(s, 2H), 3.44(s, 3H), 2.37 (s, 3H). |
| 87 | δ 7.38(m, 1H), 7.10(m, 4H), 6.92(m, 2H), 4.64(m, 3H), 2.36(s, 3H), 1.10(m, 6H). |
| 90 | δ 7.10(m, 8H), 5.20(m, 1H), 4.60(m, 1H), 2.80(m, 3H), 2.20(m, 2H) 1.20(d, 6H). |
| 91 | δ 7.22(m, 2H), 7.08(m, 2H), 4.62(m, 1H), 3.42(t, 2H), 1.62(m, 2H), 1.20(d, 6H), 0.90(t, 3H). |

INDEX TABLE D-continued

| Cmpd No. | $^1$H NMR Data ($CDCl_3$ solution unless indicated otherwise)[a] |
|---|---|
| 92 | δ 7.40(m, 2H), 7.12(m, 2H), 4.64(m, 1H), 3.42(t, 2H), 1.62(m, 2H), 1.20(d, 6H), 0.90(t, 3H). |
| 99 | δ 7.3(m, 2H), 7.1(m, 2H), 4.7(m, 1H), 4.1(m, 1H), 2.4–2.7(m, 2H), 2.2(m, 1H), 2.0(m, 1H), 1.3–1.8 (m, 5H), 1.2(d, 6H). |
| 101 | δ 6.87(t, 2H), 6.52(dd, 2H), 3.57(m, 1H), 2.91(q, 2H), 2.70(s, 3H), 1.32(t, 3H), 1.19(d, 6H). |
| 105 | δ 7.40(d, 2H), 7.20(d, 2H), 5.80(m, 1H), 5.30(m, 2H), 4.04(d, 2H), 1.20(d, 6H). |
| 106 | δ 7.40–7.08(m, 9H), 4.40(m, 3H), 1.20(d, 6H). |
| 115 | δ 7.40(d, 2H), 7.10(d, 2H), 4.62(m, 1H), 3.42(t, 2H), 1.64(q, 2H), 1.20(d, 6H), 0.92(t, 3H). |
| 126 | δ 5.87(br m, 1H), 4.41(m, 1H), 4.27(m, 2H), 3.86(t, 2H), 2.41(s, 3H), 2.35(br m, 2H), 2.25(s, 3H), 1.32(d, 6H). |
| 127 | δ 7.3(m, 1H), 6.8–7.0(m, 2H), 5.7–5.9(m, 1H), 5.2–5.4(t, 2H), 4.1(d, 2H), 3.3(m, 1H), 1.3(m, 2H), 0.7 (d, 2H). |
| 128 | δ 7.2–7.4(m, 4H), 7.1(t, 2H), 4.8(m, 1H), 4.2(g, 4H), 4.0(s, 2H), 1.3(t, 6H), 1.1(d, 6H). |
| 129 | δ 7.40–7.20(m, 5H), 4.62(m, 1H), 3.42(t, 2H), 1.58(s, 9H), 1.20(d, 6H). |
| 130 | δ 7.38(m, 1H), 6.94(m, 2H), 4.64(m, 1H), 3.43(t, 2H), 1.62(m, 2H), 1.20(m, 6H), 0.90(t, 3H). |
| 133 | δ 7.40–7.18(m, 9H), 5.18(q, 1H), 4.40(m, 1H), 1.80(d, 3H), 1.18(d, 6H). |
| 134 | δ 7.40–7.10(m, 9H), 5.18(q, 1H), 4.42(m, 1H), 1.80(d, 3H), 1.18(d, 6H). |
| 135 | δ 7.27(m, 2H), 7.11(t, 2H), 4.69(m, 1H), 2.92(m, 1H), 2.76(m, 1H), 1.32–1.14(m, 18H). |
| 144 | δ 7.40–7.27(m, 8H), 5.80(s, 1H), 4.86(s, 2H), 4.40(m, 1H), 4.22(s, 2H), 3.80(t, 2H), 2.30(s, 2H), 1.28(d, 6H). |
| 145 | δ 7.40–7.27(m, 4H), 5.80(br.s, 1H), 4.86(s, 2H), 4.30 (m, 1H), 2.38(m, 1H), 2.16(m, 4H), 1.90(m, 1H), 1.70(m, 2H), 1.26(d, 6H). |
| 147 | δ 5.8(m, 2H), 5.38(m, 2H), 4.4(m, 1H), 4.22(s, 2H), 4.08(m, 2H), 3.83(t, 2H), 2.30(br.s, 2H), 1.26(d, 6H). |
| 148 | δ 7.22(m, 2H), 7.10(m, 2H), 4.40(m, 1H), 3.80–3.50(m, 4H), 1.21(d, 6H). |
| 149 | δ 5.72(s, 1H), 4.40(m, 1H), 4.28(s, 2H), 4.16(m, 2H), 7.10(m, 2H), 4.40(m, 1H), 3.80–3.50(m, 4H), 1.21(d, 6H). |
| 150 | δ 5.82(s, 1H), 5.38(m, 2H), 4.18(d, 2H), 3.72(br.s, 2H), 3.54(br.s, 2H), 1.96(br.s, 4H). |
| 151 | δ 7.30(m, 1H), 6.92(m, 2H), 5.80(m, 1H), 5.26(m, 2H), 4.42(m, 1H), 4.06(d, 2H), 1.2(m, 6H). |
| 152 | δ 7.40(m, 5H), 4.71(s, 2H), 3.50(q, 4H), 1.24(t, 6H). |
| 153 | δ 7.31(m, 10H), 4.61(s, 2H), 3.43(s, 3H). |
| 172 | δ 7.40(m, 1H), 6.94(m, 2H), 4.62(m, 1H), 4.02(m, 1H), 3.40(m, 1H), 1.20(m, 6H), 0.78(d, 3H). |
| 174 | δ 7.20–7.40(m, 4H), 5.02(m, 1H), 4.62(m, 1H), 1.80(d, 3H), 1.18(d, 6H). |
| 178 | δ 7.40–7.20(m, 4H), 4.62(m, 1H), 3.40(m, 1H), 1.20(d, 6H), 0.78(d, 3H). |
| 180 | δ 7.3(m, 1H), 7.2–7.1(d, 2H), 5.1–5.0(m, 1H), 3.99(s, 6H), 2.22(s, 6H), 1.46(d, 6H). |
| 181 | δ 7.5–7.1(m, 4H), 5.1–5.0(m, 1H), 4.00(s, 6H), 2.26(s, 3H), 1.5(d, 6H). |
| 182 | δ 5.0(m, 1H), 4.3(m, 1H), 3.97(s, 6H), 1.5–1.4(m, 12H). |
| 183 | δ 7.3(m, 2H), 7.0(m, 1H), 6.8(m, 2H), 3.9(m, 1H), 3.4(m, 5H), 1.9–1.1(m, 13H). |
| 184 | δ 7.2(m, 2H), 7.1(m, 2H), 4.6(m, 1H), 4.1–3.8(m, 1H), 2.2–1.7(m, 9H), 1.2(d, 6H). |
| 188 | δ 7.25(m, 2H), 7.10(m, 2H), 4.65(m, 1H), 3.65(m, 2H), 3.20(m, 1H), 2.80(t, 1H), 2.62(m, 1H), 1.21(d, 6H). |
| 189 | δ 8.6(m, 2H), 7.2(m, 2H), 4.69(s, 2H), 4.3(m, 1H), 3.5(bm, 2H), 1.50(d, 6H), 1.22(t, 3H). |
| 190 | δ 8.97(s, 1H), 4.6(q, 2H), 4.4(m, 1H), 1.5(m, 9H). |
| 191 | δ 7.37(d, 2H), 7.19(d, 2H), 4.70(s, 2H), 4.55–4.67(m, 1H), 2.61(s, 3H), 2.42(s, 3H), 1.20(d, 6H). |
| 192 | δ 7.20–7.25(m, 2H), 7.04–7.10(m, 2H), 4.70(s, 2H), 4.58–4.67(m, 1H), 2.61(s, 3H), 2.42(s, 3H), 1.19(d, 6H). |
| 196 | δ 7.38–7.41(m, 2H), 7.20–7.23(m, 2H), 4.62–4.71 (m, 1H), 2.66(s, 3H), 2.21(s, 3H), 1.23(d, 6H). |
| 197 | δ 7.41–7.43(m, 3H), 7.25–7.28(m, 2H), 4.61–4.74 (m, 1H), 2.65(s, 3H), 2.19(s, 3H), 1.24(d, 6H). |

INDEX TABLE D-continued

| Cmpd No. | $^1$H NMR Data ($CDCl_3$ solution unless indicated otherwise)[a] |
|---|---|
| 198 | δ 7.25–7.28(m, 2H), 7.11(t, 2H), 4.61–4.74(m, 1H), 2.66(s, 3H), 2.21(s, 3H), 1.23(d, 6H). |
| 201 | δ 7.4(m, 3H), 7.2–7.25(m, 3H), 7.1–7.2(t, 2H), 4.6–4.8(m, 1H), 2.3–2.4(q, 2H), 2.07(s, 3H), 1.2(d, 6H), 1.0(t, 3H). |
| 206 | δ 7.40–7.20(m, 5H), 6.40(m, 1H), 6.36(m, 1H), 4.60(m, 3H), 1.20(d, 6H). |
| 207 | δ 7.40(s, 1H) 7.20(m, 2H), 7.18(m, 2H), 4.60(m, 3H), 1.20(d, 6H). |
| 208 | δ 7.40(m, 2H), 6.94(t, 2H), 6.38(m, 1H), 6.36(m, 1H), 4.62(m, 3H), 1.20(d, 6H). |
| 210 | δ 7.29(m, 7H), 7.17(m, 2H), 6.65(d, 1H), 6.1(m, 1H), 4.65(m, 1H), 4.22(d, 2H), 1.2(d, 6H). |
| 213 | δ 7.23(m, 2H), 7.09(m, 2H), 4.65(m, 1H), 4.24(s, 2H), 1.2(d, 6H), 0.14(s, 9H). |
| 214 | δ 7.24(m, 2H), 7.1(m, 2H), 6.75(m, 1H), 5.92(m, 1H), 4.65(m, 1H), 4.2(m, 4H), 1.28(t, 3H), 1.2(d, 6H). |
| 215 | δ 7.23(m, 2H), 7.09(m, 2H), 4.65(m, 1H), 4.21(s, 2H), 3.77(s, 3H), 1.2(d, 6H). |
| 216 | δ 7.27(m, 2H), 7.08(m, 2H), 4.65(m, 1H), 4.38(s, 2H), 1.21(m, 15H). |
| 217 | δ 7.2(m, 2H), 7.1(m, 2H), 4.65(m, 1H), 4.25(s, 2H), 2.22(s, 3H), 1.2(d, 6H). |
| 218 | δ 7.23(m, 2H), 7.11(m, 2H), 4.65(m, 1H), 3.7(t, 2H), 2.65(m, 2H), 1.2(d, 6H). |
| 220 | δ 7.23(m, 2H), 7.09(m, 2H), 4.65(m, 1H), 3.68(m, 4H), 3.55(m, 2H), 3.44(m, 2H), 3.31(s, 3H), 1.2(d, 6H). |
| 221 | δ 7.22(m, 2H), 7.09(m, 2H), 4.65(m, 1H), 3.47(t, 2H), 1.6(m, 2H), 1.3(m, 2H), 1.2(d, 6H), 0.9(t, 3H). |
| 222 | δ 7.40(m, 1H), 6.90(m, 2H), 4.70(m, 1H), 3.71(s, 3H), 2.31(s, 3H), 2.10(s, 3H), 1.20(m, 6H). |
| 223 | δ 7.26(m, 2H), 7.15(m, 4H), 6.70(m, 1H), 2.33(s, 3H), 2.15(s, 3H), 1.20(m, 6H). |
| 225 | δ 7.40(m, 3H), 7.30(m, 2H), 4.65(m, 1H), 2.80(s, 6H), 1.20(s, 6H). |
| 229 | δ 7.20(m, 8H), 4.66(m, 1H), 2.64(t, 2H), 2.13(s, 3H), 1.59(m, 2H), 1.35(m, 2H), 1.23(m, 6H), 0.94(t, 3H). |
| 230 | δ 7.40–7.13(m, 8H), 4.68(m, 1H), 2.69(q, 2H), 2.14 (s, 3H), 1.26(m, 9H). |
| 232 | δ 7.37(m, 3H), 7.20–7.30(m, 2H), 4.68(s, 2H), 4.61 (m, 1H), 2.61(s, 3H), 2.41(s, 3H), 1.20(d, 6H). |
| 233 | δ 7.37(dd, 1H), 6.92(dd, 1H), 4.69(s, 2H), 4.61(m, 1H), 2.61(s, 3H), 2.41(s, 3H), 1.21(d, 6H). |
| 236 | δ 7.28(m, 8H), 4.53(m, 1H), 2.33(s, 3H), 2.20(s, 1.5H), 2.07(s, 1.5H), 1.44(d, 3H), 1.16(d, 3H). |
| 238 | δ 7.40(m, 3H), 5.05(m, 1H), 4.60(m, 1H), 1.80(d, 3H), 1.20(m, 6H). |
| 241 | δ 7.37(d, 2H), 7.19(d, 2H), 4.61(m, 1H), 2.65(m, 1H), 1.119(d, 6H), 0.97(m, 4H). |
| 248 | δ 7.40(m, 2H), 7.05(m, 2H), 4.80(q, 1H), 4.25(q, 2H), 3.55(q, 2H), 1.43(d, 3H), 1.30(m, 12H). |
| 251 | δ 7.23(m, 2H), 7.11(m, 2H), 4.65(m, 1H), 3.34(d, 2H), 1.22(m, 7H), 0.55(m, 2H), 0.35(m, 2H). |
| 252 | δ 7.22(m, 2H), 7.08(m, 2H), 4.65(m, 1H), 4.25(s, 2H), 2.48(q, 2H), 1.19(d, 6H), 1.1(t, 3H). |
| 253 | δ 7.22(m, 2H), 7.08(m, 2H), 4.65(m, 1H), 3.4(m, 4H), 1.9–1.19(m, 34H), 0.88(m, 7H). |
| 254 | δ 7.23(m, 2H), 7.09(m, 2H), 4.65(m, 1H), 4.22(m, 2H), 2.13(m, 2H), 1.45(m, 2H), 1.29(m, 4H), 10.88(m, 3H). |
| 256 | δ 7.2(m, 2H), 7.04(m, 2H), 4.61(m, 3H), 3.88(s, 2H), 1.43(s, 2H), 0.04(m, 9H). |
| 257 | δ 7.23(m, 2H), 7.1(m, 2H), 4.65(m, 1H), 3.46(m, 3H), 1.67–0.9(m, 18H). |
| 258 | δ 7.23(m, 2H), 7.08(m, 2H), 4.98(s, 2H), 4.65(m, 1H), 3.71(m, 2H), 3.45(m, 2H), 3.28(s, 3H), 1.2(d, 6H). |
| 260 | δ 7.75(d, 2H), 7.6(t, 1H), 7.45(t, 2H), 7.2(m, 2H), 7.05(m, 2H), 5.38(q, 1H), 4.65(m, 1H), 1.73(d, 3H), 1.19(d, 6H). |
| 262 | δ 7.23(m, 2H), 7.08(m, 2H), 5.17(m, 1H), 5.02(m, 1H), 4.65(m, 1H), 4.06(d, 2H), 2.02(m, 4H), 11.65(s, 3H), 1.57(s, 3H), 1.19(d, 6H). |
| 263 | δ 7.22(m, 2H), 7.1(m, 2H), 6.75(m, 1H), 6.92(m, 1H), 4.65(m, 1H), 4.22(m, 2H), 3.74(s, 3H), 1.2(d, 6H). |
| 264 | δ 7.22(m, 2H), 7.08(m, 2H), 4.65(m, 1H), 4.07(s, 2H), 3.38(m, 4H), 1.24–1.14(m, 12H). |

INDEX TABLE D-continued

| Cmpd No. | $^1$H NMR Data ($CDCl_3$ solution unless indicated otherwise)[a] |
|---|---|
| 265 | δ 7.23(m, 2H), 7.08(m, 2H), 4.65(m, 1H), 4.09(s, 2H), 1.43(s, 9H), 1.19(d, 6H). |
| 266 | δ 7.21(m, 2H), 7.08(m, 2H), 4.65(m, 1H), 3.66(s, 3H), 3.55(t, 2H), 2.33(t, 2H), 1.96(m, 2H), 1.2( |
| 267 | δ 8.53(m, 1H), 7.76(m, 1H), 7.25(m, 6H), 7.08(t, 2H), 4.76(s, 2H), 4.66(m, 1H), 1.19(d, 6H). |
| 274 | δ 3.90(m, 1H), 3.40(q, 2H), 2.97(s, 6H), 1.50(m, 15H). |
| 275 | δ 3.90(m, 1H), 3.45(m, 4H), 1.70(m, 10H), 1.00(s, 9H), |
| 277 | δ 7.30(m, 1H), 6.90(m, 2H), 4.70(m, 1H), 3.20(s, 2H), 1.20(m, 6H), 0.90(s, 9H). |
| 279 | δ 7.4(m, 2H), 7.05(m, 2H), 5.80(m, 1H), 5.30(m, 1H), 5.25(m, 1H), 4.80(q, 1H), 4.25(m, 2H), 4.6(m, 2H), 1.42(d, 3H), 1.30(m, 6H). |
| 280 | δ 7.4(m, 2H), 7.05(m, 2H), 4.80(q, 1H), 4.25(q, 2H), 3.75(m, 1H), 1.00–2.00(m, 19H). |
| 283 | δ 7.40–7.20(m, 5H), 4.6(m, 1H), 4.10(m, 1H), 1.80(m, 8H), 1.20(d, 6H). |
| 284 | δ 7.40(m, 1H), 6.80(m, 2H), 4.6(m, 1H), 4.10(m, 1H), 1.80(m, 8H), 1.20(d, 6H). |
| 285 | δ 7.23(m, 2H), 7.08(m, 2H), 5.5(t, 1H), 4.65(m, 1H), 4.2(d, 2H), 2.12(s, 3H), 1.2(d, 6H). |
| 286 | δ 7.23(m, 2H), 7.11(m, 2H), 5.8(m, 1H), 5.4(m, 1H), 4.65(m, 1H), 4.0(d, 2H), 2.05(m, 2H), 1.2(d, 6H), 0.96 (t, 3H). |
| 287 | δ 7.21(m, 2H), 7.09(m, 2H), 4.65(m, 1H), 4.54(t, 1H), 4.38(t, 1H), 3.65(t, 2H), 2.05(m, 2H), 1.2(d, 6H). |
| 288 | δ 7.21(m, 2H), 7.08(m, 2H), 5.2(m, 1H), 4.65(m, 1H), 4.05(d, 2H), 1.73(d, 6H), 1.2(d, 6H). |
| 289 | δ 7.23(m, 2H), 7.09(m, 2H), 4.65(m, 1H), 4.52(t, 1H), 4.36(t, 1H), 3.53(t, 1H), 1.8–1.6(m, 4H), 1.2(d, 6H). |
| 290 | δ 7.23(m, 2H), 7.08(m, 2H), 4.65(m, 1H), 3.46(t, 2H), 1.6(m, 2H), 1.3(m, 4H), 1.19(d, 6H), 0.87(t, 3H). |
| 291 | δ 7.22(m, 2H), 7.09(m, 2H), 5.72(m, 1H), 4.99(m, 2H), 4.65(m, 1H), 3.48(t, 2H), 2.05(q, 2H), 1.7 1.2(d, 6H). |
| 292 | δ 7.38–7.35(m, 2H), 7.21–7.18(m, 2H), 4.65(m, 1H), 2.93(s, 2H), 1.2(d, 6H), 0.08(s, 9H). |
| 293 | δ 7.22(m, 2H), 7.09(m, 2H), 4.89(s, 2H), 4.65(m, 1H), 3.39(s, 3H), 1.2(d, 6H). |
| 294 | δ 7.23(m, 2H), 7.08(m, 2H), 4.65(m, 1H), 2.93(s, 2H), 1.2(d, 6H), 0.08(s, 9H). |
| 295 | δ 7.23(m, 2H), 7.09(m, 2H), 4.92(s, 2H), 4.65(m, 1H), 3.58(q, 2H), 1.2(m, 9H). |
| 296 | δ 8.59(s, 1H), 8.51(s, 2H), 4.7(m, 1H), 4.2–4.1(m, 1H), 1.4–1.3(m, 12H). |
| 297 | δ 3.49(m, 1H), 2.77(m, 1H), 1.25(,6H), 1.05(m, 4H). |
| 298 | δ 3.9(m, 1H), 3.41(q, 2H), 2.79(m, 1H), 2–1(m, 17H). |
| 302 | δ 7.4(m, 2H), 7.1(m, 2H), 4.8(m, 1H), 4.3(m, 3H), 1.5–1.2(m, 12H). |
| 303 | δ 7.4(m, 4H), 7.2–7.3(m, 1H), 7.1–7.2(m, 2H), 4.7–4.8(m, 1H), 2.306(s, 3H), 1.3–1.4(m, 9H), 1.2(m, 3H), 1.1(m, 3H). |
| 304 | δ 7.40(t, 1H), 7.26(m, 1H), 7.15(d, 2H), 7.10(m, 2H), 4.70(m, 1H), 2.38(q, 4H), 1.20(d, 6H), 1.10(t, 6H). |
| 308 | δ 3.95(m, 1H), 3.40(m, 1H), 2.10(m, 1H), 1.80(m, 3H), 1.70–1.20(m, 6H). |
| 309 | δ 4.28(m, 1H), 3.80(m, 1H), 3.40(m, 2H), 1.8(m, 2H) 1.25(d, 6H), 1.20(t, 3H). |
| 312 | δ 7.40(m, 1H), 6.42(s, 1H), 6.40(s, 1H), 4.74(s, 2H), 3.84(M, 1H), 3.40(m, 2H), 1.80(4H), 1.20(t, 3H). |
| 317 | δ 7.20(m, 2H), 7.10(m, 2H), 4.70(m, 1H), 3.50(d, 2H), 3.30(s, 6H), 1.20(d, 6H). |
| 323 | δ 7.22(m, 2H), 7.07(m, 2H), 4.6(m, 1H), 3.55(t, 2H), 2.26(t, 2H), 2.11(s, 6H), 1.8(t, 2H), 1.2(d, 6H) |
| 325 | δ 7.4(m, 2H), 7.3(m, 2H), 5.9–5.7(m, 1H), 5.3–5.2(m, 2H), 4.1(d, 2H), 3.7(q, 1H), 1.3(d, 3H), 0.7–0.4(m, 4H), 0.3(m, 1H). |
| 331 | δ 7.4(m, 2H), 7.30(t, 1H), 7.05(t, 2H), 6.95(d, 1H), 6.90(d, 1H), 4.80(q, 1H), 4.25(q, 2H), 3.75(s, 3H), 2.12 (s, 3H), 1.45(s, 3H), 1.30(t, 6H). |
| 335 | δ 8.18(d, 1H), 8.08(d, 1H), 7.82(d, 1H), 7.62–7.44(m, 6H), 7.20(m, 1H), 4.60(m, 1H), 1.20(br.s, 6H) (In DMSO). |
| 336 | δ 8.18–8.00(m, 2H), 7.60–7.43(m, 8H), 4.62(m, 1H), 2.24(s, 3H), 1.20(m, 6H) (in DMSO). |
| 337 | δ 8.14–8.00(m, 2H), 7.60–7.20(m, 7H), 4.62(m, 1H), 2.20(s, 3H), 1.20(s, 6H) (in DMSO). |
| 338 | δ 8.12–8.00(m, 2H), 7.60–7.22(m, 8H), 4.60(m, 1H), 2.24(s, 3H), 1.19(d, 6H) (in DMSO). |
| 344 | δ 8.10–8.00(m, 2H), 7.6–7.22(m, 9H), 4.62(m, 1H), 2.22(s, 3H), 1.20(m, 6H) (in DMSO). |
| 345 | δ 7.40–7.20(m, 4H), 5.60(m, 1H), 5.02(m, 1H), 4.60(m, 1H), 4.00(m, 1H), 3.60(m, 1H), 3.40(m, 1H), 1.20(d, 6H). |
| 352 | δ 7.30(m, 1H), 6.90(m, 2H), 4.65(m, 1H), 4.20(m, 1H), 3.75(t, 1H), 3.40(q, 1H), 3.20(s, 3H), 1.30(d, 3H), 1.20 (m, 6H). |
| 354 | δ |
| 355 | δ 7.30(m, 1H), 6.90(m, 2H), 4.70(m, 1H), 3.60(m, 1H), 2.20(m, 1H), 1.35(s, 3H), 1.20(m, 6H), 0.90(d, 3H), 0.80 (d, 3H). |
| 356 | δ 7.40(m, 3H), 7.28(m, 2H), 4.70(m, 1H), 3.60(m, 1H), 2.20(m, 1H), 1.35(s, 3H), 1.20(d, 6H), 0.90(d, 3H), 0.80 (d, 3H). |
| 358 | δ 7.20(m, 2H), 7.10(m, 2H), 4.70(m, 1H), 1.90(m, 2H), 1.70(m, 2H), 1.20(d, 6H), 0.80(t, 6H). |
| 359 | δ 7.2–7.4(m, 2H), 7.15(m, 2H), 7.0–7.1(t, 3H), 4.7–4.8(m, 1H), 2.308(s, 3H), 1.3–1.4(m, 12H), 1.16(s, 3H). |
| 361 | δ 7.37(d, 2H), 7.18(d, 2H), 4.64(m, 1H), 1.39(s, 3H), 1.19(d, 6H), 1.02(m, 2H), 0.86(m, 2H). |
| 362 | δ 7.24(d, 2H), 7.18(d, 2H), 4.64(m, 1H), 1.39(s, 3H), 1.19(d, 6H), 1.02(m, 2H), 0.86(m, 2H). |
| 363 | δ 7.37(d, 1H), 6.92(m, 2H), 4.64(m, 1H), 1,39(s, 3H), 1.19(d, 6H), 1.02(m, 2H), 0.86(m, 2H). |
| 364 | δ 7.40(m, 3H), 7.28(m, 2H), 4.70(m, 1H), 3.60(m, 1H), 1.90(m, 2H), 1.70(m, 2H), 1.20(d, 6H), 0.80(d, 6H). |
| 365 | δ 7.4(m, 2H), 7.2(m, 2H), 4.8(m, 1H), 4.2(m, 2H), 3.0(s, 3H), 1.4(d, 3H), 1.3(t, 3H). |
| 366 | δ 8.61(m, 2H), 7.70(br d, 1H), 7.27(m, 3H), 7.07(t, 1H), 4.73(m, 1H), 4.62(s, 2H), 1.19(d, 6H). |
| 367 | δ 7.23(m, 2H), 7.11(m, 2H), 4.67(m, 1H), 4.2(m, 1H), 3.93(m, 1H), 3.6(m, 1H), 1.48(d, 3H), 1.18(d, 6H). |
| 369 | δ 7.37(q, 1H), 7.19(d, 2H), 4.64(m, 1H), 2.31(b, 1H), 1.4–0.77(m, 12H). |
| 370 | δ 7.39(m, 3H), 7.24(m, 2H), 4.64(m, 1H), 2.28(m, 1H), 1.3–1(m, 11H), 0.78(m, 1H). |
| 372 | δ 7.37(q, 1H), 6.92(m, 2H), 4.64(m, 1H), 2.31(m, 1H), 1.4–1.0(m, 11H), 0.78(m, 1H). |
| 379 | δ 7.38(m, 3H), 7.22(m, 2H), 4.83(s, 2H), 4.62(m, 1H), 4.46(q, 2H), 1.41(t, 3H), 1.21(d, 6H). |
| 381 | δ 7.22(m, 3H), 7.06(m, 3H), 4.85(s, 2H), 4.63(m, 1H), 4.48(m, 2H), 1.42(t, 3H), 1.19(d, 6H). |
| 387 | δ 7.3(m, 2H), 7.1(m, 2H), 4.93(m, 1H), 4.65(m, 1H), 1.8 (d, 3H), 1.2(d, 6H). |
| 389 | δ 7.23(m, 2H), 7.08(m, 2H), 4.65(m, 1H), 3.46(t, 2H), 1.6(m, 2H), 1.26(m, 6H), 1.2(d, 6H), 0.86(t, 3H). |
| 394 | δ 7.28(m, 1H), 6.91(m, 2H), 4.65(m, 1H), 3.29(d, 2H), 2.11(m, 1H), 1.21(b, 6H), 0.87(D, h) |
| 399 | δ 7.24(m, 2H), 7.1(m, 2H), 4.64(m, 1H), 3.77(m, 2H), 2.45(m, 2H), 1.21(d, 6H). |
| 400 | δ 7.21(m, 2H), 7.09(m, 2H), 4.65(m, 1H), 4.47(q, 1H), 2.19(s, 3H), 1.67(d, 3H), 1.2(d, 6H). |
| 401 | δ 7.05–7.24(m, 4H), 5.37–5.44(m, 1H), 4.58–4.67(m, 1H), 2.33(s, 3H), 1.78(d, 3H), 1.19(d, 6H). |
| 408 | δ 7.27(m, 1H), 6.89(m, 2H), 4.62(m, 1H), 4.2(m, 1H), 3.98(m, 1H), 3.6(m, 1H), 1.45(d, 3H), 1.21(d, 6H). |
| 412 | δ 7.20–7.10(m, 4H), 5.80(m, 1H), 5.40(m, 1H), 4.60 (m, 1H), 4.05(d, 1H), 4.00(d, 1H), 1.70(m, 2H), 1.20(d, 6H). |
| 413 | δ 7.20(m, 2H), 7.10(m, 2H), 6.00(m, 1H), 5.20(m, 2H), 4.60(m, 2H), 1.50(d, 3H), 1.20(d, 6H). |
| 414 | δ 7.36(m, 2H), 7.19(m, 2H), 6.02(m, 2H), 5.69(m, 1H), 4.64(septet, J=6.8Hz, 1H), 2.97(s, 2H), 1.20(d, J=6.8Hz, 8H), 0.17(s, 6H). |
| 417 | δ 7.38(m, 2H), 7.17(m, 2H), 4.65(m, 1H), 3.29(d, 2H), 2.01(m, 1H), 1.21(d, 6H), 0.88(d, 6H). |
| 418 | δ 7.38(m, 2H), 7.25(m, 2H), 4.75(s, 1H), 4.63(m, 1H), 4.6(m, 1H), 3.57(t, 2H), 2.31(t, 2H), 1.71(s, 3H), 1.2(d, 6H). |
| 419 | δ 7.38(m, 2H), 7.25(m, 2H), 4.62(m, 1H), 3.68(t, 2H), 2.73(t, 2H), 2.06(s, 3H), 1.2(d, 6H). |

INDEX TABLE D-continued

| Cmpd No. | $^1$H NMR Data ($CDCl_3$ solution unless indicated otherwise)[a] |
|---|---|
| 420 | δ 7.38(m, 3H), 7.25(m, 2H), 4.53(d, 2H), 4.31(d, 2H), 3.67(s, 3H), 1.27(s, 3H), 1.2(d, 6H). |
| 424 | δ |
| 425 | δ 7.23(m, 2H), 7.08(m, 2H), 6.01(m, 2H), 5.70(dd, J=16.5Hz, J=7.3Hz, 1H), 4.65(septet, J=6.8Hz, 1H), 2.97(s, 2H), 1.19(d, J=6.8Hz, 6H), 0.17(s, 6H). |
| 426 | δ 7.23(m, 2H), 7.05(m, 2H), 5.69(m, 1H), 5.29(s, 2H), 4.85(m, 2H), 4.65(septet, J=6.8Hz, 1H), 2.95(s, 2H), 1.58(d, J=8.1Hz, 2H), 1.19(d, J=6.8Hz, 6H). |
| 427 | δ 5.82(s, 1H), 4.25(m, 1H), 4.20(s, 1H), 4.00(t, 2H), 2.25(s, 1H), 1.20(m, 6H). |
| 428 | δ 5.78(s, 1H), 4.25(m, 1H), 4.00(m, 1H), 2.25(m, 1H), 2.20(m, 4H), 1.20(d, 6H). |
| 429 | δ 4.00(m, 1H), 3.50(m, 2H), 3.00(m, 1H), 2.20(m, 2H), 1.80(m, 4H), 1.20(t, 3H). |
| 432 | δ 7.35(m, 2H), 7.0(m, 1H), 4.9(m, 1H), 4.6(m, 1H), 1.8 (d, 3H), 1.2(br, 6H). |
| 435 | δ 7.4–7.2(m, 5H), 4.9(m, 1H), 4.62(m, 1H), 1.7(d, 3H), 1.2(d, 6H). |
| 441 | δ 7.3(m, 3H), 7.2(m, 3H), 5.0(m, 1H), 4.6(m, 1H), 3.2(s, 3H), 1.6(d, 3H), 1.1(d, 6H). |
| 442 | δ 7.37(m, 3H), 7.20(m, 2H), 5.40(q, 1H), 4.61(m, 1H), 2.62(s, 3H), 2.30(s, 3H), 1.76(d, 3H), 1.20(d, 6H). |
| 443 | δ 7.30(m, 1H), 6.90(t, 2H), 5.40(q, 1H), 4.60(m, 1H), 2.62(s, 3H), 2.32(s, 3H), 1.77(d, 3H), 1.20(m, 6H). |
| 446 | δ 7.2(m, 2H), 7.1(m, 2H), 5.1(m, 1H), 4.7(m, 1H), 3.9 (m, 1H), 3.7(m, 1H), 3.4(s, 3H), 3.3(s, 3H), 1.2(s, 6H). |
| 447 | δ 7.4(m, 3H), 7.3(m, 2H), 4.6(m, 1H), 4.1(m, 4H), 3.8 (d, 2H), 1.2(m, 12H). |
| 448 | δ 7.4(m, 3H), 7.3(m, 2H), 4.6(m, 1H), 4.3(m, 1H), 4.1 (m, 4H), 1.6(m, 6H), 1.2(m, 12H). |
| 452 | δ 7.2(m, 2H), 7.1(m, 2H), 6.1–5.2(m, 3H), 4.7(m, 1H), 3.6(m, 1H), 3.4(s, 3H), 3.4(s, 3H), 1.2(d, 6H). |
| 453 | δ 7.21(m, 2H), 7.08(m, 2H), 4.6(m, 1H), 3.99(t, 2H), 3.36(t, 2H), 2.97(s, 3H), 1.18(d, 6H). |
| 454 | δ 7.39(m, 3H), 7.26(m, 2H), 5.8(m, 1H), 5.38(m, 1H), 4.68(m, 1H), 3.99(d, 2H), 2.0(m, 2H), 1.2(d, 6H), 0.95 (t, 3H). |
| 455 | δ 7.39(m, 3H), 7.26(m, 2H), 6.0(m, 1H), 5.2(dd, 2H), 4.65(m, 1H), 4.2(m, 1H), 1.9(m, 2H), 1.21(d, 6H), 0.83 (t, 3H). |
| 456 | δ 7.39(m, 2H), 7.20(m, 2H), 4.65(m, 1H), 4.2(m, 1H), 3.91(m, 1H), 3.6(dd, 1H), 1.46(d, 3H), 1.21(d, 6H). |
| 457 | δ 7.4(m, 3H), 7.2(m, 2H), 5.0(s, 2H), 4.5–4.0(br, 1H), 1.6(m, 1H), 1.2(d, 6H). |
| 458 | δ 7.3(m, 2H), 7.1(m, 2H), 5.1(m, 1H), 4.7(m, 1H), 4.1(m, 1H), 3.8(m, 1H), 3.4(s, 3H), 1.2(d, 6H). |
| 461 | δ 7.27(m, 2H), 7.11(m, 2H), 4.68(m, 1H), 3.46(t, 2H), 1.64(m, 2H), 1.22(d, 6H), 0.44(m, 2H), 0.00(s, 9H). |
| 463 | δ 7.3–7.4(q, 1H), 6.8–7.0(m, 2H), 4.6–4.7(m, 2H), 3.73(s, 3H), 1.6(d, 3H), 1.2(d, 6H). |
| 464 | δ 7.4(m, 3H), 7.2(m, 2H), 4.6–4.7(m, 2H), 3.727(s, 3H), 1.6(d, 6H), 1.3(d, 3H). |
| 465 | δ 7.3–7.4(m, 1H), 6.8–7.0(m, 2H), 4.6–4.7(m, 1H), 4.1–4.3(m, 3H), 3.5–3.9(m, 1H), 3.0–3.3(m, 1H), 2.2–2.5(m, 1H), 1.2(m, 12H). |
| 467 | δ 7.39(m, 2H), 7.22(m, 2H), 4.93(s, 2H), 4.66(septet, J=6.8Hz, 1H), 3.62(apparent t, J=8.3Hz, 2H), 1.22(d, J=6.8Hz, 6H), 0.93(apparent t, J=8.3Hz, 2H), 0.00(s, 9H). |
| 472 | δ 7.35(m, 1H), 7.00(m, 2H), 4.70(m, 1H), 4.00(m, 1H), 3.38(s, 3H), 3.23(s, 3H), 1.35(d, 3H), 1.20(m, 6H). |
| 478 | δ 1.18(d, 6H), 1.68(d, 3H), 2.95(s, 3H) 2.98(s, 3H), 4.64(m, 1H), 4.83(q, 1H) 7.05(m, 2H), 7.22(m, 2H). |
| 479 | δ 1.20(d, 6H), 1.66(d, 3H), 2.94(s, 3H), 2.96(s, 3H), 4.65(m, 3H), 4.82(q, 1H), 7.21(m, 2H), 7.38(m, 2H). |
| 481 | δ 1.20(m, 6H), 1.68(d, 3H), 2.94(s, 3H), 2.99(s, 3H), 4.64(m, 1H), 4.82(q, 1H), 6.89(m, 2H), 7.33(m, 1H). |
| 485 | δ 7.39(m, 3H), 7.24(m, 2H), 4.64(m, 1H), 4.3(s, 2H), 2.64(m, 1H) 1.21(d, 6H), 1.16(d, 6H). |
| 486 | δ 7.34(q, 1H), 6.93(m, 2H), 4.64(m, 1H), 4.3(s, 2H), 2.64(m, 1H), 1.22(b, 6H), 1.16(d, 6H). |
| 487 | δ 7.37(d, 2H), 7.18(d, 2H), 4.64(m, 1H), 2.65(m, 1H), 1.19(m, 12H). |
| 488 | δ 7.20(m, 2H), 7.09(m, 2H), 4.64(m, 1H), 4.43(s, 2H), 1.92(m, 1H), 1.19(m, 8H), 1.04(m, 2H). |
| 490 | δ 7.34(m, 1H), 6.95(m, 2H), 4.64(m, 1H), 4.42(s, 2H), 1.92(m, 1H), 1.22(m, 8H), 1.03(m, 2H). |
| 491 | δ 9.53(s, 1H), 7.24(m, 2H), 7.1(m, 2H), 4.64(m, 1H), 4.35(s, 2H), 1.2(b, 6H). |
| 492 | δ 7.3–7.2(m, 2H), 7.1(m, 2H), 6.1(bs, 1H), 4.7(m, 1H), 4.14(s, 2H), 3.7–3.6(m, 4H), 1.20(d, 6H). |
| 493 | δ 7.3–7.2(m, 2H), 7.1(m, 2H), 5.9(bs, 1H), 4.7–4.6(m, 1H), 4.09(s, 2H), 3.6–3.5(t, 2H), 3.5(dt, 2H), 2.0(m, 2H), 1.20(d, 6H). |
| 494 | δ 7.4(m, 3H), 7.3–7.2(m, 2H), 4.7(m, 1H), 4.14(t, 2H), 4.02(s, 2H), 3.3(t, 2H), 1.9–1.8(m, 2H), 1.21(d, 6H). |
| 495 | δ 7.4(m, 3H), 7.3–7.2(m, 2H), 4.7–4.6(m, 1H), 4.3(t, 2H), 4.24(s, 2H), 3.9–3.8(t, 2H), 1.21(d, 6H). |
| 496 | δ 7.4–7.3(m, 3H), 7.2–7.1(m, 2H), 5.6(bs, 1H), 4.7–4.6(m, 1H), 3.9(s, 2H), 2.0(bs, 2H), 1.9(bs, 2H), 1.6–1.4(m, 4H), 1.2(d, 6H). |
| 497 | δ 7.3(m, 3H), 7.2(m, 2H), 5.8(s, 1H), 4.7–4.6(m, 1H), 3.94(s, 2H), 2.7(m, 2H), 2.4(m, 2H), 2.2(b, 2H), 1.2(d, 6H). |
| 498 | δ 8.7–8.6(bs, 1H), 8.5(bs, 1H), 7.7(m, 1H), 7.4–7.2(m, 6H), 5.5(s, 1H), 5.3(s, 1H), 4.7–4.6(m, 1H), 4.45(s, 2H), 1.2(d, 6H). |
| 500 | δ 7.3(m, 1H), 6.9(m, 2H), 4.64(m, 1H), 4.48(d of t, 2H), 3.65(t, 2H), 2.42(m, 2H), 1.2(m, 6H). |
| 501 | δ 7.3(m, 1H), 6.9(m, 2H), 4.87(m, 1H), 4.64(m, 1H), 3.86(m, 2H), 3.77(m, 2H), 3.64(t, 2H), 2.05(m, 2H), 1.2 (m, 6H). |
| 502 | δ 7.4(m, 1H), 6.9(m, 2H), 4.64(m, 1H), 4.57(m, 1H), 3.97(m, 2H), 3.63(m, 4H), 1.97(m, 3H), 1.2(m, 7H). |
| 503 | δ 7.3(m, 1H), 6.9(m, 2H), 4.88(s, 2H), 4.64(m, 1H), 3.93(s, 3H), 1.2(m, 6H). |
| 504 | δ 7.4(m, 1H), 6.9(m, 2H), 4.92(s, 2H), 4.65(m, 1H), 3.59(q, 2H), 1.2(m, 9H). |
| 505 | δ 7.4(m, 1H), 6.9(m, 2H), 4.97(s, 2H), 4.63(m, 1H), 3.72(m, 2H), 3.45(m, 2H), 3.30(s, 3H), 1.2(m, 6H). |
| 506 | δ 7.4(m, 1H), 6.9(m, 2H), 4.63(m, 1H), 4.05(m, 2H), 3.51(m, 2H), 2.04(s, 3H), 1.67(m, 4H), 1.2(m, 6H). |
| 507 | δ 7.35(m, 2H), 6.92(m, 2H), 4.64(m, 1H), 3.7(t, 2H), 2.65(m, 2H), 1.23(br s, 6H). |
| 508 | δ 7.3(m, 4H), 7.1(m, 2H), 6.9(m, 2H), 4.62(m, 1H), 3.69(m, 2H), 2.92(m, 2H), 1.2(m, 6H) |
| 509 | δ 7.3(m, 1H), 6.9(m, 2H), 4.65(m, 1H), 3.33(m, 2H), 1.2(m, 7H), 0.54(m, 2H), 0.33(m, 2H) |
| 510 | δ 7.3(m, 1H), 6.9(m, 2H), 4.63(m, 1H), 4.37(s, 2H), 2.43(s, 3H), 2.24(s, 3H), 1.2(m, 6H). |
| 511 | δ 7.75(d, 2H), 7.6(t, 1H), 7.45(t, 2H), 7.3(m, 1H), 6.89(m, 2H), 5.37(q, 1H), 4.65(m, 1H), 1.72(d, 3H), 1.2 (br s, 6H). |
| 512 | δ 7.3(m, 1H), 6.9(m, 2H), 4.65(m, 1H), 4.23(s, 2H), 3.36(q, 2H), 3.26(q, 2H), 1.21(m, 9H), 1.11(t, 3H). |
| 513 | δ 7.35(m, 1H), 6.92(m, 2H), 4.65(m, 1H), 3.66(s, 3H), 3.53(t, 2H), 2.31(t, 2H), 1.96(m, 2H), 1.22(br s, 6H). |
| 514 | δ .35(m, 1H), 6.92(m, 2H), 5.55(t, 1H), 4.65(m, 1H), 4.2(d, 2H), 2.12(s, 3H), 1.21(br s, 6H). (3:1 cis/trans mix.) |
| 515 | δ 7.35(m, 1H), 6.92(m, 2H), 5.2(t, 1H), 4.65(m, 1H), 4.04(d, 2H), 1.72(m, 6H), 1.21(br s, 6H). |
| 516 | δ 7.35(m, 1H), 6.92(m, 2H), 5.73(m, 1H), 5.0(m, 2H), 4.65(m, 1H), 3.48(t, 2H), 2.04(q, 2H), 1.74 1.22(br s, 6H). |
| 517 | δ 7.32(m, 1H), 6.91(m, 2H), 4.65(m, 1H), 4.48(q, 1H), 2.19(s, 3H), 1.65(d, 3H), 1.22(br s, 6H). |
| 518 | δ 7.35(m, 1H), 6.89(m, 2H), 4.65(m, 1H), 2.93(s, 2H), 1.21(br s, 6H), 0.08(m, 9H). |
| 519 | δ 7.37(m, 1H), 6.92(m, 2H), 5.1(s, 1H), 4.87(s, 2H), 4.65(m, 1H), 4.13(q, 2H), 3.78(q, 2H), 1.23( |
| 520 | δ 7.3(m, 6H), 6.9(m, 2H), 4.98(s, 2H), 4.6(m, 3H), 1.21(br s, 6H). |
| 521 | δ 7.35(m, 1H), 6.9(m, 2H), 4.64(m, 1H), 3.5(d, 2H), 2.65(m, 1H), 2.0–1.7(m, 6H), 1.21(br s, 6H). |
| 522 | δ 7.35(m, 1H), 6.92(m, 2H), 4.65(m, 1H), 4.52(t, 1H), 4.36(t, 1H), 3.53(t, 2H), 1.85–1.6(m, 4H), 1.22(br s, 6H). |
| 523 | δ 7.35(m, 1H), 6.9(m, 2H), 5.8(m, 1H), 5.4(m, 1H), 4.65(m, 1H), 4.0(d, 2H), 2.03(m, 2H), 1.21(br s, 6H), 0.94(t, 3H) |

INDEX TABLE D-continued

| Cmpd No. | $^1$H NMR Data ($CDCl_3$ solution unless indicated otherwise)[a] |
|---|---|
| 524 | δ 7.32(m, 1H), 6.92(m, 2H), 4.65(m, 1H), 4.24(s, 2H), 2.47(q, 2H), 1.21(br s, 6H), 1.1(t, 3H). |
| 525 | δ 7.33(m, 1H), 6.93(m, 2H), 4.65(m, 1H), 3.75(t, 2H), 2.48(m, 2H), 1.22(br s, 6H). |
| 526 | δ 7.33(m, 1H), 6.93(m, 2H), 4.65(m, 1H), 3.55(t, 2H), 2.1(m, 2H), 1.92(m, 2H), 1.23(br s, 6H) |
| 527 | δ 7.39(m, 2H), 7.22(m, 2H), 4.93(s, 2H), 4.66(septet, J=6.8Hz, 1H), 3.62(apparent t, J=8.3Hz, 2H), 1.22(d, J=6.8Hz, 6H), 0.93(apparent t, J=8.3Hz, 2H), 0.00(s, 9H). |
| 528 | δ 7.3(d, 2H), 7.1(d, 2H), 4.6–4.7(m, 1H), 3.5(t, 2H), 1.6(m, 2H), 1.3(m, 4H), 1.1(d, 6H), 0.875(t, 3H). |
| 529 | δ 7.3(d, 2H), 7.1(d, 2H), 4.6–4.7(m, 1H), 3.4(t, 2H), 1.6(m, 2H), 1.26(brd s, 6H), 1.1(d, 6H), 0.865(t, 3H). |
| 530 | δ 7.3(d, 2H), 7.1(d, 2H), 4.6–4.7(m, 1H), 4.5(t, 1H), 4.4(t, 1H), 3.6(t, 2H), 1.9–2.1(m, 2H), 1.2(d, 6H). |
| 531 | δ 7.3(d, 2H), 7.1(d, 2H), 4.875(m, 1H), 4.6–4.7(m, 1H), 3.7–3.9(m, 4H), 3.648(t, 2H), 2.046(m, 2H), 1.1(d, 6H). |
| 532 | δ 7.3(d, 2H), 7.1(d, 2H), 4.6–4.7(m, 1H), 4.561(m, 1H), 3.9–4.0(m, 2H), 3.6(m, 4H), 1.9–2.0(m, 3H), 1.3(brd s, 1H), 1.1(d, 6H). |
| 533 | δ 7.3(d, 2H), 7.1(d, 2H), 4.886(s, 2H), 4.6–4.7(m, 1H), 3.394(s, 3H), 1.2(d, 6H). |
| 534 | δ 7.4(d, 2H), 7.2(d, 2H), 4.922(s, 2H), 4.6–4.7(m, 1H), 3.6(q, 2H), 1.1–1.2(m, 9H). |
| 535 | δ 7.3(d, 2H), 7.1(d, 2H), 4.977(s, 2H), 4.6–4.7(m, 1H), 3.708(m, 2H), 3.470(m, 2H), 3.277(s, 3H), 1.2(d, 6H). |
| 536 | δ 7.3(d, 2H), 7.1(d, 2H), 4.6–4.7(m, 1H), 4.056(t, 2H), 3.508(t, 2H), 2.039(s, 3H), 1.6–1.8(m, 4H), 1.2(d, 6H). |
| 537 | δ 7.3(d, 2H), 7.1(d, 2H), 4.6–4.7(m, 1H), 3.7(t, 2H), 2.4–2.8(m, 2H), 1.2(d, 6H). |
| 538 | δ 7.3(d, 2H), 7.238(m, 2H), 7.166(m, 1H), 7.0–7.1(m, 4H), 4.6–4.7(m, 1H), 3.7(t, 2H), 2.9(t, 2H), 1.2(d, 6H). |
| 539 | δ 7.3(d, 2H), 7.1(d, 2H), 4.6–4.7(m, 1H), 3.3(d, 2H), 1.2(d, 6H), 1.1–1.2(m, 1H), 0.56(q, 2H), 0.3(q, 2H). |
| 540 | δ 7.3(d, 2H), 7.1(d, 2H), 4.6–4.7(m, 1H), 4.369(s, 2H), 2.436(s, 3H), 2.245(s, 3H), 1.1(d, 6H). |
| 541 | δ 7.77(d, 2H), 7.6(t, 1H), 7.4(t, 2H), 7.3(d, 2H), 7.1(d, 2H), 5.3–5.4(q, 1H), 4.6–4.7(m, 1H), 1.7(d, 3H), 1.1(d, 6H). |
| 542 | δ 7.3(d, 2H), 7.1(d, 2H), 4.6–4.7(m, 1H), 4.230(s, 2H), 3.4(q, 2H), 3.2–3.2(q, 2H), 1.239(t, 3H), 1.2(d, 6H), 1.1(t, 3H). |
| 543 | δ 7.3(d, 2H), 7.1(d, 2H), 4.6–4.7(m, 1H), 3.658(s, 3H), 3.5(t, 2H), 2.3–2.4(t, 2H), 1.9–2.0(m, 2H), 1.3(d, 6H). |
| 544 | δ 7.3(d, 2H), 7.1(d, 2H), 5.5(t, 1H), 4.6–4.7(m, 1H), 4.2(d, 2H), 2.1(s, 3H), 1.1(d, 6H) (3:1 cis/trans mixture). |
| 545 | δ 7.3(d, 2H), 7.1(d, 2H), 5.2(t, 1H), 4.6–4.7(m, 1H), 4.0(d, 2H), 1.735(s, 3H), 1.719(s, 3H), 1.1(d, 6H). |
| 546 | δ 7.3(d, 2H), 7.1(d, 2H), 5.6–5.8(m, 1H), 4.9(m, 2H), 4.6–4.7(m, 1H), 3.4(t, 2H), 2.0–2.1(q, 2H), 1.7–1.8(m, 2H), 1.2(d, 6H). |
| 547 | δ 7.4–7.37(m, 2H), 7.19–7.16(m, 2H), 4.65(m, 1H), 4.48(q, 1H), 2.19(s, 3H), 1.66(d, 3H), 1.2(d, 6H). |
| 548 | δ 7.38–7.35(m, 2H), 7.21–7.18(m, 2H), 4.65(m, 1H), 2.93(s, 2H), 1.2(d, 6H), 0.08(s, 9H). |
| 549 | δ 7.4(d, 2H), 7.2(d, 2H), 5.1(s, 1H), 4.9(s, 2H), 4.6–4.7(m, 1H), 4.1–4.2(q, 2H), 3.7–3.8(q, 2H), 1.3(t, 3H), 1.1–1.2(m, 9H). |
| 550 | δ 7.3(d, 2H), 7.1(d, 2H), 4.6–4.7(m, 1H), 3.4–3.5(d, 2H), 2.6–2.7(m, 1H), 2.0–2.1(m, 2H), 1.8–1.9(q, 2H), 1.1(d, 6H). |
| 551 | δ 7.3(d, 2H), 7.1(d, 2H), 4.6–4.7(m, 1H), 4.5(t, 1H), 4.3–4.4(t, 1H), 3.5(t, 2H), 1.6–1.8(m, 4H), 1.2(d, 6H). |
| 552 | δ 7.3(d, 2H), 7.1(d, 2H), 5.7–5.9(m, 1H), 5.3–5.5 (m, 1H), 4.6–4.7(m, 1H), 4.0(d, 2H), 2.0–2.1(m, 2H), 1.1(d, 6H), 0.9(t, 3H). |
| 553 | δ 7.4(d, 2H), 7.2(d, 2H), 4.6–4.7(m, 1H), 4.244(s, 2H), 2.4(q, 2H), 1.2(d, 6H), 1.087(t, 3H). |
| 554 | δ 7.4(d, 2H), 7.2(d, 2H), 4.6–4.7(m, 1H), 3.7(t, 2H), 2.4–2.6(m, 2H), 1.2(d, 6H). |
| 555 | δ 7.4(d, 2H), 7.2(d, 2H), 4.6–4.7(m, 1H), 3.5(t, 2H), 2.0–2.2(m, 2H), 1.8–2.0(m, 2H), 1.1(d, 6H). |
| 556 | δ 7.39(m, 3H), 7.3(m, 2H), 4.6–4.7(m, 1H), 3.45(t, 2H), 1.56(m, 2H), 1.3(m, 2H), 1.2(d, 6H), 0.9(t, 3H). |

INDEX TABLE D-continued

| Cmpd No. | $^1$H NMR Data ($CDCl_3$ solution unless indicated otherwise)[a] |
|---|---|
| 557 | δ 7.38(m, 3H), 7.26(m, 2H), 4.6–4.7(m, 1H), 3.44(t, 2H), 1.6(m, 2H), 1.3(m, 4H), 1.2(d, 6H), 0.86(t, 3H). |
| 558 | δ 7.387(m, 3H), 7.38(m, 2H), 4.6–4.7(m, 1H), 3.44(t, 2H), 1.6(m, 2H), 1.25(d, 6H), 1.2(s, 6H), 0.859(t, 3H). |
| 559 | δ 7.4(m, 3H), 7.26(m, 2H), 4.6–4.7(m, 1H), 4.53(t, 1H), 4.37(t, 1H), 3.61–3.66(t, 2H), 1.9–2.1(m, 2H), 1.2(d, 6H). |
| 560 | δ 7.37(m, 3H), 7.26(m, 2H), 4.87(t, 1H), 4.6–4.7(m, 1H), 3.8–3.9(m, 2H), 3.7–3.8(m, 2H)m 3.63(t, 2H), 2.045(m, 2H), 1.2(d, 6H). |
| 561 | δ 7.3(m, 3H), 7.26(m, 2H), 4.6–4.7(m, 1H), 4.56(t, 1H), 3.9–4.0(m, 2H), 3.6(m, 4H), 1.9(m, 3H), 1.259(t, 1H), 1.2(d, 6H). |
| 562 | δ 7.39(m, 3H), 7.26(m, 2H), 4.87(s, 2H), 4.6–4.7(m, 1H), 3.377(s, 3H), 1.2(d, 6H). |
| 563 | δ 7.3(m, 3H), 7.27(m, 2H), 4.886(s, 2H), 4.6–4.7(m, 1H), 3.547–3.571(q, 2H), 1.2(d, 6H), 1.129–1.15(t, 3H). |
| 564 | δ 7.38(m, 3H), 7.26(m, 2H), 4.966(s, 2H), 4.6–4.7(m, 1H), 3.7(t, 2H), 3.4(t, 2H), 3.257(s, 3H), 1.2(d, 6H). |
| 565 | δ 7.39(m, 3H), 7.26(m, 2H), 4.6–4.7(m, 1H), 4.046(t, 2H), 3.495(t, 2H), 2.033(s, 3H), 1.6–1.8(m, 4H), 1.2 (d, 2H). |
| 566 | δ 7.38(m, 3H), 7.26(m, 2H), 4.6–4.7(m, 1H), 3.66–3.707(t, 2H), 2.6–2.7(m, 2H), 1.2(d, 6H). |
| 567 | δ 7.38(m, 3H), 7.24(m, 5H), 7.12(d, 2H), 4.63(m, 1H), 3.67(t, 2H), 2.9(t, 2H), 1.2(d, 6H). |
| 568 | δ 7.39(m, 3H), 7.26(m, 2H), 4.6–4.7(m, 1H), 3.3(d, 2H), 1.2(d, 6H), 1.1(m, 1H), 0.5(q, 2H), 0.3(q, 2H). |
| 569 | δ 7.38(m, 3H), 7.26(m, 2H), 4.6–4.7(m, 1H), 4.353(s, 2H), 2.422(s, 3H), 2.225(s, 3H), 1.2(d, 6H). |
| 570 | δ 7.759(d, 2H), 7.438(t, 1H), 7.374(t, 3H), 7.37(m, 2H), 7.26(m, 2H), 5.3–5.4(q, 1H), 4.6–4.7(m, 1H), 1.7(d, 3H), 1.2(d, 6H). |
| 571 | δ 7.37(m, 3H), 7.25(m, 2H), 4.6–4.7(m, 1H), 4.2(s, 2H), 3.2–33(q, 2H), 3.3–3.4(q, 2H), 1.2(m, 9H), 1.1(t, 3H). |
| 572 | δ 7.39(m, 3H), 7.26(m, 2H), 4.6–4.7(m, 1H), 3.6(s, 3H), 3.54(t, 2H), 2.3(t, 2H), 1.9(m, 2H), 1.2(d, 6H). |
| 573 | δ 7.39(m, 3H), 7.26(m, 2H), 5.5(t, 1H), 4.6–4.7(m, 1H), 4.2(d, 2H), 2.1(s, 3H), 1.2(d, 6H). |
| 574 | δ 7.39(m, 3H), 7.26(m, 2H), 5.1–5.2(t, 1H), 4.6–4.7(m, 1H), 4.01–4.039(d, 2H), 1.7(d, 6H), 1.2(d, 6H). |
| 575 | δ 7.39(m, 3H), 7.26(m, 2H), 5.6–5.8(m, 1H), 4.9–5.1(m, 2H), 4.6–4.7(m, 1H), 3.44–3.49(t, 2H), 2.0–2.1(q, 2H), 1.7–1.8(m, 2H), 1.2(d, 6H). |
| 576 | δ 7.39(m, 3H), 7.26(m, 2H), 4.6–4.7(m, 1H), 4.4–4.5(q, 1H), 2.166(s, 3H), 1.6(d, 2H), 1.2(d, 6H). |
| 577 | δ 7.37(m, 3H), 7.26(m, 2H), 4.6–4.7(m, 1H), 2.9(s, 2H), 1.2(d, 6H), 0.6–0.8(m, 9H). |
| 578 | δ 7.4(m, 3H), 7.26(m, 2H), 5.1(s, 1H), 4.862–4.866(s, 2H), 4.6–4.7(m, 1H), 4.1–4.2(q, 2H), 3.7–3.8(q, 2H), 1.17–1.28(m, 12H). |
| 579 | δ 7.4–7.2(m, 10H), 4.97(s, 2H), 4.63(m, 1H), 4.58(s, 2H), 1.2(d, 6H). |
| 580 | δ 7.38(m, 3H), 7.26(m, 2H), 4.6–4.7(m, 1H), 3.47–3.49 (d, 2H), 2.6–2.7(m, 1H), 1.9–2.1(m, 2H), 1.8–1.9(q, 2H), 1.7–1.8(q, 2H), 1.2(d, 6H). |
| 581 | δ 7.39(m, 3H), 7.26(m, 2H), 4.6–4.7(m, 1H), 4.5(t, 1H), 4.3–4.4(t, 1H), 3.5(t, 2H), 1.7–1.8(m, 3H), 1.6–1.7(m, 1H), 1.2(d, 6H). |
| 582 | δ 7.38(m, 3H), 7.26(m, 2H), 5.7–5.9(m, 1H), 5.3–5.4(m, 1H), 4.6–4.7(m, 1H), 4.0(d, 2H), 1.9–2.1(m, 2H), 1.2(d, 6H), 0.9–1.0(t, 3H). |
| 583 | δ 7.39(m, 3H), 7.26(m, 2H), 4.6–4.7(m, 1H), 4.23(s, 2H), 2.45–2.48(q, 2H), 1.2(d, 6H), 1.1(t, 3H). |
| 584 | δ 7.39(m, 3H), 7.26(m, 2H), 4.6–4.7(m, 1H), 3.7(t, 2H), 2.4–2.6(m, 2H), 1.2(d, 6H). |
| 585 | δ 7.3(m, 2H), 7.1(m, 2H), 4.6–4.7(m, 1H), 3.5(t, 2H), 2.0–2.2(m, 2H), 1.8–2.0(m, 2H), 1.2(d, 6H). |
| 587 | δ 7.4(m, 3H), 7.3(m, 2H), 4.6(m, 1H), 4.1(m, 4H), 3.8 (d, 2H), 1.2(m, 12H). |
| 592 | δ 7.4(m, 2H), 7.2(m, 2H), 5.1(m, 1H), 4.7(m, 1H), 3.3(s, 3H), 1.7(d, 3H), 1.2(d, 6H). |
| 593 | δ 7.3(m, 1H), 6.9(m, 2H), 5.1(m, 1H), 4.7(m, 1H), 3.3(s, 3H), 1.7(d, 3H), 1.2(m, 6H). |
| 594 | δ 7.28(m, 1H), 6.92(m, 2H), 4.6(m, 1H), 4.2(m, 1H), 3.8(m, 1H), 3.4(m, 1H), 1.31(d, 3H), 1.26(d, 6H). |

INDEX TABLE D-continued

| Cmpd No. | $^1$H NMR Data ($CDCl_3$ solution unless indicated otherwise)[a] |
|---|---|
| 596 | δ 7.22(m, 2H), 7.09(m, 2H), 4.65(m, 1h), 4.4(m, 2H), 4.2–3.6(m, 3H), 2.04(s, 3H), 1.21(d, 6H). |
| 597 | δ 7.39(m, 2H), 7.16(m, 2H), 4.6(m, 1H), 4.2–3.6(m, 2H), 1.22(d, 6H). |
| 598 | δ 7.28(m, 1H), 6.9(m, 2H), 4.63(m, 1H), 3.8(s, 2H), 1.26(b, 6H). |
| 599 | δ 7.4(d, 2H), 7.20(d, 2H), 4.65(m, 1H), 4.12(q, 4H), 4.80(d, 2H), 1.30(m, 12H). |
| 600 | δ 7.11(m, 3H), 5.80(m, 1H), 5.22(m, 3H), 4.03(d, 2H), 3.90(m, 2H), 3.26(s, 3H), 2.35(d, 6H), 1.41(d, 3H). |
| 603 | δ 7.38–7.41(m, 3H), 7.21–7.25(m, 2H), 4.82–4.89 (m, 1H), 4.59–4.68(m, 1H), 4.08–4.16(m, 1H), 3.68–3.74(m, 1H), 1.57(d, 3H), 1.21(d, 6H). |
| 604 | δ 7.29–7.37(m, 1H), 6.90–6.96(m, 2H), 4.83–4.90 (m, 1H), 4.58–4.67(m, 1H), 4.09–4.17(m, 1H), 3.68–3.74(m, 1H), 1.58(d, 3H), 1.22(br s, 6H). |
| 605 | δ 7.6(m, 1H), 7.48(m, 1H), 7.3(m, 3H), 7.2(m, 3H), 5.94 (s, 1H), 5.3(s, 1H), 4.6(m, 3H), 1.2(d, 6H). |
| 606 | δ 7.4–7.2(m, 7H), 6.9(m, 2H), 5.4(s, 1H), 5.1(s, 1H), 4.7–4.6(m, 1H), 4.4(s, 2H), 1.2(d, 6H). |
| 607 | δ 7.4(m, 3H), 7.3–7.2(m, 2H), 4.9(s, 1H), 4.8(s, 1H), 4.7–4.6(m, 1H), 3.9(s, 2H), 1.7(s, 3H), 1.2(d, 6H). |
| 608 | δ 7.4(m, 3H), 7.2(m, 2H), 5.4(s, 2H), 4.7–4.6(m, 1H), 4.2(s, 2H), 1.2(d, 6H). |
| 609 | δ 7.39(m, 3H), 7.26(m, 2H), 4.82(m, 1H), 4.64(m, 1H), 2.41(s, 1H), 1.60(d, 3H), 1.22(d, 6H). |
| 614 | δ 7.4(m, 3H), 7.2(m, 2H), 4.6–4.7(m, 1H), 4.0–4.2 (4H), 5.0(m, 1H), 3.9(m, 1H), 3.0–3.2(q of q, 2H), 1.2 (m, 16H). |
| 615 | δ 7.2(m, 2H), 7.0–7.1(t, 2H), 5.7(m, 1H), 4.6(m, 1H), 4.2(m, 2H), 3.9(m, 2H), 3.0–3.2(m, 2H), 1.1–1.3(m, 14H). |
| 616 | δ 7.2–7.3(m, 2H), 7.0–7.1(m, 2H), 4.6–4.7(m, 2H), 3.7(s, 3H), 1.66(d, 3H), 1.2(d, 6H). |
| 617 | δ 7.3(m, 2H), 7.1(m, 2H), 4.6(m, 1H), 4.3(m, 1H), 4.1(m, 4H), 1.6(m, 6H), 1.2(m, 12H). |
| 623 | δ 7.4(d, 2H), 7.2(d, 2H), 4.6–4.7(m, 2H), 3.742(s, 3H), 1.6(d, 3H), 1.2(d, 6H). |
| 627 | δ 7.20(m, 2H), 7.10(m, 2H), 4.70(m, 2H), 3.70(m, 2H), 3.60(t, 2H), 3.55(t, 2H), 3.30(s, 3H) 1.20(d, 6H). |
| 629 | δ 7.20(m, 2H), 7.10(m, 2H), 4.70(m, 2H), 3.70(m, 2H), 3.60(d, 2H), 3.45(m, 2H), 1.20(d, 6H), 1.10(t, 6H). |
| 631 | δ 7.35(m, 3H), 7.28(m, 2H), 4.70(m, 1H), 3.65(t, 2H), 3.54(t, 2H), 3.30(s, 3H), 1.22(d, 6H). |
| 632 | δ 7.35(m, 3H), 7.28(m, 2H), 4.70(m, 1H), 3.65(m, 2H), 3.55(d, 2H), 3.48(m, 2H), 1.20(d, 6H), 1.10(d, 6H). |
| 634 | δ 7.3(m, 1H), 6.92(m, 2H), 5.43(s, 2H), 4.65(m, 1H), 4.23(s, 2H), 1.21(bs, 6H). |
| 635 | δ 7.3(m, 1H), 6.9(m, 2H), 4.62(m, 1H), 3.46(t, 2H), 1.56(m, 2H), 1.2(m, 8H), 0.91(t, 3H). |
| 636 | δ 7.3(m, 1H), 6.9(m, 2H), 4.64(m, 1H), 3.45(t, 2H), 1.64(m, 2H), 1.2(m, 10H), 0.87(t, 3H). |
| 637 | δ 7.3(m, 1H), 6.9(m, 2H), 4.63(m, 1H), 3.45(t, 2H), 1.6(m, 2H), 1.2(m, 12H), 0.86(t, 3H). |
| 639 | δ 7.37(d, 2H), 7.17(d, 2H), 4.64(m, 1H), 4.43(s, 2H), 1.91(m, 1H), 1.2(m, 8H), 1.04(m, 2H). |
| 640 | δ 7.21(m, 2H), 7.09(m, 2H), 4.65(m, 1H), 4.19(s, 2H), 3.3(m, 1H), 2.4–1.8(m, 6H), 1.21(d, 6H). |
| 642 | δ 7.34(m, 1H), 6.94(m, 2H), 4.65(m, 1H), 4.19(s, 2H), 3.3(m, 1H), 2.4–1.8(m, 6H), 1.21(d, 6H). |
| 643 | δ 7.37(d, 2H), 7.17(d, 2H), 4.65(m, 1H), 4.19(s, 2H), 3.3(m, 1H), 2.4–1.8(m, 6H), 1.21(d, 6H). |
| 648 | δ 7.3(m, 2H), 7.2(m, 3H), 5.0(s, 1H), 4.8–4.6(m, 1H), 4.5(s, 1H), 4.0(s, 2H), 1.2(d, 6H). |
| 649 | δ 7.3(m, 3H), 7.2(m, 2H), 4.9(s, 1H), 4.8(s, 1H), 4.7–4.6(m, 1H), 4.0(s, 2H), 2.3–2.1(m, 1H), 1.2(d, 6H), 1.0(d, 6H). |
| 650 | δ 7.4–7.0(m, 10H), 5.0(ABm, 2H), 4.7–4.6(m, 1H), 3.9(s, 2H), 3.2(s, 2H), 1.2(d, 6H). |
| 651 | δ 7.3(m, 3H), 7.2(m, 2H), 6.5(s, 1H), 5.9(s, 1H), 5.0(m, 1H), 4.7–4.6(m, 1H), 3.66(s, 3H), 1.5(d, 3H), 1.2(d, 6H). |
| 652 | δ 7.3(m, 3H), 7.2(m, 2H), 5.6(m, 1H), 5.4(m, 1H), 4.7–4.6(m, 1H), 2.4(s, 1H), 1.73(s, 3H), 1.69(s, 3H), 1.2(d, 6H). |
| 655 | δ 7.4(m, 3H), 7.2(m, 2H), 6.4–6.3(m, 1H), 5.6–5.5(m, 1H), 4.7–4.6(m, 1H), 2.9(s, 1H), 1.6(s, 6H), 1.2(d, 6H). |
| 656 | δ 7.22(m, 2H), 7.09(m, 2H), 4.63(m, 2H), 3.95(m, 2H), 2.07(m, 2H), 1.94(m, 2H), 1.60(d, 3H), 1.18(d, 6H). |
| 657 | δ 7.40(m, 1H), 6.94(m, 2H), 4.82(m, 1H), 4.64(m, 1H), 2.40(m, 1H), 1.60(d, 3H), 1.20(d, 6H). |
| 658 | δ 7.39(m, 2H), 7.20(m, 2H), 4.80(m, 1H), 4.64(m, 1H), 2.42(m, 1H), 1.64(d, 3H), 1.21(d, 6H). |
| 672 | δ 7.26(m, 2H), 7.09(m, 2H), 4.67(m, 1H), 4.4(m, 1H), 3.9(m, 2H), 3.8(m, 2H), 1.22(d, 6H). |
| 675 | δ 7.35(m, 1H), 6.93(t, 2H), 4.6(m, 1H), 3.62(t, 2H), 2.39(t, 2H), 2.05(m, 2H), (br, 6H) |
| 677 | δ 7.39(m, 5H) 7.20(m, 2H), 7.10(m, 2H), 5.60(s, 1H), 4.60(m, 1.20(d, 6H), 3.78(s, 3H), 1.19(d, 6H). |
| 681 | δ 7.3(d, 2H), 7.2(d, 2H), 5.0(m, 1H), 4.6–4.7(m, 1H), 4.0–4.2(m, 4H), 3.0–3.3(m, 2H), 1.2–1.3(m, 12H). |
| 682 | δ 7.56(s, 1H), 7.36(m, 1H), 6.91(m, 2H), 4.60(m, 1H), 4.47(s, 2H), 4.15(q, 2H), 1.41(t, 3H), 1.21(br s, 6H). |
| 683 | δ 7.54(s, 1H), 7.38(m, 3H), 7.24(m, 2H), 4.63(m, 1H), 4.59(s, 2H), 4.14(q, 2H), 1.41(t, 3H), 1.21(d, 6H). |
| 684 | δ 7.56(s, 1H), 7.36(m, 2H), 7.19(m, 2H), 4.63(m, 1H), 4.48(s, 2H), 4.15(q, 2H), 1.41(t, 3H), 1.19(d, 6H). |
| 685 | δ 7.56(s, 1H), 7.22(m, 2H), 7.07(m, 2H), 4.63(m, 1H), 4.48(s, 2H), 4.15(q, 2H), 1.41(t, 3H), 1.19(d, 6H). |
| 686 | δ 7.68(s, 1H), 7.22(m, 2H), 7.07(m, 2H), 5.12(q, 1H), 4.63(m, 1H), 4.14(q, 2H), 1.73(d, 3H), 1.41(t, 3H), 1.18 (d, 6H). |
| 687 | δ 7.37(m, 1H), 6.92(m, 2H), 4.62(m, 1H), 3.81(t, 2H), 2.94(s, 3H), 2.92(s, 3H), 2.66(t, 2H), 1.22(m, 6H). |
| 693 | δ 9.52(s, 1H), 7.22(m, 3H), 7.1(m, 2H), 4.64(m, 1H), 4.44(q, 1H), 1.6(d, 3H), 1.2(d, 6H). |
| 694 | δ 7.37(m, 1H), 6.92(m, 2H), 5.99(m, 1H), 5.44(m, 1H), 4.64(m, 1H), 4.57(m, 1H), 2.2–1.6(m, 6H), 1.21(br, 6H). |
| 696 | δ 7.37(d, 2H), 7.17(d, 2H), 5.99(m, 1H), 5.44(m, 1H), 4.64(m, 1H), 4.57(m, 1H), 2.2–1.6(m, 6H), 1.21(d, 6H). |
| 697 | δ 7.4(m, 3H), 7.15(m, 2H), 4.65(m, 1H), 3.90(m, 8H), 2.20(m, 2H), 1.22(d, 6H). |
| 698 | δ 7.4(d, 2H), 7.20(d, 2H), 4.65(m, 1H), 3.90(m, 8H), 2.20(m, 2H), 1.22(d, 6H). |
| 701 | δ 7.35(d, 2H), 7.20(d, 2H), 4.65(m, 1H), 3.90(m, 1H), 2.85(m, 1H), 1.40–2.00(m, 6H), 1.20(d, 9H). |
| 702 | δ 7.40(m, 1H), 6.92(m, 2H), 4.65(m, 1H), 3.90(m, 1H), 2.85(m, 1H), 1.40–2.00(m, 6H), 1.25(m, 9H). |
| 705 | δ 7.22(m, 2H), 7.06(m, 2H), 4.78(q, 1H), 4.62(m, 1H), 3.64(m, 8H), 1.66(d, 3H), 1.19(d, 6H). |
| 708 | δ 7.29(m, 1H), 6.92(m, 2H), 4.65(m, 1H), 4.4–3.5(m, 5H), 2.04(s, 3H), 1.23(bs, 6H). |
| 712 | δ 7.28(m, 2H), 7.08(m, 2H), 4.62(m, 1H), 3.52(m, 4H), 1.8(m, 4H), 1.18(d, 6H). |
| 713 | δ 7.23(m, 2H), 7.08(m, 2H), 4.61(m, 1H), 3.66(t, 2H), 3.5(t, 2H), 2.11(m, 2H), 1.21(d, 6H). |
| 714 | δ 7.3(m, 1H), 6.92(m, 2H), 4.65(m, 1H), 4.25(m, 1H), 3.71(m, 2H), 1.49(d, 3H), 1.23(bs, 6H). |
| 715 | δ 7.40(m, 1H), 6.92(m, 2H), 4.65(m, 1H), 3.90(m, 1H), 3.56(q, 2H), 3.30(m, 2H), 1.82(m, 1H), 1.50(m, 5H), 1.20(m, 6H). |
| 717 | δ 7.40(m, 3H), 7.25(m, 2H), 4.65(m, 1H), 3.90(m, 1H), 2.85(m, 1H), 1.50–2.00(m, 6H), 1.25(d, 3H), 1.20(d, 6H) |
| 718 | δ 7.25(m, 2H), 7.10(m, 2H), 4.65(m, 1H), 3.90(m, 1H), 2.85(m, 1H), 1.50–2.00(m, 6H), 1.25(d, 3H), 1.20(d, 6H). |
| 720 | δ 7.3(m, 1H), 6.9(m, 2H), 4.6(m, 1H), 3.1(m, 1H), 1.5 (m, 3H), 1.4(m, 1H), 1.2(m, 6H), 0.6–0.3(m, 4H). |
| 721 | δ 7.22(m, 2H), 7.09(m, 2H), 4.92(m, 1H), 4.65(m, 1H), 4.39(m, 2H), 2.91(m, 2H), 1.68(d, 3H), 1.19(d, 6H). |
| 723 | δ 7.39(m, 7H) 7.20(m, 2H), 7.10(m, 2H), 5.60(s, 1H), 4.60(m, 1H), 3.78(s, 3H), 1.19(d, 6H). |
| 724 | δ 7.40(m, 7H), 7.15(d, 2H), 5.60(s, 1H), 4.60(m, 1H), 3.79(s, 3H), 1.20(d, 6H). |
| 725 | δ 7.4(m, 2H), 7.2(m, 2H), 5.1(m, 1H), 4.6(m, 1H), 4.1 (m, 1H), 3.8(m, 1H), 3.4(s, 3H), 1.2(d, 6H). |
| 726 | δ 7.4(m, 2H), 7.2(m, 2H), 5.1(m, 1H), 4.6(m, 1H), 4.1 (m, 1H), 3.9(m, 1H), 3.4(s, 3H), 3.3(s, 3H), 1.2(d, 6H). |
| 727 | δ 7.2(m, 2H), 7.1(m, 2H), 5.97(br, 1H), 4.65(m, 1H), 3.65(m, 2H), 3.45(m, 2H), 1.91(s, 3H), 1.19(d, 6H). |
| 729 | δ 7.39(m, 3H), 7.25(m, 2H), 4.91(q, 1H), 4.64(m, 1H), 4.37(m, 2H), 2.92(m, 2H), 1.67(d, 3H), 1.20(d, 6H). |

INDEX TABLE D-continued

| Cmpd No. | $^1$H NMR Data ($CDCl_3$ solution unless indicated otherwise)[a] |
|---|---|
| 730 | δ 7.35(m, 1H), 6.93(m, 2H), 4.93(q, 1H), 4.65(m, 1H), 4.39(m, 2H), 2.94(m, 2H), 1.68(d, 3H), 1.20(d, 6H). |
| 73 1 | δ 8.4(s, 1H), 7.6(m, 1H), 7.5(m, 1H), 7.4(m, 3H), 7.2 (m, 2H), 5.84(s, 1H), 5.3(s, 1H), 4.7(m, 1H), 4.6(s, 2H), 1.2(d, 6H). |
| 732 | δ 7.3–7.2(m, 3H), 7.1–7.0(m, 2H), 6.4(s, 1H), 5.7(s, 1H), 4.7–4.6(m, 1H), 4.3(s, 2H), 3.75(s, 3H), 1.2(d, 6H). |
| 734 | δ 7.4(m, 3H), 7.2(m, 2H), 5.1(m, 1H), 4.6(m, 1H), 4.1 (m, 1H), 3.9(m, 1H), 3.4(s, 3H), 3.3(s, 3H), 1.2(d, 6H). |
| 735 | δ 7.4(m, 3H), 7.2(m, 2H), 5.1(m, 1H), 4.6(m, 1H), 4.1 (m, 1H), 3.8(m, 1H), 3.4(s, 3H), 1.2(d, 6H). |
| 737 | δ 7.3(m, 1H), 6.9(m, 2H), 5.1(m, 1H), 4.6(m, 1H), 4.1 (m, 1H), 3.8(m, 1H), 3.4(s, 3H), 1.2(d, 6H). |
| 738 | δ 7.3(m, 1H), 6.9(m, 2H), 5.1(m, 1H), 4.6(m, 1H), 4.1 (m, 1H), 3.9(m, 1H), 3.4(s, 3H), 3.3(s, 3H), 1.2(d, 6H). |
| 742 | δ 7.3(m, 1H), 6.9(m, 2H), 4.9(m, 1H), 4.7(m, 1H), 3.4–3.6(m, 2H), 2.1(m, 1H), 1.9(m, 1h), 1.2(m, 9H), 0.9(t, 3H). |
| 744 | δ 7.40(m, 1H), 6.92(m, 2H), 4.66(m, 1H), 3.67(m, 2H), 2.56(m, 2H), 1.95(m, 1H), 1.60(d, 6H). |
| 746 | δ 7.41(m, 3H), 7.39(m, 2H), 5.60(m, 1H), 4.62(m, 1H), 3.82(m, 2H) 1.20(d, 6H). |
| 747 | δ 7.38(m, 3H) 7.25(m, 2H), 4.66(m, 1H), 4.25(m, 1H), 3.65(m, 2H), 1.49(d, 3H), 1.20(d, 6H). |
| 748 | δ 7.39(m, 2H) 7.17(m, 2H), 4.62(m, 1H), 4.25(m, 1H), 3.65(m, 2H), 1.49(d, 3H), 1.20(d, 6H). |
| 750 | δ 7.39(m, 3H) 7.26(m, 2H), 4.63(m, 1H), 3.65(m, 2H), 3.48(m, 2H), 2.10(m, 2H), 1.20(d, 6H). |
| 753 | δ 7.22(m, 2H), 7.11(m, 2H), 4.64(m, 1H), 4.58(m, 1H), 2.42(m, 1H), 2.04(m, 1H), 1.94(m, 1H), 1.20(d, 6H), 0.99(t, 3H). |
| 758 | δ 1.20(m, 6H), 4.07(m, 2H), 4.17(s, 2H), 4.32(m, 2H), 4.62(m, 1H), 6.92(m, 2H), 7.36(m, 1H). |
| 759 | δ 7.38(d, 2H), 7.18(d, 2H), 4.92(q, 1H), 4.62(m, 1H), 4.39(m, 2H), 2.91(m, 2H), 1.68(d, 3H), 1.20(d, 6H). |
| 163 | δ 7.40(m, 1H), 6.92(m, 2H), 4.66(m, 1H), 3.67(m, 2H), 2.56(m, 2H), 1.95(m, 1H), 1.60(d, 6H). |
| 764 | δ 7.38(m, 1H), 6.93(m, 2H), 4.62(m, 1H), 4.25(s, 2H), 2.37(m, 1H), 1.25(d, 6H) |
| 765 | δ 1.20(m, 6H), 4.24(S, 2H), 4.25(M, 2H), 4.38(M, 2H), 4.63(M, 1H), 7.09(M, 2H), 7.24(M, 2H). |
| 766 | δ 7.25(m, 2H), 7.15(m, 1H), 4.95(br s, 1H), 4.65(m, 1H), 4.16(m, 2H), 3.39(s, 3H), 2.19(m, 1H), 1.92(m, 3H), 1.19(d, 6H). |
| 767 | δ 7.26(m, 2H), 7.11(m, 2H), 4.64(m, 1H), 3.67(t, 2H), 2.56(m, 2H), 1.96(m, 1H), 1.21(d, 6H). |
| 768 | δ 7.38(m, 3H), 7.26(m, 2H), 4.64(m, 1H), 3.66(t, 2H), 2.54(m, 2H), 1.92(m, 1H), 1.22(d, 6H). |
| 769 | δ 7.39(m, 3H), 7.24(m, 2H), 4.74(s, 2H), 4.62(m, 1H), 3.18(m, 1H), 1.35(d, 6H), 1.21(d 6H). |
| 771 | δ 8.3(d, 1H), 7.6(dd, 1H), 7.4(d, 1H), 4.7(septet, 1H), 4.2(septet, 1H), 1.40(d, 3H), 1.21(d, 3H). |
| 772 | δ 7.4(m, 2H), 7.2(m, 2H), 4.9(m, 1H), 4.7(m, 1H), 3.4–3.6(m, 2H), 2.1(m, 1H), 1.9(m, 1H), 1.2(m, 9H), 0.9(t, 3H). |
| 773 | δ 7.4(m, 2H), 7.2(m, 2H), 4.9(m, 1H), 4.7(m, 1H), 3.4–3.6(m, 2H), 2.1(m, 1H), 1.9(m, 1H), 1.2(m, 9H), 0.9(t, 3H). |
| 774 | δ 7.3(m, 1H), 6.9(m, 2H), 4.9(m, 1H), 4.7(m, 1H), 3.4–3.6(m, 2H), 2.1(m, 1H), 1.9(m, 1H), 1.2(m, 9H), 0.9(t, 3H). |
| 776 | δ 7.3(m, 1H), 6.90(m, 2H), 4.65(m, 1H), 4.20(m, 5H), 1.70(m, 3H), 1.25(m, 12H). |
| 778 | δ 7.4(m, 1H), 6.90(m, 2H), 4.65(m, 1H), 3.60(m, 7H), 2.85(m, 3H), 1.21(m, 6H). |
| 779 | δ 7.4(d, 2H), 7.2(d, 2H), 4.65(m, 1H), 3.60(m, 7H), 2.85(m, 3H), 1.21(m, 6H). |
| 782 | δ 7.22(m, 2H), 7.09(t, 2H), 5.93(t, 1H), 4.62(m, 1H), 4.21(d, 2H), 1.2(d, 6H). |
| 783 | δ 7.38(m, 1H), 6.96(m, 2H), 4.60(m, 2H), 2.40(m, 1H), 2.10–1.80(m, 2H), 1.22(m, 1H), 0.94(m, 3H). |
| 784 | δ 7.39(m, 2H), 7.20(m, 2H), 4.64(m, 1H), 4.25(m, 2H), 2.33(m, 1H), 1.21(d, 6H). |
| 785 | δ 7.35(m, 1H), 6.92(m, 2H), 5.32(q, 1H), 4.62(m, 1H), 2.31(s, 3H), 2.24(s, 3H), 1.83(d, 3H), 1.22(br, 6H). |

INDEX TABLE D-continued

| Cmpd No. | $^1$H NMR Data ($CDCl_3$ solution unless indicated otherwise)[a] |
|---|---|
| 792 | δ 7.39(m, 3H) 7.25(m, 2H), 4.61(m, 1H), 3.52(m, 4H), 1.80(m, 4H), 1.20(d, 6H). |
| 797 | δ 7.4(m, 3H), 7.3–7.1(m, 2H), 5.5(bs, 1H), 4.7–4.6(m, 1H), 3.94(bs, 2H), 2.35(s, 2H), 2.3–2.2(m, 2H), 2.0(m, 2H), 1.2(d, 6H), 1.2(s, 6H). |
| 800 | δ 7.38(m, 3H), 7.25(m, 2H), 4.64(m, 1H), 2.35(m, 1H), 1.21(d, 6H), 1.15(s, 3H), 1.05(m, 1H), 0.94(m, 4H). |
| 801 | δ 7.37(d, 2H), 7.19(d, 2H), 4.64(m, 1H), 2.37(m, 1H), 1.19(m, 9H), 1.07(m, 1H), 0.96(m, 4H). |
| 802 | δ 737(m, 1H), 6.91(m, 2H), 4.64(m, 1H), 2.37(m, 1H), 1.19(m, 9H), 1.07(m, 1H), 0.96(m, 4H). |
| 803 | δ 7.39(m, 3H), 7.26(m, 2H), 4.64(m, 1H), 4.52(m, 1H), 2.40(m, 1H), 2.04(m, 1H), 1.92(m, 1H), 1.44 and 0.98(t, 3H), 1.22(d, 6H). |
| 804 | δ 7.38(m, 2H), 7.21(m, 2H), 4.64(m, 1H), 3.67(t, 2H), 2.56(m, 2H), 1.96(m, 1H), 1.22(d, 6H). |
| 805 | δ 7.25(m, 2H), 7.08(m, 2H), 4.65(m, 1H), 4.40(m, 1H), 3.70(m, 4H), 1.20(d, 6H). |
| 808 | δ 7.39(m, 2H), 7.20(m, 2H), 7.64(m, 1H), 4.58(m, 1H), 2.43(m, 1H), 2.40(m, 1H), 1.92(m, 1H), 1.21(d, 6H), 0.97(t, 3H). |
| 810 | δ 7.22(m, 2H), 7.09(m, 2H), 4.46(m, 1H), 4.95(m, 1), 4.64(m, 1H), 3.02(m, 1H), 2.76(m, 1H), 1.68(d, 3H), 1.20(d, 6H). |
| 811 | δ 7.21(m, 2H), 7.11(m, 2H), 4.98(m, 1H), 4.64(m, 1H), 3.89(m, 1H), 2.98(dd, 1H), 2.69(dd, 1H), 1.5(d, 3H), 1.20(d, 6H). |
| 812 | δ 7.42(m, 3H), 7.40(m, 2H), 5.44(m, 1H), 4.93(m, 1H), 4.64(m, 1H), 2.80(m, 1H), 2.70(m, 1H), 1.28(d, 3H), 1.22(d, 6H). |
| 814 | δ 7.39(d, 2H), 7.17(d, 2H), 7.11(br s, 1H), 4.92(m, 1H), 4.64(m, 1H), 3.89(m, 1H), 3.02(m, 1H), 2.70(m, 1H), 1.52(d, 3H), 1.20(d, 6H). |
| 815 | δ 7.32(m, 1H), 7.11(br s, 1H), 6.94(m, 2H), 4.88(m, 1H), 4.64(m, 1H), 3.90(m, 1H), 3.01(m, 1H), 2.70(m, 1H), 1.51(d, 3H), 1.23(br, 6H). |
| 816 | δ 7.40(m, 3H), 7.23(m, 2H), 7.09(br s, 1H), 4.91(m, 1H), 4.66(m, 1H), 3.88(m, 1H), 3.00(m, 1H), 2.70(m, 1H), 1.50(d, 3H), 1.21(d, 6H). |
| 817 | δ 7.28(m, 1H), 6.91(m, 2H), 4.63(m, 1H), 4.11(m, 1H), 1.28(d, 3H), 1.22(d, 6H). |
| 819 | δ 7.22(m, 2H), 7.08(m, 2H), 4.62(m, 1H), 3.78(d, 1H), 3.50(d, 1H), 2.70(d, 1H), 2.60(d, 1H), 1.33(s, 3H), 1.18(d, 6H). |
| 822 | δ 7.40(m, 2H), 6.92(m, 2H), 4.60(m, 1H), 3.66(m, 2H), 3.50(m, 2H), 2.05(m, 2H), 1.26(d, 6H). |
| 823 | δ 7.40(m, 2H), 6.92(m, 2H), 4.61(m, 1H), 3.54(m, 4H), 1.80(m, 4H), 1.22(d, 6H). |
| 824 | δ 7.39(m, 3H), 7.24(m, 2H), 4.62(m, 1H), 4.30(m, 1H), 3.90(m, 1H), 3.70(m, 1H), 3.60(m, 1H), 3.30(s, 3H), 1.22(d, 6H). |
| 825 | δ 7.21(m, 2H), 7.08(m, 2H), 4.62(m, 1H), 4.30(m, 1H), 3.90(m, 1H), 3.71(m, 1H), 3.60(m, 1H), 3.30(s, 3H), 1.22(d, 6H). |
| 829 | δ 4.66(s, 1H), 4.5(m, 1H), 4.3(m, 1H), 1.48(d, 6H), 1.42(s, 9H), 1.28(d, 6H). |
| 837 | δ 7.20(m, 2H), 7.10(m, 2H), 5.65(m, 2H), 5.05(d, 1H), 4.65(m, 1H), 4.20(m, 4H), 1.45(d, 3H), 1.20(d, 6H). |
| 839 | δ 7.12–7.2(m, 3H), 4.62(m, 1H), 4.17(m, 1H), 1.39 (d, 6H), 1.25(d, 6H). |
| 840 | δ 7.23(m, 2H), 7.1(m, 2H), 4.2(m, 1H), 3.80(q, 2H), 1.40(d, 6H), 1.27(t, 3H). |
| 841 | δ 7.38(d, 2H), 7.18(d, 2H), 6.0(m, 1H), 5.25(m, 2H), 4.6(m, 2H), 1.5(d, 3H), 1.2(d, 6H). |
| 842 | δ 7.38(d, 2H), 6.93(m, 2H), 5.98(m, 1H), 5.24(m, 2H), 4.6(m, 2H), 1.49(d, 3H), 1.22(br, 6H). |
| 843 | δ 7.4(m, 3H), 7.25(m, 2H), 6.0(m, 1H), 5.22(m, 2H), 4.6(m, 2H), 1.48(d, 3H), 1.2(d, 6H). |
| 845 | δ 7.38(d, 2H), 6.93(m, 2H), 4.9(s, 2H), 4.64(m, 1H), 4.41(m, 1H), 3.45(m, 2H), 2.95(m, 2H), 1.21(d, 6H). |
| 846 | δ 7.4(m, 3H), 7.25(m, 2H), 4.89(s, 2H), 4.64(m, 1H), 4.41(m, 1H), 3.45(m, 2H), 2.95(m, 2H), 1.21(d, 6H). |
| 849 | δ 9.53(s, 1H), 7.39(d, 2H), 7.19(d, 2H), 4.64(m, 1H), 4.44(q, 1H), 1.6(d, 3H), 1.21(d, 6H). |
| 850 | δ 9.51(s, 1H), 7.4(d, 3H), 7.25(m, 2H), 4.64(m, 1H), 4.42(q, 1H), 1.58(d, 3H), 1.21(d, 6H). |

INDEX TABLE D-continued

| Cmpd No. | $^1$H NMR Data ($CDCl_3$ solution unless indicated otherwise)[a] |
|---|---|
| 852 | δ 7.42(s, 1H), 7.37(m, 2H), 7.18(m, 2H), 4.63(m, 1H), 4.48(s, 2H), 3.81(s, 3H), 1.20(d, 6H). |
| 853 | δ 7.44(s, 1H), 7.38(m, 2H), 7.24(m, 3H), 4.63(m, 1H), 4.47(s, 2H), 3.80(s, 3H), 1.20(d, 6H). |
| 854 | δ 7.47(s, 1H), 7.37(m, 1H), 6.93(m, 2H), 4.62(m, 1H), 4.49(s, 2H), 3.81(s, 3H), 1.21(br s, 6H). |
| 866 | δ 7.34(m, 2H), 6.91(m, 2H), 5.33(m, 1H), 4.62(m, 1H), 3.92(s, 2H), 1.91(m, 3H), 1.21(br s, 6H). |
| 871 | δ 7.40(m, 2H), 7.19(m, 2H), 4.65(m, 1H), 4.30(m, 1H), 3.95(dd, 1H), 3.75(m, 1H), 3.60(m, 1H), 3.30(s, 3H), 1.22(d, 6H). |
| 872 | δ 7.30(m, 1H), 6.92(m, 2H), 4.62(m, 1H), 4.30(m, 1H), 3.90(m, 1H), 3.73(m, 2H), 3.60(m, 1H), 3.30(s, 3H), 1.26(d, 6H). |
| 876 | δ 7.36(m, 2H), 7.17(m, 2H), 4.60(m, 1H), 4.12(m, 1H), 1.20(d, 3H), 1.19(d, 6H). |
| 882 | δ 7.38(m, 3H), 7.25(m, 2H), 4.62(m, 2H), 2.40(m, 1H), 2.00–1.80(m, 2H), 1.50–1.30(m, 2H), 1.20(d, 6H), 0.92(t, 3H). |
| 884 | δ 7.23(m, 2H), 7.08(m, 2H), 5.75(m, 1H), 5.21(m, 2H), 4.65(m, 1H), 4.41(s, 1H), 4.32(s, 1H), 4.25(s, 1H), 3.98 (s, 1H), 3.91(d, 1H), 3.86(s, 1.5H), 3.78(d, 1H), 3.74(s, 1.5H), 1.20(d, 6H). syn/anti mixture |
| 885 | δ 7.37(m, 3H), 7.26(m, 2H), 5.75(m, 1H), 5.20(m, 2H), 4.63(m, 1H), 4.39(s, 1H), 4.31(s, 1H), 4.24(s, 1H), 3.94(s, 1H), 3.89(d, 1H), 3.84(s, 1.5H), 3.75(d, 1H), 3.73(s, 1.5H), 1.20(d, 6H). syn/anti mixture |
| 886 | δ 7.36(m, 1H), 6.91(m, 2H), 5.80(m, 1H), 5.21(m, 2H), 4.63(m, 1H), 4.40(s, 1H), 4.32(s, 1H), 4.25(s, 1H), 3.96(s, 1H), 3.92(d, 1H), 3.85(s, 1.5H), 3.80(d, 1H), 3.73(s, 1.5H), 1.20(br, 6H) syn/anti mixture |
| 887 | δ 7.36(d, 2H), 7.20(d, 2H), 5.76(m, 1H), 5.19(m, 2H), 4.64(m, 1H), 4.41(s, 1H), 4.32(s, 1H), 4.25(s, 1H), 3.95(s, 1H), 3.91(d, 1H), 3.86(s, 1.5H), 3.78(d, 1H), 3.74(s, 1.5H), 1.20(d, 6H). syn/anti mixture |
| 888 | δ 7.4(d, 2H), 7.29(d, 2H), 4.63(m, 1H), 4.15(m, 1H), 3.58(m, 2H), 1.49–1.27(m, 9H). |
| 892 | δ 7.20(m, 2H), 7.08(t, 2H), 4.65(m, 1H), 3.70(m, 1H), 3.42(m, 2H), 3.30(m, 2H), 3.12(s, 3H), 1.90(m, 3H), 1.50(m, 1H), 1.20(m, 6H). |
| 898 | δ 7.20(m, 2H), 7.08(t, 2H), 4.97(d, 1H), 4.65(m, 1H), 3.90(m, 2H), 3.80(m, 1H), 3.62(m, 1H), 3.47(m, 1H), 1.50(m, 4H), 1.40(d, 3H), 1.20(m, 6H). |
| 900 | δ 7.30(m, 9H), 4.63(m, 1H), 4.44(s, 1H), 4.39(s, 1H), 4.34(s, 1H), 4.29(s, 1H), 4.25(s, 1H), 3.96(s, 1H), 3.83(s, 1.5H), 3.71(s, 1.5H), 1.21(m, 6H). syn/anti mixture |
| 901 | δ 7.30(m, 10H), 4.63(m, 1H), 4.44(s, 1H), 4.39(s, 1H), 4.34(s, 1H), 4.29(s, 1H), 4.25(s, 1H), 3.96(s, 1H), 3.83 (s, 1.5H), 3.71(s, 1.5H), 1.21(m, 6H). syn/anti mixture |
| 902 | δ 7.23(m, 2H), 7.08(m, 2H), 4.65(m, 1H), 4.39(s, 1H), 4.29(s, 1H), 4.20(s, 1H), 3.91(s, 1H), 3.86(s, 1.5H), 3.74(s, 1.5H), 3.28(s, 1.5H), 3.14(s, 1.5H), 120(d, 6H). syn/anti mixture |
| 903 | δ 7.37(m, 3H), 7.26(m, 2H), 4.64(m, 1H), 4.38(s, 1H), 4.28(s, 1H), 4.19(s, 1H), 3.89(s, 1H), 3.85(s, 1.5H), 3.74(s, 1.5H), 3.27(s, 1.5H), 3.10(s, 1.5H), 1.20(d, 6H). syn/anti mixture |
| 904 | δ 7.37(m, 3H), 7.26(m, 2H), 4.64(m, 1H), 4.38(s, 1H), 4.28(s, 1H), 4.19(s, 1H), 3.89(s, 1H), 3.85(s, 1.5H), 3.74(s, 1.5H), 3.27(s, 1.5H), 3.10(s, 1.5H), 1.20(d, 6H). 4:1 syn/anti mixture |
| 905 | δ 7.35(d, 2H), 7.27(d, 2H), 4.39(m, 2H), 4.15(m, 1H), 3.40(s, 3H), 3.38(s, 3H), 1.39(d, 6H), 1.26(d, 3H). |
| 908 | δ 7.36(m, 3H), 7.26(m, 2H), 4.35(m, 2H), 4.15(m, 1H), 1.70(d, 3H), 1.38(m, 6H). |
| 909 | δ 7.28(m, 2H), 7.09(m, 2H), 4.38(m, 2H), 4.18(m, 1H), 1.68(d, 3H), 1.38(m, 6H). |
| 913 | δ 7.4(m, 3H), 7.25(m, 2H), 4.64(m, 1H), 3.71(t, 2H), 2.84(t, 2H), 2.14(s, 3H), 1.21(d, 6H). |
| 914 | δ 9.73(s, 1H), 7.22(m, 2H), 7.09(m, 2H), 4.64(m, 1H), 3.81(t, 2H), 2.88(t, 2H), 1.2(d, 6H). |
| 915 | δ 7.35(m, 1H), 6.92(m, 2H), 4.63(m, 1H), 3.51(t, 2H), 2.45(t, 2H), 2.11(s, 3H), 1.89(m, 2H), 1.22(br, 6H). |
| 916 | δ 7.37(m, 2H), 7.18(m, 2H), 4.64(m, 1H), 3.51(t, 2H), 2.45(t, 2H), 2.11(s, 3H), 1.89(m, 2H), 1.22(br, 6H). |
| 917 | δ 7.37(t, 2H), 7.21(m, 2H), 4.62(m, 2H), 2.40(m, 1H), 2.00–1.80(m, 2H), 1.50–1.30(m, 2H), 1.20(d, 6H), 0.92(t, 3H). |
| 919 | δ 7.34(m, 5H), 4.42(m, 2H), 4.18(m, 1H), 3.74(s, 3H), 3.42(s, 3H), 1.37(d, 6H), 1.27(m, 3H). |
| 920 | δ 7.30(m, 2H), 7.09(m, 2H), 4.38(m, 2H), 4.18(m, 1H), 3.41(s, 3H), 3.38(s, 3H), 1.39(d, 6H), 1.27(m, 3H). |
| 922 | δ 7.36(d, 2H), 7.20(d, 2H), 4.64(m, 1H), 4.39(s, 1H), 4.29(s, 1H), 4.20(s, 1H), 3.91(s, 1H), 3.86(s, 1.5H), 3.74(s, 1.5H), 3.28(s, 1.5H), 3.14(s, 1.5H), 1.20(d, 6H). syn/anti mixture |
| 923 | δ 7.38(m, 1H), 6.91(m, 2H), 4.64(m, 1H), 4.39(s, 1H), 4.29(s, 1H), 4.19(s, 1H), 3.91(s, 1H), 3.86(s, 1.5H), 3.74(s, 1.5H), 3.29(s, 1.5H), 3.15(s, 1.5H), 1.20(br, 6H). syn/anti mixture |
| 927 | δ 7.37(m, 2H), 6.91(m, 2H), 6.15(m, 1H), 5.55(m, 1H), 5.00(m, 1H), 4.64(m, 1H), 2.7(m, 1H), 2.30(m, 2H), 1.98(m, 1H), 1.2(br, 6H). |
| 929 | δ 7.4(m, 3H), 7.25(m, 2H), 6.17(m, 1H), 5.55(m, 1H), 5.00(m, 1H), 4.64(m, 1H), 2.7(m, 1H), 2.3(m, 2H), 1.99(m, 1H), 1.2(d, 6H). |
| 930 | δ 7.24(m, 3H), 7.10(m, 2H), 4.65(m, 2H), 3.8(m, 2H), 3.39(m, 2H), 1.21(d, 6H). |
| 935 | δ 7.35(m, 1H), 6.91(m, 2H), 4.63(m, 1H), 3.74(t, 2H), 2.85(t, 2H), 2.15(s, 3H), 1.21(br, 6H). |
| 947 | δ 7.31(m, 1H), 6.89(m, 2H), 4.6(m, 1H), 3.75(m, 1H), 2.72(m, 4H), 2.4(m, 2H), 2.00(m, 2H), 1.23(m, 6H). |
| 952 | δ 7.51(m, 3H), 7.24(m, 2H), 6.86(q, 1H), 4.31(m, 1H), 1.97(d, 3H), 1.49(d, 6H). |
| 953 | δ 7.34(m, 5H), 4.22(m, 1H), 2.14(s, 3H), 1.92(s, 3H), 1.44(d, 6H). |
| 955 | δ 7.43(m, 5H), 4.64(m, 1H), 4.17(m, 1H), 3.79(d, 4H), 1.38(d, 6H). |
| 956 | δ 7.44(m, 2H), 7.12(m, 2H), 4.19(m, 1H), 4.13(m, 2H), 3.78(d, 4H), 1.40(d, 6H). |
| 959 | δ 7.38(m, 3H), 7.26(m, 2H), 4.64(m, 1H), 4.26(m, 1H), 2.41(m, 2H), 1.22(m, 6H), 1.10(d, 3H), 0.85(d, 3H). |
| 962 | δ 7.22(m, 2H), 7.10(m, 2H), 4.64(m, 1H), 3.51(t, 2H), 2.45(t, 2H), 2.11(s, 3H), 1.90(m, 2H), 1.2(d, 6H). |
| 963 | δ 7.39(m, 3H), 7.26(m, 2H), 4.64(m, 1H), 3.50(t, 2H), 2.43(t, 2H), 2.11(s, 3H), 1.89(m, 2H), 1.2(d, 6H). |
| 964 | δ 9.73(s, 1H), 7.37(m, 1H), 6.93(m, 2H), 4.63(m, 1H), 3.81(t, 2H), 2.89(t, 2H), 1.22(br, 6H). |
| 965 | δ 9.72(s, 1H), 7.39(m, 3H), 7.25(m, 2H), 4.64(m, 1H), 3.79(t, 2H), 2.87(t, 2H), 1.21(br, 6H). |
| 967 | δ 7.22(m, 2H), 7.08(m, 2H), 4.64(m, 1H), 3.94(m, 1H), 2.78(m, 1H), 2.58(m, 1H), 2.00–1.70(m, 3H), 1.26(m, 2H), 1.20(m, 6H), 0.90(m, 3H). |

[a] $^1$H NMR data are in ppm downfield from tetramethylsilane. Couplings are designated by (s)-singlet, (d)-doublet, (t)-triplet, (q)-quartet, (m)-multiplet, (dd)-doublet of doublets, (dt)-doublet of triplets, (br s)-broad singlet.

Test A

Seeds of barnyardgrass (*Echinochloa crus-galli*), crabgrass (Digitaria spp.), morningglory (Ipomoea spp.), and velvetleaf (*Abutilon theophrasti*) were planted into a sandy loam soil and treated preemergence by soil drench with test chemicals formulated in a non-phytotoxic solvent mixture which includes a surfactant At the same time, these crop and weed species were also treated postemergence sprayed to runoff, with test chemicals formulated in the same manner.

Plants ranged in height from two to eighteen cm and were in the one to two leaf stage for the postemergence treatment. Treated plants and untreated controls were maintained in a greenhouse for approximately eleven days, after which all treated plants were compared to untreated controls and visually evaluated for injury. Plant response ratings, summarized in Table A, are based on a 0 to 10 scale where 0 is no effect and 10 is complete control.

TABLE A

| | COMPOUND | | | | | | | | | |
|---|---|---|---|---|---|---|---|---|---|---|
| Rate 2000 g/ha | 1 | 2 | 3 | 10 | 42 | 43 | 52 | 53 | 99 | 114 |
| Pre-emergence | | | | | | | | | | |
| Barnyardgrass | 9 | 9 | 9 | 10 | 0 | 0 | 9 | 8 | 9 | 10 |
| Crabgrass | 9 | 2 | 3 | 9 | 0 | 1 | 10 | 9 | 10 | 10 |
| Morningglory | 0 | 0 | 0 | 1 | 0 | 0 | 0 | 0 | 2 | 6 |
| Velvetleaf | 0 | 0 | 0 | 2 | 0 | 0 | 0 | 0 | 3 | 6 |

| | COMPOUND | | | | | |
|---|---|---|---|---|---|---|
| Rate 2000 g/ha | 127 | 128 | 136 | 137 | 177 | 183 |
| Pre-emergence | | | | | | |
| Barnyardgrass | 9 | 0 | 9 | 10 | 9 | 9 |
| Crabgrass | 8 | 0 | 10 | 10 | 9 | 5 |
| Morningglory | 0 | 0 | 0 | 3 | 0 | 0 |
| Velvetleaf | 0 | 0 | 0 | 5 | 1 | 0 |

| | COMPOUND | | | |
|---|---|---|---|---|
| Rate 2000 g/ha | 184 | 225 | 377 | 386 |
| Pre-emergence | | | | |
| Barnyardgrass | 9 | 10 | 0 | 0 |
| Crabgrass | 9 | 10 | 0 | 0 |
| Morningglory | 0 | 8 | 0 | 0 |
| Velvetleaf | 0 | 7 | 0 | 0 |

| | COMPOUND | | | | | | | | | |
|---|---|---|---|---|---|---|---|---|---|---|
| Rate 1000 g/ha | 1 | 2 | 3 | 10 | 42 | 43 | 52 | 53 | 99 | 114 |
| Barnyardgrass | 8 | 8 | 6 | 9 | 0 | 0 | 5 | 3 | 7 | 8 |
| Crabgrass | 5 | 0 | 0 | 8 | 0 | 0 | 8 | 6 | 7 | 7 |
| Morningglory | 0 | 0 | 0 | 0 | 0 | 0 | 1 | 0 | 2 | 10 |
| Velvetleaf | 0 | 0 | 0 | 4 | 0 | 0 | 1 | 1 | 2 | 5 |

| | COMPOUND | | | | | |
|---|---|---|---|---|---|---|
| Rate 1000 g/ha | 127 | 128 | 136 | 137 | 177 | 183 |
| Barnyardgrass | 6 | 0 | 4 | 8 | 0 | 0 |
| Crabgrass | 7 | 0 | 6 | 8 | 3 | 1 |
| Morningglory | 0 | 0 | 9 | 10 | 0 | 0 |
| Velvetleaf | 0 | 0 | 2 | 2 | 2 | 0 |

TABLE A-continued

| | COMPOUND | | | |
|---|---|---|---|---|
| Rate 1000 g/ha | 184 | 225 | 377 | 386 |
| Postemergence | | | | |
| Barnyardgrass | 2 | 9 | 0 | 0 |
| Crabgrass | 1 | 9 | 0 | 0 |
| Morningglory | 10 | 10 | 0 | 0 |
| Velvetleaf | 2 | 3 | 0 | 0 |

Test B

Seeds of bedstraw (*Galium aparine*), blackgrass (*Alopecurus myosuroides*), surinam grass (*Brachiaria decumbens*), cocklebur (*Xanthium strumarium*), corn (*Zea mays*), crabgrass (*Digitaria sanguinalis*), giant foxtail (*Setaria faberii*), morningglory (*Ipomoea hederacea*), pigweed (*Amaranthus retroflexus*), rape (*Brassica napus*), soybean (*Glycine max*), sugar beet (*Beta vulgaris*), velvetleaf (*Abutilon theophrasti*), wheat (*Triticum aestivum*), wild oat (*Avena fatua*) and purple nutsedge (*Cyperus rotundus*) tubers were planted and treated preemnergence with test chemicals formulated in a non-phytotoxic solvent mixture which included a surfactant.

At the same time, these crop and weed species were also treated with postemergence applications of test chemicals formulated in the same manner. Plants ranged in height from 2 to 18 cm (1- to 4-leaf stage) for postemergence treatments. Plant species in the flood test consisted of rice (*Oryza sativa*), smallflower flatsedge (*Cyperus difformis*), duck salad (*Heteranthera limosa*) and bamyardgrass (*Echinochloa crus-galli*) grown to the 2-leaf stage for testing. Treated plants and controls were maintained in a greenhouse for twelve to sixteen days, after which all species were compared to controls and visually evaluated. Plant response ratings, summarized in Table B, are based on a scale of 0 to 10 where 0 is no effect and 10 is complete control. A dash (–) response means no test result.

TABLE B

| | COMPOUND | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| Rate 2000 g/ha | 7 | 18 | 30 | 36 | 46 | 47 | 78 | 86 | 87 | 93 | 94 | 103 | 105 | 107 | 108 | 109 | 111 | 113 | 116 | 117 | 118 | 119 | 121 | 122 | 123 | 124 | 125 | 139 | 154 | 177 | 183 | 274 |
| Pre-emergence | | | | | | | | | | | | | | | | | | | | | | | | | | | | | | | | |
| Barnyardgrass | 0 | 9 | 0 | 0 | 9 | 8 | 3 | 0 | 0 | 0 | 7 | 0 | 0 | 0 | 0 | 9 | 9 | 9 | 9 | 3 | 6 | 0 | 9 | 0 | 0 | 0 | 0 | 6 | 0 | 0 | 0 | 0 |
| Ducksalad | 0 | 0 | 0 | 0 | 2 | 0 | 0 | 0 | 0 | 0 | 0 | 0 | 0 | 0 | 0 | 6 | 0 | 8 | 8 | 1 | 0 | 0 | 0 | 0 | 0 | 0 | 0 | 2 | 0 | 0 | 0 | 0 |
| Rice | 0 | 0 | 0 | 0 | 0 | 0 | 0 | 8 | 0 | 0 | 0 | 0 | 0 | 0 | 0 | 7 | 0 | 7 | 4 | 0 | 0 | 0 | 5 | 0 | 0 | 0 | 0 | 0 | 0 | 0 | 0 | 0 |
| S. Flatsedge | 0 | 0 | 0 | 0 | 8 | 0 | 7 | 0 | 0 | 0 | 8 | 0 | 0 | 5 | 0 | 8 | 0 | 9 | 9 | 4 | 0 | 0 | 9 | 0 | 0 | 0 | 0 | 0 | 0 | 0 | 0 | 0 |

| | COMPOUND | | |
|---|---|---|---|
| Rate 2000 g/ha | 157 | 177 | 183 |
| Postemergence | | | |
| B. signalgrass | — | 0 | 0 |
| Barnyardgrass | 0 | — | — |
| Bedstraw | — | — | — |
| Blackgrass | — | 6 | 0 |
| Cocklebur | — | 0 | 2 |
| Corn | — | 0 | 0 |
| Crabgrass | — | 0 | 0 |
| Ducksalad | 0 | — | — |
| Giant foxtail | — | 2 | 0 |
| Morningglory | — | 1 | 5 |
| Nutsedge | — | 0 | 0 |
| Rape | — | 3 | 0 |
| Redroot pigweed | — | 3 | 0 |
| Rice | 0 | — | — |
| S. Flatsedge | 0 | — | — |
| Soybean | — | 4 | 3 |
| Sugarbeets | — | 0 | 0 |
| Velvetleaf | — | 4 | 1 |
| Wheat | — | 3 | 0 |
| Wild oats | — | 2 | 0 |

| | COMPOUND | |
|---|---|---|
| Rate 2000 g/ha | 177 | 183 |
| Preemergence | | |
| B. signalgrass | 9 | 2 |
| Bedstraw | 10 | 10 |
| Blackgrass | 9 | 2 |
| Cocklebur | 2 | 0 |
| Corn | 0 | 0 |
| Crabgrass | 9 | 2 |
| Giant foxtail | 10 | 9 |

TABLE B-continued

| | | |
|---|---|---|
| Morningglory | 0 | 0 |
| Nutsedge | 0 | 0 |
| Rape | 0 | 0 |
| Redroot pigweed | 0 | 0 |
| Soybean | 0 | 0 |
| Sugarbeets | 0 | 0 |
| Velvetleaf | 3 | 0 |
| Wheat | 2 | 0 |
| Wild oats | 10 | 3 |

| | COMPOUND | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|
| Rate 1000 g/ha | 7 | 18 | 30 | 35 | 36 | 46 | 47 | 78 | 86 | 87 | 93 | 94 | 103 | 105 | 107 | 108 | 109 | 111 | 113 | 116 | 117 | 118 | 119 | 121 | 122 | 123 | 124 | 125 | 139 | 154 | 177 | 183 | 184 |
| Pre-emergence | | | | | | | | | | | | | | | | | | | | | | | | | | | | | | | | | |
| Barnyardgrass | 0 | 9 | 0 | 0 | 0 | 0 | 6 | 0 | 0 | 0 | 0 | 0 | 0 | 0 | 0 | 0 | 8 | 0 | 0 | 0 | 0 | 3 | 0 | 9 | 0 | 0 | 0 | 0 | 0 | 0 | 0 | 0 | 3 |
| Ducksalad | 0 | 0 | 0 | 0 | 0 | 2 | 3 | 0 | 0 | 0 | 0 | 0 | 0 | 0 | 0 | 0 | 1 | 0 | 1 | 1 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 3 | 0 | 0 | 0 | 0 | 0 | 0 | 0 | 0 | 0 |
| S. Flatsedge | 0 | 0 | 0 | 0 | 0 | 0 | 2 | 0 | 0 | 0 | 0 | 0 | 0 | 0 | 0 | 0 | 8 | 0 | 0 | 0 | 0 | 0 | 0 | 9 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 1000 g/ha | 244 | 247 | 248 | 274 | 279 | 280 | 302 | 306 | 307 | 308 | 309 | 310 | 317 | 322 | 331 | 332 | 333 | 365 | 447 | 448 | 587 | 599 | 600 | 616 | 617 | 623 | 662 | 677 | 678 |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 0 | 6 | 0 | 9 | 0 | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | |
|---|---|---|---|
| Rate 1000 g/ha | 679 | 680 | 681 |
| Pre-emergence | | | |
| Barnyardgrass | 0 | 0 | 0 |
| Ducksalad | 0 | 0 | 0 |
| Rice | 0 | 0 | 0 |
| S. Flatsedge | 0 | 0 | 0 |

| | COMPOUND | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|
| Rate 1000 g/ha | 1 | 2 | 3 | 4 | 5 | 6 | 7 | 8 | 9 | 12 | 13 | 99 | 127 | 157 | 176 | 177 | 183 | 184 | 247 | 279 | 280 | 302 | 365 | 447 | 448 | 587 | 599 | 600 | 616 | 617 | 623 | 662 | 677 |
| Postemergence | | | | | | | | | | | | | | | | | | | | | | | | | | | | | | | | | |
| B. signalgrass | 6 | 2 | 0 | 4 | 4 | 7 | 6 | 3 | 0 | 0 | 6 | 4 | 0 | — | 2 | 0 | 0 | 3 | 0 | 0 | 0 | 0 | 0 | 2 | 0 | 5 | 0 | 0 | 5 | 3 | 0 | 2 | 1 |
| Barnyardgrass | 0 | 0 | 0 | 4 | 4 | 8 | 0 | 0 | 0 | 0 | 0 | 8 | — | 0 | 0 | — | — | — | — | — | — | — | — | — | — | — | — | — | — | — | — | — | — |
| Bedstraw | 0 | 0 | 0 | 8 | 4 | 3 | 4 | 3 | — | 0 | 0 | — | 0 | — | 9 | — | — | — | 0 | 0 | 0 | 0 | — | — | — | 7 | — | 0 | — | — | — | — | 0 |

TABLE B-continued

| | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| Blackgrass | 8 | 9 | 3 | 6 | 8 | 7 | 6 | 5 | 3 | 0 | 8 | 5 | 0 | — | 7 | 3 | 0 | 7 | 0 | 6 | 0 | 6 | 0 | 7 | 2 | — | 6 | 0 | — | 6 | 7 | 6 | 4 |
| Cocklebur | 0 | 0 | 2 | 8 | 8 | 0 | 2 | 2 | 4 | 0 | 0 | 4 | 0 | — | 6 | 0 | 0 | 2 | 0 | 0 | 0 | 0 | 0 | 0 | 0 | 0 | 0 | 0 | 3 | 3 | 0 | 5 | 1 |
| Corn | 0 | 8 | 0 | 0 | 0 | 4 | 0 | 3 | 0 | 0 | 0 | 0 | 0 | — | 0 | 0 | 0 | 0 | 0 | 0 | 0 | 0 | 0 | 0 | 0 | 0 | 0 | 0 | 0 | 0 | 0 | 1 | 0 |
| Crabgrass | 9 | 4 | 7 | 8 | 6 | 7 | 5 | 6 | 0 | 0 | 9 | 8 | 0 | — | 9 | 0 | 0 | 2 | 0 | — | 0 | 1 | 0 | 0 | 0 | 3 | 0 | 3 | 8 | 7 | 3 | 8 | 6 |
| Ducksalad | 0 | 0 | 0 | 3 | 0 | 0 | 0 | 0 | 0 | 0 | 0 | 3 | — | 0 | 0 | — | — | — | — | — | — | — | — | — | — | — | — | — | — | — | — | — | — |
| Giant foxtail | 8 | 8 | 8 | 6 | 7 | 7 | 6 | 4 | 0 | 0 | 7 | 2 | 0 | — | 7 | 0 | 0 | 3 | 0 | 4 | 0 | 7 | 0 | 0 | 0 | 4 | 4 | 3 | 7 | 6 | 2 | 8 | 5 |
| Morningglory | 0 | 5 | 0 | 3 | 9 | 7 | 3 | 6 | 2 | 0 | 0 | 9 | 0 | — | 7 | 1 | 4 | 9 | 4 | 3 | 0 | 2 | 0 | 10 | 8 | 9 | 6 | 0 | 10 | 6 | 10 | 7 | — |
| Nutsedge | 0 | 0 | 0 | 0 | 0 | — | — | — | — | 0 | 0 | 0 | 0 | — | — | 0 | 0 | 0 | 0 | 0 | 0 | 0 | 0 | 0 | 0 | 0 | 0 | 0 | — | 0 | — | — | 0 |
| Rape | 4 | 0 | 0 | 3 | 5 | 2 | 0 | 0 | 0 | 0 | 1 | 7 | 0 | — | 0 | 0 | 0 | 3 | 0 | 0 | 0 | 0 | 0 | 0 | 0 | 0 | 0 | 0 | 3 | 0 | 0 | 0 | 0 |
| Redroot pigweed | 9 | 0 | 0 | 8 | 8 | 4 | 0 | 5 | 3 | 0 | 0 | 7 | 0 | — | 1 | 2 | 0 | 6 | 0 | 4 | 3 | 3 | 0 | 0 | 0 | 0 | 0 | 0 | 3 | 0 | 5 | 0 | 4 |
| Rice | 0 | 0 | 0 | 0 | 0 | 3 | 0 | 0 | 0 | 0 | 0 | 0 | — | 0 | 0 | — | — | — | — | — | — | — | — | — | — | — | — | — | — | — | — | — | — |
| S. Flatsedge | 0 | 0 | 0 | 4 | 2 | 3 | 0 | 0 | 0 | 0 | 0 | 3 | — | 0 | 0 | — | — | — | — | — | — | — | — | — | — | — | — | — | — | — | — | — | — |
| Soybean | 2 | 4 | 2 | 5 | 6 | 6 | 5 | 5 | 1 | 1 | 3 | 3 | 0 | — | 4 | 3 | 2 | 4 | 1 | 4 | 5 | 5 | 3 | 6 | 6 | 6 | 4 | 4 | 4 | 7 | 3 | — | 7 |
| Sugarbeets | 5 | 0 | 0 | 4 | 7 | 3 | 2 | 2 | 0 | 0 | 0 | 5 | 0 | — | 4 | 0 | 0 | 0 | 0 | 4 | 0 | 2 | 0 | 0 | 0 | 0 | 0 | 0 | 2 | 0 | 0 | 0 | 1 |
| Velvetleaf | 0 | 0 | 0 | 7 | 7 | 1 | 0 | 1 | 0 | 0 | 0 | 7 | 0 | — | 3 | 0 | 1 | 2 | 0 | 0 | 0 | 0 | 0 | 0 | 2 | 2 | 3 | 0 | 1 | 2 | 2 | 0 | 3 |
| Wheat | 0 | 0 | 0 | 0 | 2 | 0 | 2 | 3 | 0 | 0 | 0 | 2 | 0 | — | 4 | 3 | 0 | 3 | 0 | 1 | 0 | 1 | 0 | 0 | 0 | 3 | 0 | 0 | 0 | 0 | 1 | 0 | 0 |
| Wild oats | 0 | 0 | 0 | 0 | 1 | 4 | 3 | 3 | 0 | 0 | 2 | 3 | 0 | — | 4 | 2 | 0 | 5 | 0 | 0 | 0 | 0 | 0 | 0 | 4 | 0 | 0 | 0 | — | 0 | 2 | 1 | 0 |

| | COMPOUND | | | | | | | |
|---|---|---|---|---|---|---|---|---|
| Rate 1000 g/ha | 678 | 679 | 680 | 681 | 736 | 775 | 777 | 778 |
| Postemergence | | | | | | | | |
| B. signalgrass | 4 | 0 | 3 | 0 | 7 | 9 | 8 | 6 |
| Barnyardgrass | — | — | — | — | — | — | — | — |
| Bedstraw | 0 | — | — | — | — | 7 | 6 | 7 |
| Blackgrass | 6 | 1 | 3 | 4 | 7 | 4 | 4 | 4 |
| Cocklebur | 3 | 1 | 0 | 0 | 10 | 0 | 0 | 0 |
| Corn | 0 | 0 | 1 | 0 | 4 | 0 | 0 | 0 |
| Crabgrass | — | 2 | 9 | 2 | 6 | 9 | — | 9 |
| Ducksalad | — | — | — | — | — | — | — | — |
| Giant foxtail | 7 | 5 | 8 | 3 | 6 | 9 | 9 | 9 |
| Morningglory | — | 2 | 7 | — | 7 | 8 | 8 | 8 |
| Nutsedge | — | 0 | — | — | 5 | 0 | 3 | 3 |
| Rape | 2 | 0 | 0 | 0 | 0 | 0 | 0 | 3 |
| Redroot pigweed | 5 | 2 | 5 | 7 | 3 | 6 | 8 | 6 |
| Rice | — | — | — | — | — | — | — | — |
| S. Flatsedge | — | — | — | — | — | — | — | — |
| Soybean | 2 | — | — | 3 | 6 | 6 | 6 | 7 |
| Sugarbeets | 0 | 0 | 2 | 7 | 0 | 0 | 7 | 9 |
| Velvetleaf | 6 | 3 | 4 | 2 | 4 | 3 | 5 | 3 |
| Wheat | 2 | 0 | 0 | 0 | 2 | 9 | 3 | 2 |
| Wild oats | 3 | 0 | 1 | 1 | 3 | 0 | 3 | 2 |

| | COMPOUND | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| Rate 1000 g/ha | 1 | 2 | 3 | 4 | 5 | 6 | 7 | 8 | 9 | 12 | 13 | 99 | 127 | 176 | 177 | 183 | 184 | 247 | 279 | 280 | 302 | 365 | 447 | 448 | 587 | 599 | 600 | 616 | 617 | 623 | 662 | 677 | 678 |
| Preemergence | | | | | | | | | | | | | | | | | | | | | | | | | | | | | | | | | |
| B. signalgrass | 8 | 6 | 0 | 10 | 8 | 5 | 3 | 6 | 0 | 6 | 8 | 6 | 0 | 3 | 5 | 0 | 5 | 0 | 0 | 0 | 7 | 0 | 6 | 4 | 10 | 3 | 0 | 6 | 8 | 4 | 9 | 9 | 0 |

TABLE B-continued

| | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|
| Bedstraw | 0 | 0 | 0 | 6 | 0 | 0 | 0 | 0 | 0 | 0 | 3 | 0 | 0 | 6 | 10 | 7 | 2 | 0 | 0 | 0 | 0 | 0 | — | 0 | 3 | 8 | 0 | 4 | 0 | — | — | — | — |
| Blackgrass | 4 | 7 | 0 | 10 | 8 | 7 | 2 | 4 | 0 | 4 | 9 | 7 | 0 | 7 | 7 | 1 | 7 | 0 | 0 | 0 | 6 | 0 | 3 | 4 | 10 | 8 | 0 | 8 | 10 | 2 | 9 | 4 | 1 |
| Cocklebur | — | — | 0 | 0 | 0 | 2 | 0 | 0 | 0 | 0 | — | 7 | — | 0 | — | 0 | 3 | 0 | 0 | 0 | 0 | 0 | 0 | — | 0 | 3 | 0 | 0 | 0 | 0 | 9 | 0 | 0 |
| Corn | 7 | 8 | 0 | 0 | 0 | 5 | 0 | 3 | 3 | 0 | 0 | 2 | 0 | 2 | 0 | 0 | 2 | 0 | 0 | 0 | 0 | 0 | 0 | 2 | 4 | 0 | 0 | 2 | 0 | 0 | 5 | 0 | 0 |
| Crabgrass | 9 | 6 | 2 | 10 | 7 | 10 | 8 | 9 | 3 | 6 | 8 | 10 | 7 | 10 | 8 | 0 | 9 | 3 | 4 | 0 | 7 | 8 | 9 | 9 | 10 | 8 | 0 | 6 | 8 | 0 | 9 | 9 | 3 |
| Giant foxtail | 9 | 10 | 10 | 10 | 10 | 9 | 9 | 10 | 7 | 8 | 8 | 10 | 9 | 10 | 10 | 6 | 10 | 7 | 7 | 0 | 10 | 9 | 10 | 9 | 10 | 10 | 0 | 9 | 10 | 9 | 10 | 10 | 6 |
| Morningglory | 0 | 0 | 0 | 0 | 0 | 0 | 0 | 0 | 0 | 0 | 2 | 3 | 0 | 0 | 0 | 0 | 2 | 0 | 0 | 0 | 0 | 0 | 2 | 0 | 3 | 0 | 0 | 0 | 0 | 0 | 3 | 0 | 1 |
| Nutsedge | — | — | — | 0 | 0 | 0 | 0 | 0 | 0 | 0 | 0 | 10 | — | 10 | 0 | 0 | — | — | 0 | 0 | 0 | 0 | 0 | 0 | 0 | 0 | 0 | 0 | 8 | 0 | 10 | 0 | 0 |
| Rape | 0 | 0 | 0 | 3 | 0 | 0 | 0 | 0 | 0 | 0 | 0 | 6 | 0 | 3 | 0 | 0 | 0 | 0 | 0 | 0 | 8 | 0 | 0 | 0 | 2 | 3 | 0 | 6 | 0 | 2 | 4 | 3 | 0 |
| Redroot pigweed | 2 | 0 | 0 | 8 | 10 | 7 | 2 | 7 | 0 | 0 | 3 | 10 | 10 | 0 | 0 | 0 | 2 | 0 | 0 | 0 | 3 | 0 | 0 | 0 | 3 | 4 | 0 | 10 | 0 | 5 | 7 | 8 | 4 |
| Soybean | 0 | 3 | 0 | 1 | 0 | 0 | 0 | 0 | 0 | 0 | 0 | 2 | 0 | 2 | 0 | 0 | 0 | 0 | 0 | 0 | 0 | 0 | — | 0 | 2 | 0 | 3 | 5 | 1 | 0 | 3 | 0 | 0 |
| Sugarbeets | 0 | 0 | 0 | 4 | 0 | 0 | 0 | 0 | 0 | 0 | 0 | 6 | 0 | 6 | 0 | 0 | 2 | 0 | 0 | 0 | 4 | 0 | 0 | 0 | 3 | 2 | 0 | 7 | 0 | 7 | 0 | 7 | 0 |
| Velvetleaf | 3 | 2 | 0 | 0 | 0 | 4 | 0 | 4 | 0 | 0 | 2 | 0 | 0 | 5 | 0 | 0 | 3 | 0 | 0 | 0 | 4 | 0 | 0 | 0 | 4 | 0 | 0 | 5 | 0 | 0 | 2 | 0 | 5 |
| Wheat | 0 | 0 | 0 | 0 | 0 | 3 | 0 | 0 | 0 | 0 | 0 | 2 | 2 | 4 | 0 | 0 | 0 | 0 | 0 | 0 | 0 | 0 | 0 | 0 | 7 | 0 | 0 | 0 | 2 | 3 | 5 | 0 | 0 |
| Wild oats | 2 | 4 | 0 | 8 | 6 | 6 | 0 | 3 | 0 | 0 | 7 | 7 | 8 | 5 | 10 | 0 | 4 | 0 | 0 | 0 | 6 | 0 | 10 | 5 | 10 | 0 | 0 | 10 | 9 | 2 | 9 | 2 | 0 |

| | COMPOUND | | | | | | | | | | |
|---|---|---|---|---|---|---|---|---|---|---|---|
| Rate 1000 g/ha | 679 | 680 | 681 | 697 | 698 | 723 | 724 | 736 | 775 | 777 | 778 |
| Preemergence | | | | | | | | | | | |
| B. signalgrass | 0 | 0 | 4 | 9 | 4 | 6 | 0 | 9 | — | — | — |
| Bedstraw | — | — | — | 0 | 0 | 0 | 0 | — | 2 | 3 | 10 |
| Blackgrass | 5 | 4 | 6 | 10 | 9 | 6 | 2 | 10 | 10 | 10 | 10 |
| Cocklebur | 0 | 0 | — | 0 | 0 | 0 | 0 | 2 | 0 | — | 0 |
| Corn | 2 | 0 | 0 | 0 | 0 | 0 | 0 | 9 | 4 | 0 | 2 |
| Crabgrass | 3 | 3 | 8 | 9 | 9 | 9 | 9 | 9 | 10 | 10 | 10 |
| Giant foxtail | 8 | 7 | 9 | 10 | 10 | 10 | 10 | 8 | 10 | 10 | 10 |
| Morningglory | 0 | 0 | 0 | 5 | 0 | 0 | 0 | 6 | 5 | 7 | 0 |
| Nutsedge | — | 0 | 0 | 0 | — | 0 | 0 | 8 | 9 | 1 | 10 |
| Rape | 0 | 0 | 0 | 0 | 8 | 2 | 0 | 2 | 7 | 7 | 6 |
| Redroot pigweed | 6 | 7 | 5 | 0 | 0 | 5 | 3 | 2 | 10 | 9 | 10 |
| Soybean | 0 | 0 | 0 | 0 | 3 | 0 | 0 | 3 | 2 | 0 | 7 |
| Sugarbeets | 0 | 0 | 0 | 0 | 0 | 0 | 0 | 5 | 3 | 3 | 7 |
| Velvetleaf | 0 | 4 | 0 | 2 | 0 | 0 | 0 | 3 | 4 | 3 | 3 |
| Wheat | 0 | 0 | 0 | 7 | 6 | 0 | 0 | 9 | 9 | 9 | 8 |
| Wild oats | 0 | 2 | 3 | 9 | 10 | 8 | 0 | 10 | 9 | 9 | 9 |

| | COMPOUND | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|
| Rate 500 g/ha | 7 | 18 | 30 | 35 | 36 | 46 | 47 | 69 | 70 | 71 | 72 | 78 | 86 | 87 | 93 | 94 | 103 | 105 | 107 | 108 | 109 | 111 | 113 | 116 | 117 | 118 | 119 | 121 | 122 | 123 | 124 | 125 | 129 | 131 |
| Pre-emergence | | | | | | | | | | | | | | | | | | | | | | | | | | | | | | | | | | |
| Barnyardgrass | 0 | 8 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 1 | 0 | 8 | 0 | 0 | 0 | 0 | 9 | 9 |
| Ducksalad | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 5 | 9 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 6 | 8 |
| S. Flatsedge | 0 | 6 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 3 | 0 | 0 | 0 | 0 | 9 | 8 |

TABLE B-continued

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 139 | 146 | 154 | 165 | 166 | 177 | 180 | 181 | 182 | 183 | 184 | 185 | 186 | 187 | 189 | 190 | 191 | 192 | 193 | 194 | 195 | 196 | 197 | 198 | 201 | 202 | 203 | 204 | 205 |
| Pre-emergence | | | | | | | | | | | | | | | | | | | | | | | | | | | | | |
| Barnyardgrass | 0 | 5 | 0 | 1 | 0 | 0 | 0 | 0 | 0 | 0 | 6 | 0 | 0 | 0 | 0 | 0 | 0 | 0 | 0 | 0 | 0 | 0 | 0 | 0 | 9 | 0 | 0 | 0 | 0 |
| Ducksalad | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 7 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 206 | 207 | 208 | 210 | 211 | 212 | 214 | 215 | 216 | 218 | 219 | 220 | 222 | 223 | 224 | 225 | 226 | 227 | 228 | 229 | 230 | 231 | 232 | 233 | 234 | 235 | 236 | 237 | 238 |
| Pre-emergence | | | | | | | | | | | | | | | | | | | | | | | | | | | | | |
| Barnyardgrass | 0 | 7 | 0 | 0 | 0 | 0 | 0 | 0 | 0 | 0 | 9 | 3 | 0 | 0 | 0 | 0 | 0 | 0 | 0 | 0 | 0 | 0 | 0 | 0 | 0 | 0 | 0 | 0 | 0 |
| Ducksalad | 0 | 2 | 0 | 0 | 0 | 2 | 0 | 0 | 0 | 0 | 3 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 6 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 4 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 239 | 240 | 241 | 242 | 243 | 244 | 245 | 246 | 247 | 248 | 249 | 250 | 251 | 252 | 253 | 254 | 255 | 256 | 257 | 258 | 259 | 264 | 265 | 266 | 267 | 268 | 269 | 270 | 271 |
| Pre-emergence | | | | | | | | | | | | | | | | | | | | | | | | | | | | | |
| Barnyardgrass | 0 | 0 | 0 | 0 | 0 | 0 | 0 | 8 | 0 | 0 | 0 | 0 | 0 | 0 | 0 | 0 | 0 | 0 | 0 | 0 | 0 | 0 | 0 | 0 | 0 | 0 | 0 | 0 | 9 |
| Ducksalad | 0 | 0 | 0 | 0 | 0 | 0 | 0 | 0 | 0 | 0 | 0 | 4 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 272 | 273 | 274 | 276 | 277 | 278 | 279 | 280 | 281 | 282 | 283 | 284 | 286 | 290 | 291 | 293 | 294 | 297 | 298 | 299 | 300 | 301 | 302 | 303 | 304 | 305 | 306 | 307 | 308 |
| Pre-emergence | | | | | | | | | | | | | | | | | | | | | | | | | | | | | |
| Barnyardgrass | 0 | 3 | 0 | 8 | 9 | 0 | 0 | 0 | 2 | 9 | 6 | 9 | 4 | 5 | 6 | 5 | 9 | 0 | 0 | 9 | 0 | 0 | 0 | 0 | 4 | 0 | 0 | 0 | 0 |
| Ducksalad | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 2 | 0 | 0 | 0 | 0 | 0 | 1 | 0 | 0 | 0 | 0 | 5 | 0 | 0 | 0 | 0 | 0 | 0 | 0 | 0 | 0 | 0 | 0 | 0 | 0 |
| S. Flatsedge | 0 | 0 | 0 | 0 | 5 | 0 | 0 | 0 | 0 | 4 | 5 | 0 | 0 | 0 | 0 | 0 | 4 | 3 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 309 | 310 | 311 | 312 | 313 | 314 | 315 | 316 | 317 | 319 | 320 | 321 | 323 | 325 | 326 | 327 | 328 | 329 | 330 | 331 | 332 | 333 | 334 | 335 | 336 | 337 | 338 | 339 | 340 |
| Pre-emergence | | | | | | | | | | | | | | | | | | | | | | | | | | | | | |
| Barnyardgrass | 0 | 7 | 0 | 0 | 0 | 0 | 0 | 9 | 0 | 2 | 0 | 0 | 0 | 0 | 9 | 0 | 0 | 0 | 0 | 0 | 0 | 0 | 0 | 4 | 0 | 5 | 9 | 9 | 9 |
| Ducksalad | 0 | 3 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 3 | 5 |

TABLE B-continued

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rice | 0 | 0 | 0 | 0 | 0 | 0 | 0 | 0 | 0 | 0 | 0 | 0 | 0 | 0 | 0 | 0 | 7 | 0 | 0 | 0 | 0 | 0 | 0 | 0 | 0 | 0 | 0 | 1 | 0 |
| S. Flatsedge | 0 | 3 | 0 | 0 | 0 | 0 | 0 | 9 | 0 | 0 | 0 | 0 | 0 | 0 | 0 | 0 | 0 | 0 | 0 | 0 | 0 | 0 | 0 | 0 | 0 | 0 | 0 | 1 | 9 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate 500 g/ha | 341 | 346 | 350 | 351 | 353 | 354 | 358 | 365 | 366 | 367 | 368 | 369 | 370 | 371 | 372 | 373 | 374 | 375 | 376 | 378 | 379 | 380 | 381 | 382 | 383 | 384 | 385 | 387 | 388 |
| Pre-emergence | | | | | | | | | | | | | | | | | | | | | | | | | | | | | |
| Barnyardgrass | 9 | 0 | 0 | 0 | 9 | 0 | 9 | 0 | 0 | 0 | 7 | 0 | 0 | 7 | 0 | 0 | 0 | 0 | 0 | 0 | 0 | 0 | 0 | 0 | 0 | 0 | 0 | 0 | 0 |
| Ducksalad | 3 | 0 | 0 | 0 | 0 | 0 | 2 | 0 | 0 | 0 | 0 | 0 | 0 | 2 | 0 | 0 | 0 | 0 | 0 | 0 | 0 | 0 | 0 | 0 | 0 | 0 | 0 | 0 | 0 |
| Rice | 2 | 0 | 0 | 0 | 4 | 0 | 8 | 0 | 0 | 0 | 5 | 0 | 0 | 5 | 0 | 0 | 0 | 0 | 0 | 0 | 0 | 0 | 0 | 0 | 0 | 0 | 0 | 0 | 0 |
| S. Flatsedge | 9 | 0 | 0 | 0 | 7 | 0 | 8 | 0 | 0 | 0 | 4 | 0 | 0 | 3 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate 500 g/ha | 389 | 390 | 391 | 393 | 394 | 395 | 401 | 402 | 403 | 405 | 406 | 407 | 408 | 409 | 410 | 411 | 414 | 437 | 438 | 439 | 441 | 443 | 444 | 445 | 446 | 447 | 448 | 449 | 451 |
| Pre-emergence | | | | | | | | | | | | | | | | | | | | | | | | | | | | | |
| Barnyardgrass | 0 | 9 | 0 | 0 | 8 | 0 | 0 | 9 | 7 | 0 | 0 | 0 | 0 | 3 | 9 | 9 | 0 | 0 | 0 | 0 | 0 | 0 | 0 | 0 | 0 | 0 | 0 | 0 | 0 |
| Ducksalad | 3 | 3 | 0 | 0 | 3 | 0 | 0 | 0 | 0 | 0 | 0 | 0 | 0 | 0 | 2 | 2 | 0 | 0 | 0 | 0 | 0 | 0 | 0 | 0 | 0 | 0 | 0 | 0 | 0 |
| Rice | — | 4 | 0 | 0 | 1 | 0 | 0 | 2 | 0 | 0 | 0 | 0 | 0 | 0 | 5 | 0 | 0 | 0 | 0 | 0 | 0 | 0 | 0 | 0 | 0 | 0 | 0 | 0 | 0 |
| S. Flatsedge | 0 | 7 | 0 | 0 | 8 | 0 | 0 | 2 | 6 | 0 | 0 | 0 | 0 | 2 | 9 | 9 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate 500 g/ha | 452 | 453 | 454 | 455 | 456 | 457 | 458 | 459 | 460 | 461 | 462 | 463 | 465 | 466 | 467 | 468 | 469 | 470 | 471 | 472 | 473 | 474 | 476 | 477 | 478 | 479 | 480 | 482 | 485 |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate 500 g/ha | 486 | 487 | 488 | 489 | 490 | 492 | 493 | 494 | 495 | 496 | 498 | 499 | 509 | 521 | 528 | 529 | 531 | 532 | 538 | 539 | 546 | 550 | 552 | 556 | 558 | 560 | 561 | 567 | 568 |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 0 | 0 | 0 | 0 | 0 | 2 | 0 | 9 | 0 | 0 | 0 | 0 | 0 | 1 | 6 | 0 | 0 | 0 | 6 |
| Ducksalad | 0 | 0 | 0 | 0 | 0 | 0 | 0 | 0 | 0 | 0 | 0 | 0 | 0 | 0 | 0 | 0 | 0 | 9 | 0 | 0 | 0 | 0 | 0 | 0 | 0 | 0 | 0 | 0 | 2 |
| Rice | 0 | 0 | 0 | 0 | 0 | 0 | 0 | 0 | 0 | 0 | 0 | 0 | 0 | 0 | — | — | 0 | 8 | — | 0 | — | 0 | — | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 9 | 0 | 0 | 0 | 0 | 0 | 0 | 0 | 0 | 0 | 0 | 4 |

TABLE B-continued

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate 500 g/ha | 570 | 577 | 580 | 586 | 587 | 588 | 589 | 590 | 591 | 592 | 593 | 594 | 595 | 596 | 598 | 599 | 600 | 601 | 602 | 603 | 604 | 605 | 606 | 607 | 608 | 609 | 610 | 611 | 612 |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 8 | 5 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 7 | 1 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 8 | 2 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 8 | 0 | 0 |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate 500 g/ha | 613 | 615 | 616 | 617 | 618 | 619 | 620 | 621 | 622 | 623 | 624 | 625 | 627 | 628 | 629 | 630 | 631 | 632 | 633 | 634 | 636 | 637 | 638 | 639 | 640 | 641 | 642 | 643 | 645 |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 0 | 0 | 8 | 0 | 0 | 0 | 4 | 0 | 0 | 0 | 2 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | — | — | 0 | 0 | 0 | 0 | 0 | 0 | 0 |
| S. Flatsedge | 0 | 0 | 0 | 0 | 0 | 0 | 0 | 0 | 0 | 0 | 0 | 0 | 3 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate 500 g/ha | 646 | 647 | 649 | 650 | 651 | 655 | 657 | 658 | 659 | 660 | 661 | 662 | 663 | 664 | 665 | 666 | 667 | 668 | 671 | 674 | 675 | 676 | 677 | 678 | 679 | 680 | 681 | 692 | 694 |
| Pre-emergence | | | | | | | | | | | | | | | | | | | | | | | | | | | | | |
| Barnyardgrass | 0 | 0 | 2 | 0 | 0 | 0 | 0 | 0 | 7 | 0 | 0 | 0 | 0 | 0 | 6 | 5 | 0 | 0 | 0 | 0 | 0 | 0 | 0 | 0 | 0 | 0 | 0 | 9 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 100 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 8 | 0 |
| S. Flatsedge | 0 | 0 | 0 | 0 | 0 | 0 | 0 | 0 | 5 | 0 | 0 | 0 | 0 | 0 | 0 | 0 | 0 | 0 | 0 | 0 | 0 | 0 | 0 | 0 | 0 | 0 | 0 | 100 | 0 |

| | COMPOUND | | | | | | | | | | | | | | | | |
|---|---|---|---|---|---|---|---|---|---|---|---|---|---|---|---|---|---|
| Rate 500 g/ha | 695 | 696 | 697 | 699 | 701 | 702 | 705 | 706 | 715 | 720 | 721 | 724 | 740 | 741 | 758 | 765 | 793 |
| Pre-emergence | | | | | | | | | | | | | | | | | |
| Barnyardgrass | 0 | 0 | 0 | 8 | 0 | 0 | 2 | 0 | 0 | 0 | 0 | 0 | 0 | 0 | 0 | 0 | 0 |
| Ducksalad | 0 | 0 | 0 | 9 | 3 | 0 | 0 | 0 | 0 | 0 | 0 | 0 | 0 | 0 | 0 | 0 | 8 |
| Rice | 0 | 0 | 0 | 4 | — | 0 | 2 | 0 | 0 | 0 | 0 | 0 | 0 | 0 | 0 | 0 | 0 |
| S. Flatsedge | 0 | 0 | 0 | 8 | 0 | 0 | 0 | 0 | 0 | 0 | 0 | 0 | 0 | 8 | 0 | 0 | 8 |

| | COMPOUND | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Rate 500 g/ha | 1 | 2 | 3 | 4 | 5 | 6 | 7 | 8 | 9 | 10 | 11 | 12 | 13 | 14 | 15 | 16 | 17 | 18 | 19 | 20 | 21 | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 |
| Postemergence | | | | | | | | | | | | | | | | | | | | | | | | | | | | | | | | | | | | | | | | | | | | |
| B. signalgrass | 7 | 0 | 0 | 2 | 0 | 5 | 3 | 0 | 0 | 4 | 0 | 0 | 5 | 0 | 0 | 0 | 0 | 2 | 0 | 0 | 0 | 3 | 2 | — | — | — | — | — | — | — | — | 0 | 0 | 4 | 0 | 0 | 0 | 0 | 0 | 0 | 0 | 0 | 2 | 0 |
| Barnyardgrass | 0 | 0 | 0 | 4 | 2 | 0 | 0 | 0 | 0 | 0 | 0 | 0 | 0 | — | 0 | 0 | 9 | 10 | 0 | 0 | 0 | 8 | 8 | 0 | 9 | 10 | 0 | 0 | 0 | 9 | 6 | 0 | 0 | 5 | — | 0 | — | — | 0 | 0 | 0 | 0 | 0 | 0 |

TABLE B-continued

| | | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Bedstraw | 0 | 0 | 0 | 7 | 4 | 0 | 0 | 3 | 0 | 0 | 0 | 0 | 0 | 1 | 4 | 0 | 7 | 9 | 8 | 5 | 6 | 8 | 7 | — | — | — | — | — | — | — | — | 7 | 6 | — | 0 | 5 | 0 | 2 | — | — | 2 | 0 | — | — |
| Blackgrass | 2 | 8 | 0 | 6 | 4 | 7 | 3 | 2 | 2 | 7 | 0 | 0 | 4 | 3 | 3 | 2 | 5 | 3 | 2 | 2 | 0 | 6 | 7 | — | — | — | — | — | — | — | — | 9 | 7 | 6 | 0 | 8 | 0 | 7 | 4 | 0 | 4 | 0 | 4 | 6 |
| Cocklebur | 0 | 0 | 0 | 6 | 5 | 0 | 0 | 1 | 0 | 3 | 0 | 0 | 0 | 0 | 8 | 0 | 3 | 2 | 0 | 0 | 7 | 2 | 5 | — | — | — | — | — | — | — | — | 4 | 5 | 4 | 1 | 1 | 0 | 0 | 3 | 0 | 1 | 0 | 5 | 2 |
| Corn | 0 | 6 | 0 | 0 | 0 | 0 | 0 | 0 | 0 | 2 | 0 | 0 | 0 | 0 | 0 | 0 | 0 | 0 | 0 | 0 | 3 | 0 | 0 | — | — | — | — | — | — | — | — | 0 | 0 | 0 | 0 | 0 | 0 | 0 | 0 | 0 | 0 | 0 | 0 | 0 |
| Crabgrass | 8 | 0 | 6 | 8 | 6 | 5 | 3 | 0 | 0 | 9 | 0 | 0 | 9 | 8 | 8 | 0 | 9 | 9 | — | 7 | 2 | 10 | 9 | — | — | — | — | — | — | — | — | 9 | 7 | 8 | 3 | 9 | 4 | 7 | 7 | 0 | 2 | 0 | 3 | 3 |
| Ducksalad | 0 | 0 | 0 | 2 | 0 | 0 | 0 | 0 | 0 | 0 | 0 | 0 | 0 | — | 0 | 0 | 0 | 7 | 0 | 0 | 0 | 0 | 0 | 0 | 0 | 4 | 0 | 0 | 0 | 2 | 0 | 0 | 0 | 0 | — | 0 | — | — | 0 | 0 | 0 | 0 | 0 | 0 |
| Giant foxtail | 8 | 7 | 7 | 4 | 4 | 5 | 5 | 2 | 0 | 8 | 0 | 0 | 7 | 3 | 0 | 3 | 5 | 3 | 1 | 1 | 2 | 8 | 8 | — | — | — | — | — | — | — | — | 8 | 7 | 3 | 0 | 8 | 0 | 3 | 1 | 0 | 0 | 0 | 9 | 6 |
| Morningglory | 0 | 0 | 0 | 3 | — | 5 | 0 | 2 | 0 | 3 | 0 | 0 | 0 | 6 | 7 | 3 | 7 | 3 | 2 | 8 | 8 | — | 2 | — | — | — | — | — | — | — | — | 8 | 8 | 9 | 1 | 10 | 0 | 7 | 6 | 1 | 4 | 1 | 3 | 2 |
| Nutsedge | 0 | 0 | 0 | 0 | 0 | — | — | — | — | 0 | 0 | 0 | 0 | 0 | 0 | 0 | 0 | 0 | 0 | 0 | 0 | 0 | — | — | — | — | — | — | — | — | — | 0 | 0 | 0 | — | 0 | 0 | 0 | 0 | 0 | 0 | 0 | 0 | 0 |
| Rape | 2 | 0 | 0 | 2 | 4 | 0 | 0 | 0 | 0 | 0 | 0 | 0 | 1 | 0 | 0 | 0 | 0 | 1 | 0 | 0 | 0 | 2 | 0 | — | — | — | — | — | — | — | — | 0 | 2 | 0 | 0 | 0 | 0 | 0 | 0 | 0 | — | 0 | 0 | 0 |
| Redroot pigweed | 8 | 0 | 0 | 7 | 7 | 0 | 0 | 0 | 3 | 0 | 0 | 0 | 0 | 6 | 6 | 0 | 6 | 6 | 5 | 4 | 0 | 6 | 4 | — | — | — | — | — | — | — | — | 7 | 9 | 7 | 0 | 0 | 0 | — | 5 | 2 | 6 | 0 | 0 | 0 |
| Rice | 0 | 0 | 0 | 0 | 0 | 0 | 0 | 0 | 0 | 0 | 0 | 0 | 0 | — | 0 | 0 | 3 | 5 | 0 | 2 | 0 | 0 | 3 | 0 | 2 | 3 | 0 | 0 | 0 | 0 | 4 | 0 | 0 | 2 | — | 0 | — | — | 0 | 0 | 0 | 0 | 0 | 0 |
| S. Flatsedge | 0 | 0 | 0 | 2 | 0 | 0 | 0 | 0 | 0 | 0 | 0 | 0 | 0 | — | 0 | 0 | 0 | 9 | 0 | 6 | 0 | 0 | 2 | 0 | 9 | 10 | 0 | 0 | 0 | 0 | 5 | 0 | 0 | 0 | — | 0 | — | 0 | 0 | 0 | 0 | 0 | 0 | — |
| Soybean | 1 | 1 | 1 | 4 | 5 | 5 | 2 | 5 | 0 | 4 | 0 | 0 | 2 | 2 | 2 | 3 | 5 | 6 | 4 | 4 | 7 | 3 | 3 | — | — | — | — | — | — | — | — | 0 | 1 | 7 | 1 | 1 | 5 | 4 | 4 | 2 | 3 | 2 | 1 | 2 |
| Sugarbeets | 0 | 0 | 0 | 4 | 4 | 0 | 2 | 0 | 0 | 0 | 0 | 0 | 0 | 2 | 6 | 0 | 3 | 5 | 5 | 3 | 0 | 4 | 0 | — | — | — | — | — | — | — | — | 0 | 4 | 3 | 2 | 2 | 0 | 2 | 0 | 0 | 3 | 0 | 7 | 4 |
| Velvetleaf | 0 | 0 | 0 | 4 | 5 | 0 | 0 | 0 | 0 | 4 | 0 | 0 | 0 | 5 | 5 | 3 | 2 | 2 | 0 | 0 | 7 | 0 | 0 | — | — | — | — | — | — | — | — | 2 | 4 | — | 0 | 0 | 0 | 1 | — | 0 | 0 | 0 | 1 | 2 |
| Wheat | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | — | — | — | — | — | — | — | — | 0 | 0 | 0 | 0 | 0 | 0 | 0 | 0 | 0 | 0 | 0 | 0 | 0 |
| Wild oats | 0 | 0 | 0 | 0 | 1 | 2 | 0 | 0 | 0 | 0 | 0 | 0 | 0 | 0 | 0 | 0 | 0 | 0 | 0 | 0 | 0 | 2 | 2 | — | — | — | — | — | — | — | — | 0 | 0 | 0 | 0 | 0 | 0 | 0 | 2 | 0 | 0 | 0 | 0 | 0 |
| | COMPOUND | | | | | | | | | | | | | | | | | | | | | | | | | | | | | | | | | | | | | | | | | | | |
| Rate 500 g/ha | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 |
| Postemergence | | | | | | | | | | | | | | | | | | | | | | | | | | | | | | | | | | | | | | | | | | | | |
| B. signalgrass | 0 | 0 | 0 | — | 0 | 1 | 0 | 0 | 0 | 0 | 0 | 0 | 0 | 0 | 1 | 4 | 0 | 0 | 0 | 0 | 0 | 0 | — | 0 | 0 | 0 | 3 | 2 | 8 | 9 | 2 | 6 | 0 | 0 | 8 | 0 | 0 | — | 0 | 0 | 2 | 2 | 0 | 0 |
| Barnyardgrass | — | 0 | — | 0 | 0 | 0 | 0 | 0 | 0 | 0 | 0 | 0 | 0 | 0 | 0 | 0 | 0 | 0 | 2 | 3 | 0 | 0 | — | — | — | — | 0 | 0 | 0 | 0 | 0 | 7 | 9 | 9 | 0 | 0 | 0 | 0 | 0 | 0 | — | — | 0 | 0 |
| Bedstraw | — | — | — | — | — | — | — | 7 | 0 | 0 | 0 | 0 | 0 | 7 | — | — | — | 0 | 0 | 2 | 8 | — | 6 | 0 | 0 | 0 | 7 | 8 | 0 | 4 | 0 | 8 | 8 | 6 | 5 | 1 | 0 | — | 0 | 8 | 8 | 9 | 3 | — |
| Blackgrass | 0 | 0 | 0 | — | 0 | 0 | 0 | 2 | 0 | 0 | 0 | 0 | 0 | 0 | 7 | 2 | 0 | 0 | 0 | 3 | 0 | 2 | 0 | 0 | 0 | 0 | 2 | 3 | 9 | 8 | 4 | 7 | 3 | 5 | 6 | 3 | 0 | — | 0 | 3 | 4 | 6 | 0 | 0 |
| Cocklebur | 2 | 2 | 0 | — | 0 | 0 | 4 | 2 | 0 | 0 | 0 | 0 | 0 | 0 | 1 | 6 | 0 | 0 | 0 | 0 | 1 | 2 | 0 | 0 | 0 | 0 | 2 | 4 | 1 | 4 | 4 | 3 | 2 | 1 | 0 | 0 | 1 | — | 0 | 2 | 2 | 5 | 2 | 5 |
| Corn | 0 | 0 | 0 | — | 0 | 4 | 0 | 0 | 0 | 0 | 0 | 0 | 0 | 0 | 0 | 0 | 2 | 0 | 0 | 2 | 0 | 0 | 0 | 0 | 0 | 0 | 0 | 0 | 0 | 0 | 0 | 0 | 0 | 0 | 6 | 0 | 0 | — | 0 | 0 | 2 | 0 | 1 | 0 |
| Crabgrass | 2 | 8 | 9 | — | 4 | 6 | 10 | 5 | 0 | 0 | 0 | 0 | 4 | 2 | 0 | 7 | 2 | 0 | 0 | 0 | 0 | 0 | 1 | 0 | 0 | 0 | 6 | 7 | 9 | 9 | 0 | 9 | 8 | 9 | 9 | 0 | 0 | — | 0 | 9 | 9 | 9 | 2 | 4 |
| Ducksalad | — | 0 | — | 0 | 0 | 0 | 0 | 0 | 0 | 0 | 0 | 0 | 0 | 0 | 0 | 0 | 0 | 0 | 0 | 2 | 0 | 0 | — | — | — | — | 0 | 0 | 0 | 0 | 0 | 0 | 3 | 2 | 0 | 0 | 0 | 0 | 0 | 0 | — | — | 0 | 0 |
| Giant foxtail | 2 | 3 | 9 | — | 3 | 4 | 3 | 5 | 0 | 0 | 0 | 0 | 4 | 0 | 0 | 2 | 2 | 0 | 0 | 0 | 0 | 0 | 1 | 0 | 0 | 0 | 4 | 2 | 8 | 9 | 2 | 4 | 4 | 7 | 7 | 0 | 0 | — | 0 | 5 | 6 | 3 | 2 | 1 |
| Morningglory | 6 | 1 | 3 | — | 1 | 1 | 6 | 2 | 3 | 1 | 1 | 0 | 1 | 2 | 8 | 6 | 4 | 0 | 2 | 2 | 6 | 3 | 0 | 0 | 0 | 0 | 4 | 4 | 3 | 7 | 0 | 10 | 8 | 10 | 6 | 10 | 0 | — | 0 | 8 | 9 | 10 | 2 | 4 |
| Nutsedge | 0 | 0 | 0 | — | 0 | 0 | 0 | 0 | 0 | 0 | 0 | 0 | 0 | 0 | 0 | 3 | 2 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 | 0 | 0 |
| Rape | 0 | 0 | 0 | — | 0 | 0 | 3 | 0 | 0 | 0 | 0 | 0 | 0 | 4 | 3 | 0 | 0 | 0 | 0 | 0 | 2 | 0 | 0 | 0 | 0 | 0 | — | 2 | 0 | 2 | 3 | 4 | 3 | 3 | 0 | 0 | 0 | — | 0 | 4 | 3 | 3 | 0 | 0 |
| Redroot pigweed | 2 | 0 | 0 | — | 0 | 0 | 10 | 4 | 0 | 0 | 0 | 0 | 0 | 6 | 4 | 0 | 2 | 0 | 0 | 4 | 4 | 0 | 0 | 0 | 0 | 0 | 0 | 0 | 0 | 4 | 0 | 6 | 4 | 4 | 2 | 0 | 0 | — | 0 | 7 | 2 | 5 | 5 | 7 |
| Rice | — | 0 | — | 0 | 0 | 0 | 0 | 0 | 0 | 0 | 0 | 0 | 0 | 0 | 0 | 0 | 0 | 0 | 3 | 0 | 0 | 0 | — | — | — | — | 0 | 0 | 2 | 3 | 0 | 2 | 3 | 2 | 0 | 0 | 0 | 0 | 0 | 0 | — | — | 0 | 0 |
| S. Flatsedge | — | 0 | — | 0 | 0 | 0 | 0 | 0 | 0 | 0 | 0 | 0 | 0 | 0 | 0 | 0 | 0 | 0 | 0 | 3 | 0 | 0 | — | — | — | — | 0 | 0 | 0 | 0 | 3 | 4 | 10 | 3 | 0 | 0 | 0 | 0 | 0 | 0 | — | — | 0 | 0 |
| Soybean | 2 | 1 | 1 | — | 1 | 2 | 3 | 0 | 2 | 2 | 1 | 2 | 7 | 3 | 5 | 3 | 3 | 1 | 1 | 3 | 1 | 3 | 3 | 0 | 0 | 0 | 3 | 1 | 2 | 2 | 1 | 4 | 2 | 2 | 3 | 1 | 0 | — | 0 | 3 | 5 | 1 | 1 | 4 |
| Sugarbeets | 0 | 0 | 0 | — | 0 | 0 | 2 | 0 | 0 | 0 | 0 | 0 | 0 | 0 | 6 | 5 | 3 | 0 | 0 | 0 | 2 | 3 | 0 | 0 | 0 | 0 | 0 | 0 | 0 | 3 | 0 | 7 | 6 | 7 | 3 | 2 | 0 | — | 0 | 6 | 8 | 7 | 6 | 3 |
| Velvetleaf | 0 | 0 | 0 | — | 0 | 0 | 1 | 0 | 0 | 0 | 0 | 0 | 0 | 0 | 0 | 7 | 5 | 0 | 4 | 2 | 0 | 3 | 2 | 0 | 0 | 0 | 5 | 4 | 0 | 4 | 0 | 4 | 3 | 0 | 2 | 0 | 4 | — | 0 | 2 | 1 | 0 | 3 | — |
| Wheat | 3 | 0 | 0 | — | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 2 | 3 | 4 | 3 | 4 | 0 | 0 | 0 | 0 | 0 | 0 | — | 0 | 0 | 2 | 0 | 0 | 0 |
| Wild oats | 3 | 0 | 0 | — | 0 | 1 | 2 | 0 | 0 | 0 | 0 | 0 | 0 | 0 | 0 | 3 | 2 | 0 | 0 | 0 | 0 | 0 | 0 | 0 | 0 | 0 | 6 | 2 | 2 | 5 | 3 | 2 | 0 | 0 | 0 | 0 | 0 | — | 0 | 0 | 3 | 0 | 0 | 0 |

TABLE B-continued

| Rate 500 g/ha | COMPOUND 91 | 92 | 93 | 94 | 95 | 96 | 97 | 99 | 101 | 102 | 103 | 104 | 105 | 106 | 107 | 108 | 109 | 110 | 111 | 112 | 113 | 114 | 115 | 116 | 117 | 118 | 119 | 120 | 121 | 122 | 123 | 124 |
|---|---|---|---|---|---|---|---|---|---|---|---|---|---|---|---|---|---|---|---|---|---|---|---|---|---|---|---|---|---|---|---|---|
| Postemergence | | | | | | | | | | | | | | | | | | | | | | | | | | | | | | | | |
| B. signalgrass | 8 | 7 | 9 | 2 | 5 | 0 | 0 | 2 | 0 | 0 | 2 | 0 | 3 | 0 | 8 | 6 | 8 | 3 | 0 | 4 | 8 | 7 | 8 | 9 | 9 | 9 | 5 | 8 | 3 | 0 | 5 | 0 |
| Barnyardgrass | — | — | 0 | 9 | 4 | 0 | 0 | 5 | 0 | 0 | — | — | 0 | 0 | — | 0 | 0 | 0 | 0 | 0 | 0 | 0 | 0 | 4 | 3 | — | — | 0 | 6 | 0 | 0 | 0 |
| Bedstraw | — | — | 7 | — | 2 | 0 | 3 | 8 | 0 | 3 | — | 6 | 3 | 7 | 9 | 6 | — | — | — | — | — | 7 | — | — | — | — | 8 | 2 | 6 | 3 | — | 0 |
| Blackgrass | 8 | 8 | 8 | 6 | 5 | 0 | 5 | 6 | 0 | 0 | 4 | 6 | 8 | 3 | 8 | 8 | 8 | 8 | 7 | 7 | 8 | 8 | 7 | 9 | 9 | 9 | 8 | 8 | 6 | 6 | 7 | 0 |
| Cocklebur | 4 | 3 | 4 | 3 | 2 | 2 | 1 | 3 | 0 | 0 | 0 | 3 | 4 | 4 | 3 | 2 | 5 | 3 | 3 | 2 | 4 | 0 | 2 | 5 | 1 | 0 | 0 | 4 | 5 | 3 | 1 | 0 |
| Corn | 5 | 4 | 5 | 0 | 0 | 0 | 0 | 0 | 0 | 2 | 2 | 0 | 2 | 0 | 6 | 0 | 5 | 4 | 0 | 0 | 6 | 0 | 0 | 7 | 7 | 3 | 0 | 4 | 0 | 0 | 0 | 0 |
| Crabgrass | 9 | 9 | 9 | 9 | 8 | 8 | — | 8 | 0 | 5 | 9 | 8 | 9 | 6 | 9 | 9 | 9 | 8 | 9 | 9 | 9 | 9 | 6 | 9 | 9 | 9 | 8 | 9 | 9 | 5 | 9 | 0 |
| Ducksalad | — | — | 0 | 2 | 0 | 0 | 2 | 2 | 0 | 0 | — | — | 0 | 0 | — | 0 | 0 | 0 | 0 | 0 | 0 | 0 | 0 | 0 | 0 | — | — | 0 | 0 | 0 | 0 | 0 |
| Giant foxtail | 9 | 9 | 9 | 8 | 6 | 3 | 4 | 7 | 0 | 2 | 7 | 8 | 8 | 3 | 8 | 8 | 9 | 8 | 9 | 8 | 9 | 9 | 9 | 9 | 9 | 9 | 8 | 8 | 8 | 9 | 9 | 0 |
| Morningglory | 9 | 10 | 10 | 10 | 8 | 2 | 3 | 5 | 1 | 3 | 10 | 10 | 4 | 10 | 3 | 3 | 5 | 5 | 8 | 10 | 10 | 8 | 6 | 7 | 10 | 7 | 8 | 8 | 9 | 4 | 10 | 2 |
| Nutsedge | 0 | 2 | 3 | 0 | 0 | 0 | 0 | 0 | 0 | 0 | 0 | 0 | 2 | 0 | 6 | 4 | 4 | 0 | 0 | 0 | 2 | 0 | 0 | 9 | 7 | 0 | 0 | — | 0 | 0 | 0 | 0 |
| Rape | 10 | 6 | 5 | 3 | 0 | 0 | 3 | 6 | 0 | 0 | 3 | 2 | 2 | 0 | 8 | 2 | 6 | 6 | 4 | 4 | 7 | 7 | 0 | 9 | 6 | 0 | 4 | 0 | 3 | 4 | 2 | 0 |
| Redroot pigweed | 8 | 5 | 7 | 4 | 5 | 0 | 5 | 7 | 0 | 0 | 4 | 7 | 3 | 6 | 8 | 3 | 8 | 6 | 6 | 5 | 7 | 3 | 4 | 8 | 6 | 0 | 6 | 3 | 5 | 5 | 2 | 0 |
| Rice | — | — | 4 | 0 | 4 | 2 | 3 | 0 | 0 | 0 | — | — | 0 | 0 | — | 0 | 0 | 0 | 0 | 0 | 0 | 0 | 0 | 0 | 0 | — | 0 | 3 | 0 | 0 | 0 | 0 |
| S. Flatsedge | — | — | 6 | 9 | 5 | 3 | 2 | 2 | 0 | 0 | — | — | 0 | 0 | — | 0 | 0 | 0 | 0 | 0 | 0 | 0 | 0 | 0 | 0 | — | — | 0 | 6 | 0 | 0 | 0 |
| Soybean | 5 | 5 | 7 | 5 | 1 | 1 | 2 | 4 | 3 | 0 | 6 | 5 | 6 | 1 | 5 | 5 | 7 | 7 | 5 | 7 | 7 | 7 | 4 | 8 | 7 | 2 | 6 | 6 | 6 | 5 | 4 | 5 |
| Sugarbeets | 6 | 6 | 5 | 3 | 4 | 0 | 0 | 5 | 0 | 0 | 3 | 3 | 0 | 0 | 7 | 2 | 7 | 3 | 4 | 3 | 6 | 5 | 3 | 8 | 7 | 2 | 4 | 0 | 4 | 2 | 2 | 0 |
| Velvetleaf | — | — | 6 | 6 | 0 | 0 | 3 | 5 | 0 | 3 | 4 | 3 | 4 | 2 | 7 | 5 | 6 | 2 | 2 | 1 | 8 | 3 | 0 | 8 | 8 | 0 | 3 | 6 | 4 | 3 | — | 0 |
| Wheat | 6 | 6 | 5 | 0 | 0 | 0 | 0 | 0 | 0 | 0 | 0 | 0 | 2 | 0 | 8 | 2 | 6 | 1 | 0 | 0 | 6 | 0 | 0 | 8 | 8 | 2 | 3 | 4 | 0 | 0 | 4 | 0 |
| Wild oats | 5 | 5 | 5 | 1 | 3 | 0 | 0 | 0 | 0 | 0 | 0 | 2 | 4 | 0 | 9 | 3 | 7 | 2 | 2 | 1 | 6 | 2 | 0 | 8 | 8 | 2 | 6 | 2 | 0 | 0 | 2 | 0 |

| Rate 500 g/ha | COMPOUND 125 | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 | 149 | 150 | 151 | 152 | 153 |
|---|---|---|---|---|---|---|---|---|---|---|---|---|---|---|---|---|---|---|---|---|---|---|---|---|---|---|---|---|---|
| Postemergence | | | | | | | | | | | | | | | | | | | | | | | | | | | | | |
| B. signalgrass | 0 | 0 | 0 | 0 | 6 | 8 | 9 | 7 | 2 | 2 | 0 | 3 | 8 | 8 | 7 | 1 | 0 | 0 | 5 | 3 | 2 | 9 | 8 | 7 | 0 | 0 | 7 | 0 | 0 |
| Barnyardgrass | 0 | 0 | 0 | 0 | — | — | — | — | — | — | 0 | 0 | — | — | — | 8 | 3 | 9 | 10 | 8 | 9 | 9 | 9 | 4 | 0 | 0 | 8 | 0 | 0 |
| Bedstraw | 0 | 0 | 0 | 0 | 3 | 8 | 9 | 7 | 7 | — | — | — | — | 9 | 5 | 6 | 4 | 4 | 8 | 5 | 5 | 8 | 8 | 6 | 0 | 0 | 7 | 0 | 0 |
| Blackgrass | 0 | 0 | 0 | 0 | 3 | 8 | 9 | 9 | 4 | 7 | 0 | 5 | 8 | 9 | 8 | 6 | 0 | 3 | 8 | 8 | 6 | 8 | 8 | 7 | 0 | 0 | 9 | 2 | 0 |
| Cocklebur | 0 | 0 | 0 | 0 | 0 | 3 | 5 | 0 | 3 | 1 | 0 | 4 | 4 | 3 | 2 | 4 | 0 | 0 | 4 | 0 | 0 | 4 | 0 | 3 | 0 | 0 | 2 | 0 | 0 |
| Corn | 0 | 0 | 0 | 0 | 4 | 3 | 7 | 6 | 0 | 0 | 0 | 0 | 5 | 7 | 2 | 0 | 0 | 0 | 0 | 0 | 0 | 0 | 8 | 0 | 0 | 0 | 6 | 0 | 0 |
| Crabgrass | 0 | 0 | 0 | 0 | 9 | 9 | 9 | 9 | 4 | 9 | — | 9 | 9 | 9 | 9 | 9 | 9 | 5 | 9 | 9 | 8 | 9 | 9 | 9 | 0 | 5 | 9 | 3 | 0 |
| Ducksalad | 0 | 0 | 0 | 0 | — | — | — | — | — | — | 0 | 0 | — | — | — | 0 | 0 | 0 | 5 | 0 | 2 | 6 | 3 | 0 | 0 | 0 | 2 | 0 | 0 |
| Giant foxtail | 0 | 0 | 0 | 0 | 9 | 9 | 9 | 9 | 4 | 3 | 0 | 7 | 9 | 9 | 9 | 6 | 2 | 3 | 7 | 6 | 4 | 9 | 9 | 9 | 0 | 4 | 8 | 3 | 0 |
| Morningglory | 2 | 0 | 0 | 0 | 8 | 3 | 10 | 7 | 8 | 8 | 1 | 10 | 8 | 10 | 9 | 8 | 3 | 7 | 8 | 3 | 10 | 9 | 3 | 5 | 0 | 0 | 6 | 0 | 0 |
| Nutsedge | 0 | 0 | 0 | 0 | 0 | 0 | 2 | 4 | 0 | 0 | 0 | 0 | 4 | — | 4 | 0 | 0 | 0 | 0 | 0 | 0 | 6 | 2 | 0 | 0 | 0 | 5 | 0 | 0 |
| Rape | 0 | 0 | 0 | 0 | 0 | 2 | 9 | 0 | 0 | 0 | 0 | 4 | 7 | 7 | 4 | 2 | 0 | 0 | 3 | 4 | 3 | 5 | 5 | 4 | 0 | 0 | 2 | 0 | 0 |
| Redroot pigweed | 0 | 0 | 0 | 0 | 3 | 6 | 10 | 2 | 2 | 0 | 0 | 6 | 6 | 8 | 4 | 3 | 9 | 0 | 6 | 2 | 2 | 8 | 5 | 5 | 0 | 0 | 7 | 0 | 0 |
| Rice | 0 | 0 | 0 | 0 | — | — | — | — | — | — | 0 | 0 | — | — | — | 4 | 0 | 4 | 4 | 4 | 0 | 7 | 5 | 0 | 0 | 0 | 0 | 0 | 0 |
| S. Flatsedge | 0 | 0 | 0 | 0 | — | — | — | — | — | — | 0 | 0 | — | — | — | 0 | 0 | 4 | 8 | 7 | 8 | 9 | 9 | 2 | 0 | 0 | 8 | 0 | 0 |
| Soybean | 4 | 0 | 0 | 0 | 4 | 5 | 8 | 6 | 3 | 1 | 3 | 5 | 8 | 4 | 5 | 5 | 3 | 3 | 5 | 3 | 5 | 8 | 8 | 5 | 0 | 3 | 4 | 1 | 0 |
| Sugarbeets | 0 | 0 | 0 | 0 | 0 | 4 | 8 | 2 | 2 | 2 | 0 | 8 | 6 | 8 | 2 | 0 | 0 | 0 | 6 | 4 | 0 | 6 | 2 | 4 | 0 | 0 | 3 | 0 | 0 |
| Velvetleaf | 0 | 0 | 0 | 0 | 0 | 5 | 8 | 3 | 5 | 4 | 0 | 2 | 5 | 7 | 6 | 2 | 4 | 2 | 2 | 0 | 2 | 6 | 3 | 1 | 0 | 0 | 5 | 0 | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Wheat | 0 | 0 | 0 | 0 | 2 | 8 | 6 | 6 | 2 | 0 | 0 | 0 | 6 | 8 | 4 | 0 | 0 | 0 | 0 | 0 | 0 | 6 | 7 | 5 | 0 | 0 | 8 | 0 | 0 |
| Wild oats | 0 | 0 | 0 | 0 | 2 | 8 | 10 | 3 | 0 | 0 | 0 | 3 | 5 | 8 | 4 | 1 | 0 | 0 | 0 | 1 | 2 | 7 | 7 | 5 | 0 | 0 | 8 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 154 | 157 | 158 | 159 | 160 | 161 | 162 | 163 | 164 | 165 | 166 | 167 | 168 | 169 | 170 | 171 | 172 | 173 | 174 | 175 | 176 | 177 | 178 | 179 | 180 | 181 | 182 | 183 | 184 |
| Postemergence | | | | | | | | | | | | | | | | | | | | | | | | | | | | | |
| B. signalgrass | 2 | 0 | 0 | 0 | 0 | 7 | 4 | 6 | 0 | 8 | 0 | 0 | 0 | 7 | 10 | 0 | 0 | 0 | 0 | 0 | 0 | 0 | 2 | 0 | 0 | 0 | 0 | 0 | 0 |
| Barnyardgrass | 0 | 0 | 0 | 0 | 0 | — | — | — | 0 | — | — | — | — | 0 | 0 | 0 | — | — | — | — | 0 | 0 | — | — | — | — | — | — | 0 |
| Bedstraw | — | — | — | 0 | 0 | 4 | 6 | 9 | — | 8 | 5 | — | — | — | 2 | — | — | — | — | 0 | 8 | 6 | 0 | 10 | 0 | 0 | 0 | 3 | 6 |
| Blackgrass | 0 | 2 | 5 | 0 | 0 | 4 | 6 | 8 | 0 | 8 | 8 | 5 | 7 | 9 | 9 | 0 | 5 | 2 | 3 | 0 | 3 | 2 | — | 6 | 0 | 0 | 0 | 0 | 4 |
| Cocklebur | 2 | 0 | 0 | 0 | 0 | 3 | 2 | 3 | 0 | 0 | 0 | 2 | 2 | 3 | 0 | 3 | 2 | 2 | 3 | 3 | 3 | 3 | 0 | 1 | 0 | 0 | 0 | 0 | 1 |
| Corn | 0 | 0 | 0 | 0 | 0 | 0 | 0 | 0 | 0 | 3 | 0 | 0 | 0 | 0 | 0 | 0 | 0 | 0 | 0 | 0 | 0 | 0 | 0 | 0 | 0 | 0 | 0 | 0 | 0 |
| Crabgrass | 5 | 7 | 4 | 0 | 0 | 9 | 8 | 9 | 9 | 9 | 4 | 9 | 9 | 9 | 9 | 7 | 9 | 8 | 8 | 0 | 6 | 3 | 2 | 9 | 0 | 0 | 0 | 0 | 2 |
| Ducksalad | 0 | 0 | 0 | 0 | 0 | — | — | — | 0 | — | — | — | — | 0 | 0 | 0 | — | — | — | — | 0 | 2 | — | — | — | — | — | — | — |
| Giant foxtail | 3 | 4 | 5 | 0 | 0 | 7 | 3 | 8 | 7 | 8 | 4 | 0 | 3 | 9 | 8 | 0 | 0 | 0 | 1 | 0 | 6 | 0 | 2 | 4 | 0 | 0 | 0 | 0 | 2 |
| Morningglory | 2 | 1 | 2 | 4 | 0 | 10 | 10 | 8 | 2 | 4 | 2 | 8 | 10 | 7 | 2 | 2 | 8 | 10 | 5 | 4 | 3 | 4 | 3 | 5 | 0 | 0 | 0 | 2 | 7 |
| Nutsedge | 0 | 0 | 0 | 0 | 0 | 0 | 2 | 3 | 0 | 0 | 0 | 0 | 0 | 0 | 7 | 0 | 0 | 0 | 0 | 0 | 0 | 0 | 0 | 0 | 0 | 0 | 0 | 0 | 0 |
| Rape | 0 | 0 | 0 | 0 | 0 | 4 | 0 | 4 | 0 | 2 | — | 0 | 0 | 3 | 3 | 0 | 0 | 0 | 2 | 0 | 0 | 0 | 0 | 2 | 0 | 0 | 0 | 0 | 6 |
| Redroot pigweed | 6 | 0 | 4 | 0 | 0 | 5 | 0 | 3 | 0 | 4 | 3 | 7 | 0 | 3 | 6 | 5 | 7 | 0 | 6 | 0 | 0 | 3 | 7 | 8 | 0 | 0 | 0 | 0 | 7 |
| Rice | 0 | 0 | 0 | 0 | 0 | — | — | — | 0 | — | — | — | — | 0 | 0 | 0 | — | — | — | — | 0 | 0 | — | — | — | — | — | — | — |
| S. Flatsedge | 0 | 0 | 0 | 0 | 0 | — | — | — | 0 | — | — | — | — | 0 | 0 | 0 | — | — | — | — | 0 | 0 | — | — | — | — | — | — | — |
| Soybean | 3 | 2 | 5 | 3 | 0 | 4 | 4 | 3 | 2 | 6 | 3 | 5 | 2 | 6 | 7 | 3 | 5 | 4 | 4 | 1 | 4 | 4 | 2 | 1 | 0 | 0 | 0 | 2 | 3 |
| Sugarbeets | 0 | 0 | 0 | 0 | 0 | 7 | 0 | 5 | 0 | 6 | 0 | 0 | 0 | 0 | 4 | 2 | 0 | 5 | 6 | 0 | 0 | 0 | 0 | 6 | 0 | 0 | 0 | 0 | 6 |
| Velvetleaf | 0 | 0 | 0 | 0 | 0 | 6 | 4 | 6 | 0 | 1 | 0 | 2 | 1 | 0 | 5 | 3 | 2 | 0 | 0 | 3 | 2 | 3 | 0 | 3 | 0 | 0 | 0 | 0 | 5 |
| Wheat | 0 | 0 | 0 | 0 | 0 | 0 | 0 | 5 | 0 | 3 | 3 | 0 | 0 | 2 | 7 | 0 | 0 | 0 | 0 | 3 | 2 | 4 | 2 | 0 | 0 | 0 | 0 | 0 | 3 |
| Wild oats | 1 | 0 | 0 | 0 | 0 | 0 | 4 | 3 | 0 | 3 | 2 | 0 | 0 | 2 | 6 | 0 | 0 | 0 | 0 | 0 | 0 | 0 | 0 | 2 | 0 | 0 | 0 | 0 | 2 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 185 | 187 | 188 | 189 | 190 | 191 | 192 | 193 | 194 | 195 | 196 | 197 | 198 | 199 | 201 | 202 | 203 | 204 | 205 | 206 | 207 | 208 | 210 | 211 | 212 | 214 | 215 | 216 | 218 |
| Postemergence | | | | | | | | | | | | | | | | | | | | | | | | | | | | | |
| B. signalgrass | 0 | 0 | 0 | 0 | 0 | 1 | 2 | 0 | 3 | 1 | 0 | 0 | 0 | — | 0 | 0 | 0 | 0 | 0 | 0 | 0 | 3 | 0 | 0 | 7 | 0 | 3 | 8 | 7 |
| Barnyardgrass | — | — | — | — | — | — | — | — | — | — | — | — | — | 8 | — | — | — | — | — | — | — | — | — | — | — | — | — | — | — |
| Bedstraw | 3 | 0 | 5 | 0 | 0 | 0 | 0 | 0 | 0 | 7 | 0 | — | — | 2 | 0 | 4 | 0 | 7 | 0 | 0 | 5 | 5 | — | 8 | 7 | 8 | 8 | — | 8 |
| Blackgrass | 0 | 0 | 3 | 0 | 0 | 3 | — | 0 | 3 | 6 | 0 | 0 | 0 | 9 | 4 | 6 | 0 | 7 | 0 | 0 | 4 | 7 | 2 | 4 | 7 | 5 | 5 | 8 | 8 |
| Cocklebur | 2 | 0 | 0 | 0 | 0 | 3 | 5 | 0 | 2 | 2 | 0 | 0 | 0 | 3 | 0 | 2 | 0 | 1 | 2 | 0 | 3 | 0 | 2 | 0 | 5 | 0 | 0 | 3 | 4 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 3 | 0 |
| Crabgrass | 1 | 0 | 3 | 0 | 0 | 6 | 2 | 0 | 2 | 5 | 0 | 2 | 0 | 8 | 0 | 4 | 0 | 5 | 1 | 0 | 3 | 3 | 0 | 3 | 9 | 5 | 2 | 7 | 9 |
| Ducksalad | — | — | — | — | — | — | — | — | — | — | — | — | — | 2 | — | — | — | — | — | — | — | — | — | — | — | — | — | — | — |
| Giant foxtail | 1 | 0 | 4 | 0 | 0 | 2 | 1 | 0 | 2 | 3 | 0 | 3 | 0 | 7 | 0 | 2 | 0 | 3 | 0 | 0 | 2 | 1 | 0 | 3 | 9 | 4 | 5 | 6 | 8 |
| Morningglory | 2 | 0 | 0 | 0 | 0 | 8 | 6 | 2 | 2 | 3 | 0 | 0 | 3 | 8 | 3 | 9 | 0 | 8 | 2 | 5 | 3 | 3 | 7 | 6 | 8 | 7 | 3 | 10 | 9 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 2 | 0 | 2 | 0 | 0 | 0 | 0 | 0 | 0 | 4 | 0 | 0 | 0 | 0 | 2 | 0 | 0 | 3 | 3 | 3 | 0 | 3 | 7 |
| Redroot pigweed | 4 | 0 | 3 | 0 | 0 | 0 | 7 | 0 | 0 | 4 | 0 | 0 | 0 | 6 | 3 | 7 | 0 | 7 | 0 | 0 | 0 | 0 | 6 | 5 | 7 | 3 | 6 | 3 | 7 |
| Rice | — | — | — | — | — | — | — | — | — | — | — | — | — | 0 | — | — | — | — | — | — | — | — | — | — | — | — | — | — | — |
| S. Flatsedge | — | — | — | — | — | — | — | — | — | — | — | — | — | 7 | — | — | — | — | — | — | — | — | — | — | — | — | — | — | — |
| Soybean | 3 | 0 | 3 | 0 | 0 | 4 | 3 | 2 | 1 | 5 | 0 | 0 | 1 | 7 | 3 | 3 | 0 | 7 | 2 | 2 | 5 | 2 | 3 | 4 | 4 | 3 | 1 | 2 | 7 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Sugarbeets | 0 | 0 | 7 | 0 | 0 | 0 | 5 | 0 | 0 | 2 | 0 | 0 | 0 | 2 | 4 | 4 | 0 | 0 | 0 | 0 | 2 | 0 | 4 | 2 | 5 | 0 | 0 | 2 | 4 |
| Velvetleaf | 3 | 0 | 0 | 0 | 0 | 2 | 4 | 0 | 0 | 2 | 0 | 0 | 0 | 5 | 3 | 0 | 0 | 2 | 0 | 0 | 2 | 1 | 2 | 3 | 7 | 0 | 0 | 0 | 3 |
| Wheat | 0 | 0 | 0 | 0 | 0 | 0 | 0 | 0 | 0 | 0 | 0 | 0 | 0 | 4 | 0 | 0 | 0 | 0 | 0 | 0 | 0 | 0 | 0 | 0 | 7 | 6 | 8 | 2 | 0 |
| Wild oats | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 4 | 2 | 3 | 0 | 2 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 219 | 220 | 222 | 223 | 224 | 225 | 226 | 227 | 228 | 229 | 230 | 231 | 232 | 233 | 234 | 235 | 236 | 237 | 238 | 239 | 240 | 241 | 242 | 243 | 245 | 246 | 247 | 248 | 249 |
| Postemergence | | | | | | | | | | | | | | | | | | | | | | | | | | | | | |
| B. signalgrass | 8 | 8 | 1 | 0 | 0 | 9 | 9 | 0 | 0 | 0 | 0 | 0 | 8 | 1 | 0 | 0 | 0 | 0 | 0 | 0 | 0 | 6 | 9 | 9 | 8 | 1 | 0 | 0 | 0 |
| Barnyardgrass | — | — | — | — | — | — | — | — | — | — | — | — | — | — | — | — | — | — | — | — | — | — | — | — | — | — | — | — | — |
| Bedstraw | 8 | 9 | 5 | 5 | 4 | 0 | 7 | 8 | 2 | 0 | 0 | 0 | 2 | 5 | 0 | 0 | 4 | 3 | 8 | 3 | 5 | 7 | 8 | 5 | 9 | 9 | 0 | 0 | 0 |
| Blackgrass | 8 | 8 | 4 | 1 | 4 | 8 | 9 | 7 | 0 | 0 | 0 | 0 | 7 | 5 | 0 | 0 | 0 | 0 | 5 | 3 | 5 | 9 | 9 | 9 | 8 | 8 | 0 | 0 | 0 |
| Cocklebur | 4 | 5 | 0 | 2 | 1 | 0 | 2 | 3 | 0 | 0 | 0 | 0 | 4 | 2 | 3 | 0 | 0 | 0 | 0 | 1 | 1 | 1 | 7 | 0 | 1 | 2 | 0 | 0 | 0 |
| Corn | 5 | 6 | 0 | 0 | 0 | 6 | 6 | 0 | 2 | 0 | 0 | 0 | 0 | 0 | 0 | 0 | 0 | 0 | 0 | 0 | 0 | 0 | 6 | 7 | 7 | 0 | 0 | 0 | 0 |
| Crabgrass | 8 | 9 | 2 | 3 | 0 | 8 | 8 | 3 | 0 | 0 | 2 | 2 | 2 | 6 | 0 | 0 | 0 | 0 | 5 | 6 | 4 | 9 | 9 | 9 | 8 | 3 | 0 | 0 | 0 |
| Ducksalad | — | — | — | — | — | — | — | — | — | — | — | — | — | — | — | — | — | — | — | — | — | — | — | — | — | — | — | — | — |
| Giant foxtail | 9 | 8 | 1 | 1 | 0 | 9 | 7 | 0 | 0 | 0 | 1 | 0 | 3 | 6 | 0 | 0 | 0 | 0 | 2 | 6 | 2 | 8 | 9 | 8 | 8 | 8 | 0 | 0 | 0 |
| Morningglory | 7 | 8 | 3 | 6 | 6 | 6 | 7 | 10 | 9 | 0 | 7 | 4 | 8 | 8 | 2 | 7 | 6 | 6 | 5 | 9 | 10 | 8 | 8 | 8 | 9 | 9 | 2 | 0 | 3 |
| Nutsedge | 0 | 0 | — | 0 | 0 | 2 | 4 | 0 | 0 | 0 | 0 | 0 | 0 | 0 | 0 | 0 | 0 | 0 | 0 | 0 | 0 | 6 | 5 | 7 | 0 | 3 | 0 | 0 | 0 |
| Rape | 7 | 4 | 0 | 0 | 0 | 2 | 6 | 0 | 0 | 0 | 0 | 0 | 2 | 3 | 0 | 0 | 0 | 0 | 6 | 0 | 0 | 4 | 8 | 3 | 5 | 0 | 0 | 0 | 0 |
| Redroot pigweed | 8 | 4 | 0 | 5 | 7 | 2 | 0 | 7 | 2 | 0 | 0 | 0 | 4 | 4 | 0 | 0 | 0 | 3 | 5 | 7 | 7 | 7 | 8 | 7 | 9 | 3 | 0 | 0 | 3 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 7 | 7 | 2 | 4 | 2 | 4 | 6 | 5 | 1 | 2 | 5 | 1 | 4 | 5 | 1 | 0 | 3 | 1 | 2 | 3 | 3 | 4 | 6 | 8 | 5 | 4 | 0 | 1 | 4 |
| Sugarbeets | 7 | 2 | 0 | 3 | 4 | 2 | 2 | 5 | 4 | 0 | 0 | 0 | 3 | 4 | 0 | 0 | 0 | 0 | 0 | 0 | 3 | 5 | 8 | 5 | 7 | 0 | 0 | 0 | 2 |
| Velvetleaf | 4 | 2 | 3 | 3 | 4 | 3 | 0 | 3 | 0 | 2 | 0 | 0 | 3 | 3 | 0 | 0 | 3 | 2 | 2 | 3 | 3 | 1 | 7 | 7 | 7 | 3 | 0 | 0 | 0 |
| Wheat | 7 | 6 | 0 | 0 | 0 | 8 | 9 | 5 | 0 | 0 | 0 | 0 | 0 | 0 | 0 | 0 | 0 | 0 | 0 | 0 | 2 | 8 | 8 | 8 | 8 | 4 | 0 | 0 | 0 |
| Wild oats | 6 | 2 | 0 | 2 | 0 | 2 | 3 | 2 | 0 | 0 | 0 | 0 | 0 | 2 | 0 | 0 | 0 | 0 | 0 | 0 | 2 | 2 | 8 | 4 | 8 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 251 | 253 | 254 | 255 | 257 | 258 | 259 | 260 | 261 | 262 | 263 | 265 | 266 | 267 | 268 | 269 | 270 | 271 | 272 | 273 | 274 | 276 | 277 | 278 | 279 | 280 | 281 | 282 | 283 |
| Postemergence | | | | | | | | | | | | | | | | | | | | | | | | | | | | | |
| B. signalgrass | 2 | 0 | 0 | 8 | 0 | 8 | 0 | 0 | 0 | 0 | 0 | 0 | 2 | 3 | — | 0 | 0 | 5 | 0 | 0 | 0 | 0 | 3 | 0 | 0 | 0 | 0 | 2 | 2 |
| Barnyardgrass | — | — | — | — | — | — | — | — | — | — | — | — | — | — | — | — | — | — | — | — | — | — | — | — | — | — | — | — | — |
| Bedstraw | 9 | 0 | 4 | 8 | 0 | 8 | — | — | — | — | — | 8 | 6 | 7 | — | 7 | 0 | 8 | 4 | 0 | 0 | 3 | 8 | 8 | 0 | 0 | — | 8 | 6 |
| Blackgrass | 8 | 0 | 0 | 9 | 2 | 7 | 0 | 0 | 5 | 0 | 5 | 7 | 8 | 8 | — | 5 | 0 | 8 | 6 | 4 | 0 | 8 | 8 | 0 | 4 | 0 | 2 | 8 | 7 |
| Cocklebur | 3 | 0 | 0 | 2 | 0 | 1 | 3 | 0 | 1 | 0 | 0 | 0 | 2 | 3 | 0 | 2 | 0 | 4 | 1 | 0 | 0 | 0 | 2 | 3 | 0 | 0 | 0 | 2 | 2 |
| Corn | 0 | 0 | 0 | 6 | 0 | 0 | 0 | 0 | 0 | 0 | 0 | 0 | 0 | 0 | 3 | 0 | 0 | 0 | 0 | 0 | 0 | 0 | 0 | 0 | 0 | 0 | 0 | 0 | 0 |
| Crabgrass | 9 | 0 | 0 | 3 | 4 | 5 | 0 | 0 | 0 | 0 | 2 | 3 | 5 | 7 | 0 | 1 | 0 | 5 | 0 | 3 | 0 | 7 | 6 | 0 | 0 | 0 | 0 | 0 | 1 |
| Ducksalad | — | — | — | — | — | — | — | — | — | — | — | — | — | — | — | — | — | — | — | — | — | — | — | — | — | — | — | — | — |
| Giant foxtail | 8 | 0 | 0 | 8 | 2 | 7 | 0 | 0 | 0 | 0 | 3 | 2 | 7 | 7 | 0 | 2 | 0 | 7 | 0 | 2 | 0 | 6 | 6 | 0 | 1 | 0 | 0 | 2 | 7 |
| Morningglory | 9 | 0 | 9 | 8 | 8 | 10 | 8 | 4 | 6 | 7 | 7 | 8 | 8 | 8 | 7 | 7 | 0 | 8 | 7 | 3 | 0 | 8 | 9 | 4 | 2 | 0 | 5 | 9 | 10 |
| Nutsedge | 0 | 0 | 0 | 6 | 0 | 0 | 0 | 0 | 0 | 0 | 0 | 0 | 3 | 4 | 0 | 0 | 0 | 0 | 0 | 0 | 0 | 0 | 0 | 0 | 0 | 0 | 0 | 0 | 0 |
| Rape | 0 | 0 | 2 | 3 | 5 | 3 | — | 0 | 0 | 0 | 0 | 3 | 7 | 2 | — | 0 | 0 | 6 | 0 | 0 | 0 | 0 | 3 | 0 | 0 | 0 | 0 | 8 | 7 |
| Redroot pigweed | 4 | 0 | 6 | 8 | 6 | 3 | 7 | 6 | 2 | 4 | 0 | 4 | 7 | 6 | — | 6 | 0 | 8 | 4 | 4 | 1 | 2 | 5 | 4 | 2 | 1 | 6 | 8 | 7 |
| Rice | — | — | — | — | — | — | — | — | — | — | — | — | — | — | — | — | — | — | — | — | — | — | — | — | — | — | — | — | — |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| S. Flatsedge | — | — | — | — | — | — | — | — | — | — | — | — | — | — | — | — | — | — | — | — | — | — | — | — | — | — | — | — | — |
| Soybean | 6 | 0 | 2 | 6 | 4 | 6 | 6 | 1 | 4 | 4 | 1 | 4 | 8 | 6 | — | 3 | 2 | 6 | 1 | 4 | 5 | 7 | 8 | 1 | 4 | 5 | 3 | 4 | 7 |
| Sugarbeets | 2 | 0 | 7 | 3 | 5 | 2 | 3 | 3 | 0 | 0 | 0 | 3 | 7 | 4 | — | 0 | 0 | 6 | 0 | 0 | 1 | 2 | 5 | 0 | 0 | 0 | 4 | 7 | 2 |
| Velvetleaf | 0 | 0 | 2 | 1 | 1 | 0 | 1 | 1 | 1 | 2 | 2 | 3 | 5 | 3 | 0 | 3 | 0 | 3 | 0 | 2 | 0 | 0 | 1 | 2 | 0 | 0 | 1 | 3 | 3 |
| Wheat | 2 | 0 | 0 | 8 | 0 | 6 | 3 | 0 | 2 | 0 | 2 | 0 | 6 | 4 | — | 4 | 0 | 0 | 0 | 0 | 0 | 0 | 0 | 0 | 0 | 0 | 0 | 0 | 0 |
| Wild oats | 0 | 0 | 0 | 4 | 0 | 3 | 0 | 0 | 0 | 0 | 0 | 0 | 2 | 4 | — | 3 | 0 | 3 | 0 | 0 | 0 | 0 | 2 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 284 | 286 | 292 | 293 | 294 | 297 | 298 | 299 | 300 | 301 | 302 | 303 | 304 | 305 | 306 | 307 | 308 | 309 | 310 | 311 | 312 | 313 | 314 | 315 | 316 | 317 | 319 | 320 | 321 |
| Postemergence | | | | | | | | | | | | | | | | | | | | | | | | | | | | | |
| B. signalgrass | 1 | 2 | 0 | 7 | 0 | 0 | 0 | 8 | 0 | 0 | 0 | 0 | 0 | 0 | 0 | 0 | 0 | 0 | 7 | 0 | 0 | 0 | 3 | 4 | 2 | 8 | 0 | 0 | 0 |
| Barnyardgrass | — | — | — | — | — | — | — | — | — | — | — | — | — | — | — | — | — | — | — | — | — | — | — | — | — | — | — | — | — |
| Bedstraw | 9 | 6 | 0 | 9 | 9 | — | — | — | 0 | — | 0 | 0 | — | — | 0 | 0 | 0 | 0 | 5 | 2 | — | — | — | — | — | — | — | — | — |
| Blackgrass | 8 | 8 | 0 | 9 | 8 | 0 | 0 | 9 | 0 | 0 | 2 | 0 | 4 | 0 | 0 | 0 | 0 | 2 | 9 | 0 | 0 | 0 | 5 | 8 | 7 | 9 | 3 | 0 | 4 |
| Cocklebur | 2 | 0 | 0 | 0 | 0 | 0 | 0 | 5 | 0 | 0 | 0 | 0 | 0 | 0 | 0 | 0 | 0 | 0 | 7 | 0 | 0 | 0 | 1 | 0 | 0 | 1 | 0 | 0 | 0 |
| Corn | 0 | 0 | 0 | 3 | 0 | 0 | 0 | 4 | 0 | 0 | 0 | 0 | 0 | 0 | 0 | 0 | 0 | 0 | 0 | 0 | 0 | 0 | 0 | 5 | 0 | 3 | 0 | 0 | 0 |
| Crabgrass | 1 | 6 | 0 | 9 | 2 | 0 | 0 | 5 | 0 | 0 | 0 | 0 | 3 | 0 | 0 | 0 | 0 | 0 | 9 | 0 | 0 | 0 | 4 | 5 | 0 | 8 | 3 | 4 | 8 |
| Ducksalad | — | — | — | — | — | — | — | — | — | — | — | — | — | — | — | — | — | — | — | — | — | — | — | — | — | — | — | — | — |
| Giant foxtail | 8 | 3 | 0 | 9 | 4 | 0 | 0 | 8 | 0 | 0 | 4 | 0 | 2 | 0 | 0 | 0 | 0 | 0 | 8 | 0 | 0 | 0 | 7 | 7 | 3 | 8 | 0 | 3 | 8 |
| Morningglory | 8 | 8 | 2 | 7 | 9 | 0 | 3 | 9 | 0 | 0 | 2 | 0 | 6 | 2 | 5 | 3 | 2 | 2 | 8 | 10 | 0 | 7 | 6 | 3 | 8 | 6 | 4 | 3 | 9 |
| Nutsedge | 0 | 0 | 0 | 9 | 0 | 0 | 0 | 0 | 0 | 0 | 0 | 0 | 0 | 0 | 0 | 0 | 0 | 0 | 6 | 0 | 0 | 0 | 3 | 0 | 0 | — | 0 | 0 | 0 |
| Rape | 8 | 6 | 0 | 0 | 4 | 0 | 0 | 8 | 0 | 0 | 0 | 0 | 0 | 0 | 0 | 0 | 0 | 0 | 5 | 0 | 0 | 0 | 0 | 0 | 2 | 2 | 0 | 3 | 0 |
| Redroot pigweed | 8 | 7 | 0 | 6 | 4 | 0 | 0 | 8 | 0 | 0 | 2 | 3 | 6 | 6 | 0 | 0 | 0 | 0 | 7 | 0 | 0 | 2 | 2 | 0 | 5 | 6 | 0 | 7 | — |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 5 | 2 | 1 | 5 | 6 | 3 | 4 | 7 | 2 | 0 | 5 | 3 | 5 | 5 | 2 | 3 | 2 | 3 | 6 | 3 | 3 | 4 | 4 | 4 | 4 | 7 | 4 | 4 | 3 |
| Sugarbeets | 6 | 2 | 0 | 3 | 0 | 0 | 0 | 7 | 0 | 0 | 2 | 0 | 2 | 0 | 0 | 0 | 0 | 0 | 3 | 0 | 0 | 0 | 0 | 0 | 0 | 4 | 0 | 6 | 6 |
| Velvetleaf | 2 | 1 | 0 | 6 | 0 | 0 | 0 | 7 | 0 | 0 | 0 | 0 | 0 | 0 | 0 | 0 | 0 | 0 | 8 | 0 | 0 | 0 | 0 | 0 | 3 | 4 | 3 | 0 | 0 |
| Wheat | 0 | 5 | 0 | 7 | 2 | 0 | 0 | 7 | 0 | 0 | 0 | 0 | 0 | 0 | 0 | 0 | 0 | 0 | 8 | 0 | 0 | 0 | 3 | 4 | 4 | 6 | 0 | 0 | 0 |
| Wild oats | 0 | 3 | 0 | 8 | 3 | 0 | 0 | 4 | 0 | 0 | 0 | 0 | 0 | 0 | 0 | 0 | 0 | 0 | 7 | 0 | 0 | 0 | 3 | 0 | 4 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 322 | 323 | 325 | 326 | 327 | 328 | 329 | 330 | 331 | 332 | 333 | 334 | 335 | 336 | 337 | 338 | 339 | 340 | 341 | 342 | 343 | 344 | 345 | 348 | 349 | 350 | 351 | 352 | 353 |
| Postemergence | | | | | | | | | | | | | | | | | | | | | | | | | | | | | |
| B. signalgrass | 3 | 0 | 2 | 0 | 0 | 0 | 0 | 0 | 0 | 0 | 0 | 0 | 0 | 0 | 0 | 0 | 0 | 0 | 2 | 1 | 7 | 0 | 0 | 7 | 0 | 4 | 4 | 7 | 0 |
| Barnyardgrass | — | — | — | — | — | — | — | — | — | — | — | — | — | — | — | — | — | — | — | 9 | 2 | 0 | 0 | 7 | 9 | 5 | 5 | 3 | — |
| Bedstraw | 4 | — | — | — | — | — | — | — | 0 | — | 0 | 0 | 4 | 0 | 4 | 5 | 8 | 8 | 8 | 5 | 3 | 0 | 0 | 7 | 3 | — | — | 4 | — |
| Blackgrass | 8 | 0 | 7 | 1 | 7 | 5 | 0 | 0 | 0 | 0 | 0 | 0 | 0 | 0 | 0 | 0 | 2 | 8 | 2 | 4 | 6 | 0 | 0 | 7 | 6 | 7 | 4 | 8 | 9 |
| Cocklebur | 4 | 0 | 3 | 2 | 0 | 0 | 4 | 0 | 0 | 0 | 0 | 0 | 0 | 0 | — | 0 | 0 | 0 | — | 0 | 4 | 0 | 0 | 2 | 1 | 3 | 2 | 0 | 1 |
| Corn | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 3 | 0 | 0 | 0 | 6 | 0 |
| Crabgrass | 5 | 0 | 0 | 3 | 1 | 2 | 0 | 0 | 0 | 3 | 0 | 0 | 0 | 0 | 0 | 0 | 2 | 2 | 2 | 3 | 6 | 0 | 0 | 6 | 3 | 7 | 9 | 4 | 3 |
| Ducksalad | — | — | — | — | — | — | — | — | — | — | — | — | — | — | — | — | — | — | — | 4 | 0 | 0 | 0 | 4 | 4 | 3 | 4 | 2 | — |
| Giant foxtail | 4 | 0 | 0 | 2 | 0 | 1 | 0 | 0 | 0 | 0 | 0 | 0 | 0 | 0 | 0 | 0 | 0 | 6 | 2 | 7 | 9 | 0 | 0 | 9 | 9 | 9 | 9 | 9 | 8 |
| Morningglory | 8 | 3 | 8 | 10 | 10 | 10 | 0 | 4 | 0 | 0 | 0 | 0 | 0 | 0 | 0 | 2 | 10 | 10 | 10 | 9 | 9 | 0 | 0 | 10 | 10 | 9 | 6 | 8 | 10 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 3 | 0 | 0 | 6 | 0 | 0 | 0 | 2 | 0 |
| Rape | 0 | 0 | 2 | 3 | 2 | 0 | 0 | 0 | 0 | 0 | 0 | 0 | 0 | 0 | 0 | 0 | 5 | 6 | 2 | 4 | 3 | 0 | 0 | 5 | 0 | 2 | 5 | 0 | 4 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Redroot pigweed | 6 | 0 | 7 | 7 | 7 | 5 | 0 | 0 | 0 | 4 | 0 | 0 | 0 | 0 | 0 | 0 | 6 | — | 6 | 8 | 5 | 2 | 0 | 5 | 4 | 3 | 7 | 4 | 6 |
| Rice | — | — | — | — | — | — | — | — | — | — | — | — | — | — | — | — | — | — | — | 0 | 0 | 0 | 0 | 0 | 0 | 0 | 0 | 3 | — |
| S. Flatsedge | — | — | — | — | — | — | — | — | — | — | — | — | — | — | — | — | — | — | — | — | 0 | 0 | 0 | 7 | — | 8 | 8 | 7 | — |
| Soybean | 5 | 2 | 3 | 6 | 7 | 6 | 2 | 1 | 0 | 3 | 4 | 2 | 2 | 2 | 2 | 2 | 4 | 3 | 3 | 7 | 3 | 2 | 0 | 4 | 2 | 3 | 2 | 4 | 6 |
| Sugarbeets | 2 | 0 | 0 | 0 | 0 | 0 | 0 | 0 | 0 | 0 | 0 | 0 | 0 | 0 | 0 | 0 | 0 | 6 | 0 | 0 | 3 | 0 | 0 | 3 | 0 | 0 | 2 | 0 | 6 |
| Velvetleaf | 2 | 0 | 2 | 2 | 0 | 0 | 0 | 0 | 0 | 0 | 0 | 0 | 0 | 0 | 0 | 0 | 0 | 3 | 2 | 0 | 5 | 0 | 0 | 6 | 0 | 6 | 6 | 3 | 2 |
| Wheat | 3 | 0 | 5 | 0 | 1 | 0 | 0 | 0 | 0 | 0 | 0 | 0 | 0 | 0 | 0 | 0 | 0 | 0 | 0 | 0 | 5 | 0 | 0 | 4 | 3 | 2 | 2 | 7 | 0 |
| Wild oats | 2 | 0 | 4 | 0 | 0 | 0 | 0 | 0 | 0 | 0 | 0 | 0 | 0 | 0 | 0 | 0 | 0 | 0 | 3 | 0 | 4 | 0 | 0 | 7 | 3 | 5 | 5 | 7 | 2 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 354 | 355 | 356 | 357 | 358 | 359 | 360 | 361 | 363 | 364 | 365 | 367 | 368 | 369 | 370 | 371 | 372 | 373 | 374 | 375 | 376 | 378 | 379 | 380 | 381 | 382 | 383 | 384 | 385 |
| Postemergence | | | | | | | | | | | | | | | | | | | | | | | | | | | | | |
| B. signalgrass | 2 | 2 | 1 | 7 | 2 | 0 | 7 | 4 | 5 | 1 | 0 | 4 | 7 | 3 | 6 | 6 | 7 | 0 | 0 | 8 | 0 | 2 | 0 | 0 | 0 | 0 | 0 | 7 | 8 |
| Barnyardgrass | 9 | 8 | 7 | 6 | — | 0 | 7 | — | — | 0 | — | — | — | 2 | 2 | — | 6 | — | — | — | — | — | — | — | — | — | — | — | — |
| Bedstraw | — | 0 | 3 | 5 | 6 | 0 | 4 | 8 | 9 | 0 | — | — | — | — | — | — | — | — | — | — | — | — | 0 | — | 0 | 4 | 0 | 0 | 3 |
| Blackgrass | 9 | 6 | 7 | 7 | 8 | 2 | 7 | 8 | 8 | 2 | 0 | 8 | 8 | 5 | 5 | 8 | 10 | 0 | — | 8 | 0 | — | 0 | 0 | 0 | 2 | 8 | — | 8 |
| Cocklebur | 1 | 4 | 0 | 2 | 0 | 1 | 0 | 2 | 2 | 2 | 0 | 2 | 5 | 0 | 3 | 0 | 3 | 2 | 0 | 0 | 0 | 1 | 0 | 6 | 0 | 0 | 0 | 0 | 0 |
| Corn | 0 | 0 | 3 | 3 | 0 | 0 | 7 | 0 | 6 | 3 | 0 | 0 | 7 | 0 | 5 | 1 | 3 | 0 | 0 | 2 | 0 | 0 | 0 | 0 | 0 | 0 | 0 | 0 | 0 |
| Crabgrass | 3 | 2 | 3 | 5 | 7 | 0 | 5 | 5 | 9 | 2 | 0 | 8 | 8 | 9 | 9 | 9 | 9 | 2 | 3 | 9 | 0 | 2 | 0 | 7 | 0 | 1 | 4 | 8 | 9 |
| Ducksalad | 5 | 0 | 2 | 2 | — | 0 | 0 | — | — | 0 | — | — | — | 2 | 3 | — | 6 | — | — | — | — | — | — | — | — | — | — | — | — |
| Giant foxtail | 9 | 8 | 8 | 9 | 8 | 0 | 8 | 5 | 9 | 8 | 0 | 8 | 9 | 9 | 9 | 9 | 9 | 6 | 8 | 9 | 0 | 8 | 7 | 9 | 0 | 4 | 6 | 9 | 9 |
| Morningglory | 8 | 8 | 10 | 8 | 7 | 0 | 5 | — | 3 | 4 | 0 | 7 | 7 | 10 | 10 | 10 | 10 | 8 | 10 | 6 | 0 | 10 | 10 | 10 | 7 | 0 | 0 | 0 | 5 |
| Nutsedge | 0 | 0 | 0 | 2 | 0 | 0 | 4 | 0 | 0 | 0 | 0 | 3 | 0 | 3 | 5 | 0 | 0 | 0 | 0 | 6 | 0 | 0 | 0 | 0 | 0 | 0 | 0 | 0 | 0 |
| Rape | 4 | 0 | 0 | 4 | 4 | 0 | 0 | 4 | 2 | 0 | 0 | 4 | 5 | 3 | 3 | 0 | 5 | 5 | 7 | 2 | 0 | 3 | 0 | 0 | 6 | 0 | 0 | — | 0 |
| Redroot pigweed | 7 | 3 | 0 | 8 | 6 | 0 | 6 | 7 | 5 | 0 | 0 | 7 | 7 | 4 | 3 | 5 | 9 | 6 | 6 | 3 | 0 | 2 | 1 | 5 | 2 | 0 | 0 | 0 | 0 |
| Rice | 2 | 0 | 0 | 2 | 0 | 0 | 3 | — | — | 0 | — | — | — | 0 | 2 | — | 2 | — | — | — | — | — | — | — | — | — | — | — | — |
| S. Flatsedge | 9 | 8 | 7 | 8 | — | 0 | 8 | — | — | 3 | — | — | — | 4 | 7 | — | 8 | — | — | — | — | — | — | — | — | — | — | — | — |
| Soybean | 7 | 3 | 5 | 3 | 7 | 3 | 3 | 5 | 7 | 3 | 2 | 2 | 5 | 1 | 4 | 4 | 3 | 4 | 4 | 2 | 0 | 2 | 2 | 1 | 2 | 5 | 5 | 3 | 2 |
| Sugarbeets | 3 | 0 | 0 | 0 | 4 | 0 | 7 | 6 | 3 | 1 | 0 | 7 | 3 | 2 | 0 | 0 | 8 | 4 | 4 | 3 | 0 | 0 | 0 | 0 | 0 | 0 | 0 | 0 | 0 |
| Velvetleaf | 2 | 2 | 0 | 4 | 3 | 2 | 4 | 3 | 6 | 0 | 0 | 3 | 7 | 3 | 4 | 3 | 2 | 2 | 1 | 4 | 0 | 3 | 0 | 3 | 0 | 0 | 0 | 0 | 0 |
| Wheat | 0 | 3 | 4 | 7 | 5 | 2 | 6 | 2 | 6 | 0 | 0 | 6 | 6 | 4 | 3 | — | 2 | 0 | 0 | 6 | 0 | 0 | 0 | 0 | 0 | 0 | 0 | 3 | 5 |
| Wild oats | 3 | 5 | 3 | 6 | 7 | 0 | 5 | 6 | 7 | 0 | 0 | 8 | 5 | 4 | 5 | 4 | 8 | 0 | — | 8 | 0 | 0 | 0 | 0 | 0 | 0 | 0 | 4 | 3 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 387 | 388 | 389 | 390 | 391 | 393 | 394 | 395 | 396 | 397 | 398 | 400 | 401 | 402 | 403 | 404 | 405 | 406 | 407 | 408 | 409 | 410 | 411 | 414 | 415 | 416 | 417 | 418 | 419 |
| Postemergence | | | | | | | | | | | | | | | | | | | | | | | | | | | | | |
| B. signalgrass | 8 | 8 | 0 | 8 | 0 | 0 | 9 | 0 | 0 | 8 | 8 | 4 | 0 | 5 | 6 | 6 | 0 | 0 | 0 | 5 | 9 | 7 | 9 | 6 | 6 | 9 | 0 | 2 | 2 |
| Barnyardgrass | — | — | — | — | — | — | — | — | 0 | 0 | 0 | 0 | — | — | — | — | — | — | — | — | — | — | — | — | 0 | 0 | 8 | 0 | 0 |
| Bedstraw | — | 6 | 7 | 7 | 0 | — | — | 4 | — | — | 9 | — | — | 8 | 8 | — | — | — | — | 9 | 5 | 7 | 8 | — | — | 7 | 6 | — | 0 |
| Blackgrass | 9 | 10 | 6 | 9 | 0 | 8 | — | 5 | 6 | 9 | 9 | 8 | 0 | 9 | 10 | 10 | 5 | 0 | 7 | 10 | 10 | 9 | 9 | 7 | 9 | 9 | 0 | 6 | 4 |
| Cocklebur | 0 | 0 | 0 | 7 | 0 | 0 | 4 | 0 | 0 | 0 | 0 | 0 | 1 | 5 | 0 | 3 | 0 | 0 | 0 | 3 | 1 | 1 | 3 | 0 | 4 | 5 | 0 | 0 | 0 |
| Corn | 0 | 0 | 0 | 0 | 0 | 0 | 0 | 0 | 0 | 0 | 0 | 0 | 0 | 0 | 0 | 1 | 0 | 0 | 0 | 0 | 7 | 3 | 4 | 0 | 2 | 7 | 0 | 0 | 0 |
| Crabgrass | 7 | 9 | 7 | 9 | 0 | 8 | 9 | 5 | 2 | 9 | 9 | 9 | 3 | 9 | 9 | 8 | 0 | 0 | 3 | 9 | 9 | 10 | 8 | 9 | 9 | 9 | 2 | 6 | 1 |
| Ducksalad | — | — | — | — | — | — | — | — | 0 | 0 | 0 | 0 | — | — | — | — | — | — | — | — | — | — | — | — | 0 | 0 | 3 | 2 | 0 |
| Giant foxtail | 9 | 9 | 8 | 10 | 0 | 9 | 9 | 6 | 2 | 9 | 9 | 9 | 6 | 9 | 9 | 9 | 6 | 0 | 8 | 9 | 9 | 9 | 9 | 9 | 9 | 9 | 8 | 9 | 6 |
| Morningglory | 6 | 5 | 10 | 9 | 0 | 0 | 7 | — | 8 | 6 | 8 | 6 | 7 | 10 | 10 | 10 | 5 | 2 | 10 | 7 | 10 | 8 | 6 | 8 | 7 | 9 | 9 | 10 | 5 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Nutsedge | 5 | 6 | 0 | — | 0 | 0 | — | 0 | 0 | 0 | 0 | 0 | 0 | 0 | 0 | 0 | 0 | 0 | 0 | 3 | 0 | 0 | 0 | 0 | 0 | 0 | 0 | 0 | 0 |
| Rape | 0 | 0 | 4 | 10 | 0 | — | — | — | 6 | 2 | 2 | 0 | 7 | 9 | 7 | 8 | 2 | 0 | — | 2 | — | 7 | 8 | 0 | 1 | 3 | 2 | 0 | 0 |
| Redroot pigweed | 0 | 3 | 7 | 9 | 0 | 0 | 7 | 0 | 0 | 6 | 5 | 0 | 2 | 7 | 2 | 7 | 0 | 0 | 0 | 7 | 5 | 2 | 9 | 0 | 3 | 7 | 3 | 0 | 0 |
| Rice | — | — | — | — | — | — | — | — | 0 | 0 | 0 | 0 | — | — | — | — | — | — | — | — | — | — | — | — | 0 | 0 | 0 | 0 | 2 |
| S. Flatsedge | — | — | — | — | — | — | — | — | 0 | 0 | 0 | 0 | — | — | — | — | — | — | — | — | — | — | — | — | 3 | 0 | 9 | 4 | 3 |
| Soybean | 1 | 1 | 3 | 5 | 0 | 2 | 5 | 1 | 6 | 6 | 6 | 4 | 1 | 8 | 8 | 7 | 3 | 2 | 2 | 4 | 5 | 6 | 7 | 3 | 7 | 7 | 6 | 6 | 3 |
| Sugarbeets | 2 | 4 | 0 | 7 | 0 | 7 | 5 | 0 | 3 | 0 | 0 | 0 | 0 | 2 | 3 | 4 | 0 | 0 | 0 | 6 | 0 | 8 | 7 | 0 | 0 | 2 | 6 | 0 | 0 |
| Velvetleaf | 3 | 6 | 0 | 8 | 0 | 0 | 3 | 2 | 0 | 0 | 5 | 0 | 3 | 4 | 6 | 6 | 0 | 0 | 2 | 4 | 0 | 0 | 6 | 0 | 2 | 6 | 0 | 0 | 2 |
| Wheat | 0 | 8 | 0 | 7 | 0 | 0 | 4 | 3 | 0 | 4 | 3 | 0 | 0 | 0 | 4 | 3 | 0 | 0 | 0 | 2 | 7 | 4 | 8 | 0 | 3 | 7 | 0 | 0 | 0 |
| Wild oats | 0 | 6 | 0 | 9 | 0 | 0 | 6 | 3 | 0 | 5 | 0 | 0 | 0 | 3 | 5 | 8 | 0 | 0 | 0 | 3 | 4 | 5 | 9 | 2 | 3 | 7 | 0 | 3 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 420 | 421 | 422 | 423 | 424 | 425 | 426 | 427 | 428 | 429 | 430 | 431 | 432 | 433 | 434 | 435 | 436 | 437 | 438 | 439 | 440 | 441 | 443 | 444 | 445 | 446 | 447 | 448 | 449 |
| Postemergence | | | | | | | | | | | | | | | | | | | | | | | | | | | | | |
| B. signalgrass | 7 | 10 | 0 | 0 | 0 | 8 | 8 | 0 | 0 | 0 | 8 | 2 | 0 | 6 | 0 | 3 | 8 | 0 | 0 | 0 | 8 | 0 | 0 | 4 | 0 | 8 | 0 | 0 | 4 |
| Barnyardgrass | 0 | 3 | 0 | 0 | 0 | 7 | 0 | 0 | 5 | 7 | 0 | 0 | 0 | 0 | 0 | 0 | 0 | — | — | — | 0 | — | — | — | — | — | — | — | — |
| Bedstraw | 5 | 7 | — | — | 0 | — | 9 | — | — | — | 3 | — | — | 7 | — | 0 | — | — | — | — | — | — | — | — | — | — | — | — | — |
| Blackgrass | 6 | 10 | 0 | 2 | 0 | 9 | 8 | 4 | 4 | 3 | 8 | 5 | 4 | 10 | 0 | 8 | 9 | 0 | 2 | 0 | 8 | 0 | 0 | 7 | 0 | 9 | 2 | 0 | — |
| Cocklebur | 0 | 6 | 0 | 0 | 0 | 0 | 0 | 2 | 1 | 0 | 1 | 0 | 0 | 0 | 0 | 0 | 0 | 1 | 3 | 0 | 0 | 0 | 0 | 0 | 2 | 0 | 0 | 0 | 3 |
| Corn | 0 | 7 | 0 | 0 | 0 | 2 | 4 | 0 | 0 | 0 | 4 | 0 | 0 | 3 | 0 | 0 | 5 | 0 | 3 | 0 | 0 | 0 | 0 | 0 | 0 | 5 | 0 | 0 | 0 |
| Crabgrass | 8 | 8 | 0 | 1 | 0 | 9 | 9 | 2 | 3 | 3 | 9 | 2 | 6 | 9 | 4 | 8 | 9 | 3 | 9 | 0 | 9 | 0 | 0 | 9 | 7 | 9 | 0 | 0 | 2 |
| Ducksalad | 0 | 2 | 0 | 0 | 0 | 0 | 0 | 0 | 5 | 6 | 0 | 0 | 0 | 0 | 0 | 0 | 0 | — | — | — | 0 | — | — | — | — | — | — | — | — |
| Giant foxtail | 9 | 9 | 0 | 2 | 0 | 9 | 9 | 4 | 0 | 4 | 9 | 6 | 8 | 8 | 4 | 9 | 9 | 7 | 9 | 0 | 9 | 0 | 0 | 9 | 2 | 9 | 0 | 0 | 3 |
| Morningglory | 10 | 10 | 0 | 8 | 1 | 10 | 9 | 1 | 3 | 3 | 3 | 2 | 2 | 7 | 1 | 9 | 10 | 9 | 10 | 0 | — | 0 | 4 | 3 | 8 | 3 | 7 | 5 | 5 |
| Nutsedge | 0 | 2 | 0 | 0 | 0 | 0 | 3 | 0 | 0 | 0 | 6 | 0 | 0 | 0 | 0 | 3 | 3 | 0 | 0 | 0 | 0 | 0 | 0 | 0 | 0 | 0 | 0 | 0 | 0 |
| Rape | 0 | 8 | 0 | 0 | 0 | 3 | 4 | 0 | 0 | 0 | 0 | 0 | 0 | 0 | 0 | 0 | 4 | 0 | 0 | 0 | 0 | 0 | 0 | 0 | 2 | 0 | 0 | 0 | 3 |
| Redroot pigweed | 0 | 8 | 0 | 0 | 0 | 2 | 6 | 0 | 3 | 0 | 3 | 0 | 0 | 3 | 0 | 2 | 7 | 0 | 0 | 0 | 4 | 0 | 0 | 2 | 4 | 0 | 0 | 0 | 4 |
| Rice | 0 | 2 | 0 | 0 | 0 | 0 | 0 | 0 | 2 | 0 | 0 | 0 | 0 | 0 | 0 | 0 | 0 | — | — | — | 0 | — | — | — | — | — | — | — | — |
| S. Flatsedge | 0 | 0 | 0 | 0 | 0 | 6 | 0 | 0 | 9 | 9 | 0 | 0 | 0 | 0 | 0 | 0 | 0 | — | — | — | 0 | — | — | — | — | — | — | — | — |
| Soybean | 4 | 8 | 4 | 2 | 2 | 3 | 7 | 2 | 3 | 3 | 3 | 2 | 2 | 2 | 1 | 3 | 4 | 2 | 6 | 0 | 7 | 0 | 2 | 2 | 2 | 4 | 4 | 5 | 2 |
| Sugarbeets | 0 | 6 | 0 | 0 | 0 | 4 | 3 | 0 | 0 | 0 | 0 | 0 | 0 | 0 | 0 | 0 | 0 | 0 | 0 | 0 | 2 | 0 | 0 | 3 | 0 | 0 | 0 | 0 | 3 |
| Velvetleaf | 0 | 7 | 0 | 0 | 0 | 2 | 2 | 2 | 7 | 2 | 3 | 2 | 2 | 4 | 0 | 0 | 3 | 0 | 0 | 0 | 2 | 0 | 0 | 3 | 5 | 3 | 0 | 0 | 0 |
| Wheat | 5 | 7 | 0 | 0 | 0 | 6 | 2 | 0 | 0 | 0 | 0 | 0 | 0 | 3 | 0 | 0 | 7 | 0 | 0 | 0 | 4 | 0 | 0 | 0 | 0 | 3 | 0 | 0 | 3 |
| Wild oats | 2 | 8 | 0 | 0 | 0 | 3 | 2 | 0 | 0 | 0 | 0 | 0 | 3 | 2 | 0 | 3 | 3 | 3 | 0 | 0 | 5 | 0 | 0 | 2 | 0 | 3 | 0 | 0 | 4 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 451 | 452 | 453 | 454 | 455 | 456 | 457 | 458 | 459 | 460 | 461 | 462 | 463 | 465 | 466 | 467 | 468 | 469 | 470 | 471 | 472 | 473 | 474 | 476 | 477 | 478 | 479 | 480 | 482 |
| Postemergence | | | | | | | | | | | | | | | | | | | | | | | | | | | | | |
| B. signalgrass | 2 | 0 | 5 | 2 | 5 | 2 | 0 | 3 | 0 | 2 | 0 | 0 | 0 | 0 | 7 | 0 | 0 | 6 | 0 | 6 | 5 | 0 | 4 | 0 | 5 | 8 | 7 | 6 | 0 |
| Barnyardgrass | — | — | — | — | — | — | — | — | — | — | — | — | — | — | — | — | — | — | — | — | — | — | — | — | — | — | — | — | — |
| Bedstraw | — | — | — | — | — | — | — | — | 8 | 8 | — | — | — | — | — | — | — | 6 | — | — | — | — | 8 | — | — | — | — | 0 | — |
| Blackgrass | 6 | 5 | 6 | 2 | 9 | 8 | 0 | 8 | 8 | 8 | 3 | 0 | 2 | 8 | 9 | 7 | 8 | 9 | 0 | 7 | 8 | 0 | 8 | 2 | 6 | 8 | 7 | 8 | 0 |
| Cocklebur | 0 | 0 | 0 | 0 | 0 | 0 | 2 | 0 | 2 | 0 | 3 | 0 | 2 | 0 | 1 | 5 | 4 | 3 | 0 | 0 | 1 | 0 | 4 | 0 | 0 | 0 | 0 | 1 | 0 |
| Corn | 0 | 0 | 0 | 0 | 0 | 0 | 0 | 2 | 0 | 0 | 0 | 0 | 0 | 2 | 2 | 0 | 0 | 4 | 0 | 0 | 3 | 0 | 0 | 0 | 0 | 2 | 4 | 2 | 0 |
| Crabgrass | 6 | 6 | 10 | 9 | 9 | 7 | 0 | 9 | 8 | 9 | 2 | 0 | 2 | 8 | 9 | 6 | 9 | 9 | 0 | 9 | 8 | 8 | 9 | 0 | 7 | 9 | 9 | 8 | 3 |
| Ducksalad | — | — | — | — | — | — | — | — | — | — | — | — | — | — | — | — | — | — | — | — | — | — | — | — | — | — | — | — | — |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Giant foxtail | 7 | 7 | 9 | 9 | 9 | 8 | 0 | 9 | 5 | 1 | 0 | 0 | 6 | 9 | 9 | 4 | 9 | 9 | 0 | 8 | 8 | 7 | 8 | 0 | 7 | 9 | 8 | 8 | 2 |
| Morningglory | 3 | 3 | 2 | 10 | 9 | 5 | 0 | 6 | 10 | 8 | 8 | 0 | 2 | 3 | 2 | — | 5 | 10 | 1 | 5 | 7 | 2 | 2 | 2 | 10 | 8 | 10 | 8 | 8 |
| Nutsedge | 0 | 0 | 0 | 0 | 0 | 0 | 0 | 4 | 0 | 0 | 0 | — | 0 | 0 | 0 | 0 | 2 | 2 | 0 | 0 | 0 | 0 | 0 | 0 | 0 | 0 | 0 | 0 | 0 |
| Rape | 0 | 0 | 0 | 0 | 2 | 0 | 0 | 2 | 4 | 0 | 0 | 0 | 0 | 0 | 0 | 6 | 0 | 2 | 0 | 3 | 0 | 0 | 2 | 0 | 1 | 0 | 0 | 0 | 0 |
| Redroot pigweed | 3 | 0 | 3 | 6 | 8 | 5 | 0 | 0 | 3 | 2 | 0 | 0 | 0 | 3 | 7 | 6 | 7 | 6 | 0 | 5 | 4 | 0 | 6 | 4 | 2 | 6 | 3 | 2 | 3 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 1 | 2 | 2 | 3 | 4 | 2 | 2 | 4 | 7 | 4 | 4 | 2 | 1 | 1 | 5 | 2 | 3 | 5 | 1 | 3 | 2 | 1 | 4 | 2 | 2 | 3 | 3 | 4 | 1 |
| Sugarbeets | 0 | 0 | 0 | 0 | 0 | 0 | 0 | 0 | 2 | 0 | 0 | 0 | 0 | 0 | 0 | 7 | 0 | 4 | 0 | 0 | 3 | 0 | 0 | 0 | 0 | 0 | 0 | 0 | 0 |
| Velvetleaf | 0 | 2 | 2 | 3 | 3 | 3 | 0 | 0 | 0 | 0 | 0 | 0 | 0 | 4 | 1 | 5 | 5 | 2 | 0 | 4 | 2 | 0 | 2 | 2 | 0 | 0 | 1 | 0 | 0 |
| Wheat | 0 | 0 | 0 | 0 | 0 | 0 | 0 | 2 | 0 | 0 | 0 | 0 | 0 | 4 | 6 | 0 | 0 | 6 | 0 | 3 | 3 | 0 | 0 | 0 | 0 | 7 | 0 | — | 0 |
| Wild oats | 4 | 0 | 0 | 4 | 7 | 0 | 0 | 2 | 0 | 0 | 0 | 0 | 0 | 5 | 0 | 2 | 0 | 5 | 0 | 0 | 3 | 0 | — | 0 | 0 | 0 | 0 | 3 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 485 | 486 | 487 | 488 | 489 | 490 | 492 | 493 | 494 | 495 | 496 | 497 | 498 | 499 | 500 | 501 | 504 | 505 | 506 | 508 | 509 | 510 | 511 | 512 | 513 | 514 | 515 | 516 | 517 |
| Postemergence | | | | | | | | | | | | | | | | | | | | | | | | | | | | | |
| B. signalgrass | 5 | 5 | 0 | 7 | 8 | 7 | 0 | 0 | 0 | 0 | 4 | 0 | 0 | 0 | 8 | 7 | 9 | 8 | 0 | 3 | 7 | 6 | 3 | 5 | 8 | 5 | 3 | 5 | 8 |
| Barnyardgrass | — | — | — | — | — | — | — | — | — | — | — | — | — | — | — | — | — | — | — | — | — | — | — | — | — | — | — | — | — |
| Bedstraw | 6 | 8 | 6 | 9 | — | — | — | — | — | — | — | — | — | — | — | 9 | 9 | — | 9 | — | — | — | — | — | — | — | — | — | — |
| Blackgrass | 8 | 8 | 1 | 8 | 8 | 5 | 0 | 0 | 0 | 0 | 5 | 0 | 5 | 4 | 6 | 7 | 8 | 7 | 6 | 6 | 9 | 6 | 2 | 6 | 8 | 5 | 1 | 7 | 6 |
| Cocklebur | 0 | 0 | 0 | 0 | 0 | 0 | 0 | 0 | 0 | 0 | 1 | 0 | 0 | 4 | 5 | 5 | 6 | 4 | 6 | 4 | 4 | 4 | 0 | 7 | 7 | 5 | 5 | 5 | 4 |
| Corn | 0 | 3 | 0 | 0 | 4 | 0 | 0 | 0 | 0 | 0 | 0 | 0 | 0 | 0 | 6 | 6 | 6 | 6 | 0 | 3 | 1 | 0 | 0 | 0 | 3 | 5 | 0 | 0 | 4 |
| Crabgrass | 8 | 9 | 5 | 9 | 9 | 7 | 0 | 4 | — | 0 | 2 | 0 | 2 | 0 | 9 | 8 | 10 | 9 | 8 | 9 | 9 | 9 | 9 | 9 | 9 | 10 | 9 | 9 | 9 |
| Ducksalad | — | — | — | — | — | — | — | — | — | — | — | — | — | — | — | — | — | — | — | — | — | — | — | — | — | — | — | — | — |
| Giant foxtail | 8 | 9 | 8 | 9 | 9 | 8 | 0 | 0 | 0 | 0 | 0 | 0 | 3 | 2 | 9 | 8 | 9 | 9 | 8 | 8 | 8 | 9 | 9 | 8 | 8 | 9 | 9 | 9 | 9 |
| Morningglory | 10 | 2 | 10 | 8 | 10 | 3 | 8 | 0 | 0 | 7 | 8 | 0 | 4 | 6 | 3 | 4 | 6 | 7 | 5 | 7 | 5 | 6 | 5 | 7 | 9 | 7 | 6 | 7 | 2 |
| Nutsedge | 0 | 0 | 0 | 2 | 0 | 0 | 0 | 0 | 0 | 0 | 0 | 0 | 0 | 0 | 2 | 2 | 3 | 2 | 0 | 0 | — | 0 | 0 | — | 5 | 0 | 0 | — | — |
| Rape | 0 | 1 | 3 | 0 | 0 | 0 | 0 | 0 | 0 | 0 | 0 | 0 | 0 | 0 | 8 | 7 | 8 | 2 | 7 | 8 | 4 | 9 | 4 | 0 | 7 | 8 | 6 | 9 | 4 |
| Redroot pigweed | 2 | 2 | 3 | 2 | 2 | 2 | 7 | 0 | 0 | 0 | 3 | 0 | 0 | 0 | 10 | 5 | 9 | 9 | 0 | 9 | 5 | — | 7 | 9 | 7 | 8 | 5 | 8 | 7 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 5 | 4 | 5 | 5 | 7 | 6 | 0 | 2 | 1 | 0 | 3 | 2 | 1 | 3 | 4 | 5 | 7 | 5 | 4 | 5 | 5 | 8 | 4 | 7 | 8 | 7 | 7 | 7 | 8 |
| Sugarbeets | 0 | 2 | 0 | 1 | 0 | 0 | 0 | 0 | 0 | 0 | 0 | 0 | 0 | 0 | 9 | 8 | 9 | 9 | 7 | 9 | 7 | 8 | 2 | 7 | 7 | 5 | 3 | 8 | 3 |
| Velvetleaf | 4 | 6 | 2 | 1 | 5 | 1 | 0 | 0 | 0 | 0 | 0 | 0 | 2 | 0 | 5 | 3 | 7 | 4 | 4 | 2 | 7 | 7 | 2 | 1 | 7 | 5 | 8 | 4 | 6 |
| Wheat | 5 | 5 | 0 | 3 | 2 | 0 | 0 | 0 | 0 | 0 | 3 | 0 | 0 | 0 | 5 | 3 | 6 | 4 | 4 | 0 | 2 | 3 | 0 | 2 | 6 | 0 | 0 | 7 | 4 |
| Wild oats | 4 | 3 | 0 | 5 | 3 | 7 | 0 | 0 | 0 | 0 | 2 | 0 | 0 | 0 | 7 | 3 | 7 | 3 | 2 | 4 | 8 | 5 | 0 | 1 | 6 | 3 | 0 | 5 | 3 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 519 | 520 | 521 | 522 | 523 | 524 | 525 | 526 | 527 | 528 | 531 | 532 | 533 | 534 | 535 | 536 | 540 | 541 | 543 | 544 | 545 | 546 | 549 | 550 | 551 | 552 | 553 | 554 | 555 |
| Postemergence | | | | | | | | | | | | | | | | | | | | | | | | | | | | | |
| B. signalgrass | 0 | 2 | 3 | 7 | 7 | 9 | 8 | 6 | 9 | 0 | 4 | 0 | 4 | 6 | 3 | 0 | 3 | 2 | 3 | 3 | 2 | 0 | 3 | 2 | 4 | 0 | 5 | 3 | 4 |
| Barnyardgrass | — | — | — | — | — | — | — | — | — | — | — | — | — | — | — | — | — | — | — | — | — | — | — | — | — | — | — | — | — |
| Bedstraw | 0 | — | — | 10 | — | — | — | 9 | — | 8 | 3 | 0 | — | — | — | — | 9 | 5 | 2 | 3 | 7 | 9 | 8 | 0 | 9 | 10 | 7 | 9 | — |
| Blackgrass | 0 | 6 | 9 | 8 | 4 | 8 | 8 | 7 | 7 | 5 | 6 | 0 | 7 | 7 | 8 | 0 | 7 | 0 | 2 | 3 | 0 | 6 | 3 | 2 | 7 | 7 | 7 | — | 5 |
| Cocklebur | 0 | 0 | 0 | 3 | 2 | 3 | 2 | 2 | 2 | 3 | 5 | 4 | 4 | 0 | 0 | 0 | 0 | 5 | 1 | 3 | — | 0 | 4 | 2 | 0 | 4 | 2 | 3 | 3 |
| Corn | 0 | 0 | 0 | 5 | 2 | 5 | 2 | 2 | 0 | 0 | 0 | 2 | 0 | 0 | 0 | 0 | 0 | 0 | 0 | 0 | 0 | 0 | 0 | 2 | 0 | 0 | 0 | 0 | 0 |

TABLE B-continued

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Crabgrass | 6 | 9 | 10 | 9 | 10 | 9 | 9 | 10 | 10 | 10 | 10 | 9 | 9 | 8 | 6 | 3 | 8 | 3 | 7 | 9 | 9 | 10 | 9 | — | 9 | 9 | 9 | 9 | 10 |
| Ducksalad | — | — | — | — | — | — | — | — | — | — | — | — | — | — | — | — | — | — | — | — | — | — | — | — | — | — | — | — | — |
| Giant foxtail | 6 | 9 | 9 | 9 | 6 | 9 | 9 | 8 | 9 | 9 | 9 | 8 | 9 | 8 | 5 | 0 | 3 | 2 | 3 | — | 5 | 7 | 7 | 9 | 5 | 7 | 7 | 8 | 8 |
| Morningglory | 0 | 10 | 5 | 5 | 4 | 2 | 3 | 7 | 6 | 5 | — | 5 | 7 | 3 | 3 | 2 | 6 | 3 | 7 | 10 | — | 10 | 4 | 8 | 3 | 7 | 0 | 7 | 6 |
| Nutsedge | 0 | 0 | 0 | 0 | 0 | 0 | 5 | 2 | — | 6 | 3 | — | 0 | 2 | 0 | 0 | 0 | 0 | 0 | 0 | — | — | 0 | 2 | 0 | 0 | — | 0 | 0 |
| Rape | 0 | 9 | 3 | 9 | 2 | 3 | 8 | 4 | 2 | 3 | 2 | 2 | 4 | 7 | 0 | 0 | — | 3 | 0 | 3 | 3 | 7 | 7 | 3 | 5 | 7 | — | 3 | 5 |
| Redroot pigweed | 0 | 0 | 4 | 9 | 3 | 0 | 8 | 4 | 0 | 0 | 0 | 2 | 9 | 7 | 0 | 8 | 2 | 3 | 0 | 2 | 0 | 3 | 8 | 0 | 7 | 3 | 0 | — | 2 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 4 | 4 | 5 | 6 | 5 | 4 | — | 3 | 5 | 5 | 6 | 5 | 4 | 7 | 8 | 6 | 1 | 2 | 2 | 2 | 2 | 4 | 3 | 3 | 3 | 3 | — | 3 | 2 |
| Sugarbeets | 0 | 2 | 4 | 6 | 0 | 0 | 8 | 0 | 2 | 2 | 6 | 0 | 4 | 2 | 0 | 0 | 6 | 4 | 3 | 3 | 3 | 5 | 4 | 5 | 8 | 7 | 2 | — | 0 |
| Velvetleaf | 4 | 6 | 3 | 7 | 4 | 6 | 3 | 8 | 3 | 5 | 3 | 2 | 8 | 2 | 2 | 0 | 1 | 0 | 3 | 0 | — | 2 | 4 | 2 | 3 | 3 | — | 0 | 4 |
| Wheat | 0 | 0 | 2 | 5 | 2 | 5 | 5 | 0 | 0 | 0 | 0 | 0 | 2 | 5 | 2 | 0 | 0 | 0 | 0 | 0 | 0 | 0 | 2 | 0 | 3 | 3 | 3 | — | 2 |
| Wild oats | 0 | 0 | 2 | 7 | 2 | 5 | 6 | 0 | 0 | 0 | 0 | 0 | 0 | 3 | 2 | 0 | 2 | 2 | 3 | 2 | 0 | 2 | 2 | 3 | 5 | 3 | 2 | — | 2 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 556 | 557 | 558 | 559 | 560 | 561 | 562 | 563 | 564 | 565 | 566 | 567 | 568 | 569 | 570 | 571 | 572 | 573 | 574 | 575 | 576 | 577 | 578 | 579 | 580 | 581 | 582 | 584 | 585 |
| Postemergence | | | | | | | | | | | | | | | | | | | | | | | | | | | | | |
| B. signalgrass | 7 | 2 | 3 | 9 | 7 | 8 | 7 | 7 | 8 | 0 | 9 | 0 | 7 | 4 | 0 | 5 | 0 | 0 | 0 | 3 | 2 | 3 | 0 | 2 | 8 | 8 | 3 | 9 | 7 |
| Barnyardgrass | — | — | — | — | — | — | — | — | — | — | — | — | — | — | — | — | — | — | — | — | — | — | — | — | — | — | — | — | — |
| Bedstraw | 0 | — | — | 4 | — | 7 | — | 0 | 0 | 0 | — | 0 | — | — | — | — | — | — | — | — | 9 | — | — | — | 9 | 9 | — | — | — |
| Blackgrass | 6 | 0 | 2 | 7 | 7 | 6 | 3 | 4 | 4 | 0 | 6 | 0 | 9 | 3 | 0 | 0 | 0 | 0 | — | 3 | 7 | 0 | 2 | 5 | 7 | 4 | 7 | 7 | 7 |
| Cocklebur | 0 | 0 | 0 | 2 | 0 | 0 | 2 | 2 | 2 | 2 | 3 | 2 | 6 | 2 | 0 | 0 | 0 | 3 | 2 | 2 | 0 | 2 | 0 | 0 | 6 | 3 | 4 | 4 | 7 |
| Corn | 0 | 2 | 0 | 7 | 4 | 3 | 7 | 8 | 6 | 0 | 2 | 0 | 5 | 2 | 0 | 0 | 0 | 0 | 0 | 0 | 4 | 2 | 0 | 0 | 0 | 6 | 0 | 4 | 5 |
| Crabgrass | 2 | 4 | 8 | 9 | 8 | 9 | 10 | 9 | 9 | 3 | 9 | 8 | 9 | 6 | 0 | 3 | 8 | 9 | 2 | 9 | 9 | 3 | 9 | 8 | — | 9 | 3 | 9 | 9 |
| Ducksalad | — | — | — | — | — | — | — | — | — | — | — | — | — | — | — | — | — | — | — | — | — | — | — | — | — | — | — | — | — |
| Giant foxtail | 9 | 6 | 8 | 9 | 8 | 8 | 8 | 9 | 9 | 3 | 9 | 0 | 9 | 4 | 0 | 3 | 0 | 9 | 8 | — | 8 | 8 | 8 | 7 | 8 | 9 | 7 | 9 | 9 |
| Morningglory | 10 | 8 | 10 | 10 | 10 | 9 | 10 | 10 | 10 | 9 | 10 | 10 | 10 | 10 | 10 | 10 | 10 | 10 | 10 | 10 | 4 | 10 | 10 | 10 | 10 | 10 | 10 | 3 | 10 |
| Nutsedge | 0 | 0 | 0 | 2 | 5 | 4 | 5 | — | 0 | 0 | 0 | 0 | 0 | 0 | 0 | 0 | — | — | 0 | — | — | 0 | 0 | — | — | — | 0 | 3 | 0 |
| Rape | 2 | 0 | 2 | 2 | 7 | 4 | 7 | 5 | 2 | 0 | 9 | 0 | 3 | 0 | 0 | 0 | 4 | 2 | 3 | 3 | 0 | 0 | 4 | 3 | 8 | 7 | 3 | 9 | 5 |
| Redroot pigweed | 4 | 0 | 0 | 8 | 9 | 7 | 9 | 5 | 3 | 6 | 5 | 0 | 2 | 4 | 0 | 0 | 0 | 7 | 5 | 7 | 4 | 0 | 3 | 3 | 9 | 9 | 7 | 7 | 7 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 8 | 2 | 4 | 6 | 3 | 5 | 5 | 5 | 5 | 3 | 6 | 6 | 6 | 4 | 3 | 4 | 7 | 6 | 7 | 6 | 4 | 5 | 4 | 4 | 4 | 5 | 3 | 4 | 3 |
| Sugarbeets | 0 | 0 | 2 | 8 | 6 | 4 | 5 | 0 | 2 | 0 | 5 | 0 | 2 | 0 | 0 | 0 | 0 | — | 0 | 2 | 0 | — | 4 | 0 | 6 | 8 | 7 | 8 | 7 |
| Velvetleaf | 2 | 2 | 2 | 3 | 0 | 0 | 6 | 4 | 3 | 4 | 5 | 2 | 8 | 3 | 0 | 0 | 7 | 2 | 2 | 3 | 0 | 0 | 3 | 0 | 3 | 6 | 0 | 5 | 5 |
| Wheat | 3 | 0 | 0 | 3 | 6 | 7 | 5 | 0 | 2 | 0 | 4 | 0 | 5 | 0 | 0 | 0 | 0 | 0 | 2 | 2 | 0 | 0 | 0 | 0 | 3 | 4 | 0 | 6 | 4 |
| Wild oats | 2 | 0 | 0 | 5 | 2 | 2 | 4 | 0 | 2 | 0 | 4 | 0 | 6 | 0 | 0 | 0 | 0 | 0 | 0 | 0 | 0 | 0 | 0 | 0 | 7 | 5 | 3 | 7 | 2 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 586 | 587 | 588 | 589 | 590 | 591 | 592 | 593 | 594 | 595 | 596 | 598 | 599 | 600 | 601 | 602 | 603 | 604 | 605 | 606 | 607 | 608 | 609 | 610 | 611 | 612 | 613 | 615 | 616 |
| Postemergence | | | | | | | | | | | | | | | | | | | | | | | | | | | | | |
| B. signalgrass | 7 | 0 | 8 | 3 | 0 | 0 | 0 | 0 | 3 | 6 | 0 | 0 | 0 | 0 | 7 | 7 | 0 | 0 | 0 | 0 | 7 | 10 | 8 | 9 | 8 | 9 | 8 | 0 | 4 |
| Barnyardgrass | — | — | — | — | — | — | — | — | — | — | — | — | — | — | — | — | — | — | — | — | — | — | — | — | — | — | — | — | — |
| Bedstraw | — | 3 | — | — | — | — | — | — | — | — | — | — | — | 0 | 8 | — | — | — | — | 0 | — | — | — | 9 | 9 | 9 | 9 | — | — |
| Blackgrass | 8 | 6 | 8 | 3 | 0 | 0 | 0 | 0 | 5 | 9 | 0 | 0 | 0 | 0 | 8 | 9 | 0 | 0 | 0 | 1 | 7 | 9 | 8 | 10 | 9 | 10 | 9 | 0 | 5 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Cocklebur | 0 | 0 | 0 | 0 | 0 | 0 | 0 | 0 | 4 | 2 | 0 | 0 | 0 | 0 | 1 | 0 | 0 | 0 | 0 | 0 | 0 | 0 | 3 | 2 | 3 | 2 | 2 | 0 | 0 |
| Corn | 3 | 0 | 0 | 0 | 0 | 0 | 0 | 0 | 0 | 3 | 0 | 0 | 0 | 0 | 0 | 0 | 0 | 0 | 0 | 0 | 2 | 0 | 7 | 5 | 6 | 0 | 0 | 0 | 0 |
| Crabgrass | 9 | 2 | — | 3 | 2 | 0 | 2 | — | 9 | 9 | 2 | 0 | 0 | 3 | 9 | 9 | 0 | 3 | 3 | — | 9 | 7 | — | 9 | 9 | 10 | 9 | — | 7 |
| Ducksalad | — | — | — | — | — | — | — | — | — | — | — | — | — | — | — | — | — | — | — | — | — | — | — | — | — | — | — | — | — |
| Giant foxtail | 9 | 2 | 8 | 3 | 0 | 0 | 0 | 0 | 9 | 9 | 3 | 0 | 0 | 3 | 9 | 9 | 0 | 4 | 2 | 3 | 9 | 9 | 9 | 9 | 9 | 9 | 9 | 6 | 6 |
| Morningglory | — | 7 | 10 | 6 | 4 | 3 | 2 | 2 | 7 | 6 | 2 | 0 | 6 | 0 | 1 | 3 | 3 | 2 | 10 | — | 10 | 10 | 10 | 9 | 8 | 10 | 8 | 1 | 10 |
| Nutsedge | 0 | 0 | 0 | — | 0 | 0 | 0 | 0 | 3 | 5 | 0 | 0 | 0 | 0 | 0 | 0 | 0 | 0 | 0 | 0 | 7 | — | 6 | 6 | 3 | 2 | 4 | — | 0 |
| Rape | 0 | 0 | 0 | 2 | 0 | 0 | 0 | 0 | 0 | 2 | 0 | 0 | 0 | 0 | 0 | 0 | 0 | 0 | 0 | 4 | 0 | 7 | 3 | 5 | 3 | 7 | 7 | 0 | 0 |
| Redroot pigweed | 2 | 0 | 0 | 2 | 0 | 0 | 0 | 0 | 4 | 7 | 0 | 0 | 0 | 0 | 4 | 6 | 0 | 0 | 0 | 2 | 5 | 8 | 9 | 7 | 8 | 7 | 8 | 0 | 1 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 3 | 6 | 7 | 3 | 3 | 2 | 1 | 1 | 4 | 4 | 3 | 0 | 2 | 4 | 6 | 7 | 2 | 1 | 5 | — | — | — | 7 | 9 | 8 | 8 | 8 | 3 | 4 |
| Sugarbeets | 0 | 0 | 0 | 0 | 0 | 0 | 0 | 0 | 5 | 3 | 0 | 0 | 0 | 0 | 0 | 0 | 0 | 0 | 0 | 0 | 0 | 5 | 1 | 0 | 2 | 1 | 0 | 0 | 2 |
| Velvetleaf | 1 | 0 | 7 | 5 | 2 | 0 | 0 | 0 | 5 | 7 | 0 | 0 | 0 | 0 | 4 | 0 | 2 | 0 | 0 | 3 | 5 | 6 | 8 | 7 | 5 | 6 | 8 | 0 | 1 |
| Wheat | 0 | 0 | 3 | 0 | 0 | 0 | 0 | 0 | 0 | 3 | 0 | 0 | 0 | 0 | 3 | 0 | 0 | 0 | 2 | 0 | 4 | 0 | 6 | 5 | 8 | 5 | 6 | 0 | 0 |
| Wild oats | 0 | 0 | 0 | — | 0 | 0 | 0 | 0 | 0 | 4 | 0 | 0 | 0 | 0 | 0 | 3 | 0 | 0 | 2 | 0 | 4 | 6 | 4 | 9 | 7 | 9 | 9 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 617 | 618 | 619 | 620 | 621 | 622 | 623 | 624 | 625 | 627 | 628 | 629 | 630 | 631 | 632 | 633 | 634 | 635 | 636 | 638 | 639 | 640 | 641 | 642 | 643 | 645 | 646 | 647 | 648 |
| Postemergence | | | | | | | | | | | | | | | | | | | | | | | | | | | | | |
| B. signalgrass | 0 | 0 | 2 | 0 | 0 | 0 | 0 | 8 | 5 | 8 | 8 | 7 | 3 | 8 | 6 | 5 | 5 | 8 | 3 | 6 | 2 | 4 | 4 | 0 | 2 | 0 | 0 | 8 | 0 |
| Barnyardgrass | — | — | — | — | — | — | — | — | — | — | — | — | — | — | — | — | — | — | — | — | — | — | — | — | — | — | — | — | — |
| Bedstraw | — | — | — | — | — | — | — | — | — | — | — | — | — | — | — | — | — | — | — | — | — | — | — | — | — | — | — | — | — |
| Blackgrass | 0 | 0 | 0 | 0 | 0 | 0 | 6 | 9 | 7 | 9 | 9 | 8 | 9 | 9 | 8 | 8 | 8 | — | 5 | 7 | 6 | 5 | 6 | 6 | 4 | 0 | 0 | 8 | 0 |
| Cocklebur | 2 | 0 | 0 | 0 | 0 | 2 | 0 | 6 | 0 | 3 | 7 | 2 | 0 | 2 | 0 | 0 | 2 | 3 | 3 | 4 | 2 | 5 | 0 | 0 | 0 | 7 | 0 | 4 | 2 |
| Corn | 0 | 0 | 0 | 0 | 0 | 0 | 0 | 5 | 3 | 8 | 7 | 6 | 5 | 8 | 5 | 0 | 0 | 2 | 2 | 3 | 0 | 0 | 0 | 0 | 0 | 0 | 0 | 6 | 0 |
| Crabgrass | 0 | 0 | 2 | 3 | — | 5 | 0 | — | 8 | 9 | 9 | 9 | — | 9 | — | 9 | 9 | 9 | 9 | 9 | 8 | 6 | 6 | 5 | 6 | 3 | 1 | 9 | 7 |
| Ducksalad | — | — | — | — | — | — | — | — | — | — | — | — | — | — | — | — | — | — | — | — | — | — | — | — | — | — | — | — | — |
| Giant foxtail | 0 | 0 | 3 | — | 7 | 7 | 0 | 9 | 9 | 9 | 9 | 9 | 9 | 9 | 9 | 8 | 9 | 9 | 9 | 8 | 7 | 4 | 6 | 7 | 0 | 2 | 0 | 9 | 3 |
| Morningglory | 3 | 0 | 1 | — | 8 | 2 | 10 | 2 | 2 | 6 | 2 | 3 | 4 | 10 | 10 | 5 | 2 | 7 | 6 | 7 | 7 | 6 | 9 | 3 | 6 | 3 | 4 | 6 | 10 |
| Nutsedge | 0 | — | 0 | 0 | 0 | 0 | — | 3 | — | — | — | 0 | 0 | — | — | 0 | 0 | — | 0 | 7 | — | — | — | 0 | 0 | — | 0 | 6 | 0 |
| Rape | 0 | 0 | 3 | 0 | 0 | 0 | 0 | 3 | 0 | 5 | 6 | 3 | 4 | 2 | 0 | 0 | 0 | 9 | 7 | 0 | 3 | 0 | 0 | 0 | 0 | 0 | 0 | 7 | 2 |
| Redroot pigweed | 0 | 0 | 2 | 0 | 0 | 0 | 2 | 2 | 0 | 8 | 7 | 8 | 5 | 6 | 1 | 2 | 3 | 7 | 8 | 6 | 6 | 4 | 4 | 2 | 3 | 4 | 7 | 8 | 10 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 7 | — | — | 2 | 7 | — | 3 | 7 | 5 | 7 | 8 | 9 | 1 | — | — | — | — | 4 | 4 | 5 | 3 | 4 | 1 | — | — | — | — | — | 3 |
| Sugarbeets | 0 | 0 | 0 | 0 | 0 | 2 | 0 | 2 | 0 | 4 | 3 | 0 | 0 | 1 | 0 | 2 | 0 | 7 | 5 | 0 | 0 | 1 | 0 | 0 | 0 | 0 | 3 | 7 | 3 |
| Velvetleaf | 2 | 0 | 2 | 0 | 0 | 0 | 0 | 2 | 0 | 8 | 8 | 7 | 6 | 7 | 0 | 0 | 4 | 6 | 3 | 4 | 3 | 3 | 3 | 3 | 3 | 0 | 0 | 6 | 0 |
| Wheat | 0 | 0 | 0 | 0 | 0 | 0 | 1 | 4 | 0 | 8 | 7 | 0 | 3 | 7 | 5 | 0 | 0 | 2 | 2 | 3 | 4 | 0 | 0 | 0 | 0 | 0 | 0 | 6 | 0 |
| Wild oats | 0 | 0 | 0 | 0 | 0 | 0 | 1 | — | 1 | 7 | 5 | 2 | 3 | 4 | 3 | 0 | 2 | 5 | 0 | 3 | 1 | 0 | 1 | 1 | 1 | 0 | 0 | 3 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 649 | 650 | 652 | 653 | 654 | 655 | 657 | 658 | 659 | 660 | 661 | 662 | 663 | 664 | 665 | 666 | 667 | 668 | 670 | 671 | 672 | 674 | 675 | 676 | 677 | 678 | 679 | 680 | 681 |
| Postemergence | | | | | | | | | | | | | | | | | | | | | | | | | | | | | |
| B. signalgrass | 0 | 2 | 2 | 2 | 0 | 2 | 6 | 0 | 8 | 5 | 7 | 2 | 0 | 7 | 5 | 7 | 7 | 5 | 8 | 8 | 4 | 8 | 8 | 8 | 0 | 2 | 0 | 0 | 0 |
| Barnyardgrass | — | — | — | — | — | — | — | — | — | — | — | — | — | — | — | — | — | — | — | — | — | — | — | — | — | — | — | — | — |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Bedstraw | — | — | — | — | 0 | — | — | — | — | 0 | — | — | — | — | — | — | — | — | 8 | 0 | 6 | — | — | — | — | 0 | 0 | 0 | — |
| Blackgrass | 0 | 3 | 0 | 0 | 0 | 3 | 8 | 7 | 7 | 6 | — | 3 | 2 | 9 | 8 | 8 | 8 | 9 | 5 | 8 | 6 | 9 | 9 | 8 | 1 | 3 | 0 | 1 | 0 |
| Cocklebur | 2 | 0 | 0 | 0 | 0 | 0 | 5 | 5 | 2 | 2 | 0 | 0 | 2 | 6 | 2 | 7 | 5 | 2 | 3 | 1 | 7 | 4 | 3 | 2 | 1 | 2 | 0 | 0 | 0 |
| Corn | 0 | 4 | 0 | 0 | 0 | 0 | 1 | 0 | 6 | 2 | 0 | 0 | 0 | 0 | 3 | 0 | 5 | 3 | 6 | 5 | 0 | 7 | 6 | 0 | 0 | 0 | 0 | 0 | 0 |
| Crabgrass | — | 9 | 6 | 2 | 7 | 9 | 9 | — | 8 | 7 | 8 | 2 | 4 | 9 | 9 | 9 | 10 | 10 | 8 | 9 | 9 | 9 | 9 | 9 | 4 | 6 | — | 3 | 0 |
| Ducksalad | — | — | — | — | — | — | — | — | — | — | — | — | — | — | — | — | — | — | — | — | — | — | — | — | — | — | — | — | — |
| Giant foxtail | 7 | 8 | 8 | 7 | 7 | 9 | 8 | 6 | 8 | 8 | 8 | 5 | 4 | 9 | 9 | 9 | 9 | 9 | 9 | 9 | 9 | 9 | 9 | 9 | 4 | 6 | 4 | 5 | 0 |
| Morningglory | 8 | 10 | 7 | 1 | 10 | — | 9 | 10 | 10 | 7 | 0 | 7 | 4 | 10 | 8 | 7 | 6 | 4 | 4 | 6 | — | — | 4 | 2 | 7 | 8 | 2 | 1 | 7 |
| Nutsedge | 0 | 4 | 0 | 0 | — | — | — | 2 | 0 | 0 | — | 5 | 0 | 0 | 0 | 0 | 0 | 0 | 5 | 0 | 5 | — | 8 | 0 | 0 | 0 | 0 | 0 | — |
| Rape | 0 | 3 | 0 | 0 | 0 | 3 | 3 | 3 | 1 | 0 | 0 | 0 | 0 | 3 | 4 | 4 | 6 | 4 | 4 | 2 | 3 | 5 | 3 | 0 | 0 | 0 | 0 | 0 | 0 |
| Redroot pigweed | 0 | 6 | 6 | 0 | 0 | 7 | 7 | 7 | 7 | 6 | 4 | 0 | 0 | 6 | 7 | 6 | 7 | 7 | 9 | 5 | 8 | 7 | 8 | 5 | 3 | 2 | 0 | 0 | 6 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 3 | 5 | 3 | 0 | 0 | 4 | — | 4 | 7 | 6 | 3 | 2 | — | — | — | — | — | 6 | 5 | 4 | 5 | 7 | 5 | 3 | 2 | 2 | 1 | 3 | 1 |
| Sugarbeets | 0 | 0 | 2 | 0 | 0 | 2 | 3 | 2 | 4 | 0 | 0 | 0 | 4 | 0 | 4 | 4 | 3 | 6 | 2 | 3 | 3 | 5 | 4 | 2 | 1 | 0 | 0 | 0 | 0 |
| Velvetleaf | 0 | 2 | 0 | 0 | 0 | 0 | 4 | 6 | 6 | 3 | 0 | 0 | 2 | 6 | 7 | 6 | 8 | 7 | 4 | 3 | 7 | 8 | 8 | 3 | 3 | 3 | 0 | 0 | 0 |
| Wheat | 0 | 0 | 2 | 0 | 0 | 0 | 5 | 0 | 5 | 0 | 3 | 0 | 0 | 2 | 4 | 3 | 5 | 0 | 4 | 6 | 0 | 7 | 7 | 5 | 0 | 0 | 0 | 0 | 0 |
| Wild oats | 0 | 0 | 0 | 0 | 0 | 1 | 2 | 2 | 3 | 0 | 5 | 1 | 0 | 7 | 5 | 3 | 6 | 0 | 3 | 0 | 0 | 3 | 7 | 3 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 708 | 709 | 710 | 711 | 712 | 713 | 714 | 736 | 739 | 740 | 741 | 743 | 744 | 745 | 746 | 747 | 748 | 749 | 750 | 751 | 752 | 753 | 754 | 756 | 757 | 758 | 759 | 760 | 761 |
| Postemergence | | | | | | | | | | | | | | | | | | | | | | | | | | | | | |
| B. signalgrass | 2 | 0 | 7 | 8 | 8 | 7 | 6 | 0 | 7 | 2 | — | 7 | 6 | 6 | 8 | 6 | 7 | 3 | 6 | 7 | 6 | 7 | 8 | 2 | 1 | 7 | 7 | 5 | 3 |
| Barnyardgrass | — | — | — | — | — | — | — | — | — | — | — | — | — | — | — | — | — | — | — | — | — | — | — | — | — | — | — | — | — |
| Bedstraw | — | — | 8 | — | 8 | — | — | — | 6 | 0 | 9 | 8 | — | 9 | 9 | — | 9 | — | 10 | 7 | 2 | 6 | — | — | — | 8 | — | — | 3 |
| Blackgrass | 2 | 0 | 6 | 7 | 6 | 7 | 7 | 3 | 6 | 7 | 0 | 5 | 5 | 9 | 8 | 8 | 8 | 6 | 8 | 7 | 6 | 4 | 5 | 3 | 4 | 6 | 8 | 3 | 0 |
| Cocklebur | 0 | 3 | 0 | 7 | 3 | 6 | 3 | 3 | 3 | 3 | 0 | 3 | 0 | 4 | 4 | 4 | — | 4 | 3 | 2 | 3 | 4 | 0 | 0 | 2 | 4 | 2 | 1 | 0 |
| Corn | 0 | 0 | 2 | 4 | 0 | 5 | 0 | 4 | 0 | 0 | 0 | 0 | 5 | 0 | 5 | 5 | 0 | 1 | 5 | 2 | 0 | 1 | 5 | 0 | 0 | 3 | 0 | 1 | 0 |
| Crabgrass | 4 | 8 | 9 | 10 | 9 | 9 | 9 | 4 | 9 | 9 | — | 9 | 9 | 9 | 10 | 9 | 9 | 9 | — | 9 | 10 | 9 | 9 | 3 | 6 | 9 | 8 | — | 0 |
| Ducksalad | — | — | — | — | — | — | — | — | — | — | — | — | — | — | — | — | — | — | — | — | — | — | — | — | — | — | — | — | — |
| Giant foxtail | 5 | 9 | 9 | 9 | 9 | 9 | 8 | 7 | 9 | 9 | 4 | 8 | 8 | 9 | 9 | 9 | 9 | 9 | 8 | 9 | 9 | 9 | 8 | 0 | 7 | 9 | 8 | 7 | 3 |
| Morningglory | 5 | 6 | 8 | 4 | 10 | 10 | 2 | 5 | 8 | 7 | 3 | 10 | 4 | 8 | 10 | 10 | 7 | 5 | 10 | 9 | 9 | 10 | 10 | 10 | 9 | 8 | 4 | 3 | — |
| Nutsedge | 0 | 6 | 3 | 5 | 0 | 3 | 5 | 2 | 3 | 0 | 0 | 9 | 6 | 0 | 4 | 0 | 0 | 0 | — | 10 | 0 | 3 | 0 | 0 | 0 | 0 | 0 | 0 | 0 |
| Rape | 0 | 0 | 5 | 4 | 4 | 6 | 9 | 0 | 2 | 0 | 0 | 3 | 8 | 7 | 7 | 9 | 7 | 6 | 7 | 5 | 4 | 0 | 0 | 3 | 0 | 2 | 0 | 5 | 0 |
| Redroot pigweed | 5 | 8 | 9 | 10 | 8 | 9 | 9 | 0 | 5 | 8 | 7 | 8 | 8 | 6 | 9 | 8 | 8 | 7 | 7 | 9 | 9 | 7 | — | 3 | 7 | 8 | 4 | 3 | 6 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 4 | 4 | 5 | 6 | 5 | 5 | 3 | 3 | 5 | 6 | 3 | 4 | 5 | 5 | 6 | 8 | 5 | 5 | 7 | 7 | 6 | 4 | 2 | 2 | 4 | 5 | 3 | 5 | 3 |
| Sugarbeets | 0 | 0 | 6 | 3 | 6 | 5 | 7 | 0 | 4 | 2 | 4 | 4 | 5 | 4 | 4 | 3 | 7 | 4 | 6 | 3 | 3 | 5 | 3 | 0 | 3 | 8 | 0 | 0 | 6 |
| Velvetleaf | 5 | 6 | 6 | 6 | 6 | 7 | 3 | 3 | 3 | 2 | 1 | 4 | 2 | 7 | 7 | 7 | 4 | 3 | 6 | 3 | 2 | 2 | 0 | 0 | 4 | 7 | 6 | 3 | 0 |
| Wheat | 0 | 0 | 6 | 5 | 5 | 2 | 6 | 2 | 6 | 4 | 3 | 6 | 7 | 3 | 6 | 4 | — | 0 | 2 | 3 | 5 | 5 | 5 | 0 | 0 | 6 | 0 | 0 | 0 |
| Wild oats | 0 | 0 | 6 | 4 | 3 | 5 | 9 | 3 | 0 | 0 | — | 3 | 2 | 4 | 7 | 2 | 0 | 2 | 0 | 5 | 0 | 2 | 0 | 0 | 0 | 2 | 3 | 4 | 0 |

TABLE B-continued

| Rate 500 g/ha | COMPOUND 762 | 763 | 764 | 765 | 766 | 767 | 772 | 773 | 774 | 775 | 777 | 778 | 780 | 790 | 791 | 792 |
|---|---|---|---|---|---|---|---|---|---|---|---|---|---|---|---|---|
| Postemergence | | | | | | | | | | | | | | | | |
| B. signalgrass | 3 | 5 | 3 | 8 | — | 7 | 0 | 0 | 0 | 3 | 3 | 6 | 5 | 7 | 0 | 2 |
| Barnyardgrass | — | — | — | — | — | — | — | — | — | — | — | — | — | — | — | — |
| Bedstraw | 0 | 4 | 5 | — | 3 | 9 | 0 | 0 | 0 | 7 | 3 | 4 | — | 5 | 3 | — |
| Blackgrass | 0 | 5 | 8 | 7 | — | 9 | 0 | 0 | 0 | 7 | 4 | 4 | 4 | 5 | 6 | 7 |
| Cocklebur | 0 | 3 | 5 | 3 | 6 | 2 | 0 | 0 | 0 | 0 | 0 | 0 | 0 | 0 | 5 | 3 |
| Corn | 2 | 2 | 4 | 3 | 4 | 2 | 0 | 0 | 0 | 0 | 0 | 0 | 6 | 4 | 1 | 3 |
| Crabgrass | 8 | 9 | 9 | 9 | 9 | 9 | 0 | 0 | 0 | 9 | 9 | 9 | 7 | 9 | 9 | 9 |
| Ducksalad | — | — | — | — | — | — | — | — | — | — | — | — | — | — | — | — |
| Giant foxtail | — | 9 | 8 | 9 | 9 | 9 | 0 | 0 | 0 | 9 | 9 | 9 | 9 | 8 | 9 | 9 |
| Morningglory | 2 | 7 | 5 | 8 | 2 | 7 | 2 | 0 | 0 | 6 | 8 | 6 | 8 | 10 | 9 | 10 |
| Nutsedge | 3 | 6 | 3 | 3 | 5 | 7 | 0 | 0 | 0 | — | 3 | — | 4 | 7 | 0 | 0 |
| Rape | 0 | 3 | 7 | 1 | 0 | — | 0 | 0 | 0 | 0 | 0 | 3 | 0 | 3 | 6 | 7 |
| Redroot pigweed | 6 | 8 | 7 | 8 | 8 | 9 | 0 | 0 | 0 | 3 | 4 | 4 | 0 | 5 | 8 | — |
| Rice | — | — | — | — | — | — | — | — | — | — | — | — | — | — | — | — |
| S. Flatsedge | — | — | — | — | — | — | — | — | — | — | — | — | — | — | — | — |
| Soybean | 4 | 5 | 4 | 5 | 4 | 7 | 0 | 0 | 0 | 6 | 6 | 4 | 4 | 4 | 5 | 7 |
| Sugarbeets | 6 | 4 | 7 | 4 | 2 | 7 | 0 | 0 | 0 | 0 | 5 | 2 | 0 | 7 | 5 | 2 |
| Velvetleaf | 3 | 2 | 4 | 7 | 5 | 3 | 0 | 0 | 0 | 2 | 5 | 3 | 4 | 7 | 6 | 7 |
| Wheat | 0 | 3 | — | 5 | 3 | 2 | 0 | 0 | 0 | 0 | 3 | 2 | 2 | 5 | 0 | 3 |
| Wild oats | 2 | 1 | 3 | 2 | 2 | 3 | 0 | 0 | 0 | 0 | 3 | 2 | 2 | 3 | 0 | 6 |

| Rate 500 g/ha | COMPOUND 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|
| Preemergence | | | | | | | | | | | | | | | | | | | | | |
| B. signalgrass | 6 | 0 | 0 | 9 | 3 | 0 | 0 | 5 | 0 | 8 | 0 | 0 | 4 | 2 | 0 | 0 | 7 | 8 | 2 | 0 | 0 |
| Bedstraw | 0 | 0 | 0 | 4 | 0 | 0 | 0 | 0 | 0 | 0 | 0 | 0 | 0 | 4 | 7 | 0 | 2 | 3 | 0 | 6 | — |
| Blackgrass | 2 | 0 | 0 | 8 | 5 | 2 | 0 | 0 | 0 | 9 | 0 | 2 | 6 | 2 | 0 | 0 | 9 | 5 | 3 | 5 | 0 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 5 | 7 | 0 | 0 | 0 | 2 | 0 | 0 | 0 | 4 | 0 | 0 | 0 | 4 | 0 | 0 | 0 | 0 | 0 | 0 | 0 |
| Crabgrass | 8 | 0 | 0 | 10 | 6 | 9 | 8 | 6 | 3 | 7 | 8 | 0 | 5 | 9 | 10 | 2 | 10 | 10 | 10 | 7 | 7 |
| Giant foxtail | 9 | 7 | 8 | 10 | 9 | 9 | 8 | 10 | 3 | 9 | 3 | 2 | 8 | 9 | 10 | 8 | 10 | 9 | 5 | 9 | 9 |
| Morningglory | 0 | 0 | 0 | 0 | 0 | 0 | 0 | 0 | 0 | 0 | 0 | 0 | 0 | 0 | 0 | 0 | 0 | 2 | 0 | 0 | 2 |
| Nutsedge | — | — | — | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 2 | 3 | 0 | 0 |
| Redroot pigweed | 2 | 0 | 0 | — | 7 | 7 | 0 | 5 | 0 | 0 | 0 | 0 | 0 | 6 | 8 | 0 | 10 | 9 | — | 9 | 8 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 0 | 0 | 3 | 0 | 0 | 0 | 0 | 0 | 0 | 0 | 0 | 0 | 0 | 6 | 0 | 6 | 4 | 2 | 7 | 8 |
| Velvetleaf | 0 | 0 | 0 | 0 | 0 | 2 | 0 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 0 | 0 | 0 | 7 | 6 | 3 | 0 | 2 | 0 | 0 | 0 | 0 | 2 | 0 | 0 | 0 | 3 | 5 | 0 | 0 | 0 |

| Rate 500 g/ha | COMPOUND 24 | 25 | 34 | 35 | 36 | 37 | 38 | 39 | 40 | 41 | 42 | 43 | 44 | 45 | 46 | 47 | 48 | 49 | 51 | 52 | 53 | 54 | 55 | 56 |
|---|---|---|---|---|---|---|---|---|---|---|---|---|---|---|---|---|---|---|---|---|---|---|---|---|
| Preemergence | | | | | | | | | | | | | | | | | | | | | | | | |
| B. signalgrass | 6 | 7 | 3 | 7 | 8 | 0 | 8 | 0 | 7 | 7 | 0 | 0 | 0 | 9 | 3 | 0 | 0 | 0 | 0 | 6 | 3 | 2 | 0 | 0 |
| Bedstraw | 0 | 3 | 0 | 0 | 0 | 0 | 0 | 0 | 0 | 0 | 0 | 2 | 0 | 0 | 0 | 0 | 0 | 0 | 0 | — | — | 0 | 0 | 0 |
| Blackgrass | 4 | 8 | 6 | 3 | 7 | 0 | 10 | 0 | 6 | 4 | 0 | 1 | 1 | 0 | 7 | 0 | 2 | 0 | 0 | 4 | 4 | 2 | 0 | 0 |
| Cocklebur | — | 0 | 0 | 0 | — | — | 0 | 0 | 0 | 0 | 0 | 0 | 0 | 0 | 0 | 0 | 0 | 0 | 0 | — | 0 | 0 | 0 | 0 |
| Corn | 0 | 0 | 0 | 0 | 0 | 0 | 0 | 0 | 0 | 0 | 0 | 0 | 0 | 1 | 0 | 0 | 0 | 0 | 0 | 0 | 0 | 0 | 0 | 0 |
| Crabgrass | 10 | 10 | 10 | 10 | 10 | 5 | 10 | 6 | 10 | 10 | 0 | 0 | 2 | 9 | 10 | 5 | 7 | 9 | 2 | 10 | 10 | 8 | 0 | 0 |
| Giant foxtail | 9 | 10 | 10 | 10 | 10 | 3 | 10 | 10 | 10 | 10 | 0 | 0 | 1 | 10 | 10 | 3 | 10 | 10 | 8 | 10 | 10 | 7 | 0 | 0 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | 0 | 0 | 0 | 0 | 0 | 0 | 0 | — | 0 | 0 | 0 | 0 | 0 | 0 | 0 | 0 |
| Rape | 1 | 0 | 3 | 0 | 3 | 0 | 0 | 0 | 0 | 0 | 0 | 0 | 0 | 0 | 0 | 0 | 0 | 0 | 0 | 0 | 0 | 0 | 0 | 0 |
| Redroot pigweed | 9 | 8 | 6 | 0 | 7 | 0 | 10 | 6 | 6 | 7 | 0 | 4 | 0 | 8 | 9 | 0 | 0 | 0 | 0 | 6 | 3 | 0 | 0 | 0 |
| Soybean | 2 | 0 | 0 | 0 | 0 | 0 | 2 | 0 | 0 | 0 | 0 | 0 | 0 | 3 | 0 | 0 | 0 | 0 | 0 | 0 | 0 | 0 | 0 | 0 |
| Sugarbeets | 9 | 2 | 4 | 0 | 5 | 0 | 6 | 0 | 6 | 0 | 0 | 0 | 0 | 8 | 6 | 0 | 0 | 0 | 0 | 0 | 3 | 0 | 0 | 0 |
| Velvetleaf | 0 | 0 | 2 | 0 | 0 | 0 | 0 | 0 | 0 | 0 | 0 | 0 | 0 | 3 | 2 | 0 | 0 | 0 | 0 | 0 | 0 | 0 | 0 | 0 |
| Wheat | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 2 | 7 | 7 | 6 | 7 | 0 | 8 | 0 | 5 | 4 | 0 | 0 | 0 | 0 | 0 | 0 | 2 | 0 | 0 | 1 | 0 | 0 | 0 | 0 |

TABLE B-continued

| Rate 500 g/ha | COMPOUND 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 85 | 86 | 87 | 88 | 89 | 90 | 91 | 92 | 93 | 94 | 95 | 96 | 97 | 99 | 101 | 201 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | | | | | | | | | | | | | | | |
| B. signalgrass | 0 | 0 | 0 | 0 | 5 | 0 | 0 | 0 | 0 | 0 | 2 | 8 | 0 | 0 | 0 | 0 | 0 | 0 | 8 | 8 | 0 | 9 | 5 | 4 | 8 | 0 | 0 | 0 | 7 | 5 | 5 | 0 | 3 | 10 | — | 8 | 5 | 7 | 2 | 4 | 3 | 0 | 0 |
| Bedstraw | 0 | 0 | 0 | 5 | 2 | 4 | 3 | — | 3 | 0 | 0 | 4 | 0 | 0 | 0 | 0 | 0 | 0 | 0 | 0 | 0 | 0 | 0 | 0 | 0 | 0 | 0 | 0 | 0 | 3 | 2 | 0 | 0 | 8 | 1 | 3 | 0 | 0 | 2 | — | 0 | 0 | 0 |
| Blackgrass | 0 | 0 | 0 | 0 | 6 | 4 | 0 | 0 | 0 | 0 | 2 | 4 | 0 | 0 | 0 | 0 | 0 | 0 | 9 | 8 | 0 | 6 | 6 | 6 | 6 | 0 | 0 | 0 | 8 | 7 | 6 | 0 | 6 | 10 | 10 | 10 | 9 | 6 | 8 | 3 | 4 | 0 | 4 |
| Cocklebur | 0 | 0 | 0 | — | 0 | 5 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 3 | — | — | — | 0 | 0 | 0 | 0 | — | 0 |
| Corn | 0 | 0 | 0 | 0 | 0 | 0 | 0 | 0 | 0 | 0 | 0 | 0 | 0 | 0 | 0 | 0 | 0 | 0 | 0 | 4 | 0 | 0 | 0 | 0 | 4 | 0 | 0 | 0 | 0 | 2 | 0 | 0 | 0 | 9 | 9 | 9 | 6 | 0 | 0 | 0 | 0 | 0 | 0 |
| Crabgrass | 0 | 0 | 5 | 1 | 8 | 9 | 2 | 3 | 9 | 8 | 7 | 10 | 4 | 0 | 0 | 4 | 9 | 8 | 10 | 8 | 3 | 10 | 10 | 10 | 8 | 0 | 0 | 0 | 10 | 10 | 10 | 2 | 8 | 10 | 10 | 10 | 10 | 8 | 9 | 4 | 10 | 0 | 4 |
| Giant foxtail | 0 | 0 | 3 | 5 | 10 | 10 | 3 | 4 | 9 | 9 | 8 | 10 | 4 | 0 | 0 | 2 | 10 | 10 | 10 | 9 | 5 | 9 | 9 | 9 | 8 | 0 | 0 | 0 | 10 | 10 | 10 | 2 | 10 | 10 | 10 | 10 | 10 | 8 | 8 | 8 | 10 | 0 | 10 |
| Morningglory | 0 | 0 | 0 | 0 | 0 | 3 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 6 | 3 | 6 | 0 | 0 | 0 | 0 | 0 | 0 | 0 |
| Nutsedge | 0 | 0 | 0 | 0 | 0 | 0 | 6 | — | 3 | 6 | 0 | 10 | 0 | 0 | 0 | 0 | 0 | 0 | 0 | 0 | 6 | 0 | 0 | 0 | 0 | 0 | 0 | 0 | 0 | 0 | 0 | 0 | 0 | — | 0 | — | 0 | 0 | 0 | 0 | 6 | 0 | 0 |
| Rape | 0 | 0 | 0 | 0 | 0 | 0 | — | 0 | 3 | 0 | 0 | 6 | 0 | 0 | 0 | 0 | 0 | 5 | 10 | 0 | 0 | 5 | 0 | 5 | 0 | 0 | 0 | 0 | 4 | 5 | 0 | 0 | 0 | 10 | 10 | 10 | 5 | 3 | 3 | 6 | 3 | 0 | 0 |
| Redroot pigweed | 0 | 0 | 0 | 0 | 3 | 0 | 0 | 0 | 3 | 0 | 10 | 10 | 0 | 0 | 0 | 0 | 0 | 3 | 10 | 8 | 0 | 6 | 10 | 7 | 0 | 0 | 0 | 0 | 8 | 10 | 10 | 0 | 6 | 10 | 10 | 10 | 4 | 9 | 8 | 10 | 10 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 4 | 2 | 0 | 0 | 7 | 9 | 9 | 0 | 0 | 0 | 2 | 0 | 0 | 0 |
| Sugarbeets | 0 | 0 | 0 | 5 | 6 | 0 | 0 | 0 | 0 | 0 | 3 | 0 | 0 | 0 | 0 | 0 | 0 | 4 | 4 | 0 | 0 | 5 | 2 | 5 | 0 | 0 | 0 | 0 | 3 | 9 | 8 | 0 | 0 | 10 | 9 | 9 | 2 | 3 | 2 | 9 | 4 | 0 | 0 |
| Velvetleaf | 0 | 0 | 0 | 0 | 0 | 0 | 3 | 0 | 0 | 0 | 0 | 0 | 0 | 0 | 0 | 0 | 0 | 0 | 0 | 0 | 3 | 7 | 3 | 3 | 3 | 0 | 0 | 0 | 5 | 0 | 2 | 0 | 0 | 8 | 8 | 10 | 3 | 0 | 0 | 0 | 3 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 3 | 2 | 0 | 3 | 2 | 0 | 2 | 0 | 0 | 0 | 0 | 0 | 0 | 0 | 0 | 6 | 7 | 8 | 0 | 0 | 0 | 2 | 2 | 0 | 0 |
| Wild oats | 0 | 0 | 0 | 0 | 3 | 0 | 0 | 0 | 0 | 2 | 2 | 2 | 0 | 0 | 0 | 0 | 0 | 0 | 8 | 4 | 0 | 6 | 4 | 5 | 8 | 0 | 0 | 0 | 5 | 3 | 5 | 0 | 3 | 10 | 10 | 10 | 6 | 5 | 7 | 5 | 5 | 0 | 0 |

| Rate 500 g/ha | COMPOUND 103 | 104 | 105 | 106 | 107 | 108 | 109 | 110 | 111 | 112 | 113 | 114 | 115 | 116 | 117 | 118 | 119 | 120 | 121 | 122 | 123 | 124 | 125 | 126 | 127 | 128 | 129 | 130 | 131 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 7 | 6 | 10 | 2 | 10 | 9 | 10 | 7 | 4 | 5 | 10 | 10 | 10 | 10 | 10 | 10 | 9 | 8 | 9 | 5 | 2 | 0 | 0 | 0 | 0 | 0 | 7 | 9 | 9 |
| Bedstraw | 0 | 0 | 5 | 4 | 10 | 8 | 10 | 7 | 3 | 0 | 8 | 0 | 0 | 9 | 0 | 0 | 8 | 0 | 5 | 0 | 0 | 0 | 0 | 0 | 0 | 0 | 0 | 10 | 10 |
| Blackgrass | 5 | 7 | 10 | 2 | 10 | 10 | 10 | 7 | 5 | 5 | 10 | 10 | 6 | 10 | 10 | 7 | 9 | 8 | 9 | 3 | 7 | 0 | 0 | 0 | 0 | 2 | 4 | 10 | 10 |
| Cocklebur | 0 | 0 | 0 | 0 | 0 | 0 | 5 | 0 | 0 | 0 | 3 | — | 0 | 5 | 0 | 0 | — | 0 | 0 | — | 0 | 0 | 0 | 0 | 0 | 0 | — | 0 | 2 |
| Corn | 0 | 2 | 3 | 0 | 9 | 9 | 9 | 4 | 4 | 2 | 10 | 9 | 0 | 9 | 9 | 0 | 2 | 0 | 0 | 0 | 0 | 0 | 0 | 0 | 0 | 0 | 4 | 6 | 10 |
| Crabgrass | — | 9 | 9 | 8 | 10 | 10 | 10 | 10 | 9 | 10 | 10 | 9 | 9 | 10 | 10 | 10 | 10 | 9 | 9 | 8 | 7 | 0 | 0 | 0 | 0 | 0 | 9 | 10 | 10 |
| Giant foxtail | 9 | 10 | 10 | 10 | 10 | 10 | 10 | 10 | 10 | 10 | 10 | 10 | 10 | 10 | 10 | 10 | 10 | 10 | 10 | 9 | 10 | 0 | 0 | 0 | 4 | 8 | 9 | 10 | 10 |
| Morningglory | 0 | 0 | 0 | 0 | 7 | 0 | 10 | 0 | 0 | 2 | 8 | 1 | 0 | 8 | 6 | 0 | 5 | 0 | 0 | 0 | 0 | 0 | 0 | 0 | 0 | 0 | 0 | 4 | 7 |
| Nutsedge | 0 | 0 | 0 | 0 | 6 | 0 | 0 | 0 | 0 | 0 | 0 | 0 | 0 | 0 | 7 | 0 | 6 | 0 | 0 | 0 | 0 | 0 | 0 | 0 | 0 | 0 | 0 | 3 | 0 |
| Rape | 0 | 0 | 6 | 2 | 10 | 9 | 10 | 8 | 4 | 5 | 10 | 10 | 5 | 10 | 10 | 0 | 9 | 3 | 0 | 3 | 0 | 0 | 0 | 0 | 0 | 0 | 0 | 10 | 10 |
| Redroot pigweed | 7 | 4 | 10 | 4 | 10 | 10 | 10 | 8 | 8 | 9 | 10 | 10 | 8 | 10 | 10 | 10 | 10 | 8 | 8 | 8 | 9 | 0 | 0 | 0 | 7 | 0 | 7 | 10 | 10 |
| Soybean | 0 | 0 | 0 | 0 | 8 | 2 | 9 | 6 | 5 | 4 | 9 | 3 | 0 | 9 | 9 | 0 | 0 | 0 | 0 | 0 | 0 | 0 | 0 | 0 | 0 | 0 | 2 | 4 | 8 |
| Sugarbeets | 4 | 6 | 9 | 2 | 10 | 8 | 10 | 5 | 4 | 0 | 10 | 7 | 5 | 10 | 10 | 0 | 8 | 7 | 7 | 4 | 7 | 0 | 0 | 0 | 0 | 0 | 5 | 10 | 10 |
| Velvetleaf | 3 | 0 | 6 | 0 | 10 | 5 | 10 | 7 | 7 | 5 | 8 | 6 | 2 | 10 | 10 | 4 | 6 | 3 | 0 | 3 | 6 | 0 | 0 | 0 | 0 | 0 | 6 | 10 | 10 |
| Wheat | 2 | 4 | 2 | 0 | 8 | 3 | 10 | 3 | 3 | 0 | 8 | 8 | 0 | 8 | 8 | 0 | 5 | 6 | 3 | 0 | 7 | 0 | 0 | 0 | 0 | 0 | 3 | 4 | 10 |
| Wild oats | 6 | 7 | 9 | 0 | 10 | 9 | 10 | 5 | 4 | 6 | 10 | 10 | 4 | 10 | 10 | 6 | 9 | 8 | 6 | 5 | 6 | 0 | 0 | 0 | 0 | 0 | 6 | 10 | 10 |

TABLE B-continued

| Rate 500 g/ha | COMPOUND 132 | 133 | 134 | 135 | 136 | 137 | 138 | 139 | 140 | 141 | 142 | 143 | 144 | 145 | 146 | 147 | 148 | 149 | 150 | 151 | 152 | 153 | 154 | 157 | 158 | 159 | 160 | 161 | 162 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 9 | 7 | 8 | 4 | 5 | 9 | 9 | 9 | 2 | 0 | 0 | 5 | 7 | 5 | 10 | 10 | 7 | 0 | 0 | 7 | 6 | 0 | 4 | 0 | 0 | 0 | 0 | 5 | 7 |
| Bedstraw | 10 | 0 | 3 | 4 | 0 | 10 | 10 | 9 | 0 | 0 | 0 | 0 | 4 | 4 | 7 | 8 | 2 | 0 | 0 | 0 | 0 | 0 | 0 | 0 | 0 | 0 | 0 | 0 | 0 |
| Blackgrass | 10 | 5 | 2 | 4 | 6 | 10 | 9 | 10 | 4 | 0 | 0 | 6 | 7 | 7 | 10 | 10 | 9 | 0 | 0 | 10 | 3 | 0 | 5 | 5 | 3 | 0 | 0 | 9 | 3 |
| Cocklebur | 0 | 2 | 0 | 0 | — | 0 | 0 | 0 | 0 | 0 | 0 | 0 | 0 | 0 | 0 | 5 | 0 | 0 | 0 | 0 | 0 | 0 | 0 | 0 | 0 | 0 | 0 | 0 | 0 |
| Corn | 8 | 0 | 0 | 0 | 0 | 4 | 9 | 7 | 0 | 0 | 0 | 0 | 4 | 0 | 9 | 9 | 0 | 0 | 0 | 9 | 0 | 0 | 0 | 0 | 2 | 0 | 0 | 0 | 0 |
| Crabgrass | 9 | 5 | 9 | 4 | 8 | 10 | 10 | 10 | 10 | 7 | 4 | 10 | 9 | 8 | 10 | 10 | 9 | 0 | 6 | 10 | 3 | 0 | 0 | 6 | 7 | 0 | 0 | 9 | 10 |
| Giant foxtail | 10 | 10 | 10 | — | 10 | 10 | 10 | 10 | 10 | 6 | 6 | 10 | 8 | 8 | 10 | 10 | 10 | 0 | 5 | 10 | 5 | 0 | 8 | 10 | 8 | 0 | 0 | 10 | 9 |
| Morningglory | 2 | 0 | 1 | 0 | 0 | 1 | 4 | 0 | 0 | 0 | 0 | 0 | 0 | 1 | 4 | 7 | 1 | 0 | 0 | 0 | 0 | 0 | 0 | 3 | 2 | 0 | 0 | 0 | 0 |
| Nutsedge | 9 | 0 | 0 | 0 | — | — | 7 | 0 | 0 | 0 | 0 | 0 | 0 | 0 | 3 | 4 | 0 | 0 | — | 2 | 0 | 0 | 0 | 0 | 0 | 0 | 0 | 0 | 0 |
| Rape | 8 | 2 | 6 | 0 | 0 | 10 | 10 | 9 | 0 | 0 | 0 | 6 | 2 | 0 | 10 | 10 | 9 | 0 | 0 | 10 | 0 | 0 | 0 | 0 | 0 | 0 | 0 | 3 | 9 |
| Redroot pigweed | 7 | 3 | 2 | 4 | 10 | 10 | 10 | 10 | 0 | 0 | 0 | 10 | 5 | 4 | 10 | 10 | 10 | 0 | 9 | 10 | 0 | 0 | 9 | 0 | 2 | 0 | 0 | 10 | 7 |
| Soybean | 4 | 0 | 0 | 0 | 0 | 5 | 8 | 2 | 1 | 0 | 0 | 1 | 0 | 0 | 4 | 9 | 0 | 0 | 0 | 7 | 0 | 0 | 0 | 0 | 0 | 0 | 0 | 0 | 0 |
| Sugarbeets | 8 | 5 | 7 | 0 | 9 | 10 | 10 | 6 | 1 | 0 | 0 | 9 | 6 | 3 | 10 | 7 | 10 | 0 | 0 | 10 | 0 | 0 | 6 | 0 | 0 | 0 | 0 | 0 | 0 |
| Velvetleaf | 10 | 2 | 7 | 0 | 4 | 10 | 10 | 7 | 0 | 0 | 0 | 0 | 0 | 5 | 8 | 7 | 8 | 0 | 3 | 10 | 0 | 0 | 0 | 0 | 0 | 0 | 0 | 0 | 0 |
| Wheat | 4 | 0 | 0 | 0 | 0 | 5 | 9 | 4 | 0 | 0 | 0 | 0 | 0 | 0 | 8 | 8 | 6 | 0 | 0 | 5 | 0 | 0 | 0 | 0 | 0 | 0 | 0 | 2 | 0 |
| Wild oats | 9 | 4 | 2 | 0 | 3 | 10 | 10 | 9 | 1 | 0 | 0 | 5 | 2 | 3 | 10 | 10 | 8 | 0 | 2 | 10 | 0 | 0 | 5 | 0 | 2 | 0 | 0 | 6 | 5 |

| Rate 500 g/ha | COMPOUND 163 | 164 | 165 | 166 | 167 | 168 | 169 | 170 | 171 | 172 | 173 | 174 | 175 | 176 | 177 | 178 | 179 | 180 | 181 | 182 | 183 | 184 | 185 | 187 | 188 | 189 | 190 | 191 | 192 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 2 | 0 | 6 | 4 | 8 | 5 | 7 | 10 | 5 | 8 | 4 | 4 | 0 | 0 | 0 | 9 | 9 | 0 | 0 | 0 | 4 | 8 | 0 | 0 | 7 | 6 | 0 | 3 | 6 |
| Bedstraw | 4 | 0 | 4 | 0 | 5 | 0 | 10 | 9 | 0 | 5 | 0 | 3 | 9 | 0 | 10 | 0 | 0 | 0 | — | 0 | 7 | 2 | 0 | 0 | 0 | 0 | 4 | 0 | 0 |
| Blackgrass | 10 | 0 | 8 | 5 | 3 | 2 | 10 | 10 | 2 | 3 | 6 | 2 | 0 | 3 | 6 | 3 | 2 | 0 | 0 | 0 | 0 | 7 | 0 | 0 | 0 | 7 | 3 | 6 | 7 |
| Cocklebur | 0 | 0 | 0 | 0 | 0 | 0 | 0 | 9 | 0 | 0 | 0 | 0 | 0 | 0 | 0 | 0 | 0 | 0 | 0 | 0 | 0 | 2 | — | 0 | 0 | 0 | 0 | 0 | 0 |
| Corn | 2 | 0 | 0 | 0 | 0 | 0 | 6 | 9 | 0 | 0 | 0 | 0 | 0 | 0 | 0 | 0 | 0 | 0 | 0 | 0 | 0 | 0 | 0 | 0 | 0 | 0 | 0 | 0 | 4 |
| Crabgrass | 9 | 4 | 8 | 7 | 10 | 7 | 10 | 10 | 10 | 10 | 9 | 10 | 8 | 10 | 9 | 9 | 9 | 0 | 0 | 0 | 3 | 9 | 9 | 0 | 0 | 3 | 0 | 8 | 9 |
| Giant foxtail | 10 | 2 | 9 | 7 | 10 | 10 | 10 | 10 | 10 | 10 | 10 | 10 | 8 | 10 | 10 | 9 | 10 | 0 | 0 | 0 | 3 | 10 | 9 | 0 | 7 | 6 | 0 | 10 | 10 |
| Morningglory | 0 | 0 | 3 | 0 | 0 | 0 | 0 | 10 | 0 | 0 | 0 | 0 | 0 | 0 | 0 | 0 | 0 | 0 | 0 | 0 | 0 | 0 | 0 | 0 | 0 | 0 | 0 | 0 | 3 |
| Nutsedge | 0 | 0 | 0 | 0 | 0 | 0 | 3 | 9 | 0 | 0 | 0 | — | 3 | 0 | 0 | 0 | 10 | 0 | 0 | 0 | 0 | 0 | 0 | 0 | 0 | 0 | 0 | 0 | — |
| Rape | 8 | 0 | 10 | 0 | 5 | 0 | 10 | 10 | 4 | 5 | 0 | 4 | 0 | 0 | 0 | 0 | 4 | 0 | 0 | 0 | 0 | 0 | 0 | 0 | 0 | 0 | 0 | 0 | 9 |
| Redroot pigweed | 9 | 0 | 1 | 0 | 8 | 0 | 8 | 10 | 6 | 8 | 5 | 9 | 0 | 0 | 0 | 10 | 10 | 0 | 0 | 0 | 0 | 1 | 0 | 0 | 0 | 0 | 0 | 6 | 9 |
| Soybean | 0 | 0 | 0 | 2 | 0 | 0 | 5 | 9 | 0 | 0 | 3 | 0 | 0 | 0 | 0 | 0 | 0 | 0 | 0 | 0 | 0 | 0 | 0 | 0 | 0 | 0 | 0 | 0 | 2 |
| Sugarbeets | 6 | 0 | 4 | 0 | 5 | 7 | 8 | 10 | 0 | 5 | 6 | 6 | 0 | 2 | 0 | 0 | 0 | 0 | 0 | 0 | 0 | 0 | 0 | 0 | 6 | 0 | 0 | 0 | 8 |
| Velvetleaf | 5 | 0 | 4 | 6 | 3 | 6 | 8 | 10 | 0 | 3 | 0 | 0 | 0 | 2 | 0 | 0 | 5 | 0 | 0 | 0 | 0 | 7 | 0 | 0 | 2 | 0 | 0 | 0 | 6 |
| Wheat | 4 | 0 | 2 | 0 | 0 | 0 | 4 | 8 | 0 | 0 | 0 | 0 | 0 | 0 | 0 | 0 | 2 | 0 | 0 | 0 | 0 | 0 | 0 | 0 | 0 | 2 | 0 | 2 | 0 |
| Wild oats | 10 | 0 | 6 | 2 | 6 | 3 | 10 | 10 | 5 | 6 | 3 | 0 | 0 | 5 | 2 | 3 | 3 | 0 | 0 | 0 | 0 | 3 | 0 | 0 | 0 | 3 | 0 | 7 | 7 |

TABLE B-continued

| Rate 500 g/ha | COMPOUND 193 | 194 | 195 | 196 | 197 | 198 | 199 | 201 | 202 | 203 | 204 | 205 | 206 | 207 | 208 | 210 | 211 | 212 | 214 | 215 | 216 | 218 | 219 | 220 | 222 | 223 | 224 | 225 | 226 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 0 | 3 | 6 | 0 | 0 | 0 | 9 | 4 | 0 | 0 | 2 | 0 | 0 | 0 | 0 | 0 | 5 | 5 | 0 | 2 | 4 | 7 | 9 | 8 | 0 | 4 | 4 | 7 | 10 |
| Bedstraw | 0 | 10 | 2 | 0 | 0 | 0 | 0 | 0 | 2 | 0 | 0 | 0 | 0 | 0 | 0 | 0 | 10 | 10 | 0 | 0 | 0 | 3 | 9 | 10 | 0 | 3 | 0 | 2 | 0 |
| Blackgrass | 0 | 8 | 6 | 0 | 0 | 0 | 10 | 4 | 2 | 0 | 5 | 0 | 0 | 7 | 3 | 4 | 9 | 9 | 3 | 6 | 4 | 10 | 10 | 10 | 0 | 5 | 5 | 10 | 10 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 5 | — | 0 | 0 | 2 | 0 |
| Corn | 0 | 0 | 0 | 0 | 0 | 0 | 0 | 0 | 0 | 0 | 2 | 0 | 0 | 0 | 0 | 0 | 0 | 0 | 0 | 2 | 0 | 6 | 7 | 7 | 0 | 0 | 0 | 6 | 9 |
| Crabgrass | 7 | — | 9 | 0 | 3 | 0 | 10 | 9 | 9 | 0 | 8 | 8 | 8 | 4 | 6 | 8 | 3 | 5 | 4 | 4 | 8 | 7 | 10 | 10 | 9 | 9 | 10 | 10 | 10 |
| Giant foxtail | 6 | 9 | 10 | 0 | 3 | 3 | 10 | 10 | 10 | 0 | 10 | 3 | 9 | 10 | 10 | 5 | 8 | 10 | 6 | 5 | 9 | 10 | 10 | 10 | 9 | 9 | 10 | 10 | 10 |
| Morningglory | 0 | 0 | 0 | 0 | 0 | 0 | 0 | 0 | 1 | 0 | 0 | 0 | 0 | 0 | 0 | 0 | 0 | 0 | 0 | 0 | 0 | 0 | 1 | 6 | 0 | 1 | 0 | 8 | 8 |
| Nutsedge | 0 | 0 | — | 0 | 0 | 0 | 10 | — | — | 0 | 0 | — | 0 | 0 | 0 | 0 | — | 0 | — | 0 | 0 | 0 | — | — | — | — | — | 10 | — |
| Rape | 0 | 7 | 0 | 0 | 0 | 0 | 0 | 0 | 0 | 0 | 3 | 0 | 0 | 2 | 0 | 3 | 4 | 8 | 0 | 2 | 0 | 2 | 10 | 8 | 0 | 0 | 0 | 6 | 10 |
| Redroot pigweed | 0 | 10 | 0 | 0 | 0 | 0 | 10 | 0 | 3 | 0 | 0 | 0 | 3 | 8 | 2 | 8 | 7 | 10 | 9 | 6 | 8 | 10 | 10 | 10 | 4 | 7 | 4 | 10 | 9 |
| Soybean | 0 | 0 | 0 | 0 | 0 | 0 | 0 | 0 | 0 | 0 | 0 | 0 | 0 | 0 | 0 | 0 | 0 | 0 | 4 | 0 | 0 | 6 | 0 | 3 | 0 | 0 | 0 | 6 | 0 |
| Sugarbeets | 0 | 3 | 2 | 0 | 0 | 0 | 6 | 0 | 1 | 0 | 0 | 0 | 0 | 0 | 0 | 3 | 8 | 8 | 0 | 7 | 0 | 7 | 8 | 8 | 0 | 0 | 0 | 6 | 6 |
| Velvetleaf | 0 | 3 | 0 | 0 | 0 | 0 | 0 | 0 | 1 | 0 | 0 | 0 | 0 | 5 | 3 | 0 | 0 | 5 | 0 | 0 | 0 | 2 | 10 | 8 | 3 | 0 | 0 | 7 | 7 |
| Wheat | 0 | 2 | 0 | 0 | 0 | 0 | 0 | 2 | 2 | 0 | 2 | 0 | 0 | 0 | 0 | 0 | 5 | 7 | 0 | 0 | 0 | 3 | 9 | 8 | 0 | 0 | 0 | 8 | 8 |
| Wild oats | 0 | 8 | 4 | 0 | 0 | 0 | 7 | 5 | 5 | 0 | 6 | 0 | 0 | 0 | 3 | 2 | 5 | 7 | 0 | 2 | 0 | 9 | 9 | 8 | 1 | 4 | 2 | 10 | 10 |

| Rate 500 g/ha | COMPOUND 227 | 228 | 229 | 230 | 231 | 232 | 233 | 234 | 235 | 236 | 237 | 238 | 239 | 240 | 241 | 242 | 243 | 245 | 246 | 247 | 248 | 249 | 251 | 253 | 254 | 255 | 257 | 258 | 259 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 2 | 0 | 0 | 0 | 0 | 5 | 4 | 0 | 0 | 3 | 0 | 0 | 5 | 3 | 4 | 10 | 10 | 10 | 5 | 0 | 0 | 0 | 9 | 0 | 0 | 9 | 3 | 8 | 9 |
| Bedstraw | 3 | 0 | 0 | 0 | 0 | 0 | 0 | 0 | 0 | 0 | 0 | 3 | 0 | 0 | 10 | 10 | 9 | 10 | 2 | 0 | 0 | 0 | 10 | 0 | 0 | 0 | 0 | 10 | 10 |
| Blackgrass | 10 | 0 | 0 | 2 | 0 | 8 | 9 | 0 | 0 | 5 | 0 | 0 | 4 | 2 | 10 | 10 | 10 | 10 | 10 | 0 | 0 | 0 | 10 | 0 | 4 | 10 | 0 | 8 | 10 |
| Cocklebur | 0 | 0 | 0 | 0 | 0 | 0 | 0 | 0 | 0 | 0 | 0 | — | 0 | 0 | 0 | 3 | 5 | 6 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 5 | 9 | 9 | 8 | 3 | 0 | 0 | 0 | 5 | 0 | 0 | 8 | 0 | 5 | 3 |
| Crabgrass | 10 | 2 | 0 | 9 | 7 | 10 | 10 | 0 | 0 | 5 | 3 | 10 | 10 | 9 | 10 | 10 | 10 | 10 | 10 | 2 | 0 | 2 | 10 | 0 | 3 | 9 | 5 | 10 | 7 |
| Giant foxtail | 10 | 9 | 0 | 9 | 8 | 9 | 10 | 0 | 0 | 10 | 4 | 10 | 10 | 10 | 10 | 10 | 10 | 10 | 10 | 3 | 0 | 5 | 10 | 0 | 10 | 10 | 9 | 10 | 10 |
| Morningglory | 0 | 0 | 0 | 2 | 6 | 0 | 2 | 0 | 0 | 0 | 2 | 3 | 0 | 0 | 5 | 10 | 10 | 6 | 0 | 0 | 0 | 0 | 4 | 0 | 0 | 0 | 4 | 0 | 0 |
| Nutsedge | — | 0 | 0 | 0 | 0 | — | — | 0 | — | — | — | — | 0 | — | 10 | 10 | — | — | 0 | — | 0 | 0 | — | 0 | 0 | — | 0 | — | 0 |
| Rape | 10 | 0 | 0 | 0 | 0 | 0 | 3 | 0 | 0 | 0 | 0 | 10 | 0 | 0 | 9 | 10 | 10 | 10 | 10 | 0 | 0 | 0 | 10 | 0 | 6 | 5 | 0 | 7 | 9 |
| Redroot pigweed | 10 | 0 | 0 | 0 | 0 | 7 | 8 | 0 | 0 | 0 | 0 | 9 | 0 | 0 | 10 | 10 | 10 | 10 | 3 | 0 | 0 | 0 | 10 | 0 | 0 | 10 | 4 | 10 | 8 |
| Soybean | 2 | 0 | 0 | 0 | 0 | 0 | 0 | 0 | 0 | 0 | 0 | 0 | 0 | 0 | 4 | 7 | 9 | 8 | 2 | 0 | 0 | 0 | 0 | 0 | 0 | 0 | 0 | 3 | 0 |
| Sugarbeets | 8 | 0 | 0 | 0 | 0 | 4 | 8 | 0 | 0 | 0 | 0 | 6 | 0 | 0 | 6 | 8 | 10 | 10 | 8 | 0 | 0 | 0 | 10 | 0 | 6 | 7 | 0 | 7 | 0 |
| Velvetleaf | 2 | 0 | 0 | 0 | 0 | 0 | 7 | 0 | 0 | 0 | 0 | 3 | 5 | 2 | 7 | 10 | 10 | 10 | 5 | 0 | 0 | 0 | 7 | 0 | 0 | 7 | 0 | 7 | 5 |
| Wheat | 0 | 0 | 0 | 0 | 0 | 0 | 0 | 0 | 0 | 0 | 0 | 2 | 2 | 0 | 5 | 10 | 9 | 9 | 5 | 0 | 0 | 0 | 8 | 0 | 0 | 8 | 4 | 7 | 0 |
| Wild oats | 3 | 0 | 0 | 0 | 0 | 8 | 6 | 0 | 0 | 2 | 0 | 3 | 3 | 0 | 8 | 10 | 9 | 10 | 8 | 0 | 0 | 0 | 9 | 0 | 2 | 10 | 4 | 6 | 4 |

TABLE B-continued

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 260 | 261 | 262 | 263 | 265 | 266 | 267 | 268 | 269 | 270 | 271 | 272 | 273 | 274 | 276 | 277 | 278 | 279 | 280 | 281 | 282 | 283 | 284 | 286 | 292 | 293 | 294 | 297 | 298 |
| Preemergence | | | | | | | | | | | | | | | | | | | | | | | | | | | | | |
| B. signalgrass | 3 | 3 | 0 | 0 | 4 | 7 | 9 | 0 | 7 | 0 | 10 | 0 | 3 | 0 | 10 | 10 | 0 | 0 | 0 | 0 | 7 | 10 | 8 | 8 | 0 | 9 | 9 | 0 | 0 |
| Bedstraw | 5 | — | 0 | 0 | 0 | 9 | 2 | 0 | 0 | 0 | 10 | 3 | — | 0 | 0 | 2 | 0 | 0 | 0 | 10 | 2 | 9 | 8 | 0 | 0 | 0 | 0 | 0 | — |
| Blackgrass | 3 | 4 | 4 | 0 | — | 9 | 8 | 0 | 7 | 0 | 10 | 0 | 0 | 0 | 10 | 10 | 0 | 0 | 0 | 4 | 8 | 10 | 10 | 7 | 0 | 9 | 10 | 0 | 0 |
| Cocklebur | 0 | 0 | 0 | — | — | 0 | 0 | 0 | 0 | 0 | 4 | 0 | 0 | 0 | 0 | 0 | 0 | 0 | 0 | 0 | 0 | 0 | 0 | 0 | 0 | 0 | — | 0 | 0 |
| Corn | 0 | 0 | 0 | 0 | 0 | 0 | 3 | 0 | 0 | 0 | 3 | 0 | 0 | 0 | 0 | 3 | 0 | 0 | 0 | 0 | 0 | 0 | 0 | 0 | 0 | — | 2 | 0 | 0 |
| Crabgrass | 9 | 5 | 3 | 2 | 6 | 6 | 8 | 0 | 6 | 0 | 8 | 2 | 9 | 5 | 7 | 10 | 4 | 1 | 0 | 10 | 8 | 7 | 9 | 10 | 0 | 8 | 10 | 7 | 0 |
| Giant foxtail | 10 | 9 | 7 | 9 | 10 | 8 | 9 | 0 | — | 0 | 10 | 6 | 9 | 9 | 10 | 10 | 8 | 7 | 0 | 10 | 10 | 10 | 10 | 10 | 0 | 10 | 10 | 7 | — |
| Morningglory | 0 | 0 | 0 | 0 | 0 | 1 | 0 | 0 | 0 | 0 | 7 | 0 | 0 | 0 | 0 | 0 | 0 | 0 | 0 | 0 | 0 | 0 | 2 | 0 | 0 | 4 | 0 | 0 | 0 |
| Nutsedge | — | 0 | 0 | 0 | 0 | 0 | 0 | — | — | 0 | 0 | 0 | 0 | 0 | — | 0 | — | — | 0 | 0 | — | 0 | 0 | — | 0 | — | 0 | 0 | 0 |
| Rape | 0 | 0 | 0 | 0 | 0 | 5 | 0 | 0 | 0 | 0 | 10 | 0 | 0 | 0 | 10 | 2 | 0 | 0 | 0 | 0 | 2 | 8 | 7 | 7 | 0 | 10 | 3 | 0 | 0 |
| Redroot pigweed | 4 | 0 | 0 | 0 | 0 | 9 | 7 | 0 | 4 | 0 | 10 | 3 | 0 | 0 | 4 | 5 | 0 | 0 | 0 | 0 | 9 | 10 | 8 | 10 | 0 | 10 | 2 | 0 | 0 |
| Soybean | 0 | 0 | 0 | 0 | 0 | 0 | 0 | 0 | 4 | 0 | 1 | 0 | 0 | 0 | 0 | 4 | 0 | 0 | 0 | 0 | 0 | 0 | 3 | 0 | 0 | 2 | 0 | 0 | 0 |
| Sugarbeets | 0 | 0 | 0 | 0 | 0 | 7 | 5 | 0 | 4 | 0 | 8 | 0 | 7 | 0 | 7 | 7 | 0 | 0 | 0 | 0 | 3 | 5 | 6 | 4 | 0 | 8 | 2 | 0 | 0 |
| Velvetleaf | 0 | 0 | 0 | 3 | 0 | 4 | 3 | 0 | 0 | 0 | 8 | 0 | 1 | 0 | 3 | 7 | 0 | 0 | 0 | 0 | 0 | 7 | 7 | 5 | 0 | 8 | 4 | 0 | 0 |
| Wheat | 0 | 0 | 0 | 0 | 1 | 6 | 0 | 0 | 0 | 0 | 3 | 0 | 0 | 0 | 3 | 4 | 0 | 0 | 0 | 0 | 0 | 6 | 0 | 2 | 0 | 9 | 0 | 0 | 0 |
| Wild oats | 0 | 0 | 0 | 0 | 5 | 7 | 2 | 0 | 4 | 0 | 8 | 2 | 3 | 0 | 6 | 8 | 0 | 0 | 0 | 3 | 7 | 7 | 5 | 6 | 0 | 9 | 8 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 299 | 300 | 301 | 302 | 303 | 304 | 305 | 306 | 307 | 308 | 309 | 310 | 311 | 312 | 313 | 314 | 315 | 316 | 317 | 319 | 320 | 321 | 322 | 323 | 325 | 326 | 327 | 328 | 329 |
| Preemergence | | | | | | | | | | | | | | | | | | | | | | | | | | | | | |
| B. signalgrass | 10 | 2 | 0 | 3 | 0 | 0 | 5 | 0 | 4 | 0 | 2 | 8 | 0 | 0 | 0 | 6 | 6 | 9 | 8 | 3 | 3 | 5 | 3 | 0 | 0 | 7 | 7 | 5 | 0 |
| Bedstraw | 10 | 8 | 0 | 0 | — | 0 | 0 | 0 | 0 | 0 | 0 | 10 | 0 | 0 | 0 | 3 | — | 6 | — | 7 | 0 | 3 | 2 | — | 0 | — | — | — | — |
| Blackgrass | 10 | 0 | 0 | 5 | 0 | 0 | 4 | 0 | 4 | 0 | 6 | 10 | 0 | 0 | 0 | 10 | 10 | 10 | 10 | 4 | 6 | 7 | 7 | 0 | 7 | 8 | 7 | 7 | 0 |
| Cocklebur | 0 | — | — | 0 | 0 | 0 | 0 | 0 | — | 0 | 0 | 4 | 0 | 0 | 0 | 0 | 0 | 2 | 0 | 0 | 0 | 0 | 4 | 0 | 0 | 0 | 0 | 0 | 0 |
| Corn | 8 | 0 | 0 | 0 | 0 | 0 | 0 | 0 | 2 | 0 | 4 | 5 | 0 | 0 | 0 | 0 | 3 | 5 | 5 | 0 | 0 | 0 | 0 | 0 | 0 | 2 | 0 | 0 | 0 |
| Crabgrass | 9 | 7 | 0 | 7 | — | 8 | 7 | 0 | 2 | 0 | 6 | 7 | 0 | 0 | 0 | 8 | 7 | 10 | 8 | 3 | 7 | 4 | 7 | 2 | 2 | 5 | 5 | 5 | 3 |
| Giant foxtail | 10 | 10 | 0 | 9 | 0 | 6 | 10 | 9 | 9 | 0 | 9 | 10 | 0 | 0 | 0 | 10 | 10 | 10 | 10 | 9 | 7 | 10 | 10 | 2 | 10 | 9 | 9 | 9 | 3 |
| Morningglory | 7 | 0 | 0 | 0 | 3 | 0 | 0 | 0 | 0 | 0 | 0 | 8 | 0 | 0 | 0 | 0 | 0 | 0 | 0 | 0 | 0 | 0 | 0 | 0 | 0 | 0 | 0 | 4 | 0 |
| Nutsedge | — | 0 | 0 | 0 | 0 | 0 | — | 0 | 0 | 0 | 0 | 10 | 0 | 0 | 0 | 0 | 0 | — | 0 | 0 | 0 | 0 | 0 | 0 | — | 0 | 0 | 0 | — |
| Rape | 10 | 0 | 0 | — | 0 | 0 | 0 | 0 | 0 | 0 | 0 | 10 | 0 | 0 | 0 | 7 | 0 | 4 | 10 | 0 | 0 | 0 | 2 | 0 | 0 | 1 | 2 | 0 | — |
| Redroot pigweed | 10 | 0 | 0 | 0 | 0 | 0 | 7 | 0 | 4 | 0 | 2 | 10 | 0 | 0 | 0 | 9 | 3 | 10 | 10 | 0 | 0 | 0 | 8 | 0 | 0 | 7 | 3 | 4 | 0 |
| Soybean | 7 | 0 | 0 | 0 | 0 | 0 | 0 | 0 | 0 | 0 | 0 | 5 | 0 | 0 | 0 | 0 | 0 | 0 | 4 | 0 | 0 | 0 | 0 | 0 | 0 | 0 | 0 | 0 | 0 |
| Sugarbeets | 10 | 0 | 0 | 2 | 0 | 6 | 3 | 0 | 2 | 0 | 0 | 10 | 0 | 0 | 0 | 6 | 2 | 4 | 8 | 0 | 0 | 0 | 4 | 0 | 0 | 2 | 3 | 0 | 0 |
| Velvetleaf | 8 | 0 | 0 | 0 | 0 | 0 | 0 | 0 | 2 | 0 | 2 | 8 | 0 | 0 | 0 | 5 | 0 | 6 | 8 | 0 | 0 | 0 | 0 | 0 | 0 | 0 | 0 | 0 | 0 |
| Wheat | 8 | 2 | 0 | 0 | 0 | 0 | 0 | 0 | 0 | 0 | 0 | 7 | 0 | 0 | 0 | 3 | 7 | 2 | 8 | 0 | 0 | 0 | 0 | 0 | 0 | 2 | 4 | 0 | 0 |
| Wild oats | 8 | 3 | 0 | 5 | 0 | 0 | 1 | 0 | 8 | 0 | 2 | 9 | 0 | 0 | 0 | 3 | 3 | 6 | 10 | 0 | 0 | 5 | 3 | 0 | 2 | 3 | 4 | 1 | 0 |

TABLE B-continued

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 330 | 331 | 332 | 333 | 334 | 335 | 336 | 337 | 338 | 339 | 340 | 341 | 342 | 343 | 344 | 345 | 348 | 349 | 350 | 351 | 352 | 353 | 354 | 355 | 356 | 357 | 358 | 359 | 360 |
| Preemergence | | | | | | | | | | | | | | | | | | | | | | | | | | | | | |
| B. signalgrass | 0 | 0 | 0 | 0 | 0 | 0 | 0 | 0 | 0 | 0 | 2 | 0 | 6 | 8 | 0 | 0 | 7 | 4 | 4 | 4 | 7 | 5 | 5 | 6 | 5 | 7 | 7 | 0 | 7 |
| Bedstraw | 0 | 0 | — | 0 | 0 | — | 0 | 0 | 0 | 0 | 5 | 2 | — | — | — | 0 | 9 | — | 10 | 10 | — | 3 | 0 | 9 | 9 | 10 | 10 | 0 | — |
| Blackgrass | — | 0 | 0 | 0 | 0 | 0 | 0 | 3 | 0 | 3 | 8 | 7 | 7 | 10 | 0 | 0 | 9 | 4 | 8 | 8 | 10 | 8 | 9 | 10 | 9 | 10 | 10 | 0 | 10 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | — | — | — | 0 | 0 | 0 | 0 | 0 |
| Corn | 0 | 0 | 0 | 0 | 0 | 0 | 0 | 0 | 0 | 0 | 0 | 0 | 0 | 4 | 0 | 0 | 9 | 2 | 7 | 6 | 9 | 7 | 6 | 4 | 6 | 9 | 6 | 0 | 9 |
| Crabgrass | 0 | 0 | 5 | 3 | 0 | 2 | 0 | 3 | 0 | 5 | 9 | 8 | 9 | 10 | 1 | 0 | 10 | 9 | 10 | 10 | 10 | 10 | 10 | 10 | 10 | 10 | 10 | 0 | 10 |
| Giant foxtail | 0 | 0 | 7 | 2 | 0 | 10 | 0 | 9 | 9 | 10 | 10 | 10 | 10 | 10 | 8 | 0 | 10 | 10 | 10 | 10 | 10 | 10 | 10 | 10 | 10 | 10 | 10 | 0 | 10 |
| Morningglory | 0 | 0 | 0 | 0 | 0 | 0 | 0 | 0 | 0 | 0 | 0 | 0 | 0 | 3 | 0 | 0 | 0 | 0 | 2 | 0 | 2 | 1 | 0 | 2 | 0 | 7 | 5 | 0 | 10 |
| Nutsedge | 0 | 0 | 0 | 0 | 0 | 0 | 0 | 0 | 0 | 0 | 0 | 0 | 0 | 0 | 0 | 0 | 0 | 0 | 10 | 9 | 0 | 0 | 0 | 0 | 0 | 6 | 0 | 0 | 7 |
| Rape | 0 | 0 | 0 | 0 | 0 | 0 | 0 | 0 | 0 | 0 | 0 | 0 | 0 | 6 | — | 0 | 7 | 4 | 10 | 9 | 7 | 5 | 5 | 5 | 5 | 8 | 4 | 0 | 0 |
| Redroot pigweed | 0 | 0 | 3 | 0 | 0 | 0 | 0 | 0 | 0 | 0 | 4 | 8 | 0 | 10 | 0 | 0 | 10 | 7 | 10 | 10 | 10 | 10 | 10 | 10 | 10 | 10 | 10 | 0 | 10 |
| Soybean | 0 | 0 | 0 | 0 | 0 | 0 | 0 | 0 | 0 | 0 | 0 | 0 | 0 | 0 | 0 | — | 0 | 0 | 2 | 2 | 2 | 0 | 1 | 0 | 0 | 0 | 1 | 0 | 5 |
| Sugarbeets | 0 | 0 | 0 | 0 | 0 | 0 | 0 | 0 | 0 | 0 | 0 | 0 | 0 | 6 | 0 | 0 | 6 | 4 | 9 | 8 | 7 | 4 | 6 | 3 | 5 | 6 | 3 | 0 | 7 |
| Velvetleaf | 0 | 0 | 0 | 0 | 0 | 0 | 0 | 0 | 0 | 0 | 2 | 2 | 0 | 7 | 0 | 0 | 7 | 3 | 6 | 5 | 7 | 6 | 7 | 5 | 5 | 7 | 8 | 0 | 7 |
| Wheat | 0 | 0 | 0 | 0 | 0 | 0 | 0 | 0 | 0 | 0 | 0 | 0 | 3 | 5 | 0 | 0 | 0 | 0 | 3 | 2 | 6 | 2 | 2 | 2 | 6 | 9 | 3 | 0 | 8 |
| Wild oats | 0 | 0 | 0 | 0 | 0 | 0 | 0 | 0 | 0 | 0 | 3 | 2 | 4 | 9 | 0 | 0 | 10 | 9 | 7 | 4 | 10 | 6 | 8 | 9 | — | 10 | 10 | 0 | 10 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 361 | 363 | 364 | 365 | 367 | 368 | 369 | 370 | 371 | 372 | 373 | 374 | 375 | 376 | 378 | 379 | 380 | 381 | 382 | 383 | 384 | 385 | 387 | 388 | 389 | 390 | 391 | 393 | 394 |
| Preemergence | | | | | | | | | | | | | | | | | | | | | | | | | | | | | |
| B. signalgrass | 6 | 6 | 3 | 0 | 5 | 8 | 2 | 5 | 4 | 8 | 2 | 5 | 8 | 0 | 0 | 0 | 0 | 0 | 6 | 6 | 7 | 9 | 2 | 6 | 4 | 10 | 0 | 2 | 10 |
| Bedstraw | 2 | 10 | 3 | 0 | 10 | 10 | — | — | — | 10 | 0 | — | 10 | — | 0 | — | — | 0 | — | — | — | — | — | 7 | 10 | — | — | — | — |
| Blackgrass | 10 | 10 | 4 | 0 | 10 | 10 | 5 | 10 | 10 | 10 | 7 | 6 | 10 | 0 | 0 | 0 | 2 | 2 | 7 | 7 | 7 | 10 | 2 | 6 | 9 | 10 | 0 | 3 | 10 |
| Cocklebur | 0 | 0 | 0 | 0 | — | 0 | 0 | 10 | 0 | 2 | 0 | 0 | 0 | 0 | 0 | 0 | — | 0 | — | 0 | 0 | 0 | 0 | 0 | 0 | — | 0 | 0 | 0 |
| Corn | 6 | 7 | 0 | 0 | 5 | 10 | 0 | 9 | 7 | 9 | 3 | 0 | 7 | 0 | 0 | 0 | 0 | 2 | 2 | 0 | 5 | 0 | 0 | 9 | 4 | 7 | 0 | 0 | 5 |
| Crabgrass | 9 | 9 | 5 | 4 | 10 | 10 | 10 | 10 | 10 | 10 | 10 | 9 | 10 | 0 | 10 | 8 | 9 | 9 | 10 | 10 | 9 | 10 | 9 | 10 | 10 | 10 | 0 | 8 | 10 |
| Giant foxtail | 10 | 10 | 10 | 3 | 10 | 10 | 10 | 10 | 10 | 10 | 10 | 10 | 10 | 0 | 10 | 9 | 10 | 9 | 10 | 10 | 10 | 10 | 9 | 10 | 10 | 10 | 0 | 10 | 10 |
| Morningglory | 0 | 6 | 0 | 0 | 2 | 5 | 0 | 3 | 3 | 3 | 1 | 0 | 0 | 0 | 0 | 0 | 0 | 0 | 0 | 0 | 2 | 2 | 0 | 0 | 1 | 7 | 0 | 2 | 2 |
| Nutsedge | 0 | 2 | — | 0 | 0 | 10 | 5 | 10 | 9 | 10 | 0 | 0 | 0 | 0 | 0 | 0 | 0 | 0 | 0 | 0 | 0 | 0 | 0 | — | 0 | 2 | 0 | 0 | 6 |
| Rape | 6 | 5 | 2 | 0 | 10 | 10 | 5 | 10 | 10 | 10 | — | 7 | 8 | 0 | 0 | 0 | 0 | 0 | 0 | 0 | 0 | 4 | 0 | 8 | 8 | 8 | 0 | 0 | 9 |
| Redroot pigweed | 10 | 10 | 0 | 0 | 10 | 10 | 10 | 10 | 10 | 10 | 10 | — | 10 | 0 | 0 | 0 | 6 | 0 | 0 | 3 | 0 | 10 | 9 | 10 | 10 | 10 | 0 | 10 | 10 |
| Soybean | 1 | 0 | 0 | 0 | 0 | 8 | 4 | 7 | 2 | 2 | 2 | 0 | 0 | 0 | 0 | 0 | 0 | 0 | 0 | 0 | 3 | 0 | 0 | 4 | 3 | 3 | 0 | 0 | 2 |
| Sugarbeets | 6 | 8 | 0 | 0 | 9 | 10 | 4 | — | 10 | 10 | 7 | 4 | 7 | 0 | 0 | 0 | 0 | 0 | 0 | 0 | 2 | 7 | 2 | 6 | 4 | 8 | 0 | 3 | 7 |
| Velvetleaf | 5 | 7 | 0 | 0 | 6 | 10 | 6 | 6 | 6 | 7 | 0 | 0 | 7 | 0 | 0 | 0 | 0 | 0 | 0 | 0 | 3 | 3 | 3 | 6 | 2 | 7 | 0 | 0 | 7 |
| Wheat | 6 | 7 | 0 | 0 | 0 | 10 | 0 | 7 | 4 | 6 | 0 | 0 | 3 | 0 | 0 | 0 | 0 | 0 | 0 | 0 | 3 | 8 | 0 | 8 | 0 | 9 | 0 | 0 | 9 |
| Wild oats | 10 | 10 | 3 | 0 | 7 | 10 | 7 | 10 | 6 | 10 | 0 | 0 | 9 | 0 | 0 | 0 | 4 | 0 | 4 | 0 | 6 | 10 | 7 | 10 | 4 | 10 | 0 | 3 | 10 |

TABLE B-continued

| Rate 500 g/ha | COMPOUND 395 | 396 | 397 | 398 | 400 | 401 | 402 | 403 | 404 | 405 | 406 | 407 | 408 | 409 | 410 | 411 | 414 | 415 | 416 | 417 | 418 | 419 | 420 | 421 | 422 | 423 | 424 | 425 | 426 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 0 | 5 | 10 | 10 | 4 | 0 | 9 | 7 | 10 | 0 | 0 | 0 | 7 | 9 | 10 | 10 | 5 | 6 | 9 | 7 | 6 | 8 | 8 | 9 | 0 | 0 | 0 | 9 | 8 |
| Bedstraw | 0 | — | — | — | — | — | 10 | — | 10 | — | — | 0 | — | — | — | — | 0 | — | — | — | — | — | — | — | — | — | — | — | — |
| Blackgrass | 0 | 5 | 10 | 10 | 0 | 2 | 10 | 9 | 10 | 0 | 0 | 0 | 10 | 10 | 10 | 10 | 10 | 9 | 10 | 9 | 0 | 3 | 10 | 10 | 0 | 0 | 0 | 10 | 9 |
| Cocklebur | 0 | 0 | 0 | 0 | 0 | 0 | 0 | — | 0 | 0 | 0 | 0 | 0 | 2 | 0 | 0 | 0 | 0 | 4 | 0 | 0 | 0 | 0 | 0 | 0 | 0 | 0 | 2 | 0 |
| Corn | 0 | 0 | 8 | 8 | 2 | 0 | 9 | 6 | 6 | — | 0 | 0 | 8 | 10 | 9 | 9 | 0 | 4 | 6 | 0 | — | 0 | 2 | 8 | 0 | 0 | 0 | 9 | 6 |
| Crabgrass | 2 | 10 | 10 | 10 | 10 | 10 | 10 | 10 | 10 | 10 | 6 | 9 | 10 | 10 | 10 | 10 | 10 | 10 | 10 | 10 | 10 | 9 | 10 | 10 | 0 | 2 | 0 | 10 | 10 |
| Giant foxtail | 2 | 10 | 10 | 10 | 10 | 8 | 10 | 10 | 10 | 10 | 9 | 10 | 10 | 10 | 10 | 10 | 10 | 10 | 10 | 10 | 10 | 5 | 10 | 10 | 0 | 4 | 0 | 10 | 10 |
| Morningglory | 0 | 0 | 4 | 0 | 0 | 0 | 2 | 0 | 5 | 0 | 0 | 0 | 7 | 5 | 0 | 4 | 0 | 0 | 8 | 0 | 0 | 2 | 8 | 8 | 0 | 0 | 0 | 4 | 6 |
| Nutsedge | 0 | 0 | 0 | 0 | 0 | 0 | 0 | 0 | 0 | 0 | 0 | 0 | 0 | 8 | — | 2 | — | 0 | 4 | 0 | 0 | 0 | 10 | 0 | 0 | 0 | 0 | 5 | 0 |
| Rape | 0 | 0 | 10 | 10 | 0 | 0 | 8 | 7 | 8 | 0 | 0 | 0 | 8 | 6 | 8 | 10 | 0 | 10 | 10 | 6 | 9 | 2 | 8 | 10 | 0 | 0 | 0 | 10 | 10 |
| Redroot pigweed | 0 | 8 | 10 | 10 | 6 | 0 | 10 | 9 | 10 | 0 | 0 | 0 | 10 | 10 | 8 | 10 | 0 | 10 | 10 | 10 | 8 | 10 | 5 | 10 | 0 | 0 | 0 | 3 | 10 |
| Soybean | 0 | 0 | 0 | 0 | 0 | 3 | 1 | 2 | 3 | 3 | 0 | 0 | 0 | 8 | 3 | 1 | 0 | 0 | 9 | 0 | 0 | 0 | 0 | 10 | 0 | 0 | 0 | 0 | 0 |
| Sugarbeets | 0 | 2 | 9 | 9 | 4 | 0 | 8 | 5 | 8 | 0 | 0 | 0 | 8 | 9 | 0 | 8 | 0 | 8 | 9 | 6 | 2 | 5 | 3 | 10 | 0 | 0 | 0 | 2 | 6 |
| Velvetleaf | 0 | 0 | 6 | 7 | 2 | 0 | 8 | 5 | 7 | 0 | 0 | 0 | 7 | 8 | 8 | 8 | 0 | 7 | 8 | 6 | 6 | 4 | 7 | 10 | 0 | 0 | 0 | 6 | 5 |
| Wheat | 0 | 0 | 3 | 2 | 0 | 0 | 6 | 0 | 5 | 0 | 0 | 0 | 7 | 10 | 8 | 10 | 0 | 3 | 10 | 2 | 2 | 0 | 7 | 9 | 0 | 0 | 0 | 4 | 6 |
| Wild oats | 0 | 4 | 10 | 8 | 0 | 0 | 10 | 8 | 10 | 0 | 0 | 0 | 8 | 8 | 10 | 10 | 7 | 6 | 10 | 4 | 0 | 2 | 5 | 10 | 3 | 0 | 0 | 10 | 10 |

| Rate 500 g/ha | COMPOUND 427 | 428 | 429 | 430 | 431 | 432 | 433 | 434 | 435 | 436 | 437 | 438 | 439 | 440 | 441 | 443 | 444 | 445 | 446 | 447 | 448 | 449 | 451 | 452 | 453 | 454 | 455 | 456 | 457 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 4 | 3 | 4 | 3 | 0 | 0 | 6 | 0 | 1 | 10 | 0 | 2 | 0 | 8 | 0 | 10 | 8 | 3 | 8 | 0 | 2 | 0 | 0 | 0 | 6 | 4 | 9 | 2 | 0 |
| Bedstraw | — | — | — | — | — | — | — | — | — | — | — | — | — | — | — | — | — | — | — | — | 0 | 4 | — | — | — | — | — | — | 0 |
| Blackgrass | 6 | 2 | 3 | 9 | 3 | 2 | 9 | 0 | 2 | 9 | 0 | 3 | 0 | 10 | 0 | 0 | 8 | 1 | 10 | 0 | 2 | 3 | 0 | 2 | 5 | 6 | 7 | 6 | 0 |
| Cocklebur | 0 | 0 | 0 | 0 | — | 0 | 3 | 0 | 0 | 0 | 0 | 0 | 0 | 0 | 0 | 0 | 0 | — | 0 | 0 | — | 0 | 0 | 0 | 0 | 0 | 0 | 0 | 0 |
| Corn | 0 | 0 | 0 | 2 | 0 | 0 | 0 | 0 | 0 | 9 | 0 | 0 | 0 | 0 | 0 | 0 | 0 | 0 | 6 | 0 | 0 | 0 | 0 | 0 | 3 | 3 | 7 | 0 | 0 |
| Crabgrass | 10 | 10 | 10 | 10 | 3 | 9 | 10 | 1 | 9 | 10 | 2 | 10 | 0 | 10 | 0 | 9 | 10 | 9 | 9 | 9 | 9 | 9 | 7 | 5 | 7 | 9 | 10 | 9 | 0 |
| Giant foxtail | 10 | 10 | 10 | 10 | 3 | 9 | 10 | 2 | 9 | 10 | 3 | 10 | 0 | 10 | 0 | 10 | 10 | 9 | 10 | 8 | 9 | 10 | 7 | 7 | 10 | 10 | 10 | 10 | 8 |
| Morningglory | 0 | 0 | 0 | 0 | 0 | 0 | 3 | 0 | 0 | 1 | 0 | 2 | 0 | 0 | 0 | 0 | 0 | 0 | 9 | 0 | 0 | 0 | 0 | 0 | 3 | 0 | 4 | 3 | 0 |
| Nutsedge | 0 | 0 | 0 | 0 | 0 | 0 | 0 | 0 | 0 | 5 | 0 | — | 0 | — | 0 | 0 | 0 | 0 | 0 | 0 | 0 | 0 | 0 | 0 | — | 0 | 3 | 0 | 0 |
| Rape | 0 | 0 | 0 | 4 | 3 | 0 | 7 | 0 | 0 | 10 | 0 | 2 | 0 | 3 | 0 | 0 | 2 | 2 | 10 | 0 | 0 | 0 | 0 | 0 | 3 | 0 | 9 | 0 | 0 |
| Redroot pigweed | 0 | 0 | 0 | 7 | 0 | 0 | 10 | 4 | 8 | 10 | 0 | 10 | 0 | 10 | 0 | 6 | 10 | 10 | 10 | 0 | 0 | 3 | 0 | 0 | 10 | 10 | 10 | 5 | 0 |
| Soybean | 0 | 0 | 0 | 0 | 0 | 0 | 0 | 0 | 0 | 0 | 0 | 2 | 0 | 0 | 0 | 0 | 3 | 0 | 2 | 0 | 0 | 2 | 0 | 0 | 0 | 0 | 2 | 0 | 0 |
| Sugarbeets | 0 | 0 | 0 | 0 | 0 | 0 | 8 | 0 | 1 | 5 | 0 | 0 | 0 | 7 | 0 | 0 | 0 | 0 | 8 | 0 | 0 | 0 | 0 | 0 | 5 | 0 | 6 | 3 | 0 |
| Velvetleaf | 0 | 0 | 0 | 7 | 0 | 0 | 6 | 0 | 2 | 7 | 0 | 6 | 0 | 7 | 0 | 0 | 4 | 3 | 10 | 0 | 0 | 0 | 0 | 0 | 6 | 6 | 6 | 2 | 0 |
| Wheat | 0 | 0 | 0 | 5 | 0 | 0 | 2 | 0 | 0 | 5 | 0 | 0 | 0 | 7 | 0 | 0 | 0 | 0 | 7 | 0 | 0 | 0 | 0 | 0 | 6 | 0 | 2 | 0 | 0 |
| Wild oats | 3 | 2 | 0 | 3 | 2 | 0 | 8 | 0 | 3 | 10 | 0 | 3 | 0 | 9 | 0 | 0 | 4 | 0 | 10 | 7 | 0 | 0 | 0 | 0 | 8 | 2 | 10 | 3 | 0 |

TABLE B-continued

| Rate 500 g/ha | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| | 458 | 459 | 460 | 461 | 462 | 463 | 465 | 466 | 467 | 468 | 469 | 470 | 471 | 472 | 473 | 474 | 476 | 477 | 478 | 479 | 480 | 482 | 485 | 486 | 487 | 488 | 489 | 490 | 492 |
| Preemergence | | | | | | | | | | | | | | | | | | | | | | | | | | | | | |
| B. signalgrass | 4 | 1 | 0 | 0 | 0 | 2 | 5 | 9 | 2 | 4 | 10 | 6 | 10 | 10 | 0 | 7 | 0 | 6 | 10 | 9 | 9 | 0 | 8 | 8 | 5 | 10 | 9 | 8 | 0 |
| Bedstraw | — | — | — | — | 0 | — | — | 2 | 0 | — | — | — | — | — | — | 0 | — | 3 | — | 0 | — | — | — | — | — | — | — | — | 0 |
| Blackgrass | 9 | 6 | 3 | 0 | 0 | 4 | 10 | 8 | 2 | 9 | 10 | — | 10 | 10 | 3 | 9 | 0 | 8 | 10 | 9 | 9 | 4 | 9 | 10 | 9 | 10 | 10 | 9 | 0 |
| Cocklebur | 0 | 0 | 0 | 0 | 0 | 0 | 0 | 0 | 6 | 0 | 0 | 0 | 0 | 2 | 0 | 0 | 0 | 0 | 0 | — | 0 | 0 | 0 | 0 | 0 | 0 | 0 | — | 0 |
| Corn | 3 | 0 | 2 | 0 | 0 | 0 | 2 | 4 | 0 | 2 | 9 | 0 | 3 | 7 | 0 | 4 | 0 | 0 | 0 | 3 | 3 | 0 | 7 | 8 | 0 | 6 | 5 | 5 | 0 |
| Crabgrass | 10 | 10 | 9 | 3 | 0 | 2 | 10 | 10 | 8 | 9 | 10 | 9 | 10 | 10 | 7 | 10 | 0 | 10 | 10 | 10 | 10 | 8 | 10 | 10 | 10 | 10 | 10 | 10 | 3 |
| Giant foxtail | 10 | 10 | 9 | 3 | 0 | 10 | 10 | 10 | 9 | 10 | 10 | 3 | 10 | 10 | 7 | 10 | 0 | 10 | 10 | 10 | 10 | 9 | 10 | 10 | 10 | 10 | 10 | 10 | 9 |
| Morningglory | 0 | 0 | 0 | 0 | 0 | 0 | 0 | 0 | 0 | 2 | 1 | 0 | 0 | 5 | 0 | 0 | 0 | 0 | 2 | 4 | 0 | 0 | 4 | 0 | 0 | 0 | 1 | 0 | 0 |
| Nutsedge | 0 | 0 | 0 | 0 | 0 | 0 | 0 | — | 0 | 0 | — | 0 | 0 | 10 | — | 0 | 0 | 0 | 3 | — | 0 | 0 | 0 | 0 | 0 | 0 | 0 | 0 | 0 |
| Rape | 4 | 0 | 0 | 0 | 0 | 0 | 5 | 3 | 7 | 6 | 10 | 0 | 10 | 4 | 0 | 4 | 0 | 2 | 6 | 4 | 0 | 0 | 2 | 6 | 0 | 10 | 9 | 8 | 0 |
| Redroot pigweed | 8 | 7 | 0 | 0 | 0 | 10 | 10 | 10 | 9 | 10 | 10 | 0 | 10 | 10 | 10 | 7 | 4 | 8 | 10 | 6 | 9 | 0 | 9 | 9 | 10 | 10 | 10 | 8 | 0 |
| Soybean | 2 | 0 | 0 | 0 | 0 | 0 | — | 4 | 0 | 0 | 2 | 0 | 0 | 3 | 0 | 0 | 0 | 4 | 0 | 0 | 1 | 0 | 0 | 2 | 0 | 1 | 3 | 4 | 0 |
| Sugarbeets | 8 | 0 | 0 | 0 | 0 | 0 | 5 | 4 | 2 | 6 | 10 | 0 | 4 | 6 | 0 | 3 | 0 | 0 | 7 | 4 | 0 | 0 | 2 | 6 | 0 | 7 | 5 | 5 | 0 |
| Velvetleaf | 6 | 0 | 0 | 0 | 0 | 2 | 8 | 4 | 1 | 4 | 7 | 0 | 6 | 7 | 0 | 0 | 0 | 0 | 7 | 5 | 0 | 2 | 3 | 0 | 0 | 6 | 7 | 4 | 4 |
| Wheat | 2 | 0 | 0 | 0 | 0 | 0 | 0 | 1 | 0 | 6 | 6 | 0 | 0 | 0 | 0 | 0 | 0 | 0 | 8 | 7 | 2 | 0 | 5 | 0 | 0 | 5 | 6 | 4 | 0 |
| Wild oats | 10 | 0 | 0 | 0 | 0 | 0 | 3 | 7 | 0 | 7 | 10 | 3 | 7 | 10 | 0 | 8 | 0 | 7 | 10 | 7 | 7 | 3 | 8 | 8 | 6 | 10 | 9 | 8 | 0 |

| Rate 500 g/ha | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| | 493 | 494 | 495 | 496 | 497 | 498 | 499 | 500 | 501 | 502 | 503 | 504 | 505 | 506 | 508 | 509 | 510 | 511 | 512 | 513 | 514 | 515 | 516 | 517 | 519 | 520 | 521 | 522 | 523 |
| Preemergence | | | | | | | | | | | | | | | | | | | | | | | | | | | | | |
| B. signalgrass | 0 | 0 | 0 | 8 | 0 | 0 | 2 | 10 | 10 | 10 | 9 | 10 | 6 | 0 | 8 | 9 | 9 | 0 | 10 | 9 | 10 | 9 | 10 | 0 | 0 | 0 | 9 | 9 | 5 |
| Bedstraw | 0 | 0 | — | — | 0 | — | — | 10 | 9 | 10 | 10 | 8 | 9 | 4 | 0 | 9 | 4 | 0 | 3 | 4 | 0 | 3 | 7 | 0 | 0 | 0 | 0 | 10 | 0 |
| Blackgrass | 0 | 0 | 0 | 2 | 0 | 0 | 1 | 10 | 9 | 10 | 10 | 10 | 6 | 9 | 8 | 10 | 8 | 0 | 10 | 10 | 7 | 8 | 10 | 4 | 4 | 0 | 3 | 9 | 7 |
| Cocklebur | 0 | 0 | 0 | 0 | 0 | 0 | 4 | 2 | 3 | 9 | 3 | 0 | 2 | 0 | 0 | 5 | 0 | 0 | 0 | 0 | 0 | 0 | 0 | 0 | 0 | 0 | 0 | — | 0 |
| Corn | 0 | 0 | 0 | 0 | 0 | 0 | 0 | 8 | — | 9 | 9 | 6 | 6 | 0 | 4 | 6 | 5 | 0 | 3 | 4 | 5 | 5 | 0 | 3 | 0 | 0 | 3 | 9 | 9 |
| Crabgrass | 2 | 0 | 0 | 9 | 0 | 5 | 8 | 10 | 9 | 10 | 9 | 10 | 8 | 6 | 10 | 10 | 9 | 10 | 9 | 5 | 10 | 9 | 10 | 7 | 10 | 10 | 10 | 10 | 10 |
| Giant foxtail | 10 | 0 | 0 | 9 | 0 | 8 | 10 | 10 | 10 | 10 | 10 | 10 | 10 | 8 | 10 | 10 | 10 | 10 | 10 | 10 | 10 | 10 | 10 | 10 | 10 | 10 | 10 | 10 | 10 |
| Morningglory | 0 | 0 | 0 | 0 | 0 | 0 | 0 | 9 | 5 | 4 | 7 | 4 | 3 | 0 | 0 | 3 | 5 | 0 | 0 | 3 | 0 | 0 | 0 | 0 | 0 | 0 | 0 | 4 | 0 |
| Nutsedge | 0 | 0 | 0 | 0 | 0 | 0 | 0 | 10 | 9 | — | 2 | 8 | 8 | 10 | — | 0 | 0 | 0 | — | 0 | 0 | 0 | 0 | 0 | 0 | 0 | 0 | 10 | 0 |
| Rape | 0 | 0 | 0 | 0 | 0 | 0 | 0 | 10 | 10 | 9 | 9 | 10 | 9 | 8 | 3 | 10 | 9 | 0 | 5 | 7 | 8 | 10 | 9 | 4 | 0 | 0 | 2 | 6 | 7 |
| Redroot pigweed | 0 | 0 | 0 | 8 | 0 | 0 | 0 | 10 | 10 | 10 | 10 | 10 | 10 | 10 | 10 | 10 | 10 | 8 | 10 | 10 | 10 | 10 | 10 | 10 | 0 | 0 | 0 | 10 | 9 |
| Soybean | 0 | 1 | 0 | 0 | 0 | 0 | 0 | 8 | 8 | 5 | 7 | 5 | 5 | 0 | 0 | — | 0 | 0 | 0 | 5 | 0 | 0 | 0 | 0 | 0 | 0 | 0 | 10 | 0 |
| Sugarbeets | 0 | 0 | 0 | 0 | 0 | 0 | 0 | 10 | 8 | 7 | 9 | 9 | 8 | 0 | 6 | 7 | 7 | 0 | 5 | 0 | 6 | 7 | 7 | 5 | 0 | 0 | 3 | 7 | 9 |
| Velvetleaf | 0 | 0 | 0 | 0 | 0 | 0 | 0 | 10 | 5 | 8 | 8 | 10 | 10 | 0 | 0 | 8 | 6 | 0 | 0 | 0 | 5 | 6 | 7 | 3 | 0 | 0 | 3 | 9 | 5 |
| Wheat | 0 | 0 | 0 | 0 | 0 | 0 | 0 | 8 | 8 | 7 | 8 | 8 | 8 | 2 | 2 | 7 | 0 | 0 | 6 | 7 | 4 | 7 | 5 | 6 | 0 | 0 | 0 | 8 | 4 |
| Wild oats | 0 | 0 | 0 | 0 | 0 | 0 | 0 | 10 | 10 | 10 | 9 | 10 | 9 | 7 | 7 | 9 | 7 | 2 | 10 | 10 | 6 | 9 | 9 | 5 | 0 | 0 | 2 | 9 | 0 |

TABLE B-continued

| Rate 500 g/ha | 524 | 525 | 526 | 527 | 528 | 531 | 532 | 533 | 534 | 535 | 536 | 540 | 541 | 543 | 544 | 545 | 546 | 549 | 550 | 551 | 552 | 553 | 554 | 555 | 556 | 557 | 558 | 559 | 560 |
|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | |
| Preemergence | | | | | | | | | | | | | | | | | | | | | | | | | | | | | |
| B. signalgrass | — | 9 | — | — | — | — | 0 | 9 | — | 0 | 0 | 8 | 5 | 6 | 8 | 5 | 2 | 0 | 10 | 9 | 9 | 8 | 10 | 8 | 9 | 7 | 6 | 9 | 9 |
| Bedstraw | — | 0 | — | — | — | — | 0 | 0 | — | 0 | 0 | 0 | 3 | 0 | 9 | 10 | — | 5 | 3 | 10 | 8 | 10 | 0 | 0 | 0 | 0 | 0 | 0 | 8 |
| Blackgrass | — | 8 | — | — | — | — | 0 | 9 | — | 0 | 0 | 9 | 2 | 2 | 6 | 9 | 3 | — | 9 | 9 | 8 | — | 7 | 8 | 10 | 8 | 9 | 10 | 9 |
| Cocklebur | 2 | — | 0 | 3 | 0 | 0 | 0 | 0 | 0 | 0 | 0 | 10 | — | 10 | 0 | 0 | 0 | 0 | 0 | 0 | 0 | 10 | 0 | 9 | 0 | 0 | 0 | 2 | 0 |
| Corn | 9 | 8 | 2 | 0 | 0 | 0 | 0 | 6 | 3 | 2 | 0 | 2 | 0 | 0 | 0 | 0 | 0 | 0 | 0 | 5 | 0 | 3 | 2 | 2 | 0 | 0 | 0 | 6 | 5 |
| Crabgrass | 10 | 10 | 10 | 10 | 10 | 10 | 10 | 10 | 10 | 10 | 2 | 10 | 10 | — | 10 | 10 | 10 | 10 | 10 | 10 | 10 | 10 | 10 | 10 | 10 | 10 | 9 | 10 | 10 |
| Giant foxtail | 10 | 10 | 10 | 10 | 10 | 10 | 10 | 10 | 10 | 10 | 10 | 10 | 10 | 9 | 10 | 10 | 10 | 10 | 10 | 10 | 10 | 10 | 10 | 10 | 10 | 10 | 10 | 10 | 10 |
| Morningglory | 2 | 6 | 2 | 2 | 3 | 0 | 0 | 0 | 0 | 2 | — | 0 | 0 | 0 | 0 | 8 | 0 | 0 | 0 | 0 | 0 | 2 | 0 | 0 | 0 | 0 | 0 | 8 | 3 |
| Nutsedge | 4 | 0 | 0 | 0 | 0 | 0 | 0 | 0 | — | 0 | 0 | 0 | 0 | 8 | 0 | 0 | 0 | 0 | 6 | 0 | 0 | 0 | 0 | 0 | 0 | 0 | 0 | — | 10 |
| Rape | — | 4 | — | — | — | — | 0 | 7 | — | 3 | 0 | 7 | 0 | 0 | 6 | 2 | 0 | 0 | 9 | 9 | 0 | — | 3 | 0 | 8 | 2 | 2 | 10 | 8 |
| Redroot pigweed | — | 3 | — | 4 | — | — | 0 | 8 | — | 4 | 0 | 10 | 0 | — | 10 | 10 | — | — | 10 | 10 | 4 | — | 10 | 7 | 5 | 6 | 2 | 10 | 9 |
| Soybean | 0 | 0 | 0 | 0 | 0 | 0 | 0 | 0 | — | 0 | 0 | 0 | 0 | 2 | 0 | 0 | 0 | 0 | 0 | 0 | 0 | 3 | 3 | 2 | 0 | 0 | 0 | 3 | 3 |
| Sugarbeets | — | 9 | 8 | 6 | — | — | 3 | 7 | — | — | 3 | 4 | 2 | — | 4 | 6 | 2 | 3 | 8 | 9 | 5 | — | 6 | 5 | 0 | 4 | 2 | 9 | 7 |
| Velvetleaf | 4 | 4 | 3 | 2 | 0 | 5 | 4 | 5 | 3 | — | 0 | 0 | 0 | 0 | 0 | 0 | 2 | 0 | 4 | 4 | 0 | 2 | 0 | 6 | 3 | 0 | 0 | 9 | 5 |
| Wheat | — | 3 | — | — | — | — | 0 | 0 | — | 0 | 0 | 0 | 3 | 0 | 0 | 2 | 0 | 0 | 2 | 6 | 4 | — | 6 | 3 | 4 | 3 | 2 | 9 | 8 |
| Wild oats | — | 8 | — | — | — | — | 0 | 9 | — | 0 | 0 | 8 | 5 | 0 | 4 | 6 | 3 | 3 | 8 | 9 | 6 | — | 9 | 7 | 6 | 7 | 2 | 9 | 7 |

| Rate 500 g/ha | 561 | 562 | 563 | 564 | 565 | 566 | 567 | 568 | 569 | 570 | 571 | 572 | 573 | 574 | 575 | 576 | 577 | 578 | 579 | 580 | 581 | 582 | 584 | 585 | 586 | 587 | 588 | 589 | 590 |
|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | |
| Preemergence | | | | | | | | | | | | | | | | | | | | | | | | | | | | | |
| B. signalgrass | 9 | 10 | 10 | 7 | 0 | 9 | 9 | 9 | 9 | 0 | 9 | 0 | 10 | 9 | — | 9 | 7 | 9 | 3 | 9 | 9 | 4 | 9 | 9 | 10 | 7 | 8 | 0 | 0 |
| Bedstraw | 8 | 0 | 0 | 0 | 0 | 0 | 0 | 8 | 0 | 0 | 0 | 0 | 0 | 0 | 0 | 0 | 0 | 0 | 0 | 6 | 9 | 6 | 9 | 8 | — | 2 | — | — | — |
| Blackgrass | 9 | 10 | 9 | 9 | 0 | 10 | 7 | 9 | 9 | 0 | 9 | 0 | 6 | 2 | 2 | 9 | 6 | 4 | 0 | 7 | 7 | 0 | — | 8 | 10 | 8 | 8 | 0 | 0 |
| Cocklebur | 0 | 2 | 2 | 0 | 0 | 0 | 0 | 2 | 0 | 0 | 0 | 0 | 0 | 0 | 0 | 0 | 0 | 3 | 0 | 3 | 0 | 0 | 0 | 3 | 0 | 0 | 0 | 0 | 0 |
| Corn | 5 | 9 | 9 | 9 | 0 | 9 | 5 | 9 | 9 | 0 | 0 | 0 | 3 | 0 | 3 | 2 | 3 | 4 | 3 | 5 | 9 | 0 | 3 | 5 | 0 | 0 | 5 | 0 | 0 |
| Crabgrass | 9 | 10 | 9 | 9 | 2 | 10 | 9 | 10 | 9 | 10 | 3 | 0 | 10 | 9 | 9 | 9 | 10 | 10 | 10 | 9 | 9 | 7 | 9 | 10 | 10 | 9 | 9 | 9 | 3 |
| Giant foxtail | 7 | 8 | 10 | 9 | 2 | 10 | 9 | 10 | 10 | 9 | 9 | 7 | 10 | 10 | 10 | 9 | 10 | 10 | 10 | 10 | 10 | 8 | 10 | 10 | 10 | 9 | 10 | 10 | 7 |
| Morningglory | 4 | 8 | 3 | 4 | 0 | 0 | 0 | 6 | 0 | 0 | 4 | 0 | 4 | 0 | 2 | 0 | 9 | 0 | 0 | 0 | 6 | 2 | 3 | 5 | 4 | 0 | 0 | 0 | 0 |
| Nutsedge | — | — | — | — | 0 | 0 | 0 | 3 | 0 | 0 | 0 | 0 | 0 | 0 | — | 8 | 0 | 0 | 3 | 5 | 8 | 0 | 0 | 10 | 2 | 0 | 0 | 9 | 0 |
| Rape | 9 | 10 | 9 | 3 | 0 | 10 | 0 | 7 | 9 | 0 | 2 | 0 | 3 | 0 | 2 | 7 | 0 | 4 | 0 | 8 | 7 | 3 | 4 | 10 | 4 | 1 | 0 | 0 | 0 |
| Redroot pigweed | 9 | 10 | 9 | 3 | 9 | 10 | 9 | 8 | 10 | 8 | 9 | 5 | 9 | 9 | 10 | 10 | 0 | 10 | 3 | 10 | 10 | 9 | 9 | 10 | 10 | 2 | 9 | 0 | 0 |
| Soybean | 2 | 9 | 6 | 8 | 0 | 0 | 0 | 9 | 0 | 0 | 3 | 0 | 0 | 0 | 0 | 0 | 0 | 0 | 0 | 0 | 7 | 0 | 0 | 3 | 0 | 2 | 5 | 0 | 0 |
| Sugarbeets | 8 | 9 | 4 | 3 | 0 | 6 | 2 | 8 | 3 | 2 | 0 | 0 | 2 | 3 | 2 | 6 | 0 | 3 | 0 | 5 | 9 | 0 | 5 | 6 | 8 | 0 | 6 | 0 | 0 |
| Velvetleaf | 2 | 7 | 7 | 8 | 0 | 2 | 0 | 7 | 7 | 0 | 0 | 2 | 3 | 2 | 2 | 3 | 4 | 2 | 0 | 5 | 10 | 4 | 5 | 6 | 7 | 2 | 5 | 0 | 0 |
| Wheat | 9 | 9 | 10 | 7 | 0 | 7 | 0 | 5 | 4 | 0 | 9 | 0 | 0 | 0 | 0 | 8 | 0 | 2 | 0 | 5 | 5 | 0 | 3 | 3 | 8 | 3 | 8 | 0 | 0 |
| Wild oats | 9 | 10 | 10 | 7 | 0 | 10 | 0 | 8 | 9 | 0 | 7 | 0 | 0 | 3 | 2 | 8 | 0 | 2 | 0 | 5 | 8 | 0 | 9 | 9 | 10 | 9 | 7 | 0 | 0 |

TABLE B-continued

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 591 | 592 | 593 | 594 | 595 | 596 | 598 | 599 | 600 | 601 | 602 | 603 | 604 | 605 | 606 | 607 | 608 | 609 | 610 | 611 | 612 | 613 | 615 | 616 | 617 | 618 | 619 | 620 | 621 |
| Preemergence | | | | | | | | | | | | | | | | | | | | | | | | | | | | | |
| B. signalgrass | 0 | 0 | 0 | 7 | 9 | 0 | 0 | 3 | 0 | 8 | 7 | 0 | 0 | 0 | 0 | 8 | 10 | 10 | 10 | 10 | 10 | 9 | 0 | 1 | 5 | 0 | 3 | 0 | 0 |
| Bedstraw | — | — | — | 9 | 10 | 0 | 0 | 0 | 0 | — | 0 | — | 0 | 0 | — | — | — | — | 10 | 10 | 10 | — | 0 | 0 | 0 | 0 | 0 | 0 | 0 |
| Blackgrass | 0 | 0 | 0 | 9 | 10 | 0 | 0 | 6 | 0 | 9 | 9 | 0 | 0 | 0 | 3 | 9 | 9 | 10 | 10 | 10 | 10 | 10 | 4 | 6 | 6 | 0 | 0 | 0 | 0 |
| Cocklebur | 0 | 0 | 0 | 2 | 0 | 0 | 0 | 0 | 0 | 0 | 0 | 0 | 0 | 0 | 0 | 0 | 0 | 3 | 3 | 1 | 0 | 8 | 0 | 0 | 0 | 0 | 0 | 0 | 0 |
| Corn | 0 | 0 | 0 | 4 | 6 | 0 | 0 | 0 | 0 | 3 | 2 | 0 | 0 | 0 | 0 | 6 | 1 | 9 | 8 | 9 | 9 | 9 | 0 | 0 | 0 | 0 | 2 | 0 | 0 |
| Crabgrass | 0 | 2 | 0 | 9 | 10 | 6 | 0 | 8 | 0 | 10 | 10 | 0 | 1 | 10 | 8 | 9 | 10 | 9 | 10 | 10 | 10 | 10 | 0 | 1 | 8 | 2 | 8 | 6 | 8 |
| Giant foxtail | 0 | 0 | 0 | 10 | 9 | 4 | 0 | 10 | 0 | 10 | 10 | 0 | 7 | 10 | 9 | 10 | 10 | 10 | 10 | 10 | 10 | 10 | 7 | 5 | 9 | 0 | 8 | 9 | 10 |
| Morningglory | 0 | 0 | 0 | 6 | 6 | 0 | 0 | 0 | 0 | 0 | 0 | 0 | 0 | — | 0 | 0 | 4 | 5 | 8 | 6 | 10 | 10 | 0 | 0 | 0 | 0 | 0 | 0 | 0 |
| Nutsedge | 0 | 0 | 2 | 6 | 4 | 0 | 0 | 0 | 0 | — | 0 | 0 | 0 | 0 | 0 | 0 | 0 | 4 | 3 | 2 | 3 | 2 | 0 | 0 | 5 | 0 | — | 0 | 0 |
| Rape | 0 | 0 | 0 | 9 | 10 | 0 | 0 | 0 | 0 | 5 | 3 | 0 | 0 | 0 | 0 | 7 | 7 | 10 | 10 | 10 | 10 | 10 | 0 | 3 | 0 | 0 | 0 | 0 | 0 |
| Redroot pigweed | 0 | 0 | 0 | 10 | 10 | 0 | 0 | 0 | 0 | 10 | 8 | 0 | 0 | 0 | 0 | 10 | 7 | 10 | 10 | 10 | 10 | 10 | 4 | 10 | 0 | 0 | 0 | 0 | 0 |
| Soybean | 0 | 0 | 0 | 4 | 4 | 0 | 0 | 0 | 0 | 1 | 0 | 0 | 0 | 0 | 0 | 4 | 4 | 7 | 8 | 7 | 3 | 2 | 0 | 0 | 0 | 0 | 0 | 0 | 3 |
| Sugarbeets | 0 | 0 | 0 | 8 | 9 | 0 | 0 | 20 | 0 | 5 | 5 | 0 | 0 | 0 | 0 | 5 | 4 | 8 | 8 | 6 | 7 | 10 | 6 | 1 | 0 | 0 | 0 | 0 | 0 |
| Velvetleaf | 0 | 0 | 0 | 7 | 9 | 0 | 0 | 0 | 0 | 7 | 6 | 0 | 0 | 0 | 0 | 8 | 7 | 9 | 10 | 8 | 8 | 8 | 0 | 4 | 0 | 0 | 4 | 0 | 0 |
| Wheat | 0 | 0 | 0 | 2 | 6 | 0 | 0 | 0 | 0 | 6 | 0 | 0 | 0 | 0 | 0 | 3 | 0 | 6 | 6 | 7 | 8 | 6 | 0 | 0 | 0 | 0 | 0 | 0 | 0 |
| Wild oats | 0 | 0 | 0 | 5 | 9 | 0 | 0 | 0 | 0 | 8 | 8 | 0 | 0 | 0 | 3 | 6 | 6 | 10 | 10 | 8 | 10 | 10 | 0 | 2 | 3 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 622 | 623 | 624 | 625 | 627 | 628 | 629 | 630 | 631 | 632 | 633 | 634 | 635 | 636 | 637 | 638 | 639 | 640 | 641 | 642 | 643 | 645 | 646 | 647 | 648 | 649 | 650 | 652 | 653 |
| Preemergence | | | | | | | | | | | | | | | | | | | | | | | | | | | | | |
| B. signalgrass | 4 | 2 | 8 | 10 | 9 | 10 | 8 | 8 | 10 | 10 | 6 | 10 | 9 | 9 | 8 | 8 | 7 | 9 | 8 | 8 | 6 | 0 | 0 | 10 | 5 | 0 | 4 | 2 | 0 |
| Bedstraw | 2 | — | 3 | — | 8 | 10 | 8 | 7 | — | — | — | — | 9 | 9 | 4 | — | — | — | — | — | — | — | — | — | 0 | 0 | 5 | 0 | 0 |
| Blackgrass | 6 | — | 9 | 9 | 10 | 10 | 10 | 10 | 10 | 10 | 7 | 9 | 8 | 7 | 9 | 9 | 2 | 8 | 8 | 7 | 8 | 0 | 0 | 10 | 5 | 0 | 3 | 2 | 0 |
| Cocklebur | — | 0 | 0 | 0 | 7 | 7 | 7 | 0 | 2 | 0 | 0 | 0 | 0 | 0 | 0 | 9 | 2 | 0 | 0 | 0 | 0 | 0 | 0 | 7 | 0 | 0 | 0 | 3 | 0 |
| Corn | 0 | 0 | 6 | 3 | 9 | 9 | 8 | 5 | 9 | 5 | 2 | 0 | 8 | 3 | 0 | 8 | 0 | 0 | 2 | 0 | 0 | 0 | 0 | 10 | 0 | 0 | 0 | 0 | 0 |
| Crabgrass | 8 | — | 9 | 10 | 9 | 10 | 10 | 9 | 9 | 9 | 9 | 10 | 9 | 10 | 10 | 10 | 9 | 10 | 9 | 10 | 10 | 5 | 0 | 9 | 9 | 9 | 9 | 9 | 8 |
| Giant foxtail | 9 | 9 | 10 | 10 | 10 | 10 | 10 | 10 | 10 | 10 | 10 | 10 | 10 | 10 | 10 | 10 | 9 | 9 | 9 | 10 | 10 | 7 | 0 | 10 | 9 | 9 | 10 | 9 | 8 |
| Morningglory | 0 | 0 | 0 | 3 | 8 | 7 | 4 | 2 | 7 | 5 | 0 | 0 | 6 | 2 | 0 | 7 | 0 | 0 | 0 | 0 | 0 | 0 | 0 | 7 | 0 | 0 | 1 | 0 | 0 |
| Nutsedge | 3 | 0 | 0 | 0 | 10 | 9 | 5 | 3 | 8 | 0 | 0 | 0 | 4 | 10 | 0 | 8 | 0 | 0 | 3 | 0 | 0 | 0 | 0 | — | 0 | 0 | 5 | 3 | 0 |
| Rape | 0 | 2 | 7 | 4 | 10 | 9 | 9 | 0 | 8 | 4 | 4 | 7 | 9 | 10 | 3 | 10 | 10 | 6 | 0 | 9 | 6 | 0 | 0 | 10 | 0 | 0 | 2 | 0 | 0 |
| Redroot pigweed | 10 | 0 | 10 | 8 | 10 | 10 | 10 | 10 | 10 | 10 | 4 | 10 | 10 | 10 | 10 | 10 | 10 | 7 | 7 | 8 | 5 | 4 | 0 | 10 | 2 | 0 | 9 | 0 | 3 |
| Soybean | 0 | 0 | 7 | 0 | 5 | 7 | 0 | 3 | 9 | 0 | 0 | 0 | 2 | 4 | 0 | 3 | 3 | 0 | 0 | 0 | 0 | 0 | 0 | 1 | 0 | 0 | 0 | 0 | 0 |
| Sugarbeets | 3 | 2 | 8 | 0 | 9 | 7 | 7 | 7 | 8 | 0 | 0 | 6 | 9 | 7 | 5 | 10 | 6 | 6 | 0 | 4 | 0 | 0 | 0 | 8 | 0 | 0 | 4 | 0 | 0 |
| Velvetleaf | 4 | 0 | 8 | 6 | 10 | 10 | 8 | 7 | 9 | 7 | 0 | 6 | 7 | 4 | 2 | 10 | 3 | 0 | 0 | 3 | 0 | 0 | 0 | 9 | 0 | 0 | 0 | 1 | 0 |
| Wheat | 0 | 0 | 7 | 3 | 5 | 10 | 3 | 8 | 9 | 0 | 0 | 0 | 4 | 2 | 0 | 7 | 0 | 2 | 0 | 0 | 0 | 0 | 0 | 8 | 0 | 0 | 0 | 0 | 0 |
| Wild oats | 3 | 2 | 6 | 5 | 5 | 10 | 9 | 8 | 9 | 3 | 5 | 7 | 9 | 5 | 3 | 10 | 3 | 6 | 5 | 4 | 1 | 0 | 0 | 10 | 0 | 0 | 0 | 0 | 2 |

TABLE B-continued

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 654 | 655 | 657 | 658 | 659 | 660 | 661 | 662 | 663 | 664 | 665 | 666 | 667 | 668 | 669 | 670 | 671 | 672 | 673 | 674 | 675 | 676 | 677 | 678 | 679 | 680 | 681 | 682 | 683 |
| Preemergence | | | | | | | | | | | | | | | | | | | | | | | | | | | | | |
| B. signalgrass | 7 | 0 | 10 | 8 | 8 | 4 | 4 | 7 | 0 | 8 | 8 | 8 | 8 | 9 | 10 | 10 | 9 | 8 | 8 | 8 | 10 | 8 | 5 | 0 | 0 | 0 | 0 | 8 | 9 |
| Bedstraw | 0 | 0 | — | — | — | — | — | — | — | — | — | — | — | — | 9 | 9 | — | 0 | 6 | 0 | 10 | — | — | — | — | — | — | 0 | 0 |
| Blackgrass | 7 | 3 | 9 | 7 | 9 | 7 | 7 | 9 | 0 | 8 | 9 | 10 | 10 | 10 | 10 | 10 | 10 | 8 | 9 | 9 | 10 | 8 | 0 | 0 | 0 | 4 | 3 | 9 | 9 |
| Cocklebur | 0 | 0 | 2 | 0 | 0 | 0 | 0 | 2 | 0 | 3 | 0 | 0 | 0 | 0 | 0 | 2 | 1 | — | 2 | 0 | 0 | 0 | 0 | 0 | 0 | 0 | 0 | 0 | 0 |
| Corn | 0 | 0 | 8 | 2 | 9 | 0 | 0 | 3 | 0 | 0 | 3 | 10 | 10 | 9 | 9 | 9 | 9 | 0 | 6 | 8 | 9 | 6 | 0 | 0 | 0 | 0 | 0 | 0 | 3 |
| Crabgrass | 9 | 9 | 9 | 9 | 10 | 9 | 9 | 6 | 0 | 10 | 10 | 10 | 10 | 8 | 10 | 10 | 9 | 10 | 10 | 9 | 10 | 7 | 7 | 1 | 1 | 3 | 7 | 9 | 10 |
| Giant foxtail | 9 | 9 | 9 | 10 | 10 | 10 | 10 | 10 | 9 | 10 | 10 | 10 | 10 | 10 | 10 | 10 | 10 | 10 | 10 | 10 | 10 | 10 | 10 | 4 | 8 | 4 | 9 | 10 | 10 |
| Morningglory | 0 | 0 | 6 | 0 | 6 | 0 | 0 | 1 | 7 | 4 | 4 | 3 | 6 | 5 | 0 | 8 | 8 | 2 | 2 | 7 | 6 | 0 | 0 | 0 | 0 | 0 | 0 | 3 | 2 |
| Nutsedge | 0 | 0 | 6 | 2 | 0 | 0 | 0 | 7 | 0 | 0 | — | — | 7 | 0 | 6 | 10 | 6 | 0 | 6 | 6 | 7 | 0 | 0 | 0 | 0 | 0 | 0 | 0 | 0 |
| Rape | 0 | 0 | 10 | 8 | 10 | 4 | 0 | 0 | 4 | 6 | 9 | 10 | 10 | 9 | 9 | 10 | 8 | 8 | 2 | 8 | 10 | 6 | 0 | 0 | 0 | 0 | 0 | 7 | 0 |
| Redroot pigweed | 5 | 4 | 10 | 10 | 10 | 10 | 8 | 7 | 7 | 10 | 10 | 10 | 10 | 10 | 10 | 10 | 10 | 8 | 10 | 10 | 10 | 10 | — | 0 | 1 | 3 | 3 | 7 | 6 |
| Soybean | 0 | 0 | 3 | 3 | 2 | 0 | 1 | 0 | 2 | 0 | 2 | 4 | 7 | 6 | 6 | 9 | 3 | 0 | 0 | 7 | 4 | 3 | 0 | 0 | 0 | 0 | 0 | 0 | 0 |
| Sugarbeets | 0 | 0 | 9 | 7 | 5 | 0 | 0 | 0 | 0 | 5 | 7 | 8 | 10 | 9 | 9 | 9 | 9 | 8 | 3 | 9 | 10 | 8 | 0 | 0 | 0 | 0 | 0 | 7 | 0 |
| Velvetleaf | 0 | 0 | 10 | 5 | 7 | 0 | 0 | 2 | 3 | 5 | 7 | 8 | 10 | 8 | 0 | 8 | 9 | 4 | 8 | 10 | 10 | 7 | 0 | 2 | 0 | 0 | 0 | 0 | 0 |
| Wheat | 0 | 0 | 7 | 3 | 7 | 0 | 0 | 0 | 3 | 5 | 4 | 7 | 6 | 7 | 8 | 9 | 8 | 0 | — | 8 | 9 | 5 | 0 | 0 | 0 | 0 | 0 | 0 | 0 |
| Wild oats | 2 | 0 | 8 | 4 | 9 | 3 | 0 | 9 | 0 | 7 | 8 | 9 | 10 | 9 | 10 | 9 | 5 | 7 | 8 | 10 | 10 | 4 | 0 | 0 | 0 | 0 | 0 | 8 | 8 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 684 | 685 | 686 | 687 | 689 | 691 | 692 | 693 | 694 | 695 | 696 | 697 | 698 | 699 | 700 | 701 | 702 | 703 | 704 | 706 | 707 | 708 | 709 | 710 | 711 | 712 | 713 | 714 | 715 |
| Preemergence | | | | | | | | | | | | | | | | | | | | | | | | | | | | | |
| B. signalgrass | 5 | 9 | 9 | 10 | 10 | 10 | 9 | 0 | 8 | 6 | 9 | 5 | 5 | 10 | 10 | 0 | 8 | 8 | 9 | 10 | 10 | 0 | 0 | 9 | 8 | 8 | 9 | 10 | 10 |
| Bedstraw | 0 | 0 | 0 | 0 | 5 | — | 1 | 0 | — | 0 | 0 | 0 | 0 | 0 | 8 | 0 | 0 | 0 | — | — | 10 | 0 | 0 | 7 | 7 | 5 | 6 | — | — |
| Blackgrass | 7 | 10 | 9 | 10 | 10 | 10 | 10 | 2 | 10 | 9 | 9 | 6 | 8 | 10 | 10 | 6 | 10 | 8 | 10 | 10 | 10 | 5 | 0 | 10 | 9 | 9 | 9 | 9 | 10 |
| Cocklebur | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 4 | 2 | 9 | 7 | 3 | 0 | 1 | 3 | 5 | 0 | 0 | 9 | 6 | 0 | 4 | 0 | 2 | 7 | 2 | 0 | 0 | 5 | 5 | 0 | 6 | 6 | 8 |
| Crabgrass | 9 | 9 | 10 | 9 | 10 | 10 | 10 | 0 | 10 | 9 | 10 | 9 | 9 | 10 | 10 | 10 | 10 | 10 | 8 | 9 | 10 | 10 | 7 | 10 | 10 | 10 | 10 | 10 | 10 |
| Giant foxtail | 10 | 10 | 10 | 10 | 10 | 10 | 10 | 2 | 10 | 10 | 10 | 10 | 10 | 10 | 10 | 10 | 10 | 10 | 8 | 10 | 10 | 9 | 7 | 10 | 10 | 10 | 10 | 10 | 10 |
| Morningglory | 4 | 1 | 0 | 7 | 4 | 0 | 2 | 0 | 2 | 0 | 0 | 4 | 0 | 6 | 6 | 0 | 0 | 3 | 1 | 2 | 6 | 0 | 0 | 4 | 5 | 0 | 0 | 3 | 6 |
| Nutsedge | — | — | 0 | 4 | — | 0 | 0 | 0 | 0 | 0 | — | 0 | 0 | 0 | 0 | 0 | 0 | 0 | — | 4 | 0 | — | — | — | — | 0 | 0 | — | 0 |
| Rape | 0 | 6 | 6 | 8 | 9 | 8 | 6 | 0 | 4 | 0 | 3 | 0 | 8 | 9 | 5 | 2 | 2 | 2 | 5 | 7 | 10 | 0 | 0 | 9 | 8 | 8 | 8 | 10 | 10 |
| Redroot pigweed | 7 | 8 | 7 | 9 | 8 | 9 | 9 | 0 | 9 | 5 | 8 | 0 | 0 | 6 | 3 | 0 | 5 | 5 | 9 | 10 | 10 | 6 | 7 | 10 | 10 | 9 | 10 | 10 | 10 |
| Soybean | 0 | 0 | 0 | 4 | 2 | 2 | 0 | 0 | 0 | 0 | 0 | 0 | 2 | 2 | 0 | 0 | 0 | 0 | 0 | 4 | 0 | 0 | 0 | 6 | 1 | 0 | 3 | 0 | 6 |
| Sugarbeets | 0 | 6 | 5 | 9 | 7 | 8 | 3 | 0 | 1 | 0 | 6 | 0 | 0 | 7 | 6 | 0 | 3 | 2 | 5 | 7 | 8 | 0 | 3 | 8 | 8 | 8 | 8 | 6 | 8 |
| Velvetleaf | 5 | 0 | 0 | 9 | 4 | 0 | 1 | 0 | 2 | 0 | 4 | 0 | 0 | 7 | 6 | 4 | 2 | 0 | 0 | 7 | 8 | 6 | 0 | 8 | 7 | 6 | 6 | 0 | 7 |
| Wheat | 0 | 0 | 0 | 7 | 7 | 3 | 0 | 0 | 0 | 6 | 2 | 2 | 3 | 7 | 0 | 0 | 0 | 3 | 6 | 7 | 6 | 0 | 0 | 8 | 8 | 0 | 5 | 6 | 6 |
| Wild oats | 4 | 4 | 7 | 10 | 9 | 9 | 9 | 0 | 7 | 6 | 8 | 2 | 9 | 10 | 10 | 2 | 9 | 2 | 9 | 8 | 10 | 0 | 0 | 10 | 10 | 8 | 9 | 6 | 10 |

TABLE B-continued

| Rate 500 g/ha | COMPOUND 717 | 718 | 719 | 720 | 721 | 723 | 724 | 725 | 726 | 728 | 729 | 730 | 732 | 733 | 734 | 735 | 736 | 737 | 738 | 739 | 740 | 741 | 742 | 743 | 744 | 745 | 746 | 747 | 748 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 7 | 9 | 9 | 10 | 10 | 2 | 0 | 4 | 9 | 9 | 10 | 9 | 0 | 10 | 9 | 10 | 8 | 9 | 10 | — | — | 2 | 0 | 8 | 9 | 10 | — | 9 | 10 |
| Bedstraw | 0 | 0 | 0 | 10 | 10 | 0 | 0 | 0 | 0 | 2 | 8 | 4 | 0 | 0 | 0 | 0 | 8 | 0 | 0 | 10 | 0 | 5 | 0 | 8 | 8 | 5 | — | 0 | 0 |
| Blackgrass | 10 | 10 | 10 | 10 | 10 | 2 | 0 | 7 | 9 | 10 | 10 | 10 | 0 | 10 | 10 | 10 | 9 | 10 | 10 | 10 | 9 | 0 | 0 | 9 | 9 | 9 | — | 8 | 9 |
| Cocklebur | 0 | 0 | 0 | — | 2 | 0 | 0 | 0 | 0 | 0 | 0 | 0 | 0 | 0 | 0 | 0 | 2 | 0 | 0 | 0 | 0 | — | 0 | 10 | 0 | 0 | 4 | 0 | 0 |
| Corn | 9 | 3 | 5 | — | 8 | 0 | 0 | 0 | 2 | 0 | 9 | 9 | 0 | 0 | 9 | 9 | 2 | 6 | 9 | 2 | 0 | 0 | 0 | 0 | 7 | 2 | 4 | 9 | 4 |
| Crabgrass | 10 | 10 | 9 | 10 | 9 | 9 | 7 | 8 | 10 | 7 | 10 | 10 | 0 | 9 | 10 | 10 | 9 | 10 | 10 | 10 | 9 | 10 | 0 | 9 | 10 | 10 | 10 | 10 | 10 |
| Giant foxtail | 10 | 10 | 10 | 10 | 10 | 10 | 9 | 10 | 10 | 8 | 10 | 10 | 0 | 9 | 10 | 10 | 9 | 10 | 10 | 10 | 10 | 10 | 0 | 9 | 10 | 10 | 10 | 10 | 10 |
| Morningglory | 0 | 0 | 3 | 2 | 5 | 0 | 0 | 3 | 1 | 2 | 8 | 2 | 0 | 2 | 6 | 2 | 6 | 3 | 4 | 0 | 0 | 0 | 0 | 0 | 0 | 3 | 8 | 7 | 0 |
| Nutsedge | 0 | 0 | 0 | 0 | 3 | — | 0 | 0 | 0 | — | 2 | 3 | 0 | — | — | — | 10 | 0 | 8 | 0 | 0 | 0 | 0 | 9 | 7 | 5 | 5 | 2 | 2 |
| Rape | 4 | 3 | 6 | 9 | 10 | 0 | 0 | 0 | 7 | 8 | 10 | 7 | 0 | 5 | 7 | 8 | 2 | 6 | 8 | 2 | — | 0 | 0 | 9 | 9 | 7 | — | — | 7 |
| Redroot pigweed | 8 | 8 | 10 | 10 | 10 | 0 | 0 | 3 | 8 | 9 | 10 | 10 | 0 | 7 | 8 | 9 | 2 | 8 | 8 | 10 | 10 | 7 | 0 | 10 | 9 | 10 | — | — | 10 |
| Soybean | 0 | 0 | 0 | 0 | 7 | 0 | 0 | 0 | 0 | 0 | 2 | 3 | 0 | 0 | 7 | 0 | 2 | 0 | 0 | 0 | 0 | 0 | 0 | 0 | 0 | 0 | 5 | 9 | 0 |
| Sugarbeets | 3 | 2 | 8 | 8 | 8 | 0 | 0 | 2 | 5 | 4 | 7 | 7 | 0 | 0 | 8 | 7 | 3 | 6 | 8 | 4 | 5 | 4 | 0 | 6 | 7 | 4 | — | — | 7 |
| Velvetleaf | 0 | 0 | 0 | 3 | 10 | 0 | 0 | 0 | 0 | 0 | 8 | 6 | 0 | 1 | 7 | 3 | 4 | 5 | 8 | 3 | 3 | 3 | 0 | 3 | 2 | 6 | 8 | 7 | 0 |
| Wheat | 0 | 2 | 5 | 5 | 8 | 0 | 0 | 0 | 0 | 7 | 6 | 0 | 0 | 0 | 9 | 2 | 8 | 2 | 8 | 3 | 3 | 4 | 0 | 5 | 5 | 0 | — | — | 5 |
| Wild oats | 10 | 8 | 9 | 9 | 10 | 0 | 0 | 6 | 9 | 10 | 10 | 9 | 0 | 8 | 10 | 10 | 9 | 9 | 10 | 4 | 6 | 7 | 0 | 9 | 9 | 8 | — | — | 8 |

| Rate 500 g/ha | COMPOUND 749 | 750 | 751 | 752 | 753 | 754 | 755 | 756 | 757 | 758 | 759 | 760 | 761 | 762 | 763 | 764 | 765 | 766 | 767 | 772 | 773 | 774 | 775 | 777 | 778 | 780 | 790 | 791 | 792 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 10 | — | — | — | 9 | 9 | 0 | 3 | 7 | 8 | 8 | 10 | 3 | 9 | 8 | 10 | 7 | 10 | — | 0 | 0 | 0 | — | — | — | 4 | 9 | — | — |
| Bedstraw | 4 | — | 10 | 10 | 3 | 0 | 0 | 0 | 0 | 4 | 0 | 6 | 0 | 0 | 8 | 8 | 8 | 9 | 8 | 0 | 0 | 0 | 2 | 0 | 10 | 2 | 9 | — | — |
| Blackgrass | 9 | — | 10 | 10 | 9 | 9 | 0 | 7 | 7 | 9 | 8 | 9 | 0 | 9 | 10 | 9 | 9 | 9 | 10 | 0 | 0 | 0 | 10 | 10 | 10 | 9 | 10 | — | — |
| Cocklebur | 0 | 0 | 0 | 0 | 2 | 0 | 0 | 0 | 0 | 0 | 0 | 0 | 0 | 0 | 0 | 8 | 0 | 0 | 0 | 0 | 0 | 0 | 0 | 0 | 0 | 2 | 10 | 0 | 0 |
| Corn | 0 | 6 | 9 | 0 | 0 | 0 | 0 | 0 | 0 | 3 | 0 | 4 | 0 | 0 | 0 | 9 | 2 | 3 | 5 | 0 | 0 | 0 | 3 | 0 | 0 | 9 | 9 | 0 | 4 |
| Crabgrass | 10 | 10 | 10 | 10 | 9 | 9 | 0 | 9 | 9 | 10 | 9 | 10 | 3 | 0 | 9 | 10 | 10 | 10 | 10 | 0 | 0 | 0 | 10 | 10 | 10 | 10 | 10 | 10 | 10 |
| Giant foxtail | 10 | 10 | 10 | 10 | 9 | 9 | 2 | 9 | 9 | 10 | 10 | 10 | 9 | 9 | 9 | 10 | 10 | 10 | 10 | 0 | 0 | 0 | 10 | 10 | 10 | 10 | 10 | 10 | 10 |
| Morningglory | 0 | 6 | 5 | 0 | 0 | 1 | 0 | 0 | 0 | 0 | 0 | 0 | 0 | 0 | 5 | 2 | 0 | 3 | 0 | 0 | 0 | 0 | 2 | 5 | 0 | 2 | 7 | 0 | 0 |
| Nutsedge | — | 9 | 0 | 0 | 0 | 10 | 0 | 7 | 0 | — | 0 | 0 | 0 | 6 | 5 | 4 | 0 | 4 | 0 | 0 | 0 | 0 | 0 | — | 9 | — | 0 | 0 | 0 |
| Rape | 5 | — | 9 | 5 | 7 | 8 | 0 | 0 | 0 | 8 | 4 | 5 | 0 | 0 | 9 | 10 | 8 | 9 | 10 | 0 | 0 | 0 | 0 | 2 | 5 | 6 | 8 | — | — |
| Redroot pigweed | 9 | — | 10 | 10 | 10 | 9 | 0 | 0 | 3 | 10 | 4 | 9 | 0 | 3 | 10 | 10 | 10 | 10 | 10 | 0 | 0 | 0 | 9 | 2 | 9 | 6 | 10 | — | — |
| Soybean | 3 | 5 | 9 | 0 | 0 | 0 | 0 | 0 | 0 | 0 | 0 | 0 | 0 | 0 | 0 | 5 | 0 | 0 | 2 | 0 | 0 | 0 | 1 | 0 | 1 | 3 | 2 | 5 | 0 |
| Sugarbeets | 7 | — | 7 | 3 | 8 | 7 | 0 | 0 | 0 | 8 | 5 | 6 | 0 | 4 | 6 | 8 | 9 | 9 | 9 | 0 | 0 | 0 | 3 | 3 | 6 | 6 | 7 | — | — |
| Velvetleaf | 2 | 7 | 8 | 2 | 2 | 5 | 0 | 0 | 0 | 7 | 0 | 0 | 0 | 5 | 3 | 8 | 7 | 10 | 2 | 0 | 0 | 0 | 0 | 0 | 0 | 5 | 7 | 0 | 5 |
| Wheat | 1 | — | 10 | 0 | 3 | 9 | 0 | 0 | 3 | 7 | 8 | 3 | 0 | 0 | 7 | 7 | 8 | 10 | 5 | 0 | 0 | 0 | 8 | 9 | 8 | 9 | 9 | — | — |
| Wild oats | 8 | — | 10 | 8 | 9 | 9 | 0 | 0 | 5 | 9 | 8 | 6 | 0 | 0 | 9 | 7 | 9 | 10 | 9 | 0 | 0 | 0 | 8 | 9 | 8 | 9 | 10 | — | — |

TABLE B-continued

| Rate 250 g/ha | 7 | 18 | 30 | 35 | 36 | 46 | 47 | 69 | 70 | 71 | 72 | 78 | 86 | 87 | 93 | 94 | 103 | 105 | 107 | 108 | 109 | 111 | 113 | 116 | 117 | 118 | 119 | 121 | 122 | 123 | 124 | 125 | 129 | 131 |
|---|---|---|---|---|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | | | | | | |
| Pre-emergence | | | | | | | | | | | | | | | | | | | | | | | | | | | | | | | | | | |
| Barnyardgrass | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 9 | 9 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 5 | 7 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 8 | 5 |
| S. Flatsedge | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 9 | 8 |

| Rate 250 g/ha | 139 | 146 | 154 | 165 | 166 | 177 | 180 | 181 | 182 | 183 | 184 | 185 | 186 | 187 | 189 | 190 | 191 | 192 | 193 | 194 | 195 | 196 | 197 | 198 | 200 | 201 | 202 | 203 | 204 |
|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | |
| Pre-emergence | | | | | | | | | | | | | | | | | | | | | | | | | | | | | |
| Barnyardgrass | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| Rate 250 g/ha | 205 | 206 | 207 | 208 | 210 | 211 | 212 | 213 | 214 | 215 | 216 | 217 | 218 | 219 | 220 | 221 | 222 | 223 | 224 | 225 | 226 | 227 | 228 | 229 | 230 | 231 | 232 | 233 | 234 |
|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | |
| Pre-emergence | | | | | | | | | | | | | | | | | | | | | | | | | | | | | |
| Barnyardgrass | 0 | 0 | 2 | 0 | 0 | 0 | 0 | 0 | 0 | 0 | 0 | 0 | 0 | 8 | 2 | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| Rate 250 g/ha | 235 | 236 | 237 | 238 | 239 | 240 | 241 | 242 | 243 | 244 | 245 | 246 | 247 | 248 | 249 | 250 | 251 | 252 | 253 | 254 | 255 | 256 | 257 | 258 | 259 | 264 | 265 | 266 | 267 |
|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| Rate 250 g/ha | 268 | 269 | 270 | 271 | 272 | 273 | 274 | 276 | 277 | 278 | 279 | 280 | 281 | 282 | 283 | 284 | 285 | 286 | 288 | 289 | 290 | 291 | 293 | 294 | 295 | 296 | 297 | 298 | 299 |
|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | |
| Pre-emergence | | | | | | | | | | | | | | | | | | | | | | | | | | | | | |
| Barnyardgrass | 0 | 0 | 0 | 9 | 0 | 4 | 0 | 8 | 1 | 0 | 0 | 0 | 4 | 9 | 6 | 4 | 7 | 0 | 9 | 3 | 4 | 4 | 0 | 9 | 0 | 0 | 0 | 0 | 6 |
| Ducksalad | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rice | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 3 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 3 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 300 | 301 | 302 | 303 | 304 | 305 | 306 | 307 | 308 | 309 | 310 | 311 | 312 | 313 | 314 | 315 | 316 | 317 | 318 | 319 | 320 | 321 | 322 | 323 | 324 | 325 | 326 | 327 | 328 |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 4 | 0 | 0 | 0 | 0 | 8 | 9 | 0 | 0 | 0 | 0 | 0 | 7 | 0 | 0 | 0 | 8 | 3 | 0 |
| Ducksalad | 0 | 0 | 0 | 0 | 0 | 0 | 0 | 0 | 0 | 0 | 0 | 0 | 0 | 0 | 0 | 0 | 3 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 1 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 9 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 329 | 330 | 331 | 332 | 333 | 334 | 335 | 336 | 337 | 338 | 339 | 340 | 341 | 346 | 350 | 351 | 353 | 354 | 358 | 365 | 366 | 367 | 368 | 369 | 370 | 371 | 372 | 373 | 374 |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 9 | 10 | 9 | 0 | 0 | 0 | 0 | 0 | 9 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 2 | 9 | 0 | 0 | 0 | 2 | 0 | 8 | 0 | 0 | 0 | 2 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 375 | 376 | 378 | 379 | 380 | 381 | 382 | 383 | 384 | 385 | 387 | 388 | 389 | 390 | 391 | 392 | 393 | 394 | 395 | 401 | 402 | 403 | 404 | 405 | 406 | 407 | 408 | 409 | 411 |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 0 | 0 | 0 | 4 | 0 | 0 | 0 | 6 | 0 | 0 | 8 | 2 | 9 | 0 | 0 | 0 | 0 | 3 | 9 |
| Ducksalad | 0 | 0 | 0 | 0 | 0 | 0 | 0 | 0 | 0 | 0 | 0 | 0 | 0 | 0 | 0 | 0 | 0 | 3 | 0 | 0 | 0 | 0 | 5 | 0 | 0 | 0 | 0 | 0 | 2 |
| Rice | 0 | 0 | 0 | 0 | 0 | 0 | 0 | 0 | 0 | 0 | 0 | 0 | — | 1 | 0 | 0 | 0 | 1 | 0 | 0 | 2 | 0 | 7 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 8 | 0 | 0 | 0 | 0 | 8 | 0 | 0 | 0 | 0 | 2 | 9 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 414 | 437 | 438 | 439 | 441 | 442 | 443 | 444 | 445 | 446 | 447 | 448 | 449 | 450 | 451 | 452 | 453 | 454 | 455 | 456 | 457 | 458 | 459 | 460 | 461 | 462 | 463 | 465 | 466 |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

TABLE B-continued

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 467 | 468 | 469 | 470 | 471 | 472 | 473 | 474 | 476 | 477 | 478 | 479 | 480 | 482 | 483 | 465 | 486 | 487 | 488 | 489 | 490 | 492 | 493 | 494 | 495 | 496 | 498 | 499 | 509 |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 521 | 528 | 529 | 531 | 532 | 538 | 539 | 546 | 550 | 552 | 556 | 558 | 560 | 561 | 567 | 568 | 570 | 577 | 580 | 586 | 587 | 588 | 569 | 590 | 591 | 592 | 593 | 594 | 595 |
| Pre-emergence | | | | | | | | | | | | | | | | | | | | | | | | | | | | | |
| Barnyardgrass | 0 | 0 | 0 | 0 | 9 | 0 | 0 | 0 | 0 | 0 | 0 | 2 | 0 | 0 | 0 | 3 | 0 | 0 | 0 | 0 | 0 | 0 | 0 | 0 | 0 | 0 | 0 | 0 | 0 |
| Ducksalad | 0 | 0 | 0 | 0 | 9 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | — | — | 0 | 9 | — | 0 | — | 0 | — | 0 | — | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 9 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 596 | 598 | 599 | 600 | 601 | 602 | 603 | 604 | 605 | 606 | 607 | 608 | 609 | 610 | 611 | 612 | 613 | 614 | 615 | 616 | 617 | 618 | 619 | 620 | 621 | 622 | 623 | 624 | 625 |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 627 | 628 | 629 | 630 | 631 | 632 | 633 | 634 | 636 | 637 | 638 | 639 | 640 | 641 | 642 | 643 | 644 | 645 | 646 | 647 | 649 | 650 | 651 | 655 | 656 | 657 | 658 | 659 | 660 |
| Pre-emergence | | | | | | | | | | | | | | | | | | | | | | | | | | | | | |
| Barnyardgrass | 0 | 0 | 0 | 0 | 4 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | — | — | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 661 | 662 | 663 | 664 | 665 | 666 | 667 | 668 | 671 | 674 | 675 | 676 | 677 | 678 | 679 | 680 | 681 | 692 | 694 | 695 | 696 | 697 | 699 | 701 | 702 | 705 | 706 | 715 | 720 |
| Pre-emergence | | | | | | | | | | | | | | | | | | | | | | | | | | | | | |
| Barnyardgrass | 0 | 0 | 0 | 0 | 2 | 0 | 0 | 0 | 0 | 0 | 0 | 0 | 0 | 0 | 0 | 0 | 0 | 9 | 0 | 0 | 0 | 0 | 8 | 0 | 0 | 2 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 9 | 0 | 0 | 0 | 0 | 9 | 0 | 0 | 0 | 0 | 0 | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rice | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 5 | — | 0 | 2 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 9 | 0 | 0 | 0 | 0 | 9 | 0 | 0 | 0 | 0 | 0 | 0 |

| | COMPOUND | | | | | |
|---|---|---|---|---|---|---|
| Rate 250 g/ha | 721 | 724 | 740 | 741 | 758 | 765 |
| Pre-emergence | | | | | | |
| Barnyardgrass | 0 | 0 | 0 | 0 | 0 | 0 |
| Ducksalad | 0 | 0 | 0 | 0 | 0 | 0 |
| Rice | 0 | 0 | 0 | 0 | 0 | 0 |
| S. Flatsedge | 0 | 0 | 0 | 0 | 0 | 0 |

| | COMPOUND | | | | | | | | | | | | | | | | | | | | | |
|---|---|---|---|---|---|---|---|---|---|---|---|---|---|---|---|---|---|---|---|---|---|---|
| Rate 250 g/ha | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| Postemergence | | | | | | | | | | | | | | | | | | | | | | |
| B. signalgrass | 7 | 0 | 0 | 0 | 0 | 2 | 0 | 0 | 0 | 4 | 0 | 0 | 2 | 0 | 0 | 0 | 0 | 0 | 0 | 0 | 0 | 2 |
| Barnyardgrass | 0 | 0 | 0 | 3 | 0 | 0 | 0 | 0 | 0 | 0 | 0 | 0 | 0 | 0 | 0 | 0 | 2 | 9 | 0 | 0 | 0 | 0 |
| Bedstraw | 0 | 0 | 0 | 7 | 4 | 0 | 0 | 2 | 0 | 0 | 0 | 0 | 0 | 0 | 0 | 0 | 3 | 7 | 7 | 4 | 0 | 4 |
| Blackgrass | 0 | 4 | 0 | 5 | 5 | 7 | 2 | 2 | 0 | 4 | 0 | 0 | 3 | 0 | 0 | 0 | 4 | 3 | 0 | 0 | 0 | 3 |
| Cocklebur | 0 | 0 | 0 | 6 | 5 | 0 | 0 | 0 | 0 | 1 | 0 | 0 | 0 | 0 | 5 | 0 | 2 | 1 | 0 | 0 | 5 | 0 |
| Corn | 0 | 3 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 5 | 0 | 0 | 8 | 6 | 2 | 1 | 0 | 0 | 9 | 0 | 0 | 5 | 0 | 3 | 0 | 6 | 7 | 0 | 3 | 0 | 9 |
| Ducksalad | 0 | 0 | 0 | 2 | 0 | 0 | 0 | 0 | 0 | 0 | 0 | 0 | 0 | 0 | 0 | 0 | 0 | 7 | 0 | 0 | 0 | 0 |
| Giant foxtail | 2 | 7 | 3 | 3 | 7 | 4 | 3 | 0 | 0 | 8 | 0 | 0 | 2 | 0 | 0 | 0 | 2 | 1 | 0 | 1 | 0 | 4 |
| Morningglory | 0 | 0 | 0 | 3 | 3 | 2 | — | 0 | 0 | 2 | 0 | 0 | 0 | 4 | 6 | 1 | 7 | 2 | 0 | 7 | 2 | 2 |
| Nutsedge | 0 | 0 | 0 | 0 | 0 | — | — | — | — | 0 | 0 | 0 | 0 | 0 | 0 | 0 | 0 | 0 | 0 | 0 | 0 | 0 |
| Rape | 0 | 0 | 0 | 0 | 5 | 0 | 0 | 0 | 0 | 0 | 0 | 0 | 0 | 0 | 0 | 0 | 0 | 0 | 0 | 0 | 0 | 0 |
| Redroot pigweed | 4 | 0 | 0 | 5 | 7 | 0 | 0 | 0 | 0 | 0 | 0 | 0 | 0 | 3 | 2 | 0 | 2 | 1 | 2 | 3 | 0 | 2 |
| Rice | 0 | 0 | 0 | 0 | 0 | 0 | 0 | 0 | 0 | 0 | 0 | 0 | 0 | 0 | 0 | 0 | 0 | 2 | 0 | 0 | 0 | 0 |
| S. Flatsedge | 0 | 0 | 0 | 2 | 0 | 0 | 0 | 0 | 0 | 0 | 0 | 0 | 0 | 0 | 0 | 0 | 0 | 6 | 0 | 0 | 0 | 4 |
| Soybean | 0 | 1 | 1 | 4 | 5 | 3 | 1 | 4 | 0 | 3 | 0 | 0 | 2 | 2 | 2 | 1 | 2 | 3 | 3 | 3 | 2 | 4 |
| Sugarbeets | 0 | 0 | 0 | 3 | 4 | 0 | 0 | 0 | 0 | 0 | 0 | 0 | 0 | 0 | 0 | 0 | 3 | 0 | 0 | — | 0 | 0 |
| Velvetleaf | 0 | 0 | 0 | 3 | 5 | 0 | 0 | 0 | 0 | 0 | 0 | 0 | 0 | 0 | 0 | 0 | 0 | 1 | 0 | 0 | 0 | 0 |
| Wheat | 0 | 0 | 0 | 0 | 1 | 0 | 0 | 0 | 0 | 0 | 0 | 0 | 0 | 0 | 0 | 0 | 0 | 0 | 0 | 0 | 0 | 0 |
| Wild oats | 0 | 0 | 0 | 0 | 1 | 0 | 0 | 0 | 0 | 0 | 0 | 0 | 0 | 0 | 0 | 0 | 0 | 0 | 0 | 0 | 0 | 1 |

| | COMPOUND | | | | | | | | | | | | | | | | | | | | | |
|---|---|---|---|---|---|---|---|---|---|---|---|---|---|---|---|---|---|---|---|---|---|---|
| Rate 250 g/ha | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
| Postemergence | | | | | | | | | | | | | | | | | | | | | | |
| B. signalgrass | 0 | 3 | 0 | 0 | 0 | 0 | 0 | 0 | 0 | 0 | 1 | 0 | 0 | 0 | 0 | 0 | 0 | 0 | 0 | 0 | 0 | 0 |
| Barnyardgrass | 0 | 0 | 0 | 0 | 8 | 9 | 0 | 0 | 0 | 8 | 3 | 0 | 0 | 2 | — | 0 | — | — | 0 | 0 | 0 | 0 |
| Bedstraw | 0 | 8 | 7 | 0 | 0 | 8 | 0 | 0 | 0 | 0 | 2 | 6 | 3 | — | 0 | 0 | — | — | — | 0 | 0 | 0 |
| Blackgrass | 0 | 3 | 6 | 0 | 0 | 6 | 0 | 2 | 9 | 7 | 5 | 6 | 1 | 4 | 0 | 7 | 0 | 4 | 3 | 0 | 0 | 0 |
| Cocklebur | 0 | 1 | 2 | 0 | 0 | 3 | 0 | 0 | 1 | 0 | 6 | 0 | 4 | 0 | 0 | 1 | 0 | 0 | 1 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 6 | 9 | 9 | 1 | 0 | 9 | 0 | 9 | 9 | 3 | 2 | 3 | 1 | 3 | 0 | 8 | 3 | 6 | 5 | 0 | 2 | 0 |
| Ducksalad | 0 | 0 | 0 | 0 | 0 | 0 | 0 | 0 | 0 | 0 | 0 | 0 | 0 | 0 | — | 0 | — | — | 0 | 0 | 0 | 0 |
| Giant foxtail | 2 | 3 | 8 | 0 | 0 | 4 | 0 | 3 | 4 | 0 | 3 | 2 | 1 | 3 | 0 | 4 | 0 | 1 | 1 | 0 | 0 | 0 |
| Morningglory | 10 | 10 | 2 | 3 | 0 | 2 | 0 | 6 | 3 | 8 | 9 | 5 | 8 | 9 | 0 | 1 | 0 | 6 | 2 | 0 | 3 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 3 | 0 | 0 | 0 | 0 | 0 | 0 | 0 | 0 | 0 | 0 | 0 |
| Redroot pigweed | 0 | 6 | 0 | 0 | 0 | 2 | 0 | 0 | 0 | 0 | 3 | 6 | 9 | 7 | 0 | 0 | 0 | 2 | 3 | 0 | — | 0 |
| Rice | 0 | 0 | 0 | 0 | 0 | 2 | 0 | 0 | 0 | 0 | 2 | 0 | 0 | 0 | — | 0 | — | — | 0 | 0 | 0 | 0 |
| S. Flatsedge | 0 | 0 | 0 | 0 | 0 | 0 | 0 | 0 | 0 | 2 | 2 | 0 | 0 | 0 | — | 0 | — | — | 0 | 0 | 0 | 0 |
| Soybean | 4 | 3 | 3 | 2 | 2 | 3 | 2 | 2 | 1 | 2 | 3 | 0 | 1 | 5 | 0 | 0 | 4 | 4 | 4 | 0 | 3 | 1 |
| Sugarbeets | 0 | 0 | 0 | 0 | 0 | 1 | 0 | 0 | 0 | 0 | 6 | 0 | — | 0 | 0 | 0 | 0 | 2 | 0 | 0 | 1 | 0 |
| Velvetleaf | 0 | 0 | 0 | 0 | 0 | 0 | 0 | 0 | 0 | 0 | 2 | 2 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 0 | 0 | 1 | 0 | 0 | 0 | 0 | 0 | 0 | 0 | 1 | 0 | 0 | 0 | 0 | 0 | 0 | 0 | 0 | 0 | 0 | 0 |

| | COMPOUND | | | | | | | | | | | | | | | | | | | | | |
|---|---|---|---|---|---|---|---|---|---|---|---|---|---|---|---|---|---|---|---|---|---|---|
| Rate 250 g/ha | 45 | 46 | 47 | 48 | 49 | 50 | 51 | 52 | 53 | 54 | 55 | 56 | 57 | 58 | 59 | 60 | 61 | 62 | 63 | 64 | 65 | 66 |
| Postemergence | | | | | | | | | | | | | | | | | | | | | | |
| B. signalgrass | 0 | 0 | 0 | 0 | 0 | — | 0 | 0 | 0 | 0 | 0 | 0 | 0 | 0 | 0 | 0 | 0 | 2 | 0 | 0 | 0 | 0 |
| Barnyardgrass | 0 | 0 | — | 0 | — | 0 | 0 | 0 | 0 | 0 | 0 | 0 | 0 | 0 | 0 | 0 | 0 | 0 | 0 | 0 | 0 | 0 |
| Bedstraw | — | — | 6 | 0 | 5 | — | 0 | 8 | — | 4 | 0 | 0 | 0 | 0 | 0 | 7 | 6 | 2 | 3 | 0 | 0 | 0 |
| Blackgrass | 4 | 6 | 0 | 0 | 0 | — | 0 | 0 | 0 | 0 | 0 | 0 | 0 | 0 | 0 | 0 | 6 | 0 | 0 | 0 | 0 | 2 |
| Cocklebur | 2 | 1 | 2 | 0 | 0 | — | 0 | 0 | 4 | 0 | 0 | 0 | 0 | 0 | 0 | 0 | 0 | 6 | 0 | 0 | 0 | 0 |

| | COMPOUND | | | | | | | | | | | | | | | | | | | | | |
|---|---|---|---|---|---|---|---|---|---|---|---|---|---|---|---|---|---|---|---|---|---|---|
| Rate 250 g/ha | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
| Postemergence | | | | | | | | | | | | | | | | | | | | | | |
| B. signalgrass | 0 | 0 | 0 | 0 | 0 | 0 | 0 | 0 | 6 | 5 | 0 | 4 | 0 | 0 | 4 | 0 | 0 | — | 0 | 0 | 0 | 0 |
| Barnyardgrass | 0 | 0 | — | — | — | — | 0 | 0 | 0 | 0 | 0 | 3 | 3 | 8 | 0 | 0 | 0 | 0 | 0 | 0 | 0 | — |
| Bedstraw | 7 | 7 | 5 | 0 | 0 | 0 | 7 | 5 | 0 | 2 | 0 | 4 | 7 | 0 | 2 | 0 | 0 | — | 0 | 6 | 6 | 9 |
| Blackgrass | 0 | 2 | 0 | 0 | 0 | 0 | 0 | 0 | 7 | 6 | 0 | 3 | 3 | 3 | 4 | 0 | 0 | — | 0 | 1 | 1 | 6 |
| Cocklebur | 1 | 2 | 0 | 0 | 0 | 0 | 0 | 0 | 1 | 3 | 0 | 2 | 2 | 0 | 0 | 0 | 1 | — | 0 | 2 | 2 | 1 |

TABLE B-continued

| | | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Corn | 0 | 0 | 0 | 0 | 0 | — | 0 | 3 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | — | 0 | 00 | 0 | 0 |
| Crabgrass | 2 | 3 | 0 | 3 | 8 | — | 3 | 5 | 6 | 2 | 0 | 0 | 0 | 0 | 2 | 1 | 0 | 0 | 0 | 0 | 0 | 0 | 0 | 0 | 1 | 0 | 0 | 0 | 2 | 4 | 9 | 8 | 0 | 5 | 4 | 9 | 8 | 0 | 0 | — | 0 | 5 | 5 | 9 |
| Ducksalad | 0 | 0 | — | 0 | — | 0 | 0 | 0 | 0 | 0 | 0 | 0 | 0 | 0 | 0 | 0 | 0 | 0 | 0 | 0 | 0 | 0 | 0 | 0 | — | — | — | — | 0 | 0 | 0 | 0 | 0 | 0 | 0 | 0 | 0 | 0 | 0 | 0 | 0 | 0 | 0 | — |
| Giant foxtail | 9 | 1 | 0 | 2 | 9 | — | 0 | 3 | 3 | 3 | 0 | 0 | 0 | 0 | 2 | 0 | 0 | 0 | 0 | 0 | 0 | 0 | 0 | 0 | 0 | 0 | 0 | 0 | 2 | — | 8 | 7 | 0 | 3 | 3 | 3 | 6 | 0 | 0 | — | 0 | 3 | 3 | 3 |
| Morningglory | 0 | 1 | 4 | 0 | 0 | — | 0 | 1 | 5 | 2 | 2 | 1 | 1 | 0 | 1 | 2 | 4 | 2 | 4 | 0 | 1 | 1 | 2 | 2 | 0 | 0 | 0 | 0 | 4 | 3 | 1 | 4 | 0 | 10 | 7 | 10 | 2 | 10 | 0 | — | 0 | 7 | 7 | 10 |
| Nutsedge | 0 | 0 | 0 | 0 | 0 | — | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 |
| Rape | 0 | 0 | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 3 | 0 | 0 | 0 | — | 0 | 2 | 2 | 0 |
| Redroot pigweed | 0 | 0 | 0 | 0 | 0 | — | 0 | 0 | 6 | 2 | 0 | 0 | 0 | 0 | 0 | 4 | 3 | 0 | 0 | 0 | 0 | 0 | 0 | 0 | 0 | 0 | 0 | 0 | 0 | 0 | 0 | 0 | 0 | 3 | 3 | 4 | 0 | 0 | 0 | — | 0 | 5 | 5 | 3 |
| Rice | 0 | 0 | — | 0 | — | 0 | 0 | 0 | 0 | 0 | 0 | 0 | 0 | 0 | 0 | 0 | 0 | 0 | 0 | 0 | 0 | 0 | 0 | 0 | — | — | — | — | 0 | 0 | 2 | 3 | 0 | 0 | 0 | 0 | 0 | 0 | 0 | 0 | 0 | 0 | 0 | — |
| S. Flatsedge | 0 | 0 | — | 0 | — | 0 | 0 | 0 | 0 | 0 | 0 | 0 | 0 | 0 | 0 | 0 | 0 | 0 | 0 | 0 | 0 | 2 | 0 | 0 | — | — | — | — | 0 | 0 | 0 | 0 | 0 | 0 | 4 | 3 | 0 | 0 | 0 | 0 | 0 | 0 | 0 | — |
| Soybean | 1 | 1 | 2 | 1 | 1 | — | 0 | 2 | 3 | 0 | 1 | 2 | 1 | 1 | 2 | 3 | 4 | 2 | 2 | 0 | 1 | 2 | 1 | 3 | 2 | 0 | 0 | 0 | 3 | 1 | 2 | 2 | 1 | 2 | 1 | 1 | 1 | 0 | 0 | — | 0 | 2 | 2 | 1 |
| Sugarbeets | 1 | 0 | 0 | 0 | 0 | — | 0 | 0 | 1 | 0 | 0 | 0 | 0 | 0 | 0 | 0 | 2 | 0 | 2 | 0 | 0 | 0 | 0 | 0 | 0 | 0 | 0 | 0 | 0 | 0 | 0 | 2 | 0 | 4 | 4 | 4 | 0 | 0 | 0 | — | 0 | 3 | 3 | 7 |
| Velvetleaf | 0 | 0 | 0 | 0 | 0 | — | 0 | 0 | 1 | 0 | 0 | 0 | 0 | 0 | 0 | 0 | 0 | 2 | 5 | 0 | 3 | 0 | 0 | 2 | 0 | 0 | 0 | 0 | 4 | 4 | 0 | 3 | 0 | 3 | 0 | 0 | 0 | 0 | 2 | — | 0 | 0 | 0 | 0 |
| Wheat | 0 | 0 | 2 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | — | 0 | 0 | 0 | 0 |
| Wild oats | 0 | 0 | 0 | 0 | 0 | — | 0 | 1 | 0 | 0 | 0 | 0 | 0 | 0 | 0 | 0 | 0 | 3 | 0 | 0 | 0 | 0 | 0 | 0 | 0 | 0 | 0 | 0 | 2 | 0 | 0 | 2 | 0 | 0 | 0 | 0 | 0 | 0 | 0 | — | 0 | 0 | 0 | 0 |

| | COMPOUND | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| Rate 250 g/ha | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 | 114 | 115 | 116 | 117 | 118 | 119 | 120 | 121 |
| Postemergence | | | | | | | | | | | | | | | | | | | | | | | | | | | | | | | | | |
| B. signalgrass | 0 | 0 | 8 | 7 | 8 | 0 | 3 | 0 | 0 | 0 | 0 | 0 | 0 | 0 | 0 | 0 | 3 | 0 | 8 | 3 | 8 | 0 | 0 | 0 | 8 | 5 | 0 | 9 | 9 | 2 | 3 | 7 | 3 |
| Barnyardgrass | 0 | 0 | — | — | 0 | 0 | 0 | 0 | 0 | 9 | 0 | — | 0 | 0 | — | — | 0 | 0 | — | 0 | 0 | 0 | 0 | 0 | 0 | 0 | 0 | 0 | 2 | — | — | 0 | 0 |
| Bedstraw | 0 | — | — | — | — | — | 0 | 0 | 1 | — | 8 | 0 | — | 0 | 0 | — | 2 | 3 | 4 | 2 | 9 | 8 | 7 | 7 | 7 | 6 | 4 | 9 | 2 | 0 | 4 | — | — |
| Blackgrass | 0 | 0 | 8 | 7 | 8 | 3 | 4 | 0 | 3 | 0 | 6 | 0 | 0 | 0 | 4 | 5 | 7 | 1 | 8 | 7 | 8 | 4 | 5 | 5 | 8 | 7 | 6 | 9 | 9 | 7 | 7 | 6 | 2 |
| Cocklebur | 2 | 3 | 4 | 2 | 2 | 1 | 1 | 0 | 1 | 0 | 2 | 0 | 0 | 0 | 0 | 2 | 1 | 2 | 1 | 0 | 4 | 2 | 2 | 2 | 1 | 0 | 1 | 3 | 0 | 0 | 0 | 3 | 2 |
| Corn | 0 | 0 | 3 | 0 | 5 | 0 | 0 | 0 | 0 | 0 | 0 | 0 | 0 | 0 | 0 | 0 | 0 | 0 | 5 | 0 | 3 | 0 | 0 | 0 | 5 | 0 | 0 | 2 | 6 | 0 | 0 | 2 | 0 |
| Crabgrass | 0 | 2 | 9 | 9 | 9 | 8 | 6 | 3 | 4 | 2 | 4 | 0 | 0 | 0 | 6 | 5 | 7 | 3 | 9 | 8 | 9 | 3 | 3 | 4 | 9 | 9 | 2 | 9 | 9 | 7 | 8 | 9 | 9 |
| Ducksalad | 0 | 0 | — | — | 0 | 0 | 0 | 0 | 2 | 3 | 2 | — | 0 | 0 | — | — | 0 | 0 | — | 0 | 0 | 0 | 0 | 0 | 0 | 0 | 0 | 0 | 0 | — | — | 0 | 0 |
| Giant foxtail | 0 | 1 | 8 | 9 | 9 | 5 | 1 | 0 | 3 | 2 | 2 | 0 | 0 | 0 | 3 | 4 | 7 | 3 | 8 | 8 | 9 | 5 | 5 | 7 | 9 | 9 | 5 | 9 | 9 | 9 | 8 | 8 | 7 |
| Morningglory | 0 | 4 | 8 | 10 | 10 | 10 | 2 | 1 | 3 | 2 | 3 | 0 | 1 | 1 | 10 | 10 | 3 | 8 | 3 | 3 | 5 | 5 | 5 | 10 | 8 | 4 | 6 | 4 | 7 | 5 | 7 | 8 | 6 |
| Nutsedge | 0 | 0 | 0 | 0 | 0 | 0 | 0 | 0 | 0 | 0 | 0 | 0 | 0 | 0 | 0 | 0 | 0 | 0 | 5 | 4 | 0 | 0 | 0 | 0 | 0 | 0 | 0 | 8 | 7 | 0 | 0 | 0 | 0 |
| Rape | 0 | 0 | 4 | 4 | 4 | 2 | 0 | 0 | 0 | 0 | 4 | 0 | 0 | 0 | 1 | 0 | 0 | 0 | 3 | 0 | 4 | 4 | 3 | 3 | 7 | 3 | 0 | 8 | 2 | 0 | 2 | 0 | 2 |
| Redroot pigweed | 0 | 6 | 6 | 4 | 7 | 2 | 3 | 0 | — | 0 | 5 | 0 | 0 | 0 | 2 | 3 | 0 | 0 | 5 | 0 | 8 | 5 | 4 | 5 | 6 | 3 | 0 | 8 | 0 | 0 | 2 | 0 | 3 |
| Rice | 0 | 0 | — | — | 0 | 0 | 2 | 0 | 0 | 6 | 0 | — | 0 | 0 | — | — | 0 | 0 | — | 0 | 0 | 0 | 0 | 0 | 0 | 0 | 0 | 0 | 0 | — | 0 | 2 | 0 |
| S. Flatsedge | 0 | 0 | — | — | 0 | 0 | 0 | 0 | 0 | 8 | 0 | — | 0 | 0 | — | — | 0 | 0 | — | 0 | 0 | 0 | 0 | 0 | 0 | 0 | 0 | 0 | 0 | — | — | 0 | 5 |
| Soybean | 0 | 4 | 4 | 3 | 5 | 5 | 1 | 1 | 1 | 1 | 3 | 0 | 3 | 0 | 4 | 5 | 3 | 1 | 4 | 5 | 7 | 5 | 4 | 4 | 7 | 5 | 4 | 6 | 5 | 2 | 4 | 4 | 6 |
| Sugarbeets | 0 | 3 | 6 | 6 | 3 | 2 | 4 | 0 | 0 | 0 | 4 | 0 | 0 | 0 | 2 | 1 | 0 | 0 | 5 | 2 | 6 | 3 | 3 | 3 | 5 | 4 | 3 | 8 | 3 | 0 | 0 | 0 | 4 |
| Velvetleaf | 0 | 0 | 3 | 0 | 0 | 4 | 0 | 0 | 2 | 0 | 3 | 0 | 0 | 0 | 1 | 3 | 3 | 2 | 5 | 4 | 6 | 1 | 0 | 1 | 7 | 3 | 0 | 7 | 6 | 0 | 3 | 2 | 4 |
| Wheat | 0 | 0 | 4 | 5 | 4 | 0 | 0 | 0 | 0 | 0 | 0 | 0 | 0 | 0 | 0 | 0 | 0 | 0 | 7 | 0 | 5 | 0 | 0 | 0 | 4 | 0 | 0 | 7 | 6 | 0 | 3 | 0 | 0 |
| Wild oats | 0 | 0 | 3 | 1 | 2 | 0 | 0 | 0 | 0 | 0 | 0 | 0 | 0 | 0 | 0 | 0 | 2 | 0 | 5 | 3 | 4 | 0 | 1 | 0 | 6 | 2 | 0 | 7 | 4 | 0 | 3 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 122 | 123 | 124 | 125 | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 | 149 | 150 |
| Postemergence | | | | | | | | | | | | | | | | | | | | | | | | | | | | | |
| B. signalgrass | 0 | 3 | 0 | 0 | 0 | 0 | 0 | 4 | 7 | 8 | 4 | 2 | 0 | 0 | 1 | 5 | 8 | 6 | 0 | 0 | 0 | 0 | 1 | 0 | 8 | 8 | 5 | 0 | 0 |
| Barnyardgrass | 0 | 0 | 0 | 0 | 0 | 0 | 0 | — | — | — | — | — | — | 0 | 0 | 0 | 8 | 0 | 2 | 0 | 2 | 8 | 0 | 7 | 1 | 6 | 0 | 0 | 0 |
| Bedstraw | — | — | — | — | 0 | 0 | 0 | 3 | 6 | 9 | 2 | 7 | 4 | 2 | 8 | 8 | 8 | 5 | 5 | 2 | 3 | 6 | 3 | 3 | 7 | 7 | 6 | 0 | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Blackgrass | 4 | 6 | 0 | 0 | 0 | 0 | 0 | 3 | 7 | 8 | 8 | 2 | 0 | 0 | 3 | 8 | 9 | 7 | 4 | 0 | 0 | 5 | 5 | 5 | 8 | 8 | 7 | 0 | 0 |
| Cocklebur | 3 | 0 | 0 | 0 | 0 | 0 | 0 | 0 | 0 | 5 | 0 | 2 | 0 | 0 | 2 | 3 | 2 | 2 | 3 | 0 | 0 | 3 | 0 | 0 | 3 | 0 | 0 | 0 | 0 |
| Corn | 0 | 0 | 0 | 0 | 0 | 0 | 0 | 2 | 2 | 6 | 4 | 0 | 0 | 0 | 0 | 3 | 7 | 2 | 0 | 0 | 0 | 0 | 0 | 0 | 0 | 6 | 0 | 0 | 0 |
| Crabgrass | 4 | 8 | 0 | 0 | 0 | 0 | 0 | 8 | 9 | 8 | 8 | 4 | 4 | 0 | 8 | 9 | 9 | 9 | 9 | 4 | 4 | 8 | 9 | 8 | 9 | 9 | 8 | 0 | 2 |
| Ducksalad | 0 | 0 | 0 | 0 | 0 | 0 | 0 | — | — | — | — | — | — | 0 | 0 | 0 | 2 | 0 | 0 | 0 | 0 | 0 | 0 | 0 | 5 | 0 | 0 | 0 | 0 |
| Giant foxtail | 6 | 8 | 0 | 0 | 0 | 0 | 0 | 9 | 9 | 9 | 9 | 3 | 0 | 0 | 7 | 9 | 9 | 9 | 4 | 0 | 2 | 5 | 5 | 2 | 9 | 8 | 8 | 0 | 2 |
| Morningglory | 4 | 10 | 0 | 2 | 0 | 0 | 0 | 8 | 2 | 8 | 6 | 4 | 8 | 1 | 10 | 7 | 6 | 6 | 8 | 3 | 4 | 8 | 2 | 10 | 8 | 3 | 3 | 0 | 0 |
| Nutsedge | 0 | 0 | 0 | 0 | 0 | 0 | 0 | 0 | 0 | 0 | 3 | 0 | 0 | 0 | 0 | 3 | 6 | 0 | 0 | 0 | 0 | 0 | 0 | 0 | 0 | 0 | 0 | 0 | 0 |
| Rape | 3 | 0 | 0 | 0 | 0 | 0 | 0 | 0 | — | 7 | 0 | 0 | 0 | 0 | 2 | 6 | 2 | 2 | 1 | 0 | 0 | 0 | 0 | 3 | 3 | 4 | 3 | 0 | 0 |
| Redroot pigweed | 2 | 2 | 0 | 0 | 0 | 0 | 0 | 2 | 3 | 8 | 0 | 0 | 0 | 0 | 6 | 5 | 7 | 4 | 2 | 2 | 0 | 5 | 0 | 0 | 6 | 5 | — | 0 | 0 |
| Rice | 0 | 0 | 0 | 0 | 0 | 0 | 0 | — | — | — | — | — | — | 0 | 0 | 0 | 8 | 0 | 2 | 0 | 2 | 2 | 0 | 0 | 2 | 2 | 0 | 0 | 0 |
| S. Flatsedge | 0 | 0 | 0 | 0 | 0 | 0 | 0 | — | — | — | — | — | — | 0 | 0 | 0 | 7 | 0 | 0 | 0 | 0 | 2 | 0 | 5 | 3 | 3 | 0 | 0 | 0 |
| Soybean | 3 | 4 | 4 | 4 | 0 | 0 | 0 | 4 | 3 | 8 | 4 | 3 | 1 | 3 | 4 | 7 | 4 | 4 | 3 | 3 | 3 | 4 | 3 | 4 | 6 | 6 | 4 | 0 | 1 |
| Sugarbeets | 0 | 1 | 0 | 0 | 0 | 0 | 0 | 0 | 2 | 6 | 0 | 0 | 0 | 0 | 7 | 5 | 6 | 2 | 0 | 0 | 0 | 6 | 0 | 0 | 4 | 2 | 4 | 0 | 0 |
| Velvetleaf | 3 | 0 | 0 | 0 | 0 | 0 | 0 | 0 | 5 | 8 | 3 | 2 | 0 | 0 | 0 | 4 | 4 | 5 | 0 | 0 | 2 | 2 | 0 | 0 | 6 | 0 | 0 | 0 | 0 |
| Wheat | 0 | 1 | 0 | 0 | 0 | 0 | 0 | 2 | 3 | 5 | 2 | 0 | 0 | 0 | 0 | 5 | 8 | 4 | 0 | 0 | 0 | 0 | 0 | 0 | 5 | 5 | 3 | 0 | 0 |
| Wild oats | 0 | 0 | 0 | 0 | 0 | 0 | 0 | 2 | 5 | 9 | 2 | 0 | 0 | 0 | 0 | 4 | 3 | 4 | 0 | 0 | 0 | 0 | 0 | 0 | 6 | 5 | 5 | 0 | 0 |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate 250 g/ha | 151 | 152 | 153 | 154 | 155 | 156 | 157 | 158 | 159 | 160 | 161 | 162 | 163 | 164 | 165 | 166 | 167 | 168 | 169 | 170 | 171 | 172 | 173 | 174 | 175 | 176 | 177 | 178 |
| Postemergence | | | | | | | | | | | | | | | | | | | | | | | | | | | | |
| B. signalgrass | 6 | 0 | 0 | 0 | 0 | 0 | 0 | 0 | 0 | 0 | 2 | 0 | 5 | 0 | 5 | 0 | 0 | 0 | 0 | 9 | 0 | 0 | 0 | 0 | 0 | 0 | 0 | 0 |
| Barnyardgrass | 0 | 0 | 0 | 0 | 0 | 0 | 0 | 0 | 0 | 0 | — | — | — | 0 | — | — | — | — | 0 | 0 | 0 | — | — | — | — | 0 | 0 | — |
| Bedstraw | 4 | 0 | 0 | 0 | 0 | 0 | 0 | 0 | 0 | 0 | 4 | 3 | 7 | — | 4 | 1 | 8 | 8 | 7 | 0 | 8 | 8 | 4 | 6 | 0 | 2 | 5 | 0 |
| Blackgrass | 8 | 0 | 0 | 0 | 2 | 0 | 0 | 2 | 0 | 0 | 3 | 0 | 6 | 0 | 7 | 7 | 5 | 2 | 5 | 9 | 0 | 5 | 2 | 0 | 0 | 0 | 0 | 0 |
| Cocklebur | 2 | 0 | 0 | 0 | 0 | 0 | 0 | 0 | 0 | 0 | 0 | 0 | 3 | 0 | 0 | 0 | 0 | 2 | 0 | 0 | 3 | 0 | 1 | 2 | 2 | 2 | 0 | 0 |
| Corn | 2 | 0 | 0 | 0 | 2 | 0 | 0 | 0 | 0 | 0 | 0 | 0 | 0 | 0 | 3 | 0 | 0 | 0 | 0 | 0 | 0 | 0 | 0 | 0 | 0 | 0 | 0 | 0 |
| Crabgrass | 9 | 2 | 0 | 1 | 8 | 0 | 2 | 3 | 0 | 0 | 7 | 6 | 8 | 2 | 9 | 3 | 9 | 2 | 9 | 9 | 2 | 9 | 5 | 7 | 0 | 3 | 2 | 0 |
| Ducksalad | 0 | 0 | 0 | 0 | 0 | 0 | 0 | 0 | 0 | 0 | — | — | — | 0 | — | — | — | — | 0 | 0 | 0 | — | — | — | — | 0 | 2 | — |
| Giant foxtail | 8 | 0 | 0 | 1 | 6 | 0 | 4 | 4 | 0 | 0 | 3 | 2 | 8 | 0 | 5 | 1 | 0 | 1 | 6 | 8 | 0 | 0 | 0 | 0 | 0 | 0 | 0 | 0 |
| Morningglory | 6 | 0 | 0 | 1 | 2 | 2 | 1 | 2 | 3 | 0 | 7 | 10 | 5 | 0 | 3 | 2 | 5 | 10 | 5 | 1 | 2 | 5 | 10 | 5 | 3 | 2 | 2 | 2 |
| Nutsedge | 5 | 0 | 0 | 0 | 0 | 0 | 0 | 0 | 0 | 0 | 0 | 0 | 0 | 0 | 0 | 0 | 0 | 0 | 0 | 7 | 0 | 0 | 0 | 0 | 0 | 0 | 0 | 0 |
| Rape | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 |
| Redroot pigweed | 5 | 0 | 0 | 2 | 0 | 0 | 0 | 2 | 0 | 0 | 4 | 0 | 3 | 0 | 4 | 2 | 3 | 0 | 0 | 6 | 0 | 3 | 0 | 6 | 0 | 0 | 0 | — |
| Rice | 0 | 0 | 0 | 0 | 0 | 0 | 0 | 0 | 0 | 0 | — | — | — | 0 | — | — | — | — | 0 | 0 | 0 | — | — | — | — | 0 | 0 | — |
| S. Flatsedge | 0 | 0 | 0 | 0 | 0 | 0 | 0 | 0 | 0 | 0 | — | — | — | 0 | — | — | — | — | 0 | 0 | 0 | — | — | — | — | 0 | 0 | — |
| Soybean | 4 | 1 | 0 | 2 | 1 | 1 | 1 | 4 | 3 | 0 | 4 | 4 | 3 | 2 | 6 | 2 | 3 | 2 | 3 | 4 | 1 | 3 | 2 | 2 | 1 | 2 | 2 | 2 |
| Sugarbeets | 3 | 0 | 0 | 0 | 0 | 0 | 0 | 0 | 0 | 0 | 4 | 0 | 4 | 0 | 3 | 0 | 0 | 0 | 0 | 2 | 2 | 0 | 0 | 6 | 0 | 0 | 0 | 0 |
| Velvetleaf | 3 | 0 | 0 | 0 | 0 | 0 | 0 | 0 | 0 | 0 | 2 | 4 | 6 | 0 | 1 | 0 | 0 | 1 | 0 | 5 | 0 | 0 | 0 | 0 | 3 | 2 | 0 | 0 |
| Wheat | 4 | 0 | 0 | 0 | 0 | 0 | 0 | 0 | 0 | 0 | 0 | 0 | 2 | 0 | 2 | 0 | 0 | 0 | 0 | 6 | 0 | 0 | 0 | 0 | 0 | 0 | 0 | 0 |
| Wild oats | 6 | 0 | 0 | 0 | 0 | 0 | 0 | 0 | 0 | 0 | 0 | 0 | 3 | 0 | 3 | 0 | 0 | 0 | 0 | 3 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 179 | 180 | 181 | 182 | 183 | 184 | 185 | 186 | 187 | 188 | 189 | 190 | 191 | 192 | 193 | 194 | 195 | 196 | 197 | 198 | 199 | 200 | 201 | 202 | 203 | 204 | 205 | 206 | 207 |
| Postemergence | | | | | | | | | | | | | | | | | | | | | | | | | | | | | |
| B. signalgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

TABLE B-continued

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Barnyardgrass | — | — | — | — | — | — | — | — | — | — | — | — | — | — | — | — | — | — | — | — | 0 | — | — | — | — | — | — | — | — |
| Bedstraw | 5 | 0 | 0 | 0 | 7 | 3 | 3 | 8 | 0 | 3 | 0 | 0 | 0 | 0 | 0 | 0 | — | 0 | 0 | 0 | 0 | 0 | 0 | 4 | 0 | 6 | 0 | 0 | 5 |
| Blackgrass | 4 | 0 | 0 | 0 | 0 | 3 | 0 | 4 | 0 | 0 | 0 | 0 | 0 | 0 | 0 | 2 | 5 | 0 | 0 | 0 | 9 | 0 | 0 | 5 | 0 | 3 | 0 | 0 | 2 |
| Cocklebur | 0 | 0 | 0 | 0 | 0 | 0 | 0 | 0 | 0 | 0 | 0 | 0 | 2 | 2 | 0 | 2 | 2 | 0 | 0 | 0 | 0 | 0 | 0 | 2 | 0 | 1 | 1 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 2 | 0 | 0 | 0 | 0 | 0 | — | 2 | 0 | 3 | 0 | 0 | 3 | 1 | 0 | 0 | 2 | 0 | 0 | 0 | 8 | 2 | 0 | 1 | 0 | 2 | 1 | 0 | 2 |
| Ducksalad | — | — | — | — | — | — | — | — | — | — | — | — | — | — | — | — | — | — | — | — | 0 | — | — | — | — | — | — | — | — |
| Giant foxtail | 0 | 0 | 0 | 0 | 0 | 0 | 0 | 0 | 0 | 2 | 0 | 0 | 0 | 0 | 0 | 2 | 1 | 0 | 0 | 0 | 2 | 0 | 0 | 0 | 0 | 0 | 0 | 0 | 1 |
| Morningglory | 5 | 0 | 0 | 0 | 1 | 6 | 1 | 2 | 0 | 0 | 0 | 0 | 2 | 6 | 1 | 1 | 1 | 0 | 5 | 2 | 4 | 2 | 1 | 8 | 0 | 3 | 1 | 2 | 2 |
| Nutsedge | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | — | 0 | 0 |
| Rape | 0 | 0 | 0 | 0 | 0 | 3 | 0 | 0 | 0 | 0 | 0 | 0 | 0 | 2 | 0 | 0 | 0 | 0 | 0 | 0 | 0 | 0 | 0 | 1 | 0 | 0 | 0 | 0 | 0 |
| Redroot pigweed | 4 | 0 | 0 | 0 | 0 | 7 | 3 | 0 | 0 | 0 | 0 | 0 | 0 | 3 | 0 | 0 | 2 | 0 | 0 | 0 | 2 | 0 | 0 | 6 | 0 | 4 | 0 | 3 | 0 |
| Rice | — | — | — | — | — | — | — | — | — | — | — | — | — | — | — | — | — | — | — | — | 0 | — | — | — | — | — | — | — | — |
| S. Flatsedge | — | — | — | — | — | — | — | — | — | — | — | — | — | — | — | — | — | — | — | — | 2 | — | — | — | — | — | — | — | — |
| Soybean | 1 | 0 | 0 | 0 | 2 | 3 | 3 | 2 | 0 | 2 | 0 | 0 | 3 | 3 | 1 | 0 | 4 | 0 | 0 | 0 | 7 | 2 | 2 | 3 | 0 | 1 | 2 | 2 | 2 |
| Sugarbeets | 2 | 0 | 0 | 0 | 0 | 5 | 0 | 0 | 0 | 0 | 0 | 0 | 0 | 0 | 0 | 0 | 0 | 0 | 0 | 0 | 0 | 0 | 3 | 4 | 0 | 0 | 0 | 0 | 0 |
| Velvetleaf | 0 | 0 | 0 | 0 | 0 | 1 | 0 | 0 | 0 | 0 | 0 | 0 | 2 | 3 | 0 | 0 | 2 | 0 | 0 | 0 | 0 | 1 | 1 | 0 | 0 | 1 | 0 | 0 | 1 |
| Wheat | 0 | 0 | 0 | 0 | 0 | 2 | 0 | 0 | 0 | 0 | 0 | 0 | 0 | 0 | 0 | 0 | 0 | 0 | 0 | 0 | 3 | 0 | 0 | 0 | 0 | 0 | 0 | 0 | 0 |
| Wild oats | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| | COMPOUND | | | | | | | | | | | | | | | | | | | | | | | | | | | | |
| Rate 250 g/ha | 208 | 210 | 211 | 212 | 213 | 214 | 215 | 216 | 217 | 218 | 219 | 220 | 221 | 222 | 223 | 224 | 225 | 226 | 227 | 228 | 229 | 230 | 231 | 232 | 233 | 234 | 235 | 236 | 237 |
| Postemergence | | | | | | | | | | | | | | | | | | | | | | | | | | | | | |
| B. signalgrass | 0 | 0 | 0 | 7 | 2 | 0 | 3 | 5 | 7 | 3 | 5 | 8 | 8 | 0 | 0 | 0 | 5 | 6 | 0 | 0 | 0 | 0 | 0 | 1 | 0 | 0 | 0 | 0 | 0 |
| Barnyardgrass | — | — | — | — | — | — | — | — | — | — | — | — | — | — | — | — | — | — | — | — | — | — | — | — | — | — | — | — | — |
| Bedstraw | 0 | 4 | — | 2 | 3 | 2 | 6 | 2 | 0 | — | 8 | 8 | 9 | 4 | 4 | 4 | 0 | 5 | 8 | 0 | 0 | 0 | 0 | 2 | 3 | 0 | 0 | 0 | 2 |
| Blackgrass | 0 | 0 | 4 | 6 | 2 | 4 | 4 | 8 | 6 | 7 | 8 | 8 | 9 | 3 | 3 | 3 | 9 | 8 | 7 | 0 | 0 | 0 | 0 | 6 | 2 | 0 | 0 | 0 | 0 |
| Cocklebur | 0 | 0 | 0 | 2 | 0 | 0 | 0 | 0 | 0 | 3 | 4 | 3 | 0 | 0 | 0 | 0 | 0 | 0 | 2 | 0 | 0 | 0 | 0 | 2 | 2 | 0 | 0 | 0 | 0 |
| Corn | 0 | 0 | 0 | 0 | 0 | 0 | 0 | 2 | 0 | 0 | 4 | 6 | 0 | 0 | 0 | 0 | 2 | 0 | 0 | 0 | 0 | 0 | 0 | 0 | 0 | 0 | 0 | 0 | 0 |
| Crabgrass | 0 | 0 | 1 | 8 | 2 | 3 | 2 | 4 | 3 | 5 | 6 | 7 | 8 | 0 | 1 | 3 | g | 3 | 0 | 0 | 0 | 0 | 0 | 1 | 1 | 0 | 0 | 0 | 0 |
| Ducksalad | — | — | — | — | — | — | — | — | — | — | — | — | — | — | — | — | — | — | — | — | — | — | — | — | — | — | — | — | — |
| Giant foxtail | 0 | 0 | 2 | 6 | 2 | 0 | 3 | 4 | 7 | 7 | 8 | 8 | 7 | 0 | 0 | 4 | 8 | 7 | 0 | 0 | 0 | 0 | 0 | 2 | 3 | 0 | 0 | 0 | 0 |
| Morningglory | 1 | 3 | 6 | 4 | 7 | 6 | 3 | 7 | 0 | 8 | 7 | 8 | 0 | 3 | 4 | 5 | 6 | 7 | 8 | 3 | 0 | 2 | 3 | 8 | 3 | 1 | 6 | 5 | 3 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 2 | 0 | 3 | 3 | 0 | 0 | 0 | 6 | 7 | 3 | 4 | 0 | 0 | 0 | 0 | 0 | 0 | 0 | 0 | 0 | 0 | 2 | 2 | 0 | 0 | 0 | 0 |
| Redroot pigweed | 0 | 2 | 4 | — | 7 | 1 | 6 | 2 | 0 | 3 | 8 | 3 | 8 | 0 | 3 | 4 | 0 | 0 | 5 | 0 | 0 | 0 | 0 | 6 | 2 | 0 | 0 | 0 | 2 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 2 | 1 | 4 | 3 | 2 | 3 | 1 | 1 | 1 | 6 | 7 | 7 | 3 | 3 | 3 | 4 | 5 | 3 | 4 | 1 | 1 | 4 | 1 | 4 | 3 | 0 | 0 | 2 | 1 |
| Sugarbeets | 0 | 0 | 2 | 0 | 4 | 0 | 0 | 0 | 0 | 2 | 4 | 2 | 4 | 0 | 2 | 4 | 3 | 0 | 3 | 3 | 0 | 0 | 0 | 2 | 0 | 0 | 0 | 0 | 0 |
| Velvetleaf | 1 | 2 | 1 | 5 | 0 | 0 | 0 | 0 | 0 | 2 | 2 | 2 | 0 | 2 | 2 | 0 | 0 | 0 | 0 | 0 | 0 | 0 | 0 | 2 | 3 | 0 | 0 | 1 | 0 |
| Wheat | 0 | 0 | 0 | 0 | 2 | 3 | 6 | 0 | 3 | 0 | 7 | 6 | 4 | 0 | 0 | 0 | 7 | 7 | 3 | 0 | 0 | 0 | 0 | 0 | 0 | 0 | 0 | 0 | 0 |
| Wild oats | 0 | 0 | 0 | 0 | 2 | 0 | 2 | 0 | 0 | 1 | 4 | 2 | 2 | 0 | 0 | 0 | 3 | 0 | 0 | 0 | 0 | 0 | 0 | 0 | 2 | 0 | 0 | 0 | 0 |

TABLE B-continued

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 238 | 239 | 240 | 241 | 242 | 243 | 244 | 245 | 246 | 247 | 248 | 249 | 250 | 251 | 252 | 253 | 254 | 255 | 256 | 257 | 258 | 259 | 260 | 261 | 262 | 263 | 264 | 265 | 266 |
| Postemergence | | | | | | | | | | | | | | | | | | | | | | | | | | | | | |
| B. signalgrass | 0 | 0 | 0 | 4 | 8 | 9 | 0 | 6 | 0 | 0 | 0 | 0 | 0 | 0 | 0 | 0 | 0 | 2 | 0 | 0 | 4 | 0 | 0 | 0 | 0 | 0 | 0 | 0 | 0 |
| Barnyardgrass | — | — | — | — | — | — | — | — | — | — | — | — | — | — | — | — | — | — | — | — | — | — | — | — | — | — | — | — | — |
| Bedstraw | 8 | 3 | 3 | 7 | 7 | 5 | 0 | 9 | 9 | 0 | 0 | 0 | 9 | 7 | 0 | 0 | 4 | 2 | 0 | 0 | 7 | — | — | — | — | — | 6 | 3 | 5 |
| Blackgrass | 0 | 2 | 0 | 8 | 9 | 9 | 0 | 7 | 6 | 0 | 0 | 0 | 2 | 8 | 5 | 0 | 0 | 7 | 0 | 1 | 7 | 0 | 0 | 0 | 0 | 3 | 3 | 5 | 6 |
| Cocklebur | 0 | 1 | 1 | 1 | 7 | 4 | 0 | 0 | 1 | 0 | 0 | 0 | 1 | 0 | 0 | 0 | 0 | 0 | 0 | 0 | 0 | 2 | 0 | 0 | 0 | 0 | 0 | 0 | 2 |
| Corn | 0 | 0 | 0 | 0 | 0 | 5 | 0 | 5 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 2 | 2 | 2 | 8 | 9 | 9 | 0 | 8 | 0 | 0 | 0 | 0 | 0 | 6 | 6 | 0 | 0 | 2 | 1 | 2 | 2 | 0 | 0 | 0 | 0 | 0 | 0 | 2 | 3 |
| Ducksalad | — | — | — | — | — | — | — | — | — | — | — | — | — | — | — | — | — | — | — | — | — | — | — | — | — | — | — | — | — |
| Giant foxtail | 0 | 1 | 0 | 6 | 8 | 8 | 0 | 8 | 5 | 0 | 0 | 0 | 0 | 7 | 4 | 0 | 0 | 6 | 0 | 0 | 4 | 0 | 0 | 0 | 0 | 0 | 0 | 2 | 5 |
| Morningglory | 3 | 3 | 10 | 5 | 7 | 7 | 0 | 9 | 9 | 2 | 0 | 0 | 6 | 7 | 3 | 0 | 9 | 8 | — | 8 | 7 | 7 | 3 | 6 | 5 | 4 | 10 | 6 | 5 |
| Nutsedge | 0 | 0 | 0 | 0 | — | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 4 | 0 | 0 | 2 | 4 | 2 | 0 | 2 | 0 | 0 | 0 | 0 | 3 | 0 | 0 | 0 | 2 | 3 | 2 | 2 | 0 | 0 | 0 | 0 | 0 | 0 | 0 | 1 | 6 |
| Redroot pigweed | 0 | 3 | 2 | 0 | 4 | 7 | 0 | 9 | 2 | 0 | 0 | 0 | 0 | 2 | 0 | 0 | 3 | 2 | 4 | 4 | 2 | 6 | 3 | 1 | 3 | 0 | 0 | 3 | 5 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 1 | 1 | 2 | 3 | 6 | 5 | 0 | 4 | 3 | 0 | 0 | 4 | 2 | 4 | 1 | 0 | 2 | 6 | 4 | 3 | 5 | 4 | 1 | 4 | 3 | 1 | 3 | 3 | 7 |
| Sugarbeets | 0 | 0 | 0 | 0 | 5 | 2 | 0 | 3 | 0 | 0 | 0 | 0 | 3 | 0 | 0 | 0 | 0 | 0 | 3 | 2 | 0 | 2 | 2 | 0 | 0 | 0 | 1 | 3 | 3 |
| Velvetleaf | 2 | 3 | 1 | 0 | 7 | 4 | 0 | 4 | 0 | 0 | 0 | 0 | 0 | 0 | 0 | 0 | 0 | 0 | 0 | 0 | 0 | 1 | 1 | 1 | 1 | 0 | 0 | 2 | 5 |
| Wheat | 0 | 0 | 0 | 4 | 8 | 7 | 0 | 6 | 2 | 0 | 0 | 0 | 0 | 0 | 0 | 0 | 0 | 4 | 0 | 0 | 4 | 3 | 0 | 0 | 0 | 0 | 0 | 0 | 5 |
| Wild oats | 0 | 0 | 0 | 0 | 4 | 3 | 0 | 5 | 0 | 0 | 0 | 0 | 0 | 0 | 0 | 0 | 0 | 0 | 0 | 0 | 1 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 267 | 268 | 269 | 270 | 271 | 272 | 273 | 274 | 276 | 277 | 278 | 279 | 280 | 281 | 282 | 283 | 284 | 285 | 286 | 288 | 289 | 292 | 293 | 294 | 295 | 296 | 297 | 298 | 299 |
| Postemergence | | | | | | | | | | | | | | | | | | | | | | | | | | | | | |
| B. signalgrass | 0 | 0 | 0 | 0 | 2 | 0 | 0 | 0 | 0 | 1 | 0 | 0 | 0 | 0 | 0 | 0 | 0 | 0 | 0 | 0 | 3 | 0 | 7 | 0 | 5 | 0 | 0 | 0 | 7 |
| Barnyardgrass | — | — | — | — | — | — | — | — | — | — | — | — | — | — | — | — | — | — | — | — | — | — | — | — | — | — | — | — | — |
| Bedstraw | 4 | 0 | 4 | 0 | 8 | 0 | 0 | 0 | 3 | 8 | 6 | 0 | 0 | — | 7 | 5 | 6 | 7 | 5 | 0 | 8 | 0 | 3 | 8 | 4 | 0 | — | — | — |
| Blackgrass | 5 | 0 | 2 | 0 | 8 | 2 | 2 | 0 | 4 | 8 | 0 | 2 | 0 | 0 | 5 | 7 | 7 | 7 | 5 | 2 | 9 | 0 | 9 | 7 | 9 | 0 | 0 | 0 | 8 |
| Cocklebur | 1 | 0 | 1 | 0 | 1 | 1 | 0 | 0 | 0 | 1 | 0 | 0 | 0 | 0 | 2 | 2 | 2 | 0 | 0 | 1 | 2 | 0 | 0 | 0 | 0 | 0 | 0 | 0 | 4 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 3 |
| Crabgrass | 3 | 0 | 0 | 0 | 1 | 0 | 1 | 0 | 6 | 5 | 0 | 0 | 0 | 0 | 0 | 1 | 1 | 7 | 2 | 3 | 9 | 0 | 9 | 2 | 8 | 0 | 0 | 0 | 4 |
| Ducksalad | — | — | — | — | — | — | — | — | — | — | — | — | — | — | — | — | — | — | — | — | — | — | — | — | — | — | — | — | — |
| Giant foxtail | 2 | 0 | 0 | 0 | 4 | 0 | 0 | 0 | 4 | 4 | 0 | 0 | 0 | 0 | 0 | 4 | 3 | 0 | 2 | 0 | 7 | 0 | 8 | 2 | 9 | 0 | 0 | 0 | 8 |
| Morningglory | 3 | 2 | 5 | 0 | 8 | 1 | 2 | 0 | 6 | 8 | 4 | 2 | 0 | 3 | 7 | 9 | 7 | 5 | 8 | 8 | 8 | 2 | 5 | 9 | 7 | 1 | 0 | 3 | 6 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 8 | 0 | 0 | 0 | 0 | 0 | 0 |
| Rape | 0 | 0 | 0 | 0 | 4 | 0 | 0 | 0 | 0 | 3 | 0 | 0 | 0 | 0 | 6 | 4 | 4 | 0 | 5 | 3 | 2 | 0 | 0 | 2 | 3 | 0 | 0 | 0 | 7 |
| Redroot pigweed | 0 | 0 | 5 | 0 | 7 | 2 | 2 | 1 | 1 | 4 | 0 | 2 | 0 | 5 | 7 | 5 | 6 | 0 | 6 | 0 | 7 | 0 | 2 | 0 | 7 | 0 | 0 | 0 | 6 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 3 | 0 | 3 | 2 | 5 | 1 | 3 | 5 | 6 | 6 | 1 | 2 | 3 | 3 | 4 | 5 | 4 | 3 | 2 | 2 | 4 | 1 | 2 | 4 | 4 | 1 | 3 | 3 | 6 |
| Sugarbeets | 2 | 0 | 0 | 0 | 4 | 0 | 0 | 0 | 2 | 4 | 0 | 0 | 0 | 0 | 7 | 2 | 5 | 3 | 2 | 0 | 0 | 0 | 3 | 0 | 0 | 0 | 0 | 0 | 4 |
| Velvetleaf | 1 | 0 | 3 | 0 | 0 | 0 | 0 | 0 | 0 | 1 | 0 | 0 | 0 | 1 | 3 | 1 | 2 | 1 | 0 | 1 | 3 | 0 | 2 | 0 | 5 | 0 | 0 | 0 | 6 |
| Wheat | 3 | 0 | 2 | 0 | 0 | 0 | 0 | 0 | 0 | 0 | 0 | 0 | 0 | 0 | 0 | 0 | 0 | 0 | 3 | 0 | 7 | 0 | 7 | 0 | 3 | 0 | 0 | 0 | 6 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Wild oats | 2 | 0 | 0 | 0 | 0 | 0 | 0 | 0 | 0 | 0 | 0 | 0 | 0 | 0 | 0 | 0 | 0 | 0 | 2 | 0 | 3 | 0 | 3 | 0 | 2 | 0 | 0 | 0 | 3 |
| | COMPOUND | | | | | | | | | | | | | | | | | | | | | | | | | | | | |
| Rate 250 g/ha | 300 | 301 | 302 | 303 | 304 | 305 | 306 | 307 | 308 | 309 | 310 | 311 | 312 | 313 | 314 | 315 | 316 | 317 | 318 | 319 | 320 | 321 | 322 | 323 | 324 | 325 | 326 | 327 | 328 |
| Postemergence | | | | | | | | | | | | | | | | | | | | | | | | | | | | | |
| B. signalgrass | 0 | 0 | 0 | 0 | 0 | 0 | 0 | 0 | 0 | 0 | 7 | 0 | 0 | 0 | 0 | 0 | 0 | 7 | 0 | 0 | 0 | 0 | 0 | 0 | 0 | 0 | 0 | 0 | 0 |
| Barnyardgrass | — | — | — | — | — | — | — | — | — | — | — | — | — | — | — | — | — | — | — | — | — | — | — | — | — | — | — | — | — |
| Bedstraw | 0 | — | 0 | — | — | — | 0 | 0 | 0 | 0 | 7 | 0 | 0 | 7 | — | 6 | — | 8 | 0 | — | — | 8 | 4 | — | 0 | — | 7 | 7 | 4 |
| Blackgrass | 0 | 0 | 0 | 0 | 0 | 0 | 0 | 0 | 0 | 0 | 9 | 0 | 0 | 0 | 5 | 5 | 4 | 8 | 0 | 0 | 0 | 0 | 1 | 0 | 0 | 3 | 0 | 3 | 5 |
| Cocklebur | 0 | 0 | 0 | 0 | 0 | 0 | 0 | 0 | 0 | 0 | 2 | 0 | 0 | 0 | 1 | 0 | 0 | 0 | 5 | 0 | 0 | 0 | 0 | 0 | 2 | 0 | 0 | 0 | 0 |
| Corn | 0 | 0 | 0 | 0 | 0 | 0 | 0 | 0 | 0 | 0 | 0 | 0 | 0 | 0 | 0 | 4 | 0 | 2 | 0 | 0 | 0 | 0 | 0 | 0 | 0 | 0 | 0 | 0 | 0 |
| Crabgrass | 0 | 0 | 0 | 0 | 0 | 0 | 0 | 0 | 0 | 0 | 9 | 0 | 0 | 0 | 4 | 5 | 0 | 8 | 0 | 0 | 0 | 2 | 2 | 0 | 0 | 0 | 1 | 0 | 0 |
| Ducksalad | — | — | — | — | — | — | — | — | — | — | — | — | — | — | — | — | — | — | — | — | — | — | — | — | — | — | — | — | — |
| Giant foxtail | 0 | 0 | 2 | 0 | 0 | 0 | 0 | 0 | 0 | 0 | 8 | 0 | 0 | 0 | 3 | 4 | 2 | 8 | 0 | 0 | 0 | 1 | 1 | 0 | 0 | 0 | 0 | 0 | 0 |
| Morningglory | 0 | 0 | 2 | 0 | 3 | 0 | — | 2 | 2 | 2 | 7 | 8 | 0 | 3 | 3 | 0 | 5 | 3 | 3 | 4 | 3 | 8 | 7 | 2 | 0 | 8 | — | 8 | 10 |
| Nutsedge | 0 | 0 | 0 | 0 | 0 | 0 | 0 | 0 | 0 | 0 | 6 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 1 | 1 | 0 | 0 | 3 | 0 | 0 | 0 | 0 | 0 | 1 | 2 | 0 |
| Redroot pigweed | 0 | 0 | 2 | 2 | 5 | 4 | 0 | 0 | 0 | 0 | 3 | 0 | 0 | 2 | 0 | 0 | 3 | 3 | 0 | 0 | 6 | 4 | 3 | 0 | 0 | 4 | 4 | 6 | 3 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 2 | 0 | 3 | 3 | 5 | 4 | 2 | 2 | 1 | 2 | 4 | 3 | 3 | 3 | 4 | 3 | 4 | 6 | 1 | 1 | 3 | 3 | 4 | 2 | 1 | 1 | 5 | 6 | 5 |
| Sugarbeets | 0 | 0 | 1 | 0 | 0 | 0 | 0 | 0 | 0 | 0 | 2 | 0 | 0 | 0 | 0 | 0 | 0 | 1 | 0 | 0 | 2 | 5 | 0 | 0 | 0 | 0 | 0 | 0 | 0 |
| Velvetleaf | 0 | 0 | 0 | 0 | 0 | 0 | 0 | 0 | 0 | 0 | 4 | 0 | 0 | 0 | 0 | 0 | 2 | 0 | 0 | 0 | 0 | 0 | 0 | 0 | 0 | 0 | 2 | 0 | 0 |
| Wheat | 0 | 0 | 0 | 0 | 0 | 0 | 0 | 0 | 0 | 0 | 6 | 0 | 0 | 0 | 3 | 0 | 2 | 5 | 0 | 0 | 0 | 0 | 0 | 0 | 0 | 2 | 0 | 0 | 0 |
| Wild oats | 0 | 0 | 0 | 0 | 0 | 0 | 0 | 0 | 0 | 0 | 3 | 0 | 0 | 0 | 2 | 0 | 2 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 329 | 330 | 331 | 332 | 333 | 334 | 335 | 336 | 337 | 338 | 339 | 340 | 341 | 342 | 343 | 344 | 345 | 348 | 349 | 350 | 351 | 352 | 353 | 354 | 355 | 356 | 357 | 358 | 359 |
| Postemergence | | | | | | | | | | | | | | | | | | | | | | | | | | | | | |
| B. signalgrass | 0 | 0 | 0 | 0 | 0 | 0 | 0 | 0 | 0 | 0 | 0 | 0 | 0 | 0 | 4 | 0 | 0 | 4 | 0 | 0 | 0 | 7 | 0 | 0 | 0 | 1 | 4 | 1 | 0 |
| Barnyardgrass | — | — | — | — | — | — | — | — | — | — | — | — | — | 9 | 0 | 0 | 0 | 3 | 9 | 3 | 3 | 3 | — | 7 | 8 | 7 | 4 | 9 | 0 |
| Bedstraw | — | — | — | 0 | 0 | — | 0 | 0 | 2 | 2 | 7 | 7 | 4 | 5 | 0 | 0 | 0 | 4 | — | — | — | 2 | — | — | 0 | 3 | 0 | 3 | 0 |
| Blackgrass | 0 | 0 | 0 | 0 | 0 | 0 | 0 | 0 | 0 | 0 | 0 | 3 | 2 | 2 | 5 | 0 | 0 | 6 | 4 | 7 | 4 | 8 | 4 | 7 | 6 | 6 | 6 | 8 | 0 |
| Cocklebur | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 6 | 0 | 0 | 0 | 2 | 0 | 0 | 0 |
| Crabgrass | 0 | 0 | 0 | 1 | 0 | 0 | 0 | 0 | 0 | 0 | 0 | 0 | 0 | 0 | 3 | 0 | 0 | 6 | 1 | 7 | 4 | 3 | 2 | 2 | 2 | 0 | 2 | 4 | 0 |
| Ducksalad | — | — | — | — | — | — | — | — | — | — | — | — | — | 2 | 0 | 0 | 0 | 3 | 0 | 3 | 4 | 2 | — | 3 | 0 | 2 | 0 | 5 | 0 |
| Giant foxtail | 0 | 0 | 0 | 0 | 0 | 0 | 0 | 0 | 0 | 0 | 0 | 0 | 0 | 2 | 6 | 0 | 0 | 9 | 5 | 8 | 8 | 9 | 7 | 8 | 4 | 7 | 9 | 8 | 0 |
| Morningglory | 0 | 0 | 0 | 0 | 0 | 0 | 0 | 0 | 0 | 0 | 8 | 10 | 8 | — | 4 | 0 | 0 | 10 | 10 | 6 | 6 | 7 | 4 | 7 | 7 | 6 | 6 | 7 | 0 |
| Nutsedge | 0 | 0 | 0 | 0 | 0 | 0 | 0 | 0 | 0 | 0 | 0 | 0 | 0 | 0 | 2 | 0 | 0 | 2 | 0 | 0 | 0 | 2 | 0 | 0 | 0 | 0 | 0 | 0 | 0 |
| Rape | 0 | 0 | 0 | 0 | 0 | 0 | 0 | 0 | 0 | 0 | 3 | 6 | 2 | 4 | 0 | 0 | 0 | 0 | 0 | 0 | 2 | 0 | 2 | 3 | 0 | 0 | 0 | 2 | 0 |
| Redroot pigweed | 0 | 0 | 0 | 3 | 0 | 0 | 0 | 0 | 0 | 0 | 4 | 6 | 3 | 5 | 3 | 0 | 0 | 2 | 3 | 2 | 3 | 3 | 4 | 4 | 0 | 0 | 5 | 4 | 0 |
| Rice | — | — | — | — | — | — | — | — | — | — | — | — | — | 0 | 0 | 0 | 0 | 0 | 0 | 0 | 0 | 3 | — | 0 | 0 | 0 | 2 | 0 | 0 |
| S. Flatsedge | — | — | — | — | — | — | — | — | — | — | — | — | — | 7 | 0 | 0 | 0 | 6 | 7 | 7 | 6 | 7 | — | 8 | 8 | 7 | 0 | 9 | 0 |
| Soybean | 1 | 1 | 0 | 2 | 2 | 0 | 2 | 1 | 1 | 2 | 2 | 2 | 2 | 6 | 3 | 2 | 0 | 3 | 2 | 1 | 2 | 4 | 6 | 7 | 2 | 3 | 2 | 5 | 2 |
| Sugarbeets | 0 | 0 | 0 | 0 | 0 | 0 | 0 | 0 | 0 | 0 | 0 | 3 | 0 | 0 | 0 | 0 | 0 | 0 | 0 | 0 | 0 | 0 | 3 | 1 | 0 | 0 | 0 | 2 | 0 |

TABLE B-continued

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Velvetleaf | 0 | 0 | 0 | 0 | 0 | 0 | 0 | 0 | 0 | 0 | 0 | 0 | 1 | 0 | 2 | 0 | 0 | 5 | 0 | 0 | 2 | 2 | 2 | 0 | 0 | 0 | 3 | 2 | 0 |
| Wheat | 0 | 0 | 0 | 0 | 0 | 0 | 0 | 0 | 0 | 0 | 0 | 0 | 0 | 0 | 5 | 0 | 0 | 3 | 3 | 0 | 2 | 4 | 0 | 0 | 2 | 3 | 6 | 3 | 0 |
| Wild oats | 0 | 0 | 0 | 0 | 0 | 0 | 0 | 0 | 0 | 0 | 0 | 0 | 0 | 0 | 4 | 0 | 0 | 3 | 2 | 3 | 2 | 2 | 0 | 0 | 5 | 3 | 5 | 5 | 0 |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate 250 g/ha | 360 | 361 | 362 | 363 | 364 | 365 | 367 | 368 | 369 | 370 | 371 | 372 | 373 | 374 | 375 | 376 | 378 | 379 | 380 | 381 | 382 | 383 | 384 | 385 | 387 | 388 | 389 | 390 | 391 |
| Postemergence | | | | | | | | | | | | | | | | | | | | | | | | | | | | | |
| B. signalgrass | 5 | 3 | 7 | 1 | 0 | 0 | 0 | 6 | 0 | 4 | 3 | 4 | 0 | 0 | 2 | 0 | 0 | 0 | 0 | 0 | 0 | 0 | 6 | 6 | 3 | 8 | 0 | 5 | 0 |
| Barnyardgrass | 6 | — | — | — | 0 | — | — | — | 0 | 0 | — | 4 | — | — | — | — | — | — | — | — | — | — | — | — | — | — | — | — | — |
| Bedstraw | 2 | 8 | 9 | 7 | 0 | — | — | 4 | — | — | — | — | — | — | — | — | 0 | 0 | — | 0 | 4 | 0 | 0 | 0 | 0 | — | 5 | — | — |
| Blackgrass | 6 | 8 | 8 | 7 | 0 | 0 | 0 | 8 | 5 | 4 | 6 | 7 | 0 | 0 | 5 | 0 | 0 | 0 | 0 | 0 | 2 | 2 | 9 | 2 | 7 | — | 6 | 9 | 0 |
| Cocklebur | 0 | 0 | — | 2 | 0 | 0 | 0 | 3 | 0 | 2 | 0 | 0 | 2 | 0 | 0 | 0 | 0 | 0 | 0 | 0 | 0 | 0 | 0 | 0 | 0 | 0 | 0 | 3 | 0 |
| Corn | 6 | 0 | 0 | 2 | 2 | 0 | 0 | 6 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 5 | 2 | 6 | 5 | 0 | 0 | 8 | 8 | 2 | 7 | 8 | 8 | 1 | 0 | 7 | 0 | 0 | 0 | 2 | 0 | 0 | 4 | 8 | 9 | 2 | 8 | 4 | 7 | 0 |
| Ducksalad | 0 | — | — | — | 0 | — | — | — | 2 | 3 | — | 6 | — | — | — | — | — | — | — | — | — | — | — | — | — | — | — | — | — |
| Giant foxtail | 8 | 5 | 9 | 9 | 6 | 0 | 8 | 9 | 2 | 8 | 8 | 9 | 3 | 2 | 8 | 0 | 3 | 2 | 9 | 0 | 3 | 6 | 9 | 9 | 3 | 8 | 7 | 9 | 0 |
| Morningglory | 4 | 7 | 1 | 1 | 0 | 0 | 6 | 5 | 10 | 10 | 7 | 7 | 8 | 10 | 5 | 0 | 10 | 8 | 5 | 2 | 0 | 0 | 0 | 2 | 1 | 4 | 8 | 7 | 0 |
| Nutsedge | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 5 | 0 | 3 | 0 |
| Rape | 0 | 3 | 0 | 0 | 0 | 0 | 0 | 2 | 0 | 2 | 0 | 3 | 2 | 2 | 0 | 0 | 0 | 0 | 0 | 0 | 0 | 0 | 0 | 0 | 0 | — | 2 | 10 | 0 |
| Redroot pigweed | 3 | 6 | 6 | 2 | 0 | 0 | 0 | 4 | 0 | 0 | 2 | 6 | 4 | 2 | 0 | 0 | 0 | 1 | 0 | 0 | 0 | 0 | 0 | 0 | 0 | 0 | 0 | 9 | 0 |
| Rice | 3 | — | — | — | 0 | — | — | — | 0 | 2 | — | 2 | — | — | — | — | — | — | — | — | — | — | — | — | — | — | — | — | — |
| S. Flatsedge | 4 | — | — | — | 0 | — | — | — | 2 | 4 | — | 8 | — | — | — | — | — | — | — | — | — | — | — | — | — | — | — | — | — |
| Soybean | 2 | 5 | 6 | 6 | 3 | 2 | 1 | 5 | 1 | 3 | 1 | 2 | 4 | 2 | 1 | 0 | 0 | 1 | 1 | 2 | 4 | 3 | 3 | 2 | 0 | 1 | 2 | 3 | 0 |
| Sugarbeets | 2 | 5 | 2 | 3 | 0 | 0 | 0 | 2 | 0 | 0 | 0 | 2 | 1 | 0 | 0 | 0 | 0 | 0 | 0 | 0 | 0 | 0 | 0 | 0 | 0 | 0 | 0 | 5 | 0 |
| Velvetleaf | 0 | 0 | 7 | 3 | 0 | 0 | 2 | 3 | 0 | 0 | 2 | 2 | 1 | 0 | 2 | 0 | 0 | 0 | 0 | 0 | 0 | 0 | 0 | 0 | 0 | 2 | 0 | 7 | 0 |
| Wheat | 4 | 0 | 6 | 5 | 0 | 0 | 0 | 4 | 0 | 0 | 0 | 0 | 0 | 0 | 2 | 0 | 0 | 0 | 0 | 0 | 0 | 0 | 2 | 0 | 0 | 3 | 0 | 3 | 0 |
| Wild oats | 3 | 6 | 6 | 1 | 0 | 0 | 0 | 3 | 0 | 3 | 3 | 5 | 0 | 0 | 6 | 0 | 0 | 0 | 0 | 0 | 0 | 0 | 0 | 2 | 0 | 0 | 0 | 7 | 0 |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate 250 g/ha | 392 | 393 | 394 | 395 | 396 | 397 | 398 | 400 | 401 | 402 | 403 | 404 | 405 | 406 | 407 | 408 | 409 | 410 | 411 | 414 | 415 | 416 | 417 | 418 | 419 | 420 | 421 | 422 | 423 |
| Postemergence | | | | | | | | | | | | | | | | | | | | | | | | | | | | | |
| B. signalgrass | 7 | 0 | 2 | 0 | 0 | 2 | 2 | 3 | 0 | 2 | 3 | — | 0 | 0 | 0 | 0 | 8 | 5 | 5 | 1 | 2 | 8 | 0 | 0 | 0 | 5 | 7 | 0 | 0 |
| Barnyardgrass | — | — | — | — | 0 | 0 | 0 | 0 | — | — | — | — | — | — | — | — | — | — | — | — | 0 | 0 | 0 | 0 | 0 | 0 | 2 | 0 | 0 |
| Bedstraw | — | — | 5 | 0 | — | — | — | — | — | 7 | — | 8 | — | — | — | 8 | 2 | — | 7 | — | — | — | 0 | — | 0 | 3 | 7 | — | — |
| Blackgrass | 10 | 3 | 9 | 0 | 3 | 9 | 9 | 8 | 0 | — | 10 | 10 | 0 | 0 | 0 | 9 | 9 | 9 | 9 | 5 | 8 | 9 | 0 | 4 | 0 | 6 | 8 | 0 | 0 |
| Cocklebur | 2 | 0 | 0 | 0 | 0 | 0 | 0 | 0 | 0 | 4 | 0 | 2 | 0 | 0 | 0 | 0 | — | 0 | 3 | 0 | 1 | 0 | 0 | 0 | 0 | 0 | 1 | 0 | 0 |
| Corn | 0 | 0 | 0 | 0 | 0 | 0 | 0 | 0 | 0 | 0 | 0 | 0 | 0 | 0 | 0 | 0 | 7 | 0 | 0 | 0 | 1 | 5 | 0 | 0 | 0 | 0 | 3 | 0 | 0 |
| Crabgrass | 7 | 5 | 8 | 2 | 2 | 9 | 9 | 6 | 2 | 5 | 8 | 5 | 0 | 0 | 1 | 8 | 9 | 8 | 8 | 6 | 8 | 9 | 2 | 3 | 0 | 8 | 8 | 0 | 0 |
| Ducksalad | — | — | — | — | 0 | 0 | 0 | 0 | — | — | — | — | — | — | — | — | — | — | — | — | 0 | 0 | 2 | 2 | 0 | 0 | 2 | 0 | 0 |
| Giant foxtail | 9 | 9 | 8 | 5 | 2 | 9 | 9 | 9 | 2 | 9 | 9 | 9 | 0 | 0 | 3 | 9 | 9 | 9 | 9 | 6 | 9 | 9 | 1 | 8 | 1 | 8 | 9 | 0 | 0 |
| Morningglory | 7 | 0 | 6 | 0 | 8 | 5 | 3 | 3 | 6 | 8 | 8 | 7 | 5 | 2 | 10 | 7 | 9 | 8 | 6 | 7 | 6 | 9 | 9 | 8 | 5 | 4 | 9 | 0 | — |
| Nutsedge | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 |
| Rape | 0 | 3 | 0 | 0 | 0 | 0 | 2 | 0 | — | 8 | 4 | 4 | 0 | 0 | 0 | — | 3 | 7 | 7 | 0 | 0 | 3 | 0 | 0 | 0 | 0 | 3 | 0 | 0 |
| Redroot pigweed | 6 | 0 | 2 | 0 | 0 | 4 | 3 | 0 | 1 | 5 | 1 | 5 | 0 | 0 | 0 | 0 | 4 | 0 | 7 | 0 | 0 | 2 | 0 | 0 | 0 | 0 | 5 | 0 | 0 |
| Rice | — | — | — | — | 0 | 0 | 0 | 0 | — | — | — | — | — | — | — | — | — | — | — | — | 0 | 0 | 0 | 0 | 0 | 0 | 2 | 0 | 0 |
| S. Flatsedge | — | — | — | — | 0 | 0 | 0 | 0 | — | — | — | — | — | — | — | — | — | — | — | — | 3 | 0 | 9 | 4 | 0 | 0 | 0 | 0 | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Soybean | 2 | 2 | 5 | 1 | 3 | 5 | 4 | 4 | 1 | 6 | 6 | 6 | 2 | 2 | 2 | 3 | 5 | 5 | 5 | 2 | 4 | 6 | 4 | 4 | 3 | 3 | 7 | 3 | 2 |
| Sugarbeets | 0 | 0 | 1 | 0 | 0 | 0 | 0 | 0 | 0 | 2 | 0 | 1 | 0 | 0 | 0 | 0 | 0 | 7 | 4 | 0 | 0 | 0 | 0 | 0 | 0 | 0 | 3 | 0 | 0 |
| Velvetleaf | 2 | 0 | 0 | 2 | 0 | 0 | 0 | 0 | 0 | 4 | 0 | 0 | 0 | 0 | 0 | 0 | 0 | 0 | 4 | 0 | 2 | 0 | 0 | 0 | 0 | 0 | 4 | 0 | 0 |
| Wheat | 0 | 0 | 3 | 0 | 0 | 2 | 0 | 0 | 0 | 0 | 1 | 0 | 0 | 0 | 0 | 1 | 4 | 0 | 4 | 0 | 2 | 5 | 0 | 0 | 0 | 0 | 5 | 0 | 0 |
| Wild oats | 7 | 0 | 6 | 0 | 0 | 2 | 0 | 0 | 0 | 0 | 2 | 5 | 0 | 0 | 0 | 2 | 0 | 5 | 3 | 0 | 2 | 4 | 0 | 0 | 0 | 0 | 4 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 424 | 425 | 426 | 427 | 428 | 429 | 430 | 431 | 432 | 433 | 434 | 435 | 436 | 437 | 438 | 439 | 440 | 441 | 442 | 443 | 444 | 445 | 446 | 447 | 448 | 449 | 450 | 451 | 452 |
| Postemergence | | | | | | | | | | | | | | | | | | | | | | | | | | | | | |
| B. signalgrass | 0 | 7 | 7 | 0 | 0 | 0 | 6 | 0 | 0 | 3 | 0 | 1 | 0 | 0 | 0 | 0 | 2 | 0 | 0 | 0 | 4 | 0 | 6 | 0 | 0 | 0 | 0 | 0 | 0 |
| Barnyardgrass | 0 | 1 | 0 | 0 | 2 | 1 | 0 | 0 | 0 | 0 | 0 | 0 | 0 | — | — | — | 0 | — | — | — | — | — | — | — | — | — | — | — | — |
| Bedstraw | 0 | — | 9 | — | — | — | 0 | — | — | 5 | — | 0 | 0 | 0 | 0 | — | 2 | — | — | — | — | — | — | — | 0 | — | — | — | — |
| Blackgrass | 0 | 8 | 8 | 0 | 3 | 3 | 7 | 2 | 4 | 7 | 0 | 6 | 0 | 0 | 2 | 0 | 4 | 0 | 0 | 0 | 5 | 0 | 8 | 0 | 0 | 0 | 2 | 2 | 3 |
| Cocklebur | 0 | 0 | 0 | 0 | 0 | 0 | 0 | 0 | 0 | 0 | 0 | 0 | 0 | 0 | 3 | 0 | 0 | 0 | 0 | 0 | 0 | 2 | 0 | 0 | 0 | 2 | 0 | 0 | 0 |
| Corn | 0 | 0 | 2 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 8 | 9 | 1 | 0 | 2 | 8 | 0 | 6 | 4 | 1 | 7 | 1 | 1 | 8 | 0 | 9 | 0 | 0 | 0 | 9 | 3 | 9 | 0 | 0 | 2 | 4 | 4 | 6 |
| Ducksalad | 0 | 0 | 0 | 0 | 3 | 6 | 0 | 0 | 0 | 0 | 0 | 0 | 0 | — | — | — | 0 | — | — | — | — | — | — | — | — | — | — | — | — |
| Giant foxtail | 0 | 8 | 9 | 3 | 0 | 2 | 9 | 0 | 6 | 6 | 1 | 8 | 1 | 0 | 9 | 0 | 9 | 0 | 0 | 0 | 8 | 1 | 9 | 0 | 0 | 0 | 7 | 3 | 7 |
| Morningglory | 0 | 6 | 9 | 0 | 2 | 2 | 3 | 1 | 1 | 4 | 1 | 6 | 2 | 4 | 9 | 0 | 8 | 0 | 7 | 4 | 1 | 4 | 3 | 4 | 2 | 5 | 1 | 1 | 2 |
| Nutsedge | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 2 | 2 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 |
| Redroot pigweed | 0 | 2 | 5 | 0 | 0 | 0 | 3 | 0 | 0 | 2 | 0 | 2 | 0 | 0 | 0 | 0 | 3 | 0 | 0 | 0 | — | — | 0 | 0 | 0 | 2 | 0 | 0 | 0 |
| Rice | 0 | 0 | 0 | 0 | 2 | 0 | 0 | 0 | 0 | 0 | 0 | 0 | 0 | — | — | — | 0 | — | — | — | — | — | — | — | — | — | — | — | — |
| S. Flatsedge | 0 | 2 | 0 | 0 | 0 | 3 | 0 | 0 | 0 | 0 | 0 | 0 | 0 | — | — | — | 0 | — | — | — | — | — | — | — | — | — | — | — | — |
| Soybean | 1 | 2 | 6 | 1 | 2 | 2 | 3 | 1 | 2 | 2 | 1 | 1 | 0 | 0 | 2 | 0 | 6 | 0 | 0 | 1 | 2 | 1 | 4 | 2 | 2 | 2 | 1 | 1 | 1 |
| Sugarbeets | 0 | 3 | 3 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Velvetleaf | 0 | 0 | 1 | 2 | 2 | 2 | 0 | 0 | 0 | 2 | 0 | 0 | 0 | 0 | 0 | 0 | 0 | 0 | 0 | 0 | 0 | 3 | 2 | 0 | 0 | 0 | 2 | 0 | 0 |
| Wheat | 0 | 3 | 0 | 0 | 0 | 0 | 0 | 0 | 0 | 0 | 0 | 0 | 0 | 0 | 0 | 0 | 0 | 0 | 0 | 0 | 0 | 0 | 3 | 0 | 0 | 0 | 0 | 0 | 0 |
| Wild oats | 0 | 2 | 2 | 0 | 0 | 0 | 0 | 0 | 0 | 0 | 0 | 0 | 0 | 0 | 0 | 0 | 0 | 0 | 0 | 0 | 0 | 0 | 3 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 453 | 454 | 455 | 456 | 457 | 458 | 459 | 460 | 461 | 462 | 463 | 465 | 466 | 467 | 468 | 469 | 470 | 471 | 472 | 473 | 474 | 476 | 477 | 478 | 479 | 480 | 481 | 482 | 483 |
| Postemergence | | | | | | | | | | | | | | | | | | | | | | | | | | | | | |
| B. signalgrass | 2 | 0 | 1 | 0 | 0 | 0 | 0 | 0 | 0 | 0 | 0 | 0 | 3 | 0 | 0 | 2 | 0 | 4 | 2 | 0 | 1 | 0 | 5 | 5 | 3 | 5 | 6 | 0 | 0 |
| Barnyardgrass | — | — | — | — | — | — | — | — | — | — | — | — | — | — | — | — | — | — | — | — | — | — | — | — | — | — | — | — | — |
| Bedstraw | — | — | — | — | — | — | 6 | — | — | — | — | — | 4 | — | — | 6 | — | — | — | — | 8 | — | — | — | 0 | 0 | — | 0 | — |
| Blackgrass | 6 | 2 | 9 | 4 | 0 | 8 | 8 | — | 0 | 0 | 0 | 6 | 8 | 0 | 7 | 9 | 0 | 3 | 2 | 0 | 8 | 0 | 6 | 8 | 4 | 3 | 2 | 0 | 0 |
| Cocklebur | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 |
| Corn | 0 | 0 | 0 | 0 | 0 | 2 | 0 | 0 | 0 | 0 | 0 | 0 | 0 | 0 | 0 | 2 | 0 | 0 | 0 | 0 | 0 | 0 | 0 | 0 | 0 | 0 | 3 | 0 | 0 |
| Crabgrass | 4 | 3 | 4 | 4 | 0 | 8 | 5 | 9 | 0 | 0 | 2 | 5 | 9 | 0 | 9 | 9 | 0 | 8 | 8 | 3 | 6 | 0 | 5 | 8 | 6 | 7 | 2 | 1 | 0 |
| Ducksalad | — | — | — | — | — | — | — | — | — | — | — | — | — | — | — | — | — | — | — | — | — | — | — | — | — | — | — | — | — |
| Giant foxtail | 7 | 8 | 7 | 3 | 0 | 9 | 2 | 0 | 0 | 0 | 6 | 5 | 9 | 2 | 9 | 9 | 0 | 7 | 8 | 6 | 7 | 0 | 6 | 8 | 6 | 8 | 8 | 0 | 0 |
| Morningglory | 2 | 10 | 8 | 5 | 0 | 3 | — | 7 | 7 | 0 | 2 | 2 | 2 | 7 | 4 | 10 | 0 | 4 | 4 | 2 | 1 | 0 | 10 | 7 | 10 | 7 | 2 | 8 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 4 | 0 | 0 | 0 | 0 | 0 | 0 | 0 | 0 | 1 | 0 | 0 | 0 | 0 | 0 | 0 |
| Redroot pigweed | 0 | 2 | 5 | 3 | 0 | 0 | 0 | 1 | 0 | 0 | 0 | 0 | 3 | 3 | 4 | 2 | 0 | 2 | 3 | 0 | 2 | 0 | 2 | 3 | 2 | 1 | 0 | 2 | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 1 | 2 | 4 | 2 | 1 | 2 | 6 | 4 | 3 | — | 1 | 1 | 4 | 0 | 1 | 4 | 1 | 3 | 2 | 1 | 4 | 2 | 2 | 2 | 3 | 3 | 4 | 1 | 0 |
| Sugarbeets | 0 | 0 | 0 | 0 | 0 | 0 | 0 | 0 | 0 | 0 | 0 | 0 | 0 | 4 | 0 | 2 | 0 | 0 | 0 | 0 | 0 | 0 | 0 | 0 | 0 | 0 | 0 | 0 | 0 |
| Velvetleaf | 0 | 0 | 3 | 0 | 0 | 0 | 0 | 0 | 0 | 0 | 0 | 3 | 0 | 0 | 2 | 0 | 0 | 2 | 2 | 0 | 0 | 2 | 0 | 0 | 0 | 0 | 0 | 0 | 0 |
| Wheat | 0 | 0 | 0 | 0 | 0 | 2 | 0 | 0 | 0 | 0 | 0 | 0 | 0 | 0 | 0 | 3 | 0 | 0 | 0 | 0 | 0 | 0 | 0 | 2 | 0 | 0 | 0 | 0 | 0 |
| Wild oats | 0 | 0 | 0 | 0 | 0 | 2 | 0 | 0 | 0 | 0 | 0 | 0 | 0 | 2 | 0 | 3 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 485 | 486 | 487 | 488 | 489 | 490 | 492 | 493 | 494 | 495 | 496 | 497 | 498 | 499 | 500 | 501 | 504 | 505 | 506 | 508 | 509 | 510 | 511 | 512 | 513 | 514 | 515 | 516 | 517 |
| Postemergence | | | | | | | | | | | | | | | | | | | | | | | | | | | | | |
| B. signalgrass | 4 | 1 | 0 | 6 | 6 | 4 | 0 | 0 | 0 | 0 | 0 | 0 | 0 | 0 | 7 | 7 | 8 | 8 | 0 | 3 | 2 | 4 | 0 | 4 | 6 | 3 | 0 | 3 | 6 |
| Barnyardgrass | — | — | — | — | — | — | — | — | — | — | — | — | — | — | — | — | — | — | — | — | — | — | — | — | — | — | — | — | — |
| Bedstraw | 2 | 4 | 6 | 4 | 5 | — | — | — | — | — | 0 | — | — | — | 9 | — | — | — | — | — | — | — | — | 7 | — | — | — | — | — |
| Blackgrass | 7 | 8 | 0 | 8 | 8 | — | 0 | 0 | 0 | 0 | 3 | 0 | — | 2 | 6 | 6 | 7 | 7 | 5 | 6 | 6 | 5 | 0 | 6 | 8 | 5 | 0 | 7 | 6 |
| Cocklebur | 0 | 0 | 0 | 0 | 0 | 0 | 0 | 0 | 0 | 0 | 0 | 0 | 0 | 2 | 3 | 2 | 6 | 0 | 2 | 4 | 0 | 4 | 0 | 3 | 6 | 3 | 3 | 3 | 0 |
| Corn | 0 | 0 | 0 | 0 | 0 | 0 | 0 | 0 | 0 | 0 | 0 | 0 | 0 | 0 | 2 | 4 | 2 | 6 | 0 | 0 | 0 | 0 | 0 | 0 | 0 | 0 | 0 | 0 | 0 |
| Crabgrass | 7 | 5 | 5 | 8 | 8 | 6 | 0 | 0 | — | 0 | 0 | 0 | 0 | 0 | 8 | 9 | 9 | 9 | 7 | 9 | 9 | 8 | 7 | 5 | 6 | 9 | 9 | — | 8 |
| Ducksalad | — | — | — | — | — | — | — | — | — | — | — | — | — | — | — | — | — | — | — | — | — | — | — | — | — | — | — | — | — |
| Giant foxtail | 8 | 8 | 4 | 9 | 9 | 8 | 0 | 0 | 0 | 0 | 0 | 0 | 2 | 0 | 8 | 9 | 9 | 9 | 4 | 8 | 8 | 8 | 5 | 7 | 8 | 9 | 9 | 8 | 9 |
| Morningglory | 10 | 2 | 10 | 8 | 10 | 3 | 8 | 0 | 0 | 2 | 8 | 0 | 3 | 4 | 3 | 3 | 4 | 5 | 3 | 4 | 2 | 5 | 4 | 6 | 6 | 7 | 6 | 6 | 2 |
| Nutsedge | 0 | 0 | 0 | 0 | 0 | 0 | 0 | 0 | 0 | 0 | 0 | 0 | 0 | 0 | 0 | — | 0 | 2 | 0 | 0 | — | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 6 | 7 | 7 | 2 | 2 | 8 | 3 | 6 | 1 | 0 | 4 | 6 | 5 | 8 | 0 |
| Redroot pigweed | 0 | 0 | 2 | 1 | 0 | 0 | 4 | 0 | 0 | 0 | 3 | 0 | 0 | 0 | 8 | 5 | 9 | 0 | 0 | 7 | 0 | 8 | 7 | 8 | 6 | 6 | 5 | 8 | 4 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 4 | 4 | 5 | 5 | 5 | 5 | 0 | 2 | 1 | 0 | 3 | 2 | 1 | 2 | 4 | 3 | 6 | 6 | 4 | 5 | 5 | 7 | 4 | 5 | 8 | 7 | 7 | 7 | 6 |
| Sugarbeets | 0 | 0 | 0 | 1 | 0 | 0 | 0 | 0 | 0 | 0 | 0 | 0 | 0 | 0 | 9 | 7 | 7 | 5 | 6 | 8 | 4 | 6 | — | 2 | 6 | 4 | 3 | 7 | 2 |
| Velvetleaf | 0 | 2 | 0 | 0 | 0 | 1 | 0 | 0 | 0 | 0 | 0 | 0 | 0 | 0 | 5 | 3 | 6 | 4 | 2 | 1 | 5 | 6 | 2 | 1 | 5 | 5 | 5 | 4 | 0 |
| Wheat | 1 | 1 | 0 | 3 | 0 | 0 | 0 | 0 | 0 | 0 | 0 | 0 | 0 | 0 | 3 | 2 | 5 | 4 | 2 | 0 | 0 | 0 | 0 | 0 | 6 | 0 | 0 | 5 | 3 |
| Wild oats | 0 | 0 | 0 | 0 | 1 | 5 | 0 | 0 | 0 | 0 | 0 | 0 | 0 | 0 | 2 | 3 | 7 | 3 | 0 | 2 | 4 | 2 | 0 | 1 | — | 0 | 0 | 5 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 518 | 519 | 520 | 521 | 522 | 523 | 524 | 525 | 526 | 527 | 528 | 531 | 532 | 533 | 534 | 535 | 536 | 540 | 541 | 543 | 544 | 545 | 546 | 548 | 549 | 550 | 551 | 552 | 553 |
| Postemergence | | | | | | | | | | | | | | | | | | | | | | | | | | | | | |
| B. signalgrass | 7 | 0 | 0 | 0 | 7 | 2 | 2 | 2 | 4 | 0 | 0 | 0 | 0 | — | 0 | 0 | 0 | 0 | 0 | 3 | 0 | 2 | 0 | 0 | 0 | 2 | 2 | 0 | 3 |
| Barnyardgrass | — | — | — | — | — | — | — | — | — | — | — | — | — | — | — | — | — | — | — | — | — | — | — | — | — | — | — | — | — |
| Bedstraw | — | 0 | — | — | 9 | — | 9 | — | — | — | 0 | 0 | 0 | — | — | — | 0 | 10 | 5 | — | 2 | 2 | 9 | 9 | 0 | 0 | 4 | 10 | 2 |
| Blackgrass | 7 | 0 | 0 | 7 | 8 | 3 | 9 | 8 | 9 | 4 | 0 | 0 | 0 | — | 7 | 7 | 0 | 2 | 0 | 0 | 0 | 0 | 3 | 3 | 2 | 2 | 7 | 0 | 3 |
| Cocklebur | 0 | 0 | 0 | 0 | 3 | 2 | 0 | 2 | 0 | 2 | 2 | 2 | 2 | 2 | 0 | 0 | 0 | 0 | 5 | 0 | 3 | 8 | 0 | 0 | 0 | 1 | 0 | 2 | 0 |
| Corn | 0 | 0 | 0 | 0 | 3 | 2 | 3 | 2 | 2 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 10 | 6 | 4 | 10 | 8 | 6 | 8 | 9 | 9 | 9 | 9 | 9 | 7 | 9 | 4 | 5 | 5 | 5 | 0 | 3 | 8 | 3 | 7 | — | 6 | 10 | 8 | — | 8 |
| Ducksalad | — | — | — | — | — | — | — | — | — | — | — | — | — | — | — | — | — | — | — | — | — | — | — | — | — | — | — | — | — |
| Giant foxtail | 2 | 4 | 4 | 9 | — | 4 | 8 | 9 | 7 | 8 | 3 | 9 | 4 | 9 | 4 | 5 | 0 | 0 | 0 | 0 | 6 | 3 | 4 | 0 | 2 | 9 | 5 | 3 | 6 |
| Morningglory | 8 | 0 | 4 | 3 | 4 | 4 | 2 | 2 | 6 | 5 | 5 | 4 | 5 | 7 | 2 | 2 | 2 | 5 | 1 | 4 | 10 | 10 | 5 | 8 | 4 | 9 | 4 | 2 | 0 |
| Nutsedge | — | — | 0 | 0 | 0 | 0 | — | 5 | 0 | 0 | 0 | 0 | — | 0 | 2 | 0 | 0 | 0 | 0 | 0 | 0 | — | — | 0 | — | 0 | — | 0 | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rape | 7 | 0 | 0 | 2 | 0 | 2 | 0 | 3 | — | 0 | 3 | 0 | 2 | — | 0 | 0 | 0 | 7 | 3 | 0 | 2 | 0 | 7 | 7 | 5 | — | 7 | 4 | 7 |
| Redroot pigweed | 0 | 0 | — | 0 | 4 | 3 | 0 | 9 | 2 | 0 | 0 | 0 | 0 | — | 3 | 0 | 0 | 2 | 0 | 0 | 0 | 0 | 0 | 2 | 0 | 0 | 3 | 0 | 0 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 5 | 4 | 4 | 5 | — | 5 | 3 | 5 | 3 | 4 | 5 | 6 | 5 | 4 | 6 | 6 | 4 | 1 | 1 | 2 | 0 | 2 | 2 | 2 | 2 | 3 | 3 | 3 | 3 |
| Sugarbeets | 3 | 0 | 0 | 0 | 6 | 0 | 0 | 6 | 0 | 0 | 0 | 0 | 0 | — | 3 | 0 | 0 | 6 | 0 | 2 | 1 | 0 | 4 | 3 | 0 | 2 | 5 | 3 | 0 |
| Velvetleaf | 4 | 4 | 4 | 2 | 7 | 3 | 5 | 3 | 7 | 3 | 4 | 0 | 2 | 4 | 2 | 0 | 0 | 0 | 0 | 0 | 0 | 6 | — | 0 | 4 | 0 | 3 | 2 | 5 |
| Wheat | 0 | 0 | 0 | 0 | 5 | 0 | 0 | 5 | 0 | 0 | 0 | 0 | 0 | — | 3 | 0 | 0 | 0 | 0 | 0 | 0 | 0 | 0 | 2 | 0 | 0 | 0 | 0 | 0 |
| Wild oats | 2 | 0 | 0 | 0 | 7 | 0 | 0 | 4 | 0 | 0 | 0 | 0 | 0 | — | 0 | 0 | 0 | 0 | 0 | 0 | 0 | 0 | 0 | 0 | 0 | 4 | 0 | 0 | 2 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 554 | 555 | 556 | 557 | 558 | 559 | 560 | 561 | 562 | 563 | 564 | 565 | 566 | 567 | 568 | 569 | 570 | 571 | 572 | 573 | 574 | 575 | 576 | 577 | 578 | 579 | 580 | 581 | 582 |
| Postemergence | | | | | | | | | | | | | | | | | | | | | | | | | | | | | |
| B. signalgrass | 0 | 0 | 4 | 2 | 0 | 9 | 6 | 6 | 5 | 5 | 3 | 0 | 8 | 0 | 7 | 0 | 0 | 0 | 0 | 0 | 0 | 0 | 0 | 0 | 0 | 2 | 5 | 7 | 0 |
| Barnyardgrass | — | — | — | — | — | — | — | — | — | — | — | — | — | — | — | — | — | — | — | — | — | — | — | — | — | — | — | — | — |
| Bedstraw | 7 | 9 | 0 | 0 | 0 | 0 | 0 | — | 4 | — | — | — | — | 0 | — | — | — | — | 0 | — | — | — | 5 | — | — | 10 | 0 | — | 9 |
| Blackgrass | 7 | 2 | 3 | 0 | 2 | 7 | 7 | 6 | 3 | 4 | 4 | 0 | 3 | 0 | 8 | 2 | 0 | 0 | 0 | 0 | 6 | 0 | 2 | 0 | 0 | 2 | 7 | 4 | 3 |
| Cocklebur | 0 | 0 | 0 | 0 | 0 | 0 | 0 | 0 | 2 | 0 | 0 | 2 | 2 | 0 | 1 | 2 | 0 | 0 | 0 | 2 | 2 | 0 | 0 | 0 | 0 | 0 | 3 | 3 | 2 |
| Corn | 0 | 0 | 0 | 0 | 0 | 6 | 2 | 0 | 7 | 4 | 0 | 0 | 2 | 0 | 4 | 0 | 0 | 0 | 0 | 0 | 0 | 0 | 2 | 0 | 0 | 0 | 0 | 5 | 0 |
| Crabgrass | 9 | 9 | 2 | 4 | 8 | 9 | 3 | 4 | 7 | 8 | 8 | 0 | 10 | 7 | 9 | 6 | 0 | — | 6 | 9 | — | 9 | 9 | 3 | 4 | 6 | 9 | 7 | 3 |
| Ducksalad | — | — | — | — | — | — | — | — | — | — | — | — | — | — | — | — | — | — | — | — | — | — | — | — | — | — | — | — | — |
| Giant foxtail | 8 | 8 | 9 | 6 | 5 | 9 | 7 | 7 | 8 | 8 | 7 | 0 | 8 | 0 | 9 | 4 | 0 | 2 | 0 | 9 | 6 | 8 | 7 | 2 | 7 | 5 | 8 | 8 | 9 |
| Morningglory | 5 | 5 | 4 | — | 10 | 9 | 9 | 5 | 10 | 10 | 10 | 7 | 6 | 4 | 10 | 10 | 10 | 10 | 5 | 10 | 10 | 9 | 4 | 10 | 10 | 10 | 8 | 7 | 10 |
| Nutsedge | 0 | 0 | 0 | 0 | 0 | 2 | 3 | — | 5 | 0 | 0 | 0 | — | — | 0 | 0 | 0 | 0 | 0 | 0 | 0 | 0 | 0 | — | — | 0 | — | — | — |
| Rape | 0 | — | 0 | 0 | 0 | 2 | 4 | 4 | 0 | 5 | 2 | 0 | 9 | 0 | 2 | 0 | 0 | 0 | 3 | 3 | 0 | 3 | 0 | 0 | 4 | 0 | 7 | 7 | 0 |
| Redroot pigweed | 7 | 2 | 3 | 0 | 0 | 3 | 8 | 0 | 9 | 5 | 3 | 6 | — | 0 | 0 | 4 | 0 | 0 | 0 | 4 | 0 | 4 | 0 | 0 | 3 | 0 | 5 | 8 | 7 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 3 | 2 | 3 | 0 | 4 | 5 | 2 | 3 | 4 | 3 | 5 | 3 | 6 | 4 | 6 | 4 | 3 | 2 | 5 | 4 | 6 | 5 | 3 | 3 | 3 | 3 | 4 | 4 | 3 |
| Sugarbeets | 7 | 0 | 0 | 0 | 2 | 2 | 0 | — | 3 | 0 | 2 | 0 | — | 0 | 1 | 0 | 0 | 0 | 0 | 0 | 0 | — | 0 | 0 | 0 | 0 | 5 | 7 | 3 |
| Velvetleaf | 0 | 2 | 0 | 0 | 0 | 2 | 0 | 0 | 6 | 2 | 2 | 4 | 5 | 0 | 5 | 2 | 0 | 0 | 0 | 0 | 2 | 2 | 0 | 0 | 4 | 0 | 2 | 6 | 0 |
| Wheat | 2 | 0 | 2 | 0 | 0 | 2 | 3 | 3 | 7 | 0 | — | 0 | 0 | 0 | 4 | 0 | 0 | 0 | 0 | 0 | 0 | 0 | 0 | 0 | 0 | 0 | 0 | 4 | 0 |
| Wild oats | 2 | 0 | 2 | 0 | 0 | 4 | 2 | 2 | 0 | 0 | — | 0 | 0 | 0 | 2 | 0 | 0 | 0 | 0 | 0 | 0 | 0 | 0 | 0 | 0 | 0 | 3 | 5 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 584 | 585 | 586 | 587 | 588 | 589 | 590 | 591 | 592 | 593 | 594 | 595 | 596 | 598 | 599 | 600 | 601 | 602 | 603 | 604 | 605 | 606 | 607 | 608 | 609 | 610 | 611 | 612 | 613 |
| Postemergence | | | | | | | | | | | | | | | | | | | | | | | | | | | | | |
| B. signalgrass | 7 | 0 | 3 | 0 | 4 | 0 | 0 | 0 | 0 | 0 | 2 | 6 | 0 | 0 | 0 | 0 | 4 | 5 | 0 | 0 | 0 | 0 | 4 | — | 5 | 7 | 7 | 7 | 6 |
| Barnyardgrass | — | — | — | — | — | — | — | — | — | — | — | — | — | — | — | — | — | — | — | — | — | — | — | — | — | — | — | — | — |
| Bedstraw | 9 | — | 0 | — | — | — | — | — | — | — | — | — | — | — | — | — | 3 | 3 | — | — | — | 0 | — | — | — | 4 | 6 | 6 | 8 |
| Blackgrass | 7 | 6 | 3 | 3 | 6 | 2 | 0 | 0 | 0 | 0 | 5 | 9 | 0 | 0 | 0 | 0 | 7 | 8 | 0 | 0 | 0 | 0 | 6 | 8 | 8 | 9 | 9 | 9 | 9 |
| Cocklebur | 4 | 0 | 0 | 0 | 0 | 0 | 0 | 0 | 0 | 0 | 3 | 0 | 0 | 0 | 0 | 0 | 0 | 0 | 0 | 0 | 0 | 0 | 0 | 0 | 2 | 0 | 2 | 0 | 2 |
| Corn | 3 | 0 | 2 | 0 | 0 | 0 | 0 | 0 | 0 | 0 | 0 | 2 | 0 | 0 | 0 | 0 | 0 | 0 | 0 | 0 | 0 | 0 | 0 | 0 | 2 | 2 | 4 | 0 | 0 |
| Crabgrass | 6 | 9 | 8 | — | 6 | 1 | 0 | 0 | 0 | 0 | 9 | 9 | 0 | 0 | 0 | — | 5 | 4 | 0 | 3 | 1 | 3 | 8 | 7 | 9 | 9 | 9 | 9 | 9 |
| Ducksalad | — | — | — | — | — | — | — | — | — | — | — | — | — | — | — | — | — | — | — | — | — | — | — | — | — | — | — | — | — |
| Giant foxtail | 9 | 8 | 8 | 0 | 8 | 0 | 0 | 0 | 0 | 0 | 7 | 9 | 0 | 0 | 0 | 0 | 7 | 9 | 0 | 3 | 0 | 0 | 7 | 7 | 9 | 9 | 9 | 9 | 9 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Morningglory | 5 | 10 | 10 | 6 | 10 | 5 | 3 | 2 | 2 | 0 | 2 | 3 | 0 | 0 | 1 | 0 | 1 | 2 | 2 | 2 | 9 | 10 | 8 | 8 | 10 | 8 | 8 | 8 | 8 |
| Nutsedge | 0 | 0 | 0 | 0 | — | — | 0 | 0 | 0 | 0 | 3 | 0 | — | 0 | — | 0 | 0 | 0 | 0 | 0 | 0 | — | 0 | 0 | 0 | 5 | 3 | 0 | 2 |
| Rape | 9 | 5 | 0 | 0 | 0 | 0 | 0 | 0 | 0 | 0 | 0 | 2 | 0 | 0 | 0 | 0 | 0 | 0 | 0 | 0 | 0 | 3 | 0 | 5 | 1 | 3 | 2 | 0 | 3 |
| Redroot pigweed | 2 | 3 | 0 | 0 | 0 | 2 | 0 | 0 | 0 | 0 | 3 | 3 | 0 | 0 | 0 | 0 | 2 | 3 | 0 | 0 | 0 | 1 | 0 | 7 | 2 | 6 | 3 | 4 | 7 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 3 | 4 | 3 | 6 | 4 | 3 | 3 | 2 | 1 | 0 | — | 4 | 2 | 0 | 2 | 3 | 5 | 5 | 2 | 1 | 3 | 2 | 6 | 4 | — | 8 | 8 | 7 | 6 |
| Sugarbeets | 5 | 4 | 0 | 0 | 0 | 0 | 0 | 0 | 0 | 0 | 5 | 3 | 0 | 0 | 0 | 0 | 0 | 0 | 0 | 0 | 0 | 0 | 0 | 5 | 0 | 0 | 0 | 0 | 0 |
| Velvetleaf | 3 | 4 | 0 | 0 | 0 | 5 | 2 | 0 | 0 | 0 | 3 | 7 | 0 | 0 | 0 | 0 | 0 | 0 | 0 | 0 | 0 | 0 | 3 | 4 | 7 | 7 | 5 | 3 | 5 |
| Wheat | 3 | 2 | 0 | 0 | 0 | 0 | 0 | 0 | 0 | 0 | 0 | 2 | 0 | 0 | 0 | 0 | 0 | 0 | 0 | 0 | 1 | 0 | 2 | 0 | 2 | 4 | 2 | 2 | 2 |
| Wild oats | 2 | 0 | 0 | 0 | 0 | 0 | 0 | 0 | 0 | 0 | 0 | 2 | 0 | 0 | 0 | 0 | 0 | 0 | 0 | 0 | 1 | 0 | 0 | 5 | 0 | 5 | 4 | 6 | 9 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 614 | 615 | 616 | 617 | 618 | 619 | 620 | 621 | 622 | 623 | 624 | 625 | 627 | 628 | 629 | 630 | 631 | 632 | 633 | 634 | 635 | 636 | 638 | 639 | 640 | 641 | 642 | 643 | 644 |
| Postemergence | | | | | | | | | | | | | | | | | | | | | | | | | | | | | |
| B. signalgrass | 0 | 0 | 1 | 0 | 0 | 0 | 0 | 0 | 0 | 0 | 7 | 2 | 7 | 8 | 3 | 1 | 6 | 2 | 0 | 0 | 2 | 0 | 6 | 0 | 0 | 0 | 0 | 0 | 0 |
| Barnyardgrass | — | — | — | — | — | — | — | — | — | — | — | — | — | — | — | — | — | — | — | — | — | — | — | — | — | — | — | — | — |
| Bedstraw | 3 | — | 0 | — | — | 0 | — | — | — | — | — | — | — | — | 8 | — | — | 0 | 0 | 0 | 9 | 9 | — | — | — | — | — | — | — |
| Blackgrass | 0 | 0 | 0 | 0 | 0 | 0 | 0 | 0 | 0 | 4 | 8 | 7 | 9 | 9 | 8 | 3 | 6 | 6 | 4 | 8 | 7 | 3 | 6 | 2 | — | 2 | 6 | 0 | 0 |
| Cocklebur | 0 | 0 | 0 | 0 | 0 | 0 | 0 | 0 | 0 | 0 | 2 | 0 | 0 | 6 | 0 | 0 | 0 | 0 | 0 | 2 | 3 | 3 | 2 | 2 | 2 | 0 | 0 | 0 | 0 |
| Corn | 0 | 0 | 0 | 0 | 0 | 0 | 0 | 0 | 0 | 0 | 2 | 0 | 7 | 7 | 4 | 2 | 6 | 3 | 0 | 0 | 0 | 2 | 2 | 0 | 0 | 0 | 0 | 0 | 0 |
| Crabgrass | 5 | 4 | 4 | 2 | 0 | 0 | — | — | — | 0 | 7 | 4 | 9 | 9 | 8 | 8 | 9 | 8 | 3 | 7 | 8 | 9 | 8 | 2 | 3 | 3 | 0 | 0 | 0 |
| Ducksalad | — | — | — | — | — | — | — | — | — | — | — | — | — | — | — | — | — | — | — | — | — | — | — | — | — | — | — | — | — |
| Giant foxtail | 2 | 6 | 3 | 4 | 0 | 0 | 0 | 1 | 6 | 0 | 8 | 5 | 9 | 9 | 9 | 8 | 9 | 8 | 3 | 9 | 8 | 9 | 8 | 6 | 0 | 3 | 4 | 0 | 0 |
| Morningglory | 2 | 1 | 4 | 0 | 0 | 1 | 2 | 2 | 2 | 8 | 1 | 1 | 6 | 2 | 3 | 2 | 4 | 2 | 5 | 2 | 4 | 6 | 3 | 7 | 6 | 7 | 0 | 4 | 0 |
| Nutsedge | 0 | 0 | 0 | — | 0 | 0 | 0 | 0 | 0 | 0 | 0 | 0 | 6 | — | 0 | — | 0 | 0 | 0 | — | — | 0 | — | — | 0 | 4 | 0 | 0 | — |
| Rape | 0 | 0 | 0 | 0 | 0 | 0 | 0 | 0 | 0 | 0 | 0 | 0 | 0 | 3 | 0 | 0 | 2 | 0 | 0 | 0 | 7 | 7 | 0 | 0 | 0 | 0 | 0 | 0 | 0 |
| Redroot pigweed | 0 | 0 | 0 | 0 | 0 | 1 | 0 | 0 | 0 | 0 | 2 | 0 | 6 | 7 | 2 | 1 | — | 0 | 1 | 2 | 3 | 6 | 0 | 4 | 4 | 3 | 0 | 0 | 3 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 4 | 3 | 4 | 3 | 6 | 1 | 1 | 5 | 6 | 0 | 7 | 3 | 4 | — | 7 | 5 | 8 | 4 | 2 | 3 | 4 | 4 | 3 | 3 | 0 | 1 | 2 | 1 | — |
| Sugarbeets | 0 | 0 | 0 | 0 | 0 | 0 | 0 | 0 | 2 | 0 | 0 | 0 | 0 | 3 | 0 | 0 | 0 | 0 | 0 | 0 | 7 | 5 | 0 | 0 | 0 | 0 | 0 | 0 | 0 |
| Velvetleaf | 0 | 0 | 0 | 0 | 0 | 2 | 0 | 0 | 0 | 0 | 0 | 0 | 8 | 8 | 5 | 4 | 7 | 0 | 0 | 3 | 2 | 3 | 4 | 0 | 3 | 0 | 3 | 0 | 0 |
| Wheat | 0 | 0 | 0 | 0 | 0 | 0 | 0 | 0 | 0 | 1 | 0 | 0 | 6 | 7 | 0 | 0 | 6 | 0 | 0 | 0 | 2 | 0 | 3 | 0 | 0 | 0 | 0 | 0 | 0 |
| Wild oats | — | 0 | 0 | 0 | 0 | 0 | 0 | 0 | 0 | 0 | 0 | 0 | 6 | 5 | — | 0 | 1 | 0 | 0 | 0 | 5 | 0 | 1 | 1 | 0 | 1 | 1 | 1 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 645 | 646 | 647 | 648 | 649 | 650 | 652 | 653 | 654 | 655 | 656 | 657 | 658 | 659 | 660 | 661 | 662 | 663 | 664 | 665 | 666 | 667 | 668 | 670 | 671 | 672 | 674 | 675 | 676 |
| Postemergence | | | | | | | | | | | | | | | | | | | | | | | | | | | | | |
| B. signalgrass | 0 | 0 | 7 | 0 | 0 | 0 | 0 | 0 | 0 | 2 | 5 | 4 | 0 | 5 | 0 | 2 | 0 | 0 | 4 | 1 | 5 | 6 | 4 | 7 | 6 | 3 | 8 | 8 | 7 |
| Barnyardgrass | — | — | — | — | — | — | — | — | — | — | — | — | — | — | — | — | — | — | — | — | — | — | — | — | — | — | — | — | — |
| Bedstraw | 0 | 0 | — | — | — | — | — | — | 0 | — | — | — | 0 | — | — | — | — | — | — | 0 | — | — | — | — | 0 | 4 | 0 | 6 | — |
| Blackgrass | 0 | 0 | 7 | 0 | 0 | 0 | 0 | 0 | 0 | 0 | 9 | 8 | 6 | 7 | 3 | 4 | 0 | 0 | 9 | 8 | 8 | 8 | 8 | 5 | 8 | 6 | 8 | 7 | 6 |
| Cocklebur | 3 | 0 | 4 | 0 | 0 | 0 | 0 | 0 | 0 | 0 | 0 | 4 | 2 | 0 | 2 | 0 | 0 | 0 | 2 | 0 | 4 | 4 | 2 | 2 | 0 | 2 | 2 | 3 | 0 |
| Corn | 0 | 0 | 5 | 0 | 0 | 2 | 0 | 0 | 0 | 0 | 0 | 1 | 0 | 4 | 0 | 0 | 0 | 0 | 0 | 0 | 0 | 4 | 3 | 5 | 0 | 0 | 6 | 0 | 0 |
| Crabgrass | 0 | 0 | 9 | 0 | — | 7 | 0 | 0 | 2 | 8 | 8 | 9 | 2 | 6 | 5 | 7 | 0 | 0 | 9 | 9 | 9 | 9 | 9 | 8 | 8 | 7 | 9 | 9 | — |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Ducksalad | — | — | — | — | — | — | — | — | — | — | — | — | — | — | — | — | — | — | — | — | — | — | — | — | — | — | — | — | — |
| Giant foxtail | 0 | 0 | 9 | 0 | 2 | 8 | 4 | 2 | 5 | — | 9 | 7 | 7 | 8 | 5 | 4 | 2 | 0 | 9 | 8 | 8 | 9 | 9 | 9 | 9 | 8 | 9 | 9 | 8 |
| Morningglory | 1 | 0 | 2 | 10 | 7 | 10 | 5 | 1 | 10 | 9 | 2 | 5 | 7 | 10 | 6 | 0 | 9 | 4 | 9 | 6 | 7 | 4 | 4 | 6 | 1 | 8 | 10 | 2 | 2 |
| Nutsedge | 0 | 0 | — | 0 | 0 | 2 | — | 0 | 0 | 0 | 0 | 7 | — | — | 0 | 0 | 0 | 0 | 0 | 0 | 0 | 0 | 0 | 5 | — | 0 | 7 | 0 | 0 |
| Rape | 0 | 0 | 2 | 0 | 0 | 0 | 0 | — | 0 | 2 | 0 | 3 | 0 | 0 | 0 | 0 | 0 | 0 | 3 | 3 | 0 | — | — | 4 | 0 | 2 | 1 | 1 | 0 |
| Redroot pigweed | 2 | 0 | 6 | 10 | 0 | 0 | — | 0 | 0 | 3 | 0 | 5 | 7 | 2 | 5 | 2 | 0 | 0 | 4 | 6 | 2 | 5 | 6 | 8 | 3 | 8 | 3 | 8 | 3 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 1 | 1 | 3 | 3 | 3 | 4 | 1 | 0 | 0 | 2 | 2 | 4 | 4 | 5 | 4 | — | 2 | 3 | 5 | 4 | 7 | 5 | 3 | 4 | 3 | 5 | 5 | 5 | 3 |
| Sugarbeets | 0 | 0 | 2 | 0 | 0 | 0 | 0 | 0 | 0 | 0 | 0 | 0 | 0 | 0 | 0 | 0 | 0 | 0 | 0 | 0 | 2 | 0 | 2 | 2 | 0 | 2 | 0 | 2 | 0 |
| Velvetleaf | 0 | 0 | 6 | 0 | 0 | 0 | 0 | 0 | 0 | 0 | 0 | 4 | 2 | 6 | 3 | 0 | 0 | 0 | 5 | 6 | 6 | 7 | 4 | 5 | 0 | 7 | 7 | 4 | 3 |
| Wheat | 0 | 0 | 6 | 0 | 0 | 0 | 0 | 0 | 0 | 0 | 0 | 0 | 0 | 0 | 0 | 0 | 0 | 0 | 0 | 0 | 0 | 0 | 0 | 3 | 0 | 0 | 3 | 4 | 2 |
| Wild oats | 0 | 0 | 2 | 0 | 0 | 0 | 0 | 0 | 0 | 0 | 0 | 2 | 1 | 0 | 0 | 1 | 1 | 0 | 5 | 2 | 3 | 4 | 0 | 3 | 0 | 0 | 0 | 5 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 677 | 678 | 679 | 680 | 681 | 708 | 709 | 710 | 711 | 712 | 713 | 714 | 722 | 736 | 739 | 740 | 741 | 743 | 744 | 745 | 746 | 747 | 748 | 749 | 750 | 751 | 752 | 753 | 754 |
| Postemergence | | | | | | | | | | | | | | | | | | | | | | | | | | | | | |
| B. signalgrass | 0 | 0 | 0 | 0 | 0 | 0 | 0 | 6 | 6 | 4 | 5 | 6 | 2 | 0 | 2 | 0 | 4 | 3 | 5 | 6 | 6 | 4 | 4 | 3 | 6 | 6 | 2 | 2 | 6 |
| Barnyardgrass | — | — | — | — | — | — | — | — | — | — | — | — | — | — | — | — | — | — | — | — | — | — | — | — | — | — | — | — | — |
| Bedstraw | — | 0 | 0 | 0 | 0 | — | — | 6 | 8 | — | — | — | — | — | 4 | — | 4 | 4 | — | 7 | 8 | — | 9 | 3 | 7 | — | 2 | — | 0 |
| Blackgrass | 0 | 0 | 0 | 0 | 0 | 2 | 0 | 6 | 7 | 5 | 7 | 6 | 0 | 2 | 3 | 4 | 0 | 5 | 5 | 8 | 8 | 8 | 7 | 6 | 7 | 6 | 6 | 4 | 5 |
| Cocklebur | 0 | 0 | 0 | 0 | 0 | 0 | 0 | 0 | 2 | 3 | 3 | 2 | 0 | 0 | 2 | 3 | 0 | 0 | 0 | 0 | 2 | 2 | 0 | 4 | 1 | 2 | — | 0 | 0 |
| Corn | 0 | 0 | 0 | 0 | 0 | 0 | 0 | 0 | 0 | 0 | 0 | 0 | 0 | 3 | 0 | 0 | 0 | 0 | 3 | 0 | 4 | 4 | 0 | 0 | 0 | 0 | 0 | 0 | 2 |
| Crabgrass | 0 | 0 | 0 | 1 | 0 | 0 | 6 | 9 | 9 | 9 | 9 | 9 | 2 | 3 | — | 9 | 9 | 7 | 8 | 9 | 9 | 9 | 8 | 9 | 9 | 9 | 8 | 6 | 9 |
| Ducksalad | — | — | — | — | — | — | — | — | — | — | — | — | — | — | — | — | — | — | — | — | — | — | — | — | — | — | — | — | — |
| Giant foxtail | 2 | 1 | 0 | 0 | 0 | 4 | 8 | 9 | 9 | 8 | 9 | 7 | 4 | 2 | 9 | 8 | 3 | 8 | 8 | 9 | 9 | 9 | 8 | 9 | 8 | 9 | 9 | 8 | 8 |
| Morningglory | 4 | 6 | 0 | 1 | 0 | 2 | 2 | 4 | 4 | 10 | 7 | 2 | 10 | 6 | 6 | 3 | 5 | 2 | 2 | 3 | 10 | 10 | 6 | 5 | 8 | 8 | 8 | 9 | 10 |
| Nutsedge | 0 | 0 | 0 | 0 | 0 | 0 | 0 | 0 | 3 | 0 | 0 | 5 | 0 | 0 | 0 | 0 | 0 | 3 | 3 | 0 | 2 | 0 | 0 | 0 | 7 | 0 | 0 | 2 | — |
| Rape | 0 | 0 | 0 | 0 | 0 | 0 | 0 | 3 | 2 | 4 | 6 | 8 | 0 | 0 | 0 | 0 | 0 | 0 | 3 | 5 | 7 | 4 | 6 | 6 | 6 | 5 | 4 | 0 | 0 |
| Redroot pigweed | 3 | 0 | 0 | 0 | 2 | 0 | 8 | 9 | 9 | 6 | 9 | 9 | 8 | — | 3 | 4 | 7 | 5 | 0 | 5 | 8 | 7 | 6 | 4 | 7 | 9 | 5 | 6 | 0 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 1 | 2 | 1 | 0 | 0 | 4 | 3 | 4 | 5 | 5 | 5 | 4 | 0 | 4 | 4 | 4 | 3 | 4 | 4 | 5 | 4 | 7 | 4 | 5 | 7 | 7 | 6 | 4 | 2 |
| Sugarbeets | 0 | 0 | 0 | 0 | 0 | 0 | 0 | 3 | 2 | — | 0 | 7 | 0 | 0 | 3 | 2 | 4 | 4 | 0 | 4 | 4 | 0 | 6 | 4 | 3 | 3 | 3 | 5 | 0 |
| Velvetleaf | 0 | 0 | 0 | 0 | 0 | 3 | 4 | 6 | 6 | 6 | 6 | 2 | 0 | 2 | 0 | 2 | 0 | 0 | 0 | 3 | 6 | 4 | 0 | 3 | 5 | 2 | 2 | 2 | 0 |
| Wheat | 0 | 0 | 0 | 0 | 0 | 0 | 0 | 4 | 3 | 0 | 2 | 3 | 2 | 2 | 2 | 0 | 0 | 3 | 5 | 0 | — | 4 | 0 | 0 | 2 | 5 | 5 | 0 | 5 |
| Wild oats | 0 | 0 | 0 | 0 | 0 | 0 | 0 | 5 | 2 | 0 | 1 | 4 | 2 | 3 | 0 | 0 | 3 | 0 | 0 | 4 | 6 | 2 | 0 | 0 | 0 | 3 | 0 | 0 | 0 |

| | COMPOUND | | | | | | | | | | | | | | | | | | | | | | |
|---|---|---|---|---|---|---|---|---|---|---|---|---|---|---|---|---|---|---|---|---|---|---|---|
| Rate 250 g/ha | 756 | 757 | 758 | 759 | 760 | 761 | 762 | 763 | 764 | 765 | 766 | 767 | 772 | 773 | 774 | 775 | 776 | 777 | 778 | 780 | 790 | 791 | 792 |
| Postemergence | | | | | | | | | | | | | | | | | | | | | | | |
| B. signalgrass | 0 | 0 | 6 | 6 | 0 | 3 | 2 | 5 | 2 | 7 | 8 | 6 | 0 | 0 | 0 | 3 | 0 | 2 | 6 | 5 | 7 | 0 | 0 |
| Barnyardgrass | — | — | — | — | — | — | — | — | — | — | — | — | — | — | — | — | — | — | — | — | — | — | — |
| Bedstraw | 3 | 0 | 7 | — | — | 0 | 0 | — | — | — | 0 | 7 | 0 | 0 | 0 | 2 | 3 | 2 | 3 | — | 0 | 3 | — |
| Blackgrass | 0 | 3 | 6 | 7 | 0 | 0 | 0 | 5 | 6 | 7 | 6 | 9 | 0 | 0 | 0 | 4 | 2 | 2 | 4 | 4 | 5 | 5 | — |
| Cocklebur | 0 | 2 | 4 | 1 | 0 | 0 | 0 | 1 | 2 | 0 | 2 | 2 | 0 | 0 | 0 | 0 | 0 | 0 | 0 | 0 | 0 | 0 | 3 |

TABLE B-continued

| | | | | | | | | | | | | | | | | | | | | | | | |
|---|---|---|---|---|---|---|---|---|---|---|---|---|---|---|---|---|---|---|---|---|---|---|---|
| Corn | 0 | 0 | 0 | 0 | 1 | 0 | 2 | 0 | 0 | 0 | 4 | 0 | 0 | 0 | 0 | 0 | 0 | 0 | 0 | 3 | 4 | 1 | 2 |
| Crabgrass | 0 | 6 | 8 | 8 | 9 | 0 | 3 | 8 | 9 | 7 | 6 | 9 | 0 | 0 | 0 | 7 | 2 | 7 | 8 | 7 | 9 | 9 | — |
| Ducksalad | — | — | — | — | — | — | — | — | — | — | — | — | — | — | — | — | — | — | — | — | — | — | — |
| Giant foxtail | 0 | 5 | 9 | 8 | 7 | — | 8 | 9 | 8 | 9 | 9 | 9 | 0 | 0 | 0 | 7 | 2 | 8 | 9 | 9 | 8 | 8 | 9 |
| Morningglory | 10 | 7 | 4 | 3 | 3 | 7 | 2 | 7 | 2 | 6 | 2 | 5 | 0 | 0 | 0 | 6 | — | 8 | 4 | 7 | 7 | 9 | 10 |
| Nutsedge | 0 | 0 | 0 | 0 | 0 | 0 | 0 | 3 | 0 | 0 | — | 0 | 0 | 0 | 0 | 0 | 0 | 0 | — | 4 | 5 | 0 | 0 |
| Rape | 0 | 0 | 0 | 0 | 2 | 0 | 0 | 0 | 3 | 0 | 0 | — | 0 | 0 | 0 | 0 | 2 | 0 | 2 | 0 | 3 | 5 | 7 |
| Redroot pigweed | 0 | 5 | 8 | 0 | 2 | 6 | 6 | 3 | 7 | — | 6 | 9 | 0 | 0 | 0 | 3 | 2 | 4 | 4 | 0 | 5 | 6 | 6 |
| Rice | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — |
| Soybean | 2 | 4 | 5 | 3 | 4 | 3 | 4 | 3 | 3 | 5 | 4 | 4 | 0 | 0 | 0 | 6 | 2 | 3 | 4 | 0 | 4 | 5 | 5 |
| Sugarbeets | 0 | 3 | 3 | 0 | 0 | 3 | 6 | 2 | 3 | 0 | 2 | 5 | 0 | 0 | 0 | 0 | 3 | 3 | 0 | 0 | 0 | 2 | 2 |
| Velvetleaf | 0 | 3 | 6 | 6 | 0 | 0 | 3 | 0 | 4 | 7 | 3 | 2 | 0 | 0 | 0 | 2 | 3 | 3 | 3 | 4 | 5 | 6 | 6 |
| Wheat | 0 | 0 | 5 | 0 | 0 | 0 | 0 | 4 | 7 | 3 | 3 | 2 | 0 | 0 | 0 | 0 | 0 | 2 | 2 | 0 | 4 | 0 | 1 |
| Wild oats | 0 | 0 | 1 | 2 | 0 | 0 | 0 | — | 2 | 0 | 2 | 0 | 0 | 0 | 0 | 0 | 0 | 2 | 2 | 2 | 0 | 0 | 2 |

| | COMPOUND | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Rate 250 g/ha | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
| Preemergence | | | | | | | | | | | | | | | | | | | | | | | | | | | | | | | | | | | | | | | | | | | | |
| B. signalgrass | 0 | 0 | 0 | 8 | 3 | 0 | 0 | 4 | 0 | 8 | 0 | 0 | 2 | 0 | 0 | 0 | 6 | 7 | 2 | 0 | 0 | 4 | 0 | 4 | 7 | 2 | 0 | 0 | 0 | 4 | 6 | 2 | 7 | 2 | 3 | 8 | 0 | 8 | 0 | 5 | 4 | 0 | 0 | 0 |
| Bedstraw | 0 | 0 | 0 | 4 | 0 | 0 | 0 | 0 | 0 | 0 | 0 | 0 | 0 | 0 | 0 | 0 | 0 | 0 | 0 | 2 | 0 | 4 | 0 | 0 | 0 | 0 | 0 | 1 | 0 | 0 | 0 | 0 | 0 | 0 | 0 | — | 0 | 0 | 0 | 0 | 0 | 0 | 0 | 0 |
| Blackgrass | 0 | 0 | 0 | 8 | 3 | 0 | 0 | 0 | 0 | 8 | 0 | 0 | 0 | 0 | 0 | 0 | 3 | 5 | 2 | 1 | 0 | 6 | 2 | 4 | 8 | 0 | 0 | 3 | 2 | 7 | 2 | 4 | 0 | 6 | 2 | 6 | 0 | 10 | 0 | 1 | 2 | 0 | 0 | 0 |
| Cocklebur | 0 | 0 | 0 | 0 | 0 | 0 | 0 | 0 | 0 | — | 0 | 0 | 0 | 0 | — | 0 | 0 | 0 | 0 | 0 | 0 | 0 | — | 0 | 0 | 0 | 0 | 0 | 0 | — | 0 | 0 | 0 | 0 | 0 | 0 | 0 | — | 0 | 0 | 0 | 0 | 0 | 0 |
| Corn | 0 | 6 | 0 | 0 | 0 | 1 | 0 | 0 | 0 | 0 | 0 | 0 | 0 | 0 | — | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 8 | 0 | 0 | 10 | 3 | — | — | — | 0 | — | 0 | 0 | 5 | 9 | — | 2 | 9 | 8 | 7 | 6 | 7 | 8 | 3 | 9 | 10 | 3 | 0 | 9 | 7 | 10 | 9 | 9 | 7 | 10 | 6 | 9 | 3 | 10 | 5 | 7 | 8 | 0 | 0 | 0 |
| Giant foxtail | 8 | 7 | 1 | 10 | 8 | 4 | 5 | 9 | 0 | 9 | 0 | 0 | 8 | 9 | — | 3 | 7 | 8 | 4 | 7 | 8 | 7 | 3 | 9 | 10 | 4 | 0 | 7 | 3 | 10 | 8 | 9 | 9 | 10 | 10 | 10 | 2 | 10 | — | 10 | 10 | 0 | 0 | 0 |
| Morningglory | 0 | 0 | 0 | 0 | 0 | 0 | 0 | 0 | 0 | 0 | 0 | 0 | 0 | 0 | — | 0 | 0 | 0 | 0 | 0 | 2 | 0 | 0 | 0 | 0 | 0 | 0 | 0 | 0 | 0 | 0 | 2 | 1 | 0 | 0 | 0 | 0 | 0 | 0 | 0 | 0 | 0 | 0 | 0 |
| Nutsedge | — | — | — | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 6 | 0 | 0 | 0 | 0 | 0 | 0 | 0 | 0 | 0 | 0 | 0 | 0 | 0 | 0 | 0 | 0 | 0 | 3 | 0 | 0 | 0 | 0 | 0 | 0 | 0 | 0 | 4 | 0 | 0 | 0 | 0 | 0 | 0 | — | 0 | 0 | 0 | 0 | 0 | 0 |
| Redroot pigweed | 0 | 0 | 0 | 8 | 7 | 5 | 0 | 5 | 0 | 0 | 0 | 0 | 0 | 0 | 0 | 0 | 10 | 8 | 2 | 4 | 6 | 5 | 0 | 6 | 8 | 0 | 0 | 1 | 5 | 7 | 3 | 0 | 0 | 6 | 0 | 6 | 0 | 10 | 6 | 4 | 1 | 0 | 0 | 0 |
| Soybean | 0 | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 0 | 0 | 8 | 0 | 0 | 0 | 0 | 0 | 0 | 0 | 0 | 0 | 0 | 3 | 0 | 3 | 2 | 1 | 2 | 3 | 7 | 0 | 4 | 0 | 0 | 0 | 0 | 0 | 0 | 0 | 0 | 0 | 0 | 0 | 0 | 0 | 2 | 0 | 0 | 0 | 0 | 0 | 0 |
| Velvetleaf | 0 | 0 | 0 | 0 | 0 | 2 | 0 | — | 0 | 0 | 0 | 0 | 0 | 0 | — | 0 | 0 | 0 | 0 | 0 | 0 | 1 | 0 | 0 | 0 | 0 | 0 | 0 | 0 | 3 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 |
| Wild oats | 0 | 0 | 0 | 4 | 6 | 0 | 0 | 0 | 0 | 0 | 0 | 0 | 0 | 0 | 0 | 0 | 2 | 0 | 0 | 0 | 0 | 0 | 0 | 0 | 6 | 0 | 0 | 3 | 0 | 8 | 4 | 2 | 2 | 2 | 2 | 6 | 0 | 6 | 0 | 0 | 0 | 0 | 0 | 0 |

| | COMPOUND | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Rate 250 g/ha | 45 | 46 | 47 | 48 | 49 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 85 | 86 | 87 | 88 | 89 | 90 |
| Preemergence | | | | | | | | | | | | | | | | | | | | | | | | | | | | | | | | | | | | | | | | | | | | |
| B. signalgrass | 4 | 2 | 0 | 0 | 0 | 0 | 0 | 2 | 0 | 0 | 0 | 0 | 0 | 0 | 0 | 5 | 0 | 0 | 0 | 0 | 0 | 0 | 4 | 0 | 0 | 0 | 0 | 0 | 0 | 2 | 2 | 0 | 5 | 3 | 0 | 3 | 0 | 0 | 0 | 4 | 4 | 2 | 0 | — |
| Bedstraw | 0 | 0 | 0 | 0 | 0 | 0 | 0 | 0 | 0 | 0 | 0 | 0 | 0 | 0 | 0 | 2 | 0 | 0 | 0 | 2 | 0 | 0 | 4 | 0 | 0 | 0 | 0 | 0 | 0 | 0 | 0 | 0 | 0 | 0 | 0 | 0 | 0 | 0 | 0 | 0 | 0 | 0 | 0 | 0 |
| Blackgrass | 0 | 2 | 0 | 2 | 0 | 0 | 3 | 1 | 0 | 0 | 0 | 0 | 0 | 0 | 0 | 5 | 2 | 0 | 0 | 0 | 0 | 2 | 2 | 0 | 0 | 0 | 0 | 0 | 0 | 7 | 4 | 0 | 4 | 6 | 4 | 6 | 0 | 0 | 0 | 5 | 5 | 4 | 0 | 3 |
| Cocklebur | 0 | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 |
| Crabgrass | 1 | 10 | 2 | 7 | 9 | 2 | 6 | 7 | 3 | 0 | 0 | 0 | 0 | 0 | 1 | 7 | 6 | 1 | 2 | 4 | 4 | 4 | 10 | 2 | 0 | 0 | 0 | 8 | 5 | 10 | 8 | 2 | 9 | 9 | 10 | 8 | 0 | 0 | 0 | 10 | 10 | 10 | 0 | 8 |
| Giant foxtail | 10 | 10 | 3 | 10 | 10 | 4 | 7 | 8 | 3 | 0 | 0 | 0 | 0 | 3 | 4 | 9 | 9 | 2 | 3 | 4 | 6 | 8 | 10 | 4 | 0 | 0 | 2 | 9 | 8 | 9 | 9 | 3 | 9 | 9 | 8 | 8 | 0 | 0 | 0 | 10 | 10 | 10 | 0 | 9 |

TABLE B-continued

| | | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 | 2 | — | 0 | 10 | 0 | 0 | 0 | 0 | 0 | 0 | 0 | 0 | 3 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 5 | 0 | 4 | 0 | 0 | 0 | 0 | 0 | 0 | 0 | 0 | 0 |
| Redroot pigweed | 8 | 6 | 0 | 0 | 0 | 0 | 1 | 0 | 0 | 0 | 0 | 0 | 0 | 0 | 0 | 1 | 0 | 0 | 0 | 0 | 0 | 9 | 7 | 0 | 0 | 0 | 0 | 0 | 0 | 7 | 3 | 0 | 6 | 7 | 7 | 0 | 0 | 0 | 0 | 8 | 8 | 10 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 7 | 3 | 0 | 0 | 0 | 0 | 0 | 0 | 0 | 0 | 0 | 0 | 0 | 0 | 3 | 5 | 0 | 0 | 0 | 0 | 0 | 0 | 0 | 0 | 0 | 0 | 0 | 0 | 2 | 0 | 0 | 0 | 5 | 1 | 4 | 0 | 0 | 0 | 0 | 3 | 3 | 6 | 0 | 0 |
| Velvetleaf | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 2 | 0 | 2 | 0 | 0 | 0 | 0 | 3 | 3 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 3 | 0 | 0 | 0 | 0 | 0 | 0 | 0 | 0 | 0 | 0 | 0 |
| Wild oats | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 8 | 4 | 0 | 6 | 3 | 3 | 3 | 0 | 0 | 0 | 4 | 4 | 2 | 0 | 2 |

| | COMPOUND | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| Rate 250 g/ha | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 | 114 | 115 | 116 | 117 | 118 | 119 | 120 | 121 | 122 |
| Preemergence | | | | | | | | | | | | | | | | | | | | | | | | | | | | | | | | |
| B. signalgrass | 10 | 10 | — | 1 | 3 | 1 | 3 | 0 | 2 | 0 | 0 | 0 | 7 | 5 | 5 | 0 | 10 | 7 | 10 | — | 1 | 3 | 10 | 7 | 4 | 10 | 9 | 3 | 7 | 6 | 8 | 0 |
| Bedstraw | 5 | 0 | 0 | 0 | 0 | 0 | 0 | 0 | 0 | 0 | 0 | 0 | 0 | 0 | 0 | 3 | 10 | 8 | 10 | 5 | 0 | 0 | 7 | 0 | 0 | 9 | 0 | 0 | 2 | 0 | 2 | 0 |
| Blackgrass | 10 | 10 | 10 | 8 | 4 | 3 | 1 | 8 | 4 | 0 | 0 | 2 | 3 | 6 | 8 | 0 | 10 | 9 | 10 | 7 | 2 | 2 | 10 | 10 | 0 | 10 | 10 | 3 | 9 | 7 | 7 | 0 |
| Cocklebur | — | 0 | — | 0 | 0 | 0 | 0 | 0 | 0 | 0 | 0 | 0 | — | 0 | 0 | 0 | 0 | 0 | 0 | 0 | 0 | 0 | 3 | 0 | 0 | 0 | 0 | 0 | 0 | 0 | — | 0 |
| Corn | 8 | 5 | 8 | 3 | 0 | 0 | 0 | 0 | 0 | 0 | 0 | 0 | 0 | 0 | 2 | 0 | 9 | 6 | 7 | 4 | 4 | 0 | 8 | 7 | 0 | 6 | 7 | 0 | 0 | 0 | 0 | 0 |
| Crabgrass | 10 | 8 | 9 | 6 | 8 | 7 | 1 | 8 | 10 | 0 | 0 | 0 | 9 | 1 | 8 | 8 | 10 | 9 | 10 | 9 | 9 | 10 | 10 | 9 | 7 | 10 | 10 | 10 | 8 | 9 | 8 | 8 |
| Giant foxtail | 10 | 10 | 10 | 9 | 7 | 3 | 4 | 10 | 10 | 0 | 0 | 9 | 9 | 10 | 10 | 10 | 10 | 10 | 10 | 10 | 10 | 10 | 10 | 10 | 9 | 10 | 10 | 10 | 10 | 9 | 8 | 9 |
| Morningglory | 4 | 0 | 3 | 0 | 0 | 0 | 0 | 0 | 0 | 0 | 0 | 0 | 0 | 0 | 0 | 0 | 2 | 0 | 6 | 0 | 0 | 2 | 7 | 0 | 0 | 4 | 2 | 0 | 2 | 0 | 0 | 0 |
| Nutsedge | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 3 | 0 | 0 | 0 | 0 | 0 |
| Rape | 10 | 10 | 8 | 2 | 3 | 0 | 5 | 0 | 0 | 0 | 0 | 0 | 0 | 0 | 4 | 0 | 9 | 7 | 9 | 4 | 4 | 0 | 10 | 6 | 0 | 10 | 10 | 0 | 7 | 0 | 0 | 0 |
| Redroot pigweed | 10 | 9 | 10 | 0 | 9 | 7 | 4 | 5 | 4 | 0 | 0 | 0 | 6 | 0 | 9 | 0 | 10 | 10 | 10 | 7 | 8 | 7 | 10 | 10 | 6 | 10 | 10 | 2 | 10 | 8 | 8 | 8 |
| Soybean | 4 | 4 | 7 | 0 | 0 | 0 | 0 | 0 | 0 | 0 | 0 | 0 | 0 | 0 | 0 | 0 | 5 | 0 | 8 | 5 | 4 | 0 | 9 | 0 | 0 | 9 | 8 | 0 | 0 | 0 | 0 | 0 |
| Sugarbeets | 9 | 8 | 8 | 0 | 2 | 0 | 5 | 3 | 2 | 0 | 0 | 0 | 0 | 1 | 4 | 0 | 10 | 4 | 10 | 2 | 3 | 0 | 9 | 7 | 0 | 10 | 9 | 0 | 8 | 4 | 7 | 0 |
| Velvetleaf | 7 | 6 | 6 | 0 | 0 | 0 | 0 | 2 | 0 | 0 | 0 | 0 | 3 | 0 | 5 | 0 | 10 | 4 | 10 | 5 | 3 | 4 | 8 | 5 | 2 | 10 | 10 | 0 | 5 | 0 | 0 | 0 |
| Wheat | 4 | 7 | 6 | 0 | 0 | 0 | 0 | 1 | 2 | 0 | 0 | 0 | 0 | 0 | 0 | 0 | 7 | 2 | 9 | 0 | 0 | 0 | 7 | 2 | 0 | 8 | 7 | 0 | 3 | 2 | 0 | 0 |
| Wild oats | 10 | 9 | 10 | 4 | 2 | 2 | 2 | 2 | 3 | 0 | 0 | 0 | 3 | 4 | 3 | 0 | 10 | 9 | 10 | 5 | 2 | 2 | 10 | 9 | 0 | 10 | 10 | 6 | 6 | 6 | 5 | 3 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 123 | 124 | 125 | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 | 149 | 150 | 151 |
| Preemergence | | | | | | | | | | | | | | | | | | | | | | | | | | | | | |
| B. signalgrass | 0 | 0 | 0 | 0 | 0 | 0 | — | 9 | 8 | 7 | 5 | 6 | 3 | 5 | 7 | 6 | 8 | 0 | 0 | 0 | 2 | 5 | 3 | 10 | 8 | 7 | 0 | 0 | 5 |
| Bedstraw | 0 | 0 | 0 | 0 | 0 | 0 | 0 | 2 | 10 | 9 | 0 | 0 | 0 | 0 | 7 | 10 | 2 | 0 | 0 | 0 | 0 | 0 | 0 | 10 | 2 | 0 | 0 | 0 | 0 |
| Blackgrass | 4 | 0 | — | 0 | 0 | 0 | 2 | 9 | 10 | 9 | 3 | 2 | 0 | 4 | 9 | 9 | 9 | 4 | 0 | 0 | 5 | 4 | 4 | 10 | 10 | 7 | 0 | 0 | 10 |
| Cocklebur | 0 | 0 | 0 | 0 | 0 | 0 | 0 | 0 | 2 | — | 0 | 0 | 0 | 0 | 0 | 0 | 0 | 0 | 0 | 0 | — | 0 | 0 | 0 | 1 | 0 | 0 | 0 | 0 |
| Corn | 0 | 0 | 0 | 0 | 0 | 0 | 2 | 6 | 9 | 7 | 0 | 0 | 0 | 0 | 0 | 8 | 4 | 0 | 0 | 0 | 0 | 2 | 0 | 8 | 8 | 0 | 0 | 0 | 5 |
| Crabgrass | 5 | 0 | 0 | 0 | 0 | 0 | 7 | 9 | 9 | 9 | 5 | 9 | 0 | 7 | 10 | 10 | 10 | 5 | 3 | 2 | 8 | 7 | 4 | 9 | 8 | 9 | 0 | 5 | 10 |
| Giant foxtail | 9 | 0 | — | 0 | 2 | 0 | 8 | 10 | 10 | 9 | 9 | 10 | 0 | 10 | 10 | 10 | 10 | — | 3 | 5 | 9 | 8 | 5 | 10 | 9 | 9 | 0 | 3 | 10 |
| Morningglory | 0 | 0 | 0 | 0 | 0 | 0 | 0 | 3 | 5 | 0 | 0 | 0 | 0 | 0 | 0 | 3 | 0 | 0 | 0 | 0 | 0 | 0 | 0 | 3 | 2 | 0 | 0 | 0 | 0 |
| Nutsedge | 0 | 0 | 0 | 0 | 0 | 0 | 0 | 0 | 0 | 0 | 0 | 0 | 0 | 0 | 0 | 7 | 0 | 0 | 0 | 0 | 0 | 0 | 0 | 0 | 0 | 0 | 0 | 0 | 0 |
| Rape | 0 | 0 | 0 | 0 | 0 | 0 | 0 | 10 | 10 | 0 | 0 | 0 | 0 | 0 | 10 | 10 | 4 | 0 | 0 | 0 | 4 | 0 | 0 | 10 | 8 | 6 | 0 | 0 | 10 |
| Redroot pigweed | 5 | 0 | 0 | 0 | 3 | 0 | 2 | 10 | 10 | 7 | 0 | 0 | 4 | 10 | 10 | 10 | 10 | 0 | 0 | 0 | 4 | 0 | 2 | 10 | 9 | 9 | 0 | 8 | 10 |
| Soybean | 0 | 0 | 0 | 0 | 0 | 0 | 0 | 3 | 8 | 2 | 0 | 0 | 0 | 0 | 3 | 5 | 0 | 0 | 0 | 0 | 0 | 0 | 0 | 2 | 9 | 0 | 0 | 0 | 3 |
| Sugarbeets | 5 | 0 | 0 | 0 | 0 | 0 | 3 | 10 | 10 | 6 | 3 | 4 | 0 | 8 | 10 | 10 | 4 | 0 | 0 | 0 | 3 | 2 | 0 | 10 | 6 | 8 | 0 | 0 | 10 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Velvetleaf | 3 | 0 | 0 | 0 | 0 | 0 | 4 | 8 | 9 | 6 | 2 | 2 | 0 | 0 | 7 | 10 | 5 | 0 | 0 | 0 | 0 | 0 | 0 | 8 | 6 | 8 | 0 | 0 | 10 |
| Wheat | 5 | 0 | 0 | 0 | 0 | 0 | 3 | — | 8 | 2 | 0 | 0 | 0 | 0 | 5 | 6 | 2 | 0 | 0 | 0 | 0 | 0 | 0 | 8 | 7 | 3 | 0 | 0 | 4 |
| Wild oats | 6 | 0 | 0 | 0 | 0 | 0 | 6 | 10 | 10 | 8 | 2 | 2 | 0 | 0 | 9 | — | 8 | 1 | 0 | 0 | 5 | 2 | 0 | 10 | 9 | 6 | 0 | 0 | 10 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 152 | 153 | 154 | 155 | 156 | 157 | 158 | 159 | 160 | 161 | 162 | 163 | 164 | 165 | 166 | 167 | 168 | 169 | 170 | 171 | 172 | 173 | 174 | 175 | 176 | 177 | 178 | 179 | 180 |
| Preemergence | | | | | | | | | | | | | | | | | | | | | | | | | | | | | |
| B. signalgrass | 4 | 0 | 0 | 0 | 2 | 0 | 0 | 0 | 0 | 5 | 3 | 2 | 0 | 6 | 0 | 5 | 2 | 7 | 10 | 3 | 5 | 3 | 0 | 0 | 0 | 0 | 8 | — | 0 |
| Bedstraw | 0 | 0 | 0 | 0 | 0 | 0 | 0 | 0 | 0 | 0 | 0 | 4 | 0 | 3 | 0 | 3 | 0 | 7 | 6 | 0 | 3 | 0 | — | 9 | 0 | 9 | 0 | 0 | 0 |
| Blackgrass | 0 | 0 | 3 | 2 | 3 | 5 | — | 0 | 0 | 7 | 2 | 10 | 0 | 6 | 4 | 3 | 2 | 8 | 10 | 0 | 3 | 0 | 2 | 0 | 2 | 6 | 0 | 2 | 0 |
| Cocklebur | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 2 | 0 | 0 | 0 | 0 | 0 | 0 | 0 | 0 | 0 | 0 | 3 | 6 | 0 | 0 | 0 | 0 | 0 | 0 | 0 | 0 | 0 | 0 |
| Crabgrass | 1 | 0 | 0 | 6 | 6 | 4 | 4 | 0 | 0 | 9 | 9 | 8 | 0 | 8 | 7 | 10 | 7 | 10 | 10 | 10 | 10 | 8 | 8 | 6 | 9 | 9 | 8 | 9 | 0 |
| Giant foxtail | 3 | 0 | — | 2 | 7 | 8 | 7 | 0 | 0 | 9 | 9 | 8 | 0 | 8 | 5 | 10 | 10 | 10 | 10 | 10 | 10 | 9 | 10 | 8 | 10 | 10 | 8 | 10 | 0 |
| Morningglory | 0 | 0 | 0 | 0 | 0 | 0 | 1 | 0 | 0 | 0 | 0 | 0 | 0 | 0 | 0 | 0 | 0 | 0 | 6 | 0 | 0 | 0 | 0 | 0 | 0 | 0 | 0 | 0 | 0 |
| Nutsedge | 0 | 0 | 0 | 0 | 0 | 0 | 0 | 0 | 0 | 0 | 0 | 0 | 0 | 0 | 0 | 0 | 0 | 0 | 9 | 0 | 0 | 0 | — | 3 | 0 | 0 | 0 | 0 | 0 |
| Rape | 0 | 0 | 0 | 0 | 0 | 0 | 0 | 0 | 0 | 0 | 4 | 7 | 0 | 4 | 0 | 0 | 0 | 6 | 10 | — | 0 | 0 | 0 | 0 | 0 | 0 | 0 | 2 | 0 |
| Redroot pigweed | 0 | 0 | 8 | 3 | 9 | 0 | 0 | 0 | 0 | 4 | 0 | 6 | 0 | 0 | 0 | 8 | 0 | 8 | 10 | 5 | 8 | 0 | 8 | 0 | 0 | 0 | 6 | 7 | 0 |
| Soybean | 0 | 0 | 0 | 0 | 0 | 0 | 0 | 0 | 0 | 0 | 0 | 0 | 0 | 0 | 0 | 0 | 0 | 2 | 4 | 0 | 0 | 0 | 0 | 0 | 0 | 0 | 0 | 0 | 0 |
| Sugarbeets | 0 | 0 | 4 | 0 | 0 | 0 | 0 | 0 | 0 | 0 | 0 | 4 | 0 | 4 | 0 | 5 | 4 | 7 | 8 | 0 | 5 | 3 | 6 | 0 | 0 | 0 | 0 | 0 | 0 |
| Velvetleaf | 0 | 0 | 0 | 0 | 0 | 0 | 0 | 0 | 0 | 0 | 0 | 5 | 0 | 4 | 5 | 0 | 0 | 6 | 10 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 2 | 0 | 0 | 0 | 0 | 0 | 3 | 8 | 0 | 0 | 0 | 0 | 0 | 0 | 0 | 0 | 0 | 0 |
| Wild oats | 0 | 0 | 4 | 0 | 0 | 0 | 0 | 0 | 0 | 3 | 2 | 7 | 0 | 4 | 0 | 3 | 1 | 8 | 10 | 4 | 3 | 2 | 0 | 0 | 3 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 181 | 182 | 183 | 184 | 185 | 186 | 187 | 188 | 189 | 190 | 191 | 192 | 193 | 194 | 195 | 196 | 197 | 198 | 199 | 200 | 201 | 202 | 203 | 204 | 205 | 206 | 207 | 208 | 210 |
| Preemergence | | | | | | | | | | | | | | | | | | | | | | | | | | | | | |
| B. signalgrass | 0 | 0 | 4 | 8 | 0 | 0 | 0 | 6 | 3 | 0 | 0 | 6 | 0 | 0 | 1 | 0 | 0 | 0 | 6 | 0 | 0 | 0 | 0 | 0 | 0 | 0 | 0 | 0 | 0 |
| Bedstraw | 0 | 0 | 0 | 2 | 0 | 0 | 0 | 0 | 0 | 0 | 0 | 0 | 0 | 0 | 0 | 0 | 0 | 0 | 0 | 0 | 0 | 6 | 0 | 0 | 0 | 0 | 0 | 0 | 0 |
| Blackgrass | 0 | 0 | 0 | 5 | 0 | 3 | 0 | 0 | 4 | 0 | 4 | 6 | 0 | 3 | 3 | 0 | 0 | 0 | 10 | 7 | 4 | 5 | 0 | 2 | 0 | 0 | 4 | 0 | 0 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 7 | 7 | 6 | 0 | 0 | 0 | 0 | 8 | 7 | 6 | 9 | 5 | 0 | 0 | 0 | 10 | 6 | 9 | 6 | 0 | 8 | 1 | 3 | 3 | 6 | 3 |
| Giant foxtail | 0 | 0 | 0 | 10 | 9 | 9 | 0 | 4 | 3 | 0 | 9 | 10 | 5 | 8 | 8 | 0 | 0 | 0 | 10 | 6 | 8 | 7 | 0 | 10 | 0 | 8 | 9 | 9 | 3 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | — | 0 | 0 | 0 | 0 | 0 | — | 0 | 0 | — | 0 | 0 | 0 | 0 | — | — | — | 0 | 0 | 0 | 0 | 0 | 0 | 0 |
| Rape | 0 | 0 | 0 | 0 | 0 | 0 | 0 | 0 | 0 | 0 | 0 | 4 | 0 | 2 | 0 | 0 | 0 | 0 | 0 | 0 | 0 | 0 | 0 | 0 | 0 | 0 | 0 | 0 | 0 |
| Redroot pigweed | 0 | 0 | 0 | 0 | 0 | 2 | 0 | 0 | 0 | 0 | 1 | 5 | 0 | 8 | 0 | 0 | 0 | 0 | 10 | 0 | 0 | 8 | 0 | 0 | 0 | 0 | 2 | 0 | 2 |
| Soybean | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 |
| Sugarbeets | 0 | 0 | 0 | 0 | 0 | 0 | 0 | 0 | 0 | 0 | 0 | 0 | 0 | 2 | 0 | 0 | 0 | 0 | 5 | 0 | 0 | 3 | 0 | 0 | 0 | 0 | 0 | 0 | 0 |
| Velvetleaf | 0 | 0 | 0 | 2 | 0 | 2 | 0 | 0 | 0 | 0 | 0 | 5 | 0 | 0 | 0 | 0 | 0 | 0 | 0 | 0 | 0 | 6 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 0 | 0 | 0 | 0 | 0 | 0 | 0 | 0 | 3 | 0 | 3 | 5 | 0 | 3 | 0 | 0 | 0 | 0 | 4 | 0 | 3 | 0 | 0 | 3 | 0 | 0 | 0 | 0 | 2 |

TABLE B-continued

| Rate 250 g/ha | COMPOUND 211 | 212 | 213 | 214 | 215 | 216 | 217 | 218 | 219 | 220 | 221 | 222 | 223 | 224 | 225 | 226 | 227 | 228 | 229 | 230 | 231 | 232 | 233 | 234 | 235 | 236 | 237 | 238 | 239 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 0 | 5 | 0 | 0 | 2 | 4 | 0 | 6 | 9 | 8 | 6 | 0 | 3 | 4 | 7 | 9 | 0 | 0 | 0 | 0 | 0 | 1 | 4 | 0 | 0 | 0 | 0 | 0 | 4 |
| Bedstraw | 0 | 0 | 0 | 0 | 0 | 0 | 0 | 0 | 8 | 10 | 4 | 0 | 0 | 0 | 0 | 0 | — | 0 | 0 | 0 | 0 | 0 | 0 | 0 | 0 | 0 | 0 | 0 | 0 |
| Blackgrass | 9 | 7 | 0 | 3 | — | 4 | 8 | 9 | 10 | 10 | 7 | 0 | 4 | 3 | 10 | 10 | 10 | 0 | 0 | 0 | 0 | 8 | 8 | 0 | 0 | 5 | 0 | 0 | 4 |
| Cocklebur | 0 | 0 | — | 0 | 0 | 0 | 0 | 0 | 0 | — | 0 | 0 | 0 | 0 | 2 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 5 | 5 | 0 | 0 | 0 | 0 | 4 | 6 | 0 | 0 | 0 | 0 | 0 | 0 | 0 | 0 | 0 | 0 | 0 | 0 | 0 |
| Crabgrass | 3 | 5 | 3 | 1 | 4 | 8 | 8 | 6 | 9 | 8 | 8 | 8 | 7 | 9 | 10 | 10 | 10 | 1 | 0 | 7 | 0 | 9 | 9 | 0 | 0 | 5 | 2 | 10 | 10 |
| Giant foxtail | 7 | 9 | 4 | 6 | 3 | 7 | 10 | 10 | 10 | 10 | 10 | 7 | — | 9 | 10 | 10 | 10 | 9 | 0 | 8 | 3 | 8 | 9 | 0 | 0 | 9 | 4 | 10 | 10 |
| Morningglory | 0 | 0 | 3 | 0 | 0 | 0 | 0 | 0 | 0 | 1 | 0 | 0 | 1 | 0 | 4 | 7 | 0 | 0 | 0 | 0 | 0 | 0 | 0 | 0 | 0 | 0 | 0 | 0 | 0 |
| Nutsedge | — | 0 | — | — | 0 | 0 | 0 | — | — | — | 0 | 0 | — | — | 8 | — | 0 | 0 | 0 | 0 | 0 | — | 0 | — | — | — | — | 0 | — |
| Rape | 0 | 6 | 0 | 0 | 0 | 0 | 4 | 0 | 6 | 8 | 8 | 0 | 0 | 0 | 0 | 7 | 8 | 0 | 0 | 0 | 0 | 0 | 0 | 0 | 0 | 0 | 0 | 0 | 0 |
| Redroot pigweed | 3 | 10 | 5 | 6 | 5 | 2 | 10 | 8 | 9 | 8 | 10 | 0 | 7 | 0 | 10 | 7 | 10 | 0 | 0 | 0 | 0 | 5 | 7 | 0 | 0 | 0 | 0 | 0 | 0 |
| Soybean | 0 | 0 | 0 | 0 | 0 | 0 | 0 | 2 | 0 | 0 | 0 | 0 | 0 | 0 | 3 | 0 | 0 | 0 | 0 | 0 | 0 | 0 | 0 | 0 | 0 | 0 | 0 | 0 | 0 |
| Sugarbeets | 0 | 5 | 0 | 0 | 2 | 0 | 0 | 6 | 4 | 8 | 10 | 0 | 0 | 0 | 5 | 5 | 6 | 0 | 0 | 0 | 0 | 4 | 4 | 0 | 0 | 0 | 0 | 3 | 0 |
| Velvetleaf | 0 | 5 | 0 | 0 | 0 | 0 | 5 | 0 | 7 | 4 | 0 | 0 | 0 | 0 | 6 | 6 | 0 | 0 | 0 | 0 | 0 | 0 | 2 | 0 | 0 | 0 | 0 | 0 | 2 |
| Wheat | 0 | 5 | 0 | 0 | 0 | 0 | 8 | 0 | 8 | 8 | 2 | 0 | 0 | 0 | 8 | 8 | 0 | 0 | 0 | 0 | 0 | 0 | 0 | 0 | 0 | 0 | 0 | 0 | 0 |
| Wild oats | 5 | 3 | 0 | 0 | 2 | 0 | 2 | 7 | 8 | 7 | 4 | 0 | 2 | 0 | 10 | 9 | 3 | 0 | 0 | 0 | 0 | 3 | 2 | 0 | 0 | 0 | 0 | 0 | 3 |

| Rate 250 g/ha | COMPOUND 240 | 241 | 242 | 243 | 244 | 245 | 246 | 247 | 248 | 249 | 250 | 251 | 252 | 253 | 254 | 255 | 256 | 257 | 258 | 259 | 260 | 261 | 262 | 263 | 264 | 265 | 266 | 267 | 268 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 0 | 4 | 9 | 7 | 0 | 8 | 3 | 0 | 0 | 0 | 0 | 7 | 0 | 0 | 0 | 3 | 0 | 0 | 7 | 8 | 0 | 0 | 0 | 0 | 5 | 0 | 0 | 0 | 0 |
| Bedstraw | 0 | 7 | 9 | 5 | 0 | 9 | 0 | 0 | 0 | 0 | 0 | 10 | 0 | 0 | 0 | 0 | 0 | 0 | 3 | 10 | — | — | 0 | 0 | 0 | 0 | 8 | 0 | 0 |
| Blackgrass | 0 | 7 | 10 | 10 | 0 | 10 | 6 | 0 | 0 | 0 | 0 | 9 | 4 | 0 | 0 | 10 | 0 | 0 | 8 | 10 | 2 | 1 | 2 | 0 | 4 | 0 | 9 | 2 | 0 |
| Cocklebur | 0 | 0 | 2 | 0 | 0 | 2 | 0 | 0 | 0 | 0 | 0 | 0 | — | 0 | 0 | 0 | 0 | 0 | 0 | 0 | 0 | 0 | 0 | 0 | 0 | 0 | 0 | 0 | 0 |
| Corn | 0 | 0 | 6 | 6 | 0 | 7 | 0 | 0 | 0 | 0 | 0 | 0 | 0 | 0 | 0 | 0 | 0 | 0 | 3 | 3 | 0 | 0 | 0 | 0 | 0 | 0 | 0 | 2 | 0 |
| Crabgrass | 9 | 10 | 10 | 9 | 0 | 9 | 10 | 2 | 0 | 0 | 8 | 9 | 4 | 0 | 0 | 7 | 2 | 2 | 9 | — | 6 | 5 | 2 | 0 | 3 | 2 | 5 | 1 | 0 |
| Giant foxtail | 10 | 10 | 10 | 10 | 0 | 10 | 10 | 2 | 0 | 3 | 10 | 10 | 10 | 0 | 6 | 10 | 9 | 6 | 10 | 9 | 8 | 9 | — | 9 | 7 | 8 | 6 | 9 | 0 |
| Morningglory | 0 | 3 | 5 | 8 | 0 | 6 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 |
| Nutsedge | 0 | 10 | 10 | 0 | 0 | — | 0 | 0 | 0 | 0 | — | — | — | — | 0 | — | 0 | 0 | — | 0 | 0 | 0 | 0 | 0 | 0 | 0 | 0 | 0 | 0 |
| Rape | 0 | 5 | 10 | 9 | 0 | 10 | 10 | 0 | 0 | 0 | 0 | 9 | 3 | 0 | 2 | 0 | 0 | 0 | 5 | — | 0 | 0 | 0 | 0 | 0 | 0 | 5 | 0 | 0 |
| Redroot pigweed | 0 | 9 | 10 | 10 | 0 | 10 | 0 | 0 | 0 | 0 | 3 | 10 | 0 | 0 | 0 | 5 | 0 | 0 | 7 | 2 | 4 | 0 | 0 | 0 | 0 | 0 | 6 | 6 | 0 |
| Soybean | 0 | 0 | 6 | 8 | 0 | 2 | 0 | 0 | 0 | 0 | 0 | 0 | 0 | 0 | 0 | 0 | 0 | 0 | 2 | 0 | 0 | 0 | 0 | 0 | 3 | 0 | 0 | 0 | 0 |
| Sugarbeets | 0 | 6 | — | 7 | 0 | 10 | 2 | 0 | 0 | 0 | 5 | 10 | 3 | 0 | 2 | 6 | 0 | 0 | 5 | 0 | 0 | 0 | 0 | 0 | 1 | 0 | 7 | 0 | 0 |
| Velvetleaf | 0 | 5 | 8 | 10 | 0 | 10 | 4 | 0 | 0 | 0 | 0 | 5 | 2 | 0 | 0 | 5 | 0 | 0 | 5 | 4 | 0 | 0 | 0 | 0 | 0 | 0 | 0 | 0 | 0 |
| Wheat | 0 | 3 | 9 | 8 | 0 | 7 | 0 | 0 | 0 | 0 | 0 | 0 | 2 | 0 | 0 | 4 | 0 | 0 | 4 | 0 | 0 | 0 | 0 | 0 | 2 | 0 | 4 | 0 | 0 |
| Wild oats | 0 | 8 | 9 | 9 | 0 | 10 | 6 | 0 | 0 | 0 | 0 | 8 | 3 | 0 | 0 | 5 | 0 | 0 | 5 | 4 | 0 | 0 | 0 | 0 | 5 | 2 | 5 | 0 | 0 |

TABLE B-continued

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 269 | 270 | 271 | 272 | 273 | 274 | 276 | 277 | 278 | 279 | 280 | 281 | 282 | 283 | 284 | 285 | 286 | 288 | 289 | 292 | 293 | 294 | 295 | 296 | 297 | 298 | 299 | 300 | 301 |
| Preemergence | | | | | | | | | | | | | | | | | | | | | | | | | | | | | |
| B. signalgrass | 6 | 0 | 8 | 0 | 2 | 0 | 10 | 10 | 0 | 0 | 0 | 0 | 2 | 10 | 5 | 10 | 8 | 6 | 8 | 0 | 7 | 7 | 8 | 0 | 0 | 0 | 9 | 0 | 0 |
| Bedstraw | 0 | 0 | 10 | 0 | 0 | 0 | 0 | 0 | 0 | 0 | 0 | 6 | 2 | 1 | 8 | 8 | 0 | 10 | 7 | 0 | 0 | 0 | 0 | 0 | 0 | — | 10 | 0 | 0 |
| Blackgrass | 3 | 0 | 10 | 0 | — | 0 | 10 | 10 | 0 | 0 | 0 | 2 | 4 | 9 | 8 | 5 | 7 | 6 | 9 | 0 | 9 | 6 | 10 | 0 | 0 | 0 | 10 | 0 | 0 |
| Cocklebur | 0 | 0 | 0 | 0 | 0 | 0 | 0 | 0 | 0 | — | 0 | 0 | — | 0 | — | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 2 | 0 | 9 | 0 | 0 | 0 | 0 | 0 | 8 | 0 | 0 |
| Crabgrass | 3 | 0 | 7 | 0 | 6 | 1 | 6 | 9 | 2 | 0 | 0 | 10 | 6 | — | 8 | 8 | 10 | 10 | 4 | 0 | 8 | 9 | 7 | 0 | 7 | 0 | 9 | 4 | 0 |
| Giant foxtail | 10 | 0 | 10 | 6 | 8 | 6 | 10 | 10 | 2 | 6 | 0 | 10 | 10 | 10 | 9 | 10 | 10 | 10 | 10 | 0 | 9 | 10 | 10 | 0 | 7 | — | 10 | 9 | 0 |
| Morningglory | 0 | 0 | 2 | 0 | 0 | 0 | 0 | 0 | 0 | 0 | 0 | 0 | 0 | 0 | 1 | 0 | 0 | 0 | 0 | 0 | 0 | 0 | 0 | 0 | 0 | 0 | 6 | 0 | 0 |
| Nutsedge | — | 0 | 0 | 0 | 0 | 0 | — | 0 | 0 | 0 | 0 | 0 | 0 | 0 | 0 | 0 | 0 | 0 | 0 | 0 | 7 | 0 | 0 | — | 0 | 0 | — | 0 | 0 |
| Rape | 0 | 0 | 10 | 0 | 0 | 0 | 1 | 1 | 0 | 0 | 0 | 0 | 7 | 2 | 7 | 3 | 3 | 0 | 10 | 0 | 8 | 0 | 10 | 0 | 0 | 0 | 10 | 0 | 0 |
| Redroot pigweed | 4 | 0 | 10 | 0 | 0 | 0 | 2 | 0 | 0 | 0 | 0 | 0 | 7 | 10 | 7 | 5 | 2 | 0 | 8 | 0 | 10 | 0 | 6 | 0 | 0 | 0 | 10 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 6 | 0 | 0 |
| Sugarbeets | 0 | 0 | 8 | 0 | 6 | 0 | 1 | 2 | 0 | 0 | 0 | 0 | 0 | 2 | 6 | 0 | 0 | 0 | 8 | 0 | 4 | 0 | 3 | 0 | 0 | 0 | 9 | 0 | 0 |
| Velvetleaf | 0 | 0 | 7 | 0 | 0 | 0 | 0 | 6 | 0 | 0 | 0 | 0 | 0 | 5 | 0 | 3 | 3 | 3 | 7 | 0 | 7 | 3 | 3 | 0 | 0 | 0 | 8 | 0 | 0 |
| Wheat | 0 | 0 | 0 | 0 | 0 | 0 | 0 | 0 | 0 | 0 | 0 | 0 | 0 | 1 | 0 | 0 | 0 | 2 | 2 | 0 | 8 | 0 | 6 | 0 | 0 | 0 | 8 | 0 | 0 |
| Wild oats | 2 | 0 | 6 | 0 | 0 | 0 | 4 | 7 | 0 | 0 | 0 | 2 | 5 | 4 | 3 | 3 | 4 | 5 | 8 | 0 | 8 | 3 | 9 | 0 | 0 | 0 | 8 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 302 | 303 | 304 | 305 | 306 | 307 | 308 | 309 | 310 | 311 | 312 | 313 | 314 | 315 | 316 | 317 | 318 | 319 | 320 | 321 | 322 | 323 | 324 | 325 | 326 | 327 | 328 | 329 | 330 |
| Preemergence | | | | | | | | | | | | | | | | | | | | | | | | | | | | | |
| B. signalgrass | 0 | 0 | 0 | 0 | 0 | 0 | 0 | 0 | 7 | 0 | 0 | 0 | 6 | 3 | 9 | 7 | 0 | 2 | 2 | 3 | 1 | 0 | 0 | 0 | 3 | 1 | 0 | 0 | 0 |
| Bedstraw | 0 | 0 | 0 | 0 | 0 | 0 | 0 | 0 | 5 | 0 | 0 | 0 | 0 | — | 3 | — | 0 | 0 | — | — | — | 0 | 0 | 0 | — | — | — | — | 0 |
| Blackgrass | 2 | 0 | 0 | 0 | 0 | 2 | 0 | 2 | 10 | 0 | 0 | 0 | 10 | 7 | 10 | 8 | 0 | 2 | 5 | 6 | 5 | 0 | 0 | 2 | 7 | 4 | 4 | 0 | 0 |
| Cocklebur | 0 | 0 | 0 | 0 | 0 | 0 | 0 | 0 | 2 | 0 | 0 | 0 | 0 | — | 0 | — | 0 | 0 | — | 0 | 0 | 0 | 0 | 0 | 0 | 0 | 0 | 0 | 0 |
| Corn | 0 | 0 | 0 | 0 | 0 | 0 | 0 | 2 | 0 | 0 | 0 | 0 | 0 | 0 | 0 | — | 0 | 0 | 0 | 0 | 0 | 0 | 0 | 0 | 0 | 0 | 0 | 0 | 0 |
| Crabgrass | 2 | 0 | 6 | 6 | 0 | 0 | 0 | 2 | 7 | 0 | 0 | 0 | 7 | 7 | 8 | 8 | 0 | 2 | 3 | 3 | 5 | 0 | 0 | 1 | 3 | 3 | 3 | 0 | 0 |
| Giant foxtail | 7 | 0 | 6 | 9 | 8 | 9 | 0 | 9 | 10 | 0 | 0 | 0 | 7 | 9 | 10 | 10 | 0 | 9 | 6 | 9 | 9 | 0 | 0 | 8 | 8 | 9 | 8 | 0 | 0 |
| Morningglory | 0 | 0 | 0 | 0 | 0 | 0 | 0 | 0 | 6 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | 10 | 0 | 0 | 0 | — | — | — | 0 | — | 0 | 0 | — | 0 | — | 0 | 0 | 0 | 0 | 0 | 0 | 0 |
| Rape | 0 | 0 | 0 | 0 | 0 | 0 | 0 | 0 | 10 | 0 | 0 | 0 | 3 | 0 | 4 | 8 | 0 | 0 | 0 | 0 | 0 | 0 | 0 | 0 | 0 | 0 | 0 | — | 0 |
| Redroot pigweed | 0 | 0 | 0 | 3 | 0 | 0 | 0 | 0 | 10 | 0 | 0 | 0 | 2 | 0 | 10 | 7 | 0 | 0 | 0 | 0 | 8 | 0 | 0 | 0 | 6 | 1 | 0 | 0 | 0 |
| Soybean | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 2 | 0 | 6 | 0 | 0 | 0 | 0 | 0 | 10 | 0 | 0 | 0 | 2 | 1 | 0 | 7 | 0 | 0 | 0 | 0 | 2 | 0 | 0 | 0 | 0 | 0 | 0 | 0 | 0 |
| Velvetleaf | 0 | 0 | 0 | 0 | 0 | 0 | 0 | 0 | 7 | 0 | 0 | 0 | 3 | 0 | 3 | 6 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 5 | 0 | 0 | 0 | 0 | 2 | 2 | 7 | 0 | 0 | 0 | 0 | 0 | 0 | 0 | 0 | 0 | — | 0 | 0 | 0 |
| Wild oats | 2 | 0 | 0 | 0 | 0 | 0 | 0 | 0 | 9 | 0 | 0 | 0 | 2 | 0 | 6 | 8 | 0 | 0 | 0 | 2 | 2 | 0 | 0 | 0 | 3 | 0 | 0 | 0 | 0 |

TABLE B-continued

| Rate 250 g/ha | COMPOUND 331 | 332 | 333 | 334 | 335 | 336 | 337 | 338 | 339 | 340 | 341 | 342 | 343 | 344 | 345 | 348 | 349 | 350 | 351 | 352 | 353 | 354 | 355 | 356 | 357 | 358 | 359 | 360 | 361 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 0 | 0 | 0 | 0 | 0 | 0 | 0 | 0 | 0 | 1 | 0 | 2 | 6 | 0 | 0 | 5 | — | 2 | 2 | 7 | 5 | 5 | 3 | 5 | 6 | 5 | 0 | 7 | 4 |
| Bedstraw | — | 0 | 0 | 0 | 0 | 0 | 0 | 0 | 0 | — | — | 0 | — | — | 0 | — | — | 10 | 9 | — | — | 0 | 0 | — | 10 | 10 | 0 | — | 0 |
| Blackgrass | 0 | 0 | 0 | 0 | 0 | 0 | 2 | 0 | 2 | 3 | 6 | 3 | 9 | 0 | 0 | 9 | 4 | 8 | 3 | 10 | 7 | 8 | 5 | 9 | 9 | 10 | 0 | 9 | 10 |
| Cocklebur | 0 | 0 | 0 | 0 | 0 | 0 | 0 | 0 | 0 | 0 | 0 | — | 0 | 0 | 0 | 0 | — | 0 | 0 | 0 | — | 0 | 0 | 0 | 0 | 0 | — | — | 0 |
| Corn | 0 | 0 | 0 | 0 | 0 | 0 | 0 | 0 | 0 | 0 | 0 | 0 | 0 | 0 | 0 | 2 | 0 | 0 | 3 | 6 | 3 | 3 | 3 | 2 | 6 | 2 | 0 | 4 | 1 |
| Crabgrass | 0 | 3 | 0 | 0 | 2 | 0 | 0 | 0 | 2 | 8 | 2 | 9 | — | 0 | 0 | 10 | 8 | 10 | 10 | 10 | 10 | 9 | 10 | 9 | 9 | 10 | 0 | 10 | 7 |
| Giant foxtail | 0 | 4 | 0 | 0 | 10 | 0 | 2 | 0 | 9 | 10 | 10 | 10 | 10 | 3 | 0 | 10 | 10 | 10 | 10 | 10 | 10 | 10 | 10 | 10 | 10 | 10 | 0 | 10 | 10 |
| Morningglory | 0 | 0 | 0 | 0 | 0 | 0 | 0 | 0 | 0 | 0 | 0 | 0 | — | 0 | 0 | 0 | 0 | 0 | 0 | 0 | 1 | 0 | 0 | 0 | 2 | 3 | 0 | 7 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 4 | 0 | 0 | 2 | 0 | 7 | 6 | 0 | 1 | 5 | 0 | 4 | 8 | 4 | 0 | 0 | 5 |
| Redroot pigweed | 0 | 0 | 0 | 0 | 0 | 0 | 0 | 0 | 0 | 3 | 0 | 0 | 10 | 0 | 0 | 10 | 2 | 10 | 10 | 10 | 10 | 10 | 10 | 8 | 10 | 10 | 0 | 10 | 8 |
| Soybean | 0 | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | 0 | 0 | 0 |
| Sugarbeets | 0 | 0 | 0 | 0 | 0 | 0 | 0 | 0 | 0 | 0 | 0 | 0 | 1 | 0 | 0 | 3 | 4 | 4 | 6 | 3 | 2 | 2 | 2 | 2 | 5 | 3 | 0 | 6 | 6 |
| Velvetleaf | 0 | 0 | 0 | 0 | 0 | 0 | 0 | 0 | 0 | 0 | 0 | 0 | 7 | 0 | 0 | 7 | 3 | 4 | 4 | 6 | 4 | 6 | 3 | 3 | 5 | 5 | 0 | 7 | 4 |
| Wheat | 0 | 0 | 0 | 0 | 0 | 0 | 0 | 0 | 0 | 0 | 0 | 0 | 0 | 0 | 0 | 0 | 0 | 2 | 0 | 2 | 2 | 0 | 0 | 0 | 9 | 1 | 0 | 7 | 2 |
| Wild oats | 0 | 0 | 0 | 0 | 0 | 0 | 0 | 0 | 0 | 2 | 0 | 0 | 9 | 0 | 0 | 8 | 3 | 5 | 2 | 9 | 4 | 6 | 0 | 10 | 10 | 9 | 0 | 10 | 8 |

| Rate 250 g/ha | COMPOUND 362 | 363 | 364 | 365 | 367 | 368 | 369 | 370 | 371 | 372 | 373 | 374 | 375 | 376 | 378 | 379 | 380 | 381 | 382 | 383 | 384 | 385 | 387 | 388 | 389 | 390 | 391 | 392 | 393 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 7 | 5 | 0 | 0 | 4 | 8 | 2 | 2 | 2 | 6 | 0 | 2 | 4 | 0 | 0 | 0 | 0 | 0 | 2 | 0 | 3 | 7 | 1 | 3 | 0 | 9 | 0 | 9 | 0 |
| Bedstraw | 10 | 10 | 0 | 0 | 10 | 10 | — | 3 | — | 10 | — | 0 | 10 | — | 0 | 0 | — | 0 | — | — | — | — | — | — | — | — | — | 10 | — |
| Blackgrass | 10 | 10 | 1 | 0 | 8 | 10 | 2 | 9 | 10 | 10 | 5 | 5 | 9 | 0 | 0 | 0 | 0 | 0 | 3 | 2 | 3 | 6 | 0 | 5 | 6 | 9 | 0 | 10 | 0 |
| Cocklebur | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 2 | 0 | 0 | 0 |
| Corn | 9 | 3 | 0 | 0 | 2 | 7 | 0 | 4 | 2 | 9 | 3 | 0 | 2 | 0 | 0 | 0 | 0 | 0 | 0 | 0 | — | 0 | 0 | — | 0 | — | 0 | 9 | 0 |
| Crabgrass | 8 | 7 | 2 | 0 | 10 | 10 | 9 | 9 | 10 | 10 | 10 | 9 | 10 | 0 | 9 | 7 | 7 | 3 | 9 | 9 | 9 | 9 | 8 | 10 | 9 | 10 | 0 | 10 | 3 |
| Giant foxtail | 10 | 10 | 9 | 0 | 10 | 10 | 10 | 10 | 10 | 10 | 10 | 10 | 10 | 0 | 10 | 6 | 9 | 5 | 9 | 10 | 10 | 10 | 9 | 10 | 10 | 10 | 0 | 10 | 10 |
| Morningglory | 6 | 5 | 0 | 0 | 0 | 3 | 0 | 2 | 0 | 2 | 0 | 0 | 0 | 0 | 0 | 0 | 0 | 0 | 0 | 0 | 0 | 0 | 0 | 0 | 0 | 6 | 0 | 0 | 0 |
| Nutsedge | 3 | 0 | 0 | 0 | 0 | 10 | 0 | 5 | 5 | 0 | 0 | 0 | 0 | 0 | 0 | 0 | 0 | 0 | 0 | 0 | 0 | 0 | 0 | 0 | 0 | 0 | 0 | 0 | 0 |
| Rape | 6 | 3 | 0 | 0 | 5 | 6 | 2 | 6 | 9 | 10 | 0 | 2 | 6 | 0 | 0 | 0 | 0 | 0 | 0 | 0 | 0 | 0 | 0 | 2 | 0 | 8 | 0 | 5 | 0 |
| Redroot pigweed | 10 | 7 | 0 | 0 | 10 | 10 | 10 | 10 | 10 | 10 | 7 | 0 | 10 | 0 | 0 | 0 | 3 | 0 | 0 | 0 | 0 | 7 | 6 | 6 | 4 | 10 | 0 | 10 | 2 |
| Soybean | 6 | 0 | 0 | 0 | 0 | 7 | 0 | 2 | 0 | 0 | 0 | 0 | 0 | 0 | 0 | 0 | 0 | 0 | 0 | 0 | 0 | 0 | 0 | 0 | 0 | 2 | 0 | 0 | 0 |
| Sugarbeets | 8 | 7 | 0 | 0 | 7 | 10 | 2 | 5 | 6 | 10 | 4 | 0 | 4 | 0 | 0 | 0 | 0 | 0 | 0 | 0 | 0 | 2 | 1 | 3 | 0 | 8 | 0 | 7 | 2 |
| Velvetleaf | 6 | 6 | 0 | 0 | 5 | 10 | 0 | 5 | 5 | 6 | 0 | 0 | 4 | 0 | 0 | 0 | 0 | 0 | 0 | 0 | 1 | 3 | 0 | 2 | 0 | 6 | 0 | 5 | 0 |
| Wheat | 8 | 6 | 0 | 0 | 0 | 8 | 0 | 2 | 2 | 0 | 0 | 0 | 2 | 0 | 0 | 0 | 0 | 0 | 0 | 0 | 2 | 3 | 0 | 4 | 0 | 8 | 0 | 8 | 0 |
| Wild oats | 10 | 10 | 0 | 0 | 3 | 10 | 0 | 2 | 3 | 9 | 0 | 0 | 9 | 0 | 0 | 0 | 0 | 0 | 0 | 0 | 6 | 7 | 3 | 10 | 1 | 10 | 0 | 10 | 0 |

TABLE B-continued

| Rate 250 g/ha | COMPOUND 394 | 395 | 396 | 397 | 398 | 400 | 401 | 402 | 403 | 404 | 405 | 406 | 407 | 408 | 409 | 410 | 411 | 414 | 415 | 416 | 417 | 418 | 419 | 420 | 421 | 422 | 423 | 424 | 425 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 8 | 0 | 3 | 9 | 6 | 2 | 0 | 4 | 5 | 8 | 0 | 0 | 0 | 4 | 7 | 7 | 7 | 1 | 6 | 7 | 7 | 6 | 2 | 6 | 9 | 0 | 0 | 0 | 8 |
| Bedstraw | — | 0 | — | — | — | — | — | — | — | 10 | — | 0 | 0 | — | — | — | — | 0 | — | — | — | — | — | — | — | — | — | — | — |
| Blackgrass | 10 | 0 | 3 | 10 | 8 | 0 | 0 | 9 | 7 | 9 | 0 | 0 | 0 | 9 | 10 | 8 | 9 | 3 | 9 | 10 | 7 | 7 | 0 | 8 | 10 | 0 | 0 | 0 | 9 |
| Cocklebur | 0 | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | — | 0 | 0 | 0 | 0 |
| Corn | 3 | 0 | 0 | 3 | 0 | 2 | 0 | 3 | 2 | 2 | 0 | 0 | 0 | 4 | 8 | 4 | 8 | 0 | 3 | 3 | 0 | 2 | 0 | 0 | 8 | 0 | 0 | 0 | 0 |
| Crabgrass | 10 | 0 | 10 | 10 | 10 | 10 | 8 | 10 | 10 | 10 | 8 | 2 | 5 | 10 | 10 | 10 | 10 | 9 | 9 | 10 | 9 | 10 | 4 | 9 | 9 | 0 | — | 0 | 10 |
| Giant foxtail | 10 | 0 | 10 | 10 | 10 | 10 | 7 | 10 | 10 | 10 | 9 | 2 | 9 | 10 | 10 | 10 | 10 | 10 | 10 | 10 | 10 | 10 | 2 | 10 | 10 | 0 | 3 | 0 | 10 |
| Morningglory | 0 | 0 | 0 | 0 | 0 | 0 | 0 | 2 | 0 | 4 | 0 | 0 | 0 | 0 | 5 | 0 | 2 | 0 | 0 | 6 | 0 | 0 | 1 | 2 | 7 | 0 | 0 | 0 | 2 |
| Nutsedge | 2 | 0 | 0 | 0 | 0 | 0 | 0 | 0 | 0 | 0 | 0 | 0 | 0 | 0 | 8 | 0 | 0 | 0 | 0 | 3 | 0 | 0 | 0 | 0 | 0 | 0 | 0 | 0 | 3 |
| Rape | 7 | 0 | 0 | 10 | 8 | 0 | 0 | 5 | 5 | 7 | 0 | 0 | 0 | 6 | 4 | 2 | 9 | 0 | 10 | 9 | 5 | 0 | 2 | 0 | 10 | 0 | 0 | 0 | 2 |
| Redroot pigwee 6 | d | 0 | 4 | 10 | 10 | 6 | 0 | 4 | 9 | 10 | 0 | 0 | 0 | 10 | 8 | 2 | 10 | 0 | 6 | 10 | 4 | 8 | 6 | 2 | 10 | 0 | 0 | 0 | 3 |
| Soybean | 1 | 0 | 0 | 0 | 0 | 0 | 0 | 0 | 0 | 0 | 0 | 0 | 0 | 0 | 1 | 0 | 0 | 0 | 0 | 7 | 0 | 0 | 0 | 0 | 5 | 0 | 0 | 0 | 0 |
| Sugarbeets | 4 | 0 | 0 | 7 | 4 | 2 | 0 | 3 | 3 | 6 | 0 | 0 | 0 | 8 | 8 | 0 | 8 | 0 | 6 | 7 | 2 | 2 | 3 | 2 | 10 | 0 | 0 | 0 | 2 |
| Velvetleaf | 7 | 0 | 0 | 6 | 6 | 0 | 0 | 3 | 3 | 5 | 0 | 0 | 0 | 7 | 6 | 6 | 6 | 0 | 6 | 6 | 2 | 5 | 1 | 6 | 10 | 0 | 0 | 0 | 2 |
| Wheat | 6 | 0 | 0 | 2 | 0 | 0 | 0 | 3 | 0 | 4 | 0 | 0 | 0 | 4 | 9 | 7 | 7 | 0 | 2 | 7 | 0 | 0 | 0 | 2 | 7 | 0 | 0 | 0 | 3 |
| Wild oats | 10 | 0 | 2 | 7 | 3 | 0 | 0 | 8 | 5 | 10 | 0 | 0 | 0 | 5 | 7 | 7 | 8 | 2 | 6 | 8 | 2 | 0 | 0 | 2 | 10 | 0 | 0 | 0 | 4 |

| Rate 250 g/ha | COMPOUND 426 | 427 | 428 | 429 | 430 | 431 | 432 | 433 | 434 | 435 | 436 | 437 | 438 | 439 | 440 | 441 | 442 | 443 | 444 | 445 | 446 | 447 | 448 | 449 | 450 | 451 | 452 | 453 | 454 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 6 | 3 | 0 | 0 | 3 | 0 | 0 | 2 | 0 | 0 | 0 | 0 | 0 | 0 | 8 | 0 | 0 | 0 | 1 | 2 | 7 | 0 | 0 | 0 | 3 | 0 | 0 | 6 | 4 |
| Bedstraw | — | — | — | — | — | — | — | — | — | — | — | — | 0 | — | — | — | — | — | — | — | — | — | 0 | 0 | — | — | — | — | — |
| Blackgrass | 9 | 4 | 0 | 0 | 7 | 0 | 0 | 3 | 0 | 0 | 0 | 0 | 2 | 0 | 10 | 0 | 0 | 0 | 8 | 0 | 8 | 0 | 0 | 0 | 4 | 0 | 2 | 3 | 2 |
| Cocklebur | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 |
| Crabgrass | 10 | 9 | 9 | 10 | 10 | — | 8 | 10 | 0 | 6 | 0 | 0 | 9 | 0 | 10 | 0 | 8 | 9 | 9 | 3 | 9 | 8 | 4 | 9 | 8 | 1 | 5 | 6 | 8 |
| Giant foxtail | 10 | 10 | 8 | 10 | 10 | 2 | 6 | 10 | 0 | 3 | 0 | 0 | 10 | 0 | 10 | 0 | 3 | 10 | 10 | 5 | 10 | 7 | 3 | 8 | 9 | 4 | 4 | 10 | 10 |
| Morningglory | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 |
| Rape | 8 | 0 | 0 | 0 | 0 | 0 | 0 | 3 | 0 | 0 | 0 | 0 | 0 | 0 | 3 | 0 | 0 | 0 | 0 | 0 | 8 | 0 | 0 | 0 | 0 | 0 | 0 | 0 | 0 |
| Redroot pigweed | 8 | 0 | 0 | 0 | 2 | 0 | 0 | 7 | 0 | 4 | 0 | 0 | 5 | 0 | 7 | 0 | 0 | 0 | 10 | 4 | 10 | 0 | 0 | 0 | 7 | 0 | 0 | 6 | 9 |
| Soybean | 0 | 0 | 0 | 0 | 0 | 0 | 0 | 0 | 0 | 0 | 0 | 0 | 0 | 0 | 0 | 0 | 0 | 0 | 2 | — | 2 | 0 | 0 | 0 | 3 | 0 | 0 | 0 | 0 |
| Sugarbeets | 4 | 0 | 0 | 0 | 0 | 0 | 0 | 4 | 0 | 0 | 0 | 0 | 0 | 0 | 4 | 0 | 0 | 0 | 0 | 0 | 6 | 0 | 0 | 0 | 0 | 0 | 0 | 2 | 0 |
| Velvetleaf | 2 | 0 | 0 | 0 | 4 | 0 | 0 | 4 | 0 | 1 | 0 | 0 | 5 | 0 | 0 | 0 | 0 | 0 | 0 | 2 | 7 | 0 | 0 | 0 | 0 | 0 | 0 | 2 | 5 |
| Wheat | 2 | 0 | 0 | 0 | 0 | 0 | 0 | 0 | 0 | 0 | 0 | 0 | 0 | 0 | 5 | 0 | 0 | 0 | 0 | 0 | 3 | 0 | 0 | 0 | 0 | 0 | 0 | 3 | 0 |
| Wild oats | 8 | 2 | 0 | 0 | 3 | 2 | 0 | 6 | 0 | 2 | 0 | 0 | 1 | 0 | 9 | 0 | 0 | 0 | 0 | 0 | 8 | 2 | 0 | 0 | 0 | 0 | 0 | 2 | 0 |

TABLE B-continued

| Rate 250 g/ha | COMPOUND 455 | 456 | 457 | 458 | 459 | 460 | 461 | 462 | 463 | 465 | 466 | 467 | 468 | 469 | 470 | 471 | 472 | 473 | 474 | 476 | 477 | 478 | 479 | 480 | 481 | 482 | 483 | 485 | 486 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 9 | 0 | 0 | 4 | 1 | 0 | 0 | 0 | 0 | 3 | 6 | 0 | 3 | 7 | 4 | 10 | 9 | 0 | 7 | 0 | 4 | 9 | 6 | 7 | 9 | 0 | 0 | 8 | 6 |
| Bedstraw | — | — | 0 | — | — | — | 0 | 0 | — | — | — | 0 | — | — | — | — | — | — | — | — | — | 8 | 0 | — | — | — | 0 | — | — |
| Blackgrass | 6 | 3 | 0 | 8 | 5 | 0 | 0 | 0 | 2 | 6 | 7 | 2 | 5 | 9 | 7 | 10 | 10 | 0 | 4 | 0 | 7 | 10 | 8 | 8 | 10 | 0 | 0 | 8 | 10 |
| Cocklebur | 0 | 0 | 0 | 0 | 0 | 0 | 0 | 0 | 0 | 0 | 0 | 6 | 0 | 0 | 0 | 0 | 0 | — | 0 | 0 | 0 | 0 | 0 | 0 | 0 | 0 | 0 | 0 | — |
| Corn | 4 | 0 | 0 | 0 | 0 | 0 | 0 | 0 | 0 | 0 | 0 | 0 | 0 | 8 | 0 | 2 | 2 | 0 | 0 | 0 | 0 | 0 | 0 | 0 | 0 | 0 | 0 | 0 | 5 |
| Crabgrass | 10 | 8 | 0 | 9 | 9 | 6 | 0 | 0 | 2 | 4 | 10 | 6 | 9 | 10 | 8 | 10 | 10 | 4 | 9 | 0 | 10 | 10 | 9 | 8 | 8 | 8 | 0 | 10 | 10 |
| Giant foxtail | 10 | 10 | 0 | 10 | 10 | 8 | 0 | 0 | 3 | 10 | 10 | 9 | 9 | 10 | 0 | 10 | 10 | 4 | 10 | 0 | 9 | 10 | 10 | 10 | 9 | 8 | 0 | 10 | 10 |
| Morningglory | 0 | 3 | 0 | 0 | 0 | 0 | 0 | 0 | 0 | 0 | 0 | 0 | 0 | 0 | 0 | 0 | 0 | 0 | 0 | 0 | 0 | 1 | 4 | 0 | 0 | 0 | 0 | 0 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 6 | 0 | 0 | 0 | 0 |
| Rape | 8 | 0 | 0 | 3 | 0 | 0 | 0 | 0 | 0 | 2 | 0 | 7 | 3 | 10 | 0 | 7 | 0 | 0 | 2 | 0 | 0 | 4 | 1 | 0 | 0 | 0 | 0 | 0 | 6 |
| Redroot pigweed | 10 | 3 | 0 | 6 | 4 | 0 | 0 | 0 | 10 | 9 | 9 | 7 | 8 | 10 | 0 | 10 | 10 | 10 | 5 | 2 | 6 | 9 | 6 | 8 | 3 | 0 | 0 | — | 9 |
| Soybean | 0 | 0 | 0 | 0 | 0 | 0 | 0 | 0 | 0 | 7 | 2 | 0 | 0 | 0 | 0 | 0 | 0 | 0 | 0 | 0 | 3 | 0 | 0 | 0 | 0 | 0 | 0 | 0 | 0 |
| Sugarbeets | 3 | 2 | 0 | 2 | 0 | 0 | 0 | 0 | 0 | 3 | 2 | 1 | 2 | 8 | 0 | 2 | 3 | 0 | 0 | 0 | 0 | 3 | 2 | 0 | 2 | 0 | 0 | 0 | 4 |
| Velvetleaf | 5 | 1 | 0 | 2 | 0 | 0 | 0 | 0 | 0 | 7 | 4 | 0 | 1 | 6 | 0 | 3 | 3 | 0 | 0 | 0 | 0 | 3 | 1 | 0 | 0 | 0 | 0 | 0 | 0 |
| Wheat | 0 | 0 | 0 | 0 | 0 | 0 | 0 | 0 | 0 | 0 | 0 | 0 | 0 | 3 | 0 | 0 | 0 | 0 | 0 | 0 | 0 | 1 | 3 | 0 | 2 | 0 | 0 | 3 | 0 |
| Wild oats | 9 | 2 | 0 | 3 | 0 | 0 | 0 | 0 | 0 | 2 | 3 | 0 | 3 | 10 | 0 | 7 | 8 | 0 | 4 | 0 | 5 | 9 | 5 | 4 | 8 | 0 | 0 | 6 | 5 |

| Rate 250 g/ha | COMPOUND 487 | 488 | 489 | 490 | 492 | 493 | 494 | 495 | 496 | 497 | 498 | 499 | 500 | 501 | 502 | 503 | 504 | 505 | 506 | 508 | 509 | 510 | 511 | 512 | 513 | 514 | 515 | 516 | 517 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 3 | 7 | 8 | 6 | 0 | 0 | 0 | 0 | 1 | 0 | 0 | 0 | 9 | 9 | 10 | 8 | 10 | 2 | 0 | 8 | 8 | 8 | 0 | 10 | 5 | 8 | 8 | 9 | 0 |
| Bedstraw | — | — | — | — | 0 | 0 | 0 | — | — | 0 | — | 0 | 9 | 10 | 10 | 6 | 8 | 8 | 0 | 0 | 10 | 0 | 0 | 0 | 0 | 0 | 0 | 1 | 0 |
| Blackgrass | 7 | 8 | 9 | 9 | 0 | 0 | 0 | 0 | 2 | 0 | 0 | 0 | 10 | 9 | 10 | 9 | 10 | 7 | 4 | 5 | 8 | 7 | 0 | 9 | 4 | 5 | 5 | 8 | 4 |
| Cocklebur | 0 | 0 | 0 | 0 | 0 | 0 | 0 | 0 | 0 | 0 | 0 | 0 | 2 | 0 | 0 | 0 | 0 | 0 | 0 | 0 | 0 | — | 0 | 0 | 0 | 0 | 0 | 0 | 0 |
| Corn | 0 | 0 | 0 | 3 | 0 | 0 | 0 | 0 | 0 | 0 | 0 | 0 | — | 7 | 9 | 8 | 5 | 5 | 0 | 0 | 0 | 3 | 0 | 0 | 3 | 3 | 3 | 0 | 0 |
| Crabgrass | 10 | 10 | 10 | 9 | 3 | 2 | 0 | 0 | 9 | 0 | 3 | 8 | 9 | 9 | 10 | 8 | 9 | 7 | 0 | 10 | 9 | 9 | 6 | 7 | 4 | 9 | 7 | 9 | 7 |
| Giant foxtail | 10 | 10 | 10 | 9 | 2 | 9 | 0 | 0 | 9 | 0 | — | 9 | 10 | 10 | 10 | 9 | 10 | 9 | 5 | 10 | 9 | 9 | 6 | 10 | 7 | 10 | 10 | 10 | 9 |
| Morningglory | 0 | 0 | 0 | 0 | 0 | 0 | 0 | 0 | 0 | 0 | 0 | 0 | 7 | 5 | 4 | 6 | 1 | 0 | 0 | 0 | 3 | 1 | 0 | 0 | 0 | 0 | 0 | 0 | 0 |
| Nutsedge | 0 | 0 | 0 | 0 | 0 | 0 | — | 0 | 0 | 0 | 0 | 0 | 7 | 9 | 6 | 2 | 7 | 9 | 3 | 0 | 0 | 0 | 0 | 0 | 0 | 0 | 0 | 0 | 0 |
| Rape | 0 | 8 | 4 | 6 | 0 | 0 | 0 | 0 | 0 | 0 | 0 | 0 | 10 | 3 | 6 | 9 | 10 | 8 | 3 | 0 | 3 | 8 | 0 | 3 | 7 | 7 | 6 | 7 | 0 |
| Redroot pigweed | 8 | 10 | 4 | 8 | 0 | 0 | 0 | 0 | 2 | 0 | 0 | 0 | 10 | 10 | 10 | 10 | 10 | 10 | 10 | 9 | 8 | 10 | 6 | 10 | 8 | 9 | 9 | 8 | 9 |
| Soybean | — | 1 | 2 | 0 | 0 | 0 | 1 | 0 | 0 | 0 | 0 | 0 | 6 | 3 | 4 | 6 | 1 | 0 | 0 | 0 | 0 | 0 | 0 | 0 | 0 | 0 | 0 | 0 | 0 |
| Sugarbeets | 0 | 7 | 4 | 3 | 0 | 0 | 0 | 0 | 0 | 0 | 0 | 0 | 10 | 6 | 5 | 7 | 8 | 6 | 0 | 6 | 7 | 6 | 0 | 2 | 0 | 5 | 6 | 4 | 2 |
| Velvetleaf | 0 | 6 | 6 | 2 | 0 | 0 | 0 | 0 | 0 | 0 | 0 | 0 | 10 | 4 | 5 | 7 | 6 | 4 | 0 | 0 | 7 | 4 | 0 | 0 | 0 | 2 | 2 | 3 | 2 |
| Wheat | 0 | 0 | 0 | 4 | 0 | 0 | 0 | 0 | 0 | 0 | 0 | 0 | 8 | 7 | 7 | 6 | 6 | 7 | 2 | 0 | 3 | 0 | 0 | 4 | 5 | 3 | 5 | 4 | 6 |
| Wild oats | 3 | 8 | 9 | 7 | 0 | 0 | 0 | 0 | 0 | 0 | 0 | 0 | 9 | 9 | 10 | 10 | 10 | 9 | 3 | 7 | 7 | — | 0 | 9 | 7 | 6 | 7 | 8 | 5 |

TABLE B-continued

| Rate 250 g/ha | 518 | 519 | 520 | 521 | 522 | 523 | 524 | 525 | 526 | 527 | 528 | 531 | 532 | 533 | 534 | 535 | 536 | 540 | 541 | 543 | 544 | 545 | 546 | 548 | 549 | 550 | 551 | 552 | 553 |
|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | |
| Preemergence | | | | | | | | | | | | | | | | | | | | | | | | | | | | | |
| B. signalgrass | 10 | 0 | 0 | 0 | 9 | 9 | 2 | — | 9 | 4 | 0 | 2 | 0 | 9 | 9 | 0 | 0 | 0 | 0 | 4 | 6 | 0 | 0 | 3 | 0 | 9 | 9 | — | 9 |
| Bedstraw | 0 | 0 | 0 | 0 | 10 | 0 | — | 0 | 7 | — | 0 | 0 | — | 0 | 0 | — | 0 | 0 | 0 | 0 | 7 | 0 | 8 | 10 | 5 | 0 | — | 0 | 2 |
| Blackgrass | 7 | 4 | 0 | 0 | 9 | 7 | 4 | — | 10 | 2 | 0 | 9 | 0 | 9 | 9 | 0 | 0 | 0 | 0 | 0 | 2 | 2 | 0 | 3 | 6 | 7 | 9 | 0 | 7 |
| Cocklebur | 0 | 0 | 0 | 0 | 0 | 0 | 0 | 0 | 0 | 0 | 0 | 0 | 0 | 0 | 0 | 0 | 0 | 9 | — | 0 | 0 | 0 | 0 | 0 | 0 | 0 | 0 | 0 | 0 |
| Corn | 0 | 0 | 0 | 0 | 7 | 0 | 7 | 4 | 0 | 0 | 0 | 0 | 0 | 0 | 3 | 0 | 0 | 0 | 0 | 0 | 0 | 0 | 0 | 0 | 0 | 0 | 0 | 0 | 0 |
| Crabgrass | 0 | 10 | 10 | 10 | 10 | 10 | 9 | 10 | 10 | 10 | 10 | 10 | 10 | 10 | 10 | 10 | 0 | 10 | 10 | 6 | 10 | 10 | 10 | 10 | 10 | 10 | 10 | 8 | 10 |
| Giant foxtail | 0 | 10 | 10 | 10 | 10 | 10 | 9 | 10 | 10 | 10 | 10 | 10 | 10 | 10 | 10 | 10 | 10 | 10 | 10 | 9 | 10 | 10 | 10 | 10 | 10 | 10 | 10 | 10 | 10 |
| Morningglory | 0 | 0 | 0 | 0 | 2 | 0 | 2 | 0 | 0 | 0 | 0 | 0 | 0 | 0 | 2 | 0 | — | 0 | 0 | 0 | 0 | 0 | 0 | 0 | 0 | 0 | 0 | 0 | 0 |
| Nutsedge | 0 | — | 0 | 0 | 10 | 0 | 0 | 0 | 0 | 0 | 0 | 0 | 0 | — | — | 0 | 0 | 0 | 0 | 0 | 0 | 0 | 0 | 0 | 0 | 0 | 0 | 0 | 0 |
| Rape | 0 | 0 | 0 | 2 | 4 | 4 | 7 | — | 9 | 2 | 0 | 0 | 0 | 7 | 6 | 2 | 0 | 2 | 0 | 0 | 3 | 0 | 0 | 2 | 0 | 6 | 3 | 0 | 3 |
| Redroot pigweed | 4 | 0 | 0 | 0 | 10 | 9 | 8 | — | 4 | 4 | 0 | 0 | 0 | 8 | 0 | 4 | 0 | 3 | 0 | 9 | 3 | 9 | 10 | 2 | — | 9 | 10 | 4 | 9 |
| Soybean | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 |
| Sugarbeets | 2 | 0 | 0 | 3 | 5 | 7 | 6 | — | 8 | 6 | 0 | 3 | 2 | 7 | 6 | 5 | 2 | 0 | 0 | 6 | 0 | 2 | 2 | 2 | 0 | 5 | 7 | 0 | 3 |
| Velvetleaf | 0 | 0 | 0 | 2 | 8 | 2 | 4 | 3 | 2 | 2 | 0 | 2 | 0 | 5 | 2 | 2 | 0 | 0 | 0 | 0 | 0 | 0 | 0 | 0 | 0 | 2 | 2 | 0 | 0 |
| Wheat | 3 | 0 | 0 | 0 | 2 | 0 | 7 | — | 8 | 0 | 0 | 0 | 0 | 0 | 3 | 0 | 0 | 0 | 3 | 0 | 0 | 0 | 0 | 0 | — | 2 | 3 | 0 | 0 |
| Wild oats | 8 | 0 | 0 | 0 | 4 | 0 | 8 | — | 9 | 3 | 0 | 0 | 0 | 9 | 9 | 0 | 0 | 2 | 5 | 0 | 2 | 2 | 0 | 2 | 0 | 2 | 3 | 0 | 3 |

| Rate 250 g/ha | 554 | 555 | 556 | 557 | 558 | 559 | 560 | 561 | 562 | 563 | 564 | 565 | 566 | 567 | 568 | 569 | 570 | 571 | 572 | 573 | 574 | 575 | 576 | 577 | 578 | 579 | 580 | 581 | 582 |
|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | |
| Preemergence | | | | | | | | | | | | | | | | | | | | | | | | | | | | | |
| B. signalgrass | 6 | — | 7 | 7 | 3 | 9 | 7 | 8 | 10 | 9 | 6 | 0 | 10 | 2 | 8 | 9 | 0 | 3 | 0 | 9 | 10 | 10 | 6 | 4 | 9 | 2 | 6 | 2 | 2 |
| Bedstraw | 0 | 0 | 0 | 0 | 0 | 0 | 5 | 2 | 0 | 0 | 0 | 0 | 0 | 0 | 3 | 0 | 0 | 0 | 0 | 0 | 0 | 0 | 0 | 0 | 0 | 0 | 6 | 7 | 6 |
| Blackgrass | 4 | 0 | 10 | 8 | 6 | 10 | 9 | 9 | 10 | 9 | 5 | 0 | 10 | 0 | 8 | 9 | 0 | 3 | 0 | 2 | 2 | 7 | 6 | 3 | 0 | 0 | 7 | 0 | 0 |
| Cocklebur | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 6 | 5 | 2 | 9 | 4 | 4 | 0 | 2 | 0 | 5 | 0 | 0 | 0 | 0 | 0 | 0 | 0 | 0 | 2 | 2 | 0 | 2 | 7 | 0 |
| Crabgrass | — | 10 | 9 | 10 | 9 | 10 | 9 | 9 | 10 | 10 | 9 | 0 | 9 | 9 | 9 | 9 | 9 | 3 | 0 | 9 | 9 | 9 | 9 | 9 | 9 | 10 | 9 | 8 | 0 |
| Giant foxtail | 9 | 10 | 10 | 10 | 9 | 10 | 10 | 6 | 8 | 10 | 9 | 0 | 10 | 10 | 10 | 9 | 9 | 9 | 4 | 9 | 10 | 10 | 9 | 9 | 10 | 10 | 10 | 9 | 8 |
| Morningglory | 0 | 0 | 0 | 0 | 0 | 4 | 3 | 2 | 0 | 0 | 2 | 0 | 0 | 0 | 2 | 0 | 0 | 2 | 0 | 0 | 0 | 0 | 0 | 8 | 0 | 0 | 0 | 4 | 0 |
| Nutsedge | 0 | 0 | 0 | 0 | 0 | — | 7 | — | 0 | 0 | — | 0 | 0 | 0 | 0 | 0 | — | 0 | 0 | 0 | 0 | 0 | 0 | 0 | 0 | 0 | 0 | 4 | 0 |
| Rape | 0 | 0 | 3 | 0 | 2 | 10 | 7 | 5 | 10 | 9 | 0 | 0 | 7 | 0 | 5 | 4 | 0 | 0 | 0 | 3 | 0 | 2 | 2 | 0 | 2 | 0 | 7 | 2 | 0 |
| Redroot pigweed | — | 3 | 5 | 3 | 2 | 10 | 9 | 9 | 10 | 9 | 3 | 0 | 9 | 8 | 4 | 9 | 0 | 9 | 0 | 9 | — | 10 | 10 | 0 | 9 | 2 | 10 | 9 | 4 |
| Soybean | 3 | 0 | 0 | 0 | 0 | 3 | 1 | 0 | 9 | 3 | 4 | 0 | 0 | 0 | 3 | 0 | 0 | 0 | 0 | 0 | 0 | 0 | 0 | 0 | 0 | 0 | 0 | 5 | 0 |
| Sugarbeets | 0 | — | 0 | 3 | 0 | 9 | 3 | 2 | 9 | 3 | 3 | 0 | 6 | 0 | 6 | 0 | 0 | 0 | 0 | 2 | 0 | 0 | 4 | 0 | 3 | 0 | 4 | 0 | 0 |
| Velvetleaf | 0 | 0 | 3 | 0 | 0 | 6 | 2 | 0 | 0 | 6 | 6 | 0 | 0 | 0 | 6 | 0 | 0 | 0 | 0 | 0 | 2 | 0 | 0 | 3 | 2 | 0 | 2 | 5 | 4 |
| Wheat | — | 2 | 3 | 0 | 0 | 9 | 6 | 6 | 9 | 9 | 7 | 0 | 6 | 0 | 0 | 0 | 0 | 3 | 0 | 0 | 0 | 0 | 8 | 0 | 0 | 0 | 2 | 2 | 0 |
| Wild oats | 2 | 0 | 4 | 0 | 0 | 9 | 5 | 5 | 10 | 9 | 4 | 0 | 8 | 0 | 6 | 6 | 0 | 3 | 0 | 0 | 0 | 2 | 3 | 0 | 2 | 0 | 2 | 0 | 0 |

TABLE B-continued

| Rate 250 g/ha | 584 | 585 | 586 | 587 | 588 | 589 | 590 | 591 | 592 | 593 | 594 | 595 | 596 | 598 | 599 | 600 | 601 | 602 | 603 | 604 | 605 | 606 | 607 | 608 | 609 | 610 | 611 | 612 | 613 |
|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | |
| Preemergence | | | | | | | | | | | | | | | | | | | | | | | | | | | | | |
| B. signalgrass | — | 9 | 8 | 5 | 5 | 0 | 0 | 0 | 0 | 0 | 5 | 7 | 0 | 0 | 2 | 0 | 8 | 7 | 0 | 0 | 0 | 0 | 8 | — | 9 | 9 | 10 | 10 | 9 |
| Bedstraw | 9 | 9 | — | — | 0 | — | — | — | — | 0 | 2 | — | 0 | 0 | 0 | 0 | 0 | 0 | — | 0 | 0 | — | — | — | 8 | — | — | — | — |
| Blackgrass | 8 | 8 | 9 | 6 | 5 | 0 | 0 | 0 | 0 | 0 | 9 | 10 | 0 | 0 | 3 | 0 | 8 | 6 | 0 | 0 | 0 | 0 | 8 | 7 | 9 | 10 | 10 | 10 | 10 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 |
| Corn | 2 | 3 | 0 | 0 | 0 | 0 | 0 | 0 | 0 | 0 | 2 | 4 | 0 | 0 | 0 | 0 | 0 | 0 | 0 | 0 | 0 | 0 | 0 | 0 | 6 | 7 | 9 | 8 | 9 |
| Crabgrass | 9 | 9 | 10 | 8 | 8 | 7 | 2 | 0 | 2 | 0 | 9 | 9 | 1 | 0 | 5 | 0 | 10 | 9 | 0 | 0 | 5 | 7 | 9 | 10 | 8 | 10 | 10 | 10 | 10 |
| Giant foxtail | 9 | 9 | 10 | 9 | 8 | 10 | 7 | 0 | 0 | 0 | 10 | 10 | 0 | 0 | 9 | 0 | 10 | 10 | 0 | 3 | 10 | 9 | 10 | 10 | 10 | 10 | 10 | 10 | 10 |
| Morningglory | 4 | 2 | 1 | 0 | 0 | 0 | 0 | 0 | 0 | 0 | 3 | 2 | 0 | 0 | 0 | 0 | 0 | 0 | 0 | 0 | 0 | 0 | 0 | 0 | 4 | 6 | 3 | 2 | 7 |
| Nutsedge | 0 | 0 | 0 | 0 | 0 | — | 0 | 0 | 0 | 0 | 3 | 4 | 0 | 0 | 0 | 0 | — | 0 | 0 | 0 | 0 | 0 | 0 | 0 | 4 | 2 | 0 | 0 | 0 |
| Rape | 4 | 9 | 0 | 0 | 0 | 0 | 0 | 0 | 0 | 0 | 6 | 7 | 0 | 0 | 0 | 0 | 0 | 3 | 0 | 0 | 0 | 0 | 7 | 5 | 6 | 10 | 8 | 8 | 10 |
| Redroot pigweed | 9 | 10 | 10 | 1 | 9 | 0 | 0 | 0 | 0 | 0 | 10 | 10 | 0 | 0 | 0 | 0 | 10 | 8 | 0 | 0 | 0 | 0 | 9 | 7 | 8 | 10 | 10 | 10 | 10 |
| Soybean | 0 | 0 | 0 | 0 | 5 | 0 | 0 | 0 | 0 | 0 | 0 | 2 | 0 | 0 | 0 | 0 | 0 | 0 | 0 | 0 | 0 | 0 | 0 | 1 | 6 | 8 | 4 | 2 | 0 |
| Sugarbeets | 3 | 7 | 1 | 0 | 0 | 0 | 0 | 0 | 0 | 0 | 5 | 9 | 0 | 0 | 0 | 0 | 5 | 4 | 0 | 0 | 0 | 0 | 0 | 3 | 7 | 8 | 5 | 6 | 8 |
| Velvetleaf | 2 | 7 | 2 | 0 | 2 | 0 | 0 | 0 | 0 | 0 | 6 | 9 | 0 | 0 | 0 | 0 | 5 | 6 | 0 | 0 | 0 | 0 | 7 | 6 | 8 | 8 | 8 | 7 | 7 |
| Wheat | 0 | 5 | 3 | 1 | 3 | 0 | 0 | 0 | 0 | 0 | 0 | 3 | 0 | 0 | 0 | 0 | 2 | 0 | 0 | 0 | 0 | 0 | 3 | 0 | 3 | 5 | 6 | 5 | 5 |
| Wild oats | 4 | 9 | 10 | 7 | 2 | 0 | 0 | 0 | 0 | 0 | 2 | 9 | 0 | 0 | 0 | 0 | 8 | 5 | 0 | 0 | 0 | 0 | 2 | 3 | 8 | 9 | 8 | 9 | 9 |

| Rate 250 g/ha | 614 | 615 | 616 | 617 | 618 | 619 | 620 | 621 | 622 | 623 | 624 | 625 | 627 | 628 | 629 | 630 | 631 | 632 | 633 | 634 | 635 | 636 | 637 | 638 | 639 | 640 | 641 | 642 | 643 |
|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | |
| Preemergence | | | | | | | | | | | | | | | | | | | | | | | | | | | | | |
| B. signalgrass | 0 | 0 | 0 | 4 | 0 | 0 | 0 | 0 | 0 | 0 | 6 | 8 | 8 | 8 | 5 | 7 | 10 | 6 | 6 | 7 | 9 | 8 | 8 | 8 | 5 | 4 | 6 | 5 | 2 |
| Bedstraw | 0 | 0 | 0 | 0 | 0 | 0 | 0 | 0 | — | — | 0 | — | 8 | 10 | 3 | 0 | 0 | — | — | — | 7 | 9 | 2 | — | — | — | — | — | — |
| Blackgrass | 3 | 0 | 4 | 6 | 0 | 0 | 0 | 0 | 3 | 0 | 8 | 7 | 9 | 10 | 8 | 8 | 9 | 7 | 5 | 8 | 9 | 4 | 9 | 9 | 2 | 0 | 2 | 4 | 0 |
| Cocklebur | 0 | 0 | 0 | 0 | — | 0 | 0 | 0 | 0 | 0 | 0 | 0 | 6 | 4 | 3 | — | 0 | 0 | 0 | 0 | 0 | 0 | 0 | 4 | 0 | 0 | 0 | 0 | 0 |
| Corn | 0 | 0 | 0 | 0 | 0 | 0 | 0 | 0 | 0 | 0 | 2 | 0 | 6 | 7 | 6 | 3 | 8 | 4 | 0 | 0 | 2 | 0 | 0 | — | 0 | 0 | 0 | 0 | 0 |
| Crabgrass | 8 | 0 | 0 | 5 | 0 | 6 | 0 | 7 | 7 | 0 | 9 | 8 | 9 | 9 | 9 | 9 | 9 | 8 | 9 | 10 | 9 | 10 | 10 | 9 | 9 | 9 | 7 | 10 | 9 |
| Giant foxtail | 9 | 0 | 7 | 9 | 2 | 7 | 2 | 7 | 9 | 8 | 10 | 10 | 10 | 10 | 10 | 10 | 10 | 10 | 10 | 10 | 10 | 10 | 10 | 10 | 9 | 10 | 9 | 10 | 10 |
| Morningglory | 0 | 0 | 0 | 0 | 0 | 0 | 0 | 0 | 0 | 0 | 0 | 2 | 6 | 5 | 0 | 0 | 4 | 4 | 0 | 0 | 0 | 0 | 0 | 2 | 0 | 0 | 0 | 0 | 0 |
| Nutsedge | 0 | 0 | 0 | 0 | — | 0 | 0 | 0 | 0 | 0 | 0 | 0 | 7 | 6 | 5 | 0 | 4 | 0 | 0 | 0 | 3 | 0 | 0 | 5 | 0 | — | 0 | 0 | 0 |
| Rape | 0 | 0 | 0 | 0 | 0 | 0 | 0 | 0 | 0 | 0 | 1 | — | 9 | 4 | 4 | 0 | 6 | 0 | 1 | 6 | 7 | 7 | 2 | 8 | 3 | 3 | — | 4 | 0 |
| Redroot pigweed | 0 | 0 | 8 | 0 | 0 | 0 | 0 | 0 | 10 | 0 | 3 | 4 | 10 | 9 | 10 | 10 | 10 | 6 | 2 | 10 | 10 | 10 | 7 | 10 | 2 | 2 | 0 | 2 | 0 |
| Soybean | 0 | 0 | 0 | 0 | 0 | 0 | 0 | 0 | 0 | 0 | 3 | 0 | 0 | 4 | 0 | 0 | 9 | 0 | 0 | 0 | 0 | 0 | 0 | 3 | 0 | 0 | 0 | 0 | 0 |
| Sugarbeets | 0 | 0 | 0 | 0 | 0 | 0 | 0 | 0 | 0 | 0 | 7 | 0 | 8 | 7 | 3 | 4 | 4 | 0 | 0 | 5 | 8 | 6 | 3 | 6 | 0 | 6 | 0 | 0 | 0 |
| Velvetleaf | 0 | 0 | 0 | 0 | 0 | 0 | 0 | 0 | 0 | 0 | 1 | 1 | 10 | 9 | 6 | 6 | 7 | 6 | 0 | 4 | 3 | 2 | 0 | 5 | 0 | 0 | 0 | 0 | 0 |
| Wheat | 0 | 0 | 0 | 0 | 0 | 0 | 0 | 0 | 0 | 0 | 6 | 0 | 7 | 7 | 3 | 3 | 8 | 0 | 0 | 0 | 3 | 0 | 0 | 3 | 0 | 0 | 0 | 0 | 0 |
| Wild oats | 0 | 0 | 0 | 2 | 0 | 0 | 0 | 0 | 0 | 0 | 6 | 3 | 5 | 8 | 9 | 8 | 8 | 3 | 3 | 5 | 9 | 0 | 0 | 10 | 0 | 3 | 0 | 2 | 0 |

TABLE B-continued

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 644 | 645 | 646 | 647 | 648 | 649 | 650 | 652 | 653 | 654 | 655 | 656 | 657 | 658 | 659 | 660 | 661 | 662 | 663 | 664 | 665 | 666 | 667 | 668 | 669 | 670 | 671 | 672 | 673 |
| Preemergence | | | | | | | | | | | | | | | | | | | | | | | | | | | | | |
| B. signalgrass | 2 | 0 | 0 | 9 | 0 | 0 | 0 | 2 | 0 | 0 | 0 | 6 | 9 | 8 | 4 | 4 | 3 | 3 | 0 | 5 | 8 | 7 | 8 | 8 | 10 | 10 | 7 | 6 | 7 |
| Bedstraw | — | — | — | — | 0 | 0 | 0 | 0 | 0 | 0 | 0 | — | — | — | — | — | — | — | — | — | — | — | — | — | 9 | 9 | — | 0 | 4 |
| Blackgrass | 0 | 0 | 0 | 10 | 2 | 0 | 0 | 0 | 0 | 2 | 2 | 5 | 7 | 7 | 7 | 6 | 4 | 4 | 0 | 6 | 8 | 9 | 8 | 10 | 10 | 10 | 8 | 8 | 9 |
| Cocklebur | 0 | 0 | 0 | 1 | — | 0 | 0 | 0 | 0 | 0 | 0 | 0 | 2 | 0 | 0 | 0 | 0 | 0 | 0 | 0 | 0 | 0 | 0 | 0 | 0 | — | 0 | 0 | 0 |
| Corn | 0 | 0 | 0 | 5 | 0 | 0 | 0 | 0 | 0 | 0 | 0 | 0 | — | 2 | 7 | 0 | 0 | 0 | 0 | 0 | 0 | 8 | 7 | 4 | 9 | 8 | 3 | 0 | 4 |
| Crabgrass | 3 | 4 | 0 | 9 | 9 | 5 | 9 | 8 | 6 | 7 | 8 | 8 | 9 | 8 | — | 8 | 3 | 4 | 0 | 9 | 9 | 9 | 10 | 8 | 9 | 10 | 8 | 10 | 10 |
| Giant foxtail | 6 | 5 | 0 | 10 | 9 | 9 | 10 | 9 | 2 | 9 | 9 | 10 | 9 | 9 | 9 | 10 | 8 | 9 | 5 | 10 | 10 | 10 | 10 | 9 | 10 | 10 | 10 | 10 | 10 |
| Morningglory | 3 | 0 | 0 | 7 | 0 | 0 | 1 | 0 | 0 | 0 | 0 | 0 | 4 | 0 | 0 | 0 | 0 | 0 | 0 | 0 | 0 | 0 | 3 | 0 | 0 | 8 | 5 | 0 | 0 |
| Nutsedge | — | 0 | 0 | — | 0 | 0 | 7 | 0 | — | 0 | 0 | 0 | 5 | 0 | 0 | 0 | 0 | 4 | 0 | 0 | 0 | 0 | 3 | 0 | — | 8 | 6 | 0 | 2 |
| Rape | 2 | 0 | 0 | 10 | 0 | 0 | 0 | 0 | 0 | 0 | 0 | 0 | 10 | 5 | 2 | 3 | 0 | 0 | 0 | 1 | 8 | 10 | 10 | 8 | 8 | 10 | 0 | 7 | 2 |
| Redroot pigweed | 0 | 0 | 0 | 10 | 0 | 0 | 7 | 0 | 0 | 3 | 2 | 6 | 10 | 9 | 9 | 7 | 3 | 3 | 7 | 7 | 9 | 10 | 10 | 10 | 10 | 10 | 10 | 7 | 10 |
| Soybean | 0 | 0 | 0 | 1 | 0 | 0 | 0 | 0 | 0 | 0 | 0 | 0 | — | 0 | 0 | 0 | 0 | 0 | 0 | 0 | 0 | 3 | 6 | 1 | 3 | 8 | 0 | 0 | 0 |
| Sugarbeets | 0 | 0 | 0 | 8 | 0 | 0 | 0 | 0 | 0 | 0 | 0 | 3 | 10 | 6 | 0 | 0 | 0 | 0 | 0 | 0 | 6 | 7 | 8 | 6 | 8 | 9 | 9 | 7 | 3 |
| Velvetleaf | 0 | 0 | 0 | 8 | 0 | 0 | 0 | 0 | 0 | 0 | 0 | 6 | 8 | 3 | 6 | 0 | 0 | 0 | 0 | 5 | 4 | 7 | 8 | 7 | 0 | 8 | 7 | 3 | 3 |
| Wheat | 0 | 0 | 0 | 8 | 0 | 0 | 0 | 0 | 0 | 0 | 0 | 0 | 0 | 0 | 2 | 0 | 0 | 0 | 0 | 0 | 4 | 4 | 5 | 5 | 8 | 9 | 3 | 0 | 0 |
| Wild oats | 0 | 0 | 0 | 9 | 0 | 0 | 0 | 0 | 0 | 0 | 0 | 6 | 8 | 3 | 3 | 2 | 0 | 0 | 0 | 3 | 7 | 9 | 8 | 8 | 10 | 9 | 7 | 5 | 9 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 674 | 675 | 676 | 677 | 678 | 679 | 680 | 681 | 682 | 683 | 684 | 685 | 686 | 687 | 689 | 691 | 692 | 693 | 694 | 695 | 696 | 697 | 698 | 699 | 700 | 701 | 702 | 703 | 704 |
| Preemergence | | | | | | | | | | | | | | | | | | | | | | | | | | | | | |
| B. signalgrass | 8 | 8 | 4 | 3 | 0 | 0 | 0 | 0 | 7 | 4 | 4 | 9 | 7 | 10 | 9 | 9 | 10 | 0 | 6 | 5 | — | 0 | 3 | 9 | 8 | 0 | 2 | 3 | 8 |
| Bedstraw | — | 10 | — | — | — | — | — | — | 0 | 0 | 0 | 0 | 0 | — | 7 | 9 | 1 | 0 | 0 | 0 | 0 | 0 | 0 | 0 | 0 | 0 | 0 | 0 | 0 |
| Blackgrass | 9 | 9 | 4 | 0 | 0 | 0 | 0 | 1 | 8 | 7 | 4 | 10 | 8 | 9 | 10 | 10 | 10 | 0 | 9 | 6 | 7 | 2 | 2 | 10 | 8 | 2 | 9 | 6 | 10 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 5 | 6 | 3 | 0 | 0 | 0 | 0 | 0 | 0 | 0 | 0 | 0 | 0 | 0 | 9 | 0 | 0 | 0 | 1 | 0 | 0 | 0 | 0 | 8 | 3 | 0 | 0 | 0 | 0 |
| Crabgrass | 9 | 9 | 6 | 6 | 0 | 0 | 3 | 2 | 9 | 9 | 9 | 9 | 10 | 4 | 10 | 10 | 10 | 0 | 9 | 9 | 9 | 4 | 8 | 10 | 10 | 10 | 10 | 9 | 8 |
| Giant foxtail | 10 | 10 | 10 | 8 | 0 | 3 | 4 | 6 | 10 | 9 | 10 | 10 | 10 | 6 | 10 | 10 | 10 | 2 | 10 | 10 | 10 | 5 | 9 | 10 | 10 | 10 | 10 | 9 | 8 |
| Morningglory | 7 | 3 | 0 | 0 | 0 | 0 | 0 | 0 | 2 | 0 | 1 | 1 | 0 | 3 | 3 | 0 | 1 | 0 | 2 | 0 | 0 | 4 | 0 | 5 | 0 | 0 | 0 | 1 | 1 |
| Nutsedge | 5 | 3 | 0 | 0 | — | 0 | 0 | 0 | 0 | 0 | 0 | — | 0 | 0 | 0 | — | 0 | 0 | — | 0 | 0 | 0 | 0 | 0 | 0 | — | 0 | 0 | 0 |
| Rape | 5 | 7 | 5 | 0 | 0 | 0 | 0 | 0 | 3 | 0 | 0 | 2 | 2 | 8 | 7 | 6 | 3 | 6 | 0 | 0 | 2 | 0 | 0 | 9 | 2 | 0 | 0 | 0 | 1 |
| Redroot pigweed | 10 | 10 | — | 7 | 0 | 0 | 0 | 0 | 5 | 5 | 1 | 5 | 7 | 9 | 7 | 8 | 8 | 0 | 8 | 5 | 6 | 0 | 0 | 6 | 2 | 0 | 5 | 4 | — |
| Soybean | 5 | 0 | 0 | 0 | 0 | 0 | 0 | 0 | 0 | 0 | 0 | 0 | 0 | 0 | 2 | 2 | 0 | 0 | 0 | 0 | 0 | 0 | 0 | 2 | 0 | 0 | 0 | 0 | 0 |
| Sugarbeets | 7 | 8 | 5 | 0 | 0 | 0 | 0 | 0 | 3 | 0 | 0 | 1 | 2 | 9 | 6 | 5 | 2 | 0 | 0 | 0 | 3 | 0 | 0 | 7 | 3 | 0 | 3 | 0 | 4 |
| Velvetleaf | 8 | 10 | 4 | 0 | 0 | 0 | 0 | 0 | 0 | 0 | 0 | 0 | 0 | 6 | 6 | 0 | 1 | 0 | 1 | 0 | 2 | 0 | 0 | 5 | 0 | 0 | 0 | 0 | 0 |
| Wheat | 8 | 5 | 2 | 0 | 0 | 0 | 0 | 0 | 0 | 0 | 0 | 0 | 0 | 7 | 2 | 0 | 0 | 0 | 0 | 0 | 0 | 0 | 2 | 6 | 0 | 0 | 0 | 0 | 6 |
| Wild oats | 8 | 7 | 3 | 0 | 0 | 0 | 0 | 0 | 2 | 0 | 2 | — | 5 | 10 | 9 | 9 | 10 | 0 | 3 | 0 | 6 | 0 | 0 | 10 | 9 | 2 | 7 | 2 | 2 |

TABLE B-continued

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 706 | 707 | 708 | 709 | 710 | 711 | 712 | 713 | 714 | 715 | 716 | 717 | 718 | 719 | 720 | 721 | 722 | 723 | 724 | 725 | 726 | 727 | 728 | 729 | 730 | 732 | 733 | 734 | 735 |
| Preemergence | | | | | | | | | | | | | | | | | | | | | | | | | | | | | |
| B. signalgrass | 8 | 9 | 0 | 0 | 8 | 7 | 8 | 8 | 10 | 9 | 0 | 7 | 7 | 7 | 10 | 8 | 0 | 2 | 0 | 4 | 7 | 7 | 8 | 10 | 7 | 0 | 8 | 9 | 9 |
| Bedstraw | 0 | 10 | 0 | 0 | 5 | 6 | 2 | 2 | 9 | 0 | 0 | 0 | 0 | 0 | 10 | 10 | 0 | 0 | 0 | 0 | 0 | 0 | 0 | 8 | 0 | 0 | 0 | 0 | 0 |
| Blackgrass | 10 | 10 | 3 | 0 | 9 | 8 | 8 | 9 | 9 | 9 | 0 | 10 | 9 | 9 | 10 | 10 | 0 | 0 | 0 | 7 | 8 | 8 | 9 | 10 | 10 | 0 | 8 | 9 | 10 |
| Cocklebur | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 |
| Corn | 0 | 2 | 0 | 0 | 0 | 0 | 0 | 0 | 5 | 2 | 0 | 3 | 0 | 0 | 4 | 5 | 0 | 0 | 0 | 0 | 0 | 0 | 0 | 6 | 4 | 0 | 0 | 9 | 8 |
| Crabgrass | 8 | 9 | 10 | 7 | 10 | 10 | 10 | 10 | 10 | 10 | 0 | 10 | 10 | 8 | 10 | 9 | 0 | 2 | 7 | 8 | 9 | 9 | — | 9 | 9 | 0 | 9 | 9 | 10 |
| Giant foxtail | 7 | 10 | 8 | 7 | 10 | 10 | 10 | 10 | 10 | 10 | 0 | 10 | 10 | 8 | 10 | 10 | 4 | 9 | 7 | 10 | 10 | 10 | 8 | 9 | 10 | 0 | 9 | 10 | 10 |
| Morningglory | 1 | 4 | 0 | 0 | 0 | 3 | 0 | 0 | 0 | 2 | 0 | 0 | 0 | 3 | — | 2 | 2 | 0 | 0 | 1 | 1 | 0 | 2 | 2 | 0 | 0 | 2 | 3 | 2 |
| Nutsedge | 0 | 0 | 0 | — | 0 | 0 | 0 | 0 | 0 | 0 | — | 0 | 0 | 0 | — | 0 | 0 | 0 | 0 | — | 0 | 0 | — | — | 3 | 0 | 0 | 0 | 0 |
| Rape | 3 | 10 | 0 | 0 | 8 | 7 | 7 | 8 | 6 | 8 | 0 | 0 | 2 | 2 | 9 | 9 | 0 | 0 | 0 | 0 | 0 | 1 | 6 | 3 | 2 | 0 | 3 | 5 | 8 |
| Redroot pigweed | 10 | 10 | — | 5 | 10 | 9 | 8 | 8 | 10 | 10 | 0 | 8 | 6 | 10 | 10 | 10 | 0 | 0 | 0 | 0 | 7 | 5 | 8 | 10 | 10 | 0 | 5 | 8 | 8 |
| Soybean | 0 | 0 | 0 | 0 | 3 | 0 | 0 | 0 | 0 | 0 | 0 | 0 | 0 | 0 | 0 | 0 | 0 | 0 | 0 | 0 | 0 | 0 | 0 | 2 | 2 | 0 | 0 | 0 | 0 |
| Sugarbeets | 4 | 8 | 0 | 0 | 8 | 8 | 7 | 7 | 4 | 7 | 0 | 2 | 2 | 6 | 8 | 7 | 0 | 0 | 0 | 0 | 5 | 0 | 4 | 0 | 4 | 0 | 0 | 5 | 6 |
| Velvetleaf | 5 | 5 | 2 | 0 | 7 | 6 | 3 | 5 | 2 | 6 | 0 | 0 | 0 | 0 | 3 | 8 | 0 | 0 | 0 | 0 | 0 | 0 | 0 | 4 | 6 | 0 | 0 | 5 | 3 |
| Wheat | 5 | 2 | 0 | 0 | 7 | 8 | 0 | 1 | 6 | 3 | 0 | 0 | 0 | 3 | 5 | 3 | 0 | 0 | 0 | 0 | 0 | 0 | 5 | 4 | 0 | 0 | 0 | 8 | — |
| Wild oats | 8 | 9 | 0 | 0 | 9 | 9 | 3 | 8 | 6 | 9 | 0 | 9 | — | 9 | 9 | 8 | 0 | 0 | 0 | 4 | 8 | 3 | 10 | 10 | 7 | 0 | 2 | 10 | 8 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 736 | 737 | 738 | 739 | 740 | 741 | 742 | 743 | 744 | 745 | 746 | 747 | 748 | 749 | 750 | 751 | 752 | 753 | 754 | 755 | 756 | 757 | 758 | 759 | 760 | 761 | 762 | 763 | 764 |
| Preemergence | | | | | | | | | | | | | | | | | | | | | | | | | | | | | |
| B. signalgrass | 3 | 8 | 10 | — | — | 2 | 0 | 4 | 9 | 10 | 9 | — | 3 | 8 | 8 | — | — | 9 | 8 | 0 | 0 | 2 | 7 | 8 | 10 | 0 | 6 | 9 | 9 |
| Bedstraw | 0 | 0 | 0 | 10 | 0 | 0 | 0 | 0 | 0 | 5 | — | — | 0 | 0 | 0 | 9 | 10 | 3 | 0 | 0 | 0 | 0 | 3 | 0 | 0 | 0 | 0 | 7 | 5 |
| Blackgrass | 4 | 9 | 10 | 3 | 8 | 0 | 0 | 9 | 9 | 9 | 10 | — | — | 6 | 8 | 10 | 9 | 9 | 9 | 0 | 4 | 3 | 8 | 5 | 6 | 0 | 7 | 9 | 8 |
| Cocklebur | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 2 | 3 | 7 | 2 | 0 | 0 | 0 | 0 | 5 | 2 | 3 | 6 | 0 | 0 | — | 8 | 0 | 0 | 0 | 0 | 0 | 0 | — | 0 | 0 | 0 | 0 | 0 | 6 |
| Crabgrass | 4 | 10 | 9 | 9 | 9 | 5 | 0 | 9 | 9 | 10 | 10 | 10 | 10 | 10 | 9 | 10 | 10 | 9 | 9 | 0 | 9 | 9 | 10 | 8 | 10 | 5 | 4 | 10 | 10 |
| Giant foxtail | 9 | 10 | 10 | 9 | 9 | 9 | 0 | 9 | 9 | 10 | 10 | 10 | 10 | 10 | 10 | 10 | 10 | 9 | 9 | 0 | 9 | 9 | 10 | 10 | 10 | 8 | 9 | 9 | 10 |
| Morningglory | 2 | 2 | 2 | 0 | 0 | 0 | 0 | 0 | 0 | 0 | 6 | 0 | 0 | 0 | 6 | 5 | 0 | 0 | 1 | 0 | 0 | 0 | 0 | 0 | 0 | 0 | 0 | 0 | 0 |
| Nutsedge | 0 | 0 | 4 | 0 | 0 | 0 | 0 | 2 | 5 | 0 | — | 4 | 0 | 0 | 7 | 0 | — | 0 | 3 | 0 | 0 | 0 | 0 | 0 | 0 | 0 | 0 | — | 0 |
| Rape | 0 | 5 | 6 | 0 | 5 | 0 | 0 | 9 | 6 | 7 | 9 | 10 | 0 | 0 | 8 | 7 | 5 | 7 | 6 | 0 | 0 | 0 | 4 | 0 | 2 | 0 | 0 | 6 | 9 |
| Redroot pigweed | 2 | 6 | 8 | 9 | 9 | 0 | 0 | 9 | 9 | 10 | 10 | 8 | 10 | 7 | 10 | 10 | 10 | 9 | 9 | 0 | 0 | 2 | 8 | 3 | 9 | 0 | 3 | 10 | 10 |
| Soybean | 2 | 0 | 0 | 0 | 0 | 0 | 0 | 0 | 0 | 0 | 5 | 0 | 0 | 2 | 5 | 7 | 0 | 0 | 0 | 0 | 0 | 0 | 0 | 0 | 0 | 0 | 0 | 0 | 3 |
| Sugarbeets | 0 | 6 | 6 | 2 | 3 | 0 | 0 | 4 | 7 | 4 | 7 | 7 | 2 | 6 | 5 | 5 | 3 | 1 | 3 | 0 | 0 | 0 | 7 | 4 | 3 | 0 | 4 | 3 | 5 |
| Velvetleaf | 0 | 4 | 6 | 2 | 0 | 3 | 0 | 3 | 0 | 4 | 7 | 7 | 0 | 0 | 7 | 8 | 0 | — | 3 | 0 | 0 | 0 | 4 | 0 | 0 | 0 | 0 | 1 | 5 |
| Wheat | 3 | 2 | 5 | 0 | 0 | 0 | 0 | 0 | 3 | 0 | 8 | 0 | 0 | 1 | 5 | 5 | 0 | 3 | 7 | 0 | 0 | 0 | 5 | 3 | 0 | 0 | 0 | 5 | — |
| Wild oats | 9 | 8 | 10 | 0 | 2 | 0 | 0 | 5 | 9 | 8 | 10 | 3 | 2 | 5 | 7 | 10 | 7 | 8 | 8 | 0 | 0 | 2 | 8 | 5 | 2 | 0 | 0 | 9 | 6 |

TABLE B-continued

| Rate 250 g/ha | 765 | 766 | 767 | 772 | 773 | 774 | 775 | 776 | 777 | 778 | 780 | 790 | 791 | 792 |
|---|---|---|---|---|---|---|---|---|---|---|---|---|---|---|
| | COMPOUND | | | | | | | | | | | | | |
| Preemergence | | | | | | | | | | | | | | |
| B. signalgrass | 7 | 10 | — | 0 | 0 | 0 | — | — | — | — | 8 | 9 | 0 | 9 |
| Bedstraw | 2 | 10 | — | 0 | 0 | 0 | 0 | 0 | — | 0 | 0 | 7 | — | 4 |
| Blackgrass | 8 | 8 | 10 | 0 | 0 | 0 | 9 | 2 | 10 | 10 | 9 | 9 | 7 | 8 |
| Cocklebur | 0 | — | 0 | 0 | 0 | 0 | 0 | — | 0 | 0 | 2 | 10 | 0 | 0 |
| Corn | 0 | 0 | 0 | 0 | 0 | 0 | 0 | 1 | 0 | 0 | 6 | 8 | 0 | 4 |
| Crabgrass | 10 | 10 | 10 | 0 | 0 | 0 | 9 | 9 | 10 | 10 | 10 | 10 | 10 | 10 |
| Giant foxtail | 10 | 9 | 10 | 0 | 0 | 0 | 10 | 9 | 10 | 10 | 10 | lo | 10 | 10 |
| Morningglory | 0 | 3 | 0 | 0 | 0 | 0 | 0 | 2 | 1 | 0 | 0 | 2 | 0 | 0 |
| Nutsedge | 0 | 4 | 0 | 0 | 0 | 0 | 0 | 0 | 2 | 9 | 0 | 0 | 0 | 0 |
| Rape | 5 | 9 | 9 | 0 | 0 | 0 | 0 | 0 | 0 | 3 | 2 | 6 | 3 | 4 |
| Redroot pigweed | 10 | 10 | 10 | 0 | 0 | 0 | 8 | 0 | — | 3 | 6 | 9 | 5 | 9 |
| Soybean | 0 | 0 | 2 | 0 | 0 | 0 | 0 | 0 | 0 | 1 | 2 | 0 | 5 | 0 |
| Sugarbeets | 8 | 8 | 8 | 0 | 0 | 0 | 3 | 0 | 2 | 2 | 4 | 6 | 0 | 6 |
| Velvetleaf | 6 | 8 | 2 | 0 | 0 | 0 | 0 | 0 | 0 | 0 | 3 | 7 | 0 | 3 |
| Wheat | 7 | 4 | 5 | 0 | 0 | 0 | 7 | 2 | 3 | 4 | 5 | 7 | 0 | 0 |
| Wild oats | 8 | 7 | 9 | 0 | 0 | 0 | 2 | 2 | 8 | 8 | 4 | 5 | 5 | 8 |

| Rate 125 g/ha | 18 | 35 | 47 | 69 | 70 | 71 | 72 | 129 | 131 | 146 | 165 | 166 | 180 | 181 | 182 | 183 | 184 | 185 | 186 | 187 | 189 | 190 | 191 | 192 | 193 | 194 | 195 | 196 | 197 | 198 | 200 |
|---|---|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | | | |
| Pre-emergence | | | | | | | | | | | | | | | | | | | | | | | | | | | | | | | |
| Barnyardgrass | 2 | 0 | 0 | 0 | 0 | 0 | 0 | 3 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 5 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 5 | 3 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| Rate 125 g/ha | 201 | 202 | 203 | 204 | 205 | 206 | 207 | 208 | 210 | 211 | 212 | 214 | 215 | 216 | 217 | 218 | 219 | 220 | 221 | 222 | 223 | 224 | 225 | 226 | 227 | 228 | 229 | 230 | 231 |
|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| Rate 125 g/ha | 232 | 233 | 234 | 235 | 236 | 237 | 238 | 239 | 240 | 241 | 242 | 243 | 244 | 245 | 246 | 247 | 248 | 249 | 250 | 251 | 252 | 253 | 254 | 255 | 256 | 257 | 258 | 259 | 264 |
|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 265 | 266 | 267 | 268 | 269 | 270 | 271 | 272 | 273 | 274 | 276 | 277 | 278 | 279 | 280 | 281 | 282 | 283 | 284 | 285 | 286 | 287 | 288 | 289 | 290 | 291 | 293 | 294 | 295 |
| Pre-emergence | | | | | | | | | | | | | | | | | | | | | | | | | | | | | |
| Barnyardgrass | 0 | 0 | 0 | 0 | 0 | 0 | 3 | 0 | 4 | 0 | 6 | 2 | 0 | 0 | 0 | 0 | 7 | 3 | 1 | 0 | 0 | 0 | 4 | 0 | 4 | 4 | 0 | 3 | 0 |
| Ducksalad | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 296 | 297 | 298 | 299 | 300 | 301 | 302 | 303 | 304 | 305 | 306 | 307 | 308 | 309 | 310 | 311 | 312 | 313 | 314 | 315 | 316 | 317 | 318 | 319 | 320 | 321 | 322 | 323 | 324 |
| Pre-emergence | | | | | | | | | | | | | | | | | | | | | | | | | | | | | |
| Barnyardgrass | 0 | 0 | 0 | 2 | 0 | 0 | 0 | 0 | 0 | 0 | 0 | 0 | 0 | 0 | 0 | 0 | 0 | 0 | 0 | 0 | 6 | 0 | 0 | 0 | 0 | 0 | 3 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 325 | 326 | 327 | 328 | 329 | 330 | 331 | 332 | 333 | 334 | 335 | 336 | 337 | 338 | 339 | 340 | 341 | 346 | 350 | 351 | 353 | 354 | 358 | 365 | 366 | 367 | 368 | 369 | 370 |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 0 | 0 | 0 | 0 | 8 | 6 | 8 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 4 | 0 | 0 | 0 | 2 | 0 | 6 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 371 | 372 | 373 | 374 | 375 | 376 | 378 | 379 | 380 | 381 | 382 | 383 | 384 | 385 | 387 | 388 | 389 | 390 | 391 | 392 | 393 | 395 | 401 | 402 | 403 | 404 | 405 | 406 | 407 |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 0 | 0 | 0 | 0 | 0 | 0 | 0 | 5 | 0 | 0 | 0 | 0 | 0 | 5 | 4 | 9 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 0 |
| Rice | 0 | 0 | 0 | 0 | 0 | 0 | 0 | 0 | 0 | 0 | 0 | 0 | 0 | 0 | 0 | 0 | — | 1 | 0 | 0 | 0 | 0 | 0 | 1 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

TABLE B-continued

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 408 | 409 | 410 | 411 | 414 | 437 | 438 | 439 | 441 | 442 | 443 | 444 | 445 | 446 | 447 | 448 | 449 | 450 | 451 | 452 | 453 | 454 | 455 | 456 | 457 | 458 | 459 | 460 | 461 |
| Pre-emergence | | | | | | | | | | | | | | | | | | | | | | | | | | | | | |
| Barnyardgrass | 0 | 2 | 4 | 8 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 3 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 462 | 463 | 465 | 466 | 467 | 468 | 469 | 470 | 471 | 472 | 473 | 474 | 476 | 477 | 478 | 479 | 480 | 482 | 483 | 485 | 486 | 487 | 488 | 489 | 490 | 492 | 493 | 494 | 495 |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 496 | 498 | 499 | 509 | 521 | 528 | 529 | 531 | 532 | 538 | 539 | 546 | 550 | 552 | 556 | 558 | 560 | 561 | 567 | 568 | 570 | 577 | 580 | 586 | 587 | 588 | 589 | 590 | 591 |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 8 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | — | — | 0 | 1 | — | 0 | — | 0 | — | 0 | — | 0 | 0 | 0 | 1 | 0 | 0 | 0 | 0 | 0 | 0 | 0 | 0 | 0 |
| S. Flatsedge | 0 | 0 | 0 | 0 | 0 | 0 | 0 | 0 | 8 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 592 | 593 | 594 | 595 | 596 | 598 | 599 | 600 | 601 | 602 | 603 | 604 | 605 | 606 | 607 | 608 | 609 | 610 | 611 | 612 | 613 | 614 | 615 | 616 | 617 | 618 | 619 | 620 | 621 |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 622 | 623 | 624 | 625 | 627 | 628 | 629 | 630 | 631 | 632 | 633 | 634 | 636 | 637 | 638 | 639 | 640 | 641 | 642 | 643 | 644 | 645 | 646 | 647 | 649 | 650 | 651 | 655 | 656 |
| Pre-emergence | | | | | | | | | | | | | | | | | | | | | | | | | | | | | |
| Barnyardgrass | 0 | 0 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | — | — | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 657 | 658 | 659 | 660 | 661 | 662 | 663 | 664 | 665 | 666 | 667 | 668 | 671 | 674 | 675 | 676 | 677 | 678 | 679 | 680 | 681 | 692 | 694 | 695 | 696 | 697 | 699 | 701 | 702 |
| Pre-emergence | | | | | | | | | | | | | | | | | | | | | | | | | | | | | |
| Barnyardgrass | 0 | 0 | 2 | 0 | 0 | 0 | 0 | 0 | 0 | 0 | 0 | 0 | 0 | 0 | 0 | 0 | 0 | 0 | 0 | 0 | 0 | 8 | 0 | 0 | 0 | 0 | 4 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 9 | 0 | 0 | 0 | 0 | 8 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 0 | 0 | 0 | — | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 9 | 0 | 0 | 0 | 0 | 7 | 0 | 0 |

| | COMPOUND | | | | | | | | | | |
|---|---|---|---|---|---|---|---|---|---|---|---|
| Rate 125 g/ha | 705 | 706 | 715 | 720 | 721 | 724 | 740 | 741 | 758 | 765 | 793 |
| Pre-emergence | | | | | | | | | | | |
| Barnyardgrass | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 7 |
| Rice | 1 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 7 |

| | COMPOUND | | | | | | | | | | | | | | | | | | | | | |
|---|---|---|---|---|---|---|---|---|---|---|---|---|---|---|---|---|---|---|---|---|---|---|
| Rate 125 g/ha | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| Postemergence | | | | | | | | | | | | | | | | | | | | | | |
| B. signalgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Bedstraw | 0 | 0 | 0 | 5 | 3 | 0 | 0 | 2 | 0 | 0 | 0 | 0 | 0 | 0 | 0 | 0 | 0 | 7 | 6 | 3 | 0 | 2 |
| Blackgrass | 0 | 0 | 0 | 4 | 4 | 4 | 0 | 0 | 0 | 0 | 0 | 0 | 0 | 0 | 0 | 0 | 0 | 0 | 0 | 0 | 0 | 1 |
| Cocklebur | 0 | 0 | 0 | 2 | 5 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 5 | 3 | 0 | 0 | 0 | 0 | 6 | 0 | 0 | 1 | 0 | 1 | 0 | 3 | 3 | 0 | 0 | 0 | 4 |
| Ducksalad | 0 | 0 | 0 | 0 | 0 | 0 | 0 | 0 | 0 | 0 | 0 | 0 | 0 | 0 | 0 | 0 | 0 | 7 | 0 | 0 | 0 | 0 |
| Giant foxtail | 0 | 0 | 0 | 5 | 1 | 2 | 0 | 0 | 0 | 5 | 0 | 0 | 0 | 0 | 0 | 0 | 2 | 1 | 0 | 0 | 0 | 2 |
| Morningglory | 0 | 0 | 0 | 2 | 2 | 0 | 0 | 0 | 0 | 2 | 0 | 0 | 0 | 2 | 2 | 1 | 7 | 1 | 0 | 7 | 2 | 2 |
| Nutsedge | 0 | 0 | 0 | 0 | 0 | — | — | — | — | 0 | 0 | 0 | 0 | 0 | 0 | 0 | 0 | 0 | 0 | 0 | 0 | 0 |
| Rape | 0 | 0 | 0 | 0 | 5 | 0 | 0 | 0 | 0 | 0 | 0 | 0 | 0 | 0 | 0 | 0 | 0 | 0 | 0 | 0 | 0 | 0 |
| Redroot pigweed | 2 | 0 | 0 | 4 | 7 | 0 | 0 | 0 | 0 | 0 | 0 | 0 | 0 | 2 | 0 | 0 | 0 | 1 | 0 | 3 | 0 | 1 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Soybean | 0 | 0 | 0 | 4 | 5 | 3 | 0 | 3 | 0 | 3 | 0 | 0 | 1 | 2 | 2 | 1 | 2 | 3 | 3 | 3 | 2 | 3 |
| Sugarbeets | 0 | 0 | 0 | 2 | 3 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | |
|---|---|---|---|---|---|---|---|---|---|---|---|---|---|---|---|---|---|---|---|---|---|
| Rate 125 g/ha | 23 | 24 | 25 | 26 | 27 | 28 | 29 | 30 | 31 | 32 | 33 | 34 | 35 | 36 | 37 | 38 | 39 | 40 | 41 | 42 | 43 |
| Postemergence | | | | | | | | | | | | | | | | | | | | | |
| B. signalgrass | 0 | 3 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 0 | 0 | 0 | 0 | 0 | 8 | 0 | 0 | 0 | 0 | 0 | 0 | 0 | 0 | — | 0 | — | — | 0 | 0 | 0 |
| Bedstraw | 0 | 3 | 4 | 0 | 0 | — | 0 | 0 | 0 | 0 | 1 | 4 | 2 | — | 0 | 0 | — | — | — | 0 | 0 |
| Blackgrass | 0 | 1 | 5 | 0 | 0 | 2 | 0 | 0 | 4 | 0 | 5 | 2 | 0 | 3 | 0 | 3 | 0 | 0 | 0 | 0 | 0 |
| Cocklebur | 0 | 0 | 2 | 0 | 0 | 0 | 0 | 0 | 0 | 0 | 0 | 0 | 2 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 1 | 8 | 7 | 0 | 0 | 6 | 0 | 8 | 2 | 2 | 2 | 0 | 0 | 3 | 0 | 7 | 0 | 1 | 1 | 0 | 2 |
| Ducksalad | 0 | 0 | 0 | 0 | 0 | 0 | 0 | 0 | 0 | 0 | 0 | 0 | 0 | 0 | 0 | — | — | 0 | 0 | 0 | 0 |
| Giant foxtail | 2 | 2 | 5 | 0 | 0 | 2 | 0 | 2 | 0 | 0 | 1 | 0 | 0 | 3 | 0 | 2 | 0 | 0 | 0 | 0 | 0 |
| Morningglory | 8 | 9 | 1 | 1 | 0 | 2 | 0 | 1 | 1 | 7 | 8 | 2 | 7 | 9 | 0 | 0 | 0 | 6 | 2 | 0 | 3 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 |
| Redroot pigweed | 0 | 2 | 0 | 0 | 0 | 1 | 0 | 0 | 0 | 0 | 2 | 0 | 7 | 5 | 0 | 0 | 0 | 1 | 0 | 0 | 2 |
| Rice | 0 | 0 | 0 | 0 | 0 | 0 | 0 | 0 | 0 | 0 | 0 | 0 | 0 | 0 | — | 0 | — | — | 0 | 0 | 0 |
| S. Flatsedge | 0 | 0 | 0 | 0 | 0 | 0 | 0 | 0 | 0 | 0 | 0 | 0 | 0 | 0 | — | 0 | — | — | 0 | 0 | 0 |
| Soybean | 3 | 3 | 3 | 1 | 1 | 3 | 2 | 1 | 1 | 2 | 3 | 0 | 1 | 5 | 0 | 0 | 4 | 3 | 3 | 0 | 3 |
| Sugarbeets | 0 | 0 | 0 | 0 | 0 | 1 | 0 | 0 | 0 | 0 | 2 | 0 | 3 | 0 | 0 | 0 | 0 | 0 | 0 | 0 | 1 |

TABLE B-continued

| | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Velvetleaf | 0 | 0 | 0 | 3 | 4 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Rate 125 g/ha | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 |
| Postemergence | | | | | | | | | | | | | | | | | | | | | | | | | | | | | | | | | | | | | | | | | | | | |
| B. signalgrass | 0 | 0 | 0 | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 3 | 0 | 0 | 0 | 0 | 0 | 1 | 0 | 0 | — | 0 | 0 | 0 |
| Barnyardgrass | 0 | 0 | 0 | — | 0 | — | 0 | 0 | 0 | 0 | 0 | 0 | 0 | 0 | 0 | 0 | 0 | 0 | 0 | 0 | 0 | 0 | 0 | 0 | 0 | — | — | — | — | 0 | 0 | 0 | 0 | 0 | 0 | 0 | 3 | 0 | 0 | 0 | 0 | 0 | 0 | 0 |
| Bedstraw | 0 | 5 | 0 | 3 | 0 | 0 | — | 0 | 5 | 3 | 0 | 0 | 0 | 0 | 0 | 0 | 7 | 3 | 0 | 0 | 0 | 0 | 0 | 5 | 7 | 4 | 0 | 0 | 0 | 0 | 0 | 0 | 0 | 0 | 0 | 3 | 0 | 0 | 0 | 0 | — | 0 | 4 | 4 |
| Blackgrass | 0 | 0 | 0 | 0 | 0 | 0 | — | 0 | 0 | 0 | 0 | 0 | 0 | 0 | 0 | 0 | 0 | 3 | 0 | 0 | 0 | 0 | 0 | 0 | 0 | 0 | 0 | 0 | 0 | 0 | 0 | 5 | 2 | 0 | 3 | 0 | 2 | 3 | 0 | 0 | — | 0 | 0 | 0 |
| Cocklebur | 0 | 1 | 1 | 0 | 0 | 0 | — | 0 | 0 | 0 | 0 | 0 | 0 | 0 | 0 | 0 | 0 | 0 | 4 | 0 | 0 | 0 | 0 | 0 | 0 | 0 | 0 | 0 | 0 | 0 | 0 | 0 | 0 | 0 | 2 | 0 | 0 | 0 | 0 | 0 | — | 0 | 1 | 1 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 |
| Crabgrass | 0 | 0 | 0 | 0 | 1 | 1 | — | 0 | 1 | 4 | 0 | 0 | 0 | 0 | 0 | 0 | 0 | 0 | 0 | 0 | 0 | 0 | 0 | 0 | 0 | 0 | 0 | 0 | 0 | 0 | 2 | 2 | 4 | 0 | 2 | 4 | 9 | 5 | 0 | 0 | — | 0 | 3 | 3 |
| Ducksalad | 0 | 0 | — | 0 | — | 0 | 0 | 0 | 0 | 0 | 0 | 0 | 0 | 0 | 0 | 0 | 0 | 0 | 0 | 0 | 0 | 0 | 0 | 0 | 0 | — | — | — | — | 0 | 0 | 0 | 0 | 0 | 0 | 0 | 0 | 0 | 0 | 0 | 0 | 0 | 0 | 0 |
| Giant foxtail | 0 | 0 | 1 | 0 | 0 | 4 | — | 0 | 3 | 3 | 3 | 0 | 0 | 0 | 0 | 0 | 0 | 0 | 0 | 0 | 0 | 0 | 0 | 0 | 0 | 0 | 0 | 0 | 0 | 0 | 0 | 6 | 4 | 0 | 3 | 2 | 2 | 2 | 0 | 0 | — | 0 | 2 | 2 |
| Morningglory | 0 | 0 | 0 | 2 | 0 | 0 | — | 0 | 1 | 1 | 0 | 1 | 1 | 1 | 0 | 1 | 2 | 2 | 2 | 2 | 0 | 1 | 1 | 2 | 2 | 0 | 0 | 0 | 0 | 3 | 2 | 1 | 2 | 0 | 8 | 5 | 8 | 2 | 7 | 0 | — | 0 | 7 | 7 |
| Nutsedge | 0 | 0 | 0 | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 |
| Rape | 0 | 0 | 0 | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | — | 0 | 0 | 0 |
| Redroot pigweed | 0 | 0 | 0 | 0 | 0 | 0 | — | 0 | 0 | 3 | 0 | 0 | 0 | 0 | 0 | 0 | 4 | 2 | 0 | 0 | 0 | 0 | 0 | 0 | 0 | 0 | 0 | 0 | 0 | 0 | 0 | 0 | 0 | 0 | 3 | 0 | 3 | 0 | 0 | 0 | — | 0 | 0 | 0 |
| Rice | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | — | — | — | — | 0 | 0 | 2 | 0 | 0 | 0 | 0 | 0 | 0 | 0 | 0 | 0 | 0 | 0 | 0 |
| S. Flatsedge | 0 | 0 | 0 | — | 0 | — | 0 | 0 | 0 | 0 | 0 | 0 | 0 | 0 | 0 | 0 | 0 | 0 | 0 | 0 | 0 | 0 | 0 | 0 | 0 | — | — | — | — | 0 | 0 | 0 | 0 | 0 | 0 | 0 | 0 | 0 | 0 | 0 | 0 | 0 | 0 | 0 |
| Soybean | 0 | 1 | 1 | 2 | 1 | 1 | — | 0 | 2 | 3 | 0 | 1 | 2 | 1 | 1 | 1 | 3 | 3 | 1 | 2 | 0 | 1 | 1 | 1 | 2 | 2 | 0 | 0 | 0 | 0 | — | 1 | 1 | 0 | 1 | 1 | 1 | 0 | 0 | 0 | — | 0 | 2 | 2 |
| Sugarbeets | 0 | 0 | 0 | 0 | 0 | 0 | — | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 4 | — | 3 | 0 | 0 | 0 | — | 0 | 3 | 3 |
| Velvetleaf | 0 | 0 | 0 | 0 | 0 | 0 | — | 0 | 0 | 0 | 0 | 0 | 0 | 0 | 0 | 0 | 0 | 0 | 0 | 3 | 0 | 3 | 0 | 0 | 0 | 0 | 0 | 0 | 0 | 3 | 4 | 0 | 0 | 0 | 2 | 0 | 0 | 0 | 0 | 2 | — | 0 | 0 | 0 |
| Wheat | 0 | 0 | 0 | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 |
| Wild oats | 0 | 0 | 0 | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 |

| | COMPOUND | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|
| Rate 125 g/ha | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 | 114 | 115 | 116 | 117 | 118 | 119 | 120 |
| Postemergence | | | | | | | | | | | | | | | | | | | | | | | | | | | | | | | | | |
| B. signalgrass | 2 | 0 | 0 | 4 | 5 | 5 | 0 | 0 | 0 | 0 | 0 | 0 | 0 | 0 | 0 | 0 | 0 | 2 | 0 | 7 | 3 | 7 | 0 | 0 | 0 | 7 | 0 | 0 | 9 | 8 | 0 | 0 | 4 |
| Barnyardgrass | — | 0 | 0 | — | — | 0 | 0 | 0 | 0 | 0 | 9 | 0 | — | 0 | 0 | — | — | 0 | 0 | — | 0 | 0 | 0 | 0 | 0 | 0 | 0 | 0 | 0 | 0 | — | — | 0 |
| Bedstraw | 8 | 0 | — | — | — | — | — | 0 | 0 | 0 | — | 5 | 0 | — | 0 | — | — | 0 | 0 | 3 | 0 | 8 | — | 5 | 0 | 4 | 6 | 0 | 6 | 0 | 0 | 2 | — |
| Blackgrass | 5 | 0 | 0 | 8 | 7 | 8 | 0 | 0 | 0 | 0 | 0 | 3 | 0 | 0 | 0 | 1 | 0 | 6 | 0 | 7 | 7 | 8 | 4 | 3 | 4 | 8 | 2 | 4 | 9 | 9 | 4 | 3 | 4 |
| Cocklebur | 0 | 1 | 3 | 3 | 1 | 1 | 1 | 0 | 0 | 0 | 0 | 2 | 0 | 0 | 0 | 0 | 0 | 0 | 2 | 0 | 0 | 3 | 2 | 0 | 1 | 1 | 0 | 0 | 0 | 0 | 0 | 0 | 1 |
| Corn | 0 | 0 | 0 | 2 | 0 | 4 | 0 | 0 | 0 | 0 | 0 | 0 | 0 | 0 | 0 | 0 | 0 | 0 | 0 | 2 | 0 | 0 | 0 | 0 | 0 | 1 | 0 | 0 | 0 | 5 | 0 | 0 | 0 |
| Crabgrass | 0 | 0 | 2 | 9 | 8 | 8 | 3 | 0 | 3 | 2 | 0 | 2 | 0 | 0 | 0 | 4 | 4 | 7 | 0 | 8 | 8 | 9 | 3 | 2 | 4 | 9 | 8 | 0 | 9 | 9 | 7 | 3 | 7 |
| Ducksalad | — | 0 | 0 | — | — | 0 | 0 | 0 | 0 | 0 | 2 | 0 | — | 0 | 0 | — | — | 0 | 0 | — | 0 | 0 | 0 | 0 | 0 | 0 | 0 | 0 | 0 | 0 | — | — | 0 |
| Giant foxtail | 3 | 0 | 0 | 8 | 8 | 7 | 0 | 0 | 0 | 0 | 0 | 0 | 0 | 0 | 0 | 1 | 3 | 3 | 2 | 8 | 7 | 9 | 2 | 2 | 7 | 9 | 9 | 4 | 9 | 9 | 8 | 8 | 6 |
| Morningglory | 10 | 0 | 3 | 7 | 8 | 10 | 10 | 1 | 1 | 1 | 0 | 3 | 0 | 0 | 0 | 10 | 10 | 2 | 7 | 3 | 3 | 3 | 5 | 5 | 10 | 5 | 4 | 3 | 4 | 7 | 4 | 7 | 7 |
| Nutsedge | 0 | 0 | 0 | 0 | 0 | 0 | 0 | 0 | 0 | 0 | 0 | 0 | 0 | 0 | 0 | 0 | 0 | 0 | 0 | 3 | 3 | 0 | 0 | 0 | 0 | 0 | 0 | 0 | 7 | 7 | 0 | 0 | 0 |
| Rape | 0 | 0 | 0 | 3 | 3 | 3 | 2 | 0 | 0 | 0 | 0 | 2 | 0 | 0 | 0 | 0 | 0 | 0 | 0 | 2 | 0 | 3 | 4 | 3 | 2 | 3 | 3 | 0 | 0 | 0 | 0 | 0 | 0 |
| Redroot pigweed | 3 | 0 | 5 | 4 | 3 | 4 | 0 | 3 | 0 | 0 | 0 | 4 | 0 | 0 | 0 | 0 | 3 | 0 | 0 | 0 | 0 | 5 | 4 | 3 | 3 | 4 | 2 | 0 | 0 | 0 | 0 | 0 | 0 |
| Rice | — | 0 | 0 | — | — | 0 | 0 | 0 | 0 | 0 | 4 | 0 | — | 0 | 0 | — | — | 0 | 0 | — | 0 | 0 | 0 | 0 | 0 | 0 | 0 | 0 | 0 | 0 | — | — | 0 |
| S. Flatsedge | — | 0 | 0 | — | — | 0 | 0 | 0 | 0 | 0 | 8 | 0 | — | 0 | 0 | — | — | 0 | 0 | — | 0 | 0 | 0 | 0 | 0 | 0 | 0 | 0 | 0 | 0 | — | — | 0 |

TABLE B-continued

| | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| Soybean | 1 | 0 | 4 | 3 | 3 | 5 | 5 | 1 | 1 | 0 | 1 | 2 | 0 | 2 | 0 | 4 | 5 | 1 | 0 | 4 | 3 | 6 | 3 | 3 | 4 | 6 | 3 | 1 | 6 | 5 | 1 | 2 | 3 |
| Sugarbeets | 5 | 0 | 0 | 6 | 4 | 3 | 2 | 2 | 0 | 0 | 0 | 4 | 0 | 0 | 0 | 2 | 1 | 0 | 0 | 2 | 0 | 4 | 3 | 3 | 2 | 4 | 3 | 3 | 3 | 0 | 0 | 0 | 0 |
| Velvetleaf | 0 | 0 | 0 | 0 | 0 | 0 | 0 | 0 | 0 | 0 | 0 | 3 | 0 | 0 | 0 | 0 | 0 | 0 | 0 | 5 | 4 | 2 | 0 | 0 | 0 | 1 | 1 | 0 | 4 | 3 | 0 | 2 | 0 |
| Wheat | 0 | 0 | 0 | 1 | 2 | 3 | 0 | 0 | 0 | 0 | 0 | 0 | 0 | 0 | 0 | 0 | 0 | 0 | 0 | 5 | 0 | 0 | 0 | 0 | 0 | 3 | 0 | 0 | 6 | 6 | 0 | 0 | 0 |
| Wild oats | 0 | 0 | 0 | 2 | 1 | 0 | 0 | 0 | 0 | 0 | 0 | 0 | 0 | 0 | 0 | 0 | 0 | 0 | 0 | 3 | 0 | 0 | 0 | 0 | 0 | 2 | 0 | 0 | 7 | 3 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 121 | 122 | 123 | 124 | 125 | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 | 149 |
| Postemergence | | | | | | | | | | | | | | | | | | | | | | | | | | | | | |
| B. signalgrass | 0 | 0 | 0 | 0 | 0 | 0 | 0 | 0 | 0 | 2 | 5 | 3 | 0 | 0 | 0 | 0 | 4 | 7 | 2 | 0 | 0 | 0 | 0 | 0 | 0 | 8 | 7 | 3 | 0 |
| Barnyardgrass | 0 | 0 | 0 | 0 | 0 | 0 | 0 | 0 | — | — | — | — | — | — | 0 | 0 | 0 | 0 | 0 | 0 | 0 | 0 | 8 | 0 | 6 | 0 | 0 | 0 | 0 |
| Bedstraw | — | — | — | — | — | 0 | 0 | 0 | 0 | — | 8 | 0 | 4 | 4 | 0 | 5 | 8 | 7 | 2 | 5 | 2 | 2 | 6 | 2 | 2 | 6 | 4 | 5 | 0 |
| Blackgrass | 0 | 0 | 6 | 0 | 0 | 0 | 0 | 0 | 0 | 5 | 8 | 2 | 2 | 0 | 0 | 0 | 6 | 9 | 2 | 3 | 0 | 0 | 3 | 4 | 1 | 8 | 7 | 7 | 0 |
| Cocklebur | 2 | 2 | 0 | 0 | 0 | 0 | 0 | 0 | 0 | 0 | 3 | 0 | 2 | 0 | 0 | 2 | 0 | 0 | 0 | 0 | 0 | 0 | 3 | 0 | 0 | 2 | 0 | 0 | 0 |
| Corn | 0 | 0 | 0 | 0 | 0 | 0 | 0 | 0 | 0 | 0 | 5 | 0 | 0 | 0 | 0 | 0 | 0 | 4 | 2 | 0 | 0 | 0 | 0 | 0 | 0 | 0 | 5 | 0 | 0 |
| Crabgrass | 6 | 3 | 4 | 0 | 0 | 0 | 0 | 0 | 4 | 9 | 7 | 7 | 2 | 0 | 0 | 2 | 8 | 9 | 8 | 1 | 0 | 3 | 8 | 5 | 3 | 9 | 9 | 8 | 0 |
| Ducksalad | 0 | 0 | 0 | 0 | 0 | 0 | 0 | 0 | — | — | — | — | — | — | 0 | 0 | 0 | 0 | 0 | 0 | 0 | 0 | 0 | 0 | 0 | 3 | 0 | 0 | 0 |
| Giant foxtail | 1 | 2 | 5 | 0 | 0 | 0 | 0 | 0 | 6 | 9 | 8 | 9 | 2 | 0 | 0 | 4 | 8 | 9 | 8 | 1 | 0 | 2 | 2 | 2 | 0 | 9 | 8 | 8 | 0 |
| Morningglory | 6 | 3 | 9 | 0 | 0 | 0 | 0 | 0 | 4 | 2 | 7 | 6 | 3 | 6 | 1 | 10 | 7 | 5 | 5 | 8 | 2 | 3 | 6 | 2 | 8 | 5 | 3 | 3 | 0 |
| Nutsedge | 0 | 0 | 0 | 0 | 0 | 0 | 0 | 0 | 0 | 0 | 0 | 2 | 0 | 0 | 0 | 0 | 0 | 5 | 0 | 0 | 0 | 0 | 0 | 0 | 0 | 0 | 0 | 0 | 0 |
| Rape | 0 | 0 | 0 | 0 | 0 | 0 | 0 | 0 | 0 | 2 | 4 | 0 | 0 | 0 | 0 | 0 | — | 0 | 2 | 0 | 0 | 0 | 0 | 0 | 2 | 2 | 1 | 2 | 0 |
| Redroot pigweed | 2 | 1 | — | 0 | 0 | 0 | 0 | 0 | 0 | 3 | 6 | 0 | 0 | 0 | 0 | 4 | 4 | 5 | 3 | 1 | 0 | 0 | 5 | 0 | 0 | 6 | 3 | 2 | 0 |
| Rice | 0 | 0 | 0 | 0 | 0 | 0 | 0 | 0 | — | — | — | — | — | — | 0 | 0 | 0 | 7 | 0 | 0 | 0 | 0 | 0 | 0 | 0 | 0 | 0 | 0 | 0 |
| S. Flatsedge | 5 | 0 | 0 | 0 | 0 | 0 | 0 | 0 | — | — | — | — | — | — | 0 | 0 | 0 | 0 | 0 | 0 | 0 | 0 | 0 | 0 | 0 | 0 | 0 | 0 | 0 |
| Soybean | 5 | 3 | 4 | 3 | 4 | 0 | 0 | 0 | 2 | 2 | 7 | 3 | 3 | 1 | 2 | 4 | 6 | 3 | 2 | 3 | 3 | 3 | 3 | 3 | 3 | 6 | 5 | 4 | 0 |
| Sugarbeets | 0 | 0 | 0 | 0 | 0 | 0 | 0 | 0 | 0 | 0 | 3 | 0 | 0 | 0 | 0 | 4 | 3 | 0 | 0 | 0 | 0 | 0 | 6 | 0 | 0 | 3 | 0 | 3 | 0 |
| Velvetleaf | 0 | 0 | 0 | 0 | 0 | 0 | 0 | 0 | 0 | 3 | 7 | 2 | 0 | 0 | 0 | 0 | 0 | 4 | 4 | 0 | 0 | 1 | 2 | 0 | 0 | 2 | 0 | 0 | 0 |
| Wheat | 0 | 0 | 1 | 0 | 0 | 0 | 0 | 0 | 0 | 1 | 3 | 2 | 0 | 0 | 0 | 0 | 0 | 8 | 2 | 0 | 0 | 0 | 0 | 0 | 0 | 2 | 4 | 1 | 0 |
| Wild oats | 0 | 0 | 0 | 0 | 0 | 0 | 0 | 0 | 0 | 2 | 3 | 2 | 0 | 0 | 0 | 0 | 2 | 2 | 2 | 0 | 0 | 0 | 0 | 0 | 0 | 3 | 3 | 1 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 150 | 151 | 152 | 153 | 154 | 155 | 156 | 157 | 158 | 159 | 160 | 161 | 162 | 163 | 164 | 165 | 166 | 167 | 168 | 169 | 170 | 171 | 172 | 173 | 174 | 175 | 176 | 177 | 178 |
| Postemergence | | | | | | | | | | | | | | | | | | | | | | | | | | | | | |
| B. signalgrass | 0 | 4 | 0 | 0 | 0 | 0 | 0 | 0 | 0 | 0 | 0 | 0 | 0 | 2 | 0 | 1 | 0 | 0 | 0 | 0 | 6 | 0 | 0 | 0 | 0 | 0 | 0 | 0 | 0 |
| Barnyardgrass | 0 | 0 | 0 | 0 | 0 | 0 | 0 | — | 0 | 0 | 0 | — | — | — | 0 | — | — | — | — | 0 | 0 | 0 | — | — | — | — | 0 | 0 | — |
| Bedstraw | 0 | 3 | 0 | 0 | 0 | 0 | 0 | 0 | 0 | 0 | 0 | 3 | 2 | 4 | 0 | 0 | 0 | 0 | 3 | 2 | 0 | 7 | 0 | 0 | 4 | 0 | 0 | 0 | 0 |
| Blackgrass | 0 | 8 | 0 | 0 | 0 | 0 | 0 | 0 | 1 | 0 | 0 | 0 | 0 | 4 | 0 | 3 | 4 | 0 | 0 | 4 | 9 | 0 | 0 | 0 | 0 | 0 | 0 | 0 | 0 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 0 | 2 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 9 | 0 | 0 | 0 | 2 | 0 | 0 | 0 | 0 | 0 | 2 | 2 | 7 | 0 | 4 | 1 | 3 | 1 | 8 | 9 | 0 | 3 | 4 | 4 | 0 | 0 | 0 | 0 |
| Ducksalad | 0 | 0 | 0 | 0 | 0 | 0 | 0 | — | 0 | 0 | 0 | — | — | — | 0 | — | — | — | — | 0 | 0 | 0 | — | — | — | — | 0 | 0 | — |
| Giant foxtail | 1 | 8 | 0 | 0 | 0 | 3 | 0 | 1 | 0 | 0 | 0 | 0 | 2 | 7 | 0 | 1 | 0 | 0 | 0 | 2 | 7 | 0 | 0 | 0 | 0 | 0 | 0 | 0 | 0 |
| Morningglory | 0 | — | 0 | 0 | 0 | 0 | 1 | 1 | 2 | 2 | 0 | 5 | 6 | 2 | 0 | 3 | 1 | 5 | 8 | 1 | 1 | 1 | 5 | 10 | 5 | 1 | 2 | 0 | 2 |
| Nutsedge | 0 | 3 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Redroot pigweed | 0 | 3 | 0 | 0 | 0 | 0 | 0 | 0 | 2 | 0 | 0 | 0 | 0 | 2 | 0 | 2 | 0 | 0 | 0 | 0 | 0 | 0 | 0 | 0 | 4 | 0 | 0 | 0 | 7 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rice | 0 | 0 | 0 | 0 | 0 | 0 | 0 | — | 0 | 0 | 0 | — | — | — | 0 | — | — | — | — | 0 | 0 | 0 | — | — | — | — | 0 | 0 | — |
| S. Flatsedge | 0 | 0 | 0 | 0 | 0 | 0 | 0 | — | 0 | 0 | 0 | — | — | — | 0 | — | — | — | — | 0 | 0 | 0 | — | — | — | — | 0 | 0 | — |
| Soybean | 1 | 4 | 0 | 0 | 2 | 1 | 1 | 1 | 3 | 3 | 0 | 2 | 4 | 2 | 1 | 4 | 0 | 3 | 1 | 1 | 3 | 1 | 3 | 2 | 2 | 1 | 2 | 1 | 1 |
| Sugarbeets | 0 | 3 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 |
| Velvetleaf | 0 | — | 0 | 0 | 0 | 0 | 0 | 0 | 0 | 0 | 0 | 0 | 3 | 4 | 0 | 0 | 0 | 0 | 0 | 0 | 2 | 0 | 0 | 0 | 0 | 0 | 0 | 0 | 0 |
| Wheat | 0 | 2 | 0 | 0 | 0 | 0 | 0 | 0 | 0 | 0 | 0 | 0 | 0 | 0 | 0 | 1 | 0 | 0 | 0 | 0 | 6 | 0 | 0 | 0 | 0 | 0 | 0 | 0 | 0 |
| Wild oats | 0 | 2 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 179 | 180 | 181 | 182 | 183 | 184 | 185 | 186 | 187 | 188 | 189 | 190 | 191 | 192 | 193 | 194 | 195 | 196 | 197 | 198 | 199 | 200 | 201 | 202 | 203 | 204 | 205 | 206 | 207 |
| Postemergence | | | | | | | | | | | | | | | | | | | | | | | | | | | | | |
| B. signalgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | — | — | — | — | — | — | — | — | — | — | — | — | — | — | — | — | — | — | — | — | 0 | — | — | — | — | — | — | — | — |
| Bedstraw | 5 | 0 | 0 | 0 | 0 | 7 | 0 | 0 | 0 | 0 | 0 | 0 | 0 | 0 | 0 | 0 | 2 | 0 | 0 | 0 | 0 | 0 | 0 | 2 | 0 | 0 | 0 | 0 | 0 |
| Blackgrass | 2 | 0 | 0 | 0 | 0 | 1 | 0 | 0 | 0 | 0 | 0 | 0 | 0 | 0 | 0 | 0 | 3 | 0 | 0 | 0 | 4 | 0 | 0 | 3 | 0 | 2 | 0 | 0 | 2 |
| Cocklebur | 0 | 0 | 0 | 0 | 0 | 0 | 0 | 0 | 0 | 0 | 0 | 0 | 2 | 1 | 0 | 1 | 2 | 0 | 0 | 0 | 0 | 0 | 0 | 0 | 0 | 0 | 1 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 0 | 0 | 0 | 1 | 0 | 0 | 0 | 0 | 0 | 2 | 1 | 0 | 0 | 0 | 0 | 0 | 0 | 2 | 1 | 0 | 0 | 0 | 0 | 0 | 0 | 0 |
| Ducksalad | — | — | — | — | — | — | — | — | — | — | — | — | — | — | — | — | — | — | — | — | 0 | — | — | — | — | — | — | — | — |
| Giant foxtail | 0 | 0 | 0 | 0 | 0 | 0 | 0 | 0 | 0 | 0 | 0 | 0 | 0 | 0 | 0 | 1 | 0 | 0 | 0 | 0 | 2 | 0 | 0 | 0 | 0 | 0 | 0 | 0 | 0 |
| Morningglory | 5 | 0 | 0 | 0 | 0 | 6 | 1 | 2 | 0 | 0 | 0 | 0 | 2 | 3 | 0 | 0 | 0 | 0 | 5 | 0 | 4 | 0 | 1 | 5 | 0 | 3 | 0 | 1 | 2 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 1 | 0 | 0 | 0 | 0 | 0 |
| Redroot pigweed | 0 | 0 | 0 | 0 | 0 | 4 | 1 | 0 | 0 | 0 | 0 | 0 | 0 | 1 | 0 | 0 | 0 | 0 | 0 | 0 | 0 | 0 | 0 | 4 | 0 | 0 | 0 | 0 | 0 |
| Rice | — | — | — | — | — | — | — | — | — | — | — | — | — | — | — | — | — | — | — | — | 0 | — | — | — | — | — | — | — | — |
| S. Flatsedge | — | — | — | — | — | — | — | — | — | — | — | — | — | — | — | — | — | — | — | — | 0 | — | — | — | — | — | — | — | — |
| Soybean | 1 | 0 | 0 | 0 | 1 | 1 | 2 | 1 | 0 | 2 | 0 | 0 | 3 | 3 | 1 | 0 | 3 | 0 | 0 | 0 | 2 | 2 | 1 | 2 | 0 | 1 | 1 | 1 | 2 |
| Sugarbeets | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 3 | 0 | 0 | 0 | 0 | 0 |
| Velvetleaf | 0 | 0 | 0 | 0 | 0 | 1 | 0 | 0 | 0 | 0 | 0 | 0 | 0 | 2 | 0 | 0 | 0 | 0 | 0 | 0 | 0 | 0 | 0 | 0 | 0 | 1 | 0 | 0 | 1 |
| Wheat | 0 | 0 | 0 | 0 | 0 | 2 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 |
| Wild oats | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 208 | 210 | 211 | 212 | 213 | 214 | 215 | 216 | 217 | 218 | 219 | 220 | 221 | 222 | 223 | 224 | 225 | 226 | 227 | 228 | 229 | 230 | 231 | 232 | 233 | 234 | 235 | 236 | 237 |
| Postemergence | | | | | | | | | | | | | | | | | | | | | | | | | | | | | |
| B. signalgrass | 0 | 0 | 0 | 4 | 0 | 0 | 0 | 2 | 7 | 0 | 2 | 7 | 3 | 0 | 0 | 0 | 5 | 2 | 0 | 0 | 0 | 0 | 0 | 0 | 0 | 0 | 0 | 0 | 0 |
| Barnyardgrass | — | — | — | — | — | — | — | — | — | — | — | — | — | — | — | — | — | — | — | — | — | — | — | — | — | — | — | — | — |
| Bedstraw | 0 | 2 | 7 | 0 | 3 | 0 | 0 | 0 | 0 | 8 | 6 | 8 | 7 | 3 | 3 | 3 | 0 | 3 | 8 | 0 | 0 | 0 | 0 | 0 | 0 | 0 | 0 | 0 | 0 |
| Blackgrass | 0 | 0 | 3 | 6 | 0 | 4 | 0 | 4 | 6 | 5 | 7 | 7 | 9 | 0 | 0 | 0 | 9 | 5 | 2 | 0 | 0 | 0 | 0 | 2 | 0 | 0 | 0 | 0 | 0 |
| Cocklebur | 0 | 0 | 0 | 2 | 0 | 0 | 0 | 0 | 0 | 0 | 1 | 0 | 0 | 0 | 0 | 0 | 0 | 0 | 0 | 0 | 0 | 0 | 0 | 2 | 2 | 0 | 0 | 0 | 0 |
| Corn | 0 | 0 | 0 | 0 | 0 | 0 | 0 | 0 | 0 | 0 | 0 | 2 | 0 | 0 | 0 | 0 | 2 | 0 | 0 | 0 | 0 | 0 | 0 | 0 | 0 | 0 | 0 | 0 | 0 |
| Crabgrass | 0 | 0 | 0 | 6 | 0 | 3 | 0 | 2 | 2 | 4 | 4 | 5 | 6 | 0 | 0 | 0 | 8 | 0 | 0 | 0 | 0 | 0 | 0 | 1 | 0 | 0 | 0 | 0 | 0 |
| Ducksalad | — | — | — | — | — | — | — | — | — | — | — | — | — | — | — | — | — | — | — | — | — | — | — | — | — | — | — | — | — |
| Giant foxtail | 0 | 0 | 0 | 6 | 0 | 0 | 0 | 2 | 2 | 5 | 7 | 6 | 7 | 0 | 0 | 0 | 8 | 7 | 0 | 0 | 0 | 0 | 0 | 0 | 0 | 0 | 0 | 0 | 0 |
| Morningglory | 1 | 2 | 6 | 3 | 6 | 3 | 2 | 4 | 0 | 4 | 6 | 5 | 0 | 1 | 3 | 2 | 3 | 7 | 4 | 3 | 0 | 2 | 2 | 8 | 3 | 0 | 2 | 4 | 2 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rape | 0 | 0 | 2 | 0 | 2 | 0 | 0 | 0 | 0 | 1 | 3 | 0 | 4 | 0 | 0 | 0 | 0 | 0 | 0 | 0 | 0 | 0 | 0 | 2 | 2 | 0 | 0 | 0 | 0 |
| Redroot pigweed | 0 | 0 | 4 | 5 | 7 | 0 | 0 | 0 | 0 | 1 | 7 | 1 | 8 | 0 | 2 | 2 | 0 | 0 | 2 | 0 | 0 | 0 | 0 | 3 | 0 | 0 | 0 | 0 | 0 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 1 | 1 | 4 | 2 | 1 | 1 | 1 | 1 | 1 | 4 | 5 | 5 | 2 | 3 | 3 | 3 | 3 | 2 | 3 | 0 | 0 | 0 | 1 | 3 | 3 | 0 | 0 | 1 | 1 |
| Sugarbeets | 0 | 0 | 2 | 0 | 3 | 0 | 0 | 0 | 0 | 2 | 4 | 0 | 4 | 0 | 1 | 2 | 0 | 0 | 0 | 0 | 0 | 0 | 0 | 2 | 0 | 0 | 0 | 0 | 0 |
| Velvetleaf | 1 | 0 | 0 | 4 | 0 | 0 | 0 | 0 | 0 | 0 | 0 | 0 | 0 | 0 | 0 | 0 | 0 | 0 | 0 | 0 | 0 | 0 | 0 | 2 | 2 | 0 | 0 | 0 | 0 |
| Wheat | 0 | 0 | 0 | 0 | 0 | 0 | 3 | 0 | 2 | 0 | 6 | 4 | 2 | 0 | 0 | 0 | 6 | 4 | 0 | 0 | 0 | 0 | 0 | 0 | 0 | 0 | 0 | 0 | 0 |
| Wild oats | 0 | 0 | 0 | 0 | 0 | 0 | 0 | 0 | 0 | 0 | 3 | 0 | 0 | 0 | 0 | 0 | 2 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 238 | 239 | 240 | 241 | 242 | 243 | 244 | 245 | 246 | 247 | 248 | 249 | 250 | 251 | 252 | 253 | 254 | 255 | 256 | 257 | 258 | 259 | 260 | 261 | 262 | 263 | 264 | 265 | 266 |
| Postemergence | | | | | | | | | | | | | | | | | | | | | | | | | | | | | |
| B. signalgrass | 0 | 0 | 0 | 2 | 8 | 4 | 0 | 4 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | — | — | — | — | — | — | — | — | — | — | — | — | — | — | — | — | — | — | — | — | — | — | — | — | — | — | — | — | — |
| Bedstraw | 2 | 3 | 3 | 3 | 5 | 4 | 0 | 9 | 7 | 0 | 0 | 0 | 0 | 6 | 0 | 0 | 4 | 0 | 0 | 0 | 4 | 0 | 7 | — | 0 | 0 | 6 | 2 | 0 |
| Blackgrass | 0 | 0 | 0 | 7 | 9 | 8 | 0 | 7 | 2 | 0 | 0 | 0 | 0 | 4 | 2 | 0 | 0 | 2 | 0 | 0 | 5 | 0 | 0 | 0 | 0 | 0 | 2 | 4 | 5 |
| Cocklebur | 0 | 1 | 1 | 0 | 5 | 2 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 |
| Corn | 0 | 0 | 0 | 0 | — | 2 | 0 | 4 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 7 | 9 | 8 | 0 | 7 | 0 | 0 | 0 | 0 | 0 | 0 | 0 | 0 | 0 | 0 | 0 | 0 | 2 | 0 | 0 | 0 | 0 | 0 | 0 | 1 | 0 |
| Ducksalad | — | — | — | — | — | — | — | — | — | — | — | — | — | — | — | — | — | — | — | — | — | — | — | — | — | — | — | — | — |
| Giant foxtail | 0 | 0 | 0 | 3 | 8 | 7 | 0 | 8 | 0 | 0 | 0 | 0 | 0 | 2 | 4 | 0 | 0 | 3 | 0 | 0 | — | 0 | 0 | 0 | 0 | 0 | 0 | 0 | 0 |
| Morningglory | 2 | 2 | 5 | 4 | 7 | 7 | 0 | 9 | 8 | 1 | 0 | 0 | 6 | 7 | 2 | 0 | 9 | 7 | 8 | 8 | 6 | 7 | 2 | 4 | 4 | 2 | 10 | 6 | 4 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 2 | 0 | 0 | 0 | 0 | 2 | 0 | 2 | 0 | 0 | 0 | 0 | 0 | 0 | 0 | 0 | 3 |
| Redroot pigweed | 0 | 0 | 2 | 0 | 4 | 2 | 0 | 6 | 2 | 0 | 0 | 0 | 0 | 0 | 0 | 0 | 2 | 0 | 1 | 3 | 2 | 3 | 2 | 0 | 3 | 0 | 0 | 2 | 3 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 1 | 1 | 1 | 2 | 5 | 4 | 0 | 3 | 1 | 0 | 0 | 3 | 2 | 2 | 1 | 0 | 1 | 6 | 3 | 3 | 4 | 3 | 1 | 3 | 3 | 0 | 3 | 3 | 7 |
| Sugarbeets | 0 | 0 | 0 | 0 | 2 | 0 | 0 | 2 | 0 | 0 | 0 | 0 | 0 | 0 | 0 | 0 | 0 | 0 | 2 | 0 | 0 | 0 | 0 | 0 | 0 | 0 | 0 | 0 | 0 |
| Velvetleaf | 1 | 1 | 1 | 0 | 4 | 2 | 0 | 4 | 0 | 0 | 0 | 0 | 0 | 0 | 0 | 0 | 0 | 0 | 0 | 0 | 0 | 1 | 0 | 0 | 1 | 0 | 0 | 0 | 0 |
| Wheat | 0 | 0 | 0 | 2 | 7 | 4 | 0 | 5 | 0 | 0 | 0 | 0 | 0 | 0 | 0 | 0 | 0 | 4 | 0 | 0 | 0 | 3 | 0 | 0 | 0 | 0 | 0 | 0 | 5 |
| Wild oats | 0 | 0 | 0 | 0 | 2 | 0 | 0 | 3 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 267 | 268 | 269 | 270 | 271 | 272 | 273 | 274 | 276 | 277 | 278 | 279 | 280 | 281 | 282 | 283 | 284 | 285 | 286 | 287 | 288 | 289 | 290 | 291 | 292 | 293 | 294 | 295 | 296 |
| Postemergence | | | | | | | | | | | | | | | | | | | | | | | | | | | | | |
| B. signalgrass | 0 | 0 | 0 | 0 | 0 | 0 | 0 | 0 | 0 | 0 | 0 | 0 | 0 | 0 | 0 | 0 | 0 | 0 | 0 | 2 | 0 | 3 | 0 | 0 | 0 | 0 | 0 | 0 | 0 |
| Barnyardgrass | — | — | — | — | — | — | — | — | — | — | — | — | — | — | — | — | — | — | — | — | — | — | — | — | — | — | — | — | — |
| Bedstraw | 0 | 0 | 4 | 0 | 6 | 0 | 0 | 0 | 0 | 6 | 0 | 0 | 0 | — | 5 | 1 | 5 | 5 | 2 | 8 | 0 | 3 | 0 | 3 | 0 | 2 | 6 | 4 | 0 |
| Blackgrass | 0 | 0 | 0 | 0 | 4 | 0 | 1 | 0 | 1 | 8 | 0 | 0 | 0 | 0 | 2 | 6 | 5 | 2 | 2 | 9 | 0 | 9 | 0 | 2 | 0 | 9 | 0 | 7 | 0 |
| Cocklebur | 0 | 0 | — | 0 | 0 | 0 | 0 | 0 | 0 | 0 | 0 | 0 | 0 | 0 | 0 | 2 | 2 | 0 | 0 | 1 | 0 | 1 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 0 | 1 | 0 | 0 | 0 | 0 | 2 | 0 | 0 | 0 | 0 | 0 | 0 | 1 | 3 | 0 | 5 | 0 | 5 | 0 | 0 | 0 | 8 | 0 | 3 | 0 |
| Ducksalad | — | — | — | — | — | — | — | — | — | — | — | — | — | — | — | — | — | — | — | — | — | — | — | — | — | — | — | — | — |
| Giant foxtail | 0 | 0 | 0 | 0 | 3 | 0 | 0 | 0 | 1 | 3 | 0 | 0 | 0 | 0 | 0 | 3 | 2 | 0 | 0 | 8 | 0 | 5 | 0 | 0 | 0 | 8 | 0 | 6 | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Morningglory | 1 | 2 | 3 | 0 | 2 | 1 | 0 | 0 | 6 | 8 | 3 | 1 | 0 | 2 | 6 | 9 | 7 | 5 | 3 | 2 | 8 | 6 | 6 | 4 | 1 | 5 | 6 | 5 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 | 6 | 0 | 0 | 0 | 0 | 0 | 3 | 0 | 0 | 0 |
| Rape | 0 | 0 | 0 | 0 | 3 | 0 | 0 | 0 | 0 | 2 | 0 | 0 | 0 | 0 | 3 | 3 | 3 | 0 | 2 | 0 | 2 | 2 | 0 | 1 | 0 | 0 | 0 | 0 | 0 |
| Redroot pigweed | 0 | 0 | 4 | 0 | 5 | 0 | 0 | 0 | 0 | 2 | 0 | 0 | 0 | 2 | 6 | 4 | 4 | 0 | 3 | 6 | 0 | 5 | 0 | 0 | 0 | 2 | 0 | 5 | 0 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 2 | 0 | 1 | 0 | 5 | 1 | 3 | 3 | 5 | 4 | 1 | 0 | 1 | — | 3 | 4 | 4 | 2 | 1 | 3 | 2 | 3 | 2 | 3 | 0 | 2 | 3 | 2 | 0 |
| Sugarbeets | 0 | 0 | 0 | 0 | 2 | 0 | 0 | 0 | 0 | 2 | 0 | 0 | 0 | 0 | 6 | 2 | 3 | 2 | 2 | 0 | 0 | 0 | 0 | 0 | 0 | 0 | 0 | 0 | 0 |
| Velvetleaf | 0 | 0 | 0 | 0 | 0 | 0 | 0 | 0 | 0 | 1 | 0 | 0 | 0 | 1 | 0 | 0 | 0 | 0 | 0 | 4 | 0 | 0 | 0 | 0 | 0 | 2 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 3 | 5 | 0 | 5 | 0 | 0 | 0 | 6 | 0 | 0 | 0 |
| Wild oats | 0 | 0 | 0 | 0 | 0 | 0 | 0 | 0 | 0 | 0 | 0 | 0 | 0 | 0 | 0 | 0 | 0 | 0 | 0 | 3 | 0 | 3 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 297 | 298 | 299 | 300 | 301 | 302 | 303 | 304 | 305 | 306 | 307 | 308 | 309 | 310 | 311 | 312 | 313 | 314 | 315 | 316 | 317 | 318 | 319 | 320 | 321 | 322 | 323 | 324 | 325 |
| Postemergence | | | | | | | | | | | | | | | | | | | | | | | | | | | | | |
| B. signalgrass | 0 | 0 | 3 | 0 | 0 | 0 | 0 | 0 | 0 | 0 | 0 | 0 | 0 | 3 | 0 | 0 | 0 | 0 | 0 | 0 | 1 | 0 | 0 | 0 | 0 | 0 | 0 | 0 | 0 |
| Barnyardgrass | — | — | — | — | — | — | — | — | — | — | — | — | — | — | — | — | — | — | — | — | — | — | — | — | — | — | — | — | — |
| Bedstraw | 0 | 0 | 7 | 0 | 0 | 0 | 0 | 0 | 0 | 0 | 0 | 0 | 0 | 4 | 0 | 0 | 7 | 4 | 4 | 2 | 6 | 0 | 0 | 0 | 4 | 0 | 0 | 0 | 8 |
| Blackgrass | 0 | 0 | 8 | 0 | 0 | 0 | 0 | 0 | 0 | 0 | 0 | 0 | 0 | 7 | 0 | 0 | 0 | 4 | 3 | 1 | 8 | 0 | 0 | 0 | 0 | 0 | 0 | 0 | 0 |
| Cocklebur | 0 | 0 | 2 | 0 | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 3 | 0 | 0 | 0 | 0 | 0 | 0 | 0 | 0 | 0 | 0 | 9 | 0 | 0 | 0 | 0 | 2 | 0 | 5 | 0 | 0 | 0 | 0 | 0 | 0 | 0 | 0 |
| Ducksalad | — | — | — | — | — | — | — | — | — | — | — | — | — | — | — | — | — | — | — | — | — | — | — | — | — | — | — | — | — |
| Giant foxtail | 0 | 0 | 7 | 0 | 0 | 1 | 0 | 0 | 0 | 0 | 0 | 0 | 0 | 7 | 0 | 0 | 0 | 0 | 3 | 0 | 5 | 0 | 0 | 0 | 0 | 0 | 0 | 0 | 0 |
| Morningglory | 0 | 3 | 5 | 0 | 0 | 1 | 0 | 3 | 0 | 2 | 2 | 0 | 1 | 5 | 4 | 0 | 3 | 2 | 0 | 4 | 3 | 0 | 2 | 1 | 7 | 4 | 0 | 0 | 6 |
| Nutsedge | 0 | 0 | 0 | 0 | 0 | 0 | 0 | 0 | 0 | 0 | 0 | 0 | 0 | 3 | 0 | 0 | 0 | 0 | 0 | 0 | 0 | 0 | 0 | 0 | 0 | 0 | 0 | 0 | 0 |
| Rape | 0 | 0 | 3 | 0 | 0 | 0 | 0 | 0 | 0 | 0 | 0 | 0 | 0 | 0 | 0 | 0 | 0 | 0 | 0 | 0 | 0 | 0 | 0 | 3 | 0 | 0 | 0 | 0 | 0 |
| Redroot pigweed | 0 | 0 | 3 | 0 | 0 | 1 | 0 | 3 | 3 | 0 | 0 | 0 | 0 | 0 | 0 | 0 | 0 | 0 | 0 | 2 | 0 | 0 | 0 | 6 | 3 | 3 | 0 | 0 | 0 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 3 | 3 | 6 | 2 | 0 | 2 | 2 | 4 | 4 | 2 | 2 | 1 | 2 | 4 | 2 | 2 | 2 | 3 | 3 | 3 | 4 | 0 | 1 | 3 | — | 3 | 1 | 1 | 2 |
| Sugarbeets | 0 | 0 | 3 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 |
| Velvetleaf | 0 | 0 | 0 | 0 | 0 | 0 | 0 | 0 | 0 | 0 | 0 | 0 | 0 | 3 | 0 | 0 | 0 | 0 | 0 | 0 | 0 | 0 | 0 | 0 | 0 | 0 | 0 | 0 | 0 |
| Wheat | 0 | 0 | 3 | 0 | 0 | 0 | 0 | 0 | 0 | 0 | 0 | 0 | 0 | 4 | 0 | 0 | 0 | 0 | 0 | 0 | 1 | 0 | 0 | 0 | 0 | 0 | 0 | 0 | 0 |
| Wild oats | 0 | 0 | 0 | 0 | 0 | 0 | 0 | 0 | 0 | 0 | 0 | 0 | 0 | 3 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 326 | 327 | 328 | 329 | 330 | 331 | 332 | 333 | 334 | 335 | 336 | 337 | 338 | 339 | 340 | 341 | 342 | 343 | 344 | 345 | 348 | 349 | 350 | 351 | 352 | 353 | 354 | 355 | 356 |
| Postemergence | | | | | | | | | | | | | | | | | | | | | | | | | | | | | |
| B. signalgrass | 0 | 0 | 0 | 0 | 0 | 0 | 0 | 0 | 0 | 0 | 0 | 0 | 0 | 0 | 0 | 0 | 0 | 4 | 0 | 0 | 1 | 0 | 0 | 0 | 2 | 0 | 0 | 0 | 0 |
| Barnyardgrass | — | — | — | — | — | — | — | — | — | — | — | — | — | — | — | — | 2 | 0 | 0 | 0 | 2 | 2 | 0 | 3 | 3 | — | 4 | 8 | 0 |
| Bedstraw | 5 | 7 | 1 | 0 | 0 | 0 | 0 | 0 | 0 | 0 | 0 | 1 | 2 | 2 | 7 | 0 | 5 | 0 | 0 | 0 | 2 | 3 | — | — | 0 | — | — | 0 | 0 |
| Blackgrass | 0 | 0 | 1 | 0 | 0 | 0 | 0 | 0 | 0 | 0 | 0 | 0 | 0 | 0 | 0 | 0 | 0 | 3 | 0 | 0 | 3 | 4 | 4 | 2 | 8 | 4 | 5 | 3 | 6 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 0 | 0 | 0 | 1 | 0 | 0 | 0 | 0 | 0 | 0 | 0 | 0 | 0 | 0 | 1 | 0 | 0 | 2 | 0 | 1 | 1 | 3 | 0 | 2 | 0 | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Ducksalad | — | — | — | — | — | — | — | — | — | — | — | — | — | — | — | — | 0 | 0 | 0 | 0 | 3 | 0 | 2 | 0 | 0 | — | 3 | 0 | 0 |
| Giant foxtail | 0 | 0 | 0 | 0 | 0 | 0 | 0 | 0 | 0 | 0 | 0 | 0 | 0 | 0 | 0 | 0 | 0 | 7 | 0 | 0 | 8 | 0 | 8 | 7 | 2 | 3 | 4 | 2 | 4 |
| Morningglory | 7 | 8 | 8 | 0 | 0 | 0 | 0 | 0 | 0 | 0 | 0 | 0 | 0 | 2 | 7 | 7 | 7 | 2 | 0 | 0 | 9 | 5 | 6 | 4 | 6 | 3 | 5 | 5 | 6 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 1 | 2 | 0 | 0 | 0 | 0 | 0 | 0 | 0 | 0 | 0 | 0 | 2 | 0 | 0 | 0 |
| Redroot pigweed | 4 | 5 | 3 | 0 | 0 | 0 | 1 | 0 | 0 | 0 | 0 | 0 | 0 | 2 | 4 | 0 | 2 | 0 | 0 | 0 | 0 | 2 | 0 | 0 | 3 | 3 | 3 | 0 | 0 |
| Rice | — | — | — | — | — | — | — | — | — | — | — | — | — | — | — | — | 0 | 0 | 0 | 0 | 0 | 0 | 0 | 0 | 3 | — | 0 | 0 | 0 |
| S. Flatsedge | — | — | — | — | — | — | — | — | — | — | — | — | — | — | — | — | 4 | 0 | 0 | 0 | 6 | 5 | 2 | 6 | 7 | — | 8 | 2 | 4 |
| Soybean | 5 | 6 | 2 | 1 | 1 | 0 | 2 | 2 | 1 | 2 | 1 | 1 | 1 | 1 | 2 | 2 | 5 | 1 | 2 | 0 | 2 | 2 | 1 | 1 | 2 | 4 | 5 | 2 | 3 |
| Sugarbeets | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 1 | 0 | 0 |
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 4 | 0 | 0 | 3 | 0 | 0 | 0 | 3 | 0 | 0 | 2 | 3 |
| Wild oats | 0 | 0 | 0 | 0 | 0 | 0 | 0 | 0 | 0 | 0 | 0 | 0 | 0 | 0 | 0 | 0 | 0 | 4 | 0 | 0 | 3 | 0 | 0 | 0 | 0 | 0 | 0 | 3 | 3 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 357 | 358 | 359 | 360 | 361 | 362 | 363 | 364 | 365 | 367 | 368 | 369 | 370 | 371 | 372 | 373 | 374 | 375 | 376 | 378 | 379 | 380 | 381 | 382 | 383 | 384 | 385 | 387 | 388 |
| Postemergence | | | | | | | | | | | | | | | | | | | | | | | | | | | | | |
| B. signalgrass | 0 | 0 | 0 | 0 | 0 | 5 | 0 | 0 | 0 | 0 | 5 | 0 | 2 | 0 | 2 | 0 | 0 | 0 | 0 | 0 | 0 | 0 | 0 | 0 | 0 | 3 | 3 | 1 | 6 |
| Barnyardgrass | 2 | 2 | 0 | 2 | — | — | — | 0 | — | — | — | 0 | 0 | — | 0 | — | — | — | — | — | — | — | — | — | — | — | — | — | — |
| Bedstraw | 0 | 2 | 0 | 0 | 7 | 9 | 4 | 0 | — | — | — | — | — | — | — | — | — | — | — | — | 0 | — | 0 | — | 0 | 0 | — | 0 | — |
| Blackgrass | 6 | 6 | 0 | 5 | 7 | 8 | 7 | 0 | 0 | 0 | 7 | 0 | 4 | 2 | 4 | 0 | 0 | 5 | 0 | 0 | 0 | 0 | 0 | 0 | 0 | 4 | 0 | 3 | 8 |
| Cocklebur | 0 | 0 | 0 | 0 | 0 | 0 | 0 | 0 | 0 | 0 | 2 | 0 | 0 | 0 | 0 | 1 | 0 | 0 | 0 | 0 | 0 | 0 | 0 | 0 | 0 | 0 | 0 | 0 | 0 |
| Corn | 0 | 0 | 0 | 2 | 0 | 0 | 0 | 0 | 0 | 0 | 5 | 0 | 0 | 0 | 0 | 0 | 0 | 0 | 0 | 0 | 0 | 0 | 0 | 0 | 0 | 0 | 0 | 0 | 0 |
| Crabgrass | 2 | 0 | 0 | 2 | 2 | 6 | 2 | 0 | 0 | 2 | 8 | 0 | 7 | 4 | 2 | 0 | 0 | 4 | 0 | 0 | 0 | 1 | 0 | 0 | 1 | 7 | 7 | 2 | 4 |
| Ducksalad | 0 | 2 | 0 | 0 | — | — | — | 0 | — | — | — | 0 | 2 | — | 6 | — | — | — | — | — | — | — | — | — | — | — | — | — | — |
| Giant foxtail | 8 | 8 | 0 | 8 | 4 | 8 | 4 | 3 | 0 | 3 | 8 | 0 | 8 | 7 | 9 | 3 | 0 | 6 | 0 | 0 | 0 | 2 | 0 | 3 | 0 | 8 | 9 | 3 | 8 |
| Morningglory | 2 | 5 | 0 | 4 | 2 | 1 | 1 | 0 | 0 | 5 | 4 | 10 | 10 | 7 | 7 | 8 | 5 | 1 | 0 | 7 | 7 | 5 | 2 | 0 | 0 | 0 | 1 | 1 | 3 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — |
| Rape | 0 | 1 | 0 | 0 | 3 | 0 | 0 | 0 | 0 | 0 | 0 | 0 | 0 | 0 | — | 1 | 2 | 0 | 0 | 0 | 0 | 0 | 0 | 0 | 0 | 0 | 0 | 0 | 0 |
| Redroot pigweed | 0 | 3 | 0 | 0 | 5 | 4 | 0 | 0 | 0 | 0 | 3 | 0 | 0 | 0 | 3 | 3 | 0 | 0 | 0 | 0 | 0 | 0 | 0 | 0 | 0 | 0 | 0 | 0 | 0 |
| Rice | 0 | 0 | 0 | 0 | — | — | — | 0 | — | — | — | 0 | 0 | — | 0 | — | — | — | — | — | — | — | — | — | — | — | — | — | — |
| S. Flatsedge | 0 | 0 | 0 | 4 | — | — | — | 0 | — | — | — | 2 | 3 | — | 2 | — | — | — | — | — | — | — | — | — | — | — | — | — | — |
| Soybean | 2 | 4 | 2 | 2 | 4 | 5 | 5 | 2 | 0 | 1 | 5 | 0 | 2 | 1 | 1 | 3 | 2 | 1 | 0 | 0 | 1 | 1 | 2 | 3 | 3 | 2 | 2 | 0 | 1 |
| Sugarbeets | 0 | 0 | 0 | 0 | 5 | 0 | 1 | 0 | 0 | 0 | 0 | 0 | 0 | 0 | 2 | 0 | 0 | 0 | 0 | 0 | 0 | 0 | 0 | 0 | 0 | 0 | 0 | 0 | 0 |
| Velvetleaf | 2 | 2 | 0 | 0 | 0 | 4 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 2 |
| Wheat | 5 | 3 | 0 | 4 | 0 | 4 | 4 | 0 | 0 | 0 | 3 | 0 | 0 | 0 | 0 | 0 | 0 | 0 | 0 | 0 | 0 | 0 | 0 | 0 | 0 | 0 | 0 | 0 | 0 |
| Wild oats | 4 | 3 | 0 | 3 | 2 | 6 | 0 | 0 | 0 | 0 | 0 | 0 | 0 | 0 | 4 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 389 | 390 | 391 | 392 | 393 | 394 | 395 | 396 | 397 | 398 | 400 | 401 | 402 | 403 | 404 | 405 | 406 | 407 | 408 | 409 | 410 | 411 | 414 | 415 | 416 | 417 | 418 | 419 | 420 |
| Postemergence | | | | | | | | | | | | | | | | | | | | | | | | | | | | | |
| B. signalgrass | 0 | 5 | 0 | 5 | 0 | 1 | 0 | 0 | 0 | 0 | 2 | 0 | 2 | 2 | 2 | 0 | 0 | 0 | 0 | 5 | 0 | 3 | 0 | 0 | 6 | 0 | 0 | 0 | 2 |
| Barnyardgrass | — | — | — | — | — | — | — | 0 | 0 | 0 | 0 | — | — | — | — | — | — | — | — | — | — | — | — | 0 | 0 | 0 | 0 | 0 | 0 |
| Bedstraw | — | — | — | — | — | — | 0 | — | — | — | — | — | 3 | 2 | — | — | — | — | 6 | 2 | — | — | — | — | 3 | 0 | — | 0 | 0 |
| Blackgrass | 0 | — | — | 10 | 2 | — | 0 | 2 | 8 | 6 | 4 | 0 | — | 9 | — | 0 | 0 | 0 | 2 | 8 | 8 | — | 2 | 3 | 9 | 0 | 4 | 0 | 2 |
| Cocklebur | 0 | 0 | 0 | 2 | 0 | 0 | 0 | 0 | 0 | 0 | 0 | 0 | 1 | 0 | 2 | 0 | 0 | 0 | 0 | 0 | 0 | 1 | 0 | 0 | 0 | 0 | 0 | 0 | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Corn | 0 | 0 | 0 | 0 | 0 | 0 | 0 | 0 | 0 | 0 | 0 | 0 | 0 | 0 | 0 | 0 | 0 | 0 | 0 | 5 | 0 | 0 | 0 | 0 | 0 | 0 | 0 | 0 | 0 |
| Crabgrass | 3 | 7 | 0 | 2 | 1 | 2 | 2 | 0 | 6 | 3 | — | 0 | 3 | 3 | 3 | 0 | 0 | 0 | 4 | 9 | 4 | 4 | 3 | 1 | 6 | 0 | 0 | 0 | 2 |
| Ducksalad | — | — | — | — | — | — | — | 0 | 0 | 0 | 0 | — | — | — | — | — | — | — | — | — | — | — | — | 0 | 0 | 0 | 0 | 0 | 0 |
| Giant foxtail | 2 | 9 | 0 | 9 | 8 | 7 | 3 | 0 | 8 | 8 | 8 | 0 | 8 | 3 | 9 | 0 | 0 | 0 | 9 | 8 | 9 | 9 | — | 8 | 8 | 0 | 0 | 0 | 8 |
| Morningglory | 3 | 3 | 0 | 7 | 0 | 2 | 0 | 5 | 5 | 2 | 1 | 3 | 5 | 6 | 6 | 2 | 1 | 10 | 6 | 8 | 6 | — | 7 | 4 | 8 | 3 | 3 | 2 | 4 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | — | 8 | 0 | 0 | — | 0 | 0 | 0 | 0 | 0 | 0 | — | 8 | 3 | 3 | 0 | 0 | 0 | 0 | — | — | 6 | 0 | 0 | 0 | 0 | 0 | 0 | 0 |
| Redroot pigweed | 0 | 5 | 0 | 0 | 0 | 0 | 0 | 0 | 0 | 0 | 0 | 0 | 4 | 0 | 2 | 0 | 0 | 0 | 0 | 2 | 0 | 3 | 0 | 0 | 2 | 0 | 0 | 0 | 0 |
| Rice | — | — | — | — | — | — | — | 0 | 0 | 0 | 0 | — | — | — | — | — | — | — | — | — | — | — | — | 0 | 0 | 0 | 0 | 0 | 0 |
| S. Flatsedge | — | — | — | — | — | — | — | 0 | 0 | 0 | 0 | — | — | — | — | — | — | — | — | — | — | — | — | 2 | 0 | 6 | 3 | 0 | 0 |
| Soybean | 2 | 2 | 0 | 1 | 1 | 4 | 0 | 2 | 5 | 3 | 2 | 1 | 5 | 4 | 4 | 2 | 1 | 1 | 2 | 4 | 4 | 4 | 2 | 3 | 6 | 4 | 4 | 2 | 2 |
| Sugarbeets | 0 | 2 | 0 | 0 | 0 | 0 | 0 | 0 | 0 | 0 | 0 | 0 | 2 | 0 | 1 | 0 | 0 | 0 | 0 | 0 | 6 | 0 | 0 | 0 | 0 | 0 | 0 | 0 | 0 |
| Velvetleaf | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 4 | 0 | 0 | 0 | 0 | 0 | 0 | 0 | 0 | 0 |
| Wild oats | 0 | 1 | 0 | 7 | 0 | 0 | 0 | 0 | 0 | 0 | 0 | 0 | 0 | 0 | 0 | 0 | 0 | 0 | 0 | 0 | 0 | 3 | 0 | 0 | 2 | 0 | 0 | 0 | 0 |
| | COMPOUND | | | | | | | | | | | | | | | | | | | | | | | | | | | | |
| Rate 125 g/ha | 421 | 422 | 423 | 424 | 425 | 426 | 427 | 428 | 429 | 430 | 431 | 432 | 433 | 434 | 435 | 436 | 437 | 438 | 439 | 440 | 441 | 442 | 443 | 444 | 445 | 446 | 447 | 448 | 449 |
| Postemergence | | | | | | | | | | | | | | | | | | | | | | | | | | | | | |
| B. signalgrass | 3 | 0 | 0 | 0 | 2 | 5 | 0 | 0 | 0 | 1 | 0 | 0 | 1 | 0 | 0 | 0 | 0 | 0 | 0 | 0 | 0 | 0 | 0 | 0 | 0 | 3 | 0 | 0 | 0 |
| Barnyardgrass | 0 | 0 | 0 | 0 | 0 | 0 | 0 | 0 | 0 | 0 | 0 | 0 | 0 | 0 | 0 | 0 | — | — | — | 0 | — | — | — | — | — | — | — | — | — |
| Bedstraw | 4 | — | — | 0 | — | — | — | — | — | 0 | — | — | 2 | 0 | 0 | 0 | 0 | 0 | — | 0 | — | — | — | — | — | — | — | 0 | — |
| Blackgrass | 8 | 0 | 0 | 0 | 3 | 6 | 0 | 0 | 2 | 3 | 0 | 2 | 5 | 0 | 0 | 0 | 0 | 0 | 0 | 0 | 0 | 0 | 0 | 2 | 0 | 8 | 0 | 0 | 0 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 7 | 0 | 0 | 0 | 7 | 6 | 0 | 0 | 1 | 2 | 0 | 0 | 2 | 0 | 2 | 0 | 1 | 4 | 0 | 2 | 0 | 0 | 0 | 2 | 1 | 9 | 0 | 0 | — |
| Ducksalad | 0 | 0 | 0 | 0 | 0 | 0 | 0 | 0 | 2 | 0 | 0 | 0 | 0 | 0 | 0 | 0 | — | — | — | 0 | — | — | — | — | — | — | — | — | — |
| Giant foxtail | 9 | 0 | 0 | 0 | 7 | 7 | 2 | 0 | 1 | 8 | 0 | 3 | 4 | 0 | 3 | 0 | 0 | 5 | 0 | 4 | 0 | 0 | 0 | 7 | 0 | 9 | 0 | 0 | 0 |
| Morningglory | 8 | 0 | 2 | 0 | 5 | 7 | 0 | 1 | 1 | 2 | 1 | 1 | 2 | 0 | 2 | 0 | 1 | 8 | 0 | 8 | 0 | 4 | 3 | 0 | 4 | 2 | 2 | 0 | 5 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Redroot pigweed | 2 | 0 | 0 | 0 | 0 | 0 | 0 | 0 | 0 | 2 | 0 | 0 | 0 | 0 | 0 | 0 | 0 | 0 | 0 | 1 | 0 | 0 | 0 | 2 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | — | — | — | 0 | — | — | — | — | — | — | — | — | — |
| S. Flatsedge | 0 | 0 | 0 | 0 | 0 | 0 | 0 | 0 | 0 | 0 | 0 | 0 | 0 | 0 | 0 | 0 | — | — | — | 0 | — | — | — | — | — | — | — | — | — |
| Soybean | 6 | 3 | 2 | 0 | 1 | 4 | 1 | 1 | 2 | 1 | 1 | 1 | 2 | 0 | 1 | 0 | 0 | 1 | 0 | 6 | 0 | 0 | 1 | 1 | 1 | 2 | 1 | 1 | 1 |
| Sugarbeets | 0 | 0 | 0 | 0 | 2 | 3 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 |
| Wheat | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| | COMPOUND | | | | | | | | | | | | | | | | | | | | | | | | | | | | |
| Rate 125 g/ha | 450 | 451 | 452 | 453 | 454 | 455 | 456 | 457 | 458 | 459 | 460 | 461 | 462 | 463 | 465 | 466 | 467 | 468 | 469 | 470 | 471 | 472 | 473 | 474 | 476 | 477 | 478 | 479 | 480 |
| Postemergence | | | | | | | | | | | | | | | | | | | | | | | | | | | | | |
| B. signalgrass | 0 | 0 | 0 | 0 | 0 | 0 | 0 | 0 | 0 | 0 | 0 | 0 | 0 | 0 | 0 | 2 | 0 | 0 | 2 | 0 | 0 | 0 | 0 | 1 | 0 | 0 | 0 | 2 | 3 |
| Barnyardgrass | — | — | — | — | — | — | — | — | — | — | — | — | — | — | — | — | — | — | — | — | — | — | — | — | — | — | — | — | — |
| Bedstraw | — | 0 | — | — | — | — | — | 0 | — | — | — | — | 0 | — | — | — | — | — | — | 0 | — | — | — | 6 | — | 0 | 0 | 0 | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Blackgrass | 0 | 0 | 0 | 0 | 0 | 8 | 4 | 0 | 3 | 1 | — | 0 | 0 | 0 | 2 | — | 0 | 5 | 7 | 0 | 2 | 0 | 0 | — | 0 | 0 | 2 | 0 | 3 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 2 | 0 | — | — | — | — | — | 0 | 8 | 1 | 6 | 0 | 0 | 0 | 1 | 9 | 0 | — | 6 | 0 | 3 | 7 | 2 | 5 | 0 | 2 | 3 | 3 | 6 |
| Ducksalad | — | — | — | — | — | — | — | — | — | — | — | — | — | — | — | — | — | — | — | — | — | — | — | — | — | — | — | — | — |
| Giant foxtail | 5 | 0 | 4 | 5 | 2 | 7 | 2 | 0 | 9 | 0 | 0 | 0 | 0 | 0 | 5 | — | 0 | 3 | 9 | 0 | 1 | 7 | 2 | 6 | 0 | 2 | 6 | 3 | 5 |
| Morningglory | 0 | 1 | 2 | 0 | 9 | 8 | 3 | 0 | 0 | 8 | 7 | 7 | 0 | 0 | 1 | 2 | 7 | 3 | 9 | 0 | 3 | 3 | 1 | 1 | 0 | 7 | 3 | 10 | 4 |
| Nutsedge | 0 | 0 | 0 | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Redroot pigweed | 0 | 0 | 0 | 0 | 0 | 2 | 0 | 0 | 0 | 0 | 0 | 0 | 0 | 0 | 0 | 2 | 0 | 2 | 0 | 0 | 0 | 2 | 0 | 1 | 0 | 0 | 2 | 2 | 0 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 1 | 1 | 1 | 1 | 2 | 2 | 3 | 0 | 1 | 3 | 3 | 3 | 1 | 1 | 1 | 4 | 0 | 1 | 1 | 0 | 2 | 2 | 1 | 4 | 1 | 1 | 2 | 1 | 3 |
| Sugarbeets | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 |
| Velvetleaf 0 | | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 1 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 |
| | COMPOUND | | | | | | | | | | | | | | | | | | | | | | | | | | | | |
| Rate 125 g/ha | 481 | 482 | 483 | 485 | 486 | 487 | 488 | 489 | 490 | 492 | 493 | 494 | 495 | 496 | 497 | 498 | 499 | 500 | 501 | 504 | 505 | 506 | 508 | 509 | 510 | 511 | 512 | 513 | 514 |
| Postemergence | | | | | | | | | | | | | | | | | | | | | | | | | | | | | |
| B. signalgrass | 0 | 0 | 0 | 0 | 0 | 0 | 4 | 2 | 4 | 0 | 0 | 0 | 0 | 0 | 0 | 0 | 0 | 5 | 6 | 3 | 3 | 0 | 0 | 0 | 4 | 0 | 1 | 3 | 0 |
| Barnyardgrass | — | — | — | — | — | — | — | — | — | — | — | — | — | — | — | — | — | — | — | — | — | — | — | — | — | — | — | — | — |
| Bedstraw | — | 0 | — | 0 | 1 | 2 | 2 | 3 | 3 | — | — | — | — | — | 0 | — | — | 9 | — | 8 | — | — | — | — | — | 8 | — | — | — |
| Blackgrass | 0 | 0 | 0 | 7 | 6 | 0 | 8 | 6 | 4 | 0 | 0 | 0 | 0 | 3 | 0 | 0 | 0 | 4 | 6 | 7 | 4 | 0 | 3 | 5 | 5 | 0 | 3 | 4 | 3 |
| Cocklebur | 0 | 0 | 0 | 0 | 0 | 0 | 0 | 0 | 0 | 0 | 0 | 0 | 0 | 0 | 0 | 0 | 0 | 3 | 0 | 3 | 0 | 0 | 1 | 0 | 3 | 0 | 2 | 3 | 1 |
| Corn | 3 | 0 | 0 | 0 | 0 | 0 | 0 | 0 | 0 | 0 | 0 | 0 | 0 | 0 | 0 | 0 | 0 | 2 | 0 | 2 | 3 | 0 | 0 | 0 | 0 | 0 | 0 | 0 | 0 |
| Crabgrass | 2 | 0 | 0 | 6 | 3 | 3 | 7 | 5 | 6 | — | 0 | 0 | 0 | 0 | 0 | — | 0 | 9 | 8 | 8 | 7 | 3 | 9 | 9 | 8 | 3 | 2 | 4 | 9 |
| Ducksalad | — | — | — | — | — | — | — | — | — | — | — | — | — | — | — | — | — | — | — | — | — | — | — | — | — | — | — | — | — |
| Giant foxtail | 2 | 0 | 0 | 7 | 7 | 2 | 8 | 8 | 8 | 0 | 0 | 0 | 0 | 0 | 0 | 2 | 0 | 8 | 8 | 9 | 8 | — | 8 | 7 | 6 | 3 | 3 | 5 | 9 |
| Morningglory | 0 | 7 | 0 | 10 | 1 | 10 | 2 | 7 | 3 | 5 | 0 | 0 | 1 | 8 | 0 | 3 | 3 | 3 | 3 | 4 | 5 | 0 | 3 | — | 5 | 4 | 5 | 3 | 7 |
| Nutsedge | — | 0 | 0 | 0 | 0 | 0 | 0 | 0 | 0 | 0 | 0 | 0 | 0 | 0 | 0 | 0 | 0 | — | 0 | 0 | 2 | 0 | — | 0 | 0 | 0 | — | 0 | 0 |
| Rape | 0 | 0 | 0 | 0 | 0 | 0 | 0 | 0 | 0 | 0 | 0 | 0 | 0 | 0 | 0 | 0 | 0 | 3 | 2 | 4 | 0 | 0 | 5 | 0 | 4 | 1 | 0 | 4 | 6 |
| Redroot pigweed | 0 | 0 | 0 | 0 | 0 | 2 | 0 | 0 | 0 | 0 | 0 | 0 | 0 | 0 | 0 | 0 | 0 | 9 | 4 | 8 | 0 | 0 | 7 | 0 | 7 | 6 | 7 | 6 | 2 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 4 | 1 | 0 | 4 | 4 | 4 | 4 | 5 | 5 | 0 | 0 | 0 | 0 | 3 | 1 | 1 | 1 | 4 | 3 | 6 | 2 | 2 | 4 | 3 | 7 | 4 | 4 | 7 | 7 |
| Sugarbeets | 0 | 0 | 0 | 0 | 0 | 0 | 0 | 0 | 0 | 0 | 0 | 0 | 0 | 0 | 0 | 0 | 0 | 6 | 5 | 7 | 5 | 6 | 1 | 0 | 4 | 0 | 0 | 4 | 3 |
| Velvetleaf | 0 | 0 | 0 | 0 | 0 | 0 | 0 | 0 | 0 | 0 | 0 | 0 | 0 | 0 | 0 | 0 | 0 | 4 | 0 | 4 | 0 | 0 | 1 | 4 | 4 | 1 | 0 | 3 | 2 |
| Wheat | 0 | 0 | 0 | 0 | 0 | 0 | 0 | 0 | 0 | 0 | 0 | 0 | 0 | 0 | 0 | 0 | 0 | — | — | 3 | 2 | 0 | 0 | 0 | 0 | 0 | 0 | 5 | 0 |
| Wild oats | 0 | 0 | 0 | 0 | 0 | 0 | 0 | 1 | 5 | 0 | 0 | 0 | 0 | 0 | 0 | 0 | 0 | 0 | 0 | 6 | 2 | 0 | 0 | 0 | 0 | 0 | 0 | 4 | 0 |
| | COMPOUND | | | | | | | | | | | | | | | | | | | | | | | | | | | | |
| Rate 125 g/ha | 515 | 516 | 517 | 518 | 519 | 520 | 521 | 522 | 523 | 524 | 525 | 526 | 527 | 528 | 531 | 532 | 533 | 534 | 535 | 536 | 540 | 541 | 543 | 544 | 545 | 546 | 548 | 549 | 550 |
| Postemergence | | | | | | | | | | | | | | | | | | | | | | | | | | | | | |
| B. signalgrass | 0 | 0 | 4 | 7 | 0 | 0 | 0 | 5 | 0 | 0 | 2 | 2 | 0 | 0 | 0 | 0 | 0 | 0 | 0 | 0 | 0 | 0 | 0 | 0 | 0 | 0 | 0 | 0 | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Barnyardgrass | — | — | — | — | — | — | — | — | — | — | — | — | — | — | — | — | — | — | — | — | — | — | — | — | — | — | — | — | — |
| Bedstraw | 6 | — | 7 | — | — | — | — | 0 | 0 | — | — | — | — | 0 | 0 | 0 | — | — | — | 0 | 3 | — | 0 | 2 | 0 | 9 | 4 | 0 | 0 |
| Blackgrass | 0 | 4 | 3 | 7 | 0 | 0 | 2 | 8 | 0 | 2 | 6 | 6 | 3 | 0 | 0 | 0 | 2 | 2 | 4 | 0 | 0 | 0 | 0 | 0 | 0 | 0 | 0 | 0 | 0 |
| Cocklebur | 3 | 3 | 0 | 0 | 0 | 0 | 0 | 3 | 2 | 0 | 2 | 0 | 0 | 0 | 0 | 0 | 2 | 0 | 0 | 0 | 0 | 0 | 0 | 3 | 3 | 0 | 0 | 0 | 0 |
| Corn | 0 | 0 | 0 | 0 | 0 | 0 | 0 | 3 | 0 | 2 | 0 | 2 | 0 | 0 | 0 | 0 | 0 | 0 | 0 | 0 | 0 | 0 | 0 | 0 | 0 | 0 | 0 | 0 | 0 |
| Crabgrass | 8 | 9 | 7 | 2 | 2 | 3 | 4 | 8 | 8 | 8 | — | 9 | 4 | 9 | 8 | 4 | 8 | 5 | — | 5 | 5 | 0 | — | 8 | 2 | 7 | 5 | 3 | 7 |
| Ducksalad | — | — | — | — | — | — | — | — | — | — | — | — | — | — | — | — | — | — | — | — | — | — | — | — | — | — | — | — | — |
| Giant foxtail | 9 | 5 | 8 | 0 | 4 | 4 | 8 | 8 | 2 | 8 | 8 | 3 | 8 | 3 | 8 | 4 | 8 | 3 | — | 0 | 0 | 0 | 0 | 0 | 0 | — | 0 | 2 | 6 |
| Morningglory | 2 | 3 | 2 | 5 | 0 | 4 | 4 | 4 | 3 | 2 | 2 | 6 | 3 | 3 | 4 | 3 | 4 | 2 | 2 | 2 | 4 | 1 | 2 | 4 | 4 | 4 | — | 4 | 1 |
| Nutsedge | 0 | 0 | 0 | 0 | 0 | 0 | 0 | 0 | 0 | — | 0 | 0 | — | 0 | 0 | 0 | 0 | 2 | 0 | 0 | 0 | 0 | 0 | 0 | — | — | 0 | 0 | 0 |
| Rape | 4 | 4 | 0 | 7 | 0 | 0 | 0 | 0 | 0 | 0 | 0 | 4 | 0 | 0 | 0 | 0 | 0 | 0 | 0 | 0 | 2 | 0 | 0 | 2 | 0 | 0 | 0 | 0 | 3 |
| Redroot pigweed | 4 | — | 4 | 0 | 0 | 3 | 0 | 4 | 2 | 0 | 2 | 0 | 0 | 0 | 0 | 0 | 9 | 3 | 0 | 0 | 0 | 0 | 0 | 0 | 0 | — | 0 | 0 | 0 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 4 | 4 | 6 | 5 | 3 | 4 | 4 | 6 | 5 | — | 5 | 3 | 4 | 3 | 3 | 2 | 4 | 4 | 6 | 4 | 1 | 0 | 2 | 2 | 1 | 1 | 2 | 2 | 2 |
| Sugarbeets | 3 | 0 | 0 | 3 | 0 | 0 | 0 | 6 | 0 | 0 | 0 | 0 | 0 | 0 | 0 | 0 | 0 | 0 | 0 | 0 | 2 | 0 | 0 | 0 | 0 | 0 | 0 | 0 | 0 |
| Velvetleaf | 4 | 4 | 0 | 2 | 2 | 4 | 0 | 5 | 3 | 0 | 3 | 4 | 2 | 4 | 0 | 0 | 4 | 2 | 0 | 0 | 0 | 0 | 0 | 0 | 3 | 0 | 0 | 0 | 0 |
| Wheat | 0 | 1 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 |
| Wild oats | 0 | 2 | 0 | 2 | 0 | 0 | 0 | 4 | 0 | 0 | 2 | 0 | 0 | 0 | 0 | 0 | 0 | 0 | 0 | 0 | 0 | 0 | 0 | 0 | 0 | 0 | 0 | 0 | 2 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 551 | 552 | 553 | 554 | 555 | 556 | 557 | 558 | 559 | 560 | 561 | 562 | 563 | 564 | 565 | 566 | 567 | 568 | 569 | 570 | 571 | 572 | 573 | 574 | 575 | 576 | 577 | 578 | 579 |
| Postemergence | | | | | | | | | | | | | | | | | | | | | | | | | | | | | |
| B. signalgrass | 0 | 0 | 0 | 0 | 0 | 2 | 2 | — | 9 | 3 | 0 | — | 4 | — | 0 | 8 | 0 | 4 | 0 | 0 | 0 | 0 | 0 | 0 | 0 | 0 | 0 | 0 | 0 |
| Barnyardgrass | — | — | — | — | — | — | — | — | — | — | — | — | — | — | — | — | — | — | — | — | — | — | — | — | — | — | — | — | — |
| Bedstraw | 0 | 5 | 2 | 5 | 9 | 0 | — | 0 | 0 | — | — | — | 0 | — | 0 | — | 0 | 2 | — | — | — | — | — | — | — | — | 4 | 8 | 0 |
| Blackgrass | 7 | 0 | 0 | 3 | 2 | 3 | 0 | 0 | 7 | 5 | 5 | 3 | 0 | 4 | 0 | 2 | 0 | 8 | 0 | 0 | 0 | 0 | 0 | 6 | 0 | 0 | 0 | 0 | 0 |
| Cocklebur | 0 | 0 | — | 0 | 0 | 0 | 0 | 0 | 0 | 0 | 0 | 2 | 0 | 0 | 0 | 2 | 0 | 1 | 2 | 0 | 0 | 0 | 0 | 2 | 0 | 0 | 0 | 0 | 0 |
| Corn | 0 | 0 | 0 | 0 | 0 | 0 | 0 | 0 | 0 | 0 | 0 | 3 | 0 | 0 | 0 | 0 | 0 | 0 | 0 | 0 | 0 | 0 | 0 | 0 | 0 | 0 | 0 | 0 | 0 |
| Crabgrass | 6 | 9 | 3 | — | 0 | 2 | 5 | 0 | 4 | 4 | 3 | 5 | 9 | 3 | 0 | 8 | 7 | 8 | 0 | 0 | 0 | 0 | 9 | 2 | 2 | 3 | 0 | 2 | 6 |
| Ducksalad | — | — | — | — | — | — | — | — | — | — | — | — | — | — | — | — | — | — | — | — | — | — | — | — | — | — | — | — | — |
| Giant foxtail | — | 3 | 7 | 6 | 0 | 7 | 6 | 2 | 9 | 7 | 4 | 7 | 8 | 3 | 0 | 8 | 0 | 9 | 3 | 0 | 0 | 0 | 3 | 7 | 2 | 3 | 2 | 4 | 2 |
| Morningglory | 2 | 1 | 0 | 2 | 2 | 2 | 8 | 10 | 10 | 7 | 4 | 4 | 6 | 7 | 5 | 5 | 4 | 10 | 10 | 10 | 10 | 3 | 10 | 10 | 6 | 2 | 9 | 10 | 10 |
| Nutsedge | — | 0 | 0 | 0 | 0 | 0 | 0 | 0 | 0 | 3 | 2 | — | 0 | — | 0 | 0 | — | 0 | 0 | 0 | 0 | 0 | 0 | — | 0 | 0 | — | — | 0 |
| Rape | 7 | 6 | 6 | 0 | 5 | 0 | 0 | 0 | 0 | — | 4 | 0 | 0 | 0 | 0 | 0 | 0 | 0 | 0 | 0 | 0 | 3 | 2 | 0 | 0 | 0 | 0 | 2 | 0 |
| Redroot pigweed | 0 | 0 | 0 | 5 | 0 | 3 | 0 | 0 | 0 | 5 | 0 | 9 | 0 | 3 | 0 | 5 | 0 | 0 | 0 | 0 | 0 | 0 | 0 | 0 | 0 | 0 | 0 | 3 | 0 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 2 | 3 | 2 | 2 | 4 | 0 | 0 | 3 | 4 | 2 | 5 | 3 | 5 | 5 | 3 | 4 | 4 | 5 | 5 | 0 | 2 | 3 | 2 | 4 | 5 | 2 | 2 | 3 | 2 |
| Sugarbeets | 3 | 0 | 0 | 0 | 0 | 0 | 0 | 0 | 0 | 0 | 0 | 3 | 0 | 0 | 0 | 0 | 0 | 0 | 0 | 0 | 0 | 0 | 0 | 0 | 3 | 0 | 0 | 0 | 0 |
| Velvetleaf | 0 | 0 | 0 | 0 | 0 | 0 | 0 | 0 | 0 | 0 | 0 | 5 | 0 | 0 | 3 | 3 | 0 | 0 | 0 | 0 | 0 | 0 | 0 | 2 | 0 | 0 | 0 | 2 | 0 |
| Wheat | 0 | 0 | — | 0 | 0 | 0 | 0 | 0 | 2 | 0 | 2 | 4 | 0 | 0 | 0 | 0 | 0 | 2 | 0 | 0 | 0 | 0 | 0 | 0 | 0 | 0 | 0 | 0 | 0 |
| Wild oats | 0 | 0 | 0 | 0 | 0 | 2 | 0 | 0 | 2 | 0 | 0 | 0 | 0 | 0 | 0 | 0 | 0 | 2 | 0 | 0 | 0 | 0 | 0 | 0 | 0 | 0 | 0 | 0 | 0 |

TABLE B-continued

| Rate 125 g/ha | 580 | 581 | 582 | 584 | 585 | 586 | 587 | 588 | 589 | 590 | 591 | 592 | 593 | 594 | 595 | 596 | 598 | 599 | 600 | 601 | 602 | 603 | 604 | 605 | 606 | 607 | 608 | 609 | 610 |
|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | |
| Postemergence | | | | | | | | | | | | | | | | | | | | | | | | | | | | | |
| B. signalgrass | 2 | 5 | 0 | 3 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 10 | 1 | 6 |
| Barnyardgrass | — | — | — | — | — | — | — | — | — | — | — | — | — | — | — | — | — | — | — | — | — | — | — | — | — | — | — | — | — |
| Bedstraw | — | 8 | 7 | 5 | 8 | 0 | — | — | — | — | — | — | — | — | — | — | 0 | — | — | — | 3 | — | — | — | — | 0 | — | 0 | — |
| Blackgrass | 6 | 4 | — | 7 | 6 | 1 | 3 | 0 | 0 | 0 | 0 | 0 | 0 | 5 | 7 | 0 | 0 | 0 | 0 | — | 6 | 0 | 0 | 0 | 0 | 4 | 6 | 8 | 9 |
| Cocklebur | 3 | — | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 1 |
| Corn | 0 | 4 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 3 | 7 | 0 | 7 | 5 | 3 | 0 | 2 | 0 | 0 | 0 | 0 | 0 | 7 | 8 | 0 | 0 | 0 | 1 | 4 | 4 | 0 | — | 0 | 3 | — | 3 | 9 | 9 |
| Ducksalad | — | — | — | — | — | — | — | — | — | — | — | — | — | — | — | — | — | — | — | — | — | — | — | — | — | — | — | — | — |
| Giant foxtail | 6 | 8 | 4 | 8 | 6 | 2 | 0 | 4 | 0 | 0 | 0 | 0 | 0 | 7 | 9 | 0 | 0 | 0 | 0 | 7 | 8 | 0 | 2 | 0 | 0 | 6 | 7 | 9 | 7 |
| Morningglory | 7 | 8 | 10 | 4 | 8 | 10 | 4 | 7 | 3 | 3 | 0 | 1 | 0 | 2 | 2 | 0 | 0 | 1 | 0 | 1 | 1 | 0 | 1 | 6 | 10 | 8 | 7 | 10 | 8 |
| Nutsedge | 0 | — | 0 | 0 | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 |
| Rape | 6 | 7 | 0 | 4 | 3 | 0 | 0 | 0 | 0 | 0 | 0 | 0 | 0 | 0 | 0 | 0 | 0 | 0 | 0 | 0 | 0 | 0 | 0 | 0 | 2 | 0 | 5 | 0 | 2 |
| Redroot pigweed | 5 | 8 | 0 | 2 | 0 | 0 | 0 | 0 | 0 | 0 | 0 | 0 | 0 | 0 | 0 | 0 | 0 | 0 | 0 | 2 | 2 | 0 | 0 | 0 | 0 | 0 | 5 | 0 | 2 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 4 | 4 | 3 | 3 | 0 | 3 | 4 | 4 | 3 | 1 | 1 | 1 | 0 | 0 | — | 2 | 0 | 2 | 2 | 4 | 3 | 0 | 1 | 2 | 2 | 4 | 4 | 6 | 7 |
| Sugarbeets | 4 | 5 | 0 | 2 | 2 | 0 | 0 | 0 | 0 | 0 | 0 | 0 | 0 | 5 | 3 | 0 | 0 | 0 | 0 | 0 | 0 | 0 | 0 | 0 | 0 | 0 | 5 | 0 | 0 |
| Velvetleaf | 2 | 4 | 0 | 3 | 3 | 0 | 0 | 0 | 2 | 0 | 0 | 0 | 0 | 3 | 4 | 0 | 0 | 0 | 0 | 0 | 0 | 0 | 0 | 0 | 0 | 0 | 0 | 3 | 3 |
| Wheat | 0 | 4 | 0 | 2 | 2 | 0 | 0 | 0 | 0 | 0 | 0 | 0 | 0 | 0 | 0 | 0 | 0 | 0 | 0 | 0 | 0 | 0 | 0 | 1 | 0 | 0 | — | 0 | 1 |
| Wild oats | 0 | 5 | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 4 | 0 | 3 |

| Rate 125 g/ha | 611 | 612 | 613 | 614 | 615 | 616 | 617 | 618 | 619 | 620 | 621 | 622 | 623 | 624 | 625 | 627 | 628 | 629 | 630 | 631 | 632 | 633 | 634 | 635 | 636 | 638 | 639 | 640 | 641 |
|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | |
| Postemergence | | | | | | | | | | | | | | | | | | | | | | | | | | | | | |
| B. signalgrass | 3 | 3 | 3 | 0 | 0 | 0 | 0 | 0 | 0 | 0 | 0 | 0 | 0 | 7 | 0 | 7 | 8 | 1 | 0 | 3 | 0 | 0 | 0 | 0 | 0 | 4 | 0 | 0 | 0 |
| Barnyardgrass | — | — | — | — | — | — | — | — | — | — | — | — | — | — | — | — | — | — | — | — | — | — | — | — | — | — | — | — | — |
| Bedstraw | — | — | — | 0 | 0 | 0 | — | — | — | — | 0 | — | — | — | 0 | — | — | 5 | — | — | 0 | 0 | 0 | 7 | 7 | — | — | — | — |
| Blackgrass | 9 | 9 | 9 | 0 | 0 | 0 | 0 | 0 | 0 | 0 | 0 | 0 | 3 | 5 | 2 | 8 | 8 | 8 | 0 | 8 | 4 | 0 | 6 | 3 | 0 | 4 | 0 | 4 | 0 |
| Cocklebur | 2 | 0 | 2 | 0 | 0 | 0 | 0 | — | 0 | 0 | 0 | 0 | 0 | 0 | 0 | 0 | 1 | 0 | 0 | 0 | 0 | 0 | 1 | 2 | 3 | 0 | 0 | 0 | 0 |
| Corn | 0 | 0 | 0 | 0 | 0 | 0 | 0 | 0 | 0 | 0 | 0 | 0 | 0 | 0 | 0 | 3 | 6 | 3 | 0 | 5 | 3 | 0 | 0 | 0 | 2 | 2 | 0 | 0 | 0 |
| Crabgrass | 8 | 8 | 9 | 1 | 0 | 2 | 0 | 0 | 0 | 2 | 3 | 2 | 0 | 7 | 0 | 8 | — | 3 | 5 | 9 | 6 | 0 | 3 | 9 | 9 | 5 | — | 2 | 0 |
| Ducksalad | — | — | — | — | — | — | — | — | — | — | — | — | — | — | — | — | — | — | — | — | — | — | — | — | — | — | — | — | — |
| Giant foxtail | 8 | 9 | 9 | 0 | 0 | 3 | 0 | 0 | 0 | 0 | 0 | 3 | 0 | 8 | 3 | — | 9 | 8 | 7 | 9 | 7 | 0 | 8 | 8 | 7 | 6 | 0 | 0 | 0 |
| Morningglory | 8 | 8 | 7 | 2 | 1 | 0 | 0 | 0 | 1 | — | 2 | 1 | 6 | 1 | 1 | 6 | 2 | 2 | 2 | 4 | 1 | 2 | 1 | 4 | 2 | 2 | 3 | 3 | 1 |
| Nutsedge | 0 | 0 | 2 | 0 | 0 | 0 | 0 | 0 | 0 | 0 | 0 | 0 | 0 | 0 | 0 | — | — | 0 | 0 | 0 | 0 | 0 | 0 | 0 | 0 | 5 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 5 | 6 | 0 | 0 | 0 | 0 |
| Redroot pigweed | 2 | 2 | 2 | 0 | 0 | 0 | 0 | 0 | 0 | 0 | 0 | 0 | 0 | 0 | 0 | 3 | 3 | — | 0 | 0 | 0 | 0 | 2 | 0 | 0 | 0 | 4 | 0 | 0 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 7 | 5 | 5 | 3 | 1 | — | 1 | 0 | 1 | 1 | 5 | 4 | 0 | 3 | 2 | 4 | — | 6 | — | 5 | 2 | 2 | 2 | 4 | 2 | 1 | 0 | 0 | 0 |
| Sugarbeets | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 3 | 2 | 0 | 0 | 0 | 0 |
| Velvetleaf | 3 | 3 | 4 | 0 | 0 | 0 | 0 | 0 | 0 | 0 | 0 | 0 | 0 | 0 | 0 | 4 | 6 | 5 | 4 | 4 | 0 | 0 | 0 | 0 | 3 | 2 | 0 | 3 | 0 |
| Wheat | 0 | 2 | 0 | 0 | 0 | 0 | 0 | 0 | 0 | 0 | 0 | 0 | 0 | 0 | 0 | 3 | 4 | 0 | 0 | 2 | 0 | 0 | 0 | 0 | 0 | 0 | 0 | 0 | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Wild oats | 2 | 6 | 7 | 0 | 0 | 0 | 0 | 0 | 0 | 0 | 0 | 0 | 0 | 0 | 0 | 2 | 3 | 0 | 0 | 0 | 0 | 0 | 0 | 0 | 0 | 1 | 1 | 0 | 1 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 642 | 643 | 644 | 645 | 646 | 647 | 648 | 649 | 650 | 652 | 653 | 654 | 655 | 656 | 657 | 658 | 659 | 660 | 661 | 662 | 663 | 664 | 665 | 666 | 667 | 668 | 670 | 671 | 672 |
| Postemergence | | | | | | | | | | | | | | | | | | | | | | | | | | | | | |
| B. signalgrass | 0 | 0 | 0 | 0 | 0 | 6 | 0 | 0 | 0 | 0 | 0 | 0 | 0 | 2 | 2 | 0 | 5 | 0 | 0 | 0 | 0 | 0 | 0 | 4 | 4 | 2 | 7 | 1 | 3 |
| Barnyardgrass | — | — | — | — | — | — | — | — | — | — | — | — | — | — | — | — | — | — | — | — | — | — | — | — | — | — | — | — | — |
| Bedstraw | — | — | — | — | — | — | 0 | — | — | — | — | — | — | — | — | — | 0 | 0 | 0 | — | — | — | — | 0 | — | 0 | — | 0 | — |
| Blackgrass | 0 | 0 | 0 | 0 | 0 | — | 0 | 0 | 0 | 0 | 0 | 0 | 0 | 7 | 8 | 3 | 6 | 0 | 0 | 0 | 0 | 7 | 7 | 8 | 8 | 8 | 4 | 6 | 2 |
| Cocklebur | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 1 | 3 | 0 | 2 | 0 | 1 |
| Corn | 0 | 0 | 0 | 0 | 0 | 2 | 0 | 0 | 0 | 0 | 0 | 0 | 0 | 0 | 1 | 0 | 0 | 0 | 0 | 0 | 0 | 0 | 0 | 0 | 4 | 0 | 4 | 0 | 0 |
| Crabgrass | 0 | 0 | 0 | 0 | 0 | 9 | 0 | 2 | 1 | 0 | 0 | 0 | 8 | 0 | 8 | 2 | 6 | 1 | 2 | 0 | 0 | 1 | 7 | 9 | 8 | 9 | 8 | 1 | 6 |
| Ducksalad | — | — | — | — | — | — | — | — | — | — | — | — | — | — | — | — | — | — | — | — | — | — | — | — | — | — | — | — | — |
| Giant foxtail | 0 | 0 | 0 | 0 | 0 | 9 | 0 | 2 | 2 | 3 | 0 | 2 | 7 | 9 | 8 | 3 | 7 | 4 | 3 | 0 | 0 | 6 | 4 | 8 | 9 | 9 | 9 | 5 | 5 |
| Morningglory | 0 | 4 | 0 | 0 | 0 | 0 | 10 | 7 | 10 | 3 | 1 | 4 | — | 2 | 5 | 7 | 10 | 4 | 0 | 7 | 0 | 2 | 6 | 1 | 2 | 3 | 3 | 1 | 8 |
| Nutsedge | 0 | 0 | 0 | 0 | 0 | 0 | 0 | 0 | 2 | 0 | 0 | 0 | 0 | 0 | 3 | 0 | 0 | 0 | 0 | 0 | 0 | 0 | 0 | 0 | 0 | 0 | 4 | 0 | 0 |
| Rape | 0 | 0 | 0 | 0 | 0 | 0 | 0 | 0 | 0 | — | 0 | 0 | 2 | 0 | 2 | 0 | 0 | 0 | 0 | 0 | 0 | 0 | 0 | 0 | 4 | 3 | 2 | 0 | 3 |
| Redroot pigweed | 0 | 0 | 3 | 2 | 0 | 4 | 3 | 0 | 6 | 0 | 0 | 0 | 2 | 0 | 2 | 6 | 0 | 2 | 0 | 0 | 0 | 2 | 3 | 1 | 5 | 5 | 7 | 1 | — |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 2 | 1 | 0 | 1 | 1 | 3 | 2 | 2 | 4 | 0 | 0 | 0 | 2 | 2 | 1 | 4 | 3 | 3 | 1 | 1 | 0 | 4 | 2 | 4 | 3 | 2 | 2 | 2 | 2 |
| Sugarbeets | 0 | 0 | 0 | 0 | 0 | 2 | 0 | 0 | 0 | — | 0 | 0 | 0 | 0 | 0 | 0 | 0 | 0 | 0 | 0 | 0 | 0 | 0 | 0 | 0 | 0 | 2 | 0 | 0 |
| Velvetleaf | 0 | 0 | 0 | 0 | 0 | 5 | 0 | 0 | 0 | 0 | 0 | 0 | 0 | 0 | 3 | 0 | 3 | 2 | 0 | 0 | 0 | 0 | 2 | 2 | 6 | 0 | 5 | 0 | 6 |
| Wheat | 0 | 0 | 0 | 0 | 0 | 3 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 1 | 1 | 0 | 0 | 0 | 0 | 0 | 0 | 0 | 0 | 0 | 0 | 0 | 0 | 2 | 1 | 0 | 0 | 0 | 1 | 0 | 0 | 0 | 0 | 4 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 674 | 675 | 676 | 677 | 678 | 679 | 680 | 681 | 708 | 709 | 710 | 711 | 712 | 713 | 714 | 722 | 736 | 739 | 740 | 741 | 743 | 744 | 745 | 746 | 747 | 748 | 749 | 750 | 751 |
| Postemergence | | | | | | | | | | | | | | | | | | | | | | | | | | | | | |
| B. signalgrass | 5 | 4 | 4 | 0 | 0 | 0 | 0 | 0 | 0 | 0 | 5 | 6 | 0 | 3 | 2 | 0 | 0 | 2 | 0 | 0 | 0 | 2 | 0 | 4 | 3 | 2 | 2 | 2 | 3 |
| Barnyardgrass | — | — | — | — | — | — | — | — | — | — | — | — | — | — | — | — | — | — | — | — | — | — | — | — | — | — | — | — | — |
| Bedstraw | — | 1 | — | — | 0 | 0 | 0 | 0 | 0 | — | 1 | — | — | — | 3 | — | — | 3 | 0 | 0 | 0 | — | — | 7 | 8 | 6 | — | — | 5 |
| Blackgrass | 7 | 5 | 6 | 0 | 0 | 0 | 0 | 0 | 0 | 0 | 6 | 7 | 0 | 3 | 7 | 0 | 0 | 3 | 3 | 0 | 5 | 5 | 3 | 7 | 7 | 6 | 5 | 7 | 6 |
| Cocklebur | 0 | 3 | 0 | 0 | 0 | 0 | 0 | 0 | 0 | 0 | 0 | 1 | 0 | 2 | 2 | 0 | 0 | 2 | 0 | 0 | 0 | 0 | 0 | 2 | 0 | 0 | 2 | 0 | 2 |
| Corn | 3 | 0 | 0 | 0 | 0 | 0 | 0 | 0 | 0 | 0 | 0 | 0 | 0 | 0 | 0 | 0 | 4 | 0 | 0 | 0 | 0 | 0 | 0 | 0 | 0 | 0 | 0 | 0 | 0 |
| Crabgrass | 8 | 8 | 7 | 0 | 0 | 0 | 0 | 0 | 0 | 3 | 9 | 8 | 4 | 9 | 9 | 0 | 3 | 9 | 0 | — | 5 | 4 | 4 | 9 | 9 | 3 | 8 | 9 | 8 |
| Ducksalad | — | — | — | — | — | — | — | — | — | — | — | — | — | — | — | — | — | — | — | — | — | — | — | — | — | — | — | — | — |
| Giant foxtail | 9 | 9 | 8 | 0 | 0 | 0 | 0 | 0 | 2 | 4 | 8 | 8 | 8 | 9 | 6 | 2 | 2 | 9 | 7 | 0 | 7 | 8 | 2 | 8 | 9 | 6 | 5 | 8 | 9 |
| Morningglory | 2 | 2 | 2 | 2 | 6 | 0 | 1 | 0 | 2 | 0 | 4 | 2 | 4 | 3 | — | 9 | 6 | — | 3 | 1 | 3 | 2 | 3 | 8 | 9 | 6 | 3 | 3 | 8 |
| Nutsedge | 3 | 0 | 0 | 0 | 0 | 0 | 0 | 0 | 0 | 0 | 0 | 0 | 0 | 0 | 0 | 0 | 0 | — | 0 | 0 | 2 | — | 0 | 0 | 0 | 0 | 0 | 0 | 0 |
| Rape | 0 | 0 | 0 | 0 | 0 | 0 | 0 | 0 | 0 | 0 | 0 | 0 | 3 | 0 | 5 | 0 | 0 | 0 | 0 | 0 | 0 | 2 | 0 | 4 | 4 | 3 | 2 | 4 | 3 |
| Redroot pigweed | 3 | 2 | 2 | 2 | 0 | 0 | 0 | 0 | 0 | 5 | 8 | 7 | — | — | 8 | — | 2 | 3 | 2 | 7 | 0 | 0 | 2 | 5 | 4 | 4 | 4 | 7 | 6 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 3 | 5 | 3 | 0 | 1 | 0 | 0 | 0 | 4 | 3 | 4 | 4 | 5 | 4 | 4 | 0 | 3 | 3 | 3 | 2 | 0 | 3 | 3 | 3 | 4 | 3 | 4 | 6 | 3 |
| Sugarbeets | 0 | 2 | 0 | 0 | 0 | 0 | 0 | 0 | 0 | 0 | 0 | 2 | 3 | 0 | 6 | 0 | 0 | 3 | 0 | 0 | 0 | 0 | 2 | 0 | 0 | 2 | 3 | 3 | 3 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Velvetleaf | 6 | 2 | 3 | 0 | 0 | 0 | 0 | 0 | 0 | 4 | 6 | 5 | 5 | 6 | 2 | 0 | 2 | 0 | 0 | 0 | 0 | 0 | 0 | 6 | 4 | 0 | 3 | 3 | 2 |
| Wheat | 0 | 3 | 0 | 0 | 0 | 0 | 0 | 0 | 0 | 0 | 0 | 0 | 0 | 1 | 0 | 0 | 2 | 0 | 0 | 0 | 0 | 0 | 0 | 4 | 0 | 0 | 0 | 0 | 0 |
| Wild oats | 0 | 0 | 0 | 0 | 0 | 0 | 0 | 0 | 0 | 0 | 3 | 0 | 0 | 0 | 0 | 2 | 2 | 0 | 0 | 0 | 0 | 0 | 0 | 2 | 0 | 0 | 0 | 0 | 0 |

| | COMPOUND | | | | | | | | | | | | | | | | | | | | | | | | | | |
|---|---|---|---|---|---|---|---|---|---|---|---|---|---|---|---|---|---|---|---|---|---|---|---|---|---|---|---|
| Rate 125 g/ha | 752 | 753 | 754 | 756 | 757 | 758 | 759 | 760 | 761 | 762 | 763 | 764 | 765 | 766 | 767 | 772 | 773 | 774 | 775 | 776 | 777 | 778 | 779 | 780 | 790 | 791 | 792 |
| Postemergence | | | | | | | | | | | | | | | | | | | | | | | | | | | |
| B. signalgrass | 0 | 0 | 2 | 0 | 0 | 5 | 3 | 0 | 0 | 0 | 3 | 0 | 7 | 2 | 2 | 0 | 0 | 0 | 2 | 0 | 2 | 2 | 3 | 5 | 6 | 0 | 0 |
| Barnyardgrass | — | — | — | — | — | — | — | — | — | — | — | — | — | — | — | — | — | — | — | — | — | — | — | — | — | — | — |
| Bedstraw | 0 | — | 0 | 0 | 0 | 7 | — | — | 0 | 0 | 0 | 5 | — | 0 | 7 | 0 | 0 | 0 | 0 | 3 | 0 | 0 | 0 | 0 | 0 | — | 7 |
| Blackgrass | 2 | 2 | 4 | 0 | 0 | 6 | 5 | 0 | 0 | 0 | 5 | 6 | 5 | 5 | 9 | 0 | 0 | 0 | 0 | 2 | 0 | 4 | 0 | 2 | 5 | 2 | 7 |
| Cocklebur | 3 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 1 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 1 |
| Crabgrass | 3 | 4 | 5 | 0 | 4 | 3 | 4 | 6 | — | 0 | 5 | 6 | 5 | 6 | 8 | 0 | 0 | 0 | 3 | 2 | 4 | 3 | 4 | 4 | — | 4 | 9 |
| Ducksalad | — | — | — | — | — | — | — | — | — | — | — | — | — | — | — | — | — | — | — | — | — | — | — | — | — | — | — |
| Giant foxtail | 9 | 8 | 8 | 0 | 2 | 9 | 5 | 7 | 0 | 0 | 8 | 7 | 8 | 8 | 8 | 0 | 0 | 0 | 7 | 2 | 8 | 8 | 9 | 8 | 9 | 2 | 9 |
| Morningglory | 2 | 2 | 10 | 7 | 6 | 4 | 3 | 3 | 6 | 2 | 7 | 1 | 6 | 2 | 5 | 0 | 0 | 0 | 5 | 7 | 8 | 4 | 6 | 4 | 4 | 3 | 7 |
| Nutsedge | 0 | 0 | 0 | 0 | 0 | 0 | 0 | 0 | 0 | 0 | 0 | 0 | 0 | 3 | 0 | 0 | 0 | 0 | 0 | 0 | — | 0 | 0 | 0 | 0 | 0 | 0 |
| Rape | 2 | 0 | 0 | 0 | 0 | 0 | 0 | 1 | 0 | — | 0 | 0 | 0 | 0 | — | 0 | 0 | 0 | 0 | 2 | 0 | 2 | 0 | 0 | 0 | 3 | 3 |
| Redroot pigweed | 5 | 5 | 0 | 0 | 3 | 8 | 0 | 0 | — | 0 | 0 | 5 | 7 | 6 | 9 | 0 | 0 | 0 | 3 | 2 | 2 | 3 | 2 | 0 | 5 | 6 | 6 |
| Rice | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — |
| Soybean | 5 | 4 | 0 | 2 | 4 | 4 | 3 | 4 | 3 | 2 | 2 | 3 | 3 | 2 | 2 | 0 | 0 | 0 | 5 | 2 | 3 | 3 | 2 | 3 | 3 | 4 | 5 |
| Sugarbeets | 3 | 0 | 0 | 0 | 0 | 0 | 0 | 0 | 3 | 5 | 0 | 0 | 0 | 0 | 3 | 0 | 0 | 0 | 0 | 0 | 3 | 0 | 3 | 0 | 0 | 0 | 1 |
| Velvetleaf | 0 | 0 | 0 | 0 | 2 | 6 | 5 | 0 | 0 | 0 | 0 | 1 | 6 | 3 | 2 | 0 | 0 | 0 | 2 | 3 | 2 | 3 | 2 | 2 | 4 | 2 | 5 |
| Wheat | 5 | 0 | 3 | 0 | 0 | 0 | 0 | 0 | 0 | 0 | 0 | 3 | 0 | 0 | 0 | 0 | 0 | 0 | 0 | 0 | 1 | 2 | 0 | 0 | 4 | 0 | 0 |
| Wild oats | 0 | 0 | 0 | 0 | 0 | 1 | 0 | 0 | 0 | 0 | 0 | 0 | 0 | 0 | 0 | 0 | 0 | 0 | 0 | 0 | 1 | 2 | 0 | 0 | 0 | 0 | 0 |

| | COMPOUND | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Rate 125 g/ha | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
| Preemergence | | | | | | | | | | | | | | | | | | | | | | | | | | | | | | | | | | | | | | | | | | | | |
| B. signalgrass | 0 | 0 | 0 | 7 | 3 | 0 | 0 | 0 | 0 | 5 | 0 | 0 | 0 | 0 | 0 | 0 | 4 | 0 | 2 | 0 | 0 | 2 | 0 | 4 | 0 | 0 | 0 | 0 | 0 | 0 | 0 | 0 | 0 | 1 | 0 | 8 | 0 | 4 | 0 | 0 | 0 | 0 | 0 | 0 |
| Bedstraw | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Blackgrass | 0 | 0 | 0 | 6 | 3 | 0 | 0 | 0 | 0 | 4 | 0 | 0 | 0 | 0 | 0 | 0 | 2 | 0 | 2 | 1 | 0 | 4 | 1 | 1 | 3 | 0 | 0 | 0 | 0 | 3 | 2 | 2 | 0 | 5 | 2 | 5 | 0 | 6 | 0 | 0 | 0 | 0 | 0 | 0 |
| Cocklebur | 0 | 0 | 0 | 0 | 0 | 0 | — | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — |
| Corn | 0 | 4 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 4 | 0 | 0 | 10 | 3 | 7 | 7 | — | 3 | 7 | 0 | 0 | 2 | 0 | 2 | 2 | 6 | 5 | 5 | 2 | 7 | 4 | 3 | 6 | 8 | 0 | 0 | 7 | 4 | 9 | 9 | 6 | 3 | 7 | 3 | 9 | 0 | 5 | 3 | 4 | 4 | 0 | 0 | 0 |
| Giant foxtail | 7 | 6 | 0 | 9 | 7 | 3 | 2 | 5 | 0 | 6 | 0 | 0 | 3 | 9 | 8 | 2 | 7 | 5 | 2 | 5 | 8 | 4 | 2 | 7 | 7 | 0 | 0 | 5 | 1 | 3 | 8 | 8 | 6 | 6 | 7 | 10 | 0 | 10 | 0 | 9 | 9 | 0 | 0 | 0 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | — | — | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 3 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Redroot pigweed | 0 | 0 | 0 | 5 | 6 | 5 | 0 | 4 | 0 | 0 | 0 | 0 | 0 | 0 | 0 | 0 | 10 | 7 | 0 | 2 | 6 | 2 | 0 | 6 | 0 | 0 | 0 | 0 | 0 | 0 | 0 | 0 | 0 | 2 | 0 | 0 | 0 | 10 | 5 | 1 | 1 | 0 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 0 | 0 | 7 | 0 | 0 | 0 | 0 | 0 | 0 | 0 | 0 | 0 | 0 | 0 | 0 | 2 | 0 | 0 | 0 | 0 | 4 | 0 | 3 | 0 | 0 | 0 | 0 | 0 | 0 | 0 | 0 | 0 | 0 | 0 | 0 | 0 | 0 | 0 | 0 | 0 | 0 | 0 | 0 |
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

TABLE B-continued

| Wild oats | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 2 | 2 | 0 | 2 | 0 | 0 | 2 | 0 | 6 | 0 | 0 | 0 | 0 | 0 | 0 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | | | | | | | | | | | | | | | | |
| Rate 125 g/ha | 45 | 46 | 47 | 48 | 49 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 85 | 86 | 87 | 88 | 89 | 90 |
| Preemergence | | | | | | | | | | | | | | | | | | | | | | | | | | | | | | | | | | | | | | | | | | | | |
| B. signalgrass | 2 | 0 | 0 | 0 | 0 | 0 | 0 | 0 | 0 | 0 | 0 | 0 | 0 | 0 | 0 | 1 | 0 | 0 | 0 | 0 | 0 | 0 | 3 | 0 | 0 | 0 | 0 | 0 | 0 | 1 | 0 | 0 | 1 | 0 | 0 | 0 | 0 | 0 | 0 | 2 | 2 | 2 | 0 | 0 |
| Bedstraw | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Blackgrass | 0 | 0 | 0 | 0 | 0 | 0 | 0 | 1 | 0 | 0 | 0 | 0 | 0 | 0 | 0 | 0 | 0 | 0 | 0 | 0 | 0 | 0 | 2 | 0 | 0 | 0 | 0 | 0 | 0 | 1 | 2 | 0 | 4 | 2 | 2 | 4 | 0 | 0 | 0 | 3 | 3 | 4 | 0 | 0 |
| Cocklebur | 0 | 0 | 0 | 0 | 0 | 0 | 0 | — | 0 | 0 | 0 | 0 | 0 | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 1 | 4 | 2 | 6 | 7 | 0 | 1 | 5 | 2 | 0 | 0 | 0 | 0 | 0 | 1 | 4 | 3 | 0 | 0 | 2 | 2 | 4 | 3 | 0 | 0 | 0 | 0 | 5 | 2 | 8 | 4 | 2 | 9 | 7 | 3 | 4 | 0 | 0 | 0 | 8 | 8 | 7 | 0 | 2 |
| Giant foxtail | 10 | 10 | 2 | 9 | 8 | 2 | 5 | 3 | 3 | 0 | 0 | 0 | 0 | 0 | 3 | 7 | 5 | 0 | 0 | 4 | 4 | 7 | 9 | 0 | 0 | 0 | 0 | 7 | 7 | 9 | 9 | 0 | 8 | 8 | 8 | 7 | 0 | 0 | 0 | 9 | 9 | 6 | 0 | 8 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 3 | 0 | 0 | 0 | 0 | 0 | 0 | 0 | 0 | 0 |
| Redroot pigweed | 0 | 0 | 0 | 0 | 0 | 0 | 0 | 0 | 0 | 0 | 0 | 0 | 0 | 0 | 0 | 0 | 0 | 0 | 0 | 0 | 0 | 4 | 2 | 0 | 0 | 0 | 0 | 0 | 0 | 2 | 0 | 0 | 0 | 4 | 7 | 0 | 0 | 0 | 0 | 4 | 4 | 10 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 3 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 3 | 0 | 0 | 0 | 0 | 0 | 0 | 3 | 0 | 0 |
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 2 | 2 | 0 | 0 | 0 | 0 | 0 | 2 | 0 | 0 |

| | COMPOUND | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| Rate 125 g/ha | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 | 114 | 115 | 116 | 117 | 118 | 119 | 120 | 121 |
| Preemergence | | | | | | | | | | | | | | | | | | | | | | | | | | | | | | | |
| B. signalgrass | 10 | — | 7 | 1 | 0 | 0 | 2 | 0 | 0 | 0 | 0 | 0 | 5 | 0 | 1 | 0 | 7 | 6 | 9 | 7 | 1 | 0 | 9 | 0 | 2 | 8 | 9 | 2 | 7 | 3 | 4 |
| Bedstraw | 1 | 0 | 0 | 0 | 0 | 0 | 0 | 0 | 0 | — | 0 | 0 | 0 | 0 | 0 | 0 | 7 | 5 | 10 | 4 | 0 | 0 | 6 | 0 | 0 | 8 | 0 | 0 | 0 | 0 | 0 |
| Blackgrass | 10 | 10 | 10 | 1 | 2 | 3 | 1 | 6 | 3 | 0 | 0 | 0 | 0 | 3 | 7 | 0 | 10 | 7 | 8 | 3 | 0 | 0 | 9 | 8 | 0 | 9 | 8 | 2 | 8 | 3 | 4 |
| Cocklebur | 0 | — | 2 | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 0 | 0 | 0 | 0 | 0 | 0 |
| Corn | 6 | 2 | 7 | 2 | 0 | 0 | 0 | 0 | 0 | 0 | 0 | 0 | 0 | 0 | 0 | 0 | 7 | 0 | 3 | 3 | 1 | 0 | 4 | 0 | 0 | 2 | 2 | 0 | 0 | 0 | 0 |
| Crabgrass | 10 | 10 | 9 | 3 | 6 | 4 | 0 | 7 | 8 | 0 | 0 | 0 | 6 | 0 | 8 | 0 | 10 | 9 | 10 | 3 | 7 | 6 | 10 | 7 | 4 | 10 | 10 | 9 | — | 6 | 7 |
| Giant foxtail | 10 | 10 | 10 | 9 | 4 | 2 | 3 | 8 | 10 | 0 | 0 | 4 | 9 | 4 | 10 | 5 | 10 | 10 | 10 | 10 | 9 | 10 | 10 | 9 | 9 | 10 | 10 | 10 | 10 | 9 | 8 |
| Morningglory | 0 | 0 | 0 | 0 | 0 | 0 | 0 | 0 | 0 | 0 | 0 | 0 | 0 | 0 | 0 | 0 | 0 | 0 | 5 | 0 | 0 | 2 | 2 | 0 | 0 | 0 | 0 | 0 | 2 | 0 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 8 | 9 | 7 | 0 | 0 | 0 | 0 | 0 | 0 | 0 | 0 | 0 | 0 | 0 | 1 | 0 | 8 | 0 | 8 | 1 | 0 | 0 | 7 | 3 | 0 | 9 | 10 | 0 | 6 | 0 | 0 |
| Redroot pigweed | 9 | 7 | 8 | 0 | 6 | 6 | — | 4 | 0 | 0 | 0 | 0 | 0 | 0 | 3 | 0 | 10 | 3 | 10 | 6 | 6 | 2 | 8 | 8 | 5 | 10 | 10 | 0 | 10 | 8 | 7 |
| Soybean | 0 | 3 | 2 | 0 | 0 | 0 | 0 | 0 | 0 | 0 | 0 | 0 | 0 | 0 | 0 | 0 | 3 | 0 | 7 | 5 | 4 | 0 | 8 | 0 | 0 | 7 | 8 | 0 | 0 | 0 | 0 |
| Sugarbeets | 7 | 6 | 7 | 0 | 1 | 0 | 3 | 0 | 2 | 0 | 0 | 0 | 0 | 0 | 1 | 0 | 7 | 3 | 10 | 1 | 0 | 0 | 8 | 6 | 0 | 10 | 8 | 0 | 4 | 2 | 3 |
| Velvetleaf | 6 | 6 | 6 | 0 | 0 | 0 | 0 | 0 | 0 | 0 | 0 | 0 | 0 | 0 | 4 | 0 | 10 | 4 | 7 | 5 | 0 | 2 | 7 | 4 | 0 | 9 | 8 | 0 | 4 | 0 | 0 |
| Wheat | 4 | 6 | 3 | 0 | 0 | 0 | 0 | 0 | 0 | 0 | 0 | 0 | 0 | 0 | 0 | 0 | 5 | 0 | 5 | 0 | 0 | 0 | 4 | 0 | 0 | 5 | 4 | 0 | 0 | 0 | 0 |
| Wild oats | 9 | 8 | 8 | 3 | 0 | 0 | 2 | 0 | 3 | 0 | 0 | 0 | 0 | 2 | 3 | 0 | 9 | 9 | 10 | 3 | 0 | 0 | 10 | 7 | 0 | 7 | 6 | 1 | 6 | 2 | 0 |

TABLE B-continued

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 122 | 123 | 124 | 125 | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 | 149 | 150 |
| Preemergence | | | | | | | | | | | | | | | | | | | | | | | | | | | | | |
| B. signalgrass | 0 | 0 | 0 | 0 | 0 | 0 | 0 | 2 | 9 | 8 | 3 | 5 | 2 | 0 | 3 | 5 | 4 | 2 | 0 | 0 | 0 | 0 | 0 | 0 | 9 | 7 | 5 | 0 | 0 |
| Bedstraw | 0 | 0 | 0 | 0 | 0 | 0 | 0 | 0 | 0 | 10 | 0 | 0 | 0 | 0 | 0 | 7 | 7 | 0 | 0 | 0 | 0 | 0 | 0 | 0 | 9 | 2 | 0 | 0 | 0 |
| Blackgrass | 0 | 0 | 0 | 0 | 0 | 0 | 0 | 0 | 9 | 10 | 6 | 3 | 0 | 0 | 4 | 9 | 9 | 6 | 0 | 0 | 0 | 5 | 1 | 1 | 10 | 8 | 4 | 0 | 0 |
| Cocklebur | — | 0 | — | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | 0 |
| Corn | 0 | 0 | 0 | 0 | 0 | 0 | 0 | 0 | 3 | 5 | 0 | 0 | 0 | 0 | 0 | 0 | 3 | 0 | 0 | 0 | 0 | 0 | 0 | 0 | 5 | 7 | 0 | 0 | 0 |
| Crabgrass | 4 | 5 | 0 | 0 | 0 | 0 | 0 | 7 | 9 | 7 | 7 | 3 | 6 | 0 | 4 | 10 | 9 | 10 | 6 | 0 | 2 | 7 | 7 | 4 | 8 | 8 | 8 | 0 | 1 |
| Giant foxtail | 9 | 9 | 0 | 0 | 0 | 0 | 0 | 7 | 9 | 10 | 8 | 7 | 9 | 0 | 4 | 9 | 9 | 10 | 8 | 0 | 4 | 9 | 6 | 3 | 10 | 8 | 9 | 0 | 0 |
| Morningglory | 0 | 0 | 0 | 0 | 0 | 0 | 0 | 0 | 0 | 3 | 0 | 0 | 0 | 0 | 0 | 0 | 0 | 0 | 0 | 0 | 0 | 0 | 0 | 0 | 3 | 1 | 0 | 0 | 0 |
| Nutsedge | 0 | 0 | 0 | 0 | 0 | 0 | 0 | 0 | 0 | 0 | 0 | 0 | 0 | 0 | 0 | 0 | 5 | 0 | 0 | 0 | 0 | 0 | 0 | 0 | 0 | 0 | 0 | 0 | 0 |
| Rape | 0 | 0 | 0 | 0 | 0 | 0 | 0 | 0 | 9 | 10 | 0 | 0 | 0 | 0 | 0 | 4 | 9 | 0 | 0 | 0 | 0 | 3 | 0 | 0 | 10 | 7 | 0 | 0 | 0 |
| Redroot pigweed | 5 | 4 | 0 | 0 | 0 | 0 | 0 | 2 | 10 | 10 | 6 | 0 | 0 | 3 | 8 | 10 | 10 | 8 | 0 | 0 | 0 | 0 | 0 | 0 | 10 | 8 | 9 | 0 | 8 |
| Soybean | 0 | 0 | 0 | 0 | 0 | 0 | 0 | 0 | 0 | 3 | 0 | 0 | 0 | 0 | 0 | 0 | 4 | 0 | 0 | 0 | 0 | 0 | 0 | 0 | 0 | 3 | 0 | 0 | 0 |
| Sugarbeets | 0 | 3 | 0 | 0 | 0 | 0 | 0 | 3 | 9 | 8 | 5 | 2 | 2 | 0 | 4 | 10 | 10 | 3 | 0 | 0 | 0 | 1 | 0 | 0 | 9 | 2 | 6 | 0 | 0 |
| Velvetleaf | 0 | 0 | 0 | 0 | 0 | 0 | 0 | 0 | 8 | 8 | 4 | 0 | 0 | 0 | 0 | 6 | 8 | 3 | 0 | 0 | 0 | 0 | 0 | 0 | 7 | 4 | 6 | 0 | 0 |
| Wheat | 0 | 0 | 0 | 0 | 0 | 0 | 0 | 0 | 3 | 8 | 0 | 0 | 0 | 0 | 0 | 4 | 5 | 0 | 0 | 0 | 0 | 0 | 0 | 0 | 2 | 6 | 3 | 0 | 0 |
| Wild oats | 0 | 2 | 0 | 0 | 0 | 0 | 0 | 5 | 8 | 10 | 5 | 2 | 0 | 0 | 0 | 8 | 9 | 7 | 0 | 0 | 0 | 5 | 2 | 0 | 10 | 6 | 6 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 151 | 152 | 153 | 154 | 155 | 156 | 157 | 158 | 159 | 160 | 161 | 162 | 163 | 164 | 165 | 166 | 167 | 168 | 169 | 170 | 171 | 172 | 173 | 174 | 175 | 176 | 177 | 178 | 179 |
| Preemergence | | | | | | | | | | | | | | | | | | | | | | | | | | | | | |
| B. signalgrass | — | 4 | 0 | 0 | 0 | 0 | 0 | 0 | 0 | 0 | 0 | 2 | 2 | 0 | 4 | 0 | 5 | 2 | 7 | 9 | 1 | 5 | 0 | 0 | 0 | 0 | 0 | 7 | 8 |
| Bedstraw | 0 | 0 | 0 | 0 | 0 | 0 | 0 | 0 | 0 | 0 | 0 | 0 | 0 | 0 | 1 | 0 | 0 | 0 | 0 | 0 | 0 | 0 | 0 | 0 | 2 | 0 | 0 | 0 | 0 |
| Blackgrass | 9 | 0 | 0 | 0 | 0 | 0 | 0 | 0 | 0 | 0 | — | 2 | 7 | 0 | 3 | 0 | 0 | 1 | 3 | 10 | 0 | 0 | 0 | 2 | 0 | 0 | 0 | 0 | 0 |
| Cocklebur | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 |
| Crabgrass | 10 | 0 | 0 | 0 | 0 | 4 | 2 | 3 | 0 | 0 | 8 | 8 | — | 0 | 7 | 4 | 8 | 3 | 8 | 10 | 7 | 8 | 6 | 8 | 6 | 8 | 6 | 2 | 7 |
| Giant foxtail | 10 | 0 | 0 | 0 | 0 | 2 | 6 | 4 | 0 | 0 | 9 | 7 | 8 | 0 | 7 | 5 | 9 | 8 | 10 | 10 | 7 | 9 | 9 | 9 | 7 | 6 | 3 | 4 | 9 |
| Morningglory | 0 | 0 | 0 | 0 | 0 | 0 | 0 | 0 | 0 | 0 | 0 | 0 | 0 | 0 | 0 | 0 | 0 | 0 | 0 | 3 | 0 | 0 | 0 | 0 | 0 | 0 | 0 | 0 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 | 9 | 0 | 0 | 0 | 0 | 0 | 0 | 0 | 0 | 0 |
| Rape | 8 | 0 | 0 | 0 | 0 | 0 | 0 | 0 | 0 | 0 | 0 | 2 | 0 | 0 | 0 | 0 | 0 | 0 | 2 | 8 | 0 | 0 | 0 | 0 | 0 | 0 | 0 | 0 | 0 |
| Redroot pigweed | 10 | 0 | 0 | 7 | 0 | 4 | 0 | 0 | 0 | 0 | 0 | 0 | — | 0 | 0 | 0 | 6 | 0 | 6 | 10 | 0 | 6 | 0 | 6 | 0 | 0 | 0 | 0 | 7 |
| Soybean | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 0 | 0 | 0 | 0 | 0 | 0 | 0 |
| Sugarbeets | 8 | 0 | 0 | 0 | 0 | 0 | 0 | 0 | 0 | 0 | 0 | 0 | 3 | 0 | 4 | 0 | 2 | 0 | 0 | 8 | 0 | 2 | 2 | 3 | 0 | 0 | 0 | 0 | 0 |
| Velvetleaf | 8 | 0 | 0 | 0 | 0 | 0 | 0 | 0 | 0 | 0 | 0 | 0 | 2 | 0 | 1 | 0 | 0 | 0 | 2 | 7 | 0 | 0 | 0 | 0 | 0 | 0 | 0 | 0 | 0 |
| Wheat | 2 | 0 | 0 | 0 | 0 | 0 | 0 | 0 | 0 | 0 | 0 | 0 | 2 | 0 | 0 | 0 | 0 | 0 | 0 | 6 | 0 | 0 | 0 | 0 | 0 | 0 | 0 | 0 | 0 |
| Wild oats | 9 | 0 | 0 | 0 | 0 | 0 | 0 | 0 | 0 | 0 | 0 | 0 | 3 | 0 | 4 | 0 | 0 | 0 | 8 | 9 | 2 | 0 | 0 | 0 | 0 | 0 | 0 | 0 | 0 |

TABLE B-continued

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 180 | 181 | 182 | 183 | 184 | 185 | 186 | 187 | 188 | 189 | 190 | 191 | 192 | 193 | 194 | 195 | 196 | 197 | 198 | 199 | 200 | 201 | 202 | 203 | 204 | 205 | 206 | 207 | 208 |
| Preemergence | | | | | | | | | | | | | | | | | | | | | | | | | | | | | |
| B. signalgrass | 0 | 0 | 0 | 0 | 5 | 0 | 0 | 0 | 0 | — | 0 | 0 | 0 | 0 | 0 | 0 | 0 | 0 | 0 | 1 | 0 | 0 | 0 | 0 | 0 | 0 | 0 | 0 | 0 |
| Bedstraw | 0 | 0 | 0 | 0 | 0 | 0 | 0 | 0 | 0 | 0 | — | 0 | 0 | 0 | 0 | 0 | 0 | 0 | 0 | 0 | — | 0 | 0 | 0 | 0 | 0 | 0 | 0 | 0 |
| Blackgrass | 0 | 0 | 0 | 0 | 3 | 0 | 0 | 0 | 0 | 4 | 0 | 0 | 5 | 0 | 2 | 1 | 0 | 0 | 0 | 10 | 5 | 0 | 0 | 0 | 2 | 0 | 0 | 0 | 0 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 0 | 5 | 6 | 6 | 0 | 0 | 0 | 0 | 3 | 6 | 4 | 9 | 4 | 0 | 0 | 0 | 6 | 2 | 5 | 4 | 0 | 8 | 0 | 0 | 0 | 5 |
| Giant foxtail | 0 | 0 | 0 | 0 | 9 | 5 | 9 | 0 | 2 | 0 | 0 | 8 | 9 | 4 | 8 | 3 | 0 | 0 | 0 | 10 | 4 | 6 | 6 | 0 | 9 | 0 | 3 | 6 | 8 |
| Morningglory | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | — | 0 | 0 | 0 | 0 | — | 0 | 0 | 0 | — | — | 0 | 0 | 0 | 0 | 0 | 0 | — | 0 | 0 | — | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Redroot pigweed | 0 | 0 | 0 | 0 | 0 | 0 | 0 | 0 | 0 | 0 | 0 | 0 | 2 | 0 | 7 | 0 | 0 | 0 | 0 | 7 | 0 | 0 | 0 | 0 | 0 | 0 | 0 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 0 | 0 |
| Sugarbeets | 0 | 0 | 0 | 0 | 0 | 0 | 0 | 0 | 0 | 0 | 0 | 0 | 0 | 0 | 0 | 0 | 0 | 0 | 0 | 5 | 0 | 0 | 0 | 0 | 0 | 0 | 0 | 0 | 0 |
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 0 | 0 | 0 | 0 | 0 | 0 | 0 | 0 | 0 | 0 | 0 | 0 | 0 | 0 | 2 | 0 | 0 | 0 | 0 | 2 | 0 | 2 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 210 | 211 | 212 | 213 | 214 | 215 | 216 | 217 | 218 | 219 | 220 | 221 | 222 | 223 | 224 | 225 | 226 | 227 | 228 | 229 | 230 | 231 | 232 | 233 | 234 | 235 | 236 | 237 | 238 |
| Preemergence | | | | | | | | | | | | | | | | | | | | | | | | | | | | | |
| B. signalgrass | 0 | 0 | 1 | 0 | 0 | 0 | 1 | 0 | 4 | 6 | 7 | 5 | 0 | 0 | 3 | 7 | 6 | 0 | 0 | 0 | 0 | 0 | 0 | 2 | 0 | 0 | 0 | 0 | 0 |
| Bedstraw | 0 | 0 | 0 | 0 | 0 | 0 | 0 | 0 | 0 | 5 | 4 | 4 | 0 | 0 | 0 | 0 | 0 | 0 | 0 | 0 | 0 | 0 | 0 | 0 | 0 | 0 | 0 | 0 | 0 |
| Blackgrass | 0 | 9 | 4 | 0 | — | 6 | 2 | 6 | 9 | 10 | 9 | 7 | 0 | 1 | 2 | 10 | 10 | 5 | 0 | 0 | 0 | 0 | 6 | 2 | 0 | 0 | 2 | 0 | 0 |
| Cocklebur | 0 | 0 | — | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 3 | 0 | 0 | 0 | 0 | 3 | 0 | 0 | 0 | 0 | 0 | 0 | 0 | 0 | 0 | 0 | 0 | 0 | 0 |
| Crabgrass | 0 | 0 | 4 | 0 | 0 | 4 | 3 | 4 | 4 | 8 | 7 | 8 | 6 | 6 | 5 | 10 | 9 | 10 | 0 | 0 | 1 | 0 | 7 | 6 | 0 | 0 | 3 | 0 | 6 |
| Giant foxtail | 0 | 4 | 4 | 2 | 3 | 3 | 6 | 8 | 9 | 10 | 9 | 9 | 5 | 9 | 7 | 10 | 10 | 10 | 6 | 0 | 2 | 0 | 8 | 7 | 0 | 0 | 7 | 0 | 6 |
| Morningglory | 0 | 0 | 0 | 0 | 0 | 0 | 0 | 0 | 0 | 0 | 0 | 0 | 0 | 1 | 0 | 4 | 0 | 0 | 0 | 0 | 0 | 0 | 0 | 0 | 0 | 0 | 0 | 0 | 0 |
| Nutsedge | 0 | — | 0 | 0 | — | 0 | 0 | 0 | — | — | — | 0 | 0 | 0 | — | 7 | — | 0 | 0 | 0 | 0 | 0 | 0 | — | — | — | — | — | 0 |
| Rape | 0 | 0 | 0 | 0 | 0 | 0 | 0 | 0 | 0 | 0 | 6 | 6 | 0 | 0 | 0 | 0 | 0 | 4 | 0 | 0 | 0 | 0 | 0 | 0 | 0 | 0 | 0 | 0 | 0 |
| Redroot pigweed | 0 | 0 | 9 | 4 | 0 | 4 | 0 | 5 | 1 | 4 | 2 | 10 | 0 | 0 | 0 | 7 | 0 | 5 | 0 | 0 | 0 | 0 | 0 | 6 | 0 | 0 | 0 | 0 | 0 |
| Soybean | 0 | 0 | 0 | 0 | 0 | 0 | 0 | 0 | 2 | 0 | 0 | 0 | 0 | 0 | 0 | 2 | 0 | 0 | 0 | 0 | 0 | 0 | 0 | 0 | 0 | 0 | 0 | 0 | 0 |
| Sugarbeets | 0 | 0 | 5 | 0 | 0 | 2 | 0 | 0 | 1 | 4 | 6 | 4 | 0 | 0 | 0 | 2 | 3 | 3 | 0 | 0 | 0 | 0 | 0 | 0 | 0 | 0 | 0 | 0 | 0 |
| Velvetleaf | 0 | 0 | — | 0 | 0 | 0 | 0 | 1 | 0 | 6 | 3 | 0 | 0 | 0 | 0 | 5 | 5 | 0 | 0 | 0 | 0 | 0 | 0 | 0 | 0 | 0 | 0 | 0 | 0 |
| Wheat | 0 | 0 | 0 | 0 | 0 | 0 | 0 | 3 | 0 | 5 | 7 | 2 | 0 | 0 | 0 | 6 | 8 | 0 | 0 | 0 | 0 | 0 | 0 | 0 | 0 | 0 | 0 | 0 | 0 |
| Wild oats | 0 | 4 | — | 0 | 0 | 0 | 0 | 0 | 6 | 5 | 5 | 2 | 0 | 0 | 0 | 7 | 3 | 0 | 0 | 0 | 0 | 0 | 0 | 1 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 239 | 240 | 241 | 242 | 243 | 244 | 245 | 246 | 247 | 248 | 249 | 250 | 251 | 252 | 253 | 254 | 255 | 256 | 257 | 258 | 259 | 260 | 261 | 262 | 263 | 264 | 265 | 266 | 267 |
| B. signalgrass | 0 | 0 | 2 | 9 | 5 | 0 | 7 | 2 | 0 | 0 | 0 | 0 | 3 | 0 | 0 | 0 | 2 | 0 | 0 | 4 | 5 | 0 | 0 | 0 | 0 | 0 | 0 | 0 | 0 |
| Bedstraw | 0 | 0 | 0 | 7 | 0 | 0 | 2 | 0 | 0 | 0 | — | 0 | 0 | 0 | 0 | 0 | 0 | 0 | 0 | 3 | 10 | 0 | — | 0 | 0 | 0 | 0 | 3 | 0 |

TABLE B-continued

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Blackgrass | 3 | 0 | 6 | 10 | 10 | 0 | 10 | 5 | 0 | 0 | 0 | 0 | 8 | 2 | 0 | 0 | 10 | 0 | 0 | 8 | 10 | 0 | 0 | 0 | 0 | 0 | — | 8 | 2 |
| Cocklebur | 0 | 0 | 0 | — | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 3 | 0 | 5 | 0 | 0 | 0 | 0 | 0 | 0 | 0 | 0 | 0 | 0 | 0 | 0 | 2 | 0 | 0 | 0 | 0 | 0 | 0 | 0 | 0 | 0 |
| Crabgrass | 7 | 4 | 7 | 10 | 8 | 0 | 9 | 3 | 0 | 0 | 0 | 4 | 7 | 2 | 0 | 0 | 3 | 2 | 2 | 7 | 4 | 2 | 3 | 2 | 0 | 2 | 2 | 1 | 0 |
| Giant foxtail | 10 | 5 | 10 | 10 | 10 | 0 | 9 | 9 | 0 | 0 | 0 | 8 | 10 | 9 | 0 | 3 | 9 | 5 | 6 | 9 | 9 | 7 | 8 | 3 | 9 | 7 | 8 | 4 | 8 |
| Morningglory | 0 | 0 | 0 | 2 | 3 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | — | 0 | 10 | 0 | 0 | — | — | — | 0 | 0 | — | — | — | — | 0 | — | — | 0 | — | 0 | 0 | 0 | 0 | 0 | — | — | 0 | 0 |
| Rape | 0 | 0 | 0 | 6 | 5 | 0 | 4 | 2 | 0 | 0 | 0 | 0 | 9 | 0 | 0 | 0 | 0 | 0 | 0 | 1 | 0 | 0 | 0 | 0 | 0 | 0 | 0 | 0 | 0 |
| Redroot pigweed | 0 | 0 | 0 | 10 | 9 | 0 | 10 | 0 | 0 | 0 | 0 | 3 | 5 | 0 | 0 | 0 | 2 | 0 | 0 | 2 | 0 | 0 | 0 | 0 | 0 | 0 | 0 | 0 | 3 |
| Soybean | 0 | 0 | 0 | 2 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 0 | 0 | 7 | 3 | 0 | 8 | 1 | 0 | 0 | 0 | 0 | 10 | 3 | 0 | 2 | 3 | 0 | 0 | 2 | 0 | 0 | 0 | 0 | 0 | 0 | 0 | 5 | 0 |
| Velvetleaf | 0 | 0 | 5 | 8 | 6 | 0 | 7 | 2 | 0 | 0 | 0 | 0 | 4 | 0 | 0 | 0 | 0 | 0 | 0 | 5 | 2 | 0 | 0 | 0 | 0 | 0 | 0 | 0 | 0 |
| Wheat | 0 | 0 | 0 | 7 | 8 | 0 | 6 | 0 | 0 | 0 | 0 | 0 | 0 | 0 | 0 | 0 | 0 | 0 | 0 | 4 | 0 | 0 | 0 | 0 | 0 | 0 | 0 | 0 | 0 |
| Wild oats | 0 | 0 | 5 | 9 | 6 | 0 | 5 | 3 | 0 | 0 | 0 | 0 | 6 | 0 | 0 | 0 | 2 | 0 | 0 | 4 | 2 | 0 | 0 | 0 | 0 | 4 | 0 | 2 | 0 |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate 125 g/ha | 268 | 269 | 270 | 271 | 272 | 273 | 274 | 276 | 277 | 278 | 279 | 280 | 281 | 282 | 283 | 284 | 285 | 286 | 287 | 288 | 289 | 290 | 291 | 292 | 293 | 294 | 295 | 296 | 297 |
| Preemergence | | | | | | | | | | | | | | | | | | | | | | | | | | | | | |
| B. signalgrass | 0 | 6 | 0 | 8 | 0 | 0 | 0 | 7 | 9 | 0 | 0 | 0 | 0 | 1 | 10 | 5 | 5 | 3 | 10 | 4 | 7 | 0 | 3 | 0 | 3 | 7 | 6 | 0 | 0 |
| Bedstraw | 0 | 0 | 0 | 10 | 0 | 0 | 0 | 0 | 0 | 0 | 0 | 0 | 3 | — | 0 | 8 | 0 | 0 | 10 | 2 | 4 | 3 | 0 | 0 | 0 | 0 | 0 | 0 | 0 |
| Blackgrass | 0 | 2 | 0 | 9 | 0 | 0 | 0 | 6 | 9 | 0 | 0 | 0 | 1 | 1 | 8 | 4 | 4 | 0 | 10 | 2 | 9 | 2 | 8 | 0 | 7 | 3 | 10 | 0 | 0 |
| Cocklebur | 0 | — | 0 | 0 | 0 | 0 | 0 | 0 | 0 | 0 | — | 0 | — | 0 | 0 | — | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 2 | 0 | 5 | 0 | 6 | 0 | 4 | 4 | 1 | 0 | 0 | 10 | 1 | 7 | 4 | 8 | 2 | 9 | 2 | 3 | 3 | 0 | 0 | 3 | 9 | 7 | 0 | 2 |
| Giant foxtail | 0 | 6 | 0 | 10 | 5 | 8 | 3 | 10 | 10 | 2 | 3 | 0 | 9 | 8 | 9 | 9 | 9 | 10 | 10 | 9 | 10 | 9 | 9 | 0 | 9 | 9 | 10 | 0 | 0 |
| Morningglory | 0 | 0 | 0 | 1 | 0 | 0 | 0 | 0 | 0 | 0 | 0 | 0 | 0 | 0 | 0 | 1 | 0 | 0 | 0 | 0 | 0 | 0 | 0 | 0 | 0 | 0 | 0 | 0 | 0 |
| Nutsedge | 0 | 0 | 0 | 0 | 0 | — | 0 | 0 | 0 | 0 | — | 0 | 0 | 0 | 0 | 0 | 0 | 0 | 6 | 0 | 0 | — | 0 | 0 | 0 | 0 | 0 | 0 | 0 |
| Rape | 0 | 0 | 0 | 4 | 0 | 0 | 0 | 0 | 1 | 0 | 0 | 0 | 0 | 0 | — | 2 | 0 | 0 | 8 | 0 | 8 | 0 | 0 | 0 | 6 | 0 | 2 | 0 | 0 |
| Redroot pigweed | 0 | 0 | 0 | 8 | 0 | 0 | 0 | 0 | 0 | 0 | 0 | 0 | 0 | 6 | 6 | 6 | 2 | 0 | 8 | 0 | 6 | 7 | 0 | 0 | 8 | 0 | 6 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 6 | 0 | 0 | 0 | 0 | 0 | 0 | 0 | 0 | 0 | 0 |
| Sugarbeets | 0 | 0 | 0 | 6 | 0 | 0 | 0 | 1 | 1 | 0 | 0 | 0 | 0 | 0 | 0 | 5 | 0 | 0 | 6 | 0 | 6 | 5 | 0 | 0 | 4 | 0 | 0 | 0 | 0 |
| Velvetleaf | 0 | 0 | 0 | 4 | 0 | 0 | 0 | 0 | 1 | 0 | 0 | 0 | 0 | 0 | 2 | 0 | 2 | 0 | 7 | 0 | 6 | 0 | 0 | 0 | 4 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 7 | 0 | 2 | 0 | 0 | 0 | 7 | 0 | 3 | 0 | 0 |
| Wild oats | 0 | 2 | 0 | 5 | 0 | 0 | 0 | 2 | 7 | 0 | 0 | 0 | 0 | 2 | 1 | 0 | 0 | 0 | 8 | 2 | 8 | 4 | 0 | 0 | 2 | 0 | 8 | 0 | 0 |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate 125 g/ha | 298 | 299 | 300 | 301 | 302 | 303 | 304 | 305 | 306 | 307 | 308 | 309 | 310 | 311 | 312 | 313 | 314 | 315 | 316 | 317 | 318 | 319 | 320 | 321 | 322 | 323 | 324 | 325 | 326 |
| Preemergence | | | | | | | | | | | | | | | | | | | | | | | | | | | | | |
| B. signalgrass | 0 | 9 | 0 | 0 | 0 | 0 | 0 | 0 | 0 | 0 | 0 | 0 | 4 | 0 | 0 | 0 | 2 | 2 | 7 | 6 | 0 | 0 | 1 | 0 | 0 | 0 | 0 | 0 | 0 |
| Bedstraw | 0 | 10 | — | 0 | 0 | 0 | 0 | — | 0 | 0 | 0 | 0 | 3 | 0 | 0 | — | 0 | — | 0 | — | 0 | 0 | — | — | 0 | 0 | 0 | 0 | — |
| Blackgrass | — | 10 | 0 | 0 | 0 | 0 | 0 | 0 | 0 | 0 | 0 | 0 | 10 | 0 | 0 | 0 | 7 | 7 | 10 | 8 | 0 | 0 | 2 | 6 | 0 | 0 | 0 | 1 | 5 |
| Cocklebur | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 |
| Crabgrass | 0 | 9 | 2 | 0 | 0 | 0 | 4 | 4 | 0 | 0 | 0 | 1 | 5 | 0 | 0 | 0 | 3 | 5 | 8 | 7 | 0 | 0 | 3 | 2 | 2 | 0 | 0 | 0 | 0 |
| Giant foxtail | 0 | 10 | 5 | 0 | 6 | 0 | 4 | 8 | 2 | 8 | 0 | 9 | 10 | 0 | 0 | 0 | 6 | 9 | 10 | 10 | 0 | 7 | — | 8 | 9 | 0 | 0 | 7 | 2 |
| Morningglory | 0 | 2 | 0 | 0 | 0 | 0 | 0 | 0 | 0 | 0 | 0 | 0 | 6 | 0 | 0 | 0 | 0 | 0 | 0 | 0 | 0 | 0 | 0 | 0 | 0 | 0 | 0 | 0 | 0 |

TABLE B-continued

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Nutsedge | 0 | 0 | 0 | 0 | 0 | — | 0 | 0 | 0 | 0 | 0 | 0 | 0 | 0 | 0 | 0 | — | — | 0 | — | 0 | 0 | 0 | 0 | 0 | 0 | 0 | 0 | — |
| Rape | 0 | 8 | 0 | 0 | 0 | 0 | 0 | 0 | 0 | 0 | 0 | 0 | 6 | 0 | 0 | 0 | — | 0 | 0 | 2 | 0 | 0 | 0 | 0 | 0 | 0 | 0 | 0 | 0 |
| Redroot pigweed | 0 | 10 | 0 | 0 | 0 | 0 | 0 | 0 | 0 | 0 | 0 | 0 | 10 | 0 | 0 | 0 | 2 | 0 | 6 | 7 | 0 | 0 | 0 | 0 | 6 | 0 | 0 | 0 | 3 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 8 | 0 | 0 | 0 | 0 | 1 | 0 | 0 | 0 | 0 | 0 | 7 | 0 | 0 | 0 | 2 | 0 | 0 | 4 | 0 | 0 | 0 | 0 | 2 | 0 | 0 | 0 | 0 |
| Velvetleaf | 0 | 7 | 0 | 0 | 0 | 0 | 0 | 0 | 0 | 0 | 0 | 0 | 3 | 0 | 0 | 0 | 0 | 0 | 2 | 6 | 0 | 0 | 0 | 0 | 0 | 0 | 0 | 0 | 0 |
| Wheat | 0 | 7 | 0 | 0 | 0 | 0 | 0 | 0 | 0 | 0 | 0 | 0 | 2 | 0 | 0 | 0 | 0 | 0 | 0 | 2 | 0 | 0 | 0 | 0 | 0 | 0 | 0 | 0 | 0 |
| Wild oats | 0 | 7 | 0 | 0 | 0 | 0 | 0 | 0 | 0 | 0 | 0 | 0 | 9 | 0 | 0 | 0 | 2 | 0 | 4 | 8 | 0 | 0 | 0 | 0 | 0 | 0 | 0 | 0 | 1 |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate 125 g/ha | 327 | 328 | 329 | 330 | 331 | 332 | 333 | 334 | 335 | 336 | 337 | 338 | 339 | 340 | 341 | 342 | 343 | 344 | 345 | 348 | 349 | 350 | 351 | 352 | 353 | 354 | 355 | 356 | 357 |
| Preemergence | | | | | | | | | | | | | | | | | | | | | | | | | | | | | |
| B. signalgrass | 0 | 0 | 0 | 0 | 0 | 0 | 0 | 0 | 0 | 0 | 0 | 0 | 0 | 0 | 0 | 0 | 4 | 0 | 0 | 3 | — | 0 | 0 | 6 | 2 | 5 | 2 | 3 | 3 |
| Bedstraw | — | 0 | 0 | 0 | — | 0 | 0 | 0 | 0 | 0 | 0 | 0 | 0 | 0 | 0 | 0 | — | 0 | 0 | — | — | 10 | — | 0 | 0 | 0 | — | 0 | 10 |
| Blackgrass | 0 | 0 | 0 | 0 | 0 | 0 | 0 | 0 | 0 | 0 | 0 | 0 | 0 | 2 | 2 | 3 | 8 | 0 | 0 | 6 | 2 | 5 | 2 | 10 | — | 4 | 4 | 6 | 8 |
| Cocklebur | 0 | 0 | 0 | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 5 | 3 | 0 | 0 | 0 | 0 |
| Crabgrass | 2 | 0 | 0 | 0 | 0 | 0 | 0 | 0 | 0 | 0 | 0 | 0 | 0 | 3 | 2 | 6 | 9 | 0 | 0 | 7 | 6 | 8 | 10 | 10 | 9 | 9 | 10 | 8 | 9 |
| Giant foxtail | 8 | 5 | 0 | 0 | — | 1 | 0 | 0 | 4 | 0 | 0 | 0 | 3 | 10 | 9 | 9 | 10 | 2 | 0 | 10 | 9 | 10 | 10 | 10 | 10 | 10 | 10 | 10 | 10 |
| Morningglory | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 2 |
| Nutsedge | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 3 | 0 | 0 | 1 | 0 | 2 | 2 |
| Redroot pigweed | 0 | 0 | 0 | 0 | 0 | 0 | 0 | 0 | 0 | 0 | 0 | 0 | 0 | 0 | 0 | 0 | 10 | 0 | 0 | 0 | 0 | 10 | 10 | 3 | 10 | 7 | 7 | 4 | 10 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 0 | 0 | 0 | 0 | 0 | 0 | 0 | 0 | 0 | 0 | 0 | 0 | 0 | 0 | 0 | 0 | 0 | 0 | 0 | 2 | 2 | 2 | 3 | 2 | 0 | 0 | 0 | 3 |
| Velvetleaf | 0 | 0 | 0 | 0 | 0 | 0 | 0 | 0 | 0 | 0 | 0 | 0 | 0 | 0 | 0 | 0 | 6 | 0 | 0 | 3 | 0 | 2 | 3 | 4 | 1 | 5 | 2 | 2 | 5 |
| Wheat | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 6 |
| Wild oats | 0 | 0 | 0 | 0 | 0 | 0 | 0 | 0 | 0 | 0 | 0 | 0 | 0 | 0 | 0 | 0 | 4 | 0 | 0 | 4 | 0 | 3 | 0 | 8 | 1 | 4 | 0 | 7 | 10 |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate 125 g/ha | 358 | 359 | 360 | 361 | 362 | 363 | 364 | 365 | 367 | 368 | 369 | 370 | 371 | 372 | 373 | 374 | 375 | 376 | 378 | 379 | 380 | 381 | 382 | 383 | 384 | 385 | 387 | 388 | 389 |
| Preemergence | | | | | | | | | | | | | | | | | | | | | | | | | | | | | |
| B. signalgrass | 3 | 0 | 6 | 4 | 6 | 3 | 0 | 0 | 0 | 6 | 0 | 0 | 2 | 4 | 0 | 0 | 0 | 0 | 0 | 0 | 0 | 0 | 0 | 0 | 0 | 0 | 0 | 2 | 0 |
| Bedstraw | 9 | 0 | — | 0 | 9 | 9 | 0 | 0 | 10 | 2 | — | 3 | — | 2 | 0 | 0 | 10 | — | 0 | 0 | — | 0 | — | — | — | — | 0 | — | — |
| Blackgrass | 8 | 0 | 9 | 8 | 10 | 10 | 0 | 0 | 7 | 9 | 0 | 8 | 9 | 6 | 3 | 2 | 5 | 0 | 0 | 0 | 0 | 0 | 1 | 0 | 0 | 0 | 0 | 1 | 2 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 3 | 0 | 3 | 0 | 0 | 0 | 0 | 6 | 0 | 2 | 0 | 2 | 0 | 0 | 2 | 0 | 0 | 0 | 0 | 0 | 0 | 0 | — | 0 | 0 | 0 | 0 |
| Crabgrass | 10 | 0 | 10 | 7 | 8 | 7 | 0 | 0 | 9 | 10 | 7 | 8 | 10 | 9 | 7 | 6 | 8 | 0 | 3 | 0 | 7 | 0 | 7 | 8 | 6 | 9 | 6 | 8 | 2 |
| Giant foxtail | 10 | 0 | 10 | 9 | 10 | 10 | 6 | 0 | 10 | 10 | 9 | 10 | 10 | 10 | 8 | 9 | 10 | 0 | 4 | 1 | 8 | 0 | 9 | 7 | 10 | 10 | 3 | 8 | 8 |
| Morningglory | 0 | 0 | 5 | 0 | 4 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | — | 0 | 2 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 5 | 3 | 1 | 0 | 0 | 3 | 0 | 0 | 0 | 4 | 5 | 0 | 0 | 2 | 0 | 0 | 0 | 0 | 0 | 0 | 0 | 0 | 0 | 0 | 0 | 0 |
| Redroot pigweed | 9 | 0 | 5 | 7 | 10 | 3 | 0 | 0 | 10 | 10 | 4 | 7 | 10 | 10 | 3 | 0 | 10 | 0 | 0 | 0 | 3 | 0 | 0 | 0 | 0 | 7 | 0 | 0 | 0 |
| Soybean | 0 | 0 | 0 | 0 | 1 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 |
| Sugarbeets | 1 | 0 | 6 | 2 | 7 | 4 | 0 | 0 | 4 | 8 | 0 | 3 | 6 | 4 | 0 | 0 | 2 | 0 | 0 | 0 | 0 | 0 | 0 | 0 | 0 | 1 | 0 | 2 | 0 |
| Velvetleaf | 4 | 0 | 6 | 0 | 6 | 5 | 0 | 0 | 3 | 7 | 0 | 4 | 4 | 5 | 0 | 0 | 3 | 0 | 0 | 0 | 0 | 0 | 0 | 0 | 0 | 0 | 0 | 2 | 0 |

TABLE B-continued

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Wheat | 0 | 0 | 6 | 0 | 8 | 5 | 0 | 0 | 0 | 4 | 0 | 0 | 0 | 0 | 0 | 0 | 0 | 0 | 0 | 0 | 0 | 0 | 0 | 0 | 0 | 0 | 0 | 2 | 0 |
| Wild oats | 5 | 0 | 10 | 8 | 10 | 9 | 0 | 0 | 3 | 9 | 0 | 0 | 3 | 7 | 0 | 0 | 4 | 0 | 0 | 0 | 0 | 0 | 0 | 0 | 0 | 2 | 2 | 6 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 390 | 391 | 392 | 393 | 394 | 395 | 396 | 397 | 398 | 400 | 401 | 402 | 403 | 404 | 405 | 406 | 407 | 408 | 409 | 410 | 411 | 414 | 415 | 416 | 417 | 418 | 419 | 420 | 421 |
| Preemergence | | | | | | | | | | | | | | | | | | | | | | | | | | | | | |
| B. signalgrass | 5 | 0 | 3 | 0 | 5 | 0 | 0 | 6 | 2 | 0 | 0 | 3 | 4 | 4 | 0 | 0 | 0 | 2 | 4 | 5 | 3 | 0 | 3 | 7 | 3 | 3 | 0 | 2 | 8 |
| Bedstraw | 0 | — | 8 | — | — | 0 | — | — | — | — | 0 | 3 | 0 | — | — | 0 | 0 | — | — | — | — | 0 | — | — | — | — | — | — | — |
| Blackgrass | 9 | 0 | 8 | 0 | 8 | 0 | 0 | 9 | 8 | 0 | 0 | 7 | 7 | 7 | 0 | 0 | 0 | 9 | 7 | 8 | 7 | 0 | 5 | 9 | — | 4 | 0 | 8 | 10 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 3 | 0 | 3 | 0 | 0 | 0 | 0 | 0 | 0 | 0 | 0 | 0 | 2 | 2 | 0 | 0 | 0 | 2 | 8 | 0 | 2 | 0 | 2 | 0 | 0 | 0 | 0 | 0 | 5 |
| Crabgrass | 9 | 0 | 10 | 2 | 10 | 0 | 7 | 10 | 10 | 9 | 2 | 9 | 10 | 10 | 1 | 0 | 2 | 10 | 9 | 9 | 10 | 7 | 8 | 10 | 9 | 8 | 1 | 9 | 8 |
| Giant foxtail | 10 | 0 | 10 | 9 | 10 | 0 | 10 | 10 | 10 | 9 | 6 | 10 | 10 | 10 | 8 | 0 | 6 | 10 | 10 | 9 | 10 | 9 | 10 | 10 | 9 | 8 | 1 | 9 | 10 |
| Morningglory | 3 | 0 | 0 | 0 | 0 | 0 | 0 | 0 | 0 | 0 | 0 | 0 | 0 | 2 | 0 | 0 | 0 | 0 | 2 | 0 | 1 | 0 | 0 | 4 | 0 | 0 | 0 | 0 | 6 |
| Nutsedge | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 |
| Rape | 2 | 0 | 0 | 0 | 2 | 0 | 0 | 9 | 3 | 0 | 0 | 1 | 1 | 4 | 0 | 0 | 0 | 0 | 0 | 0 | 8 | 0 | 6 | 9 | 0 | 0 | 0 | 0 | 10 |
| Redroot pigweed | 9 | 0 | 7 | 2 | 2 | 0 | 0 | 8 | 5 | 4 | 0 | 2 | 4 | 6 | 0 | 0 | 0 | 6 | 8 | 0 | 8 | 0 | 0 | 9 | 0 | 3 | 0 | 2 | 10 |
| Soybean | 0 | 0 | 0 | 0 | — | 0 | 0 | 0 | 0 | 0 | 0 | 0 | 0 | 0 | 0 | 0 | 0 | 0 | 0 | 0 | 0 | 0 | 0 | 4 | 0 | 0 | 0 | 0 | 4 |
| Sugarbeets | 7 | 0 | 3 | 2 | 3 | 0 | 0 | 4 | 4 | 0 | 0 | 0 | 1 | 3 | 0 | 0 | 0 | 4 | 7 | 0 | 8 | 0 | 0 | 4 | 0 | 2 | 0 | 0 | 10 |
| Velvetleaf | 4 | 0 | 3 | 0 | 5 | 0 | 0 | 2 | 2 | 0 | 0 | 0 | 0 | 1 | 0 | 0 | 0 | 1 | 5 | 4 | 5 | 0 | 2 | 3 | 0 | 3 | 0 | 2 | 9 |
| Wheat | 4 | 0 | 3 | 0 | 1 | 0 | 0 | 0 | 0 | 0 | 0 | 0 | 0 | 2 | 0 | 0 | 0 | 0 | 8 | 3 | 4 | 0 | 0 | 4 | 0 | 0 | 0 | 0 | 4 |
| Wild oats | 6 | 0 | 9 | 0 | 6 | 0 | 0 | 5 | 3 | 0 | 0 | 4 | 4 | 8 | 0 | 0 | 0 | 2 | 5 | 6 | 5 | 0 | 3 | 7 | 0 | 0 | 0 | 2 | 7 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 422 | 423 | 424 | 425 | 426 | 427 | 428 | 429 | 430 | 431 | 432 | 433 | 434 | 435 | 436 | 437 | 438 | 439 | 440 | 441 | 442 | 443 | 444 | 445 | 446 | 447 | 448 | 449 | 450 |
| Preemergence | | | | | | | | | | | | | | | | | | | | | | | | | | | | | |
| B. signalgrass | 0 | 0 | 0 | 8 | 4 | 0 | 0 | 0 | 2 | 0 | 0 | 2 | 0 | 0 | 0 | 0 | 0 | 0 | 4 | 0 | 0 | 0 | 0 | 0 | 6 | 0 | 0 | 0 | 1 |
| Bedstraw | — | — | — | — | — | — | — | — | — | — | — | — | — | — | — | — | — | — | — | — | — | — | — | — | — | — | 0 | 0 | — |
| Blackgrass | 0 | 0 | 0 | 9 | 6 | 0 | 0 | 0 | 3 | 0 | 0 | 2 | 0 | 0 | 0 | 0 | 0 | 0 | 6 | 0 | 0 | 0 | 0 | 0 | 7 | 0 | 0 | 0 | 2 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 10 | 9 | 9 | 7 | 10 | 10 | — | 5 | 10 | 0 | 2 | 0 | 0 | 6 | 0 | 7 | 0 | 8 | 6 | 5 | 2 | 8 | 3 | 4 | 3 | 7 |
| Giant foxtail | 0 | 0 | 0 | 10 | 9 | 8 | 7 | 10 | 10 | 0 | 2 | 10 | 0 | 2 | 0 | 0 | 7 | 0 | 6 | 0 | 0 | 4 | 9 | 0 | 10 | 3 | 2 | 6 | 8 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Redroot pigweed | 0 | 0 | 0 | 0 | 4 | 0 | 0 | 0 | 0 | 0 | 0 | 4 | 0 | 2 | 0 | 0 | 2 | 0 | 4 | 0 | 0 | 0 | 10 | 2 | 10 | 0 | 0 | 0 | 4 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 0 | 0 | 0 | 3 | 0 | 0 | 0 | 0 | 0 | 0 | 2 | 0 | 0 | 0 | 0 | 0 | 0 | 0 | 0 | 0 | 0 | 0 | 0 | 4 | 0 | 0 | 0 | 0 |
| Velvetleaf | 0 | 0 | 0 | 0 | 2 | 0 | 0 | 0 | 2 | 0 | 0 | 2 | 0 | 0 | 0 | 0 | 0 | 0 | 0 | 0 | 0 | 0 | 0 | 0 | 3 | 0 | 0 | 0 | 0 |
| Wheat | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 |
| Wild oats | 0 | 0 | 0 | 4 | 7 | 0 | 0 | 0 | 0 | 0 | 0 | 6 | 0 | 0 | 0 | 0 | 0 | 0 | 5 | 0 | 0 | 0 | 0 | 0 | 5 | 0 | 0 | 0 | 0 |

TABLE B-continued

| Rate 125 g/ha | COMPOUND 451 | 452 | 453 | 454 | 455 | 456 | 457 | 458 | 459 | 460 | 461 | 462 | 463 | 465 | 466 | 467 | 468 | 469 | 470 | 471 | 472 | 473 | 474 | 476 | 477 | 478 | 479 | 480 | 481 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 0 | 0 | 2 | 0 | 3 | 0 | 0 | 4 | 0 | 0 | 0 | 0 | 0 | 2 | 3 | 0 | 2 | 7 | 0 | 9 | 9 | 0 | 2 | 0 | 2 | 6 | 5 | 4 | 9 |
| Bedstraw | — | — | — | — | — | — | — | — | 0 | 0 | — | 0 | — | — | 2 | 0 | — | — | — | — | — | — | — | 0 | — | 8 | — | — | 0 |
| Blackgrass | 0 | 0 | 0 | 0 | 4 | 2 | 0 | 8 | 0 | 0 | 0 | 0 | 0 | 3 | 5 | 2 | 4 | 8 | 0 | 10 | 9 | 0 | 3 | 0 | 1 | 8 | 6 | 5 | 6 |
| Cocklebur | 0 | 0 | 0 | 0 | 0 | 0 | 0 | 0 | 0 | 0 | 0 | 0 | 0 | 0 | 0 | 4 | 0 | 0 | 0 | — | 0 | 0 | 0 | 0 | 0 | 0 | 0 | 0 | 0 |
| Corn | 0 | 0 | 0 | 0 | 2 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 |
| Crabgrass | 0 | 5 | 6 | 3 | 5 | 6 | 0 | 6 | 7 | 1 | 0 | 0 | 0 | — | 9 | 6 | 9 | 10 | 7 | 10 | 9 | 2 | 9 | 0 | 8 | 9 | 8 | 8 | 8 |
| Giant foxtail | 0 | 3 | 9 | 9 | 10 | 10 | 0 | 9 | 9 | 6 | 0 | 0 | 0 | 10 | 10 | 7 | 8 | 10 | 0 | 10 | 10 | 3 | 10 | 0 | 6 | 10 | 9 | 10 | 9 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 4 |
| Rape | 0 | 0 | 0 | 0 | 3 | 0 | 0 | 0 | 0 | 0 | 0 | 0 | 0 | 2 | 0 | 7 | 0 | 2 | 0 | 2 | 0 | 0 | 0 | 0 | 0 | 1 | 0 | 0 | 0 |
| Redroot pigweed | 0 | 0 | 4 | 2 | 10 | 2 | 0 | 3 | 0 | 0 | 0 | 0 | 5 | 9 | 7 | 7 | 4 | 10 | 0 | 10 | 10 | 10 | 3 | 0 | 1 | 8 | 3 | — | 0 |
| Soybean | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 |
| Sugarbeets | 0 | 0 | 0 | 0 | 1 | 2 | 0 | 0 | 0 | 0 | 0 | 0 | 0 | 2 | 0 | 1 | 0 | 8 | 0 | 2 | 2 | 0 | 0 | 0 | 0 | 0 | 0 | 0 | 0 |
| Velvetleaf | 0 | 0 | 0 | 0 | 4 | 0 | 0 | 0 | 0 | 0 | 0 | 0 | 0 | 3 | 0 | 0 | 0 | 5 | 0 | 3 | 3 | 0 | 0 | 0 | 0 | 1 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 3 |
| Wild oats | 0 | 0 | 0 | 0 | 3 | 0 | 0 | 2 | 0 | 0 | 0 | 0 | 0 | 0 | 0 | 0 | 0 | 7 | 0 | 4 | 5 | 0 | 3 | 0 | 5 | 7 | 4 | 2 | 6 |

| Rate 125 g/ha | COMPOUND 482 | 483 | 485 | 486 | 487 | 488 | 489 | 490 | 492 | 493 | 494 | 495 | 496 | 497 | 498 | 499 | 500 | 501 | 502 | 503 | 504 | 505 | 506 | 508 | 509 | 510 | 511 | 512 | 513 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 0 | 0 | 5 | 5 | 3 | 7 | 7 | 5 | 0 | 0 | 0 | 0 | 0 | 0 | 0 | 0 | 9 | 9 | 9 | 8 | 10 | — | 0 | 7 | 3 | 7 | 0 | 8 | 0 |
| Bedstraw | — | 0 | — | — | — | — | — | — | 0 | 0 | 0 | — | 0 | — | — | 0 | 9 | 9 | — | 5 | 5 | 0 | 0 | 0 | 0 | 0 | 0 | 0 | — |
| Blackgrass | 0 | 0 | 8 | 9 | 3 | 8 | 8 | 8 | 0 | 0 | 0 | 0 | 0 | 0 | 0 | 0 | 9 | 5 | 10 | 9 | 8 | 6 | 0 | 3 | 7 | 6 | 0 | 2 | 4 |
| Cocklebur | 0 | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 5 | 2 | 8 | 5 | 5 | 2 | 0 | 0 | 0 | 0 | 0 | 0 | 0 |
| Crabgrass | 8 | 0 | 7 | 9 | 9 | 10 | 10 | 9 | 0 | 0 | 0 | 0 | 4 | 0 | 2 | 6 | 9 | 9 | 10 | 8 | 6 | 6 | 0 | 9 | 7 | 9 | 6 | 7 | 4 |
| Giant foxtail | 6 | 0 | 8 | 10 | 9 | 10 | 10 | 9 | 0 | 3 | 0 | 0 | 8 | 0 | 2 | 5 | 10 | 10 | 10 | 9 | 9 | 9 | 5 | 10 | 9 | 9 | — | 9 | 6 |
| Morningglory | 0 | 0 | 0 | 0 | 0 | 0 | 0 | 0 | 0 | 0 | 0 | 0 | 0 | 0 | 0 | 0 | 5 | 0 | 2 | 2 | 0 | 0 | 0 | 0 | 0 | 0 | 0 | 0 | 0 |
| Nutsedge | 0 | 0 | 0 | 0 | 0 | 0 | 0 | 0 | 0 | 0 | 0 | 0 | 0 | 0 | 0 | 0 | 8 | 3 | — | 0 | 0 | 10 | 0 | — | 0 | 0 | 0 | — | 0 |
| Rape | 0 | 0 | 0 | 2 | 0 | 7 | 0 | 1 | 0 | 0 | 0 | 0 | 0 | 0 | 0 | 0 | 10 | 0 | 3 | 8 | 10 | 4 | 0 | 0 | 0 | 5 | 0 | 0 | 2 |
| Redroot pigweed | 0 | 0 | 6 | 8 | 8 | 10 | — | 7 | 0 | 0 | 0 | 0 | 0 | 0 | 0 | 0 | 10 | 10 | 9 | 10 | 10 | 10 | 8 | 8 | 0 | 9 | 6 | 9 | 7 |
| Soybean | 0 | 0 | 0 | 0 | 0 | 0 | 1 | 0 | 0 | 0 | 1 | 0 | 0 | 0 | 0 | 0 | 3 | 0 | 4 | 3 | 0 | 0 | 0 | 0 | 0 | 0 | 0 | 0 | 0 |
| Sugarbeets | 0 | 0 | 0 | 0 | 0 | 4 | 2 | 0 | 0 | 0 | 0 | 0 | 0 | 0 | 0 | 0 | 10 | 3 | 2 | 6 | 6 | 3 | 0 | 1 | 4 | 0 | 0 | 0 | 0 |
| Velvetleaf | 0 | 0 | 0 | 0 | 0 | 2 | 2 | 0 | 0 | 0 | 0 | 0 | 0 | 0 | 0 | 0 | 8 | 2 | 5 | 6 | 5 | 2 | 0 | 0 | 6 | 2 | 0 | 0 | 0 |
| Wheat | 0 | 0 | 2 | 0 | 0 | 0 | 0 | 0 | 0 | 0 | 0 | 0 | 0 | 0 | 0 | 0 | 6 | 4 | 3 | 2 | 6 | 7 | 0 | 0 | 0 | 0 | 0 | 2 | 2 |
| Wild oats | 0 | 0 | 5 | 3 | 0 | 8 | 4 | 7 | 0 | 0 | 0 | 0 | 0 | 0 | 0 | 0 | 9 | 7 | 9 | 10 | 8 | 2 | 2 | 4 | 2 | 6 | 0 | 2 | 3 |

TABLE B-continued

| Rate 125 g/ha | COMPOUND 514 | 515 | 516 | 517 | 518 | 519 | 520 | 521 | 522 | 523 | 524 | 525 | 526 | 527 | 528 | 531 | 532 | 533 | 534 | 535 | 536 | 540 | 541 | 543 | 544 | 545 | 546 | 548 | 549 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 6 | 8 | 5 | 0 | 3 | 0 | 0 | 0 | 9 | 8 | 0 | — | 9 | 2 | 0 | 2 | 0 | 3 | 9 | 0 | 0 | 0 | 0 | 4 | 3 | 0 | — | 2 | 0 |
| Bedstraw | — | 0 | 0 | 0 | 0 | 0 | 0 | 0 | 10 | 0 | — | 0 | 0 | — | 0 | — | — | 0 | 0 | 0 | 0 | 0 | 0 | 0 | 2 | 0 | — | 10 | 0 |
| Blackgrass | 2 | 5 | 5 | 2 | 8 | 0 | 0 | 0 | 8 | 4 | 4 | 7 | 9 | 2 | 0 | 9 | 0 | 8 | 9 | 0 | 0 | 0 | 0 | 0 | 0 | 0 | 0 | 3 | 4 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 |
| Corn | 0 | 0 | 0 | 0 | 0 | 0 | 0 | 0 | 7 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 7 | 7 | 9 | 4 | 0 | 8 | 9 | 10 | 10 | 10 | 10 | 9 | 10 | 10 | 9 | 10 | 9 | 10 | 10 | 10 | 0 | 9 | 5 | 4 | 9 | 10 | 7 | 9 | 7 |
| Giant foxtail | 10 | 10 | 10 | 3 | 0 | 10 | 10 | 10 | 10 | 10 | 9 | 10 | 10 | 10 | 10 | 10 | 10 | 10 | 9 | 10 | 9 | 9 | 10 | 3 | 10 | 10 | 4 | 9 | 10 |
| Morningglory | 0 | 0 | 0 | 0 | 0 | 0 | 0 | 0 | 2 | 4 | 0 | 0 | 0 | 0 | 0 | 0 | 0 | 0 | 0 | 0 | 0 | 0 | 0 | 0 | 0 | 0 | 0 | 0 | 0 |
| Nutsedge | — | 0 | 0 | 0 | 0 | 0 | 0 | 0 | 9 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 4 | 1 | 0 | 0 | 0 | 0 | 0 | 2 | 0 | 2 | 0 | 4 | 2 | 0 | 0 | 0 | 0 | 6 | 2 | 0 | 0 | 0 | 0 | 0 | 0 | 0 | 0 | 0 |
| Redroot pigweed | 8 | 9 | — | 9 | 2 | 0 | 0 | 0 | 10 | 9 | 8 | 0 | 4 | 4 | 0 | 0 | 0 | 8 | 0 | 2 | 0 | 0 | 0 | 7 | 3 | 8 | 3 | 0 | 6 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 5 | 4 | 3 | 0 | 2 | 0 | 0 | 0 | 5 | 4 | 3 | 8 | 6 | 6 | 0 | 4 | 2 | 5 | 4 | 4 | 0 | 0 | 0 | 5 | 0 | 0 | 0 | 0 | 0 |
| Velvetleaf | 0 | 0 | — | 0 | 0 | 0 | 0 | 0 | 6 | 2 | 3 | 3 | 2 | 2 | 0 | 0 | 0 | 0 | 2 | 0 | 0 | 0 | 0 | 0 | 0 | 0 | 0 | 0 | 0 |
| Wheat | 0 | 0 | 0 | 0 | 2 | 0 | 0 | 0 | 0 | 0 | 5 | — | 0 | 0 | 0 | 0 | 0 | 0 | 0 | 0 | 0 | 0 | 0 | 0 | 0 | 0 | 0 | 0 | 0 |
| Wild oats | 4 | 5 | 5 | 4 | 6 | 0 | 0 | 0 | 2 | 0 | 9 | — | 9 | 0 | 0 | 0 | 0 | 0 | 8 | 0 | 0 | 2 | 0 | 0 | 0 | 0 | 0 | 0 | 0 |

| Rate 125 g/ha | COMPOUND 550 | 551 | 552 | 553 | 554 | 555 | 556 | 557 | 558 | 559 | 560 | 561 | 562 | 563 | 564 | 565 | 566 | 567 | 568 | 569 | 570 | 571 | 572 | 573 | 574 | 575 | 576 | 577 | 578 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 9 | 9 | 8 | 9 | 7 | — | 7 | 6 | 0 | 10 | 7 | 4 | 8 | 9 | 6 | 0 | 9 | 0 | 6 | 9 | 0 | 3 | 0 | 7 | 7 | 9 | 3 | 3 | 3 |
| Bedstraw | 0 | 8 | 0 | 0 | 0 | 0 | 0 | 0 | 0 | 0 | 0 | 0 | 0 | 0 | 0 | 0 | 0 | 0 | — | 3 | 0 | 0 | 0 | 0 | 0 | 0 | 0 | 0 | 0 |
| Blackgrass | 2 | 7 | 0 | 7 | 4 | 0 | 9 | 6 | 2 | 10 | 6 | 7 | 10 | 8 | 5 | 0 | 9 | 0 | 8 | 0 | 0 | 2 | 0 | 0 | 0 | 6 | 3 | 0 | 0 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 3 | 0 | 0 | 3 | 0 | 4 | 0 | 2 | 0 | 4 | 0 | 0 | 0 | 0 | 0 | 0 | 0 | 0 | 2 | 2 |
| Crabgrass | 10 | 9 | 9 | 9 | 10 | 9 | 9 | 9 | 9 | 10 | 9 | 9 | 8 | 9 | 8 | 0 | 9 | 9 | 7 | 9 | 9 | 2 | 0 | 9 | 9 | 9 | 4 | 9 | 9 |
| Giant foxtail | 9 | 10 | 10 | 10 | 9 | 10 | 9 | 9 | 9 | 10 | 10 | 6 | 9 | 9 | 9 | 0 | 10 | 9 | 10 | 9 | 0 | 3 | 0 | 9 | 10 | 10 | 4 | 8 | 9 |
| Morningglory | 0 | 0 | 0 | 0 | 0 | 0 | 0 | 0 | 0 | 2 | 0 | 0 | 0 | 0 | 2 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | 0 | — | 3 | — | 0 | 0 | 0 | 0 | 0 | 0 | 0 | 0 | 0 | 0 | 0 | 0 | 0 | 0 | 0 | 0 | 0 |
| Rape | 0 | 3 | 0 | 3 | 0 | 0 | 3 | 0 | 0 | 9 | 3 | 2 | 6 | 4 | 0 | 0 | 0 | 0 | 0 | 0 | 0 | 0 | 0 | 2 | 0 | 2 | 0 | 0 | 0 |
| Redroot pigweed | 9 | 9 | 4 | 7 | — | 0 | 5 | 0 | 0 | 10 | 8 | 5 | 10 | 9 | 0 | 0 | 9 | 0 | 4 | 9 | 0 | 0 | 0 | 0 | 0 | 9 | 9 | 0 | 4 |
| Soybean | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 6 | 0 | 3 | 0 | 5 | 0 | 3 | 0 | 6 | 0 | 0 | 8 | 3 | 2 | 0 | 4 | 0 | 5 | 0 | 0 | 0 | 0 | 2 | 0 | 0 | 0 | 0 | 2 |
| Velvetleaf | 0 | 0 | 0 | 0 | 0 | 0 | 2 | 0 | 0 | 4 | 2 | 0 | 0 | 3 | 2 | 0 | 0 | 0 | 6 | 0 | 0 | 0 | 0 | 0 | 0 | 0 | 0 | 3 | 2 |
| Wheat | 2 | 0 | 0 | 0 | 3 | 0 | 0 | 0 | 0 | 8 | 5 | 4 | 9 | 8 | 6 | 0 | 6 | 0 | 0 | 0 | 0 | 3 | 0 | 0 | 0 | 0 | 6 | 0 | 0 |
| Wild oats | 0 | 3 | 0 | 0 | 2 | 0 | 0 | 2 | 0 | 9 | 0 | 2 | 9 | 9 | 0 | 0 | 9 | 0 | 5 | 0 | 0 | 0 | 0 | 0 | 0 | 0 | 0 | 0 | 0 |

TABLE B-continued

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 579 | 580 | 581 | 582 | 584 | 585 | 586 | 587 | 588 | 589 | 590 | 591 | 592 | 593 | 594 | 595 | 596 | 598 | 599 | 600 | 601 | 602 | 603 | 604 | 605 | 606 | 607 | 608 | 609 |
| Preemergence | | | | | | | | | | | | | | | | | | | | | | | | | | | | | |
| B. signalgrass | 0 | 6 | 0 | 0 | 7 | 8 | 5 | 0 | 1 | 0 | 0 | 0 | 0 | 0 | 3 | 6 | 0 | 0 | 2 | 0 | 7 | 4 | 0 | 0 | 0 | 0 | 7 | 10 | 6 |
| Bedstraw | 0 | 4 | 9 | 0 | — | 8 | — | 0 | — | — | — | 0 | 0 | — | 0 | 8 | 0 | 0 | 0 | — | 0 | 0 | — | — | 0 | — | — | — | 8 |
| Blackgrass | 0 | 3 | 0 | 0 | — | 8 | 7 | 3 | 3 | 0 | 0 | 0 | 0 | 0 | 5 | 9 | 0 | 0 | 0 | 0 | 8 | 4 | 0 | 0 | 0 | 0 | 7 | 5 | 8 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 2 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 |
| Crabgrass | 7 | 6 | 9 | 0 | 8 | 8 | 9 | 6 | 6 | 1 | 0 | 0 | 0 | 0 | 9 | 9 | 0 | 0 | 3 | 0 | 9 | 8 | 0 | 0 | 3 | — | 8 | 9 | 7 |
| Giant foxtail | 9 | 9 | 10 | 5 | 8 | 6 | 10 | 8 | 8 | 9 | 0 | 0 | 0 | 0 | 9 | 10 | 0 | 0 | 9 | 0 | 10 | 9 | 0 | 2 | 10 | 6 | 10 | 10 | 10 |
| Morningglory | 0 | 0 | 2 | 0 | 4 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | 0 | 0 | 0 | 0 | 0 | 0 | 0 | 3 | 0 | 0 | 0 | 0 | 0 | 0 | 0 | 0 | 0 | 0 | 0 | 0 | 0 |
| Rape | 0 | 3 | 0 | 0 | 4 | 8 | 0 | 0 | 0 | 0 | 0 | 0 | 0 | 0 | 0 | 4 | 0 | 0 | 0 | 0 | 0 | 0 | 0 | 0 | 0 | 0 | 6 | 5 | 0 |
| Redroot pigweed | 0 | 10 | 5 | 0 | 8 | 9 | 8 | 0 | 1 | 0 | 0 | 0 | 0 | 0 | 0 | 10 | 0 | 0 | 0 | 0 | 10 | 7 | 0 | 0 | 0 | 0 | 7 | 5 | — |
| Soybean | 0 | 0 | 0 | 0 | 0 | 0 | 0 | 0 | 0 | 0 | 0 | 0 | 0 | 0 | 0 | 1 | 0 | 0 | 0 | 0 | 0 | 0 | 0 | 0 | 0 | 0 | 0 | 0 | 6 |
| Sugarbeets | 0 | 0 | 0 | 0 | 2 | 3 | 0 | 0 | 0 | 0 | 0 | 0 | 0 | 0 | 0 | 8 | 0 | 0 | 0 | 0 | 4 | 2 | 0 | 0 | 0 | 0 | 0 | 0 | 3 |
| Velvetleaf | 0 | 0 | 5 | 0 | 0 | 0 | 0 | 0 | 0 | 0 | 0 | 0 | 0 | 0 | 4 | 7 | 0 | 0 | 0 | 0 | 4 | 6 | 0 | 0 | 0 | 0 | 3 | 4 | 8 |
| Wheat | 0 | 0 | 0 | 0 | 0 | 3 | 0 | 0 | 2 | 0 | 0 | 0 | 0 | 0 | 0 | 1 | 0 | 0 | 0 | 0 | 1 | 0 | 0 | 0 | 0 | 0 | 0 | 0 | 0 |
| Wild oats | 0 | 0 | 0 | 0 | 2 | 3 | 3 | 2 | 0 | 0 | 0 | 0 | 0 | 0 | 0 | 8 | 0 | 0 | 0 | 0 | 8 | 3 | 0 | 0 | 0 | 0 | 2 | 3 | 7 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 610 | 611 | 612 | 613 | 614 | 615 | 616 | 617 | 618 | 619 | 620 | 621 | 622 | 623 | 624 | 625 | 627 | 628 | 629 | 630 | 631 | 632 | 633 | 634 | 635 | 636 | 637 | 638 | 639 |
| Preemergence | | | | | | | | | | | | | | | | | | | | | | | | | | | | | |
| B. signalgrass | 8 | 7 | 7 | 8 | 0 | 0 | 0 | 0 | 0 | 0 | 0 | 0 | 0 | 0 | 6 | 4 | 5 | 7 | 2 | 3 | 7 | 3 | 3 | 5 | 8 | 9 | 3 | 7 | 0 |
| Bedstraw | — | 1 | — | — | — | 0 | 0 | 0 | 0 | — | 0 | 0 | 0 | — | 0 | — | 2 | 7 | 0 | 0 | 0 | — | — | 0 | 8 | 5 | 0 | — | — |
| Blackgrass | 9 | 9 | 10 | 8 | 0 | 0 | 0 | 0 | 0 | 0 | 0 | 0 | 2 | 0 | 8 | 3 | 8 | 9 | 8 | 8 | 7 | 4 | 3 | 6 | — | 4 | 3 | 5 | 0 |
| Cocklebur | 0 | 0 | 0 | 0 | 0 | 0 | 0 | 0 | 0 | 0 | 0 | 0 | 0 | 0 | 0 | 0 | 6 | 3 | 0 | 0 | 0 | 0 | 0 | 0 | 0 | 0 | 0 | 0 | 0 |
| Corn | 3 | 3 | 3 | 3 | 0 | 0 | 0 | 0 | 0 | 0 | 0 | 0 | 0 | 0 | 0 | 0 | 4 | 6 | 2 | 0 | 6 | 4 | 0 | 0 | — | 0 | 0 | 8 | 0 |
| Crabgrass | 10 | 10 | 10 | 10 | 6 | 0 | 0 | — | 0 | 1 | 0 | 6 | 6 | 0 | — | 7 | 8 | 8 | 9 | 8 | 7 | 7 | 8 | 8 | 9 | 9 | 9 | 9 | 7 |
| Giant foxtail | 10 | 10 | 10 | 10 | 4 | 0 | 1 | 9 | 2 | 3 | 0 | 7 | — | 7 | 10 | 9 | 10 | 10 | 10 | 10 | 9 | 10 | 9 | 10 | 9 | 10 | 10 | 10 | 9 |
| Morningglory | 3 | 0 | 0 | 0 | 0 | 0 | 0 | 0 | 0 | 0 | 0 | 0 | 0 | 0 | 0 | 0 | 6 | 5 | 0 | 0 | 0 | 0 | 0 | 0 | 0 | 0 | 0 | 0 | 0 |
| Nutsedge | 0 | 0 | 0 | 0 | 0 | 0 | — | 0 | 0 | 0 | 0 | 0 | 0 | 0 | 0 | 0 | 7 | 6 | 2 | 0 | 4 | 0 | 0 | 0 | 0 | 0 | 0 | 5 | 0 |
| Rape | 8 | 3 | 3 | 9 | 0 | 0 | 0 | 0 | 0 | 0 | 0 | 0 | 0 | 0 | 0 | 0 | 3 | 2 | 0 | 0 | 0 | 0 | 0 | 2 | 6 | 2 | 0 | 5 | 0 |
| Redroot pigweed | 10 | 8 | 10 | 10 | 0 | 0 | 1 | 0 | 0 | 0 | 0 | 0 | 7 | 0 | 0 | 0 | 9 | 9 | 10 | 9 | 9 | 0 | 0 | 4 | 10 | 10 | 9 | 10 | 0 |
| Soybean | 6 | 2 | 0 | 0 | 0 | 0 | 0 | 0 | 0 | 0 | 0 | 0 | 0 | 0 | 0 | 0 | 0 | 0 | 0 | 0 | 5 | 0 | 0 | 0 | 0 | 0 | 0 | 0 | 0 |
| Sugarbeets | 7 | 2 | 5 | 5 | 0 | 0 | 0 | 0 | 0 | 0 | 0 | 0 | 0 | 0 | 1 | 0 | 4 | 4 | — | 4 | 3 | 0 | 0 | 0 | 5 | 0 | 0 | 6 | 0 |
| Velvetleaf | 7 | 6 | 7 | 7 | 0 | 0 | 0 | 0 | 0 | 0 | 0 | 0 | 0 | 0 | 0 | 0 | 8 | — | 6 | 1 | 7 | 1 | 0 | 0 | — | 0 | 0 | 5 | 0 |
| Wheat | 2 | 3 | 3 | 3 | 0 | 0 | 0 | 0 | 0 | 0 | 0 | 0 | 0 | 0 | 0 | 0 | 0 | 3 | 0 | 0 | 3 | 0 | 0 | 0 | 0 | 0 | 0 | 0 | 0 |
| Wild oats | 6 | 7 | 9 | 9 | 0 | 0 | 0 | 0 | 0 | 0 | 0 | 0 | 0 | 0 | 6 | 0 | 3 | 2 | 0 | 3 | 2 | 2 | 2 | 5 | 6 | 0 | 0 | 4 | 0 |

TABLE B-continued

| Rate 125 g/ha | 640 | 641 | 642 | 643 | 644 | 645 | 646 | 647 | 648 | 649 | 650 | 652 | 653 | 654 | 655 | 656 | 657 | 658 | 659 | 660 | 661 | 662 | 663 | 664 | 665 | 666 | 667 | 668 | 669 |
|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | |
| Preemergence | | | | | | | | | | | | | | | | | | | | | | | | | | | | | |
| B. signalgrass | 2 | 0 | 2 | 2 | 0 | 0 | 0 | 7 | 0 | 0 | 0 | 0 | 0 | 0 | 0 | 2 | 8 | 0 | 4 | 1 | 0 | 0 | 0 | 5 | 4 | 3 | 5 | 8 | 8 |
| Bedstraw | — | — | — | — | — | — | — | — | 0 | 0 | 0 | 0 | 0 | 0 | 0 | — | — | — | — | — | — | — | — | — | — | — | — | — | 7 |
| Blackgrass | 0 | 0 | 0 | 0 | 0 | 0 | 0 | 9 | 0 | 0 | 0 | 0 | 0 | 0 | 0 | 4 | 9 | 7 | 6 | 4 | 2 | 3 | 0 | 6 | 7 | 8 | 8 | 8 | 10 |
| Cocklebur | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | 0 | 0 | 0 | 0 | 0 |
| Corn | 0 | — | 0 | 0 | 0 | 0 | 0 | 3 | 0 | 0 | 0 | 0 | 0 | 0 | 0 | 0 | 1 | 0 | 0 | 0 | 0 | 0 | 0 | 0 | 0 | 4 | 4 | — | 9 |
| Crabgrass | 3 | 3 | 8 | 3 | — | 3 | 0 | 8 | 8 | 1 | 8 | 8 | 2 | 3 | 8 | 7 | 10 | 7 | 8 | 7 | 0 | 0 | 0 | 8 | 8 | 8 | 8 | 8 | 9 |
| Giant foxtail | 9 | 9 | 10 | 8 | 2 | 2 | 0 | 10 | 9 | — | 10 | 9 | 0 | 6 | 9 | 10 | 10 | 9 | 9 | 10 | 6 | 7 | 3 | 10 | 10 | 10 | 10 | 9 | 9 |
| Morningglory | 0 | 0 | 0 | 0 | 0 | 0 | 0 | 0 | 0 | 0 | 0 | 0 | 0 | 0 | 0 | 0 | 1 | 0 | 0 | 0 | 0 | 0 | 0 | 0 | 0 | 0 | 1 | 0 | 0 |
| Nutsedge | 0 | 0 | 0 | 0 | 0 | 0 | 0 | 0 | 0 | 0 | 3 | 0 | — | — | 0 | 0 | 0 | 0 | 0 | 0 | 0 | 0 | 0 | 0 | 0 | — | 0 | 0 | — |
| Rape | 0 | — | 2 | 0 | 0 | 0 | 0 | 8 | 0 | 0 | 0 | 0 | 0 | 0 | 0 | 0 | 3 | 5 | 0 | 0 | 0 | 0 | 0 | 1 | 6 | 8 | 8 | 5 | 4 |
| Redroot pigweed | 0 | 0 | 0 | 0 | 0 | 0 | 0 | 10 | 0 | 0 | 7 | 0 | 0 | 0 | 2 | 4 | 10 | 9 | 6 | 5 | 0 | 0 | 0 | 7 | 8 | 10 | 10 | 7 | 10 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 3 | 1 | 2 |
| Sugarbeets | 2 | 0 | 0 | 0 | 0 | 0 | 0 | 8 | 0 | 0 | 0 | 0 | 0 | 0 | 0 | 0 | 7 | 7 | 0 | 0 | 0 | 0 | 0 | 0 | 3 | 4 | 7 | 6 | 8 |
| Velvetleaf | 0 | 0 | 0 | 0 | 0 | 0 | 0 | 8 | 0 | 0 | 0 | 0 | 0 | 0 | 0 | 4 | 4 | 0 | 0 | 0 | 0 | 0 | 0 | 0 | 0 | 6 | 6 | 6 | 0 |
| Wheat | 0 | 0 | 0 | 0 | 0 | 0 | 0 | 6 | 0 | 0 | 0 | 0 | 0 | 0 | 0 | 0 | 0 | 0 | 0 | 0 | 0 | 0 | 0 | 0 | 3 | 3 | 2 | 0 | 5 |
| Wild oats | 0 | 0 | 0 | 0 | 0 | 0 | 0 | 8 | 0 | 0 | 0 | 0 | 0 | 0 | 0 | 0 | 6 | 2 | 0 | 0 | 0 | 0 | 0 | 3 | 5 | 6 | 8 | 7 | 10 |

| Rate 125 g/ha | 670 | 671 | 672 | 673 | 674 | 675 | 676 | 677 | 678 | 679 | 680 | 681 | 682 | 683 | 684 | 685 | 686 | 687 | 689 | 691 | 692 | 693 | 694 | 695 | 696 | 697 | 698 | 699 | 701 |
|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | |
| Preemergence | | | | | | | | | | | | | | | | | | | | | | | | | | | | | |
| B. signalgrass | 9 | 6 | 4 | 6 | 7 | 6 | 0 | 0 | 0 | 0 | 0 | 0 | 6 | 0 | 0 | 7 | 5 | 9 | 4 | 8 | 9 | 0 | 3 | 0 | 10 | 0 | 0 | 9 | 0 |
| Bedstraw | 8 | — | 0 | — | 0 | 2 | — | — | — | — | — | 0 | 0 | 0 | 0 | 0 | 0 | 0 | 0 | 9 | 1 | 0 | 0 | 0 | 0 | 0 | 0 | — | 0 |
| Blackgrass | 9 | 7 | 3 | 8 | 8 | 9 | 0 | 0 | 0 | 0 | 0 | 0 | 5 | 3 | 3 | 7 | 7 | 9 | 9 | 9 | 9 | 0 | 8 | 0 | 7 | 0 | 0 | 10 | 2 |
| Cocklebur | 0 | 0 | 0 | 0 | 0 | 0 | 0 | 0 | 0 | 0 | 0 | 0 | 0 | 0 | 0 | 0 | — | 0 | 0 | — | 0 | 0 | 0 | 0 | 0 | — | 0 | 0 | 0 |
| Corn | 4 | 0 | 0 | 2 | 3 | 3 | 0 | 0 | 0 | 0 | 0 | 0 | 0 | 0 | 0 | 0 | 0 | 0 | 6 | 0 | 0 | 0 | 1 | 0 | 0 | 0 | 0 | 6 | 0 |
| Crabgrass | 10 | 8 | 10 | 8 | 9 | 7 | 3 | 3 | 0 | 0 | 0 | 0 | 9 | 8 | 7 | 9 | 9 | — | 9 | 9 | 9 | 0 | 9 | 9 | 8 | 0 | 3 | 10 | 10 |
| Giant foxtail | 10 | 9 | 10 | 10 | 9 | 10 | 8 | 5 | 0 | 0 | 0 | 0 | 10 | 9 | 9 | 9 | 9 | 6 | 10 | 10 | 9 | 0 | 10 | 10 | 9 | 0 | 0 | 10 | 10 |
| Morningglory | 7 | 2 | 0 | 0 | 0 | 0 | 0 | 0 | 0 | 0 | 0 | 0 | 0 | 0 | 0 | 0 | 0 | 3 | 3 | 0 | 1 | 0 | 2 | 0 | 0 | 0 | 0 | 4 | 0 |
| Nutsedge | 5 | 2 | 0 | 0 | 0 | 0 | 0 | 0 | 0 | 0 | 0 | 0 | 0 | 0 | 0 | 0 | 0 | 0 | 0 | — | — | 0 | 0 | 0 | 0 | 0 | 0 | 0 | — |
| Rape | 9 | 0 | 2 | 2 | 3 | 3 | 0 | 0 | 0 | 0 | 0 | 0 | 0 | 0 | 0 | 0 | 0 | 5 | 0 | 3 | 0 | 0 | 0 | 0 | 0 | 0 | 0 | 2 | 0 |
| Redroot pigweed | 10 | 2 | 3 | 7 | 7 | 9 | 9 | 4 | 0 | 0 | 0 | 0 | 4 | 2 | 0 | 4 | 6 | 9 | 7 | 3 | 8 | 0 | 4 | 0 | 3 | 0 | 0 | 3 | 0 |
| Soybean | 3 | 0 | 0 | 0 | 3 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 2 | 0 |
| Sugarbeets | 9 | 9 | 4 | 0 | 5 | 7 | 2 | 0 | 0 | 0 | 0 | 0 | 0 | 0 | 0 | 0 | 0 | 5 | 2 | 2 | 0 | 0 | 0 | 0 | 0 | 0 | 0 | 4 | 0 |
| Velvetleaf | 8 | 7 | 3 | 3 | 7 | 7 | 4 | 0 | 0 | 0 | 0 | 0 | 0 | 0 | 0 | 0 | 0 | 5 | 3 | 0 | 1 | 0 | 0 | 0 | 0 | 0 | 0 | 2 | 0 |
| Wheat | 9 | 0 | 0 | 0 | 5 | 2 | 0 | 0 | 0 | 0 | 0 | 0 | 0 | 0 | 0 | 0 | 0 | 6 | 0 | 0 | 0 | 0 | 0 | 0 | 0 | 0 | 0 | 3 | 0 |
| Wild oats | 9 | 0 | 4 | — | 3 | 5 | 0 | 0 | 0 | 0 | 0 | 0 | 0 | 0 | 0 | 3 | 1 | 9 | 9 | 6 | 9 | 0 | 0 | 0 | 0 | 0 | 0 | 10 | 0 |

TABLE B-continued

| Rate 125 g/ha | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| | 702 | 703 | 704 | 706 | 707 | 708 | 709 | 710 | 711 | 712 | 713 | 714 | 715 | 716 | 718 | 719 | 720 | 721 | 722 | 723 | 724 | 725 | 726 | 727 | 728 | 729 | 730 | 732 | 733 |
| Preemergence | | | | | | | | | | | | | | | | | | | | | | | | | | | | | |
| B. signalgrass | 2 | 3 | 5 | 8 | 7 | 0 | 0 | 8 | 2 | 5 | 7 | 9 | 8 | 0 | 2 | 7 | 9 | 8 | 0 | 0 | 0 | 3 | 7 | 6 | 8 | 10 | 0 | 0 | 6 |
| Bedstraw | 0 | 0 | 0 | 0 | 7 | 0 | 0 | 3 | 3 | 0 | 0 | 8 | 0 | 0 | 0 | 0 | 10 | 10 | 0 | 0 | 0 | 0 | 0 | 0 | 0 | 0 | 0 | 0 | 0 |
| Blackgrass | 2 | 3 | 6 | 8 | 10 | 2 | 0 | 9 | 6 | 6 | 8 | 8 | 9 | 0 | 9 | 8 | 9 | 10 | 0 | 0 | 0 | 4 | 8 | 7 | 9 | 10 | 9 | 0 | 7 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 2 | 3 | 0 | 0 | 0 | 0 | 0 | 0 | 0 | 0 | 3 | 0 | 0 |
| Crabgrass | 10 | 8 | 8 | 5 | 9 | 7 | 3 | 10 | 9 | 9 | 10 | 10 | 9 | 0 | 10 | 3 | 9 | 9 | 0 | 2 | 3 | 6 | 9 | 8 | 6 | 9 | 9 | 0 | 5 |
| Giant foxtail | 10 | 7 | 7 | 6 | 10 | 7 | 4 | 10 | 10 | 10 | 10 | 10 | 10 | 0 | 10 | 5 | 10 | 10 | 0 | 7 | 0 | 8 | 9 | 7 | 7 | 9 | 10 | 0 | 6 |
| Morningglory | 0 | 0 | 0 | 1 | 3 | 0 | 0 | 0 | 1 | 0 | 0 | 2 | 1 | 0 | 0 | 1 | 0 | 2 | 2 | 0 | 0 | 1 | 0 | 0 | 0 | 0 | 0 | 0 | 1 |
| Nutsedge | 0 | 0 | 0 | — | 0 | 0 | 0 | 0 | — | 0 | 0 | 0 | 0 | 0 | — | 0 | 0 | 0 | — | 0 | 0 | 0 | 0 | 0 | 0 | 0 | 0 | — | 0 |
| Rape | 0 | 0 | 0 | 0 | 8 | 0 | 0 | 8 | 6 | 2 | 4 | 3 | 8 | 0 | 0 | 0 | 7 | 9 | 0 | 0 | 0 | 0 | 0 | 0 | 3 | 2 | 0 | 0 | 0 |
| Redroot pigweed | 5 | 4 | 5 | 8 | 10 | 3 | 0 | 8 | 7 | 8 | 7 | 9 | 9 | 0 | 4 | 7 | 9 | 10 | 0 | 0 | 0 | 0 | 4 | 5 | 7 | 9 | 9 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 0 | 3 | 4 | 6 | 0 | 0 | 6 | 6 | 4 | 4 | 4 | 5 | 0 | 0 | 4 | 6 | 7 | 0 | 0 | 0 | 0 | 0 | 0 | 0 | 0 | 2 | 0 | 0 |
| Velvetleaf | 0 | 0 | 0 | 1 | 5 | 0 | 0 | 6 | 6 | 3 | 5 | 5 | 5 | 0 | 0 | 0 | 2 | 5 | 0 | 0 | 0 | 0 | 0 | 0 | 0 | 2 | 2 | 0 | 0 |
| Wheat | 0 | 0 | 0 | 4 | 2 | 0 | 0 | 6 | 6 | 0 | 0 | 4 | 0 | 0 | 0 | 0 | 0 | 3 | 0 | 0 | 0 | 0 | 0 | 0 | 0 | 0 | 0 | 0 | 0 |
| Wild oats | 0 | 0 | 0 | 7 | 8 | 0 | 0 | 9 | 7 | 3 | 5 | 4 | 9 | 0 | 2 | 6 | 8 | 8 | 0 | 0 | 0 | 2 | 7 | 3 | 4 | 7 | 4 | 0 | 2 |

| Rate 125 g/ha | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| | 734 | 735 | 736 | 737 | 738 | 739 | 740 | 741 | 742 | 743 | 744 | 745 | 746 | 747 | 748 | 749 | 750 | 751 | 752 | 753 | 754 | 755 | 756 | 757 | 758 | 759 | 760 | 761 | 762 |
| Preemergence | | | | | | | | | | | | | | | | | | | | | | | | | | | | | |
| B. signalgrass | 9 | 8 | 3 | 4 | 9 | — | — | 0 | 0 | 3 | 8 | 9 | 9 | 8 | 3 | 2 | 10 | — | — | 7 | 3 | 0 | 0 | 0 | 6 | 3 | 3 | 0 | 0 |
| Bedstraw | 0 | 0 | 0 | 0 | 0 | 10 | 0 | 0 | 0 | 0 | 0 | — | — | 0 | 0 | 0 | 0 | 2 | 10 | 0 | 0 | 0 | 0 | 0 | 1 | 0 | 0 | 0 | 0 |
| Blackgrass | 9 | 10 | 2 | 9 | 10 | 3 | 6 | 0 | 0 | 8 | 9 | 6 | 9 | 8 | 3 | 2 | 8 | 10 | 9 | 9 | 9 | 0 | 2 | 2 | 8 | 5 | 4 | 0 | 0 |
| Cocklebur | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | 0 | — | 0 | 0 |
| Corn | 5 | 6 | 2 | 2 | 4 | 0 | 0 | 0 | 0 | 0 | 0 | 0 | 3 | 2 | 0 | 0 | 3 | 4 | 0 | 0 | 0 | 0 | 0 | 0 | 0 | 0 | 0 | 0 | 0 |
| Crabgrass | 9 | 10 | 3 | 9 | 9 | 2 | 4 | 5 | 0 | 9 | 9 | 10 | 10 | 10 | 10 | 10 | 9 | 10 | 9 | 9 | 9 | 0 | 9 | 9 | 9 | 7 | 7 | 3 | 4 |
| Giant foxtail | 10 | 10 | 8 | 10 | 9 | 9 | 9 | 2 | 0 | 9 | 9 | 10 | 10 | 10 | 10 | 10 | 10 | 10 | 10 | 9 | 9 | 0 | 9 | 9 | 9 | 9 | 9 | 0 | 10 |
| Morningglory | 2 | 0 | 0 | 2 | 1 | 0 | 0 | 0 | 0 | 0 | 0 | 0 | 4 | 0 | 0 | 0 | 0 | 5 | 0 | 0 | 0 | 0 | 0 | 0 | 0 | 0 | 0 | 0 | 0 |
| Nutsedge | 0 | — | 0 | 0 | — | 0 | 0 | 0 | 0 | — | 0 | — | 3 | 2 | 0 | 0 | 0 | 0 | 0 | 0 | 3 | — | 0 | 0 | 0 | 0 | 0 | 0 | 0 |
| Rape | 2 | 6 | 0 | 0 | 5 | 0 | 3 | 0 | 0 | 5 | 6 | 5 | 9 | 9 | 0 | 0 | 0 | 6 | 3 | 5 | 4 | 0 | 0 | 0 | 4 | 0 | 0 | 0 | 0 |
| Redroot pigweed | 7 | 7 | 0 | 3 | 7 | 2 | 9 | 0 | 0 | 9 | 8 | 9 | 10 | — | 10 | 5 | 9 | 10 | 2 | 8 | 8 | 0 | 0 | 0 | 8 | 2 | 7 | 0 | 2 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 2 | 2 | 0 | 5 | 6 | 2 | — | 0 | 0 | 2 | 2 | 4 | 7 | 6 | 0 | 2 | 3 | 2 | 0 | 0 | 0 | 0 | 0 | 0 | 7 | 0 | 3 | 0 | 0 |
| Velvetleaf | 3 | 0 | 0 | 0 | 1 | 0 | 0 | 3 | 0 | 2 | 0 | 0 | 6 | 6 | 0 | 0 | 0 | 8 | 0 | 0 | 1 | 0 | 0 | 0 | 4 | 0 | 0 | 0 | 0 |
| Wheat | 7 | 0 | 3 | 0 | 4 | 0 | 0 | 0 | 0 | 0 | 0 | 0 | 7 | — | 0 | 0 | 4 | 4 | 0 | 0 | 3 | 0 | 0 | 0 | 5 | 2 | 0 | 0 | 0 |
| Wild oats | 8 | 8 | 2 | 6 | 9 | 0 | 0 | 0 | 0 | 5 | 8 | 6 | 10 | — | 2 | 0 | 5 | 8 | 0 | 4 | 6 | 0 | 0 | 0 | 8 | 4 | 0 | 0 | 0 |

TABLE B-continued

| | COMPOUND | | | | | | | | | | | | | | | | |
|---|---|---|---|---|---|---|---|---|---|---|---|---|---|---|---|---|---|
| Rate 125 g/ha | 763 | 764 | 765 | 766 | 767 | 772 | 773 | 774 | 775 | 776 | 777 | 778 | 779 | 780 | 790 | 791 | 792 |
| Preemergence | | | | | | | | | | | | | | | | | |
| B. signalgrass | 9 | 7 | — | 8 | — | 0 | 0 | 0 | — | — | — | — | — | 6 | 9 | 0 | 0 |
| Bedstraw | 6 | 5 | — | 9 | 0 | 0 | 0 | 0 | 0 | 0 | 0 | 0 | 0 | 0 | 3 | 0 | 0 |
| Blackgrass | 9 | 7 | — | 7 | 10 | 0 | 0 | 0 | 5 | 0 | 2 | 9 | 9 | 6 | 9 | 0 | 4 |
| Cocklebur | 0 | — | 0 | 0 | 0 | 0 | 0 | 0 | 0 | — | 0 | 0 | 0 | 0 | 0 | 0 | — |
| Corn | 0 | 0 | 0 | 0 | 0 | 0 | 0 | 0 | 0 | 0 | 0 | 0 | 0 | 2 | 7 | 0 | 2 |
| Crabgrass | 9 | 10 | 10 | 9 | 10 | 0 | 0 | 0 | 9 | 8 | 10 | 10 | 10 | 10 | 10 | 6 | 10 |
| Giant foxtail | 9 | 10 | 10 | 9 | 10 | 0 | 0 | 0 | 9 | 9 | 10 | 10 | 10 | 10 | 10 | 10 | 10 |
| Morningglory | 0 | — | 0 | 3 | 0 | 0 | 0 | 0 | 0 | 2 | 1 | 0 | 0 | 0 | 0 | 0 | 0 |
| Nutsedge | — | 0 | — | 0 | 0 | 0 | 0 | 0 | 0 | — | 0 | 0 | 0 | 0 | 0 | 0 | 0 |
| Rape | 5 | 0 | — | 5 | 6 | 0 | 0 | 0 | 0 | 0 | 0 | 0 | 0 | 0 | 4 | 0 | 0 |
| Redroot pigweed | 9 | 10 | — | 10 | 10 | 0 | 0 | 0 | 0 | 0 | 2 | 2 | 2 | 3 | 6 | 0 | 9 |
| Soybean | 0 | 0 | 0 | 0 | 0 | 0 | 0 | 0 | 0 | 0 | 0 | 0 | 0 | 0 | 0 | 4 | 0 |
| Sugarbeets | 0 | 0 | — | 6 | 6 | 0 | 0 | 0 | 0 | 0 | 0 | 2 | 2 | 2 | 2 | 0 | 3 |
| Velvetleaf | 1 | 5 | 4 | 5 | 0 | 0 | 0 | 0 | 0 | 0 | 0 | 0 | 2 | 3 | 2 | 0 | 3 |
| Wheat | 0 | 3 | — | 4 | 5 | 0 | 0 | 0 | 0 | 2 | 0 | 0 | 0 | 6 | 2 | 0 | 0 |
| Wild oats | 8 | 3 | — | 7 | — | 0 | 0 | 0 | 2 | 2 | 3 | 0 | 3 | 0 | 6 | 0 | 0 |

| | COMPOUND | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| Rate 62 g/ha | 18 | 69 | 70 | 71 | 72 | 129 | 131 | 146 | 165 | 166 | 180 | 181 | 182 | 183 | 184 | 185 | 186 | 187 | 189 | 190 | 191 | 192 | 193 | 194 | 195 | 196 | 197 | 198 | 200 | 201 | 202 |
| Pre-emergence | | | | | | | | | | | | | | | | | | | | | | | | | | | | | | | |
| Barnyardgrass | 2 | 0 | 0 | 0 | 0 | 7 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Ducksalad | 0 | 0 | 0 | 0 | 0 | 5 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 3 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 203 | 204 | 205 | 206 | 207 | 208 | 210 | 211 | 212 | 213 | 214 | 215 | 216 | 217 | 218 | 219 | 220 | 221 | 222 | 223 | 224 | 225 | 226 | 227 | 228 | 229 | 230 | 231 | 232 |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 233 | 234 | 235 | 236 | 237 | 238 | 239 | 240 | 241 | 242 | 243 | 245 | 246 | 249 | 250 | 251 | 252 | 253 | 254 | 255 | 256 | 257 | 258 | 259 | 264 | 265 | 266 | 267 | 268 |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 269 | 270 | 271 | 272 | 273 | 274 | 276 | 277 | 278 | 281 | 282 | 283 | 284 | 285 | 286 | 287 | 288 | 289 | 290 | 291 | 293 | 294 | 295 | 296 | 297 | 298 | 299 | 300 | 301 |
| Pre-emergence | | | | | | | | | | | | | | | | | | | | | | | | | | | | | |
| Barnyardgrass | 0 | 0 | 4 | 0 | 0 | 0 | 1 | 2 | 0 | 0 | 7 | 0 | 0 | 0 | 0 | 0 | 0 | 0 | 3 | 2 | 0 | 0 | 0 | 0 | 0 | 0 | 0 | 0 | 0 |
| Ducksalad | 0 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 303 | 304 | 305 | 310 | 311 | 312 | 313 | 314 | 315 | 316 | 318 | 319 | 320 | 321 | 323 | 324 | 325 | 326 | 327 | 328 | 329 | 330 | 334 | 335 | 336 | 337 | 338 | 339 | 340 |
| Pre-emergence | | | | | | | | | | | | | | | | | | | | | | | | | | | | | |
| Barnyardgrass | 0 | 0 | 0 | 0 | 0 | 0 | 0 | 0 | 4 | 3 | 0 | 0 | 0 | 0 | 0 | 0 | 0 | 0 | 0 | 0 | 0 | 0 | 0 | 0 | 0 | 0 | 0 | 2 | 7 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 341 | 346 | 350 | 351 | 353 | 354 | 358 | 366 | 367 | 368 | 369 | 370 | 371 | 372 | 373 | 374 | 375 | 376 | 378 | 379 | 380 | 381 | 382 | 383 | 384 | 385 | 387 | 388 | 389 |
| Pre-emergence | | | | | | | | | | | | | | | | | | | | | | | | | | | | | |
| Barnyardgrass | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — |
| S. Flatsedge | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 390 | 391 | 392 | 393 | 394 | 395 | 401 | 402 | 403 | 404 | 405 | 406 | 407 | 408 | 409 | 410 | 411 | 414 | 437 | 438 | 439 | 441 | 442 | 443 | 444 | 445 | 446 | 449 | 450 |
| Pre-emergence | | | | | | | | | | | | | | | | | | | | | | | | | | | | | |
| Barnyardgrass | 2 | 0 | 0 | 0 | 0 | 0 | 0 | 5 | 2 | 4 | 0 | 0 | 0 | 0 | 1 | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 1 | 0 | 0 | 0 | 1 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 4 | 0 | 0 | 0 | 0 | 0 | 0 | 0 | 0 | 0 | 0 | 3 | 0 | 0 | 0 | 0 | 0 | 0 | 0 | 0 | 0 | 0 | 0 | 0 | 0 |

TABLE B-continued

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 451 | 452 | 453 | 454 | 455 | 456 | 457 | 458 | 459 | 460 | 461 | 462 | 463 | 465 | 466 | 467 | 468 | 469 | 470 | 471 | 472 | 473 | 474 | 476 | 477 | 478 | 479 | 480 | 482 |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 483 | 485 | 486 | 487 | 488 | 489 | 490 | 492 | 493 | 494 | 495 | 496 | 498 | 499 | 509 | 521 | 528 | 529 | 531 | 532 | 538 | 539 | 546 | 550 | 552 | 556 | 558 | 560 | 561 |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 8 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | — | — | 0 | 0 | — | 0 | — | 0 | — | 0 | — | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 9 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 567 | 568 | 570 | 577 | 580 | 586 | 588 | 589 | 590 | 591 | 592 | 593 | 594 | 595 | 596 | 598 | 601 | 602 | 603 | 604 | 605 | 606 | 607 | 608 | 609 | 610 | 611 | 612 | 613 |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 614 | 615 | 618 | 619 | 620 | 621 | 622 | 624 | 625 | 627 | 628 | 629 | 630 | 631 | 632 | 633 | 634 | 636 | 637 | 638 | 639 | 640 | 641 | 642 | 643 | 644 | 645 | 646 | 647 |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | — | — | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 649 | 650 | 651 | 655 | 656 | 657 | 658 | 659 | 660 | 661 | 663 | 664 | 665 | 666 | 667 | 668 | 671 | 674 | 675 | 676 | 692 | 694 | 695 | 696 | 697 | 699 | 701 | 702 | 705 |
| Pre-emergence | | | | | | | | | | | | | | | | | | | | | | | | | | | | | |
| Barnyardgrass | 0 | 0 | 0 | 0 | 0 | 0 | 0 | 0 | 0 | 0 | 0 | 0 | 0 | 0 | 0 | 0 | 0 | 0 | 0 | 0 | 8 | 0 | 0 | 0 | 0 | 4 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 9 | 0 | 0 | 0 | 0 | 3 | 0 | 0 | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 9 | 0 | 0 | 0 | 0 | 6 | 0 | 0 | 0 |

| | COMPOUND | | | | | | | | | |
|---|---|---|---|---|---|---|---|---|---|---|
| Rate 62 g/ha | 706 | 715 | 720 | 721 | 724 | 740 | 741 | 758 | 765 | 793 |
| Pre-emergence | | | | | | | | | | |
| Barnyardgrass | 0 | 0 | 0 | 0 | 0 | 0 | 0 | 0 | 0 | 0 |
| Ducksalad | 0 | 0 | 0 | 0 | 0 | 0 | 0 | 0 | 0 | 6 |
| Rice | 0 | 0 | 0 | 0 | 0 | 0 | 0 | 0 | 0 | 0 |
| S. Flatsedge | 0 | 0 | 0 | 0 | 0 | 0 | 0 | 0 | 0 | 6 |

| | COMPOUND | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Rate 62 g/ha | 4 | 10 | 11 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 |
| Postemergence | | | | | | | | | | | | | | | | | | | | | | | | | | | | | | | | | | | | | | | | | | | | |
| B. signalgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 |
| Barnyardgrass | 0 | 0 | 0 | 0 | 0 | 0 | 0 | 0 | 0 | 0 | 0 | 0 | 0 | 0 | 0 | 0 | 0 | 5 | 0 | 0 | 0 | 0 | 0 | 0 | 0 | 0 | — | 0 | — | — | 0 | 0 | 0 | 0 | 0 | 0 | — | 0 | — | 0 | 0 | 0 | 0 | 0 |
| Bedstraw | 0 | 0 | 0 | 0 | 0 | 0 | 0 | 2 | 2 | 3 | 0 | 1 | 0 | 2 | 4 | 0 | 0 | 3 | 0 | 0 | 0 | 0 | 0 | 4 | 0 | 0 | 0 | 0 | — | 0 | 0 | 0 | 0 | 0 | 3 | 0 | 0 | 0 | 0 | — | 0 | 1 | 2 | 0 |
| Blackgrass | 0 | 0 | 0 | 0 | 0 | 0 | 0 | 0 | 0 | 0 | 0 | 1 | 0 | 0 | 4 | 0 | 0 | 0 | 0 | 0 | 0 | 0 | 4 | 0 | 0 | 0 | 0 | 0 | 0 | 0 | 0 | 0 | 0 | 0 | 0 | 0 | 0 | 0 | 0 | — | 0 | 0 | 0 | 0 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 |
| Crabgrass | 0 | 3 | 0 | 0 | 0 | 0 | 1 | 0 | 0 | 0 | 0 | 0 | 0 | 2 | 2 | 0 | 0 | 3 | 0 | 1 | 0 | 0 | 1 | 0 | 0 | 3 | 0 | 0 | 0 | 0 | 0 | 0 | 1 | 0 | 0 | 0 | 0 | 0 | 0 | — | 0 | 1 | 1 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | — | — | 0 | 0 | 0 | 0 | 0 | 0 | — | 0 | — | 0 | 0 | 0 | 0 | 0 |
| Giant foxtail | 0 | 2 | 0 | 0 | 0 | 0 | 0 | 0 | 0 | 0 | 0 | 0 | 0 | 0 | 3 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 1 | — | 0 | 0 | 0 | 3 |
| Morningglory | 0 | 0 | 0 | 1 | 2 | 1 | 3 | 1 | 0 | 4 | 2 | 0 | 1 | 9 | 1 | 1 | 0 | 2 | 0 | 1 | 0 | 6 | 3 | 1 | 4 | 4 | 0 | 0 | 0 | 3 | 1 | 0 | 2 | 0 | 0 | 0 | 1 | 0 | 0 | — | 0 | 1 | 1 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 |
| Redroot pigweed | 0 | 0 | 0 | 0 | 0 | 0 | 0 | 1 | 0 | 3 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 1 | 0 | 0 | 0 | 0 | 0 | 0 | — | 0 | 0 | 1 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | — | — | 0 | 0 | 0 | 0 | 0 | 0 | — | 0 | — | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | — | — | 0 | 0 | 0 | 0 | 0 | 0 | — | 0 | — | 0 | 0 | 0 | 0 | 0 |
| Soybean | 2 | 3 | 0 | 2 | 2 | 1 | 2 | 2 | 2 | 3 | 2 | 3 | 3 | 3 | 2 | 1 | 1 | 3 | 2 | 1 | 1 | 2 | 2 | 0 | 1 | 5 | 0 | 0 | 3 | 3 | 3 | 0 | 2 | 0 | 1 | 1 | 2 | 1 | 1 | — | 0 | 2 | 3 | 0 |
| Sugarbeets | 0 | 0 | 0 | 0 | 0 | 0 | 0 | 0 | 0 | 0 | 0 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 |
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 | — | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 |
| Wild oats | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 |

| | COMPOUND | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Rate 62 g/ha | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 |
| Postemergence | | | | | | | | | | | | | | | | | | | | | | | | | | | | | | | | | | | | | | | | | | | | |
| B. signalgrass | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | — | 0 | 0 | 0 | 0 | 0 | 0 | 4 | 3 | 3 | 0 | 0 | 0 | 0 | 0 |
| Barnyardgrass | 0 | 0 | 0 | 0 | 0 | 0 | 0 | 0 | 0 | 0 | 0 | 0 | 0 | 0 | — | — | — | — | 0 | 0 | 0 | 0 | 0 | 0 | 0 | 0 | 0 | 0 | 0 | 0 | 0 | 0 | 0 | — | 0 | 0 | — | — | 0 | 0 | 0 | 0 | 0 | 5 |
| Bedstraw | 0 | 0 | 0 | 0 | 0 | — | 2 | 0 | 0 | 0 | 0 | 0 | 0 | 4 | 0 | 0 | 0 | 0 | 0 | 0 | 0 | 0 | 0 | 0 | 3 | 0 | 0 | 0 | 0 | — | 0 | 2 | 2 | 3 | 0 | 0 | — | — | — | — | 0 | 0 | 0 | 0 |
| Blackgrass | 0 | 0 | 0 | 0 | 0 | 0 | 0 | 0 | 0 | 0 | 0 | 0 | 0 | 0 | 0 | 0 | 0 | 0 | 0 | 0 | 3 | 0 | 0 | 0 | 0 | 2 | 2 | 0 | 0 | — | 0 | 0 | 0 | 2 | 0 | 0 | 8 | 7 | 7 | 0 | 0 | 0 | 0 | 0 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 | 0 | — | 0 | 0 | 0 | 0 | 1 | 1 | 3 | 0 | 0 | 0 | 0 | 0 | 0 | 0 |

TABLE B-continued

| | | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 | 0 | 0 | 2 | 0 | 3 | 0 | 0 | 0 | 0 | 0 |
| Crabgrass | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 3 | 2 | — | 0 | 0 | — | 0 | 2 | 2 | 0 | 0 | 1 | 5 | 6 | 7 | 3 | 0 | 1 | 0 | 0 |
| Ducksalad | 0 | 0 | 0 | 0 | 0 | 0 | 0 | 0 | 0 | 0 | 0 | 0 | 0 | 0 | — | — | — | — | 0 | 0 | 0 | 0 | 0 | 0 | 0 | 0 | 0 | 0 | 0 | 0 | 0 | 0 | 0 | — | 0 | 0 | — | — | 0 | 0 | 0 | 0 | 0 | 0 |
| Giant foxtail | 0 | 0 | 0 | 0 | 0 | 0 | 0 | 0 | 0 | 0 | 0 | 0 | 0 | 0 | 0 | 0 | 0 | 0 | 0 | 0 | 3 | 3 | 0 | 0 | 0 | 0 | 0 | 0 | 0 | — | 0 | 0 | 0 | 0 | 0 | 0 | 8 | 8 | 6 | 0 | 0 | 0 | 0 | 0 |
| Morningglory | 1 | 0 | 1 | 0 | 0 | 1 | 2 | 2 | 0 | 0 | 0 | 0 | 0 | 2 | 0 | 0 | 0 | 0 | 3 | 2 | 1 | 0 | 0 | 7 | 5 | 7 | 2 | 4 | 0 | — | 0 | 4 | 4 | 8 | 0 | 3 | 7 | 7 | 6 | 10 | 1 | 1 | 1 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | — | 0 | 0 | 0 | 0 | 0 | 0 | 2 | 2 | 2 | 1 | 0 | 0 | 0 | 0 |
| Redroot pigweed | 0 | 0 | 0 | 0 | 0 | 2 | 1 | 0 | 0 | 0 | 0 | 0 | 0 | 0 | 0 | 0 | 0 | 0 | 0 | 0 | 0 | 0 | 0 | 2 | 0 | 2 | 0 | 0 | 0 | — | 0 | 0 | 0 | 3 | 0 | 2 | 1 | 2 | 2 | 0 | 2 | 0 | 0 | 0 |
| Rice | 0 | 0 | 0 | 0 | 0 | 0 | 0 | 0 | 0 | 0 | 0 | 0 | 0 | 0 | — | — | — | — | 0 | 0 | 2 | 0 | 0 | 0 | 0 | 0 | 0 | 0 | 0 | 0 | 0 | 0 | 0 | — | 0 | 0 | — | — | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | — | — | — | — | 0 | 0 | 0 | 0 | 0 | 0 | 0 | 0 | 0 | 0 | 0 | 0 | 0 | 0 | 0 | — | 0 | 0 | — | — | 0 | 0 | 0 | 0 | 0 | 0 |
| Soybean | 1 | 2 | 1 | 1 | 1 | 2 | 1 | 1 | 2 | 0 | 1 | 1 | 0 | 1 | 2 | 0 | 0 | 0 | 0 | 0 | 1 | 0 | 0 | 1 | 0 | 0 | 0 | 0 | 0 | — | 0 | 2 | 2 | 1 | 0 | 4 | 3 | 3 | 4 | 5 | 1 | 1 | 0 | 1 |
| Sugarbeets | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 3 | — | 0 | 0 | 0 | — | 0 | 0 | 0 | 3 | 0 | 0 | 3 | 1 | 2 | 2 | 2 | 0 | 0 | 0 |
| Velvetleaf | 0 | 0 | 0 | 0 | 0 | 0 | 0 | 0 | 3 | 0 | 3 | 0 | 0 | 0 | 0 | 0 | 0 | 0 | 0 | 2 | 0 | 0 | 0 | 2 | 0 | 0 | 0 | 0 | 0 | — | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 | 0 | 0 | 1 | 0 | 0 | 0 | 0 | 0 | 0 | 0 |
| Wild oats | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 | 0 | 0 | 1 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 99 | 100 | 101 | 102 | 103 | 104 | 105 | 106 | 107 | 108 | 109 | 110 | 111 | 112 | 113 | 114 | 115 | 116 | 117 | 118 | 119 | 120 | 121 | 122 | 123 | 124 | 125 | 126 | 127 |
| Postemergence | | | | | | | | | | | | | | | | | | | | | | | | | | | | | |
| B. signalgrass | 0 | 0 | 0 | 0 | 0 | 0 | 0 | 0 | 7 | 0 | 7 | 0 | 0 | 0 | 4 | 0 | 0 | 8 | 6 | 0 | 0 | 0 | 0 | 0 | 0 | 0 | 0 | 0 | 0 |
| Barnyardgrass | 0 | — | 0 | 0 | — | — | 0 | 0 | — | 0 | 0 | 0 | 0 | 0 | 0 | 0 | 0 | 0 | 0 | — | — | 0 | 0 | 0 | 0 | 0 | 0 | 0 | 0 |
| Bedstraw | 3 | 0 | — | 0 | — | — | 0 | 0 | 2 | 0 | 6 | 2 | 5 | 0 | 1 | 3 | 0 | 0 | 0 | 0 | 0 | — | — | — | — | — | — | 0 | 0 |
| Blackgrass | 3 | 0 | 0 | 0 | 0 | 0 | 2 | 0 | 7 | 4 | 7 | 1 | 0 | 0 | 8 | 0 | 4 | 9 | 8 | 0 | 2 | 0 | 0 | 0 | 2 | 0 | 0 | 0 | 0 |
| Cocklebur | 0 | 0 | 0 | 0 | 0 | 0 | 0 | 0 | 0 | 0 | 2 | 0 | 0 | 0 | 1 | 0 | 0 | 0 | 0 | 0 | 0 | 1 | 0 | 0 | 0 | 0 | 0 | 0 | 0 |
| Corn | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 0 | 0 | 0 | — | 0 | 8 | 4 | 8 | 2 | 1 | 0 | 9 | 2 | 0 | 9 | 9 | 1 | 2 | 5 | 4 | 0 | 0 | 0 | 0 | 0 | 0 |
| Ducksalad | 0 | — | 0 | 0 | — | — | 0 | 0 | — | 0 | 0 | 0 | 0 | 0 | 0 | 0 | 0 | 0 | 0 | — | — | 0 | 0 | 0 | 0 | 0 | 0 | 0 | 0 |
| Giant foxtail | 0 | 0 | 0 | 0 | 0 | 3 | 2 | 0 | 8 | 5 | 8 | 0 | 2 | 2 | 9 | 5 | 0 | 9 | 9 | 1 | 8 | 3 | 1 | 2 | 3 | 0 | 0 | 0 | 0 |
| Morningglory | 1 | 0 | 0 | 0 | 8 | 10 | — | 6 | 3 | 0 | 3 | 4 | 4 | 8 | 5 | 1 | 3 | 2 | 2 | 1 | 3 | 4 | 5 | 1 | 8 | 0 | 0 | 0 | 0 |
| Nutsedge | 0 | 0 | 0 | 0 | 0 | 0 | 0 | 0 | 3 | 0 | 0 | 0 | 0 | 0 | 0 | 0 | 0 | 5 | 2 | 0 | 0 | 0 | 0 | 0 | 0 | 0 | 0 | 0 | 0 |
| Rape | 2 | 0 | 0 | 0 | 0 | 0 | 0 | 0 | 0 | 0 | 3 | 2 | 3 | 2 | 0 | 3 | 0 | 0 | 0 | 0 | 0 | 0 | 0 | 0 | 0 | 0 | 0 | 0 | 0 |
| Redroot pigweed | 3 | 0 | 0 | 0 | 0 | 1 | 0 | 0 | 0 | 0 | 3 | 3 | 3 | 2 | 3 | 0 | 0 | 0 | 0 | 0 | 0 | 0 | 2 | 0 | 0 | 0 | 0 | 0 | 0 |
| Rice | 0 | — | 0 | 0 | — | — | 0 | 0 | — | 0 | 0 | 0 | 0 | 0 | 0 | 0 | 0 | 0 | 0 | — | — | 0 | 0 | 0 | 0 | 0 | 0 | 0 | 0 |
| S. Flatsedge | 0 | — | 0 | 0 | — | — | 0 | 0 | — | 0 | 0 | 0 | 0 | 0 | 0 | 0 | 0 | 0 | 0 | — | — | 0 | 3 | 0 | 0 | 0 | 0 | 0 | 0 |
| Soybean | 2 | 0 | 2 | 0 | 4 | 4 | 1 | 0 | 3 | 1 | 4 | 3 | 3 | 4 | 6 | 3 | 1 | 3 | 2 | 1 | 1 | 2 | 5 | 3 | 2 | 0 | 0 | 0 | 0 |
| Sugarbeets | 2 | 0 | 0 | 0 | 1 | 0 | 0 | 0 | 0 | 0 | 3 | 0 | 2 | 2 | 4 | 3 | 2 | 2 | 0 | 0 | 0 | 0 | 0 | 0 | 0 | 0 | 0 | 0 | 0 |
| Velvetleaf | 0 | 0 | 0 | 0 | 0 | 0 | 0 | 0 | 4 | 2 | 0 | 0 | 0 | 0 | 0 | 0 | 0 | 4 | 0 | 0 | 0 | 0 | 0 | 0 | 0 | 0 | 0 | 0 | 0 |
| Wheat | 0 | 0 | 0 | 0 | 0 | 0 | 0 | 0 | 2 | 0 | 0 | 0 | 0 | 0 | 1 | 0 | 0 | 0 | 2 | 0 | 0 | 0 | 0 | 0 | 0 | 0 | 0 | 0 | 0 |
| Wild oats | 0 | 0 | 0 | 0 | 0 | 0 | 0 | 0 | 0 | 0 | 0 | 0 | 0 | 0 | 1 | 0 | 0 | 3 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 128 | 129 | 130 | 131 | 132 | 133 | 134 | 135 | 136 | 137 | 138 | 139 | 140 | 141 | 142 | 143 | 144 | 145 | 146 | 147 | 148 | 149 | 150 | 151 | 152 | 153 | 154 | 155 | 156 |
| Postemergence | | | | | | | | | | | | | | | | | | | | | | | | | | | | | |
| B. signalgrass | 0 | 0 | 1 | 4 | 0 | 0 | 0 | 0 | 0 | 0 | 5 | 2 | 0 | 0 | 0 | 0 | 0 | 0 | 4 | 7 | 0 | 0 | 0 | 3 | 0 | 0 | 0 | 0 | 0 |
| Barnyardgrass | — | — | — | — | — | — | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Bedstraw | 0 | 0 | 0 | 7 | 0 | 0 | 4 | 0 | 2 | 4 | 2 | — | 4 | 2 | 2 | 5 | 2 | 0 | 2 | 2 | 2 | 0 | 0 | 3 | 0 | 0 | 0 | 0 | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Blackgrass | 0 | 0 | 3 | 8 | 0 | 0 | 0 | 0 | 0 | 5 | 7 | 2 | 3 | 0 | 0 | 3 | 0 | 0 | 8 | 7 | 5 | 0 | 0 | 8 | 0 | 0 | 0 | 0 | 0 |
| Cocklebur | 0 | 0 | 0 | 2 | 0 | 2 | 0 | 0 | 1 | 0 | 0 | 0 | 0 | 0 | 0 | 1 | 0 | 0 | 2 | 0 | 0 | 0 | 0 | 0 | 0 | 0 | 0 | 0 | 0 |
| Corn | 0 | 0 | 0 | 3 | 0 | 0 | 0 | 0 | 0 | 0 | 0 | 0 | 0 | 0 | 0 | 0 | 0 | 0 | 0 | 4 | 0 | 0 | 0 | 0 | 0 | 0 | 0 | 0 | 0 |
| Crabgrass | 0 | 2 | 5 | 5 | 5 | 0 | 0 | 0 | 1 | 7 | 8 | 8 | 0 | 0 | 3 | 1 | 2 | 2 | 8 | 9 | 8 | 0 | 0 | 8 | 0 | 0 | 0 | 1 | 0 |
| Ducksalad | — | — | — | — | — | — | — | 0 | 0 | 0 | 0 | 0 | 0 | 0 | 0 | 0 | 0 | 0 | 2 | 0 | 0 | 0 | 0 | 0 | 0 | 0 | 0 | 0 | 0 |
| Giant foxtail | 0 | 4 | 8 | 8 | 8 | 0 | 0 | 0 | 0 | 8 | 9 | 6 | 0 | 0 | 0 | 0 | 0 | 0 | 8 | 8 | 5 | 0 | 0 | 7 | 0 | 0 | 0 | 1 | 0 |
| Morningglory | 0 | 4 | 2 | 7 | 3 | 2 | 5 | 0 | 6 | 7 | 5 | 3 | 4 | 1 | 3 | 3 | 0 | 6 | 3 | 3 | 3 | 0 | 0 | 4 | 0 | 0 | 0 | 0 | 0 |
| Nutsedge | 0 | 0 | 0 | 0 | 0 | 0 | 0 | 0 | 0 | 0 | 4 | 0 | 0 | 0 | 0 | 0 | 0 | 0 | 0 | 0 | 0 | 0 | 0 | 2 | 0 | 0 | 0 | 0 | 0 |
| Rape | 0 | 0 | 0 | 1 | 0 | 0 | 0 | 0 | 0 | 0 | 0 | 0 | 0 | 0 | 0 | 0 | 0 | 0 | 2 | 0 | 1 | 0 | 0 | 0 | 0 | 0 | 0 | 0 | 0 |
| Redroot pigweed | 0 | 0 | 0 | 2 | 0 | 0 | 0 | 0 | 3 | 2 | 3 | 3 | 0 | 0 | 0 | 3 | 0 | 0 | 4 | 0 | 2 | 0 | 0 | 3 | 0 | 0 | 0 | 0 | 0 |
| Rice | — | — | — | — | — | — | — | — | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | — | — | — | — | — | — | — | — | 0 | 0 | 0 | 0 | 0 | 0 | 0 | 0 | 0 | 0 | 0 | 0 | 0 | 0 | 0 | 0 | 0 | 0 | 0 | 0 | 0 |
| Soybean | 0 | 1 | 1 | 5 | 3 | 1 | 1 | 2 | 3 | 5 | 2 | 1 | 3 | 3 | 2 | 3 | 3 | 3 | 3 | 5 | 4 | 0 | 1 | 3 | 0 | 0 | 2 | 1 | 1 |
| Sugarbeets | 0 | 0 | 0 | 2 | 0 | 0 | 0 | 0 | 3 | 3 | 0 | 0 | 0 | 0 | 0 | 1 | 0 | 0 | 1 | 0 | 2 | 0 | 0 | 2 | 0 | 0 | 0 | 0 | 0 |
| Velvetleaf | 0 | 0 | 0 | 0 | 2 | 0 | 0 | 0 | 0 | 0 | 2 | 2 | 0 | 0 | 0 | 2 | 0 | 0 | 0 | 0 | 0 | 0 | 0 | 3 | 0 | 0 | 0 | 0 | 0 |
| Wheat | 0 | 0 | 0 | 3 | 0 | 0 | 0 | 0 | 0 | 0 | 3 | 2 | 0 | 0 | 0 | 0 | 0 | 0 | 0 | 3 | 0 | 0 | 0 | 0 | 0 | 0 | 0 | 0 | 0 |
| Wild oats | 0 | 0 | 0 | 2 | 0 | 0 | 0 | 0 | 0 | 1 | 0 | 2 | 0 | 0 | 0 | 0 | 0 | 0 | 2 | 2 | 0 | 0 | 0 | — | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 157 | 158 | 159 | 160 | 161 | 162 | 163 | 164 | 165 | 166 | 167 | 168 | 169 | 170 | 171 | 172 | 173 | 174 | 175 | 177 | 178 | 179 | 180 | 181 | 182 | 183 | 184 | 185 | 186 |
| Postemergence | | | | | | | | | | | | | | | | | | | | | | | | | | | | | |
| B. signalgrass | 0 | 0 | 0 | 0 | 0 | 0 | 0 | 0 | 0 | 0 | 0 | 0 | 0 | 3 | 0 | 0 | 0 | 0 | 0 | 0 | 0 | 0 | 0 | 0 | 0 | 0 | 0 | 0 | 0 |
| Barnyardgrass | — | 0 | 0 | 0 | — | — | — | 0 | — | — | — | — | 0 | 0 | 0 | — | — | — | — | 0 | — | — | — | — | — | — | — | — | — |
| Bedstraw | 0 | 0 | 0 | 0 | 0 | 0 | 0 | 0 | 0 | 0 | 0 | 3 | 2 | 0 | — | 0 | 0 | 0 | 0 | 0 | 0 | 0 | 0 | 0 | 0 | 0 | 0 | 0 | 0 |
| Blackgrass | 0 | 1 | 0 | 0 | 0 | 0 | 2 | 0 | 0 | 0 | 0 | 0 | 2 | 9 | 0 | 0 | 0 | 0 | 0 | 0 | 0 | 0 | 0 | 0 | 0 | 0 | 0 | 0 | 0 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 0 | 0 | 0 | 6 | 0 | 2 | 0 | 0 | 0 | 2 | 8 | 0 | 0 | 0 | 2 | 0 | 0 | 0 | 0 | 0 | 0 | 0 | 0 | 0 | 0 | 0 |
| Ducksalad | — | 0 | 0 | 0 | — | — | — | 0 | — | — | — | — | 0 | 0 | 0 | — | — | — | — | 0 | — | — | — | — | — | — | — | — | — |
| Giant foxtail | 0 | 0 | 0 | 0 | 0 | 0 | 6 | 0 | 0 | 0 | 0 | 0 | 0 | 4 | 0 | 0 | 0 | 0 | 0 | 0 | 0 | 0 | 0 | 0 | 0 | 0 | 0 | 0 | 0 |
| Morningglory | 0 | 0 | 0 | 0 | 4 | 6 | 2 | 0 | 3 | 1 | 2 | 7 | 1 | 0 | 0 | 2 | 7 | 3 | 1 | 0 | 2 | 4 | 0 | 0 | 0 | 0 | 0 | 1 | 1 |
| Nutsedge | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Redroot pigweed | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | — | 0 | 0 | 0 | — | — | — | 0 | — | — | — | — | 0 | 0 | 0 | — | — | — | — | 0 | — | — | — | — | — | — | — | — | — |
| S. Flatsedge | — | 0 | 0 | 0 | — | — | — | 0 | — | — | — | — | 0 | 0 | 0 | — | — | — | — | 0 | — | — | — | — | — | — | — | — | — |
| Soybean | 0 | 3 | 0 | 0 | 2 | 3 | 2 | 0 | 2 | 0 | 2 | 1 | 1 | 2 | 1 | 2 | 2 | 2 | 1 | 1 | 1 | 1 | 0 | 0 | 0 | 0 | 1 | 2 | 1 |
| Sugarbeets | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 |
| Velvetleaf | 0 | 0 | 0 | 0 | 0 | 3 | 3 | 0 | 0 | 0 | 0 | 0 | 0 | 2 | 0 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 3 | 0 | 0 | 0 | 0 | 0 | 0 | 0 | 0 | 0 | 0 | 0 | 0 | 0 | 0 | 0 |
| Wild oats | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 187 | 188 | 189 | 190 | 191 | 192 | 193 | 194 | 195 | 196 | 197 | 198 | 199 | 200 | 201 | 202 | 203 | 204 | 205 | 206 | 207 | 208 | 210 | 211 | 212 | 213 | 214 | 215 | 216 |
| Postemergence | | | | | | | | | | | | | | | | | | | | | | | | | | | | | |
| B. signalgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Barnyardgrass | — | — | — | — | — | — | — | — | — | — | — | — | 0 | — | — | — | — | — | — | — | — | — | — | — | — | — | — | — | — |
| Bedstraw | 0 | 0 | 0 | 0 | 0 | 0 | 0 | 0 | 2 | 0 | 0 | 0 | 0 | 0 | 0 | 1 | 0 | 0 | 0 | 0 | 0 | 0 | 0 | 4 | 0 | 0 | 0 | 0 | 0 |
| Blackgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 6 | 0 | 1 | 0 | 0 |
| Cocklebur | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 0 | 2 | 1 | 0 | 0 | 0 | 0 | 0 | 0 | 0 | 0 | 0 | 0 | 0 | 0 | 0 | 0 | 0 | 0 | 0 | 0 | 6 | 0 | 1 | 0 | 0 |
| Ducksalad | — | — | — | — | — | — | — | — | — | — | — | — | 0 | — | — | — | — | — | — | — | — | — | — | — | — | — | — | — | — |
| Giant foxtail | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 4 | 0 | 0 | 0 | 0 |
| Morningglory | 0 | 0 | 0 | 0 | 1 | 1 | 0 | 0 | 0 | 0 | 3 | 0 | 4 | 0 | 1 | 2 | 0 | 3 | 0 | 1 | 0 | 1 | 2 | 4 | 2 | 6 | 2 | 0 | 3 |
| Nutsedge | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 1 | 0 | 0 | 0 | 0 | 0 | 0 | 0 | 2 | 0 | 0 | 0 | 0 | 0 |
| Redroot pigweed | 0 | 0 | 0 | 0 | 0 | 0 | 0 | 0 | 0 | 0 | 0 | 0 | 0 | 0 | 0 | 3 | 0 | 0 | 0 | 0 | 0 | 0 | 0 | 2 | 0 | 5 | 0 | 0 | 0 |
| Rice | — | — | — | — | — | — | — | — | — | — | — | — | 0 | — | — | — | — | — | — | — | — | — | — | — | — | — | — | — | — |
| S. Flatsedge | — | — | — | — | — | — | — | — | — | — | — | — | 0 | — | — | — | — | — | — | — | — | — | — | — | — | — | — | — | — |
| Soybean | 0 | 1 | 0 | 0 | 3 | 3 | 0 | 0 | 2 | 0 | 0 | 0 | 2 | 2 | 1 | 2 | 0 | 1 | 0 | 0 | 1 | 1 | 1 | 3 | 1 | 1 | 0 | 0 | 1 |
| Sugarbeets | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 3 | 0 | 0 | 0 |
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 3 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 3 | 0 |
| Wild oats | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 217 | 218 | 219 | 220 | 221 | 222 | 223 | 224 | 225 | 226 | 227 | 228 | 229 | 230 | 231 | 232 | 233 | 234 | 235 | 236 | 237 | 238 | 239 | 240 | 241 | 242 | 243 | 244 | 245 |
| Postemergence | | | | | | | | | | | | | | | | | | | | | | | | | | | | | |
| B. signalgrass | 0 | 0 | 0 | 2 | 0 | 0 | 0 | 0 | 2 | 0 | 0 | 0 | 0 | 0 | 0 | 0 | 0 | 0 | 0 | 0 | 0 | 0 | 0 | 0 | 0 | 1 | 0 | 0 | 1 |
| Barnyardgrass | — | — | — | — | — | — | — | — | — | — | — | — | — | — | — | — | — | — | — | — | — | — | — | — | — | — | — | — | — |
| Bedstraw | 0 | 6 | 6 | 6 | 2 | 3 | 3 | 3 | 0 | 0 | 7 | 0 | 0 | 0 | 0 | 0 | 0 | 0 | 0 | 0 | 0 | 0 | 0 | 0 | 0 | 2 | 0 | 0 | 3 |
| Blackgrass | 3 | 5 | 5 | 5 | 2 | 0 | 0 | 0 | 6 | 0 | 0 | 0 | 0 | 0 | 0 | 0 | 0 | 0 | 0 | 0 | 0 | 0 | 0 | 0 | 3 | 8 | 7 | 0 | 4 |
| Cocklebur | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 5 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 1 | 3 | 3 | 2 | 0 | 0 | 0 | 5 | 0 | 0 | 0 | 0 | 0 | 0 | 0 | 0 | 0 | 0 | 0 | 0 | 0 | 0 | 0 | 2 | 8 | 3 | 0 | 2 |
| Ducksalad | — | — | — | — | — | — | — | — | — | — | — | — | — | — | — | — | — | — | — | — | — | — | — | — | — | — | — | — | — |
| Giant foxtail | 1 | 1 | 6 | 5 | 2 | 0 | 0 | 0 | 8 | 2 | 0 | 0 | 0 | 0 | 0 | 0 | 0 | 0 | 0 | 0 | 0 | 0 | 0 | 0 | 2 | 7 | 3 | 0 | 5 |
| Morningglory | 0 | 3 | 6 | 5 | 0 | 1 | 1 | 2 | 2 | 5 | 4 | 2 | 0 | 0 | 1 | 3 | 3 | 0 | 2 | 4 | 2 | 2 | 1 | 5 | 3 | 0 | 5 | 0 | 5 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 2 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 |
| Redroot pigweed | 0 | 0 | 5 | 0 | 6 | 0 | 0 | 0 | 0 | 0 | 0 | 0 | 0 | 0 | 0 | 2 | 0 | 0 | 0 | 0 | 0 | 0 | 0 | 0 | 0 | 0 | 2 | 0 | 3 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 1 | 3 | 5 | 5 | 2 | 2 | 3 | 2 | 2 | 2 | 1 | 0 | 0 | 0 | 0 | 3 | 3 | 0 | 0 | 1 | 0 | 1 | 1 | 0 | 1 | 4 | 3 | 0 | 2 |
| Sugarbeets | 0 | 2 | 4 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 1 |
| Velvetleaf | 0 | 0 | 0 | 0 | 0 | 0 | 0 | 0 | 0 | 0 | 0 | 0 | 0 | 0 | 0 | 2 | 2 | 0 | 0 | 0 | 0 | 1 | 0 | 0 | 2 | 3 | 0 | 0 | 3 |
| Wheat | 0 | 0 | 5 | 3 | 0 | 0 | 0 | 0 | 3 | 2 | 0 | 0 | 0 | 0 | 0 | 0 | 0 | 0 | 0 | 0 | 0 | 0 | 0 | 0 | 0 | 4 | 2 | 0 | 4 |
| Wild oats | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

TABLE B-continued

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 246 | 248 | 249 | 250 | 251 | 252 | 253 | 254 | 255 | 256 | 257 | 258 | 259 | 260 | 261 | 262 | 263 | 264 | 265 | 266 | 267 | 268 | 269 | 270 | 271 | 272 | 273 | 274 | 276 |
| Postemergence | | | | | | | | | | | | | | | | | | | | | | | | | | | | | |
| B. signalgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | — | — | — | — | — | — | — | — | — | — | — | — | — | — | — | — | — | — | — | — | — | — | — | — | — | — | — | — | — |
| Bedstraw | 7 | 0 | 0 | 0 | 2 | 0 | 0 | 0 | 0 | 0 | 0 | 2 | 0 | 6 | 0 | 0 | 0 | 0 | 0 | 0 | 0 | 0 | — | 0 | 4 | 0 | 0 | 0 | 0 |
| Blackgrass | 0 | 0 | 0 | 0 | 0 | 0 | 0 | 0 | 0 | 0 | 0 | 1 | 0 | 0 | 0 | 0 | 0 | 2 | 4 | 3 | 0 | 0 | 0 | 0 | 3 | 0 | 0 | 0 | 0 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 0 | 0 | 0 | 0 | 0 | 0 | 0 | 0 | 0 | 0 | 0 | 0 | 0 | 0 | 0 | 1 | 0 | 0 | 0 | 0 | 0 | 0 | 0 | 0 | 0 | 0 |
| Ducksalad | — | — | — | — | — | — | — | — | — | — | — | — | — | — | — | — | — | — | — | — | — | — | — | — | — | — | — | — | — |
| Giant foxtail | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 1 | 0 | 0 | 0 | 0 |
| Morningglory | 8 | 0 | 0 | 4 | 6 | 2 | 0 | 7 | 3 | 8 | 6 | 3 | 6 | 2 | 3 | 3 | 2 | 7 | 6 | 4 | 1 | 1 | 3 | 0 | 2 | 0 | 0 | 0 | 3 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 0 | 0 | 0 | 0 | 0 | 0 | 0 |
| Redroot pigweed | 0 | 0 | 0 | 0 | 0 | 0 | 0 | 0 | 0 | 0 | 3 | 0 | 2 | 0 | 0 | 1 | 0 | 0 | 2 | 2 | 0 | 0 | 3 | 0 | 3 | 0 | 0 | 0 | 0 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 1 | 0 | 2 | 1 | 2 | 1 | 0 | 0 | 2 | 3 | 3 | 3 | 3 | 1 | 2 | 1 | 0 | 0 | 3 | 5 | 2 | 0 | 1 | 0 | 4 | 1 | 2 | 2 | 3 |
| Sugarbeets | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 |
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 2 | 0 | 0 | 0 | 0 | 0 | 0 | 4 | 0 | 0 | 0 | 0 | 0 | 0 | 0 | 0 | 0 |
| Wild oats | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 277 | 278 | 281 | 282 | 283 | 284 | 285 | 286 | 287 | 288 | 289 | 290 | 291 | 292 | 293 | 294 | 295 | 296 | 297 | 298 | 299 | 300 | 301 | 303 | 304 | 305 | 306 | 307 | 308 |
| Postemergence | | | | | | | | | | | | | | | | | | | | | | | | | | | | | |
| B. signalgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | — | — | — | — | — | — | — | — | — | — | — | — | — | — | — | — | — | — | — | — | — | — | — | — | — | — | — | — | — |
| Bedstraw | 5 | 0 | — | 5 | 0 | 2 | 0 | 2 | 4 | 0 | 0 | 0 | 0 | 0 | 0 | 3 | 0 | 0 | 0 | 0 | 2 | 0 | 0 | — | 0 | — | 0 | 0 | 0 |
| Blackgrass | 2 | 0 | 0 | 0 | 2 | 3 | 0 | 0 | 8 | 0 | 5 | 0 | 1 | 0 | 5 | 0 | 2 | 0 | 0 | 0 | 7 | 0 | 0 | 0 | 0 | 0 | 0 | 0 | 0 |
| Cocklebur | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 1 | 0 | 0 | 0 | 0 | 0 | 0 | 0 | 2 | 0 | 3 | 0 | 0 | 0 | 6 | 0 | 0 | 0 | 0 | 0 | 0 | 0 | 0 | 0 | 0 | 0 | 0 | 0 | 0 |
| Ducksalad | — | — | — | — | — | — | — | — | — | — | — | — | — | — | — | — | — | — | — | — | — | — | — | — | — | — | — | — | — |
| Giant foxtail | 2 | 0 | 0 | 0 | 0 | 0 | 0 | 0 | 7 | 0 | 2 | 0 | 0 | 0 | 5 | 0 | 0 | 0 | 0 | 0 | 7 | 0 | 0 | 0 | 0 | 0 | 0 | 0 | 0 |
| Morningglory | 7 | 3 | 2 | 6 | 8 | 7 | 3 | 1 | 2 | 7 | 3 | 4 | 4 | 0 | 1 | 6 | 1 | 0 | 0 | 0 | 3 | 0 | 0 | 0 | 3 | 0 | 2 | 0 | 0 |
| Nutsedge | 0 | 0 | 0 | 0 | 0 | 0 | 0 | 0 | 6 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 2 | 2 | 1 | 0 | 0 | 0 | 1 | 0 | 0 | 0 | 0 | 0 | 0 | 0 | 0 | 0 | 0 | 1 | 0 | 0 | 0 | 0 | 0 | 0 | 0 | 0 |
| Redroot pigweed | 1 | 0 | 0 | 4 | 4 | 3 | 0 | 0 | 2 | 0 | 0 | 0 | 0 | 0 | 0 | 0 | 0 | 0 | 0 | 0 | 2 | 0 | 0 | 0 | 3 | 3 | 0 | 0 | 0 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 3 | 1 | 2 | 3 | 4 | 4 | 2 | 1 | 1 | 0 | 2 | 2 | 1 | 0 | 1 | 2 | 2 | 0 | 2 | 0 | — | 1 | 0 | 2 | 3 | 4 | 1 | 0 | 1 |
| Sugarbeets | 1 | 0 | 0 | 2 | 0 | 1 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 |
| Velvetleaf | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 5 | 0 | 2 | 0 | 0 | 0 | 2 | 0 | 0 | 0 | 0 | 0 | 0 | 0 | 0 | 0 | 0 | 0 | 0 | 0 | 0 |

TABLE B-continued

| Wild oats | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 |
|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | |
| Rate 62 g/ha | 309 | 310 | 311 | 312 | 313 | 314 | 315 | 316 | 317 | 318 | 319 | 320 | 321 | 322 | 323 | 324 | 325 | 326 | 327 | 328 | 329 | 330 | 332 | 333 | 334 | 335 | 336 | 337 | 338 |
| Postemergence | | | | | | | | | | | | | | | | | | | | | | | | | | | | | |
| B. signalgrass | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | — | — | — | — | — | — | — | — | — | — | — | — | — | — | — | — | — | — | — | — | — | — | — | — | — | — | — | — | — |
| Bedstraw | 0 | 4 | 0 | 0 | 5 | 2 | 0 | — | 2 | 0 | 0 | 0 | 0 | 0 | 0 | 0 | 2 | — | 7 | 0 | 0 | 0 | 0 | 0 | 0 | 0 | 0 | 0 | 0 |
| Blackgrass | 0 | 5 | 0 | 0 | 0 | 2 | 0 | 0 | 8 | 0 | 0 | 0 | 0 | 0 | 0 | 0 | 0 | 0 | 0 | 0 | 0 | 0 | 0 | 0 | 0 | 0 | 0 | 0 | 0 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 8 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 |
| Ducksalad | — | — | — | — | — | — | — | — | — | — | — | — | — | — | — | — | — | — | — | — | — | — | — | — | — | — | — | — | — |
| Giant foxtail | 0 | 7 | 0 | 0 | 0 | 0 | 0 | 0 | 5 | 0 | 0 | 0 | 0 | 0 | 0 | 0 | 0 | 0 | 0 | 0 | 0 | 0 | 0 | 0 | 0 | 0 | 0 | 0 | 0 |
| Morningglory | 1 | 4 | 0 | 0 | 2 | 2 | 0 | 3 | 1 | 0 | 2 | 1 | 2 | 4 | 0 | 0 | 4 | 5 | 7 | 7 | 0 | 0 | 0 | 0 | 0 | 0 | 0 | 0 | 0 |
| Nutsedge | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Redroot pigweed | 0 | 0 | 0 | 0 | 0 | 0 | 0 | 2 | 0 | 0 | 0 | 3 | 2 | 2 | 0 | 0 | 0 | 3 | 4 | 2 | 0 | 0 | 0 | 0 | 0 | 0 | 0 | 0 | 0 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 2 | 4 | 2 | 2 | 1 | 2 | 3 | 3 | 3 | 0 | 0 | 2 | 2 | 1 | 0 | 0 | 2 | 3 | 5 | — | 1 | 1 | 2 | 2 | 1 | 1 | 1 | 1 | 1 |
| Sugarbeets | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Velvetleaf | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wheat | 0 | 4 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 0 | 3 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 339 | 340 | 341 | 342 | 343 | 344 | 345 | 348 | 349 | 350 | 351 | 352 | 353 | 354 | 355 | 356 | 357 | 358 | 359 | 360 | 361 | 362 | 363 | 364 | 367 | 368 | 369 | 370 | 371 |
| Postemergence | | | | | | | | | | | | | | | | | | | | | | | | | | | | | |
| B. signalgrass | 0 | 0 | 0 | 0 | 2 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 |
| Barnyardgrass | — | — | — | 0 | 0 | 0 | 0 | 2 | 2 | 0 | 0 | 0 | — | 0 | 1 | — | 0 | 2 | 0 | 2 | — | — | — | 0 | — | — | 0 | 0 | — |
| Bedstraw | 0 | 3 | 0 | 4 | 0 | 0 | 0 | — | 2 | — | — | 0 | — | — | 0 | 0 | 0 | 0 | 0 | 0 | 7 | 5 | 4 | 0 | — | 0 | — | — | — |
| Blackgrass | 0 | 0 | 0 | 0 | 3 | 0 | 0 | 2 | 1 | 4 | 0 | 8 | 0 | 3 | 3 | 3 | 3 | 2 | 0 | 5 | 5 | 8 | 5 | 0 | 0 | 7 | 0 | 2 | 2 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 |
| Crabgrass | 0 | 0 | 0 | 0 | 1 | 0 | 0 | 1 | 0 | 1 | 0 | 1 | 0 | 0 | 0 | 0 | 2 | 0 | 0 | 2 | 0 | 3 | 1 | 0 | 0 | 6 | 0 | 3 | 3 |
| Ducksalad | — | — | — | 0 | 0 | 0 | 0 | 0 | 0 | 0 | 0 | 0 | — | 0 | 0 | — | 0 | 0 | 0 | 0 | — | — | — | 0 | — | — | 0 | 0 | — |
| Giant foxtail | 0 | 0 | 0 | 0 | 7 | 0 | 0 | 3 | 0 | 5 | 0 | 2 | 0 | 0 | 2 | 2 | 8 | 3 | 0 | 8 | 1 | 6 | 4 | 0 | 0 | 8 | 0 | 6 | 5 |
| Morningglory | 2 | 2 | 7 | 7 | 2 | 0 | 0 | 2 | 5 | 3 | 3 | 0 | 3 | 0 | 2 | 4 | 2 | 3 | 0 | 4 | 1 | 1 | 1 | 0 | 5 | 2 | 7 | 10 | 7 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 2 | 0 | 0 | 0 | 0 | 0 | 0 | 0 | 0 | 0 | 0 | 2 | 0 | 0 | 0 | 0 | 1 | 0 | 0 | 2 | 0 | 0 | 0 | 0 | 0 | 0 | 0 | 0 |
| Redroot pigweed | 0 | 2 | 0 | 2 | 0 | 0 | 0 | 0 | 0 | 0 | 0 | 0 | 2 | 2 | 0 | 0 | 0 | 3 | 0 | 0 | 3 | 2 | 0 | 0 | 0 | 2 | 0 | 0 | 0 |
| Rice | — | — | — | 0 | 0 | 0 | 0 | 0 | 0 | 0 | 0 | 0 | — | 0 | 0 | 0 | 0 | 0 | 0 | 0 | — | — | — | 0 | — | — | 0 | 0 | — |
| S. Flatsedge | — | — | — | 0 | 0 | 0 | 0 | 4 | 0 | 0 | 0 | 2 | — | 5 | 0 | — | 0 | 0 | 0 | 2 | — | — | — | 0 | — | — | 0 | 2 | — |
| Soybean | 1 | 1 | 1 | 3 | 1 | 2 | 0 | 1 | 1 | 1 | 1 | 2 | 4 | 3 | 1 | 2 | 2 | 4 | 0 | 1 | 2 | 4 | 4 | 0 | 0 | 4 | 0 | 1 | 1 |
| Sugarbeets | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 |

TABLE B-continued

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Velvetleaf | 0 | 0 | 0 | 0 | 0 | 0 | 0 | 2 | 0 | 0 | 0 | 0 | 0 | 0 | 0 | 0 | 2 | 2 | 0 | 0 | 0 | 1 | 0 | 0 | 0 | 0 | 0 | 0 | 0 |
| Wheat | 0 | 0 | 0 | 0 | 2 | 0 | 0 | 2 | 0 | 0 | 0 | 0 | 0 | 0 | 0 | 2 | 4 | 2 | 0 | 3 | 0 | 2 | 0 | 0 | 0 | 0 | 0 | 0 | 0 |
| Wild oats | 0 | 0 | 0 | 0 | 0 | 0 | 0 | 2 | 0 | 0 | 0 | 0 | 0 | 0 | 0 | 2 | 3 | 0 | 0 | 3 | 0 | 3 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate 62 g/ha | 372 | 373 | 374 | 375 | 376 | 378 | 379 | 380 | 381 | 382 | 383 | 384 | 385 | 387 | 388 | 389 | 390 | 391 | 392 | 393 | 394 | 395 | 396 | 397 | 398 | 400 | 401 | 402 | 403 |
| Postemergence | | | | | | | | | | | | | | | | | | | | | | | | | | | | | |
| B. signalgrass | 0 | 0 | 0 | 0 | 0 | 0 | 0 | 0 | 0 | 0 | 0 | 0 | 0 | 0 | 1 | 0 | 2 | 0 | 1 | 0 | 0 | 0 | 0 | 0 | 0 | 0 | 0 | 0 | 0 |
| Barnyardgrass | 0 | — | — | — | — | — | — | — | — | — | — | — | — | — | — | — | — | — | — | — | — | — | 0 | 0 | 0 | 0 | — | — | — |
| Bedstraw | — | — | — | — | — | — | 0 | — | 0 | — | — | 0 | — | 0 | — | — | — | — | — | — | — | 0 | — | — | — | — | — | 3 | 0 |
| Blackgrass | 4 | 0 | 0 | 2 | 0 | 0 | 0 | 0 | 0 | 0 | 0 | 3 | 0 | 3 | — | 0 | 8 | — | 7 | 0 | 2 | 0 | 0 | 6 | 0 | 0 | 0 | — | 6 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 2 | 0 | 0 | 0 | 0 | 0 | 0 | 0 | 0 | 0 | 0 | 1 | 6 | 0 | 4 | 0 | 2 | 0 | 2 | 0 | 2 | 0 | 0 | 2 | 2 | 0 | 0 | 3 | 2 |
| Ducksalad | 3 | — | — | — | — | — | — | — | — | — | — | — | — | — | — | — | — | — | — | — | — | — | 0 | 0 | 0 | 0 | — | — | — |
| Giant foxtail | 4 | 0 | 0 | 0 | 0 | 0 | 0 | 1 | 0 | 0 | 0 | 4 | 7 | 2 | 7 | 0 | 9 | 0 | 7 | 5 | — | 0 | 0 | 8 | 3 | 5 | 0 | 8 | 3 |
| Morningglory | 5 | 8 | — | 1 | 0 | 5 | 5 | 5 | 2 | 0 | 0 | 0 | 1 | 0 | 1 | 2 | 2 | 0 | 5 | 0 | 0 | 0 | 0 | 0 | 2 | 0 | 3 | 3 | 2 |
| Nutsedge | 0 | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | 0 | 0 | 0 |
| Rape | 2 | 0 | 0 | 0 | 0 | 0 | 0 | 0 | 0 | 0 | 0 | 0 | 0 | 0 | 0 | — | 7 | 0 | 0 | — | 0 | 0 | 0 | 0 | 0 | 0 | 0 | 1 | 2 |
| Redroot pigweed | 2 | 2 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 2 | 0 |
| Rice | 0 | — | — | — | — | — | — | — | — | — | — | — | — | — | — | — | — | — | — | — | — | — | 0 | 0 | 0 | 0 | — | — | — |
| S. Flatsedge | 2 | — | — | — | — | — | — | — | — | — | — | — | — | — | — | — | — | — | — | — | — | — | 0 | 0 | 0 | 0 | — | — | — |
| Soybean | 1 | 3 | 2 | 1 | 0 | 0 | 1 | 0 | 1 | 1 | 2 | 1 | 2 | 0 | 1 | 2 | 2 | 0 | 1 | 1 | 3 | 0 | 2 | 3 | 3 | 1 | 0 | 4 | 4 |
| Sugarbeets | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 0 |
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate 62 g/ha | 404 | 405 | 406 | 407 | 408 | 409 | 410 | 411 | 414 | 415 | 416 | 417 | 418 | 419 | 420 | 421 | 422 | 423 | 424 | 425 | 426 | 427 | 428 | 429 | 430 | 431 | 432 | 433 | 434 |
| Postemergence | | | | | | | | | | | | | | | | | | | | | | | | | | | | | |
| B. signalgrass | 2 | 0 | 0 | 0 | 0 | 3 | 0 | 0 | 0 | 0 | 2 | 0 | 0 | 0 | 0 | 0 | 0 | 0 | 0 | 0 | 2 | 0 | 0 | 0 | 0 | 0 | 0 | 0 | 0 |
| Barnyardgrass | — | — | — | — | — | — | — | — | — | 0 | 0 | 0 | 0 | 0 | 0 | 0 | 0 | 0 | 0 | 0 | 0 | 0 | 0 | 0 | 0 | 0 | 0 | 0 | 0 |
| Bedstraw | — | — | — | — | 6 | 0 | — | — | — | — | — | 0 | — | 0 | 0 | — | — | — | 0 | — | — | — | — | — | — | — | — | — | 0 |
| Blackgrass | 5 | 0 | 0 | 0 | 0 | 6 | — | — | 0 | 0 | 6 | 0 | 2 | 0 | 0 | 8 | 0 | 0 | 0 | 2 | 3 | 0 | 0 | 0 | 2 | 0 | 0 | 2 | 0 |
| Cocklebur | 0 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 0 | 3 | 6 | 4 | 4 | 1 | 0 | 2 | 0 | 0 | 0 | 2 | 4 | 0 | 0 | 0 | 4 | 1 | 0 | 0 | 0 | 1 | 0 | 0 | 2 | 0 |
| Ducksalad | — | — | — | — | — | — | — | — | — | 0 | 0 | 0 | 0 | 0 | 0 | 0 | 0 | 0 | 0 | 0 | 0 | 0 | 0 | 0 | 0 | 0 | 0 | 0 | 0 |
| Giant foxtail | 5 | 0 | 0 | 0 | 9 | 8 | 8 | 6 | 3 | 5 | 7 | 0 | 0 | 0 | 7 | 8 | 0 | 0 | 0 | 6 | 3 | 0 | 0 | 0 | 6 | 0 | 0 | 4 | 0 |
| Morningglory | — | 2 | 0 | 6 | 1 | 4 | 4 | 6 | 1 | 2 | 4 | 3 | 3 | 2 | 4 | 2 | 0 | 2 | 0 | 2 | 6 | 0 | 0 | 1 | 1 | 0 | 1 | 2 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 2 | 0 | 0 | 0 | 0 | 0 | 2 | 6 | 0 | 0 | 0 | 0 | 0 | 0 | 0 | 0 | 0 | 0 | 0 | 0 | 0 | 0 | 0 | 0 | 0 | 0 | 0 | 0 | 0 |
| Redroot pigweed | 2 | 0 | 0 | 0 | 0 | 0 | 0 | 0 | 0 | 0 | 1 | 0 | 0 | 0 | 0 | 1 | 0 | 0 | 0 | 0 | 0 | 0 | 0 | 0 | 0 | 0 | 0 | 0 | 0 |
| Rice | — | — | — | — | — | — | — | — | — | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | — | — | — | — | — | — | — | — | — | 0 | 0 | 2 | 0 | 0 | 0 | 0 | 0 | 0 | 0 | 0 | 0 | 0 | 0 | 0 | 0 | 0 | 0 | 0 | 0 |

TABLE B-continued

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Soybean | 4 | 2 | 1 | 0 | 1 | 4 | 4 | 3 | 2 | 3 | 5 | 3 | 3 | 2 | 2 | 4 | 2 | 2 | 0 | 1 | 4 | 0 | 1 | 1 | — | 1 | 1 | 1 | 0 |
| Sugarbeets | 1 | 0 | 0 | 0 | 0 | 0 | 0 | 0 | 0 | 0 | 0 | 0 | 0 | 0 | 0 | 0 | 0 | 0 | 0 | 2 | 2 | 0 | 0 | 0 | 0 | 0 | 0 | 0 | 0 |
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate 62 g/ha | 435 | 436 | 437 | 438 | 439 | 440 | 441 | 442 | 443 | 444 | 445 | 446 | 449 | 450 | 451 | 452 | 453 | 454 | 455 | 456 | 457 | 458 | 459 | 460 | 461 | 462 | 463 | 465 | 466 |
| Postemergence | | | | | | | | | | | | | | | | | | | | | | | | | | | | | |
| B. signalgrass | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 2 |
| Barnyardgrass | 0 | 0 | — | — | — | 0 | — | — | — | — | — | — | — | — | — | — | — | — | — | — | — | — | — | — | — | — | — | — | — |
| Bedstraw | 0 | 0 | 0 | 0 | — | — | — | 0 | 0 | — | — | 0 | — | — | 0 | — | — | — | — | — | 0 | — | — | — | — | 0 | — | — | 4 |
| Blackgrass | 0 | 0 | 0 | 0 | 0 | 0 | 0 | 0 | 0 | 0 | 0 | 4 | 0 | 0 | 0 | 0 | 0 | 0 | 6 | 4 | 0 | 0 | 0 | 2 | 0 | 0 | 0 | 0 | 8 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 2 | 0 | 1 | 0 | 0 | 0 | 2 | 0 | 5 | 0 | 0 | 0 | 3 | 0 | 2 | 4 | 4 | 0 | 2 | 0 | 3 | 0 | 0 | 0 | 1 | 9 |
| Ducksalad | 0 | 0 | — | — | — | 0 | — | — | — | — | — | — | — | — | — | — | — | — | — | — | — | — | — | — | — | — | — | — | — |
| Giant foxtail | 0 | 0 | 0 | 5 | 0 | 0 | 0 | 0 | 0 | 4 | 0 | 6 | 0 | 2 | 0 | 2 | 3 | 2 | 7 | 2 | 0 | 7 | 0 | 0 | 0 | 0 | 0 | 2 | 9 |
| Morningglory | 1 | 0 | 0 | 4 | 0 | 2 | 0 | 4 | 2 | 0 | 3 | 2 | 2 | 0 | 1 | 1 | 0 | 7 | 3 | 3 | 0 | 0 | 6 | 7 | 3 | 0 | 0 | 0 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Redroot pigweed | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 2 |
| Rice | 0 | 0 | — | — | — | 0 | — | — | — | — | — | — | — | — | — | — | — | — | — | — | — | — | — | — | — | — | — | — | — |
| S. Flatsedge | 0 | 0 | — | — | — | 0 | — | — | — | — | — | — | — | — | — | — | — | — | — | — | — | — | — | — | — | — | — | — | — |
| Soybean | 0 | 0 | 0 | 1 | 0 | 5 | 0 | 0 | 1 | 1 | 1 | 1 | 0 | 1 | 0 | 1 | 1 | 1 | 1 | 1 | 0 | 0 | 3 | 3 | 2 | 0 | 1 | 1 | 4 |
| Sugarbeets | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate 62 g/ha | 467 | 468 | 469 | 470 | 471 | 472 | 473 | 474 | 476 | 477 | 478 | 479 | 480 | 481 | 482 | 483 | 485 | 486 | 487 | 488 | 489 | 490 | 492 | 493 | 494 | 495 | 496 | 497 | 498 |
| Postemergence | | | | | | | | | | | | | | | | | | | | | | | | | | | | | |
| B. signalgrass | 0 | 0 | 0 | 0 | 0 | 0 | 0 | 0 | 0 | 0 | 0 | 0 | 0 | 0 | 0 | 0 | 0 | 0 | 0 | 0 | 1 | 2 | 0 | 0 | 0 | 0 | 0 | 0 | 0 |
| Barnyardgrass | — | — | — | — | — | — | — | — | — | — | — | — | — | — | — | — | — | — | — | — | — | — | — | — | — | — | — | — | — |
| Bedstraw | — | — | 0 | 0 | — | — | — | 6 | — | — | 0 | 0 | 0 | 0 | 0 | — | 0 | 0 | 0 | 0 | 0 | — | — | — | 0 | — | — | 0 | — |
| Blackgrass | 0 | 0 | 7 | 0 | 0 | 0 | 0 | 7 | 0 | 0 | 0 | 0 | 0 | 0 | 0 | 0 | 3 | 0 | 0 | 1 | 1 | 2 | 0 | 0 | 0 | 0 | 2 | 0 | 0 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 3 | 3 | 0 | 1 | 7 | 1 | 2 | 0 | 1 | 2 | 2 | 2 | 0 | 0 | 0 | 3 | 0 | 0 | — | 2 | 3 | 0 | 0 | 0 | 0 | 0 | 0 | 0 |
| Ducksalad | — | — | — | — | — | — | — | — | — | — | — | — | — | — | — | — | — | — | — | — | — | — | — | — | — | — | — | — | — |
| Giant foxtail | 0 | 1 | 8 | 0 | 0 | 7 | 1 | 3 | 0 | 2 | 3 | 0 | 3 | 2 | 0 | 0 | 5 | 2 | 0 | 5 | 2 | 2 | 0 | 0 | 0 | 0 | 0 | 0 | 0 |
| Morningglory | 3 | 2 | 9 | 0 | 3 | 3 | 0 | 1 | 0 | 6 | 3 | 7 | 2 | 0 | 5 | 0 | 8 | 1 | 2 | 1 | 2 | 2 | 0 | 0 | 0 | 1 | 8 | 0 | 1 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Redroot pigweed | — | 0 | 0 | 0 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 0 | 1 | 0 | 0 | 2 | 2 | 1 | 3 | 0 | 1 | 2 | 1 | 2 | 4 | 1 | 0 | 2 | 4 | 3 | 4 | 3 | 4 | 0 | — | 0 | 0 | 2 | 0 | 1 |
| Sugarbeets | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Velvetleaf | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 0 | 0 | 0 | 0 | 0 | 0 | 0 | 0 | 0 | 0 | 0 | 0 | 0 | 0 | 0 | 0 | 0 | 0 | 0 | 0 | 0 | 5 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 499 | 500 | 501 | 504 | 505 | 506 | 508 | 509 | 510 | 511 | 512 | 513 | 514 | 515 | 516 | 517 | 518 | 519 | 520 | 521 | 522 | 523 | 524 | 525 | 526 | 527 | 528 | 531 | 532 |
| Postemergence | | | | | | | | | | | | | | | | | | | | | | | | | | | | | |
| B. signalgrass | 0 | 3 | 2 | 0 | 0 | 0 | 0 | 0 | 2 | 0 | 0 | 0 | 0 | 0 | 0 | 0 | — | 0 | 0 | 0 | 0 | 0 | 0 | 0 | 0 | 0 | 0 | 0 | 0 |
| Barnyardgrass | — | — | — | — | — | — | — | — | — | — | — | — | — | — | — | — | — | — | — | — | — | — | — | — | — | — | — | — | — |
| Bedstraw | — | — | — | — | — | — | — | — | — | — | — | 6 | — | 6 | — | 4 | — | 0 | — | — | 0 | 0 | — | — | — | 0 | 0 | 0 | 0 |
| Blackgrass | 0 | 3 | 3 | 6 | 2 | 0 | 0 | 2 | 5 | 0 | 2 | 4 | 0 | 0 | 0 | 0 | 4 | 0 | 0 | 2 | 8 | 0 | 0 | 4 | 3 | 0 | 0 | 0 | 0 |
| Cocklebur | 0 | 3 | 0 | 2 | 0 | 0 | 0 | 0 | 3 | 0 | 0 | 3 | 0 | 0 | 2 | 0 | 0 | 0 | 0 | 0 | 0 | 0 | 0 | 2 | 0 | 0 | 0 | 0 | 0 |
| Corn | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 |
| Crabgrass | 0 | 6 | 7 | 8 | 7 | 0 | 9 | 3 | 3 | 3 | 2 | 1 | 7 | 4 | 3 | 7 | 0 | 0 | 2 | 2 | 8 | 3 | 3 | 6 | 6 | 4 | 3 | 2 | 4 |
| Ducksalad | — | — | — | — | — | — | — | — | — | — | — | — | — | — | — | — | — | — | — | — | — | — | — | — | — | — | — | — | — |
| Giant foxtail | 0 | 7 | 8 | 8 | 8 | 2 | 8 | 3 | 4 | 3 | 2 | 1 | 6 | 8 | 0 | 8 | 0 | 4 | 2 | 4 | 8 | 2 | 4 | 5 | 3 | 5 | 0 | 0 | 0 |
| Morningglory | 3 | 3 | 0 | 4 | 5 | 0 | 3 | — | 4 | 4 | 5 | 3 | 2 | 2 | 2 | 2 | 5 | 0 | 3 | 3 | 3 | 2 | 0 | 2 | 6 | 3 | 2 | 2 | 0 |
| Nutsedge | 0 | 0 | — | 0 | 0 | 0 | — | 0 | — | 0 | 0 | 0 | 0 | 0 | 0 | 0 | 0 | — | 0 | 0 | 0 | 0 | — | 0 | 0 | 0 | — | 0 | 4 |
| Rape | 0 | 3 | 2 | 1 | 0 | 0 | 1 | 0 | 1 | 0 | 0 | 0 | 6 | 4 | 1 | 0 | 0 | 0 | 0 | 0 | 0 | 0 | 0 | 0 | 0 | 0 | 0 | 0 | 0 |
| Redroot pigweed | 0 | 7 | 0 | 7 | 0 | 0 | 3 | 0 | 7 | 5 | 1 | 3 | 0 | 3 | 4 | 0 | 0 | 0 | 0 | 0 | 0 | 0 | 0 | 2 | 0 | 0 | 0 | 0 | 0 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 0 | 3 | 4 | 3 | 1 | 2 | 4 | 1 | 4 | 1 | 4 | 1 | 6 | 4 | 4 | 0 | 4 | 3 | 2 | 4 | 4 | 4 | 3 | 3 | 2 | 3 | 3 | 3 | 0 |
| Sugarbeets | 0 | 6 | 5 | 5 | 3 | 2 | 0 | 0 | 2 | 0 | 0 | 2 | 3 | 3 | 0 | 0 | 0 | 0 | 0 | 0 | 6 | 0 | 0 | 0 | 0 | 0 | 0 | 0 | 0 |
| Velvetleaf | 0 | 4 | 0 | 1 | 0 | 0 | 0 | 2 | 4 | 0 | 0 | 3 | 2 | 2 | 3 | 0 | — | 2 | 3 | 0 | 2 | 0 | 0 | 2 | 4 | 3 | 0 | 0 | 0 |
| Wheat | 0 | 0 | 2 | 0 | 0 | 0 | 0 | 0 | 0 | 0 | 0 | 3 | 0 | 0 | 0 | 0 | 0 | 0 | 0 | 0 | 0 | 0 | 0 | 0 | 0 | 0 | 0 | 0 | 0 |
| Wild oats | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 533 | 534 | 535 | 536 | 540 | 541 | 543 | 544 | 545 | 546 | 548 | 549 | 550 | 551 | 552 | 553 | 554 | 555 | 556 | 557 | 558 | 559 | 560 | 561 | 562 | 563 | 564 | 565 | 566 |
| Postemergence | | | | | | | | | | | | | | | | | | | | | | | | | | | | | |
| B. signalgrass | 0 | 0 | 0 | 0 | 0 | 0 | 0 | 0 | 0 | 0 | 0 | 0 | 0 | 0 | 0 | 0 | 0 | 0 | 0 | 0 | 0 | 4 | 0 | 0 | — | 0 | 0 | 0 | 2 |
| Barnyardgrass | — | — | — | — | — | — | — | — | — | — | — | — | — | — | — | — | — | — | — | — | — | — | — | — | — | — | — | — | — |
| Bedstraw | — | — | — | — | 0 | 0 | 0 | 0 | 0 | 0 | 0 | 0 | 0 | 0 | 2 | 0 | 5 | 2 | 0 | 0 | — | — | 0 | 0 | — | 0 | 0 | 0 | — |
| Blackgrass | — | 0 | 0 | 0 | 0 | 0 | 0 | 0 | 0 | 0 | 0 | 0 | 0 | 4 | 0 | 0 | 0 | 0 | 0 | 0 | 0 | 7 | 2 | 2 | 3 | 0 | 0 | 0 | 0 |
| Cocklebur | 2 | 0 | 0 | 0 | 0 | 0 | 0 | 3 | 0 | 0 | 0 | 0 | 0 | 0 | 0 | 0 | 0 | 0 | 0 | 0 | 0 | 0 | 0 | 0 | 2 | 0 | 0 | 0 | 2 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 3 | — | 5 | 0 | 5 | 0 | 0 | 0 | 0 | 1 | — | 2 | — | 0 | 3 | 0 | 0 | 0 | 0 | 0 | 0 | 5 | 0 | 2 | 7 | 9 | 2 | 0 | 2 |
| Ducksalad | — | — | — | — | — | — | — | — | — | — | — | — | — | — | — | — | — | — | — | — | — | — | — | — | — | — | — | — | — |
| Giant foxtail | 8 | — | 5 | 0 | 0 | 0 | 0 | 0 | 0 | 0 | 0 | 2 | 2 | 0 | 0 | 0 | 2 | 0 | 4 | 0 | 2 | 9 | 2 | 2 | 7 | 6 | 2 | 0 | 0 |
| Morningglory | 4 | 2 | 4 | 2 | 2 | 0 | 1 | 3 | 4 | 0 | 5 | 4 | 1 | 1 | 1 | 0 | 1 | 1 | 0 | 5 | 10 | 9 | 4 | 1 | 4 | 4 | 5 | 3 | 5 |
| Nutsedge | 0 | 0 | 0 | 0 | 0 | 0 | 0 | 0 | 0 | — | — | — | 0 | — | 0 | 0 | 0 | 0 | 0 | 0 | 0 | 0 | 3 | 0 | — | 0 | 0 | — | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rape | 0 | 0 | 0 | 0 | 0 | 0 | 0 | 0 | 0 | 0 | — | 0 | 0 | 3 | 2 | 2 | 0 | 4 | 0 | 0 | 0 | 0 | 0 | 4 | 0 | 0 | 0 | 0 | 0 |
| Redroot pigweed | 9 | 0 | 0 | 0 | 0 | 0 | 0 | 0 | 0 | 0 | 0 | 0 | 0 | 0 | 0 | 0 | 0 | 0 | 3 | 0 | 0 | 0 | 2 | 0 | 9 | 0 | 3 | 0 | 3 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 4 | — | 3 | 2 | 1 | 0 | 0 | 0 | 1 | 1 | 2 | 2 | 2 | 2 | 2 | 1 | 2 | 1 | 0 | 0 | 3 | 4 | 2 | 2 | 3 | 5 | 0 | 2 | 4 |
| Sugarbeets | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 3 | 0 | 0 | 0 | 0 |
| Velvetleaf | 0 | 0 | 0 | 0 | 0 | 0 | 0 | 0 | 0 | 0 | 0 | — | 0 | 0 | 0 | — | 0 | 0 | 0 | 0 | 0 | 0 | 0 | 0 | 3 | 0 | 0 | 3 | 3 |
| Wheat | 0 | 0 | 0 | 0 | 0 | 0 | 0 | 0 | 0 | 0 | 0 | 0 | 0 | 0 | 0 | 0 | 0 | 6 | 0 | 0 | 0 | 2 | 0 | 0 | 0 | 0 | 0 | 0 | 0 |
| Wild oats | 0 | 0 | 0 | 0 | 0 | 0 | 0 | 0 | 0 | 0 | 0 | 0 | 0 | 0 | 0 | 0 | 0 | 0 | 2 | 0 | 0 | 2 | 0 | 0 | 0 | 0 | 0 | 0 | 0 |
| | COMPOUND | | | | | | | | | | | | | | | | | | | | | | | | | | | | |
| Rate 62 g/ha | 567 | 568 | 569 | 570 | 571 | 572 | 573 | 574 | 575 | 576 | 577 | 578 | 579 | 580 | 581 | 582 | 584 | 585 | 586 | 588 | 589 | 590 | 591 | 592 | 593 | 594 | 595 | 596 | 598 |
| Postemergence | | | | | | | | | | | | | | | | | | | | | | | | | | | | | |
| B. signalgrass | 0 | 1 | 0 | 0 | 0 | 0 | 0 | 0 | 0 | 0 | 0 | 0 | 0 | 0 | 5 | 0 | 3 | 0 | 0 | 0 | 0 | 0 | 0 | 0 | 0 | 0 | 0 | 0 | 0 |
| Barnyardgrass | — | — | — | — | — | — | — | — | — | — | — | — | — | — | — | — | — | — | — | — | — | — | — | — | — | — | — | — | — |
| Bedstraw | 0 | 0 | 0 | 0 | — | 0 | — | — | — | — | — | — | 0 | 3 | 0 | — | 5 | 0 | 0 | 0 | — | — | — | — | — | — | — | — | 0 |
| Blackgrass | 0 | 8 | 0 | 0 | 0 | 0 | 0 | 2 | 0 | 0 | 0 | 0 | 0 | 2 | 4 | 3 | 5 | 3 | 0 | 0 | 0 | 0 | 0 | 0 | 0 | — | 3 | 0 | 0 |
| Cocklebur | 0 | 1 | 0 | 0 | 0 | 0 | 0 | 0 | 0 | 0 | 0 | 0 | 0 | 3 | 2 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 |
| Crabgrass | 3 | 8 | 0 | 0 | 0 | 0 | 6 | 0 | 0 | 2 | 0 | 0 | 0 | 0 | 3 | 0 | 1 | — | 2 | 0 | 0 | 0 | 0 | 0 | 0 | 5 | 5 | 0 | 0 |
| Ducksalad | — | — | — | — | — | — | — | — | — | — | — | — | — | — | — | — | — | — | — | — | — | — | — | — | — | — | — | — | — |
| Giant foxtail | 0 | 7 | 0 | 0 | 0 | 0 | 2 | 2 | — | 2 | 0 | 0 | 0 | 0 | 7 | 3 | 7 | 6 | 2 | 0 | 0 | 0 | 0 | 0 | 0 | 6 | 8 | 0 | 0 |
| Morningglory | 0 | 7 | 3 | 4 | 4 | 3 | 10 | 10 | 4 | 2 | 6 | 9 | 10 | 7 | 4 | 9 | 1 | 4 | 6 | 7 | 3 | 2 | 0 | 1 | 0 | 0 | 1 | 0 | 0 |
| Nutsedge | 4 | 0 | 0 | 0 | 0 | 0 | 0 | 0 | — | 0 | 0 | — | — | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 2 | 0 | 0 | 0 | 0 | 0 | 2 | 0 | 4 | 0 | 0 | 3 | 0 | 0 | 0 | 0 | 0 | 0 | 0 | 0 | 0 | 0 | 0 | 0 |
| Redroot pigweed | 0 | 0 | 0 | 0 | 0 | 0 | 0 | 0 | 0 | 0 | 0 | 3 | 0 | 0 | 5 | 0 | 0 | — | 0 | 0 | 0 | 0 | 0 | 0 | 0 | — | 0 | 0 | 0 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 0 | 4 | 0 | 0 | 2 | 2 | 2 | 4 | 3 | 2 | 2 | 3 | 2 | 2 | 0 | 1 | 2 | — | 2 | 2 | 2 | 1 | 1 | 1 | 0 | 0 | 0 | 1 | 0 |
| Sugarbeets | 0 | 0 | 0 | 0 | 0 | 0 | 0 | 0 | 0 | 0 | 0 | 0 | 0 | 0 | 3 | 0 | 0 | 0 | 0 | 0 | 0 | 0 | 0 | 0 | 0 | 0 | 0 | 0 | 0 |
| Velvetleaf | 0 | 0 | 0 | 0 | 0 | 0 | 0 | 0 | 0 | 0 | 0 | 0 | 0 | 0 | 3 | 0 | 0 | 3 | 0 | 0 | 0 | 0 | 0 | 0 | 0 | 0 | 2 | 0 | 0 |
| Wheat | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 |
| Wild oats | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| | COMPOUND | | | | | | | | | | | | | | | | | | | | | | | | | | | | |
| Rate 62 g/ha | 601 | 602 | 603 | 604 | 605 | 606 | 607 | 608 | 609 | 610 | 611 | 612 | 613 | 614 | 615 | 618 | 619 | 620 | 621 | 622 | 624 | 625 | 627 | 628 | 629 | 630 | 631 | 632 | 633 |
| Postemergence | | | | | | | | | | | | | | | | | | | | | | | | | | | | | |
| B. signalgrass | 0 | 0 | 0 | 0 | 0 | 0 | 0 | 3 | 0 | 0 | 0 | 1 | 1 | 0 | 0 | 0 | 0 | 0 | 0 | 0 | 4 | 0 | 3 | 2 | 0 | 0 | 1 | 0 | 0 |
| Barnyardgrass | — | — | — | — | — | — | — | — | — | — | — | — | — | — | — | — | — | — | — | — | — | — | — | — | — | — | — | — | — |
| Bedstraw | — | — | — | — | 0 | 0 | 0 | — | 0 | 0 | — | 3 | 8 | — | 0 | — | 0 | 0 | — | 0 | 0 | 0 | — | 0 | 3 | 0 | — | 0 | 0 |
| Blackgrass | — | 4 | 0 | 0 | 0 | 0 | 0 | 4 | 5 | 8 | 7 | 7 | 8 | 0 | 0 | 0 | 0 | 0 | 0 | 0 | 4 | 0 | 8 | 6 | 3 | 0 | 1 | 0 | 0 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 3 | 0 | 5 | 0 | 0 |
| Crabgrass | 3 | 2 | 0 | 1 | 0 | 0 | 5 | 3 | 5 | 9 | 8 | 4 | 8 | 0 | 0 | 0 | 0 | 1 | 0 | 2 | 6 | 1 | 8 | 8 | 1 | 1 | 8 | 0 | 0 |
| Ducksalad | — | — | — | — | — | — | — | — | — | — | — | — | — | — | — | — | — | — | — | — | — | — | — | — | — | — | — | — | — |
| Giant foxtail | 7 | 1 | 0 | 1 | 0 | 0 | 6 | 5 | 6 | 8 | 8 | 7 | 5 | 0 | 0 | 0 | 0 | 0 | 0 | 0 | 4 | 0 | 9 | 8 | 3 | 2 | 8 | 3 | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Morningglory | 1 | 0 | 0 | 0 | — | 6 | 6 | 0 | 8 | 8 | 7 | 5 | 7 | 2 | 0 | 0 | 0 | 2 | 1 | 0 | 1 | 0 | 3 | 1 | 2 | 1 | 0 | 1 | 1 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 3 | 0 | 0 | 0 | 0 | 0 | 0 |
| Rape | 0 | 0 | 0 | 0 | 0 | — | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 |
| Redroot pigweed | 0 | 2 | 0 | 0 | 0 | 0 | 0 | 3 | 0 | 0 | 0 | 0 | 1 | 0 | 0 | 0 | 0 | 0 | 0 | 0 | 0 | 0 | 2 | 3 | 0 | 0 | 0 | 0 | 0 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 4 | 3 | 0 | 0 | 2 | 1 | 3 | 3 | 5 | 5 | 5 | 4 | 4 | 3 | 1 | 0 | 1 | 1 | 1 | 4 | 2 | 0 | 2 | 4 | 4 | 4 | 5 | 1 | 2 |
| Sugarbeets | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Velvetleaf | 0 | 0 | 0 | 0 | 0 | 0 | 0 | 0 | 3 | 0 | 0 | 2 | 0 | 0 | 0 | 0 | 0 | 0 | 0 | 0 | 0 | 0 | 3 | 6 | 0 | 0 | 4 | 0 | 0 |
| Wheat | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 |
| Wild oats | 0 | 0 | 0 | 0 | 2 | 0 | 0 | 3 | 0 | 0 | 0 | 0 | 1 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 634 | 635 | 636 | 638 | 639 | 640 | 641 | 642 | 643 | 644 | 645 | 646 | 647 | 648 | 649 | 650 | 652 | 653 | 654 | 655 | 656 | 657 | 658 | 659 | 660 | 661 | 663 | 664 | 665 |
| Postemergence | | | | | | | | | | | | | | | | | | | | | | | | | | | | | |
| B. signalgrass | 0 | 0 | 0 | 0 | 0 | 0 | 0 | 0 | 0 | 0 | 0 | 0 | 4 | 0 | 0 | 0 | 0 | 0 | 0 | 0 | 0 | 0 | 0 | 0 | 0 | 0 | 0 | 0 | 0 |
| Barnyardgrass | — | — | — | — | — | — | — | — | — | — | — | — | — | — | — | — | — | — | — | — | — | — | — | — | — | — | — | — | — |
| Bedstraw | 0 | 5 | 7 | — | — | — | — | — | — | — | 0 | 0 | 0 | — | — | — | — | — | — | — | — | — | — | 0 | 0 | — | — | 0 | — |
| Blackgrass | 2 | 2 | 0 | 0 | 0 | 0 | 0 | 0 | 0 | 0 | 0 | 0 | 6 | 0 | 0 | 0 | 0 | 0 | 0 | 0 | 6 | 6 | 0 | 1 | 0 | 0 | 0 | 4 | 3 |
| Cocklebur | 1 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 2 | 0 | 0 | 0 | 0 | 0 | 0 | 0 | 0 | 0 | 0 | 0 | 0 | 0 | 0 | 0 | 0 | 0 | 0 | 1 | 0 | 0 | 0 | 0 | 0 | 0 | 0 |
| Crabgrass | 0 | 4 | 3 | 2 | 0 | 0 | 0 | 0 | 0 | 0 | 0 | 0 | 7 | 0 | 0 | 0 | 0 | 0 | 0 | 1 | 0 | 3 | 0 | 1 | 0 | 0 | 0 | 0 | 1 |
| Ducksalad | — | — | — | — | — | — | — | — | — | — | — | — | — | — | — | — | — | — | — | — | — | — | — | — | — | — | — | — | — |
| Giant foxtail | 4 | 5 | 2 | 5 | 0 | 0 | 0 | 0 | 0 | 0 | 0 | 0 | 8 | 0 | 0 | 0 | 0 | 0 | 0 | 1 | 3 | 5 | 0 | 5 | 3 | 2 | 0 | 2 | 2 |
| Morningglory | 1 | 1 | 2 | 0 | 0 | 0 | 0 | 0 | 0 | 0 | 0 | 0 | 0 | 6 | 4 | 4 | 3 | 0 | 3 | 9 | 1 | 2 | 7 | 4 | 1 | 0 | 0 | 0 | 4 |
| Nutsedge | 0 | 0 | 0 | 0 | 0 | 0 | 0 | 0 | 0 | — | 0 | 0 | 0 | 0 | 0 | 2 | — | 0 | 0 | 0 | 0 | — | 0 | 0 | 0 | 0 | 0 | 0 | — |
| Rape | 0 | 2 | 2 | 0 | 0 | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 |
| Redroot pigweed | 1 | 0 | 0 | 0 | 3 | 0 | — | 0 | 0 | 2 | 0 | 0 | 0 | 0 | 0 | 2 | 0 | 0 | 0 | 1 | 0 | 0 | 6 | 0 | 2 | 0 | 0 | 0 | 3 |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 3 | 3 | 2 | 1 | 0 | 0 | 0 | 2 | 1 | 0 | 1 | 0 | 2 | 0 | 2 | 2 | 0 | 0 | 0 | 2 | 2 | 1 | 2 | 2 | 2 | 1 | — | 3 | 2 |
| Sugarbeets | 0 | 3 | 2 | 0 | 0 | 0 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 |
| Velvetleaf | 0 | 0 | 3 | 0 | 0 | 0 | 0 | 0 | 0 | 0 | 0 | 0 | 5 | 0 | 0 | 0 | 0 | 0 | 0 | 0 | 0 | 2 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 0 | 0 | 0 | 1 | 1 | 0 | 0 | 1 | 0 | 0 | 0 | 0 | 0 | 0 | 0 | 0 | 0 | 0 | 0 | 0 | 0 | 1 | 1 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 666 | 667 | 668 | 670 | 671 | 672 | 674 | 675 | 676 | 708 | 709 | 710 | 711 | 712 | 713 | 714 | 722 | 739 | 740 | 741 | 743 | 744 | 745 | 746 | 747 | 748 | 749 | 750 | 751 |
| Postemergence | | | | | | | | | | | | | | | | | | | | | | | | | | | | | |
| B. signalgrass | 0 | 0 | 1 | 3 | 0 | 0 | 3 | 1 | 0 | 0 | 0 | 5 | 4 | 0 | 0 | 2 | 0 | 0 | 0 | 0 | 0 | 0 | 0 | 3 | 1 | 2 | 2 | 0 | 3 |
| Barnyardgrass | — | — | — | — | — | — | — | — | — | — | — | — | — | — | — | — | — | — | — | — | — | — | — | — | — | — | — | — | — |
| Bedstraw | — | 0 | — | — | — | — | — | 0 | — | 0 | — | — | — | — | — | — | — | 3 | 0 | 0 | 0 | — | — | — | 8 | 5 | 3 | 5 | 0 |
| Blackgrass | 6 | 6 | 7 | 2 | 0 | 0 | 4 | 5 | 2 | 0 | 0 | 5 | 3 | 0 | 1 | 7 | 0 | 0 | 3 | 0 | 3 | 5 | 3 | 5 | 5 | 5 | 5 | 4 | 6 |
| Cocklebur | 0 | 2 | 0 | 2 | 0 | 0 | 0 | 0 | 0 | 0 | 0 | 0 | 1 | 0 | 1 | 0 | 0 | 2 | 0 | 0 | 0 | 0 | 0 | 0 | 0 | 0 | 0 | 0 | 0 |
| Corn | 0 | 4 | 0 | 3 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 3 | 6 | 6 | 9 | 1 | 5 | 6 | 6 | 4 | 0 | 2 | 8 | 4 | 1 | 2 | 4 | 0 | 4 | 0 | 9 | 2 | 3 | 4 | 7 | 3 | 2 | 4 | 7 | 7 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Ducksalad | — | — | — | — | — | — | — | — | — | — | — | — | — | — | — | — | — | — | — | — | — | — | — | — | — | — | — | — | — |
| Giant foxtail | 2 | 5 | 8 | 9 | 5 | 3 | 7 | 8 | 4 | 0 | 3 | 8 | 6 | 3 | 4 | 6 | 0 | 7 | 2 | 0 | 7 | 6 | 2 | 6 | 8 | 2 | 3 | 9 | 8 |
| Morningglory | 0 | 2 | 1 | 3 | 1 | 4 | 2 | 1 | 0 | 0 | — | 4 | 2 | 3 | 2 | 0 | 4 | 6 | 2 | — | 5 | 2 | 3 | 4 | 2 | 0 | 2 | 3 | 8 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 2 | 0 | 0 | 0 | 0 | 0 | 0 | 0 | 0 | 0 | 0 | 2 | 0 | 5 | 0 | 0 | 0 | 0 | 0 | 0 | 0 | 4 | 4 | 0 | 2 | 0 | 2 |
| Redroot pigweed | 0 | 2 | 3 | 7 | 0 | 7 | 0 | 2 | 0 | 0 | 5 | 8 | 3 | 3 | 2 | 5 | 8 | 0 | 0 | 3 | 0 | 0 | 2 | 6 | 4 | 2 | 4 | 4 | — |
| Rice | — | — | — | — | — | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — | — | — | — | — | — |
| Soybean | 4 | 2 | 2 | 3 | 2 | 2 | 2 | 4 | 2 | 3 | 1 | 3 | 1 | 2 | 3 | 2 | 0 | 3 | 2 | 2 | 0 | 2 | 3 | 2 | 4 | 3 | 3 | 2 | 2 |
| Sugarbeets | 0 | 0 | 0 | 0 | 0 | 0 | 0 | 0 | 0 | 0 | 0 | 0 | 1 | 1 | 0 | 0 | 0 | 3 | 0 | 0 | 0 | 0 | 2 | 0 | 0 | 0 | 1 | 0 | 3 |
| Velvetleaf | 0 | 5 | 0 | 5 | 0 | 6 | 4 | 0 | 0 | 0 | 4 | 5 | 3 | 0 | 3 | 2 | 0 | 0 | 0 | 0 | 0 | 0 | 0 | 2 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 0 | 0 | 0 | 0 | 0 | 0 | 0 | 0 | 0 | 0 | 0 | 1 | 0 | 0 | 0 | 0 | 2 | 0 | 0 | 0 | 0 | 0 | 0 | 0 | 0 | 0 | 0 | 0 | 0 |

| | COMPOUND | | | | | | | | | | | | | | | | | | | | | | | |
|---|---|---|---|---|---|---|---|---|---|---|---|---|---|---|---|---|---|---|---|---|---|---|---|---|
| Rate 62 g/ha | 752 | 753 | 754 | 756 | 757 | 758 | 759 | 760 | 761 | 762 | 763 | 764 | 765 | 766 | 767 | 772 | 773 | 774 | 776 | 779 | 780 | 790 | 791 | 792 |
| Postemergence | | | | | | | | | | | | | | | | | | | | | | | | |
| B. signalgrass | 0 | 0 | 0 | 0 | 0 | 4 | 0 | 0 | 0 | 0 | 0 | 0 | 3 | 0 | 2 | 0 | 0 | 0 | 0 | 2 | 0 | 2 | 0 | 0 |
| Barnyardgrass | — | — | — | — | — | — | — | — | — | — | — | — | — | — | — | — | — | — | — | — | — | — | — | — |
| Bedstraw | 0 | — | — | 0 | — | — | 0 | — | — | 0 | — | 0 | — | 0 | 7 | 0 | 0 | 0 | 0 | 0 | 0 | 0 | 0 | — |
| Blackgrass | 0 | 0 | 2 | 0 | 0 | 3 | 4 | 0 | 0 | 0 | 5 | 3 | 3 | 0 | 9 | 0 | 0 | 0 | 2 | 0 | 0 | 4 | 0 | 4 |
| Cocklebur | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 3 | 0 | 5 | 0 | 3 | 2 | 2 | 5 | — | 0 | 2 | 0 | 3 | 2 | 8 | 0 | 0 | 0 | 2 | 3 | 3 | 9 | 1 | 2 |
| Ducksalad | — | — | — | — | — | — | — | — | — | — | — | — | — | — | — | — | — | — | — | — | — | — | — | — |
| Giant foxtail | — | 3 | 4 | 0 | 2 | 8 | 3 | 0 | 0 | — | 6 | 3 | 5 | 0 | 8 | 0 | 0 | 0 | 2 | 8 | 7 | 9 | 0 | 2 |
| Morningglory | 2 | — | 10 | 4 | 6 | 2 | 3 | 3 | 0 | 0 | 2 | 1 | 5 | 2 | 5 | 0 | 0 | 0 | 7 | 5 | 4 | 2 | 3 | 6 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 2 | 0 | 0 | 0 | 0 | 0 | 0 | 2 | 0 | 0 | 0 | 0 | 0 | 0 | — | 0 | 0 | 0 | 2 | 0 | 0 | 0 | 3 | 3 |
| Redroot pigweed | 0 | 4 | — | 0 | 1 | 7 | 0 | 0 | 0 | 0 | 0 | 0 | 6 | 5 | 6 | 0 | 0 | 0 | 2 | 2 | 0 | 0 | 2 | 0 |
| Rice | — | — | — | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — | — | — | — |
| Soybean | 4 | 1 | 0 | 2 | 3 | 4 | 3 | 4 | 2 | 2 | 2 | 1 | 2 | 2 | 1 | 0 | 0 | 0 | 2 | 2 | 3 | 2 | 4 | 4 |
| Sugarbeets | 3 | 0 | 0 | 0 | 0 | 0 | 0 | 0 | 2 | 0 | 0 | 0 | 0 | 0 | 3 | 0 | 0 | 0 | 0 | 2 | 0 | 0 | 0 | 0 |
| Velvetleaf | 0 | 0 | 0 | 0 | 0 | 5 | 2 | 0 | 0 | 0 | 0 | 0 | 6 | 0 | 2 | 0 | 0 | 0 | 3 | 2 | 0 | 4 | 2 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 |
| Wild oats | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Rate 62 g/ha | 4 | 10 | 11 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 51 | 52 | 53 | 54 | 55 |
| Preemergence | | | | | | | | | | | | | | | | | | | | | | | | | | | | | | | | | | | | | | | | | | | | |
| B. signalgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 5 | 0 | 3 | 0 | 0 | 0 | 0 | 0 | 0 | 0 | 0 | 0 | 0 | 0 | 0 | 0 | 0 | 0 | 0 |
| Bedstraw | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 | 0 | 0 | 0 |
| Blackgrass | 0 | 1 | 0 | 0 | 0 | 0 | 0 | 2 | 0 | 0 | 0 | 0 | 0 | 0 | 3 | 0 | 0 | 0 | 0 | 3 | 0 | 1 | 0 | 3 | 0 | 4 | 0 | 4 | 0 | 0 | 0 | 0 | 0 | 0 | 0 | 0 | 0 | 0 | 0 | 0 | 0 | 0 | 0 | 0 |
| Cocklebur | 0 | 0 | 0 | 0 | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

TABLE B-continued

| | | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Crabgrass | 3 | 2 | 0 | 0 | 0 | 0 | 0 | 6 | 3 | 1 | 4 | 3 | 3 | 0 | 5 | 0 | 0 | 3 | 3 | 3 | 9 | 4 | 3 | 7 | 3 | 8 | 0 | 2 | 0 | 2 | 3 | 0 | 0 | 0 | 0 | 1 | 0 | 1 | 2 | 0 | 0 | 3 | 2 | 0 |
| Giant foxtail | 9 | 3 | 0 | 6 | 6 | 0 | 3 | 2 | 0 | 3 | 8 | 3 | 2 | 6 | 5 | 0 | 0 | 2 | 0 | 2 | 6 | 4 | 4 | 2 | 3 | 10 | 0 | 10 | 0 | 9 | 4 | 0 | 0 | 0 | 7 | 10 | 0 | 6 | 8 | 0 | 3 | 3 | 2 | 0 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 |
| Redroot pigweed | 2 | 0 | 0 | 0 | 0 | 0 | 3 | 4 | 0 | 0 | 6 | 0 | 0 | 2 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 |
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 4 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Rate 62 g/ha | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 85 | 86 | 87 | 88 | 89 | 90 | 91 | 92 | 93 | 94 | 95 | 96 | 97 | 98 | 99 |
| Preemergence | | | | | | | | | | | | | | | | | | | | | | | | | | | | | | | | | | | | | | | | | | | |
| B. signalgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 7 | 10 | — | 0 | 0 | 0 | 0 | 0 | 0 |
| Bedstraw | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 |
| Blackgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 2 | 0 | 0 | 0 | 2 | 2 | 1 | 0 | 0 | 10 | 9 | 9 | 0 | 0 | 0 | 0 | 2 | 0 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 3 | 0 | 3 | 0 | 0 | 0 | 0 | 0 | 0 |
| Crabgrass | 0 | 0 | 0 | 0 | 0 | 0 | 2 | 0 | 0 | 0 | 0 | 2 | 2 | 0 | 0 | 0 | 0 | 1 | 2 | 3 | 3 | 0 | 7 | 2 | 3 | 1 | 0 | 0 | 0 | 5 | 5 | 5 | 0 | 0 | 10 | 8 | 7 | 3 | 2 | 1 | 0 | 4 | 5 |
| Giant foxtail | 0 | 0 | 0 | 0 | 3 | 3 | 5 | 0 | 0 | 3 | 4 | 3 | 5 | 0 | 0 | 0 | 0 | 2 | 3 | 6 | 4 | 0 | 8 | 4 | 6 | 2 | 0 | 0 | 0 | 8 | 8 | 4 | 0 | 4 | 10 | 10 | 10 | 8 | 2 | 2 | 0 | 5 | — |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 7 | 4 | 3 | 0 | 0 | 0 | 0 | 0 | 0 |
| Redroot pigweed | 0 | 0 | 0 | 0 | 0 | 0 | 0 | 0 | 0 | 0 | 0 | 4 | 0 | 0 | 0 | 0 | 0 | 0 | 0 | 0 | 0 | 0 | 0 | 0 | — | 0 | 0 | 0 | 0 | 2 | 4 | 9 | 0 | 0 | 6 | 2 | 9 | 0 | 5 | — | 0 | 4 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 7 | 2 | 6 | 0 | 0 | 0 | 0 | 0 | 0 |
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 6 | 4 | 5 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 3 | 3 | 3 | 0 | 0 | 0 | 0 | 0 | 0 |
| Wild oats | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 8 | 7 | 8 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 100 | 101 | 102 | 103 | 104 | 105 | 106 | 107 | 108 | 109 | 110 | 111 | 112 | 113 | 114 | 115 | 116 | 117 | 118 | 119 | 120 | 121 | 122 | 123 | 124 | 125 | 126 | 127 | 128 |
| Preemergence | | | | | | | | | | | | | | | | | | | | | | | | | | | | | |
| B. signalgrass | 0 | 0 | 0 | 1 | 0 | 0 | 0 | 5 | 4 | 9 | 3 | 0 | 0 | 7 | 0 | 2 | 4 | 6 | 0 | 5 | 0 | 0 | 0 | 0 | 0 | 0 | 0 | 0 | 0 |
| Bedstraw | 0 | 0 | 0 | 0 | 0 | 0 | 0 | 2 | 0 | 8 | 0 | 0 | 0 | 4 | 0 | 0 | 2 | 0 | 0 | — | 0 | 0 | 0 | 0 | 0 | 0 | 0 | 0 | 0 |
| Blackgrass | 0 | 0 | 0 | 0 | 0 | 5 | 0 | 9 | 5 | 8 | 0 | 0 | 0 | 8 | 6 | 0 | 9 | 8 | 0 | 5 | 0 | 0 | 0 | 0 | 0 | 0 | 0 | 0 | 0 |
| Cocklebur | 0 | 0 | 0 | 0 | — | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 4 | 0 | 0 | 2 | 0 | 0 | 3 | 0 | 0 | 0 | 0 | 0 | 0 | 0 | 0 | 0 | 0 | 0 | 0 | 0 | 0 | 0 |
| Crabgrass | 0 | 0 | 0 | 2 | 0 | 2 | 0 | 10 | 7 | 10 | 3 | 6 | 5 | 7 | 2 | 4 | 8 | 9 | 7 | 7 | 6 | 2 | 4 | 4 | 0 | 0 | 0 | 0 | 0 |
| Giant foxtail | 0 | 0 | 2 | 8 | 0 | 10 | 2 | 10 | 10 | 10 | 10 | 8 | 8 | 9 | 5 | 9 | 10 | 10 | 9 | 9 | 8 | 8 | 7 | 7 | 0 | 0 | 0 | 0 | 0 |
| Morningglory | 0 | 0 | 0 | 0 | 0 | 0 | 0 | 0 | 0 | 0 | 0 | 0 | 0 | 1 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 3 | 0 | 7 | 0 | 0 | 0 | 4 | 0 | 0 | 6 | 6 | 0 | 4 | 0 | 0 | 0 | 0 | 0 | 0 | 0 | 0 | 0 |
| Redroot pigweed | 0 | 0 | 0 | 0 | 0 | 0 | 0 | 10 | — | 10 | 3 | 3 | 0 | 8 | 5 | 5 | 10 | 9 | 0 | 10 | 7 | 4 | 0 | 0 | 0 | 0 | 0 | 0 | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Soybean | 0 | 0 | 0 | 0 | 0 | 0 | 0 | 0 | 0 | 0 | 1 | 0 | 0 | 3 | 0 | 0 | 0 | 0 | 0 | 0 | 0 | 0 | 0 | 0 | 0 | 0 | 0 | 0 | 0 |
| Sugarbeets | 0 | 0 | 0 | 0 | 0 | 0 | 0 | 4 | 3 | 8 | 0 | 0 | 0 | 7 | 4 | 0 | 9 | 0 | 0 | 3 | 0 | 0 | 0 | 0 | 0 | 0 | 0 | 0 | 0 |
| Velvetleaf | 0 | 0 | 0 | 0 | 0 | 0 | 0 | 7 | 3 | 5 | 0 | 0 | 0 | 6 | 4 | 0 | 8 | 6 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 2 | 0 | 0 | 3 | 2 | 0 | 0 | 0 | 0 | 0 | 0 | 0 | 0 | 0 | 0 | 0 |
| Wild oats | 0 | 0 | 0 | 0 | 0 | 2 | 0 | 9 | 9 | 8 | 0 | 0 | 0 | 6 | 5 | 0 | 7 | 3 | 0 | 5 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 129 | 130 | 131 | 132 | 133 | 134 | 135 | 136 | 137 | 138 | 139 | 140 | 141 | 142 | 143 | 144 | 145 | 146 | 147 | 148 | 149 | 150 | 151 | 152 | 153 | 154 | 155 | 156 | 157 |
| Preemergence | | | | | | | | | | | | | | | | | | | | | | | | | | | | | |
| B. signalgrass | 0 | 6 | 7 | 0 | 0 | 0 | 0 | 3 | 3 | 2 | 0 | 0 | 0 | 0 | 0 | 0 | 0 | 9 | 6 | 0 | 0 | 0 | 4 | 0 | 0 | 0 | 0 | 0 | 0 |
| Bedstraw | 0 | 0 | — | 0 | 0 | 0 | — | — | 4 | 5 | 0 | 0 | 0 | 0 | 0 | 0 | 0 | 9 | 1 | 0 | 0 | 0 | 0 | 0 | 0 | 0 | 0 | 0 | 0 |
| Blackgrass | 0 | 5 | 10 | 3 | 3 | 0 | 0 | 0 | 7 | 9 | 4 | 0 | 0 | 0 | 4 | 0 | 0 | 8 | 8 | 4 | 0 | 0 | 8 | 0 | 0 | 0 | 0 | 0 | 0 |
| Cocklebur | 0 | 0 | 0 | 0 | 0 | 0 | 0 | 0 | 0 | 0 | 0 | 0 | — | 0 | 0 | — | 0 | 0 | 0 | — | 0 | 0 | 0 | 0 | 0 | 0 | 0 | 0 | 0 |
| Corn | 0 | 3 | 0 | 0 | 0 | 0 | 0 | 0 | 0 | 0 | 0 | 0 | 0 | 0 | 0 | 0 | 0 | 3 | 6 | 0 | 0 | 0 | 0 | 0 | 0 | 0 | 0 | 0 | 0 |
| Crabgrass | 6 | 6 | 2 | 7 | 1 | 2 | 0 | 0 | 8 | 9 | 7 | 4 | 0 | 0 | 3 | 4 | 0 | 8 | 8 | 5 | 0 | 0 | 10 | 0 | 0 | 0 | 0 | 0 | 0 |
| Giant foxtail | 7 | 7 | 10 | 8 | 3 | 6 | 0 | 0 | 8 | 7 | 10 | 1 | 0 | 0 | 3 | 3 | 0 | 10 | 7 | 7 | 0 | 0 | 9 | 0 | 0 | 0 | 0 | 0 | 3 |
| Morningglory | 0 | 0 | 3 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 |
| Nutsedge | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 |
| Rape | 0 | 4 | 8 | 0 | 0 | 0 | 0 | 0 | 0 | 7 | 0 | 0 | 0 | 0 | 0 | 0 | 0 | 2 | 1 | 0 | 0 | 0 | 2 | 0 | 0 | 0 | 0 | 0 | 0 |
| Redroot pigweed | 0 | 6 | 7 | 2 | 0 | 0 | — | 7 | 9 | 9 | 6 | 0 | 0 | 0 | — | 0 | 0 | 10 | 6 | 7 | 0 | 4 | 10 | 0 | 0 | 6 | 0 | 0 | 0 |
| Soybean | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 2 | 7 | 7 | 2 | 0 | 0 | 0 | 4 | 6 | 9 | 3 | 0 | 0 | 0 | 0 | 0 | 0 | 8 | 2 | 4 | 0 | 0 | 1 | 0 | 0 | 0 | 0 | 0 | 0 |
| Velvetleaf | 0 | 5 | 7 | 3 | 0 | 0 | 0 | 0 | 3 | 5 | 2 | 0 | 0 | 0 | 0 | 0 | 0 | 7 | 3 | 0 | 0 | 0 | 6 | 0 | 0 | 0 | 0 | 0 | 0 |
| Wheat | 0 | 2 | 2 | 0 | 0 | 0 | 0 | 0 | 0 | 3 | 0 | 0 | 0 | 0 | 0 | 0 | 0 | 2 | 5 | 0 | 0 | 0 | 2 | 0 | 0 | 0 | 0 | 0 | 0 |
| Wild oats | 3 | 7 | 10 | 3 | 0 | 0 | 0 | 0 | 5 | 5 | 3 | 0 | 0 | 0 | 0 | 0 | 0 | 9 | 2 | 6 | 0 | 0 | 8 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 158 | 159 | 160 | 161 | 162 | 163 | 164 | 165 | 166 | 167 | 168 | 169 | 170 | 171 | 172 | 173 | 174 | 175 | 177 | 178 | 179 | 180 | 181 | 182 | 183 | 184 | 185 | 186 | 187 |
| Preemergence | | | | | | | | | | | | | | | | | | | | | | | | | | | | | |
| B. signalgrass | 0 | 0 | 0 | 0 | 0 | 0 | 0 | 0 | 0 | 2 | 0 | 7 | 2 | 0 | 2 | 0 | 0 | 0 | 0 | 6 | 7 | 0 | 0 | 0 | 0 | 5 | 0 | 0 | 0 |
| Bedstraw | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Blackgrass | 0 | 0 | 0 | 3 | 0 | 7 | 0 | 0 | 0 | 0 | 0 | 3 | 10 | 0 | 0 | 0 | 0 | 0 | 0 | 0 | 0 | 0 | 0 | 0 | 0 | 0 | 0 | 0 | 0 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 3 | 0 | 0 | 4 | 6 | 8 | 0 | 4 | 4 | 7 | 0 | 8 | 8 | 2 | 7 | 2 | 2 | 5 | 1 | 0 | 6 | 0 | 0 | 0 | 0 | 0 | 2 | 2 | 0 |
| Giant foxtail | 3 | 0 | 0 | 4 | 7 | 8 | 0 | 6 | 3 | 8 | 6 | 10 | 9 | 5 | 8 | 6 | 8 | 5 | 3 | 4 | 6 | 0 | 0 | 0 | 0 | 0 | 0 | 5 | 0 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 2 | 2 | 0 | 0 | 0 | 0 | 0 | 0 | 0 | 0 | 0 | 0 | 0 | 0 | 0 | — | 0 | 0 |
| Redroot pigweed | 0 | 0 | 0 | 0 | 0 | — | 0 | 0 | 0 | 0 | 0 | 6 | 10 | 0 | 0 | 0 | 0 | 0 | 0 | 0 | 7 | 0 | 0 | 0 | 0 | 0 | 0 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 0 | 0 | 0 | 0 | 0 | 0 | 0 | 0 | 0 | 0 | 0 | 4 | 0 | 0 | 0 | 3 | 0 | 0 | 0 | 0 | 0 | 0 | 0 | 0 | 0 | 0 | 0 | 0 |
| Velvetleaf | 0 | 0 | 0 | 0 | 0 | 0 | 0 | 0 | 0 | 0 | 0 | 2 | 3 | 0 | 0 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 5 | 0 | 0 | 0 | 0 | 0 | 0 | 0 | 0 | 0 | 0 | 0 | 0 | 0 | 0 | 0 | 0 |
| Wild oats | 0 | 0 | 0 | 0 | 0 | 3 | 0 | 4 | 0 | 0 | 0 | 8 | 7 | 0 | 0 | 0 | 0 | 0 | 0 | 0 | 0 | 0 | 0 | 0 | 0 | 0 | 0 | 0 | 0 |

TABLE B-continued

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 188 | 189 | 190 | 191 | 192 | 193 | 194 | 195 | 196 | 197 | 198 | 199 | 200 | 201 | 202 | 203 | 204 | 205 | 206 | 207 | 208 | 210 | 211 | 212 | 213 | 214 | 215 | 216 | 217 |
| Preemergence | | | | | | | | | | | | | | | | | | | | | | | | | | | | | |
| B. signalgrass | 0 | 3 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Bedstraw | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | 0 | 0 | 0 | 0 | 0 |
| Blackgrass | 0 | 1 | 0 | 0 | 5 | 0 | 0 | 0 | 0 | 0 | 0 | 6 | 0 | 0 | 0 | 0 | 0 | 0 | 0 | 0 | 0 | 0 | 6 | 4 | 0 | 0 | 4 | 0 | 6 |
| Cocklebur | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 0 | 2 | — | 4 | 3 | 0 | 0 | 0 | 6 | 0 | 0 | 3 | 0 | 6 | 0 | 0 | 0 | 4 | 0 | 0 | 0 | 0 | 0 | 3 | 0 | 3 |
| Giant foxtail | 0 | 0 | 0 | 3 | 8 | 2 | 3 | 3 | 0 | 0 | 0 | 7 | 0 | 2 | 2 | 0 | 7 | 0 | 0 | 3 | 2 | 0 | 3 | 2 | 0 | 2 | 3 | 0 | 6 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | — | 0 | 0 | 0 | 0 | 0 | 0 | 0 | 0 | 0 | — | 0 | 0 | 0 | 0 | — | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Redroot pigweed | 0 | 0 | 0 | 0 | 0 | 0 | 5 | 0 | 0 | 0 | 0 | 7 | 0 | 0 | 0 | 0 | 0 | 0 | 0 | 0 | 0 | 0 | 0 | 9 | 0 | 0 | 4 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 0 | 0 | 0 | 0 | 0 | 0 | 0 | 0 | 0 | 0 | 4 | 0 | 0 | 0 | 0 | 0 | 0 | 0 | 0 | 0 | 0 | 0 | 0 | 0 | 0 | 0 | 0 | 0 |
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 218 | 219 | 220 | 221 | 222 | 223 | 224 | 225 | 226 | 227 | 228 | 229 | 230 | 231 | 232 | 233 | 234 | 235 | 236 | 237 | 238 | 239 | 240 | 241 | 242 | 243 | 244 | 245 | 246 |
| Preemergence | | | | | | | | | | | | | | | | | | | | | | | | | | | | | |
| B. signalgrass | 0 | 4 | 7 | 5 | 0 | 0 | 0 | 1 | 3 | 0 | 0 | 0 | 0 | 0 | 0 | 0 | 0 | 0 | 0 | 0 | 0 | 0 | 0 | 0 | 6 | 4 | 0 | 3 | 0 |
| Bedstraw | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 | 0 |
| Blackgrass | 8 | 7 | 8 | 5 | 0 | 0 | 2 | 2 | 10 | 2 | 0 | 0 | 0 | 0 | 2 | 2 | 0 | 0 | 0 | 0 | 0 | 0 | 0 | 6 | 9 | 8 | 0 | 10 | — |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 3 | 0 |
| Crabgrass | 4 | 5 | 7 | 6 | 0 | 4 | 2 | 9 | 5 | 1 | 0 | 0 | 1 | 0 | 5 | 5 | 0 | 0 | 2 | 0 | 2 | — | 2 | 3 | 9 | 7 | 0 | 9 | 3 |
| Giant foxtail | 9 | 10 | 9 | 5 | 0 | 7 | 3 | 8 | 9 | 9 | — | 0 | 2 | 0 | 6 | 7 | 0 | 0 | 7 | 0 | 5 | 4 | 5 | 10 | 10 | 10 | 0 | 9 | 8 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 2 | 0 | 0 | 0 |
| Nutsedge | — | — | — | 0 | — | 0 | 0 | 7 | — | 0 | 0 | 0 | 0 | 0 | 0 | 0 | — | — | — | — | 0 | 0 | — | — | 10 | 0 | 0 | — | — |
| Rape | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 3 | 0 |
| Redroot pigweed | 6 | 0 | 0 | 9 | 0 | 0 | 0 | 6 | 0 | 3 | 0 | 0 | 0 | 0 | 0 | 3 | 0 | 0 | 0 | 0 | 0 | 0 | 0 | 0 | 9 | 6 | 0 | 8 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 3 | 5 | 0 | 0 | 0 | 0 | 0 | 0 | 2 | 0 | 0 | 0 | 0 | 0 | 0 | 0 | 0 | 0 | 0 | 0 | 0 | 0 | 0 | 3 | 2 | 0 | 3 | 0 |
| Velvetleaf | 0 | 3 | 1 | 0 | 0 | 0 | 0 | 4 | 2 | 0 | 0 | 0 | 0 | 0 | 0 | 0 | 0 | 0 | 0 | 0 | 0 | 0 | 0 | 2 | 6 | 4 | 0 | 7 | 0 |
| Wheat | 0 | 3 | 6 | 0 | 0 | 0 | 0 | 5 | 6 | 0 | 0 | 0 | 0 | 0 | 0 | 0 | 0 | 0 | 0 | 0 | 0 | 0 | 0 | 0 | 5 | 5 | 0 | 6 | 0 |
| Wild oats | 5 | 2 | 3 | 2 | 0 | — | 0 | 4 | 1 | 0 | 0 | 0 | 0 | 0 | 0 | 0 | 0 | 0 | 0 | 0 | 0 | 0 | 0 | 3 | 7 | 3 | 0 | 3 | 2 |

TABLE B-continued

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 248 | 249 | 250 | 251 | 252 | 253 | 254 | 255 | 256 | 257 | 258 | 259 | 260 | 261 | 262 | 263 | 264 | 265 | 266 | 267 | 268 | 269 | 270 | 271 | 272 | 273 | 274 | 276 | 277 |
| Preemergence | | | | | | | | | | | | | | | | | | | | | | | | | | | | | |
| B. signalgrass | 0 | 0 | 0 | 2 | 0 | 0 | 0 | 0 | 0 | 0 | 0 | 2 | 0 | 0 | 0 | 0 | 0 | 0 | 0 | 0 | 0 | 0 | 0 | 8 | 0 | 0 | 0 | 4 | — |
| Bedstraw | 0 | 0 | 0 | 0 | 0 | 0 | 0 | 0 | 0 | 0 | 0 | 7 | 0 | — | 0 | 0 | 0 | 0 | 0 | 0 | 0 | 0 | 0 | 3 | 0 | 0 | 0 | 0 | — |
| Blackgrass | 0 | 0 | 0 | 6 | 0 | 0 | 0 | 10 | 0 | 0 | 6 | 2 | 0 | 0 | 0 | 0 | 0 | 0 | 8 | 0 | 0 | 0 | 0 | 8 | 0 | 0 | 0 | — | — |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 2 | 3 | 0 | 0 | 0 | 0 | 0 | 0 | 3 | 4 | 0 | 2 | 0 | 0 | 0 | 1 | 0 | 2 | 0 | 0 | 0 | 3 | 0 | 2 | 0 | 3 | 4 |
| Giant foxtail | 0 | 0 | 8 | 8 | 3 | 0 | 0 | 8 | 0 | 3 | 8 | 9 | 3 | 8 | 0 | 2 | 2 | 6 | 0 | 8 | 0 | 3 | 0 | 8 | 2 | 7 | 0 | 9 | 10 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 0 | 0 | 0 |
| Nutsedge | 0 | 0 | — | — | — | — | 0 | — | — | — | — | 0 | 0 | — | 0 | 0 | — | 0 | — | 0 | 0 | 0 | 0 | 0 | 0 | — | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | — |
| Redroot pigweed | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 3 | 0 | 0 | 0 | 0 | — |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 0 | 0 | 6 | 0 | 0 | 0 | 0 | 0 | 0 | 0 | 0 | 0 | 0 | 0 | 0 | 0 | 0 | 0 | 0 | 0 | 0 | 0 | 5 | 0 | 0 | 0 | 0 | — |
| Velvetleaf | 0 | 0 | 0 | 0 | 0 | 0 | 0 | 0 | 0 | 0 | 2 | 2 | 0 | 0 | 0 | 0 | 0 | 0 | 0 | 0 | 0 | 0 | 0 | 2 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — |
| Wild oats | 0 | 0 | 0 | 0 | 0 | 0 | 0 | 0 | 0 | 0 | 2 | 2 | 0 | 0 | 0 | 0 | 2 | 0 | 0 | 0 | 0 | 0 | 0 | 2 | 0 | 0 | 0 | 0 | — |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 278 | 281 | 282 | 283 | 284 | 285 | 286 | 287 | 288 | 289 | 290 | 291 | 292 | 293 | 294 | 295 | 296 | 297 | 298 | 299 | 300 | 301 | 303 | 304 | 306 | 307 | 308 | 309 | 310 |
| Preemergence | | | | | | | | | | | | | | | | | | | | | | | | | | | | | |
| B. signalgrass | 0 | 0 | 0 | 6 | 5 | 2 | 0 | 6 | 0 | 7 | 0 | 0 | 0 | 2 | 0 | 6 | 0 | 0 | 0 | 6 | 0 | 0 | 0 | 0 | 0 | 0 | 0 | 0 | 4 |
| Bedstraw | — | 0 | 0 | 0 | 0 | 0 | 0 | 9 | 0 | 0 | 0 | 0 | 0 | 0 | 0 | 0 | 0 | — | — | 10 | — | 0 | 0 | 0 | 0 | 0 | 0 | 0 | 2 |
| Blackgrass | 0 | 0 | 0 | 7 | 0 | 0 | 0 | 10 | 0 | 8 | 2 | 0 | 0 | 7 | 0 | 5 | 0 | 0 | 0 | 9 | 0 | 0 | 0 | 0 | 0 | 0 | 0 | 0 | 10 |
| Cocklebur | 0 | — | — | 0 | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 2 | 1 | 2 | 4 | 4 | 0 | 8 | 1 | 2 | 1 | 0 | 0 | 1 | 1 | 2 | 0 | 0 | 0 | 6 | 0 | 0 | 0 | 3 | 0 | 0 | 0 | 0 | 5 |
| Giant foxtail | 0 | 7 | 8 | 8 | 9 | 8 | 8 | 10 | 5 | 10 | 8 | 8 | 0 | 9 | 7 | 8 | 0 | 0 | 0 | 9 | 0 | 0 | 0 | 0 | 2 | 6 | 0 | 5 | 10 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 |
| Nutsedge | — | 0 | 0 | 0 | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 |
| Rape | 0 | 0 | 0 | 0 | 2 | 0 | 0 | 4 | 0 | 0 | 0 | 0 | 0 | 0 | 0 | 0 | 0 | 0 | 0 | 1 | 0 | 0 | 0 | 0 | 0 | 0 | 0 | 0 | 5 |
| Redroot pigweed | 0 | 0 | 1 | 2 | 5 | 0 | 0 | 5 | 0 | 5 | 2 | 0 | 0 | 6 | 0 | 3 | 0 | 0 | 0 | 9 | 0 | 0 | 0 | 0 | 0 | 0 | 0 | 0 | 9 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 0 | 0 | 0 | 2 | 0 | 0 | 3 | 0 | 2 | 2 | 0 | 0 | 0 | 0 | 0 | 0 | 0 | 0 | 3 | 0 | 0 | 0 | 0 | 0 | 0 | 0 | 0 | 5 |
| Velvetleaf | 0 | 0 | 0 | 0 | 0 | 0 | 0 | 6 | 0 | 3 | 0 | 0 | 0 | 4 | 0 | 0 | 0 | 0 | 0 | 6 | 0 | 0 | 0 | 0 | 0 | 0 | 0 | 0 | 2 |
| Wheat | 0 | 0 | 0 | 0 | 0 | 0 | 0 | 0 | 0 | 0 | 0 | 0 | 0 | 2 | 0 | 0 | 0 | 0 | 0 | 3 | 0 | 0 | 0 | 0 | 0 | 0 | 0 | 0 | 2 |
| Wild oats | 0 | 0 | 0 | 0 | 0 | 0 | 0 | 8 | 0 | 1 | 0 | 0 | 0 | 1 | 0 | 2 | 0 | 0 | 0 | 2 | 0 | 0 | 0 | 0 | 0 | 0 | 0 | 0 | 8 |

TABLE B-continued

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 311 | 312 | 313 | 314 | 315 | 316 | 317 | 318 | 319 | 320 | 321 | 322 | 323 | 324 | 325 | 326 | 327 | 328 | 329 | 330 | 332 | 333 | 334 | 335 | 336 | 337 | 338 | 339 | 340 |
| Preemergence | | | | | | | | | | | | | | | | | | | | | | | | | | | | | |
| B. signalgrass | 0 | 0 | 0 | 0 | 2 | 6 | 5 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Bedstraw | 0 | 0 | 0 | 0 | 0 | 0 | 0 | — | 0 | 0 | 0 | 0 | 0 | 0 | 0 | — | — | 0 | 0 | — | 0 | 0 | 0 | 0 | 0 | 0 | 0 | 0 | 0 |
| Blackgrass | 0 | 0 | 0 | 5 | 4 | 8 | 3 | 0 | 0 | 0 | 3 | 0 | 0 | 0 | 0 | 0 | 0 | 0 | 0 | 0 | 0 | 0 | 0 | 0 | 0 | 0 | 0 | 0 | 0 |
| Cocklebur | 0 | 0 | 0 | 0 | 0 | 0 | — | 0 | 0 | 0 | 0 | 0 | 0 | 0 | 0 | 0 | 0 | — | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 1 | 2 | 6 | 6 | 0 | 0 | 2 | 0 | 1 | 0 | 0 | 0 | 0 | 0 | 0 | 0 | 0 | 0 | 0 | 0 | 0 | 0 | 0 | 0 | 0 | 0 |
| Giant foxtail | 0 | 0 | 0 | 3 | 7 | 9 | 9 | 0 | 6 | 0 | 4 | 6 | 0 | 0 | 3 | 0 | 7 | 0 | 0 | 0 | 0 | 0 | 0 | 2 | 0 | 0 | 0 | 1 | 8 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | — | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Redroot pigweed | 0 | 0 | 0 | 0 | 0 | 4 | 2 | 0 | 0 | 0 | 0 | 0 | 0 | 0 | 0 | 1 | 0 | 0 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Velvetleaf | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 0 | 0 | 0 | 0 | 0 | 4 | 5 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 341 | 342 | 343 | 344 | 345 | 348 | 349 | 350 | 351 | 352 | 353 | 354 | 355 | 356 | 357 | 358 | 359 | 360 | 361 | 362 | 363 | 364 | 367 | 368 | 369 | 370 | 371 | 372 | 373 |
| Preemergence | | | | | | | | | | | | | | | | | | | | | | | | | | | | | |
| B. signalgrass | 0 | 0 | 3 | 0 | 0 | — | — | 0 | 0 | 2 | 0 | 1 | 0 | 0 | 1 | 1 | 0 | 5 | 3 | 4 | 3 | 0 | 0 | 1 | 0 | 0 | 0 | 0 | 0 |
| Bedstraw | 0 | 0 | — | 0 | 0 | — | — | 10 | — | 0 | 0 | 0 | 0 | 0 | 10 | 0 | 0 | — | 0 | 9 | 9 | 0 | 10 | 0 | — | 0 | — | 0 | 0 |
| Blackgrass | 0 | 0 | 7 | 0 | 0 | 4 | 2 | 4 | 0 | 9 | 2 | 3 | 2 | 5 | 7 | 4 | 0 | 9 | 3 | 9 | 8 | 0 | 2 | 8 | 0 | 6 | 5 | 5 | 1 |
| Cocklebur | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | — | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 3 | 0 | 0 | 0 | 2 | 0 |
| Crabgrass | 2 | 4 | 6 | 0 | 0 | 7 | 3 | 8 | 7 | 9 | 7 | 9 | 4 | 7 | 9 | 9 | 0 | 9 | 2 | 5 | 3 | 0 | 6 | 10 | 5 | 7 | 8 | 8 | 4 |
| Giant foxtail | 9 | 8 | 10 | 0 | 0 | 9 | 8 | 10 | 10 | 10 | 9 | 10 | 10 | 10 | 10 | 10 | 0 | 10 | 7 | 10 | — | 3 | 10 | 10 | 8 | 9 | 10 | 10 | 8 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 4 | 0 | 0 | 0 | 0 | 0 | 0 | 0 | 0 | 5 | 0 |
| Redroot pigweed | 0 | 0 | 10 | 0 | 0 | 0 | 0 | 4 | 10 | — | 7 | 5 | — | 0 | 7 | 7 | 0 | 5 | 1 | 8 | 2 | 0 | 10 | 10 | 0 | 5 | 4 | 6 | 0 |
| Soybean | 0 | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 0 | 0 | 0 | 0 | 0 | 0 | 2 | 2 | 2 | 0 | 0 | 0 | 0 | 2 | 0 | 0 | 2 | 0 | 5 | 0 | 0 | 2 | 6 | 0 | 2 | 0 | 2 | 0 |
| Velvetleaf | 0 | 0 | 5 | 0 | 0 | 3 | 0 | 2 | 0 | 2 | 0 | 1 | 0 | 1 | 4 | 3 | 0 | 3 | 0 | 4 | 1 | 0 | 3 | 4 | 0 | 2 | 0 | 3 | 0 |
| Wheat | 0 | 0 | 0 | 0 | 0 | 0 | 0 | 0 | 0 | 0 | 0 | 0 | 0 | 0 | 4 | 0 | 0 | 3 | 0 | 7 | 3 | 0 | 0 | 0 | 0 | 0 | 0 | 0 | 0 |
| Wild oats | 0 | 0 | 2 | 0 | 0 | 3 | 0 | 0 | 0 | 8 | 0 | 0 | 0 | 5 | 9 | 4 | 0 | 3 | 7 | 7 | 5 | 0 | 0 | 4 | 0 | 0 | 0 | 4 | 0 |

TABLE B-continued

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate 62 g/ha | 374 | 375 | 376 | 378 | 379 | 380 | 381 | 382 | 383 | 384 | 385 | 387 | 388 | 389 | 390 | 391 | 392 | 393 | 394 | 395 | 396 | 397 | 398 | 400 | 401 | 402 | 403 | 404 | 405 |
| Preemergence | | | | | | | | | | | | | | | | | | | | | | | | | | | | | |
| B. signalgrass | 0 | 0 | 0 | 0 | 0 | 0 | 0 | 0 | 0 | 0 | 0 | 0 | 0 | 0 | 1 | 0 | 2 | 0 | 2 | 0 | 0 | 3 | 0 | 0 | 0 | 0 | 3 | 2 | 0 |
| Bedstraw | 0 | 6 | — | 0 | 0 | — | 0 | — | 0 | — | 0 | 0 | — | — | — | — | — | 0 | — | 0 | — | — | — | — | 0 | 2 | 0 | 0 | — |
| Blackgrass | 0 | 3 | 0 | 0 | 0 | 0 | 0 | 0 | 0 | 0 | 0 | 0 | 0 | 0 | 6 | 0 | 6 | 0 | 7 | 0 | 0 | 7 | 3 | 0 | 0 | 3 | 2 | 6 | 0 |
| Cocklebur | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 6 | 7 | 0 | 0 | 0 | 1 | 0 | 6 | 6 | 6 | 3 | 0 | 6 | 1 | 8 | 0 | 10 | 0 | 9 | 0 | 0 | 10 | 9 | 6 | 0 | 9 | 10 | 10 | 0 |
| Giant foxtail | 8 | 10 | 0 | 4 | 0 | 2 | 0 | 9 | 0 | 9 | 3 | 3 | 8 | 2 | 10 | 0 | 10 | 1 | 9 | 0 | 2 | 10 | 10 | 9 | 0 | 10 | 10 | 10 | 0 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 3 | 0 | 0 | 0 | 0 | 0 | 1 | 0 |
| Redroot pigweed | 0 | 10 | 0 | 0 | 0 | 0 | 0 | 0 | 0 | 0 | 2 | 0 | 0 | 0 | 8 | 0 | 2 | 0 | 1 | 0 | 0 | 8 | 2 | 3 | 0 | 0 | 0 | 2 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 0 | 0 | 0 | 0 | 0 | 0 | 0 | 0 | 0 | 0 | 0 | 0 | 0 | 5 | 0 | 0 | 0 | 0 | 0 | 0 | 0 | 0 | 0 | 0 | 0 | 0 | 0 | 0 |
| Velvetleaf | 0 | 0 | 0 | 0 | 0 | 0 | 0 | 0 | 0 | 0 | 0 | 0 | 0 | 0 | 2 | 0 | 0 | 0 | 1 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 0 | 0 | 0 | 0 | 0 | 0 | 0 | 0 | 0 | 0 | 0 | 0 | 3 | 0 | 3 | 0 | 2 | 0 | 4 | 0 | 0 | 2 | 0 | 0 | 0 | 1 | 0 | 3 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 406 | 407 | 408 | 409 | 410 | 411 | 414 | 415 | 416 | 417 | 418 | 419 | 420 | 421 | 422 | 423 | 424 | 425 | 426 | 427 | 428 | 429 | 430 | 431 | 432 | 433 | 434 | 435 | 436 |
| Preemergence | | | | | | | | | | | | | | | | | | | | | | | | | | | | | |
| B. signalgrass | 0 | 0 | 0 | 0 | 1 | 0 | 0 | 2 | 7 | 2 | 0 | 0 | 2 | 7 | 0 | 0 | 0 | 3 | 4 | 0 | 0 | 0 | 1 | 0 | 0 | 2 | 0 | 0 | 0 |
| Bedstraw | 0 | 0 | — | — | — | — | 0 | — | — | — | — | — | — | — | — | — | — | — | — | — | — | — | — | 0 | — | — | — | — | — |
| Blackgrass | 0 | 0 | 6 | 4 | 3 | 6 | 0 | 5 | 8 | 3 | 4 | 0 | 4 | 8 | 0 | 0 | 0 | 7 | 4 | 0 | 0 | 0 | 0 | 0 | 0 | 2 | 0 | 0 | 0 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 7 | 0 | 0 | 0 | 0 | 0 | 0 | 0 | 0 | 0 | 4 | 0 | 0 | 0 | 0 | 0 | 0 | 0 | 0 | 0 | 0 | 0 | 0 | 0 | 0 | 0 |
| Crabgrass | 0 | 0 | 9 | 9 | 7 | 9 | 2 | 8 | 7 | 6 | 6 | 0 | 7 | 8 | 0 | 0 | 0 | 9 | 8 | 5 | 2 | 7 | 9 | 0 | 3 | 9 | 0 | — | 0 |
| Giant foxtail | 0 | 0 | 10 | 9 | 9 | 10 | 2 | 9 | 8 | 4 | 7 | 0 | 5 | 9 | 0 | 0 | 0 | 10 | 9 | 7 | 0 | 3 | 10 | 0 | 0 | 10 | 0 | 0 | 0 |
| Morningglory | 0 | 0 | 0 | 0 | 0 | 0 | 0 | 0 | 0 | 0 | 0 | 0 | 0 | 4 | 0 | 0 | 0 | 0 | 0 | 0 | 0 | 0 | 0 | 0 | 0 | 0 | 0 | 0 | 0 |
| Nutsedge | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 2 | 0 | 2 | 7 | 0 | 0 | 0 | 0 | 8 | 0 | 0 | 0 | 0 | 0 | 0 | 0 | 0 | 0 | 0 | 0 | 0 | 0 | 0 | 0 |
| Redroot pigweed | 0 | 0 | 4 | 7 | 0 | 3 | 0 | 0 | 7 | 0 | 2 | 0 | 0 | 8 | 0 | 0 | 0 | 0 | 2 | 0 | 0 | 0 | 0 | 0 | 0 | 0 | 0 | 2 | 0 |
| Soybean | 0 | 0 | 0 | 0 | 0 | 0 | 0 | 0 | 0 | 0 | 0 | 0 | 0 | 4 | 0 | 0 | 0 | 0 | 0 | 0 | 0 | 0 | 0 | 0 | 0 | 0 | 0 | 0 | 0 |
| Sugarbeets | 0 | 0 | 2 | 2 | 0 | 5 | 0 | 0 | 3 | 0 | 0 | 0 | 0 | 8 | 0 | 0 | 0 | 0 | 0 | 0 | 0 | 0 | 0 | 0 | 0 | 0 | 0 | 0 | 0 |
| Velvetleaf | 0 | 0 | 0 | 2 | 3 | 2 | 0 | 0 | 0 | 0 | 0 | 0 | 0 | 8 | 0 | 0 | 0 | 0 | 0 | 0 | 0 | 0 | 0 | 0 | 0 | 2 | 0 | 0 | 0 |
| Wheat | 0 | 0 | 0 | 4 | 0 | 0 | 0 | 0 | 2 | 0 | 0 | 0 | 0 | 4 | 0 | 0 | 0 | 2 | 0 | 0 | 0 | 0 | 0 | 0 | 0 | 0 | 0 | 0 | 0 |
| Wild oats | 0 | 0 | 0 | 0 | 3 | 0 | 0 | 0 | 6 | 0 | 0 | 0 | 0 | 6 | 0 | 0 | 0 | 2 | 2 | 0 | 0 | 0 | 0 | 0 | 0 | 2 | 0 | 0 | 0 |

TABLE B-continued

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 437 | 438 | 439 | 440 | 441 | 442 | 443 | 444 | 445 | 446 | 449 | 450 | 451 | 452 | 453 | 454 | 455 | 456 | 457 | 458 | 459 | 460 | 461 | 462 | 463 | 465 | 466 | 467 | 468 |
| Preemergence | | | | | | | | | | | | | | | | | | | | | | | | | | | | | |
| B. signalgrass | 0 | 0 | 0 | 1 | 0 | 0 | 0 | 0 | 0 | 0 | 0 | 0 | 0 | 0 | 0 | 0 | 0 | 0 | 0 | 4 | 0 | 0 | 0 | 0 | 0 | 0 | 0 | 0 | 0 |
| Bedstraw | — | — | — | — | — | — | — | — | — | — | 0 | — | — | — | — | — | — | — | — | — | 0 | 0 | — | 0 | — | — | — | 0 | — |
| Blackgrass | 0 | 0 | 0 | 2 | 0 | 0 | 0 | 0 | 0 | 5 | 0 | 0 | 0 | 0 | 0 | 0 | 3 | 0 | 0 | 6 | 0 | 0 | 0 | 0 | 0 | 2 | 2 | 0 | 3 |
| Cocklebur | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 3 | 0 | 7 | 0 | 7 | 5 | 4 | 0 | 8 | 0 | 2 | 0 | 5 | 5 | 2 | 5 | 6 | 0 | 6 | 5 | 0 | 0 | 0 | 0 | 2 | 6 | 5 | 9 |
| Giant foxtail | 0 | 2 | 0 | 6 | 0 | 0 | 3 | 9 | 0 | 9 | 2 | 2 | 0 | 2 | 7 | 6 | 10 | 5 | 0 | 9 | 8 | 0 | 0 | 0 | 0 | 7 | 9 | 0 | 6 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 4 | 0 |
| Redroot pigweed | 0 | 2 | 0 | 0 | 0 | 0 | 0 | 10 | 0 | 6 | 0 | 0 | 0 | 0 | 0 | 0 | 7 | 0 | 0 | 0 | 0 | 0 | 0 | 0 | 2 | 3 | 1 | 7 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | 0 |
| Sugarbeets | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 0 |
| Velvetleaf | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha | 469 | 470 | 471 | 472 | 473 | 474 | 476 | 477 | 478 | 479 | 480 | 481 | 482 | 483 | 485 | 486 | 487 | 488 | 489 | 490 | 492 | 493 | 494 | 495 | 496 | 497 | 498 | 499 | 500 |
| Preemergence | | | | | | | | | | | | | | | | | | | | | | | | | | | | | |
| B. signalgrass | 3 | 0 | 6 | 3 | 0 | 0 | 0 | 0 | 4 | 0 | 0 | 7 | 0 | 0 | 3 | 5 | 3 | 4 | 6 | 3 | 0 | 0 | 0 | 0 | 0 | 0 | 0 | 0 | 9 |
| Bedstraw | — | — | — | — | — | 0 | 0 | 0 | — | — | — | 0 | 0 | 0 | — | — | — | — | — | — | 0 | 0 | 0 | — | 0 | 0 | — | 0 | 8 |
| Blackgrass | 6 | 0 | 9 | 9 | 0 | 3 | 0 | 0 | 4 | 2 | 3 | 6 | 0 | 0 | 4 | 7 | 2 | 5 | 7 | 7 | 0 | 0 | 0 | 0 | 0 | 0 | 0 | 0 | 9 |
| Cocklebur | 0 | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 | 0 | 0 | 0 | — | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 9 | 1 | 9 | 9 | — | 6 | 0 | 8 | 8 | — | 7 | 7 | 3 | 0 | 6 | 8 | 6 | 8 | 9 | 8 | 0 | 0 | 0 | 0 | 0 | 0 | 0 | 4 | 7 |
| Giant foxtail | 9 | 0 | 10 | 10 | 2 | 7 | 0 | 6 | 9 | 7 | 10 | 9 | 1 | 0 | 7 | 9 | 9 | 9 | 9 | 9 | 2 | 3 | 0 | 0 | 2 | 0 | 0 | 3 | 9 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | — | 0 | 0 | 0 | — | 0 | 0 | 0 | 0 | 0 | 0 | 0 | 0 | 0 | — | 0 | 0 | 0 | 0 | 0 | — | 0 |
| Rape | 0 | 0 | 2 | 0 | 0 | 0 | 0 | 0 | 0 | 0 | 0 | 0 | 0 | 0 | 0 | 2 | 0 | 1 | 0 | 0 | 0 | 0 | 0 | 0 | 0 | 0 | 0 | 0 | 9 |
| Redroot pigweed | 5 | 0 | 10 | 10 | 2 | 1 | 0 | 0 | 8 | 0 | 2 | 0 | 0 | 0 | 1 | 6 | 1 | 4 | 0 | 5 | 0 | 0 | 0 | 0 | 0 | 0 | 0 | 0 | 10 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 6 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 9 |
| Velvetleaf | 4 | 0 | 2 | 1 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 5 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 |
| Wild oats | 7 | 0 | 2 | 2 | 0 | 0 | 0 | 0 | 2 | 0 | 0 | 4 | 0 | 0 | 2 | 0 | 0 | 3 | 0 | 6 | 0 | 0 | 0 | 0 | 0 | 0 | 0 | 0 | 7 |

TABLE B-continued

| Rate 62 g/ha | 501 | 502 | 503 | 504 | 505 | 506 | 508 | 509 | 510 | 511 | 512 | 513 | 514 | 515 | 516 | 517 | 518 | 519 | 520 | 521 | 522 | 523 | 524 | 525 | 526 | 527 | 528 | 531 | 532 |
|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | |
| Preemergence | | | | | | | | | | | | | | | | | | | | | | | | | | | | | |
| B. signalgrass | 8 | 6 | 6 | 7 | 0 | 0 | 4 | 2 | 7 | 0 | 3 | 0 | 6 | 2 | 1 | 0 | 0 | 0 | 0 | 0 | 10 | 4 | 0 | 9 | 8 | 2 | 0 | 2 | 0 |
| Bedstraw | 2 | 10 | 5 | 2 | 0 | 0 | 0 | 0 | 0 | 0 | 0 | 0 | 0 | 0 | 0 | 0 | 0 | 0 | 0 | 0 | 10 | 0 | — | 0 | 0 | 0 | 0 | 0 | 0 |
| Blackgrass | 5 | 10 | 10 | 6 | 0 | 0 | 1 | 5 | 6 | 0 | 0 | 1 | 2 | 3 | 3 | 2 | 7 | 0 | 0 | 0 | 4 | 2 | 4 | 8 | 7 | 0 | 0 | 2 | 0 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | — | 0 | 3 | 0 | 2 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 |
| Crabgrass | 8 | 10 | 8 | 6 | — | 0 | 6 | 3 | 5 | 5 | 3 | 4 | 5 | 6 | 6 | 4 | 0 | 7 | 9 | 10 | 9 | 9 | 9 | 9 | 9 | 9 | 7 | 8 | 9 |
| Giant foxtail | 9 | 10 | 9 | 9 | 9 | 0 | 10 | 9 | 9 | 5 | 5 | 2 | 9 | 10 | 10 | 2 | 0 | 10 | 9 | 10 | 10 | 10 | 9 | 9 | 9 | 9 | 9 | 9 | 10 |
| Morningglory | 0 | 0 | 2 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 |
| Nutsedge | 0 | 0 | 0 | 2 | 3 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 2 | 4 | 5 | 4 | 0 | 0 | 0 | 2 | 0 | 0 | 0 | 0 | 0 | 0 | 0 | 0 | 0 | 0 | 0 | 0 | 0 | 2 | 0 | 4 | 0 | 0 | 0 | 0 |
| Redroot pigweed | 9 | 9 | 8 | 10 | 9 | 2 | 7 | 0 | 7 | 4 | 3 | 7 | 7 | 8 | 7 | 8 | 2 | 0 | 0 | 0 | 10 | 2 | 8 | 0 | 4 | 0 | 0 | 0 | 0 |
| Soybean | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 0 | 2 | 4 | 3 | 0 | 1 | 0 | 0 | 0 | 0 | 0 | 0 | 0 | 1 | 0 | 0 | 0 | 0 | 0 | 5 | 3 | 0 | 5 | 4 | 0 | 0 | 0 | 0 |
| Velvetleaf | 0 | 0 | 6 | 1 | 0 | 0 | 0 | 3 | 1 | 0 | 0 | 0 | 0 | 0 | 0 | 0 | 0 | 0 | 0 | 0 | 2 | 0 | 0 | 2 | 0 | 0 | 0 | 0 | 0 |
| Wheat | 4 | 0 | 0 | 2 | 3 | 0 | 0 | 0 | 0 | 0 | 0 | 0 | 0 | 0 | 0 | 0 | 0 | 0 | 0 | 0 | 0 | 0 | 0 | 3 | 0 | 0 | 0 | 0 | 0 |
| Wild oats | 0 | 9 | 6 | 6 | 2 | 0 | 3 | 0 | 4 | 0 | 2 | 3 | 3 | 3 | 0 | 4 | 4 | 0 | 0 | 0 | 10 | 0 | 7 | 5 | 7 | 0 | 0 | 0 | 0 |

| Rate 62 g/ha | 533 | 534 | 535 | 536 | 540 | 541 | 543 | 544 | 545 | 546 | 548 | 549 | 550 | 551 | 552 | 553 | 554 | 555 | 556 | 557 | 558 | 559 | 560 | 561 | 562 | 563 | 564 | 565 | 566 |
|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | |
| Preemergence | | | | | | | | | | | | | | | | | | | | | | | | | | | | | |
| B. signalgrass | 2 | 9 | — | 0 | 0 | 0 | 0 | 3 | 0 | 0 | 0 | 0 | 6 | 4 | 4 | 6 | 7 | 6 | 6 | 4 | 0 | 8 | 4 | 4 | 5 | 3 | 2 | 0 | 9 |
| Bedstraw | 0 | 0 | 0 | 0 | 0 | 0 | — | 0 | 0 | 0 | 8 | 0 | 0 | — | 0 | 0 | 0 | 0 | 0 | 0 | 0 | 0 | 0 | 0 | 0 | 0 | 0 | 0 | 0 |
| Blackgrass | 4 | 8 | — | 0 | 0 | 0 | 0 | 0 | 0 | 0 | 0 | 0 | 0 | 3 | 0 | 7 | — | 0 | 6 | 6 | 2 | 9 | 4 | 5 | 4 | 2 | 0 | 0 | 3 |
| Cocklebur | 0 | 0 | 0 | 0 | 0 | — | — | 0 | 0 | 0 | 0 | 0 | 0 | 0 | 0 | — | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 2 | 0 | 0 |
| Crabgrass | 9 | 9 | 10 | 0 | 8 | 5 | 4 | 9 | 8 | 7 | 9 | 3 | 4 | 9 | 9 | 10 | 9 | 9 | 9 | 9 | 8 | 9 | 9 | 9 | 8 | 8 | 7 | 0 | 9 |
| Giant foxtail | 9 | 9 | 10 | 7 | 9 | 7 | 3 | 9 | 10 | — | 9 | 9 | 7 | 10 | 9 | 10 | 9 | 9 | 9 | 9 | 8 | 10 | 10 | 0 | 4 | 9 | 9 | 0 | 9 |
| Morningglory | 0 | 0 | 0 | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | 0 |
| Nutsedge | 0 | 0 | 0 | 0 | — | — | 0 | 0 | 0 | 0 | 0 | — | 0 | 0 | 0 | 0 | 0 | 0 | 0 | 0 | 0 | — | 0 | — | 0 | 0 | 0 | 0 | 0 |
| Rape | 0 | 2 | 2 | 0 | 0 | 0 | 0 | 0 | 0 | 0 | 0 | 0 | 0 | 0 | 0 | 0 | 0 | 0 | 0 | 0 | 0 | 7 | 0 | 2 | 0 | 0 | 0 | 0 | 0 |
| Redroot pigweed | 8 | 0 | 2 | 0 | 0 | 0 | 7 | 3 | 3 | — | 0 | 6 | 7 | 8 | 0 | 0 | 9 | 0 | 0 | 0 | 0 | 7 | 3 | 3 | 10 | 4 | 0 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 3 | 3 | 4 | 0 | 0 | 0 | 4 | 0 | 0 | 0 | 0 | 0 | 0 | 2 | 0 | 0 | 0 | 2 | 0 | 2 | 0 | 3 | 0 | 0 | 6 | 2 | 2 | 0 | 0 |
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | 0 | 3 | 0 | 0 | 0 | 3 | 0 | 0 | 0 |
| Wheat | 0 | 0 | 0 | 0 | 0 | 0 | 0 | 0 | 0 | 0 | 0 | 0 | 0 | 0 | 0 | — | 3 | 0 | 0 | 0 | 0 | 3 | 3 | 0 | 3 | 3 | 0 | 0 | 0 |
| Wild oats | 0 | 3 | 0 | 0 | 0 | 0 | 0 | 0 | 0 | 0 | 0 | 0 | 0 | 0 | 0 | 0 | 0 | 0 | 0 | 0 | 0 | — | 0 | 0 | 4 | 2 | 0 | 0 | 3 |

TABLE B-continued

| Rate 62 g/ha | COMPOUND 567 | 568 | 569 | 570 | 571 | 572 | 573 | 574 | 575 | 576 | 577 | 578 | 579 | 580 | 581 | 582 | 584 | 585 | 586 | 588 | 589 | 590 | 591 | 592 | 593 | 594 | 595 | 596 | 598 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 0 | 3 | 0 | 0 | 0 | 0 | 7 | 4 | 6 | 0 | 0 | 0 | 0 | 2 | 0 | 0 | 7 | 3 | 0 | 0 | 0 | 0 | 0 | 0 | 0 | 3 | 2 | 0 | 0 |
| Bedstraw | 0 | 0 | 0 | 0 | 0 | 0 | 0 | 0 | 0 | 0 | 0 | 0 | 0 | 0 | 8 | 0 | 9 | 7 | — | — | — | 0 | 0 | 0 | 0 | 0 | 0 | 0 | 0 |
| Blackgrass | 0 | 5 | 0 | 0 | 0 | 0 | 0 | 0 | 2 | 0 | 0 | 0 | 0 | 0 | 0 | 0 | 9 | 3 | 3 | 0 | 0 | 0 | 0 | 0 | 0 | 5 | 6 | 0 | 0 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | — | 0 | 0 |
| Corn | 0 | 0 | 0 | 0 | 0 | 0 | 0 | 0 | 0 | 0 | 2 | 3 | 0 | 0 | 0 | 0 | 0 | 0 | 0 | 0 | 0 | 0 | 0 | 0 | 0 | 0 | 0 | 0 | 0 |
| Crabgrass | 0 | 7 | 7 | 9 | 2 | 0 | 3 | 2 | 8 | 0 | 7 | 0 | 7 | 6 | 4 | 0 | 8 | 5 | 9 | 3 | 0 | 0 | 0 | 0 | 0 | 9 | 7 | 0 | 0 |
| Giant foxtail | 3 | 9 | 9 | 0 | 3 | 0 | 9 | 9 | 8 | 2 | 7 | 2 | 8 | 9 | 4 | 0 | 9 | 7 | 9 | 7 | 3 | 0 | 0 | 0 | 0 | 9 | 10 | 0 | 0 |
| Morningglory | 0 | 0 | 0 | 0 | 0 | 0 | 0 | 0 | 0 | 0 | 0 | 0 | 0 | 0 | 0 | 0 | 4 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | — | 0 | 0 | 0 | 0 | 0 | 0 | 0 | 0 | 0 | 0 | 0 | 0 | 0 | 0 | 0 | 0 | 0 | — | 0 | 0 |
| Rape | 0 | 0 | 0 | 0 | 0 | 0 | 2 | 0 | 0 | 0 | 0 | 0 | 0 | 0 | 0 | 0 | 3 | 3 | 0 | 0 | 0 | 0 | 0 | 0 | 0 | 0 | 4 | 0 | 0 |
| Redroot pigweed | 0 | 2 | 7 | 0 | 0 | 0 | 0 | 0 | 9 | 0 | 0 | 2 | 0 | 9 | — | 0 | 7 | 6 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | 0 | 0 | 0 | 0 |
| Sugarbeets | 0 | 5 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 6 | 0 | 0 |
| Velvetleaf | 0 | 5 | 0 | 0 | 0 | 0 | 0 | 0 | 0 | 0 | 4 | 0 | 0 | 0 | 5 | 0 | 0 | 0 | 0 | 0 | 0 | 0 | 0 | 0 | 0 | 2 | 7 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 0 | 5 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 3 | 0 | 0 |

| Rate 62 g/ha | COMPOUND 601 | 602 | 603 | 604 | 605 | 606 | 607 | 608 | 609 | 610 | 611 | 612 | 613 | 614 | 615 | 618 | 619 | 620 | 621 | 622 | 624 | 625 | 627 | 628 | 629 | 630 | 631 | 632 | 633 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 3 | 0 | 0 | 0 | 0 | 0 | 4 | 1 | 3 | 6 | 7 | 4 | 7 | 0 | 0 | 0 | 0 | 0 | 0 | 0 | 3 | 0 | 5 | 3 | 0 | 0 | 6 | 0 | 0 |
| Bedstraw | 0 | 0 | — | — | 0 | — | — | — | 4 | — | 1 | — | — | 0 | 0 | 0 | — | 0 | 0 | 0 | 0 | — | 2 | 6 | 0 | 0 | 0 | — | — |
| Blackgrass | — | 0 | 0 | 0 | 0 | 0 | 4 | 2 | 7 | 8 | 9 | 8 | 8 | 0 | 0 | 0 | 0 | 0 | 0 | 1 | 1 | 0 | 8 | 6 | 4 | 5 | 6 | 2 | 0 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 6 | 2 | 0 | 0 | 0 | 0 | 0 |
| Corn | 0 | 0 | 0 | 0 | 0 | 0 | 0 | 0 | 2 | 0 | 2 | 0 | 2 | 0 | 0 | 0 | 0 | 0 | 0 | 0 | 0 | 0 | 3 | 3 | 1 | 0 | 5 | 0 | 0 |
| Crabgrass | 6 | 7 | 0 | 0 | 0 | 0 | 7 | 7 | 7 | 9 | 9 | 10 | 9 | 0 | 0 | 0 | 0 | 0 | 5 | 6 | 7 | 2 | 7 | 8 | 7 | 7 | 7 | 2 | 5 |
| Giant foxtail | 10 | 9 | 0 | 0 | 2 | 0 | 9 | 9 | 10 | 9 | 10 | 10 | 10 | 0 | 0 | 2 | 0 | 0 | 0 | 4 | 10 | 6 | 9 | 10 | 8 | 9 | 9 | 8 | 6 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 6 | 5 | 0 | 0 | 0 | 0 | 0 |
| Nutsedge | 0 | 0 | 0 | 0 | 0 | 0 | — | — | 0 | 0 | 0 | 0 | 0 | — | 0 | — | 0 | 0 | 0 | 0 | 0 | 0 | 7 | 3 | 0 | 0 | 0 | 0 | 0 |
| Rape | 0 | 0 | 0 | 0 | 0 | 0 | 0 | 1 | 0 | 3 | 3 | 0 | 7 | 0 | 0 | 0 | 0 | 0 | 0 | 0 | 0 | 0 | 1 | 0 | 0 | 0 | 0 | 0 | 0 |
| Redroot pigweed | 4 | 2 | 0 | 0 | 0 | 0 | 4 | 5 | 8 | 10 | 6 | 8 | 10 | 0 | 0 | 0 | 0 | 0 | 0 | 4 | 0 | 0 | 9 | 8 | 2 | 2 | 7 | 0 | 0 |
| Soybean | 0 | — | 0 | 0 | 0 | 0 | 0 | 0 | 4 | 0 | 2 | 0 | 0 | 0 | 0 | 0 | 0 | 0 | 0 | 0 | 0 | 0 | 0 | 0 | 0 | 0 | 2 | 0 | 0 |
| Sugarbeets | 0 | 0 | 0 | 0 | 0 | 0 | 0 | 0 | 0 | 3 | 2 | 3 | 3 | 0 | 0 | 0 | 0 | 0 | 0 | 0 | 0 | 0 | 5 | 3 | 2 | 0 | 0 | 0 | 0 |
| Velvetleaf | 1 | 0 | 0 | 0 | 0 | 0 | 0 | 0 | 7 | 7 | 6 | 6 | 7 | 0 | 0 | 0 | 0 | 0 | 0 | 0 | 0 | 0 | 7 | 7 | 3 | 0 | 6 | 0 | 0 |
| Wheat | 0 | 0 | 0 | 0 | 0 | 0 | 0 | 0 | 0 | 2 | 1 | 0 | 0 | 0 | 0 | 0 | 0 | 0 | 0 | 0 | 0 | 0 | 0 | 3 | 0 | 0 | 0 | 0 | 0 |
| Wild oats | 3 | 0 | 0 | 0 | 0 | 0 | 0 | 0 | 3 | 5 | 5 | 5 | 7 | 0 | 0 | 0 | 0 | 0 | 0 | 0 | 2 | 0 | 0 | — | 0 | 0 | 0 | 0 | 0 |

TABLE B-continued

| Rate 62 g/ha | COMPOUND 634 | 635 | 636 | 637 | 638 | 639 | 640 | 641 | 642 | 643 | 644 | 645 | 646 | 647 | 648 | 649 | 650 | 652 | 653 | 654 | 655 | 656 | 657 | 658 | 659 | 660 | 661 | 663 | 664 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 1 | 4 | 3 | 0 | 4 | 0 | 0 | 0 | 0 | 0 | 0 | 0 | 0 | 3 | 0 | 0 | 0 | 0 | 0 | 0 | 0 | 0 | 2 | 0 | 2 | 0 | 0 | 0 | 1 |
| Bedstraw | — | 9 | — | 0 | — | — | — | — | — | — | — | — | 0 | — | 0 | 0 | 0 | 0 | 0 | 0 | 0 | — | — | — | — | — | — | — | — |
| Blackgrass | 4 | 9 | 2 | 2 | 4 | 0 | 0 | 0 | 0 | 0 | 0 | 0 | 0 | 7 | 0 | 0 | 0 | 0 | 0 | 0 | 0 | 4 | 5 | 3 | 3 | 0 | 0 | 0 | 5 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 7 | 9 | 8 | 9 | 9 | 7 | 3 | 0 | 6 | 0 | 2 | 2 | — | 8 | 0 | 0 | 3 | 4 | 0 | 0 | — | 7 | 3 | 3 | 8 | 4 | 0 | 0 | 4 |
| Giant foxtail | 9 | 9 | 9 | 9 | 10 | 7 | 9 | 5 | 8 | 6 | 0 | 1 | 0 | 9 | 5 | 0 | 7 | 8 | 0 | 0 | 3 | 4 | 10 | 9 | 9 | 8 | 2 | 0 | 9 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 0 | 0 | 0 | 0 |
| Nutsedge | 0 | 0 | 0 | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | 0 |
| Rape | 0 | 6 | 0 | 0 | 0 | 0 | 0 | 0 | 0 | 0 | 0 | 0 | 0 | 5 | 0 | 0 | 0 | 0 | 0 | 0 | 0 | 0 | 3 | 2 | 0 | 0 | 0 | 0 | 0 |
| Redroot pigweed | 0 | 10 | 10 | 4 | 7 | 0 | 0 | 0 | 0 | 0 | 0 | 0 | 0 | 10 | 0 | 0 | 1 | 0 | 0 | 0 | 0 | 0 | 7 | 2 | 6 | 0 | 0 | 0 | 2 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 3 | 0 | 0 | 0 | 0 | 0 | 0 | 0 | 0 | 0 | 0 | 0 | 7 | 0 | — | 0 | 0 | 0 | 0 | 0 | 0 | 7 | 3 | 0 | 0 | 0 | 0 | 0 |
| Velvetleaf | 0 | 0 | 0 | 0 | 3 | 0 | 0 | 0 | 0 | 0 | 0 | 0 | 0 | 6 | 0 | 0 | 0 | 0 | 0 | 0 | 0 | 2 | 3 | 0 | 0 | 0 | 0 | 0 | 0 |
| Wheat | 0 | 0 | 0 | 0 | 0 | 0 | 0 | 0 | 0 | 0 | 0 | 0 | 0 | 1 | 0 | 0 | 0 | 0 | 0 | 0 | 0 | 0 | 0 | 0 | 0 | 0 | 0 | 0 | 0 |
| Wild oats | 2 | 2 | 0 | 0 | 4 | 0 | 0 | 0 | 0 | 0 | 0 | 0 | 0 | 5 | 0 | 0 | 0 | 0 | 0 | 0 | 0 | 0 | 3 | 0 | 0 | 0 | 0 | 0 | 0 |

| Rate 62 g/ha | COMPOUND 665 | 666 | 667 | 668 | 669 | 670 | 671 | 672 | 673 | 674 | 675 | 676 | 682 | 683 | 684 | 685 | 686 | 687 | 689 | 691 | 692 | 693 | 694 | 695 | 696 | 699 | 700 | 701 | 702 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| B. signalgrass | 1 | 2 | 3 | 5 | 8 | 8 | 4 | 2 | 4 | 6 | 4 | 0 | 2 | 0 | 0 | 5 | 2 | 6 | 2 | 0 | 2 | 0 | 3 | 0 | 0 | 8 | 4 | 0 | 0 |
| Bedstraw | — | — | — | — | 0 | 8 | — | 0 | 3 | 0 | 0 | — | 0 | 0 | 0 | — | 0 | 0 | 0 | 0 | 0 | 0 | 0 | — | 0 | 0 | 0 | 0 | 0 |
| Blackgrass | 5 | 6 | 8 | 6 | 9 | 8 | 5 | 1 | 3 | 6 | 5 | 0 | 3 | 1 | 1 | 5 | 4 | 8 | 9 | 4 | 8 | 0 | 7 | 0 | 6 | 8 | 4 | 0 | 2 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 2 | 2 | 0 | 0 | 0 | 2 | 0 | 0 | 0 | 0 | 0 | 0 | 0 | 0 | 0 | 0 | 0 | 0 | 1 | 0 | 0 | 3 | 0 | 0 | 0 |
| Crabgrass | 6 | 7 | 8 | 8 | 9 | 10 | 4 | 8 | 4 | 8 | 6 | 0 | 5 | 6 | 3 | 9 | 8 | 4 | 9 | 9 | 9 | 0 | 8 | 8 | 8 | 10 | 10 | 0 | 9 |
| Giant foxtail | 9 | 9 | 10 | 9 | 9 | 10 | 8 | 9 | 9 | 6 | 9 | 8 | 9 | 8 | 7 | 9 | 9 | 6 | 10 | 9 | 9 | 0 | 9 | 8 | 8 | 10 | 10 | 6 | 10 |
| Morningglory | 0 | 0 | 0 | 0 | 0 | 2 | 0 | 0 | 0 | 0 | 0 | 0 | 0 | 0 | 0 | 0 | 0 | 2 | 0 | 0 | 1 | 0 | 0 | 0 | 0 | 2 | 0 | 0 | 0 |
| Nutsedge | 0 | 0 | 0 | 0 | 0 | — | 0 | 0 | 0 | 0 | 0 | 0 | 0 | 0 | 0 | — | 0 | — | 0 | 0 | 0 | — | 0 | 0 | — | 0 | — | 0 | 0 |
| Rape | 4 | 0 | 7 | 0 | 2 | 8 | 0 | 0 | 1 | 0 | 2 | 0 | 0 | 0 | 0 | 0 | 0 | 0 | 0 | 0 | 0 | 0 | 0 | 0 | 0 | 0 | 0 | 0 | 0 |
| Redroot pigweed | 7 | 8 | 10 | 0 | 6 | 9 | 0 | 0 | 6 | 7 | 5 | 4 | 4 | 0 | 0 | 0 | 0 | 8 | 3 | 2 | 7 | 0 | 0 | 0 | 3 | 3 | 0 | 0 | 2 |
| Soybean | 0 | 0 | 0 | 0 | 0 | 0 | 0 | 0 | 0 | 3 | 0 | 0 | 0 | 0 | 0 | 0 | 0 | 0 | 0 | 2 | 0 | 0 | 0 | 0 | 0 | 0 | 0 | 0 | 0 |
| Sugarbeets | 0 | 0 | 5 | 0 | 6 | 8 | 1 | 3 | 0 | 2 | 5 | 2 | 0 | 0 | 0 | 0 | 0 | 4 | 0 | 0 | 0 | 0 | 0 | 0 | 0 | 3 | 0 | 0 | 0 |
| Velvetleaf | 0 | 5 | 6 | 3 | 0 | 6 | 2 | 0 | 0 | 6 | 6 | 4 | 0 | 0 | 0 | 0 | 0 | 2 | 2 | 0 | 0 | 0 | 0 | 0 | 0 | 0 | 0 | 0 | 0 |
| Wheat | 0 | 0 | 2 | 0 | 6 | 7 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 3 | 5 | 4 | 2 | 10 | 7 | 0 | 0 | 5 | 1 | 4 | 0 | 0 | 0 | 0 | 0 | 0 | 7 | 7 | 2 | 0 | 0 | 0 | 0 | 0 | 9 | 4 | 0 | — |

TABLE B-continued

| Rate 62 g/ha | 703 | 704 | 706 | 707 | 708 | 709 | 710 | 711 | 712 | 713 | 714 | 715 | 716 | 717 | 718 | 719 | 720 | 721 | 722 | 725 | 726 | 727 | 728 | 729 | 730 | 732 | 733 | 734 | 735 |
|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | |
| Preemergence | | | | | | | | | | | | | | | | | | | | | | | | | | | | | |
| B. signalgrass | 2 | 2 | 2 | 6 | 0 | 0 | 8 | 2 | 3 | 5 | 7 | 8 | 0 | 4 | 0 | 3 | 8 | 7 | 0 | 0 | 4 | 0 | 5 | 5 | 0 | 0 | 6 | 9 | 7 |
| Bedstraw | 0 | 0 | 0 | 7 | 0 | 0 | 3 | 2 | 0 | 0 | 0 | 0 | 0 | 0 | 0 | 0 | — | 3 | 0 | 0 | 0 | 0 | 0 | 0 | 0 | 0 | 0 | 0 | 0 |
| Blackgrass | 0 | 2 | 8 | 9 | 0 | 0 | 9 | 6 | 3 | 5 | 7 | 9 | 0 | 9 | 8 | 6 | 9 | 9 | 0 | 2 | 7 | 0 | 0 | 6 | 6 | 0 | 4 | 7 | 8 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 5 | 5 | 5 | 5 | 6 | 2 | 10 | 8 | 8 | 10 | 10 | 9 | 0 | 10 | 9 | — | 9 | 9 | 0 | 6 | 9 | 3 | 6 | 7 | 9 | 0 | 2 | 9 | 10 |
| Giant foxtail | 5 | 4 | 6 | 6 | 5 | 2 | 10 | 10 | 10 | 10 | 10 | 10 | 0 | 10 | 10 | — | 9 | 9 | 0 | 7 | 9 | 7 | 4 | 9 | 10 | 0 | 3 | 9 | 9 |
| Morningglory | 0 | 0 | 1 | 3 | 0 | 0 | 0 | 0 | 0 | 0 | 0 | 0 | 0 | 0 | 0 | 0 | 0 | 1 | 0 | 1 | 0 | 0 | 0 | 0 | 0 | 0 | 1 | 2 | 0 |
| Nutsedge | 0 | 0 | 0 | 0 | — | 0 | — | 0 | 0 | 0 | 0 | 0 | 0 | 0 | 0 | 0 | — | 0 | 0 | 0 | 0 | — | 0 | 0 | 0 | 0 | 0 | 0 | 0 |
| Rape | 0 | 0 | 0 | 8 | 0 | 0 | 7 | 1 | 0 | 4 | 2 | 2 | 0 | 0 | 0 | 0 | 6 | 1 | 0 | 0 | 0 | 0 | 0 | 0 | 0 | 0 | 0 | 0 | 1 |
| Redroot pigweed | 0 | 0 | 8 | — | 0 | 0 | 8 | 7 | 6 | 6 | 10 | 8 | 0 | 6 | 0 | 7 | 8 | 9 | 0 | 0 | 0 | 0 | 0 | 7 | 6 | 0 | 0 | 2 | 5 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 0 | 0 | 6 | 0 | 0 | 6 | 5 | 0 | 3 | 2 | 4 | 0 | 0 | 0 | 4 | 4 | 3 | 0 | 0 | 0 | 0 | 0 | 0 | 0 | 0 | 0 | 0 | 0 |
| Velvetleaf | 0 | 0 | 0 | 3 | 0 | 0 | 5 | 4 | 0 | 2 | 6 | 0 | 0 | 0 | 0 | 0 | 1 | 0 | 0 | 0 | 0 | 0 | 0 | 0 | 0 | 0 | 0 | 2 | 0 |
| Wheat | 0 | 0 | 0 | 2 | 0 | 0 | 5 | 2 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 0 | 0 | 4 | 8 | 0 | 0 | 8 | 7 | 0 | 2 | 0 | 9 | 0 | 9 | 2 | 2 | 7 | 6 | 0 | 0 | 1 | 0 | 0 | 2 | 0 | 0 | 2 | 3 | 6 |

| Rate 62 g/ha | 737 | 738 | 739 | 740 | 741 | 742 | 743 | 744 | 745 | 746 | 747 | 748 | 749 | 750 | 751 | 752 | 753 | 754 | 755 | 756 | 757 | 758 | 759 | 760 | 761 | 762 | 763 | 764 | 765 |
|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | |
| Preemergence | | | | | | | | | | | | | | | | | | | | | | | | | | | | | |
| B. signalgrass | 4 | 6 | — | — | 0 | 0 | 0 | 5 | 8 | 7 | 7 | 0 | 0 | 5 | — | — | 2 | 3 | 0 | 0 | 0 | 6 | 3 | 2 | 0 | 0 | 0 | 8 | 5 |
| Bedstraw | 0 | 0 | 0 | 0 | 0 | 0 | 0 | 0 | 0 | 8 | 0 | — | 0 | 0 | — | 0 | 0 | 0 | 0 | 0 | 0 | 0 | 0 | 0 | 0 | 0 | 0 | 0 | 0 |
| Blackgrass | 6 | 8 | 2 | 3 | 0 | 0 | 8 | 6 | 3 | 9 | 8 | 0 | 0 | 7 | 9 | 4 | 5 | 7 | 0 | 0 | 1 | 6 | 4 | 0 | 0 | 0 | 8 | 7 | 7 |
| Cocklebur | 0 | 0 | 0 | 0 | 0 | 0 | 0 | 0 | 0 | — | 0 | 0 | — | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 |
| Crabgrass | 8 | 8 | 2 | 4 | 5 | 0 | 9 | 9 | 7 | 9 | 10 | 9 | 9 | 9 | 10 | 9 | 9 | 8 | 0 | 4 | 6 | 9 | 7 | 2 | 3 | — | 9 | 10 | 9 |
| Giant foxtail | 9 | 8 | 9 | 4 | 0 | 0 | 9 | 9 | 10 | 10 | 10 | 9 | 9 | 9 | 10 | 10 | 9 | 8 | 0 | 7 | 9 | 9 | 9 | 8 | 0 | 5 | 9 | 10 | 9 |
| Morningglory | 1 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | — | 0 | 0 | 0 | 0 | 0 | — | 0 | 0 | 0 | 0 | 0 | 0 | 0 | 0 | 0 | 3 | 0 | — | 0 | 0 | 0 | 0 | 0 | 0 | 0 | 0 | 0 |
| Rape | 0 | 2 | 0 | 0 | 0 | 0 | 5 | 4 | 0 | 2 | 7 | 0 | 0 | 0 | 4 | 0 | 2 | 0 | 0 | 0 | 0 | 0 | 0 | 0 | 0 | 0 | 0 | 0 | 2 |
| Redroot pigweed | 2 | 6 | 2 | 3 | 0 | 0 | 7 | 4 | 7 | 10 | 8 | 4 | 0 | 7 | 10 | 0 | 6 | 8 | 0 | 0 | 0 | 8 | 0 | 7 | 0 | 2 | 8 | 9 | 8 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 1 | 3 | 2 | 0 | 0 | 0 | 0 | 0 | 0 | 5 | 4 | 0 | 0 | 1 | 2 | 0 | 0 | 0 | 0 | 0 | 0 | 5 | 0 | 3 | 0 | 0 | 0 | 0 | 6 |
| Velvetleaf | 0 | 0 | 0 | 0 | 0 | 0 | 0 | 0 | 0 | 4 | 4 | 0 | 0 | 0 | 7 | 0 | 0 | 0 | 0 | 0 | 0 | 2 | 0 | 0 | 0 | 0 | 0 | 3 | 0 |
| Wheat | 0 | 2 | 0 | 0 | 0 | 0 | 0 | 0 | 0 | 6 | 0 | 0 | 0 | 2 | 0 | 0 | 0 | 0 | 0 | 0 | 0 | 4 | 0 | 0 | 0 | 0 | 0 | 0 | 3 |
| Wild oats | 5 | 4 | 0 | 0 | 0 | 0 | 5 | 3 | 2 | 7 | 3 | 0 | 0 | 0 | 3 | 0 | 0 | 0 | 0 | 0 | 0 | 5 | 0 | 0 | 0 | 0 | 2 | 0 | 4 |

TABLE B-continued

| Rate 62 g/ha | COMPOUND 766 | 767 | 772 | 773 | 774 | 776 | 779 | 780 | 790 | 791 | 792 |
|---|---|---|---|---|---|---|---|---|---|---|---|
| Preemergence | | | | | | | | | | | |
| B. signalgrass | 6 | — | 0 | 0 | 0 | — | — | 6 | 8 | 0 | 0 |
| Bedstraw | 4 | — | 0 | 0 | 0 | 0 | 0 | 0 | 0 | — | 0 |
| Blackgrass | 0 | 10 | 0 | 0 | 0 | 0 | 2 | 2 | 8 | 0 | 1 |
| Cocklebur | 0 | 0 | 0 | 0 | 0 | — | 0 | 0 | 0 | 0 | 0 |
| Corn | 0 | 0 | 0 | 0 | 0 | 0 | 0 | 2 | 2 | 0 | 0 |
| Crabgrass | 9 | 10 | 0 | 0 | 0 | 5 | 9 | 10 | 10 | 6 | 10 |
| Giant foxtail | 9 | 10 | 0 | 0 | 0 | 9 | 9 | 10 | 10 | 10 | 10 |
| Morningglory | 2 | 0 | 0 | 0 | 0 | 0 | 0 | 0 | 0 | 0 | 0 |
| Nutsedge | 0 | 0 | 0 | 0 | 0 | 0 | 0 | 0 | 0 | 0 | 0 |
| Rape | 2 | 4 | 0 | 0 | 0 | 0 | 0 | 0 | 2 | 0 | 0 |
| Redroot pigweed | 9 | 10 | 0 | 0 | 0 | 0 | 0 | 0 | 2 | 0 | 7 |
| Soybean | 0 | 0 | 0 | 0 | 0 | 0 | 0 | 0 | 0 | 4 | 0 |
| Sugarbeets | 2 | 2 | 0 | 0 | 0 | 0 | 0 | 2 | 1 | 0 | 0 |
| Velvetleaf | 5 | 0 | 0 | 0 | 0 | 0 | 2 | 0 | 0 | 0 | 0 |
| Wheat | 0 | 0 | 0 | 0 | 0 | 0 | 0 | 0 | 0 | 0 | 0 |
| Wild oats | 3 | 9 | 0 | 0 | 0 | 2 | 0 | 0 | 0 | 0 | 0 |

| Rate 31 g/ha | COMPOUND 196 | 200 | 217 | 221 | 285 | 287 | 288 | 289 | 290 | 291 | 295 | 296 | 318 | 324 | 392 | 442 | 450 | 483 | 614 | 644 | 656 |
|---|---|---|---|---|---|---|---|---|---|---|---|---|---|---|---|---|---|---|---|---|---|
| Pre-emergence | | | | | | | | | | | | | | | | | | | | | |
| Barnyardgrass | 0 | 0 | 0 | 0 | 0 | 0 | 0 | 0 | 6 | 2 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 |
| S. Flatsedge | 0 | 0 | 0 | 0 | 0 | 0 | 0 | 0 | 0 | 0 | 0 | 0 | 0 | 0 | 0 | 0 | 0 | 0 | 0 | 0 | 0 |

| Rate 31 g/ha | COMPOUND 4 | 14 | 22 | 23 | 26 | 27 | 28 | 29 | 30 | 31 | 32 | 33 | 87 | 98 | 100 | 137 | 138 | 139 | 146 | 155 | 156 | 200 | 213 | 217 | 221 | 225 | 244 | 250 | 252 | 256 | 264 | 285 | 287 | 288 |
|---|---|---|---|---|---|---|---|---|---|---|---|---|---|---|---|---|---|---|---|---|---|---|---|---|---|---|---|---|---|---|---|---|---|---|
| Postemergence | | | | | | | | | | | | | | | | | | | | | | | | | | | | | | | | | | |
| B. signalgrass | 0 | — | 0 | 0 | 0 | 0 | 0 | 0 | 0 | 0 | 0 | 0 | — | 0 | 0 | — | — | — | 0 | 0 | 0 | 0 | 0 | 0 | 0 | 0 | 0 | 0 | 0 | 0 | 0 | 0 | 0 | 0 |
| Barnyardgrass | 0 | 0 | 0 | 0 | — | — | — | — | — | — | — | — | 0 | 3 | — | 0 | 0 | 0 | 0 | 0 | 0 | — | — | — | — | — | — | — | — | — | — | — | — | — |
| Bedstraw | 0 | — | 0 | 0 | 0 | 0 | 3 | 0 | 0 | 0 | 0 | 0 | — | 0 | 0 | — | — | — | 0 | 0 | 0 | 0 | 0 | 0 | 2 | — | 0 | 0 | 0 | 0 | 0 | 0 | 0 | 0 |
| Blackgrass | 0 | — | 0 | 0 | 0 | 0 | 0 | 0 | 0 | 0 | 0 | 3 | — | 0 | 0 | — | — | — | 4 | 0 | 0 | 0 | 0 | 0 | 2 | 0 | 0 | 0 | 0 | 0 | 0 | 0 | 8 | 0 |
| Cocklebur | 0 | — | 0 | 0 | 0 | 0 | 0 | 0 | 0 | 0 | 0 | 0 | — | 0 | 0 | — | — | — | 0 | 0 | 0 | 0 | 0 | 0 | 0 | 0 | 0 | 0 | 0 | 0 | 0 | 0 | 0 | 0 |
| Corn | 0 | — | 0 | 0 | 0 | 0 | 0 | 0 | 0 | 0 | 0 | 0 | — | 0 | 0 | — | — | — | 0 | 0 | 0 | 0 | 0 | 0 | 0 | 0 | 0 | 0 | 0 | 0 | 0 | 0 | 0 | 0 |
| Crabgrass | 0 | — | 0 | 0 | 0 | 0 | 1 | 0 | 0 | 0 | 0 | 0 | — | 0 | 0 | — | — | — | 5 | 0 | 0 | 0 | 0 | 0 | 0 | 0 | 0 | 0 | 0 | 0 | 0 | 0 | 2 | 0 |
| Ducksalad | 0 | 0 | 0 | 0 | — | — | — | — | — | — | — | — | 0 | 0 | — | 0 | 0 | 0 | 0 | 0 | 0 | — | — | — | — | — | — | — | — | — | — | — | — | — |
| Giant foxtail | 0 | — | 0 | 0 | 0 | 0 | 1 | 0 | 0 | 0 | 0 | 0 | — | 0 | 0 | — | — | — | 3 | 0 | 0 | 0 | 0 | 0 | 0 | 0 | 0 | 0 | 0 | 0 | 0 | 0 | 2 | 0 |
| Morningglory | 0 | — | 0 | 0 | 0 | 0 | 0 | 0 | 1 | 0 | 6 | 3 | — | 0 | 0 | — | — | — | 2 | 0 | 0 | 0 | 5 | 0 | 0 | 2 | 0 | 4 | 2 | 6 | 6 | 1 | 2 | 3 |
| Nutsedge | 0 | — | 0 | 0 | 0 | 0 | 0 | 0 | 0 | 0 | 0 | 0 | — | 0 | 0 | — | — | — | 0 | 0 | 0 | 0 | 0 | 0 | 0 | 0 | 0 | 0 | 0 | 0 | 0 | 0 | 5 | 0 |
| Rape | 0 | — | 0 | 0 | 0 | 0 | 0 | 0 | 0 | 0 | 0 | 0 | — | 0 | 0 | — | — | — | 0 | 0 | 0 | 0 | 0 | 0 | 0 | 0 | 0 | 0 | 0 | 0 | 0 | 0 | 0 | 0 |

TABLE B-continued

| | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|
| Redroot pigweed | 0 | — | 0 | 0 | 0 | 0 | 0 | 0 | 0 | 0 | 0 | 0 | — | 0 | 0 | — | — | — | 0 | 0 | 0 | 0 | 0 | 0 | 2 | 0 | 0 | 0 | 0 | 0 | 0 | 0 | 0 | 0 |
| Rice | 0 | 0 | 0 | 0 | — | — | — | — | — | — | — | — | 0 | 0 | — | 0 | 0 | 0 | 0 | 0 | 0 | — | — | — | — | — | — | — | — | — | — | — | — | — |
| S. Flatsedge | 0 | 0 | 0 | 0 | — | — | — | — | — | — | — | — | 0 | 0 | — | 0 | 0 | 0 | 0 | 0 | 0 | — | — | — | — | — | — | — | — | — | — | — | — | — |
| Soybean | 1 | — | 3 | 3 | 1 | 1 | 3 | 1 | 1 | 0 | 2 | 2 | — | 1 | 0 | — | — | — | 2 | 1 | 1 | 1 | 1 | 1 | 1 | 1 | 0 | 1 | 1 | 3 | 0 | 0 | 1 | 0 |
| Sugarbeets | 0 | — | 0 | 0 | 0 | 0 | 0 | 0 | 0 | 0 | 0 | 0 | — | 0 | 0 | — | — | — | 0 | 0 | 0 | 0 | 0 | 0 | 0 | 0 | 0 | 0 | 0 | 0 | 0 | 0 | 0 | 0 |
| Velvetleaf | 0 | — | 0 | 0 | 0 | 0 | 0 | 0 | 0 | 0 | 0 | 0 | — | 0 | 0 | — | — | — | 0 | 0 | 0 | 0 | 0 | 0 | 0 | 0 | 0 | 0 | 0 | 0 | 0 | 0 | 0 | 0 |
| Wheat | 0 | — | 0 | 0 | 0 | 0 | 0 | 0 | 0 | 0 | 0 | 0 | — | 0 | 0 | — | — | — | 0 | 0 | 0 | 0 | 0 | 0 | 0 | 0 | 0 | 0 | 0 | 0 | 0 | 0 | 2 | 0 |
| Wild oats | 0 | — | 0 | 0 | 0 | 0 | 0 | 0 | 0 | 0 | 0 | 0 | — | 0 | 0 | — | — | — | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | |
|---|---|---|---|---|---|---|---|---|---|---|---|---|---|---|---|---|---|---|---|---|---|
| Rate 31 g/ha | 289 | 290 | 291 | 295 | 296 | 318 | 324 | 362 | 392 | 442 | 450 | 481 | 483 | 518 | 548 | 614 | 644 | 656 | 722 | 776 | 779 |
| Postemergence | | | | | | | | | | | | | | | | | | | | | |
| B. signalgrass | 0 | 0 | 0 | 0 | 0 | 0 | 0 | 1 | 0 | 0 | 0 | 0 | 0 | 3 | 0 | 0 | 0 | 0 | 0 | 0 | 2 |
| Barnyardgrass | — | — | — | — | — | — | — | — | — | — | — | — | — | — | — | — | — | — | — | — | — |
| Bedstraw | 0 | 0 | 0 | 0 | 0 | 0 | 0 | 5 | — | 0 | 0 | — | — | — | 0 | — | — | — | — | 0 | 0 |
| Blackgrass | 2 | 0 | 0 | 0 | 0 | 0 | 0 | 8 | 7 | 0 | 0 | 0 | 0 | 4 | 0 | 0 | 0 | 6 | 0 | 2 | 0 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 0 | 0 | 0 | 0 | 3 | 1 | 0 | 0 | 0 | 0 | 0 | 0 | 0 | 0 | 0 | 0 | 2 | 3 |
| Ducksalad | — | — | — | — | — | — | — | — | — | — | — | — | — | — | — | — | — | — | — | — | — |
| Giant foxtail | 2 | 0 | 0 | 0 | 0 | 0 | 0 | 5 | 7 | 0 | 0 | 0 | 0 | 0 | 0 | 0 | 0 | 0 | 0 | 2 | 5 |
| Morningglory | 2 | 4 | 1 | 1 | 0 | 0 | 0 | 0 | 3 | 1 | 0 | 0 | 0 | 5 | 1 | 0 | 0 | 0 | 3 | 4 | 5 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 |
| Redroot pigweed | 0 | 0 | 0 | 0 | 0 | 0 | 0 | 0 | 0 | 0 | 0 | 0 | 0 | 0 | 0 | 0 | 2 | 0 | 0 | 0 | 2 |
| Rice | — | — | — | — | — | — | — | — | — | — | — | — | — | — | — | — | — | — | — | — | — |
| S. Flatsedge | — | — | — | — | — | — | — | — | — | — | — | — | — | — | — | — | — | — | — | — | — |
| Soybean | 0 | 1 | 1 | 1 | 0 | 0 | 0 | 4 | 1 | 0 | 0 | 4 | 0 | 4 | 1 | 2 | 0 | 1 | 0 | 1 | 2 |
| Sugarbeets | 0 | 0 | 0 | 0 | 0 | 0 | 0 | 0 | 0 | 0 | 0 | 0 | 0 | 0 | 0 | 0 | 0 | 0 | 0 | 0 | 2 |
| Velvetleaf | 0 | 0 | 0 | 0 | 0 | 0 | 0 | 0 | 0 | 0 | 0 | 0 | 0 | — | 0 | 0 | 0 | 0 | 0 | 2 | 2 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 0 | 0 | 0 | 0 | 0 | 0 | 0 | 0 | 0 | 0 | 0 | 0 | 0 | 0 | 0 | 0 | 0 | 0 | 2 | 0 | 0 |

| | COMPOUND | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|
| Rate 31 g/ha | 4 | 22 | 23 | 26 | 27 | 28 | 29 | 30 | 31 | 32 | 33 | 98 | 100 | 146 | 155 | 156 | 200 | 213 | 217 | 221 | 225 | 244 | 250 | 252 | 256 | 264 | 285 | 287 | 288 | 289 | 290 | 291 | 295 |
| Preemergence | | | | | | | | | | | | | | | | | | | | | | | | | | | | | | | | | |
| B. signalgrass | 0 | 0 | 0 | 0 | 0 | 0 | 0 | 0 | 0 | 0 | 0 | 0 | 0 | 7 | 0 | 0 | 0 | 0 | 0 | 2 | 0 | 0 | 0 | 0 | 0 | 0 | 0 | 3 | 0 | 2 | 0 | 0 | 3 |
| Bedstraw | 0 | 0 | 0 | 0 | 0 | 0 | 0 | 0 | 0 | 0 | 0 | 0 | — | 0 | 0 | 0 | 0 | 0 | 0 | 0 | — | 0 | 0 | 0 | 0 | 0 | 0 | 4 | 0 | 0 | 0 | 0 | 0 |
| Blackgrass | 0 | 0 | 0 | 0 | 0 | 0 | 0 | 0 | 0 | 0 | 0 | 0 | 0 | 7 | 0 | 0 | 0 | 0 | 0 | 5 | 0 | 0 | 0 | 0 | 0 | 0 | 0 | 7 | 0 | 6 | 0 | 0 | 4 |
| Cocklebur | 0 | 0 | 0 | 0 | 0 | 0 | 0 | 0 | 0 | 0 | 0 | 0 | 0 | 0 | 0 | 0 | 0 | — | 0 | — | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 3 | 3 | 0 | 0 | 0 | 2 | 0 | 2 | 2 | 0 | 3 | 2 | 0 | 5 | 0 | 0 | 0 | 0 | 0 | 2 | 2 | 0 | 0 | 0 | 0 | 0 | 0 | 2 | 0 | 1 | 0 | 0 | 2 |
| Giant foxtail | 8 | 3 | 1 | 0 | 0 | 0 | 0 | 2 | 1 | 1 | 3 | 4 | 0 | 9 | 0 | 0 | 0 | 0 | 3 | 5 | 8 | 0 | 7 | 3 | 0 | 0 | 7 | 9 | 0 | 9 | 2 | 8 | 8 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | 0 | 0 | 0 | 0 | 0 | 0 | 0 | 0 | 0 | — | 0 | 0 | 0 | 0 | — | — | — | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 4 | 0 | 0 | 0 | 0 | 0 |

TABLE B-continued

| | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|
| Redroot pigweed | 0 | 0 | 0 | 0 | 0 | 0 | 0 | 0 | 0 | 0 | 0 | 0 | 0 | 10 | 0 | 0 | 0 | 0 | 0 | 7 | 6 | 0 | 0 | 0 | 0 | 0 | 0 | 4 | 0 | 5 | 0 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 0 | 0 | 0 | 0 | 0 | 0 | 0 | 0 | 0 | 0 | 0 | 0 | 5 | 0 | 0 | 0 | 0 | 0 | 0 | 0 | 0 | 0 | 0 | 0 | 0 | 0 | 0 | 0 | 0 | 0 | 0 | 0 |
| Velvetleaf | 0 | 0 | 0 | 0 | 0 | 0 | 0 | 0 | 0 | 0 | 0 | 0 | 0 | 3 | 0 | 0 | 0 | 0 | 0 | 0 | 0 | 0 | 0 | 0 | 0 | 0 | 0 | 3 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oats | 0 | 0 | 0 | 0 | 0 | 0 | 0 | 0 | 0 | 0 | 0 | 0 | 0 | 1 | 0 | 0 | 0 | 0 | 0 | 2 | 0 | 0 | 0 | 0 | 0 | 0 | 0 | 1 | 0 | 0 | 0 | 0 | 0 |

| | COMPOUND | | | | | | | | | | | | | | | | | | |
|---|---|---|---|---|---|---|---|---|---|---|---|---|---|---|---|---|---|---|---|
| Rate 31 g/ha | 296 | 318 | 324 | 362 | 392 | 442 | 450 | 481 | 483 | 518 | 548 | 614 | 644 | 656 | 716 | 722 | 727 | 776 | 779 |
| Preemergence | | | | | | | | | | | | | | | | | | | |
| B. signalgrass | 0 | 0 | 0 | 2 | 0 | 0 | 0 | 7 | 0 | 0 | 0 | 0 | 0 | 0 | 0 | 0 | 0 | — | — |
| Bedstraw | 0 | — | 0 | 8 | 0 | — | — | 0 | 0 | 0 | 9 | 0 | — | — | 0 | 0 | 0 | 0 | 0 |
| Blackgrass | 0 | 0 | 0 | 8 | 2 | 0 | 0 | 3 | 0 | 4 | 0 | 0 | 0 | 2 | 0 | 0 | 0 | 0 | 0 |
| Cocklebur | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | — | 8 | 5 | 0 | 7 | 0 | 0 | 4 | 0 | 2 | 6 | 0 | 0 | 3 | 5 | 8 |
| Giant foxtail | 0 | 0 | 0 | — | 10 | 0 | 0 | 8 | 0 | 0 | 9 | 0 | 0 | 4 | 0 | 0 | 5 | 5 | 9 |
| Morningglory | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 |
| Redroot pigweed | 0 | 0 | 0 | 3 | 0 | 0 | 0 | 0 | 0 | 2 | 0 | 0 | 0 | 0 | 0 | 0 | 0 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 |
| Sugarbeets | 0 | 0 | 0 | 3 | 0 | 0 | 0 | 0 | 0 | 0 | 0 | 0 | 0 | 0 | 0 | 0 | 0 | 0 | 0 |
| Velvetleaf | 0 | 0 | 0 | 2 | 0 | 0 | 0 | 0 | 0 | 0 | 0 | 0 | 0 | 0 | 0 | 0 | 0 | 0 | 0 |
| Wheat | 0 | 0 | 0 | 4 | 0 | 0 | 0 | 0 | 0 | 0 | 0 | 0 | 0 | 0 | 0 | 0 | 0 | 0 | 0 |
| Wild oats | 0 | 0 | 0 | 7 | 2 | 0 | 0 | 4 | 0 | 4 | 0 | 0 | 0 | 0 | 0 | 0 | 0 | 2 | 0 |

| | COMPOUND | | |
|---|---|---|---|
| Rate 16 g/ha | 287 | 290 | 291 |
| Pre-emergence | | | |
| Barnyardgrass | 0 | 0 | 0 |
| Ducksalad | 0 | 0 | 0 |
| Rice | 0 | 0 | 0 |
| S. Flatsedge | 0 | 0 | 0 |

| | COMPOUND | | | |
|---|---|---|---|---|
| Rate 16 g/ha | 287 | 290 | 291 | 779 |
| Postemergence | | | | |
| B. signalgrass | 0 | 0 | 0 | 0 |
| Barnyardgrass | — | — | — | — |
| Bedstraw | 0 | 0 | 0 | 0 |
| Blackgrass | 0 | 0 | 0 | 0 |
| Cocklebur | 0 | 0 | 0 | 0 |

TABLE B-continued

| | | | | |
|---|---|---|---|---|
| Corn | 0 | 0 | 0 | 0 |
| Crabgrass | 0 | 0 | 0 | 2 |
| Ducksalad | — | — | — | — |
| Giant foxtail | 0 | 0 | 0 | 2 |
| Morningglory | 2 | 3 | 1 | 5 |
| Nutsedge | 0 | 0 | 0 | 0 |
| Rape | 0 | 0 | 0 | 0 |
| Redroot pigweed | 0 | 0 | 0 | 2 |
| Rice | — | — | — | — |
| S. Flatsedge | — | — | — | — |
| Soybean | 1 | 1 | 1 | 2 |
| Sugarbeets | 0 | 0 | 0 | 2 |
| Velvetleaf | 0 | 0 | 0 | 2 |
| Wheat | 0 | 0 | 0 | 0 |
| Wild oats | 0 | 0 | 0 | 0 |

| | COMPOUND | | | |
|---|---|---|---|---|
| Rate 16 g/ha | 287 | 290 | 291 | 779 |
| Preemergence | | | | |
| B. signalgrass | 0 | 0 | 0 | — |
| Bedstraw | 0 | 0 | 0 | 0 |
| Blackgrass | 0 | 0 | 0 | 0 |
| Cocklebur | 0 | 0 | 0 | 0 |
| Corn | 0 | 0 | 0 | 0 |
| Crabgrass | 0 | 0 | 0 | 3 |
| Giant foxtail | 8 | 2 | 7 | 3 |
| Morningglory | 0 | 0 | 0 | 0 |
| Nutsedge | 0 | 0 | 0 | 0 |
| Rape | 0 | 0 | 0 | 0 |
| Redroot pigweed | 0 | 0 | 0 | 0 |
| Soybean | 0 | 0 | 0 | 0 |
| Sugarbeets | 0 | 0 | 0 | 0 |
| Velvetleaf | 1 | 0 | 0 | 0 |
| Wheat | 0 | 0 | 0 | 0 |
| Wild oats | 0 | 0 | 0 | 0 |

Test C

Compounds evaluated in this test were formulated in a non-phytotoxic solvent mixture which included a surfactant and applied to plants that were grown for various periods of time before treatment (postemergence application). A mixture of sandy loam soil and greenhouse potting mix in a 60:40 ratio was used for the postemergence test.

Plantings of these crops and weed species were adjusted to produce plants of appropriate size for the postemergence test. All plant species were grown using normal greenhouse practices. Crop and weed species include arrowleaf sida (*Sida rhombifolia*), barnyardgrass (*Echinochloa crus-galli*), cocklebur (*Xanthium strumarium*), common ragweed (*Ambrosia elatior*), corn (*Zea mays*), cotton (*Gossypium hirsutum*), eastern black nightshade (*Solanum ptycanthum*), fall panicum (*Panicum dichotomiflorum*), field bindweed (*Convolvulus arvensis*), giant foxtail (*Setaria faberii*), hairy beggarticks (*Bidens pilosa*), ivyleaf morningglory (*Ipomoea hederacea*), johnsongrass (*Sorghum halepense*), ladysthumb smartweed (*Polygonum persicaria*), lambsquarters (*Chenopodium album*), large crabgrass (*Digitaria sanguinalis*), purple nutsedge (*Cyperus rotundus*), redroot pigweed (*Amaranthus retroflexus*), soybean (*Glycine max*), surinam grass (*Brachiaria decumbens*), velvetleaf (*Abutilon theophrasti*) and wild poinsettia (*Euphorbia heterophylla*).

Treated plants and untreated controls were maintained in a greenhouse for approximately 14, to 21 days, after which all treated plants were compared to untreated controls and visually evaluated. Plant response ratings, summarized in Table C, were based upon a 0 to 100 scale where 0 was no effect and 100 was complete control. A dash response (–) means no test result.

TABLE C

| | COMPOUND | | | | | | | | | | | | | |
|---|---|---|---|---|---|---|---|---|---|---|---|---|---|---|
| | 80 | 93 | 94 | 103 | 107 | 109 | 113 | 116 | 117 | 131 | 132 | 138 | 146 | 242 |
| Rate 1120 g/ha Postemergence | | | | | | | | | | | | | | |
| Arrowleaf sida | 30 | 60 | 80 | — | 85 | 95 | 95 | 90 | 50 | 60 | 80 | 70 | 90 | 90 |
| Barnyardgrass | 20 | 95 | 65 | 80 | 95 | 95 | 95 | 90 | 90 | 95 | 95 | 85 | 95 | 95 |
| Cocklebur | 50 | — | — | 0 | — | — | 50 | 50 | 0 | 10 | 0 | 0 | 70 | 20 |
| Common ragweed | 5 | 20 | 5 | 5 | 50 | 20 | 20 | 0 | 50 | 0 | 0 | — | 30 | 80 |
| Corn | 0 | 45 | 0 | 0 | 60 | 55 | 60 | 20 | 85 | 40 | 10 | 60 | 50 | 20 |
| Cotton | 40 | 85 | 80 | 80 | 90 | 70 | 80 | — | 60 | 65 | 40 | 70 | 70 | 70 |
| E. blacknightsh | 60 | 85 | 95 | 0 | 95 | 95 | 95 | 50 | 80 | 80 | 0 | 70 | 85 | 90 |
| Fall panicum | 10 | 90 | 70 | 30 | 85 | 95 | 85 | 90 | 80 | 90 | 50 | 90 | 90 | 90 |
| Field bindweed | 0 | 50 | 0 | 0 | 60 | 10 | 50 | 50 | 40 | 60 | 70 | 50 | 0 | 0 |
| Giant foxtail | 20 | 95 | 40 | 40 | 95 | 85 | 80 | 85 | 80 | 80 | 0 | 85 | 85 | 85 |
| H. beggarticks | 10 | 70 | 20 | 5 | 95 | 85 | 50 | — | 0 | 70 | — | 80 | 85 | 90 |
| I. morningglory | 50 | 70 | — | 10 | 95 | 70 | 50 | 20 | 0 | 50 | 0 | 0 | 50 | 0 |
| Johnsongrass | 0 | 90 | 0 | 0 | 90 | 95 | 95 | 80 | 85 | 70 | 60 | 90 | 90 | 90 |
| Ladysthumb | 70 | — | 90 | 10 | — | 95 | 85 | — | — | — | — | — | — | — |
| Lambsquarters | 20 | 40 | 30 | 20 | 40 | 70 | 50 | 0 | 0 | 0 | 0 | 20 | 50 | 0 |
| Large crabgrass | 10 | 95 | — | 10 | 95 | 90 | 95 | 90 | 80 | 85 | 80 | 85 | 80 | 85 |
| Purple nutsedge | 0 | 10 | 0 | 0 | 10 | 0 | 10 | 10 | 80 | 80 | 0 | 70 | 0 | 80 |
| Redroot pigweed | 80 | 85 | 0 | 85 | 80 | 85 | 90 | 20 | 30 | 30 | 30 | 70 | 20 | 50 |
| Soybean | — | 85 | 55 | 35 | 85 | 85 | 85 | 40 | 60 | 45 | 40 | 40 | 85 | 65 |
| Surinam grass | 10 | 85 | 10 | 5 | 95 | 95 | 90 | 90 | 90 | 90 | 30 | 90 | 95 | 90 |
| Velvetleaf | 20 | 70 | 40 | 45 | 75 | 75 | 75 | 80 | 60 | 70 | 0 | 80 | 60 | 60 |
| Wild poinsettia | 5 | 70 | 85 | 60 | 80 | 90 | 95 | — | 0 | 80 | 0 | 70 | 70 | 85 |
| Rate 560 g/ha Postemergence | | | | | | | | | | | | | | |
| Arrowleaf sida | — | 60 | 80 | 0 | 75 | 85 | 70 | 85 | 0 | 30 | 10 | — | 85 | 70 |
| Barnyardgrass | 20 | 90 | 30 | 10 | 90 | 85 | 85 | 90 | 90 | 95 | 80 | 85 | 85 | 90 |
| Cocklebur | 50 | 40 | — | 0 | — | 60 | 50 | 0 | 0 | 0 | 0 | 0 | 70 | 0 |
| Common ragweed | 5 | 10 | 5 | 0 | 50 | 10 | — | 0 | 20 | 0 | 0 | 0 | 30 | 80 |
| Corn | 0 | 0 | 0 | 0 | 55 | 5 | 45 | 15 | 40 | 5 | 0 | 50 | 5 | 0 |
| Cotton | 40 | 70 | 70 | 40 | 80 | 70 | 50 | 50 | 30 | 40 | 20 | 40 | 65 | 45 |
| E. blacknightsh | 50 | — | 75 | 0 | 70 | — | — | 10 | 70 | 50 | 0 | 70 | 85 | 60 |
| Fall panicum | 0 | 90 | 10 | 0 | 85 | 80 | 85 | 85 | 40 | 90 | 50 | 60 | 90 | 90 |
| Field bindweed | 0 | 0 | 0 | 0 | 30 | 10 | 50 | 50 | 30 | 0 | 40 | 0 | 0 | 0 |
| Giant foxtail | 0 | 80 | 10 | 0 | 95 | 80 | 80 | 60 | 75 | 60 | 0 | 80 | 80 | 80 |
| H. beggarticks | 10 | 5 | 5 | 0 | 70 | 70 | 30 | 90 | — | 40 | — | — | 85 | — |
| I. morningglory | 30 | 10 | 90 | 0 | 30 | 50 | 50 | 0 | 0 | 20 | 0 | 0 | 20 | 0 |
| Johnsongrass | 0 | 85 | 0 | 0 | 90 | 60 | 60 | 60 | 40 | 60 | 0 | 60 | 60 | 60 |
| Ladysthumb | 70 | 80 | 85 | 10 | 30 | 30 | 85 | — | — | — | — | — | 85 | — |
| Lambsquarters | 20 | 10 | 10 | 5 | 40 | 30 | 20 | 0 | 0 | — | 0 | 10 | 10 | 0 |
| Large crabgrass | 10 | 50 | 70 | 0 | 95 | 90 | 95 | 30 | 60 | 70 | 40 | 85 | 60 | 85 |
| Purple nutsedge | 0 | 0 | 0 | 0 | 10 | 0 | 0 | 10 | 10 | 0 | 0 | 50 | 0 | 10 |
| Redroot pigweed | 50 | 10 | 0 | 70 | 80 | 70 | 0 | 0 | 0 | 20 | — | 40 | — | 10 |
| Soybean | 60 | 80 | 30 | 35 | 85 | 85 | 85 | 30 | 40 | 30 | 30 | 30 | 60 | 25 |
| Surinam grass | 0 | 50 | 0 | 0 | 80 | 50 | 90 | — | 40 | 85 | 0 | 85 | 50 | 85 |
| Velvetleaf | 20 | 40 | 20 | 10 | 70 | 50 | 60 | 40 | 20 | 10 | 0 | 70 | 40 | 40 |
| Wild poinsettia | 5 | 30 | 60 | 10 | 40 | 50 | 80 | 0 | 0 | 30 | 0 | 0 | 50 | 0 |
| Rate 280 g/ha | | | | | | | | | | | | | | |

TABLE C-continued

| | COMPOUND | | | | | | | | | | | | | |
|---|---|---|---|---|---|---|---|---|---|---|---|---|---|---|
| | 80 | 93 | 94 | 103 | 107 | 109 | 113 | 116 | 117 | 131 | 132 | 138 | 146 | 242 |
| Postemergence | | | | | | | | | | | | | | |
| Arrowleaf sida | 5 | 10 | 10 | 0 | 30 | 70 | 40 | — | 0 | 10 | 0 | — | 45 | 30 |
| Barnyardgrass | 10 | 90 | 0 | 0 | 85 | 85 | 80 | 85 | 80 | 70 | 50 | 70 | 80 | 85 |
| Cocklebur | 10 | 35 | 0 | 0 | 50 | 30 | 50 | — | 0 | 0 | 0 | 0 | 40 | 0 |
| Common ragweed | 0 | 10 | 0 | 0 | 50 | 10 | 5 | 0 | 0 | 0 | 0 | 0 | — | 10 |
| Corn | 0 | 0 | 0 | 0 | 5 | 0 | 40 | 0 | 0 | 0 | 0 | 20 | 0 | 0 |
| Cotton | 35 | 30 | 70 | 20 | 60 | 50 | 15 | 50 | 10 | 10 | 10 | 30 | 65 | 20 |
| E. blacknightsh | 5 | 40 | 40 | 0 | 50 | 80 | 50 | 0 | 0 | 10 | 0 | 10 | 30 | 40 |
| Fall panicum | 0 | 80 | 0 | 0 | 60 | 50 | 80 | 60 | — | 40 | 30 | 0 | 60 | 85 |
| Field bindweed | 0 | 0 | 0 | 0 | 0 | 0 | 0 | 0 | 30 | 0 | 0 | 0 | 0 | — |
| Giant foxtail | 0 | 55 | 0 | 0 | 70 | 80 | 70 | 60 | 60 | 40 | 0 | 15 | 40 | 60 |
| H. beggarticks | — | 0 | 0 | 0 | 60 | 5 | 30 | — | — | — | 0 | 10 | 20 | — |
| I. morningglory | 10 | 10 | 10 | 0 | 30 | 50 | 50 | 0 | 0 | 0 | 0 | 0 | 20 | 0 |
| Johnsongrass | 0 | 5 | 0 | 0 | 50 | 10 | 20 | 40 | 35 | 40 | 0 | 20 | 30 | 45 |
| Ladysthumb | 10 | 0 | 10 | 0 | — | 10 | 0 | — | — | — | — | — | 10 | — |
| Lambsquarters | 15 | 10 | 5 | 5 | 0 | 10 | — | — | 0 | 0 | 0 | 0 | 5 | 0 |
| Large crabgrass | 0 | 30 | 0 | 0 | 85 | 60 | 85 | 0 | 20 | 20 | 10 | 10 | 60 | 30 |
| Purple nutsedge | 0 | 0 | 0 | 0 | 0 | 0 | 10 | 0 | 0 | 0 | 0 | 0 | 0 | 0 |
| Redroot pigweed | 0 | — | — | 60 | 75 | 40 | 0 | 0 | 0 | 10 | 10 | 10 | — | 0 |
| Soybean | 20 | 60 | 15 | 30 | 70 | 70 | 70 | 10 | 35 | 25 | 20 | 30 | 50 | 25 |
| Surinam grass | 0 | 45 | 0 | 0 | 70 | 5 | 40 | 0 | 0 | 80 | 0 | 40 | 5 | 40 |
| Velvetleaf | 5 | 5 | 5 | 5 | 60 | 20 | 0 | 0 | — | 0 | 0 | 60 | 40 | 0 |
| Wild poinsettia | 0 | 0 | 0 | 0 | 15 | 30 | 50 | 0 | 0 | 10 | 0 | 0 | 40 | 0 |
| Rate 140 g/ha | | | | | | | | | | | | | | |
| Postemergence | | | | | | | | | | | | | | |
| Arrowleaf sida | 0 | — | — | 0 | — | 60 | 30 | 0 | 0 | — | 0 | 0 | 40 | 10 |
| Barnyardgrass | 0 | 70 | 0 | 0 | 70 | 60 | 80 | 55 | 70 | 70 | 50 | 40 | 60 | 80 |
| Cocklebur | 5 | 0 | 0 | 0 | 0 | 30 | 5 | 0 | 0 | 0 | 0 | 0 | 40 | 0 |
| Common ragweed | 0 | 5 | 0 | 0 | 0 | 5 | 5 | 0 | 0 | 0 | 0 | 0 | 10 | 0 |
| Corn | 0 | 0 | 0 | 0 | 0 | 0 | 0 | 0 | 0 | 0 | 0 | — | 0 | 0 |
| Cotton | 20 | 15 | 20 | 0 | 45 | 10 | 10 | 10 | 5 | 10 | 5 | 5 | 40 | 0 |
| E. blacknightsh | 0 | 10 | 0 | 0 | 50 | 50 | 50 | 0 | 0 | 0 | 0 | 0 | 0 | 0 |
| Fall panicum | 0 | 0 | 0 | 0 | 50 | 50 | 60 | 10 | 0 | 0 | 0 | 0 | 50 | 30 |
| Field bindweed | 0 | 0 | 0 | 0 | 0 | 0 | 0 | 0 | 0 | 0 | 0 | 0 | 0 | 0 |
| Giant foxtail | 0 | 10 | 0 | 0 | — | 50 | 20 | — | 0 | 10 | 0 | 0 | 0 | 40 |
| H. beggarticks | 0 | — | 0 | 0 | 5 | — | 5 | 80 | — | 0 | 0 | — | 10 | — |
| I. morningglory | 0 | 5 | 0 | 0 | 10 | 0 | 10 | 0 | 0 | 0 | 0 | 0 | 0 | 0 |
| Johnsongrass | 0 | 0 | 0 | 0 | 35 | 0 | 0 | 10 | 10 | 15 | 0 | 0 | 0 | 45 |
| Ladysthumb | 10 | 0 | 5 | 0 | 0 | — | 0 | — | — | — | — | — | 0 | — |
| Lambsquarters | 0 | 10 | 0 | 0 | 0 | 10 | 0 | 0 | 0 | 0 | 0 | 0 | 0 | 0 |
| Large crabgrass | 0 | 0 | 0 | 0 | 70 | 10 | 0 | 0 | 0 | 0 | 0 | 0 | 0 | 10 |
| Purple nutsedge | 0 | 0 | 0 | 0 | 0 | 0 | 0 | 0 | 0 | 0 | 0 | 0 | 0 | 0 |
| Redroot pigweed | — | 5 | — | 0 | — | 0 | 0 | 0 | 0 | 10 | 0 | 0 | 0 | 0 |
| Soybean | 5 | 40 | 15 | 30 | 45 | 35 | 40 | 10 | 10 | 20 | 5 | 10 | 40 | 20 |
| Surinam grass | 0 | 0 | 0 | 0 | 10 | 0 | 0 | 0 | 0 | 0 | 0 | 10 | 0 | 0 |
| Velvetleaf | 5 | 0 | 5 | 0 | 5 | 10 | 0 | 0 | 0 | 0 | 0 | 0 | 0 | 0 |
| Wild poinsettia | 0 | 0 | 0 | 0 | 0 | 10 | 10 | 0 | 0 | 0 | 0 | 0 | 0 | 0 |

Test D

Seeds, tubers, or plant parts of Alexandergrass (*Brachiaria plantaginea*), bermuda-grass (*Cynodon dactylon*), common pursiane (*Portulaca oleracea*), common ragweed (*Ambrosia elatior*), common groundsel (*Senecio vulgaris*), dallisgrass (*Paspalum dilatatum*), goosegrass (*Eleusine indica*), guineagrass (*Panicum maximum*), itchgrass (*Rottboellia exaltata*), Johnson grass (*Sorghum halepense*), large crabgrass (*Digitaria sanguinalis*), pitted morningglory (*Ipomoea lacunosa*), purple nutsedge (*Cyperus rotundus*), sandbur (*Cenchrus echinatus*), sourgrass (*Trichachne insularis*), Spanishneedles (*Bidens bipinnata*), surinam grass (*Brachiaria decumbens*) and tall mallow (*Malva sylvestris*) were planted into greenhouse pots of flats containing greenhouse planting medium. Plant species were grown in separate pots or individual compartments. Preemergence applications were made within one day of planting the seed or plant part.

Test chemicals were formulated in a non-phytotoxic solvent mixture which included a surfactant and applied preemergence to the surface of the pot containing seeds in a sandy loam soil. Untreated control pots and treated pots were placed in the greenhouse for growth and visually evaluated for injury 14 to 21 days after herbicide application. Plant response ratings, summarized in Table C, are based on a 0 to 100 scale where 0 is no injury and 100 is complete control. A dash (–) response means no test result.

TABLE D

| Rate 500 g/ha | COMPOUND 146 | 147 | 299 |
|---|---|---|---|
| Postemergence | | | |
| Alexandergrass | 65 | 75 | 100 |
| Bermudagrass | 35 | 40 | 100 |
| C. purslane | 20 | 10 | 0 |
| C. ragweed | 40 | 0 | 100 |
| Com. groundsel | 0 | 0 | 100 |
| Dallisgrass | 80 | 85 | 100 |
| Goosegrass | 80 | 65 | 100 |
| Green foxtail | — | — | 100 |
| Guineagrass | 60 | 60 | 100 |
| Itchgrass | 65 | 65 | 100 |
| Johnsongrass | 65 | 70 | 100 |
| Large crabgrass | 65 | 60 | 100 |
| P. morninglory | 65 | 30 | 0 |
| Purple nutsedge | 35 | 60 | 100 |
| Sandbur | 80 | 90 | 100 |
| Sourgrass | 80 | 80 | — |
| Spanishneedles | 20 | 20 | 100 |
| Surinam grass | 80 | 70 | 100 |
| Tall Mallow | 50 | 20 | 100 |

| Rate 500 g/ha | 4 | 24 | 30 | 36 | 46 | 78 | 93 | 94 | 103 | 105 | 107 | 108 | 109 | 110 | 112 | 115 | 117 | 131 | 138 | 146 | 147 | 151 | 170 | 242 |
|---|---|---|---|---|---|---|---|---|---|---|---|---|---|---|---|---|---|---|---|---|---|---|---|---|
| Preemergence | | | | | | | | | | | | | | | | | | | | | | | | |
| Alexandergrass | 100 | 98 | 90 | 98 | 80 | 100 | 100 | 80 | 95 | 100 | 100 | 100 | 100 | 100 | 100 | 100 | 98 | 100 | 100 | 100 | 100 | 100 | 100 | 100 |
| Bermudagrass | 98 | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 |
| C. purslane | 0 | 0 | 0 | 0 | 0 | 0 | 0 | 0 | 0 | 0 | 0 | 0 | 0 | 0 | 0 | 0 | 0 | 10 | 100 | 0 | 0 | 0 | 10 | 0 |
| C. ragweed | 0 | 0 | 0 | 10 | 0 | 0 | 80 | 10 | 0 | 0 | 100 | 80 | 55 | 0 | 0 | 20 | 65 | 100 | 100 | 75 | 0 | 20 | 45 | 100 |
| Com. groundsel | — | 0 | 100 | 100 | 0 | 0 | 100 | 100 | 0 | 80 | 100 | 100 | 0 | 20 | 10 | 98 | 100 | 100 | 100 | 100 | 0 | 100 | 100 | — |
| Dallisgrass | 98 | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 |
| Goosegrass | 100 | 100 | 98 | 100 | 100 | 100 | 100 | 100 | 100 | 100 | 100 | 100 | 100 | 100 | 100 | 100 | 100 | 100 | 100 | 100 | 100 | 100 | 100 | 100 |
| Green foxtail | — | — | 100 | 100 | 100 | 100 | 100 | 100 | 100 | 100 | 100 | 100 | 100 | 100 | 0 | 100 | 100 | 100 | 100 | 100 | — | 100 | 100 | 100 |
| Guineagrass | 100 | 100 | 98 | 100 | 85 | 100 | 100 | 100 | 100 | 100 | 100 | 100 | 100 | 100 | 100 | 100 | 100 | 100 | 100 | 100 | 100 | 100 | 100 | 100 |
| Itchgrass | 80 | 40 | — | 80 | 10 | 20 | 100 | 40 | 0 | 85 | 100 | 100 | 100 | 40 | 80 | 50 | 100 | 100 | 100 | 100 | 85 | 100 | 50 | 100 |
| Johnsongrass | 30 | 85 | 40 | 0 | 60 | 20 | 85 | 20 | 40 | 90 | 100 | 85 | 100 | 45 | 50 | 90 | 100 | 100 | 100 | 95 | 95 | 100 | 95 | 100 |
| Large crabgrass | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 |
| P. morninglory | 0 | 0 | 0 | 0 | 0 | 0 | 20 | 0 | 0 | 0 | 100 | 0 | 100 | 0 | 10 | 10 | 40 | 100 | 65 | 20 | 30 | 20 | 85 | 100 |
| Purple nutsedge | 0 | 0 | 0 | 0 | 0 | 0 | 100 | 50 | 10 | 75 | 85 | 30 | 85 | 0 | 40 | 0 | 100 | 85 | 80 | 100 | 85 | 70 | 65 | 60 |
| Sandbur | 100 | 100 | 100 | 100 | 0 | 80 | 100 | 100 | 100 | 100 | 100 | 100 | 100 | 98 | 100 | 100 | 100 | 100 | 100 | 100 | 80 | 100 | 98 | 100 |
| Sourgrass | 100 | 100 | — | — | — | — | — | — | — | — | — | — | — | — | — | — | — | — | 100 | 100 | — | — | — | |
| Spanishneedles | 0 | 0 | 0 | 10 | 20 | 0 | 45 | 0 | 20 | 0 | 100 | 20 | 30 | 0 | 10 | 10 | 0 | 90 | 75 | 100 | 30 | 40 | 85 | 40 |
| Surinam grass | 98 | 65 | 85 | 85 | 30 | 98 | 100 | 90 | 40 | 100 | 100 | 100 | 100 | 85 | 98 | 85 | 100 | 100 | 100 | 100 | 100 | 100 | 100 | 100 |
| Tall Mallow | 30 | 0 | 0 | 0 | 10 | 0 | 98 | 20 | 0 | 75 | 100 | 98 | 100 | 0 | 20 | 0 | 100 | 100 | 100 | 100 | 70 | 85 | 45 | 85 |

TABLE D-continued

| | COMPOUND | | | | | | | | | | | | | | | | | | | | | | | |
|---|---|---|---|---|---|---|---|---|---|---|---|---|---|---|---|---|---|---|---|---|---|---|---|---|
| Rate 250 g/ha | 131 | 146 | 147 | 241 | 242 | 243 | 299 | 342 | 343 | 348 | 349 | 352 | 357 | 358 | 360 | | | | | | | | | |
| Postemergence | | | | | | | | | | | | | | | | | | | | | | | | |
| Alexandergrass | 100 | 40 | 50 | 100 | 100 | 100 | 100 | 80 | 100 | 100 | 90 | 100 | 100 | 100 | 100 | | | | | | | | | |
| Bermudagrass | 100 | 0 | 20 | 100 | 100 | 100 | 100 | 100 | 100 | 100 | 100 | 100 | 100 | 100 | 100 | | | | | | | | | |
| C. purslane | 0 | 20 | 0 | 0 | 0 | 0 | 0 | 0 | 0 | 0 | 0 | 0 | 0 | 0 | 0 | | | | | | | | | |
| C. ragweed | 100 | 30 | 0 | 100 | 100 | 60 | 100 | 100 | 90 | 20 | 20 | 100 | 50 | 70 | 30 | | | | | | | | | |
| Com. groundsel | 100 | 0 | 0 | 100 | 100 | 100 | 100 | 0 | 100 | 100 | 50 | 100 | 100 | 40 | 100 | | | | | | | | | |
| Dallisgrass | 100 | 60 | 85 | 100 | 100 | 100 | 100 | 100 | 100 | 100 | 90 | 100 | 100 | 100 | 100 | | | | | | | | | |
| Goosegrass | 100 | 30 | 50 | 100 | 100 | 100 | 100 | 100 | 100 | 100 | 90 | 100 | 100 | 100 | 100 | | | | | | | | | |
| Green foxtail | 100 | — | — | 100 | 100 | 100 | 100 | 100 | 100 | 100 | 100 | 100 | 100 | 100 | 100 | | | | | | | | | |
| Guineagrass | 100 | 35 | 50 | 100 | 100 | 100 | 100 | 90 | 100 | 80 | 40 | 100 | 100 | 100 | 100 | | | | | | | | | |
| Itchgrass | 100 | 50 | 50 | 100 | 100 | 100 | 50 | 0 | 30 | 100 | 0 | 60 | 50 | 100 | 30 | | | | | | | | | |
| Johnsongrass | 100 | 50 | 60 | 0 | 90 | 100 | 100 | 0 | 100 | 90 | 40 | 80 | 90 | 100 | 70 | | | | | | | | | |
| Large crabgrass | 100 | 50 | — | 100 | 100 | 100 | 100 | 100 | 100 | 100 | 100 | 100 | 100 | 100 | 100 | | | | | | | | | |
| P. morninglory | 100 | 50 | 30 | 0 | 0 | 40 | 0 | 0 | 0 | 0 | 0 | 0 | 0 | 0 | 10 | | | | | | | | | |
| Purple nutsedge | 100 | 0 | 35 | 0 | 100 | 100 | 0 | 0 | 0 | 0 | 0 | 0 | 50 | 10 | 20 | | | | | | | | | |
| Sandbur | 100 | 85 | 35 | 90 | 100 | 100 | 100 | 0 | 50 | 100 | 80 | 100 | 100 | 90 | 100 | | | | | | | | | |
| Sourgrass | —80 | 80 | — | — | — | — | — | — | — | — | — | — | — | — | | | | | | | | | | |
| Spanishneedles | 60 | 10 | 0 | 10 | 100 | 100 | 20 | 0 | 20 | 0 | 0 | 30 | 20 | 0 | 20 | | | | | | | | | |
| Surinam grass | 100 | — | 80 | 100 | 100 | 100 | 100 | 40 | 100 | 100 | 60 | 100 | 100 | 50 | 100 | | | | | | | | | |
| Tall Mallow | 100 | 0 | 0 | 40 | 100 | 60 | 70 | 10 | 30 | 40 | 0 | 20 | 100 | 80 | 90 | | | | | | | | | |
| Rate 250 g/ha | 4 | 24 | 28 | 30 | 34 | 46 | 78 | 93 | 103 | 105 | 107 | 108 | 109 | 110 | 112 | 115 | 119 | 131 | 138 | 146 | 147 | 151 | 170 | 242 |
| Preemergence | | | | | | | | | | | | | | | | | | | | | | | | |
| Alexandergrass | 90 | 65 | 75 | 80 | 60 | 75 | 75 | 100 | 85 | 98 | 100 | 100 | 100 | 100 | 80 | 85 | 100 | 100 | 98 | 100 | 90 | 100 | 98 | 100 |
| Bermudagrass | 98 | 100 | 100 | 98 | 100 | 100 | 100 | 100 | 100 | 100 | 100 | 100 | 100 | 100 | 98 | 100 | 100 | 100 | 100 | 90 | 100 | 100 | 100 | 100 |
| C. purslane | 0 | 0 | 0 | 0 | 0 | 0 | 0 | 0 | 0 | 0 | 0 | 0 | 0 | 0 | 0 | 0 | 0 | 10 | 100 | 0 | 0 | 0 | 0 | 0 |
| C. ragweed | 0 | 0 | 0 | 0 | 0 | 0 | 0 | 0 | 0 | 0 | 100 | 0 | 10 | 0 | 0 | 20 | 0 | 100 | 60 | 60 | 0 | 20 | 40 | 100 |
| Com. groundsel | — | 0 | 0 | 0 | 0 | 0 | 0 | 0 | 0 | 0 | 100 | 100 | 0 | 20 | 0 | 10 | 100 | 100 | 100 | 85 | 0 | 100 | 45 | — |
| Dallisgrass | 98 | 98 | 100 | 80 | 100 | 100 | 100 | 100 | 98 | 100 | 100 | 100 | 100 | 100 | 100 | 98 | 98 | 100 | 100 | 100 | 100 | 100 | 100 | 100 |
| Goosegrass | 98 | 98 | 100 | 85 | 98 | 98 | 98 | 100 | 98 | 100 | 100 | 100 | 100 | 100 | 100 | 100 | 100 | 100 | 100 | 100 | 100 | 100 | 98 | 100 |
| Green foxtail | — | — | — | 100 | — | 100 | 100 | 100 | 100 | 100 | 100 | 100 | 100 | 100 | 98 | 100 | 100 | 100 | 100 | 100 | — | 100 | 100 | 100 |
| Guineagrass | 100 | 98 | 98 | 98 | 98 | 65 | 100 | 100 | 90 | 100 | 100 | 100 | 100 | 100 | 90 | 98 | 98 | 100 | 100 | 100 | 100 | 100 | 100 | 100 |
| Itchgrass | 80 | 40 | 40 | 75 | 20 | 0 | 10 | 90 | 0 | 85 | 100 | 98 | 100 | 40 | 0 | 50 | 75 | 100 | 100 | 100 | 75 | 100 | 45 | 98 |
| Johnsongrass | 30 | 85 | 0 | 0 | 30 | 40 | 20 | 95 | 0 | 75 | 98 | 85 | 100 | 20 | 0 | 75 | 85 | 98 | 100 | 90 | 95 | 50 | 100 | 98 |
| Large crabgrass | 100 | 100 | 100 | 98 | 100 | 100 | 100 | 100 | 98 | 100 | 100 | 100 | 100 | 100 | 100 | 100 | 100 | 100 | 100 | 100 | 100 | 100 | 100 | 100 |
| P. morninglory | 0 | 0 | 0 | 0 | 0 | 0 | 0 | 0 | 0 | 0 | 75 | 0 | 85 | 0 | 0 | 0 | 0 | 85 | 65 | 0 | 0 | 0 | 65 | 20 |
| Purple nutsedge | 0 | 0 | 0 | 0 | 0 | 0 | 0 | 30 | 0 | 0 | 85 | 10 | 75 | 0 | 0 | 0 | 0 | 85 | 75 | 75 | 40 | 65 | 65 | 60 |
| Sandbur | 90 | 20 | 0 | 40 | 40 | 0 | 75 | 100 | 75 | 98 | 100 | 98 | 100 | 98 | 0 | 50 | 100 | 100 | 98 | 100 | 85 | 100 | 40 | 100 |
| Sourgrass | 100 | 100 | 100 | — | 100 | — | — | — | — | — | — | — | — | — | — | — | — | — | — | 100 | 100 | — | — | — |
| Spanishneedles | 0 | 0 | 75 | 0 | 40 | 10 | 0 | 0 | 20 | 0 | 100 | 0 | 30 | 0 | 0 | 10 | 10 | 75 | 70 | 90 | 30 | 85 | 100 | 100 |
| Surinam grass | 85 | 10 | 75 | 85 | 20 | 10 | 85 | 98 | 0 | 98 | 100 | 98 | 100 | 70 | 0 | 75 | 98 | 100 | 30 | 100 | 10 | 0 | 40 | 10 |
| Tall Mallow | 30 | 0 | 0 | 0 | 0 | 10 | 0 | 90 | 0 | 75 | 98 | 45 | 98 | 0 | 0 | 0 | 0 | 90 | 98 | 100 | 90 | 100 | 40 | 60 |

TABLE D-continued

| | COMPOUND | | | | | | | | | | | | | | |
|---|---|---|---|---|---|---|---|---|---|---|---|---|---|---|---|
| Rate 125 g/ha | 131 | 146 | 147 | 241 | 242 | 243 | 299 | 342 | 343 | 348 | 349 | 352 | 357 | 358 | 360 |
| Postemergence | | | | | | | | | | | | | | | |
| Alexandergrass | 100 | 20 | 35 | 100 | 100 | 100 | 100 | 70 | 100 | 100 | 70 | 100 | 100 | 90 | 100 |
| Bermudagrass | 100 | 0 | 0 | 100 | 100 | 100 | 100 | 100 | 100 | 100 | 100 | 100 | 100 | 100 | 100 |
| C. purslane | 0 | 0 | 0 | 0 | 0 | 0 | 0 | 0 | 0 | 0 | 0 | 0 | 0 | 0 | 0 |
| C. ragweed | 90 | 0 | 0 | 100 | 90 | 10 | 50 | 0 | 60 | 0 | 0 | 20 | 0 | 70 | 30 |
| Com. groundsel | 100 | 0 | 0 | 100 | 90 | 100 | 100 | 0 | 100 | 100 | 20 | 100 | 100 | — | 100 |
| Dallisgrass | 100 | 30 | 70 | 90 | 100 | 100 | 100 | 90 | 90 | 100 | 60 | 100 | 100 | 100 | 100 |
| Goosegrass | 100 | 35 | 50 | 100 | 100 | 100 | 100 | 100 | 90 | 100 | 100 | 100 | 100 | 100 | 100 |
| Green foxtail | 100 | — | — | 100 | 100 | 100 | 100 | 60 | 100 | 100 | 80 | 100 | 100 | 100 | 100 |
| Guineagrass | 100 | 10 | 30 | 100 | 100 | 100 | 80 | 50 | 50 | 100 | 0 | 80 | 70 | 100 | 100 |
| Itchgrass | 100 | 30 | 50 | 100 | 80 | 10 | 10 | 0 | 20 | 0 | 0 | 20 | 30 | 0 | 20 |
| Johnsongrass | 60 | 35 | 50 | 0 | 30 | 30 | 60 | 0 | 20 | 20 | 10 | 40 | 60 | 0 | 50 |
| Large crabgrass | 100 | 20 | 60 | 100 | 100 | 100 | 100 | 100 | 100 | 100 | 100 | 100 | 100 | 100 | 100 |
| P. morninglory | 0 | 40 | 0 | 0 | 0 | 0 | 0 | 0 | 0 | 0 | 0 | 0 | 0 | 0 | 0 |
| Purple nutsedge | 30 | 0 | 0 | 0 | 0 | 10 | 0 | 0 | 0 | 0 | 0 | 0 | 0 | 0 | 10 |
| Sandbur | 100 | — | 0 | 100 | 100 | 30 | 100 | — | 50 | 60 | 20 | 100 | 0 | 100 | 100 |
| Sourgrass | — | 50 | 30 | — | — | — | — | — | — | — | — | — | — | — | — |
| Spanishneedles | 70 | 10 | 0 | 0 | 0 | 20 | 0 | 0 | 0 | 0 | 0 | 40 | 10 | 0 | 0 |
| Surinam grass | 100 | — | 20 | 100 | 100 | 100 | 100 | 30 | 70 | 80 | 10 | 70 | 100 | 50 | 90 |
| Tall Mallow | 90 | 0 | 0 | 10 | 90 | 40 | 90 | 0 | 0 | 20 | 0 | 30 | 50 | 70 | 60 |

| Rate 125 g/ha | 4 | 18 | 24 | 28 | 30 | 34 | 46 | 78 | 93 | 94 | 103 | 105 | 107 | 108 | 109 | 113 | 114 | 115 | 117 | 119 | 131 | 138 | 146 | 147 | 151 | 170 | 242 |
|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | |
| Alexandergrass | 80 | 30 | 10 | 60 | 50 | 30 | 65 | 75 | 85 | 50 | 40 | 98 | 100 | 98 | 100 | 98 | 98 | 75 | 90 | 98 | 100 | 80 | 98 | 85 | 98 | 85 | 98 |
| Bermudagrass | 30 | 100 | 98 | 100 | 98 | 100 | 100 | 98 | 100 | 90 | 80 | 100 | 100 | 100 | 100 | 100 | 100 | 100 | 100 | 100 | 100 | 100 | 90 | 98 | 100 | 100 | 98 |
| C. purslane | 0 | 0 | 0 | 0 | 0 | 0 | 0 | 0 | 0 | 0 | 0 | 0 | 0 | 0 | 0 | 0 | 0 | 0 | 0 | 0 | 0 | 30 | 0 | 0 | 0 | 0 | 0 |
| C. ragweed | 0 | 0 | 0 | 0 | 0 | 0 | 0 | 0 | 10 | 0 | 0 | 0 | 85 | 0 | 10 | 0 | 0 | 10 | 0 | 0 | 30 | 30 | 0 | 0 | 0 | 0 | 100 |
| Com. groundsel | — | 0 | 0 | 0 | 0 | 0 | 0 | 0 | 35 | 75 | 0 | 0 | 100 | 100 | 0 | 100 | 85 | 10 | 75 | 100 | 100 | 100 | 75 | 0 | 100 | 45 | — |
| Dallisgrass | 98 | 100 | 98 | 85 | 60 | 98 | 100 | 100 | 98 | 98 | 65 | 100 | 100 | 100 | 100 | 100 | 100 | 98 | 95 | 90 | 100 | 100 | 100 | 98 | 100 | 85 | 98 |
| Goosegrass | 98 | 85 | 98 | 98 | 85 | 85 | 85 | 98 | 100 | 85 | 85 | 98 | 100 | 100 | 100 | 100 | 100 | 98 | 100 | 100 | 100 | 100 | 100 | 98 | 100 | 75 | 100 |
| Green foxtail | — | 85 | — | — | 85 | — | 40 | 100 | 100 | 90 | 100 | 100 | 100 | 100 | 100 | 100 | 100 | 100 | 100 | 100 | 100 | 100 | 100 | — | 100 | 100 | 100 |
| Guineagrass | 90 | 65 | 90 | 75 | 75 | 85 | 30 | 85 | 100 | 0 | 85 | 98 | 100 | 98 | 100 | 100 | 100 | 85 | 100 | 98 | 100 | 100 | 100 | 90 | 100 | 100 | 100 |
| Itchgrass | 0 | 0 | 40 | 40 | 75 | 0 | 0 | 0 | 75 | 0 | 0 | 20 | 98 | 40 | 75 | 60 | 20 | 50 | 75 | 60 | 90 | 80 | 90 | 65 | 85 | 30 | 80 |
| Johnsongrass | 0 | 0 | 0 | 0 | 0 | 20 | 40 | 0 | 75 | 0 | 0 | 20 | 90 | 40 | 98 | 90 | 0 | 60 | 90 | 75 | 90 | 65 | 80 | 85 | 50 | 75 | 85 |
| Large crabgrass | 100 | 100 | 100 | 100 | 98 | 100 | 98 | 100 | 100 | 98 | 95 | 100 | 100 | 100 | 100 | 100 | 100 | 100 | 98 | 100 | 100 | 100 | 100 | 100 | 100 | 100 | 100 |
| P. morninglory | 0 | 0 | 0 | 0 | 0 | 0 | 0 | 0 | 0 | 0 | 0 | 0 | 30 | 0 | 65 | 10 | 0 | 0 | 20 | 0 | 50 | 65 | 0 | 0 | 0 | 40 | 20 |
| Purple nutsedge | 0 | 0 | 0 | 0 | 0 | 0 | 0 | 0 | 0 | 50 | 0 | 0 | 65 | 10 | 40 | 30 | 20 | 0 | 0 | 0 | 60 | 65 | 70 | 30 | 30 | 0 | 40 |
| Sandbur | 30 | 0 | 20 | 0 | 40 | 30 | 0 | 0 | 65 | 20 | 0 | 0 | 98 | 98 | 100 | 100 | 85 | 40 | 0 | 98 | 100 | 65 | 100 | 0 | 100 | 40 | 90 |
| Sourgrass | 100 | — | 100 | 100 | — | 100 | — | — | — | — | — | — | — | — | — | — | — | — | — | — | — | 100 | 100 | — | — | — | |
| Spanishneedles | 40 | 0 | 0 | 75 | 0 | 0 | 10 | 0 | 10 | 0 | 0 | 0 | 20 | 0 | 10 | 0 | 0 | 0 | 0 | 10 | 60 | 10 | 90 | 10 | 0 | 0 | 10 |
| Surinam grass | 90 | 20 | 10 | 65 | 40 | 0 | 0 | 30 | 90 | 80 | 0 | 40 | 100 | 98 | 98 | 100 | 75 | 75 | 100 | 85 | 100 | 85 | 100 | 85 | 100 | 75 | 90 |
| Tall Mallow | 0 | 0 | 0 | 0 | 0 | 0 | 10 | 0 | 30 | 0 | 0 | 40 | 90 | 10 | 85 | 30 | 10 | 0 | 65 | 0 | 80 | 40 | 80 | 0 | 75 | 30 | 0 |

TABLE D-continued

| | COMPOUND | | | | | | | | | | | | | | | |
|---|---|---|---|---|---|---|---|---|---|---|---|---|---|---|---|---|
| Rate 64 g/ha | 131 | 146 | 147 | 169 | 241 | 242 | 243 | 299 | 342 | 343 | 348 | 349 | 352 | 357 | 358 | 360 |
| Postemergence | | | | | | | | | | | | | | | | |
| Alexandergrass | 100 | 10 | 20 | 65 | 10 | 90 | 20 | 90 | 0 | 50 | 70 | 40 | 80 | 100 | 100 | 50 |
| Bermudagrass | 100 | 0 | 0 | 100 | 100 | 100 | 100 | 90 | 90 | 60 | 100 | 70 | 100 | 100 | 100 | 100 |
| C. purslane | 0 | 0 | 0 | 0 | 0 | 0 | 0 | 0 | 0 | 0 | 0 | 0 | 0 | 0 | 0 | 0 |
| C. ragweed | 0 | 0 | 0 | 0 | 20 | 30 | 10 | 100 | 0 | 0 | 0 | 0 | 20 | 0 | —30 | |
| Com. groundsel | 100 | 0 | 0 | 65 | 0 | 90 | 0 | 100 | — | 100 | 50 | — | 50 | 100 | 0 | 0 |
| Dallisgrass | 100 | — | 10 | 90 | 50 | 90 | 70 | 100 | 0 | 90 | 90 | 0 | 80 | 100 | 100 | 100 |
| Goosegrass | 100 | 0 | 0 | 100 | 100 | 100 | 100 | 90 | 90 | 90 | 100 | 100 | 100 | 100 | 100 | 100 |
| Green foxtail | 100 | — | — | 100 | 10 | 100 | 100 | 100 | 0 | 100 | 100 | 10 | 100 | 100 | 100 | 100 |
| Guineagrass | 100 | 10 | 0 | 100 | 80 | 0 | 20 | 0 | 80 | 0 | 0 | 20 | 60 | 20 | 100 | |
| Itchgrass | 20 | 30 | 0 | 0 | 0 | 40 | 0 | 0 | 0 | 20 | 0 | 0 | 0 | 0 | 0 | 0 |
| Johnsongrass | 30 | 20 | 0 | 0 | 0 | 40 | 0 | 0 | 0 | 20 | 0 | 0 | 0 | 0 | 0 | 0 |
| Large crabgrass | 100 | 20 | 10 | 100 | 100 | 100 | 100 | 100 | 40 | 90 | 100 | 70 | 100 | 100 | 100 | 100 |
| P. morninglory | 0 | 30 | 0 | 0 | 0 | 0 | 0 | 0 | 0 | 0 | 0 | 0 | 0 | 0 | 0 | 0 |
| Purple nutsedge | 0 | 0 | 0 | 0 | 0 | 0 | 0 | 0 | 0 | 0 | 0 | 0 | 0 | 0 | 0 | 0 |
| Sandbur | 100 | 0 | 0 | 40 | 20 | 50 | 30 | 90 | 0 | 0 | 20 | 0 | 70 | 0 | 100 | 50 |
| Sourgrass | — | 50 | 0 | — | — | — | — | — | — | — | — | — | — | — | — | — |
| Spanishneedles | 0 | 10 | 0 | 0 | 0 | 0 | 50 | 0 | 0 | 0 | 0 | 0 | 0 | 10 | 0 | 0 |
| Surinam grass | 60 | — | — | 65 | 60 | 100 | 90 | 50 | 20 | 20 | 20 | 0 | 30 | 80 | 0 | 100 |
| Tall Mallow | 40 | 0 | 0 | 0 | 0 | 50 | 30 | 30 | 0 | 0 | 0 | 0 | 30 | 20 | 50 | 40 |

| Rate 64 g/ha | 4 | 18 | 24 | 28 | 30 | 34 | 46 | 78 | 93 | 103 | 105 | 107 | 108 | 109 | 112 | 113 | 115 | 117 | 119 | 130 | 131 | 132 | 138 | 139 | 146 | 147 | 151 | 170 | 242 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| Alexandergrass | 80 | 0 | 10 | 0 | 40 | 20 | 40 | 30 | 30 | 0 | 85 | 100 | 85 | 98 | 0 | 98 | 50 | 90 | 75 | 98 | 98 | 98 | 80 | 60 | 95 | 75 | 98 | 30 | 100 |
| Bermudagrass | 0 | 85 | 95 | 100 | 98 | 98 | 98 | 90 | 90 | 60 | 98 | 100 | 100 | 100 | 85 | 100 | 98 | 98 | 100 | 100 | 100 | 100 | 100 | 98 | 95 | 95 | 90 | 100 | 85 |
| C. purslane | 0 | 0 | 0 | 0 | 0 | — | 0 | 0 | 0 | 0 | 0 | 0 | 0 | 0 | 0 | 0 | 0 | 0 | 0 | 0 | 0 | 10 | 0 | 0 | 0 | 0 | 0 | 0 | 0 |
| C. ragweed | 0 | 0 | 0 | 0 | 0 | 0 | 0 | 0 | 0 | 0 | 0 | 0 | 0 | 10 | 0 | 0 | 0 | 0 | 0 | 30 | 30 | 0 | 10 | 0 | 0 | 0 | 0 | 0 | 100 |
| Com. groundsel | — | 0 | 0 | 0 | 0 | 0 | 0 | 0 | 0 | 0 | 0 | 98 | 85 | 0 | 0 | 100 | 10 | 0 | 100 | 0 | 85 | 0 | 40 | 0 | 0 | 0 | 0 | 0 | — |
| Dallisgrass | 90 | 85 | 30 | 75 | 50 | 80 | 40 | 75 | 98 | 45 | 98 | 100 | 100 | 100 | 70 | 100 | 75 | 85 | 85 | 100 | 100 | 98 | 100 | 90 | 98 | 80 | 100 | 85 | 98 |
| Goosegrass | 95 | 85 | 50 | 85 | 70 | 75 | 75 | 85 | 98 | 65 | 98 | 100 | 98 | 100 | 85 | 100 | 90 | 85 | 98 | 100 | 100 | 98 | 98 | 98 | 100 | 98 | 100 | 75 | 95 |
| Green foxtail | — | 85 | — | — | 85 | — | 30 | 85 | 100 | 50 | 100 | 100 | 100 | 100 | 85 | 100 | 85 | 100 | 90 | 100 | 100 | 100 | 100 | 98 | 100 | — | 100 | 100 | 100 |
| Guineagrass | 50 | 30 | 75 | 65 | 40 | 80 | 30 | 65 | 100 | 0 | 98 | 100 | 98 | 100 | 40 | 100 | 30 | 100 | 85 | 100 | 100 | 85 | 100 | 65 | 100 | 85 | 100 | 98 | 98 |
| Itchgrass | 75 | 0 | 40 | 20 | 40 | 0 | 0 | 0 | 60 | 0 | 20 | 85 | 30 | 75 | 0 | 50 | 40 | 40 | 50 | 80 | 90 | 10 | 30 | 20 | 90 | 20 | 75 | 0 | 70 |
| Johnsongrass | 30 | 0 | 0 | 0 | 0 | 0 | 0 | 0 | 40 | 0 | 0 | 90 | 20 | 75 | 0 | 80 | 40 | 90 | 65 | 65 | 65 | 35 | 40 | 10 | 60 | 20 | 40 | 0 | 40 |
| Large crabgrass | 98 | 98 | 70 | 98 | 85 | 98 | 40 | 98 | 98 | 85 | 100 | 100 | 100 | 100 | 10 | 100 | 85 | 98 | 98 | 100 | 100 | 100 | 100 | 90 | 100 | 98 | 100 | 100 | 100 |
| P. morninglory | 0 | 0 | 0 | 0 | 0 | 0 | 0 | 0 | 0 | 0 | 0 | 30 | 0 | 0 | 0 | 10 | 0 | 0 | 0 | 65 | 0 | 0 | 65 | 30 | 0 | 0 | 0 | 20 | 10 |
| Purple nutsedge | 0 | 0 | 0 | 0 | 0 | 0 | 0 | 0 | 20 | 0 | 0 | 20 | 0 | 40 | 0 | 20 | 0 | 0 | 0 | 0 | 40 | 0 | 30 | 0 | 65 | 0 | 0 | 0 | 0 |
| Sandbur | 65 | 0 | 20 | 0 | 0 | 0 | 0 | 0 | 65 | 0 | 0 | 65 | 30 | 98 | 0 | 75 | 0 | 0 | 65 | 100 | 85 | 0 | 65 | 40 | 100 | 0 | 90 | 40 | 0 |
| Sourgrass | 90 | 100 | 85 | — | 100 | — | — | — | — | — | — | — | — | — | — | — | — | — | — | — | — | 100 | 98 | — | — | — | | | |
| Spanishneedles | 0 | 0 | 0 | 60 | 0 | 0 | 0 | 0 | 0 | 0 | 0 | 0 | 0 | 10 | 0 | 0 | 0 | 0 | 0 | 60 | 40 | 0 | 10 | 20 | 85 | 0 | 0 | 0 | 0 |
| Surinam grass | 65 | 0 | 10 | 0 | 40 | 0 | 0 | 20 | 85 | 0 | 0 | 100 | 65 | 85 | 0 | 98 | 65 | 80 | 50 | 80 | 85 | 30 | 40 | 20 | 60 | 75 | 85 | 30 | 85 |
| Tall Mallow | 0 | 0 | 0 | 0 | 0 | 0 | 0 | 0 | 0 | 0 | 0 | 0 | 0 | 60 | 0 | 0 | 0 | 40 | 0 | 85 | 80 | 40 | 40 | 20 | 50 | 0 | 0 | 30 | 0 |

TABLE D-continued

| | COMPOUND | | | | | | | | | | | |
|---|---|---|---|---|---|---|---|---|---|---|---|---|
| Rate 32 g/ha | 131 | 241 | 242 | 243 | 342 | 343 | 348 | 349 | 352 | 357 | 358 | 360 |
| Postemergence | | | | | | | | | | | | |
| Alexandergrass | 50 | 10 | 50 | 0 | 0 | 0 | 0 | 0 | 60 | 20 | 0 | 60 |
| Bermudagrass | 90 | 30 | 100 | 60 | 30 | 80 | 20 | 40 | 80 | 100 | 90 | 100 |
| C. purslane | 0 | 0 | 0 | 0 | 0 | 0 | 0 | 0 | 0 | 0 | 0 | 0 |
| C. ragweed | 0 | 0 | 30 | 0 | 0 | 0 | 0 | 0 | 0 | — | 0 | 0 |
| Com. groundsel | 100 | 0 | 100 | 0 | 0 | 40 | — | — | 0 | 40 | 0 | — |
| Dallisgrass | 60 | 40 | 90 | 50 | 0 | 30 | 50 | 0 | 70 | 20 | 30 | 40 |
| Goosegrass | 100 | 100 | 100 | 80 | 30 | 80 | 90 | 20 | 90 | 100 | 20 | 100 |
| Green foxtail | 60 | 10 | 100 | 100 | 0 | 100 | 20 | 0 | 100 | 30 | 30 | 70 |
| Guineagrass | 20 | 0 | 100 | 0 | 0 | 0 | 0 | 0 | 0 | 0 | 0 | 100 |
| Itchgrass | 0 | 0 | 0 | 0 | 0 | 0 | 0 | 0 | 0 | 0 | 0 | 0 |
| Johnsongrass | 0 | 0 | 0 | 0 | 0 | 0 | 0 | 0 | 0 | 0 | 0 | 0 |
| Large crabgrass | 100 | 70 | 100 | 70 | 0 | 30 | 60 | 0 | 100 | 100 | 40 | 80 |
| P. morninglory | 0 | 0 | 0 | 0 | 0 | 0 | 0 | 0 | 0 | 0 | 0 | 0 |
| Purple nutsedge | 0 | 0 | 0 | 0 | 0 | 0 | 0 | 0 | 0 | 0 | 0 | 0 |
| Sandbur | 0 | 40 | 30 | 20 | 0 | 0 | 0 | 0 | 90 | 0 | 20 | 90 |
| Sourgrass | — | — | — | — | — | — | — | — | — | — | — | — |
| Spanishneedles | 0 | 0 | 0 | 50 | 0 | 0 | 0 | 0 | 0 | 10 | 0 | — |
| Surinam grass | 40 | 0 | 30 | 20 | 0 | 20 | 0 | 0 | 0 | 20 | 0 | 0 |
| Tall Mallow | 30 | 0 | 0 | 20 | 0 | 0 | 0 | 0 | 0 | 10 | 30 | 0 |

| Rate 32 g/ha | 4 | 18 | 24 | 28 | 30 | 34 | 46 | 78 | 93 | 103 | 105 | 107 | 108 | 109 | 112 | 113 | 115 | 119 | 131 | 146 | 147 | 151 | 170 | 242 |
|---|---|---|---|---|---|---|---|---|---|---|---|---|---|---|---|---|---|---|---|---|---|---|---|---|
| Preemergence | | | | | | | | | | | | | | | | | | | | | | | | |
| Alexandergrass | 20 | 0 | 10 | 0 | 0 | 0 | 0 | 0 | 10 | 0 | 30 | 90 | 20 | 90 | 0 | 85 | 20 | 50 | 90 | 85 | 0 | 40 | 20 | 85 |
| Bermudagrass | 0 | 60 | 75 | 85 | 65 | 85 | 85 | 85 | 80 | 30 | 98 | 100 | 98 | 100 | 75 | 100 | 98 | 65 | 100 | 100 | 85 | 90 | 90 | 85 |
| C. purslane | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| C. ragweed | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 100 |
| Com. groundsel | — | 0 | 0 | 0 | 0 | 0 | 0 | 0 | 0 | 0 | 0 | 75 | 75 | 0 | 0 | 65 | 0 | 98 | 75 | 0 | 0 | 0 | 0 | — |
| Dallisgrass | 85 | 0 | 30 | 30 | 0 | 0 | 40 | 0 | 98 | 20 | 98 | 85 | 50 | 98 | 65 | 95 | 75 | 65 | 95 | 90 | 60 | 85 | 0 | 85 |
| Goosegrass | 85 | 0 | 50 | 0 | 40 | 0 | 20 | 10 | 98 | 30 | 98 | 98 | 85 | 98 | 40 | 100 | 85 | 85 | 98 | 98 | 65 | 85 | 65 | 85 |
| Green foxtail | — | 0 | — | — | 50 | — | 0 | 75 | 75 | 0 | 85 | 100 | 100 | 100 | 0 | 98 | 70 | 75 | 100 | — | — | 100 | 75 | 100 |
| Guineagrass | 20 | 0 | 60 | 40 | 30 | 30 | 0 | 20 | 75 | 0 | 85 | 75 | 85 | 100 | 0 | 100 | 30 | 75 | 100 | 95 | 0 | 90 | 85 | 85 |
| Itchgrass | 0 | 0 | 40 | 0 | 20 | 0 | 0 | 0 | 60 | 0 | 0 | 75 | 20 | 65 | 0 | 40 | 40 | 10 | 50 | 90 | 0 | 0 | 0 | 65 |
| Johnsongrass | 0 | 0 | 0 | 0 | 0 | 0 | 0 | 0 | 0 | 0 | 0 | 85 | 20 | 0 | 0 | 60 | 40 | 0 | 40 | 60 | 0 | 0 | 0 | 40 |
| Large crabgrass | 100 | 0 | 70 | 85 | 40 | 85 | 20 | 40 | 98 | 0 | 98 | 98 | 100 | 100 | 10 | 100 | 75 | 90 | 100 | 100 | 98 | 98 | 85 | 100 |
| P. morninglory | 0 | 0 | 0 | 0 | 0 | 0 | 0 | 0 | 0 | 0 | 0 | 0 | 0 | 0 | 0 | 10 | 0 | 0 | 0 | 0 | 0 | 0 | 20 | 0 |
| Purple nutsedge | 0 | 0 | 0 | 0 | 0 | 0 | 0 | 0 | 0 | 0 | 0 | 0 | 0 | 0 | 0 | 0 | 0 | 0 | 0 | 40 | 0 | 0 | 0 | 0 |
| Sandbur | 0 | 0 | 20 | 0 | 0 | 0 | 0 | 0 | 0 | 0 | 0 | 30 | 0 | 0 | 0 | 65 | 0 | 0 | 60 | 85 | 0 | 20 | 0 | 0 |
| Sourgrass | 65 | — | 40 | 60 | — | 98 | — | — | — | — | — | — | — | — | — | — | — | — | — | 98 | 75 | — | — | — |
| Spanishneedles | — | 0 | 0 | 0 | 0 | 0 | 0 | 0 | 0 | 0 | 0 | 0 | 0 | 10 | 0 | 0 | 0 | 0 | 0 | 75 | 0 | 0 | 0 | 0 |
| Surinam grass | 0 | 0 | 10 | 0 | 40 | 0 | 0 | 0 | 0 | 0 | 0 | 75 | 65 | 30 | 0 | 90 | 20 | 0 | 75 | 60 | 0 | 30 | 0 | 85 |
| Tall Mallow | 0 | 0 | 0 | 0 | 0 | 0 | 0 | 0 | 0 | 0 | 0 | 0 | 0 | 20 | 0 | 0 | 0 | 0 | 30 | 40 | 0 | 0 | 30 | 0 |

TABLE D-continued

| | COMPOUND | | | | | | | | | | | |
|---|---|---|---|---|---|---|---|---|---|---|---|---|
| Rate 16 g/ha | 131 | 241 | 242 | 243 | 342 | 343 | 348 | 349 | 352 | 357 | 358 | 360 |
| Postemergence | | | | | | | | | | | | |
| Alexandergrass | 0 | 0 | 0 | 0 | 0 | 0 | 0 | 0 | 0 | 0 | 0 | 20 |
| Bermudagrass | 30 | 0 | 90 | 20 | 20 | 0 | 0 | 0 | 0 | 90 | 0 | 0 |
| C. purslane | 0 | 0 | 0 | 0 | 0 | 0 | 0 | 0 | 0 | 0 | 0 | 0 |
| C. ragweed | 0 | 0 | 50 | 0 | — | 0 | 0 | 0 | 0 | 0 | 0 | |
| Com. groundsel | 90 | — | 0 | 0 | — | 0 | 30 | — | — | — | 0 | — |
| Dallisgrass | 20 | 0 | 60 | 0 | 0 | 0 | 0 | 0 | 0 | 0 | 0 | 0 |
| Goosegrass | 90 | 0 | 90 | 70 | 20 | 40 | 50 | 0 | 0 | 90 | 0 | 20 |
| Green foxtail | 0 | 0 | 30 | 10 | 0 | 0 | 0 | 0 | 0 | 10 | 0 | 0 |
| Guineagrass | 0 | 0 | 0 | 0 | 0 | 0 | 0 | 0 | 0 | 0 | 0 | 0 |
| Itchgrass | 0 | 0 | 0 | 0 | 0 | 0 | 0 | 0 | 0 | 0 | 0 | 0 |
| Johnsongrass | 0 | 80 | 0 | 0 | 0 | 0 | 0 | 0 | 0 | 0 | 0 | 0 |
| Large crabgrass | 90 | 0 | 0 | 0 | 0 | 0 | 20 | 0 | 0 | 100 | 0 | 0 |
| P. morninglory | 0 | 0 | 0 | 0 | 0 | 0 | 0 | 0 | 0 | 0 | 0 | 0 |
| Purple nutsedge | 0 | 0 | 0 | 0 | 0 | 0 | 0 | 0 | 0 | 0 | 0 | 0 |
| Sandbur | 0 | 0 | 20 | 10 | 0 | 0 | 0 | 0 | 0 | 0 | 0 | 0 |
| Sourgrass | — | — | — | — | — | — | — | — | — | — | — | |
| Spanishneedles | 0 | 0 | 0 | 0 | 0 | 0 | 0 | 0 | 0 | 10 | 0 | 0 |
| Surinam grass | 0 | 0 | 0 | 0 | 0 | 0 | 0 | 0 | 0 | 0 | 0 | 0 |
| Tall Mallow | 0 | 0 | 0 | 50 | 0 | 0 | 0 | 0 | 0 | 10 | 0 | 0 |

| Rate 16 g/ha | 4 | 18 | 30 | 46 | 78 | 93 | 103 | 105 | 107 | 108 | 109 | 112 | 113 | 115 | 119 | 131 | 146 | 147 | 151 | 170 | 242 |
|---|---|---|---|---|---|---|---|---|---|---|---|---|---|---|---|---|---|---|---|---|---|
| Preemergence | | | | | | | | | | | | | | | | | | | | | |
| Alexandergrass | 20 | 0 | 0 | 0 | 0 | 0 | 0 | 0 | 0 | 20 | 40 | 0 | 65 | 0 | 0 | 20 | 65 | 0 | 40 | 20 | 65 |
| Bermudagrass | 0 | 40 | 50 | 65 | 75 | 80 | 30 | 85 | 85 | 85 | 98 | 60 | 98 | 75 | 50 | 100 | 65 | 0 | 90 | 80 | 80 |
| C. purslane | 0 | 0 | 0 | 0 | 0 | 0 | 0 | 0 | 0 | 0 | 0 | 0 | 0 | 0 | 0 | 0 | 0 | 0 | 0 | 0 | 0 |
| C. ragweed | 0 | 0 | 0 | 0 | 0 | 0 | 0 | 0 | 0 | 0 | 0 | 0 | 0 | 0 | 0 | 0 | 0 | 0 | 0 | 0 | 100 |
| Com. groundsel | — | 0 | 0 | 0 | 0 | 0 | 0 | 0 | 40 | 65 | 0 | 0 | 0 | 0 | 85 | 75 | 65 | 0 | 0 | 0 | — |
| Dallisgrass | 75 | 0 | 0 | 20 | 0 | 60 | 10 | 60 | 30 | 40 | 40 | 30 | 0 | 0 | 30 | 85 | 80 | 0 | 100 | 0 | 65 |
| Goosegrass | 70 | 0 | 30 | 0 | 10 | 65 | 0 | 85 | 85 | 60 | 85 | 40 | 90 | 20 | 30 | 75 | 90 | 0 | 85 | 50 | 75 |
| Green foxtail | — | 0 | 0 | 0 | 0 | 65 | 0 | 75 | 100 | 40 | 98 | 0 | 80 | 0 | 10 | 90 | — | — | 100 | 65 | 80 |
| Guineagrass | 20 | 0 | 30 | 0 | 20 | 65 | 0 | 40 | 65 | 0 | 90 | 0 | 85 | 0 | 65 | 0 | 90 | 0 | 85 | 0 | 70 |
| Itchgrass | 0 | 0 | 20 | 0 | 0 | 50 | 0 | 0 | 40 | 0 | 0 | 0 | 10 | 40 | 0 | 30 | 85 | 0 | 0 | 0 | 65 |
| Johnsongrass | 0 | 0 | 0 | 0 | 0 | 0 | 0 | 0 | 20 | 0 | 0 | 0 | 0 | 0 | 0 | 10 | 60 | 0 | 0 | 0 | 10 |
| Large crabgrass | 100 | 0 | 40 | 0 | 0 | 90 | 0 | 40 | 85 | 85 | 85 | 10 | 85 | 75 | 85 | 100 | 90 | 50 | 98 | 30 | 90 |
| P. morninglory | 0 | 0 | 0 | 0 | 0 | 0 | 0 | 0 | 0 | 0 | 0 | 0 | 10 | 0 | 0 | 0 | 0 | 0 | 0 | 20 | 0 |
| Purple nutsedge | 0 | 0 | 0 | 0 | 0 | 0 | 0 | 0 | 0 | 0 | 0 | 0 | 0 | 0 | 0 | 0 | 40 | 0 | 0 | 0 | 0 |
| Sandbur | 0 | 0 | 0 | 0 | 0 | 0 | 0 | 0 | 30 | 0 | 0 | 0 | 0 | 0 | 0 | 0 | 0 | 0 | 0 | 0 | 0 |
| Sourgrass | 50 | — | — | — | — | — | — | — | — | — | — | — | — | — | — | — | — | — | | | |
| Spanishneedles | 0 | 0 | 0 | 0 | 0 | 0 | 0 | 0 | 0 | 0 | 0 | 0 | 0 | 0 | 0 | 0 | 0 | 0 | 0 | 0 | 0 |
| Surinam grass | 0 | 0 | — | 0 | 0 | 0 | 0 | 0 | 30 | 0 | 0 | 0 | 85 | 0 | 0 | 20 | 40 | 0 | 30 | 0 | 20 |
| Tall Mallow | 0 | 0 | 0 | 0 | 0 | 0 | 0 | 0 | 0 | 0 | 0 | 0 | 0 | 0 | 0 | 30 | 40 | 0 | 0 | 30 | 0 |

TABLE D-continued

| | COMPOUND | | |
|---|---|---|---|
| Rate 500 g/ha | 146 | 147 | 299 |
| Postemergence | | | |
| Alexandergrass | 65 | 75 | 100 |
| Bermudagrass | 35 | 40 | 100 |
| C. purslane | 20 | 10 | 0 |
| C. ragweed | 40 | 0 | 100 |
| Com. groundsel | 0 | 0 | 100 |
| Dallisgrass | 80 | 85 | 100 |
| Goosegrass | 80 | 65 | 100 |
| Green foxtail | — | — | 100 |
| Guineagrass | 60 | 60 | 100 |
| Itchgrass | 65 | 65 | 100 |
| Johnsongrass | 65 | 70 | 100 |
| Large crabgrass | 65 | 60 | 100 |
| P. morninglory | 65 | 30 | 0 |
| Purple nutsedge | 35 | 60 | 100 |
| Sandbur | 80 | 90 | 100 |
| Sourgrass | 80 | 80 | — |
| Spanishneedles | 20 | 20 | 100 |
| Surinam grass | 80 | 70 | 100 |
| Tall Mallow | 50 | 20 | 100 |

| Rate 500 g/ha | 4 | 24 | 30 | 36 | 46 | 78 | 93 | 94 | 103 | 105 | 107 | 108 | 109 | 110 | 112 | 115 | 117 | 131 | 138 | 146 | 147 | 151 | 170 | 242 |
|---|---|---|---|---|---|---|---|---|---|---|---|---|---|---|---|---|---|---|---|---|---|---|---|---|
| Preemergence | | | | | | | | | | | | | | | | | | | | | | | | |
| Alexandergrass | 100 | 98 | 90 | 98 | 80 | 100 | 100 | 80 | 95 | 100 | 100 | 100 | 100 | 100 | 100 | 100 | 98 | 100 | 100 | 100 | 100 | 100 | 100 | 100 |
| Bermudagrass | 98 | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 |
| C. purslane | 0 | 0 | 0 | 10 | 0 | 0 | 80 | 10 | 0 | 0 | 100 | 80 | 55 | 0 | 0 | 20 | 65 | 100 | 100 | 0 | 0 | 0 | 10 | 0 |
| C. ragweed | 0 | 0 | 0 | 10 | 0 | 0 | 80 | 10 | 0 | 0 | 100 | 80 | 55 | 0 | 0 | 20 | 65 | 100 | 100 | 75 | 0 | 20 | 45 | 100 |
| Com. groundsel | — | 0 | 100 | 100 | 0 | 0 | 100 | 100 | 0 | 80 | 100 | 100 | 0 | 20 | 10 | 98 | 100 | 100 | 100 | 100 | 0 | 100 | 100 | — |
| Dallisgrass | 98 | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 |
| Goosegrass | 100 | 100 | 98 | 100 | 100 | 100 | 100 | 100 | 100 | 100 | 100 | 100 | 100 | 100 | 100 | 100 | 100 | 100 | 100 | 100 | 100 | 100 | 100 | 100 |
| Green foxtail | — | — | 100 | 100 | 100 | 100 | 100 | 100 | 100 | 100 | 100 | 100 | 100 | 100 | 0 | 100 | 100 | 100 | 100 | 100 | — | 100 | 100 | 100 |
| Guineagrass | 100 | 100 | 98 | 100 | 85 | 100 | 100 | 100 | 100 | 100 | 100 | 100 | 100 | 100 | 100 | 100 | 100 | 100 | 100 | 100 | 100 | 100 | 100 | 100 |
| Itchgrass | 80 | 40 | — | 80 | 10 | 20 | 100 | 40 | 0 | 85 | 100 | 100 | 100 | 40 | 80 | 50 | 100 | 100 | 100 | 100 | 85 | 100 | 50 | 100 |
| Johnsongrass | 30 | 85 | 40 | 0 | 60 | 20 | 85 | 20 | 40 | 90 | 100 | 85 | 100 | 45 | 50 | 90 | 100 | 100 | 100 | 95 | 95 | 100 | 95 | 100 |
| Large crabgrass | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 |
| P. morninglory | 0 | 0 | 0 | 0 | 0 | 0 | 20 | 0 | 0 | 0 | 100 | 0 | 100 | 0 | 10 | 10 | 40 | 100 | 65 | 20 | 30 | 20 | 85 | 100 |
| Purple nutsedge | 0 | 0 | 0 | 0 | 0 | 0 | 100 | 50 | 10 | 75 | 85 | 30 | 85 | 0 | 40 | 0 | 100 | 85 | 80 | 100 | 85 | 70 | 65 | 60 |
| Sandbur | 100 | 100 | 100 | 100 | 0 | 80 | 100 | 100 | 100 | 100 | 100 | 100 | 100 | 98 | 100 | 100 | 100 | 100 | 100 | 100 | 80 | 100 | 98 | 100 |
| Sourgrass | 100 | 100 | — | — | — | — | — | — | — | — | — | — | — | — | — | — | — | — | — | 100 | 100 | — | — | — |
| Spanishneedles | 0 | 0 | 0 | 10 | 20 | 0 | 45 | 0 | 20 | 0 | 100 | 20 | 30 | 0 | 10 | 10 | 0 | 90 | 75 | 100 | 30 | 40 | 85 | 40 |
| Surinam grass | 98 | 65 | 85 | 85 | 30 | 96 | 100 | 90 | 40 | 100 | 100 | 100 | 100 | 85 | 98 | 85 | 100 | 100 | 100 | 100 | 100 | 100 | 100 | 100 |
| Tall Mallow | 30 | 0 | 0 | 0 | 10 | 0 | 98 | 20 | 0 | 75 | 100 | 98 | 100 | 0 | 20 | 0 | 100 | 100 | 100 | 100 | 70 | 85 | 45 | 85 |

TABLE D-continued

| | COMPOUND | | | | | | | | | | | | | | |
|---|---|---|---|---|---|---|---|---|---|---|---|---|---|---|---|
| Rate 250 g/ha | 131 | 146 | 147 | 241 | 242 | 243 | 299 | 342 | 343 | 348 | 349 | 352 | 357 | 358 | 360 |
| Postemergence | | | | | | | | | | | | | | | |
| Alexandergrass | 100 | 40 | 50 | 100 | 100 | 100 | 100 | 80 | 100 | 100 | 90 | 100 | 100 | 100 | 100 |
| Bermudagrass | 100 | 0 | 20 | 100 | 100 | 100 | 100 | 100 | 100 | 100 | 100 | 100 | 100 | 100 | 100 |
| C. purslane | 0 | 20 | 0 | 0 | 0 | 0 | 0 | 0 | 0 | 0 | 0 | 0 | 0 | 0 | 0 |
| C. ragweed | 100 | 30 | 0 | 100 | 100 | 60 | 100 | 100 | 90 | 20 | 20 | 100 | 50 | 70 | 30 |
| Com. groundsel | 100 | 0 | 0 | 100 | 100 | 100 | 100 | 0 | 100 | 100 | 50 | 100 | 100 | 40 | 100 |
| Dallisgrass | 100 | 60 | 85 | 100 | 100 | 100 | 100 | 100 | 100 | 100 | 90 | 100 | 100 | 100 | 100 |
| Goosegrass | 100 | 30 | 50 | 100 | 100 | 100 | 100 | 100 | 100 | 100 | 90 | 100 | 100 | 100 | 100 |
| Green foxtail | 100 | — | — | 100 | 100 | 100 | 100 | 100 | 100 | 100 | 100 | 100 | 100 | 100 | 100 |
| Guineagrass | 100 | 35 | 50 | 100 | 100 | 100 | 100 | 90 | 100 | 80 | 40 | 100 | 100 | 100 | 100 |
| Itchgrass | 100 | 50 | 50 | 100 | 100 | 100 | 50 | 0 | 30 | 100 | 0 | 60 | 50 | 100 | 30 |
| Johnsongrass | 100 | 50 | 60 | 0 | 90 | 100 | 100 | 0 | 100 | 90 | 40 | 80 | 90 | 100 | 70 |
| Large crabgrass | 100 | 50 | — | 100 | 100 | 100 | 100 | 100 | 100 | 100 | 100 | 100 | 100 | 100 | 100 |
| P. morninglory | 100 | 50 | 30 | 0 | 0 | 40 | 0 | 0 | 0 | 0 | 0 | 0 | 0 | 0 | 10 |
| Purple nutsedge | 100 | 0 | 35 | 0 | 100 | 100 | 0 | 0 | 0 | 0 | 0 | 0 | 50 | 10 | 20 |
| Sandbur | 100 | 85 | 35 | 90 | 100 | 100 | 100 | 0 | 50 | 100 | 80 | 100 | 100 | 90 | 100 |
| Sourgrass | — | 80 | 80 | — | — | — | — | — | — | — | — | — | — | — | — |
| Spanishneedles | 60 | 10 | 0 | 10 | 100 | 100 | 20 | 0 | 20 | 0 | 0 | 30 | 20 | 0 | 20 |
| Surinam grass | 100 | — | 80 | 100 | 100 | 100 | 100 | 40 | 100 | 100 | 60 | 100 | 100 | 50 | 100 |
| Tall Mallow | 100 | 0 | 0 | 40 | 100 | 60 | 70 | 10 | 30 | 40 | 0 | 20 | 100 | 80 | 90 |

| Rate 250 g/ha | 4 | 24 | 28 | 30 | 34 | 46 | 78 | 93 | 103 | 105 | 107 | 108 | 109 | 110 | 112 | 115 | 119 | 131 | 138 | 146 | 147 | 151 | 170 | 242 |
|---|---|---|---|---|---|---|---|---|---|---|---|---|---|---|---|---|---|---|---|---|---|---|---|---|
| Preemergence | | | | | | | | | | | | | | | | | | | | | | | | |
| Alexandergrass | 90 | 65 | 75 | 80 | 60 | 75 | 75 | 100 | 85 | 98 | 100 | 100 | 100 | 100 | 80 | 85 | 100 | 100 | 98 | 100 | 90 | 100 | 98 | 100 |
| Bermudagrass | 98 | 100 | 100 | 98 | 100 | 100 | 100 | 100 | 100 | 100 | 100 | 100 | 100 | 100 | 98 | 100 | 100 | 100 | 100 | 90 | 100 | 100 | 100 | 100 |
| C. purslane | 0 | 0 | 0 | 0 | 0 | 0 | 0 | 0 | 0 | 0 | 0 | 0 | 0 | 0 | 0 | 0 | 0 | 10 | 100 | 0 | 0 | 0 | 0 | 0 |
| C. ragweed | 0 | 0 | 0 | 0 | 0 | 0 | 0 | 0 | 0 | 0 | 100 | 0 | 10 | 0 | 0 | 20 | 0 | 100 | 60 | 60 | 0 | 20 | 40 | 100 |
| Com. groundsel | — | 0 | 0 | 0 | 0 | 0 | 0 | 0 | 0 | 0 | 100 | 100 | 0 | 20 | 0 | 10 | 100 | 100 | 100 | 85 | 0 | 100 | 45 | — |
| Dallisgrass | 98 | 98 | 100 | 80 | 100 | 100 | 100 | 100 | 98 | 100 | 100 | 100 | 100 | 100 | 100 | 98 | 98 | 100 | 100 | 100 | 100 | 100 | 100 | 100 |
| Goosegrass | 98 | 98 | 100 | 85 | 98 | 98 | 98 | 100 | 98 | 100 | 100 | 100 | 100 | 100 | 100 | 100 | 100 | 100 | 100 | 100 | 100 | 100 | 98 | 100 |
| Green foxtail | — | — | — | 100 | — | 100 | 100 | 100 | 100 | 100 | 100 | 100 | 100 | 100 | 98 | 100 | 100 | 100 | 100 | 100 | — | 100 | 100 | 100 |
| Guineagrass | 100 | 98 | 98 | 98 | 98 | 65 | 100 | 100 | 90 | 100 | 100 | 100 | 100 | 100 | 90 | 98 | 98 | 100 | 100 | 100 | 100 | 100 | 100 | 100 |
| Itchgrass | 80 | 40 | 40 | 75 | 20 | 0 | 10 | 90 | 0 | 85 | 100 | 98 | 100 | 40 | 0 | 50 | 75 | 100 | 100 | 100 | 75 | 100 | 45 | 98 |
| Johnsongrass | 30 | 85 | 0 | 0 | 30 | 40 | 20 | 95 | 0 | 75 | 98 | 85 | 100 | 20 | 0 | 75 | 85 | 98 | 100 | 90 | 95 | 50 | 100 | 98 |
| Large crabgrass | 100 | 100 | 100 | 98 | 100 | 100 | 100 | 100 | 98 | 100 | 100 | 100 | 100 | 100 | 100 | 100 | 100 | 100 | 100 | 100 | 100 | 100 | 100 | 100 |
| P. morninglory | 0 | 0 | 0 | 0 | 0 | 0 | 0 | 0 | 0 | 0 | 75 | 0 | 85 | 0 | 0 | 0 | 0 | 85 | 65 | 0 | 0 | 0 | 65 | 20 |
| Purple nutsedge | 0 | 0 | 0 | 0 | 0 | 0 | 0 | 30 | 0 | 0 | 85 | 10 | 75 | 0 | 0 | 0 | 0 | 85 | 75 | 75 | 40 | 65 | 65 | 60 |
| Sandbur | 90 | 20 | 0 | 40 | 40 | 0 | 75 | 100 | 75 | 98 | 100 | 98 | 100 | 98 | 0 | 50 | 100 | 100 | 98 | 100 | 85 | 100 | 40 | 100 |
| Sourgrass | 100 | 100 | 100 | — | 100 | — | — | — | — | — | — | — | — | — | — | — | — | — | — | 100 | 100 | — | — | — |
| Spanishneedles | 0 | 0 | 75 | 0 | 40 | 10 | 0 | 0 | 20 | 0 | 100 | 0 | 30 | 0 | 0 | 10 | 10 | 75 | 30 | 100 | 10 | 0 | 40 | 10 |
| Surinam grass | 85 | 10 | 75 | 85 | 20 | 10 | 85 | 98 | 0 | 98 | 100 | 98 | 100 | 70 | 0 | 75 | 98 | 100 | 98 | 100 | 90 | 100 | 100 | 100 |
| Tall Mallow | 30 | 0 | 0 | 0 | 0 | 10 | 0 | 90 | 0 | 75 | 98 | 45 | 98 | 0 | 0 | 0 | 0 | 90 | 70 | 90 | 30 | 85 | 40 | 60 |

TABLE D-continued

| | COMPOUND | | | | | | | | | | | | | | |
|---|---|---|---|---|---|---|---|---|---|---|---|---|---|---|---|
| Rate 125 g/ha | 131 | 146 | 147 | 241 | 242 | 243 | 299 | 342 | 343 | 348 | 349 | 352 | 357 | 358 | 360 |
| Postemergence | | | | | | | | | | | | | | | |
| Alexandergrass | 100 | 20 | 35 | 100 | 100 | 100 | 100 | 70 | 100 | 100 | 70 | 100 | 100 | 90 | 100 |
| Bermudagrass | 100 | 0 | 0 | 100 | 100 | 100 | 100 | 100 | 100 | 100 | 100 | 100 | 100 | 100 | 100 |
| C. purslane | 0 | 0 | 0 | 0 | 0 | 0 | 0 | 0 | 0 | 0 | 0 | 0 | 0 | 0 | 0 |
| C. ragweed | 90 | 0 | 0 | 100 | 90 | 10 | 50 | 0 | 60 | 0 | 0 | 20 | 0 | 70 | 30 |
| Com. groundsel | 100 | 0 | 0 | 100 | 90 | 100 | 100 | 0 | 100 | 100 | 20 | 100 | 100 | — | 100 |
| Dallisgrass | 100 | 30 | 70 | 90 | 100 | 100 | 100 | 90 | 90 | 100 | 60 | 100 | 100 | 100 | 100 |
| Goosegrass | 100 | 35 | 50 | 100 | 100 | 100 | 100 | 100 | 90 | 100 | 100 | 100 | 100 | 100 | 100 |
| Green foxtail | 100 | — | — | 100 | 100 | 100 | 100 | 60 | 100 | 100 | 80 | 100 | 100 | 100 | 100 |
| Guineagrass | 100 | 10 | 30 | 100 | 100 | 100 | 80 | 50 | 50 | 100 | 0 | 80 | 70 | 100 | 100 |
| Itchgrass | 100 | 30 | 50 | 100 | 80 | 10 | 10 | 0 | 20 | 0 | 0 | 20 | 30 | 0 | 20 |
| Johnsongrass | 60 | 35 | 50 | 0 | 30 | 30 | 60 | 0 | 20 | 20 | 10 | 40 | 60 | 0 | 50 |
| Large crabgrass | 100 | 20 | 60 | 100 | 100 | 100 | 100 | 100 | 100 | 100 | 100 | 100 | 100 | 100 | 100 |
| P. morninglory | 0 | 40 | 0 | 0 | 0 | 0 | 0 | 0 | 0 | 0 | 0 | 0 | 0 | 0 | 0 |
| Purple nutsedge | 30 | 0 | 0 | 0 | 0 | 10 | 0 | 0 | 0 | 0 | 0 | 0 | 0 | 0 | 10 |
| Sandbur | 100 | — | 0 | 100 | 100 | 30 | 100 | — | 50 | 60 | 20 | 100 | 0 | 100 | 100 |
| Sourgrass | 50 | 30 | — | — | — | — | — | — | — | — | — | — | — | | |
| Spanishneedles | 70 | 10 | 0 | 0 | 0 | 20 | 0 | 0 | 0 | 0 | 0 | 40 | 10 | 0 | 0 |
| Surinam grass | 100 | — | 20 | 100 | 100 | 100 | 100 | 30 | 70 | 80 | 10 | 70 | 100 | 50 | 90 |
| Tall Mallow | 90 | 0 | 0 | 10 | 90 | 40 | 90 | 0 | 0 | 20 | 0 | 30 | 50 | 70 | 60 |

| Rate 125 g/ha | 4 | 18 | 24 | 28 | 30 | 34 | 46 | 78 | 93 | 94 | 103 | 105 | 107 | 108 | 109 | 113 | 114 | 115 | 117 | 119 | 131 | 138 | 146 | 147 | 151 | 170 | 242 |
|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | |
| Alexandergrass | 80 | 30 | 10 | 60 | 50 | 30 | 65 | 75 | 85 | 50 | 40 | 98 | 100 | 98 | 100 | 98 | 98 | 75 | 90 | 98 | 100 | 80 | 98 | 85 | 98 | 85 | 98 |
| Bermudagrass | 30 | 100 | 98 | 100 | 98 | 100 | 100 | 98 | 100 | 90 | 80 | 100 | 100 | 100 | 100 | 100 | 100 | 100 | 100 | 100 | 100 | 100 | 90 | 98 | 100 | 100 | 98 |
| C. purslane | 0 | 0 | 0 | 0 | 0 | 0 | 0 | 0 | 0 | 0 | 0 | 0 | 0 | 0 | 0 | 0 | 0 | 0 | 0 | 0 | 0 | 30 | 0 | 0 | 0 | 0 | 0 |
| C. ragweed | 0 | 0 | 0 | 0 | 0 | 0 | 0 | 0 | 10 | 0 | 0 | 0 | 85 | 0 | 10 | 0 | 0 | 10 | 0 | 0 | 30 | 30 | 0 | 0 | 0 | 0 | 100 |
| Com. groundsel | — | 0 | 0 | 0 | 0 | 0 | 0 | 0 | 35 | 75 | 0 | 0 | 100 | 100 | 0 | 100 | 85 | 10 | 75 | 100 | 100 | 100 | 75 | 0 | 100 | 45 | — |
| Dallisgrass | 98 | 100 | 98 | 85 | 60 | 98 | 100 | 100 | 98 | 98 | 65 | 100 | 100 | 100 | 100 | 100 | 100 | 98 | 95 | 90 | 100 | 100 | 100 | 98 | 100 | 85 | 98 |
| Goosegrass | 98 | 85 | 98 | 98 | 85 | 85 | 85 | 98 | 100 | 85 | 85 | 98 | 100 | 100 | 100 | 100 | 100 | 98 | 100 | 100 | 100 | 100 | 100 | 98 | 100 | 75 | 100 |
| Green foxtail | — | 85 | — | — | 85 | — | 40 | 100 | 100 | 90 | 100 | 100 | 100 | 100 | 100 | 100 | 100 | 100 | 100 | 100 | 100 | 100 | 100 | — | 100 | 100 | 100 |
| Guineagrass | 90 | 65 | 90 | 75 | 75 | 85 | 30 | 85 | 100 | 0 | 85 | 98 | 100 | 98 | 100 | 100 | 100 | 85 | 100 | 98 | 100 | 100 | 100 | 90 | 100 | 100 | 100 |
| Itchgrass | 0 | 0 | 40 | 40 | 75 | 0 | 0 | 0 | 75 | 0 | 0 | 20 | 98 | 40 | 75 | 60 | 20 | 50 | 75 | 60 | 90 | 80 | 90 | 65 | 85 | 30 | 80 |
| Johnsongrass | 0 | 0 | 0 | 0 | 0 | 20 | 40 | 0 | 75 | 0 | 0 | 20 | 90 | 40 | 98 | 90 | 0 | 60 | 90 | 75 | 90 | 65 | 80 | 85 | 50 | 75 | 85 |
| Large crabgrass | 100 | 100 | 100 | 100 | 98 | 100 | 98 | 100 | 100 | 98 | 95 | 100 | 100 | 100 | 100 | 100 | 100 | 100 | 98 | 100 | 100 | 100 | 100 | 100 | 100 | 100 | 100 |
| P. morninglory | 0 | 0 | 0 | 0 | 0 | 0 | 0 | 0 | 0 | 0 | 0 | 0 | 30 | 0 | 65 | 10 | 0 | 0 | 20 | 0 | 50 | 65 | 0 | 0 | 0 | 40 | 20 |
| Purple nutsedge | 0 | 0 | 0 | 0 | 0 | 0 | 0 | 0 | 0 | 50 | 0 | 0 | 65 | 10 | 40 | 30 | 20 | 0 | 0 | 0 | 60 | 65 | 70 | 30 | 30 | 0 | 40 |
| Sandbur | 30 | 0 | 20 | 0 | 40 | 30 | 0 | 0 | 65 | 20 | 0 | 0 | 98 | 98 | 100 | 100 | 85 | 40 | 0 | 98 | 100 | 65 | 100 | 0 | 100 | 40 | 90 |
| Sourgrass | 100 | — | 100 | 100 | — | 100 | — | — | — | — | — | — | — | — | — | — | — | — | — | — | — | — | 100 | 100 | — | — | — |
| Spanishneedles | 40 | 0 | 0 | 75 | 0 | 0 | 10 | 0 | 10 | 0 | 0 | 0 | 20 | 0 | 10 | 0 | 0 | 0 | 0 | 10 | 60 | 10 | 90 | 10 | 0 | 0 | 10 |
| Surinam grass | 90 | 20 | 10 | 65 | 40 | 0 | 0 | 30 | 90 | 80 | 0 | 40 | 100 | 98 | 98 | 100 | 75 | 75 | 100 | 85 | 100 | 85 | 100 | 85 | 100 | 75 | 90 |
| Tall Mallow | 0 | 0 | 0 | 0 | 0 | 0 | 10 | 0 | 30 | 0 | 0 | 45 | 90 | 10 | 85 | 30 | 10 | 0 | 65 | 0 | 80 | 40 | 80 | 0 | 75 | 30 | 0 |

TABLE D-continued

| Rate 64 g/ha | COMPOUND 131 | 146 | 147 | 169 | 241 | 242 | 243 | 299 | 342 | 343 | 348 | 349 | 352 | 357 | 358 | 360 |
|---|---|---|---|---|---|---|---|---|---|---|---|---|---|---|---|---|
| Postemergence | | | | | | | | | | | | | | | | |
| Alexandergrass | 100 | 10 | 20 | 65 | 10 | 90 | 20 | 90 | 0 | 50 | 70 | 40 | 80 | 100 | 100 | 50 |
| Bermudagrass | 100 | 0 | 0 | 100 | 100 | 100 | 100 | 90 | 90 | 60 | 100 | 70 | 100 | 100 | 100 | 100 |
| C. purslane | 0 | 0 | 0 | 0 | 0 | 0 | 0 | 0 | 0 | 0 | 0 | 0 | 0 | 0 | 0 | 0 |
| C. ragweed | 0 | 0 | 0 | 0 | 20 | 30 | 10 | 100 | 0 | 0 | 0 | 0 | 20 | 0 | — | 30 |
| Com. groundsel | 100 | 0 | 0 | 65 | 0 | 90 | 0 | 100 | — | 100 | 50 | — | 50 | 100 | 0 | 0 |
| Dallisgrass | 100 | — | 10 | 90 | 50 | 90 | 70 | 100 | 0 | 90 | 90 | 0 | 80 | 100 | 100 | 100 |
| Goosegrass | 100 | 0 | 0 | 100 | 100 | 100 | 100 | 90 | 90 | 90 | 100 | 100 | 100 | 100 | 100 | 100 |
| Green foxtail | 100 | — | — | 100 | 10 | 100 | 100 | 100 | 0 | 100 | 100 | 10 | 100 | 100 | 100 | 100 |
| Guineagrass | 100 | 10 | 0 | 0 | 100 | 80 | 0 | 20 | 0 | 80 | 0 | 0 | 20 | 60 | 20 | 100 |
| Itchgrass | 20 | 30 | 0 | 0 | 0 | 40 | 0 | 0 | 0 | 20 | 0 | 0 | 0 | 0 | 0 | 0 |
| Johnsongrass | 30 | 20 | 0 | 0 | 0 | 40 | 0 | 0 | 0 | 20 | 0 | 0 | 0 | 0 | 0 | 0 |
| Large crabgrass | 100 | 20 | 10 | 100 | 100 | 100 | 100 | 100 | 40 | 90 | 100 | 70 | 100 | 100 | 100 | 100 |
| P. morningglory | 0 | 30 | 0 | 0 | 0 | 0 | 0 | 0 | 0 | 0 | 0 | 0 | 0 | 0 | 0 | 0 |
| Purple nutsedge | 0 | 0 | 0 | 0 | 0 | 0 | 0 | 0 | 0 | 0 | 0 | 0 | 0 | 0 | 0 | 0 |
| Sandbur | 100 | 0 | 0 | 40 | 20 | 50 | 30 | 90 | 0 | 0 | 20 | 0 | 70 | 0 | 100 | 50 |
| Sourgrass | — | 50 | 0 | — | — | — | — | — | — | — | — | — | — | — | — | — |
| Spanishneedles | 0 | 10 | 0 | 0 | 0 | 0 | 50 | 0 | 0 | 0 | 0 | 0 | 0 | 10 | 0 | 0 |
| Surinam grass | 60 | — | — | 65 | 60 | 100 | 90 | 50 | 20 | 20 | 20 | 0 | 30 | 80 | 0 | 100 |
| Tall Mallow | 40 | 0 | 0 | 0 | 0 | 50 | 30 | 30 | 0 | 0 | 0 | 0 | 30 | 20 | 50 | 40 |

| Rate 64 g/ha | 4 | 18 | 24 | 28 | 30 | 34 | 46 | 78 | 93 | 103 | 105 | 107 | 108 | 109 | 112 | 113 | 115 | 117 | 119 | 130 | 131 | 132 | 138 | 139 | 146 | 147 | 151 | 170 | 242 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| Alexandergrass | 80 | 0 | 10 | 0 | 40 | 20 | 40 | 30 | 30 | 0 | 85 | 100 | 85 | 98 | 0 | 98 | 50 | 90 | 75 | 98 | 98 | 98 | 80 | 60 | 95 | 75 | 98 | 30 | 100 |
| Bermudagrass | 0 | 85 | 95 | 100 | 98 | 98 | 98 | 90 | 90 | 60 | 98 | 100 | 100 | 100 | 85 | 100 | 98 | 98 | 100 | 100 | 100 | 100 | 100 | 98 | 95 | 95 | 90 | 100 | 85 |
| C. purslane | 0 | 0 | 0 | 0 | 0 | — | 0 | 0 | 0 | 0 | 0 | 0 | 0 | 0 | 0 | 0 | 0 | 0 | 0 | 0 | 0 | 10 | 0 | 0 | 0 | 0 | 0 | 0 | 0 |
| C. ragweed | 0 | 0 | 0 | 0 | 0 | 0 | 0 | 0 | 0 | 0 | 0 | 0 | 0 | 10 | 0 | 0 | 0 | 0 | 0 | 30 | 30 | 0 | 10 | 0 | 0 | 0 | 0 | 0 | 100 |
| Com. groundsel | — | 0 | 0 | 0 | 0 | 0 | 0 | 0 | 0 | 0 | 0 | 98 | 85 | 0 | 0 | 100 | 10 | 0 | 100 | 0 | 85 | 0 | 40 | 0 | 0 | 0 | 0 | 0 | — |
| Dallisgrass | 90 | 85 | 30 | 75 | 50 | 80 | 40 | 75 | 98 | 45 | 98 | 100 | 100 | 100 | 70 | 100 | 75 | 85 | 85 | 100 | 100 | 98 | 100 | 90 | 98 | 80 | 100 | 85 | 98 |
| Goosegrass | 95 | 85 | 50 | 85 | 70 | 75 | 75 | 85 | 98 | 65 | 98 | 100 | 98 | 100 | 85 | 100 | 90 | 85 | 98 | 100 | 100 | 98 | 98 | 98 | 100 | 98 | 100 | 75 | 95 |
| Green foxtail | — | 85 | — | — | 85 | — | 30 | 85 | 100 | 50 | 100 | 100 | 100 | 100 | 85 | 100 | 85 | 100 | 90 | 100 | 100 | 100 | 100 | 98 | 100 | — | 100 | 100 | 100 |
| Guineagrass | 50 | 30 | 75 | 65 | 40 | 80 | 30 | 65 | 100 | 0 | 98 | 100 | 98 | 100 | 40 | 100 | 30 | 100 | 85 | 100 | 100 | 85 | 100 | 65 | 100 | 85 | 100 | 98 | 98 |
| Itchgrass | 75 | 0 | 40 | 20 | 40 | 0 | 0 | 0 | 60 | 0 | 20 | 85 | 30 | 75 | 0 | 50 | 40 | 40 | 50 | 80 | 90 | 10 | 30 | 20 | 90 | 20 | 75 | 0 | 70 |
| Johnsongrass | 30 | 0 | 0 | 0 | 0 | 0 | 0 | 0 | 40 | 0 | 0 | 90 | 20 | 75 | 0 | 80 | 40 | 90 | 65 | 65 | 65 | 35 | 40 | 10 | 60 | 20 | 40 | 0 | 40 |
| Large crabgrass | 98 | 98 | 70 | 98 | 85 | 98 | 40 | 98 | 98 | 85 | 100 | 100 | 100 | 100 | 10 | 100 | 85 | 98 | 98 | 100 | 100 | 100 | 100 | 90 | 100 | 98 | 100 | 100 | 100 |
| P. morningglory | 0 | 0 | 0 | 0 | 0 | 0 | 0 | 0 | 0 | 0 | 0 | 30 | 0 | 0 | 0 | 10 | 0 | 0 | 0 | 65 | 0 | 0 | 65 | 30 | 0 | 0 | 0 | 20 | 10 |
| Purple nutsedge | 0 | 0 | 0 | 0 | 0 | 0 | 0 | 0 | 20 | 0 | 0 | 20 | 0 | 40 | 0 | 20 | 0 | 0 | 0 | 0 | 40 | 0 | 30 | 0 | 65 | 0 | 0 | 0 | 0 |
| Sandbur | 65 | 0 | 20 | 0 | 0 | 0 | 0 | 0 | 65 | 0 | 0 | 65 | 30 | 98 | 0 | 75 | 0 | 0 | 65 | 100 | 85 | 0 | 65 | 40 | 100 | 0 | 90 | 40 | 0 |
| Sourgrass | 90 | — | 100 | 85 | — | 100 | — | — | — | — | — | — | — | — | — | — | — | — | — | — | — | — | — | — | 100 | 98 | — | — | — |
| Spanishneedles | 0 | 0 | 0 | 60 | 0 | 0 | 0 | 0 | 0 | 0 | 0 | 0 | 0 | 10 | 0 | 0 | 0 | 0 | 0 | 60 | 40 | 0 | 10 | 20 | 85 | 0 | 0 | 0 | 0 |
| Surinam grass | 65 | 0 | 10 | 0 | 40 | 0 | 0 | 20 | 85 | 0 | 0 | 100 | 65 | 85 | 0 | 98 | 65 | 80 | 50 | 80 | 85 | 30 | 40 | 20 | 60 | 75 | 85 | 30 | 85 |
| Tall Mallow | 0 | 0 | 0 | 0 | 0 | 0 | 0 | 0 | 0 | 0 | 0 | 0 | 0 | 60 | 0 | 0 | 0 | 40 | 0 | 85 | 80 | 40 | 40 | 20 | 50 | 0 | 0 | 30 | 0 |

TABLE D-continued

| | COMPOUND | | | | | | | | | | | |
|---|---|---|---|---|---|---|---|---|---|---|---|---|
| Rate 32 g/ha | 131 | 241 | 242 | 243 | 342 | 343 | 348 | 349 | 352 | 357 | 358 | 360 |
| Postemergence | | | | | | | | | | | | |
| Alexandergrass | 50 | 10 | 50 | 0 | 0 | 0 | 0 | 0 | 60 | 20 | 0 | 60 |
| Bermudagrass | 90 | 30 | 100 | 60 | 30 | 80 | 20 | 40 | 80 | 100 | 90 | 100 |
| C. purslane | 0 | 0 | 0 | 0 | 0 | 0 | 0 | 0 | 0 | 0 | 0 | 0 |
| C. ragweed | 0 | 0 | 30 | 0 | 0 | 0 | 0 | 0 | 0 | — | 0 | 0 |
| Com. groundsel | 100 | 0 | 100 | 0 | 0 | 40 | — | — | 0 | 40 | 0 | — |
| Dallisgrass | 60 | 40 | 90 | 50 | 0 | 30 | 50 | 0 | 70 | 20 | 30 | 40 |
| Goosegrass | 100 | 100 | 100 | 80 | 30 | 80 | 90 | 20 | 90 | 100 | 20 | 100 |
| Green foxtail | 60 | 10 | 100 | 100 | 0 | 100 | 20 | 0 | 100 | 30 | 30 | 70 |
| Guineagrass | 20 | 0 | 100 | 0 | 0 | 0 | 0 | 0 | 0 | 0 | 0 | 100 |
| Itchgrass | 0 | 0 | 0 | 0 | 0 | 0 | 0 | 0 | 0 | 0 | 0 | 0 |
| Johnsongrass | 0 | 0 | 0 | 0 | 0 | 0 | 0 | 0 | 0 | 0 | 0 | 0 |
| Large crabgrass | 100 | 70 | 100 | 70 | 0 | 30 | 60 | 0 | 100 | 100 | 40 | 80 |
| P. morninglory | 0 | 0 | 0 | 0 | 0 | 0 | 0 | 0 | 0 | 0 | 0 | 0 |
| Purple nutsedge | 0 | 0 | 0 | 0 | 0 | 0 | 0 | 0 | 0 | 0 | 0 | 0 |
| Sandbur | 0 | 40 | 30 | 20 | 0 | 0 | 0 | 0 | 90 | 0 | 20 | 90 |
| Sourgrass | — | — | — | — | — | — | — | — | — | — | — | — |
| Spanishneedles | 0 | 0 | 0 | 0 | 0 | 0 | 0 | 0 | 0 | 10 | 0 | — |
| Surinam grass | 40 | 0 | 30 | 20 | 0 | 20 | 0 | 0 | 0 | 20 | 0 | 0 |
| Tall Mallow | 30 | 0 | 0 | 20 | 0 | 0 | 0 | 0 | 0 | 10 | 30 | 0 |

| Rate 32 g/ha | 4 | 18 | 24 | 28 | 30 | 34 | 46 | 78 | 93 | 103 | 105 | 107 | 108 | 109 | 112 | 113 | 115 | 119 | 131 | 146 | 147 | 151 | 170 | 242 |
|---|---|---|---|---|---|---|---|---|---|---|---|---|---|---|---|---|---|---|---|---|---|---|---|---|
| Preemergence | | | | | | | | | | | | | | | | | | | | | | | | |
| Alexandergrass | 20 | 0 | 10 | 0 | 0 | 0 | 0 | 0 | 10 | 0 | 30 | 90 | 20 | 90 | 0 | 85 | 20 | 50 | 90 | 85 | 0 | 40 | 20 | 85 |
| Bermudagrass | 0 | 60 | 75 | 85 | 65 | 85 | 85 | 85 | 80 | 30 | 98 | 100 | 98 | 100 | 75 | 100 | 98 | 65 | 100 | 100 | 85 | 90 | 90 | 85 |
| C. purslane | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| C. ragweed | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 100 |
| Com. groundsel | — | 0 | 0 | 0 | 0 | 0 | 0 | 0 | 0 | 0 | 0 | 75 | 75 | 0 | 0 | 65 | 0 | 98 | 75 | 0 | 0 | 0 | 0 | — |
| Dallisgrass | 85 | 0 | 30 | 30 | 0 | 0 | 40 | 0 | 98 | 20 | 98 | 85 | 50 | 98 | 65 | 95 | 75 | 65 | 95 | 90 | 60 | 85 | 0 | 85 |
| Goosegrass | 85 | 0 | 50 | 0 | 40 | 0 | 20 | 10 | 98 | 30 | 98 | 98 | 85 | 98 | 40 | 100 | 85 | 85 | 98 | 98 | 65 | 85 | 65 | 85 |
| Green foxtail | — | 0 | — | — | — | 0 | 75 | 75 | 0 | 85 | 100 | 100 | 100 | 0 | 98 | 70 | 75 | 100 | — | — | 100 | 75 | 100 | |
| Guineagrass | 20 | 0 | 60 | 40 | 30 | 30 | 0 | 20 | 75 | 0 | 85 | 75 | 85 | 100 | 0 | 100 | 30 | 75 | 100 | 95 | 0 | 90 | 85 | 85 |
| Itchgrass | 0 | 0 | 40 | 0 | 20 | 0 | 0 | 0 | 60 | 0 | 0 | 75 | 20 | 65 | 0 | 40 | 40 | 10 | 50 | 90 | 0 | 0 | 0 | 65 |
| Johnsongrass | 0 | 0 | 0 | 0 | 0 | 0 | 0 | 0 | 0 | 0 | 0 | 85 | 20 | 0 | 0 | 60 | 40 | 0 | 40 | 60 | 0 | 0 | 0 | 40 |
| Large crabgrass | 100 | 0 | 70 | 85 | 40 | 85 | 20 | 40 | 98 | 0 | 98 | 98 | 100 | 100 | 10 | 100 | 75 | 90 | 100 | 100 | 98 | 98 | 85 | 100 |
| P. morninglory | 0 | 0 | 0 | 0 | 0 | 0 | 0 | 0 | 0 | 0 | 0 | 0 | 0 | 0 | 0 | 10 | 0 | 0 | 0 | 0 | 0 | 0 | 20 | 0 |
| Purple nutsedge | 0 | 0 | 0 | 0 | 0 | 0 | 0 | 0 | 0 | 0 | 0 | 0 | 0 | 0 | 0 | 0 | 0 | 0 | 0 | 40 | 0 | 0 | 0 | 0 |
| Sandbur | 0 | 0 | 20 | 0 | 0 | 0 | 0 | 0 | 0 | 0 | 0 | 30 | 0 | 0 | 0 | 65 | 0 | 0 | 60 | 85 | 0 | 20 | 0 | 0 |
| Sourgrass | 65 | — | 40 | 60 | — | 98 | — | — | — | — | — | — | — | — | — | — | — | — | — | 98 | 75 | — | — | — |
| Spanishneedles | — | 0 | 0 | 0 | 0 | 0 | 0 | 0 | 0 | 0 | 0 | 0 | 0 | 10 | 0 | 0 | 0 | 0 | 0 | 75 | 0 | 0 | 0 | 0 |
| Surinam grass | 0 | 0 | 10 | 0 | 40 | 0 | 0 | 0 | 0 | 0 | 0 | 75 | 65 | 30 | 0 | 90 | 20 | 0 | 75 | 60 | 0 | 30 | 0 | 85 |
| Tall Mallow | 0 | 0 | 0 | 0 | 0 | 0 | 0 | 0 | 0 | 0 | 0 | 0 | 0 | 20 | 0 | 0 | 0 | 0 | 30 | 40 | 0 | 0 | 30 | 0 |

TABLE D-continued

| | COMPOUND | | | | | | | | | | | |
|---|---|---|---|---|---|---|---|---|---|---|---|---|
| Rate 16 g/ha | 131 | 241 | 242 | 243 | 342 | 343 | 348 | 349 | 352 | 357 | 358 | 360 |
| Postemergence | | | | | | | | | | | | |
| Alexandergrass | 0 | 0 | 0 | 0 | 0 | 0 | 0 | 0 | 0 | 0 | 0 | 20 |
| Bermudagrass | 30 | 0 | 90 | 20 | 20 | 0 | 0 | 0 | 0 | 90 | 0 | 0 |
| C. purslane | 0 | 0 | 0 | 0 | 0 | 0 | 0 | 0 | 0 | 0 | 0 | 0 |
| C. ragweed | 0 | 0 | 50 | 0 | — | 0 | 0 | 0 | — | 0 | 0 | 0 |
| Com. groundsel | 90 | — | 0 | 0 | — | 0 | 30 | — | — | — | 0 | — |
| Dallisgrass | 20 | 0 | 60 | 0 | 0 | 0 | 0 | 0 | 0 | 0 | 0 | 0 |
| Goosegrass | 90 | 0 | 90 | 70 | 20 | 40 | 50 | 0 | 0 | 90 | 0 | 20 |
| Green foxtail | 0 | 0 | 30 | 10 | 0 | 0 | 0 | 0 | 0 | 10 | 0 | 0 |
| Guineagrass | 0 | 0 | 0 | 0 | 0 | 0 | 0 | 0 | 0 | 0 | 0 | 0 |
| Itchgrass | 0 | 0 | 0 | 0 | 0 | 0 | 0 | 0 | 0 | 0 | 0 | 0 |
| Johnsongrass | 0 | 80 | 0 | 0 | 0 | 0 | 0 | 0 | 0 | 0 | 0 | 0 |
| Large crabgrass | 90 | 0 | 0 | 0 | 0 | 0 | 20 | 0 | 0 | 100 | 0 | 0 |
| P. morningglory | 0 | 0 | 0 | 0 | 0 | 0 | 0 | 0 | 0 | 0 | 0 | 0 |
| Purple nutsedge | 0 | 0 | 0 | 0 | 0 | 0 | 0 | 0 | 0 | 0 | 0 | 0 |
| Sandbur | 0 | 0 | 20 | 10 | 0 | 0 | 0 | 0 | 0 | 0 | 0 | 0 |
| Sourgrass | — | — | — | — | — | — | — | — | — | — | — | — |
| Spanishneedles | 0 | 0 | 0 | 0 | 0 | 0 | 0 | 0 | 0 | 10 | 0 | 0 |
| Surinam grass | 0 | 0 | 0 | 0 | 0 | 0 | 0 | 0 | 0 | 0 | 0 | 0 |
| Tall Mallow | 0 | 0 | 0 | 50 | 0 | 0 | 0 | 0 | 0 | 10 | 0 | 0 |

| Rate 16 g/ha | 4 | 18 | 30 | 46 | 78 | 93 | 103 | 105 | 107 | 108 | 109 | 112 | 113 | 115 | 119 | 131 | 146 | 147 | 151 | 170 | 242 |
|---|---|---|---|---|---|---|---|---|---|---|---|---|---|---|---|---|---|---|---|---|---|
| Preemergence | | | | | | | | | | | | | | | | | | | | | |
| Alexandergrass | 20 | 0 | 0 | 0 | 0 | 0 | 0 | 0 | 0 | 20 | 40 | 0 | 65 | 0 | 0 | 20 | 65 | 0 | 40 | 20 | 65 |
| Bermudagrass | 0 | 40 | 50 | 65 | 75 | 80 | 30 | 85 | 85 | 85 | 98 | 60 | 98 | 75 | 50 | 100 | 65 | 0 | 90 | 80 | 80 |
| C. purslane | 0 | 0 | 0 | 0 | 0 | 0 | 0 | 0 | 0 | 0 | 0 | 0 | 0 | 0 | 0 | 0 | 0 | 0 | 0 | 0 | 0 |
| C. ragweed | 0 | 0 | 0 | 0 | 0 | 0 | 0 | 0 | 0 | 0 | 0 | 0 | 0 | 0 | 0 | 0 | 0 | 0 | 0 | 0 | 100 |
| Com. groundsel | — | 0 | 0 | 0 | 0 | 0 | 0 | 0 | 40 | 65 | 0 | 0 | 0 | 0 | 85 | 75 | 65 | 0 | 0 | 0 | — |
| Dallisgrass | 75 | 0 | 0 | 20 | 0 | 60 | 10 | 60 | 30 | 40 | 40 | 30 | 0 | 0 | 30 | 85 | 80 | 0 | 100 | 0 | 65 |
| Goosegrass | 70 | 0 | 30 | 0 | 10 | 65 | 0 | 85 | 85 | 60 | 85 | 40 | 90 | 20 | 30 | 75 | 90 | 0 | 85 | 50 | 75 |
| Green foxtail | — | 0 | 0 | 0 | 0 | 65 | 0 | 75 | 100 | 40 | 98 | 0 | 80 | 0 | 10 | 90 | — | — | 100 | 65 | 80 |
| Guineagrass | 20 | 0 | 30 | 0 | 20 | 65 | 0 | 40 | 65 | 0 | 90 | 0 | 85 | 0 | 65 | 0 | 90 | 0 | 85 | 0 | 70 |
| Itchgrass | 0 | 0 | 20 | 0 | 0 | 50 | 0 | 0 | 40 | 0 | 0 | 0 | 10 | 40 | 0 | 30 | 85 | 0 | 0 | 0 | 65 |
| Johnsongrass | 0 | 0 | 0 | 0 | 0 | 0 | 0 | 0 | 20 | 0 | 0 | 0 | 0 | 0 | 0 | 10 | 60 | 0 | 0 | 0 | 10 |
| Large crabgrass | 100 | 0 | 40 | 0 | 0 | 90 | 0 | 40 | 85 | 85 | 85 | 10 | 85 | 75 | 85 | 100 | 90 | 50 | 98 | 30 | 90 |
| P. morningglory | 0 | 0 | 0 | 0 | 0 | 0 | 0 | 0 | 0 | 0 | 0 | 0 | 10 | 0 | 0 | 0 | 0 | 0 | 0 | 20 | 0 |
| Purple nutsedge | 0 | 0 | 0 | 0 | 0 | 0 | 0 | 0 | 0 | 0 | 0 | 0 | 0 | 0 | 0 | 0 | 40 | 0 | 0 | 0 | 0 |
| Sandbur | 0 | 0 | 0 | 0 | 0 | 0 | 0 | 0 | 30 | 0 | 0 | 0 | 0 | 0 | 0 | 0 | 0 | 0 | 0 | 0 | 0 |
| Sourgrass | 50 | — | — | — | — | — | — | — | — | — | — | — | — | — | — | 90 | 0 | — | — | — | |
| Spanishneedles | 0 | 0 | 0 | 0 | 0 | 0 | 0 | 0 | 0 | 0 | 0 | 0 | 0 | 0 | 0 | 0 | 0 | 0 | 0 | 0 | 0 |
| Surinam grass | 0 | 0 | — | 0 | 0 | 0 | 0 | 0 | 30 | 0 | 0 | 0 | 85 | 0 | 0 | 20 | 40 | 0 | 30 | 0 | 20 |
| Tall Mallow | 0 | 0 | 0 | 0 | 0 | 0 | 0 | 0 | 0 | 0 | 0 | 0 | 0 | 0 | 0 | 30 | 40 | 0 | 0 | 30 | 0 |

Test E

Compounds evaluated in this test were formulated in a non-phytotoxic solvent mixture which included a surfactant and applied to plants that were in the 1- to 4-leaf stage (postemergence application). A mixture of sandy loam soil and greenhouse potting mix in a 60:40 ratio was used for the postemergence test.

Plantings of these crops and weed species were adjusted to produce plants of appropriate size for the postemergence test. All plant species were grown using normal greenhouse practices. Crop and weed species include annual bluegrass (*Poa annua*), blackgrass (*Alopecurus myosuroides*), black nightshade (*Solanum nigra*), chickweed (*Stellaria media*), common poppy (*Papaver rhoeas*), deadnettle (*Lamium amplexicaule*), downy brome (*Bromus tectorum*), field violet (*Viola arvensis*), galium (*Galium aparine*), green foxtail (*Setaria viridis*), Italian ryegrass (*Lolium multiflorum*), jointed goatgrass (*Aegilops cylindrica*), kochia (*Kochia scoparia*), lambsquarters (*Chenopodium album*), littleseed canarygrass (*Phalaris minor*), rape (*Brassica napus*), redroot pigweed (*Amaranthus retroflexus*), Russian thistle (*Salsola kali*), scentless chamomile (*Matricaria inodora*), spring barley (*Hordeum vulgare*), sugar beet (*Beta vulgaris*), sunflower (*Helianthus annuus*), ivyleaf speedwell (*Veronica hederaefolia*), spring wheat (*Triticum aestivum*), winter wheat (*Triticum aestivum*), wild buckwheat (*Polygonum convolvulus*), wild mustard (*Sinapis arvensis*), wild oat (*Avena fatua*), windgrass (*Apera spica-venti*) and winter barley (*Hordeum vulgare*).

Treated plants and untreated controls were maintained in a greenhouse for approximately 21 to 28 days, after which all treated plants were compared to untreated controls and visually evaluated. Plant response ratings, summarized in Table E, are based upon a 0 to 100 scale where 0 is no effect and 100 is complete control. A dash response (-) means no test result.

TABLE E

| Rate 2000 g/ha | COMPOUND 177 | Rate 2000 g/ha | COMPOUND 177 |
|---|---|---|---|
| Postemergence | | Preemergence | |
| Annual bluegras | — | Annual bluegras | — |
| Barley (winter) | — | Barley (winter) | 80 |
| Blackgrass | — | Blackgrass | 60 |
| Blk nightshade | — | Blk nightshade | — |
| Chickweed | — | Chickweed | — |
| Common poppy | — | Common poppy | — |
| Deadnettle | — | Deadnettle | — |
| Downy brome | — | Downy brome | — |
| Field violet | — | Field violet | — |
| Galium | — | Galium | — |
| Green foxtail | — | Green foxtail | 100 |
| I. Ryegrass | — | I. Ryegrass | 65 |
| Jointed goatgra | — | Jointed goatgra | — |
| Kochia | — | Kochia | — |
| Lambsquarters | — | Lambsquarters | — |
| LS canarygrass | — | LS canarygrass | — |
| Rape | — | Rape | — |
| Redroot pigweed | — | Redroot pigweed | — |
| Russian thistle | — | Russian thistle | — |
| Scentless chamo | — | Scentless chamo | — |
| Spring Barley | — | Spring Barley | — |
| Spring Wheat | — | Spring Wheat | — |
| Sugar beet | — | Sugar beet | — |
| Sunflower | — | Sunflower | — |
| Veronica hedera | — | Wheat (winter) | 70 |
| Wheat (winter) | 70 | Wild buckwheat | — |
| Wild buckwheat | — | Wild mustard | — |
| Wild mustard | — | Wild oat | 70 |
| Wild oat | — | Windgrass | — |
| Windgrass | — | | |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 1000 g/ha | 4 | 30 | 40 | 46 | 67 | 75 | 86 | 88 | 94 | 103 | 115 | 123 | 157 | 161 | 162 | 163 | 165 | 167 | 169 | 172 | 173 | 174 | 176 | 177 | 202 | 204 | 207 | 208 | 212 |
| Postemergence | | | | | | | | | | | | | | | | | | | | | | | | | | | | | |
| Annual bluegras | — | — | — | — | — | — | — | — | — | — | — | — | — | — | — | — | — | — | — | — | — | — | — | — | — | — | — | — | — |
| Barley (winter) | — | — | — | — | — | — | — | — | — | — | — | — | — | — | — | — | — | — | — | — | — | — | — | — | — | — | — | — | — |
| Blackgrass | — | — | — | — | — | — | — | — | — | — | — | — | — | — | — | — | — | — | — | — | — | — | — | — | — | — | — | — | — |
| Blk nightshade | — | — | — | — | — | — | — | — | — | — | — | — | — | — | — | — | — | — | — | — | — | — | — | — | — | — | — | — | — |
| Chickweed | — | — | — | — | — | — | — | — | — | — | — | — | — | — | — | — | — | — | — | — | — | — | — | — | — | — | — | — | — |
| Common poppy | — | — | — | — | — | — | — | — | — | — | — | — | — | — | — | — | — | — | — | — | — | — | — | — | — | — | — | — | — |
| Deadnettle | — | — | — | — | — | — | — | — | — | — | — | — | — | — | — | — | — | — | — | — | — | — | — | — | — | — | — | — | — |
| Downy brome | — | — | — | — | — | — | — | — | — | — | — | — | — | — | — | — | — | — | — | — | — | — | — | — | — | — | — | — | — |
| Field violet | — | — | — | — | — | — | — | — | — | — | — | — | — | — | — | — | — | — | — | — | — | — | — | — | — | — | — | — | — |
| Galium | — | — | — | — | — | — | — | — | — | — | — | — | — | — | — | — | — | — | — | — | — | — | — | — | — | — | — | — | — |

TABLE E-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Green foxtail | — | — | — | — | — | — | — | — | — | — | — | — | — | — | — | — | — | — | — | — | — | — | — | — | — | — | — | — | — |
| I. Ryegrass | — | — | — | — | — | — | — | — | — | — | — | — | — | — | — | — | — | — | — | — | — | — | — | — | — | — | — | — | — |
| Jointed goatgra | — | — | — | — | — | — | — | — | — | — | — | — | — | — | — | — | — | — | — | — | — | — | — | — | — | — | — | — | — |
| Kochia | — | — | — | — | — | — | — | — | — | — | — | — | — | — | — | — | — | — | — | — | — | — | — | — | — | — | — | — | — |
| Lambsquarters | — | — | — | — | — | — | — | — | — | — | — | — | — | — | — | — | — | — | — | — | — | — | — | — | — | — | — | — | — |
| LS canarygrass | — | — | — | — | — | — | — | — | — | — | — | — | — | — | — | — | — | — | — | — | — | — | — | — | — | — | — | — | — |
| Rape | — | — | — | — | — | — | — | — | — | — | — | — | — | — | — | — | — | — | — | — | — | — | — | — | — | — | — | — | — |
| Redroot pigweed | — | — | — | — | — | — | — | — | — | — | — | — | — | — | — | — | — | — | — | — | — | — | — | — | — | — | — | — | — |
| Russian thistle | — | — | — | — | — | — | — | — | — | — | — | — | — | — | — | — | — | — | — | — | — | — | — | — | — | — | — | — | — |
| Scentless chamo | — | — | — | — | — | — | — | — | — | — | — | — | — | — | — | — | — | — | — | — | — | — | — | — | — | — | — | — | — |
| Spring Barley | — | — | — | — | — | — | — | — | — | — | — | — | — | — | — | — | — | — | — | — | — | — | — | — | — | — | — | — | — |
| Spring Wheat | — | — | — | — | — | — | — | — | — | — | — | — | — | — | — | — | — | — | — | — | — | — | — | — | — | — | — | — | — |
| Sugar beet | — | — | — | — | — | — | — | — | — | — | — | — | — | — | — | — | — | — | — | — | — | — | — | — | — | — | — | — | — |
| Sunflower | — | — | — | — | — | — | — | — | — | — | — | — | — | — | — | — | — | — | — | — | — | — | — | — | — | — | — | — | — |
| Veronica hedera | — | — | — | — | — | — | — | — | — | — | — | — | — | — | — | — | — | — | — | — | — | — | — | — | — | — | — | — | — |
| Wheat (winter) | 0 | 0 | 0 | 70 | 40 | 70 | 60 | 10 | 0 | 10 | 40 | 65 | 40 | 50 | 50 | 70 | 85 | 50 | 65 | 50 | 60 | 50 | 40 | 65 | 60 | 30 | 50 | 60 | 75 |
| Wild buckwheat | — | — | — | — | — | — | — | — | — | — | — | — | — | — | — | — | — | — | — | — | — | — | — | — | — | — | — | — | — |
| Wild mustard | — | — | — | — | — | — | — | — | — | — | — | — | — | — | — | — | — | — | — | — | — | — | — | — | — | — | — | — | — |
| Wild oat | — | — | — | — | — | — | — | — | — | — | — | — | — | — | — | — | — | — | — | — | — | — | — | — | — | — | — | — | — |
| Windgrass | — | — | — | — | — | — | — | — | — | — | — | — | — | — | — | — | — | — | — | — | — | — | — | — | — | — | — | — | — |

| | COMPOUND | | | | | | | | | | | | | | | | | | | | | | | |
|---|---|---|---|---|---|---|---|---|---|---|---|---|---|---|---|---|---|---|---|---|---|---|---|---|
| Rate 1000 g/ha | 232 | 233 | 236 | 238 | 246 | 269 | 271 | 273 | 274 | 277 | 281 | 282 | 283 | 284 | 285 | 288 | 290 | 291 | 297 | 309 | 328 | 340 | 341 | 369 |
| Postemergence | | | | | | | | | | | | | | | | | | | | | | | | |
| Annual bluegras | — | — | — | — | — | — | — | — | — | — | — | — | — | — | — | — | — | — | — | — | — | — | — | — |
| Barley (winter) | — | — | — | — | — | — | — | — | — | — | — | — | — | — | — | — | — | — | — | — | — | — | — | — |
| Blackgrass | — | — | — | — | — | — | — | — | — | — | — | — | — | — | — | — | — | — | — | — | — | — | — | — |
| Blk nightshade | — | — | — | — | — | — | — | — | — | — | — | — | — | — | — | — | — | — | — | — | — | — | — | — |
| Chickweed | — | — | — | — | — | — | — | — | — | — | — | — | — | — | — | — | — | — | — | — | — | — | — | — |
| Common poppy | — | — | — | — | — | — | — | — | — | — | — | — | — | — | — | — | — | — | — | — | — | — | — | — |
| Deadnettle | — | — | — | — | — | — | — | — | — | — | — | — | — | — | — | — | — | — | — | — | — | — | — | — |
| Downy brome | — | — | — | — | — | — | — | — | — | — | — | — | — | — | — | — | — | — | — | — | — | — | — | — |
| Field violet | — | — | — | — | — | — | — | — | — | — | — | — | — | — | — | — | — | — | — | — | — | — | — | — |
| Galium | — | — | — | — | — | — | — | — | — | — | — | — | — | — | — | — | — | — | — | — | — | — | — | — |
| Green foxtail | — | — | — | — | — | — | — | — | — | — | — | — | — | — | — | — | — | — | — | — | — | — | — | — |
| I. Ryegrass | — | — | — | — | — | — | — | — | — | — | — | — | — | — | — | — | — | — | — | — | — | — | — | — |
| Jointed goatgra | — | — | — | — | — | — | — | — | — | — | — | — | — | — | — | — | — | — | — | — | — | — | — | — |
| Kochia | — | — | — | — | — | — | — | — | — | — | — | — | — | — | — | — | — | — | — | — | — | — | — | — |
| Lambsquarters | — | — | — | — | — | — | — | — | — | — | — | — | — | — | — | — | — | — | — | — | — | — | — | — |
| LS canarygrass | — | — | — | — | — | — | — | — | — | — | — | — | — | — | — | — | — | — | — | — | — | — | — | — |
| Rape | — | — | — | — | — | — | — | — | — | — | — | — | — | — | — | — | — | — | — | — | — | — | — | — |
| Redroot pigweed | — | — | — | — | — | — | — | — | — | — | — | — | — | — | — | — | — | — | — | — | — | — | — | — |
| Russian thistle | — | — | — | — | — | — | — | — | — | — | — | — | — | — | — | — | — | — | — | — | — | — | — | — |
| Scentless chamo | — | — | — | — | — | — | — | — | — | — | — | — | — | — | — | — | — | — | — | — | — | — | — | — |
| Spring Barley | — | — | — | — | — | — | — | — | — | — | — | — | — | — | — | — | — | — | — | — | — | — | — | — |
| Spring Wheat | — | — | — | — | — | — | — | — | — | — | — | — | — | — | — | — | — | — | — | — | — | — | — | — |
| Sugar beet | — | — | — | — | — | — | — | — | — | — | — | — | — | — | — | — | — | — | — | — | — | — | — | — |
| Sunflower | — | — | — | — | — | — | — | — | — | — | — | — | — | — | — | — | — | — | — | — | — | — | — | — |
| Veronica bedera | — | — | — | — | — | — | — | — | — | — | — | — | — | — | — | — | — | — | — | — | — | — | — | — |

TABLE E-continued

| | | | | | | | | | | | | | | | | | | | | | | | | |
|---|---|---|---|---|---|---|---|---|---|---|---|---|---|---|---|---|---|---|---|---|---|---|---|---|
| Wheat (winter) | 60 | 60 | 10 | 40 | 0 | 55 | 0 | 60 | 60 | 10 | 80 | 50 | 75 | 85 | 30 | 40 | 70 | 55 | 70 | 80 | 80 | 60 | 65 | 70 |
| Wild buckwheat | — | — | — | — | — | — | — | — | — | — | — | — | — | — | — | — | — | — | — | — | — | — | — | — |
| Wild mustard | — | — | — | — | — | — | — | — | — | — | — | — | — | — | — | — | — | — | — | — | — | — | — | — |
| Wild oat | — | — | — | — | — | — | — | — | — | — | — | — | — | — | — | — | — | — | — | — | — | — | — | — |
| Windgrass | — | — | — | — | — | — | — | — | — | — | — | — | — | — | — | — | — | — | — | — | — | — | — | — |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 1000 g/ha | 4 | 18 | 30 | 40 | 46 | 67 | 75 | 86 | 88 | 94 | 103 | 115 | 123 | 157 | 161 | 162 | 163 | 165 | 167 | 169 | 172 | 173 | 174 | 176 | 177 | 202 | 204 | 207 | 208 |
| Preemergence | | | | | | | | | | | | | | | | | | | | | | | | | | | | | |
| Annual bluegras | — | — | — | — | — | — | — | — | — | — | — | — | — | — | — | — | — | — | — | — | — | — | — | — | — | — | — | — | — |
| Barley (winter) | 10 | 50 | 10 | 50 | 50 | 40 | 60 | 70 | 0 | 50 | 50 | 30 | 50 | 30 | 40 | 40 | 50 | 50 | 20 | 50 | 20 | 40 | 10 | 50 | 70 | 70 | 30 | 80 | 50 |
| Blackgrass | 100 | 85 | 30 | 70 | 70 | 40 | 85 | 65 | 50 | 60 | 70 | 60 | 65 | 50 | 55 | 55 | 50 | 100 | 80 | 55 | 80 | 98 | 55 | 75 | 60 | 30 | 95 | 85 | 85 |
| Blk nightshade | — | — | — | — | — | — | — | — | — | — | — | — | — | — | — | — | — | — | — | — | — | — | — | — | — | — | — | — | — |
| Chickweed | — | — | — | — | — | — | — | — | — | — | — | — | — | — | — | — | — | — | — | — | — | — | — | — | — | — | — | — | — |
| Common poppy | — | — | — | — | — | — | — | — | — | — | — | — | — | — | — | — | — | — | — | — | — | — | — | — | — | — | — | — | — |
| Deadnettle | — | — | — | — | — | — | — | — | — | — | — | — | — | — | — | — | — | — | — | — | — | — | — | — | — | — | — | — | — |
| Downy brome | — | — | — | — | — | — | — | — | — | — | — | — | — | — | — | — | — | — | — | — | — | — | — | — | — | — | — | — | — |
| Field violet | — | — | — | — | — | — | — | — | — | — | — | — | — | — | — | — | — | — | — | — | — | — | — | — | — | — | — | — | — |
| Galium | — | — | — | — | — | — | — | — | — | — | — | — | — | — | — | — | — | — | — | — | — | — | — | — | — | — | — | — | — |
| Green foxtail | 100 | 70 | 60 | 90 | 80 | 60 | 60 | 100 | 85 | 100 | 100 | 90 | 40 | 50 | 90 | 85 | 100 | 65 | 100 | 95 | 100 | 100 | 85 | 100 | 85 | 100 | 100 | 100 | 70 |
| I. Ryegrass | 85 | 70 | 50 | 70 | 70 | 50 | 50 | 60 | 50 | 60 | 70 | 80 | 50 | 50 | 85 | 70 | 60 | 70 | 80 | 90 | 80 | 98 | 40 | 98 | 60 | 60 | 65 | 30 | 95 |
| Jointed goatgra | — | — | — | — | — | — | — | — | — | — | — | — | — | — | — | — | — | — | — | — | — | — | — | — | — | — | — | — | — |
| Kochia | — | — | — | — | — | — | — | — | — | — | — | — | — | — | — | — | — | — | — | — | — | — | — | — | — | — | — | — | — |
| Lambsquarters | — | — | — | — | — | — | — | — | — | — | — | — | — | — | — | — | — | — | — | — | — | — | — | — | — | — | — | — | — |
| LS canarygrass | — | — | — | — | — | — | — | — | — | — | — | — | — | — | — | — | — | — | — | — | — | — | — | — | — | — | — | — | — |
| Rape | — | — | — | — | — | — | — | — | — | — | — | — | — | — | — | — | — | — | — | — | — | — | — | — | — | — | — | — | — |
| Redroot pigweed | — | — | — | — | — | — | — | — | — | — | — | — | — | — | — | — | — | — | — | — | — | — | — | — | — | — | — | — | — |
| Russian thistle | — | — | — | — | — | — | — | — | — | — | — | — | — | — | — | — | — | — | — | — | — | — | — | — | — | — | — | — | — |
| Scentless chamo | — | — | — | — | — | — | — | — | — | — | — | — | — | — | — | — | — | — | — | — | — | — | — | — | — | — | — | — | — |
| Spring Barley | — | — | — | — | — | — | — | — | — | — | — | — | — | — | — | — | — | — | — | — | — | — | — | — | — | — | — | — | — |
| Spring Wheat | — | — | — | — | — | — | — | — | — | — | — | — | — | — | — | — | — | — | — | — | — | — | — | — | — | — | — | — | — |
| Sugar beet | — | — | — | — | — | — | — | — | — | — | — | — | — | — | — | — | — | — | — | — | — | — | — | — | — | — | — | — | — |
| Sunflower | — | — | — | — | — | — | — | — | — | — | — | — | — | — | — | — | — | — | — | — | — | — | — | — | — | — | — | — | — |
| Wheat (winter) | 0 | 20 | 0 | 40 | 50 | 20 | 65 | 65 | 10 | 40 | 30 | 20 | 20 | 40 | 45 | 40 | 55 | 70 | 30 | 65 | 30 | 50 | 40 | 50 | 50 | 70 | 50 | 70 | 30 |
| Wild buckwheat | — | — | — | — | — | — | — | — | — | — | — | — | — | — | — | — | — | — | — | — | — | — | — | — | — | — | — | — | — |
| Wild mustard | — | — | — | — | — | — | — | — | — | — | — | — | — | — | — | — | — | — | — | — | — | — | — | — | — | — | — | — | — |
| Wild oat | 50 | 50 | 20 | 60 | 70 | 50 | 10 | 70 | 20 | 50 | 70 | 60 | 55 | 50 | 60 | 60 | 70 | 70 | 50 | 40 | 50 | 50 | 50 | 50 | 80 | 80 | 50 | 70 | 50 |
| Windgrass | — | — | — | — | — | — | — | — | — | — | — | — | — | — | — | — | — | — | — | — | — | — | — | — | — | — | — | — | — |

| | COMPOUND | | | | | | | | | | | | | | | | | | | | | | | | |
|---|---|---|---|---|---|---|---|---|---|---|---|---|---|---|---|---|---|---|---|---|---|---|---|---|---|
| Rate 1000 g/ha | 212 | 232 | 233 | 236 | 238 | 246 | 269 | 271 | 273 | 274 | 277 | 281 | 282 | 283 | 284 | 285 | 288 | 290 | 291 | 297 | 309 | 328 | 340 | 341 | 369 |
| Preemergence | | | | | | | | | | | | | | | | | | | | | | | | | |
| Annual bluegras | — | — | — | — | — | — | — | — | — | — | — | — | — | — | — | — | — | — | — | — | — | — | — | — | — |
| Barley (winter) | 50 | 55 | 60 | 50 | 30 | 60 | 60 | 60 | 80 | 55 | 50 | 80 | 70 | 80 | 60 | 20 | 10 | 70 | 20 | 60 | 70 | 70 | 50 | 80 | 60 |
| Blackgrass | 65 | 50 | 85 | 70 | 75 | 100 | 40 | 100 | 100 | 65 | 100 | 50 | 70 | 85 | 70 | 70 | — | 95 | 50 | 50 | 75 | 40 | 85 | 90 | 100 |
| Blk nightshade | — | — | — | — | — | — | — | — | — | — | — | — | — | — | — | — | — | — | — | — | — | — | — | — | — |

TABLE E-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Chickweed | — | — | — | — | — | — | — | — | — | — | — | — | — | — | — | — | — | — | — | — | — | — | — | — | — | | | | |
| Common poppy | — | — | — | — | — | — | — | — | — | — | — | — | — | — | — | — | — | — | — | — | — | — | — | — | — | | | | |
| Deadnettle | — | — | — | — | — | — | — | — | — | — | — | — | — | — | — | — | — | — | — | — | — | — | — | — | — | | | | |
| Downy brome | — | — | — | — | — | — | — | — | — | — | — | — | — | — | — | — | — | — | — | — | — | — | — | — | — | | | | |
| Field violet | — | — | — | — | — | — | — | — | — | — | — | — | — | — | — | — | — | — | — | — | — | — | — | — | — | | | | |
| Galium | — | — | — | — | — | — | — | — | — | — | — | — | — | — | — | — | — | — | — | — | — | — | — | — | — | | | | |
| Green foxtail | 100 | 100 | 100 | 100 | 100 | 100 | 100 | 100 | 60 | 40 | 100 | 100 | 100 | 100 | 100 | 65 | 100 | 85 | 100 | 60 | 100 | 100 | 100 | 85 | 100 | | | | |
| I. Ryegrass | 70 | 55 | 60 | 55 | 85 | 100 | 70 | 100 | 60 | 50 | 100 | 60 | 70 | 98 | 85 | 70 | 60 | 90 | 90 | 40 | 70 | 70 | 65 | 55 | 70 | | | | |
| Jointed goatgra | — | — | — | — | — | — | — | — | — | — | — | — | — | — | — | — | — | — | — | — | — | — | — | — | — | | | | |
| Kochia | — | — | — | — | — | — | — | — | — | — | — | — | — | — | — | — | — | — | — | — | — | — | — | — | — | | | | |
| Lambsquarters | — | — | — | — | — | — | — | — | — | — | — | — | — | — | — | — | — | — | — | — | — | — | — | — | — | | | | |
| LS canarygrass | — | — | — | — | — | — | — | — | — | — | — | — | — | — | — | — | — | — | — | — | — | — | — | — | — | | | | |
| Rape | — | — | — | — | — | — | — | — | — | — | — | — | — | — | — | — | — | — | — | — | — | — | — | — | — | | | | |
| Redroot pigweed | — | — | — | — | — | — | — | — | — | — | — | — | — | — | — | — | — | — | — | — | — | — | — | — | — | | | | |
| Russian thistle | — | — | — | — | — | — | — | — | — | — | — | — | — | — | — | — | — | — | — | — | — | — | — | — | — | | | | |
| Scentless chamo | — | — | — | — | — | — | — | — | — | — | — | — | — | — | — | — | — | — | — | — | — | — | — | — | — | | | | |
| Spring Barley | — | — | — | — | — | — | — | — | — | — | — | — | — | — | — | — | — | — | — | — | — | — | — | — | — | | | | |
| Spring Wheat | — | — | — | — | — | — | — | — | — | — | — | — | — | — | — | — | — | — | — | — | — | — | — | — | — | | | | |
| Sugar beet | — | — | — | — | — | — | — | — | — | — | — | — | — | — | — | — | — | — | — | — | — | — | — | — | — | | | | |
| Sunflower | — | — | — | — | — | — | — | — | — | — | — | — | — | — | — | — | — | — | — | — | — | — | — | — | — | | | | |
| Wheat (winter) | 60 | 50 | 60 | 20 | 50 | 50 | 50 | 75 | 60 | 50 | 50 | 80 | 70 | 80 | 80 | 50 | 55 | 50 | 60 | 70 | 70 | 70 | 60 | 85 | 70 | | | | |
| Wild buckwheat | — | — | — | — | — | — | — | — | — | — | — | — | — | — | — | — | — | — | — | — | — | — | — | — | — | | | | |
| Wild mustard | — | — | — | — | — | — | — | — | — | — | — | — | — | — | — | — | — | — | — | — | — | — | — | — | — | | | | |
| Wild oat | 70 | 60 | 60 | 50 | 50 | 85 | 70 | 60 | 80 | 60 | 70 | 80 | 80 | 70 | 70 | 40 | 50 | 70 | 60 | 70 | 70 | 60 | 60 | 80 | 75 | | | | |
| Windgrass | — | — | — | — | — | — | — | — | — | — | — | — | — | — | — | — | — | — | — | — | — | — | — | — | — | | | | |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 4 | 18 | 30 | 38 | 40 | 46 | 67 | 75 | 86 | 94 | 98 | 103 | 105 | 109 | 114 | 115 | 116 | 118 | 131 | 132 | 146 | 147 | 157 | 158 | 161 | 162 | 163 | 165 | 167 |
| Postemergence | | | | | | | | | | | | | | | | | | | | | | | | | | | | | |
| Annual bluegras | — | — | — | — | — | — | — | — | — | — | — | — | — | 50 | 60 | — | 75 | — | 70 | — | 65 | — | — | — | — | — | — | — | — |
| Barley (winter) | — | — | — | — | — | — | — | — | — | — | — | — | — | 10 | 20 | — | 10 | — | 20 | — | 20 | — | — | — | — | — | — | — | — |
| Blackgrass | — | — | — | — | — | — | — | — | — | — | — | — | — | 70 | 65 | — | 80 | — | 75 | — | 40 | — | — | — | — | — | — | — | — |
| Blk nightshade | — | — | — | — | — | — | — | — | — | — | — | — | — | 60 | 80 | — | 60 | — | 70 | — | 70 | — | — | — | — | — | — | — | — |
| Chickweed | — | — | — | — | — | — | — | — | — | — | — | — | — | 10 | 10 | — | 50 | — | 50 | — | 30 | — | — | — | — | — | — | — | — |
| Common poppy | — | — | — | — | — | — | — | — | — | — | — | — | — | 10 | 20 | — | 10 | — | 0 | — | 10 | — | — | — | — | — | — | — | — |
| Deadnettle | — | — | — | — | — | — | — | — | — | — | — | — | — | 30 | 70 | — | 50 | — | 50 | — | 20 | — | — | — | — | — | — | — | — |
| Downy brome | — | — | — | — | — | — | — | — | — | — | — | — | — | 0 | 30 | — | 60 | — | 70 | — | 5 | — | — | — | — | — | — | — | — |
| Field violet | — | — | — | — | — | — | — | — | — | — | — | — | — | 40 | 15 | — | 0 | — | 0 | — | 10 | — | — | — | — | — | — | — | — |
| Galium | — | — | — | — | — | — | — | — | — | — | — | — | — | 50 | 85 | — | 70 | — | 50 | — | 60 | — | — | — | — | — | — | — | — |
| Green foxtail | — | — | — | — | — | — | — | — | — | — | — | — | — | 80 | 90 | — | 75 | — | 75 | — | 80 | — | — | — | — | — | — | — | — |
| I. Ryegrass | — | — | — | — | — | — | — | — | — | — | — | — | — | 65 | 20 | — | 0 | — | 40 | — | 50 | — | — | — | — | — | — | — | — |
| Jointed goatgra | — | — | — | — | — | — | — | — | — | — | — | — | — | 30 | 50 | — | 50 | — | 60 | — | 40 | — | — | — | — | — | — | — | — |
| Kochia | — | — | — | — | — | — | — | — | — | — | — | — | — | 50 | 30 | — | 0 | — | 0 | — | 40 | — | — | — | — | — | — | — | — |
| Lambsquarters | — | — | — | — | — | — | — | — | — | — | — | — | — | 30 | 40 | — | 0 | — | 0 | — | 50 | — | — | — | — | — | — | — | — |
| LS canarygrass | — | — | — | — | — | — | — | — | — | — | — | — | — | 65 | 60 | — | 50 | — | 50 | — | 65 | — | — | — | — | — | — | — | — |
| Rape | — | — | — | — | — | — | — | — | — | — | — | — | — | 60 | 55 | — | 30 | — | 0 | — | 60 | — | — | — | — | — | — | — | — |
| Redroot pigweed | — | — | — | — | — | — | — | — | — | — | — | — | — | 15 | 20 | — | 0 | — | 0 | — | 50 | — | — | — | — | — | — | — | — |
| Russian thistle | — | — | — | — | — | — | — | — | — | — | — | — | — | 0 | 0 | — | 0 | — | 0 | — | 0 | — | — | — | — | — | — | — | — |
| Scentless chamo | — | — | — | — | — | — | — | — | — | — | — | — | — | 10 | 0 | — | 40 | — | 50 | — | 10 | — | — | — | — | — | — | — | — |

TABLE E-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Spring Barley | — | — | — | — | — | — | — | — | — | — | — | — | — | 20 | 35 | — | 0 | — | 20 | — | 20 | — | — | — | — | — | — | — | — |
| Spring Wheat | — | — | — | — | — | — | — | — | — | — | — | — | — | 10 | 30 | — | 10 | — | 40 | — | 20 | — | — | — | — | — | — | — | — |
| Sugar beet | — | — | — | — | — | — | — | — | — | — | — | — | — | 30 | 50 | — | 0 | — | 0 | — | 40 | — | — | — | — | — | — | — | — |
| Sunflower | — | — | — | — | — | — | — | — | — | — | — | — | — | 40 | 15 | — | 0 | — | 0 | — | 50 | — | — | — | — | — | — | — | — |
| Veronica hedera | — | — | — | — | — | — | — | — | — | — | — | — | — | 70 | 70 | — | 70 | — | 20 | — | 70 | — | — | — | — | — | — | — | — |
| Wheat (winter) | 0 | 65 | 0 | 10 | 0 | 70 | 30 | 75 | 70 | 0 | 55 | 0 | 20 | 0 | 20 | 20 | 10 | 70 | 20 | 80 | 20 | 80 | 30 | 30 | 35 | 40 | 50 | 65 | 40 |
| Wild buckwheat | — | — | — | — | — | — | — | — | — | — | — | — | — | 10 | 30 | — | 0 | — | 0 | — | 50 | — | — | — | — | — | — | — | — |
| Wild mustard | — | — | — | — | — | — | — | — | — | — | — | — | — | 20 | 70 | — | 40 | — | 30 | — | 60 | — | — | — | — | — | — | — | — |
| Wild oat | — | — | — | — | — | — | — | — | — | — | — | — | — | 10 | 0 | — | 70 | — | 70 | — | 10 | — | — | — | — | — | — | — | — |
| Windgrass | — | — | — | — | — | — | — | — | — | — | — | — | — | 95 | 90 | — | 80 | — | 100 | — | 100 | — | — | — | — | — | — | — | — |
| | COMPOUND | | | | | | | | | | | | | | | | | | | | | | | | | | | | |
| Rate 500 g/ha | 169 | 172 | 173 | 174 | 176 | 177 | 191 | 192 | 202 | 207 | 208 | 211 | 212 | 218 | 219 | 232 | 233 | 236 | 241 | 242 | 243 | 246 | 267 | 269 | 271 | 273 | 274 | 276 | 277 |
| Postemergence | | | | | | | | | | | | | | | | | | | | | | | | | | | | | |
| Annual bluegras | — | — | — | — | — | — | — | — | — | — | — | — | — | — | — | — | — | — | — | 80 | — | — | — | — | — | — | — | — | — |
| Barley (winter) | — | — | — | — | — | — | — | — | — | — | — | — | — | — | — | — | — | — | — | 20 | — | — | — | — | — | — | — | — | — |
| Blackgrass | — | — | — | — | — | — | — | — | — | — | — | — | — | — | — | — | — | — | — | 50 | — | — | — | — | — | — | — | — | — |
| Blk nightshade | — | — | — | — | — | — | — | — | — | — | — | — | — | — | — | — | — | — | — | 75 | — | — | — | — | — | — | — | — | — |
| Chickweed | — | — | — | — | — | — | — | — | — | — | — | — | — | — | — | — | — | — | — | 50 | — | — | — | — | — | — | — | — | — |
| Common poppy | — | — | — | — | — | — | — | — | — | — | — | — | — | — | — | — | — | — | — | 0 | — | — | — | — | — | — | — | — | — |
| Deadnettle | — | — | — | — | — | — | — | — | — | — | — | — | — | — | — | — | — | — | — | 50 | — | — | — | — | — | — | — | — | — |
| Downy brome | — | — | — | — | — | — | — | — | — | — | — | — | — | — | — | — | — | — | — | 40 | — | — | — | — | — | — | — | — | — |
| Field violet | — | — | — | — | — | — | — | — | — | — | — | — | — | — | — | — | — | — | — | 40 | — | — | — | — | — | — | — | — | — |
| Galium | — | — | — | — | — | — | — | — | — | — | — | — | — | — | — | — | — | — | — | 40 | — | — | — | — | — | — | — | — | — |
| Green foxtail | — | — | — | — | — | — | — | — | — | — | — | — | — | — | — | — | — | — | — | 70 | — | — | — | — | — | — | — | — | — |
| I. Ryegrass | — | — | — | — | — | — | — | — | — | — | — | — | — | — | — | — | — | — | — | 60 | — | — | — | — | — | — | — | — | — |
| Jointed goatgra | — | — | — | — | — | — | — | — | — | — | — | — | — | — | — | — | — | — | — | 40 | — | — | — | — | — | — | — | — | — |
| Kochia | — | — | — | — | — | — | — | — | — | — | — | — | — | — | — | — | — | — | — | 20 | — | — | — | — | — | — | — | — | — |
| Lambsquarters | — | — | — | — | — | — | — | — | — | — | — | — | — | — | — | — | — | — | — | 0 | — | — | — | — | — | — | — | — | — |
| LS canarygrass | — | — | — | — | — | — | — | — | — | — | — | — | — | — | — | — | — | — | — | 50 | — | — | — | — | — | — | — | — | — |
| Rape | — | — | — | — | — | — | — | — | — | — | — | — | — | — | — | — | — | — | — | 50 | — | — | — | — | — | — | — | — | — |
| Redroot pigweed | — | — | — | — | — | — | — | — | — | — | — | — | — | — | — | — | — | — | — | 40 | — | — | — | — | — | — | — | — | — |
| Russian thistle | — | — | — | — | — | — | — | — | — | — | — | — | — | — | — | — | — | — | — | 0 | — | — | — | — | — | — | — | — | — |
| Scentless chamo | — | — | — | — | — | — | — | — | — | — | — | — | — | — | — | — | — | — | — | 20 | — | — | — | — | — | — | — | — | — |
| Spring Barley | — | — | — | — | — | — | — | — | — | — | — | — | — | — | — | — | — | — | — | 20 | — | — | — | — | — | — | — | — | — |
| Spring Wheat | — | — | — | — | — | — | — | — | — | — | — | — | — | — | — | — | — | — | — | 20 | — | — | — | — | — | — | — | — | — |
| Sugar beet | — | — | — | — | — | — | — | — | — | — | — | — | — | — | — | — | — | — | — | 30 | — | — | — | — | — | — | — | — | — |
| Sunflower | — | — | — | — | — | — | — | — | — | — | — | — | — | — | — | — | — | — | — | 20 | — | — | — | — | — | — | — | — | — |
| Veronica hedera | — | — | — | — | — | — | — | — | — | — | — | — | — | — | — | — | — | — | — | — | — | — | — | — | — | — | — | — | — |
| Wheat (winter) | 50 | 40 | 40 | 40 | 50 | 70 | 60 | 50 | 55 | 30 | 50 | 40 | 70 | 85 | 60 | 50 | 55 | 0 | 50 | 90 | 80 | 0 | 70 | 40 | 0 | 50 | 50 | 20 | 0 |
| Wild buckwheat | — | — | — | — | — | — | — | — | — | — | — | — | — | — | — | — | — | — | — | 0 | — | — | — | — | — | — | — | — | — |
| Wild mustard | — | — | — | — | — | — | — | — | — | — | — | — | — | — | — | — | — | — | — | 5 | — | — | — | — | — | — | — | — | — |
| Wild oat | — | — | — | — | — | — | — | — | — | — | — | — | — | — | — | — | — | — | — | 20 | — | — | — | — | — | — | — | — | — |
| Windgrass | — | — | — | — | — | — | — | — | — | — | — | — | — | — | — | — | — | — | — | 95 | — | — | — | — | — | — | — | — | — |

TABLE E-continued

| Rate 500 g/ha | 281 | 282 | 283 | 284 | 285 | 288 | 290 | 291 | 293 | 297 | 309 | 315 | 317 | 328 | 340 | 341 | 350 | 351 | 353 | 354 | 369 | 370 | 371 | 372 | 375 | 388 |
|---|---|---|---|---|---|---|---|---|---|---|---|---|---|---|---|---|---|---|---|---|---|---|---|---|---|---|
| Postemergence | | | | | | | | | | | | | | | | | | | | | | | | | | |
| Annual bluegras | — | — | — | — | — | — | — | — | — | — | — | — | — | — | — | — | — | — | — | — | — | — | — | — | — | — |
| Barley (winter) | — | — | — | — | — | — | — | — | — | — | — | — | — | — | — | — | — | — | — | — | — | — | — | — | — | — |
| Blackgrass | — | — | — | — | — | — | — | — | — | — | — | — | — | — | — | — | — | — | — | — | — | — | — | — | — | — |
| Blk nightshade | — | — | — | — | — | — | — | — | — | — | — | — | — | — | — | — | — | — | — | — | — | — | — | — | — | — |
| Chickweed | — | — | — | — | — | — | — | — | — | — | — | — | — | — | — | — | — | — | — | — | — | — | — | — | — | — |
| Common poppy | — | — | — | — | — | — | — | — | — | — | — | — | — | — | — | — | — | — | — | — | — | — | — | — | — | — |
| Deadnettle | — | — | — | — | — | — | — | — | — | — | — | — | — | — | — | — | — | — | — | — | — | — | — | — | — | — |
| Downy brome | — | — | — | — | — | — | — | — | — | — | — | — | — | — | — | — | — | — | — | — | — | — | — | — | — | — |
| Field violet | — | — | — | — | — | — | — | — | — | — | — | — | — | — | — | — | — | — | — | — | — | — | — | — | — | — |
| Galium | — | — | — | — | — | — | — | — | — | — | — | — | — | — | — | — | — | — | — | — | — | — | — | — | — | — |
| Green foxtail | — | — | — | — | — | — | — | — | — | — | — | — | — | — | — | — | — | — | — | — | — | — | — | — | — | — |
| I. Ryegrass | — | — | — | — | — | — | — | — | — | — | — | — | — | — | — | — | — | — | — | — | — | — | — | — | — | — |
| Jointed goatgra | — | — | — | — | — | — | — | — | — | — | — | — | — | — | — | — | — | — | — | — | — | — | — | — | — | — |
| Kochia | — | — | — | — | — | — | — | — | — | — | — | — | — | — | — | — | — | — | — | — | — | — | — | — | — | — |
| Lambsquarters | — | — | — | — | — | — | — | — | — | — | — | — | — | — | — | — | — | — | — | — | — | — | — | — | — | — |
| LS canarygrass | — | — | — | — | — | — | — | — | — | — | — | — | — | — | — | — | — | — | — | — | — | — | — | — | — | — |
| Rape | — | — | — | — | — | — | — | — | — | — | — | — | — | — | — | — | — | — | — | — | — | — | — | — | — | — |
| Redroot pigweed | — | — | — | — | — | — | — | — | — | — | — | — | — | — | — | — | — | — | — | — | — | — | — | — | — | — |
| Russian thistle | — | — | — | — | — | — | — | — | — | — | — | — | — | — | — | — | — | — | — | — | — | — | — | — | — | — |
| Scentless chamo | — | — | — | — | — | — | — | — | — | — | — | — | — | — | — | — | — | — | — | — | — | — | — | — | — | — |
| Spring Barley | — | — | — | — | — | — | — | — | — | — | — | — | — | — | — | — | — | — | — | — | — | — | — | — | — | — |
| Spring Wheat | — | — | — | — | — | — | — | — | — | — | — | — | — | — | — | — | — | — | — | — | — | — | — | — | — | — |
| Sugar beet | — | — | — | — | — | — | — | — | — | — | — | — | — | — | — | — | — | — | — | — | — | — | — | — | — | — |
| Sunflower | — | — | — | — | — | — | — | — | — | — | — | — | — | — | — | — | — | — | — | — | — | — | — | — | — | — |
| Veronica hedera | — | — | — | — | — | — | — | — | — | — | — | — | — | — | — | — | — | — | — | — | — | — | — | — | — | — |
| Wheat (winter) | 70 | 30 | 50 | 20 | 40 | 30 | 60 | 40 | 50 | 60 | 70 | 80 | 95 | 70 | 55 | 65 | 40 | 75 | 40 | 50 | 70 | 85 | 80 | 80 | 50 | 65 |
| Wild buckwheat | — | — | — | — | — | — | — | — | — | — | — | — | — | — | — | — | — | — | — | — | — | — | — | — | — | — |
| Wild mustard | — | — | — | — | — | — | — | — | — | — | — | — | — | — | — | — | — | — | — | — | — | — | — | — | — | — |
| Wild oat | — | — | — | — | — | — | — | — | — | — | — | — | — | — | — | — | — | — | — | — | — | — | — | — | — | — |
| Windgrass | — | — | — | — | — | — | — | — | — | — | — | — | — | — | — | — | — | — | — | — | — | — | — | — | — | — |

| Rate 500 g/ha | 4 | 18 | 30 | 38 | 40 | 46 | 67 | 75 | 86 | 94 | 98 | 103 | 105 | 109 | 114 | 115 | 116 | 118 | 131 | 132 | 146 | 147 | 157 | 158 | 161 | 162 | 163 | 165 | 167 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| Annual bluegras | — | — | — | — | — | — | — | — | — | — | — | — | — | 75 | 60 | — | 100 | — | 100 | — | 90 | — | — | — | — | — | — | — | — |
| Barley (winter) | 10 | 30 | 10 | 0 | 40 | 40 | 40 | 20 | 80 | 50 | 30 | 40 | 10 | 5 | 40 | 20 | 80 | 50 | 100 | 60 | 95 | 45 | 10 | 30 | 40 | 30 | 40 | 55 | 40 |
| Blackgrass | 90 | 25 | — | 35 | 60 | 55 | 20 | 40 | 55 | 60 | 55 | 50 | 50 | 90 | 100 | 50 | 100 | 100 | 100 | 75 | 70 | 65 | 40 | 50 | 50 | 60 | 40 | 60 | 60 |
| Blk nightshade | — | — | — | — | — | — | — | — | — | — | — | — | — | 90 | 90 | — | 100 | — | 90 | — | 100 | — | — | — | — | — | — | — | — |
| Chickweed | — | — | — | — | — | — | — | — | — | — | — | — | — | 100 | 100 | — | 100 | — | 100 | — | 70 | — | — | — | — | — | — | — | — |
| Common poppy | — | — | — | — | — | — | — | — | — | — | — | — | — | — | — | — | — | — | — | — | 100 | — | — | — | — | — | — | — | — |
| Deadnettle | — | — | — | — | — | — | — | — | — | — | — | — | — | 30 | 20 | — | 80 | — | 100 | — | 50 | — | — | — | — | — | — | — | — |
| Downy brome | — | — | — | — | — | — | — | — | — | — | — | — | — | 60 | 50 | — | 70 | — | 100 | — | 60 | — | — | — | — | — | — | — | — |
| Field violet | — | — | — | — | — | — | — | — | — | — | — | — | — | 20 | 10 | — | 90 | — | 40 | — | 50 | — | — | — | — | — | — | — | — |

TABLE E-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Galium | — | — | — | — | — | — | — | — | — | — | — | — | — | 100 | 70 | — | 100 | — | 100 | — | 95 | — | — | — | — | — | — | — | — |
| Green foxtail | 100 | 50 | 60 | 100 | 90 | 85 | 55 | 60 | 55 | 90 | 65 | 70 | 100 | 85 | 85 | 70 | — | 65 | — | 100 | 100 | 65 | 40 | 50 | 70 | 65 | 100 | 55 | 85 |
| I. Ryegrass | 50 | 60 | 40 | 80 | 70 | 65 | 30 | 30 | 50 | 60 | 60 | 50 | 85 | 70 | 95 | 50 | 100 | 60 | 100 | 100 | 90 | 50 | 30 | 50 | 65 | 65 | 50 | 55 | 65 |
| Jointed goatgra | — | — | — | — | — | — | — | — | — | — | — | — | — | 70 | 50 | — | 65 | — | 95 | — | 50 | — | — | — | — | — | — | — | — |
| Kochia | — | — | — | — | — | — | — | — | — | — | — | — | — | 100 | 30 | — | 70 | — | 100 | — | 75 | — | — | — | — | — | — | — | — |
| Lambsquarters | — | — | — | — | — | — | — | — | — | — | — | — | — | 100 | 100 | — | 100 | — | 100 | — | 100 | — | — | — | — | — | — | — | — |
| LS canarygrass | — | — | — | — | — | — | — | — | — | — | — | — | — | 50 | 80 | — | 100 | — | 100 | — | 85 | — | — | — | — | — | — | — | — |
| Rape | — | — | — | — | — | — | — | — | — | — | — | — | — | 65 | 50 | — | 100 | — | 90 | — | 60 | — | — | — | — | — | — | — | — |
| Redroot pigweed | — | — | — | — | — | — | — | — | — | — | — | — | — | 100 | 100 | — | 100 | — | 95 | — | 100 | — | — | — | — | — | — | — | — |
| Russian thistle | — | — | — | — | — | — | — | — | — | — | — | — | — | 0 | 0 | — | 50 | — | 0 | — | 10 | — | — | — | — | — | — | — | — |
| Scentless chamo | — | — | — | — | — | — | — | — | — | — | — | — | — | 30 | 10 | — | — | — | — | — | 80 | — | — | — | — | — | — | — | — |
| Spring Barley | — | — | — | — | — | — | — | — | — | — | — | — | — | 50 | 20 | — | 100 | — | 85 | — | 90 | — | — | — | — | — | — | — | — |
| Spring Wheat | — | — | — | — | — | — | — | — | — | — | — | — | — | 50 | 20 | — | 100 | — | 100 | — | 100 | — | — | — | — | — | — | — | — |
| Sugar beet | — | — | — | — | — | — | — | — | — | — | — | — | — | 70 | 50 | — | 95 | — | 90 | — | 80 | — | — | — | — | — | — | — | — |
| Sunflower | — | — | — | — | — | — | — | — | — | — | — | — | — | 5 | 5 | — | 70 | — | 20 | — | 30 | — | — | — | — | — | — | — | — |
| Wheat (winter) | 0 | 10 | 0 | 10 | 30 | 70 | 10 | 20 | 40 | 30 | 40 | 30 | 10 | 10 | 0 | 10 | 100 | 70 | 95 | 60 | 100 | 70 | 30 | — | 20 | 15 | — | 50 | 20 |
| Wild buckwheat | — | — | — | — | — | — | — | — | — | — | — | — | — | 90 | 80 | — | 95 | — | 100 | — | 100 | — | — | — | — | — | — | — | — |
| Wild mustard | — | — | — | — | — | — | — | — | — | — | — | — | — | 80 | 90 | — | 65 | — | 100 | — | 100 | — | — | — | — | — | — | — | — |
| Wild oat | 25 | 40 | 10 | 20 | 50 | 60 | 40 | — | 60 | 40 | 50 | 50 | 55 | 80 | 70 | 50 | 80 | 70 | 100 | 65 | 85 | 0 | 30 | 60 | 50 | 50 | 60 | 60 | 40 |
| Windgrass | — | — | — | — | — | — | — | — | — | — | — | — | — | 100 | 100 | — | 100 | — | 100 | — | 100 | — | — | — | — | — | — | — | — |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 500 g/ha | 169 | 172 | 173 | 174 | 176 | 177 | 191 | 192 | 201 | 202 | 207 | 208 | 211 | 212 | 218 | 219 | 232 | 233 | 236 | 241 | 242 | 243 | 246 | 267 | 269 | 271 | 273 | 274 | 276 |
| Preemergence | | | | | | | | | | | | | | | | | | | | | | | | | | | | | |
| Annual bluegras | — | — | — | — | — | — | — | — | — | — | — | — | — | — | — | — | — | — | — | — | 100 | — | — | — | — | — | — | — | — |
| Barley (winter) | 30 | 40 | 40 | 0 | 40 | 60 | 20 | 30 | 20 | 40 | 70 | 40 | 10 | 40 | 65 | 70 | 20 | 50 | 40 | 60 | 85 | 70 | 50 | 70 | 50 | 50 | 65 | 60 | 50 |
| Blackgrass | 60 | 60 | 70 | 50 | 50 | 60 | 30 | 50 | 50 | 50 | 80 | 85 | 50 | 50 | 100 | 70 | 50 | 60 | 60 | 98 | 98 | 100 | 100 | 60 | 30 | 80 | 80 | 30 | 50 |
| Blk nightshade | — | — | — | — | — | — | — | — | — | — | — | — | — | — | — | — | — | — | — | — | 95 | — | — | — | — | — | — | — | — |
| Chickweed | — | — | — | — | — | — | — | — | — | — | — | — | — | — | — | — | — | — | — | — | — | — | — | — | — | — | — | — | — |
| Common poppy | — | — | — | — | — | — | — | — | — | — | — | — | — | — | — | — | — | — | — | — | — | — | — | — | — | — | — | — | — |
| Deadnettle | — | — | — | — | — | — | — | — | — | — | — | — | — | — | — | — | — | — | — | — | 100 | — | — | — | — | — | — | — | — |
| Downy brome | — | — | — | — | — | — | — | — | — | — | — | — | — | — | — | — | — | — | — | — | 100 | — | — | — | — | — | — | — | — |
| Field violet | — | — | — | — | — | — | — | — | — | — | — | — | — | — | — | — | — | — | — | — | 100 | — | — | — | — | — | — | — | — |
| Galium | — | — | — | — | — | — | — | — | — | — | — | — | — | — | — | — | — | — | — | — | 100 | — | — | — | — | — | — | — | — |
| Green foxtail | 70 | 85 | — | 50 | 70 | 60 | 50 | 65 | 65 | 85 | 90 | 60 | 20 | 65 | 85 | 70 | 90 | 100 | 100 | 90 | 100 | 100 | 100 | 100 | 70 | 100 | 30 | 30 | 98 |
| I. Ryegrass | 80 | 65 | 45 | 20 | 60 | 60 | 30 | 60 | 60 | 60 | 55 | 60 | 10 | 70 | 70 | 70 | 50 | 50 | 40 | 100 | 100 | 100 | 90 | 50 | 60 | 85 | 55 | 30 | 50 |
| Jointed goatgra | — | — | — | — | — | — | — | — | — | — | — | — | — | — | — | — | — | — | — | — | 90 | — | — | — | — | — | — | — | — |
| Kochia | — | — | — | — | — | — | — | — | — | — | — | — | — | — | — | — | — | — | — | — | 60 | — | — | — | — | — | — | — | — |
| Lambsquarters | — | — | — | — | — | — | — | — | — | — | — | — | — | — | — | — | — | — | — | — | 100 | — | — | — | — | — | — | — | — |
| LS canarygrass | — | — | — | — | — | — | — | — | — | — | — | — | — | — | — | — | — | — | — | — | 100 | — | — | — | — | — | — | — | — |
| Rape | — | — | — | — | — | — | — | — | — | — | — | — | — | — | — | — | — | — | — | — | 85 | — | — | — | — | — | — | — | — |
| Redroot pigweed | — | — | — | — | — | — | — | — | — | — | — | — | — | — | — | — | — | — | — | — | 100 | — | — | — | — | — | — | — | — |
| Russian thistle | — | — | — | — | — | — | — | — | — | — | — | — | — | — | — | — | — | — | — | — | 50 | — | — | — | — | — | — | — | — |
| Scentless chamo | — | — | — | — | — | — | — | — | — | — | — | — | — | — | — | — | — | — | — | — | — | — | — | — | — | — | — | — | — |
| Spring Barley | — | — | — | — | — | — | — | — | — | — | — | — | — | — | — | — | — | — | — | — | 85 | — | — | — | — | — | — | — | — |
| Spring Wheat | — | — | — | — | — | — | — | — | — | — | — | — | — | — | — | — | — | — | — | — | 100 | — | — | — | — | — | — | — | — |
| Sugar beet | — | — | — | — | — | — | — | — | — | — | — | — | — | — | — | — | — | — | — | — | 65 | — | — | — | — | — | — | — | — |
| Sunflower | — | — | — | — | — | — | — | — | — | — | — | — | — | — | — | — | — | — | — | — | 60 | — | — | — | — | — | — | — | — |
| Wheat (winter) | 40 | 20 | 30 | 50 | 30 | 70 | 50 | 40 | 40 | 40 | 70 | 30 | 30 | 30 | 50 | 60 | 30 | 50 | 10 | 60 | 95 | 75 | — | 70 | 40 | 50 | 60 | 50 | 50 |

TABLE E-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Wild buckwheat | — | — | — | — | — | — | — | — | — | — | — | — | — | — | — | — | — | — | — | — | 100 | — | — | — | — | — | — | — | — |
| Wild mustard | — | — | — | — | — | — | — | — | — | — | — | — | — | — | — | — | — | — | — | — | 70 | — | — | — | — | — | — | — | — |
| Wild oat | 30 | 40 | 45 | 40 | 50 | 80 | 50 | 55 | 40 | 60 | 70 | 60 | 40 | 70 | 70 | 60 | 50 | 60 | 30 | 55 | 100 | 90 | 65 | 70 | 70 | 65 | 70 | 50 | 60 |
| Windgrass | — | — | — | — | — | — | — | — | — | — | — | — | — | — | — | — | — | — | — | — | 100 | — | — | — | — | — | — | — | — |

| | COMPOUND | | | | | | | | | | | | | | | | | | | | | | | | | | |
|---|---|---|---|---|---|---|---|---|---|---|---|---|---|---|---|---|---|---|---|---|---|---|---|---|---|---|---|
| Rate 500 g/ha | 277 | 281 | 282 | 283 | 284 | 285 | 288 | 290 | 291 | 293 | 297 | 309 | 315 | 317 | 328 | 340 | 341 | 350 | 351 | 353 | 354 | 369 | 370 | 371 | 372 | 375 | 388 |
| Preemergence | | | | | | | | | | | | | | | | | | | | | | | | | | | |
| Annual bluegras | — | — | — | — | — | — | — | — | — | — | — | — | — | — | — | — | — | — | — | — | — | — | — | — | — | — | — |
| Barley (winter) | 65 | 70 | 50 | 75 | 30 | 10 | 5 | 60 | 30 | 50 | 55 | 20 | 80 | 70 | 50 | 40 | 60 | 25 | 80 | 30 | 40 | 50 | 70 | 70 | 70 | 30 | 70 |
| Blackgrass | 70 | — | 60 | 60 | — | 55 | 50 | 70 | 40 | 50 | 20 | 60 | 85 | 60 | 50 | 60 | 60 | 60 | 100 | 55 | 30 | 70 | 100 | 100 | 100 | 65 | 40 |
| Blk nightshade | — | — | — | — | — | — | — | — | — | — | — | — | — | — | — | — | — | — | — | — | — | — | — | — | — | — | — |
| Chickweed | — | — | — | — | — | — | — | — | — | — | — | — | — | — | — | — | — | — | — | — | — | — | — | — | — | — | — |
| Common poppy | — | — | — | — | — | — | — | — | — | — | — | — | — | — | — | — | — | — | — | — | — | — | — | — | — | — | — |
| Deadnettle | — | — | — | — | — | — | — | — | — | — | — | — | — | — | — | — | — | — | — | — | — | — | — | — | — | — | — |
| Downy brome | — | — | — | — | — | — | — | — | — | — | — | — | — | — | — | — | — | — | — | — | — | — | — | — | — | — | — |
| Field violet | — | — | — | — | — | — | — | — | — | — | — | — | — | — | — | — | — | — | — | — | — | — | — | — | — | — | — |
| Galium | — | — | — | — | — | — | — | — | — | — | — | — | — | — | — | — | — | — | — | — | — | — | — | — | — | — | — |
| Green foxtail | 100 | 100 | 100 | 100 | 100 | 60 | 60 | 70 | 85 | 60 | 60 | 100 | 100 | 100 | 85 | 60 | 55 | 85 | 85 | 100 | 100 | 85 | 100 | 85 | 100 | 70 | 85 |
| I. Ryegrass | 95 | 60 | 70 | 90 | 70 | 70 | 50 | 70 | 100 | 50 | 50 | 60 | 85 | 95 | 60 | 60 | 55 | 85 | 60 | 90 | 90 | 65 | 90 | 90 | 85 | 65 | 60 |
| Jointed goatgra | — | — | — | — | — | — | — | — | — | — | — | — | — | — | — | — | — | — | — | — | — | — | — | — | — | — | — |
| Kochia | — | — | — | — | — | — | — | — | — | — | — | — | — | — | — | — | — | — | — | — | — | — | — | — | — | — | — |
| Lambsquarters | — | — | — | — | — | — | — | — | — | — | — | — | — | — | — | — | — | — | — | — | — | — | — | — | — | — | — |
| LS canarygrass | — | — | — | — | — | — | — | — | — | — | — | — | — | — | — | — | — | — | — | — | — | — | — | — | — | — | — |
| Rape | — | — | — | — | — | — | — | — | — | — | — | — | — | — | — | — | — | — | — | — | — | — | — | — | — | — | — |
| Redroot pigweed | — | — | — | — | — | — | — | — | — | — | — | — | — | — | — | — | — | — | — | — | — | — | — | — | — | — | — |
| Russian thistle | — | — | — | — | — | — | — | — | — | — | — | — | — | — | — | — | — | — | — | — | — | — | — | — | — | — | — |
| Scentless chamo | — | — | — | — | — | — | — | — | — | — | — | — | — | — | — | — | — | — | — | — | — | — | — | — | — | — | — |
| Spring Barley | — | — | — | — | — | — | — | — | — | — | — | — | — | — | — | — | — | — | — | — | — | — | — | — | — | — | — |
| Spring Wheat | — | — | — | — | — | — | — | — | — | — | — | — | — | — | — | — | — | — | — | — | — | — | — | — | — | — | — |
| Sugar beet | — | — | — | — | — | — | — | — | — | — | — | — | — | — | — | — | — | — | — | — | — | — | — | — | — | — | — |
| Sunflower | — | — | — | — | — | — | — | — | — | — | — | — | — | — | — | — | — | — | — | — | — | — | — | — | — | — | — |
| Wheat (winter) | 10 | 65 | 60 | 65 | 70 | 25 | 30 | 30 | 50 | 55 | 60 | 65 | 85 | 60 | 70 | 50 | 50 | 50 | 70 | 60 | 60 | 55 | 60 | 65 | 70 | 50 | 60 |
| Wild buckwheat | — | — | — | — | — | — | — | — | — | — | — | — | — | — | — | — | — | — | — | — | — | — | — | — | — | — | — |
| Wild mustard | — | — | — | — | — | — | — | — | — | — | — | — | — | — | — | — | — | — | — | — | — | — | — | — | — | — | — |
| Wild oat | 65 | 65 | 70 | 50 | 60 | 20 | 30 | 70 | 50 | 50 | 60 | 50 | 70 | 70 | 50 | 50 | 70 | 65 | 80 | 85 | 40 | 70 | 90 | 90 | 80 | 70 | 30 |
| Windgrass | — | — | — | — | — | — | — | — | — | — | — | — | — | — | — | — | — | — | — | — | — | — | — | — | — | — | — |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 4 | 18 | 30 | 38 | 40 | 46 | 67 | 75 | 86 | 88 | 93 | 94 | 98 | 103 | 105 | 107 | 108 | 109 | 110 | 111 | 112 | 113 | 114 | 115 | 116 | 117 | 118 | 119 | 123 |
| Postemergence | | | | | | | | | | | | | | | | | | | | | | | | | | | | | |
| Annual bluegras | — | — | — | — | — | — | — | — | — | — | 50 | — | — | — | — | 50 | 50 | 10 | — | — | — | — | 30 | — | 70 | — | — | — | — |
| Barley (winter) | — | — | — | — | — | — | — | — | — | — | 0 | — | — | — | — | 10 | 15 | 20 | — | — | — | — | 10 | — | 10 | — | — | — | — |
| Blackgrass | — | — | — | — | — | — | — | — | — | — | 40 | — | — | — | — | 85 | 10 | 10 | — | — | — | — | 20 | — | 80 | — | — | — | — |
| Blk nightshade | — | — | — | — | — | — | — | — | — | — | 50 | — | — | — | — | 60 | 50 | 40 | — | — | — | — | 40 | — | 50 | — | — | — | — |
| Chickweed | — | — | — | — | — | — | — | — | — | — | 0 | — | — | — | — | 0 | 0 | 0 | — | — | — | — | 0 | — | 20 | — | — | — | — |

TABLE E-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Common poppy | — | — | — | — | — | — | — | — | — | — | 0 | — | — | — | — | 5 | 0 | 10 | — | — | — | — | 10 | — | 0 | — | — | — | — |
| Deadnettle | — | — | — | — | — | — | — | — | — | — | 0 | — | — | — | — | 50 | 30 | 30 | — | — | — | — | 10 | — | 20 | — | — | — | — |
| Downy brortie | — | — | — | — | — | — | — | — | — | — | 0 | — | — | — | — | 0 | 0 | 0 | — | — | — | — | 0 | — | 30 | — | — | — | — |
| Field violet | — | — | — | — | — | — | — | — | — | — | 0 | — | — | — | — | 0 | 20 | 20 | — | — | — | — | 0 | — | 0 | — | — | — | — |
| Galium | — | — | — | — | — | — | — | — | — | — | 0 | — | — | — | — | 30 | 50 | 30 | — | — | — | — | 50 | — | 40 | — | — | — | — |
| Green foxtail | — | — | — | — | — | — | — | — | — | — | 0 | — | — | — | — | 85 | 75 | 65 | — | — | — | — | 50 | — | 75 | — | — | — | — |
| I. Ryegrass | — | — | — | — | — | — | — | — | — | — | 0 | — | — | — | — | 30 | 40 | 10 | — | — | — | — | 20 | — | 70 | — | — | — | — |
| Jointed goatgra | — | — | — | — | — | — | — | — | — | — | 0 | — | — | — | — | 10 | 10 | 5 | — | — | — | — | 5 | — | 40 | — | — | — | — |
| Kochia | — | — | — | — | — | — | — | — | — | — | 0 | — | — | — | — | 15 | 30 | 30 | — | — | — | — | 30 | — | 0 | — | — | — | — |
| Lambsquarters | — | — | — | — | — | — | — | — | — | — | 0 | — | — | — | — | 5 | 20 | 30 | — | — | — | — | 30 | — | 0 | — | — | — | — |
| LS canarygrass | — | — | — | — | — | — | — | — | — | — | 0 | — | — | — | — | 60 | 70 | 50 | — | — | — | — | 30 | — | 40 | — | — | — | — |
| Rape | — | — | — | — | — | — | — | — | — | — | 0 | — | — | — | — | 50 | 50 | 50 | — | — | — | — | 50 | — | 0 | — | — | — | — |
| Redroot pigweed | — | — | — | — | — | — | — | — | — | — | 0 | — | — | — | — | 20 | 30 | 15 | — | — | — | — | 10 | — | 0 | — | — | — | — |
| Russian thistle | — | — | — | — | — | — | — | — | — | — | 0 | — | — | — | — | 0 | 0 | 0 | — | — | — | — | 0 | — | 0 | — | — | — | — |
| Scentless chamo | — | — | — | — | — | — | — | — | — | — | 0 | — | — | — | — | 10 | 10 | 0 | — | — | — | — | 0 | — | 0 | — | — | — | — |
| Spring Barley | — | — | — | — | — | — | — | — | — | — | 0 | — | — | — | — | 30 | 25 | 20 | — | — | — | — | 30 | — | 10 | — | — | — | — |
| Spring Wheat | — | — | — | — | — | — | — | — | — | — | 0 | — | — | — | — | 10 | 20 | 20 | — | — | — | — | 20 | — | 10 | — | — | — | — |
| Sugar beet | — | — | — | — | — | — | — | — | — | — | 0 | — | — | — | — | 40 | 20 | 35 | — | — | — | — | 55 | — | 0 | — | — | — | — |
| Sunflower | — | — | — | — | — | — | — | — | — | — | 0 | — | — | — | — | 30 | 35 | 30 | — | — | — | — | 10 | — | 0 | — | — | — | — |
| Veronica hedera | — | — | — | — | — | — | — | — | — | — | 0 | — | — | — | — | 10 | 40 | 50 | — | — | — | — | 50 | — | 0 | — | — | — | — |
| Wheat (winter) | 0 | 55 | 0 | 10 | 0 | 60 | 20 | 60 | 55 | 0 | 0 | 0 | 50 | 0 | 10 | 0 | 40 | 75 | 0 | 0 | 10 | 70 | 60 | 10 | 45 | 25 | 65 | 20 | 55 |
| Wild buckwheat | — | — | — | — | — | — | — | — | — | — | 0 | — | — | — | — | 10 | 10 | 20 | — | — | — | — | 30 | — | 0 | — | — | — | — |
| Wild mustard | — | — | — | — | — | — | — | — | — | — | 10 | — | — | — | — | 40 | 80 | 50 | — | — | — | — | 50 | — | 40 | — | — | — | — |
| Wild oat | — | — | — | — | — | — | — | — | — | — | 0 | — | — | — | — | 0 | 20 | 0 | — | — | — | — | 0 | — | 30 | — | — | — | — |
| Windgrass | — | — | — | — | — | — | — | — | — | — | 80 | — | — | — | — | 90 | 100 | 90 | — | — | — | — | 85 | — | 75 | — | — | — | — |
| | COMPOUND | | | | | | | | | | | | | | | | | | | | | | | | | | | | |
| Rate 250 g/ha | 131 | 132 | 137 | 138 | 146 | 147 | 148 | 157 | 158 | 161 | 162 | 163 | 165 | 167 | 169 | 170 | 172 | 173 | 174 | 176 | 191 | 199 | 201 | 202 | 204 | 207 | 208 | 211 | 212 |
| Postemergence | | | | | | | | | | | | | | | | | | | | | | | | | | | | | |
| Annual bluegras | 40 | — | — | 10 | 10 | — | — | — | — | — | — | — | — | — | — | — | — | — | — | — | — | — | — | — | — | — | — | — | — |
| Barley (winter) | 0 | — | — | 0 | 10 | — | — | — | — | — | — | — | — | — | — | — | — | — | — | — | — | — | — | — | — | — | — | — | — |
| Blackgrass | 60 | — | — | 0 | 15 | — | — | — | — | — | — | — | — | — | — | — | — | — | — | — | — | — | — | — | — | — | — | — | — |
| Blk nightshade | 60 | — | — | 60 | 40 | — | — | — | — | — | — | — | — | — | — | — | — | — | — | — | — | — | — | — | — | — | — | — | — |
| Chickweed | 20 | — | — | 0 | 0 | — | — | — | — | — | — | — | — | — | — | — | — | — | — | — | — | — | — | — | — | — | — | — | — |
| Common poppy | 0 | — | — | 40 | 0 | — | — | — | — | — | — | — | — | — | — | — | — | — | — | — | — | — | — | — | — | — | — | — | — |
| Deadnettle | 30 | — | — | 50 | — | — | — | — | — | — | — | — | — | — | — | — | — | — | — | — | — | — | — | — | — | — | — | — | — |
| Downy brome | 50 | — | — | 2 | 0 | — | — | — | — | — | — | — | — | — | — | — | — | — | — | — | — | — | — | — | — | — | — | — | — |
| Field violet | 0 | — | — | 30 | 0 | — | — | — | — | — | — | — | — | — | — | — | — | — | — | — | — | — | — | — | — | — | — | — | — |
| Galium | 0 | — | — | 50 | 15 | — | — | — | — | — | — | — | — | — | — | — | — | — | — | — | — | — | — | — | — | — | — | — | — |
| Green foxtail | 50 | — | — | 70 | 70 | — | — | — | — | — | — | — | — | — | — | — | — | — | — | — | — | — | — | — | — | — | — | — | — |
| I. Ryegrass | 30 | — | — | 0 | 10 | — | — | — | — | — | — | — | — | — | — | — | — | — | — | — | — | — | — | — | — | — | — | — | — |
| Jointed goatgra | 0 | — | — | 0 | 10 | — | — | — | — | — | — | — | — | — | — | — | — | — | — | — | — | — | — | — | — | — | — | — | — |
| Kochia | 0 | — | — | 0 | 10 | — | — | — | — | — | — | — | — | — | — | — | — | — | — | — | — | — | — | — | — | — | — | — | — |
| Lambsauarters | 0 | — | — | 30 | 10 | — | — | — | — | — | — | — | — | — | — | — | — | — | — | — | — | — | — | — | — | — | — | — | — |
| LS canarygrass | 20 | — | — | 10 | 30 | — | — | — | — | — | — | — | — | — | — | — | — | — | — | — | — | — | — | — | — | — | — | — | — |
| Rape | 0 | — | — | 0 | 50 | — | — | — | — | — | — | — | — | — | — | — | — | — | — | — | — | — | — | — | — | — | — | — | — |
| Redroot pigweed | 0 | — | — | 10 | 10 | — | — | — | — | — | — | — | — | — | — | — | — | — | — | — | — | — | — | — | — | — | — | — | — |
| Russian thistle | 0 | — | — | 0 | 0 | — | — | — | — | — | — | — | — | — | — | — | — | — | — | — | — | — | — | — | — | — | — | — | — |
| Scentless chamo | 20 | — | — | 0 | 10 | — | — | — | — | — | — | — | — | — | — | — | — | — | — | — | — | — | — | — | — | — | — | — | — |

TABLE E-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Spring Barley | 0 | — | — | 5 | 10 | — | — | — | — | — | — | — | — | — | — | — | — | — | — | — | — | — | — | — | — | — | — | — | — |
| Spring Wheat | 0 | — | — | 0 | 10 | — | — | — | — | — | — | — | — | — | — | — | — | — | — | — | — | — | — | — | — | — | — | — | — |
| Sugar beet | 0 | — | — | 10 | 30 | — | — | — | — | — | — | — | — | — | — | — | — | — | — | — | — | — | — | — | — | — | — | — | — |
| Sunflower | 0 | — | — | 0 | 40 | — | — | — | — | — | — | — | — | — | — | — | — | — | — | — | — | — | — | — | — | — | — | — | — |
| Veronica hedera | 0 | — | — | — | 40 | — | — | — | — | — | — | — | — | — | — | — | — | — | — | — | — | — | — | — | — | — | — | — | — |
| Wheat (winter) | 0 | 50 | 20 | 80 | 60 | 80 | 80 | 20 | 40 | 30 | 30 | 40 | 40 | 30 | 40 | — | — | — | — | — | — | — | — | — | — | — | — | — | — |
| Wild buckwheat | 0 | — | — | 0 | 10 | — | — | — | — | — | — | — | — | — | — | — | — | — | — | — | — | — | — | — | — | — | — | — | — |
| Wild mustard | 0 | — | — | 0 | 40 | — | — | — | — | — | — | — | — | — | — | — | — | — | — | — | — | — | — | — | — | — | — | — | — |
| Wild oat | 20 | — | — | 0 | 0 | — | — | — | — | — | — | — | — | — | — | — | — | — | — | — | — | — | — | — | — | — | — | — | — |
| Windgrass | 90 | — | — | 95 | 95 | — | — | — | — | — | — | — | — | — | — | — | — | — | — | — | — | — | — | — | — | — | — | — | — |
| | COMPOUND | | | | | | | | | | | | | | | | | | | | | | | | | | | | |
| Rate 250 g/ha | 218 | 219 | 225 | 232 | 233 | 236 | 238 | 241 | 242 | 243 | 246 | 267 | 269 | 271 | 273 | 274 | 276 | 277 | 281 | 282 | 283 | 284 | 285 | 287 | 288 | 290 | 291 | 293 | 295 |
| Postemergence | | | | | | | | | | | | | | | | | | | | | | | | | | | | | |
| Annual bluegras | — | — | — | — | — | — | — | — | 10 | — | — | — | — | — | — | — | — | — | — | — | — | — | — | — | — | — | — | — | — |
| Barley (winter) | — | — | — | — | — | — | — | — | 10 | — | — | — | — | — | — | — | — | — | — | — | — | — | — | — | — | — | — | — | — |
| Blackgrass | — | — | — | — | — | — | — | — | 10 | — | — | — | — | — | — | — | — | — | — | — | — | — | — | — | — | — | — | — | — |
| Blk nightshade | — | — | — | — | — | — | — | — | 50 | — | — | — | — | — | — | — | — | — | — | — | — | — | — | — | — | — | — | — | — |
| Chickweed | — | — | — | — | — | — | — | — | 0 | — | — | — | — | — | — | — | — | — | — | — | — | — | — | — | — | — | — | — | — |
| Common poppy | — | — | — | — | — | — | — | — | 20 | — | — | — | — | — | — | — | — | — | — | — | — | — | — | — | — | — | — | — | — |
| Deadnettle | — | — | — | — | — | — | — | — | 10 | — | — | — | — | — | — | — | — | — | — | — | — | — | — | — | — | — | — | — | — |
| Downy brome | — | — | — | — | — | — | — | — | 30 | — | — | — | — | — | — | — | — | — | — | — | — | — | — | — | — | — | — | — | — |
| Field violet | — | — | — | — | — | — | — | — | 0 | — | — | — | — | — | — | — | — | — | — | — | — | — | — | — | — | — | — | — | — |
| Galium | — | — | — | — | — | — | — | — | 30 | — | — | — | — | — | — | — | — | — | — | — | — | — | — | — | — | — | — | — | — |
| Green foxtail | — | — | — | — | — | — | — | — | 60 | — | — | — | — | — | — | — | — | — | — | — | — | — | — | — | — | — | — | — | — |
| I. Ryegrass | — | — | — | — | — | — | — | — | 70 | — | — | — | — | — | — | — | — | — | — | — | — | — | — | — | — | — | — | — | — |
| Jointed goatgra | — | — | — | — | — | — | — | — | 0 | — | — | — | — | — | — | — | — | — | — | — | — | — | — | — | — | — | — | — | — |
| Kochia | — | — | — | — | — | — | — | — | 0 | — | — | — | — | — | — | — | — | — | — | — | — | — | — | — | — | — | — | — | — |
| Lambsquarters | — | — | — | — | — | — | — | — | 0 | — | — | — | — | — | — | — | — | — | — | — | — | — | — | — | — | — | — | — | — |
| LS canarygrass | — | — | — | — | — | — | — | — | 15 | — | — | — | — | — | — | — | — | — | — | — | — | — | — | — | — | — | — | — | — |
| Rape | — | — | — | — | — | — | — | — | 0 | — | — | — | — | — | — | — | — | — | — | — | — | — | — | — | — | — | — | — | — |
| Redroot pigweed | — | — | — | — | — | — | — | — | 0 | — | — | — | — | — | — | — | — | — | — | — | — | — | — | — | — | — | — | — | — |
| Russian thistle | — | — | — | — | — | — | — | — | 0 | — | — | — | — | — | — | — | — | — | — | — | — | — | — | — | — | — | — | — | — |
| Scentless chamo | — | — | — | — | — | — | — | — | 0 | — | — | — | — | — | — | — | — | — | — | — | — | — | — | — | — | — | — | — | — |
| Spring Barley | — | — | — | — | — | — | — | — | 20 | — | — | — | — | — | — | — | — | — | — | — | — | — | — | — | — | — | — | — | — |
| Spring Wheat | — | — | — | — | — | — | — | — | 10 | — | — | — | — | — | — | — | — | — | — | — | — | — | — | — | — | — | — | — | — |
| Sugar beet | — | — | — | — | — | — | — | — | 40 | — | — | — | — | — | — | — | — | — | — | — | — | — | — | — | — | — | — | — | — |
| Sunflower | — | — | — | — | — | — | — | — | 0 | — | — | — | — | — | — | — | — | — | — | — | — | — | — | — | — | — | — | — | — |
| Veronica hedera | — | — | — | — | — | — | — | — | — | — | — | — | — | — | — | — | — | — | — | — | — | — | — | — | — | — | — | — | — |
| Wheat (winter) | 70 | 50 | 70 | 40 | 50 | 0 | 60 | 60 | 10 | 75 | 0 | 70 | 50 | 10 | 30 | 30 | 10 | 0 | 55 | 20 | 60 | 60 | 20 | 50 | 35 | 50 | 30 | 30 | 50 |
| Wild buckwheat | — | — | — | — | — | — | — | — | 10 | — | — | — | — | — | — | — | — | — | — | — | — | — | — | — | — | — | — | — | — |
| Wild mustard | — | — | — | — | — | — | — | — | 20 | — | — | — | — | — | — | — | — | — | — | — | — | — | — | — | — | — | — | — | — |
| Wild oat | — | — | — | — | — | — | — | — | 20 | — | — | — | — | — | — | — | — | — | — | — | — | — | — | — | — | — | — | — | — |
| Windgrass | — | — | — | — | — | — | — | — | 95 | — | — | — | — | — | — | — | — | — | — | — | — | — | — | — | — | — | — | — | — |

TABLE E-continued

| | COMPOUND | | | | | | | | | | | | | | | | | | | | | |
|---|---|---|---|---|---|---|---|---|---|---|---|---|---|---|---|---|---|---|---|---|---|---|
| Rate 250 g/ha | 297 | 299 | 309 | 310 | 314 | 315 | 317 | 328 | 340 | 341 | 350 | 351 | 353 | 354 | 367 | 369 | 370 | 371 | 372 | 375 | 387 | 388 |
| Postemergence | | | | | | | | | | | | | | | | | | | | | | |
| Annual bluegras | — | — | — | — | — | — | — | — | — | — | — | — | — | — | — | — | — | — | — | — | — | — |
| Barley (winter) | — | — | — | — | — | — | — | — | — | — | — | — | — | — | — | — | — | — | — | — | — | — |
| Blackgrass | — | — | — | — | — | — | — | — | — | — | — | — | — | — | — | — | — | — | — | — | — | — |
| Blk nightshade | — | — | — | — | — | — | — | — | — | — | — | — | — | — | — | — | — | — | — | — | — | — |
| Chickweed | — | — | — | — | — | — | — | — | — | — | — | — | — | — | — | — | — | — | — | — | — | — |
| Common poppy | — | — | — | — | — | — | — | — | — | — | — | — | — | — | — | — | — | — | — | — | — | — |
| Deadnettle | — | — | — | — | — | — | — | — | — | — | — | — | — | — | — | — | — | — | — | — | — | — |
| Downy brome | — | — | — | — | — | — | — | — | — | — | — | — | — | — | — | — | — | — | — | — | — | — |
| Field violet | — | — | — | — | — | — | — | — | — | — | — | — | — | — | — | — | — | — | — | — | — | — |
| Galium | — | — | — | — | — | — | — | — | — | — | — | — | — | — | — | — | — | — | — | — | — | — |
| Green foxtail | — | — | — | — | — | — | — | — | — | — | — | — | — | — | — | — | — | — | — | — | — | — |
| I. Ryegrass | — | — | — | — | — | — | — | — | — | — | — | — | — | — | — | — | — | — | — | — | — | — |
| Jointed goatgra | — | — | — | — | — | — | — | — | — | — | — | — | — | — | — | — | — | — | — | — | — | — |
| Kochia | — | — | — | — | — | — | — | — | — | — | — | — | — | — | — | — | — | — | — | — | — | — |
| Lambsquarters | — | — | — | — | — | — | — | — | — | — | — | — | — | — | — | — | — | — | — | — | — | — |
| LS canarygrass | — | — | — | — | — | — | — | — | — | — | — | — | — | — | — | — | — | — | — | — | — | — |
| Rape | — | — | — | — | — | — | — | — | — | — | — | — | — | — | — | — | — | — | — | — | — | — |
| Redroot pigweed | — | — | — | — | — | — | — | — | — | — | — | — | — | — | — | — | — | — | — | — | — | — |
| Russian thistle | — | — | — | — | — | — | — | — | — | — | — | — | — | — | — | — | — | — | — | — | — | — |
| Scentless chamo | — | — | — | — | — | — | — | — | — | — | — | — | — | — | — | — | — | — | — | — | — | — |
| Spring Barley | — | — | — | — | — | — | — | — | — | — | — | — | — | — | — | — | — | — | — | — | — | — |
| Spring Wheat | — | — | — | — | — | — | — | — | — | — | — | — | — | — | — | — | — | — | — | — | — | — |
| Sugar beet | — | — | — | — | — | — | — | — | — | — | — | — | — | — | — | — | — | — | — | — | — | — |
| Sunflower | — | — | — | — | — | — | — | — | — | — | — | — | — | — | — | — | — | — | — | — | — | — |
| Veronica hedera | — | — | — | — | — | — | — | — | — | — | — | — | — | — | — | — | — | — | — | — | — | — |
| Wheat (winter) | 50 | 70 | 50 | 80 | 70 | 80 | 95 | 65 | 30 | 70 | 30 | 70 | 30 | 40 | 40 | 60 | 80 | 65 | 70 | 35 | 30 | 30 |
| Wild buckwheat | — | — | — | — | — | — | — | — | — | — | — | — | — | — | — | — | — | — | — | — | — | — |
| Wild mustard | — | — | — | — | — | — | — | — | — | — | — | — | — | — | — | — | — | — | — | — | — | — |
| Wild oat | — | — | — | — | — | — | — | — | — | — | — | — | — | — | — | — | — | — | — | — | — | — |
| Windgrass | — | — | — | — | — | — | — | — | — | — | — | — | — | — | — | — | — | — | — | — | — | — |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate 250 g/ha | 4 | 18 | 30 | 38 | 40 | 46 | 67 | 75 | 86 | 88 | 93 | 94 | 98 | 103 | 105 | 107 | 108 | 109 | 110 | 111 | 112 | 113 | 114 | 115 | 116 | 117 | 118 | 119 | 123 |
| Preemergence | | | | | | | | | | | | | | | | | | | | | | | | | | | | | |
| Annual bluegras | — | — | — | — | — | — | — | — | — | — | 65 | — | — | — | — | 85 | 60 | 90 | — | — | — | — | 50 | — | 85 | — | — | — | — |
| Barley (winter) | 10 | 20 | 10 | 0 | 30 | 30 | 20 | 10 | 70 | 0 | 50 | 40 | 10 | 30 | 0 | 15 | 10 | 20 | 5 | 0 | 10 | 85 | 10 | 10 | 70 | 30 | 65 | 10 | 30 |
| Blackgrass | 50 | 10 | 30 | 45 | 40 | 40 | 10 | 20 | 60 | 50 | 75 | 60 | 20 | 30 | 50 | 80 | 90 | 65 | 60 | 0 | 50 | 85 | 50 | 30 | 45 | 60 | 80 | 50 | 30 |
| Blk nightshade | — | — | — | — | — | — | — | — | — | — | 80 | — | — | — | — | 95 | 90 | 90 | — | — | — | — | 60 | — | 90 | — | — | — | — |
| Chickweed | — | — | — | — | — | — | — | — | — | — | 100 | — | — | — | 85 | 50 | 30 | — | — | — | — | — | 50 | — | 100 | — | — | — | — |
| Common poppy | — | — | — | — | — | — | — | — | — | — | — | — | — | — | — | — | — | — | — | — | — | — | — | — | — | — | — | — | — |
| Deadnettle | — | — | — | — | — | — | — | — | — | — | 85 | — | — | — | — | 85 | 40 | 30 | — | — | — | — | 20 | — | 80 | — | — | — | — |
| Downy brome | — | — | — | — | — | — | — | — | — | — | 20 | — | — | — | — | 75 | 70 | 80 | — | — | — | — | 60 | — | 50 | — | — | — | — |
| Field violet | — | — | — | — | — | — | — | — | — | — | 30 | — | — | — | — | 20 | 20 | 15 | — | — | — | — | 0 | — | 40 | — | — | — | — |

TABLE E-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Galium | — | — | — | — | — | — | — | — | — | — | 100 | — | — | — | — | 100 | 95 | 100 | — | — | — | — | 60 | — | 100 | — | — | — | — |
| Green foxtail | 55 | 30 | 30 | 90 | 70 | 60 | 30 | 60 | 40 | 60 | — | 80 | 60 | 70 | 90 | 95 | 90 | 100 | 85 | 10 | 50 | 85 | 100 | 65 | 100 | 80 | 55 | 60 | 20 |
| I. Ryegrass | 20 | 40 | 20 | 20 | 30 | 50 | 40 | 20 | 30 | 10 | 100 | 40 | 50 | 50 | 30 | 95 | 95 | 100 | 20 | 0 | 20 | 100 | 100 | 45 | 60 | 85 | 60 | 60 | 40 |
| Jointed goatgra | — | — | — | — | — | — | — | — | — | — | 60 | — | — | — | — | 50 | 60 | 65 | — | — | — | — | 65 | — | 100 | — | — | — | — |
| Kochia | — | — | — | — | — | — | — | — | — | — | 20 | — | — | — | — | 80 | 40 | 50 | — | — | — | — | 30 | — | 85 | — | — | — | — |
| Lambsquarters | — | — | — | — | — | — | — | — | — | — | 100 | — | — | — | — | 100 | 90 | 100 | — | — | — | — | 100 | — | 100 | — | — | — | — |
| LS canarygrass | — | — | — | — | — | — | — | — | — | — | 60 | — | — | — | — | 80 | 70 | 60 | — | — | — | — | 60 | — | 80 | — | — | — | — |
| Rape | — | — | — | — | — | — | — | — | — | — | 10 | — | — | — | — | 100 | 50 | 55 | — | — | — | — | 20 | — | 100 | — | — | — | — |
| Redroot pigweed | — | — | — | — | — | — | — | — | — | — | 90 | — | — | — | — | 100 | 90 | 100 | — | — | — | — | 65 | — | 100 | — | — | — | — |
| Russian thistle | — | — | — | — | — | — | — | — | — | — | 0 | — | — | — | — | 10 | 15 | 0 | — | — | — | — | 0 | — | 0 | — | — | — | — |
| Scentless chamo | — | — | — | — | — | — | — | — | — | — | — | — | — | — | — | 90 | 80 | 30 | — | — | — | — | 30 | — | — | — | — | — | — |
| Spring Barley | — | — | — | — | — | — | — | — | — | — | 60 | — | — | — | — | 70 | 5 | 20 | — | — | — | — | 0 | — | 75 | — | — | — | — |
| Spring Wheat | — | — | — | — | — | — | — | — | — | — | 80 | — | — | — | — | 85 | 30 | 40 | — | — | — | — | 10 | — | 80 | — | — | — | — |
| Sugar beet | — | — | — | — | — | — | — | — | — | — | 5 | — | — | — | — | 100 | 60 | 60 | — | — | — | — | 40 | — | 85 | — | — | — | — |
| Sunflower | — | — | — | — | — | — | — | — | — | — | 20 | — | — | — | — | 40 | 10 | 10 | — | — | — | — | 0 | — | 40 | — | — | — | — |
| Wheat (winter) | 0 | 0 | 0 | 0 | 20 | 40 | 10 | 10 | 60 | 0 | 100 | 30 | 40 | 20 | 0 | 40 | 10 | 55 | 0 | 0 | 0 | 60 | 0 | 5 | 30 | 90 | 50 | 30 | 10 |
| Wild buckwheat | — | — | — | — | — | — | — | — | — | — | 40 | — | — | — | — | 95 | 80 | 85 | — | — | — | — | 50 | — | 60 | — | — | — | — |
| Wild mustard | — | — | — | — | — | — | — | — | — | — | 80 | — | — | — | — | 100 | 65 | 85 | — | — | — | — | 40 | — | 85 | — | — | — | — |
| Wild oat | 20 | 20 | 10 | 20 | 40 | 55 | 30 | 0 | 70 | 10 | 60 | 40 | 46 | 40 | 50 | 80 | 75 | 50 | 10 | 0 | 0 | 60 | 70 | 40 | 95 | 60 | 70 | 30 | 50 |
| Windgrass | — | — | — | — | — | — | — | — | — | — | 100 | — | — | — | — | 100 | 100 | 100 | — | — | — | — | 100 | — | 100 | — | — | — | — |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 131 | 132 | 137 | 138 | 146 | 147 | 148 | 157 | 158 | 161 | 162 | 163 | 165 | 167 | 169 | 170 | 172 | 173 | 174 | 176 | 191 | 199 | 201 | 202 | 204 | 207 | 208 | 211 | 212 |
| Preemergence | | | | | | | | | | | | | | | | | | | | | | | | | | | | | |
| Annual bluegras | 80 | — | — | 70 | 80 | — | — | — | — | — | — | — | — | — | — | — | — | — | — | — | — | — | — | — | — | — | — | — | — |
| Barley (winter) | 100 | 50 | 20 | 90 | 10 | 20 | 10 | 0 | 30 | 30 | 30 | 30 | 20 | 40 | 30 | 70 | 40 | 30 | 0 | 30 | 30 | 70 | 0 | 20 | 50 | 65 | 30 | 20 | 20 |
| Blackgrass | 60 | 60 | 30 | 70 | 90 | 55 | 50 | 20 | 50 | 30 | 55 | 30 | 40 | 50 | 30 | 85 | 50 | 50 | 30 | 40 | 20 | 60 | 30 | 30 | 55 | 30 | 40 | 0 | 20 |
| Blk nightshade | 85 | — | — | 95 | 10 | — | — | — | — | — | — | — | — | — | — | — | — | — | — | — | — | — | — | — | — | — | — | — | — |
| Chickweed | 100 | — | — | — | 80 | — | — | — | — | — | — | — | — | — | — | — | — | — | — | — | — | — | — | — | — | — | — | — | — |
| Common poppy | — | — | — | — | 100 | — | — | — | — | — | — | — | — | — | — | — | — | — | — | — | — | — | — | — | — | — | — | — | — |
| Deadnettle | 60 | — | — | 70 | 40 | — | — | — | — | — | — | — | — | — | — | — | — | — | — | — | — | — | — | — | — | — | — | — | — |
| Downy brome | 80 | — | — | 90 | 0 | — | — | — | — | — | — | — | — | — | — | — | — | — | — | — | — | — | — | — | — | — | — | — | — |
| Field violet | 20 | — | — | 70 | 30 | — | — | — | — | — | — | — | — | — | — | — | — | — | — | — | — | — | — | — | — | — | — | — | — |
| Galium | 50 | — | — | 70 | 50 | — | — | — | — | — | — | — | — | — | — | — | — | — | — | — | — | — | — | — | — | — | — | — | — |
| Green foxtail | 100 | 98 | 50 | 75 | 65 | 65 | 55 | 30 | 20 | 60 | 60 | 100 | 50 | 60 | 60 | 100 | 60 | 85 | 30 | 50 | 40 | 100 | 50 | 70 | 75 | 80 | 40 | 10 | 55 |
| I. Ryegrass | 100 | 100 | 50 | 80 | 60 | 55 | 30 | 20 | 50 | 60 | 50 | 30 | 60 | 30 | 75 | 70 | 30 | 35 | 0 | 50 | 0 | 70 | 50 | 30 | 50 | 40 | 50 | 0 | 60 |
| Jointed goatgra | 70 | — | — | 80 | 50 | — | — | — | — | — | — | — | — | — | — | — | — | — | — | — | — | — | — | — | — | — | — | — | — |
| Kochia | 10 | — | — | 40 | 50 | — | — | — | — | — | — | — | — | — | — | — | — | — | — | — | — | — | — | — | — | — | — | — | — |
| Lambsquarters | 100 | — | — | 100 | 100 | — | — | — | — | — | — | — | — | — | — | — | — | — | — | — | — | — | — | — | — | — | — | — | — |
| LS canarygrass | 70 | — | — | 85 | 75 | — | — | — | — | — | — | — | — | — | — | — | — | — | — | — | — | — | — | — | — | — | — | — | — |
| Rape | 75 | — | — | 95 | 80 | — | — | — | — | — | — | — | — | — | — | — | — | — | — | — | — | — | — | — | — | — | — | — | — |
| Redroot pigweed | 100 | — | — | 90 | 100 | — | — | — | — | — | — | — | — | — | — | — | — | — | — | — | — | — | — | — | — | — | — | — | — |
| Russian thistle | 0 | — | — | 20 | 0 | — | — | — | — | — | — | — | — | — | — | — | — | — | — | — | — | — | — | — | — | — | — | — | — |
| Scentless chamo | — | — | — | — | 100 | — | — | — | — | — | — | — | — | — | — | — | — | — | — | — | — | — | — | — | — | — | — | — | — |
| Spring Barley | 70 | — | — | 90 | 10 | — | — | — | — | — | — | — | — | — | — | — | — | — | — | — | — | — | — | — | — | — | — | — | — |
| Spring Wheat | 100 | — | — | 100 | 80 | — | — | — | — | — | — | — | — | — | — | — | — | — | — | — | — | — | — | — | — | — | — | — | — |
| Sugar beet | 60 | — | — | 50 | 60 | — | — | — | — | — | — | — | — | — | — | — | — | — | — | — | — | — | — | — | — | — | — | — | — |
| Sunflower | 20 | — | — | 60 | 30 | — | — | — | — | — | — | — | — | — | — | — | — | — | — | — | — | — | — | — | — | — | — | — | — |
| Wheat (winter) | 60 | 40 | 30 | 80 | 0 | 30 | 0 | 20 | 30 | 10 | 30 | 30 | 40 | 10 | 10 | 70 | 10 | 20 | 60 | 20 | 30 | 50 | 40 | 50 | 30 | 60 | 30 | 35 | 10 |

TABLE E-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Wild buckwheat | 70 | — | — | 100 | 85 | — | — | — | — | — | — | — | — | — | — | — | — | — | — | — | — | — | — | — | — | — | — | — | — |
| Wild mustard | 100 | — | — | 55 | 95 | — | — | — | — | — | — | — | — | — | — | — | — | — | — | — | — | — | — | — | — | — | — | — | — |
| Wild oat | 60 | 50 | 10 | 65 | 50 | 0 | 40 | 50 | 50 | 50 | 50 | 50 | 55 | 30 | 50 | 70 | 30 | 50 | 50 | 30 | 40 | 80 | 50 | 50 | 50 | 65 | 50 | — | 60 |
| Windgrass | 100 | — | — | 100 | 100 | — | — | — | — | — | — | — | — | — | — | — | — | — | — | — | — | — | — | — | — | — | — | — | — |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha | 218 | 219 | 225 | 232 | 233 | 236 | 238 | 241 | 242 | 243 | 246 | 267 | 269 | 271 | 273 | 274 | 276 | 277 | 281 | 282 | 283 | 284 | 286 | 287 | 288 | 290 | 291 | 293 | 295 |
| Preemergence | | | | | | | | | | | | | | | | | | | | | | | | | | | | | |
| Annual bluegras | — | — | — | — | — | — | — | — | 100 | — | — | — | — | — | — | — | — | — | — | — | — | — | — | — | — | — | — | — | — |
| Barley (winter) | 50 | 30 | 60 | 20 | 30 | 20 | 40 | 50 | 60 | 60 | 40 | 30 | 30 | 45 | 70 | 50 | 30 | 50 | 70 | 50 | 60 | 50 | 5 | 35 | 0 | 55 | 10 | 40 | 30 |
| Blackgrass | 70 | 20 | 80 | 30 | 50 | 60 | 50 | 100 | 100 | 85 | 60 | 50 | 40 | 100 | 55 | 0 | 50 | 100 | 50 | 60 | 50 | 65 | 10 | 60 | 50 | 60 | 30 | — | 10 |
| Blk nightshade | — | — | — | — | — | — | — | — | 95 | — | — | — | — | — | — | — | — | — | — | — | — | — | — | — | — | — | — | — | — |
| Chickweed | — | — | — | — | — | — | — | — | — | — | — | — | — | — | — | — | — | — | — | — | — | — | — | — | — | — | — | — | — |
| Common poppy | — | — | — | — | — | — | — | — | — | — | — | — | — | — | — | — | — | — | — | — | — | — | — | — | — | — | — | — | — |
| Deadnettle | — | — | — | — | — | — | — | — | 70 | — | — | — | — | — | — | — | — | — | — | — | — | — | — | — | — | — | — | — | — |
| Downy brome | — | — | — | — | — | — | — | — | 100 | — | — | — | — | — | — | — | — | — | — | — | — | — | — | — | — | — | — | — | — |
| Field violet | — | — | — | — | — | — | — | — | 65 | — | — | — | — | — | — | — | — | — | — | — | — | — | — | — | — | — | — | — | — |
| Galium | — | — | — | — | — | — | — | — | 100 | — | — | — | — | — | — | — | — | — | — | — | — | — | — | — | — | — | — | — | — |
| Green foxtail | 55 | 60 | 60 | 95 | 100 | 85 | 70 | 90 | 98 | 100 | 100 | 100 | 60 | 100 | 20 | 20 | 100 | 100 | 100 | 80 | 100 | 100 | 55 | 90 | 50 | 65 | 55 | 70 | 100 |
| I. Ryegrass | 60 | 55 | 90 | 40 | 40 | 20 | 50 | 70 | 98 | 85 | 80 | 50 | 50 | 100 | 30 | 20 | 60 | 75 | 60 | 70 | 70 | 85 | 40 | 60 | 30 | 60 | 70 | 50 | 50 |
| Jointed goatgra | — | — | — | — | — | — | — | — | 80 | — | — | — | — | — | — | — | — | — | — | — | — | — | — | — | — | — | — | — | — |
| Kochia | — | — | — | — | — | — | — | — | 50 | — | — | — | — | — | — | — | — | — | — | — | — | — | — | — | — | — | — | — | — |
| Lambsquarters | — | — | — | — | — | — | — | — | 100 | — | — | — | — | — | — | — | — | — | — | — | — | — | — | — | — | — | — | — | — |
| LS canarygrass | — | — | — | — | — | — | — | — | 100 | — | — | — | — | — | — | — | — | — | — | — | — | — | — | — | — | — | — | — | — |
| Rape | — | — | — | — | — | — | — | — | 60 | — | — | — | — | — | — | — | — | — | — | — | — | — | — | — | — | — | — | — | — |
| Redroot pigweed | — | — | — | — | — | — | — | — | 100 | — | — | — | — | — | — | — | — | — | — | — | — | — | — | — | — | — | — | — | — |
| Russian thistle | — | — | — | — | — | — | — | — | 30 | — | — | — | — | — | — | — | — | — | — | — | — | — | — | — | — | — | — | — | — |
| Scentless chamo | — | — | — | — | — | — | — | — | — | — | — | — | — | — | — | — | — | — | — | — | — | — | — | — | — | — | — | — | — |
| Spring Barley | — | — | — | — | — | — | — | — | 70 | — | — | — | — | — | — | — | — | — | — | — | — | — | — | — | — | — | — | — | — |
| Spring Wheat | — | — | — | — | — | — | — | — | 60 | — | — | — | — | — | — | — | — | — | — | — | — | — | — | — | — | — | — | — | — |
| Sugar beet | — | — | — | — | — | — | — | — | 50 | — | — | — | — | — | — | — | — | — | — | — | — | — | — | — | — | — | — | — | — |
| Sunflower | — | — | — | — | — | — | — | — | 70 | — | — | — | — | — | — | — | — | — | — | — | — | — | — | — | — | — | — | — | — |
| Wheat (winter) | 40 | 60 | 70 | 30 | 50 | 0 | 40 | 50 | 55 | 70 | 50 | 55 | 60 | 60 | 50 | 30 | 30 | 20 | 60 | 60 | 50 | 70 | 40 | 50 | 40 | 10 | 35 | 50 | 60 |
| Wild buckwheat | — | — | — | — | — | — | — | — | 70 | — | — | — | — | — | — | — | — | — | — | — | — | — | — | — | — | — | — | — | — |
| Wild mustard | — | — | — | — | — | — | — | — | 65 | — | — | — | — | — | — | — | — | — | — | — | — | — | — | — | — | — | — | — | — |
| Wild oat | 65 | 50 | 60 | 55 | 55 | 20 | 50 | 60 | 98 | 55 | 50 | 55 | 70 | 60 | 80 | 40 | 60 | 60 | 70 | 70 | 65 | 70 | 10 | 60 | 20 | 60 | 20 | 10 | 10 |
| Windgrass | — | — | — | — | — | — | — | — | 100 | — | — | — | — | — | — | — | — | — | — | — | — | — | — | — | — | — | — | — | — |

| | COMPOUND | | | | | | | | | | | | | | | | | | | | | |
|---|---|---|---|---|---|---|---|---|---|---|---|---|---|---|---|---|---|---|---|---|---|---|
| Rate 250 g/ha | 297 | 299 | 309 | 310 | 314 | 315 | 317 | 328 | 340 | 341 | 350 | 351 | 353 | 354 | 367 | 369 | 370 | 371 | 372 | 375 | 387 | 388 |
| Preemergence | | | | | | | | | | | | | | | | | | | | | | |
| Annual bluegras | — | — | — | — | — | — | — | — | — | — | — | — | — | — | — | — | — | — | — | — | — | — |
| Barley (winter) | 50 | 50 | 50 | 70 | 60 | 70 | 50 | 40 | 50 | 70 | 10 | 70 | 20 | 30 | 30 | 70 | 60 | 60 | 70 | — | 15 | 20 |
| Blackgrass | 40 | 100 | 60 | 85 | 50 | 60 | 100 | 50 | 50 | 40 | 30 | 85 | 50 | 55 | 30 | 85 | 70 | 100 | 60 | 60 | 20 | 0 |
| Blk nightshade | — | — | — | — | — | — | — | — | — | — | — | — | — | — | — | — | — | — | — | — | — | — |
| Chickweed | — | — | — | — | — | — | — | — | — | — | — | — | — | — | — | — | — | — | — | — | — | — |

TABLE E-continued

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Common poppy | — | — | — | — | — | — | — | — | — | — | — | — | — | — | — | — | — | — | — | — | — | — | | | | | | | |
| Deadnettle | — | — | — | — | — | — | — | — | — | — | — | — | — | — | — | — | — | — | — | — | — | — | | | | | | | |
| Downy brome | — | — | — | — | — | — | — | — | — | — | — | — | — | — | — | — | — | — | — | — | — | — | | | | | | | |
| Field violet | — | — | — | — | — | — | — | — | — | — | — | — | — | — | — | — | — | — | — | — | — | — | | | | | | | |
| Galium | — | — | — | — | — | — | — | — | — | — | — | — | — | — | — | — | — | — | — | — | — | — | | | | | | | |
| Green foxtail | 60 | 100 | 65 | 100 | 85 | 100 | 100 | 100 | 30 | 25 | 55 | 90 | 100 | 80 | 50 | 50 | 100 | 60 | 60 | 60 | 20 | 40 | | | | | | | |
| I. Ryegrass | 60 | 85 | 50 | 70 | 55 | 70 | 85 | 65 | 55 | 50 | 90 | 60 | 90 | 60 | 60 | 50 | 85 | 70 | 70 | 70 | 10 | 40 | | | | | | | |
| Jointed goatgra | — | — | — | — | — | — | — | — | — | — | — | — | — | — | — | — | — | — | — | — | — | — | | | | | | | |
| Kochia | — | — | — | — | — | — | — | — | — | — | — | — | — | — | — | — | — | — | — | — | — | — | | | | | | | |
| Lambsquarters | — | — | — | — | — | — | — | — | — | — | — | — | — | — | — | — | — | — | — | — | — | — | | | | | | | |
| LS canarygrass | — | — | — | — | — | — | — | — | — | — | — | — | — | — | — | — | — | — | — | — | — | — | | | | | | | |
| Rape | — | — | — | — | — | — | — | — | — | — | — | — | — | — | — | — | — | — | — | — | — | — | | | | | | | |
| Redroot pigweed | — | — | — | — | — | — | — | — | — | — | — | — | — | — | — | — | — | — | — | — | — | — | | | | | | | |
| Russian thistle | — | — | — | — | — | — | — | — | — | — | — | — | — | — | — | — | — | — | — | — | — | — | | | | | | | |
| Scentless chamo | — | — | — | — | — | — | — | — | — | — | — | — | — | — | — | — | — | — | — | — | — | — | | | | | | | |
| Spring Barley | — | — | — | — | — | — | — | — | — | — | — | — | — | — | — | — | — | — | — | — | — | — | | | | | | | |
| Spring Wheat | — | — | — | — | — | — | — | — | — | — | — | — | — | — | — | — | — | — | — | — | — | — | | | | | | | |
| Sugar beet | — | — | — | — | — | — | — | — | — | — | — | — | — | — | — | — | — | — | — | — | — | — | | | | | | | |
| Sunflower | — | — | — | — | — | — | — | — | — | — | — | — | — | — | — | — | — | — | — | — | — | — | | | | | | | |
| Wheat (winter) | 30 | 65 | 70 | 70 | 70 | 70 | 50 | 40 | 40 | 40 | 40 | 60 | 40 | 50 | 40 | 60 | 40 | 60 | 50 | 40 | 55 | 50 | | | | | | | |
| Wild buckwheat | — | — | — | — | — | — | — | — | — | — | — | — | — | — | — | — | — | — | — | — | — | — | | | | | | | |
| Wild mustard | — | — | — | — | — | — | — | — | — | — | — | — | — | — | — | — | — | — | — | — | — | — | | | | | | | |
| Wild oat | 70 | 70 | 50 | 70 | 70 | 60 | 60 | 70 | 50 | 60 | 60 | 70 | 55 | 30 | 50 | 65 | 75 | 85 | 60 | 60 | 0 | 20 | | | | | | | |
| Windgrass | — | — | — | — | — | — | — | — | — | — | — | — | — | — | — | — | — | — | — | — | — | — | | | | | | | |
| | COMPOUND | | | | | | | | | | | | | | | | | | | | | | | | | | | | |
| Rate 125 g/ha | 4 | 38 | 93 | 98 | 105 | 107 | 108 | 109 | 110 | 111 | 112 | 113 | 114 | 116 | 117 | 119 | 131 | 132 | 137 | 138 | 146 | 147 | 148 | 151 | 158 | 170 | 191 | 192 | 199 |
| Postemergence | | | | | | | | | | | | | | | | | | | | | | | | | | | | | |
| Annual bluegras | — | — | 20 | — | — | 5 | 15 | 10 | — | — | — | — | 0 | 50 | — | — | 40 | — | — | 0 | 10 | — | — | — | — | — | — | — | — |
| Barley (winter) | — | — | 0 | — | — | 5 | 10 | 40 | — | — | — | — | 5 | 10 | — | — | 0 | — | — | 0 | 10 | — | — | — | — | — | — | — | — |
| Blackgrass | — | — | 30 | — | — | 80 | 5 | 30 | — | — | — | — | 0 | 40 | — | — | 20 | — | — | 20 | 25 | — | — | — | — | — | — | — | — |
| Blk nightshade | — | — | 0 | — | — | 30 | 30 | 40 | — | — | — | — | 50 | 50 | — | — | 50 | — | — | 20 | 50 | — | — | — | — | — | — | — | — |
| Chickweed | — | — | 0 | — | — | 0 | 0 | 0 | — | — | — | — | 10 | 0 | — | — | 10 | — | — | 0 | 0 | — | — | — | — | — | — | — | — |
| Comnion poppy | — | — | 0 | — | — | 0 | 0 | 30 | — | — | — | — | 0 | 0 | — | — | 0 | — | — | 20 | 10 | — | — | — | — | — | — | — | — |
| Deadnettle | — | — | 0 | — | — | 5 | 20 | 0 | — | — | — | — | 20 | 0 | — | — | 30 | — | — | 0 | 10 | — | — | — | — | — | — | — | — |
| Downy brome | — | — | 0 | — | — | 10 | 0 | 0 | — | — | — | — | 0 | 0 | — | — | 0 | — | — | 0 | 10 | — | — | — | — | — | — | — | — |
| Field violet | — | — | 0 | — | — | 25 | 0 | 10 | — | — | — | — | 0 | 0 | — | — | 0 | — | — | 10 | 0 | — | — | — | — | — | — | — | — |
| Galium | — | — | 0 | — | — | 30 | 10 | 50 | — | — | — | — | 10 | 40 | — | — | 10 | — | — | 20 | 0 | — | — | — | — | — | — | — | — |
| Green foxtail | — | — | 0 | — | — | 30 | 15 | 30 | — | — | — | — | 20 | 70 | — | — | 70 | — | — | 15 | 20 | — | — | — | — | — | — | — | — |
| I. Ryegrass | — | — | 0 | — | — | 50 | 5 | 10 | — | — | — | — | 10 | 50 | — | — | 0 | — | — | 0 | 10 | — | — | — | — | — | — | — | — |
| Jointed goatgra | — | — | 0 | — | — | 10 | 10 | 10 | — | — | — | — | 15 | 20 | — | — | 0 | — | — | 0 | 15 | — | — | — | — | — | — | — | — |
| Kochia | — | — | 0 | — | — | 20 | 40 | 30 | — | — | — | — | 20 | 0 | — | — | 0 | — | — | 15 | 10 | — | — | — | — | — | — | — | — |
| Lambsquarters | — | — | 0 | — | — | 15 | 20 | 20 | — | — | — | — | 30 | 30 | — | — | 0 | — | — | 10 | 20 | — | — | — | — | — | — | — | — |
| LS canarygrass | — | — | 0 | — | — | 20 | 20 | 25 | — | — | — | — | 0 | 30 | — | — | 0 | — | — | 10 | 30 | — | — | — | — | — | — | — | — |
| Rape | — | — | 0 | — | — | 30 | 40 | 50 | — | — | — | — | 55 | 0 | — | — | 0 | — | — | 10 | 40 | — | — | — | — | — | — | — | — |
| Redroot pigweed | — | — | 0 | — | — | 10 | 20 | 20 | — | — | — | — | 15 | 0 | — | — | 0 | — | — | 20 | 20 | — | — | — | — | — | — | — | — |
| Russian thistle | — | — | 0 | — | — | 0 | 0 | 0 | — | — | — | — | 0 | 0 | — | — | 0 | — | — | 0 | 0 | — | — | — | — | — | — | — | — |
| Scentless chamo | — | — | 0 | — | — | 0 | 0 | 0 | — | — | — | — | 0 | 0 | — | — | 0 | — | — | 20 | 10 | — | — | — | — | — | — | — | — |
| Spring Barley | — | — | 0 | — | — | 0 | 20 | 30 | — | — | — | — | 20 | 0 | — | — | 0 | — | — | 0 | 10 | — | — | — | — | — | — | — | — |

TABLE E-continued

| | 211 | 218 | 219 | 225 | 241 | 242 | 243 | 245 | 271 | 276 | 277 | 285 | 287 | 293 | 295 | 299 | 310 | 314 | 315 | 317 | 350 | 351 | 353 | 354 | 367 | 370 | 371 | 372 | 375 |
|---|---|---|---|---|---|---|---|---|---|---|---|---|---|---|---|---|---|---|---|---|---|---|---|---|---|---|---|---|---|
| Spring Wheat | — | — | 0 | — | — | 5 | 10 | 30 | — | — | — | — | 10 | 0 | — | — | 0 | — | — | 0 | 10 | — | — | — | — | — | — | — | — |
| Sugar beet | — | — | 0 | — | — | 10 | 10 | 30 | — | — | — | — | 50 | 0 | — | — | 0 | — | — | 30 | 20 | — | — | — | — | — | — | — | — |
| Sunflower | — | — | 0 | — | — | 20 | 30 | 30 | — | — | — | — | 10 | 0 | — | — | 0 | — | — | 0 | 40 | — | — | — | — | — | — | — | — |
| Veronica hedera | — | — | 0 | — | — | 0 | 10 | 20 | — | — | — | — | 10 | 0 | — | — | 0 | — | — | — | 60 | — | — | — | — | — | — | — | — |
| Wheat (winter) | 0 | 10 | 65 | 30 | 10 | 30 | 20 | 55 | 0 | 0 | 0 | 30 | 10 | 10 | 10 | 10 | 60 | 20 | 10 | 70 | 40 | 70 | 10 | 70 | 15 | 75 | 30 | 30 | 55 |
| Wild buckwheat | — | — | 0 | — | — | 0 | 20 | 10 | — | — | — | — | 20 | 0 | — | — | 0 | — | — | 0 | 0 | — | — | — | — | — | — | — | — |
| Wild mustard | — | — | 0 | — | — | 90 | 10 | 40 | — | — | — | — | 75 | 20 | — | — | 0 | — | — | 0 | 50 | — | — | — | — | — | — | — | — |
| Wild oat | — | — | 0 | — | — | 5 | 5 | 0 | — | — | — | — | 0 | 0 | — | — | 0 | — | — | 0 | 5 | — | — | — | — | — | — | — | — |
| Windgrass | — | — | 70 | — | — | 90 | 90 | 90 | — | — | — | — | 85 | 70 | — | — | 60 | — | — | 90 | 90 | — | — | — | — | — | — | — | — |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 211 | 218 | 219 | 225 | 241 | 242 | 243 | 245 | 271 | 276 | 277 | 285 | 287 | 293 | 295 | 299 | 310 | 314 | 315 | 317 | 350 | 351 | 353 | 354 | 367 | 370 | 371 | 372 | 375 |
| Postemergence | | | | | | | | | | | | | | | | | | | | | | | | | | | | | |
| Annual bluegras | — | — | — | — | — | 20 | — | — | — | — | — | — | — | — | — | — | — | — | — | — | — | — | — | — | — | — | — | — | — |
| Barley (winter) | — | — | — | — | — | 0 | — | — | — | — | — | — | — | — | — | — | — | — | — | — | — | — | — | — | — | — | — | — | — |
| Blackgrass | — | — | — | — | — | 0 | — | — | — | — | — | — | — | — | — | — | — | — | — | — | — | — | — | — | — | — | — | — | — |
| Blk nightshade | — | — | — | — | — | 30 | — | — | — | — | — | — | — | — | — | — | — | — | — | — | — | — | — | — | — | — | — | — | — |
| Chickweed | — | — | — | — | — | 30 | — | — | — | — | — | — | — | — | — | — | — | — | — | — | — | — | — | — | — | — | — | — | — |
| Common poppy | — | — | — | — | — | 40 | — | — | — | — | — | — | — | — | — | — | — | — | — | — | — | — | — | — | — | — | — | — | — |
| Deadnettle | — | — | — | — | — | 10 | — | — | — | — | — | — | — | — | — | — | — | — | — | — | — | — | — | — | — | — | — | — | — |
| Downy brome | — | — | — | — | — | 30 | — | — | — | — | — | — | — | — | — | — | — | — | — | — | — | — | — | — | — | — | — | — | — |
| Field violet | — | — | — | — | — | 60 | — | — | — | — | — | — | — | — | — | — | — | — | — | — | — | — | — | — | — | — | — | — | — |
| Galium | — | — | — | — | — | 20 | — | — | — | — | — | — | — | — | — | — | — | — | — | — | — | — | — | — | — | — | — | — | — |
| Green foxtail | — | — | — | — | — | 30 | — | — | — | — | — | — | — | — | — | — | — | — | — | — | — | — | — | — | — | — | — | — | — |
| I. Ryegrass | — | — | — | — | — | 0 | — | — | — | — | — | — | — | — | — | — | — | — | — | — | — | — | — | — | — | — | — | — | — |
| Jointed goatgra | — | — | — | — | — | 0 | — | — | — | — | — | — | — | — | — | — | — | — | — | — | — | — | — | — | — | — | — | — | — |
| Kochia | — | — | — | — | — | 60 | — | — | — | — | — | — | — | — | — | — | — | — | — | — | — | — | — | — | — | — | — | — | — |
| Lambsquarters | — | — | — | — | — | 0 | — | — | — | — | — | — | — | — | — | — | — | — | — | — | — | — | — | — | — | — | — | — | — |
| LS canarygrass | — | — | — | — | — | 10 | — | — | — | — | — | — | — | — | — | — | — | — | — | — | — | — | — | — | — | — | — | — | — |
| Rape | — | — | — | — | — | 10 | — | — | — | — | — | — | — | — | — | — | — | — | — | — | — | — | — | — | — | — | — | — | — |
| Redroot pigweed | — | — | — | — | — | 0 | — | — | — | — | — | — | — | — | — | — | — | — | — | — | — | — | — | — | — | — | — | — | — |
| Russian thistle | — | — | — | — | — | 0 | — | — | — | — | — | — | — | — | — | — | — | — | — | — | — | — | — | — | — | — | — | — | — |
| Scentless chamo | — | — | — | — | — | 40 | — | — | — | — | — | — | — | — | — | — | — | — | — | — | — | — | — | — | — | — | — | — | — |
| Spring Barley | — | — | — | — | — | 20 | — | — | — | — | — | — | — | — | — | — | — | — | — | — | — | — | — | — | — | — | — | — | — |
| Spring Wheat | — | — | — | — | — | 20 | — | — | — | — | — | — | — | — | — | — | — | — | — | — | — | — | — | — | — | — | — | — | — |
| Sugar beet | — | — | — | — | — | 50 | — | — | — | — | — | — | — | — | — | — | — | — | — | — | — | — | — | — | — | — | — | — | — |
| Sunflower | — | — | — | — | — | 10 | — | — | — | — | — | — | — | — | — | — | — | — | — | — | — | — | — | — | — | — | — | — | — |
| Veronica hedera | — | — | — | — | — | — | — | — | — | — | — | — | — | — | — | — | — | — | — | — | — | — | — | — | — | — | — | — | — |
| Wheat (winter) | 20 | 65 | 20 | 75 | 20 | 10 | 70 | 0 | 10 | 10 | 0 | 20 | 40 | 50 | 30 | 60 | 80 | 65 | 70 | 70 | 50 | 60 | 20 | 30 | 50 | 70 | 70 | 65 | 35 |
| Wild buckwheat | — | — | — | — | — | 10 | — | — | — | — | — | — | — | — | — | — | — | — | — | — | — | — | — | — | — | — | — | — | — |
| Wild mustard | — | — | — | — | — | 20 | — | — | — | — | — | — | — | — | — | — | — | — | — | — | — | — | — | — | — | — | — | — | — |
| Wild oat | — | — | — | — | — | 0 | — | — | — | — | — | — | — | — | — | — | — | — | — | — | — | — | — | — | — | — | — | — | — |
| Windgrass | — | — | — | — | — | 95 | — | — | — | — | — | — | — | — | — | — | — | — | — | — | — | — | — | — | — | — | — | — | — |

TABLE E-continued

| Rate 125 g/ha | COMPOUND 387 | 388 |
|---|---|---|
| Postemergence | | |
| Annual bluegras | — | — |
| Barley (winter) | — | — |
| Blackgrass | — | — |
| Blk nightshade | — | — |
| Chickweed | — | — |
| Common poppy | — | — |
| Deadnettle | — | — |
| Downy brome | — | — |
| Field violet | — | — |
| Galium | — | — |
| Green foxtail | — | — |
| I. Ryegrass | — | — |
| Jointed goatgra | — | — |
| Kochia | — | — |
| Lambsquarters | — | — |
| LS canarygrass | — | — |
| Rape | — | — |
| Redroot pigweed | — | — |
| Russian thistle | — | — |
| Scentless chamo | — | — |
| Spring Barley | — | — |
| Spring Wheat | — | — |
| Sugar beet | — | — |
| Sunflower | — | — |
| Veronica hedera | — | — |
| Wheat (winter) | 20 | 30 |
| Wild buckwheat | — | — |
| Wild mustard | — | — |
| Wild oat | — | — |
| Windgrass | — | — |

| Rate 125 g/ha | 4 | 38 | 93 | 98 | 105 | 107 | 108 | 109 | 110 | 111 | 112 | 113 | 114 | 116 | 117 | 119 | 131 | 132 | 137 | 138 | 146 | 147 | 148 | 151 | 158 | 170 | 191 | 192 | 199 |
|---|---|---|---|---|---|---|---|---|---|---|---|---|---|---|---|---|---|---|---|---|---|---|---|---|---|---|---|---|---|
| Preemergence | | | | | | | | | | | | | | | | | | | | | | | | | | | | | |
| Annual bluegras | — | — | 50 | — | — | 80 | 60 | 40 | — | — | — | — | 50 | 60 | — | — | 70 | — | — | — | 60 | — | — | — | — | — | — | — | — |
| Barley (winter) | 10 | 0 | 50 | 20 | 0 | 20 | 20 | 10 | 0 | 0 | 10 | 10 | 5 | 30 | 20 | 10 | 65 | 10 | 20 | 60 | 10 | 10 | 10 | 20 | 20 | 60 | 10 | 20 | 70 |
| Blackgrass | 30 | 25 | 70 | 30 | 20 | 85 | 75 | 65 | 50 | 0 | 20 | 30 | 50 | 50 | 50 | 10 | 50 | 20 | 20 | 60 | 85 | 20 | 50 | 75 | 20 | 60 | 10 | 40 | 65 |
| Blk nightshade | — | — | 65 | — | — | 95 | 85 | 75 | — | — | — | — | 20 | 80 | — | — | 70 | — | — | 85 | 85 | — | — | — | — | — | — | — | — |
| Chickweed | — | — | 20 | — | — | 50 | 40 | 40 | — | — | — | — | 15 | 100 | — | — | 100 | — | — | — | 30 | — | — | — | — | — | — | — | — |
| Common poppy | — | — | — | — | — | — | — | — | — | — | — | — | — | — | — | — | — | — | — | — | 100 | — | — | — | — | — | — | — | — |
| Deadnettle | — | — | 10 | — | — | 60 | 10 | 20 | — | — | — | — | 20 | 95 | — | — | 30 | — | — | 65 | 40 | — | — | — | — | — | — | — | — |
| Downy brome | — | — | 60 | — | — | 60 | 30 | 0 | — | — | — | — | 10 | 60 | — | — | 85 | — | — | 90 | 60 | — | — | — | — | — | — | — | — |
| Field violet | — | — | 10 | — | — | 30 | 0 | 50 | — | — | — | — | 0 | 50 | — | — | 20 | — | — | 50 | 10 | — | — | — | — | — | — | — | — |
| Galium | — | — | 15 | — | — | 70 | 50 | 100 | — | — | — | — | 100 | 100 | — | — | 60 | — | — | 50 | 40 | — | — | — | — | — | — | — | — |
| Green foxtail | 50 | 80 | 80 | 60 | 55 | 100 | — | 85 | 60 | 0 | 20 | 70 | 100 | 50 | 60 | 50 | 100 | 60 | 15 | 70 | 50 | 55 | 30 | 80 | 10 | 100 | 30 | 50 | 100 |

TABLE E-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| I. Ryegrass | 20 | 0 | 70 | 50 | 30 | 98 | 45 | 100 | 0 | 0 | 0 | 50 | 30 | 30 | 45 | 35 | 100 | 20 | 20 | 70 | 50 | 20 | 20 | 50 | 20 | 70 | 0 | 20 | 60 |
| Jointed goatgra | — | — | 70 | — | — | 50 | 40 | 20 | — | — | — | — | 20 | 30 | — | — | 50 | — | — | 65 | 45 | — | — | — | — | — | — | — | — |
| Kochia | — | — | 0 | — | — | 60 | 50 | 0 | — | — | — | — | 25 | 0 | — | — | 0 | — | — | 20 | 0 | — | — | — | — | — | — | — | — |
| Lambsquarters | — | — | 100 | — | — | 100 | 100 | 60 | — | — | — | — | 50 | 100 | — | — | 100 | — | — | 100 | 100 | — | — | — | — | — | — | — | — |
| LS canarygrass | — | — | 80 | — | — | 80 | 50 | 50 | — | — | — | — | 50 | 70 | — | — | 70 | — | — | 70 | 40 | — | — | — | — | — | — | — | — |
| Rape | — | — | 0 | — | — | 70 | 60 | 10 | — | — | — | — | 0 | 60 | — | — | 70 | — | — | 30 | 60 | — | — | — | — | — | — | — | — |
| Redroot pigweed | — | — | 100 | — | — | 100 | 90 | 70 | — | — | — | — | 50 | 100 | — | — | 100 | — | — | 90 | 70 | — | — | — | — | — | — | — | — |
| Russian thistle | — | — | 0 | — | — | 0 | 0 | 0 | — | — | — | — | 0 | 0 | — | — | 10 | — | — | 10 | 0 | — | — | — | — | — | — | — | — |
| Scentless chamo | — | — | — | — | — | 80 | 60 | 0 | — | — | — | — | 30 | — | — | — | — | — | — | — | 15 | — | — | — | — | — | — | — | — |
| Spring Barley | — | — | 10 | — | — | 70 | 10 | 5 | — | — | — | — | 0 | 40 | — | — | 20 | — | — | 60 | 20 | — | — | — | — | — | — | — | — |
| Spring Wheat | — | — | 50 | — | — | 75 | 20 | 20 | — | — | — | — | 0 | 15 | — | — | 70 | — | — | 55 | 50 | — | — | — | — | — | — | — | — |
| Sugar beet | — | — | 10 | — | — | 100 | 40 | 0 | — | — | — | — | 20 | 50 | — | — | 80 | — | — | 0 | 60 | — | — | — | — | — | — | — | — |
| Sunflower | — | — | 5 | — | — | 30 | 0 | 0 | — | — | — | — | 0 | 15 | — | — | 20 | — | — | 55 | 20 | — | — | — | — | — | — | — | — |
| Wheat (winter) | 0 | 10 | 40 | 30 | 10 | 30 | 10 | 30 | 0 | 0 | 0 | 50 | 10 | 55 | 60 | 20 | 35 | 30 | 20 | 70 | 10 | 20 | 0 | 10 | 10 | 70 | 10 | 10 | 70 |
| Wild buckwheat | — | — | 30 | — | — | 90 | 100 | 20 | — | — | — | — | 20 | 40 | — | — | 30 | — | — | 50 | 70 | — | — | — | — | — | — | — | — |
| Wild mustard | — | — | 65 | — | — | 85 | 90 | 30 | — | — | — | — | 50 | 75 | — | — | 60 | — | — | 40 | 60 | — | — | — | — | — | — | — | — |
| Wild oat | 10 | 0 | 60 | 50 | 30 | 60 | 30 | 30 | 0 | 0 | 0 | 30 | 40 | 30 | 20 | 10 | 50 | 35 | 20 | 60 | 30 | 0 | 15 | 20 | 50 | 70 | 30 | 30 | 70 |
| Windgrass | — | — | 100 | — | — | 100 | 100 | 100 | — | — | — | — | 100 | 100 | — | — | 100 | — | — | 100 | 100 | — | — | — | — | — | — | — | — |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 125 g/ha | 211 | 218 | 219 | 225 | 241 | 242 | 243 | 245 | 271 | 276 | 277 | 285 | 287 | 293 | 295 | 299 | 310 | 314 | 315 | 317 | 350 | 351 | 353 | 354 | 367 | 370 | 371 | 372 | 375 |
| Preemergence | | | | | | | | | | | | | | | | | | | | | | | | | | | | | |
| Annual bluegras | — | — | — | — | — | 100 | — | — | — | — | — | — | — | — | — | — | — | — | — | — | — | — | — | — | — | — | — | — | — |
| Barley (winter) | 10 | 40 | 20 | 50 | 40 | 40 | 30 | 70 | 35 | 50 | 30 | 0 | 30 | 40 | 20 | 40 | 60 | 50 | 55 | 40 | 5 | 70 | 10 | 20 | 20 | 60 | 40 | 60 | 35 |
| Blackgrass | 0 | 65 | 0 | 60 | 60 | 95 | 65 | 50 | 30 | 30 | 60 | 20 | 50 | 40 | 0 | 60 | 85 | 40 | 50 | 50 | 50 | 35 | 10 | 50 | 60 | 50 | 85 | 70 | 20 |
| Blk nightshade | — | — | — | — | — | 70 | — | — | — | — | — | — | — | — | — | — | — | — | — | — | — | — | — | — | — | — | — | — | — |
| Chickweed | — | — | — | — | — | — | — | — | — | — | — | — | — | — | — | — | — | — | — | — | — | — | — | — | — | — | — | — | — |
| Common poppy | — | — | — | — | — | — | — | — | — | — | — | — | — | — | — | — | — | — | — | — | — | — | — | — | — | — | — | — | — |
| Deadnettle | — | — | — | — | — | — | — | — | — | — | — | — | — | — | — | — | — | — | — | — | — | — | — | — | — | — | — | — | — |
| Downy brome | — | — | — | — | — | 70 | — | — | — | — | — | — | — | — | — | — | — | — | — | — | — | — | — | — | — | — | — | — | — |
| Field violet | — | — | — | — | — | 50 | — | — | — | — | — | — | — | — | — | — | — | — | — | — | — | — | — | — | — | — | — | — | — |
| Galium | — | — | — | — | — | 0 | — | — | — | — | — | — | — | — | — | — | — | — | — | — | — | — | — | — | — | — | — | — | — |
| Green foxtail | 0 | 30 | 65 | 50 | 65 | 70 | 75 | 100 | 70 | 60 | 95 | 20 | 60 | 55 | 50 | 100 | 100 | 60 | 90 | 100 | 65 | 40 | 70 | 85 | 70 | 70 | 35 | 60 | 50 |
| I. Ryegrass | — | 55 | 30 | 50 | 60 | 95 | 70 | 60 | 60 | 30 | 65 | 20 | 55 | 30 | 40 | 70 | 70 | 50 | 55 | 60 | 60 | 55 | 40 | 50 | 60 | 55 | 60 | 60 | 50 |
| Jointed goatgra | — | — | — | — | — | 65 | — | — | — | — | — | — | — | — | — | — | — | — | — | — | — | — | — | — | — | — | — | — | — |
| Kochia | — | — | — | — | — | 35 | — | — | — | — | — | — | — | — | — | — | — | — | — | — | — | — | — | — | — | — | — | — | — |
| Lambsquarters | — | — | — | — | — | 100 | — | — | — | — | — | — | — | — | — | — | — | — | — | — | — | — | — | — | — | — | — | — | — |
| LS canarygrass | — | — | — | — | — | 100 | — | — | — | — | — | — | — | — | — | — | — | — | — | — | — | — | — | — | — | — | — | — | — |
| Rape | — | — | — | — | — | 50 | — | — | — | — | — | — | — | — | — | — | — | — | — | — | — | — | — | — | — | — | — | — | — |
| Redroot pigweed | — | — | — | — | — | 90 | — | — | — | — | — | — | — | — | — | — | — | — | — | — | — | — | — | — | — | — | — | — | — |
| Russian thistle | — | — | — | — | — | 20 | — | — | — | — | — | — | — | — | — | — | — | — | — | — | — | — | — | — | — | — | — | — | — |
| Scentless chamo | — | — | — | — | — | — | — | — | — | — | — | — | — | — | — | — | — | — | — | — | — | — | — | — | — | — | — | — | — |
| Spring Barley | — | — | — | — | — | 60 | — | — | — | — | — | — | — | — | — | — | — | — | — | — | — | — | — | — | — | — | — | — | — |
| Spring Wheat | — | — | — | — | — | 55 | — | — | — | — | — | — | — | — | — | — | — | — | — | — | — | — | — | — | — | — | — | — | — |
| Sugar beet | — | — | — | — | — | 30 | — | — | — | — | — | — | — | — | — | — | — | — | — | — | — | — | — | — | — | — | — | — | — |
| Sunflower | — | — | — | — | — | 55 | — | — | — | — | — | — | — | — | — | — | — | — | — | — | — | — | — | — | — | — | — | — | — |
| Wheat (winter) | 50 | 50 | 35 | 65 | 40 | 65 | 50 | 50 | 30 | 20 | 30 | 30 | 45 | 40 | 40 | 50 | 40 | 65 | 55 | 50 | 40 | 50 | 20 | 30 | 60 | 50 | 60 | 60 | 30 |
| Wild buckwheat | — | — | — | — | — | 60 | — | — | — | — | — | — | — | — | — | — | — | — | — | — | — | — | — | — | — | — | — | — | — |
| Wild mustard | — | — | — | — | — | 65 | — | — | — | — | — | — | — | — | — | — | — | — | — | — | — | — | — | — | — | — | — | — | — |

TABLE E-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Wild oat | 20 | 70 | 30 | 50 | 50 | 60 | 60 | 30 | 50 | 50 | 50 | 10 | 70 | 0 | 0 | 65 | 50 | 70 | 65 | 60 | 40 | 70 | 30 | 0 | 55 | 60 | 70 | 50 | 55 |
| Windgrass | — | — | — | — | — | 100 | — | — | — | — | — | — | — | — | — | — | — | — | — | — | — | — | — | — | — | — | — | — | — |

| | COMPOUND | |
|---|---|---|
| Rate 125 g/ha | 387 | 388 |
| Preemergence | | |
| Annual bluegras | — | — |
| Barley (winter) | 20 | 10 |
| Blackgrass | 0 | 0 |
| Blk nightshade | — | — |
| Chickweed | — | — |
| Common poppy | — | — |
| Deadnettle | — | — |
| Downy brome | — | — |
| Field violet | — | — |
| Galium | — | — |
| Green foxtail | 10 | 30 |
| I. Ryegrass | 0 | 30 |
| Jointed goatgra | — | — |
| Kochia | — | — |
| Lambsquarters | — | — |
| LS canarygrass | — | — |
| Rape | — | — |
| Redroot pigweed | — | — |
| Russian thistle | — | — |
| Scentless chamo | — | — |
| Spring Barley | — | — |
| Spring Wheat | — | — |
| Sugar beet | — | — |
| Sunflower | — | — |
| Wheat (winter) | 50 | 50 |
| Wild buckwheat | — | — |
| Wild mustard | — | — |
| Wild oat | 0 | 20 |
| Windgrass | — | — |

| | COMPOUND | | | | | | | | | | | | | | | | | | | | | | | | | |
|---|---|---|---|---|---|---|---|---|---|---|---|---|---|---|---|---|---|---|---|---|---|---|---|---|---|---|
| Rate 62 g/ha | 91 | 93 | 107 | 108 | 109 | 110 | 111 | 112 | 113 | 114 | 116 | 117 | 119 | 131 | 138 | 146 | 148 | 151 | 158 | 170 | 199 | 225 | 242 | 245 | 287 | 310 |
| Postemergence | | | | | | | | | | | | | | | | | | | | | | | | | | |
| Annual bluegras | — | 20 | 20 | 0 | — | — | — | — | — | — | 100 | — | — | 55 | — | 85 | — | — | — | — | — | — | 95 | — | — | — |
| Barley (winter) | — | 0 | 5 | 10 | — | — | — | — | — | — | 0 | — | — | 5 | — | 5 | — | — | — | — | — | — | 20 | — | — | — |
| Blackgrass | — | 10 | 5 | 5 | — | — | — | — | — | — | 0 | — | — | 85 | — | 70 | — | — | — | — | — | — | 60 | — | — | — |
| Blk nightshade | — | 0 | 10 | 20 | — | — | — | — | — | — | 10 | — | — | 50 | — | 50 | — | — | — | — | — | — | 60 | — | — | — |
| Chickweed | — | 0 | 10 | 10 | — | — | — | — | — | — | 0 | — | — | 60 | — | 30 | — | — | — | — | — | — | 0 | — | — | — |
| Common poppy | — | 0 | 0 | 10 | — | — | — | — | — | — | 30 | — | — | 65 | — | 60 | — | — | — | — | — | — | 55 | — | — | — |
| Deadnettle | — | 0 | 0 | 10 | — | — | — | — | — | — | 0 | — | — | 30 | — | 50 | — | — | — | — | — | — | 100 | — | — | — |

TABLE E-continued

| | | | | | | | | | | | | | | | | | | | | | | | | | |
|---|---|---|---|---|---|---|---|---|---|---|---|---|---|---|---|---|---|---|---|---|---|---|---|---|---|
| Downy brome | — | 0 | 0 | 0 | — | — | — | — | — | — | 0 | — | — | 55 | — | 55 | — | — | — | — | — | — | 30 | — | — | — |
| Field violet | — | 0 | 0 | 0 | — | — | — | — | — | — | 60 | — | — | 60 | — | 50 | — | — | — | — | — | — | 30 | — | — | — |
| Galium | — | 0 | 5 | 0 | — | — | — | — | — | — | 30 | — | — | 50 | — | 50 | — | — | — | — | — | — | 0 | — | — | — |
| Green foxtail | — | 0 | 20 | 10 | — | — | — | — | — | — | 20 | — | — | 55 | — | 70 | — | — | — | — | — | — | 60 | — | — | — |
| I. Ryegrass | — | 0 | 0 | 20 | — | — | — | — | — | — | 0 | — | — | 50 | — | 50 | — | — | — | — | — | — | 50 | — | — | — |
| Jointed goatgra | — | 0 | 0 | 10 | — | — | — | — | — | — | 30 | — | — | 30 | — | 55 | — | — | — | — | — | — | 55 | — | — | — |
| Kochia | — | 0 | 5 | 20 | — | — | — | — | — | — | 0 | — | — | 45 | — | 30 | — | — | — | — | — | — | 20 | — | — | — |
| Lambsquarters | — | 0 | 15 | 10 | — | — | — | — | — | — | 20 | — | — | 0 | — | 50 | — | — | — | — | — | — | 10 | — | — | — |
| LS canarygrass | — | 0 | 15 | 0 | — | — | — | — | — | — | 10 | — | — | 50 | — | 30 | — | — | — | — | — | — | 65 | — | — | — |
| Rape | — | 0 | 20 | 60 | — | — | — | — | — | — | 10 | — | — | 10 | — | 60 | — | — | — | — | — | — | 20 | — | — | — |
| Redroot pigweed | — | 0 | 20 | 5 | — | — | — | — | — | — | 0 | — | — | 5 | — | 30 | — | — | — | — | — | — | 0 | — | — | — |
| Russian thistle | — | 0 | 0 | 0 | — | — | — | — | — | — | 40 | — | — | 10 | — | 20 | — | — | — | — | — | — | 50 | — | — | — |
| Scentless chamo | — | 0 | 10 | 10 | — | — | — | — | — | — | 50 | — | — | 55 | — | 20 | — | — | — | — | — | — | 55 | — | — | — |
| Spring Barley | — | 0 | 20 | 10 | — | — | — | — | — | — | 5 | — | — | 5 | — | 20 | — | — | — | — | — | — | 5 | — | — | — |
| Spring Wheat | — | 0 | 0 | 10 | — | — | — | — | — | — | 5 | — | — | 5 | — | 10 | — | — | — | — | — | — | 15 | — | — | — |
| Sugar beet | — | 0 | 10 | 5 | — | — | — | — | — | — | 0 | — | — | 0 | — | 0 | — | — | — | — | — | — | 50 | — | — | — |
| Sunflower | — | 0 | 10 | 20 | — | — | — | — | — | — | 20 | — | — | 10 | — | 0 | — | — | — | — | — | — | 10 | — | — | — |
| Veronica hedera | — | 0 | 10 | 0 | — | — | — | — | — | — | — | — | — | — | — | — | — | — | — | — | — | — | — | — | — | — |
| Wheat (winter) | 10 | 20 | 40 | 0 | 0 | 0 | 0 | 0 | 15 | 0 | 20 | 0 | 10 | 50 | 60 | 20 | 0 | 10 | 10 | 80 | 50 | 60 | 65 | 10 | 30 | 75 |
| Wild buckwheat | — | 0 | 0 | 0 | — | — | — | — | — | — | 0 | — | — | 50 | — | 20 | — | — | — | — | — | — | 50 | — | — | — |
| Wild mustard | — | 0 | 5 | 5 | — | — | — | — | — | — | 70 | — | — | 30 | — | 60 | — | — | — | — | — | — | 0 | — | — | — |
| Wild oat | — | 0 | 5 | 0 | — | — | — | — | — | — | 20 | — | — | 40 | — | 20 | — | — | — | — | — | — | — | — | — | |
| Windgrass | — | 60 | 85 | 80 | — | — | — | — | — | — | 70 | — | — | 85 | — | 85 | — | — | — | — | — | — | 90 | — | — | — |

| | COMPOUND | | | | | | | | | | | | | | | | | | | | | | | | |
|---|---|---|---|---|---|---|---|---|---|---|---|---|---|---|---|---|---|---|---|---|---|---|---|---|---|
| Rate 62 g/ha | 91 | 93 | 107 | 108 | 109 | 110 | 111 | 112 | 113 | 114 | 116 | 117 | 119 | 131 | 138 | 146 | 148 | 151 | 158 | 170 | 199 | 225 | 242 | 245 | 287 | 310 |
| Preemergence | | | | | | | | | | | | | | | | | | | | | | | | | | |
| Annual bluegras | — | 10 | 70 | 20 | — | — | — | — | — | — | — | — | — | — | — | — | — | — | — | — | — | — | — | — | — | — |
| Barley (winter) | 40 | 50 | 20 | 10 | 10 | 0 | 0 | 0 | 10 | 0 | 10 | 25 | 5 | 40 | 30 | 10 | 10 | 10 | 10 | 60 | 70 | 50 | 30 | 50 | 20 | 50 |
| Blackgrass | 60 | 50 | 60 | 40 | 30 | 20 | 0 | 10 | 60 | 30 | 40 | 50 | 20 | 60 | 50 | 70 | 20 | 45 | 10 | 60 | 60 | 50 | 70 | 60 | 30 | 85 |
| Blk nightshade | — | 60 | 70 | 50 | — | — | — | — | — | — | — | — | — | — | — | — | — | — | — | — | — | — | — | — | — | — |
| Chickweed | — | 60 | 80 | 30 | — | — | — | — | — | — | — | — | — | — | — | — | — | — | — | — | — | — | — | — | — | — |
| Common poppy | — | — | — | — | — | — | — | — | — | — | — | — | — | — | — | — | — | — | — | — | — | — | — | — | — | — |
| Deadnettle | — | 10 | 50 | 10 | — | — | — | — | — | — | — | — | — | — | — | — | — | — | — | — | — | — | — | — | — | — |
| Downy brome | — | 40 | 50 | 30 | — | — | — | — | — | — | — | — | — | — | — | — | — | — | — | — | — | — | — | — | — | — |
| Field violet | — | 0 | 70 | 15 | — | — | — | — | — | — | — | — | — | — | — | — | — | — | — | — | — | — | — | — | — | — |
| Galium | — | 10 | 50 | 95 | — | — | — | — | — | — | — | — | — | — | — | — | — | — | — | — | — | — | — | — | — | — |
| Green foxtail | 80 | 70 | 80 | 65 | 50 | 30 | 0 | 10 | 55 | 45 | 65 | 50 | 10 | 60 | 60 | 55 | 20 | 30 | 0 | 100 | 100 | 60 | — | 100 | 60 | 100 |
| I. Ryegrass | 40 | 50 | 55 | 20 | 20 | 0 | 0 | 0 | 50 | 20 | 50 | 50 | 10 | 70 | 60 | 40 | 20 | 30 | 10 | 60 | 70 | 30 | 70 | 40 | 50 | 70 |
| Jointed goatgra | — | 15 | 40 | 30 | — | — | — | — | — | — | — | — | — | — | — | — | — | — | — | — | — | — | — | — | — | — |
| Kochia | — | 0 | 50 | 50 | — | — | — | — | — | — | — | — | — | — | — | — | — | — | — | — | — | — | — | — | — | — |
| Lambsquarters | — | 100 | 100 | 80 | — | — | — | — | — | — | — | — | — | — | — | — | — | — | — | — | — | — | — | — | — | — |
| LS canarygrass | — | 40 | 50 | 60 | — | — | — | — | — | — | — | — | — | — | — | — | — | — | — | — | — | — | — | — | — | — |
| Rape | — | 0 | 60 | 40 | — | — | — | — | — | — | — | — | — | — | — | — | — | — | — | — | — | — | — | — | — | — |
| Redroot pigweed | — | 100 | 100 | 70 | — | — | — | — | — | — | — | — | — | — | — | — | — | — | — | — | — | — | — | — | — | — |
| Russian thistle | — | 0 | 0 | 0 | — | — | — | — | — | — | — | — | — | — | — | — | — | — | — | — | — | — | — | — | — | — |
| Scentless chamo | — | — | 70 | 50 | — | — | — | — | — | — | — | — | — | — | — | — | — | — | — | — | — | — | — | — | — | — |
| Spring Barley | — | 5 | 30 | 10 | — | — | — | — | — | — | — | — | — | — | — | — | — | — | — | — | — | — | — | — | — | — |
| Spring Wheat | — | 30 | 60 | 10 | — | — | — | — | — | — | — | — | — | — | — | — | — | — | — | — | — | — | — | — | — | — |

TABLE E-continued

| | | | | | | | | | | | | | | | | | | | | | | | | | | |
|---|---|---|---|---|---|---|---|---|---|---|---|---|---|---|---|---|---|---|---|---|---|---|---|---|---|---|
| Sugar beet | — | 0 | 70 | 60 | — | — | — | — | — | — | — | — | — | — | — | — | — | — | — | — | — | — | — | — | — | — |
| Sunflower | — | 10 | 20 | 0 | — | — | — | — | — | — | — | — | — | — | — | — | — | — | — | — | — | — | — | — | — | — |
| Wheat (winter) | 40 | 40 | 50 | 0 | 20 | 0 | 0 | 0 | 40 | 0 | 30 | 30 | 0 | 50 | 60 | 0 | 0 | 0 | 0 | 70 | 60 | 30 | 40 | 20 | 30 | 60 |
| Wild buckwheat | — | 30 | 60 | 60 | — | — | — | — | — | — | — | — | — | — | — | — | — | — | — | — | — | — | — | — | — | — |
| Wild mustard | — | 30 | 100 | 50 | — | — | — | — | — | — | — | — | — | — | — | — | — | — | — | — | — | — | — | — | — | — |
| Wild oat | 60 | 50 | 50 | 15 | 20 | 0 | 0 | 0 | 20 | 20 | 20 | 20 | 20 | 50 | 50 | 25 | 10 | 10 | 50 | 65 | 60 | 40 | 60 | 40 | 30 | 70 |
| Windgrass | — | 100 | 100 | 100 | — | — | — | — | — | — | — | — | — | — | — | — | — | — | — | — | — | — | — | — | — | — |

| | COMPOUND | | | | | | | | |
|---|---|---|---|---|---|---|---|---|---|
| Rate 31 g/ha | 91 | 93 | 107 | 146 | 151 | 225 | 242 | 245 | 287 |
| Postemergence | | | | | | | | | |
| Annual bluegras | — | — | — | — | — | — | — | — | — |
| Barley (winter) | — | — | — | — | — | — | — | — | — |
| Blackgrass | — | — | — | — | — | — | — | — | — |
| Blk nightshade | — | — | — | — | — | — | — | — | — |
| Chickweed | — | — | — | — | — | — | — | — | — |
| Common poppy | — | — | — | — | — | — | — | — | — |
| Deadnettle | — | — | — | — | — | — | — | — | — |
| Downy brome | — | — | — | — | — | — | — | — | — |
| Field violet | — | — | — | — | — | — | — | — | — |
| Galium | — | — | — | — | — | — | — | — | — |
| Green foxtail | — | — | — | — | — | — | — | — | — |
| I. Ryegrass | — | — | — | — | — | — | — | — | — |
| Jointed goatgra | — | — | — | — | — | — | — | — | — |
| Kochia | — | — | — | — | — | — | — | — | — |
| Lambsquarters | — | — | — | — | — | — | — | — | — |
| LS canarygrass | — | — | — | — | — | — | — | — | — |
| Rape | — | — | — | — | — | — | — | — | — |
| Redroot pigweed | — | — | — | — | — | — | — | — | — |
| Russian thistle | — | — | — | — | — | — | — | — | — |
| Scentless chamo | — | — | — | — | — | — | — | — | — |
| Spring Barley | — | — | — | — | — | — | — | — | — |
| Spring Wheat | — | — | — | — | — | — | — | — | — |
| Sugar beet | — | — | — | — | — | — | — | — | — |
| Sunflower | — | — | — | — | — | — | — | — | — |
| Veronica hedera | — | — | — | — | — | — | — | — | — |
| Wheat (winter) | 0 | 0 | 50 | 30 | 10 | 50 | 55 | 0 | 30 |
| Wild buckwheat | — | — | — | — | — | — | — | — | — |
| Wild mustard | — | — | — | — | — | — | — | — | — |
| Wild oat | — | — | — | — | — | — | — | — | — |
| Windgrass | — | — | — | — | — | — | — | — | — |

| | COMPOUND | | | | | | | | |
|---|---|---|---|---|---|---|---|---|---|
| Rate 31 g/ha | 91 | 93 | 107 | 146 | 151 | 225 | 242 | 245 | 287 |
| Preemergence | | | | | | | | | |
| Annual bluegras | — | — | — | — | — | — | — | — | — |
| Barley (winter) | 20 | 20 | 10 | 20 | 10 | 0 | 30 | 40 | 30 |
| Blackgrass | 20 | 0 | 30 | 20 | 30 | 30 | 55 | 60 | 30 |
| Blk nightshade | — | — | — | — | — | — | — | — | — |
| Chickweed | — | — | — | — | — | — | — | — | — |
| Common poppy | — | — | — | — | — | — | — | — | — |
| Deadnettle | — | — | — | — | — | — | — | — | — |
| Downy brome | — | — | — | — | — | — | — | — | — |
| Field violet | — | — | — | — | — | — | — | — | — |
| Galium | — | — | — | — | — | — | — | — | — |
| Green foxtail | 60 | 30 | 55 | 50 | 20 | 30 | 50 | 60 | 30 |
| I. Ryegrass | 40 | 30 | 40 | 50 | 20 | 20 | 65 | 20 | 20 |
| Jointed goatgra | — | — | — | — | — | — | — | — | — |
| Kochia | — | — | — | — | — | — | — | — | — |
| Lambsquarters | — | — | — | — | — | — | — | — | — |
| LS canarygrass | — | — | — | — | — | — | — | — | — |
| Rape | — | — | — | — | — | — | — | — | — |
| Redroot pigweed | — | — | — | — | — | — | — | — | — |
| Russian thistle | — | — | — | — | — | — | — | — | — |
| Scentless chamo | — | — | — | — | — | — | — | — | — |
| Spring Barley | — | — | — | — | — | — | — | — | — |
| Spring Wheat | — | — | — | — | — | — | — | — | — |
| Sugar beet | — | — | — | — | — | — | — | — | — |
| Sunflower | — | — | — | — | — | — | — | — | — |
| Wheat (winter) | 10 | 20 | 0 | 20 | 0 | 10 | 30 | 20 | 40 |
| Wild buckwheat | — | — | — | — | — | — | — | — | — |
| Wild mustard | — | — | — | — | — | — | — | — | — |
| Wild oat | 40 | 40 | 20 | 40 | 10 | 30 | 50 | 30 | 0 |
| Windgrass | — | — | — | — | — | — | — | — | — |

Test F Protocol

*Abutilon theophrasti* (ABUTH), *Chenopodium album* (CHEAL), *Amaranthus rudis* (AMATA), *Setaria faberii* (SETFA), *Panicum dichotomiflorum* (PANDI), and *Digitaria sanguinalis* (DIGSA) were grown from seed in pots of an artificial potting mixture in a greenhouse. Compounds of the present invention were applied at 70 and 105 g ai/ha preemergence. Rimsulfuron was applied at 8.8 and 17.5 g ai/ha. Mixtures of the compounds of the present invention and rimsulfuron were also applied.

Following application, the plants were maintained by watering as needed. A fertilizer solution of Peter's 20-20-20 (10 pounds/5 gallons of water) plus Sprint 330, a Iron Chelate micronutrient, (113.5 grams/5 gallons of water) was injected into the water with an Anderson fertilizer injection system to provide approximately 219 ppm of nitrogen with each watering. Artificial lighting was used to supplement natural light to produce a 14 hour photoperiod and: an additional one hour light period was used between 1:00 am to 2:00 am for a night interruption. Greenhouse temperatures were targeted for 27° C. in the day and 21° C. at night. At 21 days after treatment, all plants were evaluated for injury as compared to control plants that were sprayed only with non-phytotoxic solvent. Mean plant response ratings, summarized in Table F, are based upon a 0 to 100 scale where 0 is no effect and 100 is complete control.

Colby's equation was used to calculate the expected additive herbicidal effect of the mixtures of Compound 21 and the mixture partners listed above. Colby's equation (Colby, S. R. "Calculating Synergistic and Antagonistic Responses of Herbicide Combinations," *Weeds*, 15(1), pp 20–22 (1967)) calculates the expected additive effect of herbicidal mixtures, and for two active ingredients is of the form:

$$P_{a+b}=P_a+P_b-(P_aP_b/100)$$

wherein $P_{a+b}$ is the percentage effect of the mixture expected from additive contribution of the individual components, $P_a$ is the observed percentage effect of the first active ingredient at the same use rate as in the mixture, and $P_b$ is the observed percentage effect of the second active ingredient at the same use rate as in the mixture.

Combinations of Compound 113, Compound 131, and Compound 242 with rimsulfuron are surprisingly found to provide better control of certain weeds than expected by calculation from the Colby's equation, thus demonstrating synergism. Weeds other than those specifically listed are also controlled by mixtures of compounds of the present invention and rimsulfuron. Different ratios of compounds of the present invention with rimsulfuron, and different formulation types, also provide useful weed control from the combination of the two herbicides.

TABLE F

| Cmpd. | | ABUTH | | CHEAL | |
|---|---|---|---|---|---|
| 113 | Rimsulfuron | Observed | Expected† | Observed | Expected† |
| Alone | | | | | |
| 70 | 0 | 45 | — | 15 | — |
| 105 | 0 | 65 | — | 35 | — |
| 0 | 8.8 | 20 | — | 25 | — |
| 0 | 17.5 | 40 | — | 60 | — |
| Mixtures | | | | | |
| 70 | 8.8 | 75 | 56 | 60 | 36 |
| 70 | 17.5 | 85 | 67 | 95 | 66 |
| 105 | 8.8 | 90 | 72 | 100 | 51 |
| 105 | 17.5 | 80 | 79 | 100 | 74 |

TABLE F-continued

| Cmpd. | | AMATA | | SETFA | |
|---|---|---|---|---|---|
| 113 | Rimsulfuron | Observed | Expected† | Observed | Expected† |
| Alone | | | | | |
| 70 | 0 | 35 | — | 60 | — |
| 105 | 0 | 25 | — | 65 | — |
| 0 | 8.8 | 10 | — | 75 | — |
| 0 | 17.5 | 15 | — | 90 | — |
| Mixtures | | | | | |
| 70 | 8.8 | 15 | 23 | 95 | 90 |
| 70 | 17.5 | 70 | 45 | 100 | 96 |
| 105 | 8.8 | 25 | 33 | 100 | 91 |
| 105 | 17.5 | 90 | 36 | 100 | 97 |

| Cmpd. | | PANDI | | DIGSA | |
|---|---|---|---|---|---|
| 113 | Rimsulfuron | Observed | Expected† | Observed | Expected† |
| Alone | | | | | |
| 70 | 0 | 100 | — | 95 | — |
| 105 | 0 | 95 | — | 70 | — |
| 0 | 8.8 | 75 | — | 95 | — |
| 0 | 17.5 | 95 | — | 100 | — |
| Mixtures | | | | | |
| 70 | 8.8 | 90 | 100 | 100 | 100 |
| 70 | 17.5 | 100 | 100 | 100 | 100 |
| 105 | 8.8 | 100 | 99 | 90 | 99 |
| 105 | 17.5 | 85 | 99 | 100 | 100 |

| Cmpd. | | ABUTH | | CHEAL | |
|---|---|---|---|---|---|
| 131 | Rimsulfuron | Observed | Expected† | Observed | Expected† |
| Alone | | | | | |
| 70 | 0 | 40 | — | 60 | — |
| 105 | 0 | 60 | — | 95 | — |
| 0 | 8.8 | 20 | — | 25 | — |
| 0 | 17.5 | 40 | — | 60 | — |
| Mixtures | | | | | |
| 70 | 8.8 | 50 | 52 | 95 | 70 |
| 70 | 17.5 | 85 | 64 | 100 | 84 |
| 105 | 8.8 | 80 | 68 | 95 | 96 |
| 105 | 17.5 | 75 | 76 | 100 | 98 |

| Cmpd. | | AMATA | | SETFA | |
|---|---|---|---|---|---|
| 131 | Rimsulfuron | Observed | Expected† | Observed | Expected† |
| Alone | | | | | |
| 70 | 0 | 50 | — | 35 | — |
| 105 | 0 | 40 | — | 65 | — |
| 0 | 8.8 | 10 | — | 75 | — |
| 0 | 17.5 | 15 | — | 90 | — |
| Mixtures | | | | | |
| 70 | 8.8 | 95 | 54 | 85 | 84 |
| 70 | 17.5 | 100 | 58 | 100 | 93 |
| 105 | 8.8 | 95 | 46 | 95 | 91 |
| 105 | 17.5 | 85 | 49 | 100 | 97 |

TABLE F-continued

| Cmpd. | | PANDI | | DIGSA | |
|---|---|---|---|---|---|
| 131 | Rimsulfuron | Observed | Expected† | Observed | Expected† |
| Alone | | | | | |
| 70 | 0 | 100 | — | 100 | — |
| 105 | 0 | 95 | — | 100 | — |
| 0 | 8.8 | 75 | — | 95 | — |
| 0 | 17.5 | 95 | — | 100 | — |
| Mixtures | | | | | |
| 70 | 8.8 | 75 | 100 | 100 | 100 |
| 70 | 17.5 | 95 | 100 | 100 | 100 |
| 105 | 8.8 | 100 | 99 | 100 | 100 |
| 105 | 17.5 | 100 | 100 | 100 | 100 |

| Cmpd. | | ABUTH | | CHEAL | |
|---|---|---|---|---|---|
| 242 | Rimsulfuron | Observed | Expected† | Observed | Expected† |
| Alone | | | | | |
| 70 | 0 | 50 | — | 30 | — |
| 105 | 0 | 70 | — | 100 | — |
| 0 | 8.8 | 20 | — | 25 | — |
| 0 | 17.5 | 40 | — | 60 | — |
| Mixtures | | | | | |
| 70 | 8.8 | 85 | 60 | 100 | 48 |
| 70 | 17.5 | 80 | 81 | 85 | 72 |
| 105 | 8.8 | 85 | 76 | 100 | 100 |
| 105 | 17.5 | 80 | 82 | 100 | 100 |

| Cmpd. | | AMATA | | SETFA | |
|---|---|---|---|---|---|
| 242 | Rimsulfuron | Observed | Expected† | Observed | Expected† |
| Alone | | | | | |
| 70 | 0 | 20 | — | 60 | — |
| 105 | 0 | 55 | — | 75 | — |
| 0 | 8.8 | 10 | — | 75 | — |
| 0 | 17.5 | 15 | — | 90 | — |
| Mixtures | | | | | |
| 70 | 8.8 | 70 | 28 | 90 | 90 |
| 70 | 17.5 | 85 | 32 | 100 | 96 |
| 105 | 8.8 | 35 | 60 | 75 | 94 |
| 105 | 17.5 | 65 | 62 | 100 | 97 |

| Cmpd. | | PANDI | | DIGSA | |
|---|---|---|---|---|---|
| 242 | Rimsulfuron | Observed | Expected† | Observed | Expected† |
| Alone | | | | | |
| 70 | 0 | 60 | — | 100 | — |
| 105 | 0 | 80 | — | 100 | — |
| 0 | 8.8 | 75 | — | 95 | — |
| 0 | 17.5 | 95 | — | 100 | — |
| Mixtures | | | | | |
| 70 | 8.8 | 95 | 90 | 100 | 100 |
| 70 | 17.5 | 100 | 98 | 100 | 100 |
| 105 | 8.8 | 100 | 85 | 100 | 100 |
| 105 | 17.5 | 100 | 99 | 100 | 100 |

*Data are reported as percent control.
†Expected from the Colby Equation

Test G Protocol

In soil-containing pots were planted seeds of maize hybrid P33G26 that was previously treated with dichlomid, fenchlorazole-ethyl, and naphthalic anhydride (or no safener). The soil surface was then treated with several rates of Compound 131 or Compound 146 dissolved in a non-phytotoxic solvent using a flat-fan sprayer calibrated to deliver 310 L/ha. Treatmemtes were replicated 4 or 5 times. The treated and untreated plants were allowed to grow in a greenhouse using supplementary artificial lighting with a day-length of 14 hours, with the temperature maintained at about 27° C. during the day and 24° C. during the night. Plants were kept watered with a dilute balanced fertilizer solution.

At 28 days after application, the treated plants were compared with untreated controls and vissually evaluated. Mean plant response ratings, summarized in Table G, are based upon a 0 to 100 scale where 0 is no effect and 100 is complete control.

TABLE G*

| | | Safener | | | |
|---|---|---|---|---|---|
| Compd | Rate (g ai/ha) | None | Dichlormid | Fenchlorazole-ethyl | naphthalic anhydride |
| 131 | 560 | 95 | 40 | 96 | ND† |
| 131 | 280 | 91 | 3 | 92 | ND† |
| 131 | 140 | 88 | 3 | 91 | 0 |
| 131 | 70 | 80 | 3 | 85 | ND† |
| 146 | 1120 | 85 | 4 | 85 | 35 |
| 146 | 560 | 80 | 4 | 78 | ND† |
| 146 | 280 | 73 | 1 | 74 | ND† |
| 146 | 140 | 49 | 1 | 3 | 0 |

*Data are reported as percent control.
†naphthalic anhydride treatment severely inhibited corn germination. Where corn did satisfactorily emerge, it was safened against the herbicide damage.

As can be seen from Table F, in the absence of any safener, both Compound 131 and Compound 14 at rates ranging from 70 to 560 g/ha, and 140 to 1120 g/ha respectively, were severely injurious to maize. With the exception of Compound 131 at the rate of 560 g/ha (entry 1 in Table F), the presence of dichlormid reduced the injury to an insignificant level from which the corn would be expected to recover with no long-term deleterious effects. The presence of fenchlorazole-ethyl, however, did not provide safening effects except for low rate of Compound 146 (Entry 8 in Table F). The dramatic safening effects observed here were unexpected and surprising. Based on this discovery, it is anticipated that other compounds known to safen herbicides on corn, soybeans or other crops are useful in safening compounds of the present invention on corn, soybeans or other crops.

Test H Protocol

Mixtures of the herbicide and safeners were applied to pots of a soil mixture previously sown with corn. Pioneer hybrid P33G26 corn was sown in pots containing a sterile mix of 60% sassafras soil and 40% Metro Mix 360® growing medium (pH 6.7, O.M. 2%). Test compounds were dissolved in AGWT (a mixture of 0.25% Tween 20 surfactant, 5% water, 5% glycerin and 89.75% acetone) and sprayed on the soil as pots passed under a stationary 8002E nozzle. Treatments were applied at a 33 gal/acre rate of the AGWT carrier. After treatment, the test pots were placed in the greenhouse and watered. There were two replications for each treatment. Each pot contained eight corn seeds. The pots within each replication were placed in random positions on greenhouse benches. Test plants were fertilized as they were watered with approximately 200 ppm of N (as water soluble 20-20-20 fertilizer) which was metered into the water lines with a fertilizer injector. Daytime temperatures was 23–30° C. and night time temperature was 18–25° C. The test plants were supplemented with artificial lighting. The lights were activated whenever the natural light intensity dropped below the programmed threshold. Day length was maintained for approximately 14 hours.

The test was evaluated approximately 12 days after treatment. Treated plants were visually compared to untreated controls and rated on a scale from 0 to 100 where 0 is no effect and 100 is plant death. The results summarized in Table H are the averages from the two replications for each treatment.

TABLE H

| Compd | Rate (g ai/ha) | None | Dichlormid 70 g/ha | Dichlormid 140 g/ha | Dichlormid 280 g/ha |
|---|---|---|---|---|---|
| 113 | 70 | 18 | 0 | 0 | 0 |
| 113 | 140 | 25 | 20 | 0 | 0 |
| 113 | 280 | 53 | 35 | 28 | 33 |
| Compd | Rate (g ai/ha) | None | Benoxacor 70 g/ha | Benoxacor 140 g/ha | Benoxacor 280 g/ha |
| 113 | 70 | 18 | 0 | 0 | 0 |
| 113 | 140 | 25 | 0 | 0 | 8 |
| 113 | 280 | 53 | 38 | 18 | 20 |

As shown in Table H, both dichlormid and benoxacor functioned very effectively as safeners for Compound 113. Without safener, Compound 113 at rates from 70 to 280 g/ha produced corn injury of 18 to 53%. In the presence of dichlormid or benoxacor at rates from 70 to 280 g/ha, corn injury was reduced to from 0 to 38%. The dramatic and unexpected safening by dichlormid and benoxacor demonstrates the potential utility of mixtures of these compounds with Compound 113, or other similar compounds of this invention, for the control of undesired vegetation in corn production.

What is claimed is:

1. A compound selected from Formula 1, an N-oxide or an agriculturally suitable salt thereof,

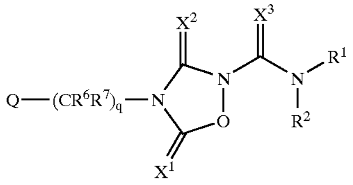

1 wherein

Q is H; or $C_1$–$C_{12}$ alkyl, $C_3$–$C_{10}$ cycloalky, $C_6$–$C_{14}$ bicycloalkyl, $C_3$–$C_{12}$ alkenyl, $C_3$–$C_{10}$ cycloalkenyl, $C_6$–$C_{14}$ bicycloalkenyl or $C_3$–$C_{12}$ alkynyl, each optionally substituted with one or more $R^{21}$; or Q is a 3- to 7-membered fully saturated or 5- to 7-membered partially saturated heterocyclic ring containing one or two X, provided that (a) when X is other than O or $S(O)_n$, then only one X may be present and (b) when two X are present in the ring, they cannot be bonded directly to each other; or Q is a 5- or 6-membered aromatic heterocyclic ring system containing 1 to 3 heteroatoms independently selected from the group consisting of nitrogen, oxygen and sulfur, provided that the heterocyclic ring system contains no more than one oxygen and no more than one sulfur, and each heterocyclic ring system is optionally substituted with one or more $R^{16}$; and when Q is a 5- or 6-membered aromatic heterocyclic ring system containing a nitrogen, then Q is bonded through any available carbon or nitrogen atom by replacement of a hydrogen on said carbon or nitrogen atom; or Q is phenyl optionally substituted with one or more substituents independently selected from the group consisting of $R^{16}$, phenoxy and Z; or Q is

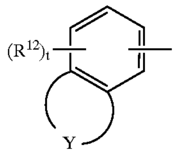

;

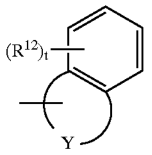

or

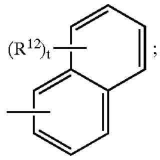

; or

Q is —$C(R^{14})(=NOR^{15})$, —$C(O)R^{19}$, —$C(O)OR^{19}$, —$C(O)SR^{19}$, —$C(S)R^{19}$, —$C(S)OR^{19}$, —$C(S)SR^{19}$, —$C(O)NR^{23}R^{24}$, —$C(S)NR^{23}R^{24}$, —$OR^{19}$, —$NR^{19}R^{20}$, —$S(O)_nR^{19}$ or —$S(O)_nNR^{19}R^{20}$;

each X is —O—, —$S(O)_n$—, —N═, —$NR^{10}$— or —$Si(R^{11})_2$—;

Y is, together with the carbons to which it is attached, a fully or partially saturated 5-, 6- or 7-membered carbocyclic ring optionally substituted with one or more $C_1$–$C_4$ alkyl groups; or Y is, together with the carbons to which it is attached, a fully or partially saturated 5-, 6- or 7-membered heterocyclic ring which contains one or two X and is optionally substituted with one or more $R^{12}$, provided that when said heterocyclic ring contains two X, then one X is other than O;

Z is phenyl or a 5- or 6-membered aromatic heterocyclic ring system containing 1 to 3 heteroatoms independently selected from the group consisting of nitrogen, oxygen and sulfur, provided that the heterocyclic ring system contains no more than one oxygen and no more than one sulfur, and each phenyl and heterocyclic ring system is optionally substituted with one or more $R^{16}$;

$R^1$ is $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl, $C_3$–$C_6$ haloalkynyl, $C_1$–$C_6$ alkoxy, $C_2$–$C_6$ alkoxyalkyl or $C_2$–$C_6$ haloalkoxyalkyl; or $R^1$ is $C_3$–$C_7$ cycloalkyl or $C_3$–$C_7$ cycloalkenyl, each optionally substituted with one or more $R^5$; or $R^1$ is phenyl optionally substituted with one or more $R^{13}$; or $R^1$ is a 5- or 6-membered aromatic heterocyclic ring system containing 1 to 3 heteroatoms independently selected from the group consisting of nitrogen, oxygen and sulfur, provided that the heterocyclic ring system contains no more than one oxygen and no more than one sulfur, and each heterocyclic ring system is optionally substituted with one or more $R^{16}$;

$R^2$ is $C_1$–$C_6$ alkyl, $C_1$–$C_6$ haloalkyl, $C_3$–$C_7$ cycloalkyl, $C_3$–$C_6$ alkenyl, $C_3$–$C_6$ haloalkenyl, $C_3$–$C_6$ alkynyl, $C_3$–$C_6$ haloalkynyl, $C_1$–$C_6$ alkoxy, $C_2$–$C_6$ alkoxyalkyl, $C_2$–$C_6$ haloalkoxyalkyl or $NR^3R^4$; or $R^2$ is

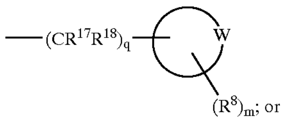

$R^1$ and $R^2$ are taken together as $-CH_2CH_2-$, $-CH_2CH_2CH_2-$, $-CH_2CH_2CH_2CH_2-$, $-CH_2CH_2CH_2CH_2CH_2-$ or $-CH_2CH_2OCH_2CH_2-$;

$R^3$ is $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl, $C_3$–$C_6$ haloalkynyl; or $R^3$ is $C_3$–$C_7$ cycloalkyl or $C_3$–$C_7$ cycloalkenyl, each optionally substituted with one or more $R^5$; or $R^3$ is a saturated or partially saturated 5-, 6- or 7-membered heterocyclic ring containing 1 to 2 heteroatoms independently selected from the group consisting of nitrogen, oxygen and sulfur, and each heterocyclic ring is optionally substituted with one or more $R^5$; or $R^3$ is phenyl optionally substituted with one or more $R^{26}$ groups; or $R^1$ and $R^3$ are taken together with the two nitrogen atoms to which they are attached to form a saturated or partially saturated 5-, 6- or 7-membered heterocyclic ring containing an optional third heteroatom selected from the group consisting of oxygen, sulfur and nitrogen, and said heterocyclic ring is optionally substituted with one or more $R^9$; or $R^2$ and $R^{13}$, together with the two atoms to which they are attached and the atom between them, form a fully saturated 5-, 6- or 7-membered carbocyclic or heterocyclic ring containing one oxygen, one sulfur or one or two nitrogen atoms, said heterocyclic ring is optionally substituted with one or more $R^{12}$ provided that when said heterocyclic ring contains two nitrogen atoms, they are other than bonded directly to each other;

$R^4$ is H or $C_1$–$C_4$ alkyl; or $R^3$ and $R^4$ are taken together with the nitrogen atom to which they are attached to form a saturated or partially saturated 5-, 6- or 7-membered heterocyclic ring containing an optional second heteroatom selected from the group consisting of oxygen, sulfur and nitrogen, and said heterocyclic ring is optionally substituted with 1–4 $R^9$;

each $R^5$ is independently halogen, $C_1$–$C_4$ alkyl or $C_1$–$C_4$ alkoxy; or when two $R^5$ are attached to the same carbon, then said two $R^5$ groups are taken together as (=O);

each $R^6$ and, $R^7$ are independently H or $C_1$–$C_4$ alkyl;

$R^8$ is independently $C_1$–$C_4$ alkyl, $C_1$–$C_4$ haloalkyl or $C_1$–$C_4$ alkoxy;

each $R^9$ is independently $C_1$–$C_4$ alkyl or $C_1$–$C_4$ alkoxy; or when two $R^9$ are attached to the same carbon, then said two $R^9$ groups are taken together as (=O);

W is, together with the carbons to which it is attached, a fully or partially saturated 5-, 6- or 7-membered heterocyclic ring containing one or two X, provided that (a) when X is other than O or $S(O)_n$, then only one X may be present; (b) when two X are present in the ring, they cannot be bonded directly to each other; and (c) said heterocyclic ring is bonded to the group $(CR^{17}R^{18})_q$ through other than X;

$R^{10}$ is H, $C_1$–$C_4$ alkyl, $C_1$–$C_4$ haloalkyl, $C_3$–$C_4$ alkenyl, $C_3$–$C_4$ alkynyl, $C_2$–$C_4$ alkoxycarbonyl or $C_2$–$C_4$ alkylcarbonyl; or $R^{10}$ is phenyl optionally substituted with $C_1$–$C_3$ alkyl, halogen, cyano, nitro or $C_2$–$C_4$ alkoxycarbonyl;

each $R^{11}$ is $C_1$–$C_4$ alkyl;

each $R^{12}$ is independently halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ haloalkylthio, $C_1$–$C_4$ alkylsulfinyl, $C_1$–$C_4$ alkylsulfonyl or $C_2$–$C_4$ alkoxycarbonyl;

each $R^{13}$ is independently halogen, $C_1$–$C_3$ alkyl, $C_1$–$C_3$ haloalkyl, $C_1$–$C_3$ alkoxy, $C_1$–$C_3$ haloalkoxy, $C_3$–$C_6$ alkenyloxy, $C_3$–$C_6$ alkynyloxy, $C_1$–$C_4$ alkylthio, $C_1$–$C_4$ haloalkylthio, $C_1$–$C_4$ alkylsulfinyl, $C_1$–$C_4$ alkylsulfonyl, cyano, amino, nitro or $C_2$–$C_4$ alkoxycarbonyl;

$R^{14}$ is H, $C_1$–$C_6$ alkyl, $C_1$–$C_6$ haloalkyl or $C_2$–$C_6$ alkoxyalkyl; or $R^{14}$ and $R^6$, together with the carbon atoms to which they are bonded, form a 5- or 6-membered saturated carbocyclic ring optionally substituted with one or more $C_1$–$C_4$ alkyl groups;

$R^{15}$ is H, $C_1$–$C_6$ alkyl, $C_1$–$C_6$ haloalkyl, $C_3$–$C_4$ alkenyl or $C_3$–$C_4$ alkynyl;

each $R^{16}$ is independently halogen, nitro, cyano, $C_1$–$C_4$ alkyl, $C_1$–$C_4$ haloalkyl, $C_3$–$C_4$ alkenyl, $C_3$–$C_4$ alkynyl, $OR^{22}$, $NR^{23}R^{24}$ or $S(O)_nR^{19}$;

each $R^{17}$ and $R^{18}$ are independently H or $C_1$–$C_4$ alkyl;

each $R^{19}$ and $R^{20}$ are independently $C_1$–$C_{12}$ alkyl, $C_3$–$C_8$ cycloalkyl, $C_3$–$C_{12}$ alkenyl, $C_3$–$C_8$ cycloalkenyl or $C_3$–$C_{12}$ alkynyl, each optionally substituted with one or more $R^{21}$;

each $R^{21}$ is halogen, $C_4$–$C_8$ trialkylsilylalkyl, CN, $NO_2$, $-OR^{22}$, $-NR^{23}R^{24}$, $-S(O)_nR^{22}$, $-S(O)_nNR^{23}R^{24}$, $-C(O)R^{22}$, $-C(S)R^{22}$, $-C(O)OR^{22}$, $-C(S)OR^{22}$, $-C(S)SR^{22}$, $-C(O)NR^{23}R^{24}$, $-C(S)NR^{23}R^{24}$, $-CHR^2$, $COR^{22}$, $-CHR^{25}P(O)(OR^{22})_2$, $-CHR^{25}P(S)(OR^{22})_2$, $-CHR^{25}C(O)NR^{23}R^{24}$, $-CHR^{25}C(O)NH_2$, $-CHR^{25}CO_2R^{22}$, phenyl optionally substituted with one or more $R^{26}$ groups or benzyl optionally substituted with one or more $R^{26}$ groups;

each $R^{22}$ is $C_1$–$C_8$ alkyl, $C_3$–$C_8$ cycloalkyl, $C_3$–$C_8$ alkenyl, $C_3$–$C_8$ alkynyl, $C_1$–$C_8$ haloalkyl, $C_2$–$C_8$ alkoxyalkyl, $C_2$–$C_8$ alkylthioalkyl, $C_2$–$C_8$ alkylsulfinylalkyl, $C_2$–$C_8$ alkylsulfonylalkyl, $C_4$–$C_8$ alkoxyalkoxyalkyl, $C_4$–$C_8$ cycloalkylalkyl, $C_4$–$C_8$ alkenoxyalkyl, $C_4$–$C_8$ alkynyloxyalkyl, $C_6$–$C_8$ cycloalkoxyalkyl, $C_4$–$C_8$ alkenyloxyalkyl, $C_4$–$C_8$ alkynyloxyalkyl, $C_3$–$C_8$ haloalkoxyalkyl, $C_4$–$C_8$ haloalkenoxyalkyl, $C_4$–$C_8$ haloalkynyloxyalkyl, $C_6$–$C_8$ cycloalkylthioalkyl, $C_4$–$C_8$ alkenylthioalkyl, $C_4$–$C_8$ alkynylthioalkyl, $C_1$–$C_4$ alkyl substituted with phenoxy or benzyloxy, each ring optionally substituted with halogen, $C_1$–$C_3$ alkyl or $C_1$–$C_3$ haloalkyl, $C_4$–$C_8$ trialkylsilylalkyl, $C_3$–$C_8$ cyanoalkyl, $C_3$–$C_8$ halocycloalkyl, $C_3$–$C_8$ haloalkenyl, $C_5$–$C_8$ alkoxyalkenyl, $C_5$–$C_8$ haloalkoxyalkenyl, $C_5$–$C_8$ alkylthioalkenyl, $C_3$–$C_8$ haloalkynyl, $C_5$–$C_8$ alkoxyalkynyl, $C_5$–$C_8$ haloalkoxyalkynyl, $C_5$–$C_8$ alkylthioalkynyl, $C_2$–$C_8$ alkyl carbonyl, $C_2$–$C_8$ alkoxy carbonyl, phenyl optionally substituted with halogen, CN, $C_1$–$C_2$ haloalkyl and $C_1$–$C_2$ haloalkoxy or benzyl optionally substituted with halogen, $C_1$–$C_3$ alkyl and $C_1$–$C_3$ haloalkyl;

each $R^{23}$ is H or $C_1$–$C_4$ alkyl;

each $R^{24}$ is $C_1$–$C_4$ alkyl or phenyl optionally substituted with one or more $R^{26}$ groups;

$R^{23}$ and $R^{24}$ may be taken together as —$(CH_2)_5$—, —$(CH_2)_4$— or —$CH_2CH_2OCH_2CH_2$—, each ring optionally substituted with $C_1$–$C_3$alkyl, phenyl or benzyl;

each $R^{25}$ is H or $C_1$–$C_4$ alkyl;

each $R^{26}$ is $C_1$–$C_3$ alkyl, $C_1$–$C_3$ haloalkyl, $C_1$–$C_3$ alkoxy, $C_1$–$C_3$ haloalkoxy, $C_1$–$C_3$ alkylthio, $C_2$–$C_5$ alkylcarbonyl, $C_2$–$C_5$ alkoxycarbonyl, halogen, amino, cyano or nitro;

$R^{28}$ is H or $C_1$–$C_4$ alkyl;

$X^1$ and $X^2$ are independently O or S;

$X^3$ is O, S or $NR^{28}$;

m is 0, 1, 2, 3 or 4;

each n is independently 0, 1 or 2;

p is 0 or 1;

each q is independently 0, 1 or 2; and t is 0, 1 or 2;

provided that when Q is unsubstituted phenyl, $X^1$, $X^2$ and $X^3$ are O, q is 0 and $R^2$ is methyl, then $R^1$ is other than methyl;

provided that when q is 0, and $X^1$, $X^2$ and $X^3$ are O, and $R^1$ and $R^2$ are $CH_3$, then Q is other than ethyl.

2. The compound of claim 1 wherein

Q is H; or $C_1$–$C_{12}$ alkyl, $C_3$–$C_{10}$ cycloalkyl, $C_6$–$C_{14}$ bicycloalkyl, $C_3$–$C_{12}$ alkenyl, $C_3$–$C_{10}$ cycloalkenyl, $C_6$–$C_{14}$ bicycloalkenyl or $C_3$–$C_{12}$ alkynyl, each optionally substituted with one or more $R^{21}$; or Q is a 3- to 7-membered partially saturated or 5- to 7-membered partially saturated heterocyclic ring containing one or two X, provided that (a) when X is other than O or $S(O)_n$, then only one X may be present and (b) when two X are present in the ring, they cannot be bonded directly to each other; or Q is a 5- or 6-membered aromatic heterocyclic ring system containing 1 to 3 heteroatoms independently selected from the group consisting of nitrogen, oxygen and sulfur, provided that the heterocyclic ring system contains no more than one oxygen and no more than one sulfur, and each heterocyclic ring system is optionally substituted with one or more $R^{16}$; and when Q is a 5- or 6-membered aromatic heterocyclic ring system containing a nitrogen, then Q is bonded through any available carbon or nitrogen atom by replacement of a hydrogen on said carbon or nitrogen atom; or Q is phenyl optionally substituted with one or more substituents independently selected from the group consisting of $R^{16}$, phenoxy and Z.

3. The compound of claim 2 wherein

Q is H; or $C_1$–$C_{12}$ alkyl, $C_3$–$C_{10}$ cycloalkyl, $C_6$–$C_{14}$ bicycloalkyl, $C_3$–$C_{12}$ alkenyl, $C_3$–$C_{10}$ cycloalkenyl, $C_6$–$C_{14}$ bicycloalkenyl or $C_3$–$C_{12}$ alkynyl, each optionally substituted with one or more $R^{21}$.

4. The compound of claim 2 wherein

Q is a 3- to 7-membered fully saturated or 5- to 7-membered partially saturated heterocyclic ring containing one or two X, provided that (a) when X is other than O or $S(O)_n$, then only one X may be present and (b) when two X are present in the ring, they cannot be bonded directly to each other; or Q is a 5- or 6-membered aromatic heterocyclic ring system containing 1 to 3 heteroatoms independently selected from the group consisting of nitrogen, oxygen and sulfur, provided that the heterocyclic ring system contains no more than one oxygen and no more than one sulfur, and each heterocyclic ring system is optionally substituted with one or more $R^{16}$; and when Q is a 5- or 6-membered aromatic heterocyclic ring system containing a nitrogen, then Q is bonded through any available carbon or nitrogen atom by replacement of a hydrogen on said carbon or nitrogen atom.

5. The compound of claim 2 wherein

Q is phenyl optionally substituted with one or more substituents independently selected from the group consisting of $R^{16}$, phenoxy and Z.

6. The compound of claim 3 wherein

Q is $C_1$–$C_6$ alkyl optionally substituted with one or more $R^{21}$, $C_3$–$C_7$ cycloalkyl, $C_3$–$C_7$ alkenyl or $C_3$–$C_6$ alkynyl.

7. The compound of claim 4 wherein

Q is a 5- or 6-membered aromatic heterocyclic ring system containing 1 to 3 heteroatoms independently selected from the group consisting of nitrogen, oxygen and sulfur, provided that the heterocyclic ring system contains no more than one oxygen and no more than one sulfur, and each heterocyclic ring system is optionally substituted with one or more $R^{16}$; and when Q is a 5- or 6-membered aromatic heterocyclic ring system containing a nitrogen, then Q is bonded through any available carbon or nitrogen atom by replacement of a hydrogen on said carbon or nitrogen atom.

8. The compound of claim 5 wherein

Q is phenyl optionally substituted with one or more substituents independently selected from the group consisting of $R^{16}$.

9. The compounds of claim 3, claim 4 or claim 5 wherein $X^1$, $X^2$ and $X^3$ are O.

10. The compound of claim 8 wherein

Q is phenyl with substituents on the 2-, and 6-position independently selected from the group consisting of $R^{16}$.

11. The compound of claim 6 wherein q is 0 or 1.

12. The compound of claim 7 wherein q is 0 or 1.

13. The compound of claim 8 wherein q is 0 or 1.

14. The compound of claim 1 wherein $R^1$ is phenyl substituted with one or more $R^{13}$.

15. The compound of claim 1 wherein $R^2$ is $C_2$–$C_6$ alkyl, $C_2$–$C_6$ haloalkyl or $C_2$–$C_6$ alkoxyalkyl.

16. The compound of claim 1 which is selected from the group consisting of:

(a) N-(4-fluorophenyl)-N-(1-methylethyl)-4-(2-methylphenyl)-3,5-dioxo-1,2,4-oxadiazolidine-2-carboxamide;

(b) 4-(2,6-dimethylphenyl)-N-(4-fluorophenyl)-N-(1-methylethyl)-3,5-dioxo-1,2,4-oxadiazolidine-2-carboxamide;

(c) 4-(2,6-dimethylphenyl)-N-(1-methylethyl)-3,5-dioxo-N-phenyl-1,2,4-oxadiazolidine-2-carboxamide;

(d) 4-cyclohexyl-N-(1-methylethyl)-3,5-dioxo-N-phenyl-1,2,4-oxadiazolidine-2-carboxamide;

(e) 4-cyclohexyl-N-(4-fluorophenyl)-N-(1-methylethyl)-3,5-dioxo-1,2,4-oxadiazolidine-2-carboxamide;

(f) N,4-bis(1-methylethyl)-3,5-dioxo-N-phenyl-1,2,4-oxadiazolidine-2-carboxamide;

(g) N-(4-fluorophenyl)-N-(1-methylethyl)-3,5-dioxo-4-(cyclopropyl)-1,2,4-oxadiazolidine-2-carboxamide; and (h) N-(4-fluorophenyl)-N,4-bis(1-methylethyl)-3,5-dioxo-1,2,4-oxadiazolidine-carboxamide.

17. A process for preparing a compound of Formula 1

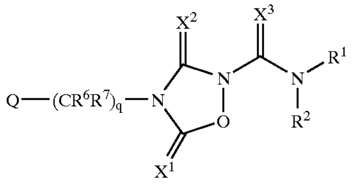

1 wherein Q, $R^6$, $R^7$, q, $X^1$, $X^2$, $X^3$, $R^1$ and $R^2$ are as defined for Formula 1 in claim 1, comprising:

(a) contacting a compound of Formula 5

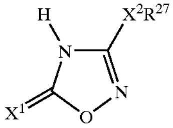

5 wherein $R^{27}$ is —$(CR^6R^7)_q$—Q, with a compound of Formula 4

$$Q—(CR^6R^7)_q—X^4 \qquad 4$$

wherein $X^4$ is halogen or mesylate, in the presence of a base to provide a compound of Formula 3

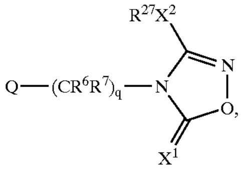

, and

3

(b) contacting the compound of Formula 34 with a carbamoyl or thiocarbamoyl chloride of Formula 2

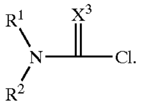

2

18. A process for preparing a compound of Formula 1

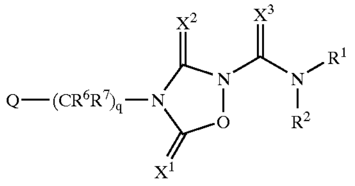

1 wherein Q, $R^6$, $R^7$, q, $X^1$, $X^2$, $X^3$, $R^1$ and $R^2$ are as defined for Formula 1 in claim 1, comprising:

(a) contacting a compound of Formula 5

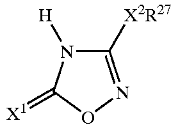

5 wherein $R^{27}$ is —$(CR^6R^7)_q$—Q with an alcohol of Formula 6

$$Q—(CR^6R^7)_q—OH \qquad 6$$

under reaction conditions involving a tertiary phosphine and an azo compound to provide a compound of Formula 3

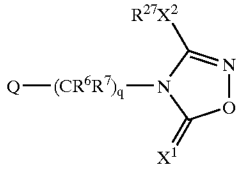

, and

3

(b) contacting the compound of Formula 3 with a carbamoyl or thiocarbamoyl chloride of Formula 2.

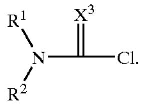

2

19. A process for preparing a compound of Formula 1

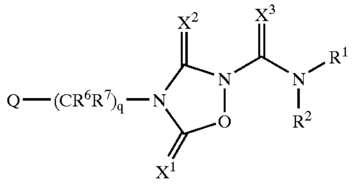

1 wherein Q, $R^6R^7$, q, $X^1$, $X^2$, $X^3$, $R^1$ and $R^2$ are as defined for Formula 1 in claim 1, comprising:

(a) concting a compound of Formula 5

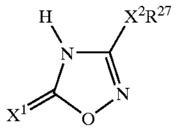

5 wherein $R^{27}$ is —$(CR^6R^7)_q$—Q, with a carbamoyl thiocarbamoyl chloride of Formula 2

2

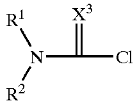

in the presence of a base to provide the compound of Formula 1

1

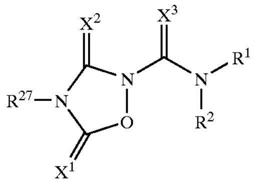

directly or a compound of Formula 7

7

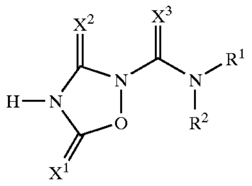

, and (b) contacting the compound of Formula 7 with an alcohol of Formula 6

$$Q—(CR^6R^7)_q—OH \quad 6$$

under reaction conditions involving a tertiary phosphine and an azo compound or with a compound of Formula 4

$$O—(CR^6R^7)_q—X^4 \quad 4$$

in the presence of a base.

20. A process for preparing a compound of Formula 1

1

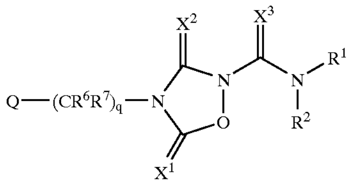

wherein Q, $R^6$, $R^7$, q, $X^2$, $X^3$, $R^1$ and $R^2$ are as defined for Formula 1 in claim 1, and $X^1$ is O, comprising:

(a) contacting a compound of Formula 19

19

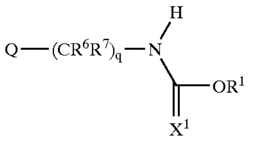

with phosgene or thiophosgene to provide a compound of Formula 20

20

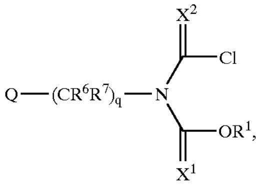

(b) contacting the compound of Formula 20 with hydroxylamine, following by treatment with a base, and then an acid, to provide a compound of Formula 8

8

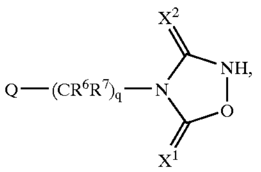

and (c) contacting the compound of Formula 8 with a compound of Formula 2

2

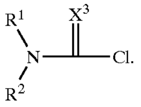

21. A process for preparing a compound of Formula 1

1

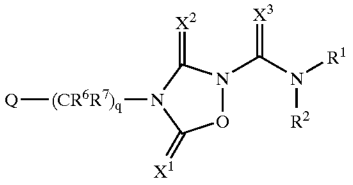

wherein Q, $R^6$, $R^7$, q, $X^1$, $X^2$, $X^3$, $R^1$ and $R^2$ are as defined for Formula 1 in claim 1, comprising:

(a) contacting a compound of Formula 2

2

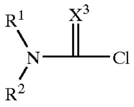

with hydroxylamine in the presence of a base to provide a compound of Formula 22

22

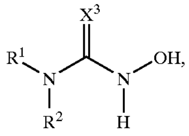

(b) contacting the compound of Formula 22 with a compound of Formula 23

23

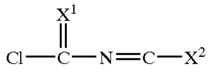

in the presence of a base to provide a compound of Formula 7

7

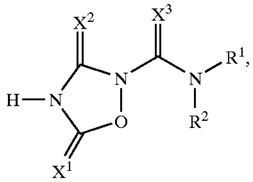 and (c) contacting the compound of Formula 7 with an alcohol of Formula 6

$Q—(CR^6R^7)_q—OH$ 6 under reaction conditions involving a tertiary phosphine and an azo compound or with a compound of Formula 4

$Q—(CR^6R^7)_q—X^4$ 4 in the presence of a base.

22. A process for preparing a compound of Formula 1

1

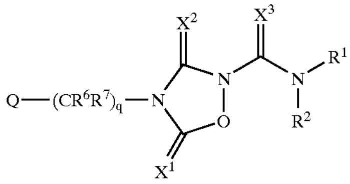

wherein Q, $R^6$, $R^7$, q, $X^1$, $X^2$, $X^3$, $R^1$ and $R^2$ are as defined for Formula 1 in claim 1, comprising contacting a compound of Formula 7

7

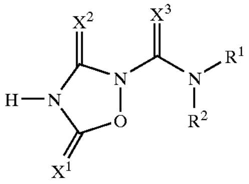

with an orthoformate of Formula 24

$(R^{27}O)_3CH$ 24 wherein $R^{27}$ is $—(CR^6R^7)_q—Q$, in the presence of a base.

23. A process for preparing a compound of Formula 1

1

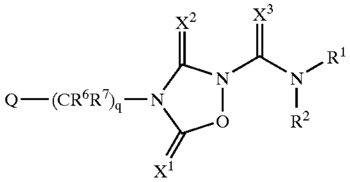

wherein Q, $R^6$, $R^7$, q, $X^1$, $X^2$, $X^3$, $R^1$ and $R^2$ are as defined for Formula 1 in claim 1, comprising:

(a) contacting a compound of Formula 8

8

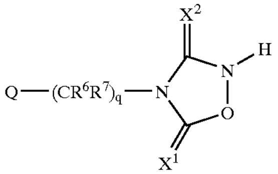

with a compound of Formula 26

26

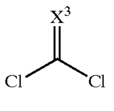

to provide a compound of Formula 25

25

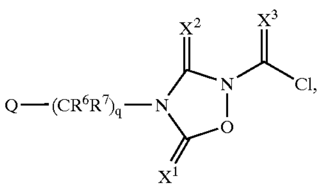

or a compound of Formula 27

27

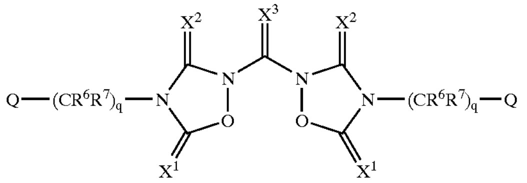

in the presence of a catalyst such as hexamethylguanidinium chloride; and (c) contacting the compound of Formula 25 or Formula 27 with an amine of Formula 13

13

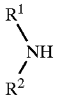

in the presence of a base.

24. A herbicidal composition comprising a herbicidally effective amount of a compound selected from Formula 1, an N-oxide or an agriculturally suitable salt thereof,

1

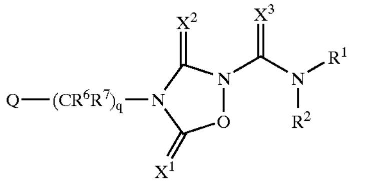

wherein

Q is H; or $C_1$–$C_{12}$ alkyl, $C_3$–$C_{10}$ cycloalky, $C_6$–$C_{14}$ bicycloalkyl, $C_3$–$C_{12}$ alkenyl, $C_3$–$C_{10}$ cycloalkenyl, $C_6$–$C_{14}$ bicycloalkenyl or $C_3$–$C_{12}$ alkynyl, each optionally substituted with one or more $R^{21}$; or Q is a 3- to 7-membered fully saturated or 5- to 7-membered partially saturated heterocyclic ring containing one or two X, provided that (a) when X is other than O, or $S(O)_n$, then only one X may be present and (b) when two X are present in the ring, they cannot be bonded directly to each other; or Q is a 5- or 6-membered aromatic heterocyclic ring system containing 1 to 3 heteroatoms independently selected from the group consisting of nitrogen, oxygen and sulfur, provided that the heterocyclic ring system contains no more than one oxygen and no more than one sulfur, and each heterocyclic ring system is optionally substituted with one or more $R^{16}$; and when Q is a 5- or 6-membered aromatic heterocyclic ring system containing a nitrogen, then Q is bonded through any available carbon or nitrogen atom by replacement of a hydrogen on said carbon or nitrogen atom; or Q is phenyl optionally substituted with one or more substituents independently selected from the group consisting of $R^{16}$, phenoxy and Z; or Q is

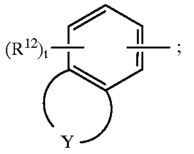

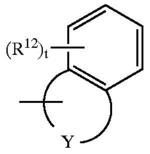

or

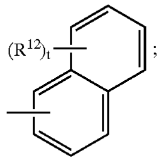

; or

Q is $—C(R^{14})(=NOR^{15})$, $—C(O)R^{19}$, $—C(O)OR^{19}$, $—C(O)SR^{19}$, $—C(S)R^{19}$, $—C(S)OR^{19}$, $—C(S)SR^{19}$, $—C(O)NR^{23}R^{24}$, $—C(S)NR^{23}R^{24}$, $—OR^{19}$, $—N^{19}R^{20}$, $—S(O)_nR^{19}$ or $—S(O)_nNR^{19}R^{20}$;

each X is —O—, $—S(O)_n—$, —N=, $—NR^{10}—$ or $—Si(R^{11})_2—$;

Y is, together with the carbons to which it is attached, a fully or partially saturated 5-, 6- or 7-membered carbocyclic ring optionally substituted with one or more $C_1$–$C_4$ alkyl groups; or Y is, together with the carbons to which it is attached, a fully or partially saturated 5-, 6- or 7-membered heterocyclic ring which contains one or two X and is optionally substituted with one or more $R^{12}$, provided that when said heterocyclic ring contains two X, then one X is other than O;

Z is phenyl or a 5- or 6-membered aromatic heterocyclic ring system containing 1 to 3 heteroatoms independently selected from the group consisting of nitrogen, oxygen and sulfur, provided that the heterocyclic ring system contains no more than one oxygen and no more than one sulfur, and each phenyl and heterocyclic ring system is optionally substituted with one or more $R^{16}$;

$R^1$ is $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl, $C_3$–$C_6$ haloalkynyl, $C_1$–$C_6$ alkoxy, $C_2$–$C_6$ alkoxyalkyl or $C_2$–$C_6$ haloalkoxyalkyl; or $R^1$, is $C_3$–$C_7$ cycloalkyl or $C_3$–$C_7$ cycloalkenyl, each optionally substituted with one or more $R^5$; or $R^1$ is phenyl optionally substituted with one or more $R^{13}$; or $R^1$ is a 5- or 6-membered aromatic heterocyclic ring system containing 1 to 3 heteroatoms independently selected from the group consisting of nitrogen, oxygen and sulfur, provided that the heterocyclic ring system contains no more than one oxygen and no more than one sulfur, and each heterocyclic ring system is optionally substituted with one or more $R^{16}$;

$R^2$ is $C_1$–$C_6$ alkyl, $C_1$–$C_6$ haloalkyl, $C_3$–$C_7$ cycloalkyl, $C_3$–$C_6$ alkenyl, $C_3$–$C_6$ haloalkenyl, $C_3$–$C_6$ alkynyl, $C_3$–$C_6$ haloalkynyl, $C_1$–$C_6$ alkoxy, $C_2$–$C_6$ alkoxyalkyl, $C_2$–$C_6$ haloalkoxyalkyl or $NR^3R^4$; or $R^2$ is

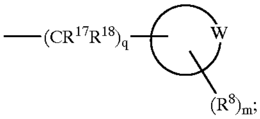

; or $R^1$ and $R^2$ are taken together as $—CH_2CH_2—$, $—CH_2CH_2CH_2—$, $—CH_2CH_2CH_2CH_2—$, $—CH_2CH_2CH_2CH_2CH_2—$ or $—CH_2CH_2OCH_2CH_2—$;

$R^3$ is $C_1$–$C_6$ alkyl, $C_3$–$C_6$ haloalkyl, $C_3$–$C_6$ alkenyl, $C_3$–$C_6$ haloalkenyl, $C_3$–$C_6$ alkynyl, $C_3$–$C_6$ haloalkynyl; or $R^3$ is $C_3$–$C_7$ cycloalkyl or $C_3$–$C_7$ cycloalkenyl, each optionally substituted with one or more $R^5$; or $R^3$ is a saturated or partially saturated 5-, 6- or 7-membered heterocyclic ring containing 1 to 2 heteroatoms independently selected from the group consisting of nitrogen, oxygen and sulfur, and each heterocyclic ring is optionally substituted with one or more $R^5$; or $R^3$ is phenyl optionally substituted with one or more $R^{26}$ groups; or $R^1$ and $R^3$ are taken together with the two nitrogen atoms to which they are attached to form a saturated or partially saturated 5-, 6- or 7-membered heterocyclic ring containing an optional third heteroatom selected from the group consisting of oxygen, sulfur and nitrogen, and said heterocyclic ring is optionally substituted with one or more $R^9$; or $R^2$ and $R^{13}$, together with the two atoms to which they are attached and the atom between them, form a fully saturated 5-, 6- or 7-membered carbocyclic or heterocyclic ring containing one oxygen, one sulfur or one or two nitrogen atoms, said heterocyclic ring is optionally substituted with one or more $R^{12}$, provided that when said heterocyclic ring contains two nitrogen atoms, they are other than bonded directly to each other;

$R^4$ is H or $C_1$–$C_4$ alkyl; or $R^3$ and $R^4$ are taken together with the nitrogen atom to which they are attached to form a saturated or partially saturated 5-, 6- or 7-membered heterocyclic ring containing an optional second heteroatom selected from the group consisting of oxygen, sulfur and nitrogen, and said heterocyclic ring is optionally substituted with 1–4 $R^9$;

each $R^5$ is independently halogen, $C_1$–$C_4$ alkyl or $C_1$–$C_4$ alkoxy; or when two $R^5$ are attached to the same carbon, then said two $R^5$ groups are taken together as (=O);

each $R^6$ and $R^7$ are independently H or $C_1$–$C_4$ alkyl $R^8$ is independently $C_1$–$C_4$ alkyl, $C_1$–$C_4$ haloalkyl or $C_1$–$C_4$ alkoxy;

each $R^9$ is independently $C_1$–$C_4$ alkyl or $C_1$–$C_4$ alkoxy; or when two $R^9$ are attached to the same carbon, then said two $R^9$ groups are taken together as (=O);

W is, together with the carbons to which it is attached, a fully or partially saturated 5-, 6- or 7-membered heterocyclic ring containing one or two X, provided that (a) when X is other than O or $S(O)_n$, then only one X may be present; (b) when two X are present in the ring, they cannot be bonded directly to each other; and (c) said heterocyclic ring is bonded to the group $(CR^{17}R^{18})_q$ through other than X;

$R^{10}$ is H, $C_1$–$C_4$ alkyl, $C_1$–$C_4$ haloalkyl, $C_3$–$C_4$ alkenyl, $C_3$–$C_4$ alkynyl, $C_2$–$C_4$ alkoxycarbonyl or $C_2$–$C_4$ alkylcarbonyl; or $R^{10}$ is phenyl optionally substituted with $C_1$–$C_3$ alkyl, halogen, cyano, nitro or $C_2$–$C_4$ alkoxycarbonyl;

each $R^{11}$ is $C_1$–$C_4$ alkyl;

each $R^{12}$ is independently halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ haloalkylthio, $C_1$–$C_4$ alkylsulfinyl, $C_1$–$C_4$ alkylsulfonyl or $C_2$–$C_4$ alkoxycarbonyl;

each $R^{13}$ is independently halogen, $C_1$–$C_3$ alkyl, $C_1$–$C_3$ haloalkyl, $C_1$–$C_3$ alkoxy, $C_1$–$C_3$ haloalkoxy, $C_3$–$C_6$ alkenyloxy, $C_3$–$C_6$ alkynyloxy, $C_1$–$C_4$ alkylthio, $C_1$–$C_4$ haloalkylthio, $C_1$–$C_4$ alkylsulfinyl, $C_1$–$C_4$ alkylsulfonyl, cyano, amino, nitro or $C_2$–$C_4$ alkoxycarbonyl;

$R^{14}$ is H, $C_1$–$C_6$ alkyl, $C_1$–$C_6$ haloalkyl or $C_2$–$C_6$ alkoxyalkyl; or $R^{14}$ and $R^6$, together with the carbon atoms to which they are bonded, form a 5- or 6-membered saturated carbocyclic ring optionally substituted with one or more $C_1$–$C_4$ alkyl groups;

$R^{15}$ is H, $C_1C_6$ alkyl, $C_1$–$C_6$ haloalkyl, $C_3$–$C_4$ alkenyl or $C_3$–$C_4$ alkynyl;

each $R^{16}$ is independently halogen, nitro, cyano, $C_1$–$C_4$ alkyl, $C_1$–$C_4$ haloalkyl, $C_3$–$C_4$ alkenyl, $C_3$–$C_4$ alkynyl, $OR^{22}$, $NR^{23}R^{24}$ or $S(O)_nR^{19}$;

each $R^{17}$ and $R^{18}$ are independently H or $C_1$–$C_4$ alkyl;

each $R^{19}$ and $R^{20}$ are independently $C_1$–$C_{12}$ alkyl, $C_3$–$C_8$ cycloalkyl, $C_3$–$C_{12}$ alkenyl, $C_3$–$C_8$ cycloalkenyl or $C_3$–$C_{12}$ alkynyl, each optionally substituted with one or more $R^{21}$;

each $R^{21}$ is halogen, $C_4$–$C_8$ trialkylsilylalkyl, CN, $NO_2$, $—OR^{22}$, $—NR^{23}R^{24}$, $—S(O)_nR^{22}$, $—S(O)_nNR^{23}R^{24}$, $—C(O)R^{22}$, $—C(S)R^{22}$, $—C(O)OR^{22}$, $—C(S)OR^{22}$, $—C(S)SR^{22}$, $—C(O)NR^{23}R^{24}$, $—C(S)NR^{23}R^{24}$, $—CHR^{25}COR^{22}$, $—CHR^{25}P(O)(OR^{22})_2$, $—CHR^{25}P(S)(OR^{22})_2$, $—CHR^{25}C(O)NR^{23}R^{24}$, $—CHR^{25}C(O)NH_2$, $—CHR^{25}CO_2R^{22}$, phenyl optionally substituted with one or more $R^{26}$ groups or benzyl optionally substituted with one or more $R^{26}$ groups;

each $R^{22}$ is $C_1$–$C_8$ alkyl, $C_3$–$C_8$ cycloalkyl, $C_3$–$C_8$ alkenyl, $C_3$–$C_8$ alkynyl, $C_1$–$C_8$ haloalkyl, $C_2$–$C_8$ alkoxyalkyl, $C_2$–$C_8$ alkylthioalkyl, $C_2$–$C_8$ alkylsulfinylalkyl, $C_2$–$C_8$ alkylsulfonylalkyl, $C_4$–$C_8$ alkoxyalkoxyalkyl, $C_4$–$C_8$ cycloalkylalkyl, $C_4$–$C_8$ alkenoxyalkyl, $C_4$–$C_8$ alkynyloxyalkyl, $C_6$–$C_8$ cycloalkoxyalkyl, $C_4$–$C_8$ alkenyloxyalkyl, $C_4$–$C_8$ alkynyloxyalkyl, $C_3$–$C_8$ haloalkoxyalkyl, $C_4$–$C_8$ haloalkenoxyalkyl, $C_4$–$C_8$ haloalkynyloxyalkyl, $C_6$–$C_8$ cycloalkylthioalkyl, $C_4$–$C_8$ alkenylthioalkyl, $C_4$–$C_8$ alkynylthioalkyl, $C_1$–$C_4$ alkyl substituted with phenoxy or benzyloxy, each ring optionally substituted with halogen, $C_1$–$C_3$ alkyl or $C_1$–$C_3$ haloalkyl, $C_4$–$C_8$ trialkylsilylalkyl, $C_3$–$C_8$ cyanoalkyl, $C_3$–$C_8$ halocycloalkyl, $C_3$–$C_8$ haloalkenyl, $C_5$–$C_8$ alkoxyalkenyl, $C_5$–$C_8$ haloalkoxyalkenyl, $C_5$–$C_8$ alkylthioalkenyl, $C_3$–$C_8$ haloalkynyl, $C_5$–$C_8$ alkoxyalkynyl, $C_5$–$C_8$ haloalkoxyalkynyl, $C_5$–$C_8$ alkylthioalkynyl, $C_2$–$C_8$ alkyl carbonyl, $C_2$–$C_8$ alkoxy carbonyl, phenyl optionally substituted with halogen, CN, $C_1$–$C_2$ haloalkyl and $C_1$–$C_2$ haloalkoxy or benzyl optionally substituted with halogen, $C_1$–$C_3$ alkyl and $C_1$–$C_3$ haloalkyl;

each $R^{23}$ is H or $C_1$–$C_4$ alkyl;

each $R^{24}$ is $C_1$–$C_4$ alkyl or phenyl optionally substituted with one or more $R^{26}$ groups;

$R^{23}$ and $R^{24}$ may be taken together as $—(CH_2)_5—$, $—(CH_2)_4—$ or $—CH_2CH_2OCH_2CH_2—$, each ring optionally substituted with $C_1$–$C_3$ alkyl, phenyl or benzyl;

each $R^{25}$ is H or $C_1$–$C_4$ alkyl;

each $R^{26}$ is $C_1$–$C_3$ alkyl, $C_1$–$C_3$ haloalkyl, $C_1$–$C_3$ alkoxy, $C_1$–$C_3$ haloalkoxy, $C_1$–$C_3$ alkylthio, $C_2$–$C_5$ alkylcarbonyl, $C_2$–$C_5$ alkoxycarbonyl, halogen, amino, cyano or nitro;

$R^{28}$ is H or $C_1$–$C_4$ alkyl;

$X^1$ and $X^2$ are independently O or S;

$X^3$ is O, S or $NR^{28}$;

m is 0, 1, 2, 3 or 4;

each n is independently 0, 1 or 2;

p is 0 or 1;

each q is independently 0, 1 or 2; and t is 0, 1 or 2;

provided that when Q is unsubstituted phenyl, $X^1$, $X^2$ and $X^3$ are O, q is 0 and $R^2$ is methyl, then $R^1$ is other than methyl; and at least one of a surfactant, a solid diluent or a liquid diluent.

25. A method for controlling the growth of undesired vegetation comprising contacting the vegetation or its environment with a herbicidally effective amount of a compound of claim 1.

* * * * *